US012668600B2

(12) United States Patent
Wu et al.

(10) Patent No.: US 12,668,600 B2
(45) Date of Patent: Jun. 30, 2026

(54) SUBSTITUTED HETEROAROMATIC AMINES AND USES THEREOF

(71) Applicant: Kumquat Biosciences Inc., San Diego, CA (US)

(72) Inventors: Baogen Wu, San Diego, CA (US); Pingda Ren, San Diego, CA (US); Liansheng Li, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 19/353,426

(22) Filed: Oct. 8, 2025

(65) Prior Publication Data

US 2026/0028358 A1 Jan. 29, 2026

Related U.S. Application Data

(63) Continuation of application No. PCT/US2024/036174, filed on Jun. 28, 2024.

(60) Provisional application No. 63/646,597, filed on May 13, 2024, provisional application No. 63/600,560, filed on Nov. 17, 2023, provisional application No. 63/582,484, filed on Sep. 13, 2023, provisional application No. 63/513,796, filed on Jul. 14, 2023, provisional application No. 63/511,279, filed on Jun. 30, 2023.

(51) Int. Cl.

| | |
|---|---|
| ***C07D 519/00*** | (2006.01) |
| ***A61K 31/553*** | (2006.01) |
| ***A61K 31/675*** | (2006.01) |
| ***A61P 35/00*** | (2006.01) |
| ***C07D 498/06*** | (2006.01) |
| ***C07D 498/16*** | (2006.01) |
| ***C07F 9/6561*** | (2006.01) |

(52) U.S. Cl.

CPC .......... *C07D 519/00* (2013.01); *A61K 31/553* (2013.01); *A61K 31/675* (2013.01); *A61P 35/00* (2018.01); *C07D 498/06* (2013.01); *C07D 498/16* (2013.01); *C07F 9/6561* (2013.01)

(58) Field of Classification Search

CPC ..... C07D 519/00; A61P 35/00; A61K 31/353; A61K 31/675

See application file for complete search history.

(56) References Cited

U.S. PATENT DOCUMENTS

| | | | |
|---|---|---|---|
| 12,209,102 | B2 | 1/2025 | Ren et al. |
| 2020/0331911 | A1 | 10/2020 | Marx et al. |
| 2024/0270736 | A1 | 8/2024 | Wu et al. |

FOREIGN PATENT DOCUMENTS

| | | | |
|---|---|---|---|
| CN | 116332948 | A | 6/2023 |
| WO | WO-2013155223 | A1 | 10/2013 |
| WO | WO-2015054572 | A1 | 4/2015 |
| WO | WO-2017172979 | A1 | 10/2017 |
| WO | WO-2018206539 | A1 | 11/2018 |
| WO | WO-2018217651 | A1 | 11/2018 |
| WO | WO-2019099524 | A1 | 5/2019 |
| WO | WO-2019215203 | A1 | 11/2019 |
| WO | WO-2020081282 | A1 | 4/2020 |
| WO | WO-2020097537 | A2 | 5/2020 |
| WO | WO-2020113071 | A1 | 6/2020 |
| WO | WO-2021041671 | A1 | 3/2021 |
| WO | WO-2021118877 | A1 | 6/2021 |
| WO | WO-2022047260 | A1 | 3/2022 |
| WO | WO-2022173870 | A1 | 8/2022 |
| WO | WO-2022177917 | A2 | 8/2022 |
| WO | WO 2022/216762 | * | 10/2022 |
| WO | WO-2022216762 | A1 | 10/2022 |
| WO | WO-2023004102 | A2 | 1/2023 |
| WO | WO-2023172737 | A1 | 9/2023 |
| WO | WO-2023244615 | A1 | 12/2023 |
| WO | WO-2024009191 | A1 | 1/2024 |
| WO | WO-2024015262 | A1 | 1/2024 |
| WO | WO-2024032702 | A1 | 2/2024 |
| WO | WO-2024032747 | A1 | 2/2024 |
| WO | WO-2024041573 | A1 | 2/2024 |
| WO | WO-2024041621 | A1 | 2/2024 |
| WO | WO-2024083168 | A1 | 4/2024 |
| WO | WO-2024085661 | A1 | 4/2024 |
| WO | WO 2024/104453 | * | 5/2024 |
| WO | WO-2024091409 | A1 | 5/2024 |
| WO | WO-2024104453 | A1 | 5/2024 |
| WO | WO-2024197503 | A1 | 10/2024 |
| WO | WO-2024218686 | A1 | 10/2024 |
| WO | WO-2024235286 | A1 | 11/2024 |
| WO | WO-2024254334 | A1 | 12/2024 |
| WO | WO-2025007000 | A1 | 1/2025 |
| WO | WO-2025076523 | A1 | 4/2025 |

(Continued)

OTHER PUBLICATIONS

Hensbergen, Albertus Wijnand. et al. An Expedient Synthesis of Oxazepino and Oxazocino Quinazolines. Tetrahedron Letters 55(46):6478-6483 (2015).

(Continued)

*Primary Examiner* — Marcos L Sznaidman

(74) *Attorney, Agent, or Firm* — Wilson Sonsini Goodrich & Rosati

(57) ABSTRACT

The present disclosure provides compounds and pharmaceutically acceptable salts thereof, and methods of using the same. The compounds and methods have a range of utilities as therapeutics, diagnostics, and research tools. In particular, the subject compositions and methods are useful for reducing signaling output of oncogenic protein.

16 Claims, 1 Drawing Sheet

Specification includes a Sequence Listing.

(56) References Cited

FOREIGN PATENT DOCUMENTS

| | | | |
|---|---|---|---|
| WO | WO-2025130912 | A1 | 6/2025 |
| WO | WO-2025167948 | A1 | 8/2025 |
| WO | WO-2025171055 | A1 | 8/2025 |

OTHER PUBLICATIONS

McGregor, Lynn M. et al. Expanding the Scope of Electrophiles Capable of Targeting K-Ras Oncogenes. Biochemistry 56(25):3178-3183 (2017).

PCT/US2024/036174 International Search Report and Written Opinion dated Oct. 1, 2024.

Wang, Zhijun and Neidlein, Richard. A Novel Fused Heterocyclic System—synthesis of Substituted 9,10-dihydro-1,3,4,6,7,10-hexaazacyclohepta[de]naphthalen-8(7H)-ones. Tetrahedron 54(33):9903-9910 (1998).

KR-10-2022-0134463 filed on Oct. 18, 2022 (first priority document for WO2024085661 Ildong) including machine English translation.

KR-10-2023-0056594 filed on Apr. 28, 2023 (second priority document for WO2024085661 Ildong) including certified English translation.

* cited by examiner

| | 1 | | 20 | | 40 | |
|---|---|---|---|---|---|---|
| **K-Ras** (SEQ ID No. 9) | mte-------- ----yklvvv | gaggvgksal | tiqliqnhfv | deydptieds | yrkqvvidge | **49** |
| **H-Ras** (SEQ ID No. 10) | mte-------- ----yklvvv | gaggvgksal | tiqliqnhfv | deydptieds | yrkqvvidge | **49** |
| **N-Ras** (SEQ ID No. 11) | mte-------- ----yklvvv | gaggvgksal | tiqliqnhfv | deydptieds | yrkqvvidge | **49** |
| **RalA** (SEQ ID No. 12) | maankpkgqn slalhkvimv | gsggvgksal | tlqfmydefv | edyeptkads | yrkkvvldge | **60** |
| **RalB** (SEQ ID No. 13) | maankskgqs slalhkvimv | gsggvgksal | tlqfmydefv | edyeptkads | yrkkvvldge | **60** |

| | 60 | | 80 | | 100 | |
|---|---|---|---|---|---|---|
| **K-Ras** | tclldildta | gqeeysamrd qymrtgegfl | cvfainntks | fedihhyreq | ikrvkdsed- | **108** |
| **H-Ras** | tclldildta | gqeeysamrd qymrtgegfl | cvfainntks | fedihqyreq | ikrvkdsdd- | **108** |
| **N-Ras** | tclldildta | gqeeysamrd qymrtgegfl | cvfainnsks | fadinlyreq | ikrvkdsdd- | **108** |
| **RalA** | evqidildta | gqedyaaird nyfrsgegfl | cvfsitemes | faatadfreq | ilrvk-eden | **119** |
| **RalB** | evqidildta | gqedyaaird nyfrsgegfl | lvfsitehes | ftataefreq | ilrvkaeedk | **120** |

SEQUENCE LISTING

```
Sequence total quantity: 13
SEQ ID NO: 1            moltype = AA  length = 188
FEATURE                 Location/Qualifiers
source                  1..188
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 2            moltype = AA  length = 188
FEATURE                 Location/Qualifiers
source                  1..188
                        mol_type = protein
```

```
                        organism = Homo sapiens
SEQUENCE: 2
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 3            moltype = AA  length = 188
FEATURE                 Location/Qualifiers
source                  1..188
                        mol_type = protein
                        organism = Homo sapiens
SEQUENCE: 3
MTEYKLVVVG AVGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 4            moltype = AA  length = 188
FEATURE                 Location/Qualifiers
source                  1..188
                        mol_type = protein
                        organism = Homo sapiens
SEQUENCE: 4
MTEYKLVVVG ASGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 5            moltype = AA  length = 189
FEATURE                 Location/Qualifiers
source                  1..189
                        mol_type = protein
                        organism = Homo sapiens
SEQUENCE: 5
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 6            moltype = AA  length = 189
FEATURE                 Location/Qualifiers
source                  1..189
                        mol_type = protein
                        organism = Homo sapiens
SEQUENCE: 6
MTEYKLVVVG ADGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                         189

SEQ ID NO: 7            moltype = AA  length = 189
FEATURE                 Location/Qualifiers
source                  1..189
                        mol_type = protein
                        organism = Homo sapiens
SEQUENCE: 7
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                         189

SEQ ID NO: 8            moltype = AA  length = 189
FEATURE                 Location/Qualifiers
source                  1..189
                        mol_type = protein
                        organism = Homo sapiens
SEQUENCE: 8
MTEYKLVVVG ADGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                         189

SEQ ID NO: 9            moltype = AA  length = 108
FEATURE                 Location/Qualifiers
source                  1..108
                        mol_type = protein
                        organism = Homo sapiens
SEQUENCE: 9
```

-continued

```
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSED               108

SEQ ID NO: 10          moltype = AA  length = 108
FEATURE                Location/Qualifiers
source                 1..108
                       mol_type = protein
                       organism = Homo sapiens
SEQUENCE: 10
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHQYREQI KRVKDSDD               108

SEQ ID NO: 11          moltype = AA  length = 108
FEATURE                Location/Qualifiers
source                 1..108
                       mol_type = protein
                       organism = Homo sapiens
SEQUENCE: 11
MTEYKLVVVG AGGVGKSALT IQLIQNHFVD EYDPTIEDSY RKQVVIDGET CLLDILDTAG  60
QEEYSAMRDQ YMRTGEGFLC VFAINNSKSF ADINLYREQI KRVKDSDD               108

SEQ ID NO: 12          moltype = AA  length = 119
FEATURE                Location/Qualifiers
source                 1..119
                       mol_type = protein
                       organism = Homo sapiens
SEQUENCE: 12
MAANKPKGQN SLALHKVIMV GSGGVGKSAL TLQFMYDEFV EDYEPTKADS YRKKVVLDGE  60
EVQIDILDTA GQEDYAAIRD NYFRSGEGFL CVFSITEMES FAATADFREQ ILRVKEDEN   119

SEQ ID NO: 13          moltype = AA  length = 120
FEATURE                Location/Qualifiers
source                 1..120
                       mol_type = protein
                       organism = Homo sapiens
SEQUENCE: 13
MAANKSKGQS SLALHKVIMV GSGGVGKSAL TLQFMYDEFV EDYEPTKADS YRKKVVLDGE  60
EVQIDILDTA GQEDYAAIRD NYFRSGEGFL LVFSITEHES FTATAEFREQ ILRVKAEEDK  120
```

SUBSTITUTED HETEROAROMATIC AMINES AND USES THEREOF

CROSS-REFERENCE

This application is a continuation of International Application No. PCT/US2024/036174, filed Jun. 28, 2024, which claims the benefit of U.S. Provisional Application No. 63/511,279, filed Jun. 30, 2023; U.S. Provisional Application No. 63/513,796, filed Jul. 14, 2023; U.S. Provisional Application No. 63/582,484, filed Sep. 13, 2023; U.S. Provisional Application No. 63/600,560, filed Nov. 17, 2023; and U.S. Provisional Application No. 63/646,597, filed May 13, 2024, each incorporated herein by reference in its entirety.

SEQUENCE LISTING

The instant application contains a Sequence Listing which has been submitted electronically in XML format and is hereby incorporated by reference in its entirety. Said XML copy, created on Oct. 7, 2025, is named 56690_771_301_SL.xml and is 14,004 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) are one of the most frequent Ras mutations detected in human cancers, including lung adenocarcinomas (LUADs) and pancreatic ductal adenocarcinoma (PDAC).

Ras proteins have long been considered "undruggable," due to, in part, high affinity to their substrate guanosine-5'-triphosphate (GTP) and/or their smooth surfaces without any obvious targeting region. The specific G12C Ras gene mutation has been identified as a druggable target to which a number of G12C specific inhibitors have been developed. However, such therapeutics are still of limited application, as the G12C mutation in Ras exhibits a much lower prevalence rate as compared to other known Ras mutations, such as G12D and G12V. Drug resistance and lack of durability impose further limitations to such therapeutics.

SUMMARY

In view of the foregoing, there remains a considerable need for a new design of therapeutics and diagnostics that can specifically target Ras, including wildtype Ras, mutants and/or associated proteins of Ras to reduce Ras signaling output. Of particular interest are Ras inhibitors, including pan Ras inhibitors capable of inhibiting two or more Ras mutants and/or wildtype Ras, as well as mutant-selective inhibitors targeting mutant Ras proteins such as Ras G12D, G12C, G12S, G13D, and/or G12V, for the treatment of Ras-associated diseases (e.g., cancer). Such compositions and methods can be particularly useful for treating a variety of diseases including, but not limited to, cancers and neoplasia conditions. The present disclosure addresses these needs, and provides additional advantages applicable for diagnosis, prognosis, and/or treatment for a wide diversity of diseases.

In certain aspects, the present disclosure provides a compound of Formula (I):

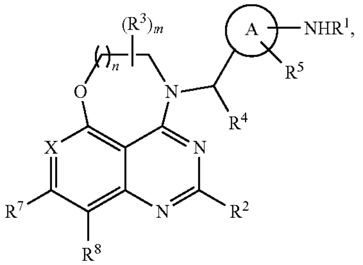

(I)

or a pharmaceutically acceptable salt or solvate thereof, wherein:

X is selected from $C(R^6)$ and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)OC(O)R^{12}$, —C(O)O—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})_2$;

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^7$ is benzothiophenyl optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)OR^{12}$, —$C(O)R^{12}$, —$P(O)(Y—R^{16})(Z—R^{17})$, and —$CH_2P(O)(Y—R^{16})(Z—R^{17})$;

Y and Z are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, for a compound of Formula (I), (III), or (IV), X is C($R^6$). In some embodiments, X is N.

In some embodiments, for a compound of Formula (I), (III), or (IV), A is selected from pyridinyl, pyridazinyl, pyrimidinyl, and pyrazinyl, such as A is pyridinyl. In some embodiments, $R^1$ is hydrogen. In some embodiments, $R^5$ is selected from hydrogen and halogen; or $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^5$ is hydrogen. In some embodiments,

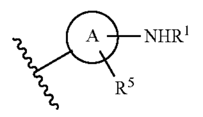

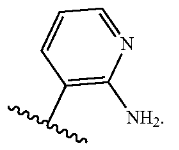 [SMILES: *c1cccnc1N]

In some embodiments, for a compound of Formula (I), (III), or (IV), $R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^4$ is $CH_3$.

In some embodiments, for a compound of Formula (I), (III), or (IV), $R^7$ is benzo[b]thiophen-4-yl optionally substituted with one, two, three, or four $R^{20}$. In some embodiments, $R^7$ is substituted with one, two, or three substituents independently selected from halogen, —CN, and —N($R^{22}$)($R^{23}$). In some embodiments, $R^7$ is substituted with fluorine, —CN, and —$NH_2$. In some embodiments, $R^7$ is

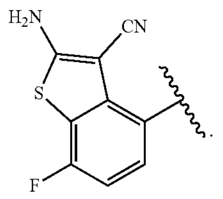 [SMILES: *c1ccc(F)c2sc(N)c(C#N)c12]

In some embodiments, for a compound of Formula (I), (III), or (IV), X is C($R^6$); A is selected from pyridinyl, pyridazinyl, pyrimidinyl, and pyrazinyl; $R^1$ is hydrogen; $R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, —$C_{3-8}$ carbocycle, 3- to 8-membered heterocycle, —$OR^{12}$, —N($R^{12}$)($R^{13}$), —C(O)$OR^{12}$, —N($R^{12}$)C(O)N($R^{12}$)($R^{13}$), —C(O)$R^{12}$, —OC(O)$R^{12}$, —C(O)N($R^{12}$)($R^{13}$), and —N($R^{12}$)C(O)$R^{12}$, wherein $C_{1-6}$ alkyl, $C_{2-6}$ alkenyl, $C_{2-6}$ alkynyl, —$C_{3-8}$ carbocycle, and 3- to 8-membered heterocycle are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =C($R^{14}$)$_2$; $R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; $R^7$ is benzo[b]thiophen-4-yl optionally substituted with one, two, three, or four $R^{20}$; m is 0 or 1; and n is 1 or 2.

In certain aspects, the present disclosure provides a compound of Formula (II):

(II)

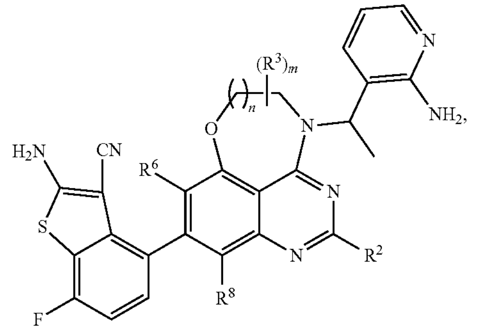

or a pharmaceutically acceptable salt or solvate thereof, wherein:

$R^2$, $R^3$, $R^6$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, $=NR^{12}$, or $=C(R^4)_2$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, $=NR^{22}$, $=C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, $=NR^{22}$, $=C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, the compound of Formula (I) or (II) is a compound of Formula (II-a):

(II-a)

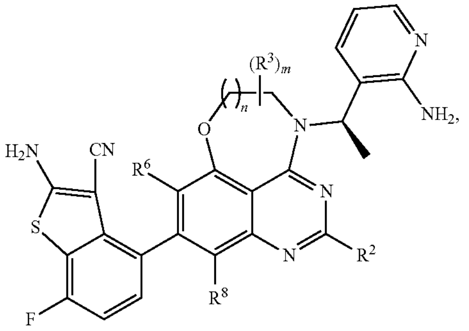

or a pharmaceutically acceptable salt or solvate thereof.

In some embodiments, for a compound of Formula (I), (II), (II-a), (III), or (IV), $R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$. In some embodiments, $R^2$ is —$OR^{12}$. In some embodiments, $R^2$ is —O($C_{1-3}$ alkyl)(4- to 10-membered heterocycle) optionally substituted with one, two, or three substituents independently selected from halogen, $C_{1-3}$ alkyl, $C_{1-3}$ haloalkyl, and $=C(R^{21})_2$, wherein $R^{21}$ is independently selected at each occurrence from hydrogen, halogen, and $C_{1-3}$ alkyl. In some embodiments, $R^2$ is selected from

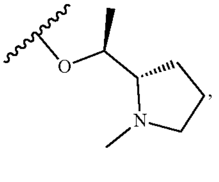,
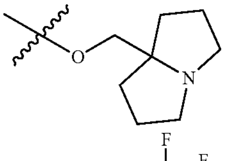,
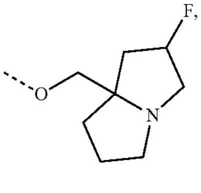,
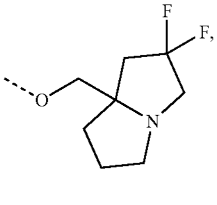,

-continued

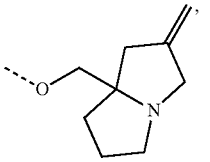

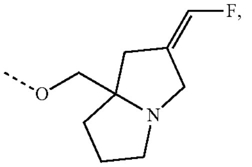

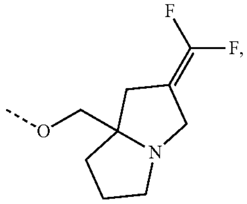

and

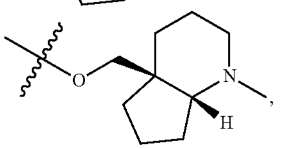

such as $R^2$ is

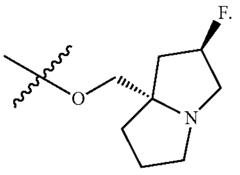 [SMILES: *OC[C@@]12CCCN1C[C@H](F)C2]

In some embodiments, for a compound of Formula (I), (II), (II-a), (III), or (IV), $R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$. In some embodiments, $R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$. In some embodiments, m is 0 or 1, such as m is 0.

In some embodiments, for a compound of Formula (I), (II), (II-a), (III), or (IV), $R^6$ and $R^8$ are independently selected from hydrogen, halogen, and $C_{1-3}$ haloalkyl. In some embodiments, $R^6$ is chlorine. In some embodiments, $R^8$ is fluorine. In some embodiments, n is 1.

In certain aspects, the present disclosure provides a compound disclosed in Table 1, or a pharmaceutically acceptable salt or solvate thereof.

In certain aspects, the present disclosure provides a compound having the formula B-$L^{BE}$-E wherein:

B is a monovalent form of a compound disclosed herein, such as a compound of Table 1;

$L^{BE}$ is a covalent linker bonded to B and E; and

E is a monovalent form of a degradation enhancer.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2HI, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1. In some embodiments, $L^{BE}$ is -$L^{BE1}$-$L^{BE2}$-$L^{BE3}$-$L^{BE4}$-$L^{BE5}$-$L^{BE1}$, $L^{BE2}$, $L^{BE3}$, $L^{BE4}$, and $L^{BE5}$ are independently a bond, —O—, —N($R^{12}$)—, —C(O)—, —N($R^{12}$)C(O)—, —C(O)N($R^{12}$)—, —S—, —S(O)$_2$—, —S(O)—, —S(O)$_2$N($R^{12}$)—, —S(O)N($R^{12}$)—, —N($R^{12}$)S(O)—, —N($R^{12}$)S(O)$_2$—, $C_{1-6}$ alkylene, (—O—$C_{1-6}$ alkyl)$_z$-, (—$C_{1-6}$ alkyl-O)$_z$—, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$; and wherein each $C_{1-6}$ alkyl of (—O—$C_{1-6}$ alkyl)$_z$- and (—$C_{1-6}$ alkyl-O)$_z$— is optionally substituted with one, two, or three $R^{20}$; and z is independently an integer from 0 to 10. In some embodiments, $L^{BE}$ is —(O—$C_2$ alkyl)$_z$- and z is an integer from 1 to 10. In some embodiments, $L^{BE}$ is —($C_2$ alkyl-O—)$_z$- and z is an integer from 1 to 10. In some embodiments, $L^{BE}$ is —($CH_2$)$_{zz1}$$L^{BE2}$($CH_2O$)$_{zz2}$—, wherein $L^{BE2}$ is a bond, a 5 or 6 membered heterocycloalkylene or heteroarylene, phenylene, —$C_{2-4}$alkynylene, —$SO_2$— or —NH—; and zz1 and zz2 are independently an integer from 0 to 10. In some embodiments, $L^{BE}$ is —($CH_2$)$_{zz1}$($CH_2O$)$_{zz2}$—, wherein zz1 and zz2 are each independently an integer from 0 to 10. In some embodiments $L^{BE}$ is a PEG linker. In some embodiments E is a monovalent form of a compound selected from

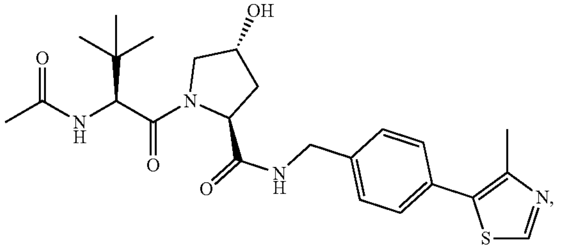

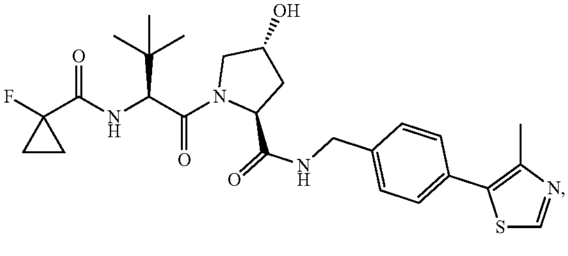

-continued

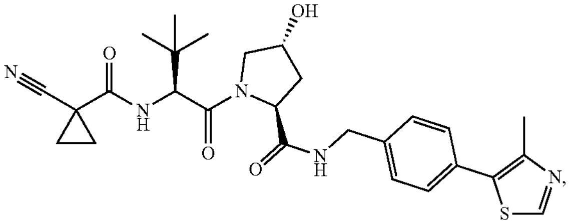

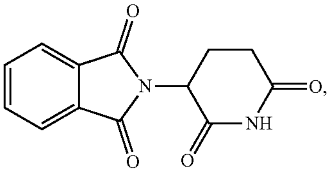

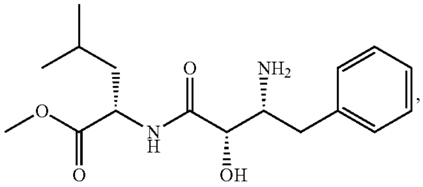

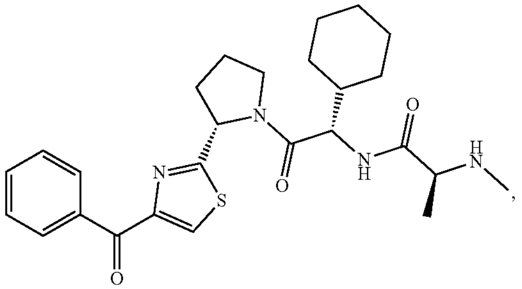

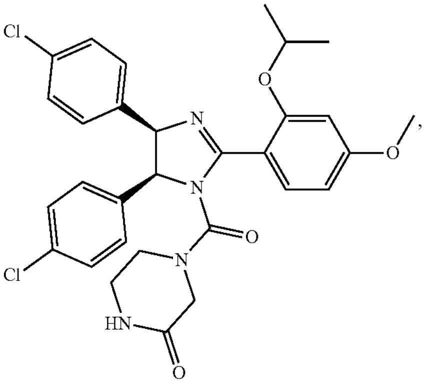

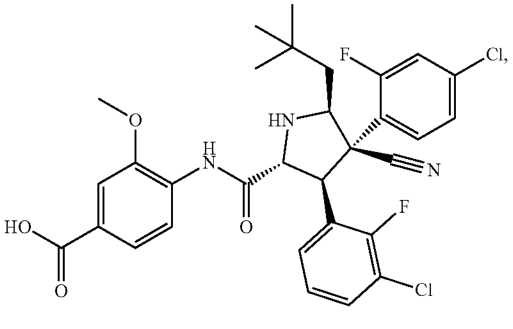

-continued

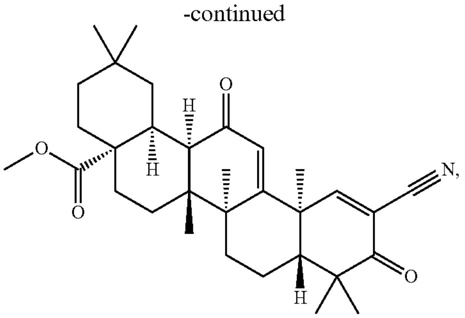

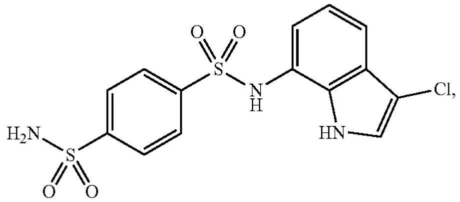

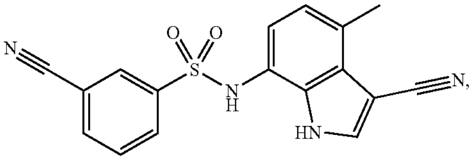

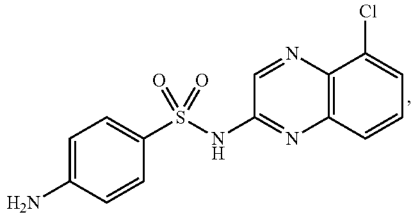

and

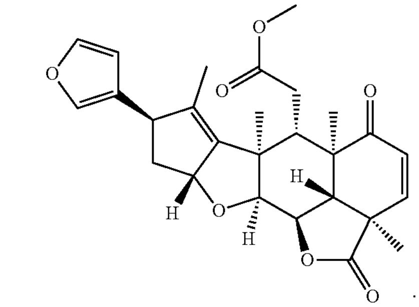

In certain aspects, the present disclosure provides a pharmaceutical composition comprising a compound described herein, such as a compound of Table 1, or a pharmaceutically acceptable salt or solvate thereof, and a pharmaceutically acceptable excipient.

In certain aspects, the present disclosure provides a method of treating cancer in a subject in need thereof, comprising administering to the subject a therapeutically effective amount of a compound described herein, such as a compound of Table 1, or a pharmaceutically acceptable salt or solvate thereof. In certain aspects, the present disclosure provides a method of treating cancer in a subject comprising a Ras mutant protein, the method comprising: inhibiting the Ras mutant protein of said subject by administering to said subject a compound described herein, such as a compound of Table 1, wherein the compound is characterized in that upon contacting the Ras mutant protein, said Ras mutant protein exhibits reduced Ras signaling output. In some embodiments, the cancer is a solid tumor or a hematological cancer. In some embodiments, the cancer comprises a K-Ras G12C, G12D, G12S, or G12V mutant protein.

In certain aspects, the present disclosure provides a method of modulating signaling output of a Ras protein, comprising contacting a Ras protein with an effective amount of a compound described herein, such as a compound of Table 1, or a pharmaceutically acceptable salt or solvate thereof, thereby modulating the signaling output of the Ras protein. In certain aspects, the present disclosure provides a method of inhibiting cell growth, comprising administering an effective amount of a compound described herein, such as a compound of Table 1, or a pharmaceutically acceptable salt or solvate thereof, to a cell expressing a Ras protein, thereby inhibiting growth of said cells.

A method of the present disclosure may further comprise administering an additional agent. In some embodiments, the additional agent comprises (1) an inhibitor of MEK; (2) an inhibitor of epidermal growth factor receptor (EGFR) and/or mutants thereof; (3) an immunotherapeutic agent; (4) a taxane; (5) an anti-metabolite; (6) an inhibitor of FGFR1 and/or FGFR2 and/or FGFR3 and/or mutants thereof; (7) a mitotic kinase inhibitor; (8) an anti-angiogenic drug; (9) a topoisomerase inhibitor; (10) a platinum-containing compound; (11) an inhibitor of c-MET and/or mutants thereof; (12) an inhibitor of BCR-ABL and/or mutants thereof; (13) an inhibitor of ErbB2 (Her2) and/or mutants thereof; (14) an inhibitor of AXL and/or mutants thereof; (15) an inhibitor of NTRK1 and/or mutants thereof; (16) an inhibitor of RET and/or mutants thereof; (17) an inhibitor of A-Raf and/or B-Raf and/or C-Raf and/or mutants thereof; (18) an inhibitor of ERK and/or mutants thereof; (19) an MDM2 inhibitor; (20) an inhibitor of mTOR; (21) an inhibitor of IGF1/2 and/or IGF1-R; (22) an inhibitor of CDK9; (23) an inhibitor of farnesyl transferase; (24) an inhibitor of SHIP pathway; (25) an inhibitor of SRC; (26) an inhibitor of JAK; (27) a PARP inhibitor, (28) a ROS1 inhibitor; (29) an inhibitor of SHP pathway; (30) an inhibitor of Src, FLT3, HDAC, VEGFR, PDGFR, LCK, Bcr-Abl or AKT; (31) an inhibitor of KRAS G12C; (32) an SHC inhibitor; (33) a GAB inhibitor; (34) a PI-3 kinase inhibitor; (35) a MARPK inhibitor; (36) a CDK4/6 inhibitor; (37) a MAPK inhibitor; (38) a SHP2 inhibitor; (39) a checkpoint immune blockade agent; (40) a SOS1 inhibitor; or (41) a SOS2 inhibitor. In some embodiments, the additional agent comprises an inhibitor of SHP2 selected RMC-4630, ERAS-601, TNO155, JAB-3068, IACS-13909/BBP-398, SHP099, and RMC-4550. In some embodiments, the additional agent comprises an inhibitor of SOS selected from RMC-5845, BI-1701963, BI-3406, MRTX0902, and BAY 293. In some embodiments, the additional agent comprises an inhibitor of EGFR selected from afatinib, erlotinib, gefitinib, lapatinib, cetuximab panitumumab, osimertinib, olmutinib, and EGF-816. In some embodiments, the additional agent comprises an inhibitor of MEK selected from trametinib, cobimetinib, binimetinib, selumetinib, refametinib, and AZD6244. In some embodiments, the additional agent comprises an inhibitor of ERK selected from ulixertinib, MK-8353, LTT462, AZD0364, SCH772984, BIX02189, LY3214996, and ravoxertinib. In some embodiments, the additional agent comprises an inhibitor of CDK4/6 selected from palbociclib, ribociclib, and abemaciclib. In some embodiments, the additional agent comprises an inhibitor of BRAF selected from Sorafenib, Vemurafenib, Dabrafenib, Encorafenib, regorafenib, and GDC-879.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a sequence alignment of various wild type Ras proteins including K-Ras, H-Ras, N-Ras, RalA, and RalB, from top to bottom.

DETAILED DESCRIPTION

Unless defined otherwise, all technical and scientific terms used herein have the same meaning as is commonly understood by one of skill in the art to which this disclosure belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Chemical structures are named herein according to IUPAC conventions as implemented in ChemDraw® software (Perkin Elmer, Inc., Cambridge, MA). The section headings used herein are for organizational purposes only and are not to be construed as limiting the subject matter described. As used in the specification and claims, the singular forms "a", "an" and "the" include plural references unless the context clearly dictates otherwise. Furthermore, use of the term "including" as well as other forms, such as "include", "includes", and "included", is not limiting. The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl, or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{5-12}$ bicyclic rings, $C_{5-18}$ polycyclic rings, $C_{5-12}$ spirocyclic rings, and $C_{5-12}$ bridged rings. Each ring of a bicyclic or polycyclic carbocycle may be selected from saturated, unsaturated, and aromatic rings. A polycyclic carbocycle contains a number or rings equal to the minimum number of scissions required to convert the carbocycle into an acyclic skeleton (e.g., bicyclic, tricyclic, tetracyclic, etc.). In some embodiments, the carbocycle is a $C_{6-12}$ aryl group, such as $C_{6-10}$ aryl. In some embodiments, the carbocycle is a $C_{3-12}$ cycloalkyl group. In some embodiments, the carbocycle is a $C_{5-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic rings, as valence permits, are included in the definition of carbocycle. A carbocycle may comprise a fused ring, a bridged ring, a spirocyclic ring, a saturated ring, an unsaturated ring, an aromatic ring, or any combination thereof. Exemplary carbocycles include cyclopentyl, cyclohexyl, cyclohexenyl, adamantly, phenyl, indanyl, and naphthyl. Unless state otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2, 3, or 4 heteroatoms selected from O, S, P, and N. Heterocycle may include 3- to 10-membered monocyclic rings, 5- to 12-membered bicyclic rings, 5- to 18-membered polycyclic rings, 5- to 12-membered spirocyclic rings, and 5- to 12-membered bridged rings. Each ring of a bicyclic or polycyclic heterocycle may be selected from saturated, unsaturated, and aromatic rings. A polycyclic heterocycle contains a number or rings equal to the minimum number of scissions required to convert the heterocycle into an acyclic skeleton (e.g., bicyclic, tricyclic, tetracyclic, etc.). The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. A heterocycle may comprise a fused ring, a bridged ring, a spirocyclic ring, a saturated ring, an unsaturated ring, an aromatic ring, or any combination thereof. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, benzothienyl, benzoxazolyl, and quinolinyl. Unless stated otherwise specifically in the specification, a heterocycle is optionally substituted by one or more substituents such as those substituents described herein.

"Heteroaryl" refers to an aromatic ring that comprises at least one heteroatom, for example 1, 2, 3, or 4 heteroatoms selected from O, S and N. Heteroaryl may include 5- to 10-membered monocyclic rings, 6- to 12-membered bicyclic rings, 6- to 18-membered polycyclic rings, 5- to 12-membered spirocyclic rings, and 6- to 12-membered bridged rings. As used herein, the heteroaryl ring may be selected from monocyclic, bicyclic, or polycyclic-including fused, spirocyclic and bridged ring systems—wherein at least one of the rings in the ring system is aromatic and comprises at least one heteroatom. A polycyclic heteroaryl contains a number or rings equal to the minimum number of scissions required to convert the heteroaryl into an acyclic skeleton (e.g., bicyclic, tricyclic, tetracyclic, etc.). The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line “~” drawn across or at the end of a bond or a dashed bond “- - -” are used interchangeably herein to denote where a bond disconnection or attachment occurs. For example, in the structure

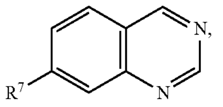

if $R^7$ is benzo[b]thiophen-4-yl as in

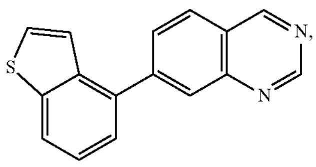 [SMILES: c1cc(-c2ccc3cncnc3c2)c2ccsc2c1]

then $R^7$ may be depicted as

“ 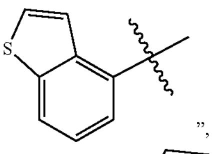 ”, “ 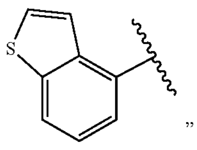 ” or

“ 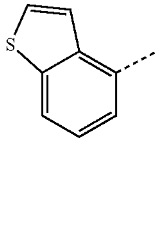 ”.

The term “substituted” refers to moieties having substituents replacing a hydrogen on one or more carbons or heteroatoms of the structure. It will be understood that “substitution” or “substituted with” includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I), (II), (II-a), (III), (IV), (V), (Va), (Vb), (Vc), (VI), (VII), (VIII), (IX), (X), (XI), or (XII), is optionally substituted by one or more-such as 1, 2 or 3-substituents selected from: halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, and —$S(=O)(=NR^{22})N(R^{22})(R^{23})$; wherein two substituents attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl; and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I), (II), (II-a), (III), (IV), (V), (Va), (Vb), (Vc), (VI), (VII), (VIII), (IX), (X), (XI), or (XII), is optionally substituted by one or more-such as 1, 2 or 3-substituents selected from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, and —$S(O)_2N(R^{22})(R^{23})$—, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, and =$C(R^{21})_2$;

$R^{21}$ is independently selected at each occurrence from hydrogen, halogen, $C_{1-6}$ alkyl, and $C_{1-6}$ haloalkyl;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl; and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I), (II), (II-a), (III), (IV), (V), (Va), (Vb), (Vc), (VI), (VII), (VIII), (IX), (X), (XI), or (XII), is optionally substituted by one or more—such as 1, 2 or 3-substituents selected from halogen, oxo, =NH, —CN, —$NO_2$, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —OH, —$OCH_3$, —$OCH_2CH_3$, —$NH_2$, —$NHCH_3$, and —$NHCH_2CH_3$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, —$NO_2$, —$CH_3$, —$CH_2CH_3$, —$CH(CH_3)_2$, —$C(CH_3)_3$, —OH, —$OCH_3$, —$OCH_2CH_3$, —$NH_2$, —$NHCH_3$, and —$NHCH_2CH_3$.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$—is also intended to encompass —$OCH_2$—.

"Optional" or "optionally" means that the subsequently described event or circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^{1}H$ (protium), $^{2}H$ (deuterium), and $^{3}H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^{2}H$, $^{3}H$, $^{13}C$, $^{14}C$, $^{15}N$, $^{18}O$, $^{17}O$, $^{35}S$, $^{36}Cl$, and $^{18}F$. Of particular interest are compounds of Formula (I), (II), (II-a), (III), or (IV) enriched in tritium or carbon-14, which can be used, for example, in tissue distribution studies; compounds of the disclosure enriched in deuterium-especially at a site of metabolism-resulting, for example, in compounds having greater metabolic stability; and compounds of Formula (I), (II), (II-a), (III), or (IV) enriched in a positron emitting isotope, such as $^{11}C$, $^{18}F$, $^{15}O$ and $^{13}N$, which can be used, for example, in Positron Emission Topography (PET) studies. Isotopically-enriched compounds may be prepared by conventional techniques well known to those skilled in the art.

As used herein, the phrase "of the formula", "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat cancer, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds described herein are included with the scope of the disclosure unless otherwise specified.

The term "pharmaceutically acceptable" refers to a material that is not biologically or otherwise unacceptable when used in the subject compositions and methods. For example, the term "pharmaceutically acceptable carrier" refers to a material-such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term “effective amount” also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, “treating” or “treatment” refers to an approach for obtaining beneficial or desired results with respect to a disease, disorder, or medical condition (such as cancer) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, “treating cancer” would include preventing cancer from occurring, ameliorating cancer, suppressing cancer, and alleviating the symptoms of cancer. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some embodiments, treating does not include preventing a disease or medical condition from occurring. In some embodiments, “treating” or “treatment” refers to an approach for obtaining beneficial or desired results with respect to a disease, disorder, or medical condition (such as cancer) in a subject, including but not limited to the following: (a) ameliorating the disease or medical condition, e.g., eliminating or causing regression of the disease or medical condition in a subject; (b) suppressing the disease or medical condition, e.g., slowing or arresting the development of the disease or medical condition in a subject; or (c) alleviating symptoms of the disease or medical condition in a subject. In some embodiments treating includes preventing the reoccurrence of a disease.

A “therapeutic effect”, as that term is used herein, encompasses a therapeutic benefit and/or prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms “antagonist” and “inhibitor” are used interchangeably, and they refer to a compound having the ability to inhibit a biological function (e.g., activity, expression, binding, protein-protein interaction) of a target protein (e.g., K-Ras). Accordingly, the terms “antagonist” and “inhibitor” are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term “selective inhibition” or “selectively inhibit” refers to the ability of a biologically active agent to preferentially reduce the target signaling activity as compared to off-target signaling activity, via direct or indirect interaction with the target.

The terms “subject” and “patient” refer to an animal, such as a mammal, for example a human. The methods described herein can be useful in both human therapeutics and veterinary applications. In some embodiments, the subject is a mammal, such as a human. “Mammal” includes humans and both domestic animals such as laboratory animals and household pets (e.g., cats, dogs, swine, cattle, sheep, goats, horses, rabbits), and non-domestic animals such as wildlife and the like.

The terms “therapeutic agent”, “therapeutic capable agent” or “treatment agent” are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms “polypeptide”, “peptide” and “protein” are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term “amino acid” refers to either natural and/or unnatural or synthetic amino acids, including glycine and both the D or L optical isomers, and amino acid analogs and peptidomimetics.

The terms “polynucleotide”, “nucleotide sequence”, “nucleic acid” and “oligonucleotide” are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, “expression” refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

An "antigen" is a moiety or molecule that contains an epitope, and, as such, also specifically binds to an antibody. An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, e.g., "nanobody") that comprises a single antigen-binding domain, Fv, Fd, Fab, Fab', F(ab')2, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH3)2, (scFv-CH3)2, ((scFv)2-CH3+CH3), ((scFv)2-CH3) or (scFv-CH3-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

"Prodrug" is meant to indicate a compound that may be converted under physiological conditions or by solvolysis to a biologically active compound described herein (e.g., a compound of Formula (I), (II), (II-a), (III), or (IV)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press each of which is incorporated in full by reference herein). The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body. The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body. The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound disclosed herein to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS (also used interchangeably herein as K-Ras, K-ras, or Kras), HRAS (or H-Ras), NRAS (or N-Ras), MRAS (or M-Ras), ERAS (or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "mutant Ras" and "Ras mutant", as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, 96 (e.g., Y96D), or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230,220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

As used herein, the term "corresponding to" or "corresponds to" as applied to an amino acid residue in a polypeptide sequence refers to the correspondence of such amino acid relative to a reference sequence when optimally aligned (e.g., taking into consideration of gaps, insertions and mismatches; wherein alignment may be primary sequence alignment or three-dimensional structural alignment of the folded proteins). For instance, the serine residue in a K-Ras G12S mutant refers to the serine corresponding to residue 12 of SEQ ID No. 4, which can serve as a reference sequence. For instance, the aspartate residue in a K-Ras G12D mutant refers to the aspartate corresponding to residue 12 of SEQ ID No. 2, which can serve as a reference sequence. When an amino acid of a mutant Ras protein corresponds to an amino acid position in the WT Ras protein, it will be understood that although the mutant Ras protein amino acid may be a different amino acid (e.g., G12D, wherein the wildtype G at position 12 is replaced by an aspartate at position 12 of SEQ ID. No. 1), the mutant amino acid is at the position corresponding to the wildtype amino acid (e.g., of SEQ ID No. 1). In some embodiments, a modified Ras mutant protein disclosed herein may comprise truncations at the C-terminus, or truncations at the N-terminal end preceding the serine residue. The serine residue in such N-terminal truncated modified mutant is still considered corresponding to position 12 of SEQ ID No. 1. In addition, an aspartate residue at position 12 of SEQ ID No. 2 finds a corresponding residue in SEQ ID Nos. 6 and 8.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In some embodiments, the degradation enhancer is capable of binding to an E3 ubiquitin ligase protein or a protein complex comprising an E3 ubiquitin ligase protein. In some embodiments, the degradation enhancer is capable of binding to an E2 ubiquitin-conjugating enzyme. In some embodiments, the degradation enhancer is capable of binding to a protein complex comprising an E2 ubiquitin-conjugating enzyme and an E3 ubiquitin ligase protein.

Compounds

In certain aspects, the present disclosure provides a compound of Formula (I):

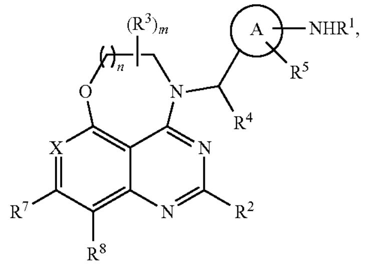

(I)

or a pharmaceutically acceptable salt or solvate thereof, wherein:

X is selected from $C(R^6)$ and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —C(O)OC(O)$R^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^7$ is benzothiophenyl optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)OR^{12}$, —$C(O)R^{12}$, —$P(O)(Y—R^{16})(Z—R^{17})$, and —$CH_2P(O)(Y—R^{16})(Z—R^{17})$;

Y and Z are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =0, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In certain aspects, the present disclosure provides a compound of Formula (II):

(II)

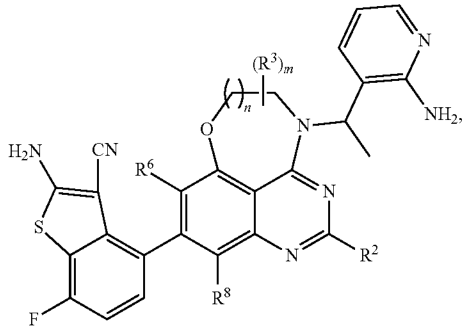

or a pharmaceutically acceptable salt or solvate thereof, wherein:

$R^2$, $R^3$, $R^6$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^4)_2$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, the compound of Formula (II) is a compound of Formula (II-a):

(II-a)

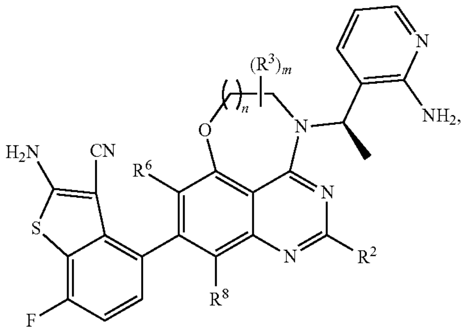

or a pharmaceutically acceptable salt or solvate thereof.

In certain aspects, the present disclosure provides a compound of Formula (III):

(III)

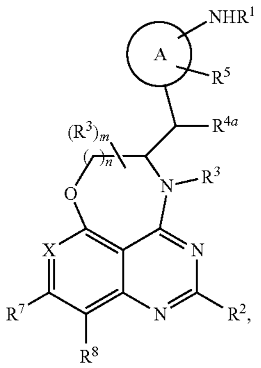

or a pharmaceutically acceptable salt or solvate thereof, wherein:

X is selected from C($R^6$) and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —C(O)OC(O)$R^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =C($R^{14}$).

$R^{4a}$ is selected from hydrogen and $R^4$;

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^7$ is selected from benzothiophenyl and naphthalenyl, each of which is optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$OR^{12}$, —C(O)$R^{12}$, —P(O)(Y—$R^{16}$)(Z—$R^{17}$), and —$CH_2$P(O)(Y—$R^{16}$)(Z—$R^{17}$);

Y and Z are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S$(O)_2R^{12}$, —N($R^{12}$)S$(O)_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)($NR^{12}$)$R^{12}$, —S$(O)_2$N($R^{12}$)($R^{13}$), —S(O)($NR^{12}$)N($R^{12}$)($R^{13}$), —P(O)$(OR^{12})_2$, —P(O)$(R^{12})_2$, —OP(O)$(OR^{12})_2$, =0, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —OS$(O)_2R^{22}$, —S$(O)_2R^{22}$, —S(O)($NR^{22}$)$R^{22}$, —S$(O)_2$N($R^{22}$)($R^{23}$)—, —S(O)($NR^{22}$)N($R^{22}$)($R^{23}$), and —$OCH_2$C(O)$OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —OS$(O)_2R^{22}$, —S$(O)_2R^{22}$, —S(O)($NR^{22}$)$R^{22}$, —S$(O)_2$N($R^{22}$)($R^{23}$), and —S(O)($NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In certain aspects, the present disclosure provides a compound of Formula (IV):

(IV)

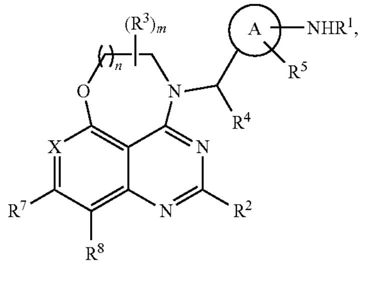

or a pharmaceutically acceptable salt or solvate thereof, wherein:

X is selected from C($R^6$) and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)OR$^{12}$, —C(O)OC(O)R$^{12}$, —C(O)O—($C_{1-6}$ alkyl)-OR$^{15}$, —($C_{1-6}$ alkyl)-OR$^{15}$, —C(O)R$^{12}$, —C(O)N(R$^{12}$)(R$^{13}$), —C(O)C(O)N(R$^{12}$)(R$^{13}$), —S(O)$_2$R$^{12}$, —S(O)(NR$^{12}$)R$^{12}$, —S(O)$_2$N(R$^{12}$)(R$^{13}$), and —S(O)(NR$^{12}$)N(R$^{12}$)(R$^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three R$^{20}$;

R$^2$, R$^3$, R$^5$, R$^6$, and R$^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —OR$^{12}$, —OR$^{15}$, —O—($C_{1-6}$ alkyl)-OR$^{15}$, —SR$^{12}$, —N(R$^{12}$)(R$^{13}$), —C(O)OR$^{12}$, —OC(O)N(R$^{12}$)(R$^{13}$), —N(R$^{12}$)C(O)N(R$^{12}$)(R$^{13}$), —N(R$^{12}$)C(O)OR$^{12}$, —N(R$^{12}$)S(O)$_2$R$^{12}$, —C(O)R$^{12}$, —S(O)R$^{12}$, —OC(O)R$^{12}$, —C(O)N(R$^{12}$)(R$^{13}$), —C(O)C(O)N(R$^{12}$)(R$^{13}$), —N(R$^{12}$)C(O)R$^{12}$, —S(O)$_2$R$^{12}$, —S(O)(NR$^{12}$)R$^{12}$, —S(O)$_2$N(R$^{12}$)(R$^{13}$), —S(O)(NR$^{12}$)N(R$^{12}$)(R$^{13}$), and —OCH$_2$C(O)OR$^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three R$^{20}$; wherein two R$^3$ are optionally taken together with the atom or atoms to which they are attached to form $C_{3-8}$ carbocycle or 3- to 8-membered heterocycle, each of which is optionally substituted with one, two, or three R$^{20}$; and further wherein two R$^3$ are optionally taken together to form ═O, ═NR$^{12}$, or ═C(R$^{14}$).

R$^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —OR$^{12}$, —OR$^{15}$, —O—($C_{0-6}$ alkyl)-OR$^{15}$, —SR$^{12}$, —N(R$^{12}$)(R$^{13}$), —C(O)OR$^{12}$, —OC(O)N(R$^{12}$)(R$^{13}$), —N(R$^{12}$)C(O)N(R$^{12}$)(R$^{13}$), —N(R$^{12}$)C(O)OR$^{12}$, —N(R$^{12}$)S(O)$_2$R$^{12}$, —C(O)R$^{12}$, —S(O)R$^{12}$, —OC(O)R$^{12}$, —C(O)N(R$^{12}$)(R$^{13}$), —C(O)C(O)N(R$^{12}$)(R$^{13}$), —N(R$^{12}$)C(O)R$^{12}$, —S(O)$_2$R$^{12}$, —S(O)(NR$^{12}$)R$^{12}$, —S(O)$_2$N(R$^{12}$)(R$^{13}$), —S(O)(NR$^{12}$)N(R$^{12}$)(R$^{13}$), and —OCH$_2$C(O)OR$^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three R$^{20}$; or R$^4$ and R$^5$, together with the atoms to which they are attached, form $C_{4-8}$ carbocycle or 4- to 8-membered heterocycle, each of which is optionally substituted with one, two, or three R$^{20}$; or R$^3$ and R$^4$, together with the atoms to which they are attached, form 4- to 8-membered heterocycle optionally substituted with one, two, or three R$^{20}$;

R$^7$ is selected from benzothiophenyl and naphthalenyl, each of which is optionally substituted with one, two, three, or four substituents independently selected from —OR$^{15}$, —O—($C_{1-6}$ alkyl)-OR$^{15}$, —NH($C_{1-6}$ alkyl)-OR$^{15}$, —NHC(O)O—($C_{1-6}$ alkyl)-OR$^{15}$, (5-methyl-2-oxo-1,3-dioxol-4-yl)methyl-NH—, and R$^{20}$;

m is 0, 1, 2, or 3;

n is 1 or 2;

R$^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three R$^{20}$;

R$^{13}$ is independently selected at each occurrence from hydrogen, $C_{1-6}$ alkyl, and $C_{1-6}$ haloalkyl; or R$^{12}$ and R$^{13}$ attached to the same nitrogen atom form 3- to 10-membered heterocycle optionally substituted with one, two, or three R$^{20}$;

R$^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two R$^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three R$^{20}$;

R$^{15}$ is independently selected at each occurrence from (5-methyl-2-oxo-1,3-dioxol-4-yl)methyl, —C(O)OR$^{12}$, —C(O)R$^{12}$, —P(O)(Y—R$^{16}$)(Z—R$^{17}$), and —CH$_2$P(O)(Y—R$^{16}$)(Z—R$^{17}$);

Y and Z are independently selected at each occurrence from —O— and —N(R$^{12}$)—;

R$^{16}$ and R$^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —NO$_2$, —CN, $C_{3-12}$ carbocycle, 3- to 12-membered heterocycle, —OR$^{12}$, —SR$^{12}$, —N(R$^{12}$)(R$^{13}$), —C(O)OR$^{12}$, —OC(O)N(R$^{12}$)(R$^{13}$), —N(R$^{12}$)C(O)N(R$^{12}$)(R$^{13}$), —N(R$^{12}$)C(O)OR$^{12}$, —N(R$^{12}$)S(O)$_2$R$^{12}$, —N(R$^{12}$)S(O)$_2$N(R$^{12}$)(R$^{13}$), —S—S—R$^{12}$, —S—C(O)R$^{12}$, —C(O)R$^{12}$, —S(O)R$^{12}$, —OC(O)R$^{12}$, —OC(O)OR$^{12}$, —C(O)N(R$^{12}$)(R$^{13}$), —C(O)C(O)N(R$^{12}$)(R$^{13}$), —N(R$^{12}$)C(O)R$^{12}$, —S(O)$_2$R$^{12}$, —S(O)(NR$^{12}$)R$^{12}$, —S(O)$_2$N(R$^{12}$)(R$^{13}$), —S(O)(NR$^{12}$)N(R$^{12}$)(R$^{13}$), —P(O)(OR$^{12}$)$_2$, —P(O)(R$^{12}$)$_2$, —OP(O)(OR$^{12}$)$_2$, ═0, ═S, and ═NR$^{12}$; or R$^{16}$ and R$^{17}$ are taken together with the atoms to which they are attached to form 3- to 12-membered heterocycle optionally substituted with one, two, or three R$^{20}$;

R$^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In certain aspects, the present disclosure provides a compound of Formula (V):

(V)

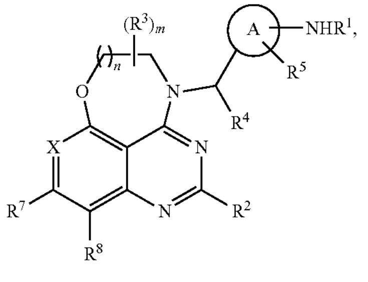

or a pharmaceutically acceptable salt or solvate thereof, wherein:

i) X is N and $R^7$ is selected from benzothiophenyl, thienopyridinyl, furopyridinyl, and naphthalenyl, each of which is optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$; or ii) X is C($R^6$) and $R^7$ is selected from benzothiophenyl, thienopyridinyl, and furopyridinyl, each of which is optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —$C(O)OC(O)R^{12}$, —C(O)O—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^3$, $R^5$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —OC(O)$R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})_2$;

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^6$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$SF_5$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)OR^{12}$, —$C(O)R^{12}$, —P(O)(Y—$R^{16}$)(Z—$R^{17}$), and —$CH_2$P(O)(Y—$R^{16}$)(Z—$R^{17}$);

Y and Z are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =0, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON═$R^{22}$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —OS(O)$_2R^{22}$, —S(O)$_2R^{22}$, —S(O)(N$R^{22}$)$R^{22}$, —S(O)$_2$N($R^{22}$)($R^{23}$), and —S(O)(N$R^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, the compound of Formula (V) is a compound of Formula (Va):

(Va)

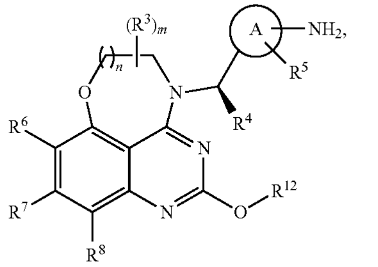

or a pharmaceutically acceptable salt or solvate thereof, wherein:

A is 6-membered heteroaryl comprising one or two ring nitrogen atoms;

$R^3$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{12}$, —O$R^{15}$, —O—($C_{1-6}$ alkyl)-O$R^{15}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)(N$R^{12}$)$R^{12}$, —S(O)$_2$N($R^{12}$)($R^{13}$), —S(O)(N$R^{12}$)N($R^{12}$)($R^{13}$), and —OC$H_2$C(O)O$R^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form ═O, ═N$R^{12}$, or ═C($R^4$)$_2$;

$R^4$ is selected from $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^5$ selected from hydrogen, halogen, —CN, $C_{1-6}$ alkyl, —$C_{0-6}$ alkyl-($C_{3-12}$ carbocycle), —O$R^{12}$, and —C(O)$R^{12}$, wherein $C_{1-6}$ alkyl and —$C_{0-6}$ alkyl-($C_{3-12}$ carbocycle) are optionally substituted with one, two, or three $R^{20}$; $R^6$ is selected from halogen, $C_{1-6}$ alkyl, $C_{2-6}$ alkenyl, and —$C_{0-6}$ alkyl-($C_{3-12}$ carbocycle), wherein $C_{1-6}$ alkyl, $C_{2-6}$ alkenyl, and —$C_{0-6}$ alkyl-($C_{3-12}$ carbocycle) are optionally substituted with one, two, or three $R^{20}$;

$R^7$ is selected from benzothiophenyl, thienopyridinyl, and furopyridinyl, each of which is optionally substituted with one, two, three, or four substituents independently selected from —O$R^{15}$, —O—($C_{1-6}$ alkyl)-O$R^{15}$, —NH($C_{1-6}$ alkyl)-O$R^{15}$, —NHC(O)O—($C_{0-6}$ alkyl)-O$R^{15}$, (5-methyl-2-oxo-1,3-dioxol-4-yl)methyl-NH—, and $R^{20}$;

$R^8$ is halogen; m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)O$R^{12}$, —C(O)$R^{12}$, —P(O)(Y—$R^{16}$)(Z—$R^{17}$), and —C$H_2$P(O)(Y—$R^{16}$)(Z—$R^{17}$);

Y and Z are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, the compound of Formula (V) or (Va) is a compound of Formula (Vb):

(Vb)

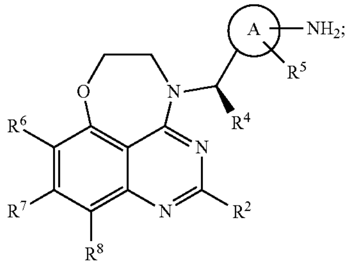

or a pharmaceutically acceptable salt or solvate thereof, wherein:

Ring A is 6-membered heteroaryl comprising one or two ring nitrogen atoms;

$R^2$ is selected from —O—$CH_2$-(8- to 10-membered saturated heterocycle), —O—$CH_2$-(cyclopropylene)-$CH_2$-(5- to 8-membered saturated heterocycle), and —O—($C_{1-3}$ alkyl)-(5- to 8-membered non-aromatic heterocycle), each of which is optionally substituted with one or more substituents independently selected from —F, =$CF_2$, =$CH_2$, =CHF, halogen, —CN, —$OCH_3$, —$CHF_2$, $C_{1-3}$ alkyl, —CH=N—$OCH_2CH_3$, =N—$OCH_2CH_3$, —$S(O)(CH_2CH_3)$, —O—, =$NOCH_2CH_3$, =$NOCH_3$, $CH_2P(O)(CH_3)_2$, —$CH_2O$(6-membered heteroaryl)- $CF_3$, —$CH_2O$(6-membered heteroaryl)-$CHF_2$, —$OCH_2CH_2CH_2P(O)(CH_3)_2$, and —$CH_2N(C_{1-3}$ alkyl$)_2$;

$R^4$ is selected from $C_{1-5}$ alkyl, $C_{2-4}$ alkenyl, $C_{2-3}$ alkynyl, —$C_{1-2}$ alkyl-($C_3$-4 saturated carbocycle), —$C_{1-2}$ alkyl-(5- to 6-membered saturated heterocycle), —$C_{1-2}$ alkyl-(phenyl), and —$C_{1-2}$ alkyl-(5- to 6-membered heteroaryl), each of which is optionally substituted with one or more substituents independently selected from halogen, —OH, —$OCH_3$, —$C(O)N(C_{1-3}$ alkyl$)_2$, —$N(C_{1-3}$ alkyl$)_2$, —$P(O)(CH_3)_2$, —$S(O)(CH_3)$, $S(O)_2CH_3$, and =N—$OCH_2CH_3$;

$R^5$ is selected from hydrogen, halogen, CN, cyclopropyl, $C_{1-4}$ alkyl, —$CF_3$, —$C(O)CH_3$, —$OCH_3$, —$CH_2NH_2$, —$OCHF_2$, and —$CH_2N(C_{1-3}$ alkyl$)_2$, $R^6$ is selected from halogen and —$CF_3$;

$R^7$ is benzothiophenyl optionally substituted with one or more substituents independently selected from —$NH_2$, —CN, and —F; and $R^8$ is halogen.

In certain aspects, the present disclosure provides a compound of Formula (Vc):

(Vc)

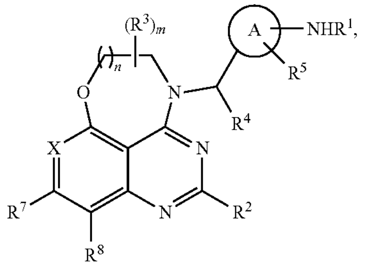

or a pharmaceutically acceptable salt or solvate thereof, wherein:

X is selected from $C(R^6)$ and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —C(O)OC(O)$R^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^5$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^3$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =C($R^{14}$)$_2$;

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^6$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$SF_5$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)

$(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^7$ is selected from benzothiophenyl and thienopyridinyl, each of which is optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)OR^{12}$, —$C(O)R^{12}$, —$P(O)(Y\text{-}R^{16})(Z—R^{17})$, and —$CH_2P(O)(Y—R^{16})(Z—R^{17})$;

Y and Z are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =0, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

Embodiments disclosed herein that refer to a compound of Formula (I), (II), (II-a), (III), (IV), (V), or (VI) are also intended to apply to a compound of Formula (Va), (Vb), and/or (Vc). If any provision of an embodiment that refers to a compound of Formula (I), (II), (II-a), (III), (IV), (V), or (VI) recites a substituent or variable not depicted in the compound of Formula (Va), (Vb), or (Vc), then the remainder of said embodiment shall be considered severable and not affected by the missing substituent or variable.

In certain aspects, the present disclosure provides a compound of Formula (VI):

(VI)

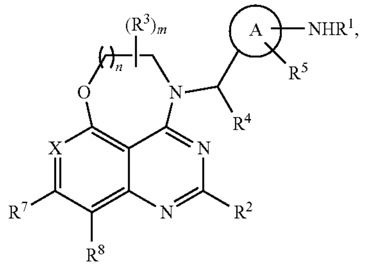

or a pharmaceutically acceptable salt or solvate thereof, wherein:

X is selected from $C(R^6)$ and N;

A is 6-membered heteroaryl comprising one, two, or three ring nitrogen atoms;

$R^1$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —C(O)OC(O)$R^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^2$, $R^3$, $R^5$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =C($R^{14}$)$_2$.

$R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;

$R^6$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$SF_5$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), and —$OCH_2$C(O)$OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^7$ is selected from phenyl and pyridyl, each of which is optionally substituted with one or more substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;

m is 0, 1, 2, or 3;

n is 1 or 2;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and $—C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, $—C_{0-6}$ alkyl-($C_{3-12}$ carbocycle), and $—C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, $—C_{0-6}$ alkyl-($C_{3-12}$ carbocycle), $—C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, $—C(O)OR^{12}$, $—C(O)R^{12}$, $—P(O)(Y—R^{16})(Z—R^{17})$, and $—CH_2P(O)(Y—R^{16})(Z—R^{17})$;

Y and Z are independently selected at each occurrence from —O— and $—N(R^{12})—$;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, $—NO_2$, —CN, $C_{3-12}$ carbocycle, 3- to 12-membered heterocycle, $—OR^{12}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—N(R^{12})S(O)_2N(R^{12})(R^{13})$, $—S—S—R^{12}$, $—S—C(O)R^{12}$, $—C(O)R^{12}$, $—S(O)R^{12}$, $—OC(O)R^{12}$, $—OC(O)OR^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, $—S(O)(NR^{12})N(R^{12})(R^{13})$, $—P(O)(OR^{12})_2$, $—P(O)(R^{12})_2$, $—OP(O)(OR^{12})_2$, =0, =S, and $=NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{22}$, $—SR^{22}$, $—N(R^{22})(R^{23})$, $=NR^{22}$, $=C(R^{21})_2$, $—SF_5$, $=N—OR^{22}$, $=N—N(R^{22})(R^{23})$, $—P(O)(R^{22})(R^{23})$, $—ON=R^{22}$, $—C(O)OR^{22}$, $—OC(O)N(R^{22})(R^{23})$, $—N(R^{22})C(O)N(R^{22})(R^{23})$, $—N(R^{22})C(O)OR^{22}$, $—N(R^{22})S(O)_2R^{22}$, $—C(O)R^{22}$, $—S(O)R^{22}$, $—OC(O)R^{22}$, $—C(O)N(R^{22})(R^{23})$, $—C(O)C(O)N(R^{22})(R^{23})$, $—N(R^{22})C(O)R^{22}$, $—OS(O)_2R^{22}$, $—S(O)_2R^{22}$, $—S(O)(NR^{22})R^{22}$, $—S(O)_2N(R^{22})(R^{23})—$, $—S(O)(NR^{22})N(R^{22})(R^{23})$, and $—OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, $—OR^{22}$, $—SR^{22}$, $—N(R^{22})(R^{23})$, $=NR^{22}$, $=C(R^{21})_2$, $—SF_5$, $=N—OR^{22}$, $=N—N(R^{22})(R^{23})$, $—P(O)(R^{22})(R^{23})$, $—ON=R^{22}$, $—C(O)OR^{22}$, $—OC(O)N(R^{22})(R^{23})$, $—N(R^{22})C(O)N(R^{22})(R^{23})$, $—N(R^{22})C(O)OR^{22}$, $—N(R^{22})S(O)_2R^{22}$, $—C(O)R^{22}$, $—S(O)R^{22}$, $—OC(O)R^{22}$, $—C(O)N(R^{22})(R^{23})$, $—C(O)C(O)N(R^{22})(R^{23})$, $—N(R^{22})C(O)R^{22}$, $—OS(O)_2R^{22}$, $—S(O)_2R^{22}$, $—S(O)(NR^{22})R^{22}$, $—S(O)_2N(R^{22})(R^{23})$, and $—S(O)(NR^{22})N(R^{22})(R^{23})$;

$R^{21}$ is independently selected at each occurrence from hydrogen, halogen, $C_{1-6}$ alkyl, $C_{1-6}$ haloalkyl, $—C_{0-6}$ alkyl-($C_{3-12}$ carbocycle), and $—C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $—C_{0-6}$ alkyl-($C_{3-12}$ carbocycle), and $—C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle;

provided that:

i) X is N; and/or ii) $R^3$ is independently selected at each occurrence from $C_{2-6}$ alkenyl, $C_{2-6}$ alkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle), wherein $C_{2-6}$ alkenyl, $C_{2-6}$ alkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, $=NR^{12}$, or $=C(R^{14})_2$; and/or iii) $R^4$ is selected from $C_{1-6}$ alkyl, $C_{2-6}$ alkenyl and $C_{2-6}$ alkynyl, wherein $C_{1-6}$ alkyl is substituted with $=N—OR^{22}$, $=N—N(R^{22})(R^{23})$, or $—ON=R^{22}$, and wherein $C_{2-6}$ alkenyl and $C_{2-6}$ alkynyl are optionally substituted with one, two, or three $R^{20}$; and/or iv) $R^6$ is selected from $C_{1-6}$ alkyl, $C_{2-6}$ alkenyl, $C_{2-6}$ alkynyl, $—C_{0-6}$ alkyl-($C_{3-12}$ carbocycle), $—OR^{12}$, $—OR^{15}$, $—O—(C_{1-6}$ alkyl)-$OR^{15}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, $—S(O)(NR^{12})N(R^{12})(R^{13})$, $—OCH_2C(O)OR^{12}$, and $—SF_5$, wherein $C_{2-6}$ alkenyl and $C_{2-6}$ alkynyl are optionally substituted with one, two, or three $R^{20}$; and wherein $C_{1-6}$ alkyl and —$C_{0-6}$ alkyl-($C_{3-12}$ carbocycle) are each substituted with one, two, or three $R^{20}$.

In certain aspects, the present disclosure provides a compound of Formula (VII):

(VII)

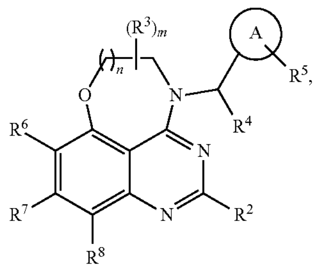

or a pharmaceutically acceptable salt or solvate thereof, wherein:

- $R^7$ is selected from benzothiophenyl, thienopyridinyl, and furopyridinyl, each of which is optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$;
- A is 6-membered heteroaryl comprising one, two, or three ring nitrogen atoms;
- $R^2$, $R^3$, $R^5$, and $R^8$ are each independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.
- $R^4$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{0-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$;
- $R^6$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, —$SF_5$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;
- m is 0, 1, 2, or 3;
- n is 1 or 2;
- $R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;
- $R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;
- $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$OR^{12}$, —C(O)$R^{12}$, —P(O)(Y—$R^{16}$)(Z—$R^{17}$), and —$CH_2$P(O)(Y—$R^{16}$)(Z—$R^{17}$);

Y and Z are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S$(O)_2R^{12}$, —N($R^{12}$)S$(O)_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)($NR^{12}$)$R^{12}$, —S$(O)_2$N($R^{12}$)($R^{13}$), —S(O)($NR^{12}$)N($R^{12}$)($R^{13}$), —P(O)$(OR^{12})_2$, —P(O)$(R^{12})_2$, —OP(O)$(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C$(R^{21})_2$, —$SF_5$, =N—$OR^{22}$, =N—N($R^{22}$)($R^{23}$), —P(O)($R^{22}$)($R^{23}$), —ON=$R^{22}$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —OS$(O)_2R^{22}$, —S$(O)_2R^{22}$, —S(O)($NR^{22}$)$R^{22}$, —S$(O)_2$N($R^{22}$)($R^{23}$)—, —S(O)($NR^{22}$)N($R^{22}$)($R^{23}$), and —$OCH_2$C(O)$OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C$(R^{21})_2$, —$SF_5$, =N—$OR^{22}$, =N—N($R^{22}$)($R^{23}$), —P(O)($R^{22}$)($R^{23}$), —ON=$R^{22}$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —OS$(O)_2R^{22}$, —S$(O)_2R^{22}$, —S(O)($NR^{22}$)$R^{22}$, —S$(O)_2$N($R^{22}$)($R^{23}$), and —S(O)($NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, for a compound of Formula (VII), $R^5$ is halogen. In some embodiments, for a compound of Formula (VII), $R^5$ is —F. In some embodiments, for a compound of Formula (VII), $R^5$ is —Cl. In some embodiments, for a compound of Formula (VII), $R^5$ is —Br. In some embodiments, for a compound of Formula (VII), $R^5$ is $C_{1-6}$ alkyl optionally substituted with one, two, or three $R^{20}$. In some embodiments, for a compound of Formula (VII), $R^5$ is $C_{1-6}$ alkyl optionally substituted with one, two, or three halogen. In some embodiments, for a compound of Formula (VII), $R^5$ is $C_{1-6}$ alkyl optionally substituted with one, two, or three —F. In some embodiments, for a compound of Formula (VII), $R^5$ is unsubstituted methyl. In some embodiments, for a compound of Formula (VII), $R^5$ is unsubstituted $C_{1-6}$ alkyl. In some embodiments, for a compound of Formula (VII), $R^5$ is —$CF_3$. In some embodiments, for a compound of Formula (VII), $R^5$ is —$CHF_2$. In some embodiments, for a compound of Formula (VII), $R^5$ is —OH. In some embodiments, the substituents (for example, $R^2$, $R^3$, $R^4$, $R^5$, $R^6$, $R^7$, and $R^8$) of formula (VII) are the same as the corresponding substituents in Formula (I), (II), (III), (IV), (V), and/or (VI). In some embodiments, for a compound of Formula (VII), $R^7$ is benzothiophenyl optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$. In some embodiments, for a compound of Formula (VII),

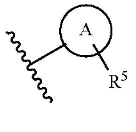

is selected from

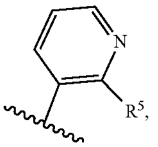

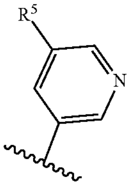

,

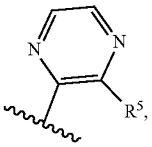

-continued

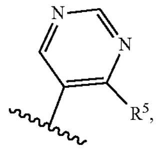 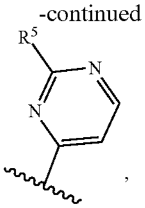 , 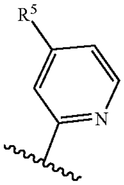 , and

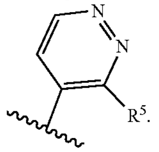

In some embodiments, for a compound of Formula (VII),

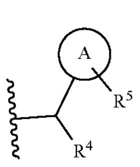

is selected from

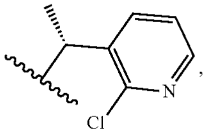 , 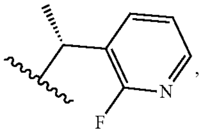 ,

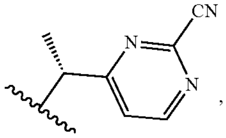 , 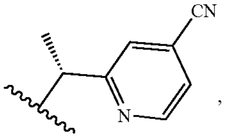 ,

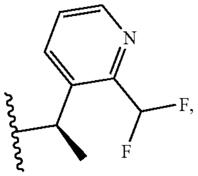 and 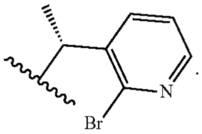 .

In some embodiments, for a compound of Formula (I), (III), (IV), (V), or (VI), X is $C(R^6)$, such as C(Cl). In some embodiments, X is $C(CF_3)$. In some embodiments, X is N.

In some embodiments, for a compound of Formula (I), (III), (IV), (V), or (VI), A is 6-membered heteroaryl comprising one or two ring nitrogen atoms. In some embodiments, A is selected from pyridinyl, pyridazinyl, pyrimidinyl, and pyrazinyl. In some embodiments, A is selected from pyridin-3-yl, pyridazin-4-yl, pyrimidin-5-yl, and pyrazin-2-yl. In some embodiments, A is pyridinyl. In some embodiments, A is pyridin-3-yl.

In some embodiments, for a compound of Formula (I), (III), (IV), (V), or (VI), $R^1$ is selected from hydrogen, $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), —$C(O)R^{12}$, and —$C(O)N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$. In some embodiments, $R^1$ is selected from hydrogen, $C_{1-6}$ alkyl, and —$C(O)R^{12}$. In some embodiments, $R^1$ is hydrogen. In some embodiments, $R^1$ is $C_{1-6}$ alkyl, such as —$CH_3$. In some embodiments, $R^1$ is —$C(O)R^{12}$.

In some embodiments, for a compound of Formula (I), (III), (IV), (V), or (VI), $R^1$ is selected from hydrogen, (5-methyl-2-oxo-1,3-dioxol-4-yl)methyl, —$C(O)OR^{12}$, —$C(O)OC(O)R^{12}$, —C(O)O—($C_{1-6}$ alkyl)-$OR^{15}$, and —($C_{1-6}$ alkyl)-$OR^{15}$, wherein $C_{1-6}$ alkyl is optionally substituted with one, two, or three $R^{20}$. In some embodiments, $R^1$ is selected from hydrogen and —($C_{1-6}$ alkyl)-$OR^{15}$. In some embodiments, $R^1$ is —($C_{1-6}$ alkyl)-$OR^{15}$. In some embodiments, $R^1$ is selected from —$CH(R^{20})OC(O)R^{12}$ and —$CH_2OP(O)(Y—R^{16})(Z—R^{17})$. In some embodiments, $R^1$ is selected from —$CH(R^{20})OC(O)R^{12}$ and —$CH_2OP(O)(Y—R^{16})(Z—R^{17})$; and $R^{12}$ is $C_{1-6}$ alkyl optionally substituted with one, two, or three $R^{20}$. In some embodiments, $R^1$ is selected from —$CH(R^{20})OC(O)R^{12}$ and —$CH_2OP(O)(Y—R^{16})(Z—R^{17})$; and $R^{12}$ is $C_{1-6}$ alkyl. In some embodiments, $R^1$ is selected from —$CH_2OC(O)R^{12}$, —$CH(CH_3)OC(O)R^{12}$, and —$CH_2OP(O)(Y—R^{16})(Z—R^{17})$. In some embodiments, $R^1$ is selected from —$CH_2OC(O)R^{12}$, —$CH(CH_3)OC(O)R^{12}$, and —$CH_2OP(O)(Y—R^{16})(Z—R^{17})$; and $R^{12}$ is $C_{1-6}$ alkyl optionally substituted with one, two, or three $R^{20}$. In some embodiments, $R^1$ is selected from —$CH_2OC(O)R^{12}$, —$CH(CH_3)OC(O)R^{12}$, and —$CH_2OP(O)(Y—R^{16})(Z—R^{17})$; and $R^{12}$ is $C_{1-6}$ alkyl. In some embodiments, $R^1$ is selected from —$CH_2OC(O)R^{12}$, —$CH(CH_3)OC(O)R^{12}$, and —$CH_2OP(O)(OH)_2$. In some embodiments, $R^1$ is selected from —$CH_2OC(O)R^{12}$, —$CH(CH_3)OC(O)R^{12}$, and —$CH_2OP(O)(OH)_2$; and $R^{12}$ is $C_{1-6}$ alkyl optionally substituted with one, two, or three $R^{20}$. In some embodiments, $R^1$ is selected from —$CH_2OC(O)R^{12}$, —$CH(CH_3)OC(O)R^{12}$, and —$CH_2OP(O)(OH)_2$; and $R^{12}$ is $C_{1-6}$ alkyl. In some embodiments, $R^1$ is selected from —$CH_2OP(O)(OHI)_2$, —$CH(CH_3)OP(O)(OH)_2$, —$CH_2OP(O)(OCH_2OC(O)OCH(CH_3)_2)_2$, —$CH_2OC(O)CH(NH_2)(CH(CH_3)_2)$, —$CH(CH_3)OC(O)CH(NH_2)(CH(CH_3)_2)$, and —$CH_2OC(O)CH(CH_3)_2$.

In some embodiments, for a compound of Formula (I), (III), (IV), (V), or (VI), $R^5$ is selected from hydrogen, halogen, —CN, $C_{1-6}$ alkyl, $C_{2-6}$ alkenyl, $C_{2-6}$ alkynyl, 2- to 6-membered heteroalkyl, —$OR^{12}$, and —$N(R^{12})(R^{13})$, wherein $C_{1-6}$ alkyl, $C_{2-6}$ alkenyl, $C_{2-6}$ alkynyl, and 2- to 6-membered heteroalkyl are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^5$ is selected from hydrogen, halogen, —CN, $C_{1-6}$ alkyl, $C_{2-6}$ alkenyl, $C_{2-6}$ alkynyl, 2- to 6-membered heteroalkyl, —$OR^{12}$, and —$N(R^{12})(R^{13})$, wherein $C_{1-6}$ alkyl, $C_{2-6}$ alkenyl, $C_{2-6}$ alkynyl, and 2- to 6-membered heteroalkyl are optionally substituted with one, two, or three $R^{20}$. In some embodiments, $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^5$ is selected from hydrogen and halogen; or $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^5$ is selected from hydrogen and halogen. In some embodiments, $R^5$ is hydrogen.

In embodiments, $R^5$ is independently selected at each occurrence from hydrogen, halogen, —CN, methyl, $C_{3-6}$ carbocycle, —$OR^{12}$, and —$N(R^{12})(R^{13})$, wherein $C_{1-6}$ alkyl is optionally substituted with one, two, or three substituents selected from halogen and —$N(R^{22})(R^{23})$. In embodiments, $R^5$ is independently selected at each occurrence from hydrogen, F, Cl, Br, I, —CN, methyl, cyclopropyl, —$OCH_3$, —$OCHF_2$, —$NH_2$, and —$N(CH_3)_2$, wherein methyl is optionally substituted with one, two, or three substituents selected from F and —$N(CH_3)_2$.

In some embodiments, for a compound of Formula (I), (III), (IV), (V), or (VI),

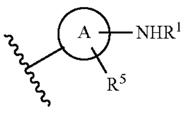

is selected from

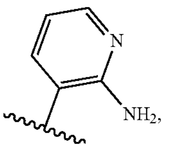

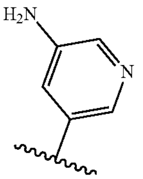

,

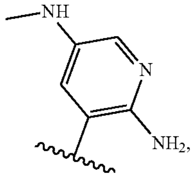

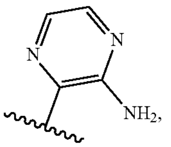

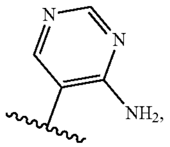

and

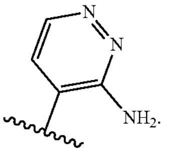

In some embodiments,

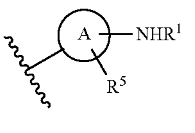

is

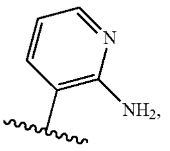 [SMILES: *c1cccnc1N]

In some embodiments, for a compound of Formula (I), (III), (IV), (V), or (VI), $R^4$ is selected from halogen, —CN, $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, and —$N(R^{12})(R^{13})$, wherein $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$; or $R^3$ and $R^4$, together with the atoms to which they are attached, form 4- to 8-membered heterocycle optionally substituted with one, two, or three $R^{20}$. In some embodiments, $R^4$ is selected from halogen, —CN, $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, and —$N(R^{12})(R^{13})$, wherein $C_{1-6}$ alkyl, $C_{2-6}$ alkenyl, $C_{2-6}$ alkynyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$. In some embodiments, $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^3$ and $R^4$, together with the atoms to which they are attached, form 4- to 8-membered heterocycle optionally substituted with one, two, or three $R^{20}$. In some embodiments, $R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$. In some embodiments, $R^4$ is $C_{1-3}$ alkyl optionally substituted with one, two, or three $R^{20}$. In some embodiments, $R^4$ is $C_{1-6}$ alkyl substituted with —$N(R^{12})C(O)R^{12}$, such as —NHC(O)($C_{2-6}$ alkenyl). In some embodiments, $R^4$ is $C_{1-3}$ alkyl substituted with —$N(R^{12})C(O)R^{12}$, such as —NHC(O)($C_{2-6}$ alkenyl). In some embodiments, $R^4$ is $C_{1-6}$ alkyl substituted with —$N(R^{22})C(O)R^{22}$, such as —NHC(O)($C_{2-6}$ alkenyl). In some embodiments, $R^4$ is $C_{1-3}$ alkyl substituted with —$N(R^{22})C(O)R^{22}$, such as —NHC(O)($C_{2-6}$ alkenyl). In some embodiments, $R^4$ is $C_{1-6}$ alkyl substituted with —NHC(O)$CHCH_2$. In some embodiments, $R^4$ is $C_{1-3}$ haloalkyl, such as —$CH_2F$, —$CHF_2$, —$CF_3$, —$CH_2CH_2F$, —$CH_2CHF_2$, or —$CH_2CF_3$. In some embodiments, $R^4$ is selected from —$CH_3$, —$CHF_2$, —$CH_2CH_3$, and $CH_2CHF_2$. In some embodiments, $R^4$ is $C_{1-3}$ alkyl. In some embodiments, $R^4$ is $CH_3$. In some embodiments, $R^4$ is selected from

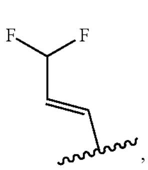
,
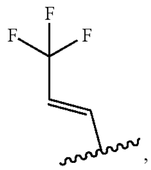
,
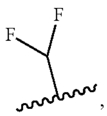
,
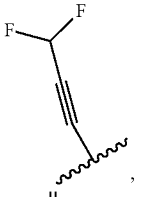
,
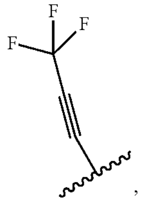
,
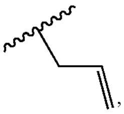
,
,
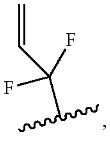
,
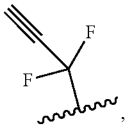
,
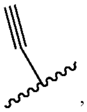
,
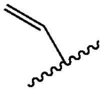
, -continued

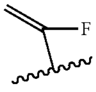, 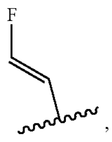, 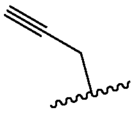, and 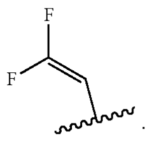.

In some embodiments, $R^4$ is selected from

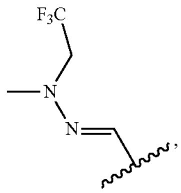, 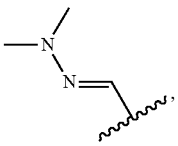,

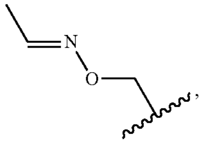, and 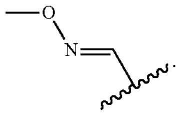.

In embodiments, $R^4$ is selected from $C_{2-6}$ alkenyl and $C_{2-6}$ alkynyl, wherein $C_{2-6}$ alkenyl and $C_{2-6}$ alkynyl are optionally substituted with one, two, or three substituents selected from halogen, and $C_{3-6}$ carbocycle. In embodiments, $R^4$ is selected from $C_{2-4}$ alkenyl and $C_{2-4}$ alkynyl, wherein $C_{2-4}$ alkenyl and $C_{2-4}$ alkynyl are optionally substituted with one, two, or three substituents selected from F and cyclopropyl. In embodiments, $R^4$ is selected from

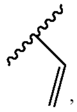, 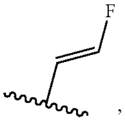, 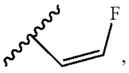, 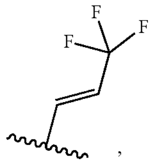,

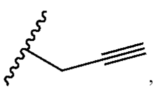, 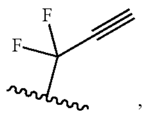, 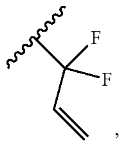,

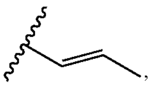, 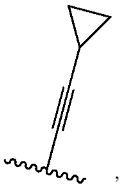, 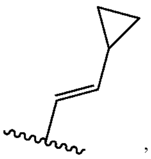,

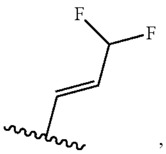, 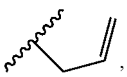, 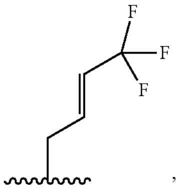,

-continued

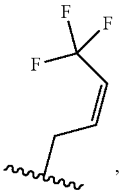, 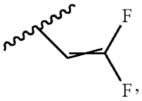, 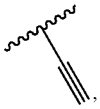, 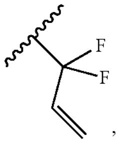,

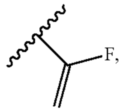, 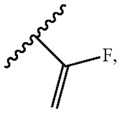, 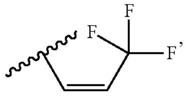, and

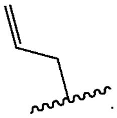.

In embodiments, $R^4$ is selected from —$C_{1-6}$ alkyl-($C_{3-6}$ carbocycle), -(2- to 6-membered heteroalkyl)-($C_{3-6}$ carbocycle), —$C_{1-6}$ alkyl-(3- to 6-membered heterocycle), and -(2- to 6-membered heteroalkyl)-(3- to 6-membered heterocycle), wherein —$C_{1-6}$ alkyl-($C_{3-6}$ carbocycle), -(2- to 6-membered heteroalkyl)-($C_{3-6}$ carbocycle), —$C_{1-6}$ alkyl-(3- to 6-membered heterocycle), and -(2- to 6-membered heteroalkyl)-(3- to 6-membered heterocycle) are each optionally substituted with one, two, or three substituents selected from oxo, —$OR^{22}$, and $C_{1-6}$ alkyl optionally substituted with one or more substituents independently selected from oxo, —$OR^{22}$, and —$N(R^{22})(R^{23})$. In embodiments, $R^4$ is selected from —$C_{1-3}$ alkyl-($C_{3-6}$ carbocycle), -(2- to 3-membered heteroalkyl)-($C_{3-6}$ carbocycle), —$C_{1-3}$ alkyl-(4- to 6-membered heterocycle), and -(2- to 3-membered heteroalkyl)-(4- to 6-membered heterocycle), wherein —$C_{1-3}$ alkyl-($C_{3-6}$ carbocycle), -(2- to 3-membered heteroalkyl)-($C_{3-6}$ carbocycle), —$C_{1-3}$ alkyl-(4- to 6-membered heterocycle), and -(2- to 3-membered heteroalkyl)-(4- to 6-membered heterocycle) are each optionally substituted with one, two, or three substituents selected from oxo, —$OCH_3$, and $C_{1-6}$ alkyl optionally substituted with one or more substituents independently selected from oxo and —$NH_2$. In embodiments, $R^4$ is selected from —$C_{1-3}$ alkyl-($C_{3-6}$ saturated carbocycle), -(2- to 3-membered heteroalkyl)-($C_{3-6}$ saturated carbocycle), —$C_{1-3}$ alkyl-(4- to 6-membered saturated heterocycle), -(2- to 3-membered heteroalkyl)-(4- to 6-membered saturated heterocycle), —$C_{1-3}$ alkyl-(5- to 6-membered heteroaryl), and -(2- to 3-membered heteroalkyl)-(5- to 6-membered heteroaryl), wherein —$C_{1-3}$ alkyl-($C_{3-6}$ saturated carbocycle), -(2- to 3-membered heteroalkyl)-($C_{3-6}$ saturated carbocycle), —$C_{1-3}$ alkyl-(4- to 6-membered saturated heterocycle), -(2- to 3-membered heteroalkyl)-(4- to 6-membered saturated heterocycle), —$C_{1-3}$ alkyl-(5- to 6-membered heteroaryl), and -(2- to 3-membered heteroalkyl)-(5- to 6-membered heteroaryl) are each optionally substituted with one, two, or three substituents selected from oxo, —$OCH_3$, —$CH_3$, $C(O)CH_3$, $C(O)C(NH_2)(CH(CH_3)_2)$. In embodiments, $R^4$ is selected from

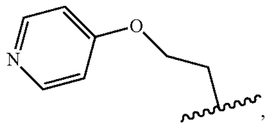, 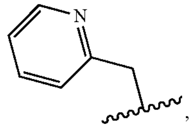,

-continued
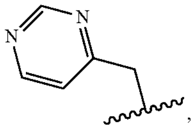, 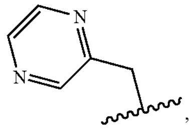,
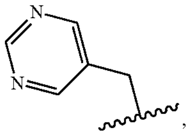, 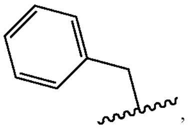,
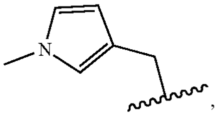, 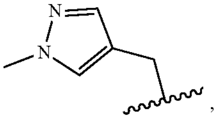,
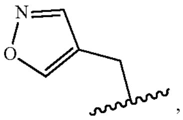, 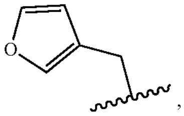, 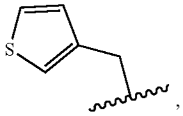,
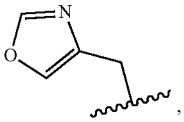, 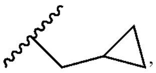, 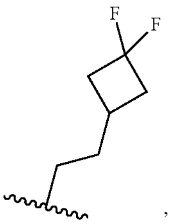,
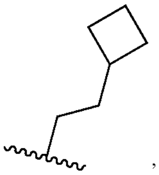, 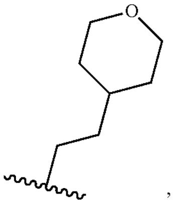, 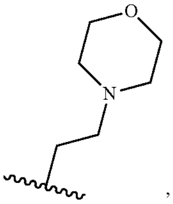,
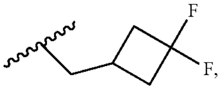 F, 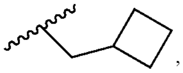,
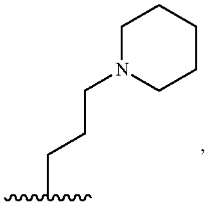, 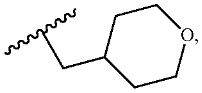 O,
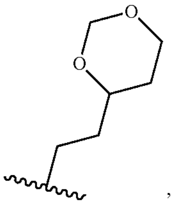, 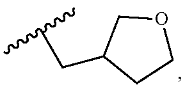, 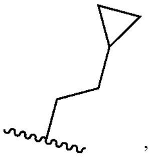,
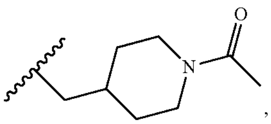, 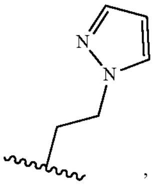,
-continued
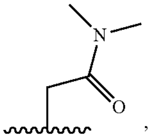, 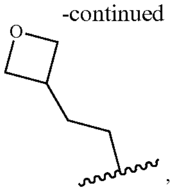, 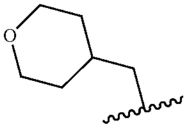,
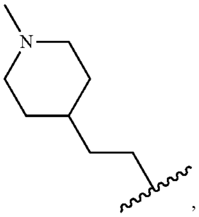, 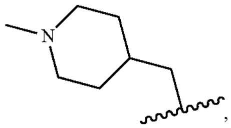,
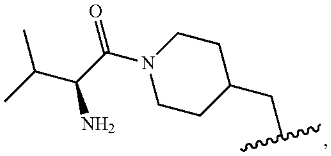,
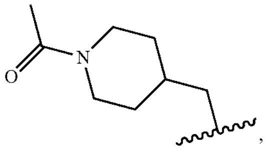, 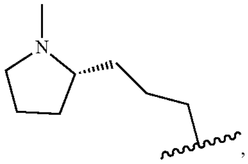,
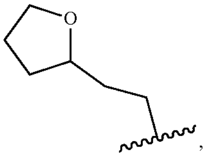, 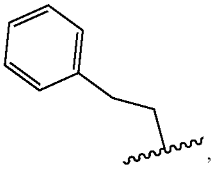,
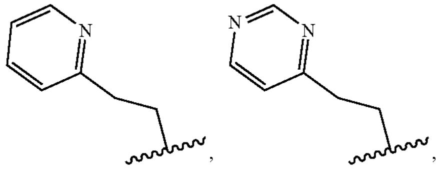,
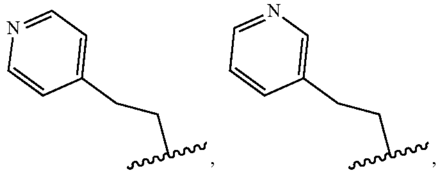,
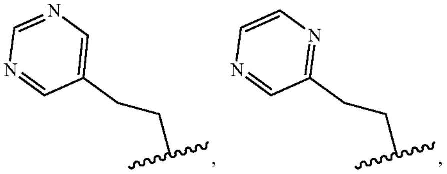,
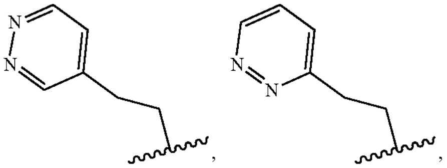,
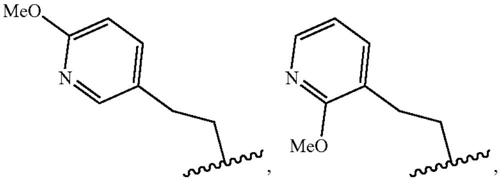, -continued

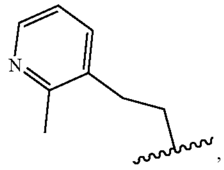,
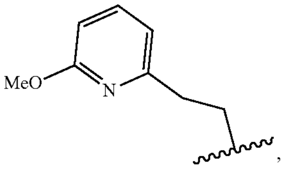,
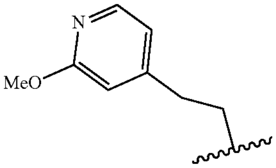,
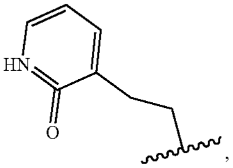,
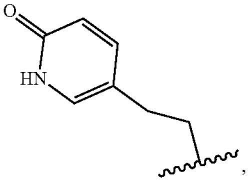,
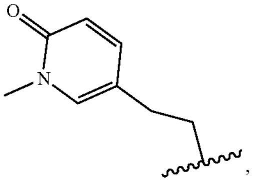,
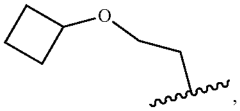,
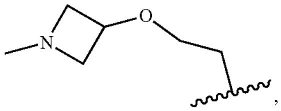, and
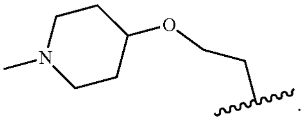.

In embodiments, $R^4$ is $C_{1-6}$ alkyl optionally substituted with one, two, or three substituents selected from halogen, oxo, —$OR^{22}$, —$N(R^{22})(R^{23})$, —$S(O)R^{22}$, —$C(O)N(R^{22})(R^{23})$, —$N(R^{22})C(O)R^{22}$, —$S(O)_2R^{22}$, —$P(O)(R^{22})(R^{23})$, and ═N—$OR^{22}$. In embodiments, $R^4$ is $C_{1-6}$ alkyl optionally substituted with one, two, or three substituents selected from F, —$NH_2$, —$N(CH_3)_2$, —$N(CH_2CH_3)_2$, oxo, —OH, —$OCH_3$, —$OCHF_2$, —$OCF_3$, —$S(O)CH_3$, —$C(O)N(H)(CH_3)$, —$N(CH_3)C(O)CH_3$, —$S(O)_2CH_3$, —$P(O)(CH_3)_2$, and ═N—$OCH_2CH_3$. In embodiments, $R^4$ is selected from

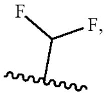, 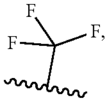, 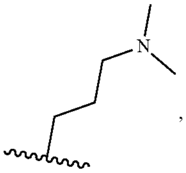,
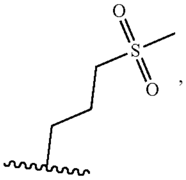, 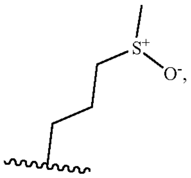,
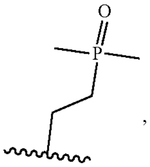, 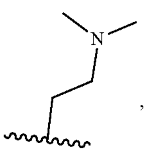, 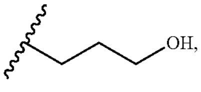

-continued

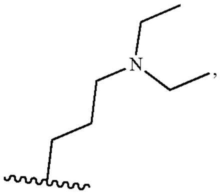,
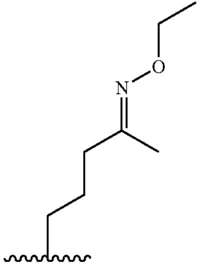,
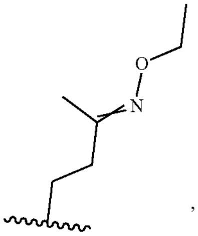,
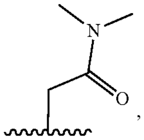,
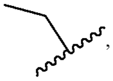,
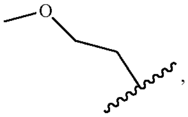,
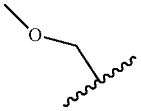,
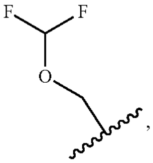,
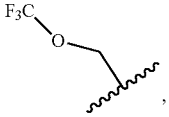,
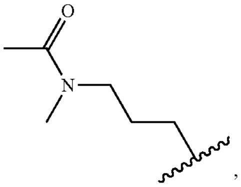,
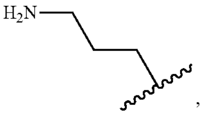, and
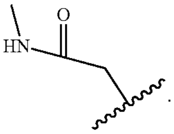.

embodiments, $R^4$ is

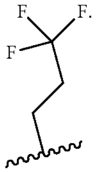

In embodiments, $R^4$ is

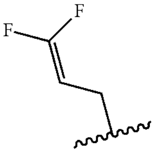.

In embodiments, $R^4$ is
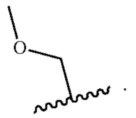
In embodiments, $R^4$ is
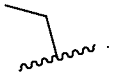
In some embodiments, for a compound of Formula (I), (III), (LV), (V), or (VI)
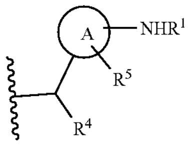
is selected from
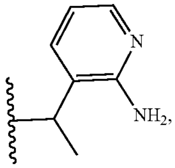
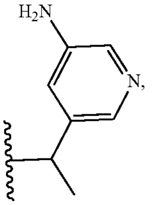
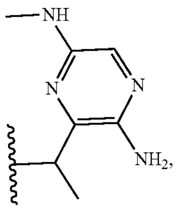
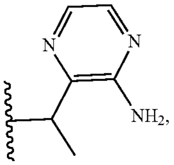
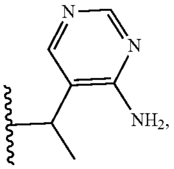
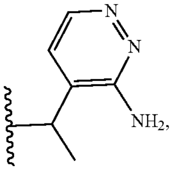
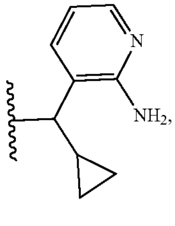
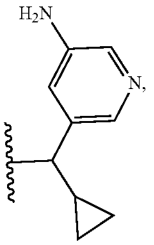
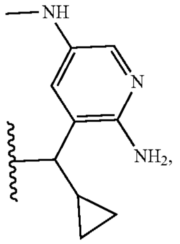
-continued
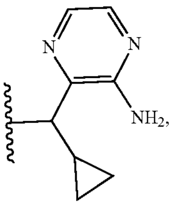
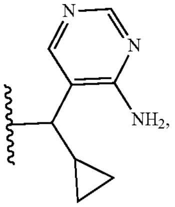
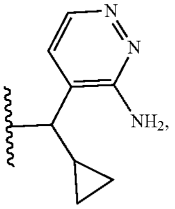
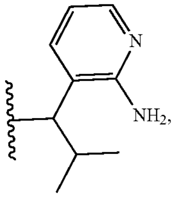
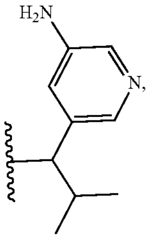
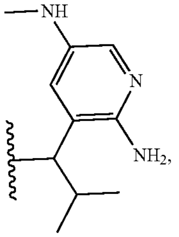
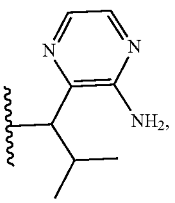
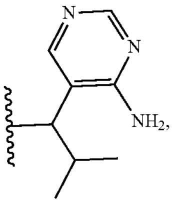
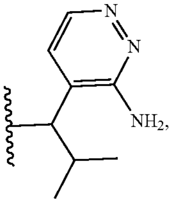
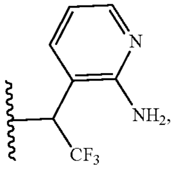
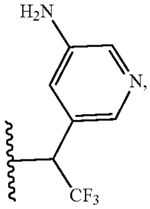
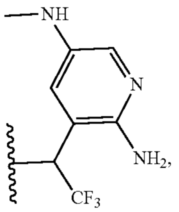
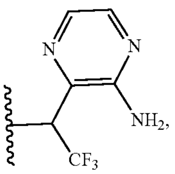
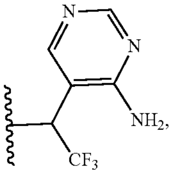
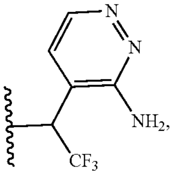
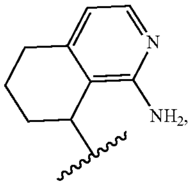
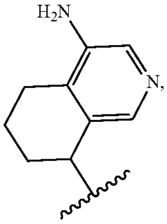
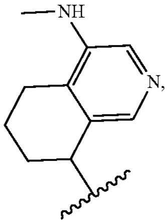
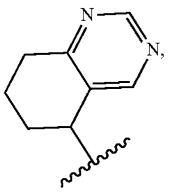
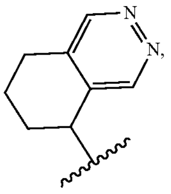
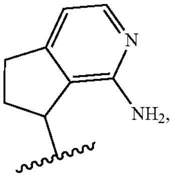

-continued
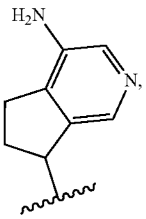
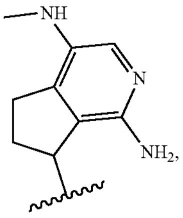
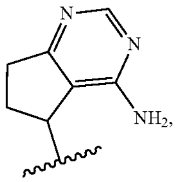
and
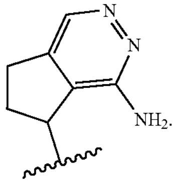
In some embodiments
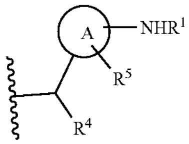
is
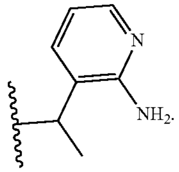 [SMILES: *C(C)c1cccnc1N]
In some embodiments, for a compound of Formula (I), (III), (LV), (V), or (VI),
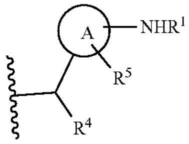
is selected from
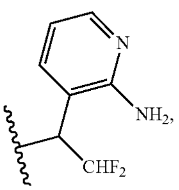
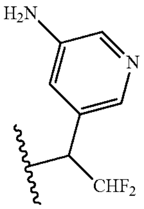
,
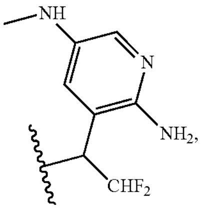
-continued
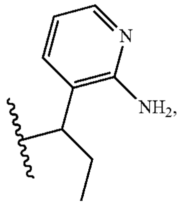
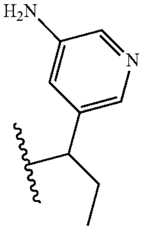
,
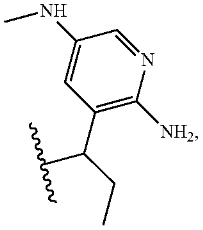
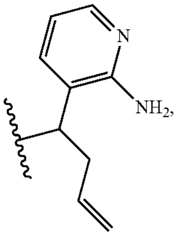
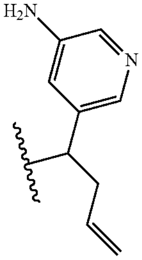
,
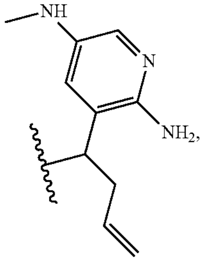
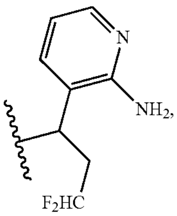
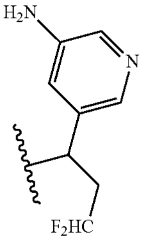
,
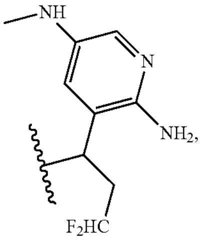
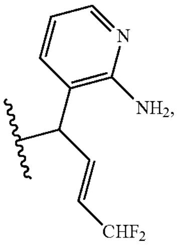
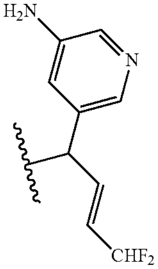
,
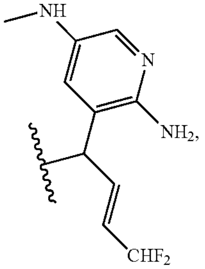
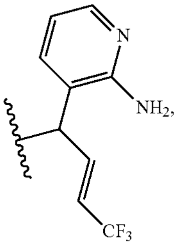
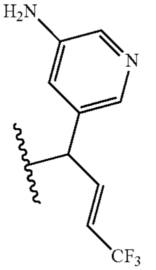
,
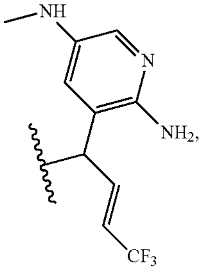
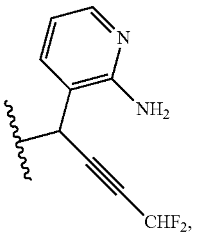
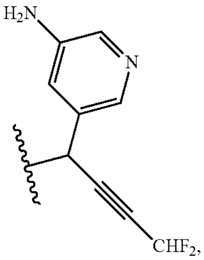

-continued
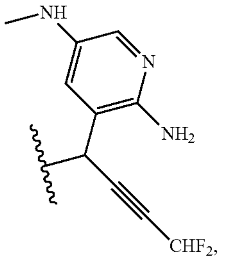
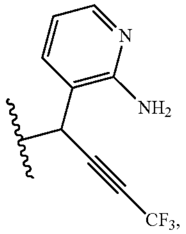
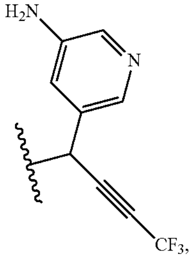
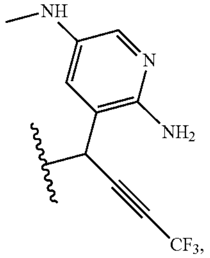
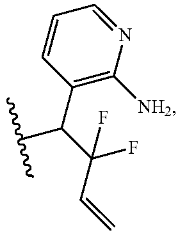
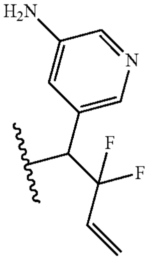
,
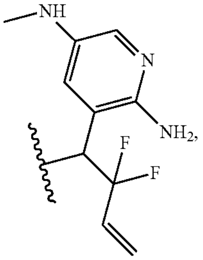
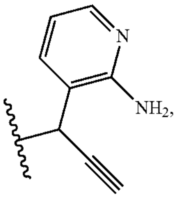
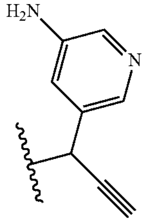
,
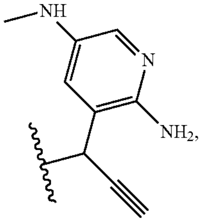
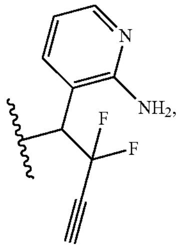
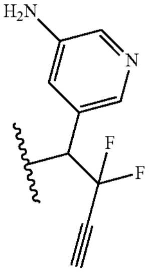
,
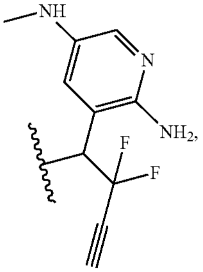
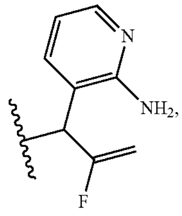
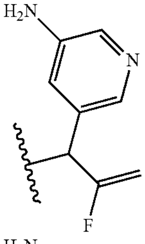
,
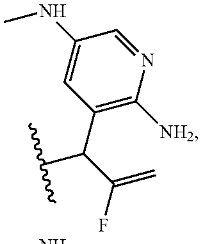
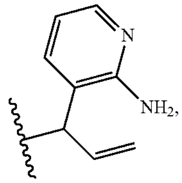
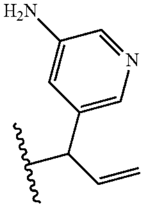
,
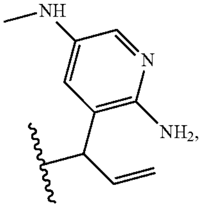
-continued
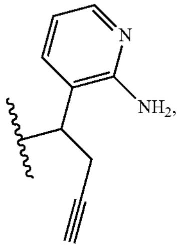
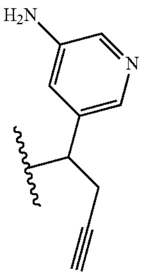
,
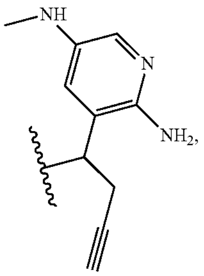
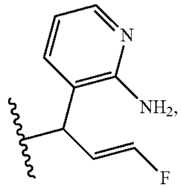
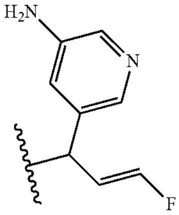
,
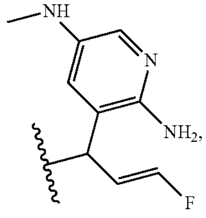
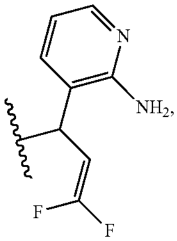
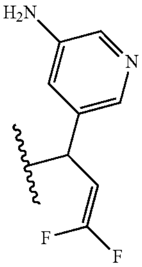
,
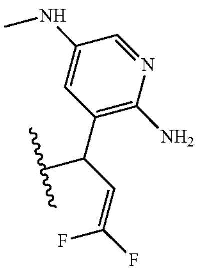
,
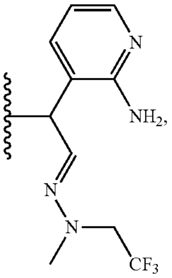
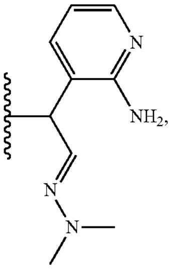
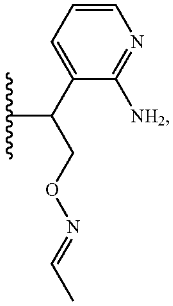
and
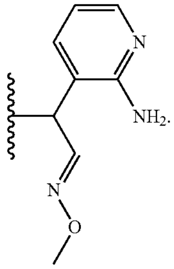
In some embodiments, for a compound of Formula (I), (III), (IV), (V), or (VI),
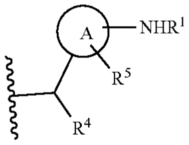

is selected from
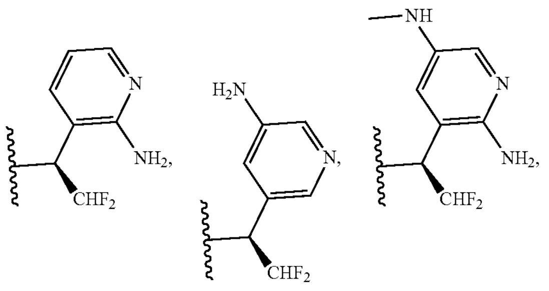
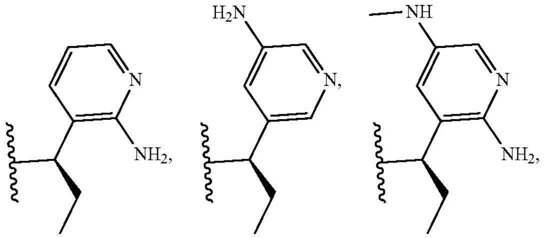
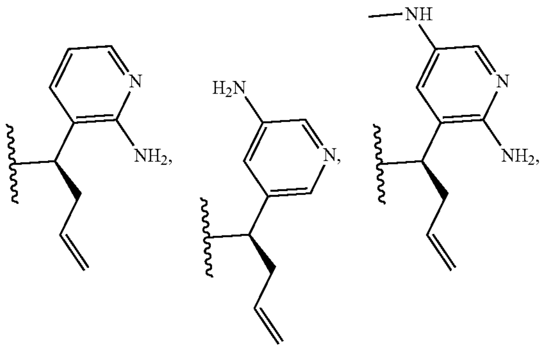
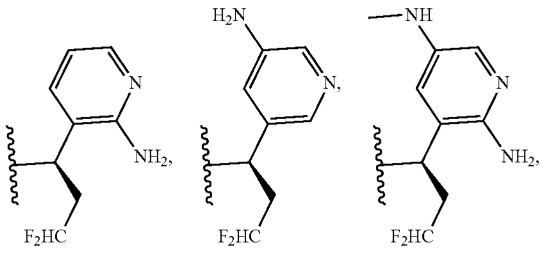
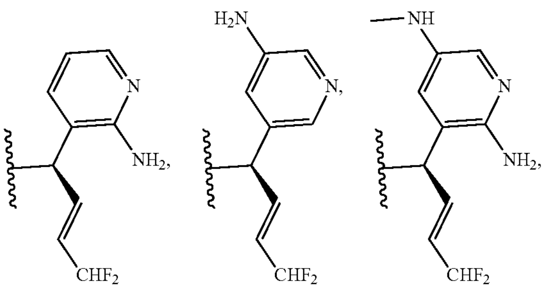
-continued
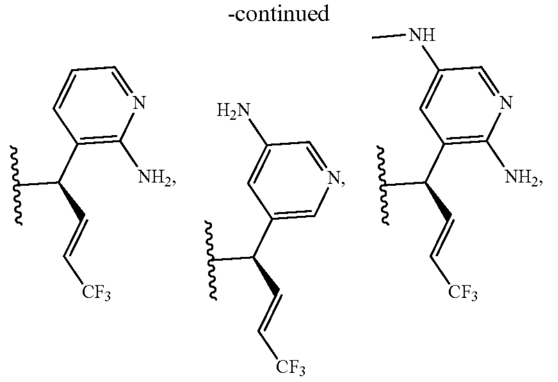
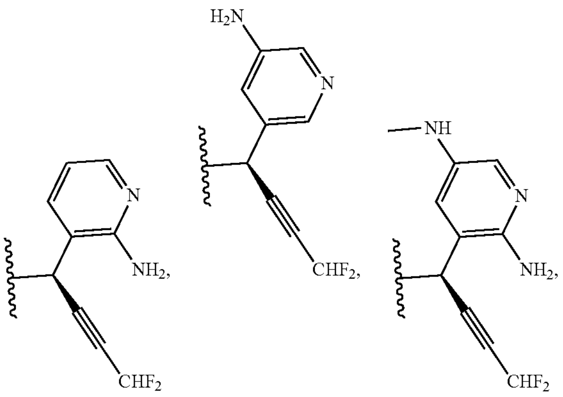
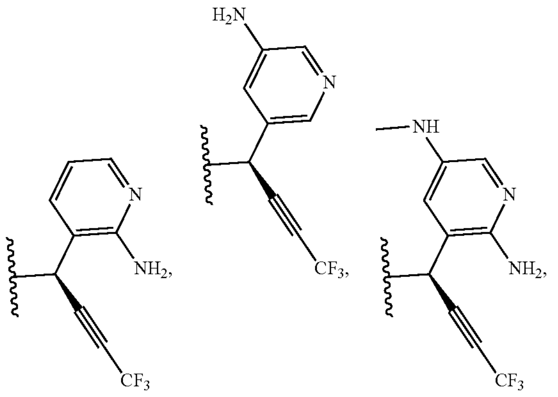
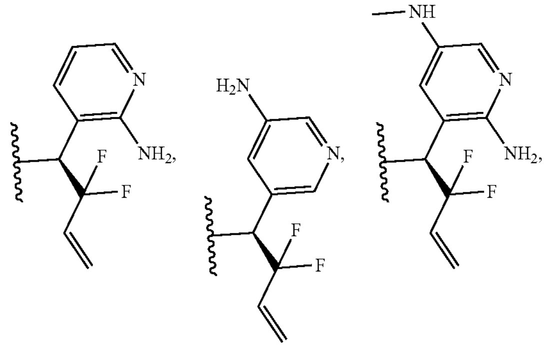

-continued
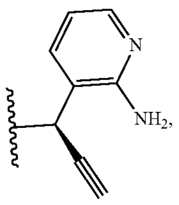
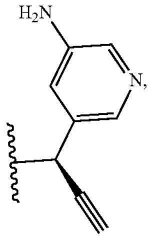
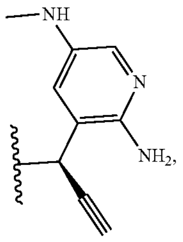
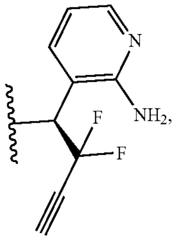
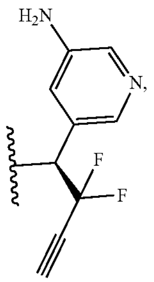
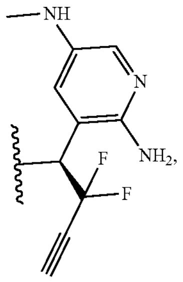
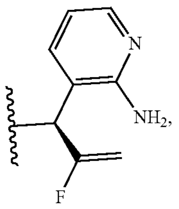
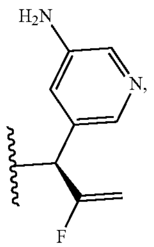
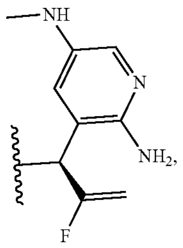
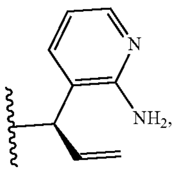
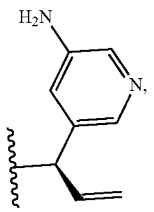
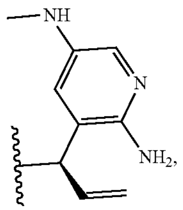
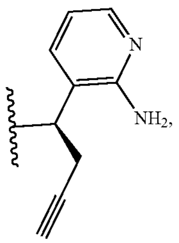
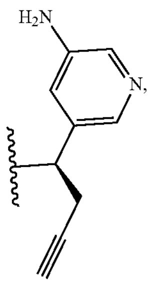
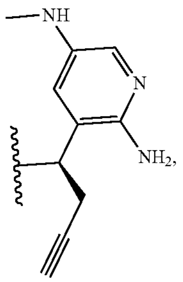
-continued
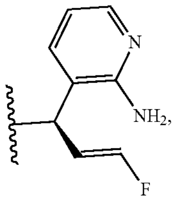
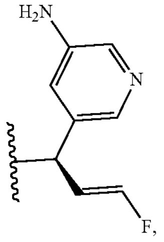
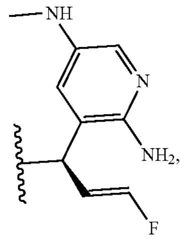
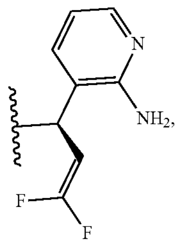
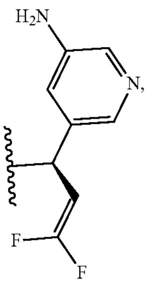
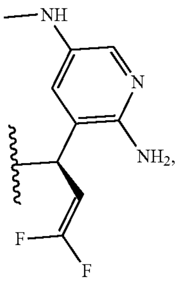
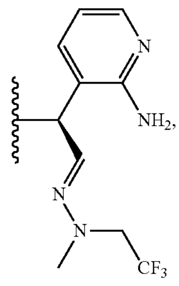
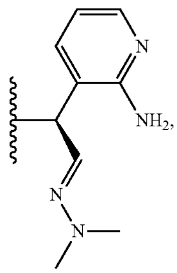
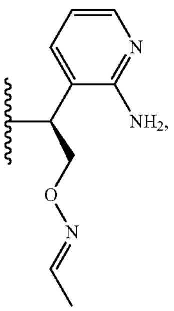
and
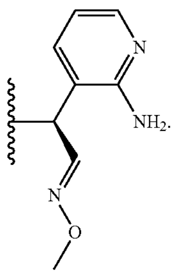
In some embodiments, for a compound of Formula (I), (III), (IV), (V), or (VI),
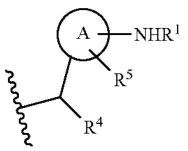

is selected from
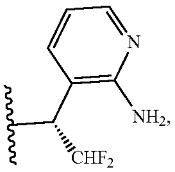
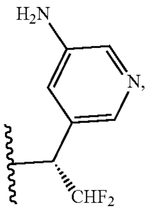
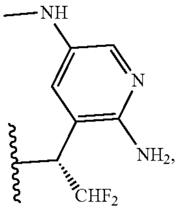
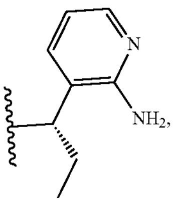
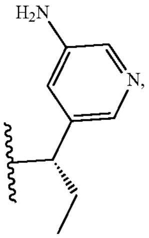
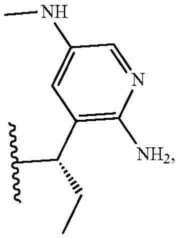
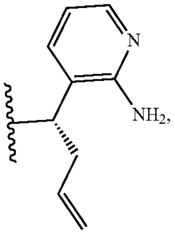
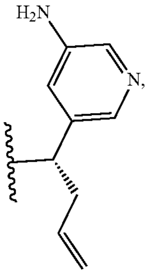
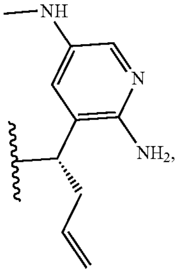
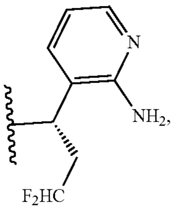
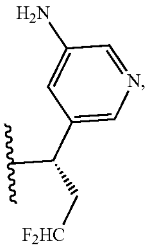
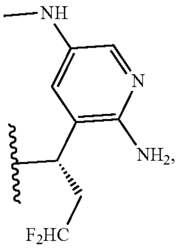
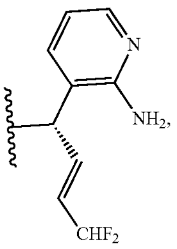
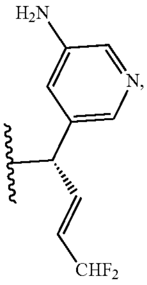
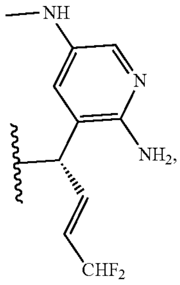
-continued
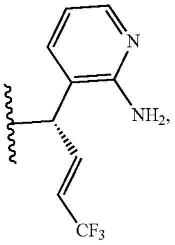
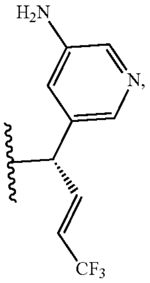
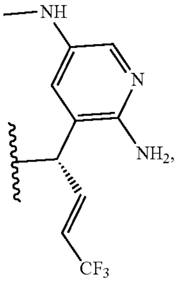
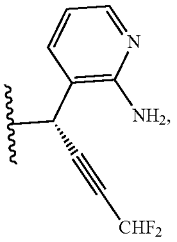
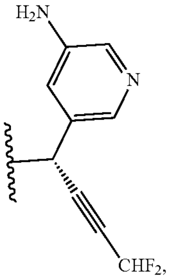
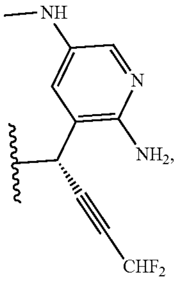
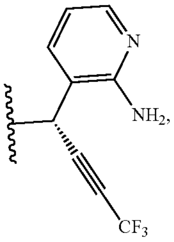
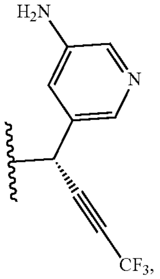
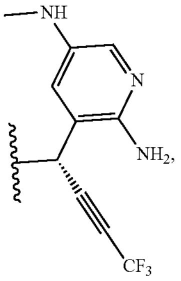
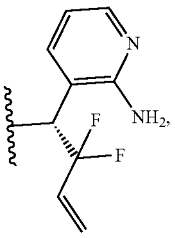
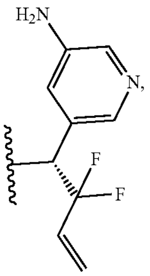
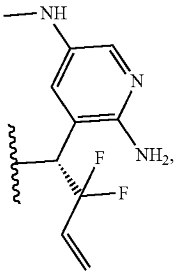

-continued
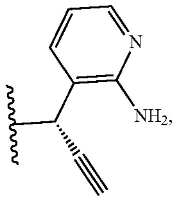,
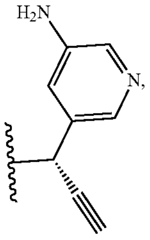,
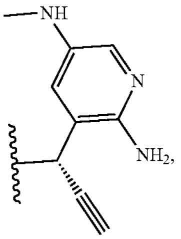,
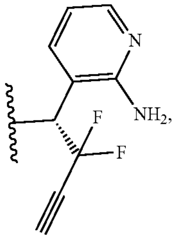,
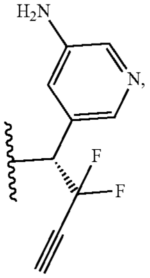,
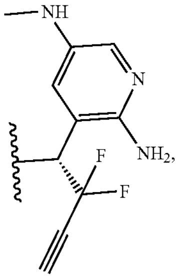,
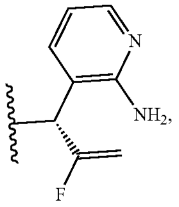,
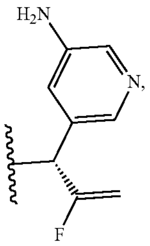,
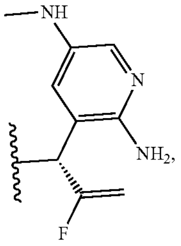,
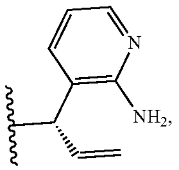,
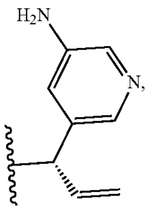,
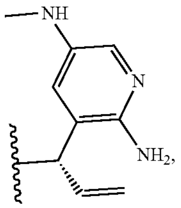,
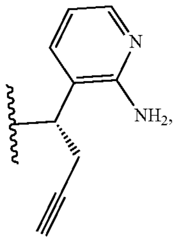,
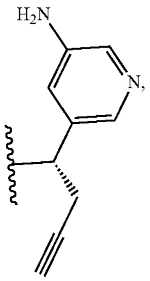,
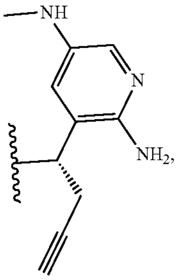,
-continued
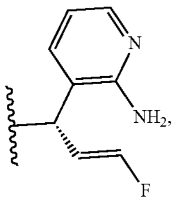,
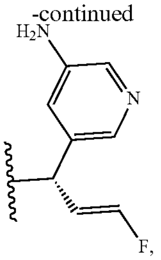,
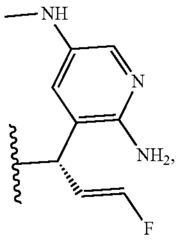,
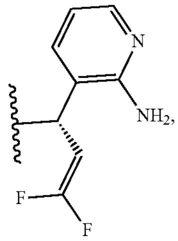,
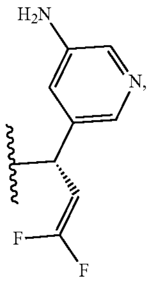,
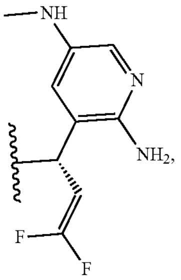,
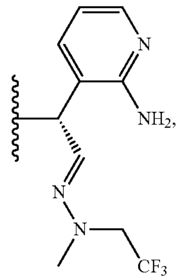,
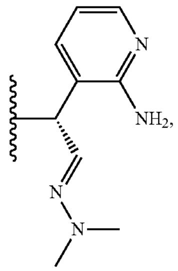,
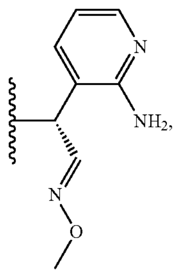, and
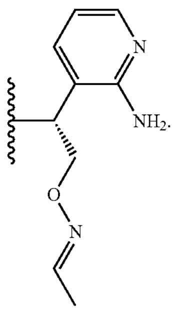.
In some embodiments, for a compound of Formula (I), (III), (IV), (V), or (VI),
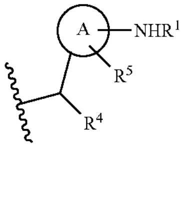

is selected from
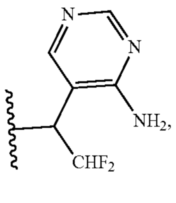
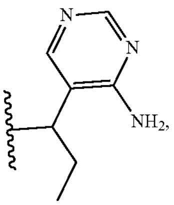
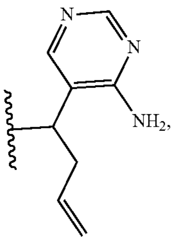
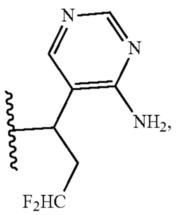
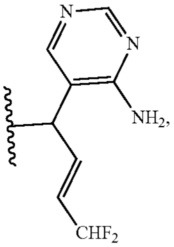
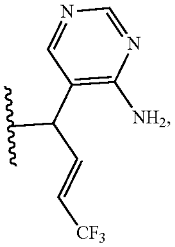
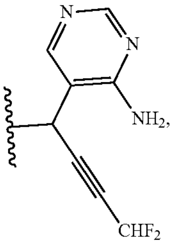
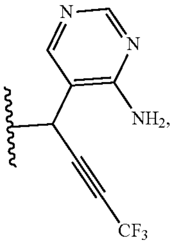
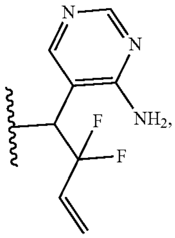
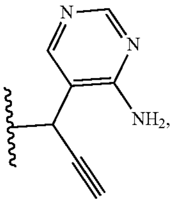
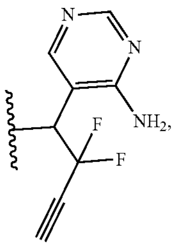
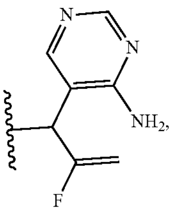
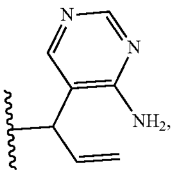
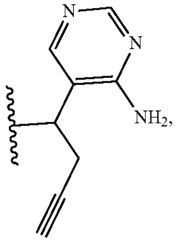
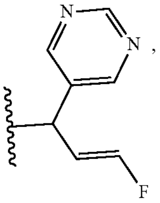
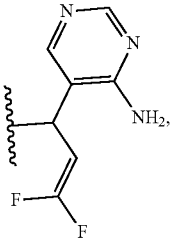
-continued
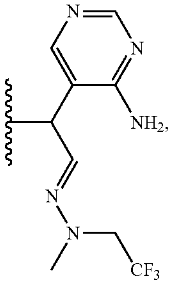
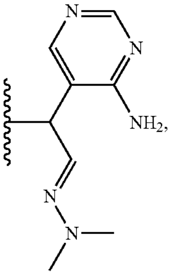
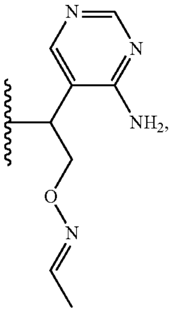
and
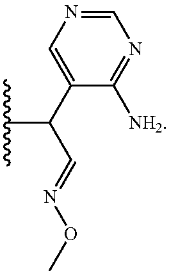
In some embodiments, for a compound of Formula (I), (III), (IV), (V), or (VI),
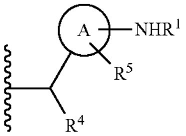
is selected from
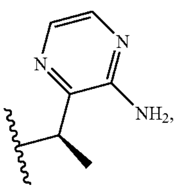
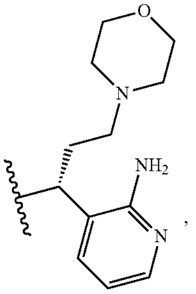
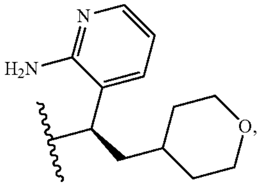
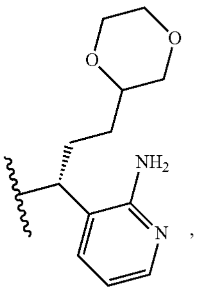

-continued
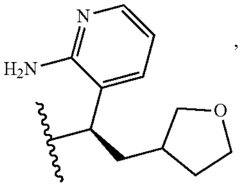,
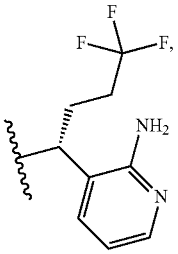
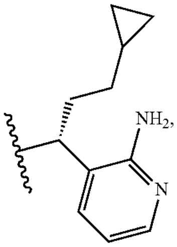
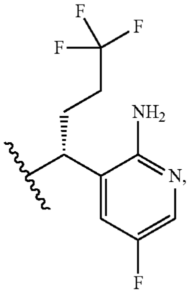
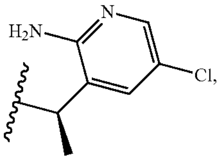
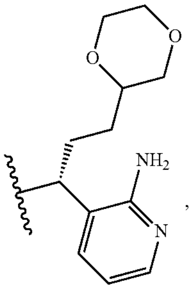,
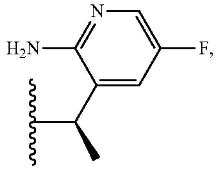
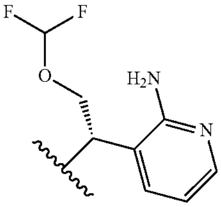,
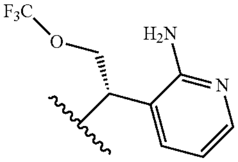,
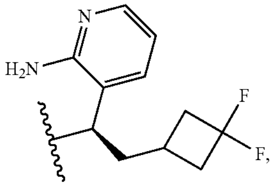
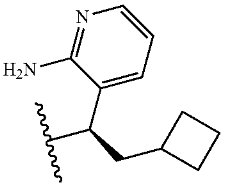,
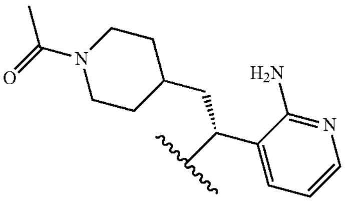,
-continued
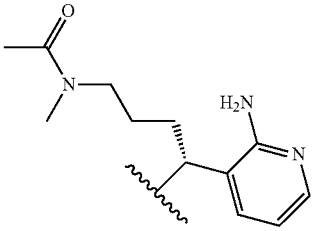,
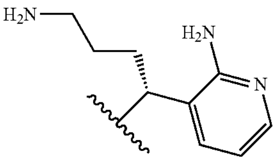,
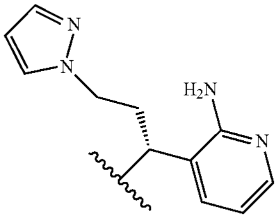,
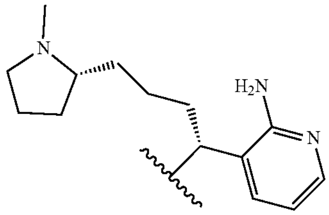,
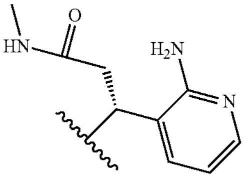,
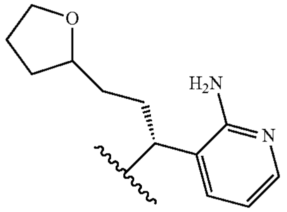,
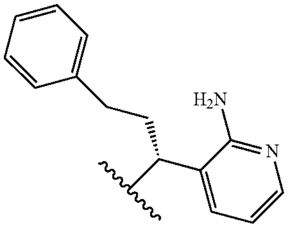,
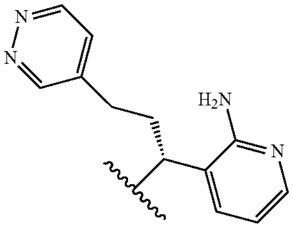, -continued
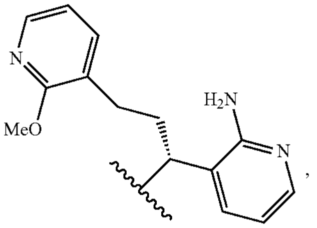
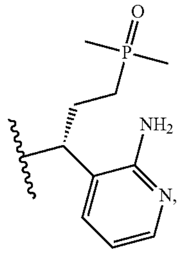
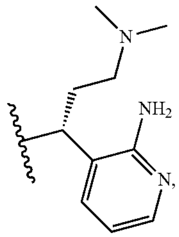
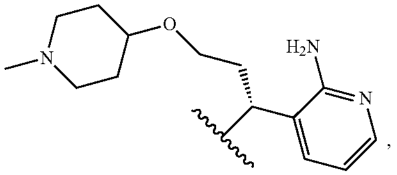
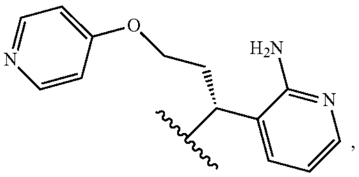
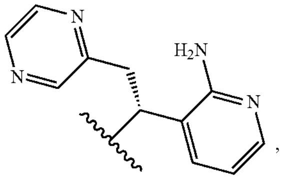
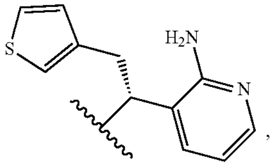
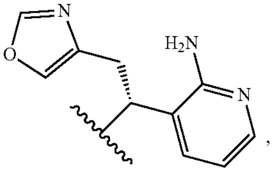
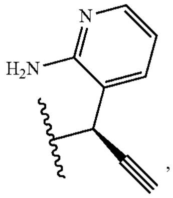
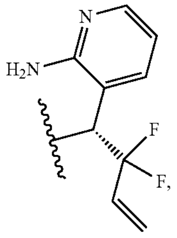
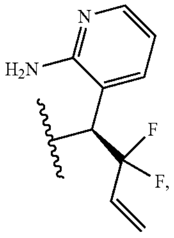
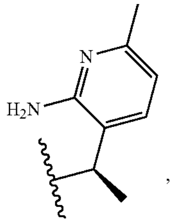
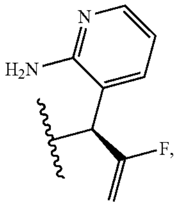
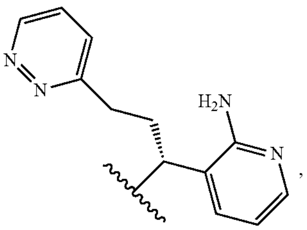
-continued
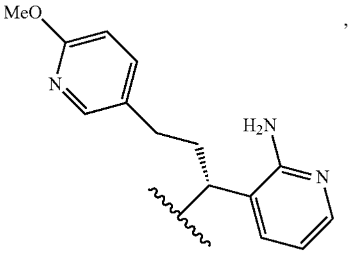
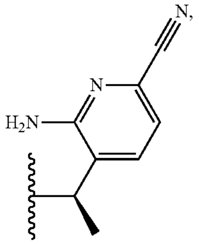
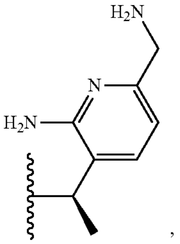
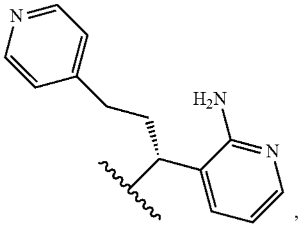
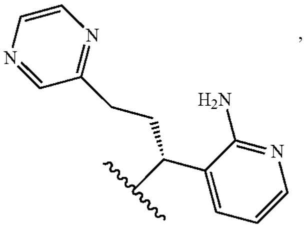
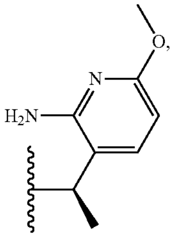
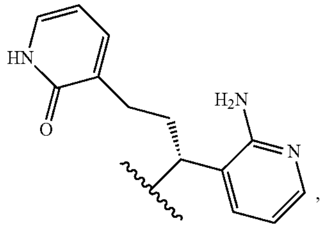
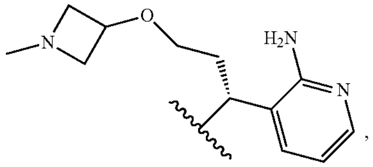
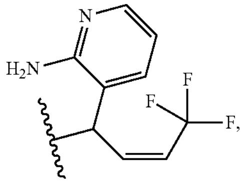
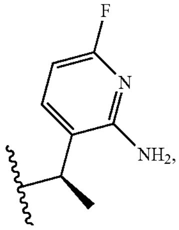
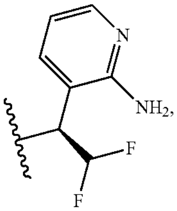
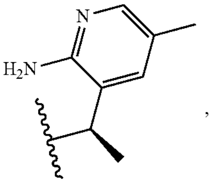

-continued
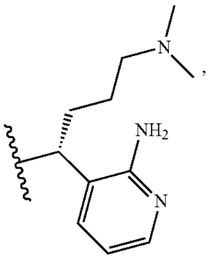,
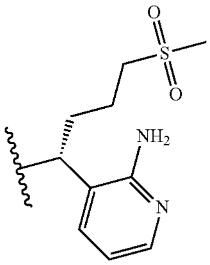,
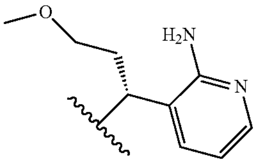,
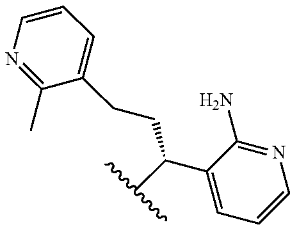,
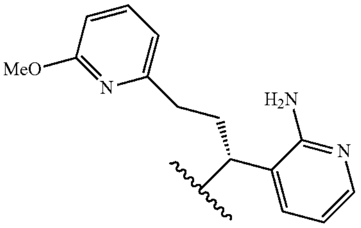,
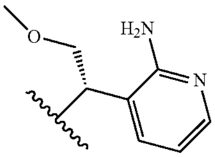,
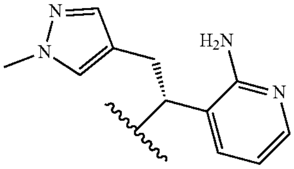,
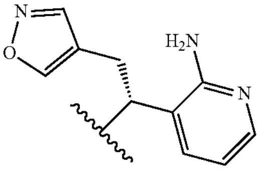,
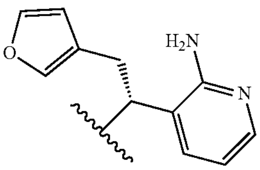,
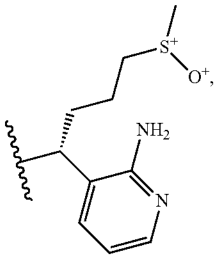,
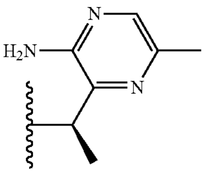,
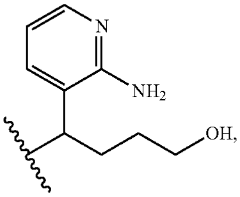,
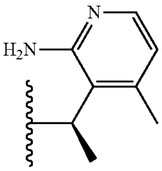,
-continued
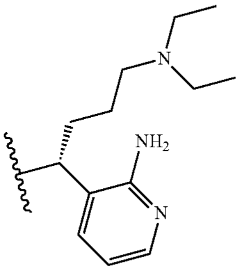,
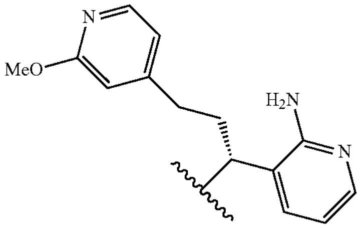,
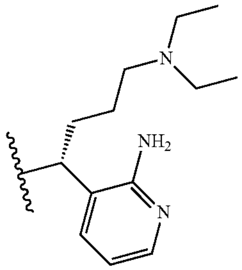,
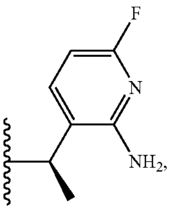,
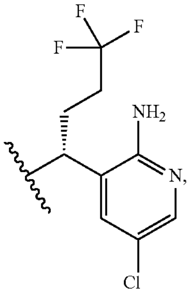,
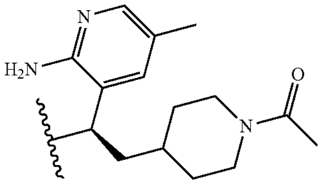,
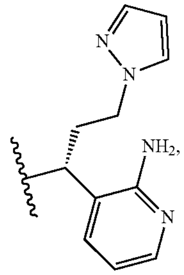,
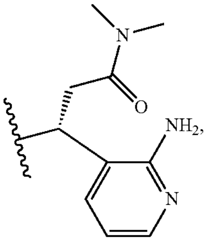,
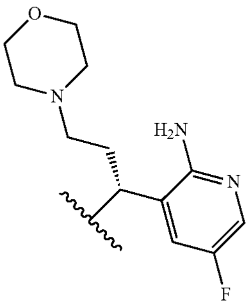,
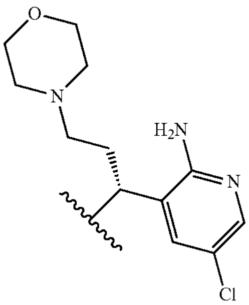, -continued
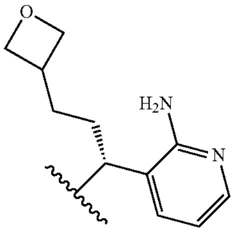,
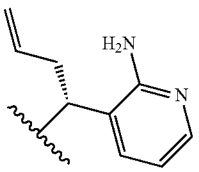,
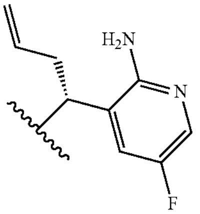,
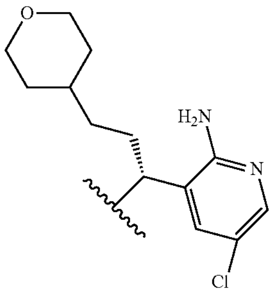,
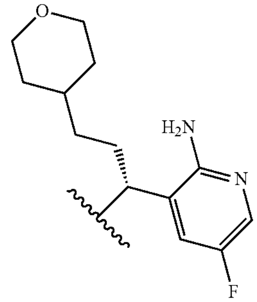,
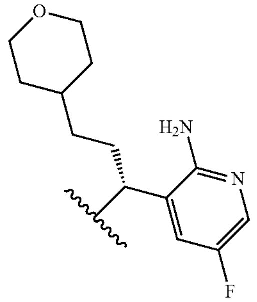,
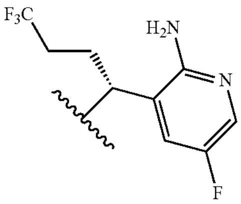,
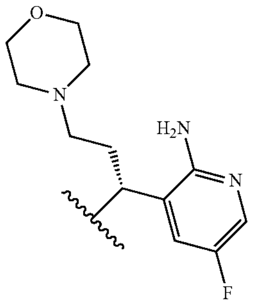,
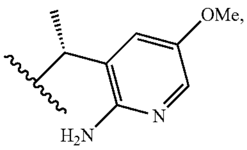,
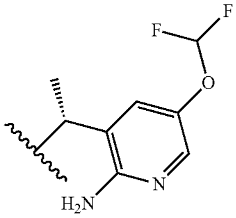,
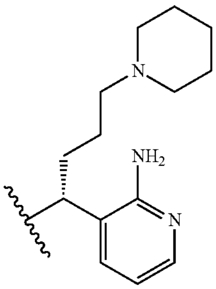,
-continued
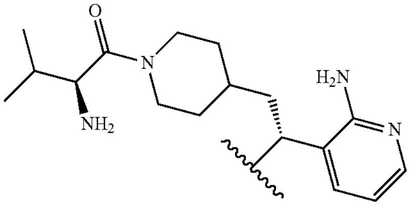,
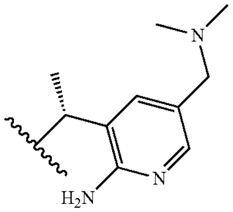,
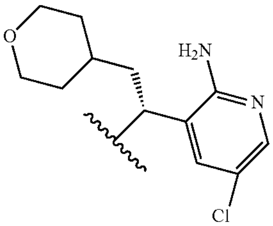,
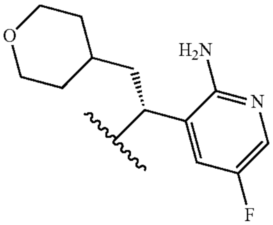,
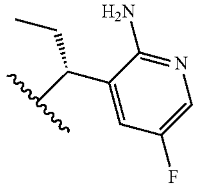,
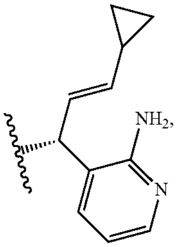,
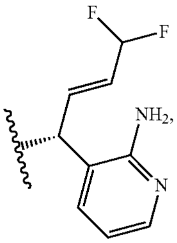,
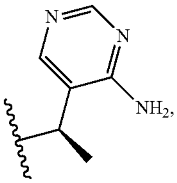,
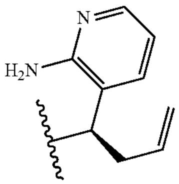,
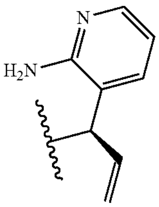,
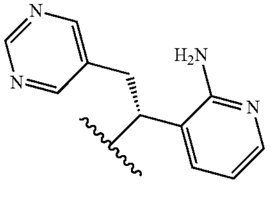,
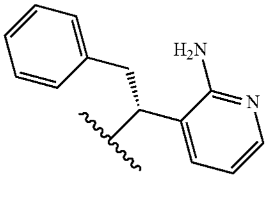,
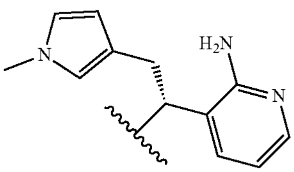,
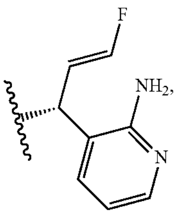

-continued
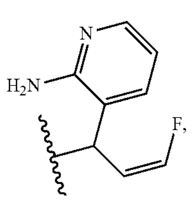
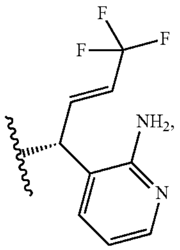
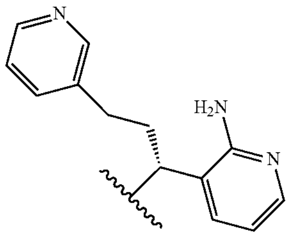
,
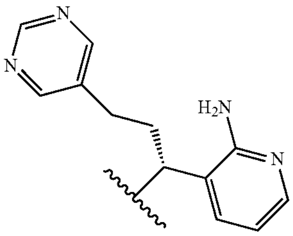
,
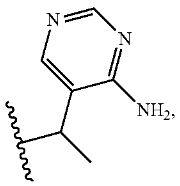
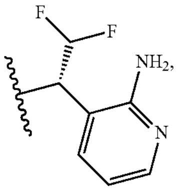
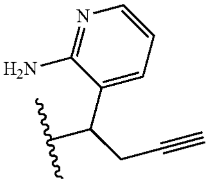
,
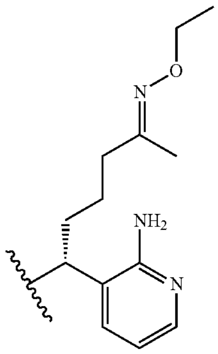
,
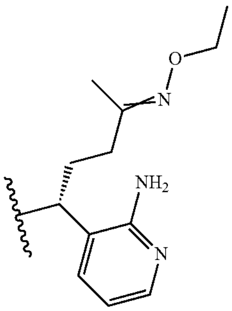
,
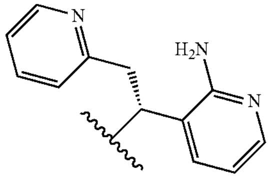
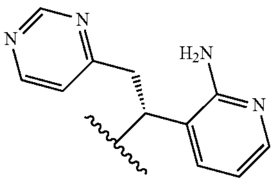
,
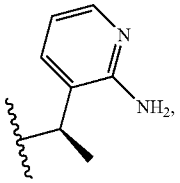
-continued
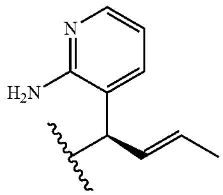
,
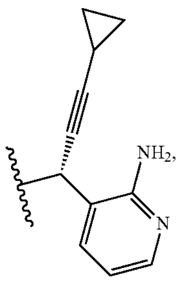
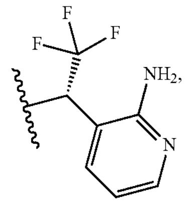
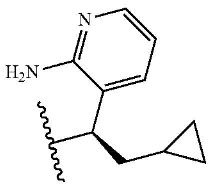
,
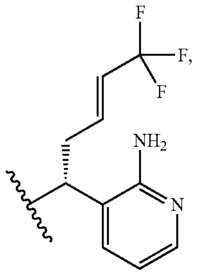
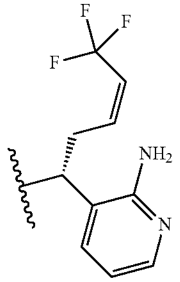
,
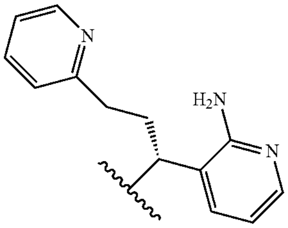
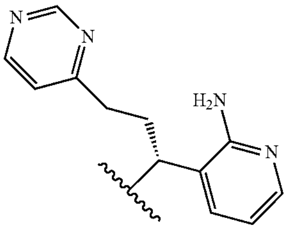
,
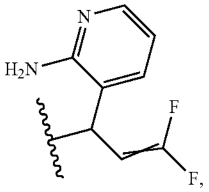
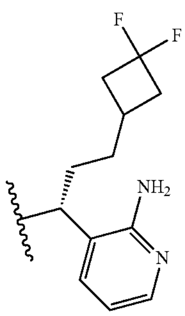
,
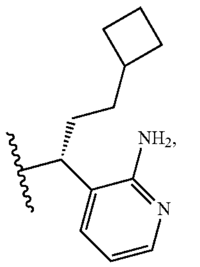

-continued
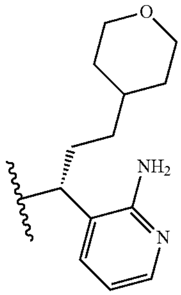,
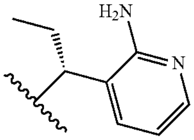,
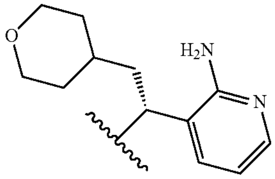,
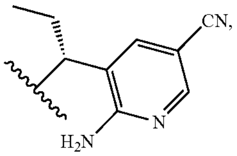
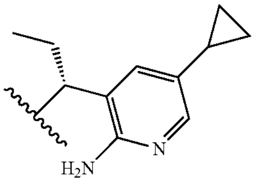,
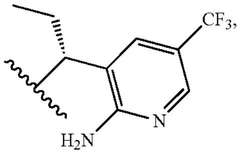
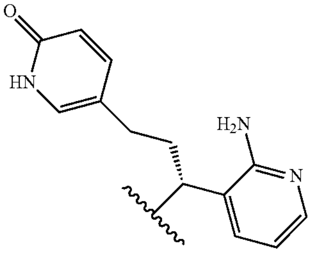,
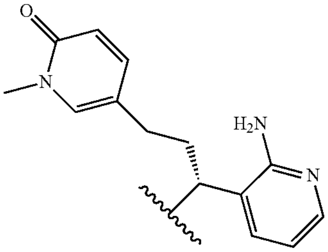,
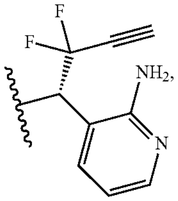
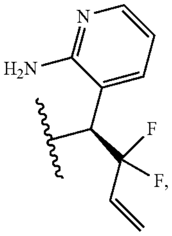
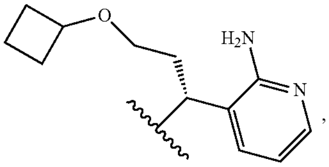,
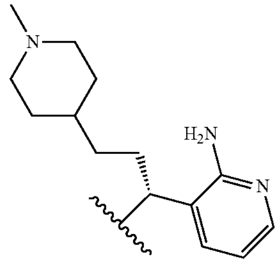,
-continued
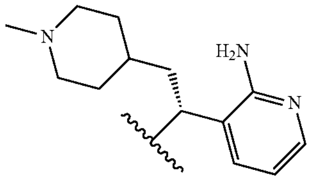,
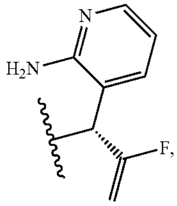 and
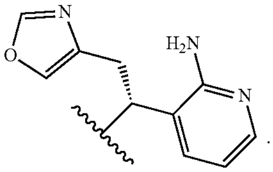.
In some embodiments, for a compound of Formula (I), (III), (IV), (V), or (VI),
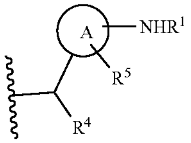
is selected from
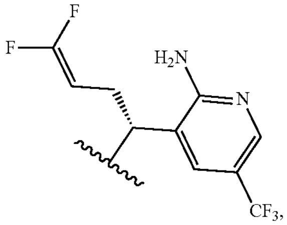
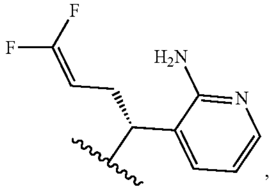,
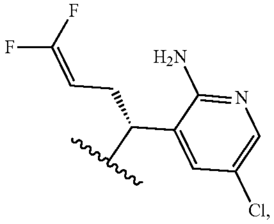
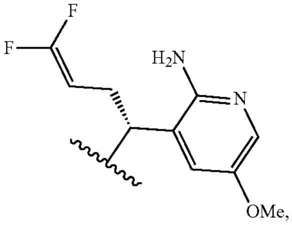
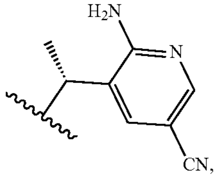
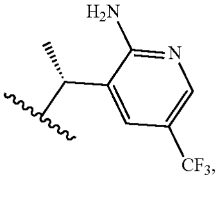
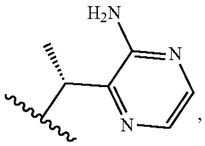, -continued
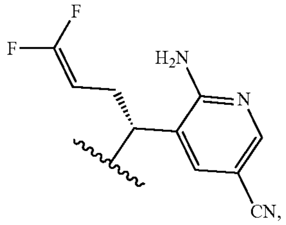
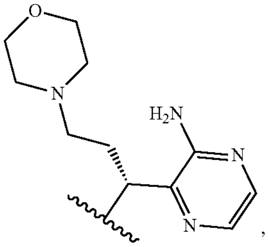
,
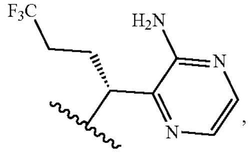
,
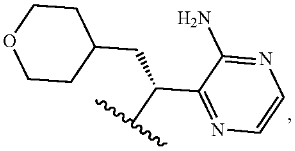
,
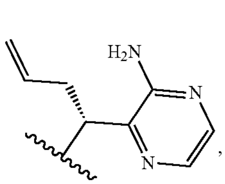
,
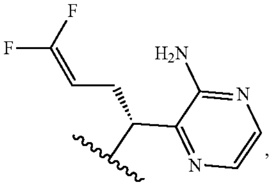
,
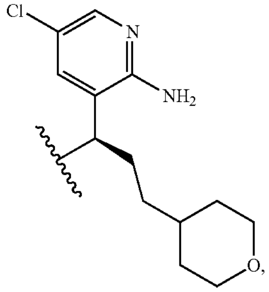
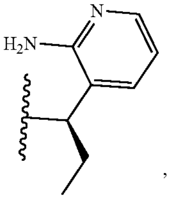
,
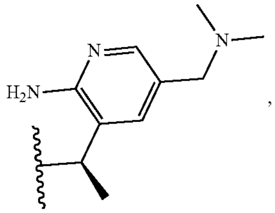
,
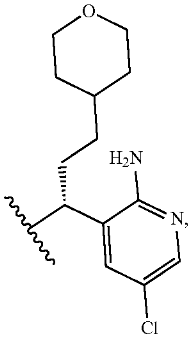
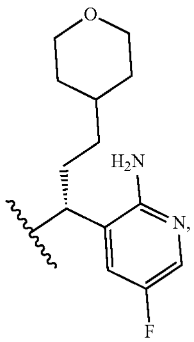
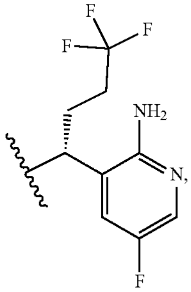
-continued
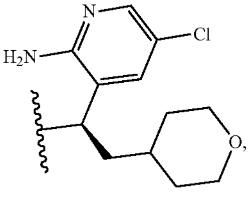
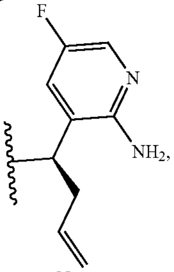
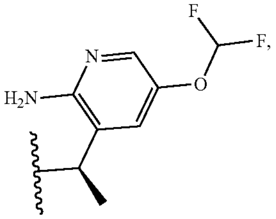
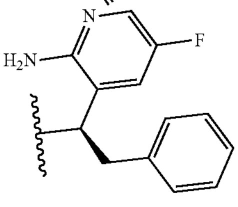
,
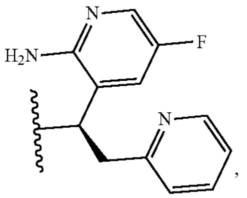
,
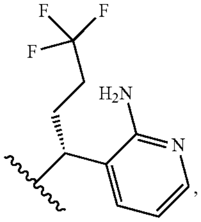
,
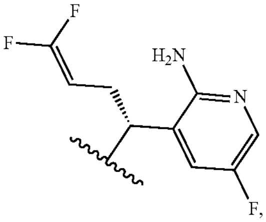
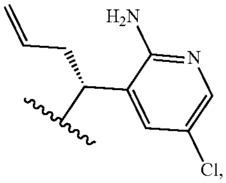
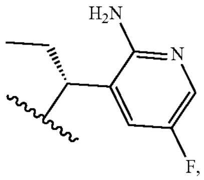
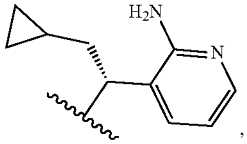
,
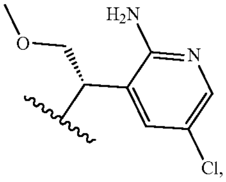
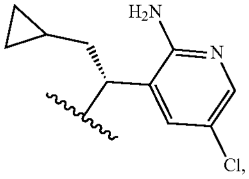
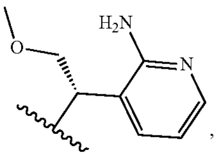
,
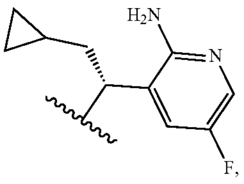
and
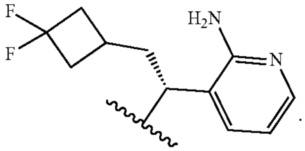
In some embodiments, for a compound of Formula (I), (III), (IV), or (V), $R^7$ is benzothiophenyl optionally substituted with one or more $R^{20}$. In some embodiments, $R^7$ is benzothiophenyl optionally substituted with one, two, three, or four $R^{20}$. In some embodiments, $R^7$ is benzothiophenyl substituted with two $R^{20}$. In some embodiments, $R^7$ is benzothiophenyl substituted with three $R^{20}$. In some embodiments, $R^7$ is benzo[b]thiophen-4-yl optionally substituted with one, two, three, or four $R^{20}$. In some embodiments, $R^7$ is benzo[b]thiophen-4-yl substituted with two $R^{20}$. In some embodiments, $R^7$ is benzo[b]thiophen-4-yl substituted with three $R^{20}$. In some embodiments, $R^7$ is selected from

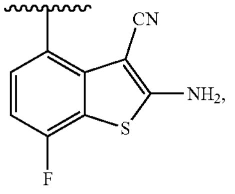
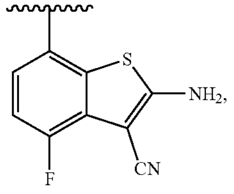
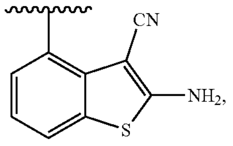
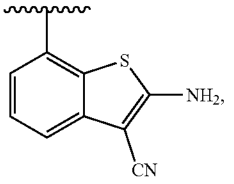
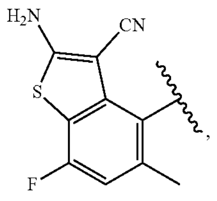
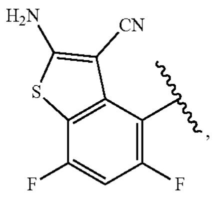
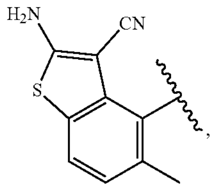
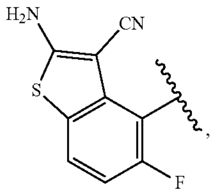
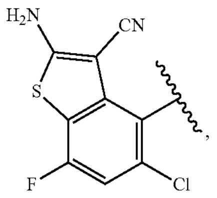
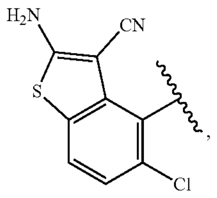
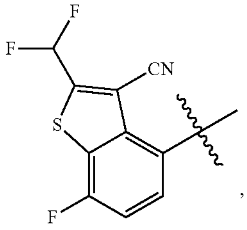
, and
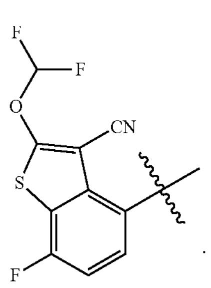
.

In some embodiments, $R^7$ is

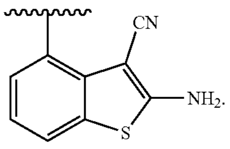 [SMILES: *c1cccc2sc(N)c(C#N)c12]

In some embodiments, $R^7$ is

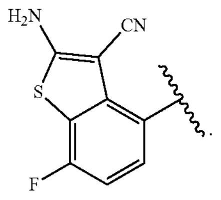 [SMILES: *c1ccc(F)c2sc(N)c(C#N)c12]

In some embodiments, $R^7$ is

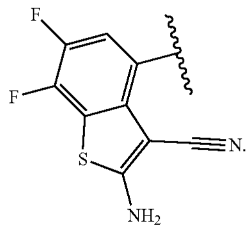 [SMILES: *c1cc(F)c(F)c2sc(N)c(C#N)c12]

In some embodiments, $R^7$ is

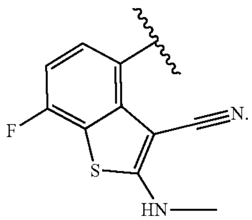 [SMILES: *c1ccc(F)c2sc(NC)c(C#N)c12]

In some embodiments, $R^7$ is

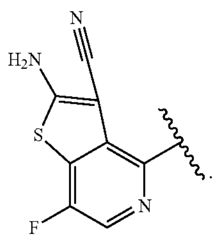 [SMILES: *c1ncc(F)c2sc(N)c(C#N)c12]

In some embodiments, for a compound of Formula (III), (IV), or (V), $R^7$ is naphthalenyl optionally substituted with one or more $R^{20}$. In some embodiments, $R^7$ is naphthalenyl optionally substituted with one, two, three, or four $R^{20}$. In some embodiments, $R^7$ is naphthalenyl substituted with two $R^{20}$. In some embodiments, $R^7$ is naphthalenyl substituted with three $R^{20}$. In some embodiments,

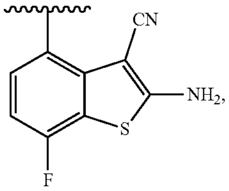,
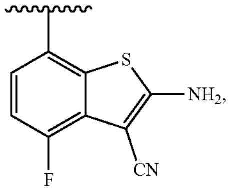,
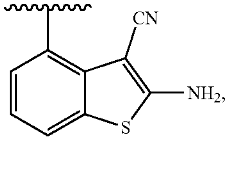,
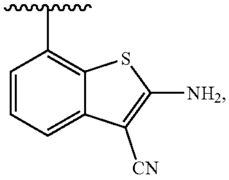,
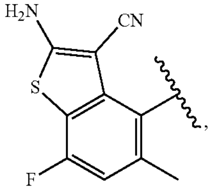,
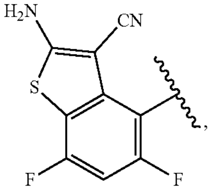,
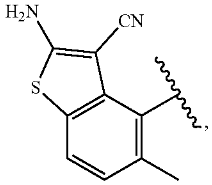,
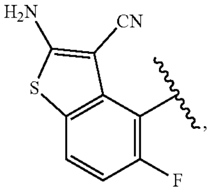,
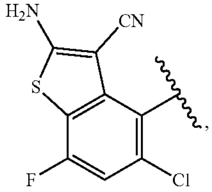,
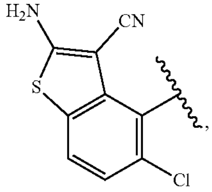,
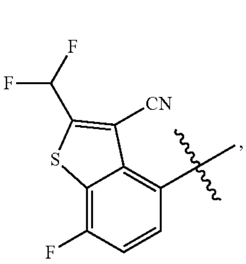,
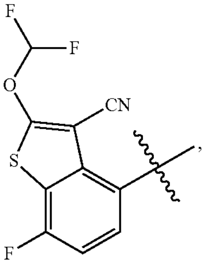,
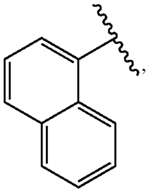,
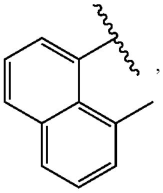,
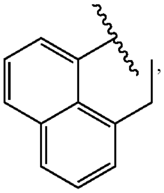,
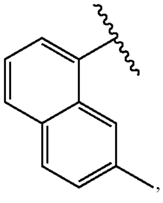,
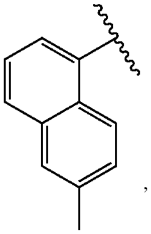,
-continued
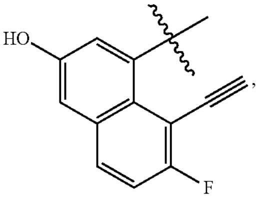,
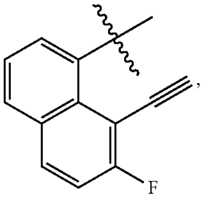,
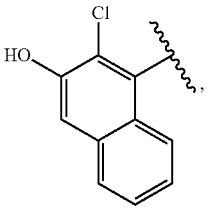,
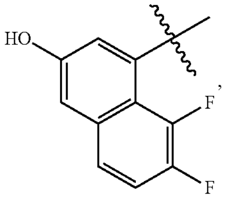,
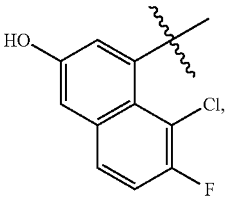,
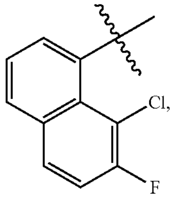,
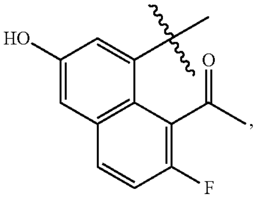,
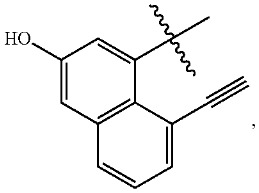,
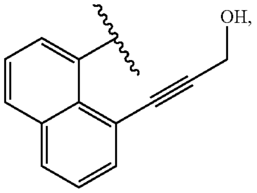,
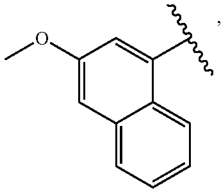,
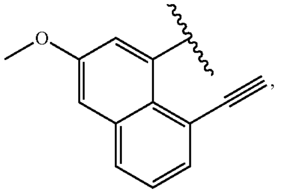,
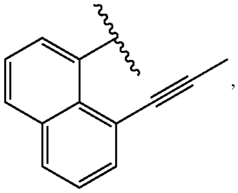,
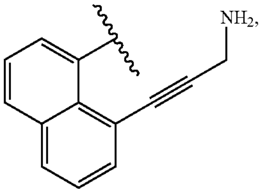,
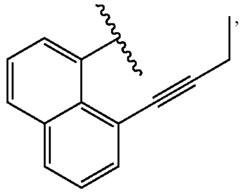,
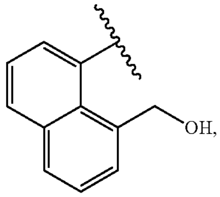,
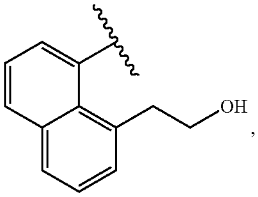, -continued
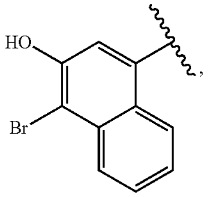
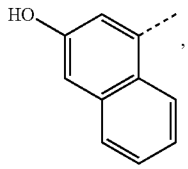
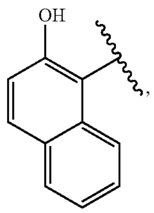
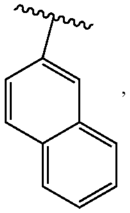
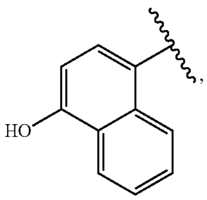
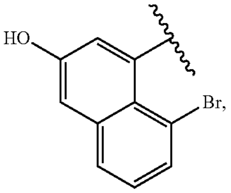
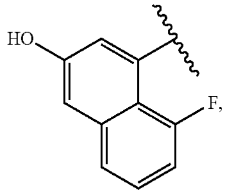
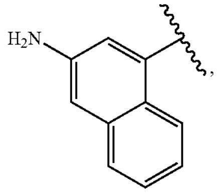
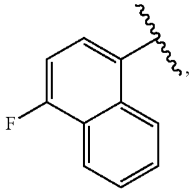
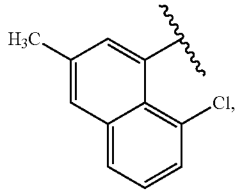
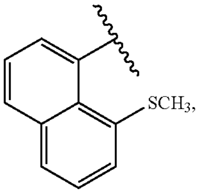
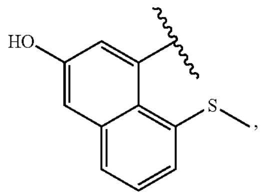
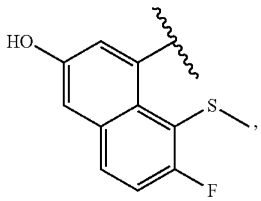
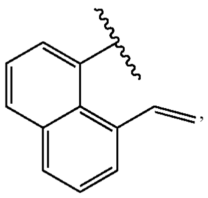
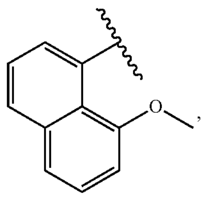
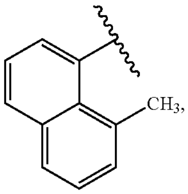
-continued
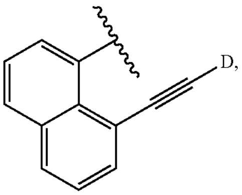
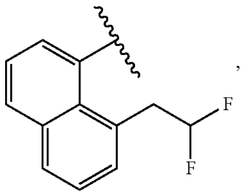
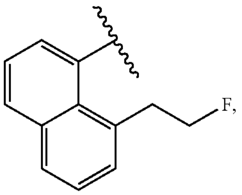
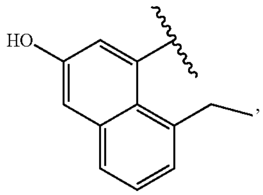
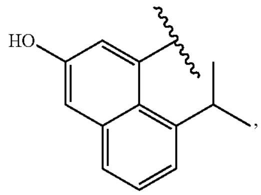
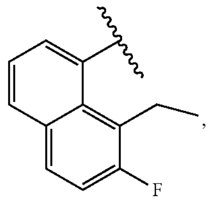
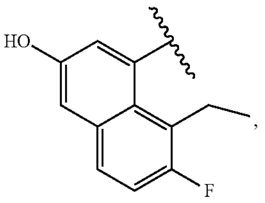
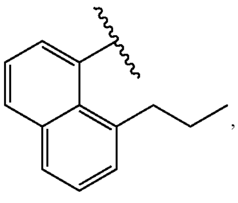
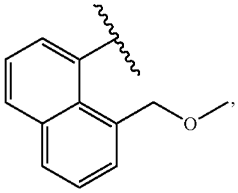
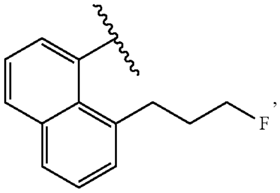
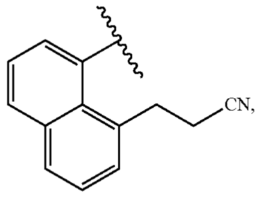
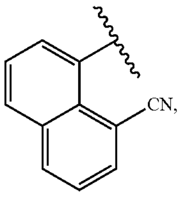
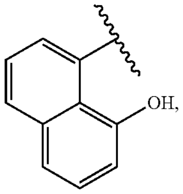
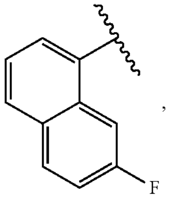
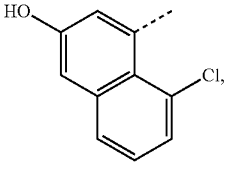
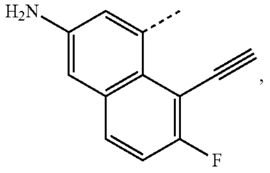

-continued
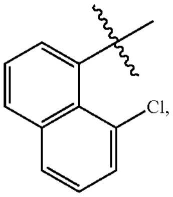
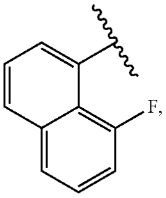
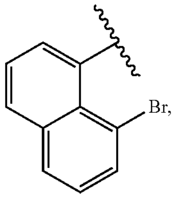
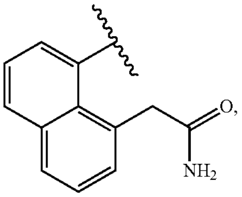
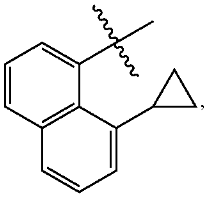
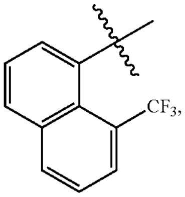
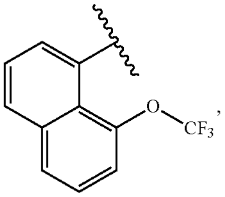
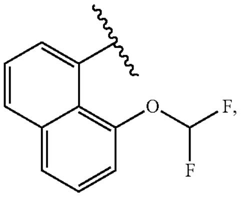
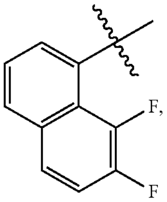
and
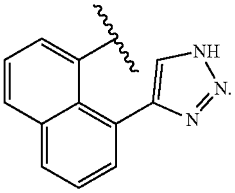 [SMILES: *c1cccc2cccc(-c3c[nH]nn3)c12]
In some embodiments, $R^7$ is selected from
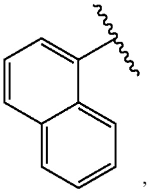
,
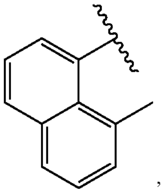
,
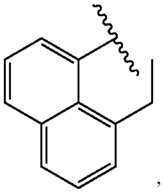
,
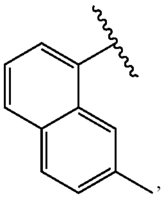
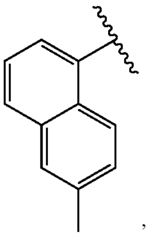
,
-continued
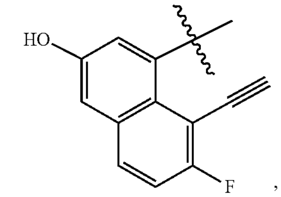
,
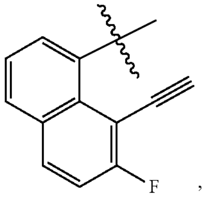
,
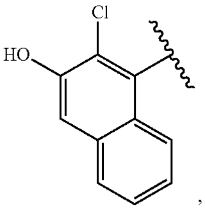
,
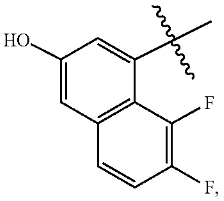
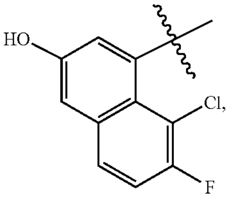
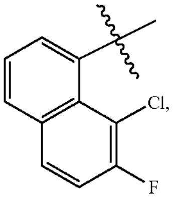
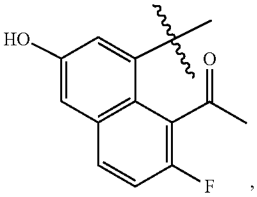
,
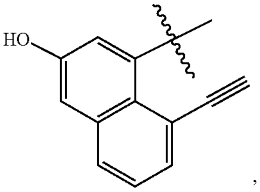
,
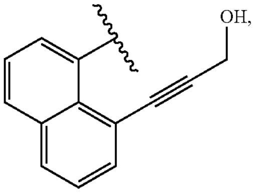
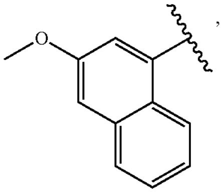
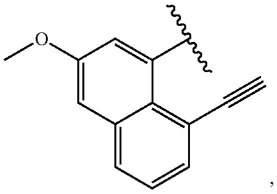
,
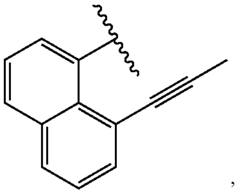
,
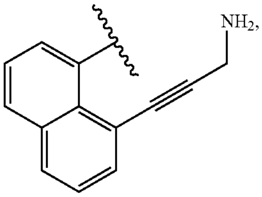
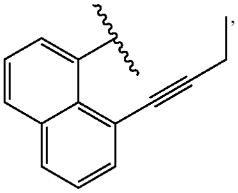
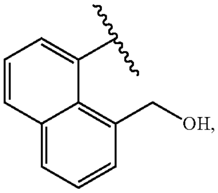
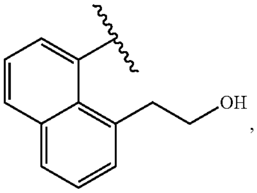

-continued
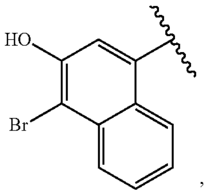,
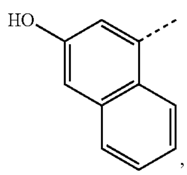,
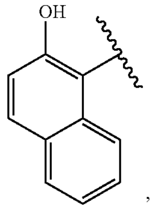,
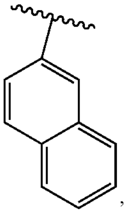,
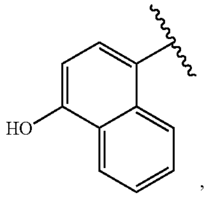,
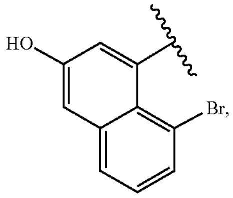
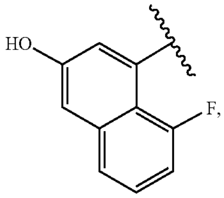
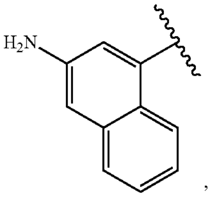,
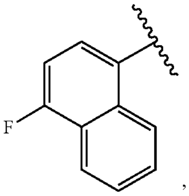,
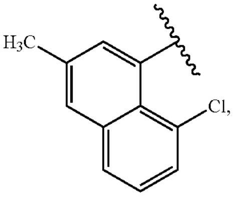
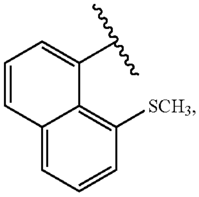
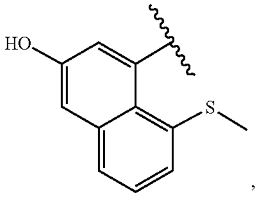,
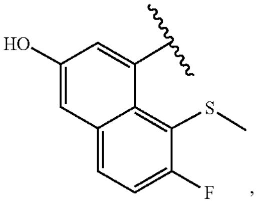,
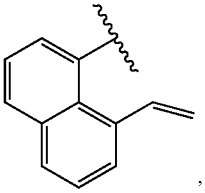,
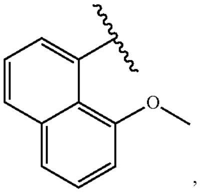,
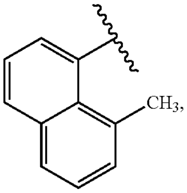
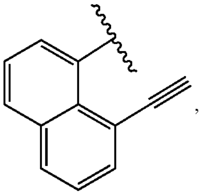
-continued
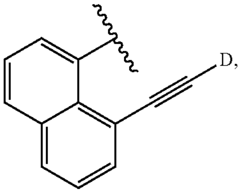
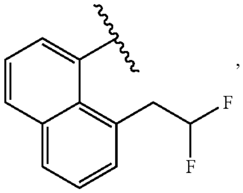,
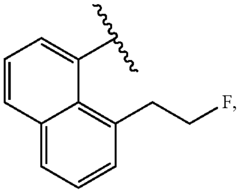
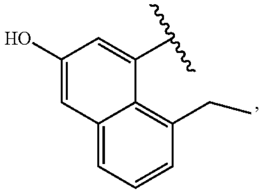
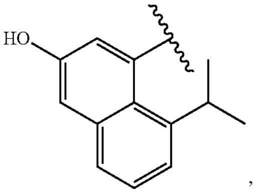,
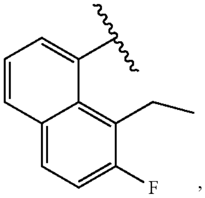,
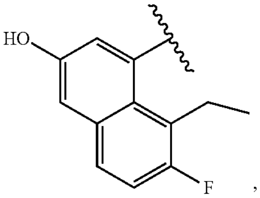,
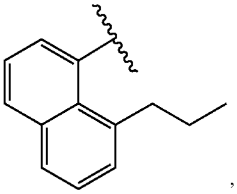,
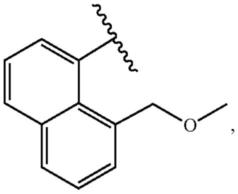,
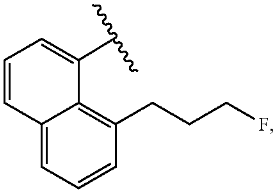
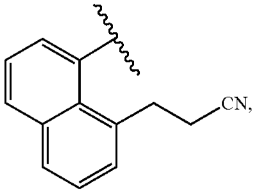
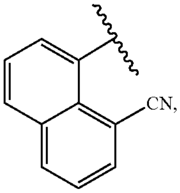
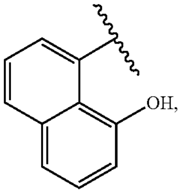
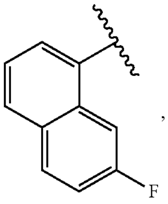,
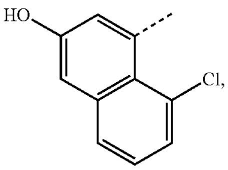
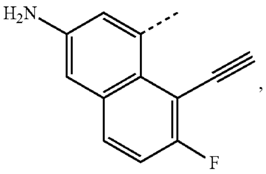, -continued
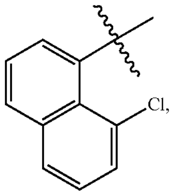 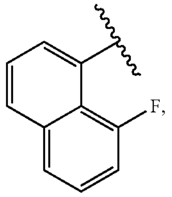 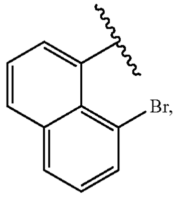
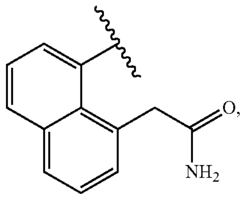 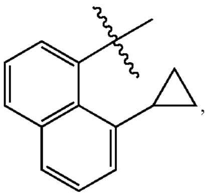
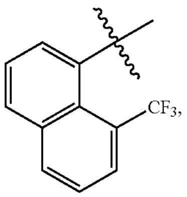 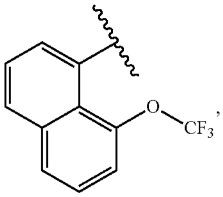
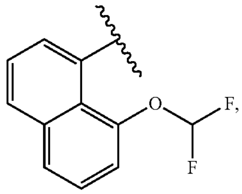 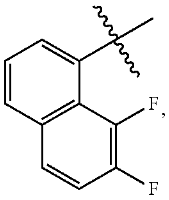 and
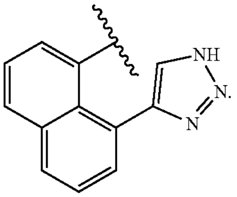
In some embodiments, $R^7$ is selected from
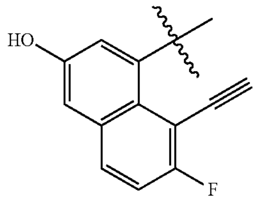 ,
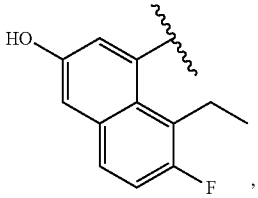 , and 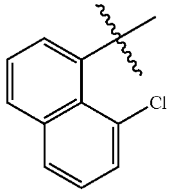 .
In some embodiments, $R^7$ is
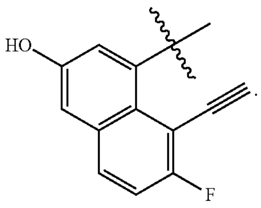 [SMILES: *c1cc(O)cc2ccc(F)c(C#C)c12]
In some embodiments, $R^7$ is
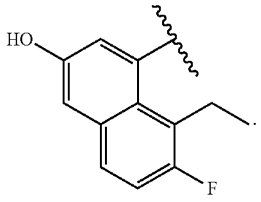 [SMILES: *c1cc(O)cc2ccc(F)c(CC)c12]
In some embodiments, $R^7$ is
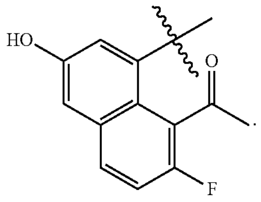 [SMILES: *c1cc(O)cc2ccc(F)c(C(C)=O)c12]
In some embodiments, $R^7$ is
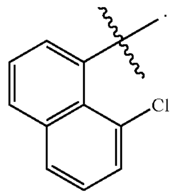 [SMILES: *c1cccc2cccc(Cl)c12]
In some embodiments of Formula (V), $R^7$ is selected from
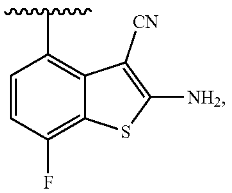 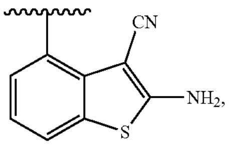
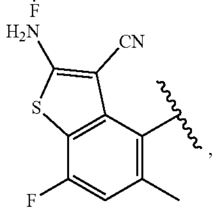 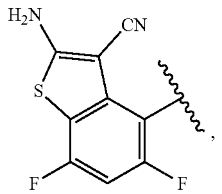

-continued

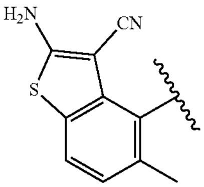,
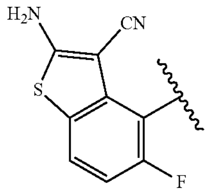,
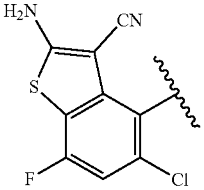,
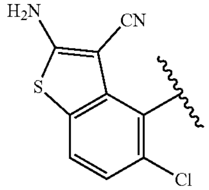,
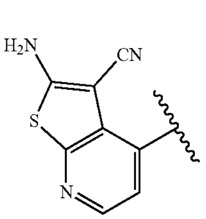,
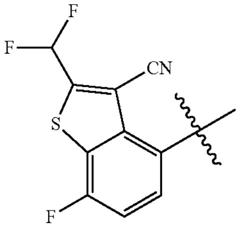,
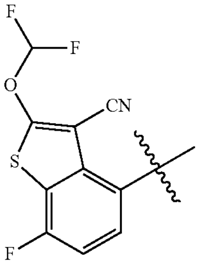,
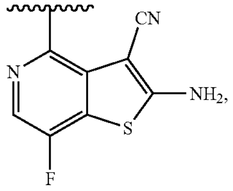,
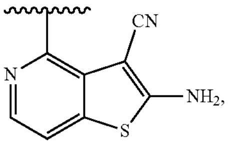,
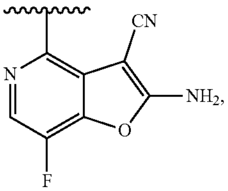,
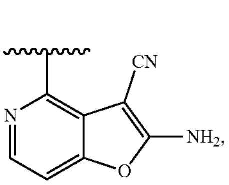, and
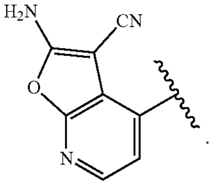.

In some embodiments of Formula (V), $R^7$ is thienopyridinyl optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$. In some embodiments of Formula (V), $R^7$ is furopyridinyl optionally substituted with one, two, three, or four substituents independently selected from —$OR^{15}$, —O—($C_{1-6}$ alkyl)-$OR^{15}$, —NH($C_{1-6}$ alkyl)-$OR^{15}$, —NHC(O)O—($C_{1-6}$ alkyl)-$OR^{15}$, (5-methyl-2-oxo-1,3-dioxol-4-yl)methyl-NH—, and $R^{20}$. In some embodiments, $R^7$ is

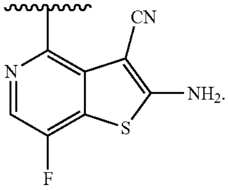 [SMILES: *c1ncc(F)c2sc(N)c(C#N)c12].

In some embodiments, $R^7$ is

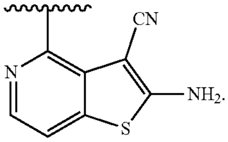 [SMILES: *c1nccc2sc(N)c(C#N)c12].

In some embodiments, $R^7$ is

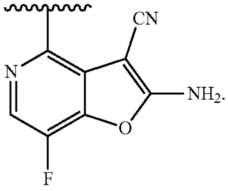 [SMILES: *c1ncc(F)c2oc(N)c(C#N)c12].

In some embodiments, $R^7$ is

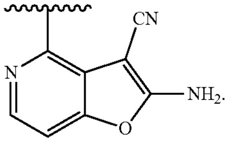 [SMILES: *c1nccc2oc(N)c(C#N)c12].

In some embodiments of Formula (I), (III), (IV), or (V), $R^7$ is

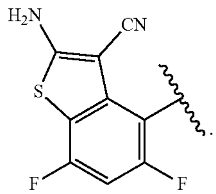.

In some embodiments, $R^7$ is

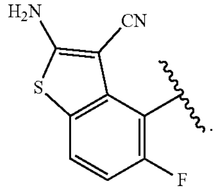.

In some embodiments of Formula (VI), $R^7$ is selected from
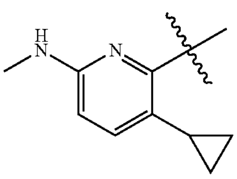,
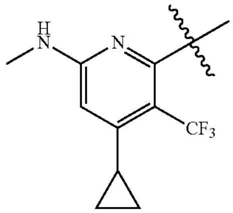,
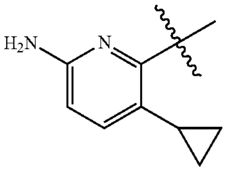,
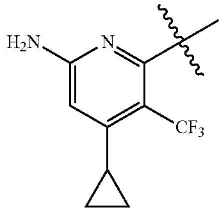,
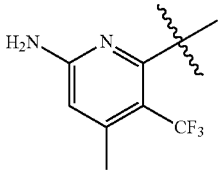,
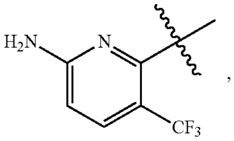,
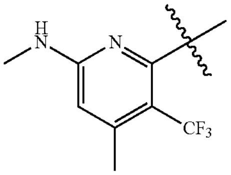,
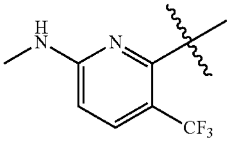,
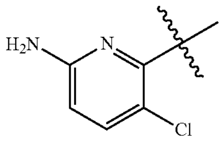,
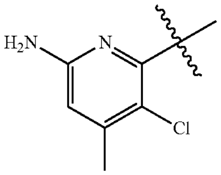,
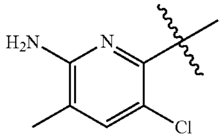,
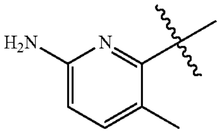,
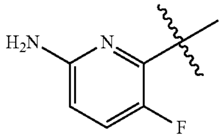,
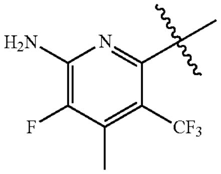,
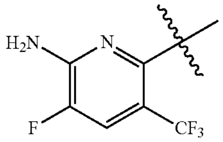,
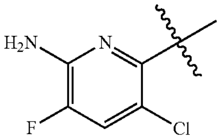,
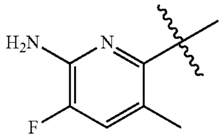,
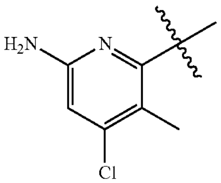,
-continued
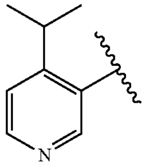,
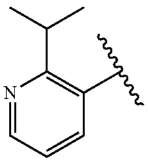,
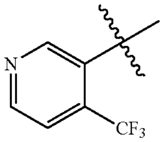,
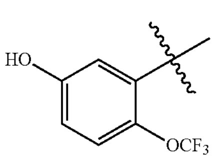,
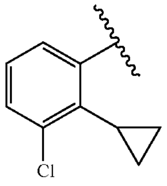,
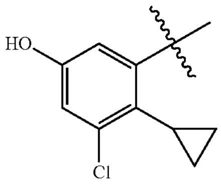,
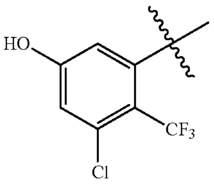,
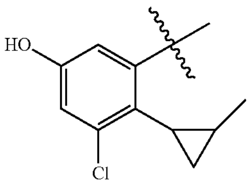,
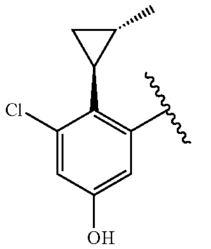,
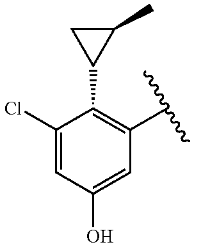,
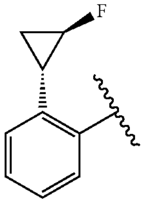,
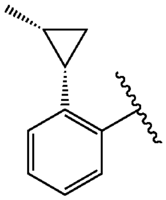,
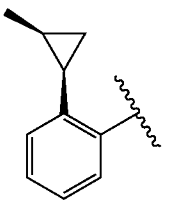,
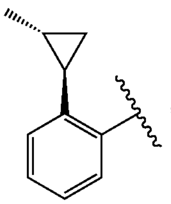,
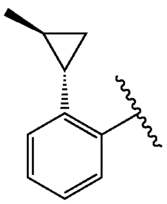,
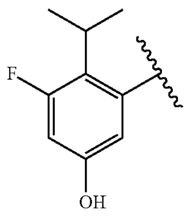,
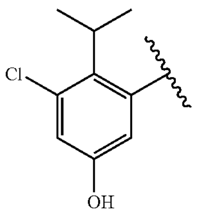,
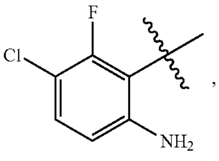,
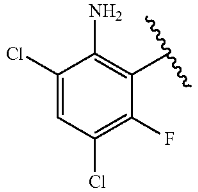, -continued
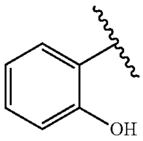, 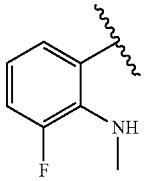, 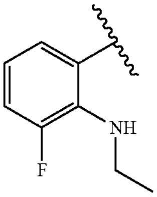,
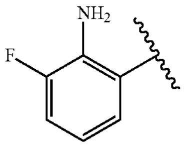, 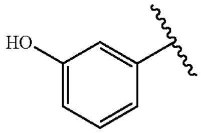,
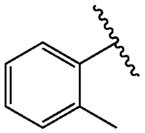, 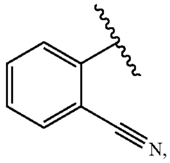, 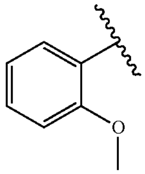,
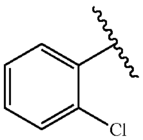, 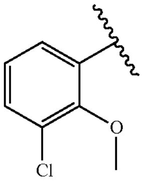, 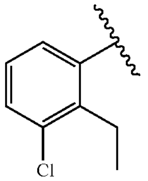,
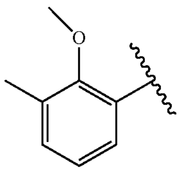, 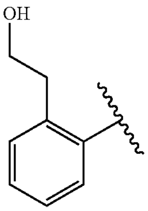, 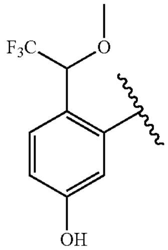,
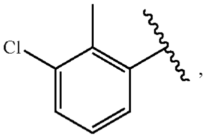, 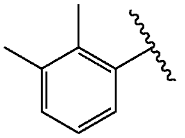,
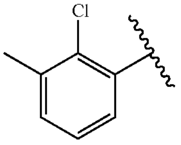, 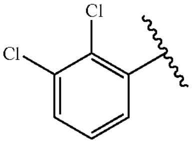,
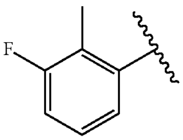, 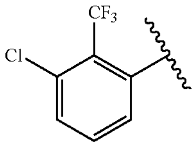,
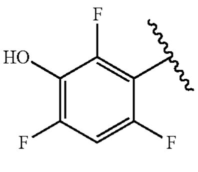, 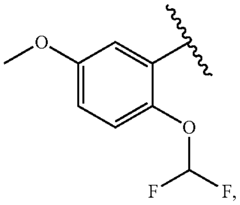
-continued
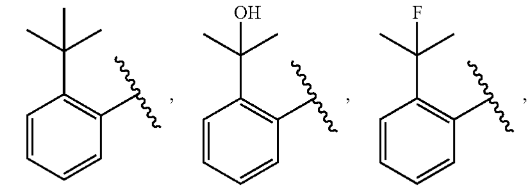
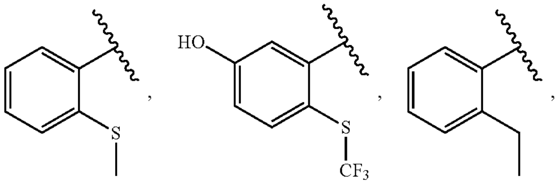
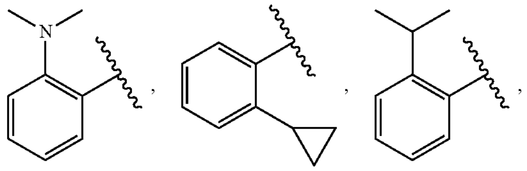
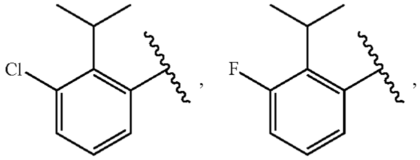
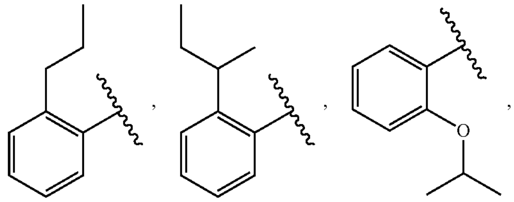
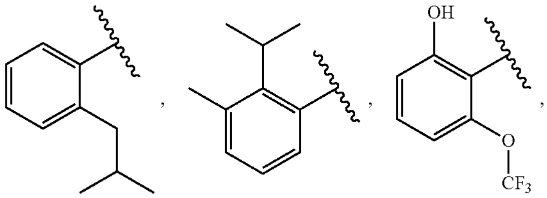
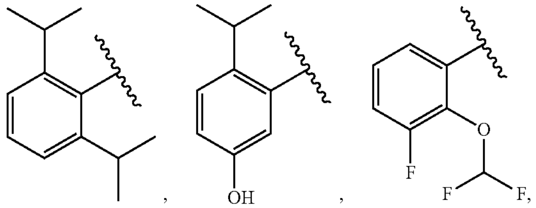
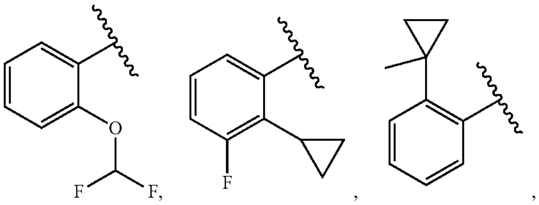
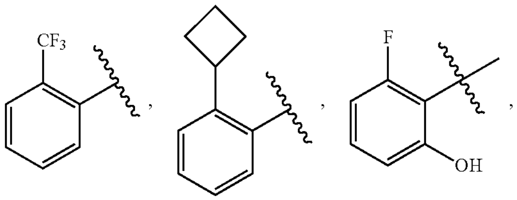

-continued
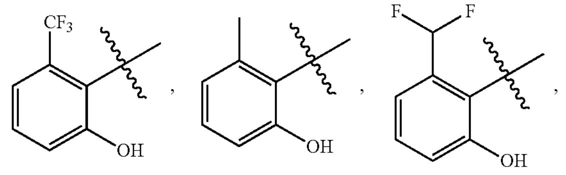
, , ,
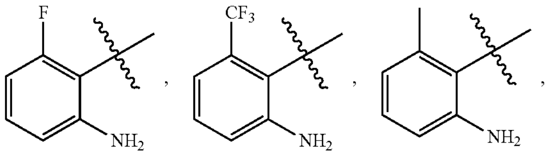
, , ,
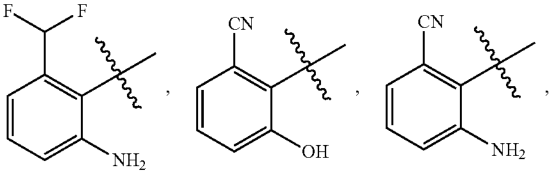
, , ,
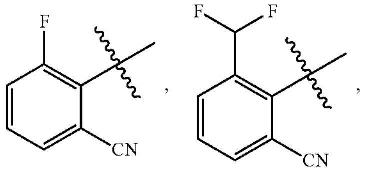
, ,
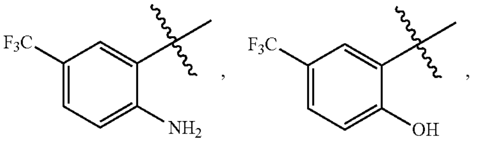
, ,
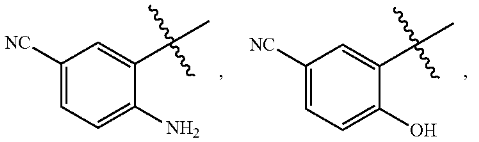
, ,
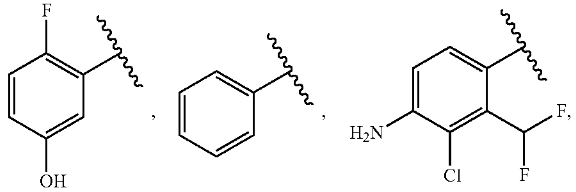
, ,
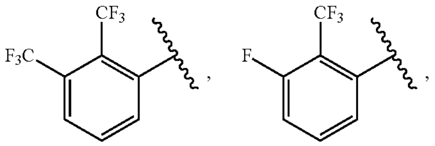
, ,
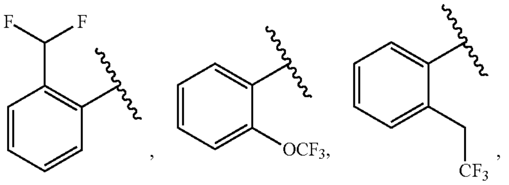
, ,
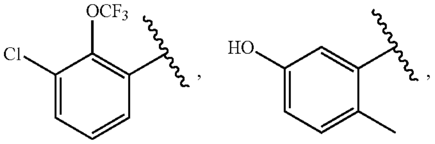
, ,
-continued
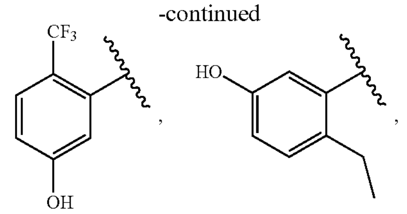
, ,
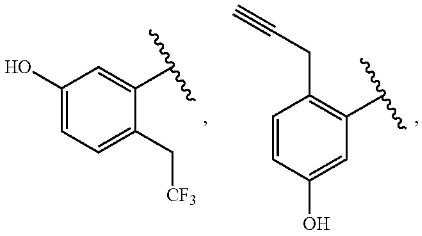
, ,
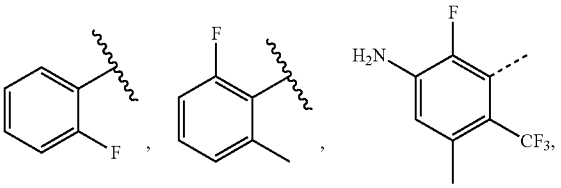
, ,
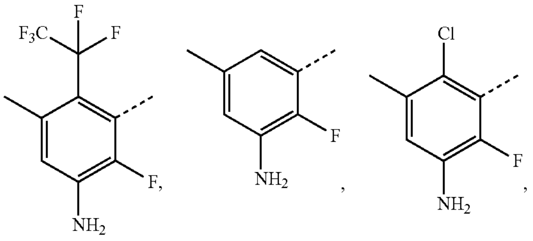
, ,
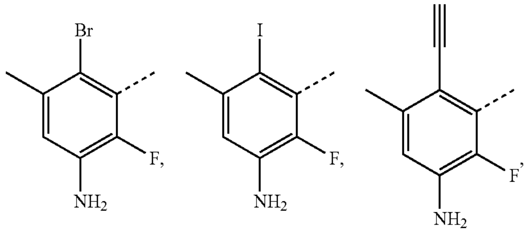
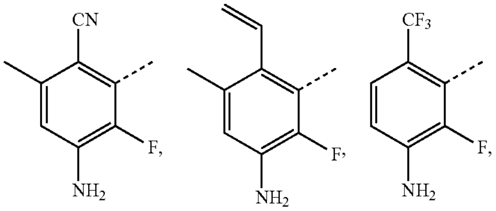
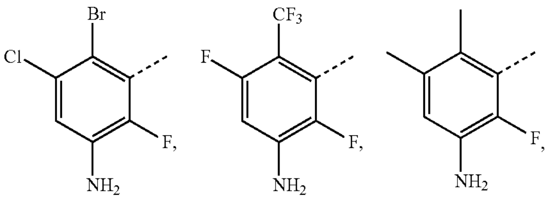
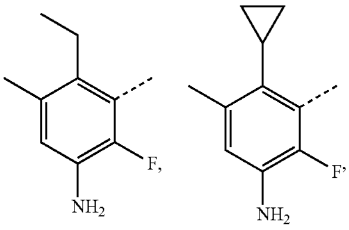
and -continued

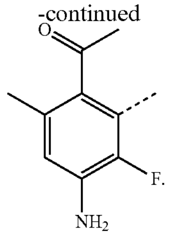

In some embodiments of Formula (VI), $R^7$ is

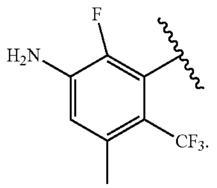 [SMILES: *c1c(F)c(N)cc(C)c1C(F)(F)F]

In some embodiments of Formula (VI), $R^7$ is

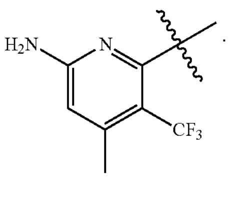 [SMILES: *c1nc(N)cc(C)c1C(F)(F)F]

In some embodiments of Formula (VI), $R^7$ is

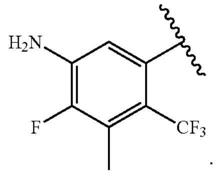 [SMILES: *c1cc(N)c(F)c(C)c1C(F)(F)F]

In some embodiments, for a compound of Formula (I), (III), (IV), (V), or (VI), $R^7$ is substituted with one, two, three, or four substituents independently selected from halogen, —CN, $C_{1-6}$ alkyl, $C_{2-6}$ alkenyl, $C_{2-6}$ alkynyl, $C_{3-6}$ cycloalkyl, —$OR^{22}$, —$SR^{22}$, and —N $(R^{22})(R^{23})$, wherein $C_{1-6}$ alkyl, $C_{2-6}$ alkenyl, $C_{2-6}$ alkynyl, and $C_{3-6}$ cycloalkyl are optionally substituted with one, two, or three substituents independently selected from halogen, $C_{1-6}$ alkyl, $C_{1-6}$ haloalkyl, and —$OR^{22}$. In some embodiments, $R^7$ is substituted with one, two, three, or four substituents independently selected from halogen, —CN, $C_{1-3}$ alkyl, $C_{1-3}$ haloalkyl, $C_{2-3}$ alkenyl, $C_{2-3}$ alkynyl, —$OR^{22}$, —$N(R^{22})(R^{23})$, and $C_{3-6}$ cycloalkyl. In some embodiments, $R^7$ is substituted with one, two, three, or four substituents independently selected from halogen, —CN, $C_{1-3}$ alkyl, $C_{2-3}$ alkenyl, $C_{2-3}$ alkynyl, —$OR^{22}$, and —$N(R^{22})(R^{23})$. In some embodiments, $R^7$ is substituted with one, two, three, or four substituents independently selected from halogen, —CN, —$CH_3$, —C≡CH, —OH, and —$NH_2$. In some embodiments, $R^7$ is substituted with —F, —CN, and —$NH_2$. In some embodiments, $R^7$ is substituted with —CN and —$NH_2$. In some embodiments, $R^7$ is substituted with —F, —C≡CH, and —OH. In some embodiments, $R^7$ is substituted with —$CF_3$, —$CH_3$, and —$NH_2$. In some embodiments, $R^7$ is substituted with —$CF_3$ and —$NH_2$. In some embodiments, $R^7$ is substituted with —$CF_3$, —$CH_3$, —F, and —$NH_2$. In some embodiments, $R^7$ is substituted with —$CF_3$, —F, and —$NH_2$. In some embodiments, $R^7$ is substituted with one, two, three, or four substituents independently selected from halogen, —CN, —$CH_3$, —$CH_2CH_3$, —CH—$CH_2$, —$CF_3$, —C≡CH, —OH, —$NH_2$, and -cyclopropyl. In some embodiments, $R^7$ is substituted with one, two, or three substituents independently selected from halogen, —CN, and —$N(R^{22})(R^{23})$. In some embodiments, $R^7$ is substituted with one, two, or three substituents independently selected from fluorine, chlorine, —CN, and —$NH_2$. In some embodiments, $R^7$ is substituted with fluorine, —CN, and —$NH_2$. In some embodiments, $R^7$ is substituted with one, two, three, or four substituents independently selected from halogen, —CN, $C_{1-6}$ alkyl, $C_{2-6}$ alkenyl, $C_{2-6}$ alkynyl, $C_{3-6}$ cycloalkyl, —$C(O)R^{22}$, —$OR^{22}$, —$SR^{22}$, and —$N(R^{22})(R^{23})$, wherein $C_{1-6}$ alkyl, $C_{2-6}$ alkenyl, $C_{2-6}$ alkynyl, and $C_{3-6}$ cycloalkyl are optionally substituted with one, two, or three substituents independently selected from halogen, $C_{1-6}$ alkyl, $C_{1-6}$ haloalkyl, and —$OR^{22}$. In some embodiments, $R^7$ is substituted with one, two, three, or four substituents independently selected from halogen, —$CH_2CH_3$, —C≡CH, —OH, and —$C(O)CH_3$. In some embodiments, $R^7$ is substituted with —F, —OH, and —$C(O)CH_3$. In some embodiments, $R^7$ is substituted with —F, —$CH_2CH_3$, and —OH.

In some embodiments, for a compound of Formula (I), (III), (IV), (V), or (VI), $R^7$ is substituted with halogen, —CN, and an additional substituent selected from —NHC(O)O—($C_{1-6}$ alkyl)-$OR^{15}$ and —NH($C_{1-6}$ alkyl)-$OR^{15}$, wherein $C_{1-6}$ alkyl is optionally substituted with one, two, or three $R^{20}$. In some embodiments, $R^7$ is substituted with halogen, —CN, and —NH($C_{1-6}$ alkyl)-$OR^{15}$. In some embodiments, $R^7$ is substituted with halogen, —CN, and an additional substituent selected from —$NHCH(R^{20})OC(O)R^{12}$ and —$NHCH_2OP(O)$(Y—$R^{16}$)(Z—$R^{17}$). In some embodiments, $R^7$ is substituted with halogen, —CN, and an additional substituent selected from —$NHCH(R^{20})OC(O)R^{12}$ and —$NHCH_2OP(O)$(Y—$R^{16}$)(Z—$R^{17}$); and $R^{12}$ is $C_{1-6}$ alkyl optionally substituted with one, two, or three $R^{20}$. In some embodiments, $R^7$ is substituted with halogen, —CN, and an additional substituent selected from —$NHCH(R^{20})OC(O)R^{12}$ and —$NHCH_2OP(O)$(Y—$R^{16}$)(Z—$R^{17}$); and $R^{12}$ is $C_{1-6}$ alkyl. In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)$(Y—$R^{16}$)(Z—$R^{17}$). In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)$(Y—$R^{16}$)(Z—$R^{17}$); and $R^{12}$ is $C_{1-6}$ alkyl optionally substituted with one, two, or three $R^{20}$. In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)$(Y—$R^{16}$)(Z—$R^{17}$); and $R^{12}$ is $C_{1-6}$ alkyl. In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)(OH)_2$. In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)(OH)_2$; and $R^{12}$ is $C_{1-6}$ alkyl optionally substituted with one, two, or three $R^{20}$. In some embodiments, $R^7$ is substituted with halogen, —CN, and an additional substituent selected from —$NHCH_2OC(O)R^{12}$, —$NHCH(CH_3)OC(O)R^{12}$, and —$NHCH_2OP(O)(OH)_2$; and $R^{12}$ is $C_{1-6}$ alkyl. In some embodiments, $R^7$ is substituted with halogen, —CN, and an additional substituent selected from —$NHCH_2OP(O)(OH)_2$, —$NHCH(CH_3)OP(O)(OH)_2$, —$NHCH_2OP(O)(OCH_2OC(O)OCH(CH_3)_2)_2$, —$NHCH_2OC(O)CH(NH_2)(CH(CH_3)_2)$, —$NHCH(CH_3)OC(O)CH(NH_2)(CH(CH_3)_2)$, and —$NHCH_2OC(O)CH(CH_3)_2$.

In some embodiments, for a compound of Formula (I), (III), (IV), or (V):

X is $C(R^6)$;

A is selected from pyridinyl, pyridazinyl, pyrimidinyl, and pyrazinyl;

$R^1$ is hydrogen;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, —$C_{3-8}$ carbocycle, 3- to 8-membered heterocycle, —$OR^{12}$, —$N(R^{12})(R^{13})$, —$C(O)OR^{12}$, —$N(R^{12})C(O)N(R^{12})(R^{13})$, —$C(O)R^{12}$, —$OC(O)R^{12}$, —$C(O)N(R^{12})(R^{13})$, and —$N(R^{12})C(O)R^{12}$, wherein $C_{1-6}$ alkyl, $C_{2-6}$ alkenyl, $C_{2-6}$ alkynyl, —$C_{3-8}$ carbocycle, and 3- to 8-membered heterocycle are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^7$ is benzo[b]thiophen-4-yl optionally substituted with one, two, three, or four $R^{20}$;

m is 0 or 1; and n is 1 or 2.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1; and $R^6$ and $R^8$ are independently selected from hydrogen and halogen.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1; and $R^6$ and $R^8$ are independently selected from hydrogen, halogen, and —$CF_3$.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ and $R^8$ are independently selected from hydrogen and halogen; and n is 1.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ and $R^8$ are independently selected from hydrogen, halogen, and —$CF_3$; and n is 1.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is chlorine; and $R^8$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is —$CF_3$; and $R^8$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is chlorine;

$R^1$ is fluorine; and n is 1.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is —$CF_3$;

$R^8$ is fluorine; and n is 1.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is

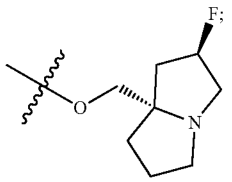 [SMILES: *OC[C@@]12CCCN1C[C@H](F)C2]

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is chlorine; and $R^8$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from

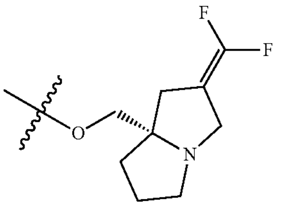

and

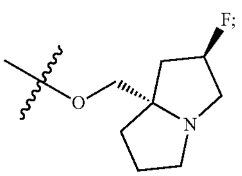

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$; and $R^1$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is

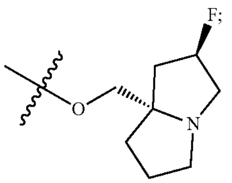 [SMILES: *OC[C@@]12CCCN1C[C@H](F)C2]

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is chlorine;

$R^8$ is fluorine; and n is 1.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from

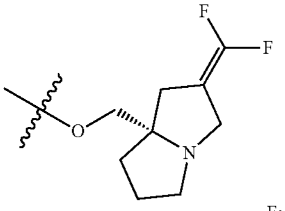

and

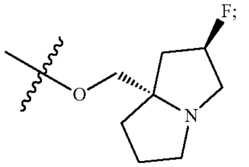

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$;

$R^8$ is fluorine; and n is 1.

In some embodiments, for a compound of Formula (I), (III), (IV), or (V):

X is $C(R^6)$;

A is selected from pyridinyl, pyridazinyl, pyrimidinyl, and pyrazinyl;

$R^1$ is hydrogen;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, —$C_{3-8}$ carbocycle, 3- to 8-membered heterocycle, —$OR^{12}$, —$N(R^{12})(R^{13})$, —$C(O)OR^{12}$, —$N(R^{12})C(O)N(R^{12})(R^{13})$, —$C(O)R^{12}$, —$OC(O)R^{12}$, —$C(O)N(R^{12})(R^{13})$, and —$N(R^{12})C(O)R^{12}$, wherein $C_{1-6}$ alkyl, $C_{2-6}$ alkenyl, $C_{2-6}$ alkynyl, —$C_{3-8}$ carbocycle, and 3- to 8-membered heterocycle are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.

$R^4$ is $C_{1-3}$ alkyl optionally substituted with one, two, or three halogen (e.g., —F); or $R^4$ and $R^5$, together with the atoms to which they are attached, form $C_{4-8}$ carbocycle or 4- to 8-membered heterocycle, each of which is optionally substituted with one, two, or three $R^{20}$;

$R^7$ is benzo[b]thiophen-4-yl optionally substituted with one, two, three, or four $R^{20}$;

m is 0 or 1; and n is 1 or 2.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is selected from

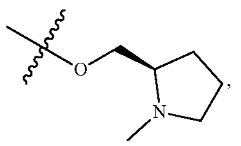

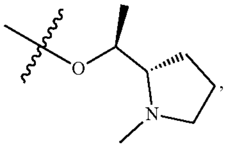

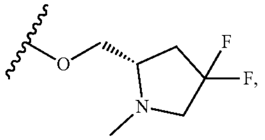

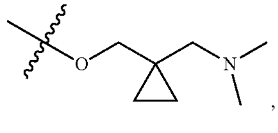

, and

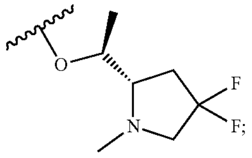

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$; and $R^8$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is

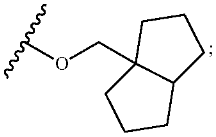 [SMILES: *OCC12CCCC1CCC2];

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$; and $R^8$ is fluorine.

In some embodiments, for a compound of Formula (I), (II), (II-a), (III), (IV), (V), or (VI):

A is selected from pyridinyl, pyridazinyl, pyrimidinyl, and pyrazinyl;

$R^1$ is hydrogen;

$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;

$R^2$ is

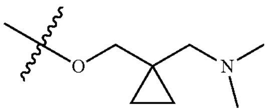;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$; and $R^8$ is fluorine.

In some embodiments, for a compound of Formula (III):

A is selected from pyridinyl, pyridazinyl, pyrimidinyl, and pyrazinyl;

$R^1$ is hydrogen;

$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, —$C_{3-8}$ carbocycle, 3- to 8-membered heterocycle, —$OR^{12}$, —$N(R^{12})(R^{13})$, —$C(O)OR^{12}$, —$N(R^{12})C(O)N(R^{12})(R^{13})$, —$C(O)R^{12}$, —$OC(O)R^{12}$, —$C(O)N(R^{12})(R^{13})$, and —$N(R^{12})C(O)R^{12}$, wherein $C_{1-6}$ alkyl, $C_{2-6}$ alkenyl, $C_{2-6}$ alkynyl, —$C_{3-8}$ carbocycle, and 3- to 8-membered heterocycle are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.

$R^{4a}$ is hydrogen;

$R^7$ is benzo[b]thiophen-4-yl optionally substituted with one, two, three, or four $R^{20}$;

m is 0 or 1; and n is 1 or 2.

In some embodiments, for a compound of Formula (III):

A is selected from pyridinyl, pyridazinyl, pyrimidinyl, and pyrazinyl;

$R^1$ is hydrogen;

$R^{4a}$ is hydrogen;

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from hydrogen, $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1; and $R^6$ and $R^8$ are independently selected from hydrogen, halogen, and —$CF_3$.

In some embodiments, for a compound of Formula (III):

A is selected from pyridinyl, pyridazinyl, pyrimidinyl, and pyrazinyl;

$R^1$ is hydrogen;

$R^{4a}$ is hydrogen;

$R^2$ is

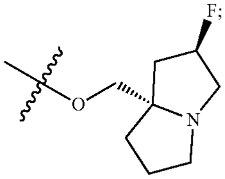 [SMILES: *OC[C@@]12CCCN1C[C@H](F)C2];

$R^3$ is independently selected at each occurrence from hydrogen, $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is chlorine; and $R^1$ is fluorine.

In some embodiments, for a compound of Formula (III):

A is selected from pyridinyl, pyridazinyl, pyrimidinyl, and pyrazinyl;

$R^1$ is hydrogen;
$R^{4a}$ is hydrogen;
$R^2$ is selected from and

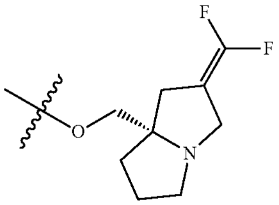

and

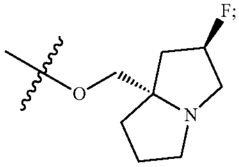

$R^3$ is independently selected at each occurrence from hydrogen, $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;
m is 0 or 1;
$R^6$ is selected from chlorine and —$CF_3$; and
$R^8$ is fluorine.

In some embodiments, for a compound of Formula (I), (III), (IV), or (V):
A is selected from pyridinyl, pyridazinyl, pyrimidinyl, and pyrazinyl;
$R^1$ is hydrogen;
$R^2$, $R^3$, $R^5$, $R^6$, and $R^8$ are each independently selected at each occurrence from hydrogen, halogen, —CN, $C_{1-6}$ alkyl, $C_{2-6}$ alkenyl, $C_{2-6}$ alkynyl, —$C_{3-8}$ carbocycle, 3- to 8-membered heterocycle, —$OR^{12}$, —$N(R^{12})(R^{13})$, —$C(O)OR^{12}$, —$N(R^{12})C(O)N(R^{12})(R^{13})$, —$C(O)R^{12}$, —$OC(O)R^{12}$, —$C(O)N(R^{12})(R^{13})$, and —$N(R^{12})C(O)R^{12}$, wherein $C_{1-6}$ alkyl, $C_{2-6}$ alkenyl, $C_{2-6}$ alkynyl, —$C_{3-8}$ carbocycle, and 3- to 8-membered heterocycle are optionally substituted with one, two, or three $R^{20}$;
wherein two $R^3$, together with the atom or atoms to which they are attached, form $C_{3-8}$ carbocycle or 3- to 8-membered heterocycle, each of which is optionally substituted with one, two, or three $R^{20}$; and further wherein two $R^3$ are optionally taken together to form =O, =$NR^{12}$, or =$C(R^{14})$.
$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;
$R^7$ is selected from benzo[b]thiophen-4-yl and naphthalenyl, wherein each is optionally substituted with one, two, three, or four $R^{20}$;
m is 0 or 1; and
n is 1 or 2.

In some embodiments, for a compound of Formula (I), (II), (II-a), (III), (IV), (V), or (VI):
A is selected from pyridinyl, pyridazinyl, pyrimidinyl, and pyrazinyl;
$R^1$ is hydrogen;
$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;
$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;
$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;
two $R^3$, together with the atoms to which they are attached, form 4- to 8-membered heterocycle, which is optionally substituted with one, two, or three $R^{20}$;
m is 0 or 1; and
$R^6$ and $R^8$ are independently selected from hydrogen, halogen, and —$CF_3$.

In some embodiments, for a compound of Formula (I), (II), (II-a), (III), (IV), (V), or (VI):
A is selected from pyridinyl, pyridazinyl, pyrimidinyl, and pyrazinyl;
$R^1$ is hydrogen;
$R^4$ is $C_{1-3}$ alkyl optionally substituted with one, two, or three $R^{20}$; or $R^4$ and $R^5$, together with the atoms to which they are attached, form $C_{4-8}$ carbocycle or 4- to 8-membered heterocycle, each of which is optionally substituted with one, two, or three $R^{20}$;
$R^2$ is selected from

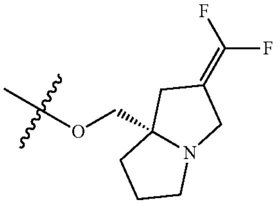

and

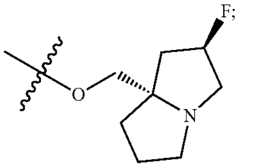

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;
two $R^3$ bonded to adjacent atoms, together with the atoms to which they are attached, form 5-membered heterocycle, which is optionally substituted with one, two, or three $R^{20}$;
m is 0 or 1;
$R^6$ is selected from chlorine and —$CF_3$; and
$R^8$ is fluorine.

In some embodiments, for a compound of Formula (V):
A is selected from pyridinyl and pyrimidinyl;
i) X is N and $R^7$ is selected from

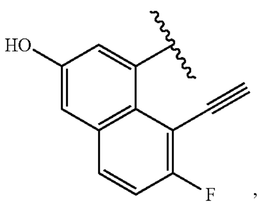

,

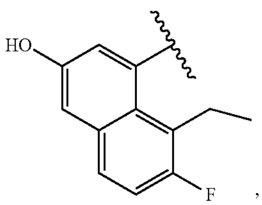

,

-continued

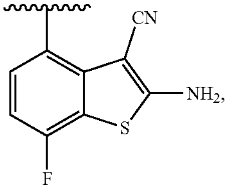

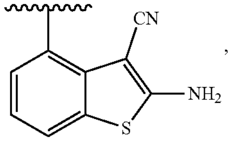

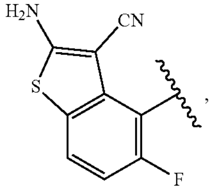

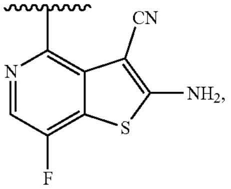

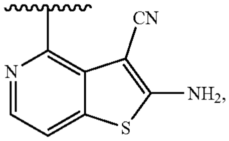

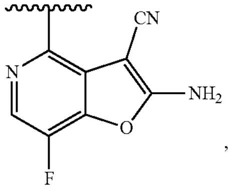

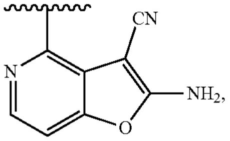

and

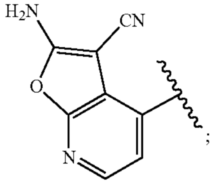

or i)) X is C($R^6$) and $R^7$ is selected from

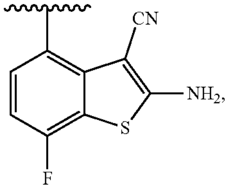

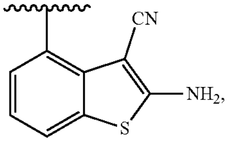

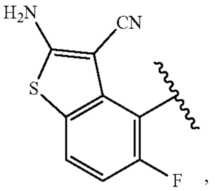

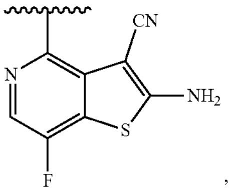

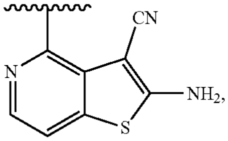

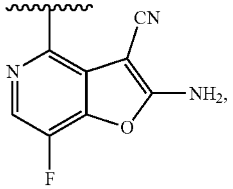

-continued

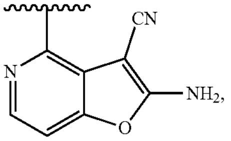

and

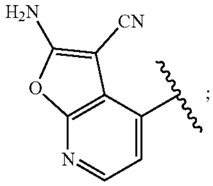

$R^1$ is hydrogen;

$R^2$ is selected from —O($C_{1-4}$ alkyl), —S($C_{1-4}$ alkyl),

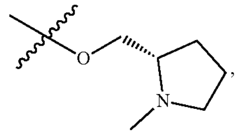

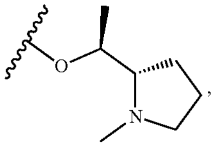

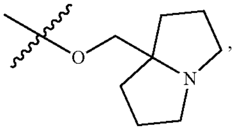

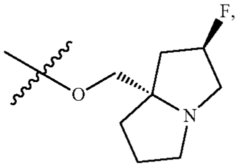

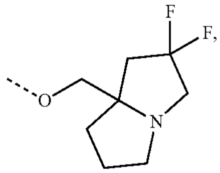

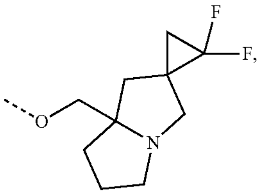

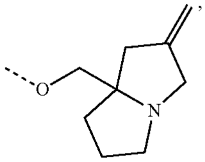

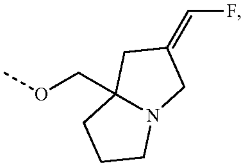

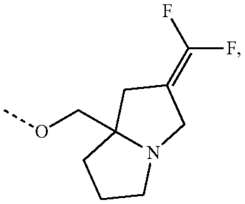

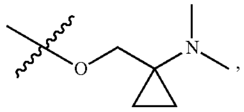

and

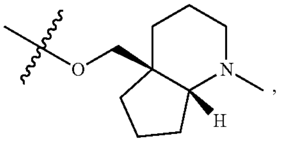

wherein $C_{1-4}$ alkyl is optionally substituted with one, two, or three $R^{20}$;

$R^3$ is independently selected at each occurrence from $C_{1-4}$ alkyl, $C_{2-4}$ alkenyl, $C_{2-4}$ alkynyl, $C_{3-5}$ carbocycle, and 3- to 5-membered heterocycle, each of which is optionally substituted with one, two, or three substituents independently selected from halogen, —CN, —OH, and —$OCH_3$;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three $R^{20}$;

m is 0 or 1;

n is 1;

$R^5$ is hydrogen;

$R^6$ is selected from halogen, —O($C_{1-4}$ alkyl), $C_{1-4}$ alkyl, $C_{2-4}$ alkenyl, $C_{2-4}$ alkynyl, $C_{3-4}$ carbocycle, and —$SF_5$, wherein $C_1$0.4 alkyl, $C_{2-4}$ alkenyl, $C_{2-4}$ alkynyl, and $C_{3-4}$ carbocycle are optionally substituted with one, two, or three $R^{20}$; and $R^8$ is fluorine.

In some embodiments, for a compound of Formula (I), (III), (IV), or (V):

A is selected from pyridinyl and pyrimidinyl;

$R^7$ is selected from

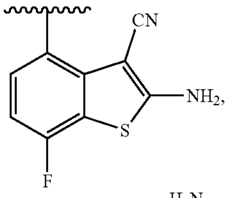

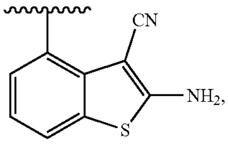

and

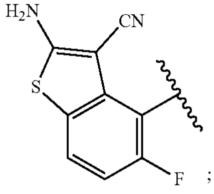

;

$R^1$ is hydrogen;

$R^2$ is selected from —O($C_{1-4}$ alkyl), —S($C_{1-4}$ alkyl)

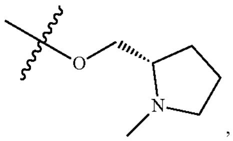

,

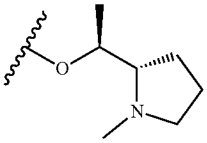

,

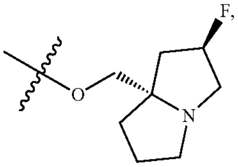

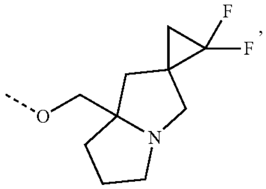

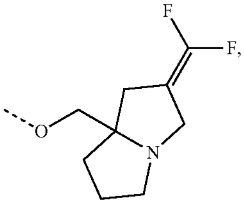

and

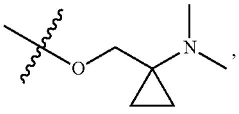

, wherein $C_{1-4}$ alkyl is optionally substituted with one, two, or three $R^{20}$;

$R^3$ is independently selected at each occurrence from $C_{1-4}$ alkyl, $C_{2-4}$ alkenyl, and $C_{2-4}$ alkynyl, each of which is optionally substituted with one, two, or three —F;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three —F;

m is 0 or 1;

n is 1;

$R^5$ is hydrogen;

$R^6$ is selected from —Cl, —Br, —$OCF_3$, —$CF_3$, —CH═$CH_2$, and —$SF_5$; and $R^8$ is fluorine.

In some embodiments, for Formula (I), (III), (IV), or (V):

A is selected from pyridinyl and pyrimidinyl;

$R^1$ is hydrogen;

$R^2$ is selected from —O($C_{1-4}$ alkyl), —S($C_{1-4}$ alkyl),

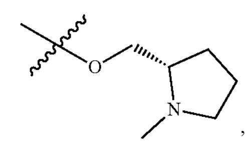

,

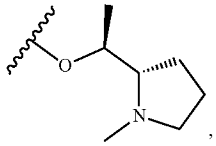

,

,

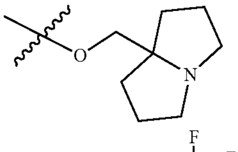

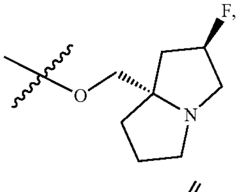

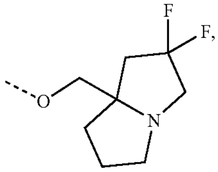

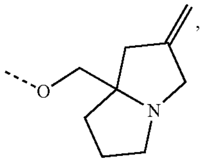

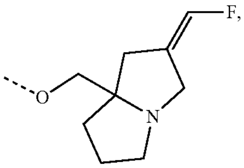

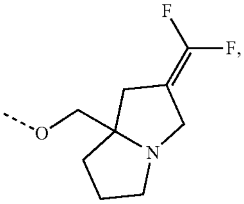

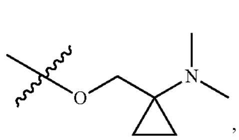

, and

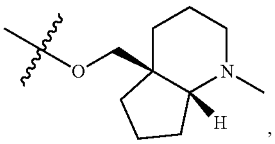

, wherein $C_{1-4}$ alkyl is optionally substituted with one, two, or three $R^{20}$;

$R^3$ is independently selected at each occurrence from $C_{1-4}$ alkyl, $C_{2-4}$ alkenyl, $C_{2-4}$ alkynyl, $C_{3-5}$ carbocycle, and 3- to 5-membered heterocycle, each of which is optionally substituted with one, two, or three substituents independently selected from halogen, —CN, —OH, and —$OCH_3$;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three $R^{20}$;

m is 0 or 1;

n is 1;

$R^5$ is hydrogen;

$R^6$ is selected from halogen, —O($C_{1-4}$ alkyl), $C_{1-4}$ alkyl, $C_{2-4}$ alkenyl, $C_{2-4}$ alkynyl, and $C_{3-4}$ carbocycle, wherein $C_{1-4}$ alkyl, $C_{2-4}$ alkenyl, $C_{2-4}$ alkynyl, and $C_{3-4}$ carbocycle are optionally substituted with one, two, or three $R^{20}$;

$R^7$ is selected from

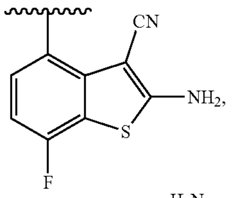

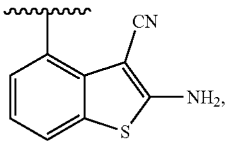

and

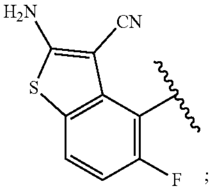

;

and $R^8$ is fluorine.

In some embodiments, for Formula (I), (III), (IV), or (V):

A is selected from pyridinyl and pyrimidinyl;

$R^1$ is hydrogen;

$R^2$ is selected from —$OCH_3$, —$SCH_3$,

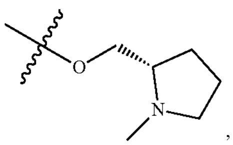

,

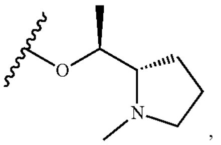

,

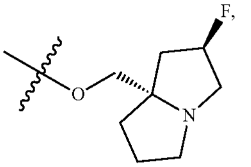

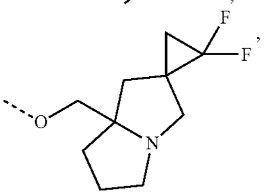

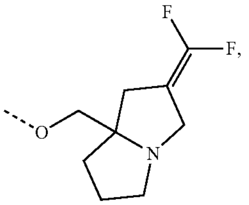

and

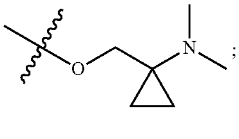

;

$R^3$ is independently selected at each occurrence from $C_{1-4}$ alkyl, $C_{2-4}$ alkenyl, and $C_{2-4}$ alkynyl, each of which is optionally substituted with one, two, or three-F;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three-F;

m is 0 or 1;

n is 1;

$R^5$ is hydrogen;

$R^6$ is selected from —Cl, —Br, —$OCF_3$, —$CF_3$, and $C_2$ alkenyl;

$R^7$ is selected from

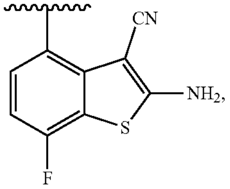

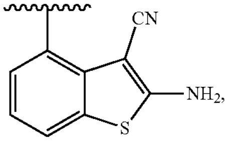

and

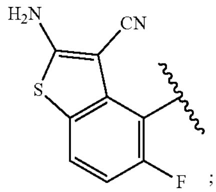

;

and $R^8$ is fluorine.

In some embodiments, for a compound of Formula (V):

A is selected from pyridinyl and pyrimidinyl;

i) X is N and $R^7$ is selected from

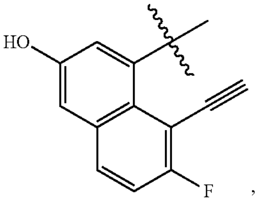

,

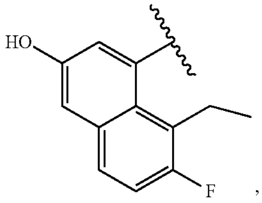

,

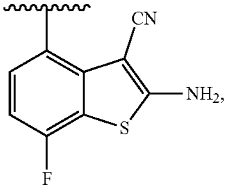

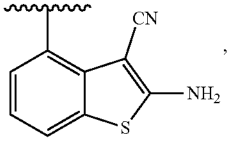

,

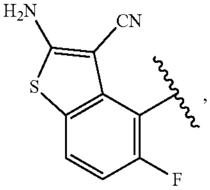

,

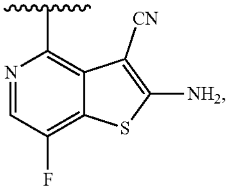

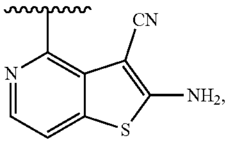

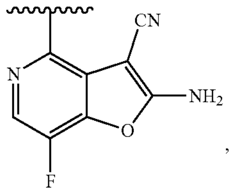

,

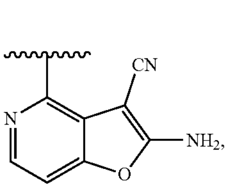

and

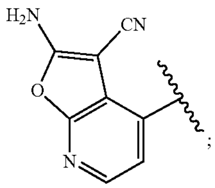

;

or
ii) X is C(R) and $R^7$ is selected from
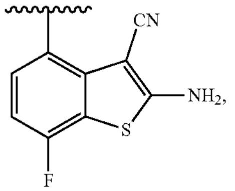
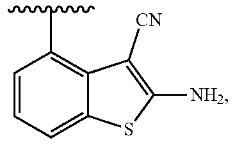
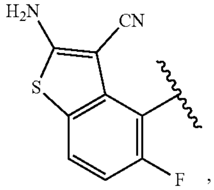
,
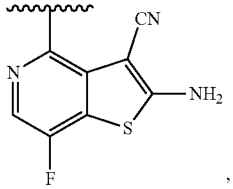
,
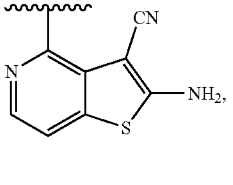
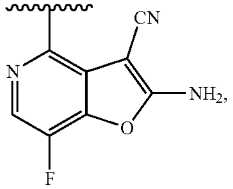
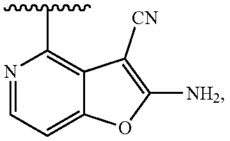
and
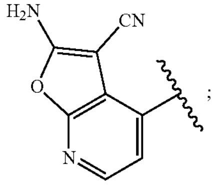
;
$R^1$ is hydrogen;
$R^2$ is selected from —O($C_{1-4}$ alkyl), —S($C_{1-4}$ alkyl),
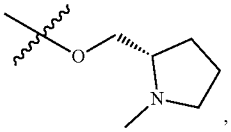
,
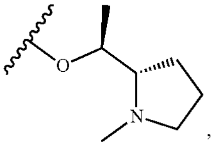
,
,
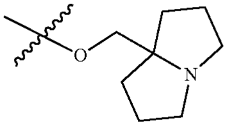
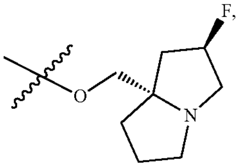
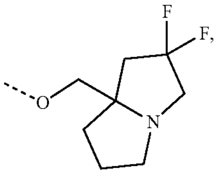
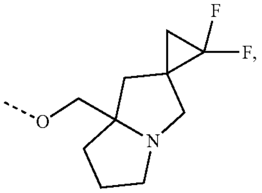
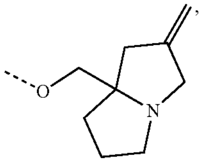
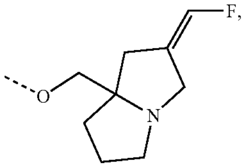
-continued
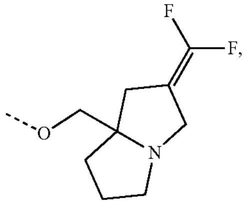
,
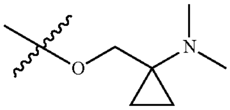
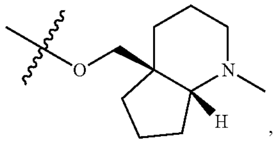
,
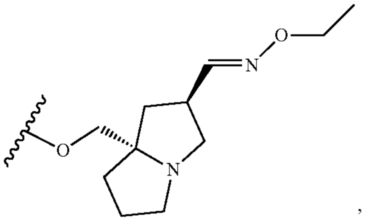
,
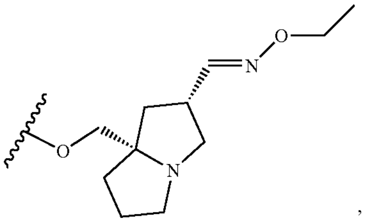
,
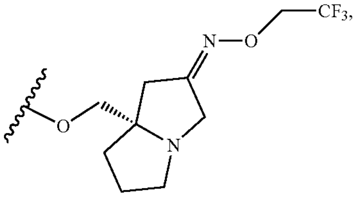
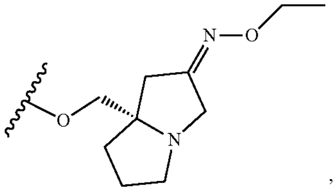
,
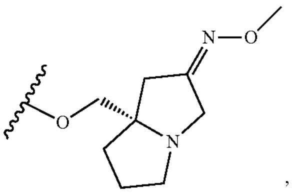
,
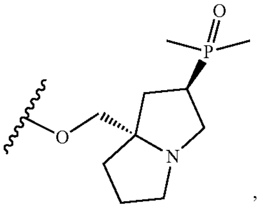
,
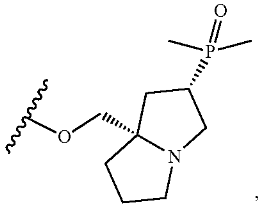
,
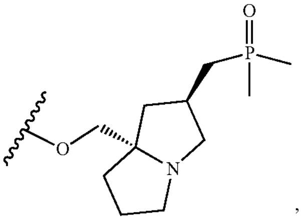
, -continued
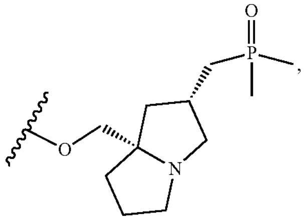,
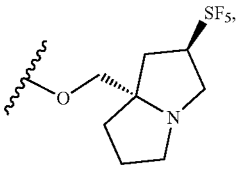,
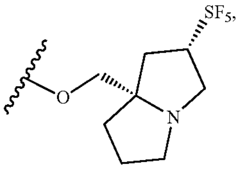,
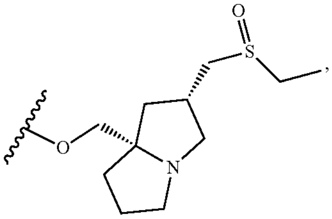,
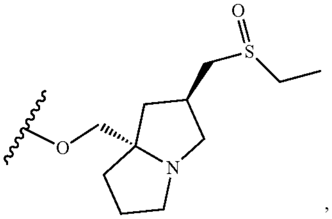,
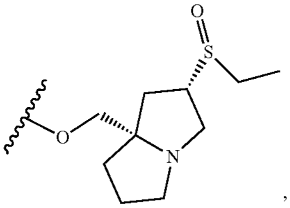,
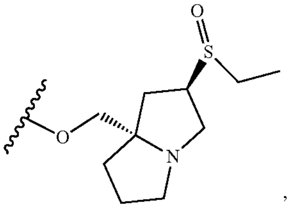,
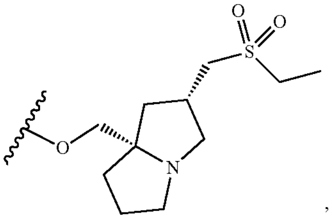,
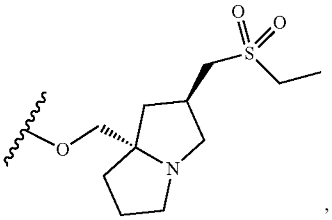,
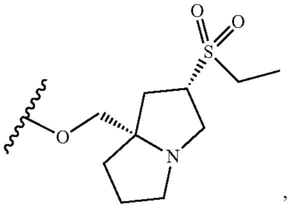,
-continued
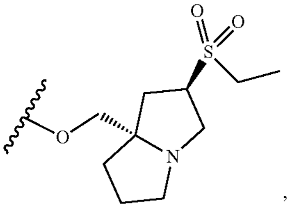,
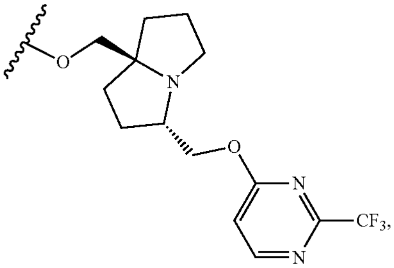,
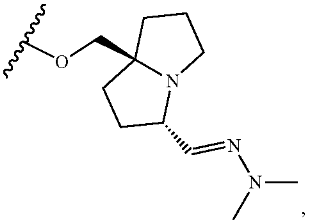,
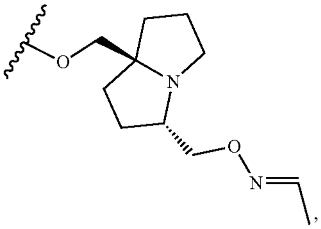,
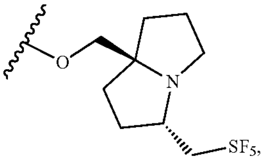,
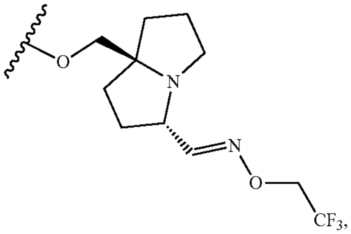,
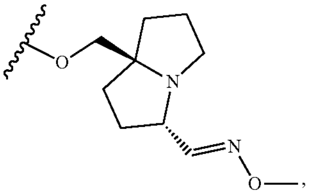,
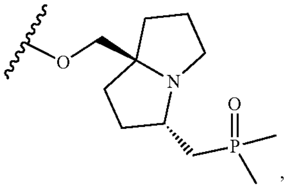, -continued

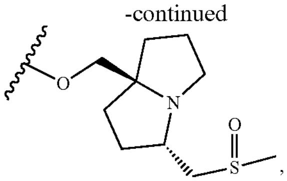

, and

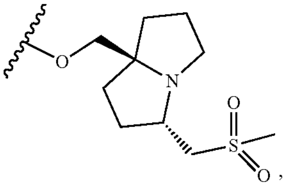

, wherein $C_{1-4}$ alkyl is optionally substituted with one, two, or three $R^{20}$;

$R^3$ is independently selected at each occurrence from $C_{1-4}$ alkyl, $C_{2-4}$ alkenyl, $C_{2-4}$ alkynyl, Cas carbocycle, and 3- to 5-membered heterocycle, each of which is optionally substituted with one, two, or three substituents independently selected from halogen, —CN, —OH, and —$OCH_3$;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three $R^{20}$;

m is 0 or 1;

n is 1;

$R^5$ is hydrogen;

$R^6$ is selected from halogen, —O($C_{1-4}$ alkyl), $C_{1-4}$ alkyl, $C_{2-4}$ alkenyl, $C_{2-4}$ alkynyl, $C_{3-4}$ carbocycle, and -SFs, wherein $C_{1-4}$ alkyl, $C_{2-4}$ alkenyl, $C_{2-4}$ alkynyl, and $C_{3-4}$ carbocycle are optionally substituted with one, two, or three $R^{20}$; and $R^8$ is fluorine.

In some embodiments, for a compound of Formula (I), (III), (IV), or (V):

A is selected from pyridinyl and pyrimidinyl;

$R^7$ is selected from

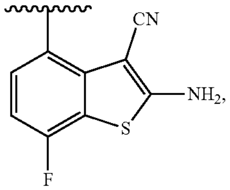

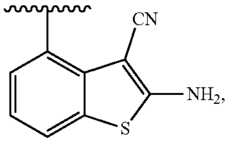

and

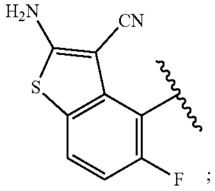

;

$R^1$ is hydrogen;

$R^2$ is selected from —O($C_{1-4}$ alkyl), —S($C_{1-4}$ alkyl),

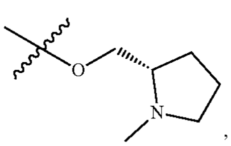

,

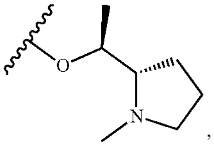

,

-continued

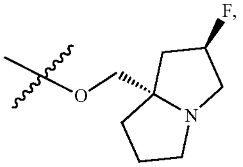

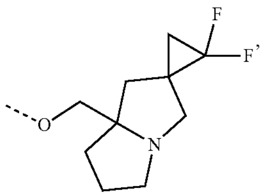

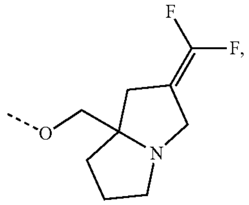

,

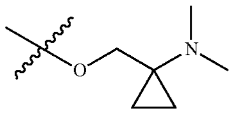

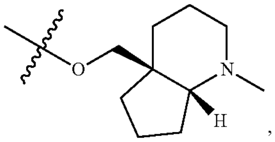

,

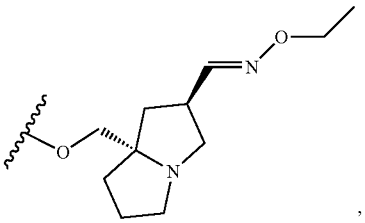

,

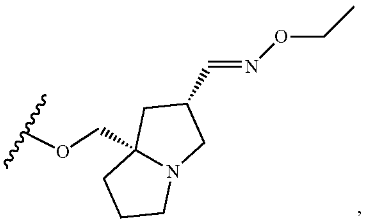

,

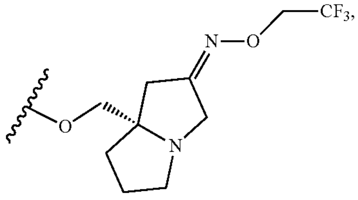

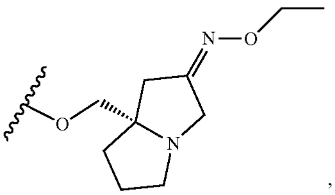

,

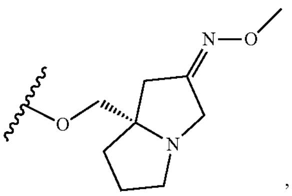

,

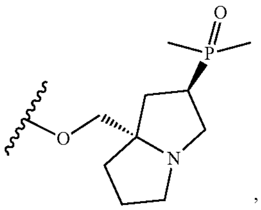

,

-continued
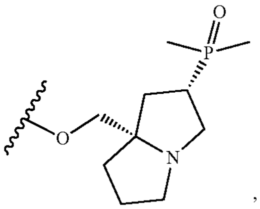
,
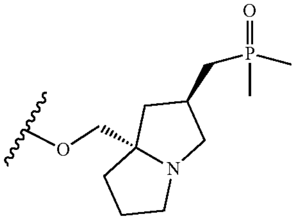
,
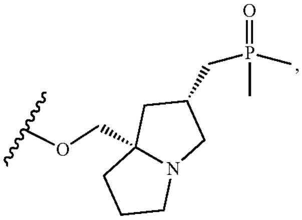
,
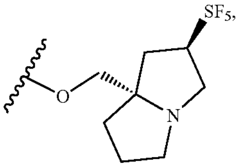
,
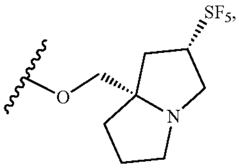
,
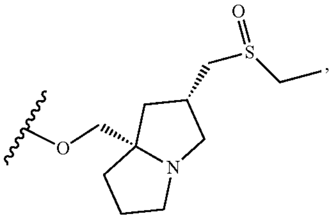
,
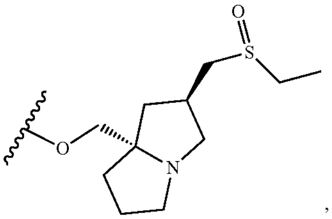
,
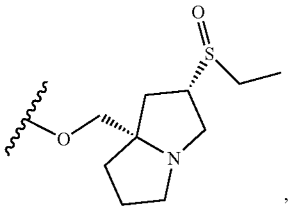
,
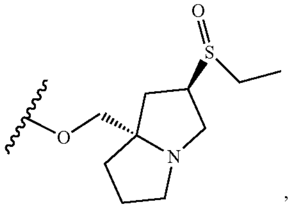
,
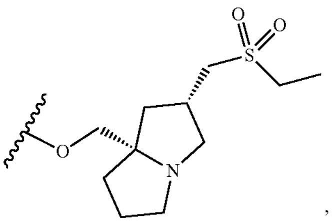
,
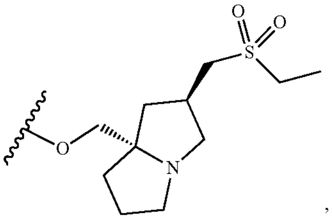
,
-continued
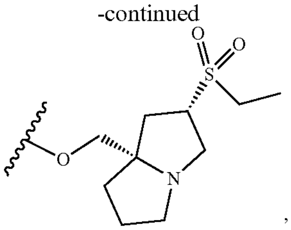
,
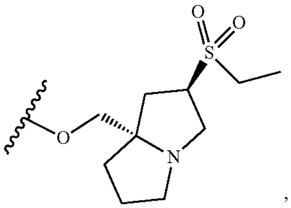
,
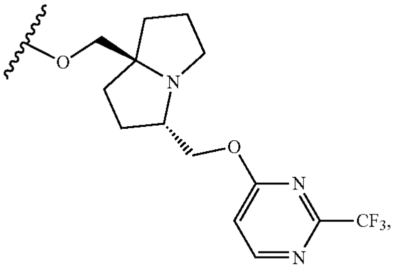
,
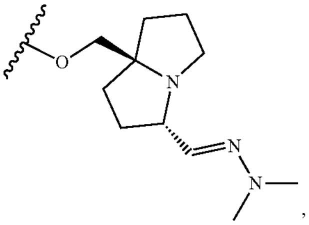
,
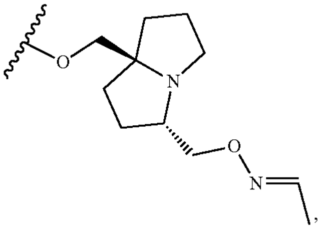
,
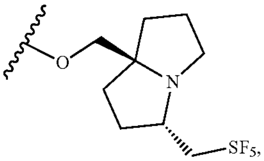
,
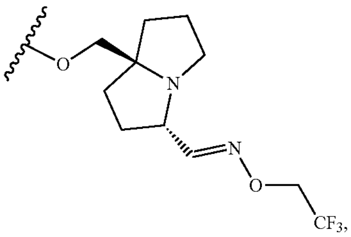
,
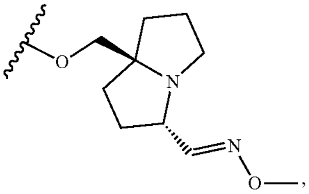
, -continued

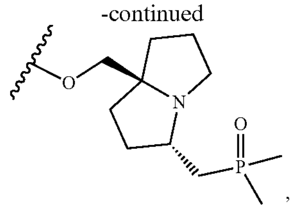

,

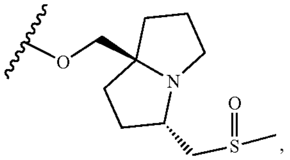

, and

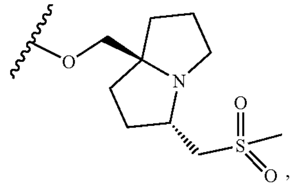

, wherein $C_{1-4}$ alkyl is optionally substituted with one, two, or three $R^{20}$;

$R^3$ is independently selected at each occurrence from $C_{1-4}$ alkyl, $C_{2-4}$ alkenyl, and $C_{2-4}$ alkynyl, each of which is optionally substituted with one, two, or three-F;

$R^4$ is selected from $C_{1-4}$ alkyl, $C_{2-4}$ alkenyl, and $C_{2-4}$ alkynyl, wherein $C_{1-4}$ alkyl, $C_{2-4}$ alkenyl, and $C_{2-4}$ alkynyl are optionally substituted with one, two, or three substituents independently selected from —$SF_5$, =N—$OR^{22}$, =N—$N(R^{22})(R^{23})$, —$P(O)(R^{22})(R^{23})$, —ON=$R^{22}$, and —F;

m is 0 or 1;

n is 1;

$R^5$ is hydrogen;

$R^6$ is selected from —Cl, —Br, —$OCF_3$, —$CF_3$, $C_2$ alkenyl, and —$SF_5$;

$R^8$ is fluorine; and $R^{22}$ and $R^{23}$ are independently selected from $C_{1-4}$ alkyl and $C_{1-4}$ haloalkyl.

In some embodiments, for a compound of Formula (I), (II), (III), (IV), (V), or (VI), the compound, or a pharmaceutically acceptable salt or solvate thereof, has the formula:

(VIII)

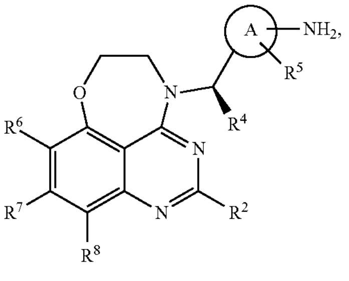

wherein:

Ring A is 6-membered heteroaryl comprising one or two ring nitrogen atoms;

$R^2$ is selected from —O—$CH_2$-(8- to 10-membered saturated heterocycle) and —O—$CH_2$-(cyclopropylene)-$CH_2$-(5- to 8-membered saturated heterocycle); wherein-O—$CH_2$-(8- to 10-membered saturated heterocycle) and —O—$CH_2$-(cyclopropylene)-$CH_2$-(5- to 8-membered saturated heterocycle) are optionally substituted with one or more substituents independently selected from —F, —$CF_2$, =$CH_2$, and =CHF;

$R^4$ is selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle); wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen, $R^5$ is selected from hydrogen and halogen;

$R^6$ is selected from halogen and —$CF_3$;

$R^7$ is benzothiophenyl optionally substituted with one or more substituents independently selected from —$NH_2$, —CN, and —F; and $R^8$ is halogen.

In embodiments of a compound of Formula (VIII), $R^6$ is —$CF_3$. In embodiments of a compound of Formula (VIII), $R^5$ is halogen. In embodiments of a compound of Formula (VIII), $R^8$ is —F. In some embodiments, the substituents (for example, $R^2$, $R^4$, $R^5$, $R^6$, $R^7$, and $R^8$) of formula (VIII) are the same as the corresponding substituents in Formula (I), (II), (III), (IV), (V), (VI), and/or (VII), including in embodiments thereof. In embodiments, a compound of Formula (VIII) is a compound of Formula (I), (II), (III), (IV), (V), (VI), and/or (VII).

In some embodiments, for a compound of Formula (I), (II), (III), (IV), (V), or (VI), the compound, or a pharmaceutically acceptable salt or solvate thereof, has the formula:

(IX)

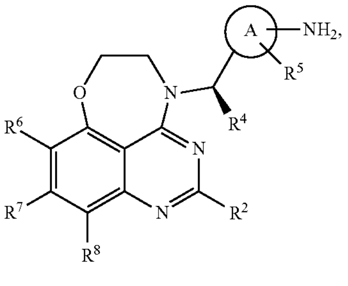

wherein:

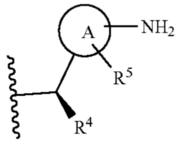

is selected from

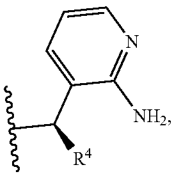

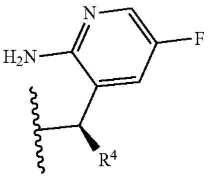

,

-continued

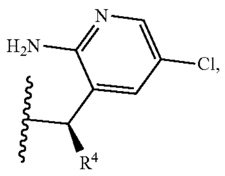

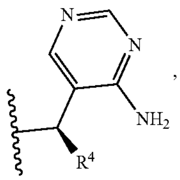

, and

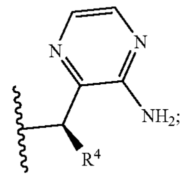

$R^2$ is selected from —O—$CH_2$-(8- to 10-membered saturated heterocycle) and —O—$CH_2$-(cyclopropylene)-$CH_2$-(5- to 8-membered saturated heterocycle); wherein-O—$CH_2$-(8- to 10-membered saturated heterocycle) and —O—$CH_2$-(cyclopropylene)-$CH_2$-(5- to 8-membered saturated heterocycle) are optionally substituted with one or more substituents independently selected from —F, —$CF_2$, ═$CH_2$, and ═CHF;

$R^4$ is selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle); wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more-F, $R^6$ is selected from —Cl and —$CF_3$;

$R^7$ is benzothiophenyl optionally substituted with one or more substituents independently selected from —$NH_2$, —CN, and —F; and $R^8$ is —F.

In embodiments of a compound of Formula (IX), $R^6$ is —$CF_3$. In some embodiments, the substituents (for example, $R^2$, $R^4$, $R^5$, $R^6$, $R^7$, and $R^8$) of formula (IX) are the same as the corresponding substituents in Formula (I), (II), (III), (IV), (V), (VI), and/or (VII) including in embodiments thereof. In embodiments, a compound of Formula (IX) is a compound of Formula (I), (II), (III), (IV), (V), (VI), and/or (VII).

In some embodiments, for a compound of Formula (I), (II), (III), (IV), (V), or (VI), the compound, or a pharmaceutically acceptable salt or solvate thereof, has the formula:

(X)

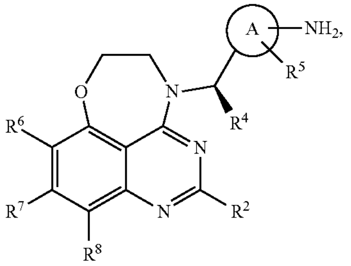

wherein:

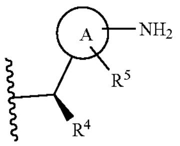

is selected from

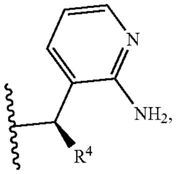

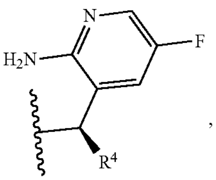

,

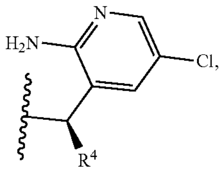

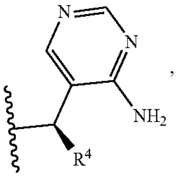

, and

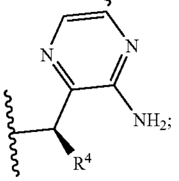

$R^2$ is selected from

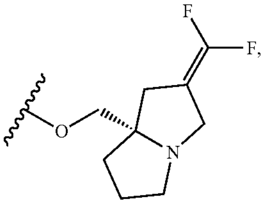

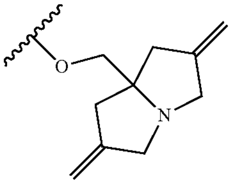

,

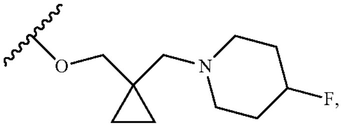

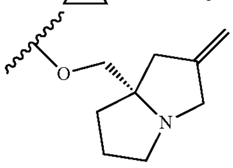

,

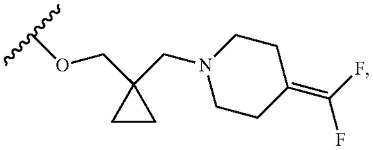

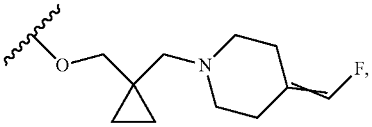

-continued

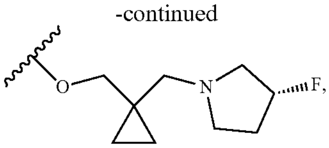

,

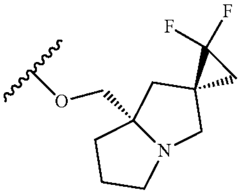

,

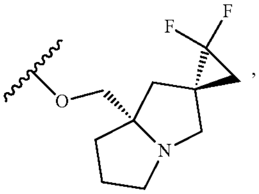

,

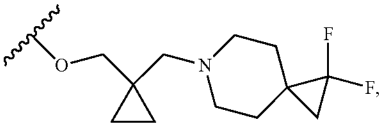

, and

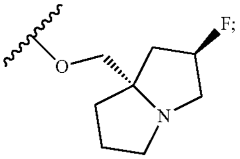

;

$R^4$ is selected from

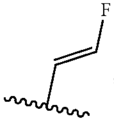

,

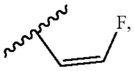

,

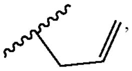

,

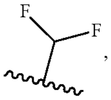

,

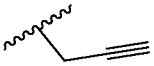

,

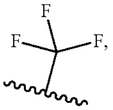

,

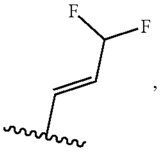

,

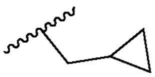

,

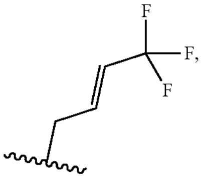

,

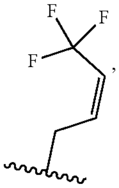

,

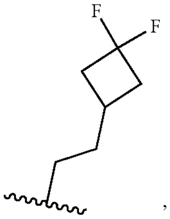

,

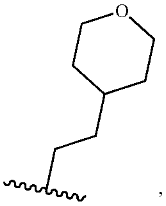

,

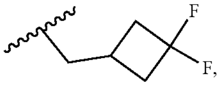

,

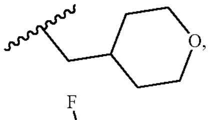

,

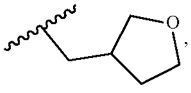

,

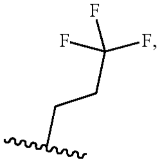

,

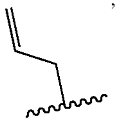

,

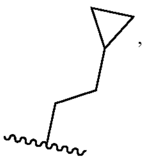

,

—$CH_2CH_3$, and —$CH_3$;

$R^6$ is selected from —Cl and —$CF_3$;

$R^7$ is selected from

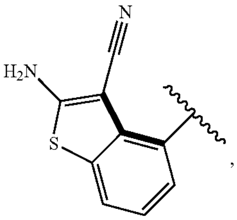

,

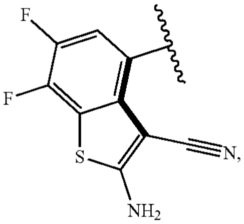

, and

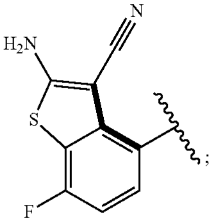

;

and $R^8$ is —F.

In embodiments of a compound of Formula (X), $R^6$ is —$CF_3$. In some embodiments, the substituents (for example, $R^2$, $R^4$, $R^5$, $R^6$, $R^7$, and $R^8$) of formula (X) are the same as the corresponding substituents in Formula (I), (II), (III), (IV), (V), (VI), and/or (VII) including in embodiments thereof. In embodiments, a compound of Formula (X) is a compound of Formula (I), (II), (III), (IV), (V), (VI), and/or (VII). In some embodiments of the formulae above,

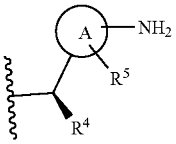

is

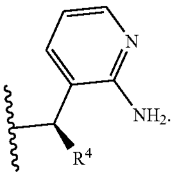

In some embodiments of the formulae above,

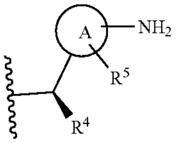

is

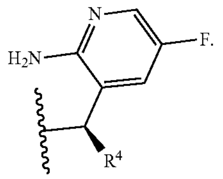

In some embodiments of the formulae above,

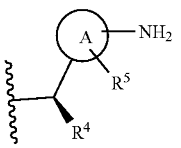

is

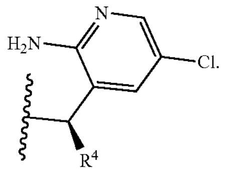

In some embodiments of the formulae above,

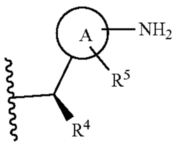

is

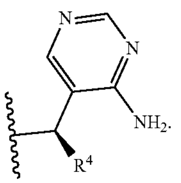

In some embodiments of the formulae above,

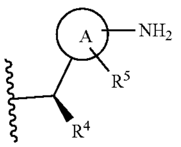

is

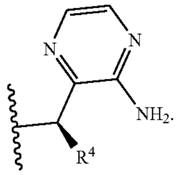

In some embodiments of the formulae above, $R^2$ is

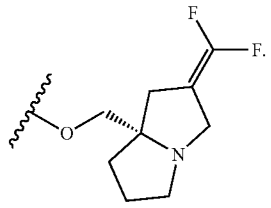 [SMILES: *OC[C@@]12CCCN1CC(=C(F)F)C2]

In some embodiments of the formulae above, $R^2$ is

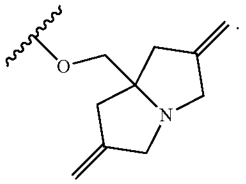 [SMILES: *OCC12CC(=C)CN1CC(=C)C2]

In some embodiments of the formulae above, $R^2$ is

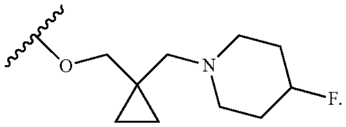 [SMILES: *OCC1(CN2CCC(F)CC2)CC1]

In some embodiments of the formulae above, $R^2$ is

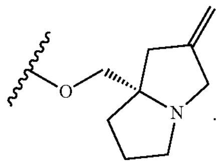 [SMILES: *OC[C@@]12CCCN1CC(=C)C2]

In some embodiments of the formulae above, $R^2$ is

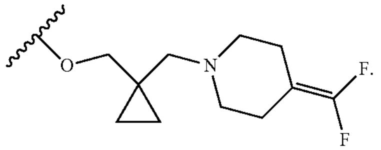 [SMILES: *OCC1(CN2CCC(=C(F)F)CC2)CC1]

In some embodiments of the formulae above, $R^2$ is

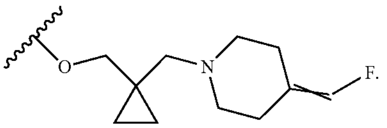

In some embodiments of the formulae above, $R^2$ is

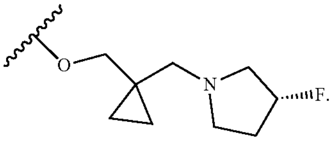 [SMILES: *OCC1(CN2CC[C@@H](F)C2)CC1]

In some embodiments of the formulae above, $R^2$ is

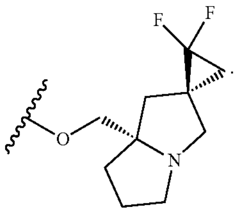 [SMILES: *OC[C@@]12CCCN1C[C@@]1(CC1(F)F)C2]

In some embodiments of the formulae above, $R^2$ is

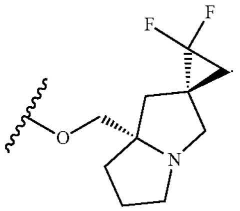 [SMILES: *OC[C@@]12CCCN1C[C@]1(CC1(F)F)C2]

In some embodiments of the formulae above, $R^2$ is

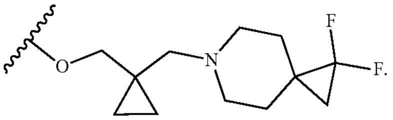 [SMILES: *OCC1(CN2CCC3(CC2)CC3(F)F)CC1]

In some embodiments of the formulae above, $R^2$ is

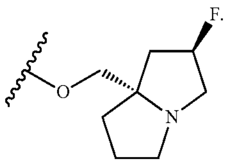 [SMILES: *OC[C@@]12CCCN1C[C@H](F)C2]

In some embodiments of the formulae above, $R^4$ is

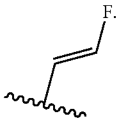

In some embodiments of the formulae above, $R^4$ is

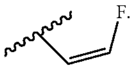

In some embodiments of the formulae above, $R^4$ is

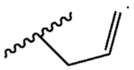

In some embodiments of the formulae above, $R^4$ is

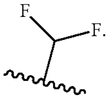

In some embodiments of the formulae above, $R^4$ is

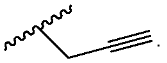 [SMILES: *CC#C]

In some embodiments of the formulae above, $R^4$ is

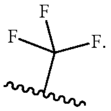

In some embodiments of the formulae above, $R^4$ is

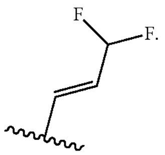 [SMILES: */C=C/C(F)F]

In some embodiments of the formulae above, $R^4$ is

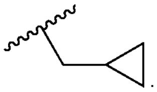 [SMILES: *CC1CC1]

In some embodiments of the formulae above, $R^4$ is

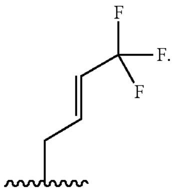 [SMILES: *C/C=C/C(F)(F)F]

In some embodiments of the formulae above, $R^4$ is

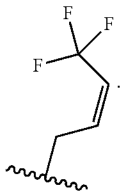 [SMILES: *C/C=C\C(F)(F)F]

In some embodiments of the formulae above, $R^4$ is

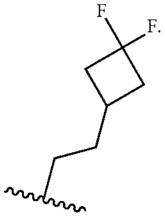 [SMILES: *CCC1CC(F)(F)C1]

In some embodiments of the formulae above, $R^4$ is

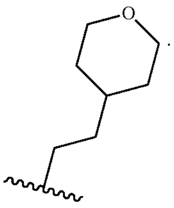 [SMILES: *CCC1CCOCC1]

In some embodiments of the formulae above, $R^4$ is

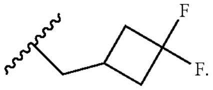 [SMILES: *CC1CC(F)(F)C1]

In some embodiments of the formulae above, $R^4$ is

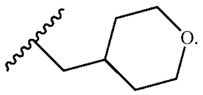 [SMILES: *CC1CCOCC1]

In some embodiments of the formulae above, $R^4$ is

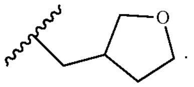 [SMILES: *CC1CCOC1]

In some embodiments of the formulae above, $R^4$ is

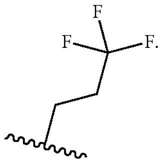 [SMILES: *CCC(F)(F)F]

In some embodiments of the formulae above, $R^4$ is

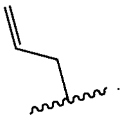 [SMILES: *CC=C]

In some embodiments of the formulae above, $R^4$ is

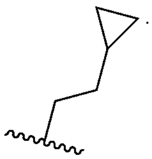 [SMILES: *CCC1CC1]

In some embodiments of the formulae above, $R^4$ is $—CH_3$. In some embodiments of the formulae above, $R^4$ is $—CH_2CH_3$. In some embodiments of the formulae above, $R^6$ is —Cl. In some embodiments of the formulae above, $R^6$ is $—CF_3$. In some embodiments of the formulae above, $R^7$ is

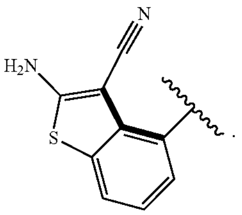

In some embodiments of the formulae above, $R^7$ is

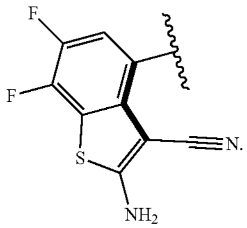

In some embodiments of the formulae above, $R^7$ is

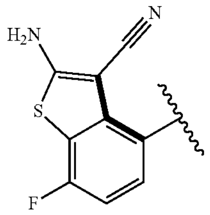

.

In some embodiments, one embodiment of each of

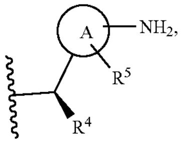

Ring A, $R^2$, $R^4$, $R^5$, R°, $R^7$, and $R^8$ is combined with a formulae above to generate a single compound.

In some embodiments, for a compound of Formula (I), (II), (III), (IV), (V), or (VI), the compound, or a pharmaceutically acceptable salt or solvate thereof, has the formula:

(XI)

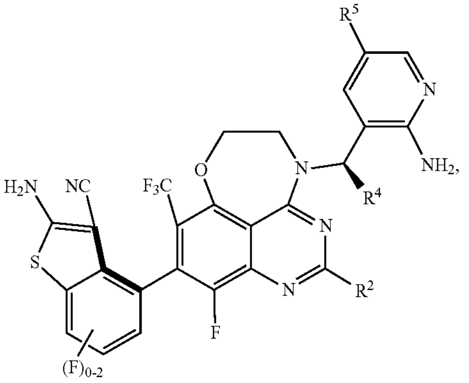

wherein:

$R^2$ is selected from

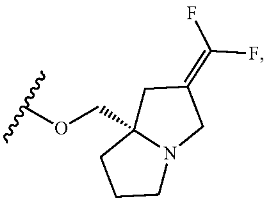

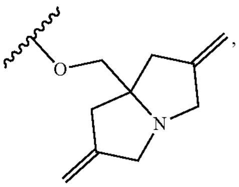

,

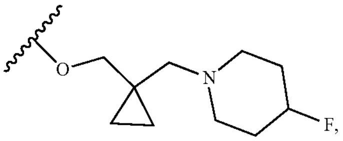

-continued

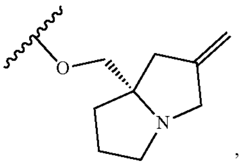

,

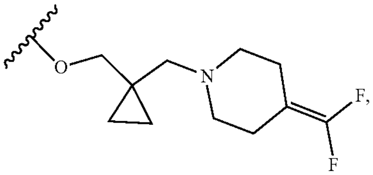

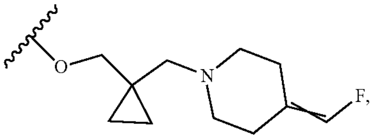

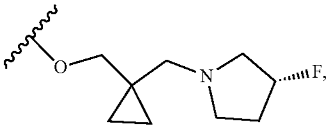

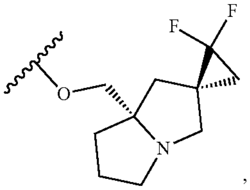

,

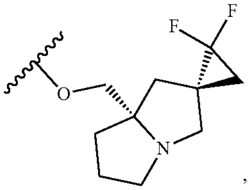

,

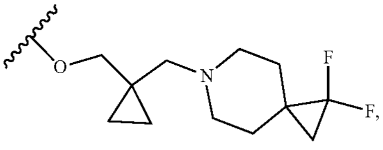

and

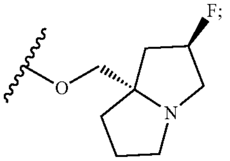

$R^4$ is selected from

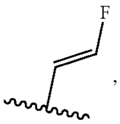

,

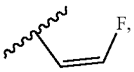

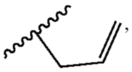

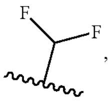

,

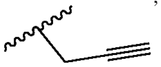

,

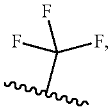

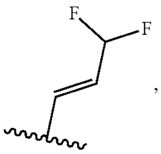

,

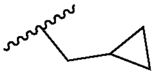

,

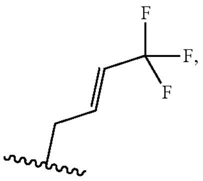

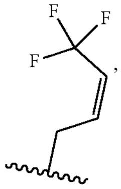

,

-continued

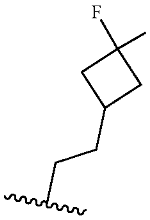, 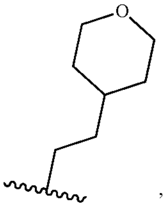, 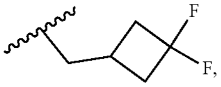

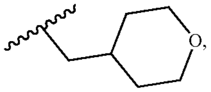 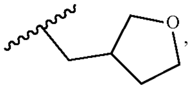

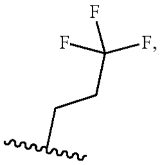 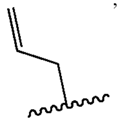, 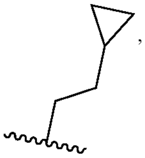,

—$CH_2CH_3$, and —$CH_3$;

$R^5$ is selected from hydrogen and halogen; and

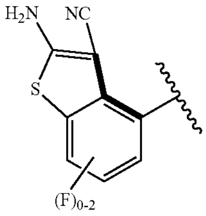

is selected from

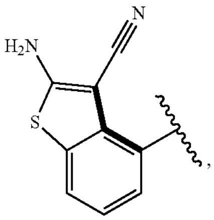 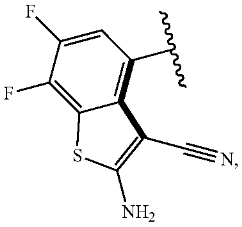 and

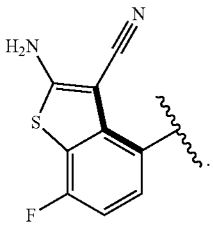

In embodiments, $R^4$ is —$CH_3$ and $R^5$ is hydrogen. In embodiments, $R^4$ is

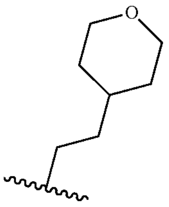 [SMILES: *CCC1CCOCC1]

and $R^5$ is hydrogen. In embodiments, $R^4$ is —$CH_3$ and $R^5$ is halogen. In embodiments, $R^4$ is —$CH_2CH_3$ and $R^5$ is halogen. In embodiments, $R^4$ is —$CH_3$ and $R^5$ is —F. In embodiments, $R^4$ is selected from

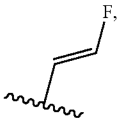 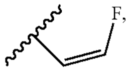 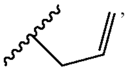

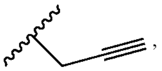 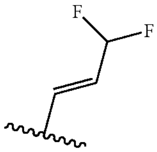, 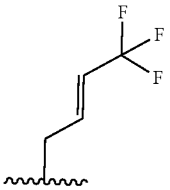,

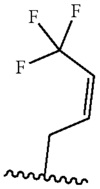, and 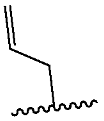;

and $R^5$ is hydrogen. In embodiments,

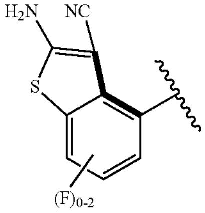

is

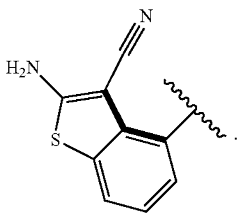

In embodiments,

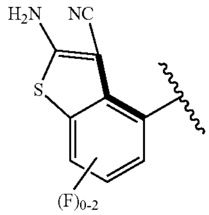

is

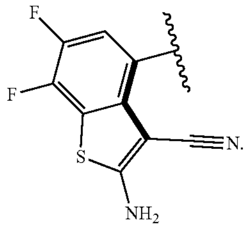

In embodiments,

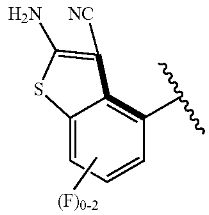

is

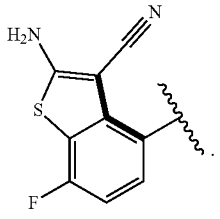

In some embodiments of the formulae above, $R^2$ is

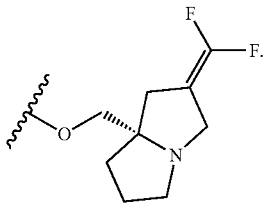 [SMILES: *OC[C@@]12CCCN1CC(=C(F)F)C2]

In some embodiments of the formulae above, $R^2$ is

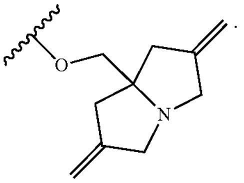 [SMILES: *OCC12CC(=C)CN1CC(=C)C2]

In some embodiments of the formulae above, $R^2$ is

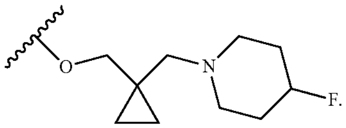 [SMILES: *OCC1(CN2CCC(F)CC2)CC1]

In some embodiments of the formulae above, $R^2$ is

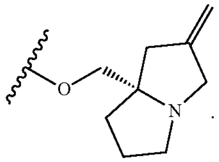 [SMILES: *OC[C@@]12CCCN1CC(=C)C2]

In some embodiments of the formulae above, $R^2$ is

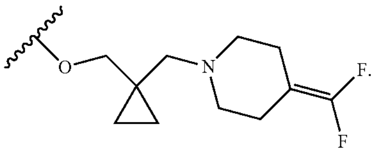 [SMILES: *OCC1(CN2CCC(=C(F)F)CC2)CC1]

In some embodiments of the formulae above, $R^2$ is

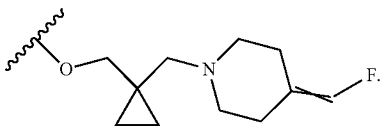

In some embodiments of the formulae above, $R^2$ is

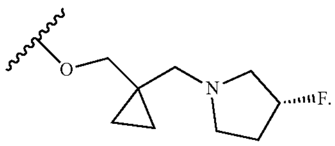 [SMILES: *OCC1(CN2CC[C@@H](F)C2)CC1]

In some embodiments of the formulae above, $R^2$ is

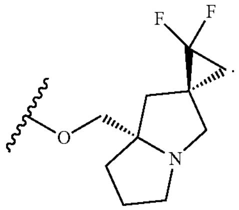 [SMILES: *OC[C@@]12CCCN1C[C@@]1(CC1(F)F)C2]

In some embodiments of the formulae above, $R^2$ is

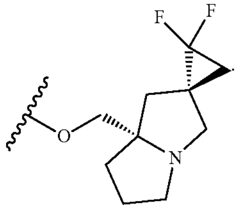 [SMILES: *OC[C@@]12CCCN1C[C@]1(CC1(F)F)C2]

In some embodiments of the formulae above, $R^2$ is

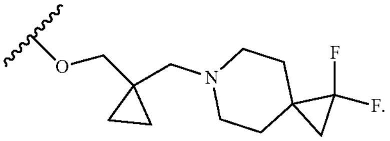 [SMILES: *OCC1(CN2CCC3(CC2)CC3(F)F)CC1]

In some embodiments of the formulae above, $R^2$ is

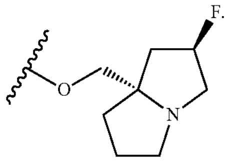 [SMILES: *OC[C@@]12CCCN1C[C@H](F)C2]

In some embodiments, the substituents (for example, $R^2$, $R^4$, $R^5$, $R^6$, $R^7$, and $R^8$) of formula (XI) are the same as the corresponding substituents in Formula (I), (II), (III), (IV), (V), (VI), and/or (VII) including in embodiments thereof. In embodiments, a compound of Formula (XI) is a compound of Formula (I), (II), (III), (IV), (V), (VI), and/or (VII).

In some embodiments, for a compound of Formula (I), (II), (III), (IV), (V), or (VI), the compound, or a pharmaceutically acceptable salt or solvate thereof, has the formula:

(XII)

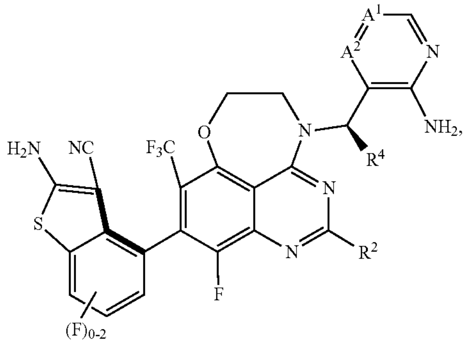

wherein:

$A^1$ is N and $A^3$ is CH; or $A^1$ is CH and $A^2$ is N;

$R^3$ is selected from

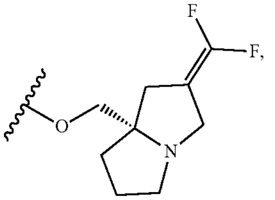

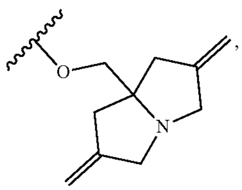

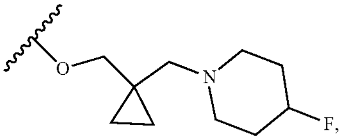

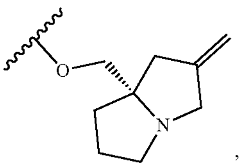

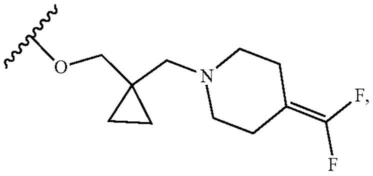

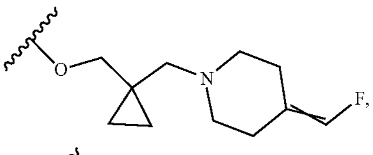

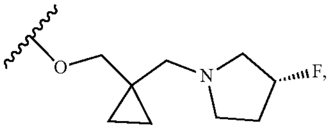

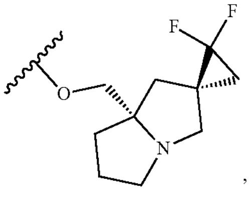

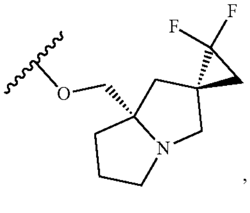

-continued

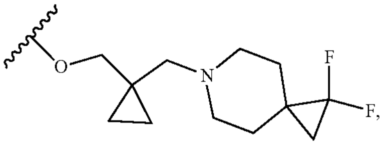

and

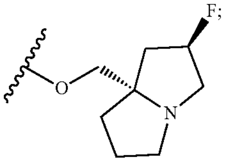

$R^4$ is selected from

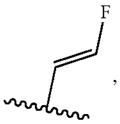

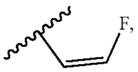

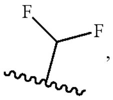

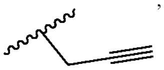

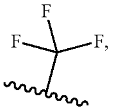

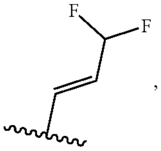

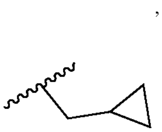

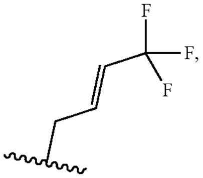

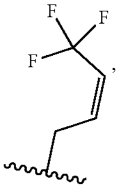

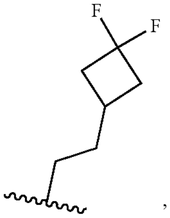

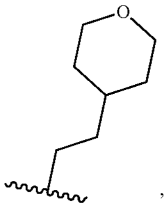

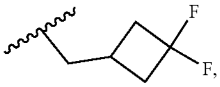

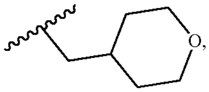

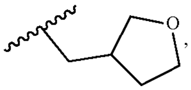

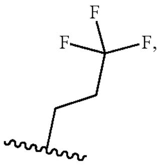

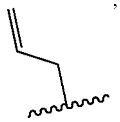

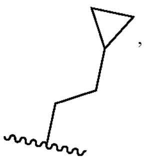

and —$CH_3$; and

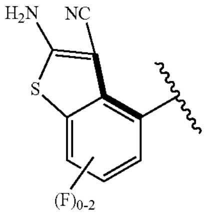

is selected from

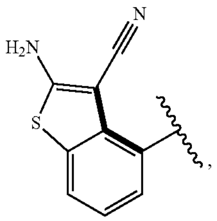

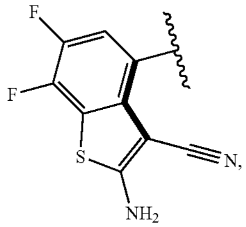

and

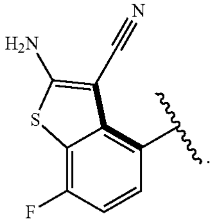

In embodiments, $R^4$ is —$CH_3$, $A^1$ is N, and $A^2$ is CH. In embodiments, $R^4$ is —$CH_3$, $A^1$ is CH, and $A^3$ is N. In embodiments, R is

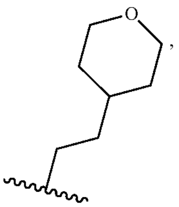 [SMILES: *CCC1CCOCC1]

$A^1$ is N, and $A^3$ is CH. In embodiments, $R^4$ is

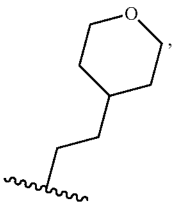 [SMILES: *CCC1CCOCC1]

$A^1$ is CH, and $A^2$ is N. In embodiments, $R^4$ is —$CH_3$ and $R^5$ is halogen. In embodiments, $R^4$ is —$CH_3$ and $R^5$ is —F. In embodiments, $R^4$ is selected from

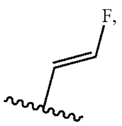

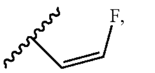

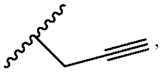

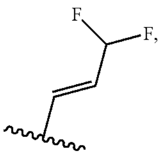

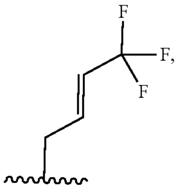

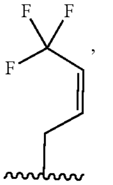

and

-continued
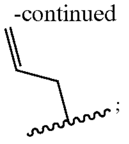
$A^1$ is CH; and $A^2$ is N. In embodiments, $R^4$ is selected from
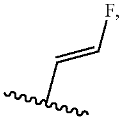
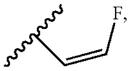
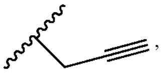
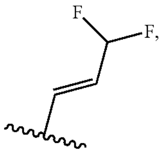
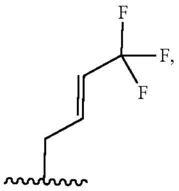
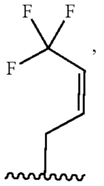
and
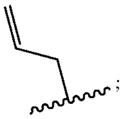
$A^1$ is N; and $A^2$ is CH. In embodiments,
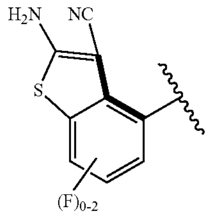
is
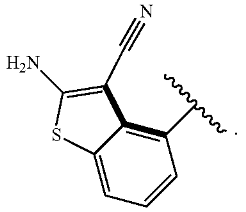
In embodiments,
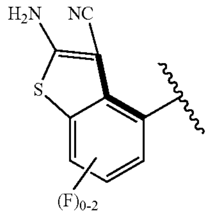
is
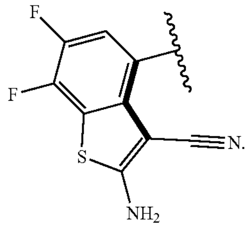
In embodiments,
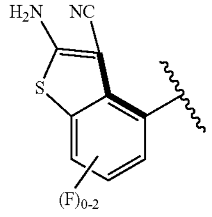
is
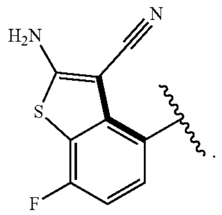
In some embodiments of the formulae above, $R^2$ is
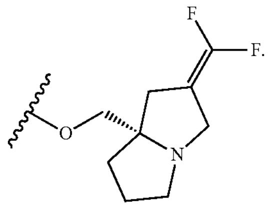 [SMILES: *OC[C@@]12CCCN1CC(=C(F)F)C2]
In some embodiments of the formulae above, $R^2$ is
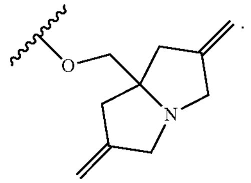 [SMILES: *OCC12CC(=C)CN1CC(=C)C2]

In some embodiments of the formulae above, $R^2$ is

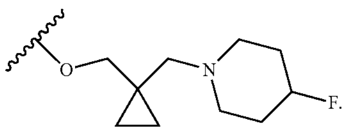 [SMILES: *OCC1(CN2CCC(F)CC2)CC1]

In some embodiments of the formulae above, $R^2$ is

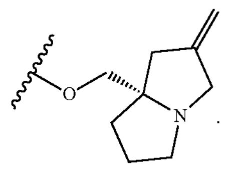 [SMILES: *OC[C@@]12CCCN1CC(=C)C2]

In some embodiments of the formulae above, $R^2$ is

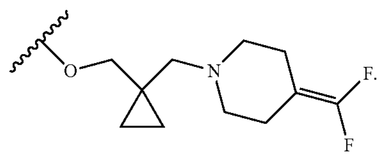 [SMILES: *OCC1(CN2CCC(=C(F)F)CC2)CC1]

In some embodiments of the formulae above, $R^2$ is

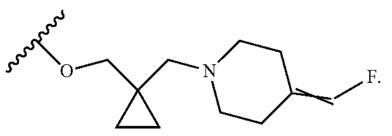

In some embodiments of the formulae above, $R^2$ is

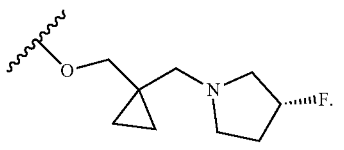 [SMILES: *OCC1(CN2CC[C@@H](F)C2)CC1]

In some embodiments of the formulae above, $R^2$ is

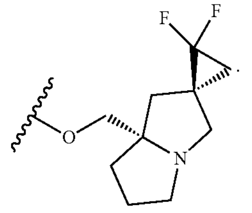 [SMILES: *OC[C@@]12CCCN1C[C@@]1(CC1(F)F)C2]

In some embodiments of the formulae above, $R^2$ is

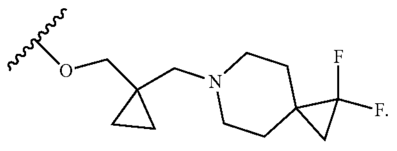 [SMILES: *OCC1(CN2CCC3(CC2)CC3(F)F)CC1]

In some embodiments of the formulae above, $R^2$ is

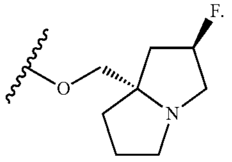 [SMILES: *OC[C@@]12CCCN1C[C@H](F)C2]

In some embodiments of the formulae above, $R^2$ is

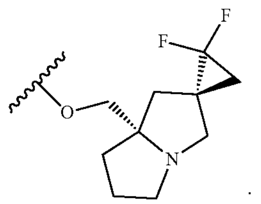 [SMILES: *OC[C@@]12CCCN1C[C@]1(CC1(F)F)C2]

In some embodiments, the substituents (for example, $R^2$, $R^4$, $R^5$, $R^6$, $R^7$, and $R^8$) of formula (XII) are the same as the corresponding substituents in Formula (I), (II), (III), (IV), (V), (VI), and/or (VII) including in embodiments thereof. In embodiments, a compound of Formula (XII) is a compound of Formula (I), (II), (III), (IV), (V), (VI), and/or (VII).

In some embodiments, the compound of Formula (I), (IV), or (V), is selected from:

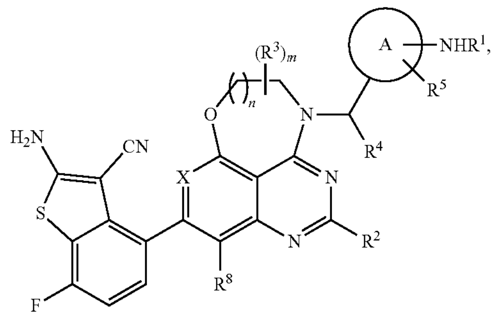

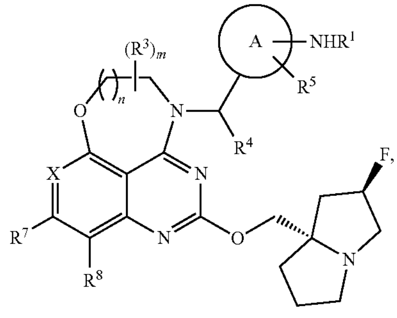

-continued
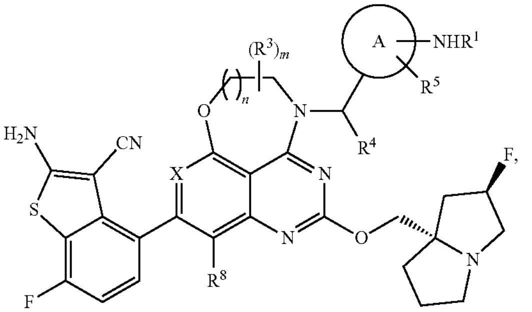
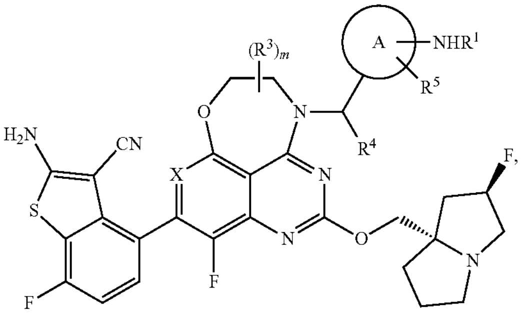
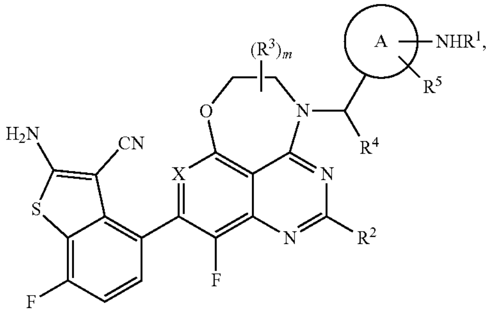
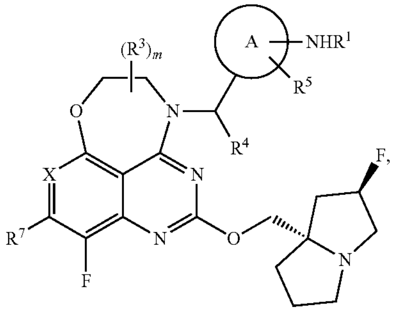
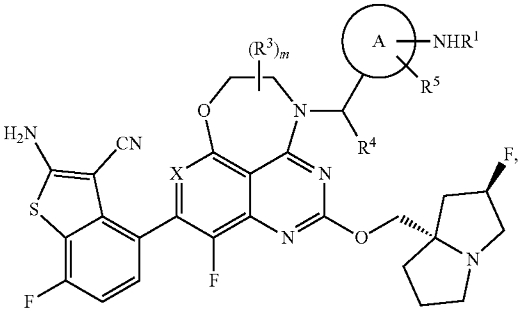
-continued
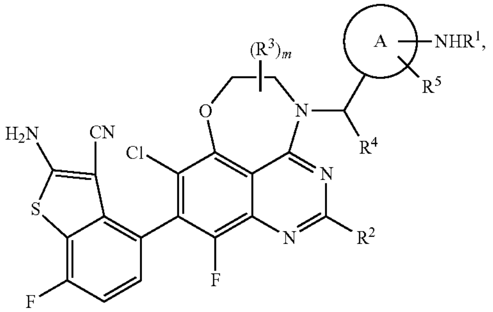
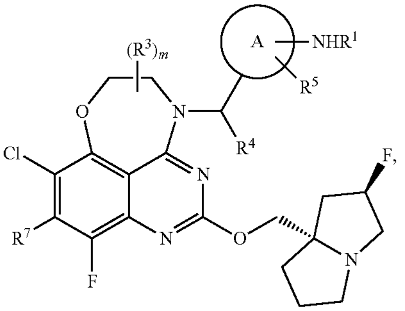
and
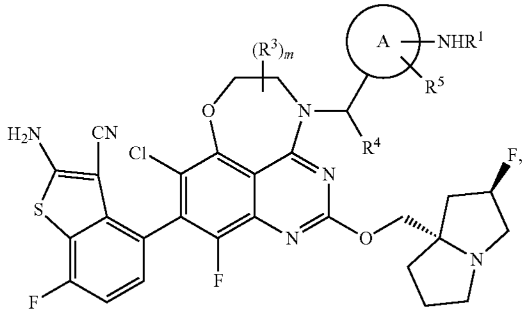
or a pharmaceutically acceptable salt or solvate thereof.
In some embodiments, the compound of Formula (I), (IV), or (V), is selected from:
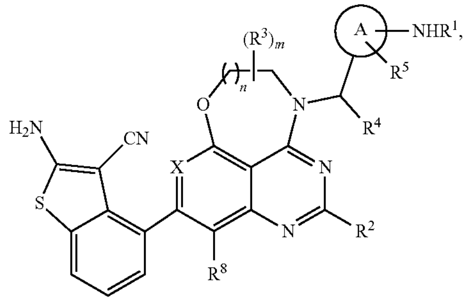
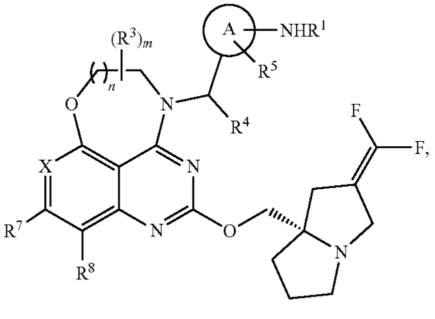

-continued
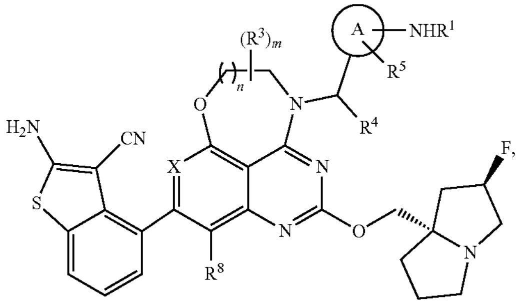
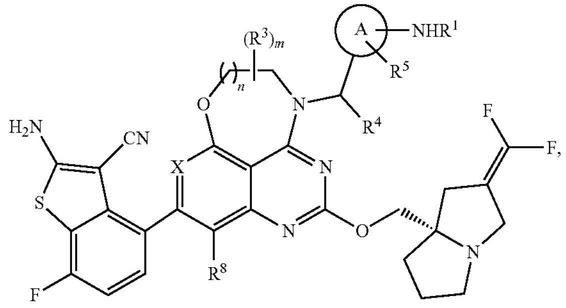
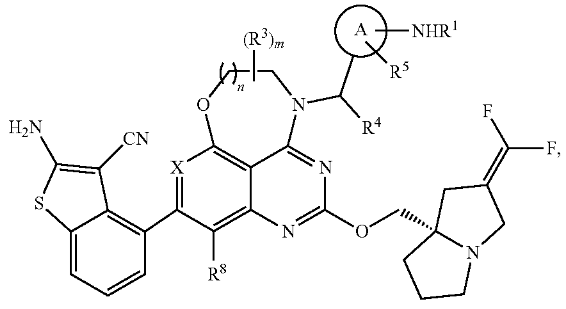
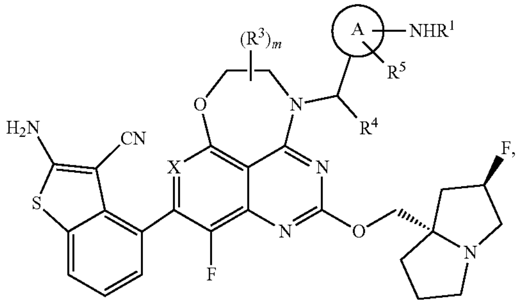
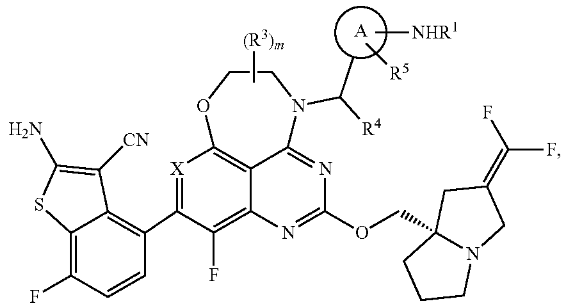
-continued
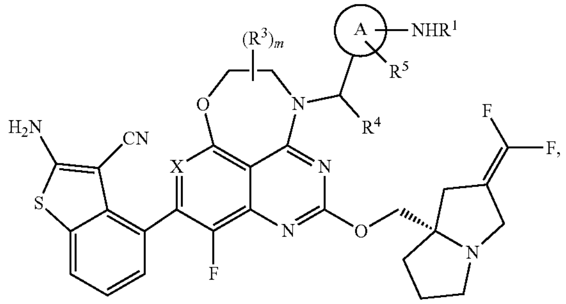
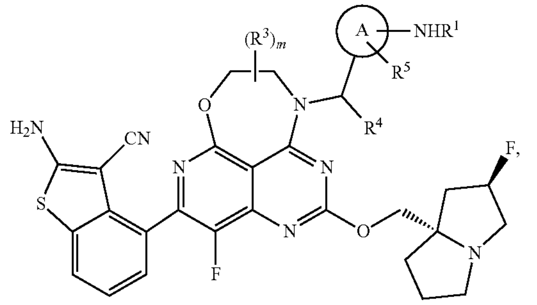
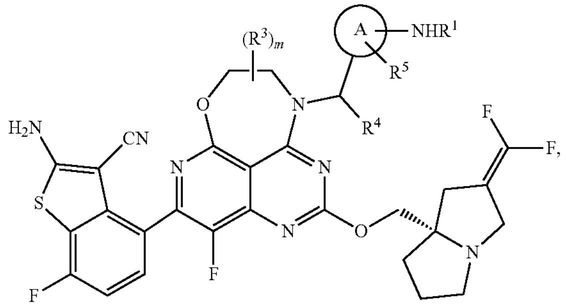
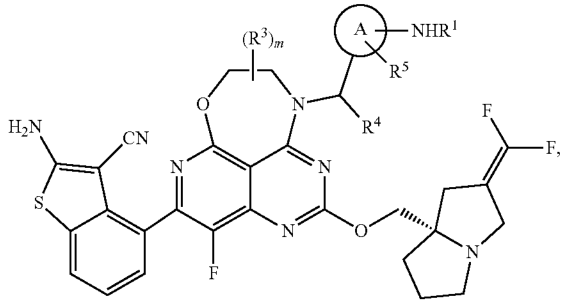
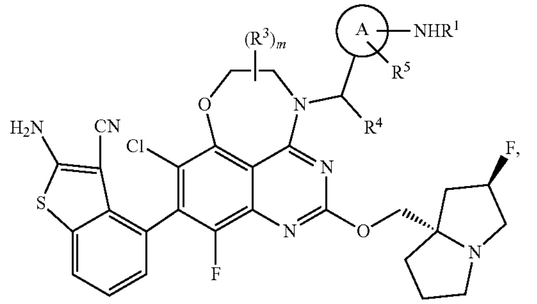

-continued
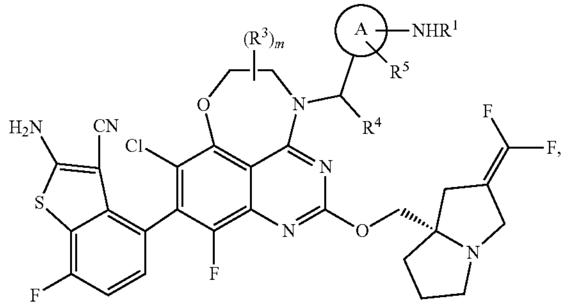
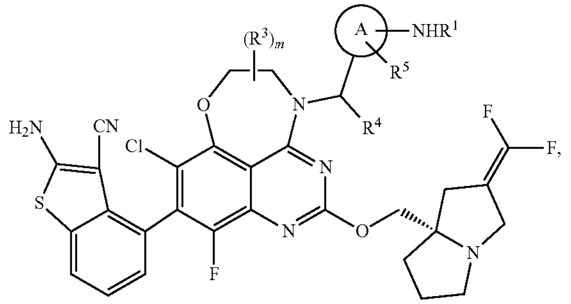
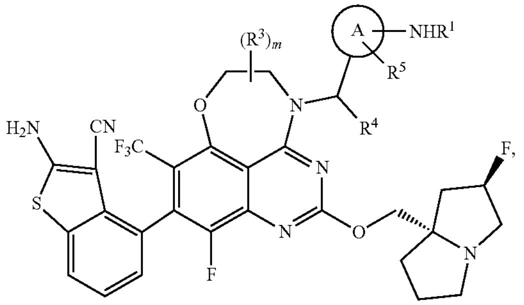
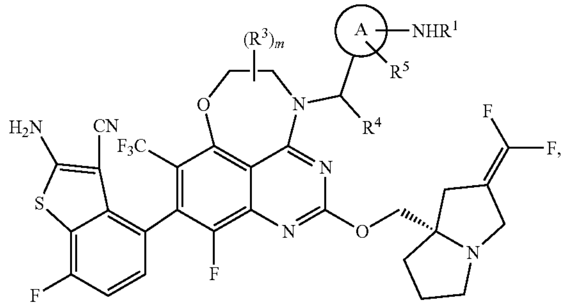
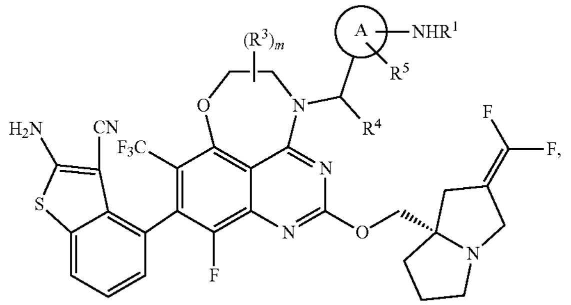
-continued
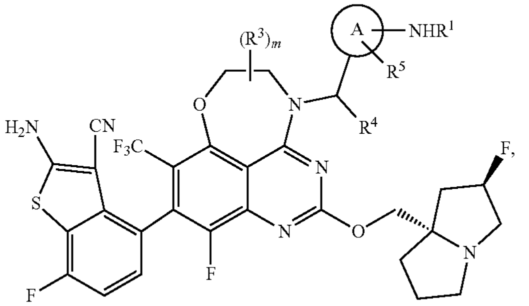
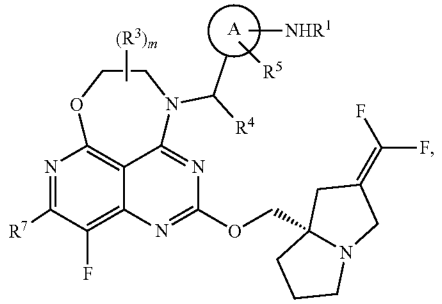
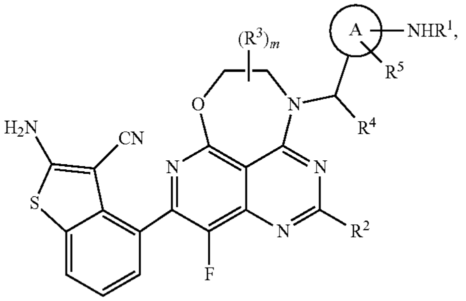
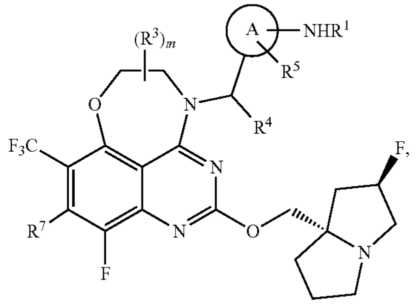
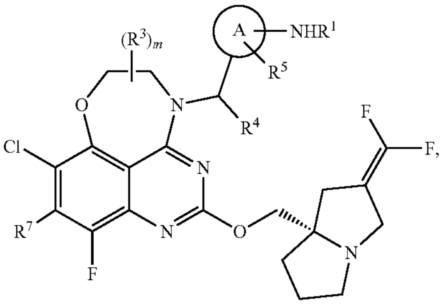

-continued
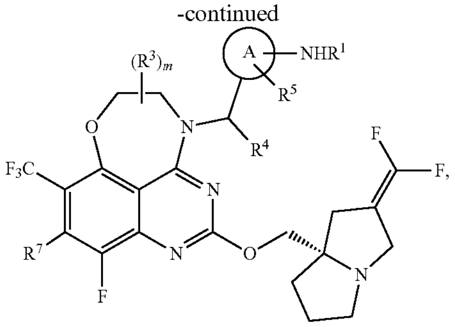
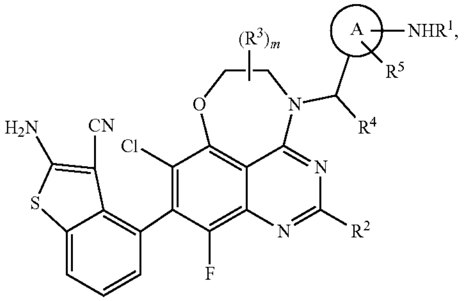
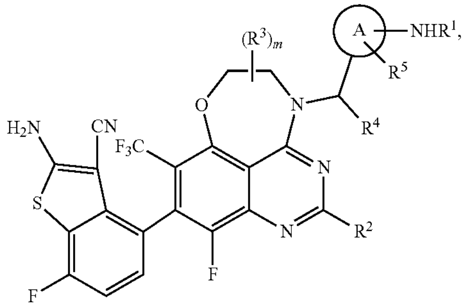
and
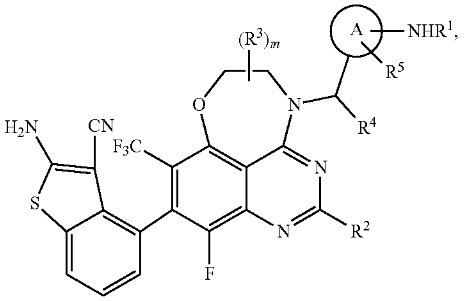
or a pharmaceutically acceptable salt or solvate thereof.
In some embodiments, the compound of Formula (I), (IV), or (V), is selected from:
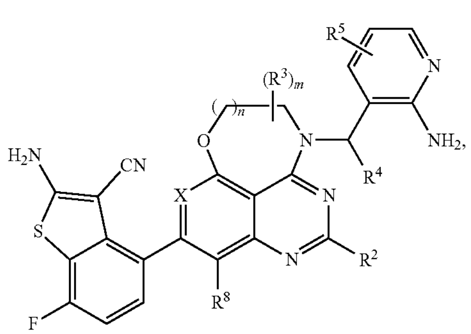
-continued
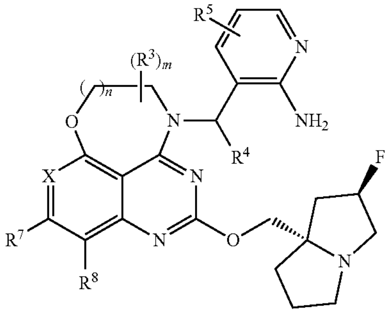
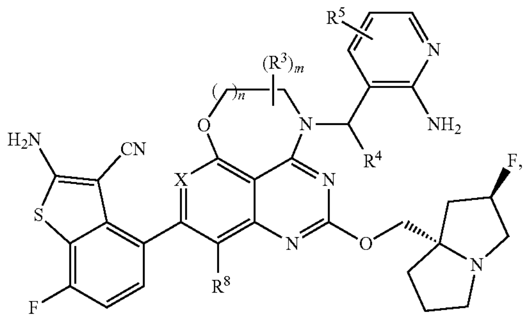
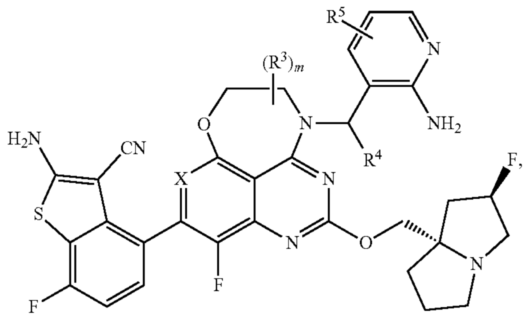
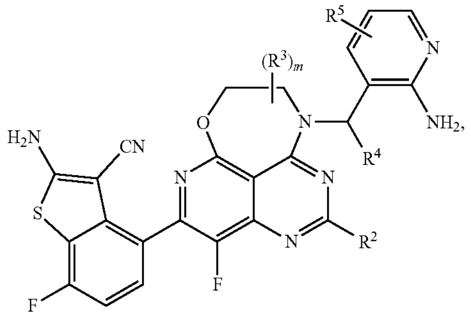
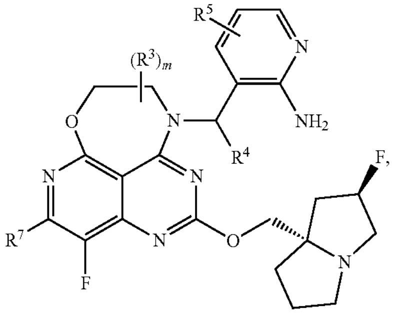

-continued
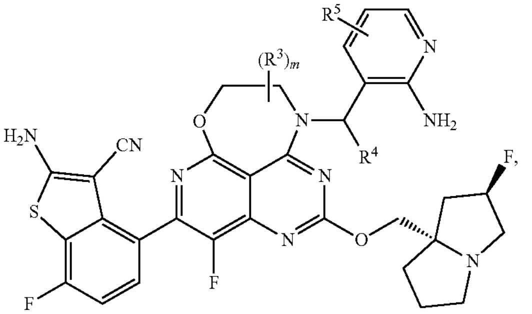
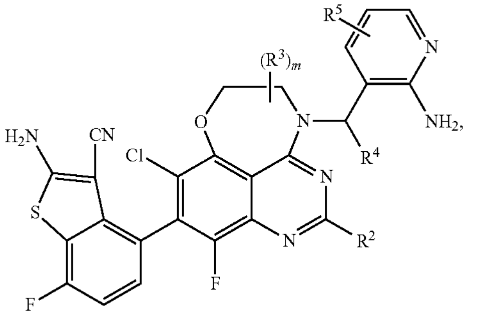
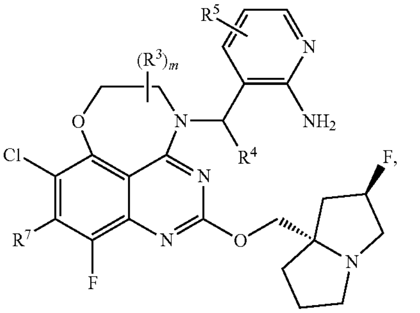
and
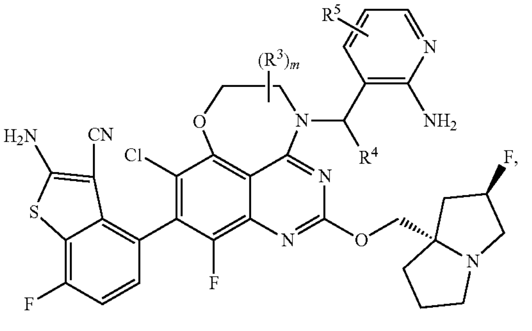
or a pharmaceutically acceptable salt or solvate thereof.
In some embodiments, the compound of Formula (I) is selected from:
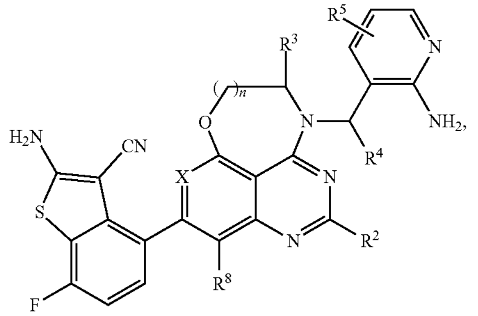
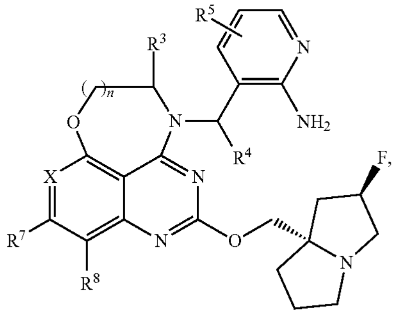
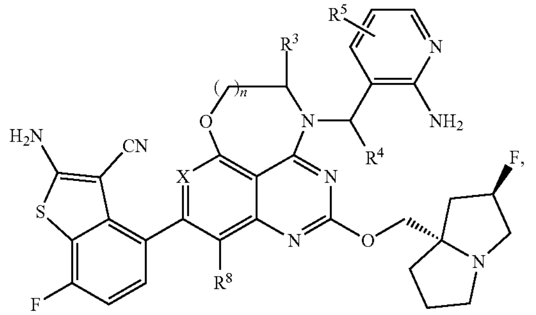
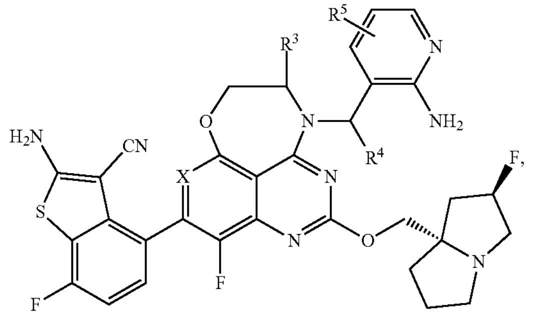
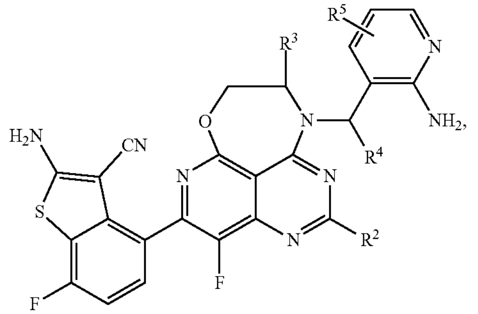

-continued

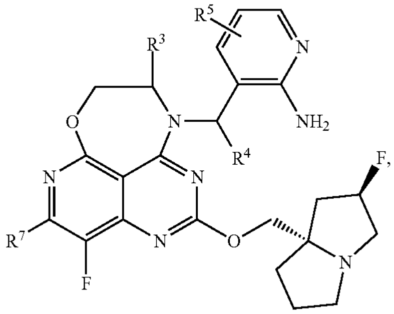

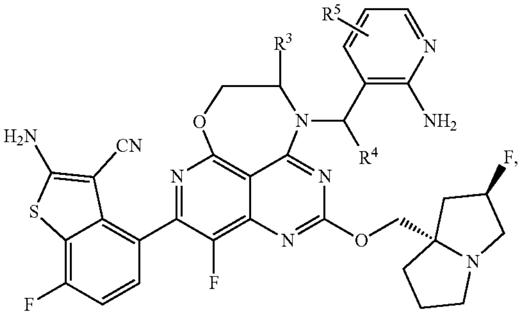

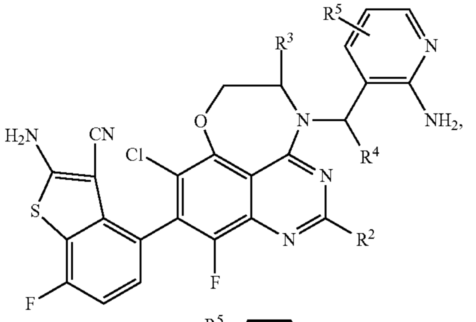

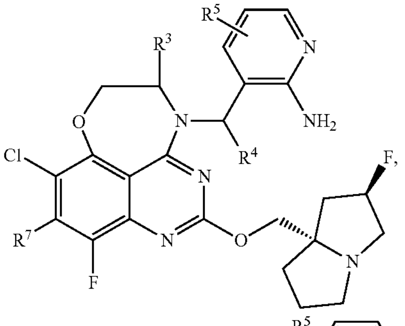

and

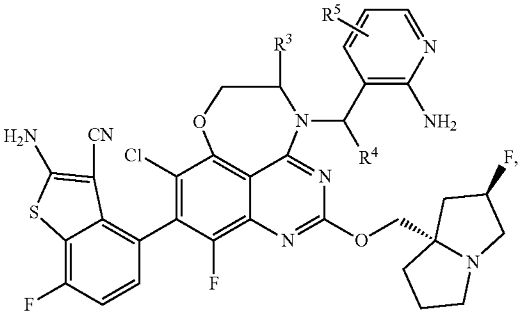

or a pharmaceutically acceptable salt or solvate thereof.

In some embodiments, for a compound of Formula (I), (II), (II-a), (III), (IV), (V), or (VI), $R^2$ is selected from hydrogen, $C_{1-6}$ alkyl, $C_{2-6}$ alkenyl, $C_{3-10}$ carbocycle, 3- to 10-membered heterocycle, —$OR^{12}$, and —$N(R^{12})(R^{13})$, wherein $C_{1-6}$ alkyl, $C_{2-6}$ alkenyl, $C_{3-10}$ carbocycle, and 3- to 10-membered heterocycle are optionally substituted with one, two, or three $R^{20}$. In some embodiments, $R^2$ is selected from hydrogen, —($C_{0-3}$ alkylene)-O—($C_{0-3}$ alkylene)-$R^{20}$, $C_{1-3}$ alkyl, and 3- to 10-membered heterocycle, wherein each $C_{0-3}$ alkylene, $C_{1-3}$ alkyl, and 3- to 10-membered heterocycle is optionally substituted with one, two, or three $R^{20}$. In some embodiments, $R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$. In some embodiments, $R^2$ is $OR^{12}$. In some embodiments, $R^2$ is —O($C_{1-3}$ alkylene)(4- to 10-membered heterocycle), wherein 4- to 10-membered heterocycle is optionally substituted with one, two, or three substituents independently selected from halogen, $C_{1-3}$ alkyl, $C_{1-3}$ haloalkyl, and —$C(R^{21})_2$, wherein $R^{21}$ is independently selected at each occurrence from hydrogen, halogen, and $C_{1-3}$ alkyl. In some embodiments, $R^2$ is —$OCH_2$ (hexahydro-1H-pyrrolizine) optionally substituted with one, two, or three $R^{20}$. In some embodiments, $R^2$ is —$OCH_2$ (hexahydro-1H-pyrrolizine) optionally substituted with one, two, or three substituents independently selected from halogen, $C_{1-3}$ alkyl, $C_{1-3}$ haloalkyl, and —$C(R^{21})_2$, wherein $R^{21}$ is independently selected at each occurrence from hydrogen, halogen, and $C_{1-3}$ alkyl.

In some embodiments, for a compound of Formula (I), (II), (II-a), (III), (IV), (V), (VI), (VII), (VIII), or (IX), $R^2$ is selected from

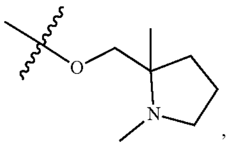,
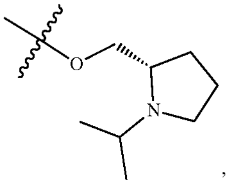,
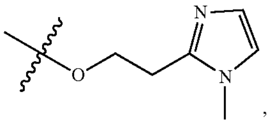,
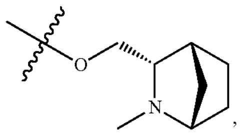,
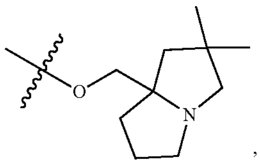,
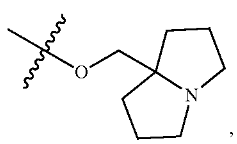,
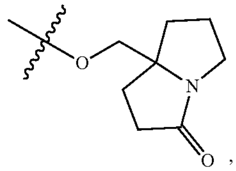,
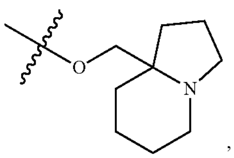,
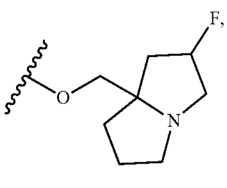
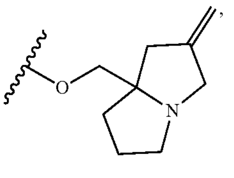

-continued
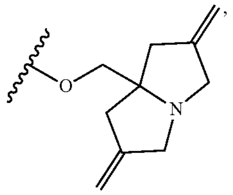
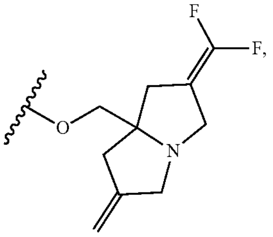
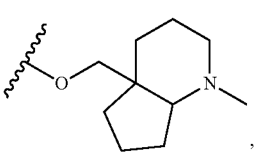
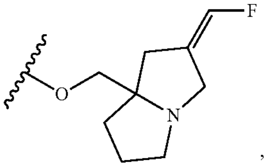
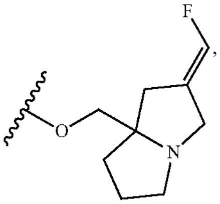
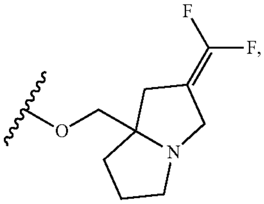
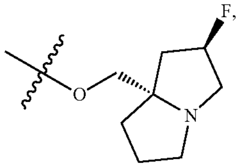
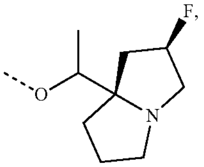
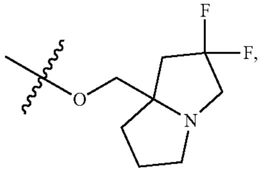
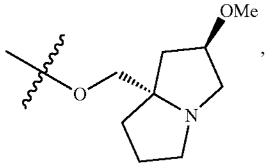
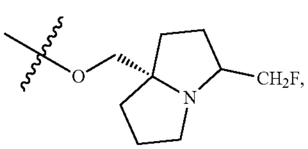
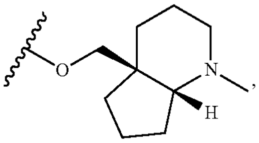
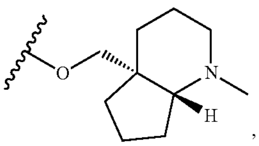
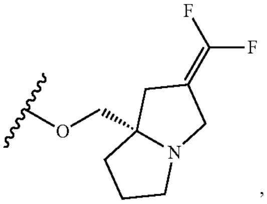
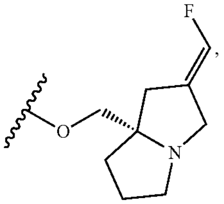
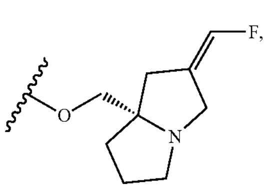
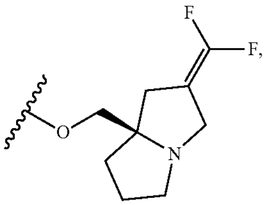
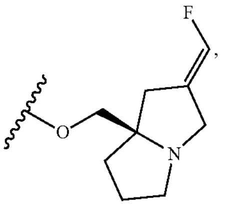
-continued
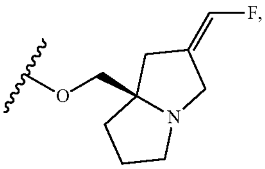
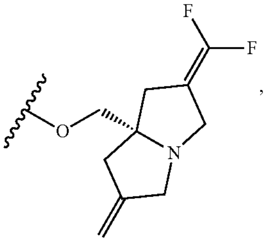
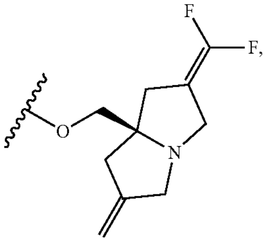
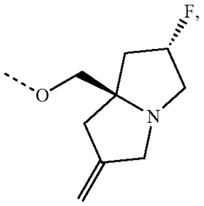
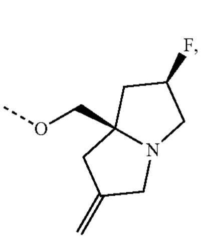
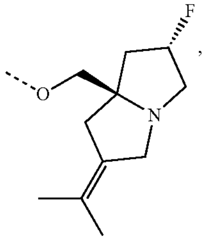
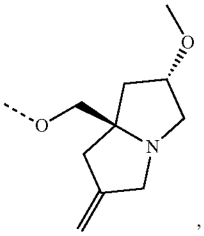
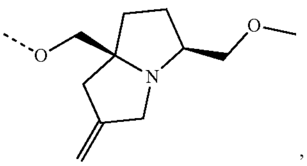
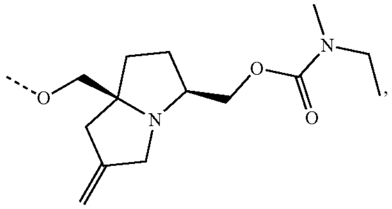
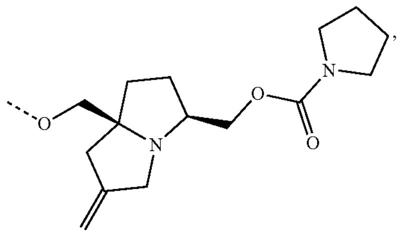
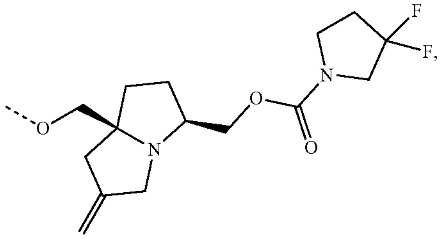

-continued
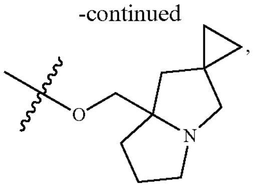,
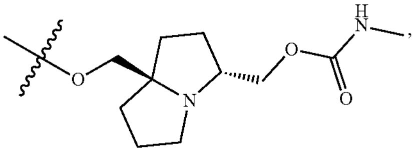,
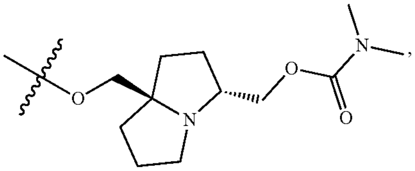,
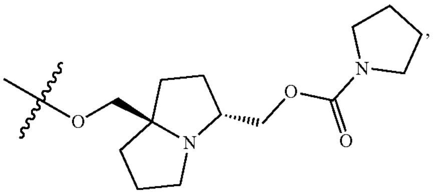,
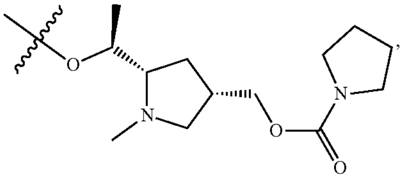,
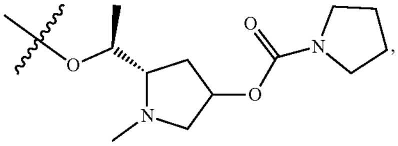,
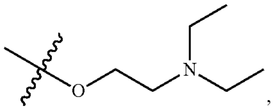,
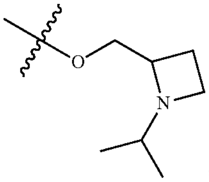,
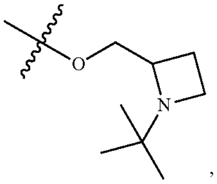,
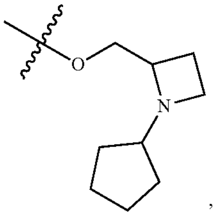,
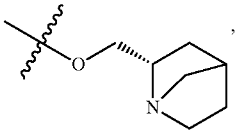,
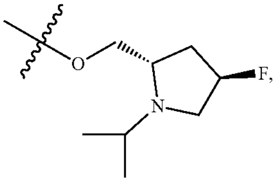,
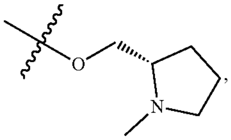,
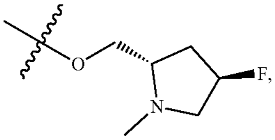,
-continued
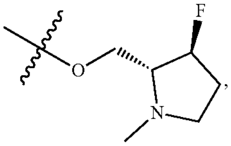,
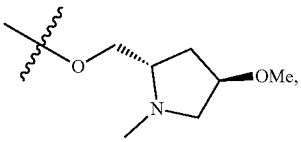,
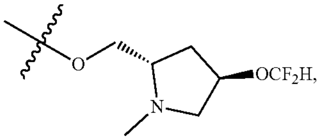,
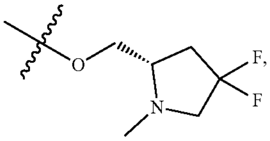,
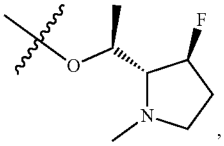,
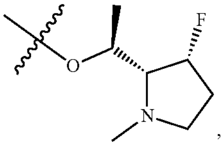,
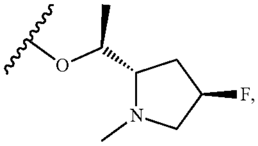,
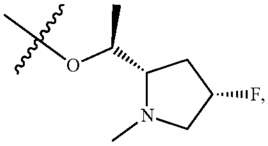,
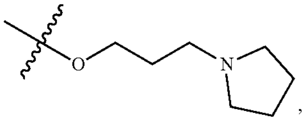,
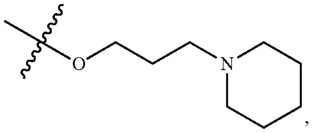,
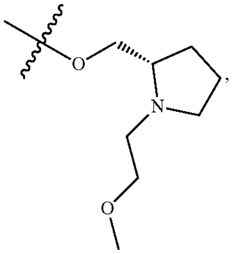,
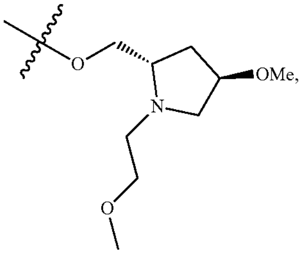,
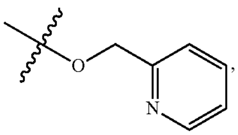,
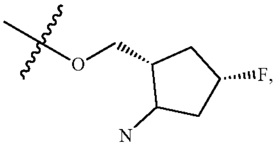,
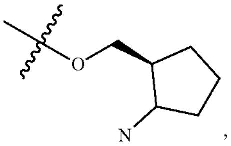,
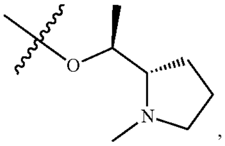,
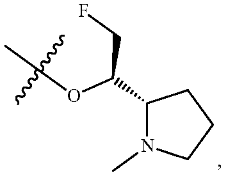,
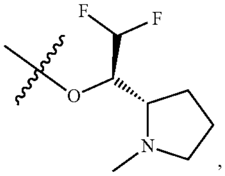, -continued
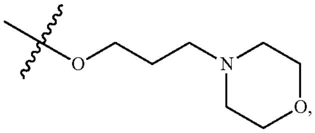
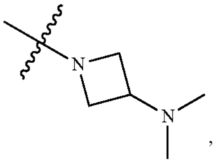
,
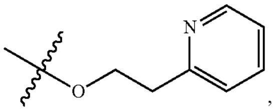
,
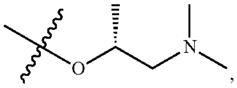
,
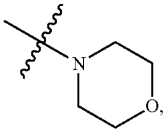
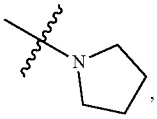
,
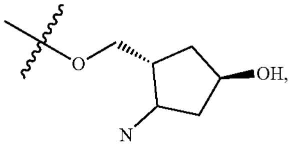
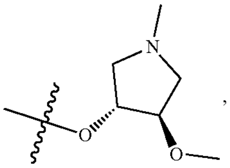
,
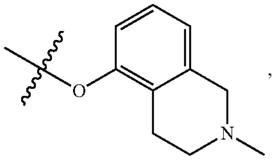
,
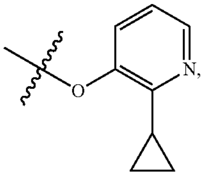
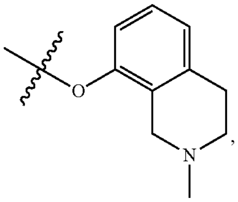
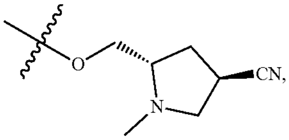
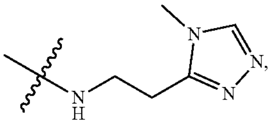
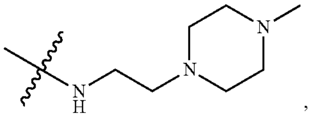
,
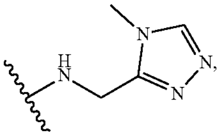
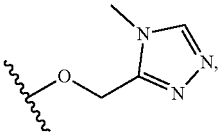
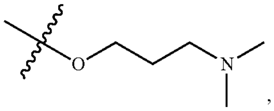
,
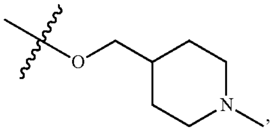
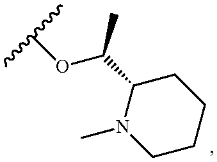
,
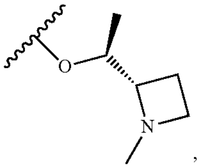
,
-continued
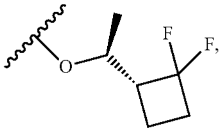
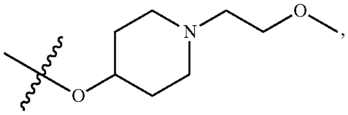
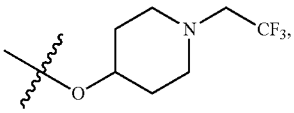
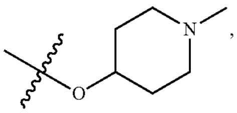
,
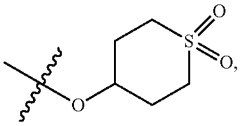
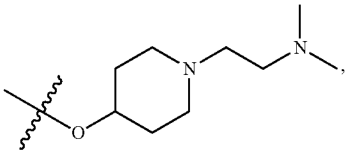
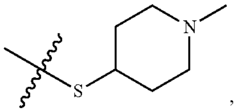
,
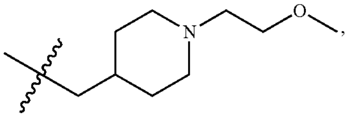
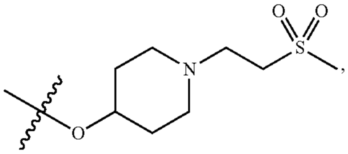
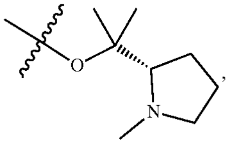
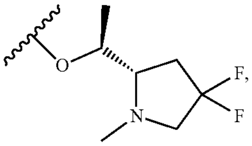
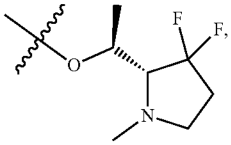
,
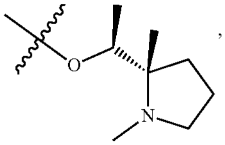
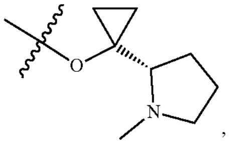
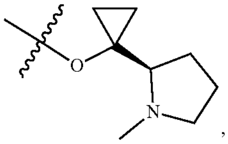
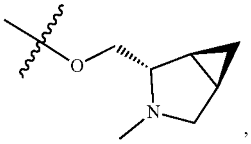
,
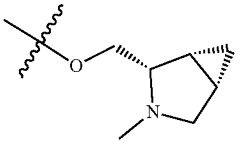
,
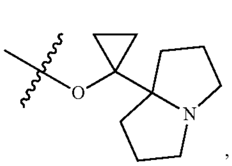
,
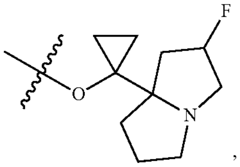
, -continued
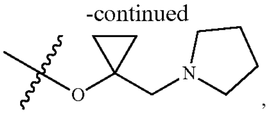,
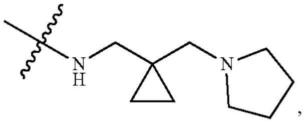,
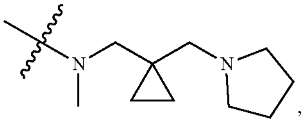,
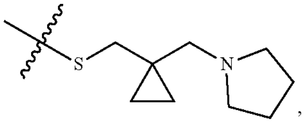,
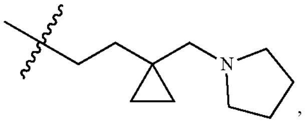,
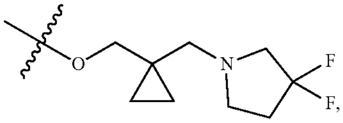
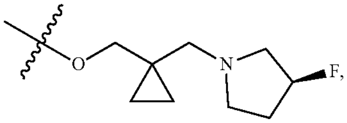
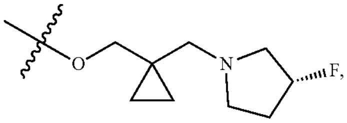
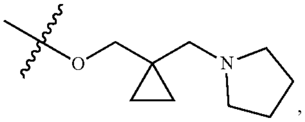,
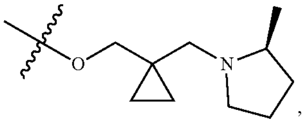,
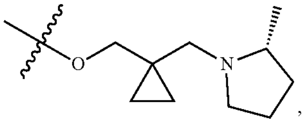,
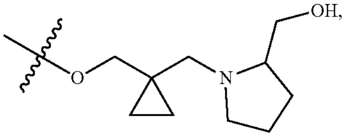
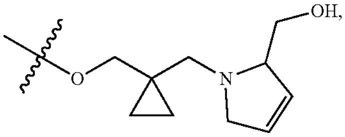
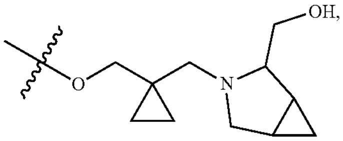
-continued
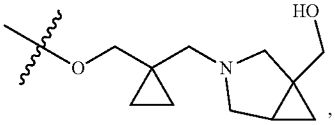,
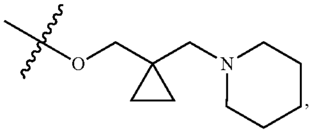
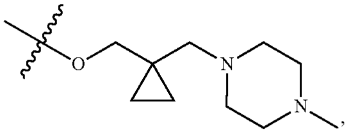,
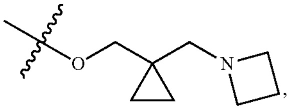
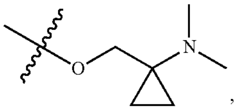, 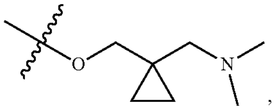,
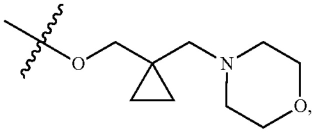
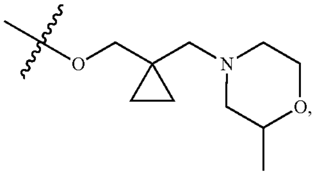
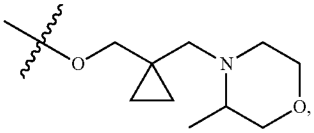 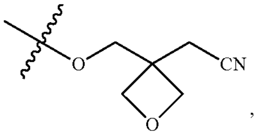,
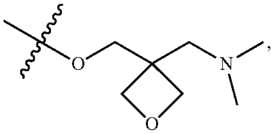 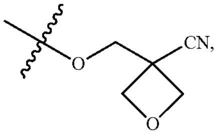
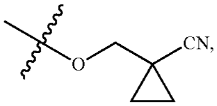 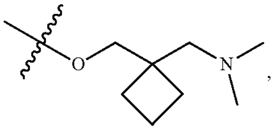,
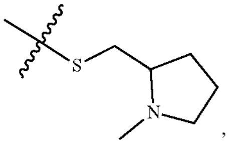, 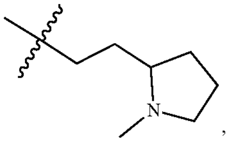,
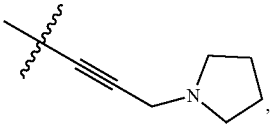, 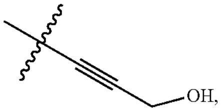

-continued
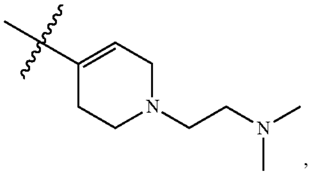,
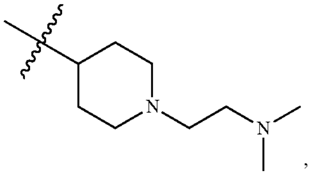,
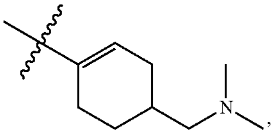, 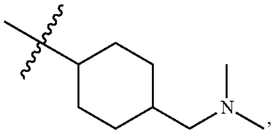,
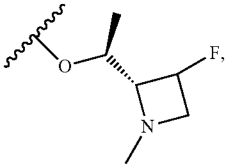 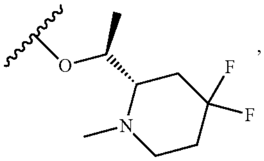,
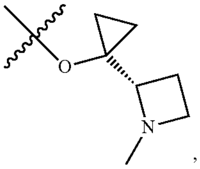, 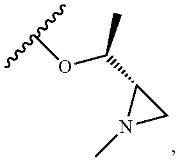,
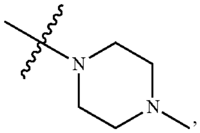, 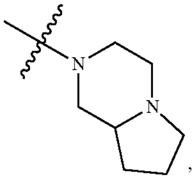,
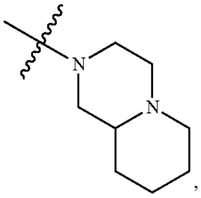, 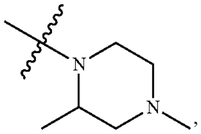,
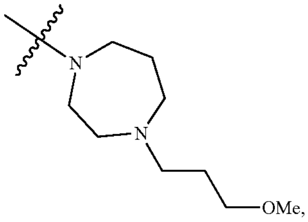
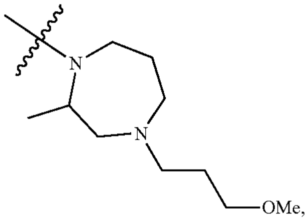
-continued
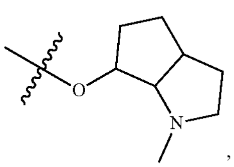, 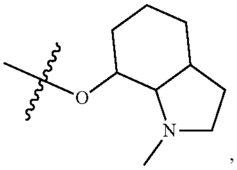,
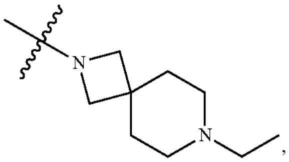
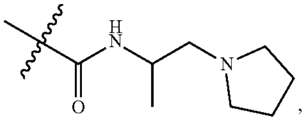,
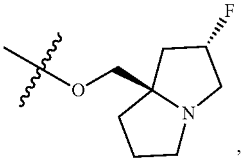, 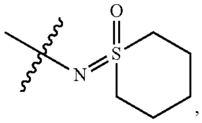,
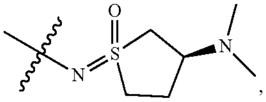,
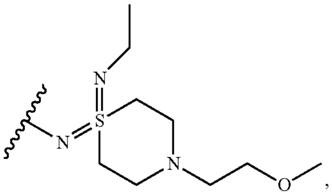, and
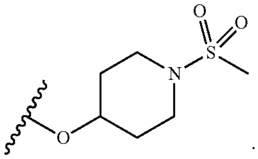.
In some embodiments, $R^2$ is selected from
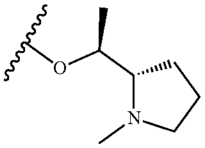, 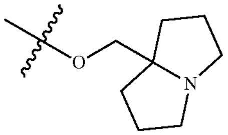,
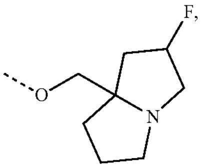 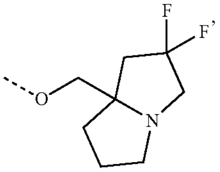
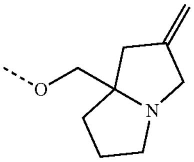, 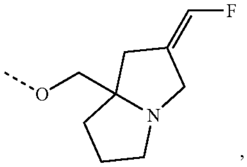, -continued
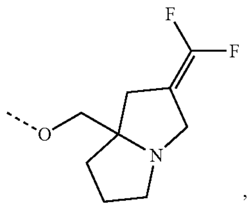
, and
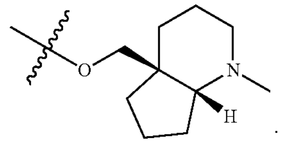
In some embodiments, $R^2$ is selected from
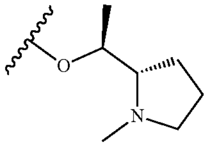
and
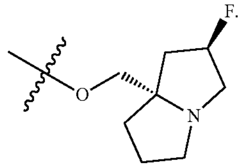
In some embodiments, $R^2$ is
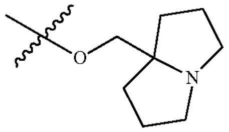 [SMILES: *OCC12CCCN1CCC2]
optionally substituted with one or more $R^{20}$. In some embodiments, $R^2$ is
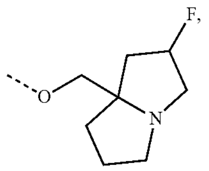
such as
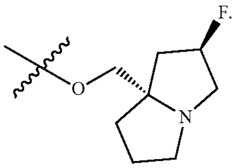 [SMILES: *OC[C@@]12CCCN1C[C@H](F)C2]
In some embodiments, $R^2$ is
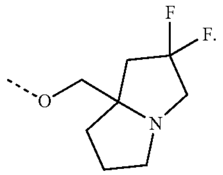
In some embodiments, $R^2$ is
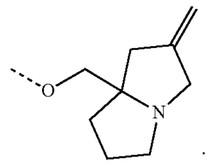
In some embodiments, $R^2$ is
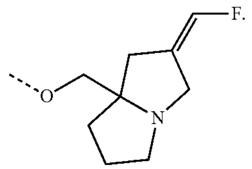
In some embodiments, $R^2$ is
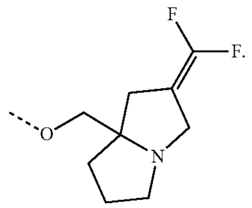
In some embodiments, $R^2$ is
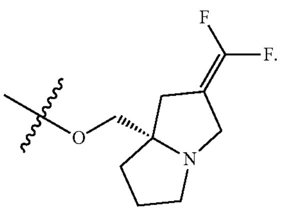 [SMILES: *OC[C@@]12CCCN1CC(=C(F)F)C2]
In some embodiments, $R^2$ is
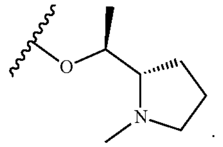 [SMILES: *O[C@@H](C)[C@@H]1CCCN1C]

In some embodiments, $R^2$ is
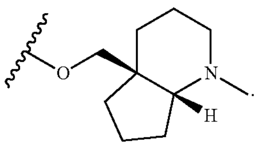 [SMILES: *OC[C@]12CCC[C@H]1N(C)CCC2]
In some embodiments, $R^2$ is
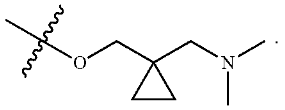 [SMILES: *OCC1(CN(C)C)CC1]
In some embodiments, $R^2$ is
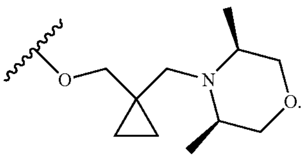 [SMILES: *OCC1(CN2[C@H](C)COC[C@@H]2C)CC1]
In some embodiments, $R^2$ is
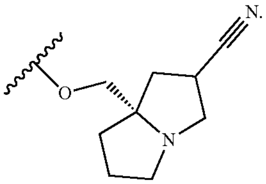 [SMILES: *OC[C@@]12CCCN1CC(C#N)C2]
In some embodiments, $R^2$ is
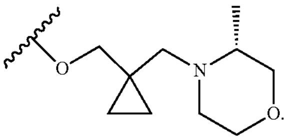 [SMILES: *OCC1(CN2CCOC[C@H]2C)CC1]
In some embodiments, $R^2$ is
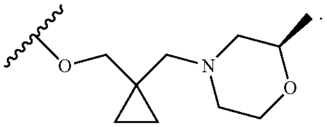 [SMILES: *OCC1(CN2CCO[C@H](C)C2)CC1]
In some embodiments, $R^2$ is
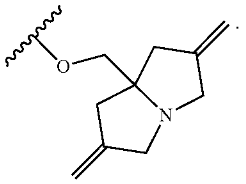 [SMILES: *OCC12CC(=C)CN1CC(=C)C2]
In some embodiments, $R^2$ is
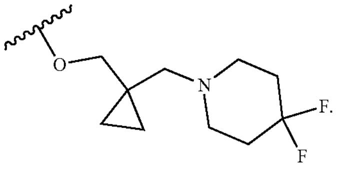 [SMILES: *OCC1(CN2CCC(F)(F)CC2)CC1]
In some embodiments, $R^2$
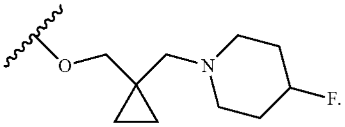 [SMILES: *OCC1(CN2CCC(F)CC2)CC1]
In some embodiments, $R^2$ is
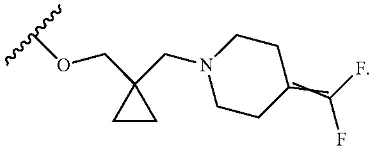 [SMILES: *OCC1(CN2CCC(=C(F)F)CC2)CC1]
In some embodiments, $R^2$ is
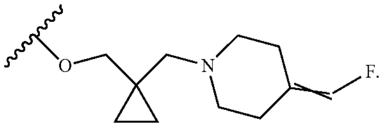
In some embodiments, $R^2$ is
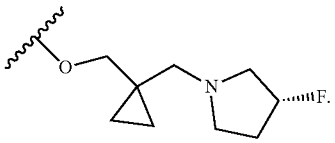 [SMILES: *OCC1(CN2CC[C@@H](F)C2)CC1]

In some embodiments, $R^2$ is
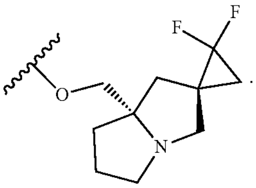 [SMILES: *OC[C@@]12CCCN1C[C@@]1(CC1(F)F)C2]
In some embodiments, $R^2$ is
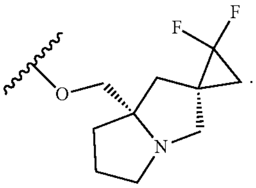 [SMILES: *OC[C@@]12CCCN1C[C@]1(CC1(F)F)C2]
In some embodiments, $R^2$ is
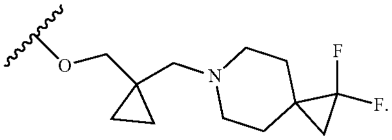 [SMILES: *OCC1(CN2CCC3(CC2)CC3(F)F)CC1]
In some embodiments of Formula (I), (II), (II-a), (III), (IV), (V), (VI), (VII), (VIII), or (IX), $R^2$ is
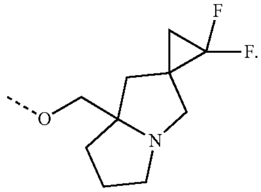
In some embodiments of the formulae above, $R^2$ is selected from
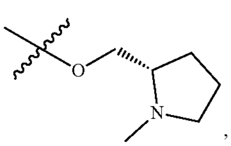
,
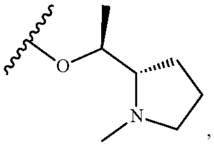
,
,
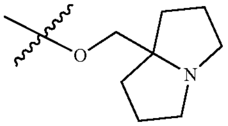
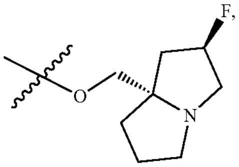
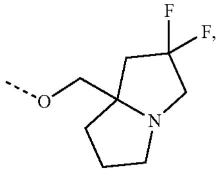
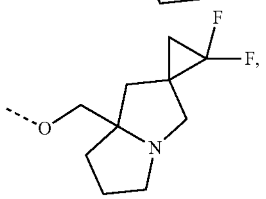
-continued
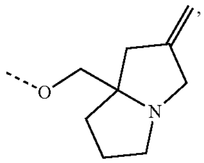
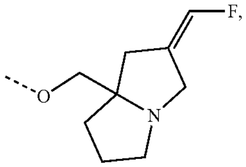
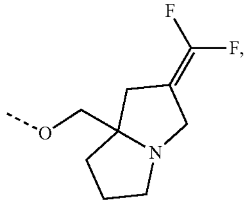
, and
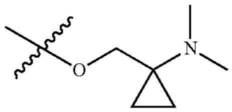
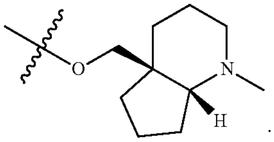
.
In some embodiments of Formula (I), (II), (II-a), (III), (IV), (V), (VI), (VII), (VIII), or (IX), $R^2$ is selected from
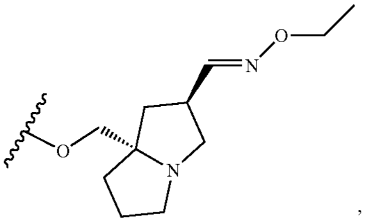
,
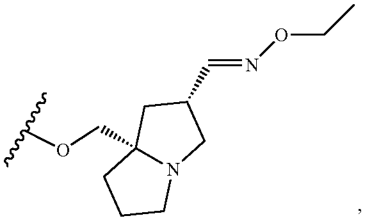
,
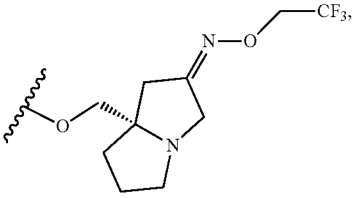
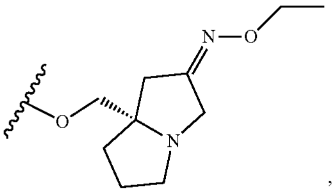
,
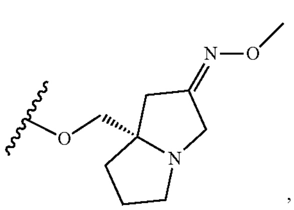
,
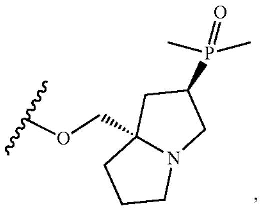
, -continued
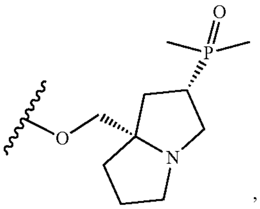
,
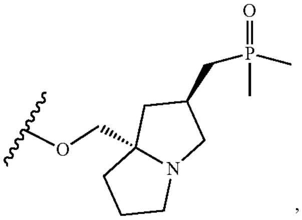
,
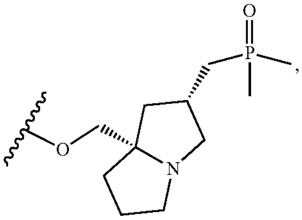
,
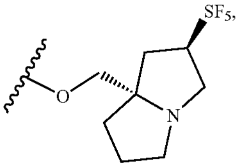
,
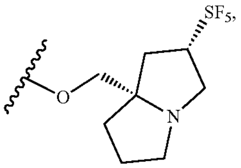
,
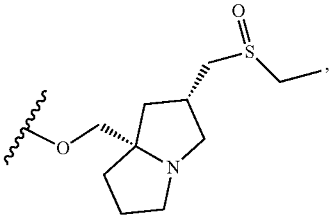
,
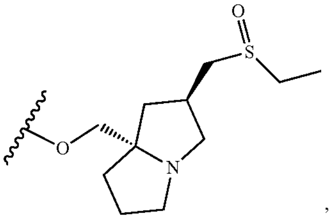
,
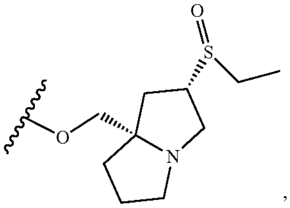
,
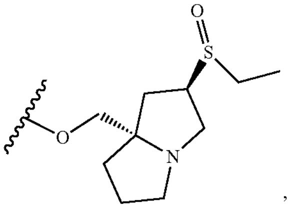
,
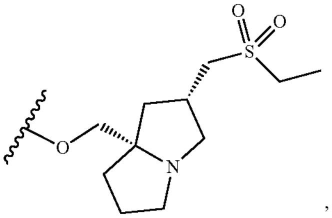
,
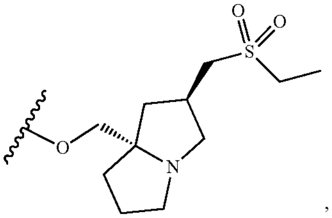
,
-continued
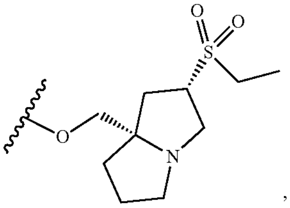
,
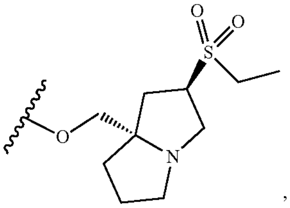
,
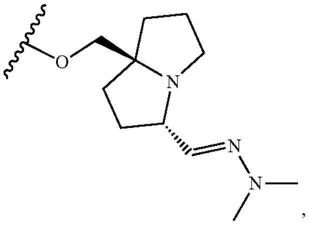
,
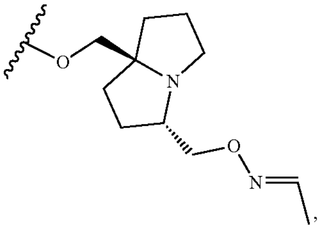
,
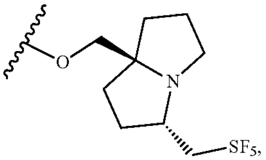
,
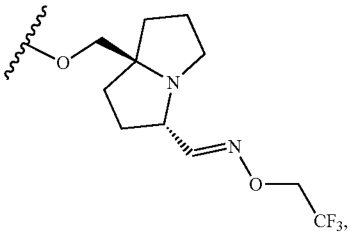
,
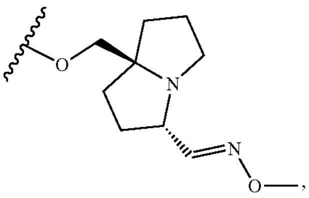
,
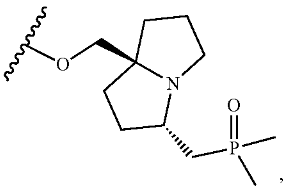
, -continued
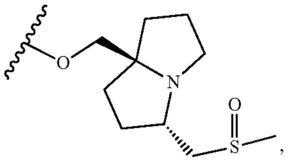
and
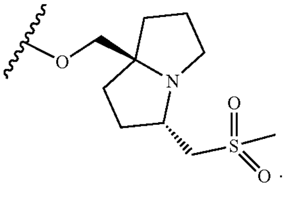
In some embodiments of Formula (I), (II), (II-a), (III), (IV), (V), (VI), (VII), (VIII), or (IX), $R^2$ is
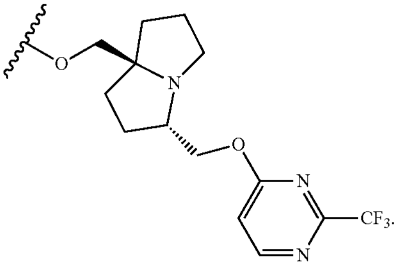 [SMILES: *OC[C@@]12CCCN1[C@H](COc1ccnc(C(F)(F)F)n1)CC2]
In some embodiments of Formula (I), (II), (II-a), (III), (IV), (V), (VI), (VII), (VIII), or (IX), $R^2$ is
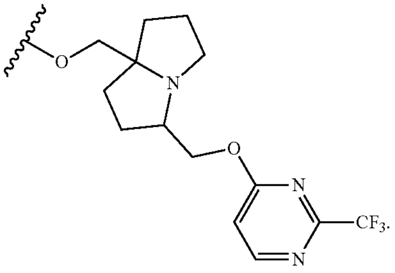 [SMILES: *OCC12CCCN1C(COc1ccnc(C(F)(F)F)n1)CC2]
In some embodiments of Formula (I), (II), (II-a), (III), (IV), (V), (VI), (VII), (VIII), or (IX), $R^2$ is selected from
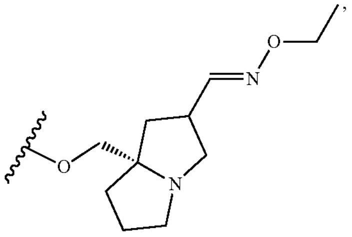
-continued
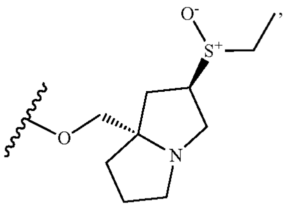
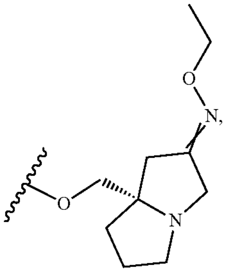
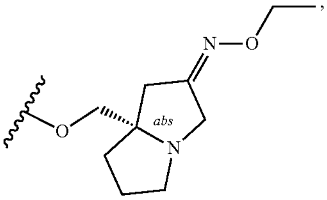
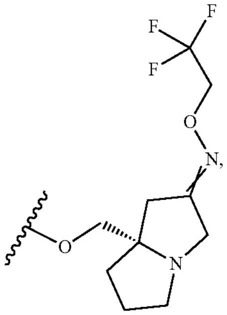
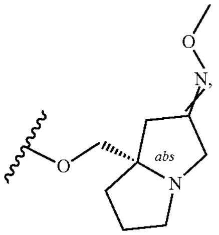
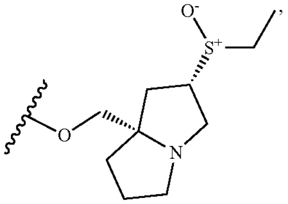
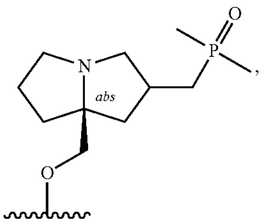
and
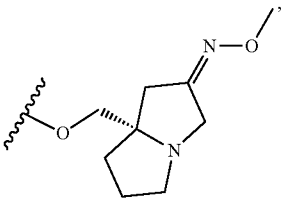
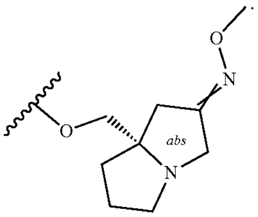 [SMILES: *OC[C@@]12CCCN1CC(=NOC)C2]
In some embodiments of Formula (I), (II), (II-a), (III), (IV), (V), (VI), (VII), (VIII), or (IX), $R^2$ is

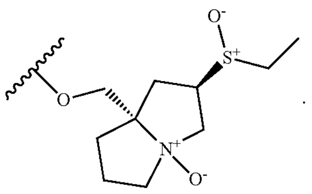 [SMILES: *OC[C@@]12CCC[N+]1([O-])C[C@H]([S+]([O-])CC)C2]

In some embodiments of Formula (I), (II), (II-a), (III), (IV), (V), (VI), (VII), (VIII), or (IX), $R^2$ is

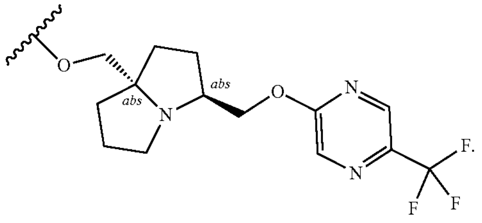 [SMILES: *OC[C@@]12CCCN1[C@H](COc1cnc(C(F)(F)F)cn1)CC2]

In some embodiments of Formula (I), (II), (II-a), (III), (IV), (V), (VI), (VII), (VIII), or (IX), $R^2$ is

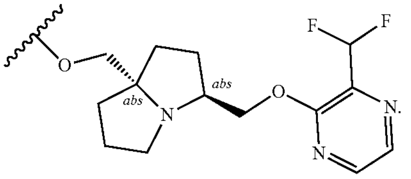 [SMILES: *OC[C@@]12CCCN1[C@H](COc1nccnc1C(F)F)CC2]

In some embodiments of Formula (I), (II), (II-a), (III), (IV), (V), (VI), (VII), (VIII), or (IX), $R^2$ is

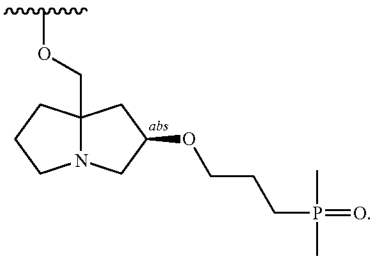 [SMILES: *OCC12CCCN1C[C@H](OCCCP(C)(C)=O)C2]

In some embodiments of Formula (I), (II), (II-a), (III), (IV), (V), (VI), (VII), (VIII), or (IX), $R^2$ is

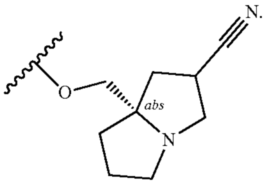 [SMILES: *OC[C@@]12CCCN1CC(C#N)C2]

In some embodiments of Formula (I), (II), (II-a), (III), (IV), (V), (VI), (VII), (VIII), or (IX), $R^2$ is

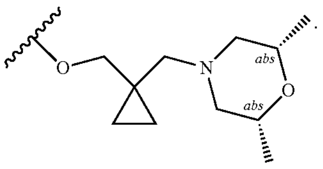 [SMILES: *OCC1(CN2C[C@@H](C)O[C@@H](C)C2)CC1]

In some embodiments of Formula (I), (II), (II-a), (III), (IV), (V), (VI), (VII), (VIII), or (IX), $R^2$ is

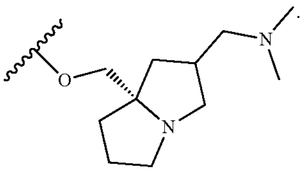 [SMILES: *OC[C@@]12CCCN1CC(CN(C)C)C2]

In some embodiments of Formula (I), (II), (II-a), (III), (IV), (V), (VI), (VII), (VIII), or (IX), $R^2$ is

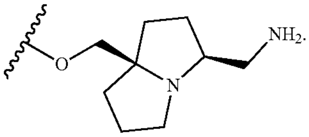 [SMILES: *OC[C@]12CCCN1[C@H](CN)CC2]

In some embodiments of Formula (I), (II), (II-a), (III), (IV), (V), (VI), (VII), (VIII), or (IX), $R^2$ is

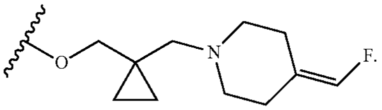 [SMILES: *OCC1(CN2CCC(=CF)CC2)CC1]

In some embodiments of Formula (I), (II), (II-a), (III), (IV), (V), (VI), (VII), (VIII), or (IX), $R^2$ is

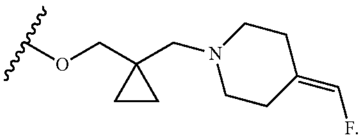 [SMILES: *OCC1(CN2CCC(=CF)CC2)CC1]

In some embodiments of Formula (I), (II), (II-a), (III), (IV), (V), (VI), (VII), (VIII), or (IX), $R^2$ is

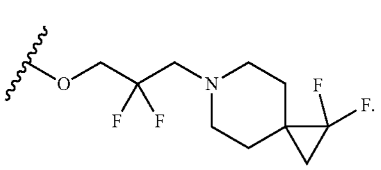 [SMILES: *OCC(F)(F)CN1CCC2(CC1)CC2(F)F]

In some embodiments of Formula (I), (II), (II-a), (III), (IV), (V), (VI), (VII), (VIII), or (IX), $R^2$ is

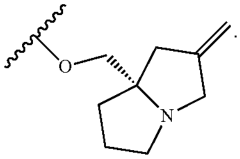 [SMILES: *OC[C@@]12CCCN1CC(=C)C2]
In some embodiments of Formula (I), (II), (II-a), (III), (IV), (V), (VI), (VII), (VIII), or (IX), $R^2$ is
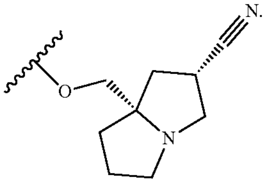 [SMILES: *OC[C@@]12CCCN1C[C@@H](C#N)C2]
In some embodiments, for a compound of Formula (I), (II), (II-a), (III), (IV), (V), (VI), (VII), (VIII), or (IX), $R^2$ is selected from
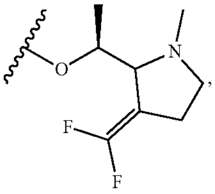
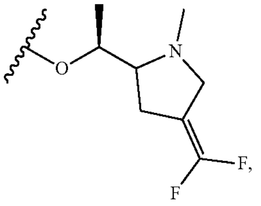
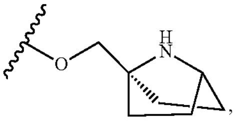
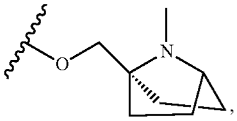
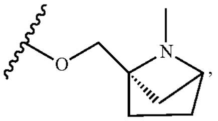
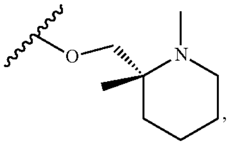
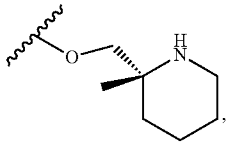
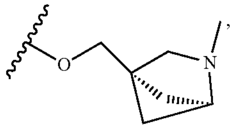
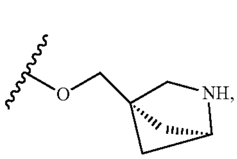
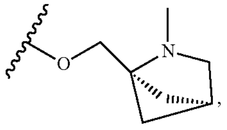
-continued
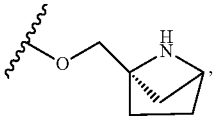
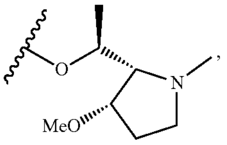
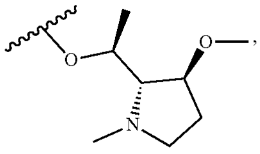
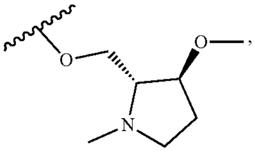
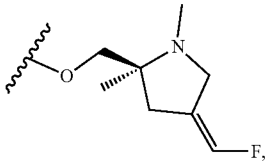
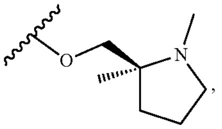
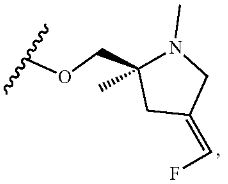
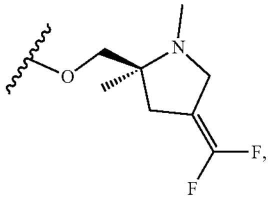
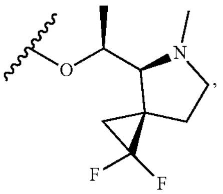
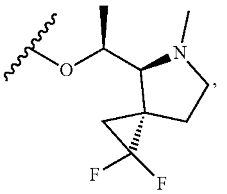
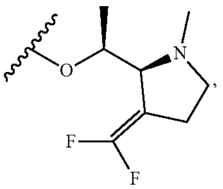
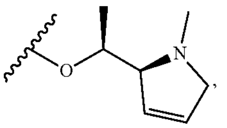
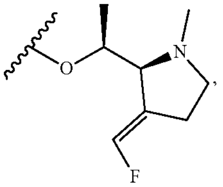
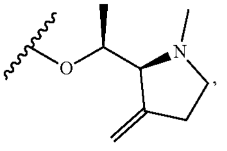
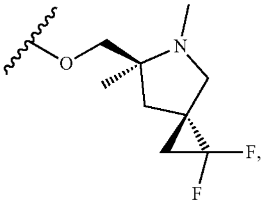
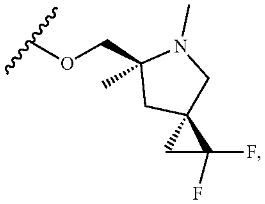
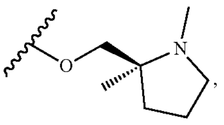
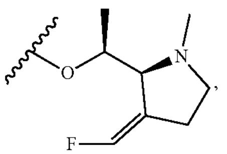

-continued

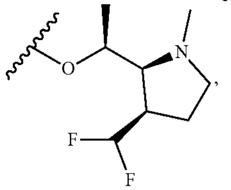, 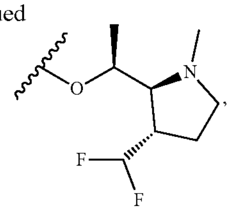

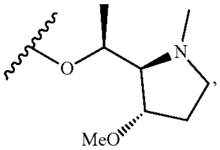, 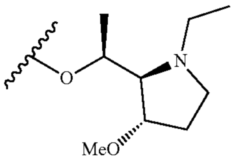,

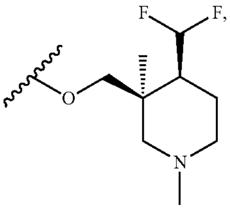, and 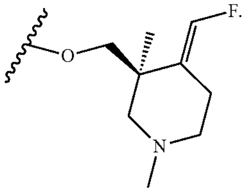.

In some embodiments, for a compound of Formula (I), (II), (II-a), (III), (IV), (V), (VI), (VII), (VIII), or (IX), $R^2$ is substituted with one, two, three, or four substituents independently selected from halogen, oxo, $C_{1-6}$ alkyl, —$OR^{22}$, —$N(R^{22})(R^{23})$, —$C(R^{21})_2$, and —$OC(O)N(R^{22})(R^{23})$, wherein $C_{1-6}$ alkyl is optionally substituted with one or more substituents independently selected from halogen, —CN, —$OR^{22}$, —$N(R^{22})(R^{23})$, and —$OC(O)N(R^{22})(R^{23})$. In some embodiments, $R^2$ is substituted with one, two, three, or four substituents independently selected from halogen, $C_{1-3}$ alkyl, $C_{1-3}$ haloalkyl, and —$C(R^{21})_2$, wherein $R^{21}$ is independently selected at each occurrence from hydrogen, halogen, and $C_{1-3}$ alkyl. In some embodiments, $R^2$ is substituted with one, two, three, or four substituents independently selected from halogen, $C_{1-3}$ alkyl, $C_{1-3}$ haloalkyl, —$CH_2$, —CHF, and —$CF_2$. In some embodiments, $R^2$ is substituted with =$C(R^{21})_2$, such as =$CF_2$. In some embodiments, $R^2$ is substituted with halogen, such as fluorine. In some embodiments, $R^2$ is substituted with one, two, three, or four substituents independently selected from

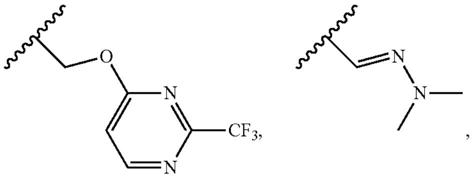

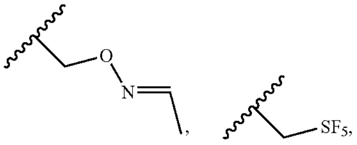

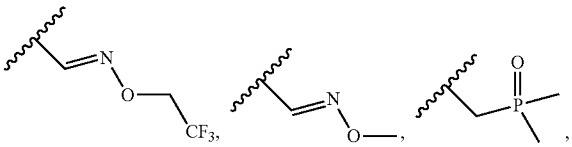

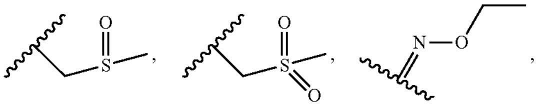

-continued

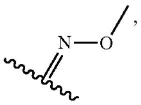, 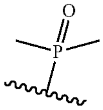, 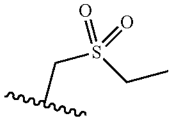,

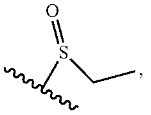, 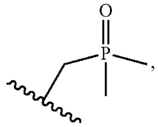, 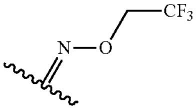,

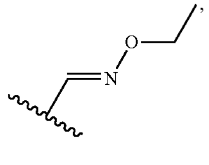, 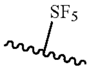, 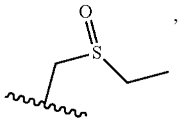, and

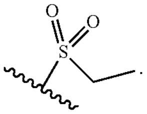.

In some embodiments, $R^2$ is substituted with a substituent selected from

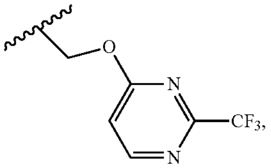, 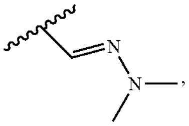,

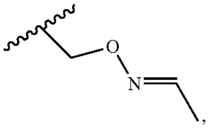, 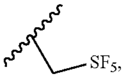, 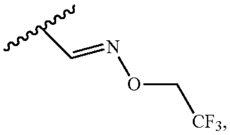,

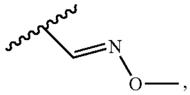, 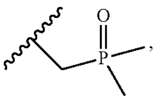, 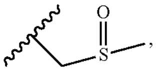,

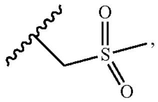, 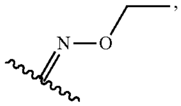, 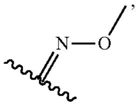,

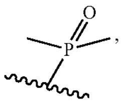, 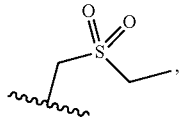, 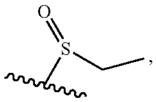,

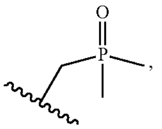, 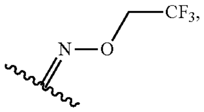, 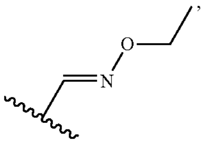,

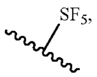, 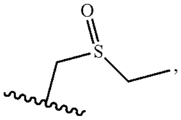, and 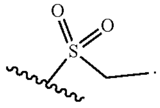.

In some embodiments, $R^2$ is substituted with a substituent selected from

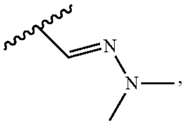, 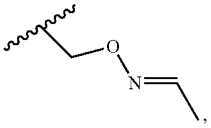, 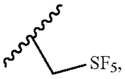, 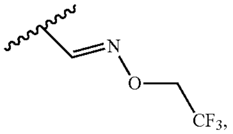, 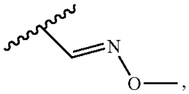, 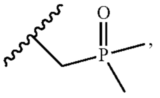, 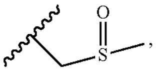, 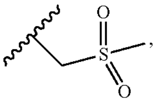, 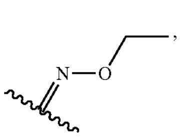, 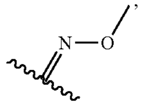, 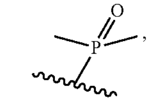, 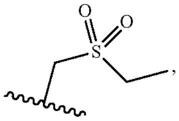, 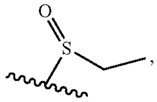, 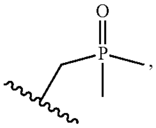, 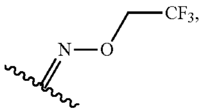, 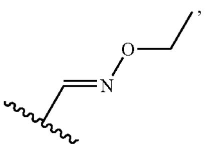, , 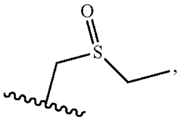, and 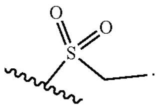.

In some embodiments, $R^2$ is substituted with a substituent selected from $—SF_5$, $—N—OR^{22}$, $=N—N(R^{22})(R^{23})$, $—P(O)(R^{22})(R^{23})$, $—ON=R^{22}$, $—S(O)R^{22}$, and $—S(O)_2R^{22}$. In some embodiments, $R^2$ is substituted with a substituent selected from $—SF_5$, $=N—OR^{22}$, $—N—N(R^{22})(R^{23})$, $—P(O)(R^{22})(R^{23})$, $—ON=R^{22}$, $—S(O)R^{22}$, and $—S(O)_2R^{22}$; wherein $R^{22}$ and $R^{23}$ are independently selected from $C_{1-4}$ alkyl and $C_{1-4}$ haloalkyl. In some embodiments, $R^2$ is substituted with $C_{1-6}$ alkyl, wherein the $C_{1-6}$ alkyl is substituted with a substituent selected from $—SF_5$, $—N—OR^{22}$, $=N—N(R^{22})(R^{23})$, $—P(O)(R^{22})(R^{23})$, $—ON=R^{22}$, $—S(O)R^{22}$, and $—S(O)_2R^{22}$. In some embodiments, $R^2$ is substituted with $C_{1-6}$ alkyl, wherein the $C_{1-6}$ alkyl is substituted with a substituent selected from $—SF_5$, $=N—OR^{22}$, $—N—N(R^{22})(R^{23})$, $—P(O)(R^{22})(R^{23})$, $—ON=R^{22}$, $—S(O)R^{22}$, and $—S(O)_2R^{22}$; wherein $R^{22}$ and $R^{23}$ are independently selected from $C_{1-4}$ alkyl and $C_{1-4}$ haloalkyl.

In some embodiments, for a compound of Formula (I), (II), (II-a), (III), (IV), (V), (VI), or (VII), $R^3$ is independently selected at each occurrence from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{12}$, $—SR^{12}$, $—N(R^{12})(R^{13})$, $—C(O)OR^{12}$, $—OC(O)N(R^{12})(R^{13})$, $—N(R^{12})C(O)N(R^{12})(R^{13})$, $—N(R^{12})C(O)OR^{12}$, $—N(R^{12})S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, $—S(O)(NR^{12})N(R^{12})(R^{13})$, and $—OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), and -(2- to 6-membered heteroalkyl)-(3- to 12-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form $=O$, $=NR^{12}$, or $=C(R^{14})_2$. In some embodiments, two $R^3$ are taken together with the atom or atoms to which they are attached to form $C_{3-8}$ carbocycle or 3- to 8-membered heterocycle, each of which is optionally substituted with one, two, or three $R^{20}$. In some embodiments, two $R^3$ are taken together with the atom to which they are attached to form $C_{3-8}$ carbocycle or 3- to 8-membered heterocycle, each of which is optionally substituted with one, two, or three $R^{20}$. In some embodiments, two $R^3$ attached to adjacent atoms are taken together with the atoms to which they are attached to form $C_{3-8}$ carbocycle or 3- to 8-membered heterocycle, each of which is optionally substituted with one, two, or three $R^{20}$. In some embodiments, two $R^3$ are taken together to form $=O$, $=NR^{12}$, or $=C(R^{14})_2$.

In some embodiments, for a compound of Formula (I), (II), (II-a), (III), (IV), (V), (VI), or (VII), $R^3$ is independently selected at each occurrence from halogen, —CN, $C_{1-6}$ alkyl, $C_{2-6}$ alkenyl, $C_{2-6}$ alkynyl, $—C_{0-6}$ alkyl-($C_{3-6}$ carbocycle), -(2- to 6-membered heteroalkyl)-($C_{3-6}$ carbocycle), $—C_{0-6}$ alkyl-(3- to 6-membered heterocycle), -(2- to 6-membered heteroalkyl)-(3- to 6-membered heterocycle), $—OR^{12}$, and $—N(R^{12})(R^{13})$, wherein $C_{1-6}$ alkyl, $C_{2-6}$ alkenyl, $C_{2-6}$ alkynyl, $—C_{0-6}$ alkyl-($C_{3-6}$ carbocycle), -(2- to 6-membered heteroalkyl)-($C_{3-6}$ carbocycle), $—C_{0-6}$ alkyl-(3- to 6-membered heterocycle), and -(2- to 6-membered heteroalkyl)-(3- to 6-membered heterocycle) are optionally substituted with one, two, or three $R^{20}$; wherein two $R^3$ are optionally taken together with the atom or atoms to which they are attached to form $C_{3-8}$ carbocycle or 3- to 8-membered heterocycle, each of which is optionally substituted with one, two, or three $R^{20}$; and further wherein two $R^3$ are optionally taken together to form $=O$, $=NR^{12}$, or $=C(R^{14})_2$. In some embodiments, $R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$. In some embodiments, $R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and $—OCH_3$. In some embodiments, $R^3$ is $C_{2-3}$ alkenyl. In some embodiments, $R^3$ is $C_{2-3}$ alkynyl. In some embodiments, $R^3$ is $C_{1-3}$ haloalkyl. In some embodiments, $R^3$ is selected from $—CHCH_2$, —CCH, $—CH_2CN$, and $—CHF_2$.

In some embodiments, for a compound of Formula (I), (II), (II-a), (III), (IV), (V), (VI), or (VII), $R^3$ is independently selected at each occurrence from
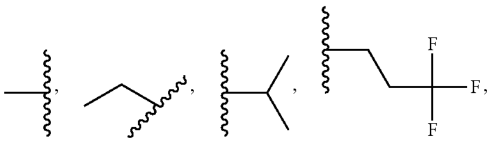
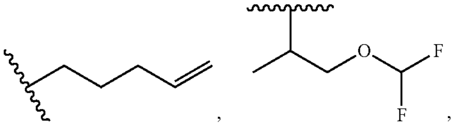
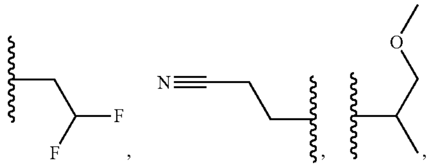
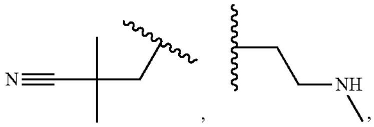
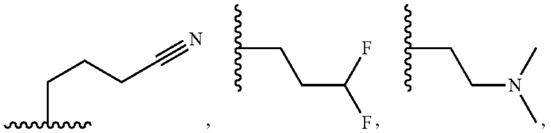
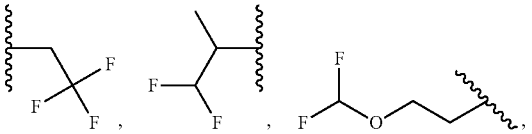
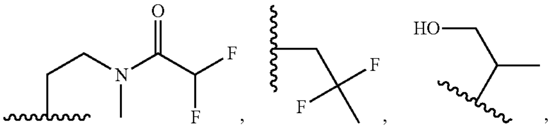
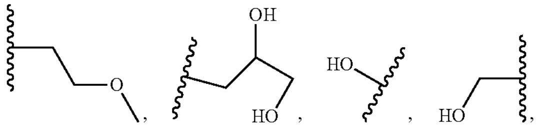
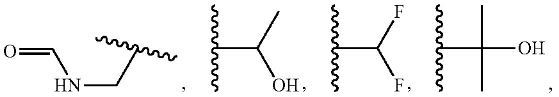
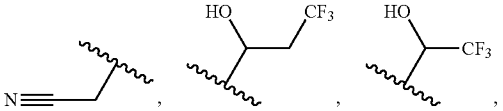
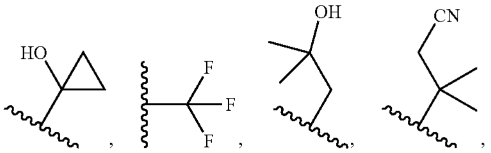
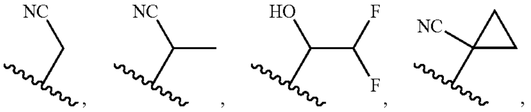
-continued
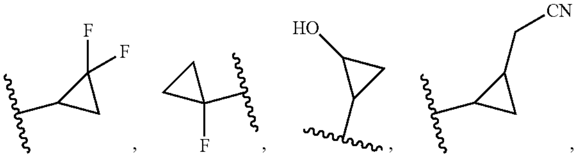
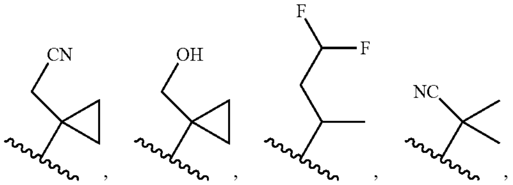
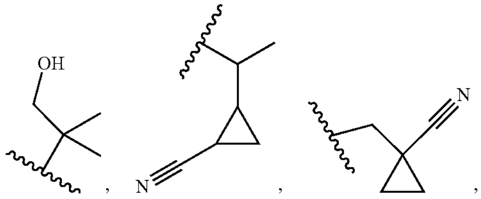
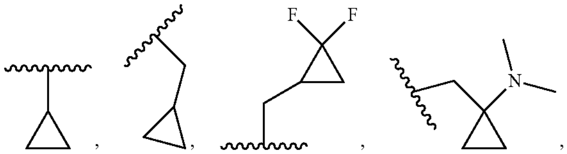
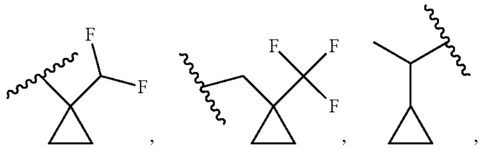
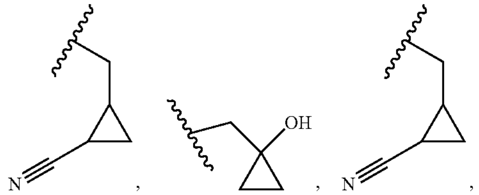
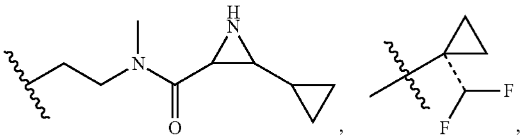
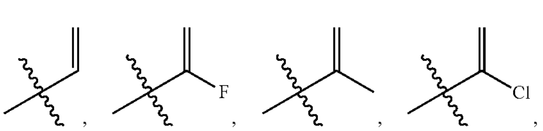
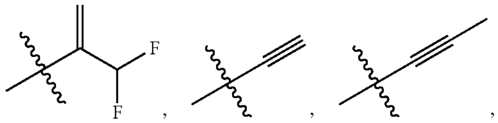
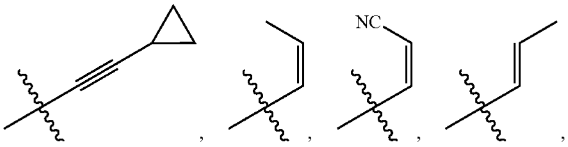

-continued
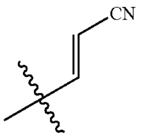, 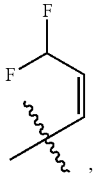, 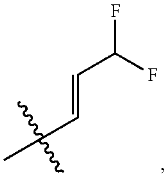,
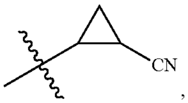, 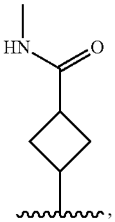, 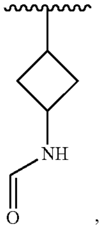,
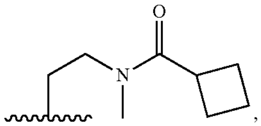, 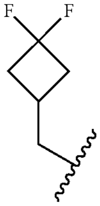, 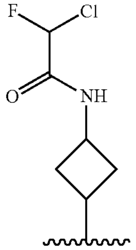,
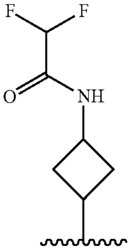, 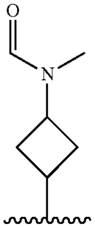, 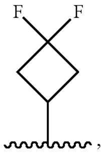, 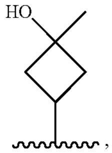,
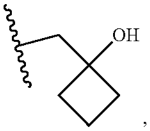, 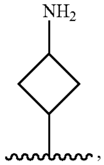, 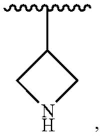, 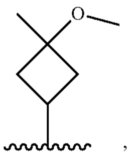,
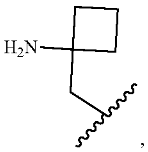, 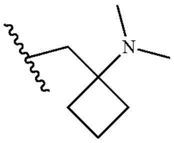, 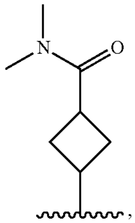,
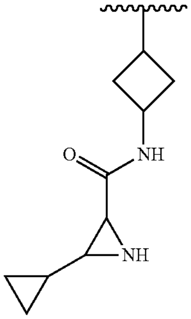, 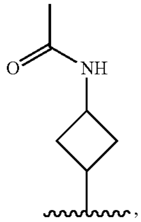, 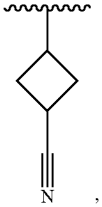,
-continued
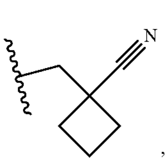, 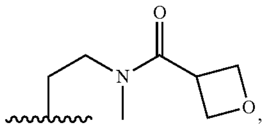, 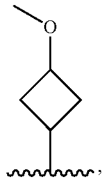,
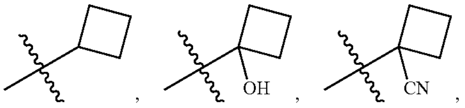
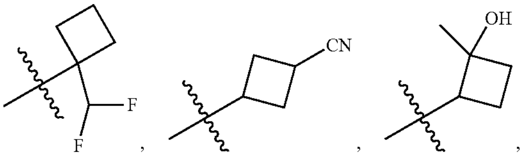
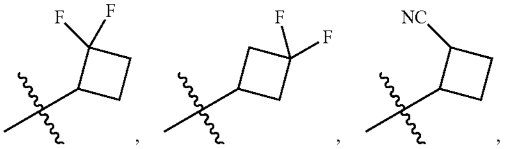
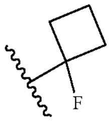, 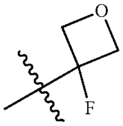, 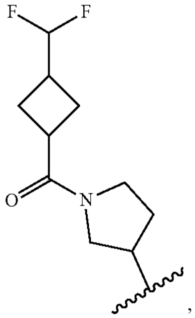,
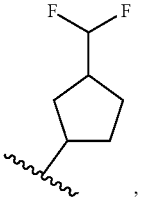, 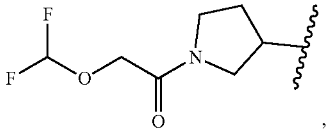,
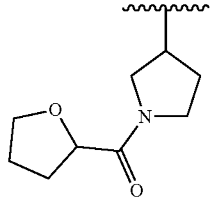, 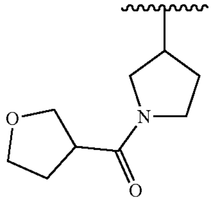,
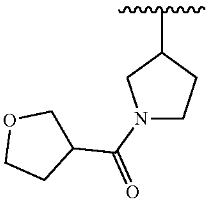, 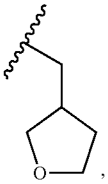, 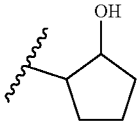, -continued
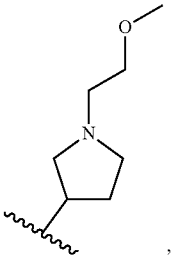,
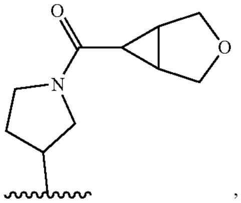,
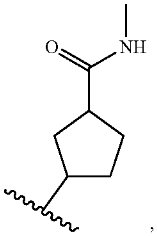,
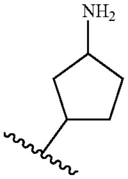,
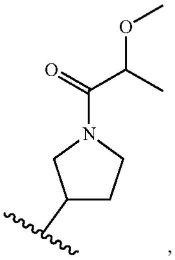,
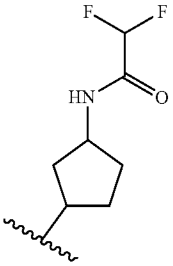,
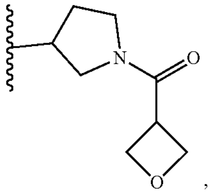,
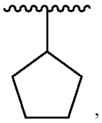,
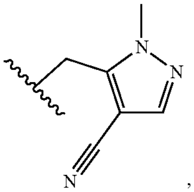,
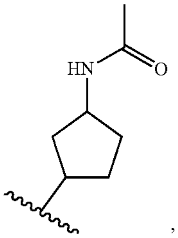,
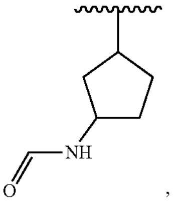,
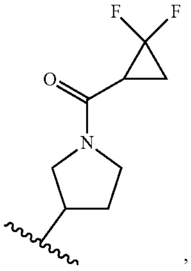,
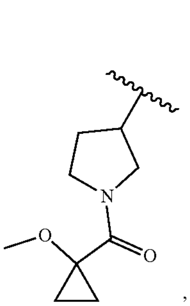,
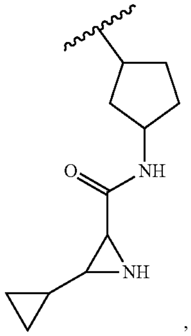,
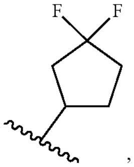,
-continued
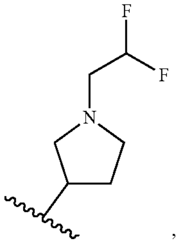,
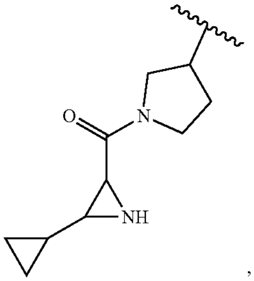,
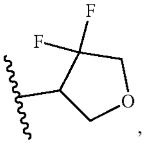,
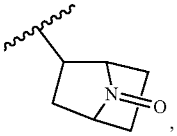,
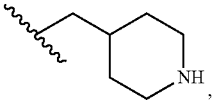
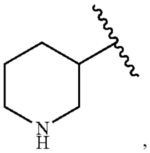,
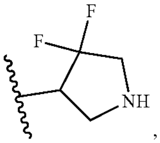,
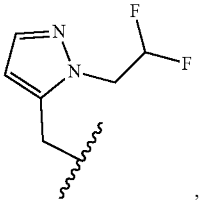,
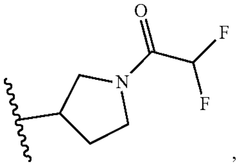,
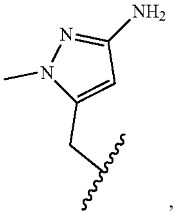,
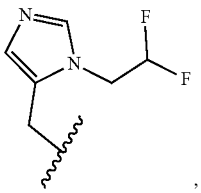,
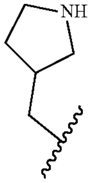,
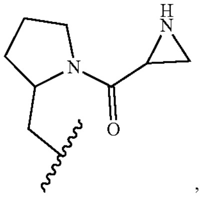,
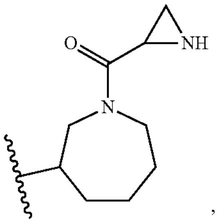,
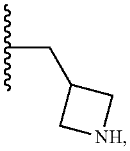
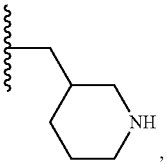,
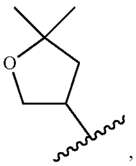,
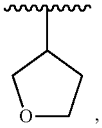,
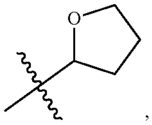,
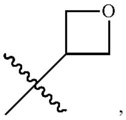,
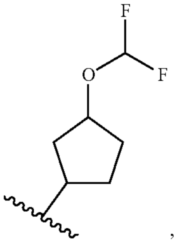,
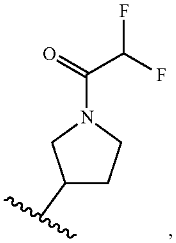,
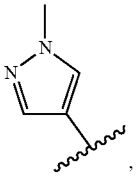, -continued
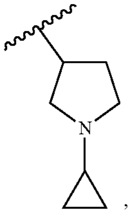, 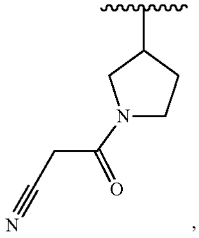, 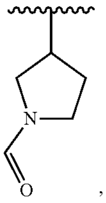,
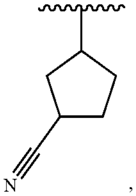, 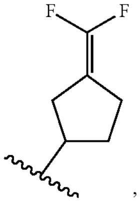, 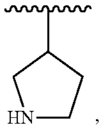,
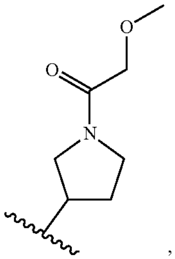, 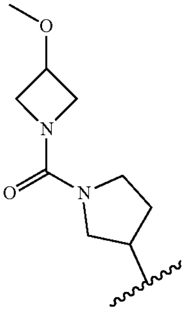, 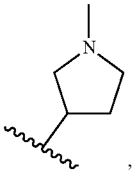,
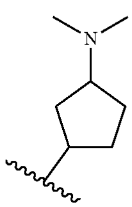, 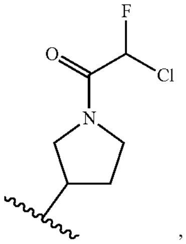, 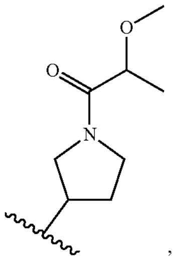,
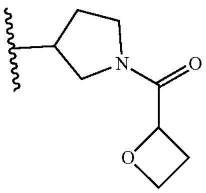, 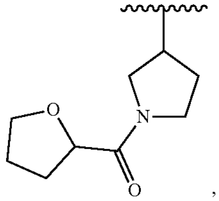,
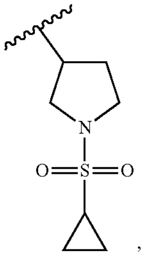, 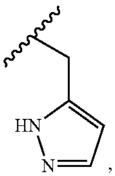, 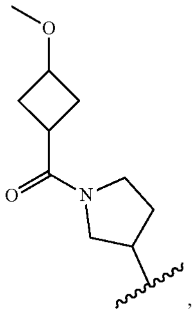,
-continued
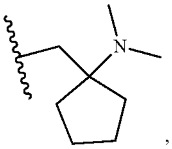, 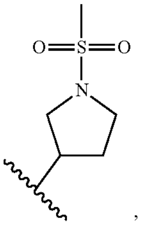, 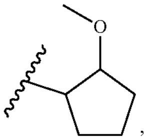,
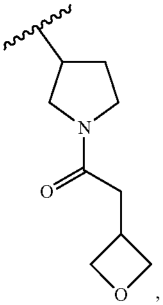, 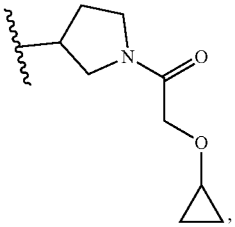,
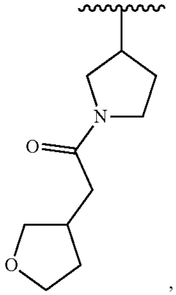, 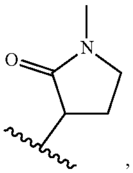, 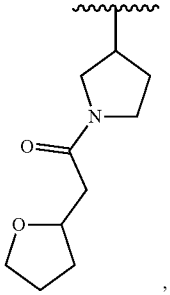,
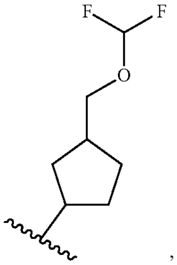, 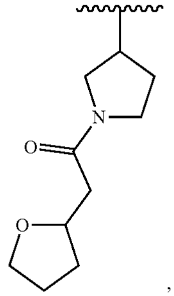, 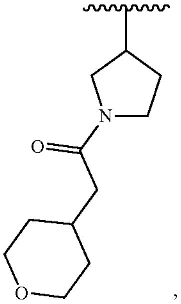,
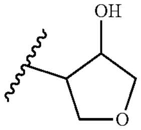, 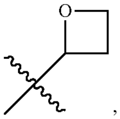, 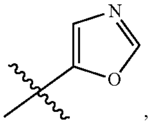,
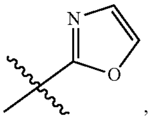, 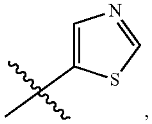, 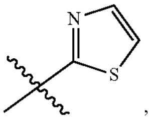,
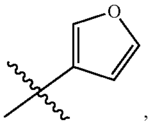, 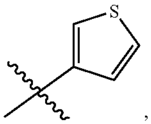, 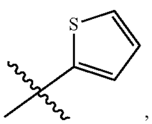,
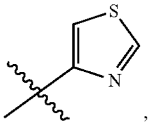, 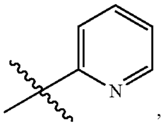, 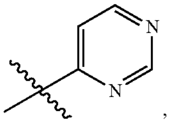, -continued
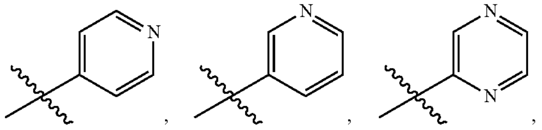
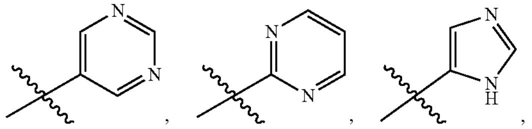
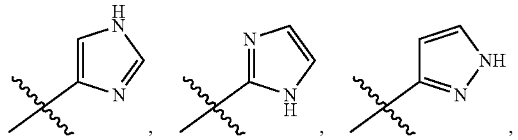
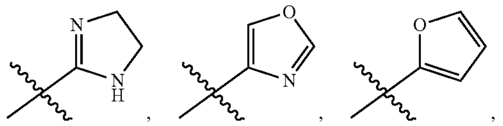
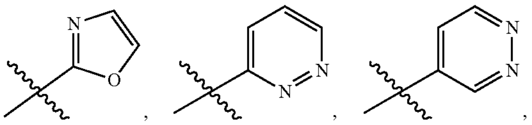
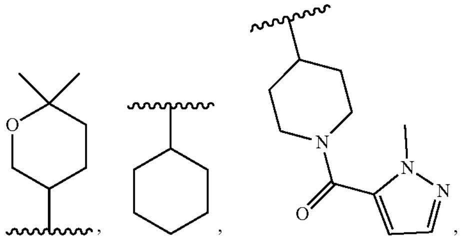
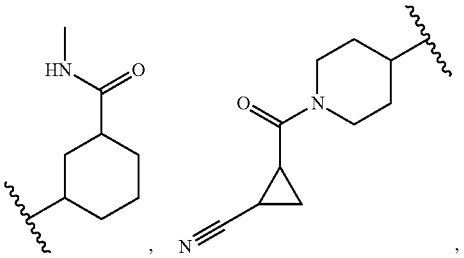
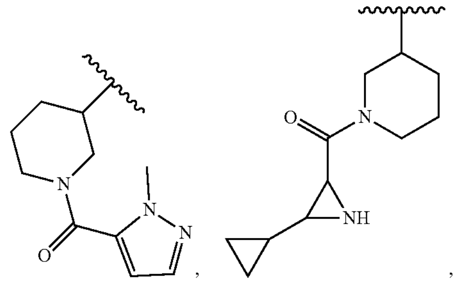
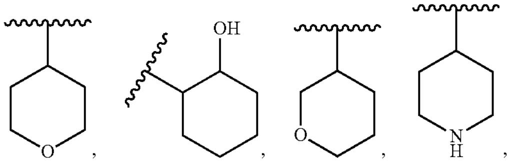
-continued
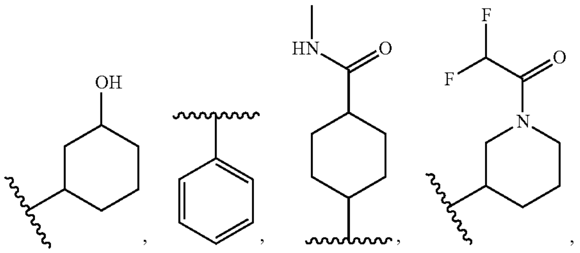
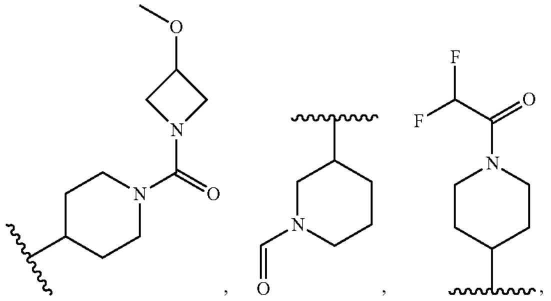
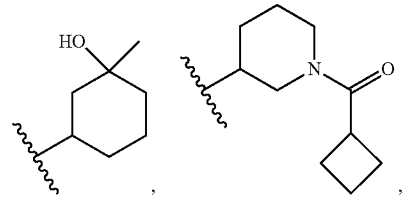
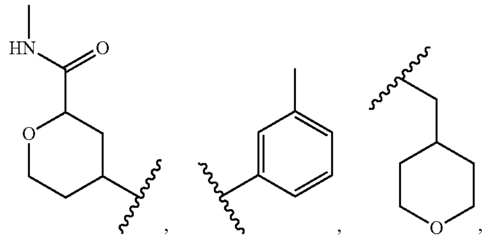
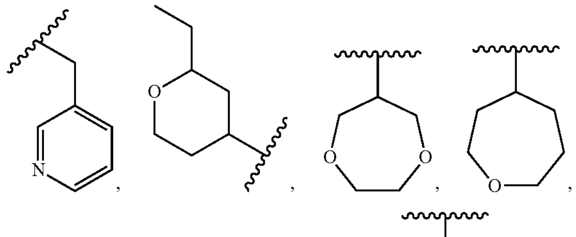
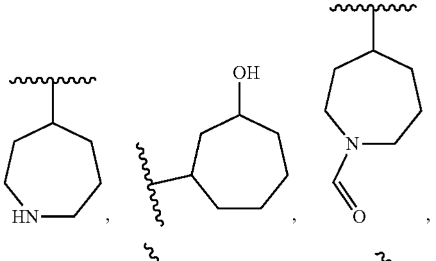
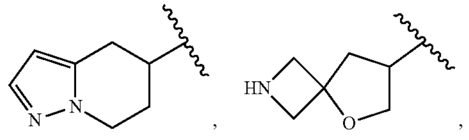
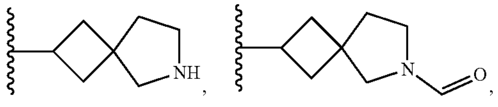

-continued

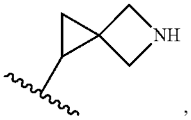, 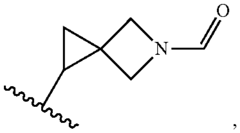,

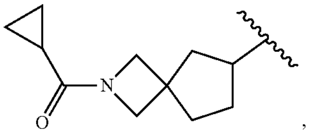, 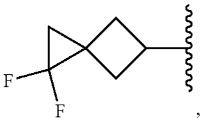,

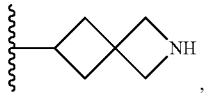,

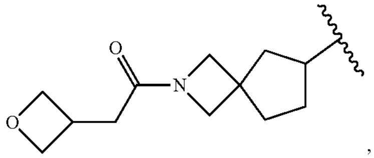,

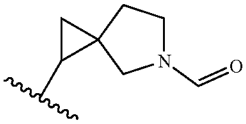, 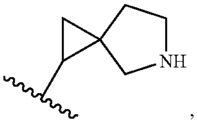,

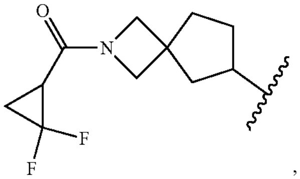, 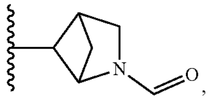,

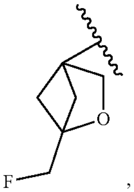, 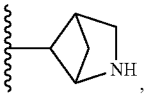, 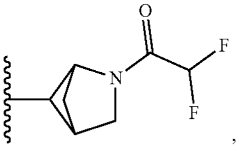,

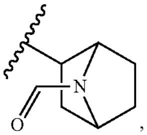, 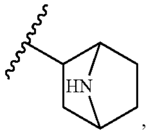, 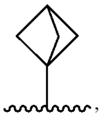,

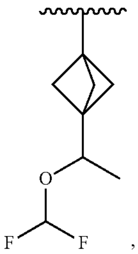, 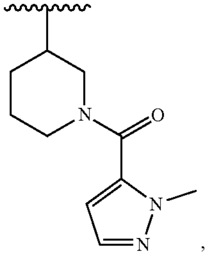,

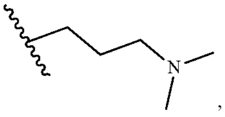, 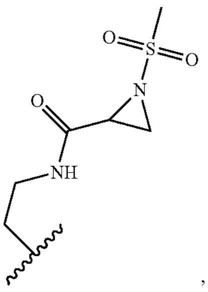,

-continued

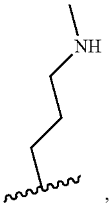, and 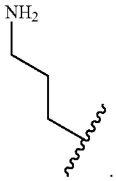.

In some embodiments, for a compound of Formula (I), (II), (II-a), (III), (IV), (V), (VI), or (VII), m is 0, 1, or 2. In some embodiments, m is 0 or 1. In some embodiments, m is 1 or 2. In some embodiments, m is 0. In some embodiments, m is 1. In some embodiments, m is 2. In some embodiments, m is 3.

In some embodiments, for a compound of Formula (I), (II), (II-a), (III), (IV), (V), (VI), or (VII), $R^6$ is selected from hydrogen, halogen, —CN, $C_{1-6}$ alkyl, 2- to 6-membered heteroalkyl, —$C_{0-6}$ alkyl-($C_{3-12}$ carbocycle), —$C_{0-6}$ alkyl-(3- to 12-membered heterocycle), —$OR^{12}$, and —$N(R^{12})(R^{13})$, wherein $C_{1-6}$ alkyl, 2- to 6-membered heteroalkyl, —$C_{0-6}$ alkyl-($C_{3-12}$ carbocycle), and —$C_{0-6}$ alkyl-(3- to 12-membered heterocycle) are optionally substituted with one or more $R^{20}$. In some embodiments, $R^6$ is selected from hydrogen, halogen, and $C_{1-3}$ alkyl. In some embodiments, $R^6$ is selected from hydrogen, halogen, and $C_{1-3}$ haloalkyl. In some embodiments, $R^6$ is selected from hydrogen and halogen. In some embodiments, $R^6$ is hydrogen. In some embodiments, $R^6$ is halogen, such as fluorine. In some embodiments, $R^6$ is chlorine. In some embodiments, $R^6$ is —$CF_3$. In some embodiments, $R^6$ is —$CHF_2$. In some embodiments, $R^6$ is —$CH_2CN$. In some embodiments, $R^6$ is —$NH_2$. In some embodiments, $R^6$ is —$N(CH_3)_2$. In some embodiments, $R^6$ is —$N(CH_2CH_3)_2$. In some embodiments, $R^6$ is —$SF_5$.

In some embodiments, for a compound of Formula (I), (II), (II-a), (III), (IV), (V), (VI), or (VII), $R^8$ is selected from hydrogen, halogen, —CN, $C_{1-6}$ alkyl, 2- to 6-membered heteroalkyl, —$C_{0-6}$ alkyl-($C_{3-12}$ carbocycle), —$C_{0-6}$ alkyl-(3- to 12-membered heterocycle), —$OR^{12}$, and —$N(R^{12})(R^{13})$, wherein $C_{1-6}$ alkyl, 2- to 6-membered heteroalkyl, —$C_{0-6}$ alkyl-($C_{3-12}$ carbocycle), and —$C_{0-6}$ alkyl-(3- to 12-membered heterocycle) are optionally substituted with one or more $R^{20}$. In some embodiments, $R^8$ is selected from hydrogen, halogen, and $C_{1-3}$ alkyl. In some embodiments, $R^8$ is selected from hydrogen and halogen. In some embodiments, $R^8$ is hydrogen. In some embodiments, $R^8$ is halogen, such as chlorine. In some embodiments, $R^8$ is fluorine. In some embodiments, $R^6$ and $R^8$ are independently selected from hydrogen, halogen, and $C_{1-3}$ haloalkyl. In some embodiments, $R^6$ and $R^8$ are independently selected from $C_{1-3}$ haloalkyl and halogen. In some embodiments, $R^6$ and $R^8$ are independently selected from hydrogen, halogen, and —$CF_3$. In some embodiments, $R^6$ and $R^8$ are independently selected from —Cl, —F, and —$CF_3$. In some embodiments, $R^6$ and $R^8$ are independently selected from hydrogen and halogen.

In some embodiments, for a compound of Formula (I), (II), (II-a), (III), (IV), (V), (VI), or (VII), n is 0, 1, 2, or 3. In some embodiments, n is 1. In some embodiments, n is 2.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1; and $R^6$ and $R^8$ are independently selected from hydrogen and halogen.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1; and $R^6$ and $R^8$ are independently selected from hydrogen, halogen, and —$CF_3$.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ and $R^8$ are independently selected from hydrogen and halogen; and n is 1.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ and $R^8$ are independently selected from hydrogen, halogen, and —$CF_3$; and n is 1.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is chlorine; and $R^8$ is fluorine.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is —$CF_3$; and $R^8$ is fluorine.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is chlorine;

$R^8$ is fluorine; and n is 1.

In some embodiments, for a compound of Formula (I), (II), (II-a), (III), (IV), (V), or (VI):

$R^2$ is selected from hydrogen, $C_{1-3}$ alkyl, —$OR^{12}$, and 3- to 10-membered heterocycle, wherein $C_{1-3}$ alkyl and 3- to 10-membered heterocycle are optionally substituted with one, two, or three $R^{20}$;

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three $R^{20}$;

m is 0 or 1;

$R^6$ is —$CF_3$;

$R^8$ is fluorine; and n is 1.

In some embodiments, for a compound of Formula (I), (II), (II-a), (III), (IV), (V), or (VI):

$R^2$ is

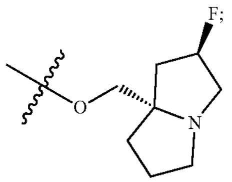 [SMILES: *OC[C@@]12CCCN1C[C@H](F)C2]

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is chlorine; and $R^8$ is fluorine.

In some embodiments, for a compound of Formula (I), (II), (II-a), (III), (IV), (V), or (VI):

$R^2$ is selected from

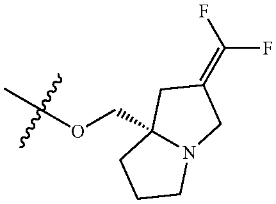

and

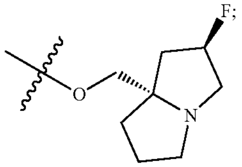

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$; and $R^8$ is fluorine.

In some embodiments, for a compound of Formula (I), (II), (II-a), (III), (IV), (V), or (VI):

$R^2$ is

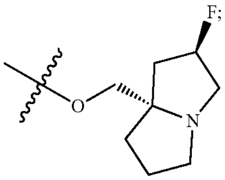 [SMILES: *OC[C@@]12CCCN1C[C@H](F)C2]

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is chlorine;

$R^8$ is fluorine; and n is 1.

In some embodiments, for a compound of Formula (I), (II), (II-a), (III), (IV), (V), or (VI):

$R^2$ is selected from

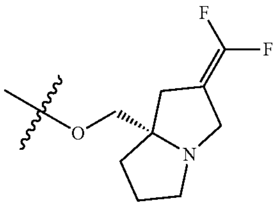

and

-continued

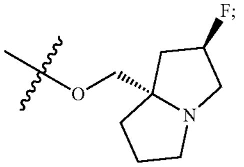

$R^3$ is independently selected at each occurrence from $C_{1-6}$ alkyl, $C_{2-6}$ alkenyl, $C_{2-6}$ alkynyl, $C_{3-8}$ carbocycle, and 3- to 8-membered heterocycle, each of which is optionally substituted with one, two, or three substituents independently selected from halogen, —CN, —OH, and —$OCH_3$;

m is 0 or 1;

$R^6$ is selected from chlorine and —$CF_3$;

$R^8$ is fluorine; and n is 1.

In some embodiments, the compound of Formula (I), (II), (IV), or (V), is selected from:

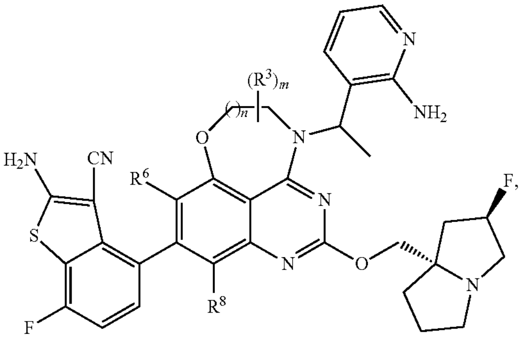

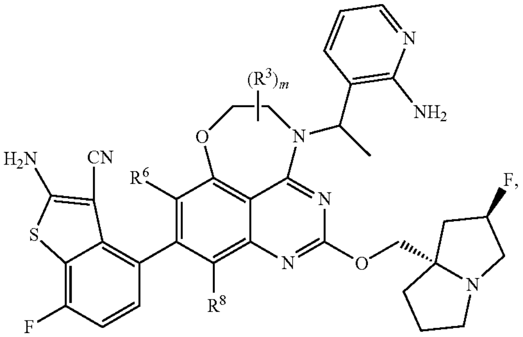

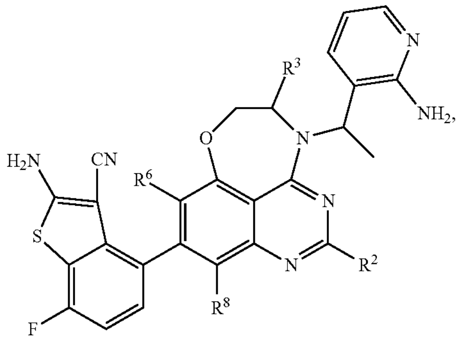

-continued
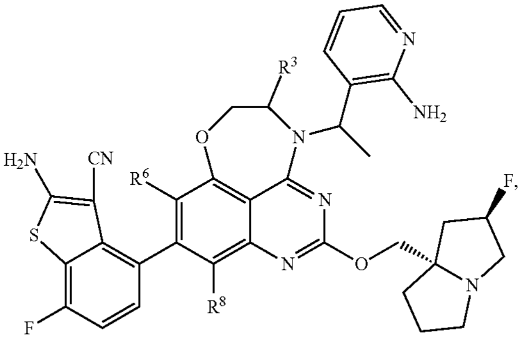
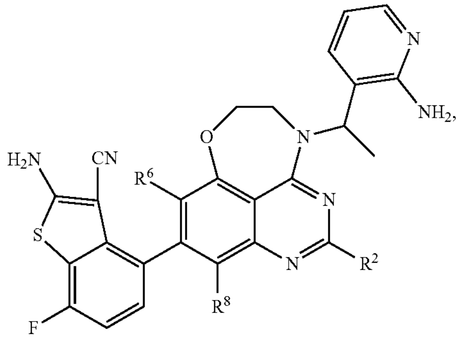
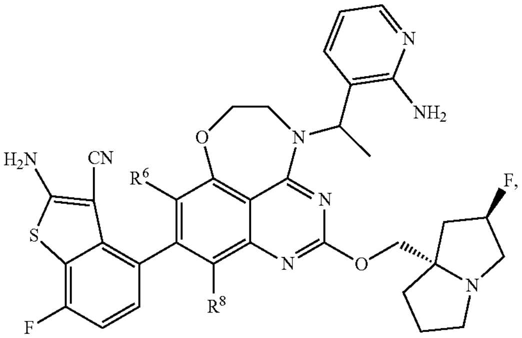
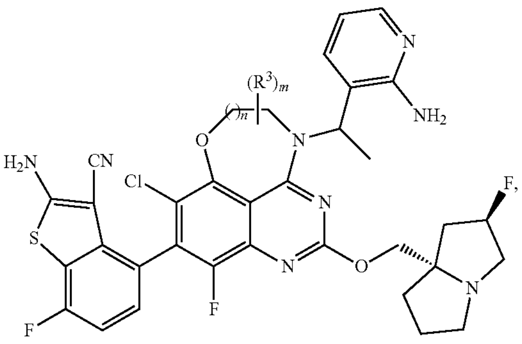
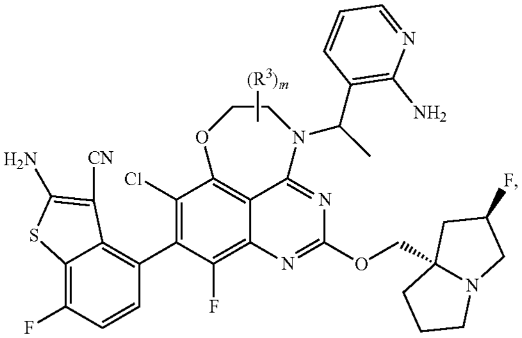
-continued
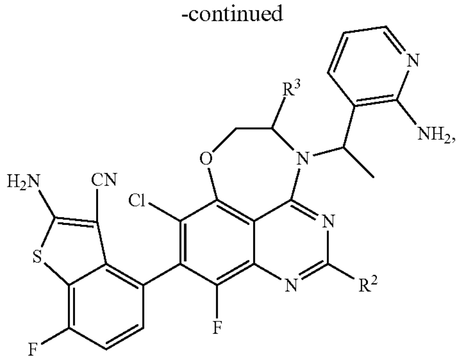
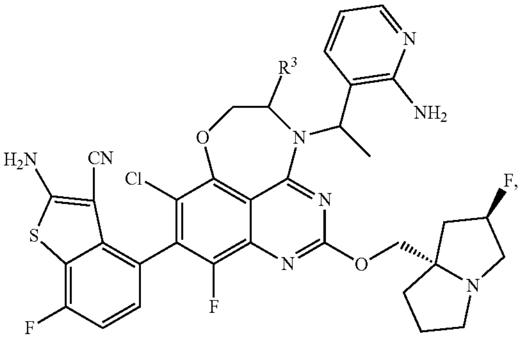
and
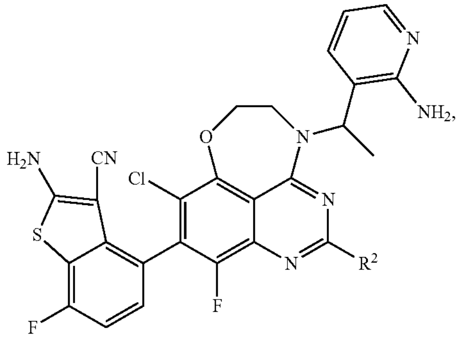
or a pharmaceutically acceptable salt or solvate thereof.
In some embodiments, the compound of Formula (I), (II), (II-a), (IV), or (V) is selected from:
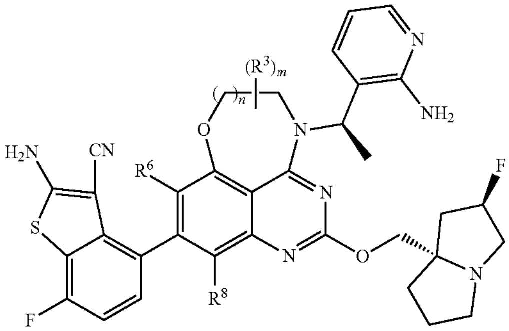
, -continued
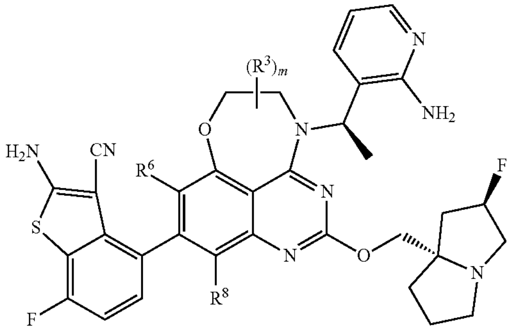
,
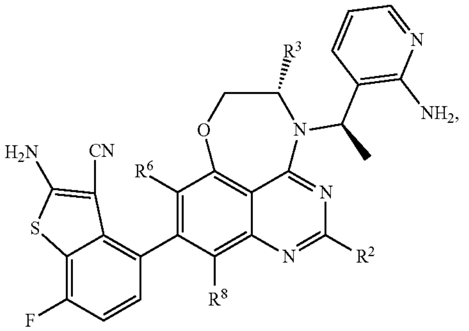
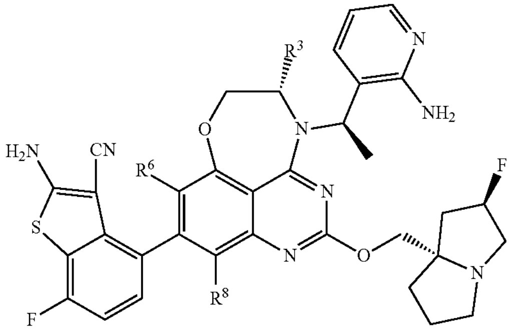
,
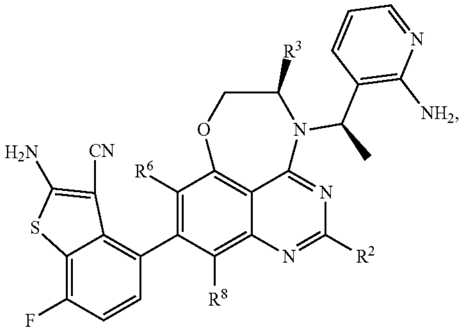
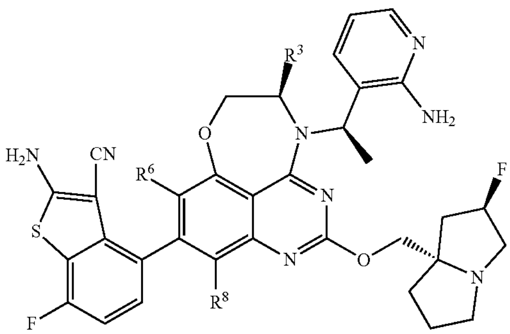
,
-continued
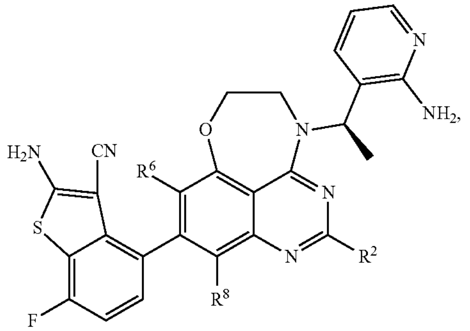
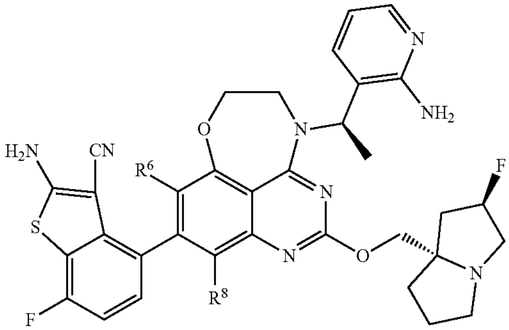
,
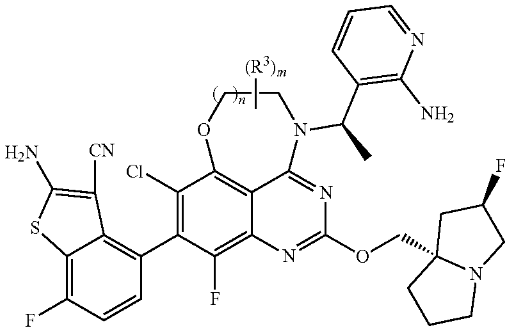
,
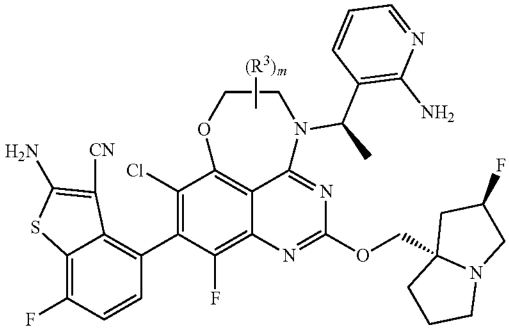
,
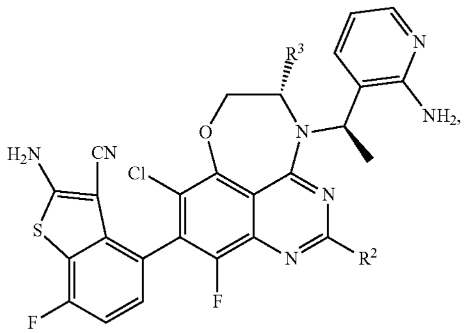

-continued
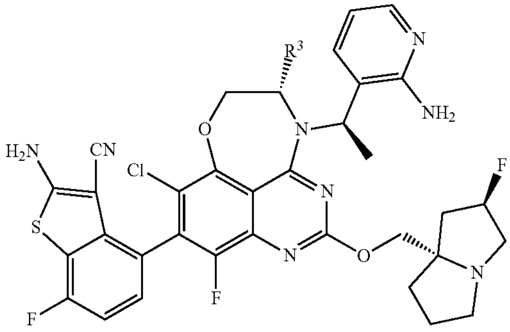
,
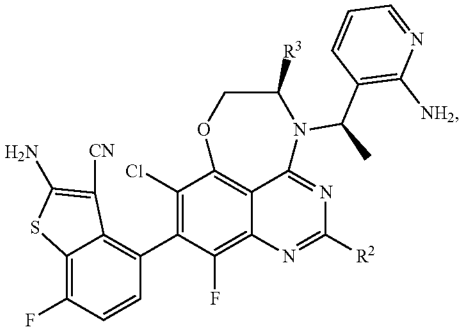
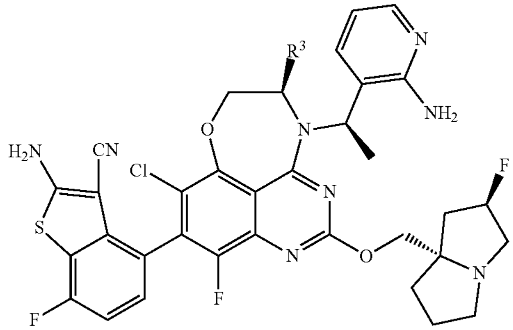
, and
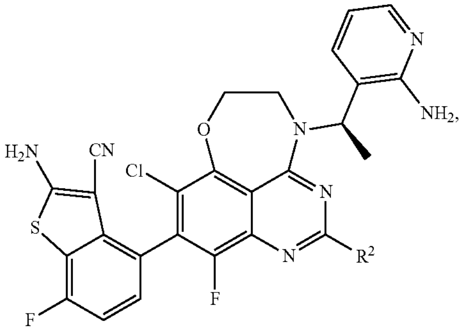
or a pharmaceutically acceptable salt or solvate thereof.
In some embodiments, the compound of Formula (I), (IV), or (V) is selected from:
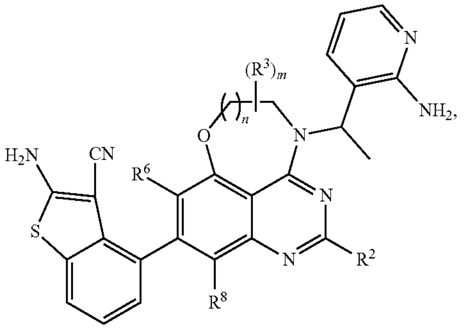
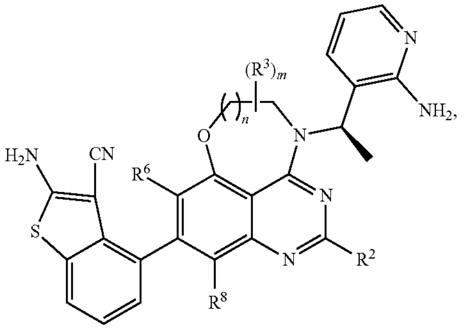
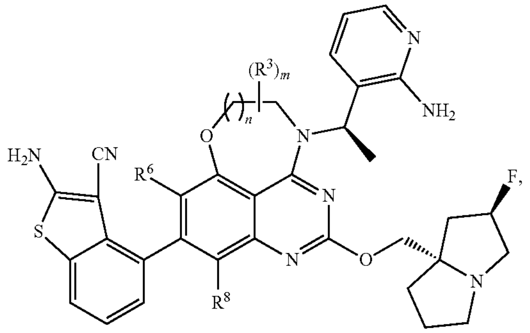
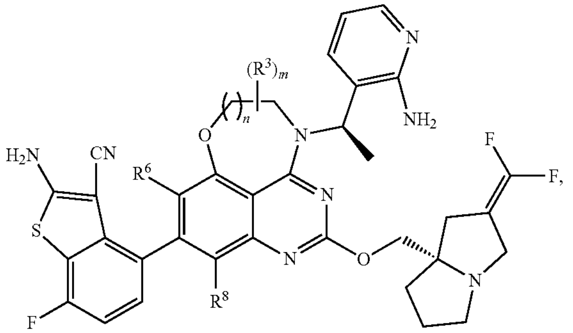
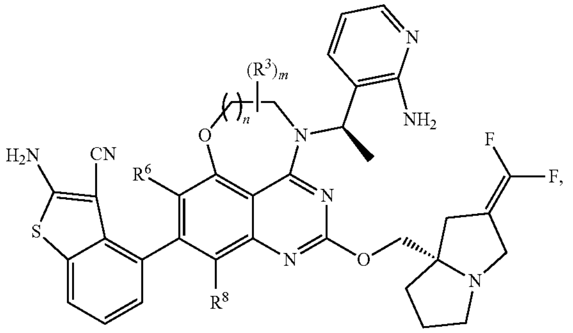

-continued
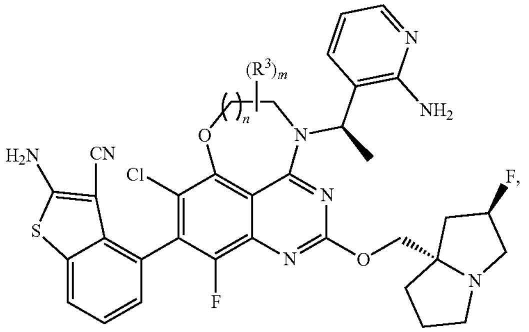
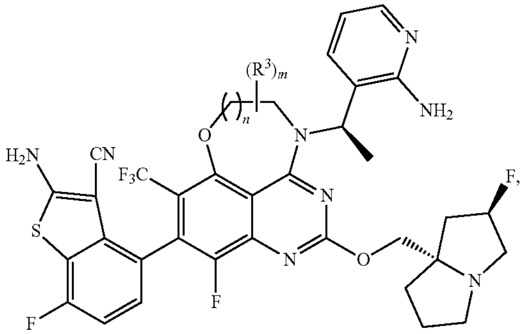
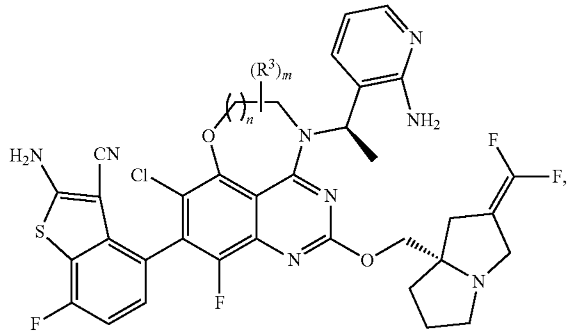
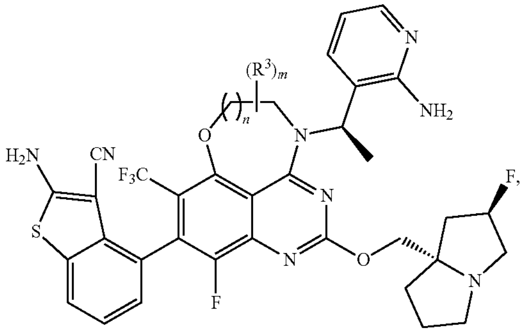
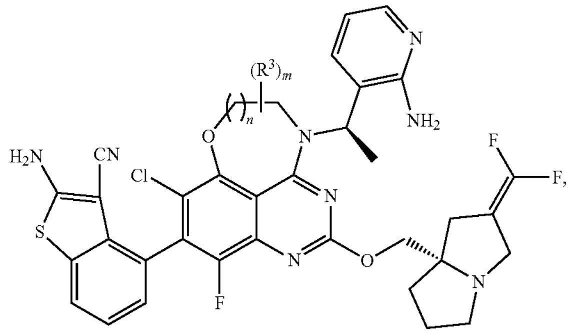
-continued
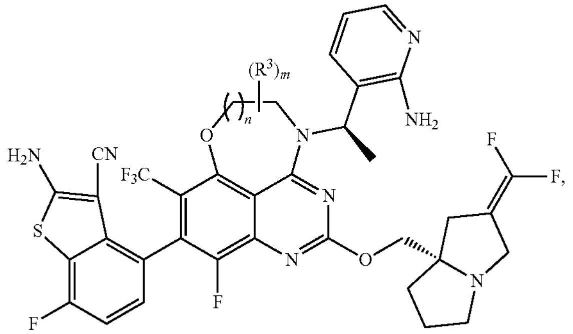
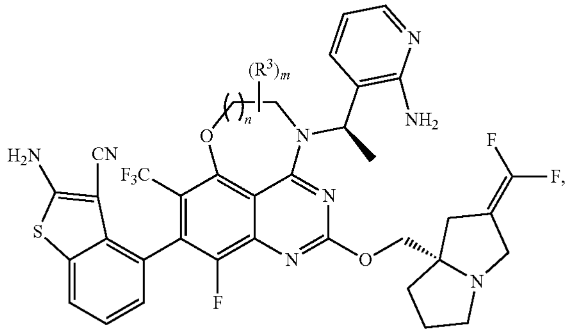
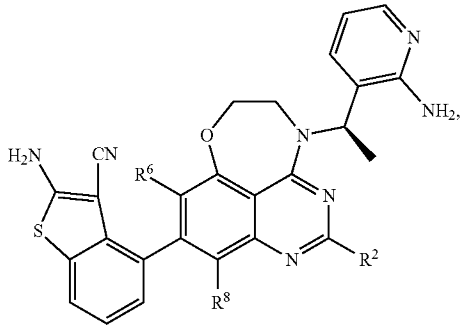
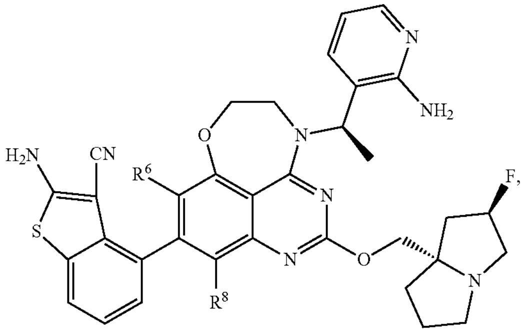
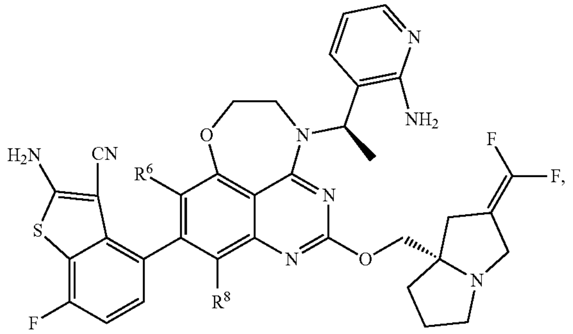

-continued
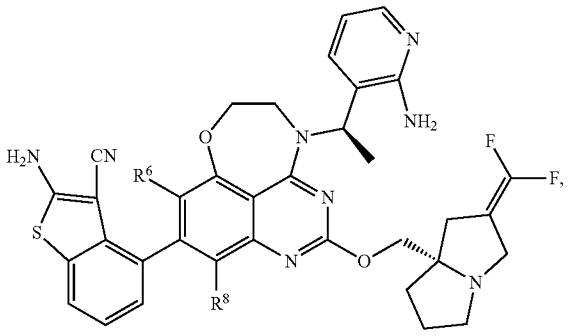
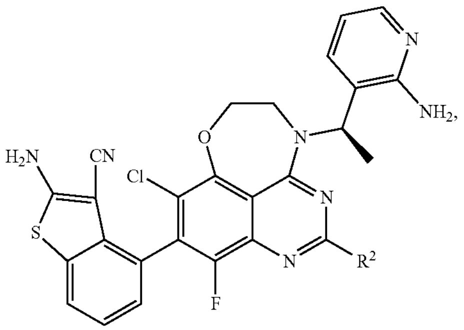
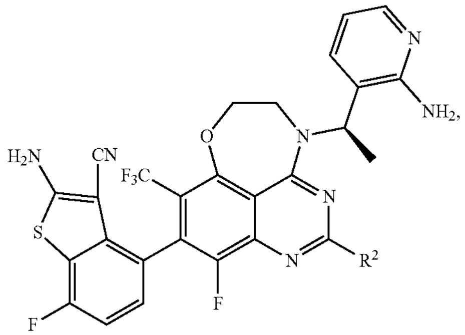
and
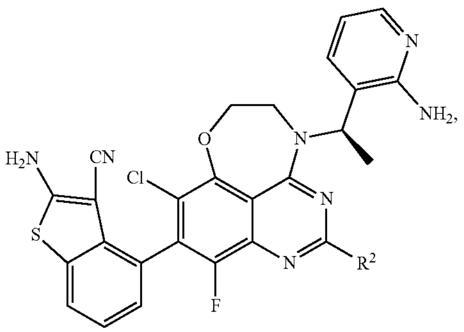
or a pharmaceutically acceptable salt or solvate thereof.
In certain aspects, the present disclosure provides a compound selected from:
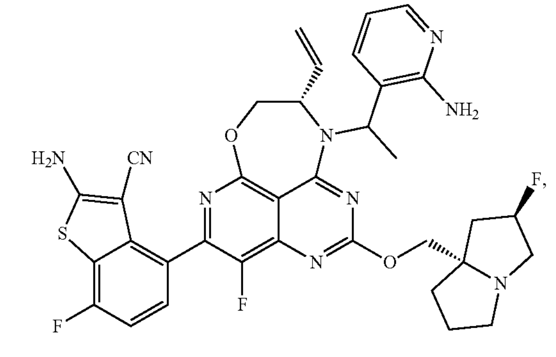
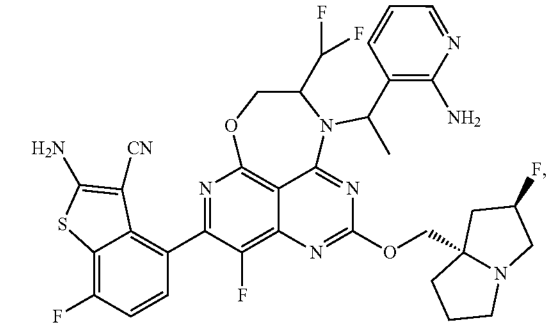
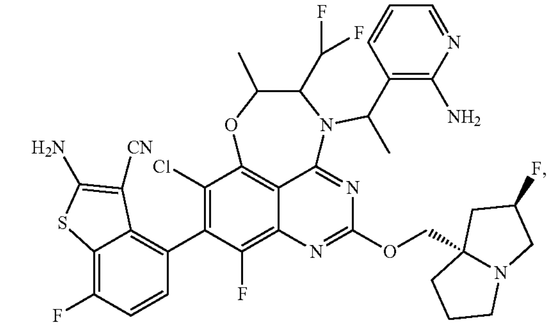
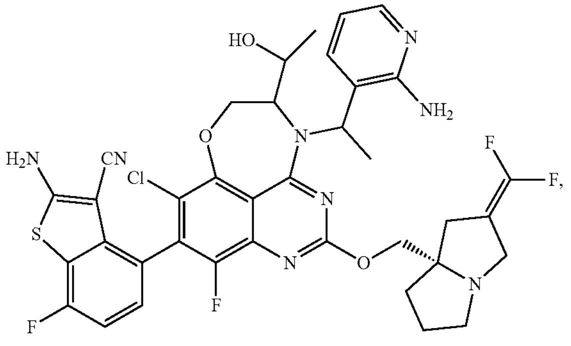
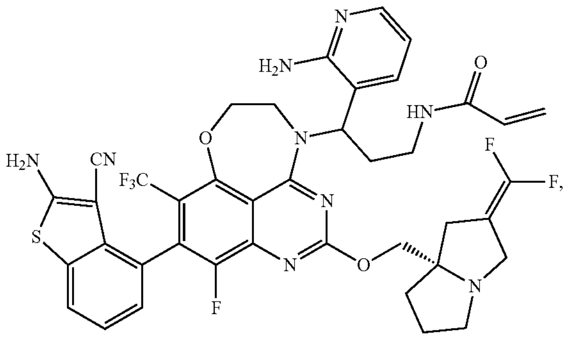

-continued
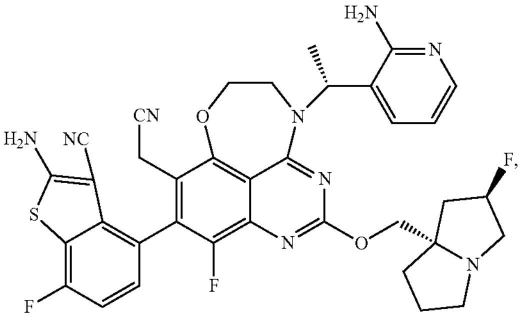
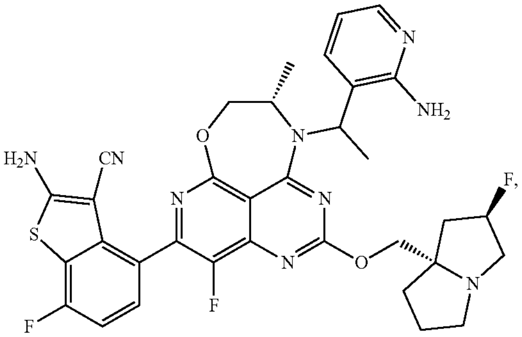
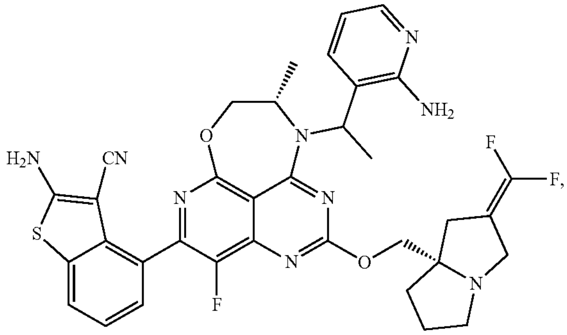
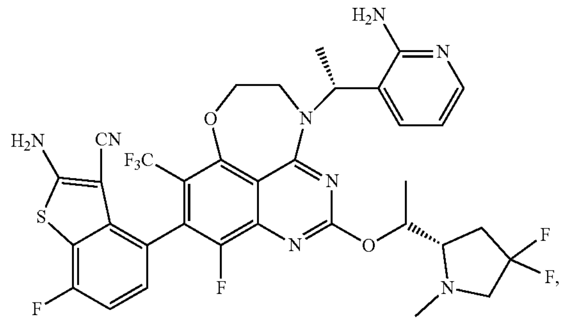
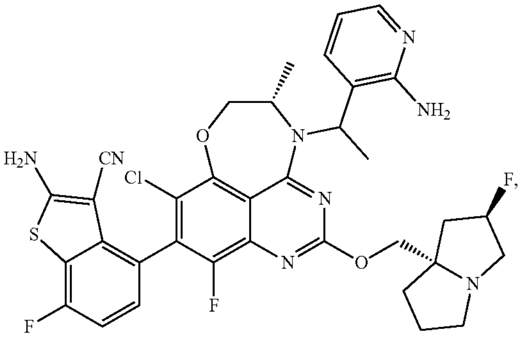
-continued
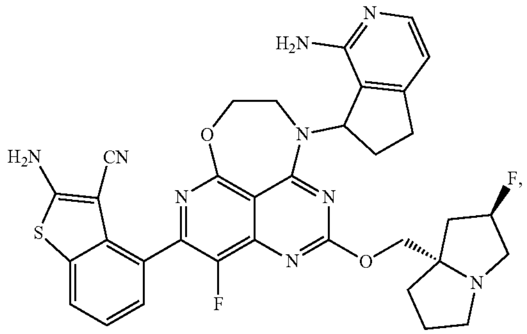
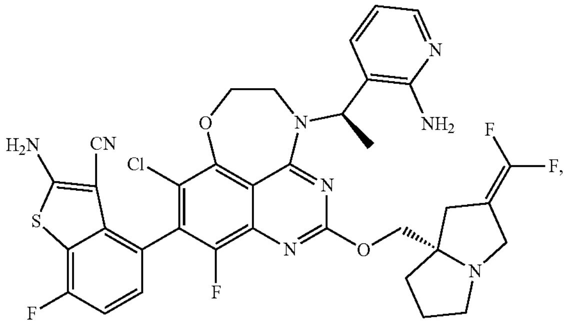
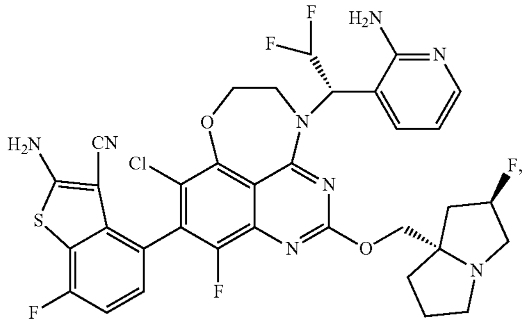
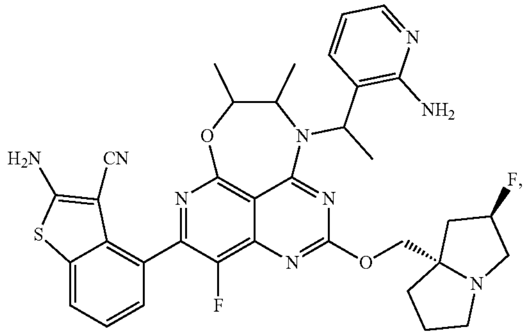
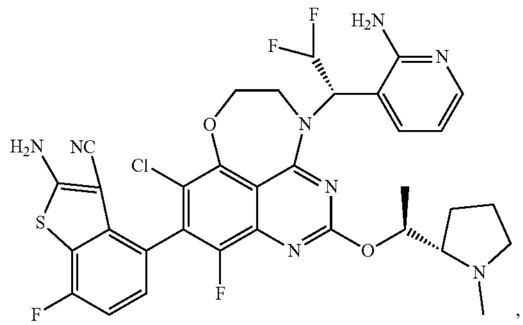
, -continued
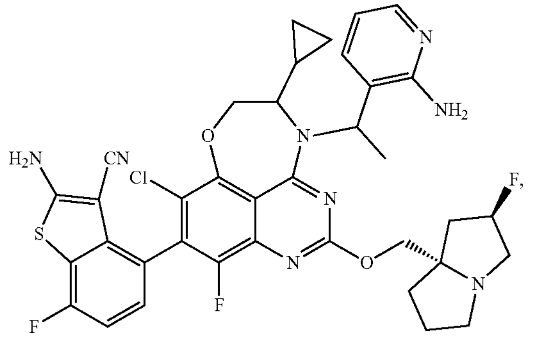
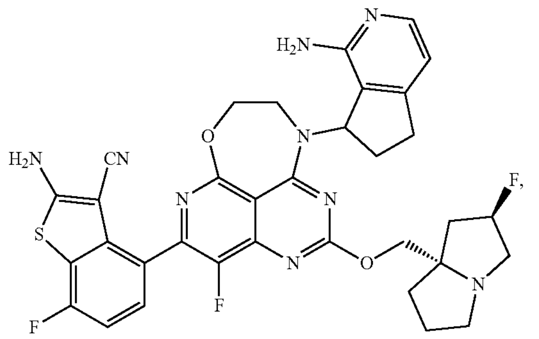
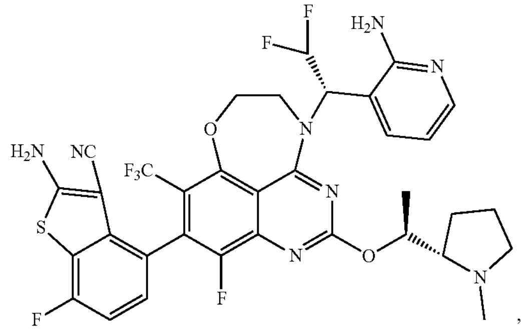
,
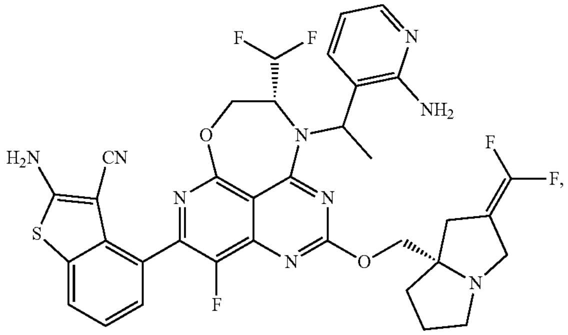
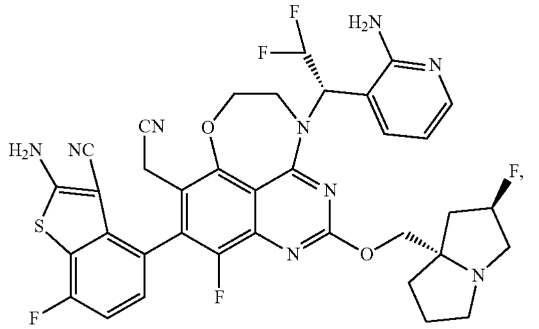
-continued
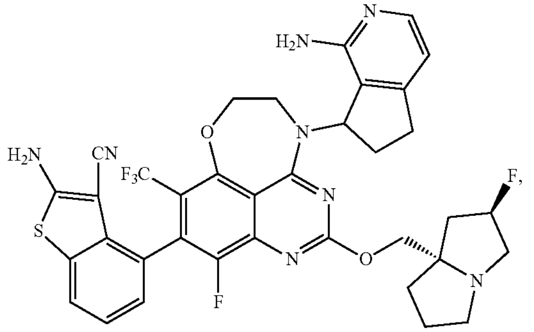
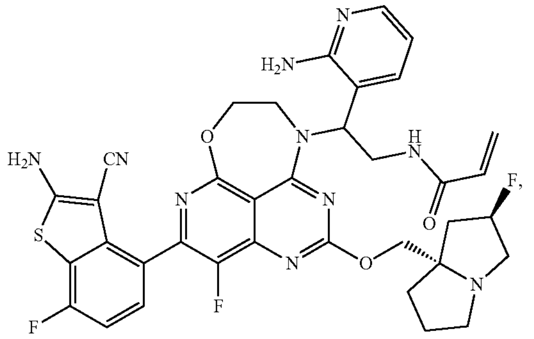
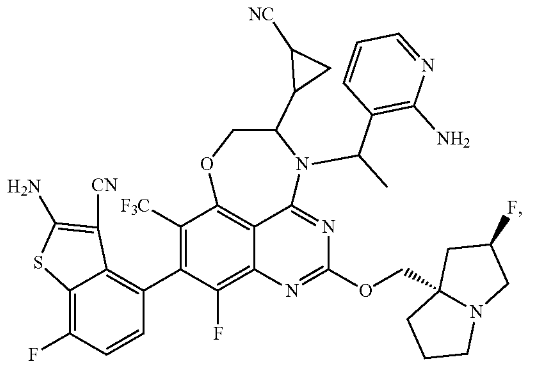
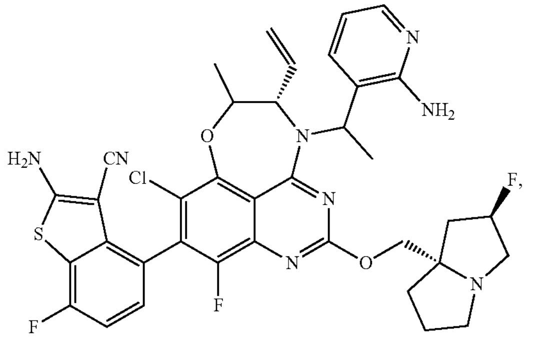
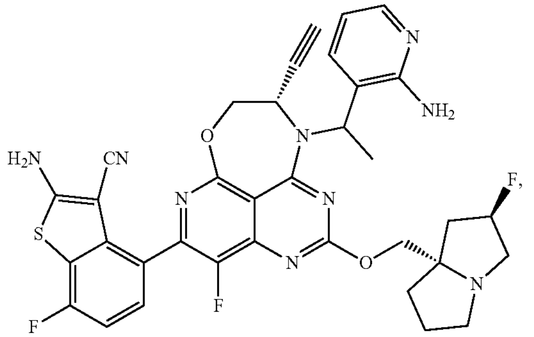

-continued
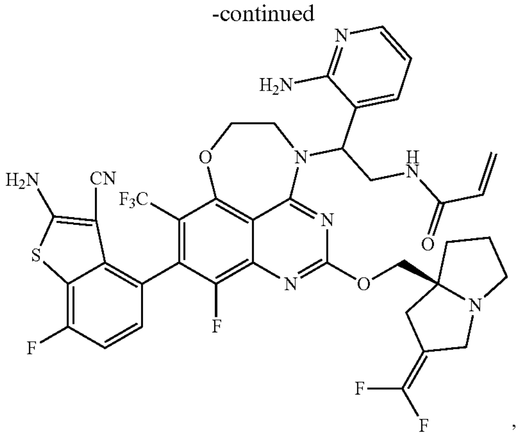
,
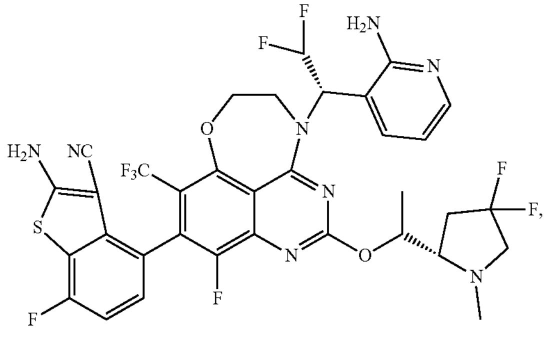
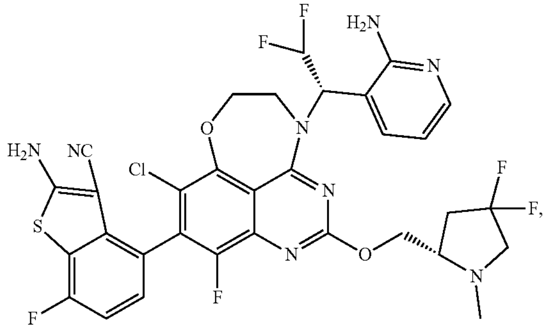
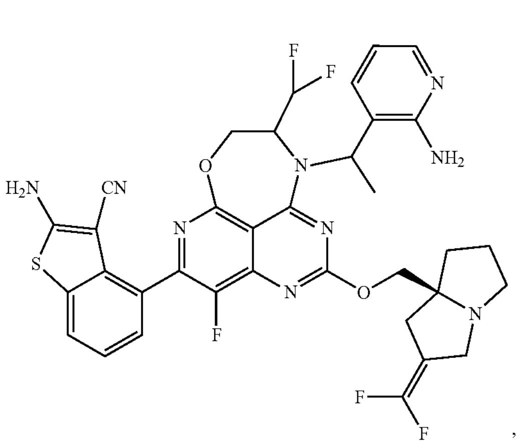
,
-continued
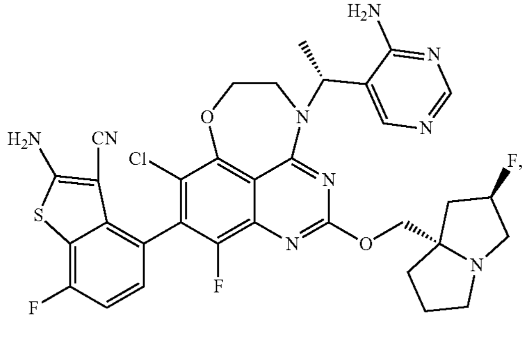
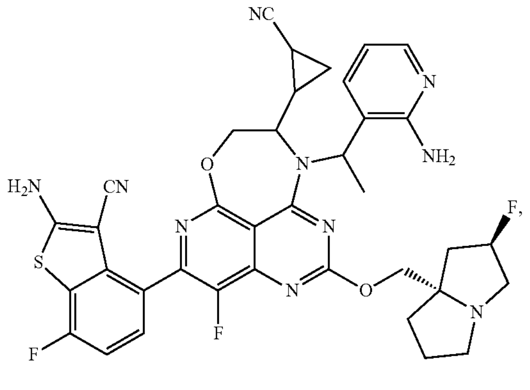
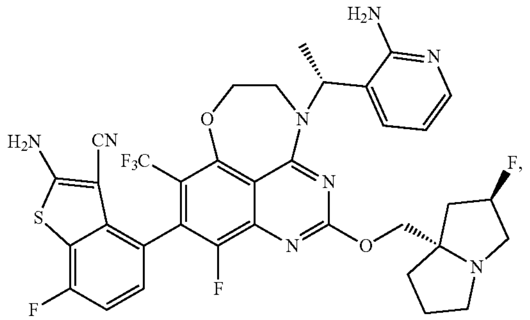
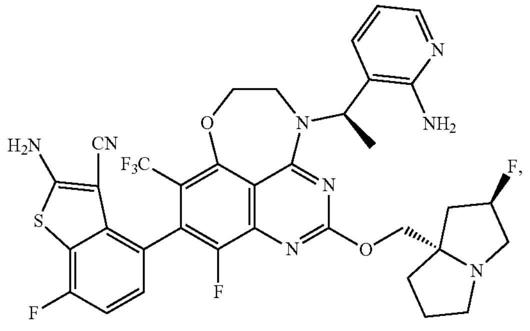
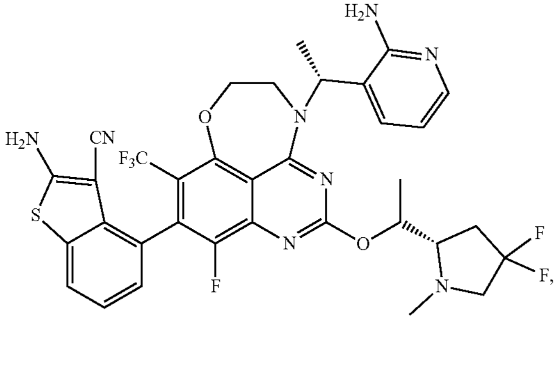

-continued
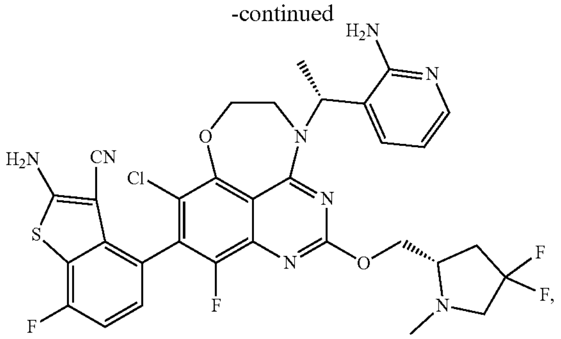
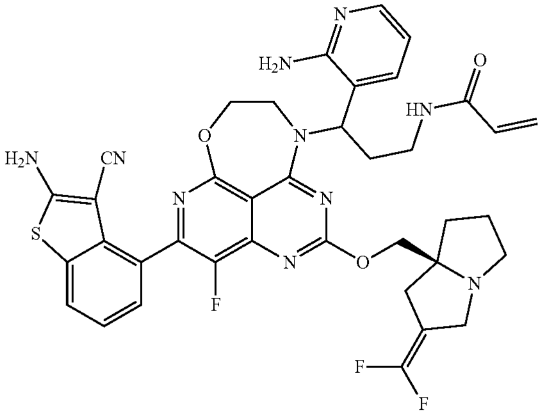
,
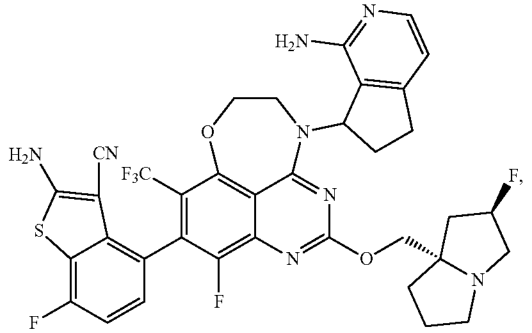
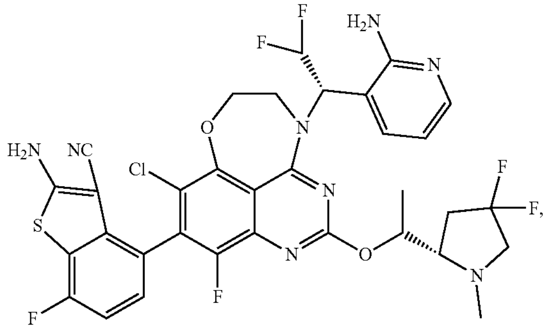
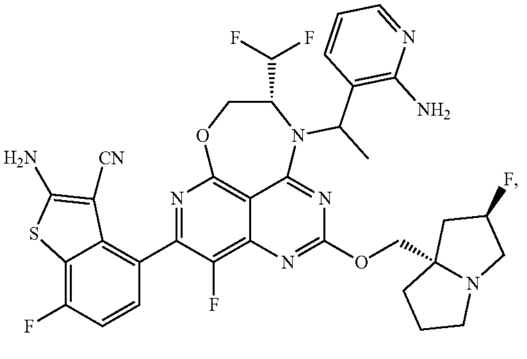
-continued
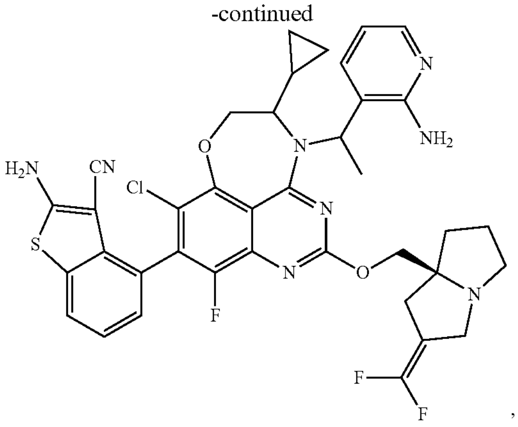
,
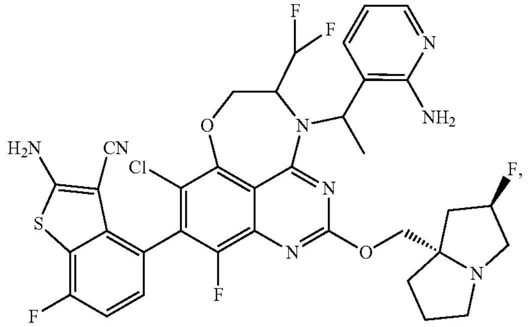
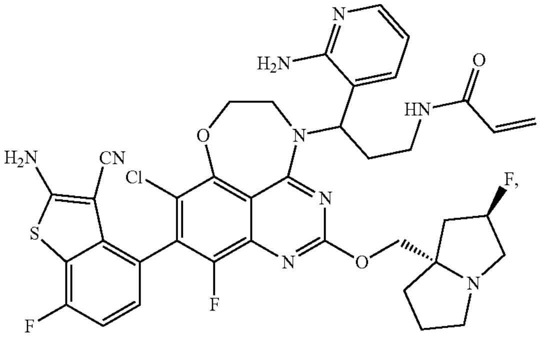
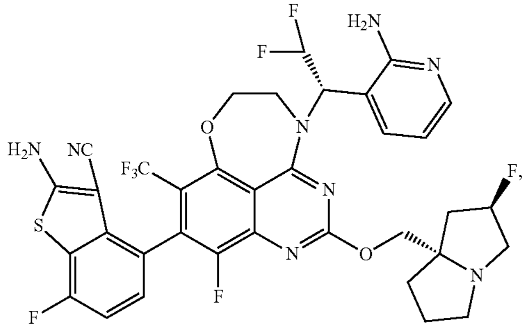
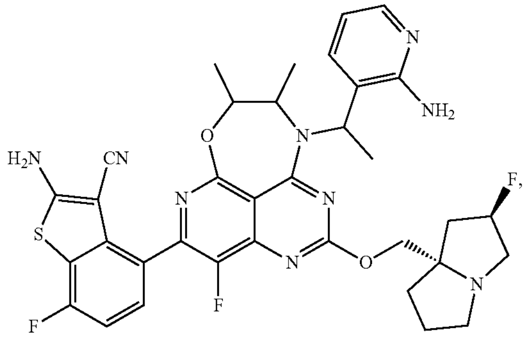

-continued
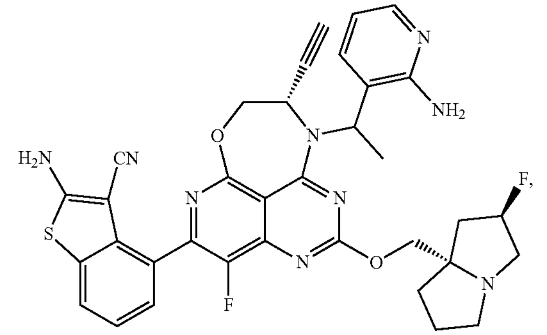
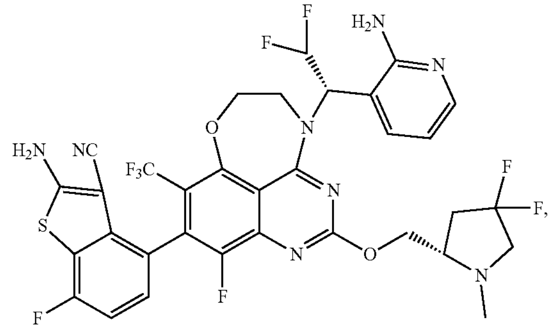
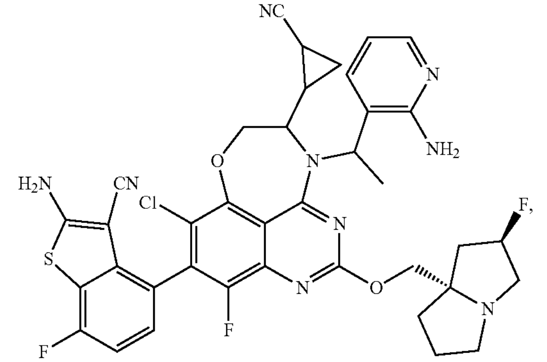
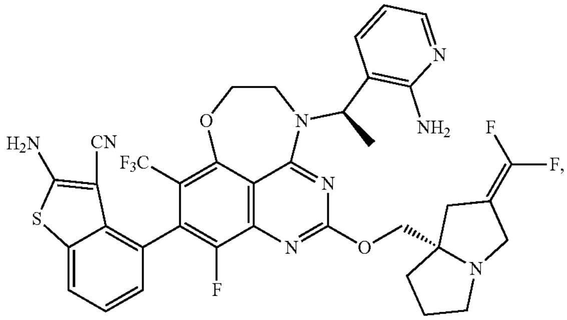
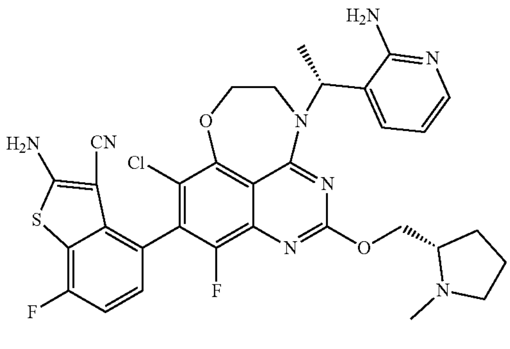
,
-continued
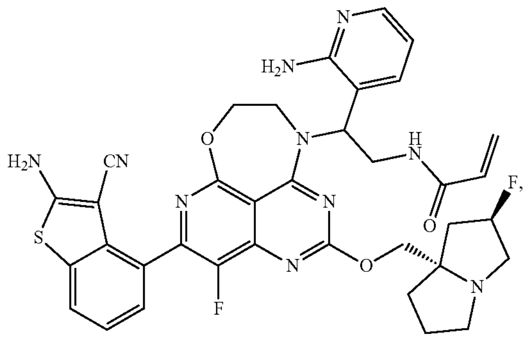
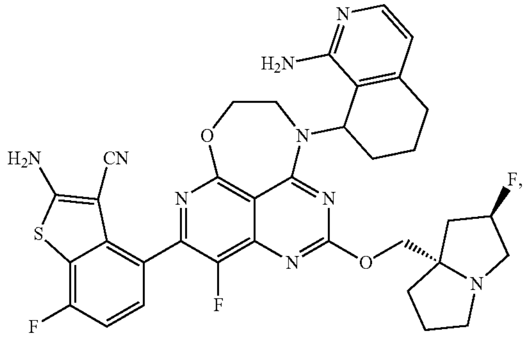
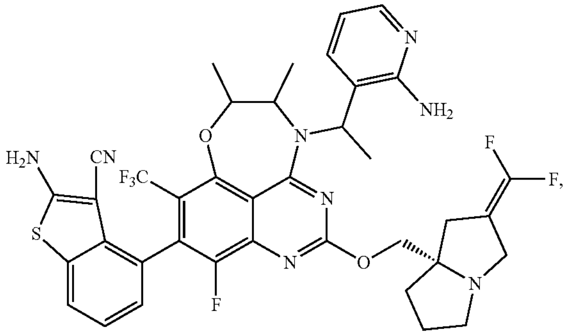
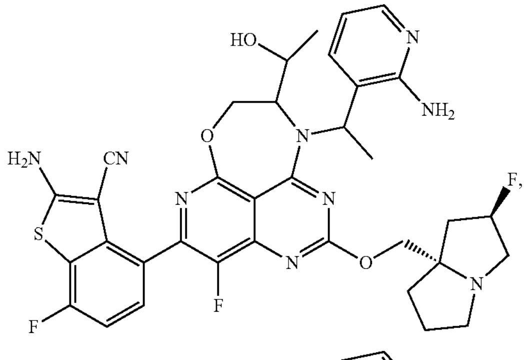
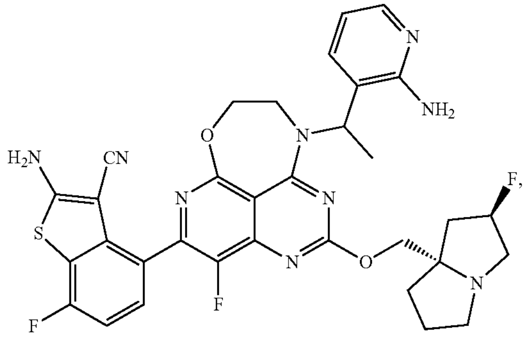

-continued
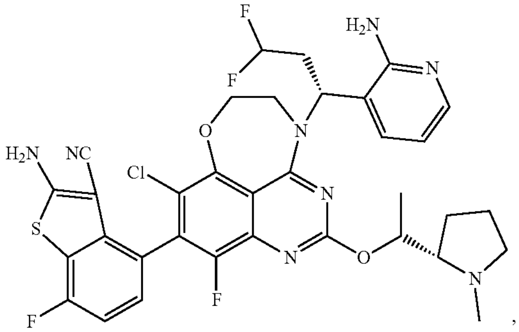
,
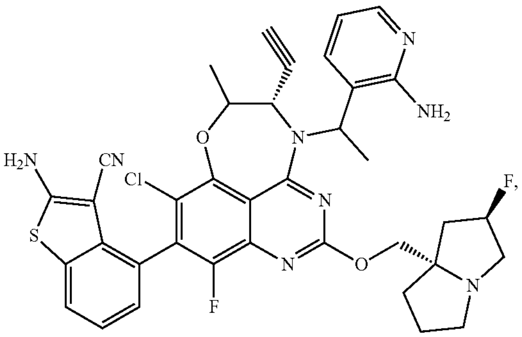
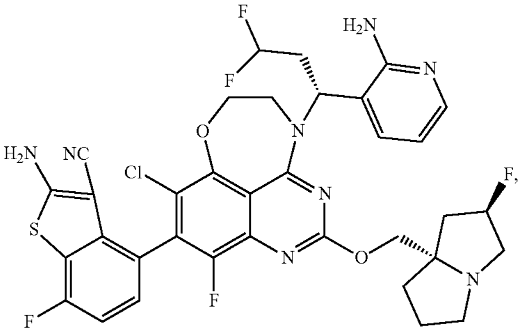
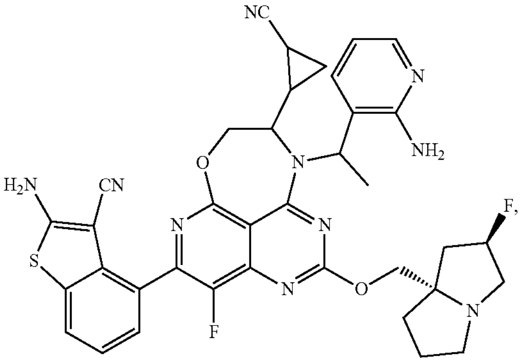
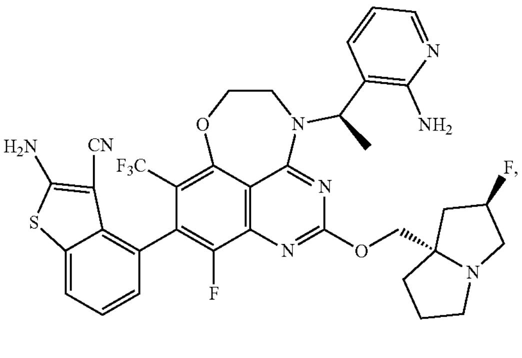
-continued
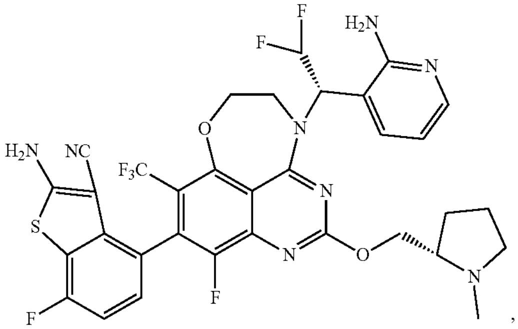
,
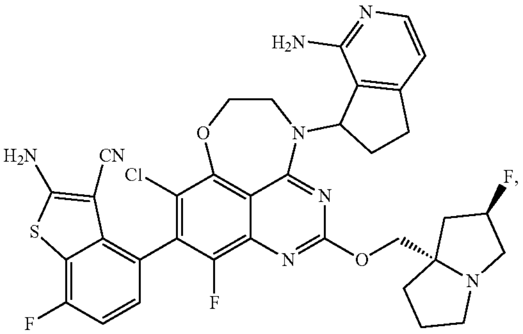
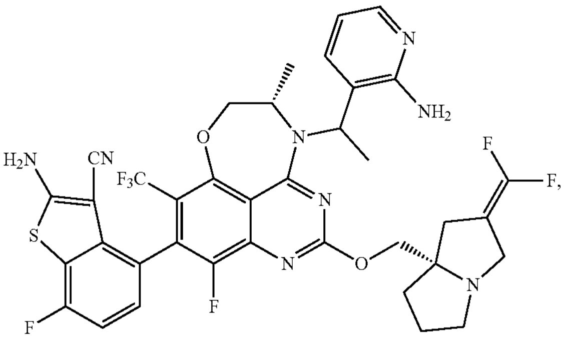
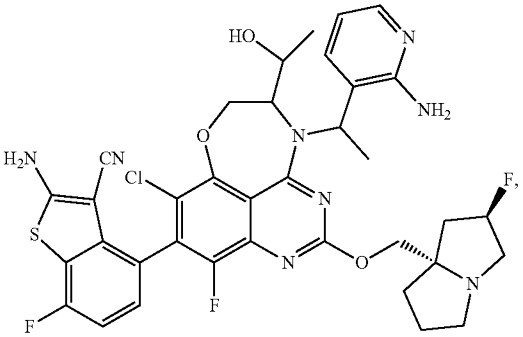
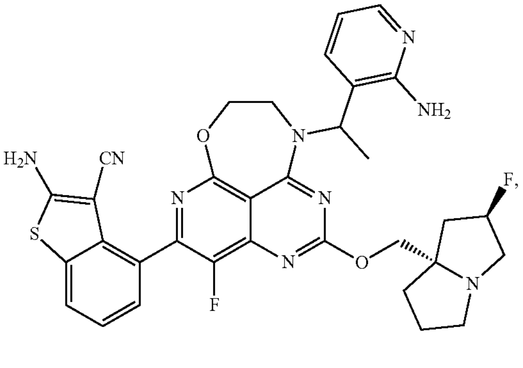

-continued
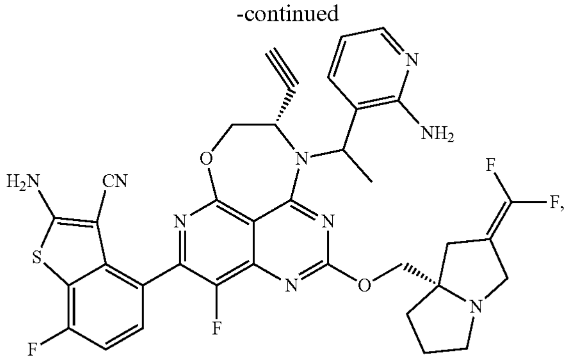
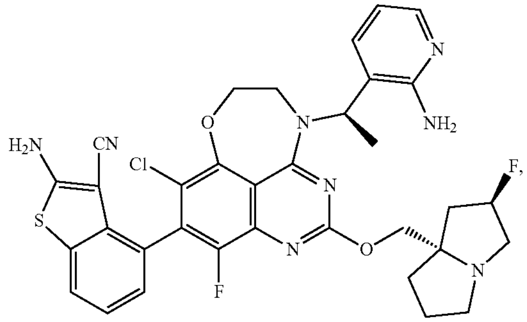
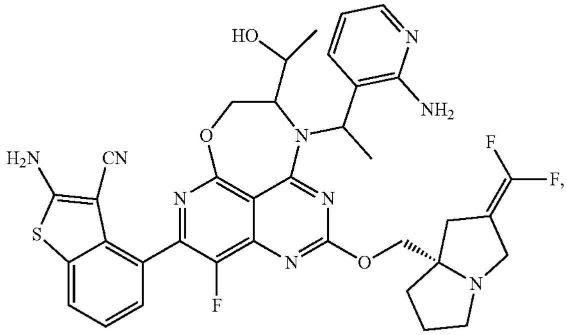
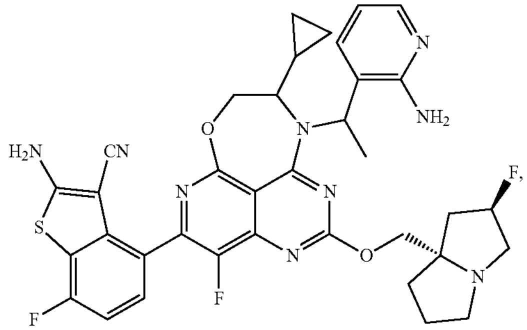
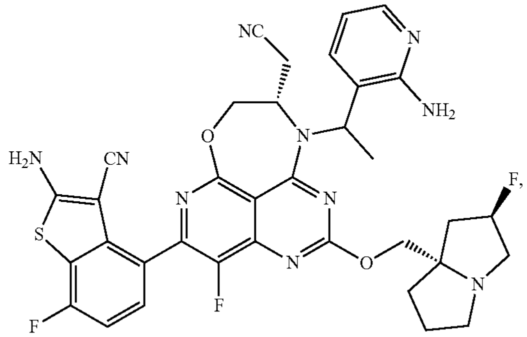
-continued
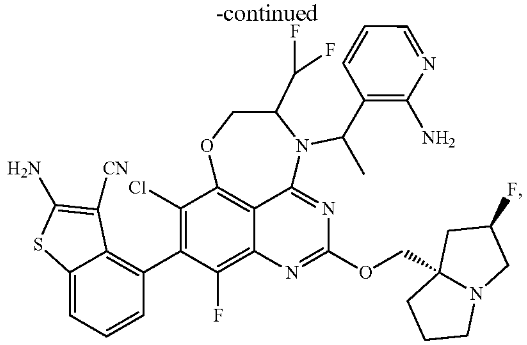
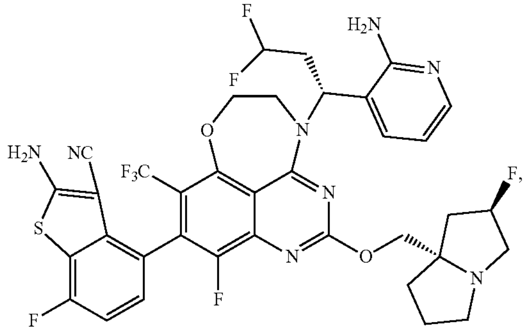
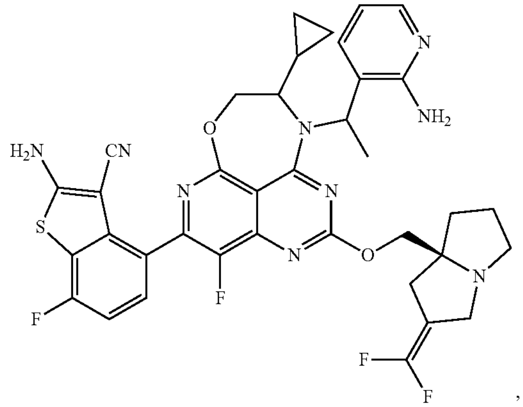
,
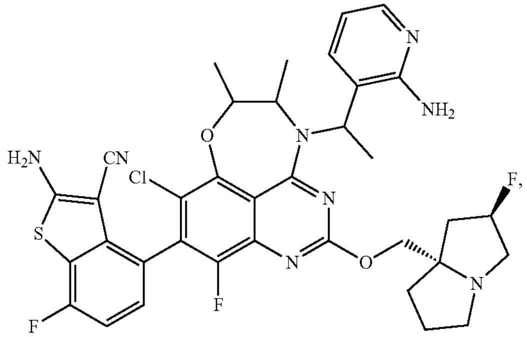
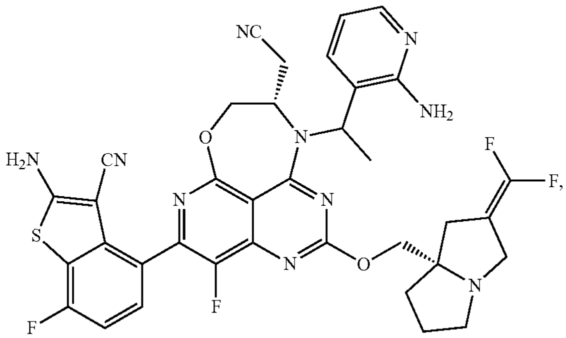

-continued
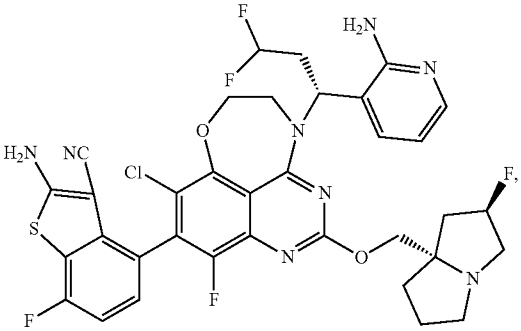
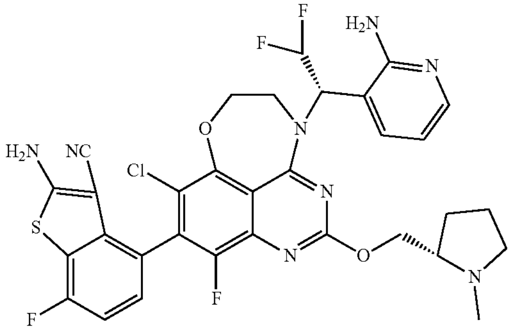
,
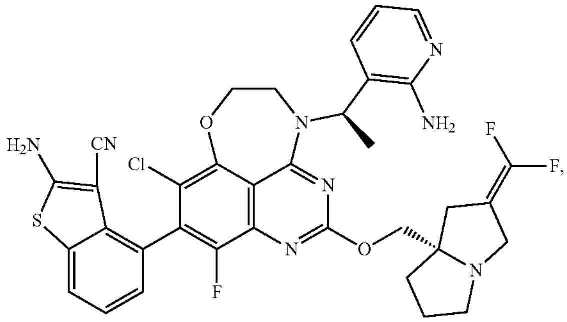
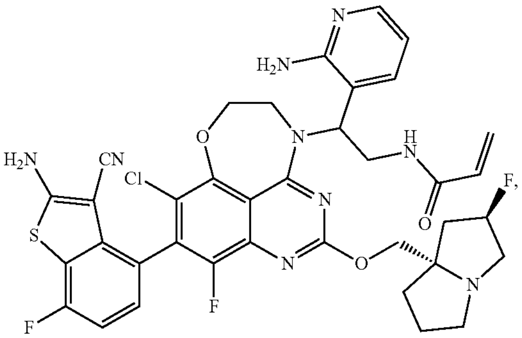
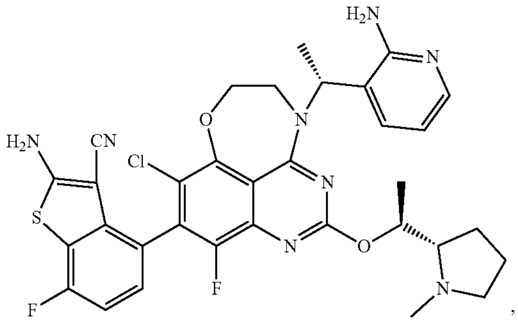
,
-continued
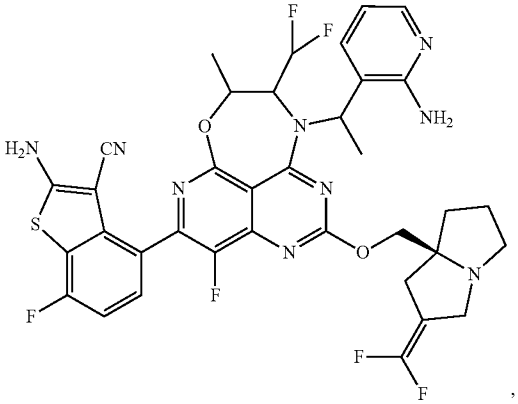
,
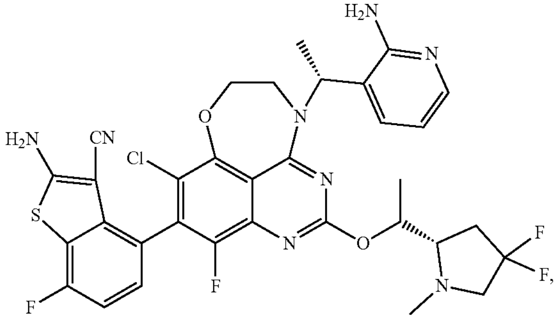
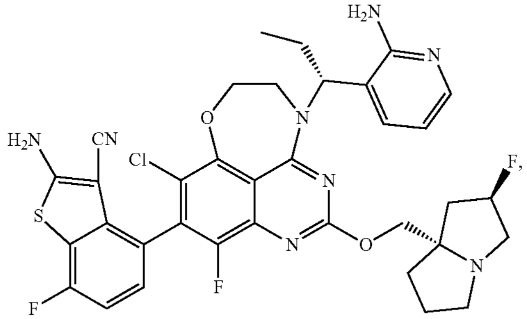
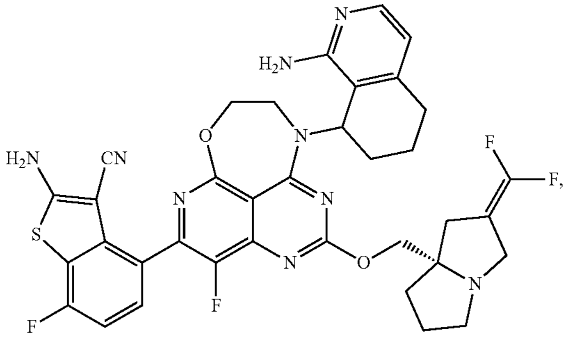
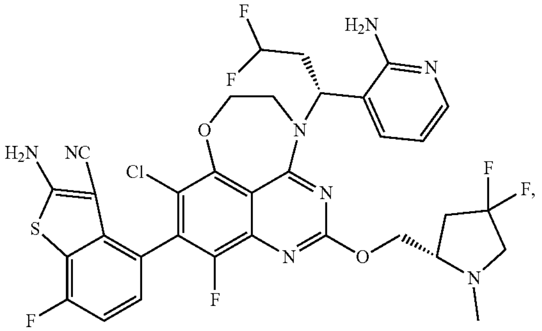

-continued
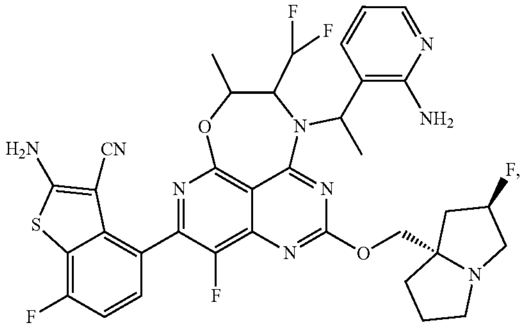
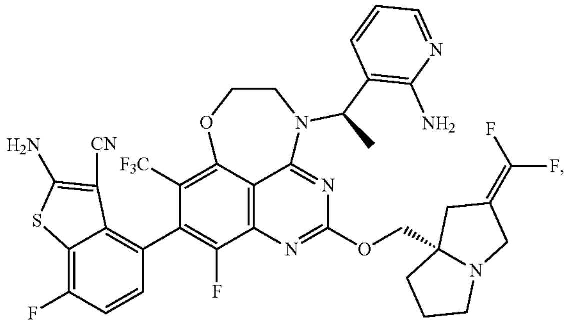
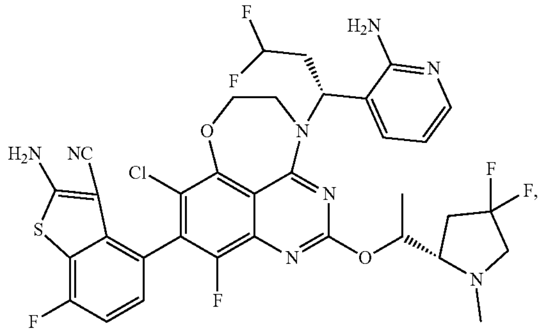
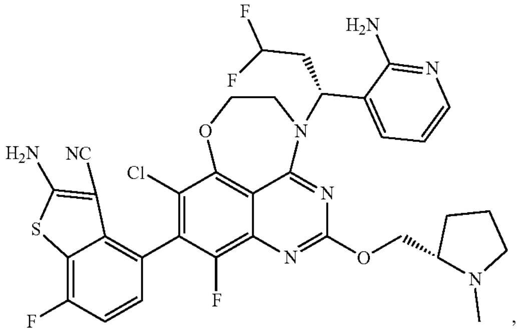
,
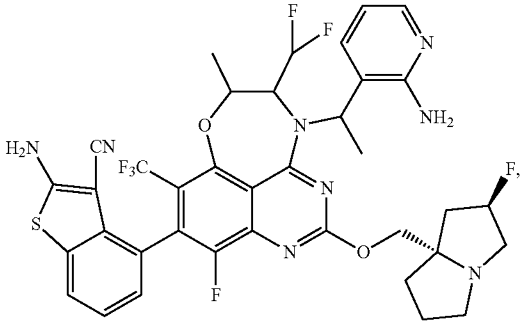
-continued
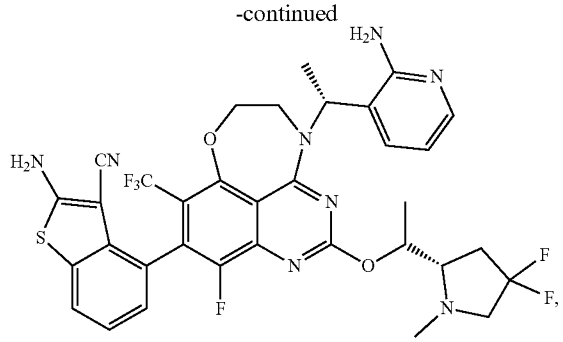
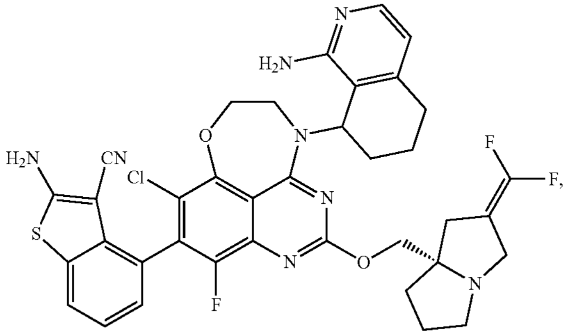
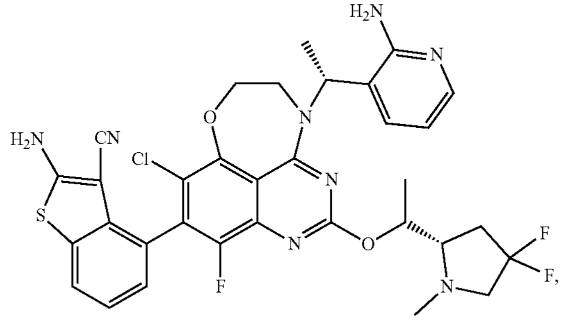
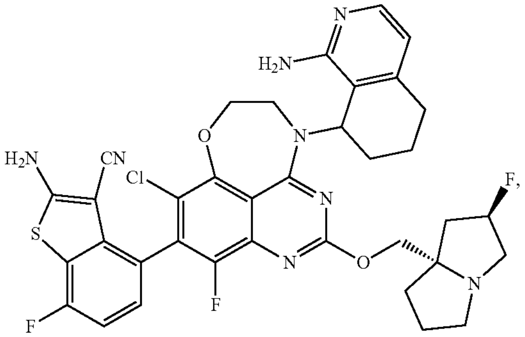
and
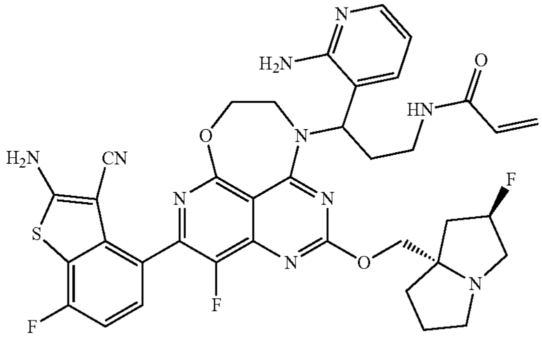
,
or a pharmaceutically acceptable salt or solvate thereof.
In certain aspects, the present disclosure provides a compound selected from:

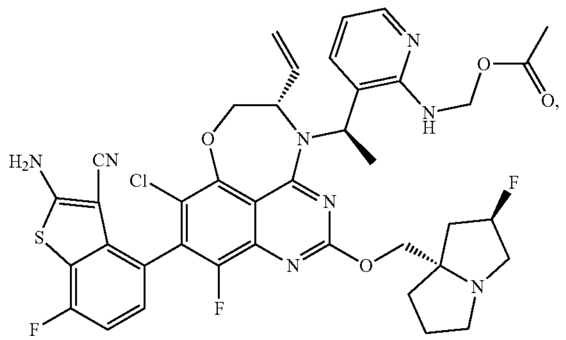
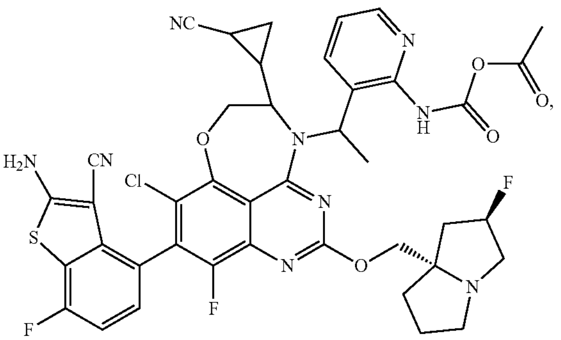
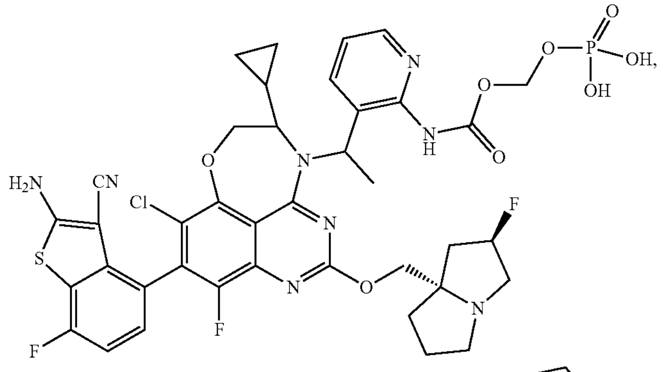
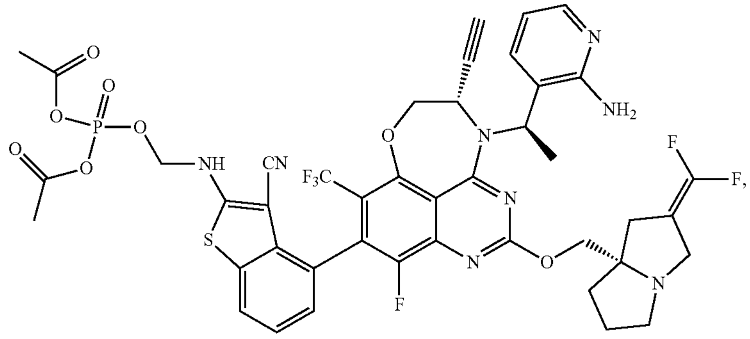
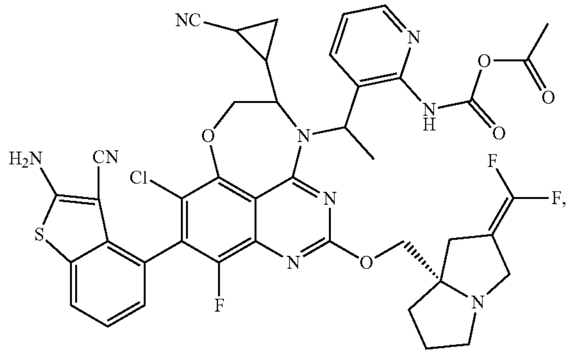
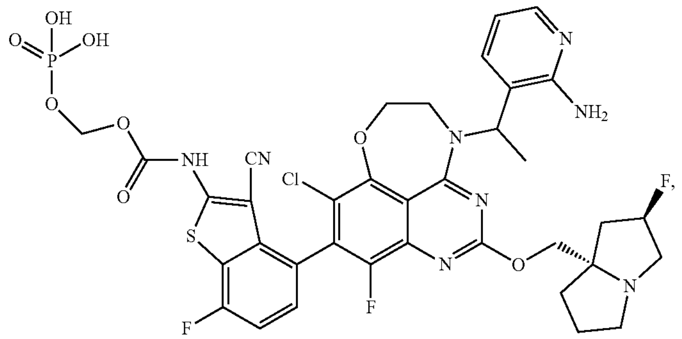

-continued
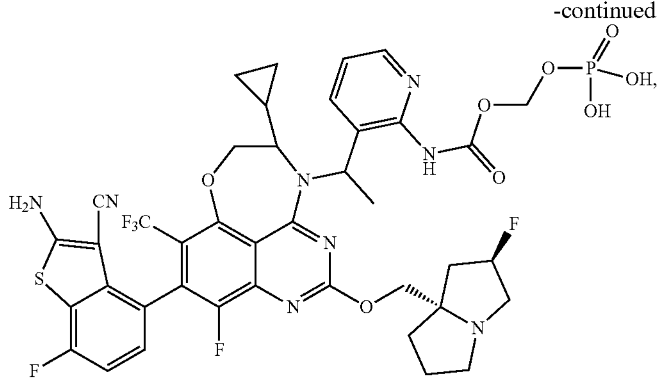
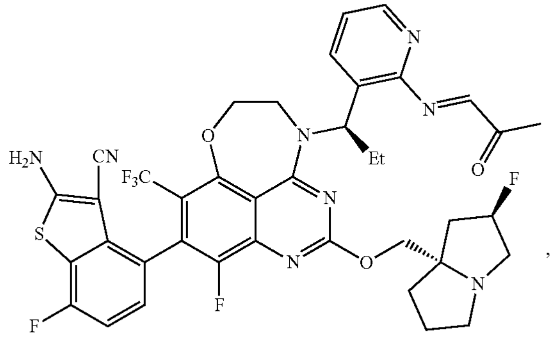
,
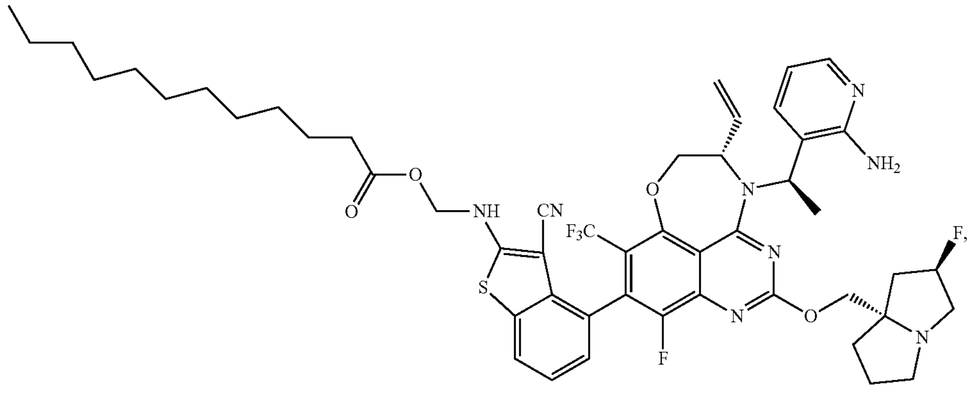
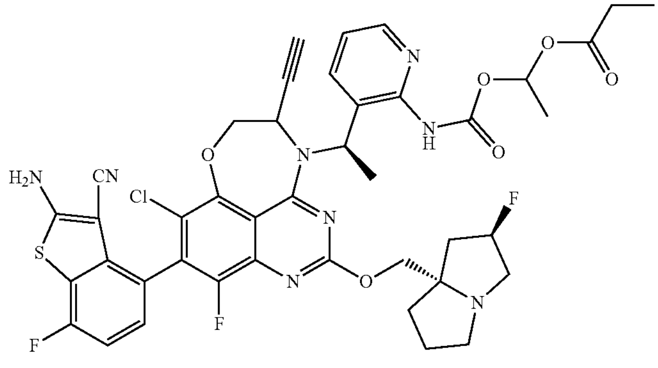
,

-continued
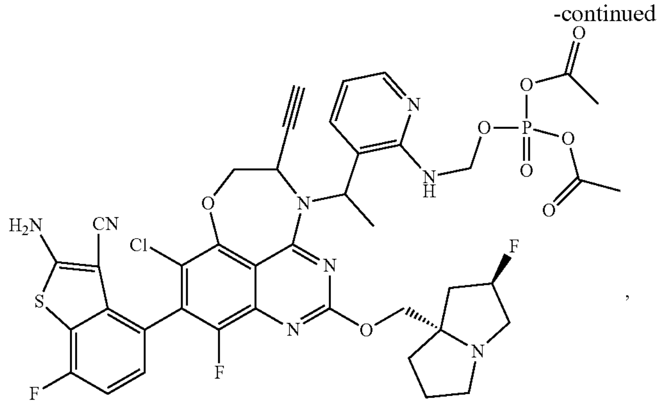
,
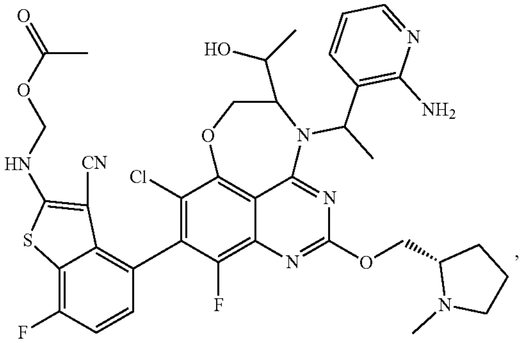
,
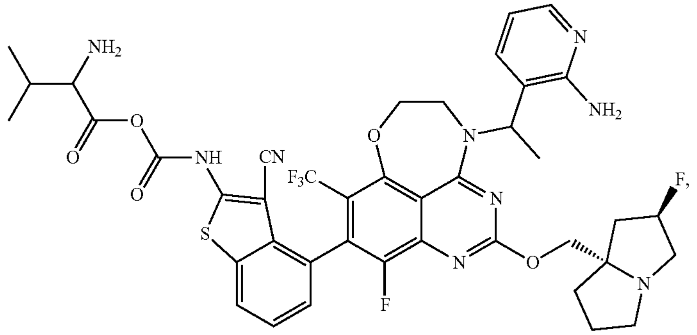
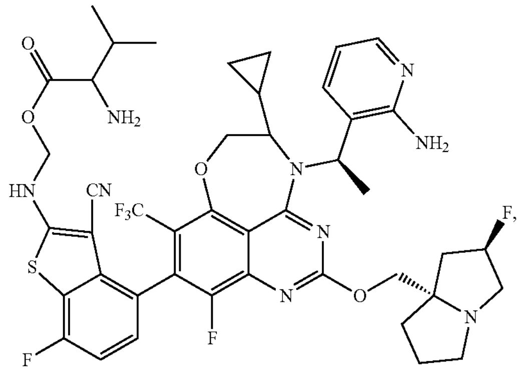
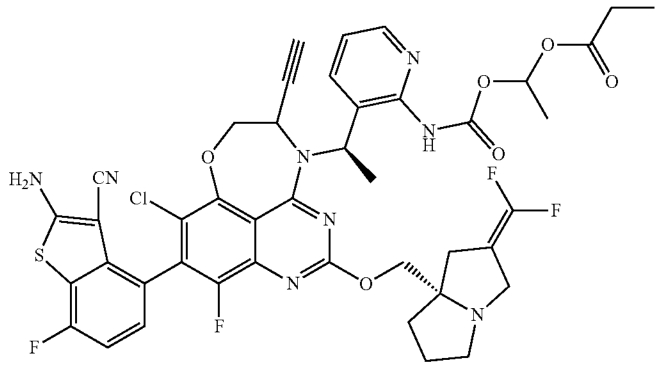
, -continued
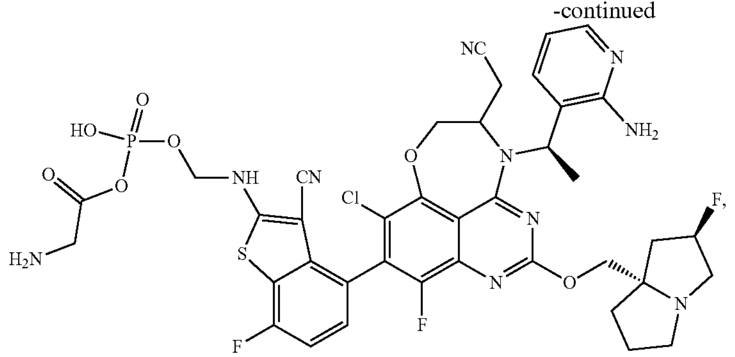
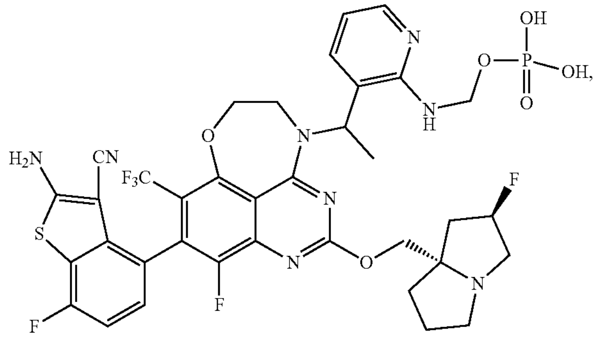
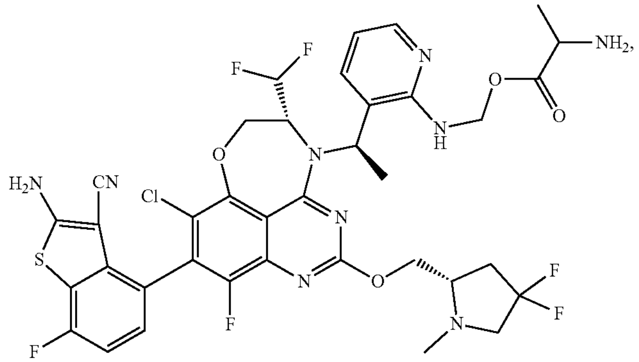
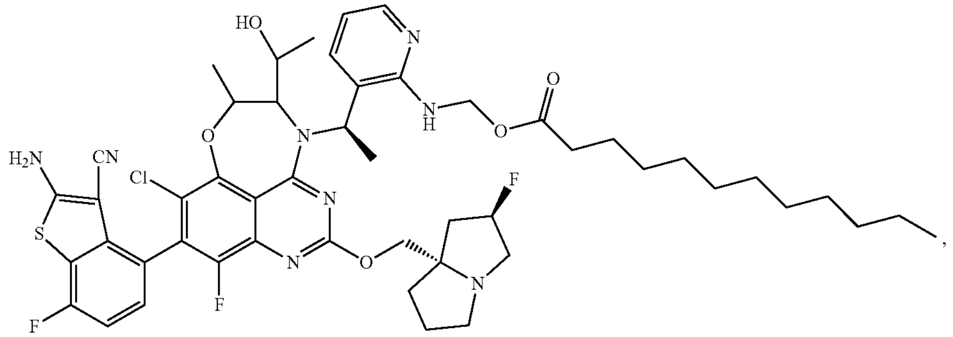
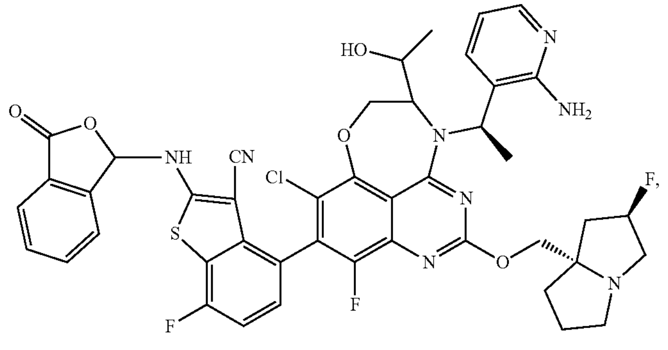

-continued
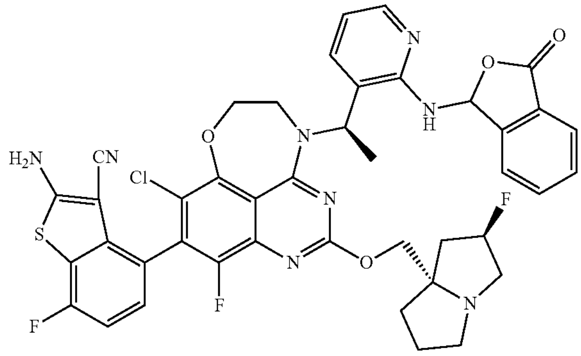
,
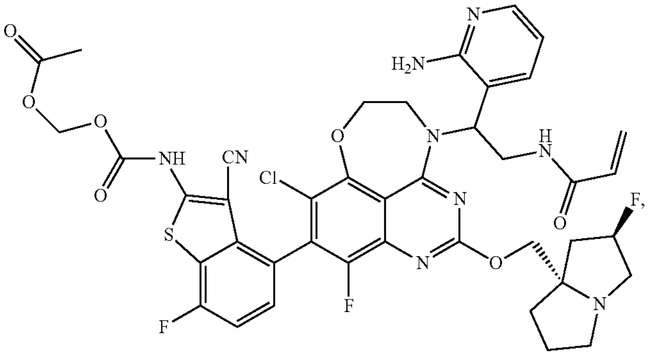
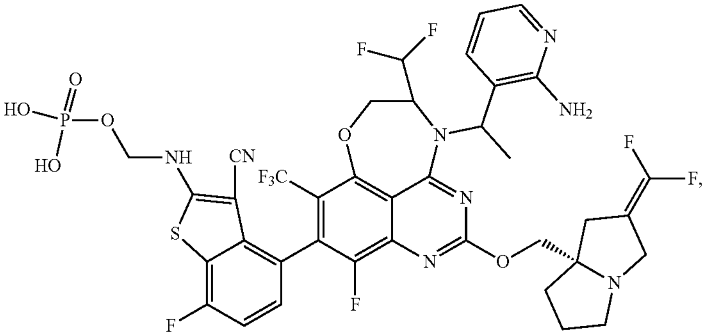
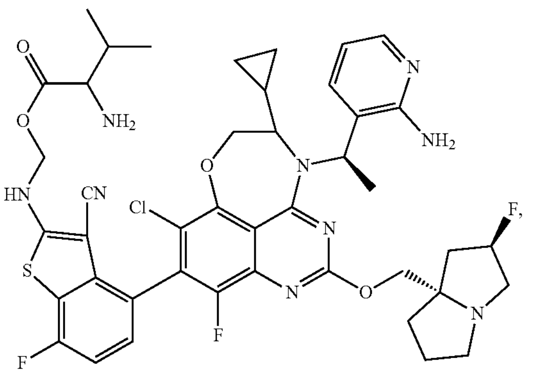
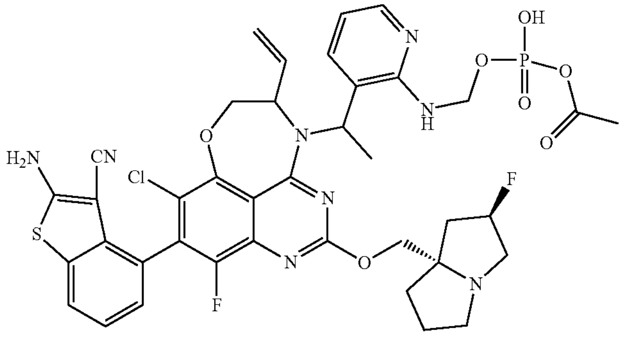
,

-continued
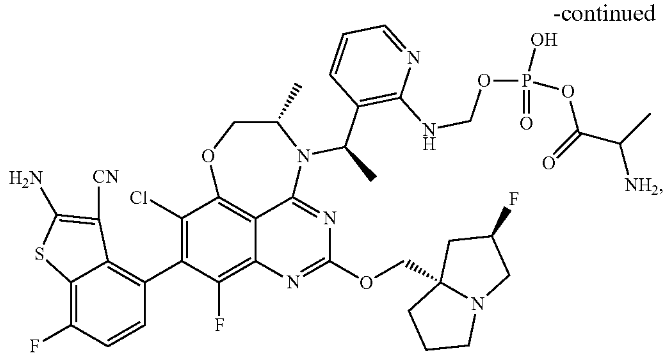
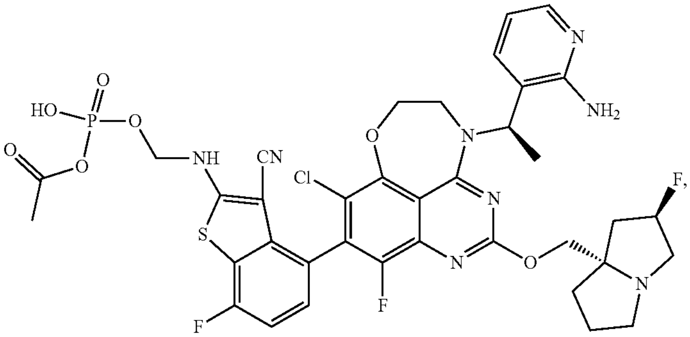
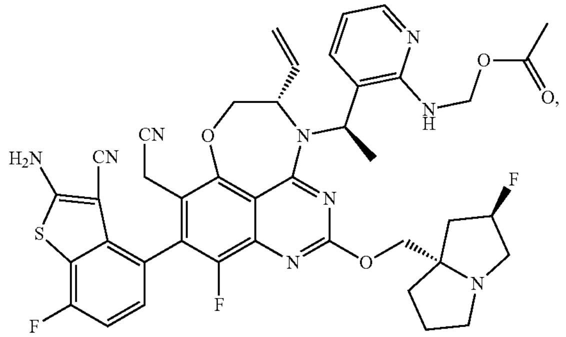
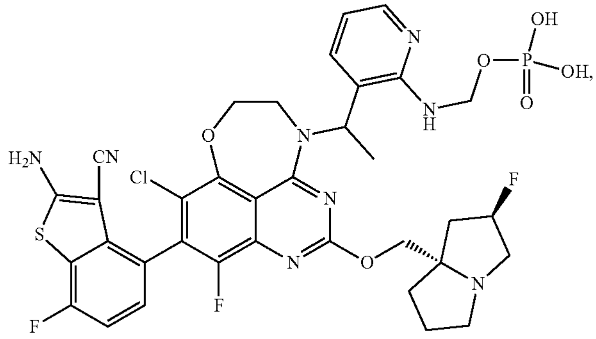
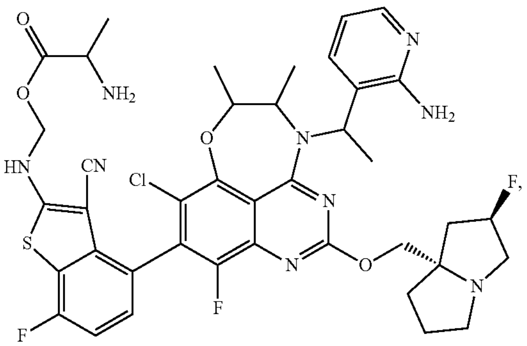
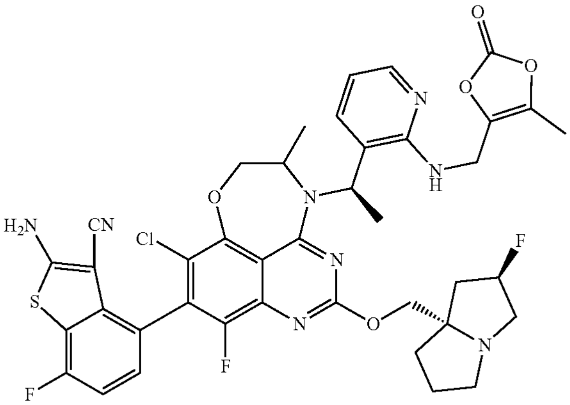
, -continued
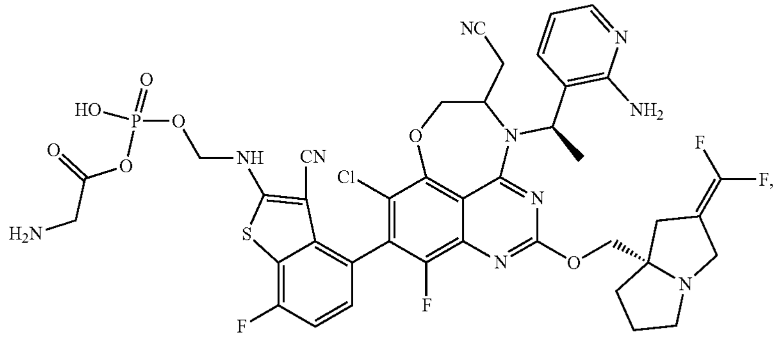
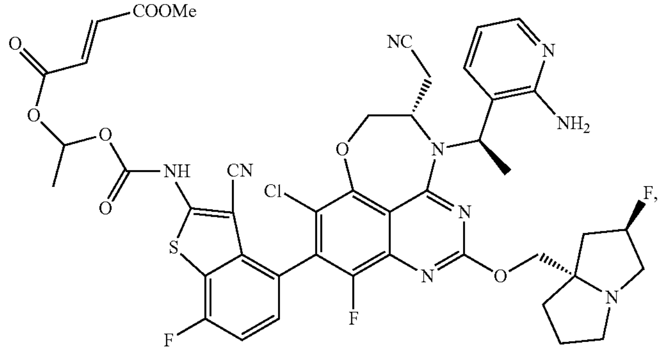
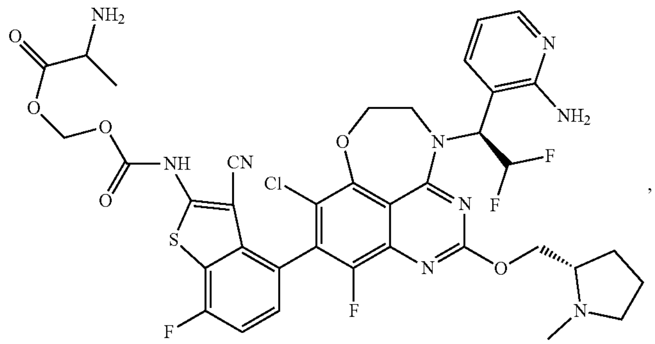
,
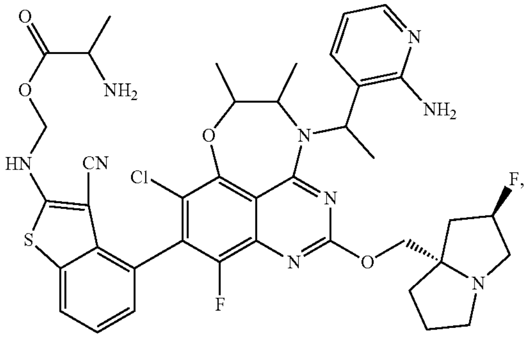
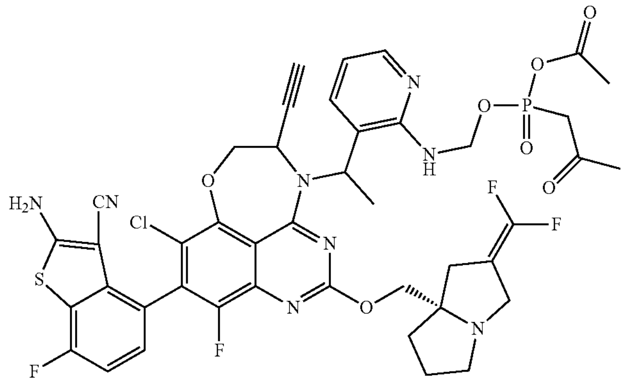
,
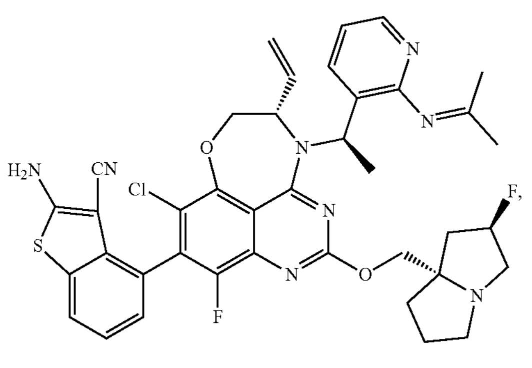

-continued
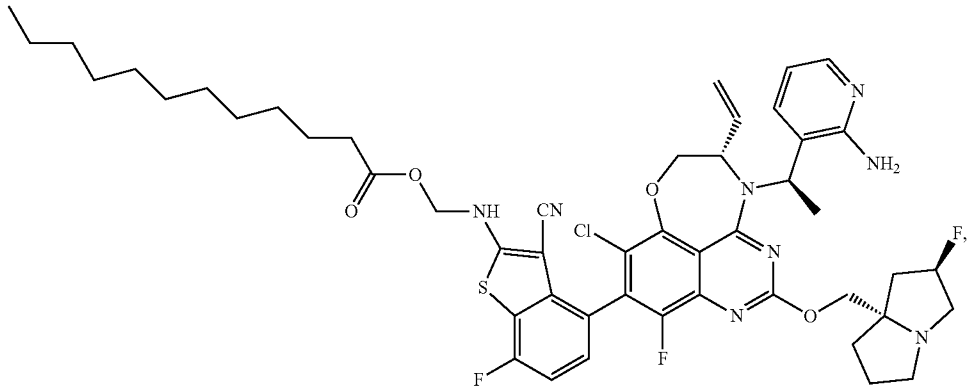
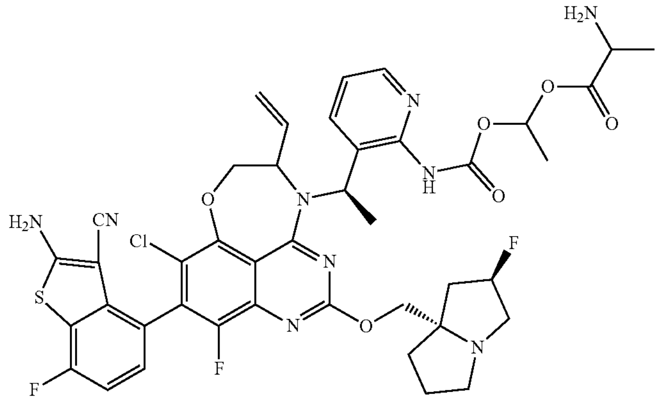
,
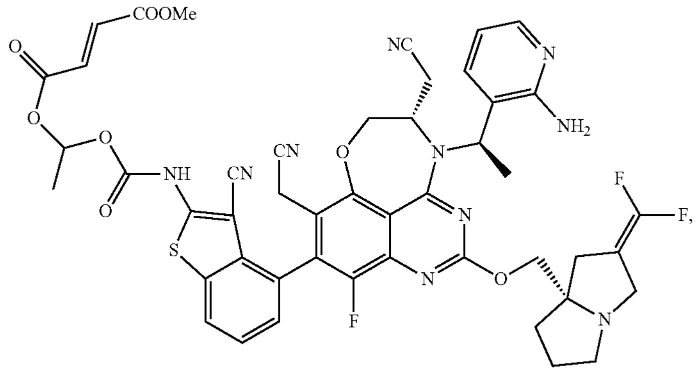
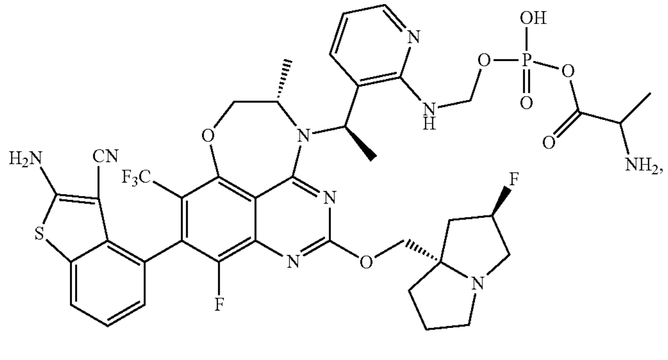

-continued
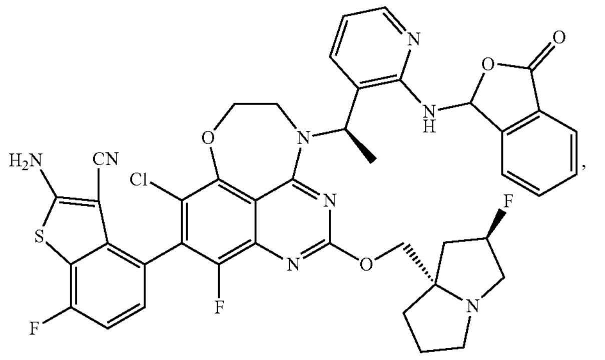
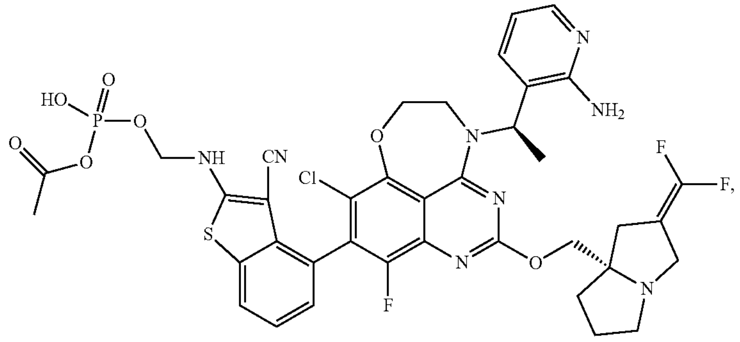
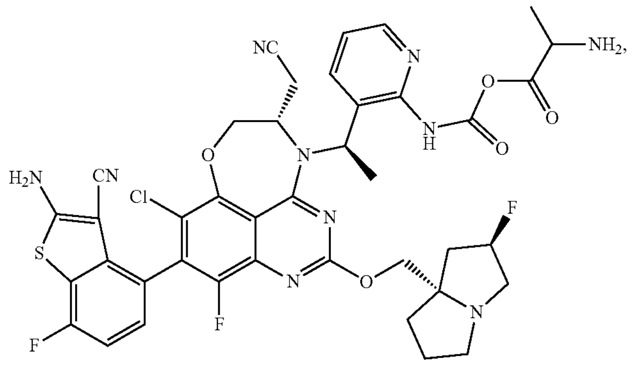
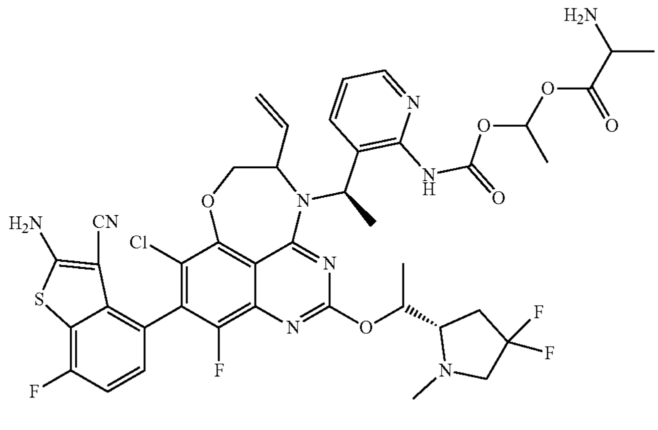
,

-continued
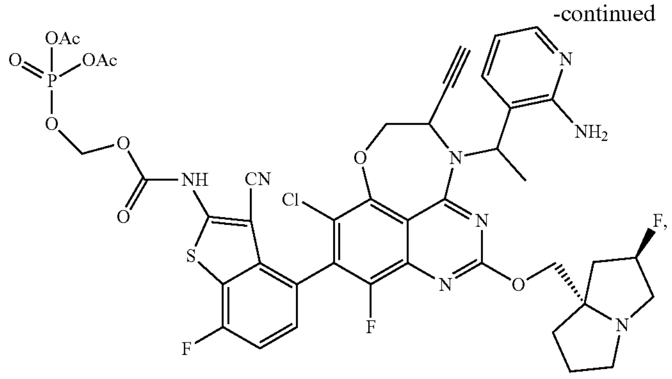
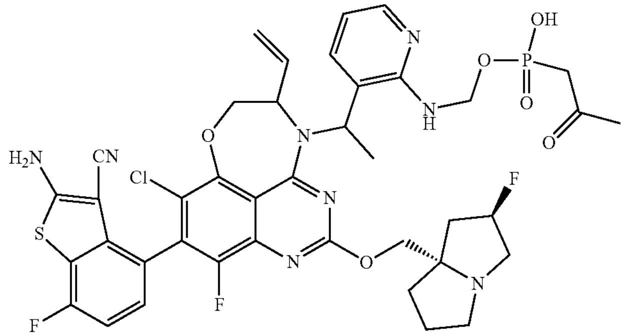
,
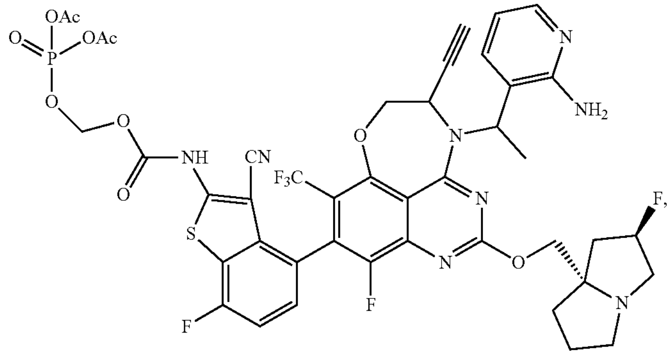
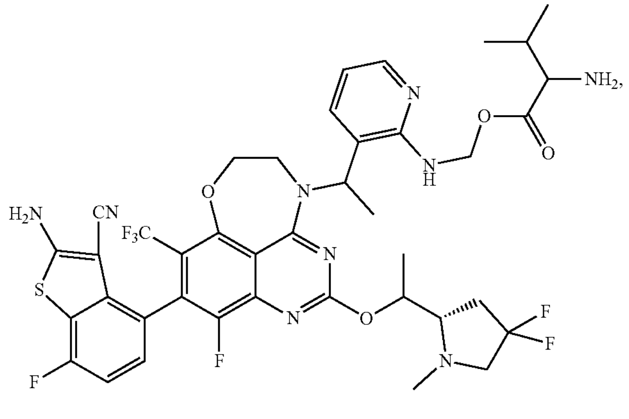

-continued
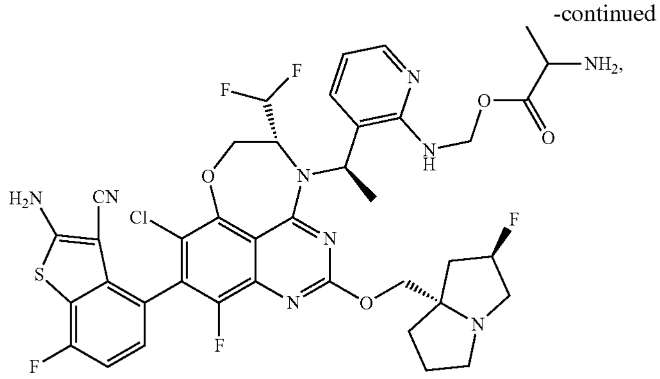
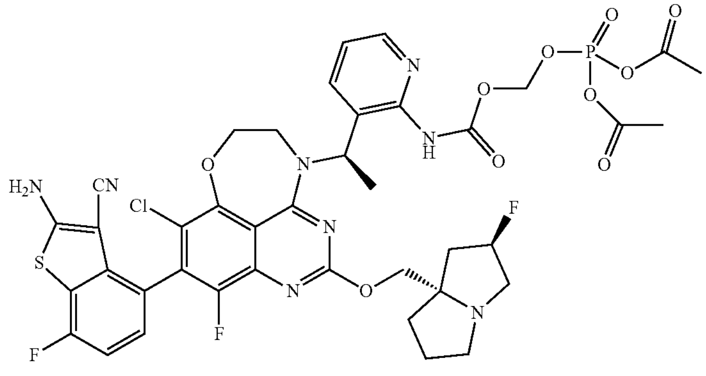
,
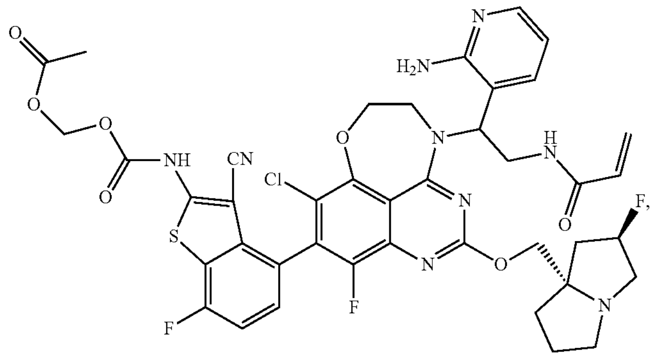
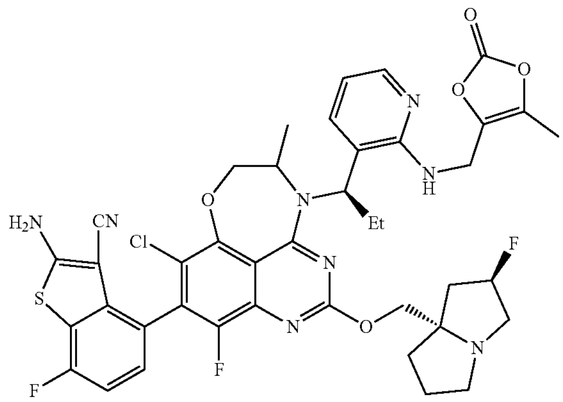
,

-continued
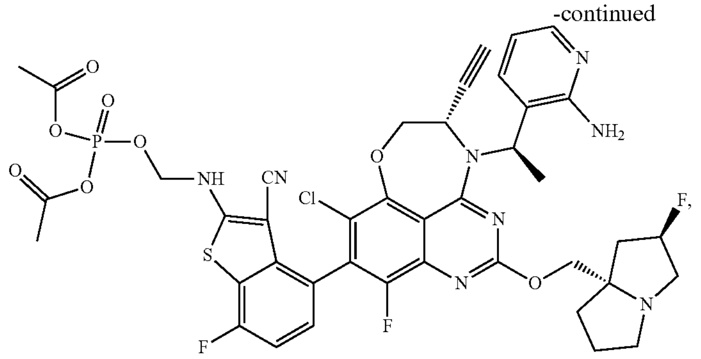
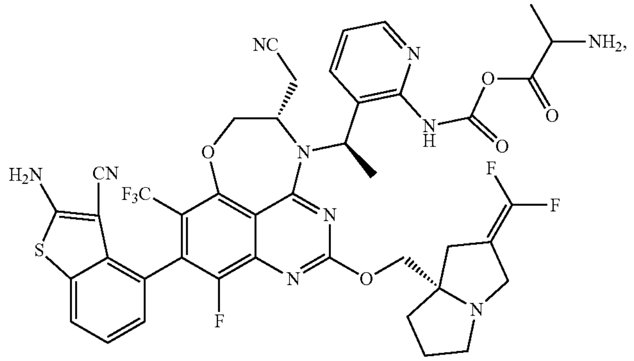
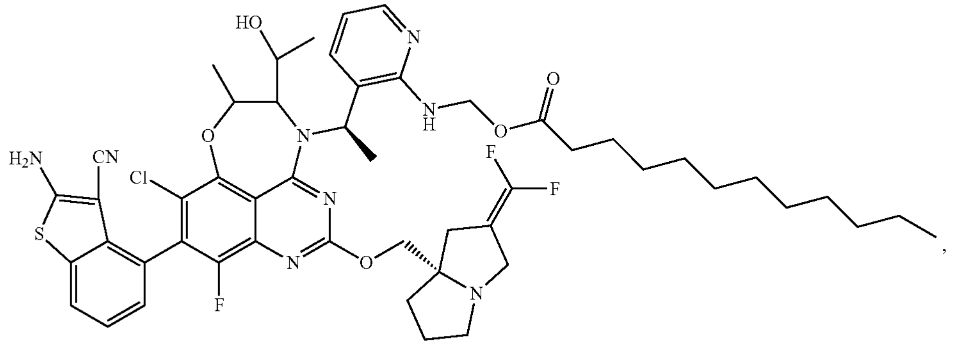
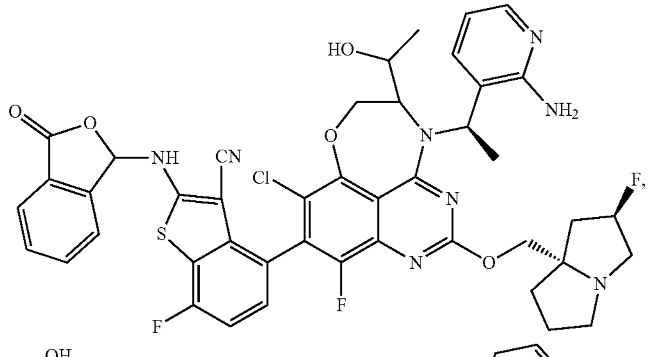
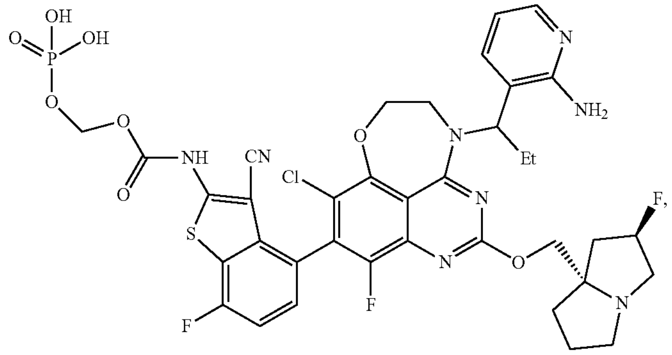

-continued
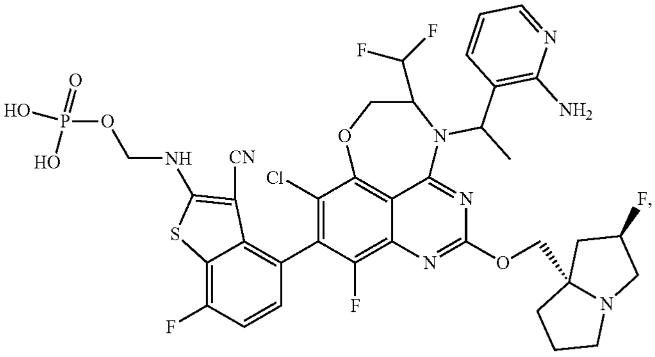
,
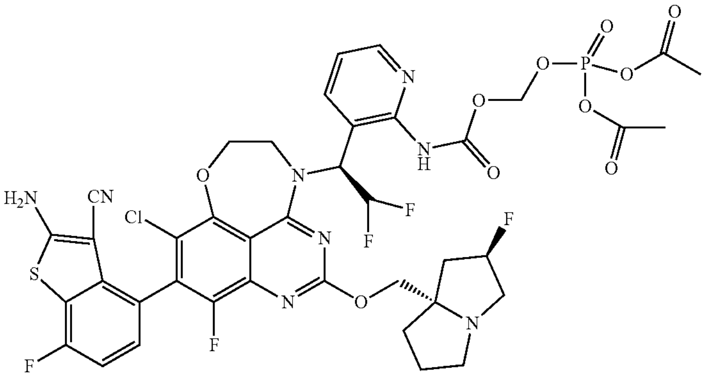
,
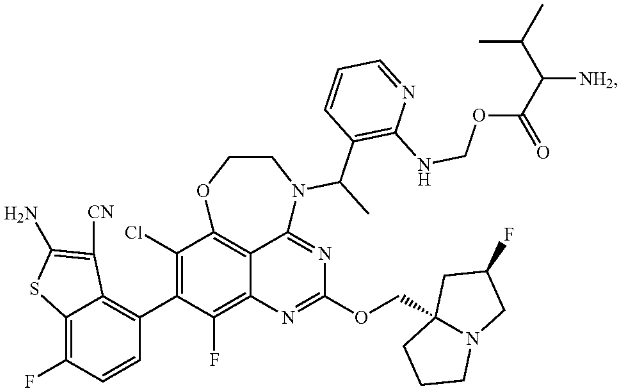
,
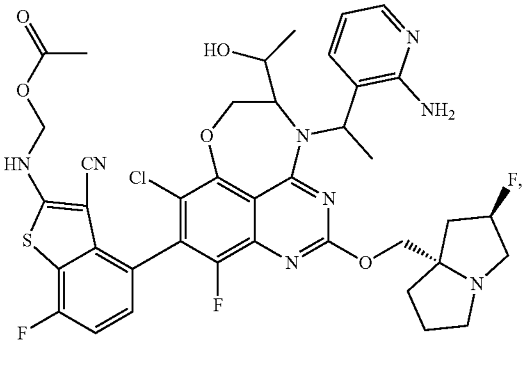
, and

-continued
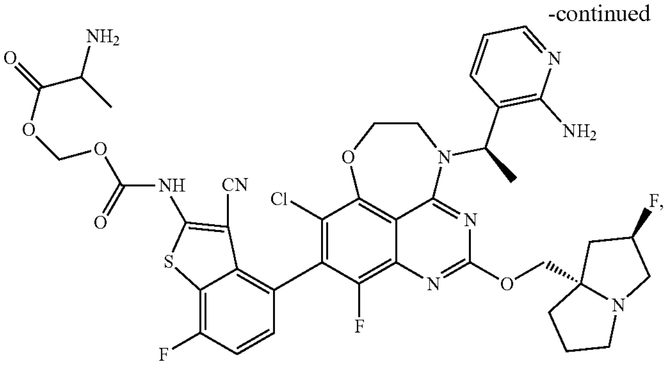
or a pharmaceutically acceptable salt or solvate thereof.
In certain aspects, the present disclosure provides a compound selected from:
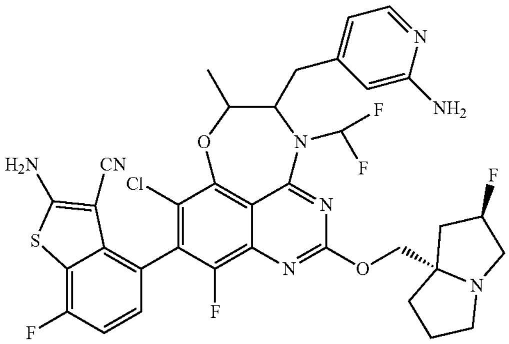
,
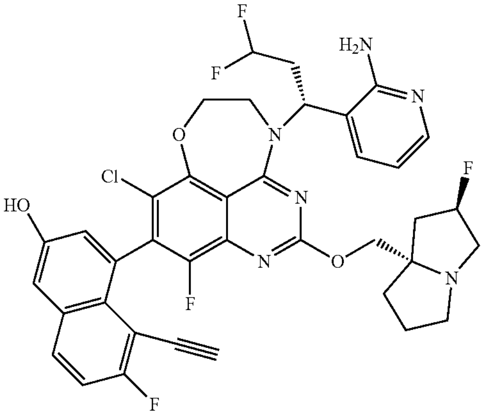
,
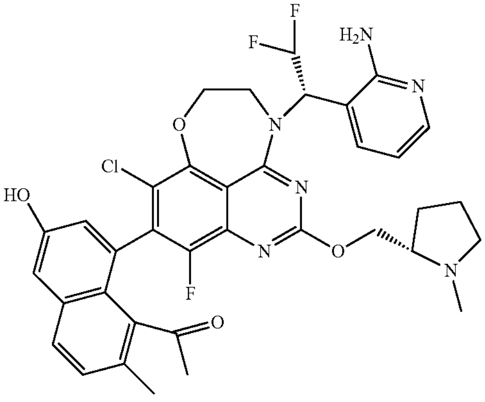
,
-continued
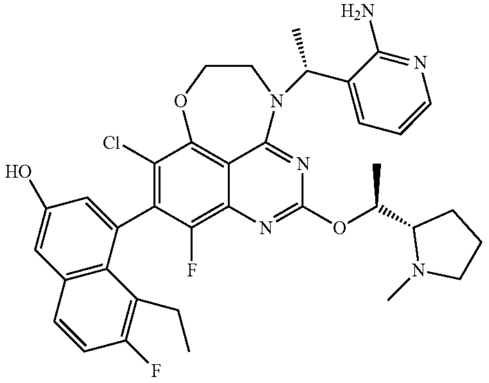
,
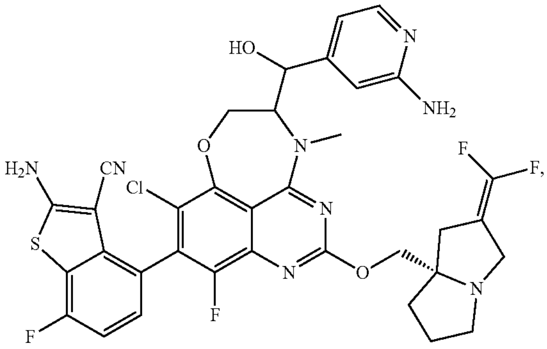
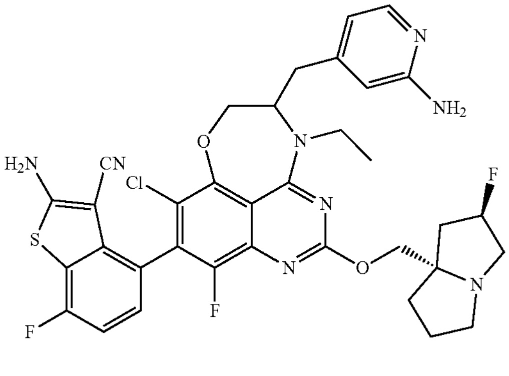
, -continued
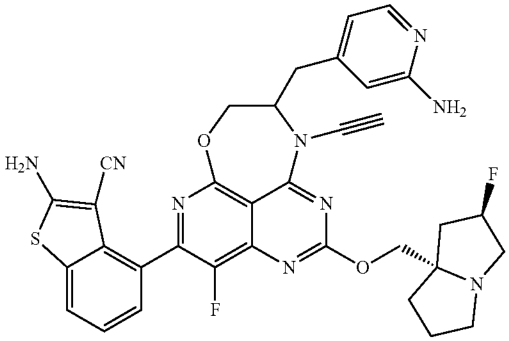
,
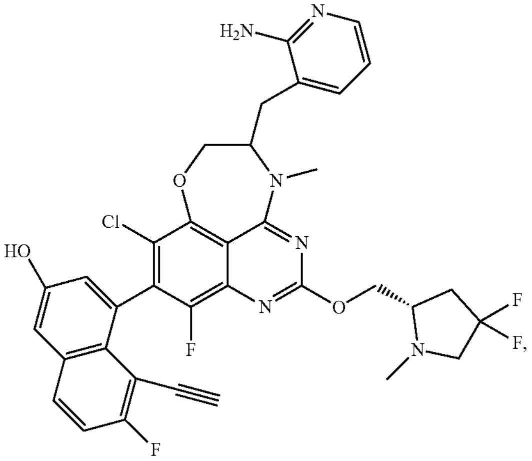
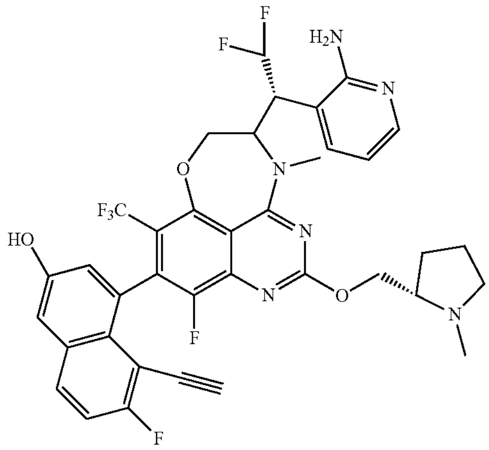
,
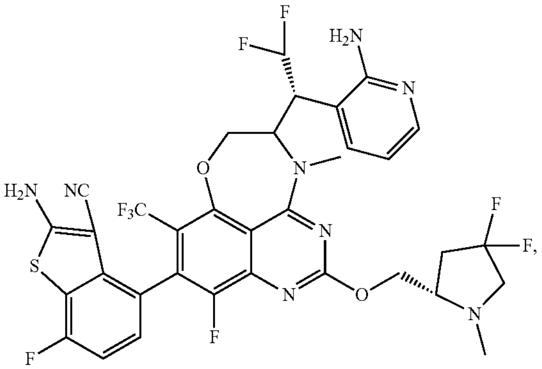
-continued
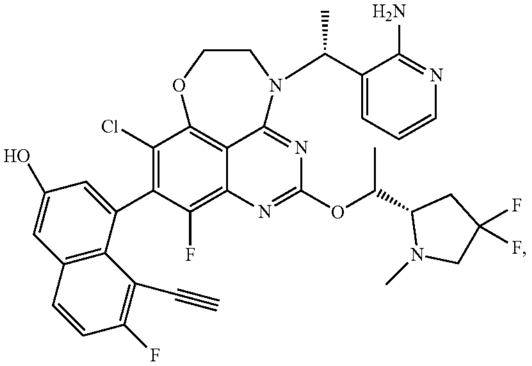
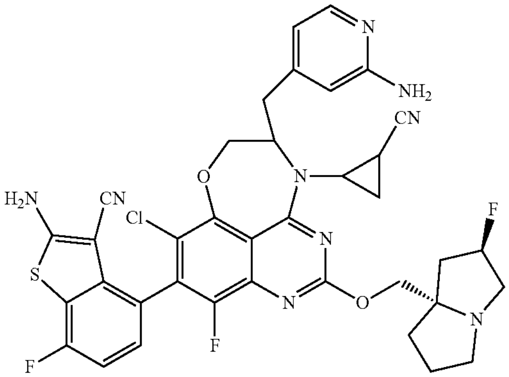
,
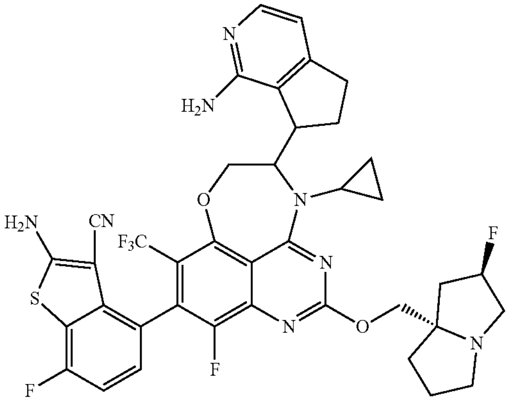
,
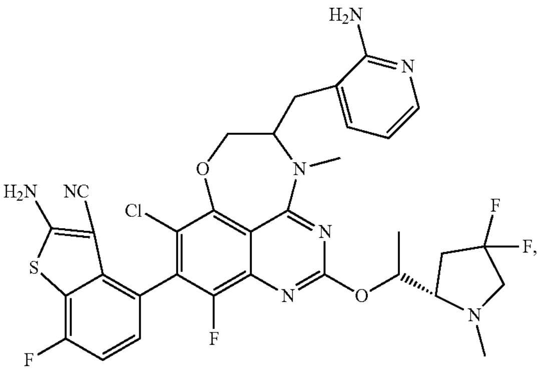

-continued
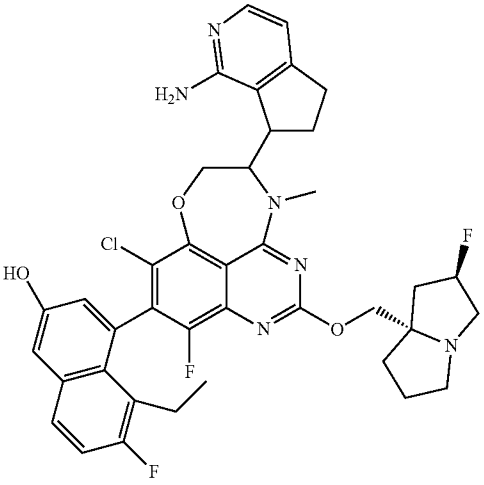
,
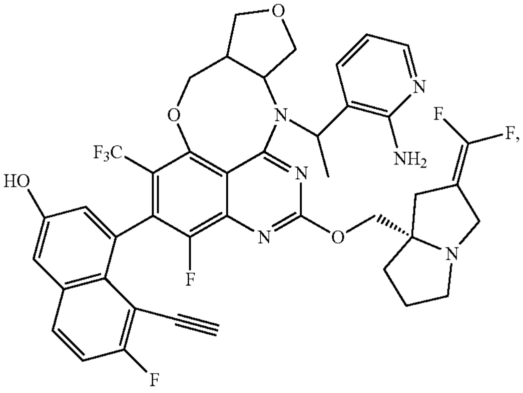
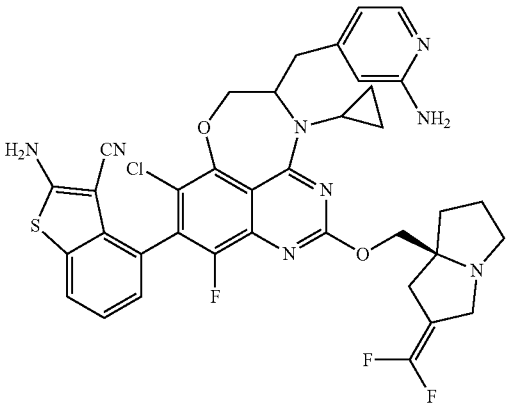
,
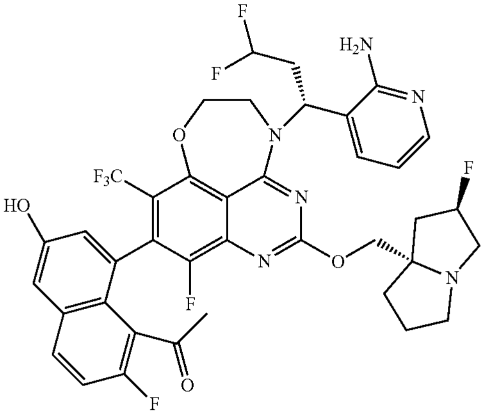
,
-continued
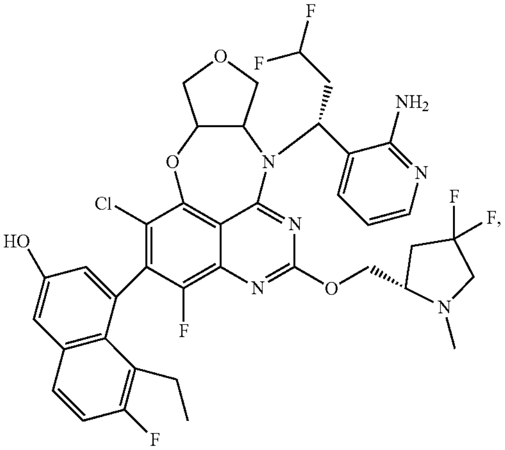
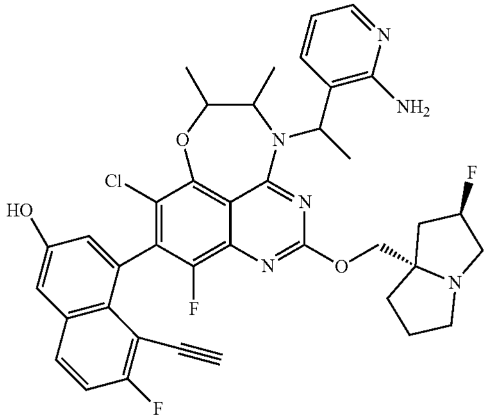
,
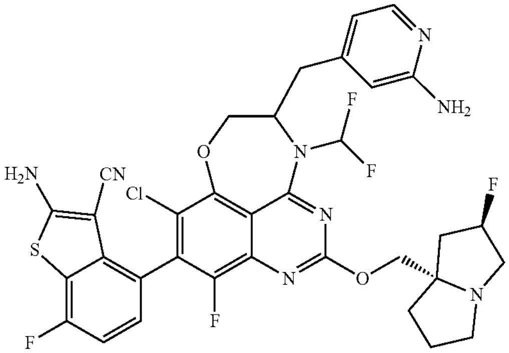
,
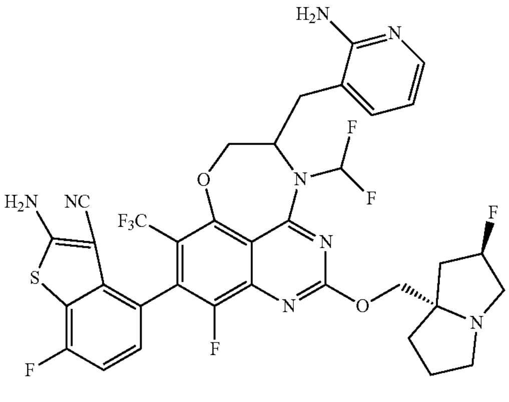
, -continued
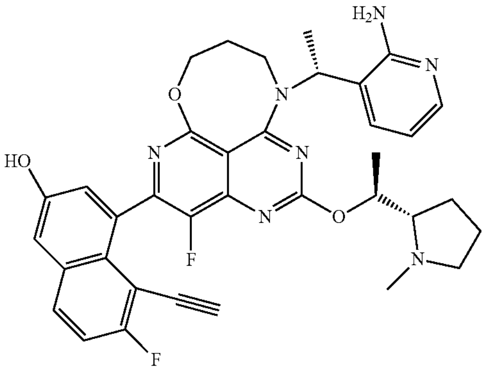
,
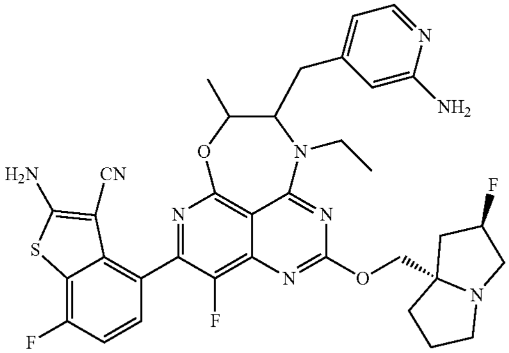
,
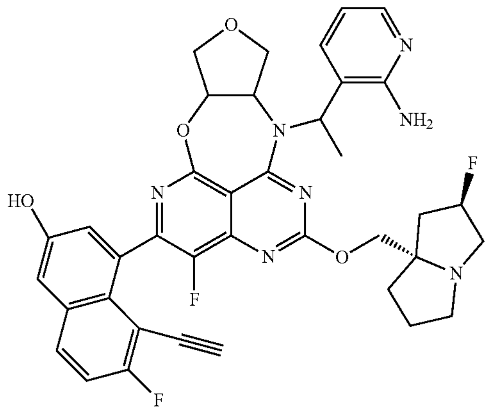
,
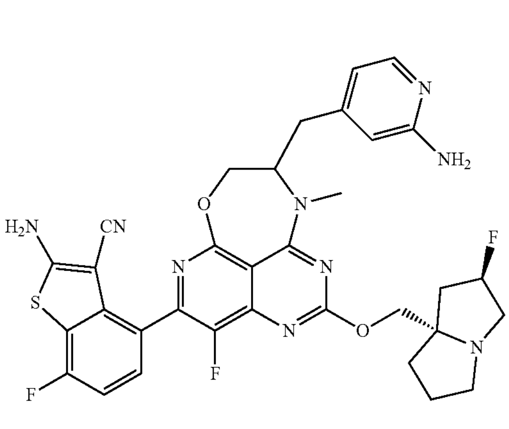
,
-continued
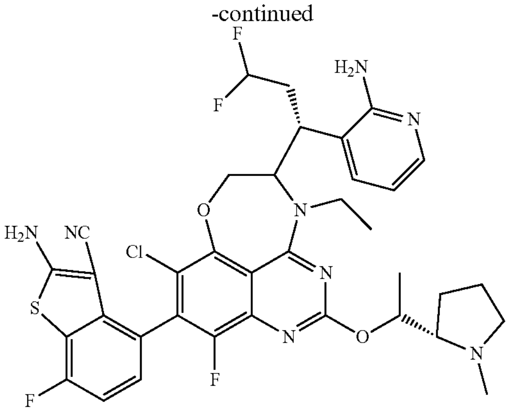
,
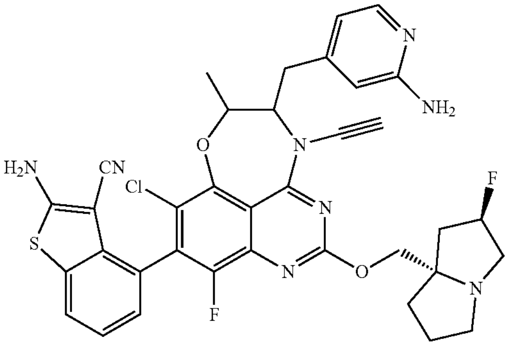
,
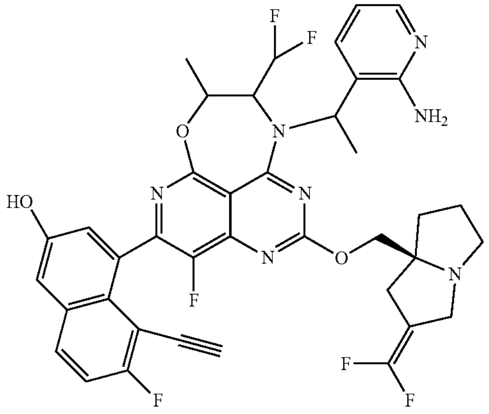
,
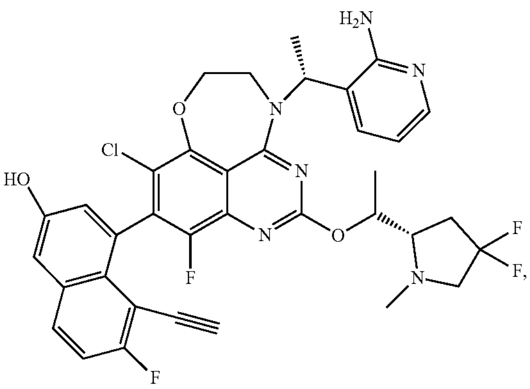
, -continued
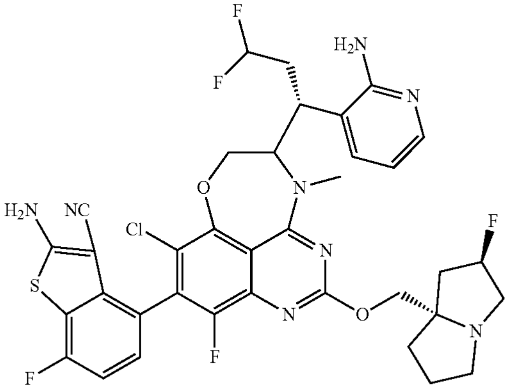
,
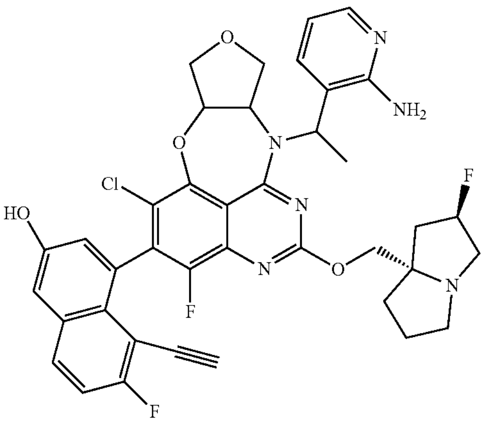
,
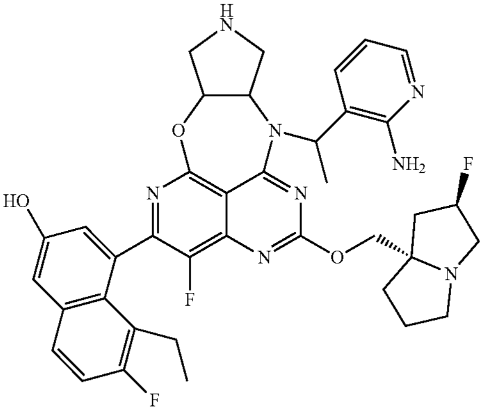
,
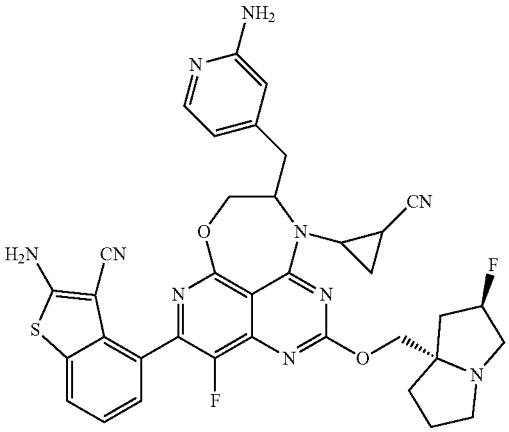
,
-continued
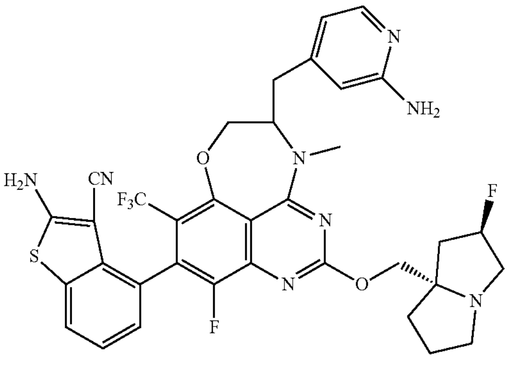
,
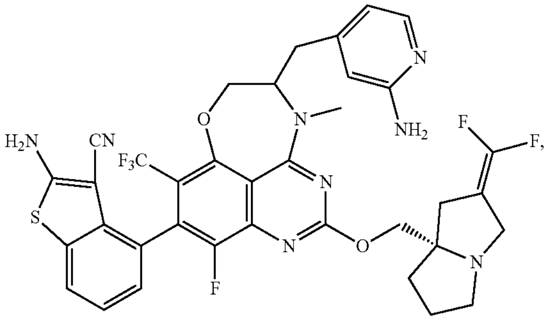
,
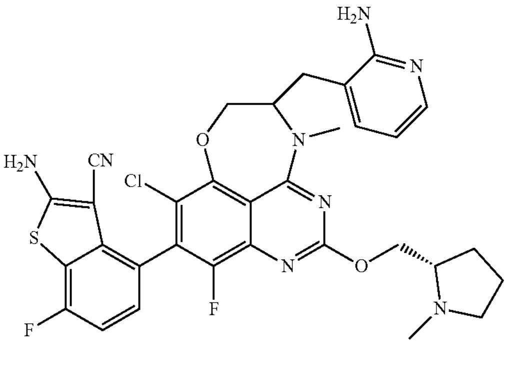
,
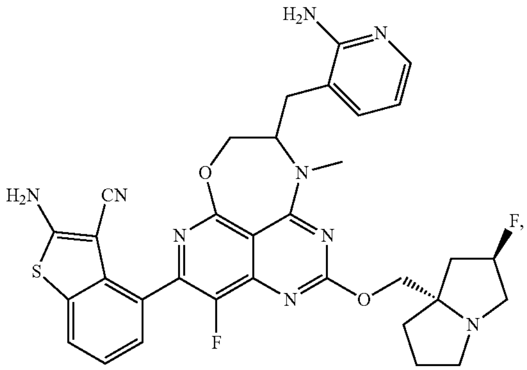
, -continued
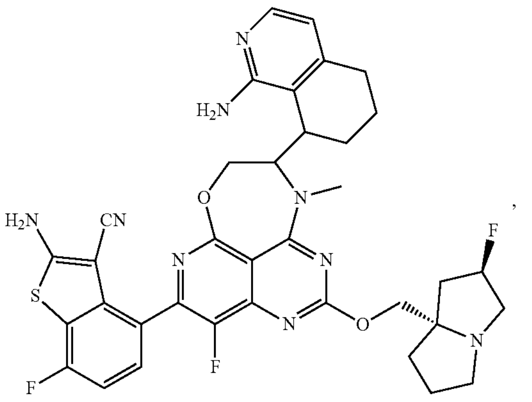
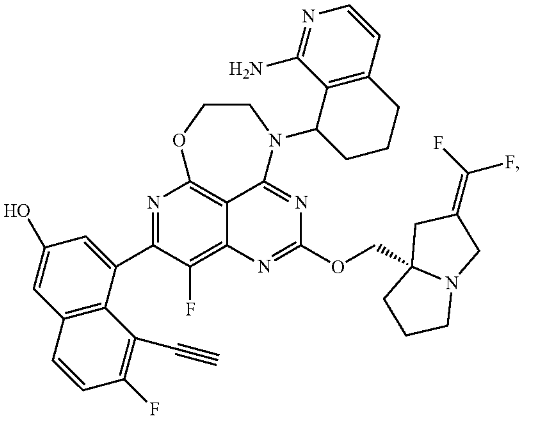
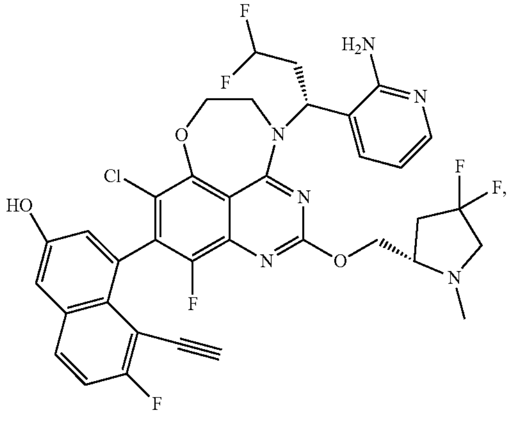
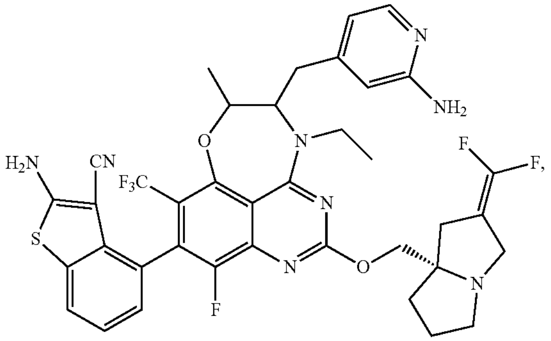
-continued
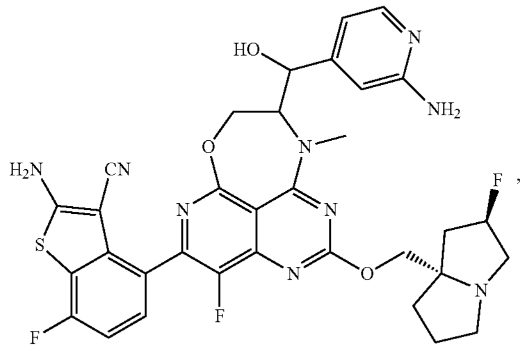
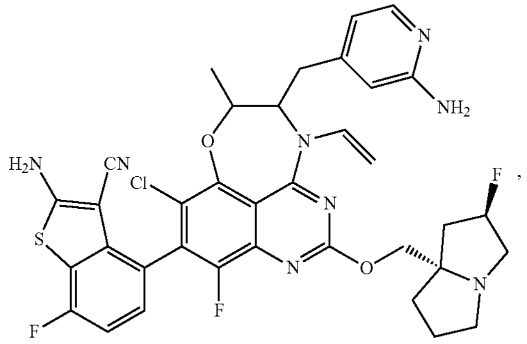
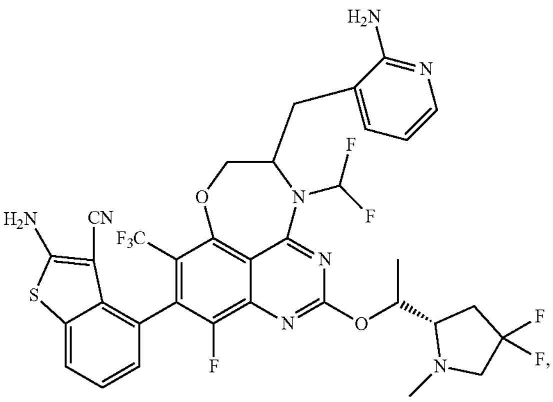
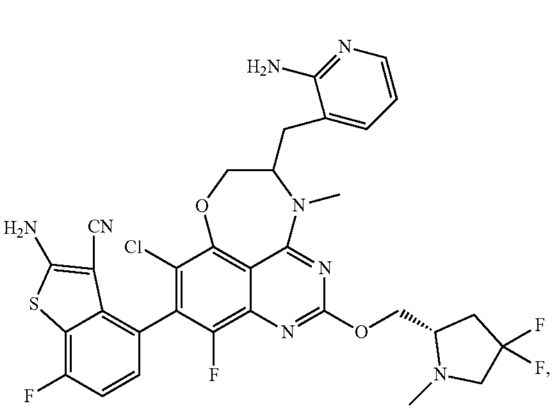

-continued
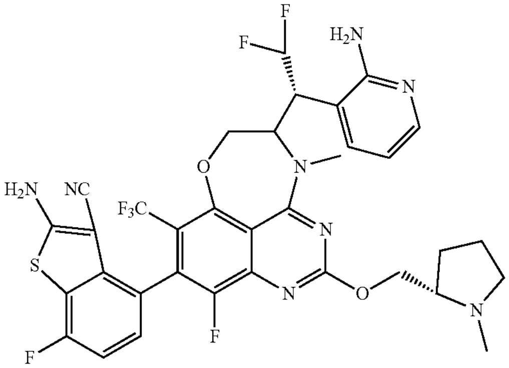
,
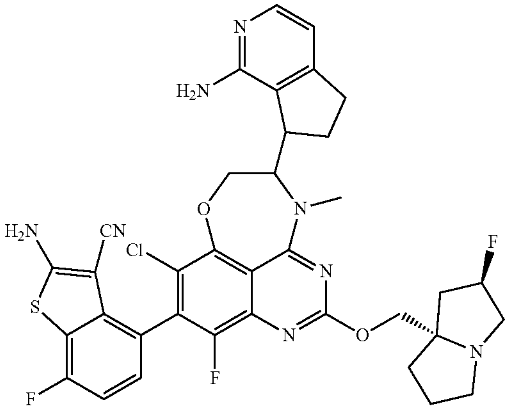
,
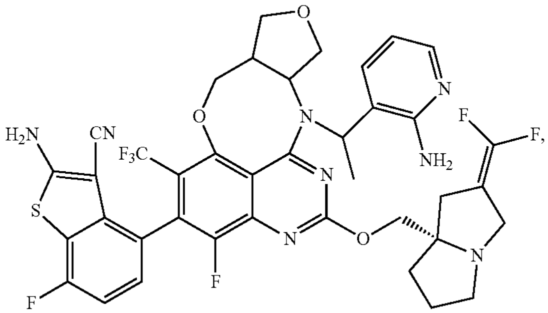
,
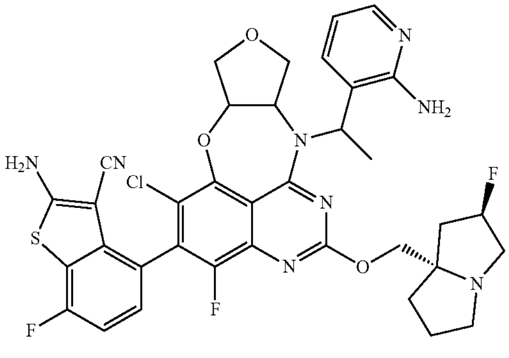
,
-continued
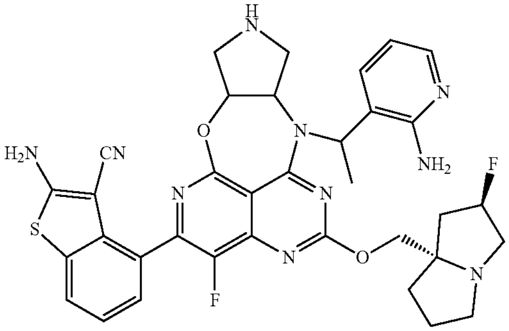
,
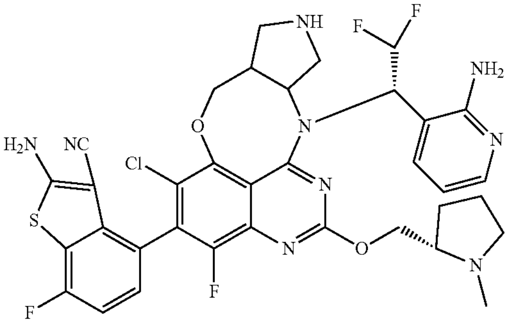
,
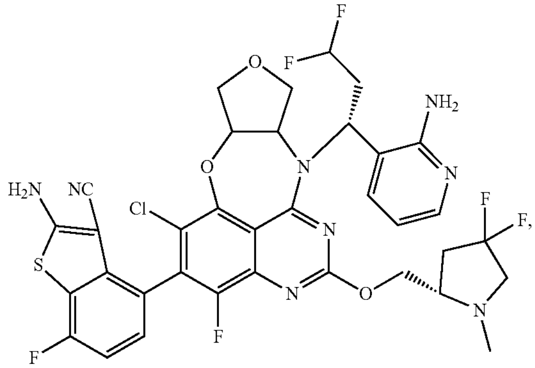
,
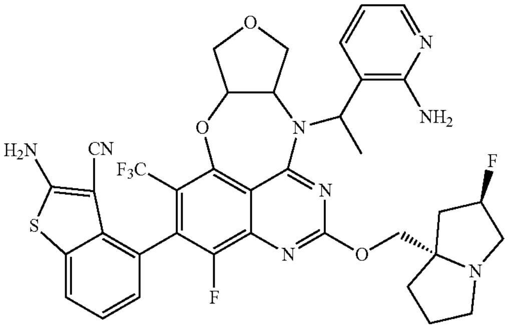
,
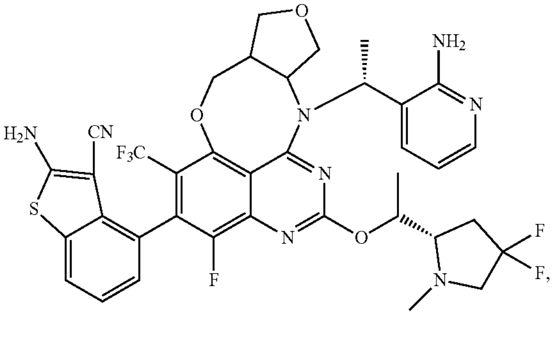
, -continued
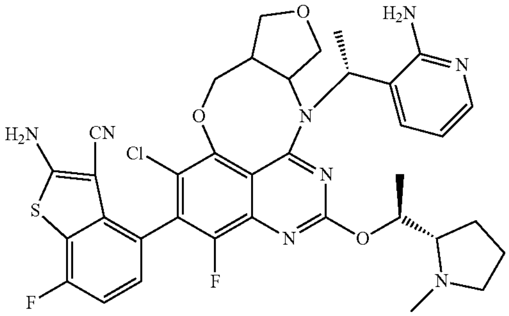
,
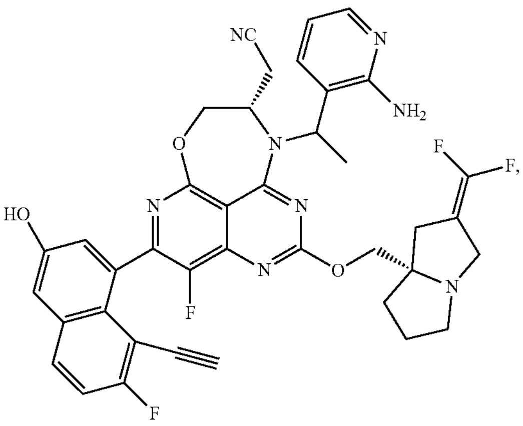
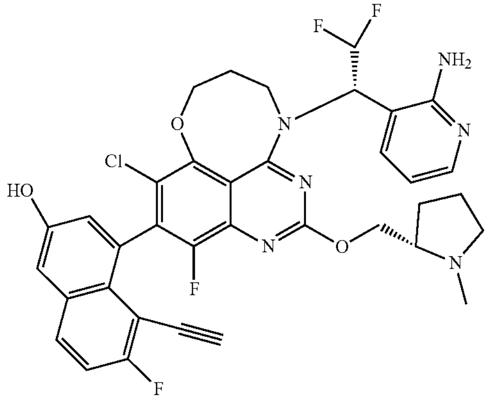
,
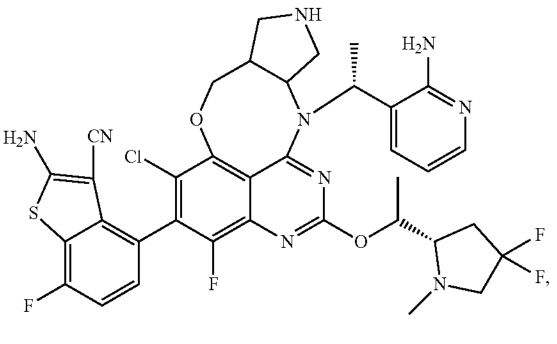
-continued
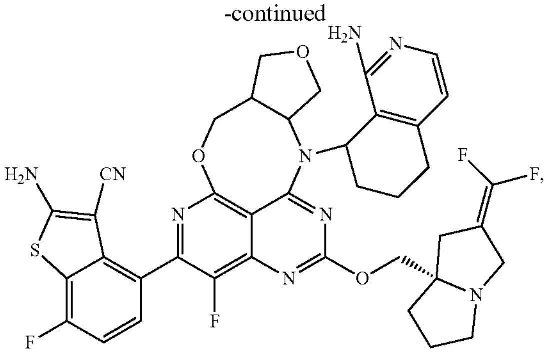
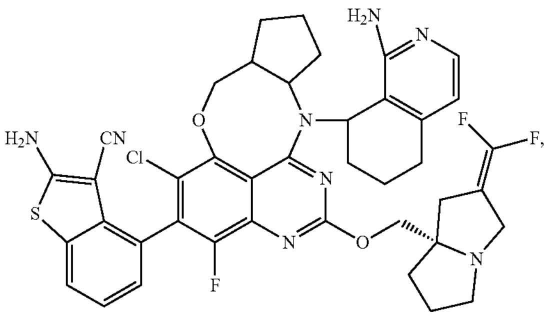
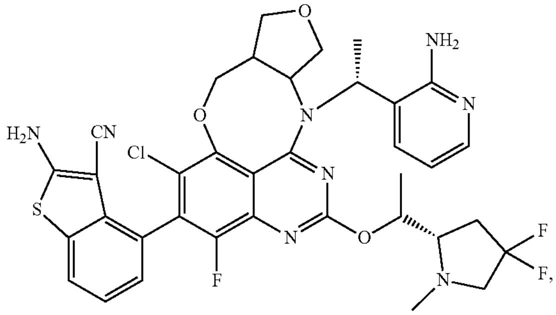
or a pharmaceutically acceptable salt or solvate thereof.
In certain aspects, the present disclosure provides a compound selected from:
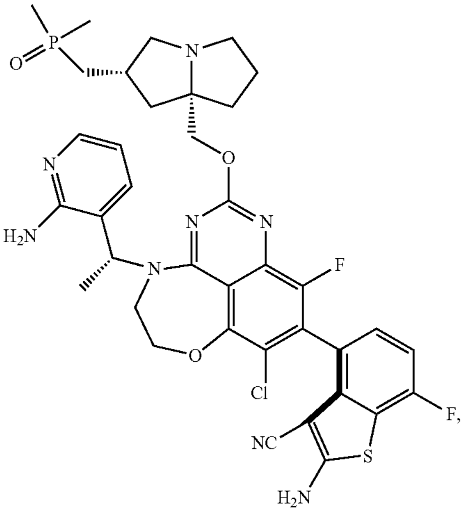

-continued
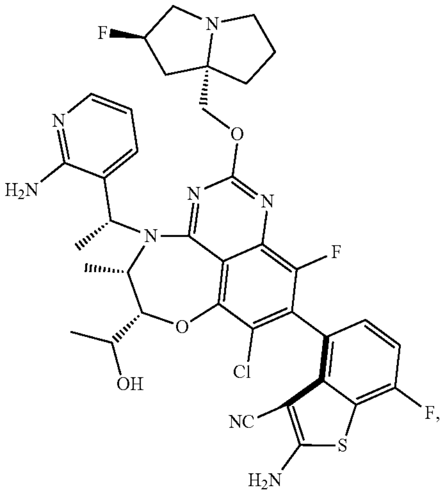
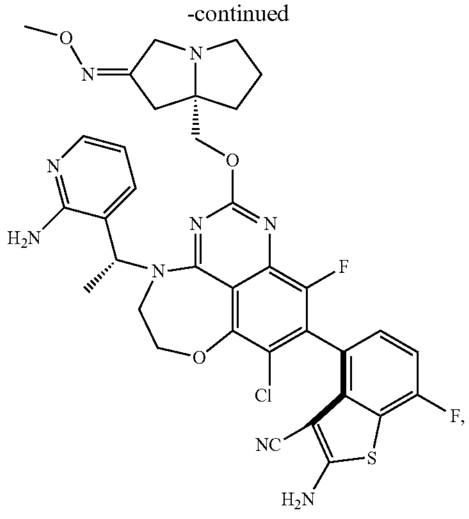
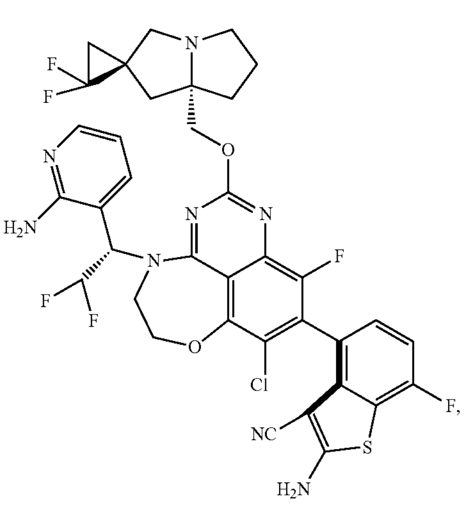
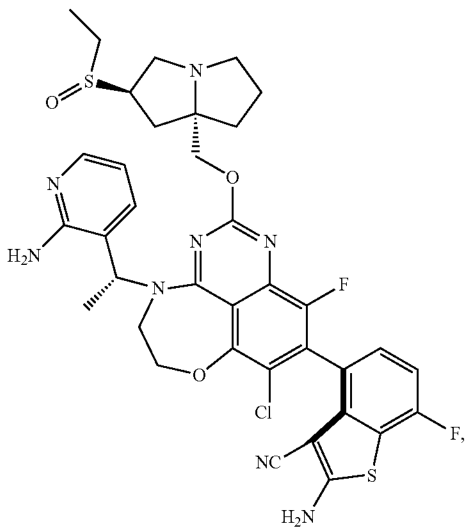
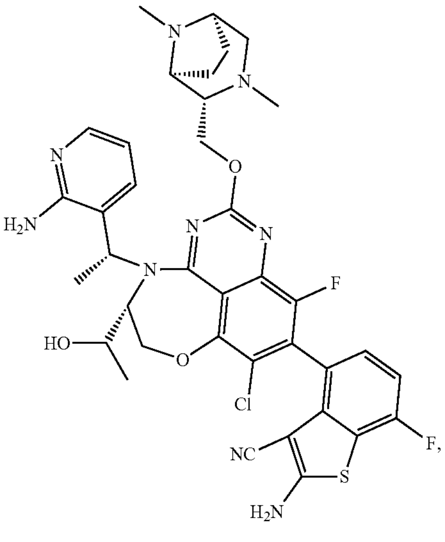
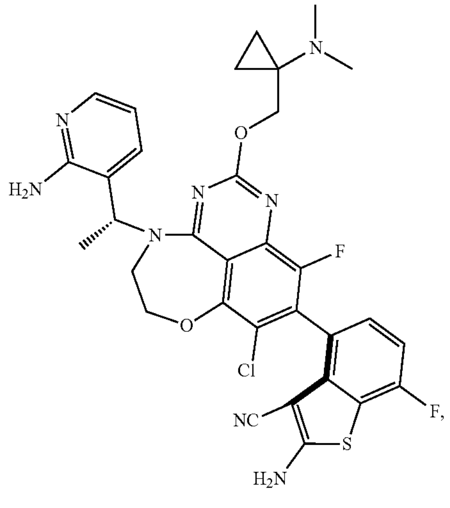

-continued
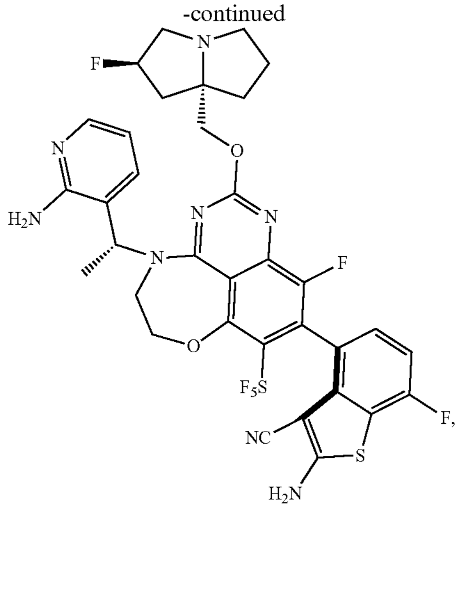
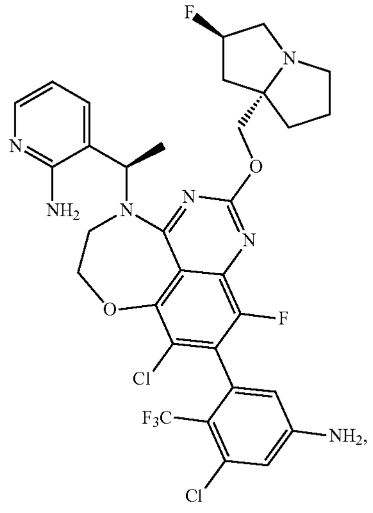
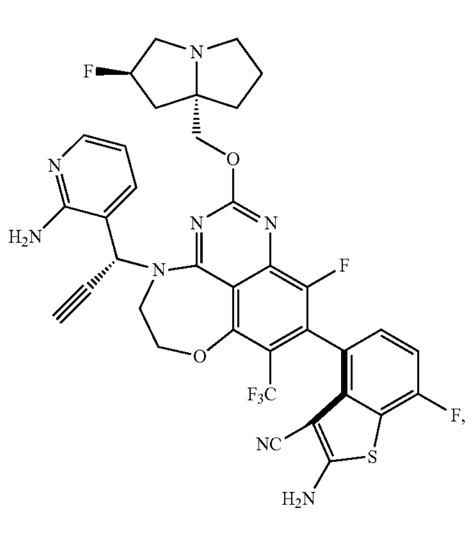
-continued
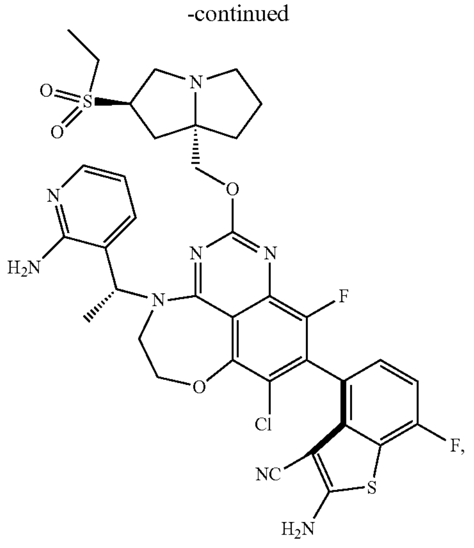
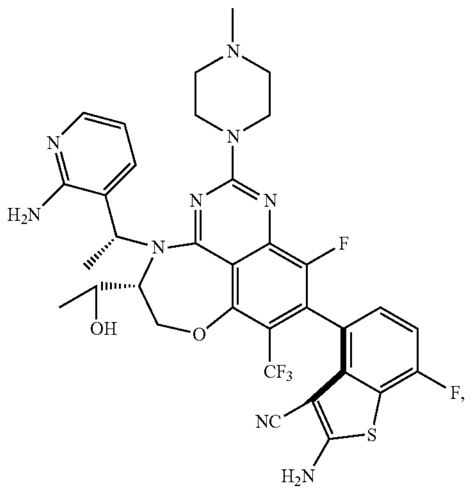
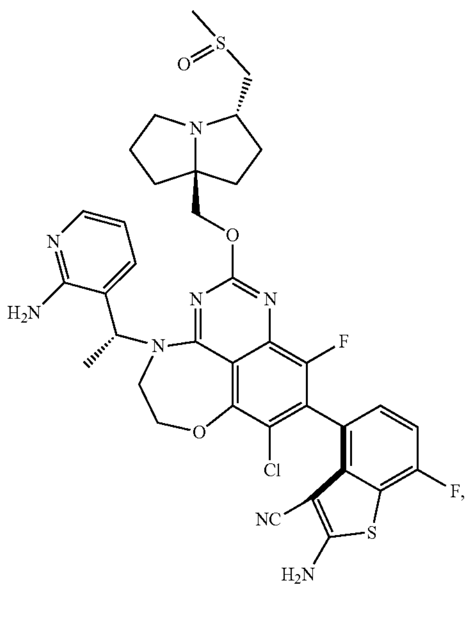

-continued
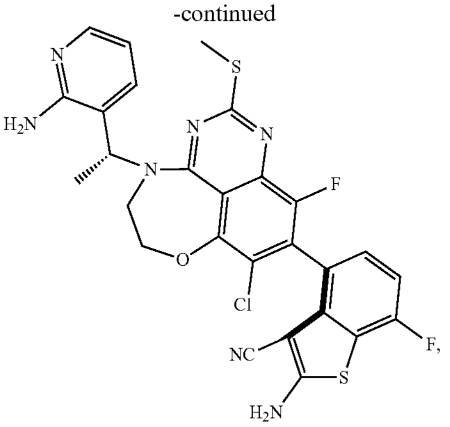
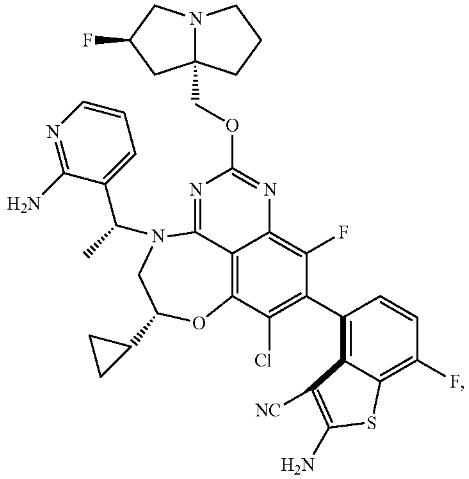
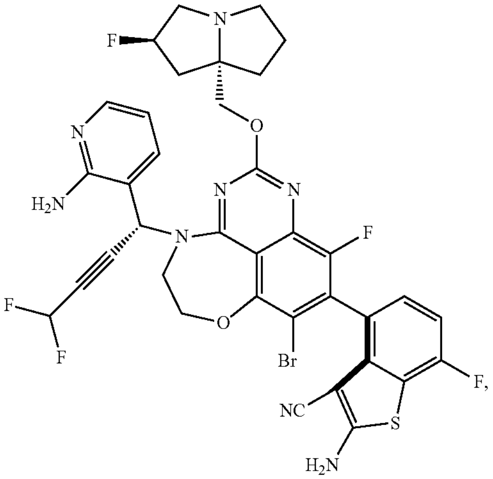
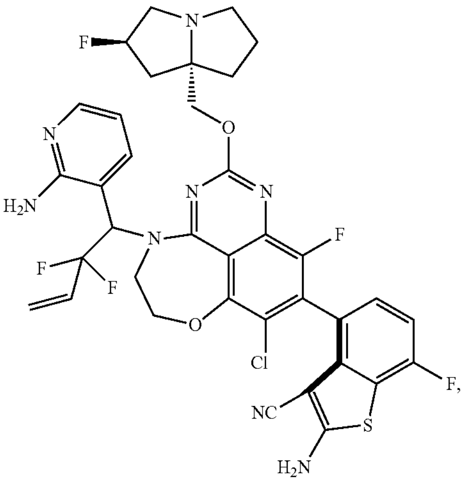
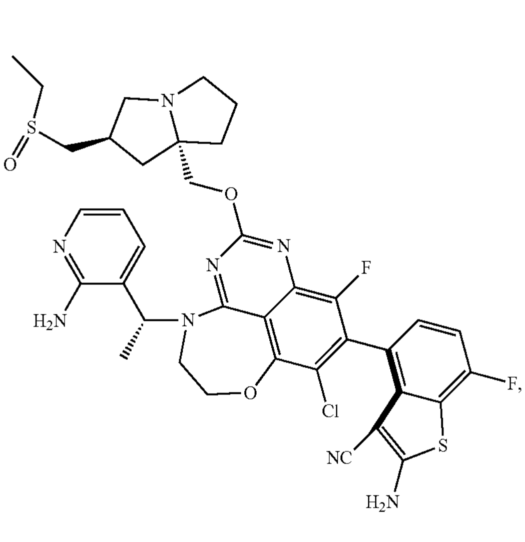
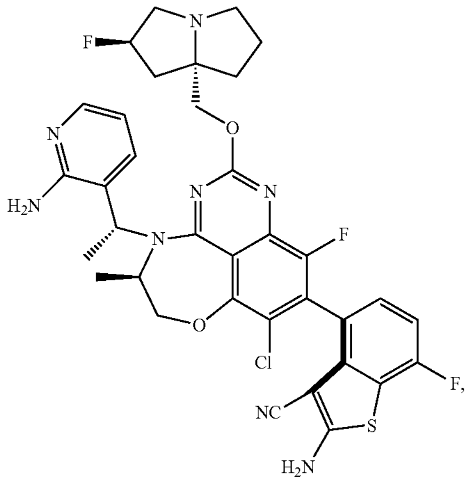
-continued -continued
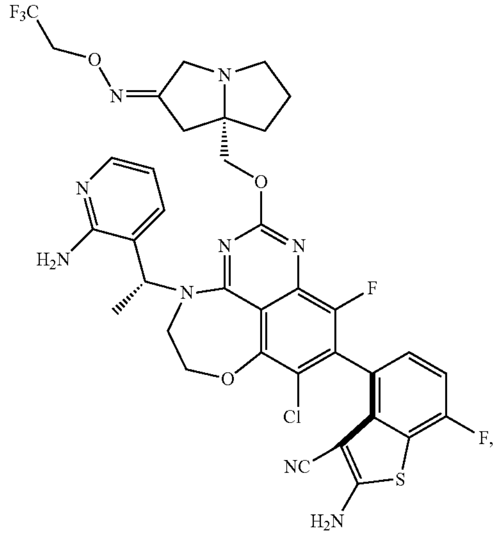
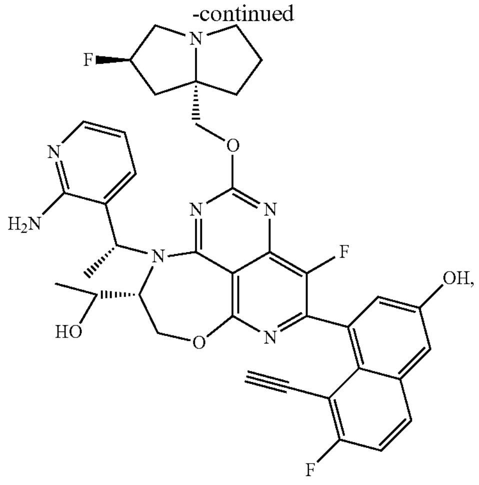
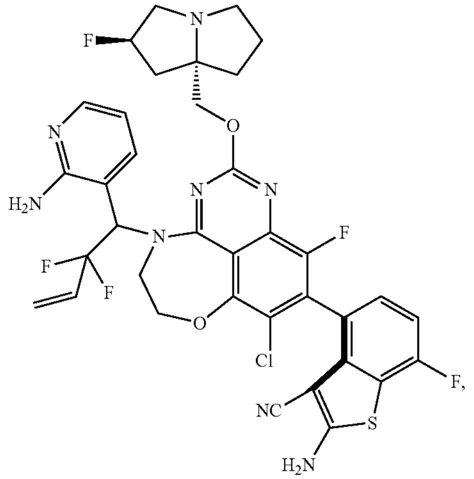
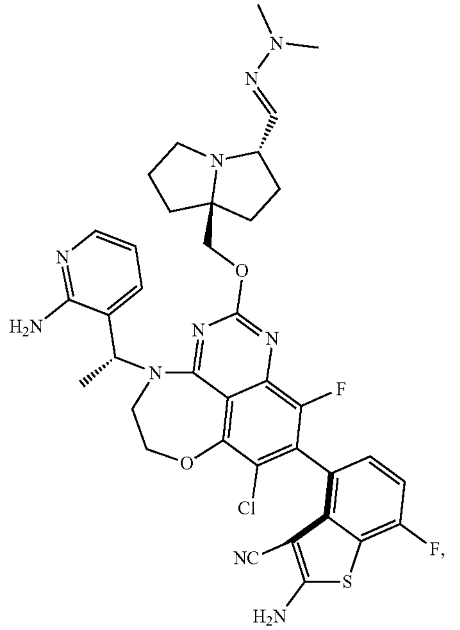
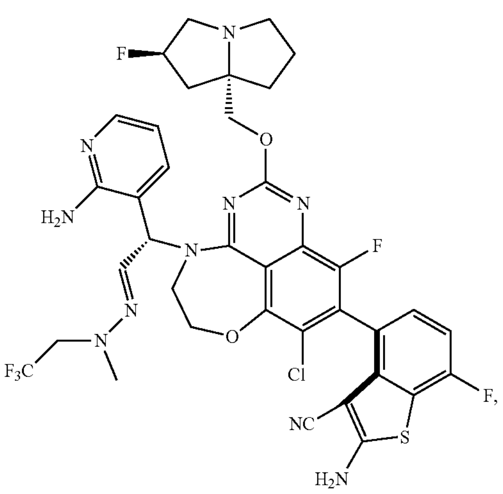
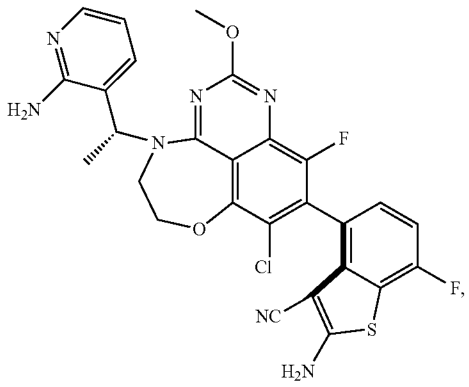

-continued
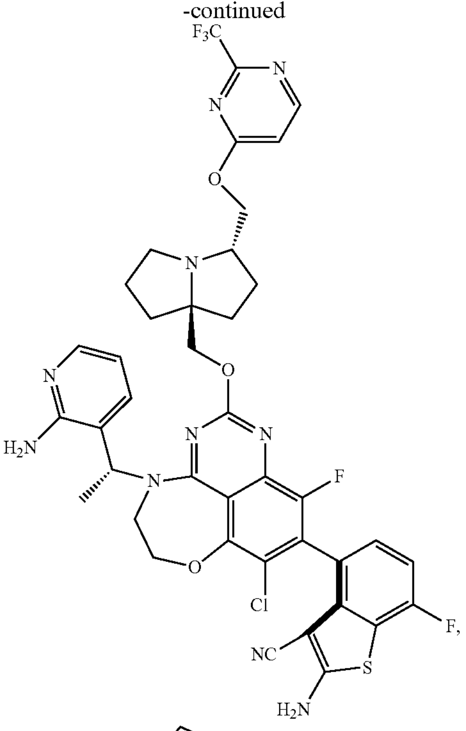
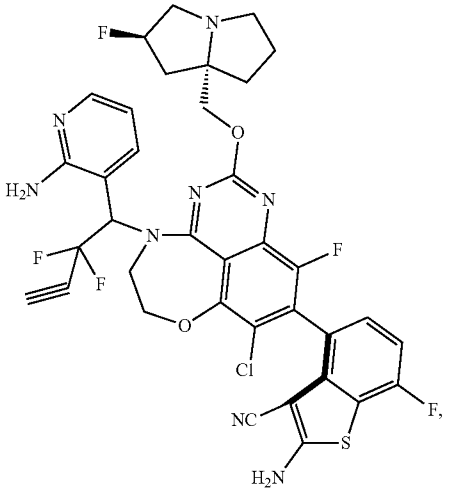
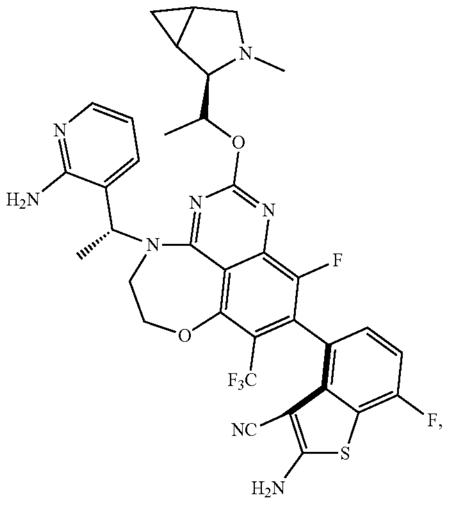
-continued
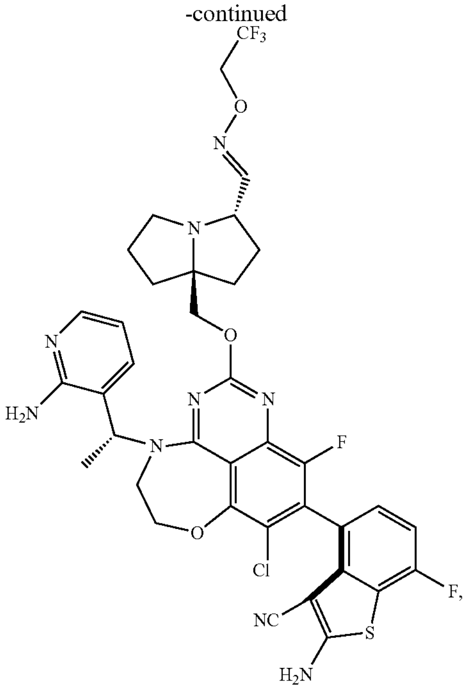
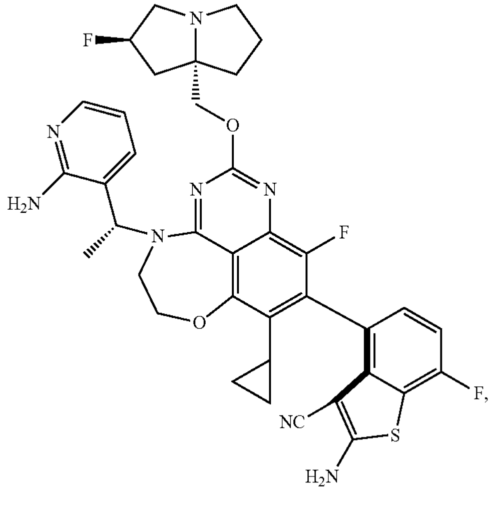

-continued
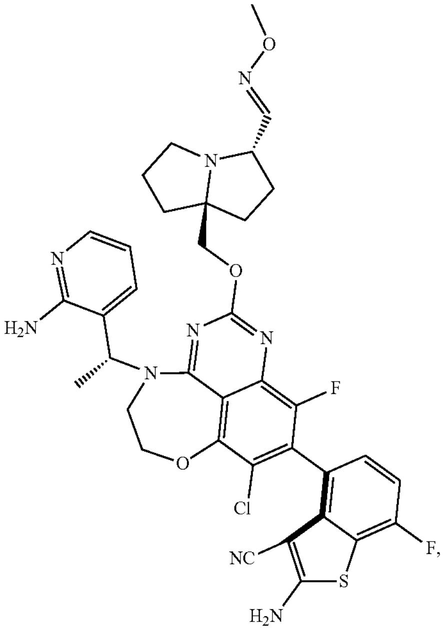
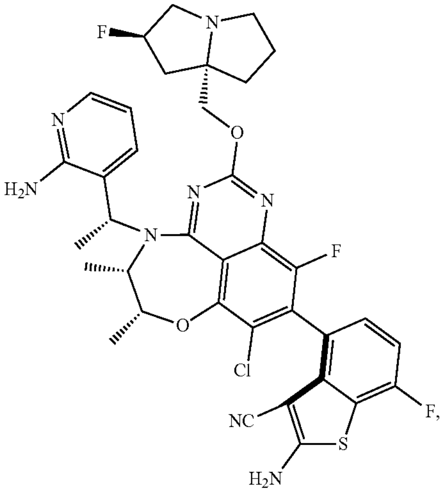
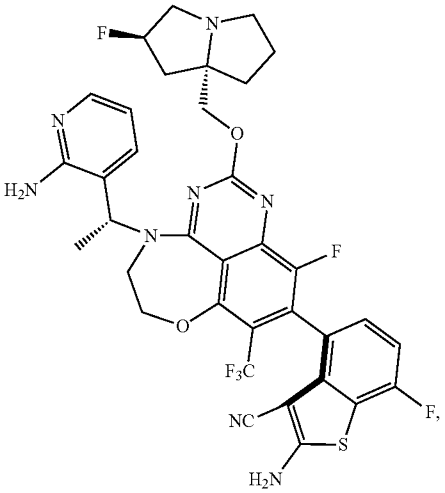
-continued
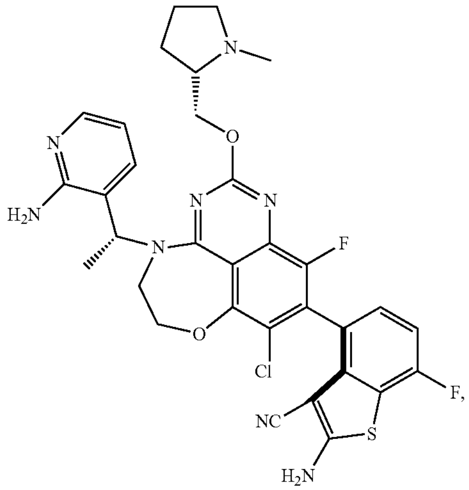
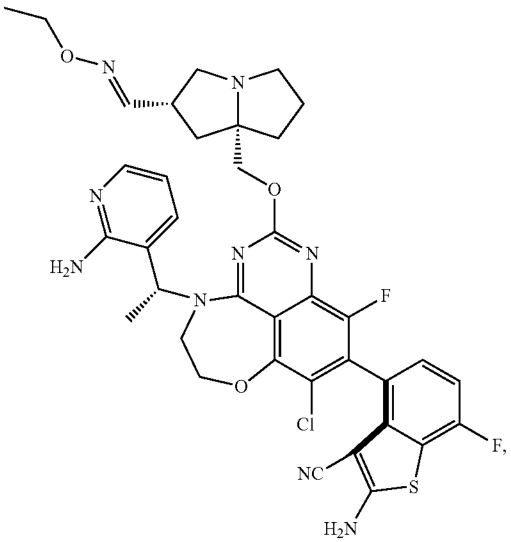
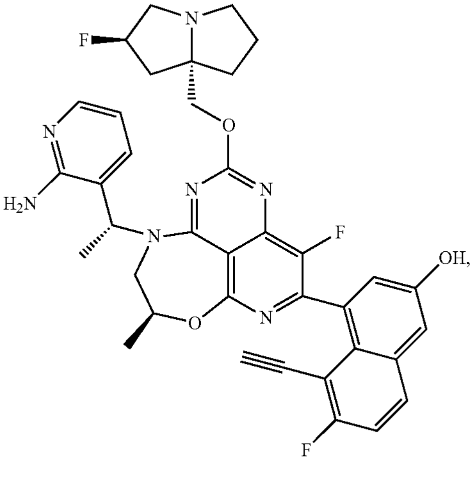

-continued
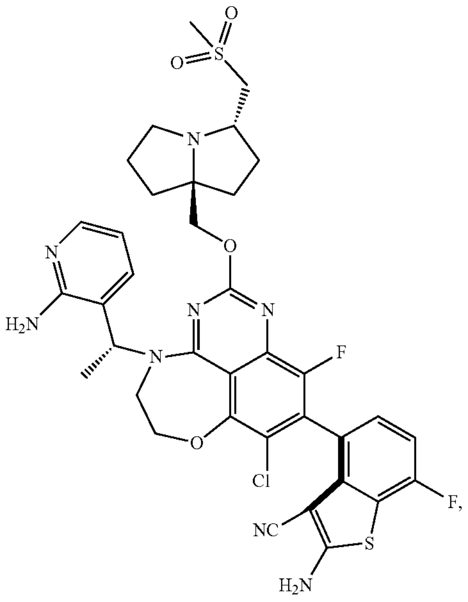
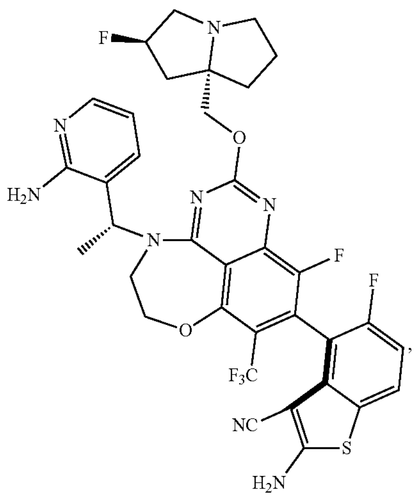
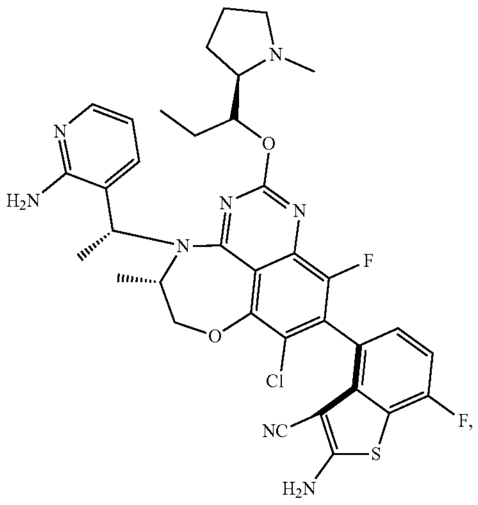
-continued
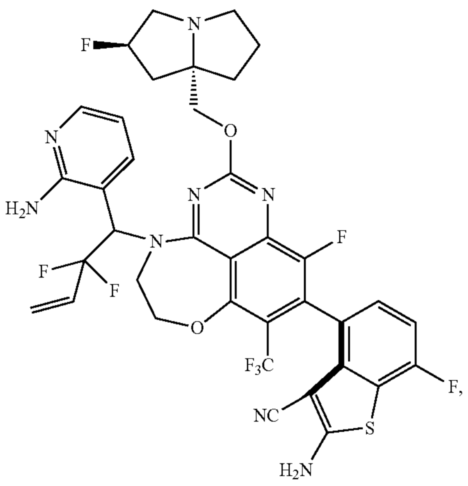
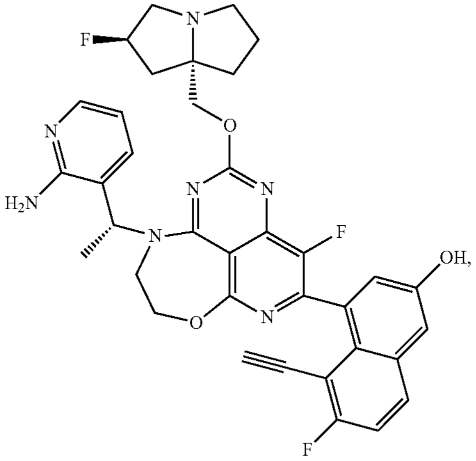
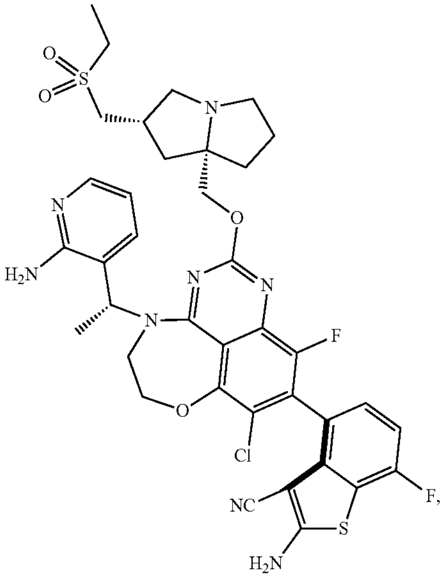

-continued
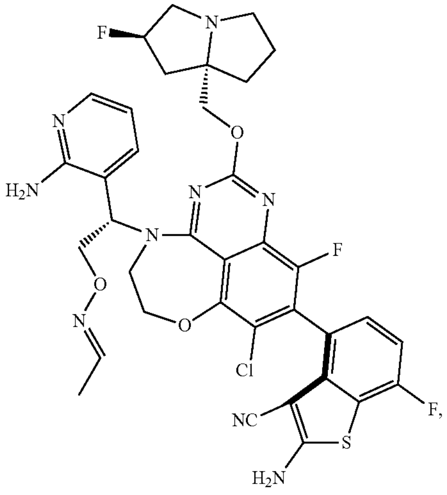
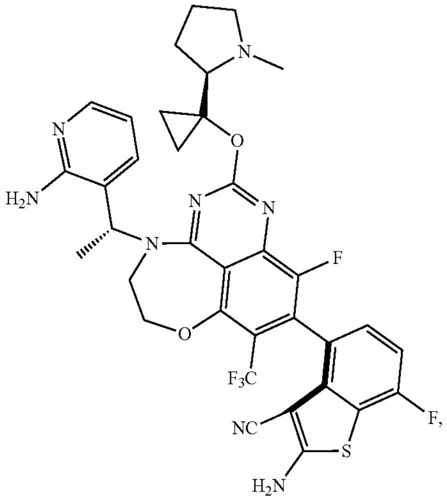
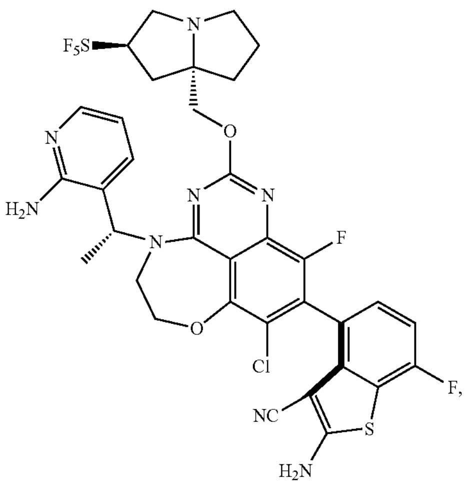
-continued
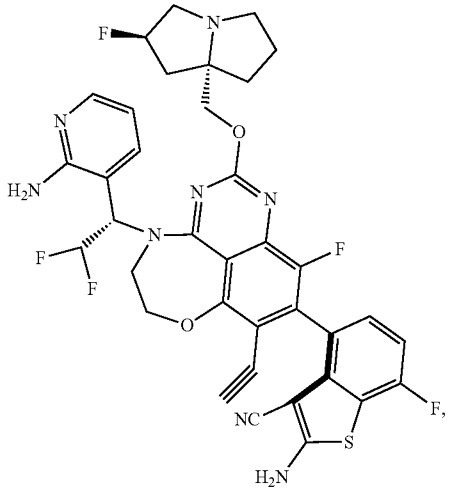
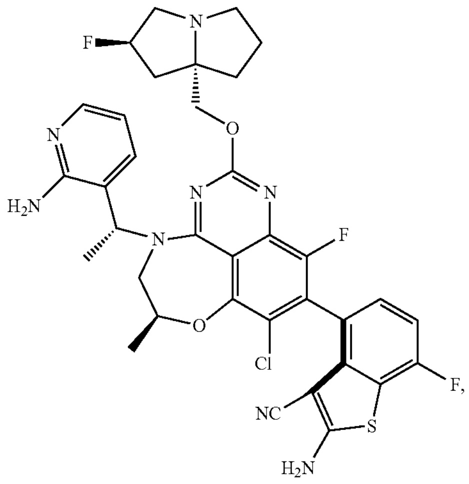
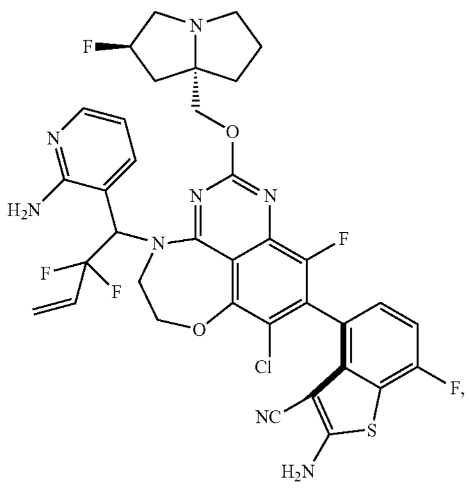

-continued
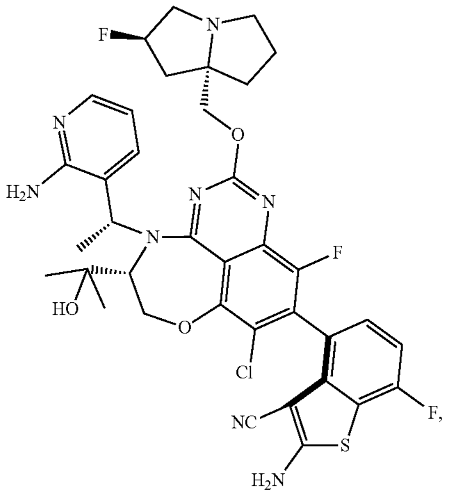
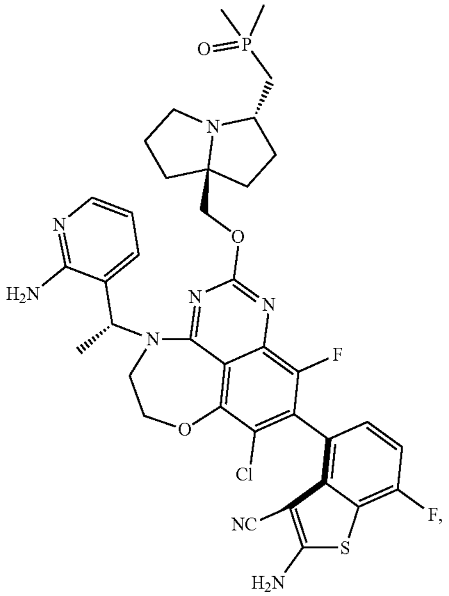
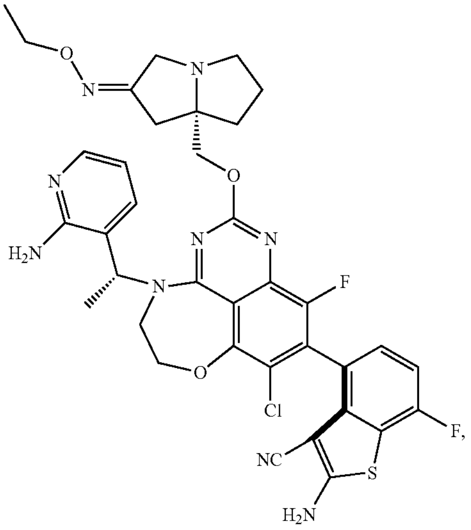
-continued
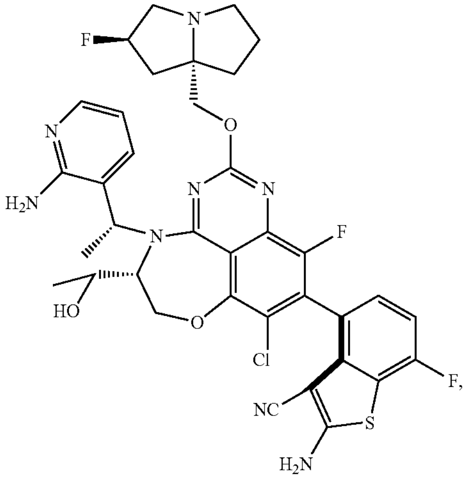
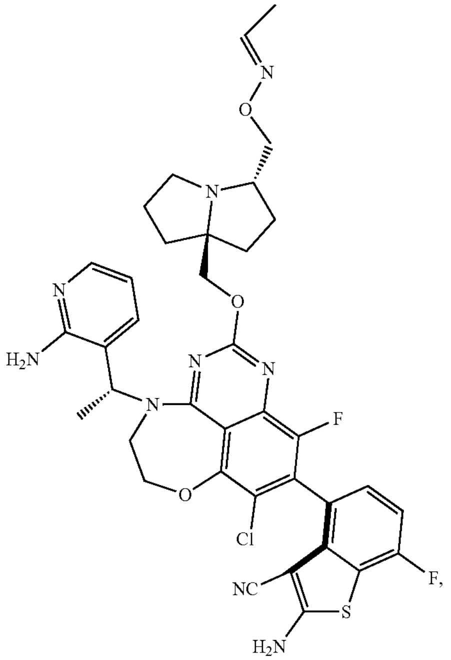
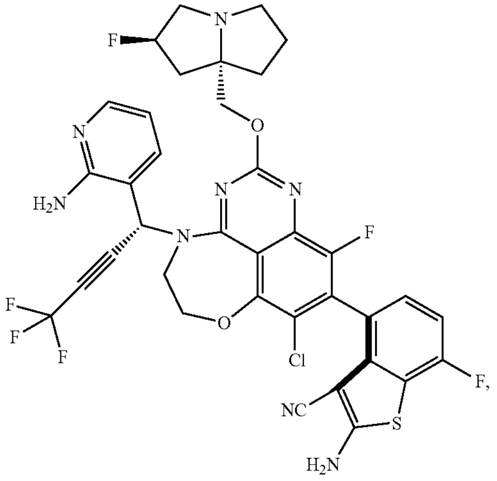

-continued
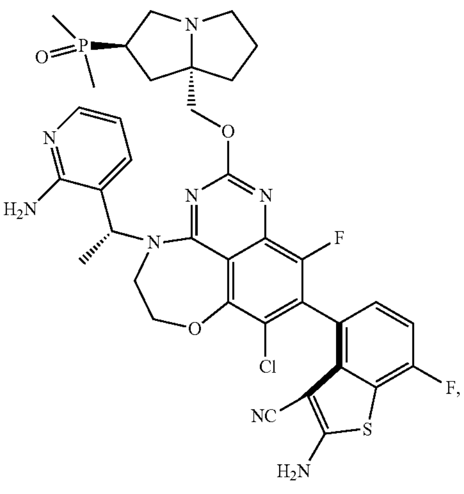
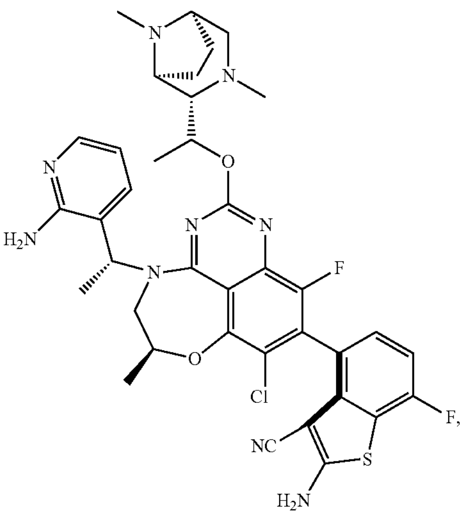
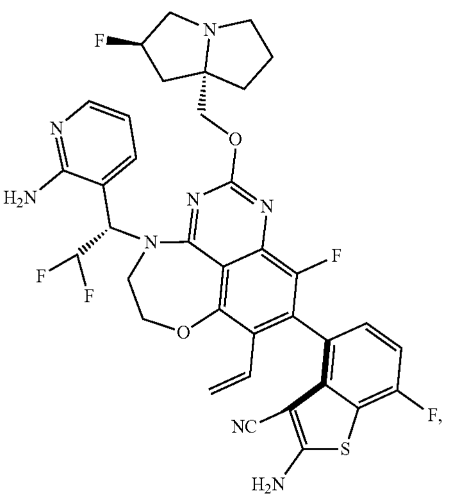
-continued
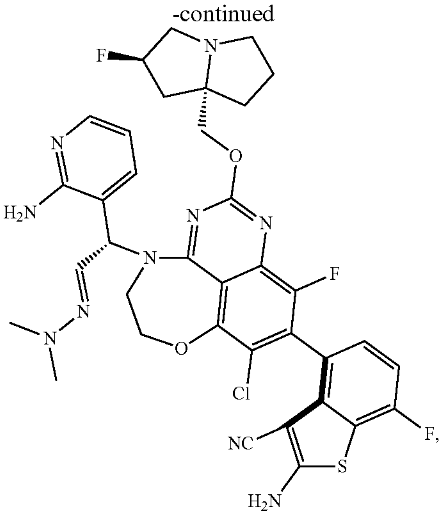
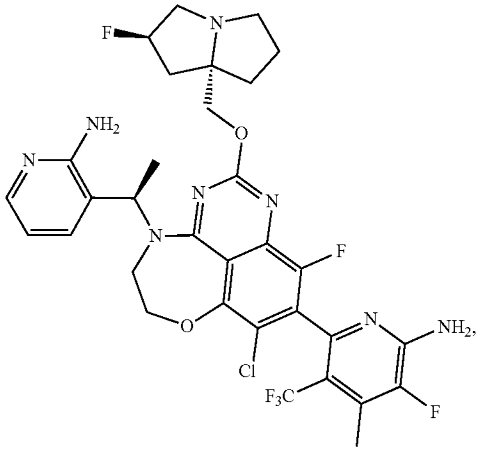
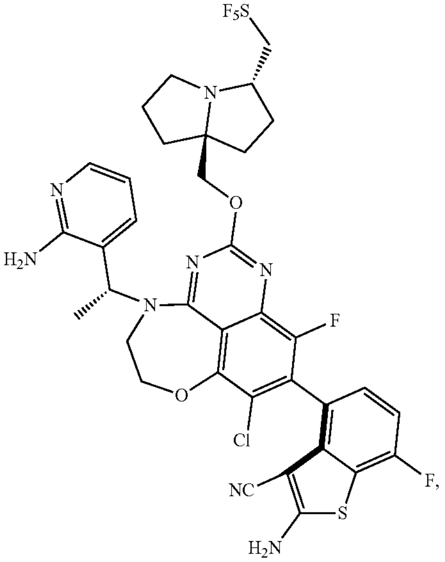

-continued
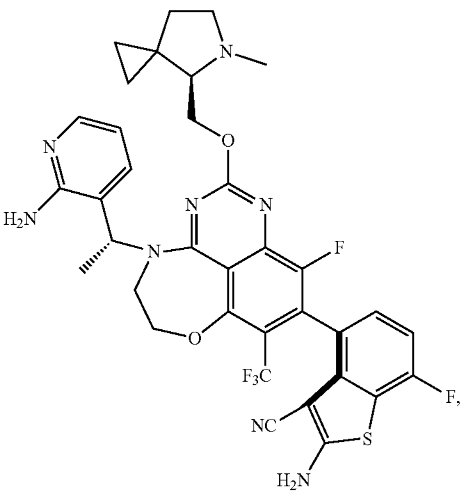
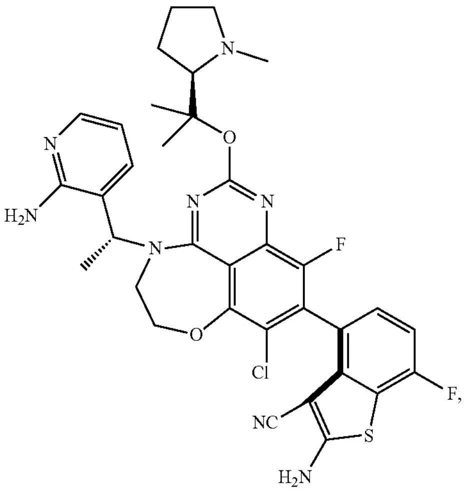
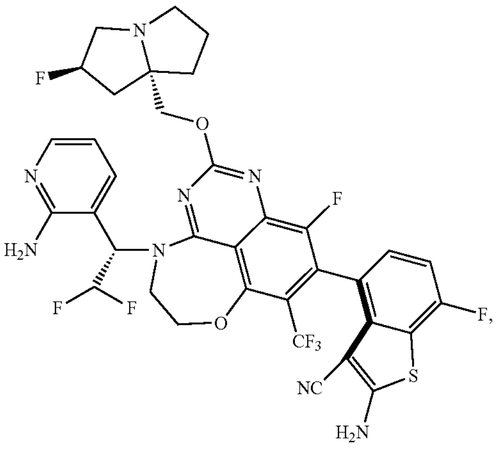
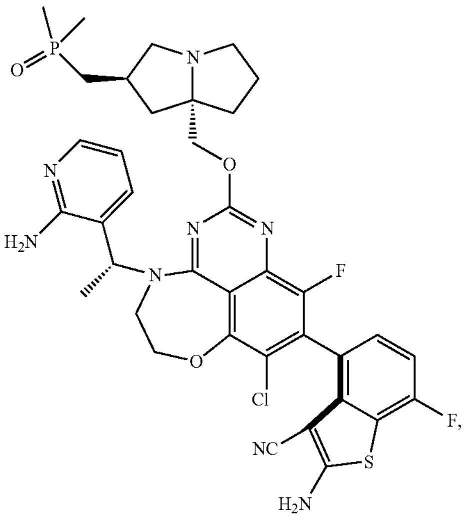
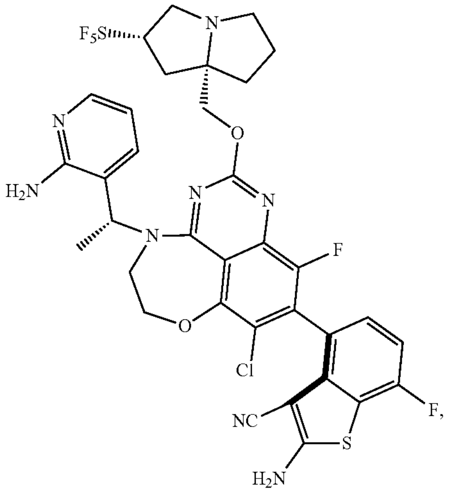
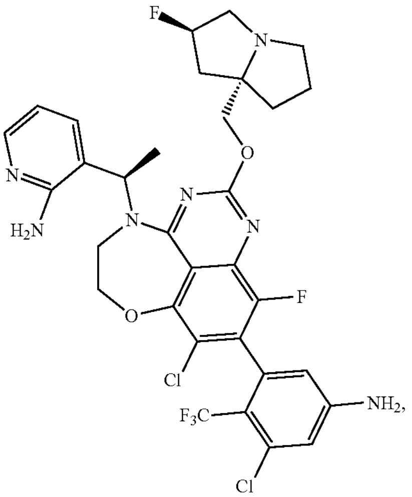
-continued -continued
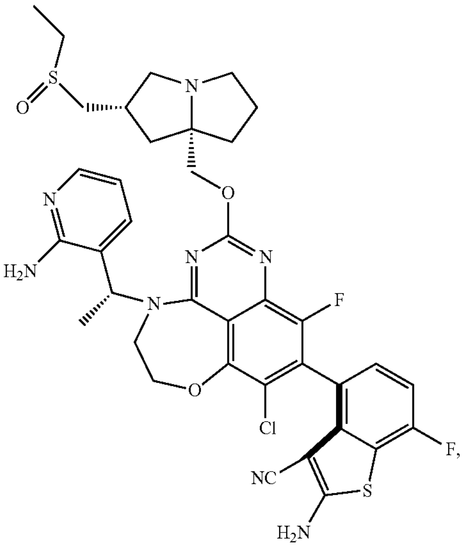
-continued
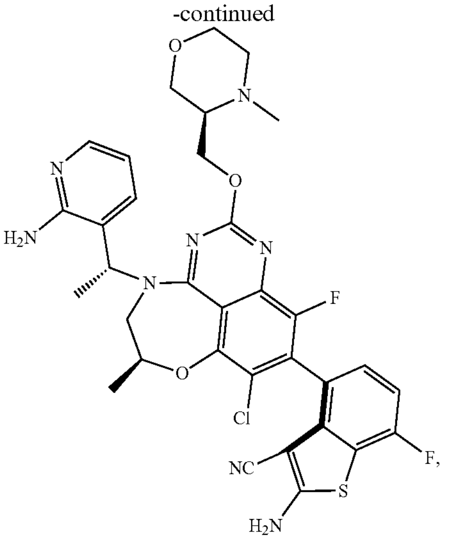
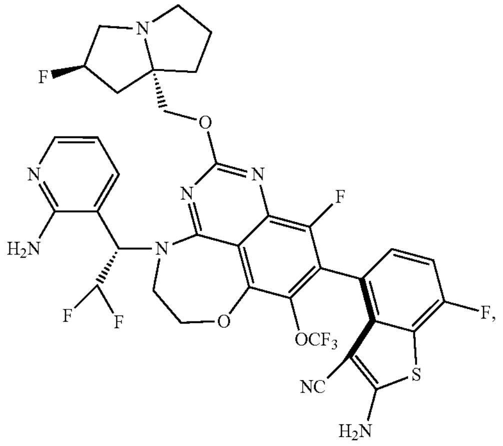
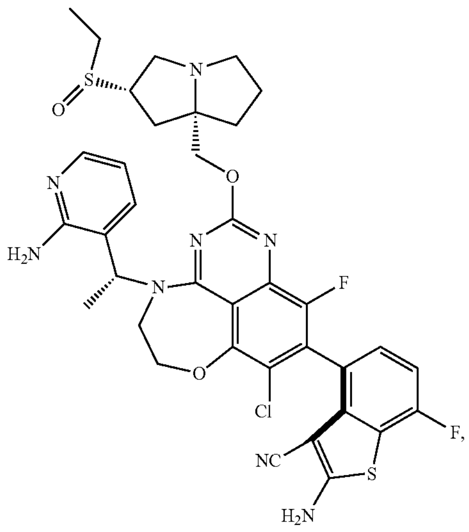
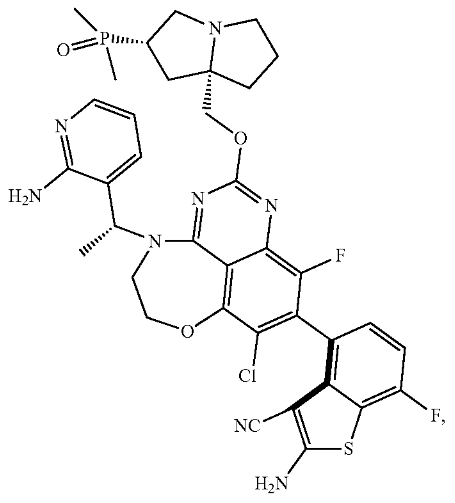
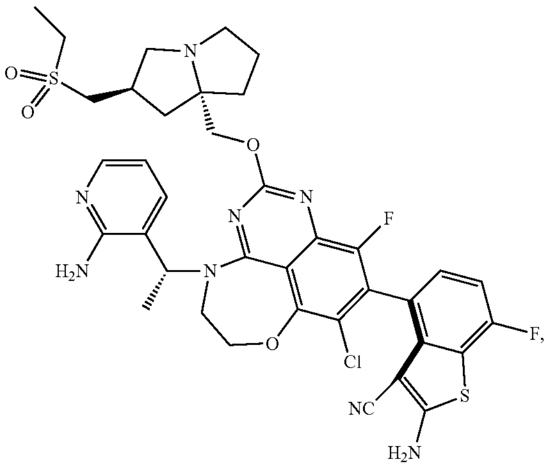

-continued
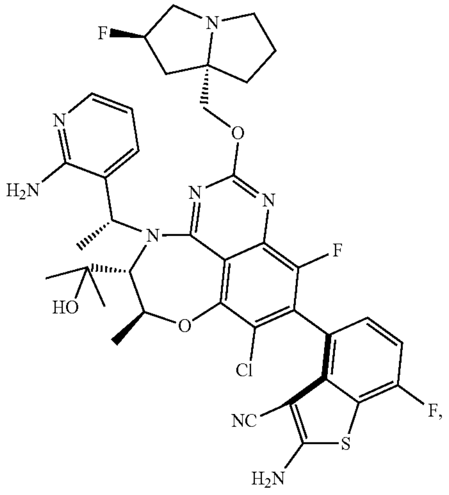
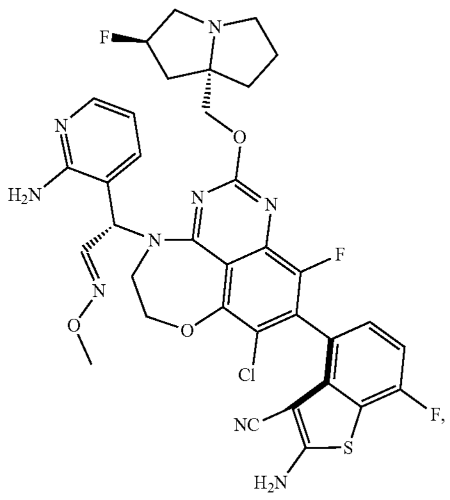
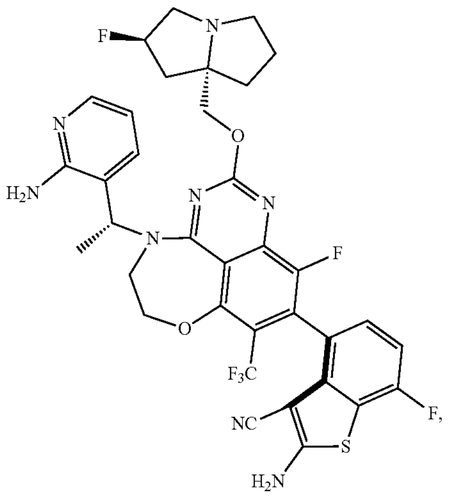
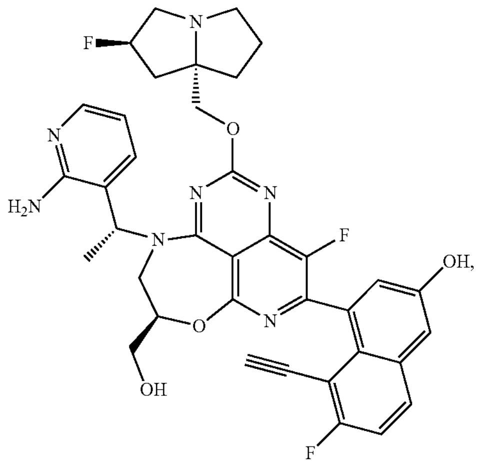
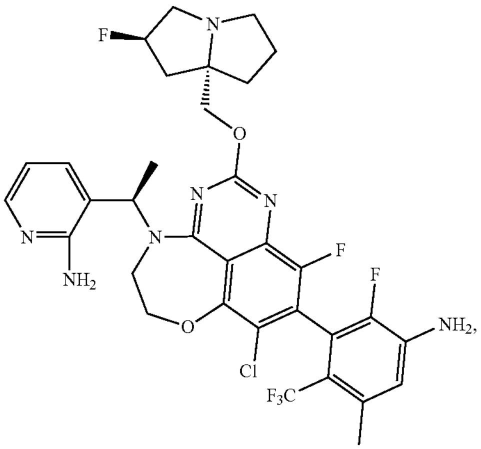
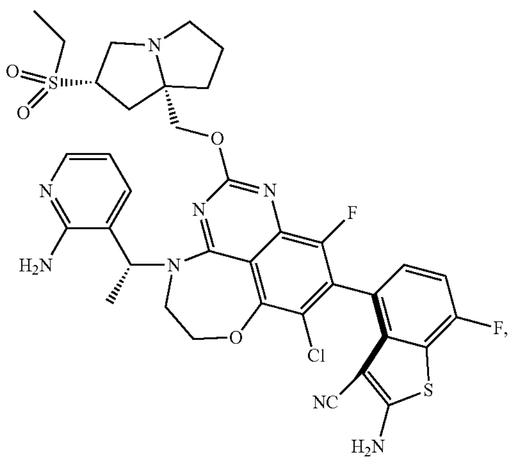
and

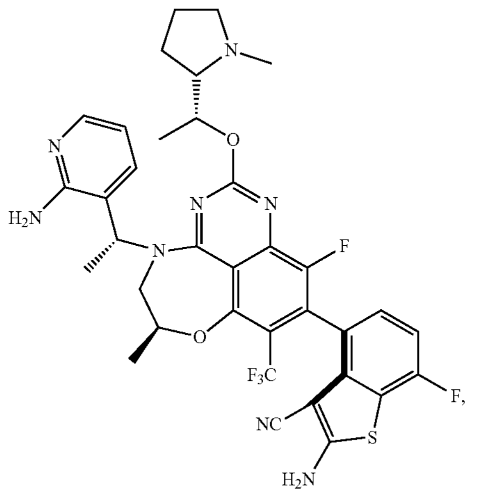
or a pharmaceutically acceptable salt or solvate thereof.
In certain aspects, the present disclosure provides a compound selected from:
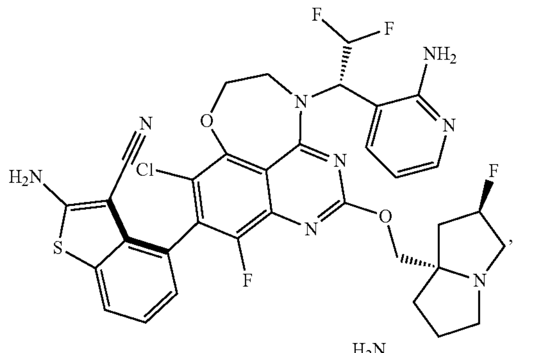
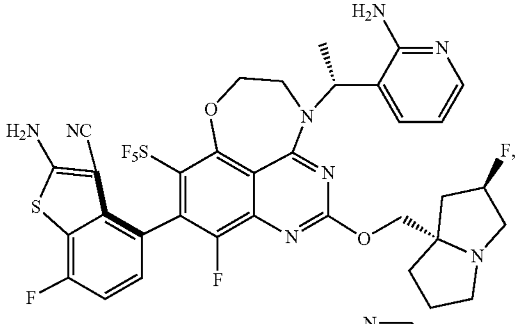
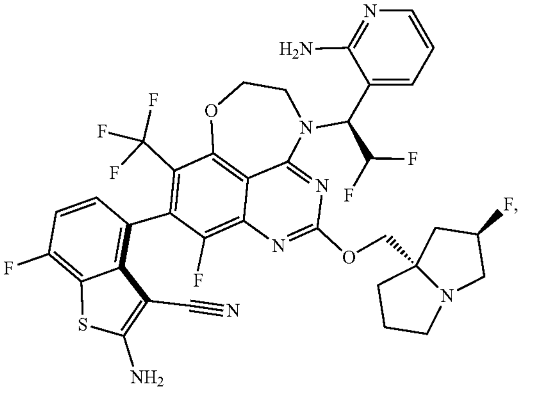
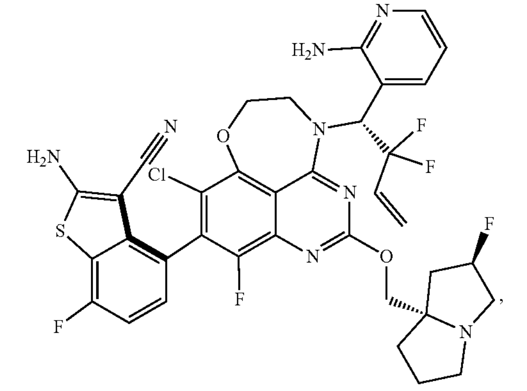
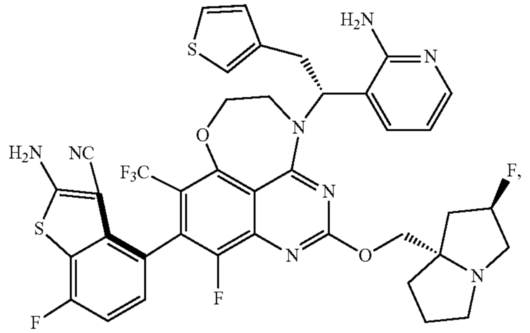
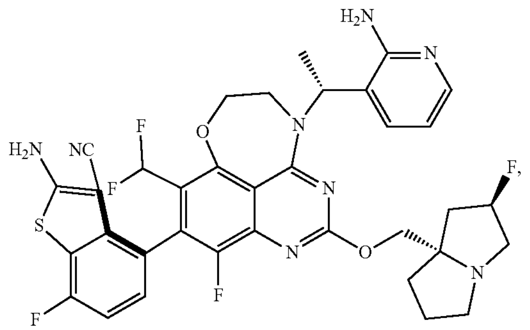
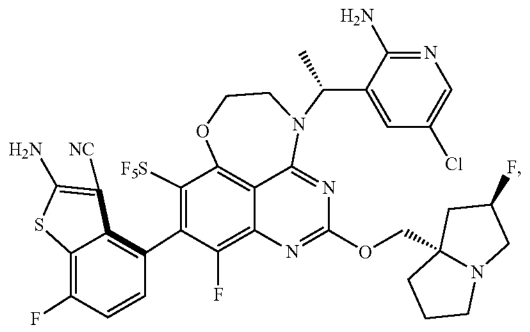
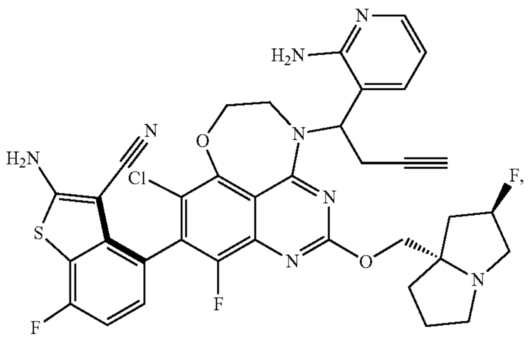

-continued
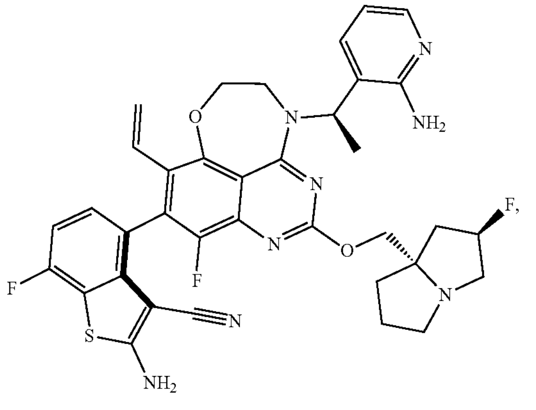
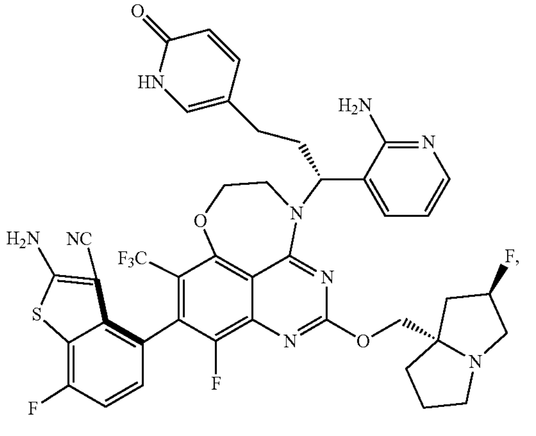
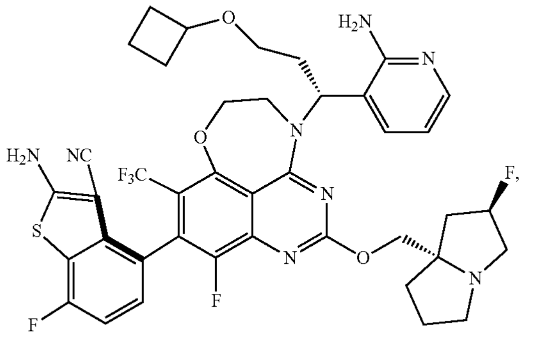
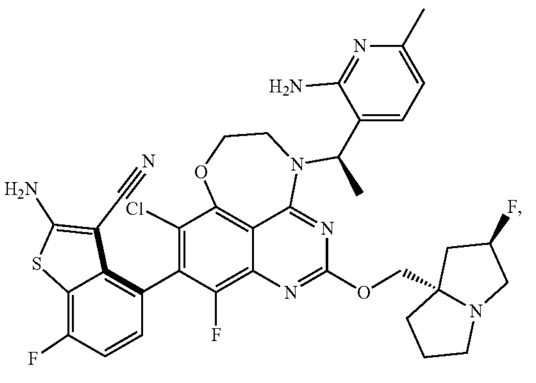
-continued
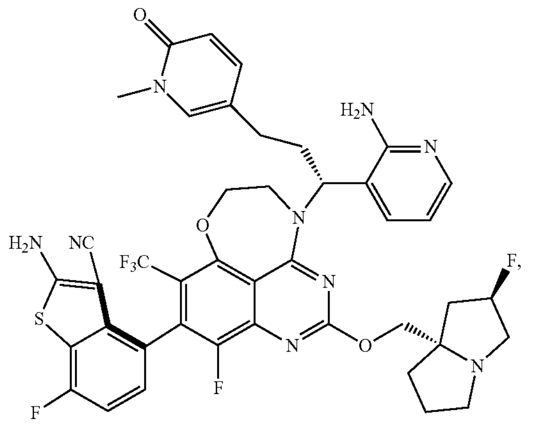
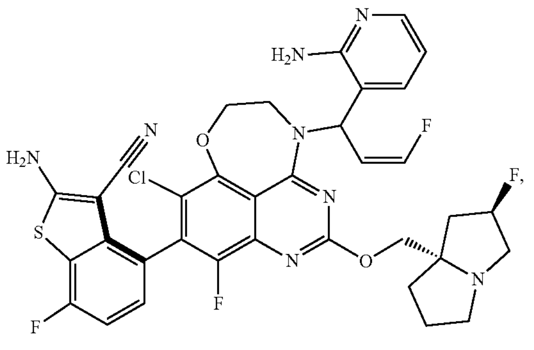
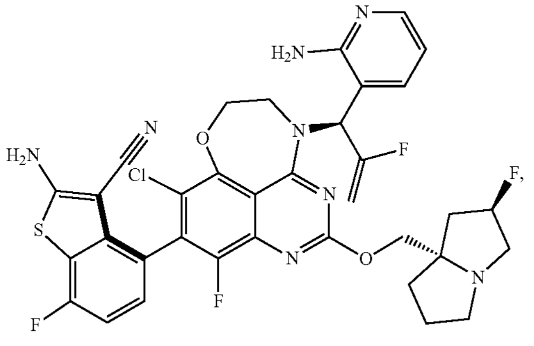
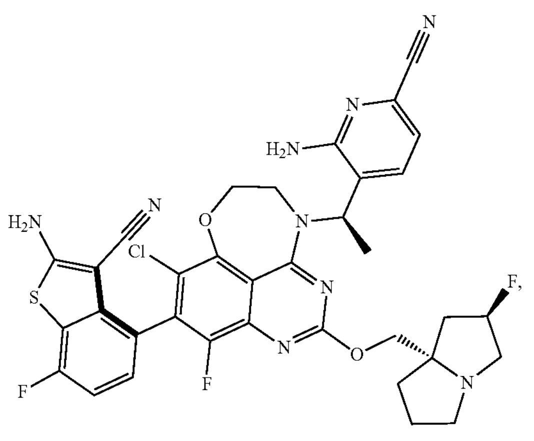

-continued
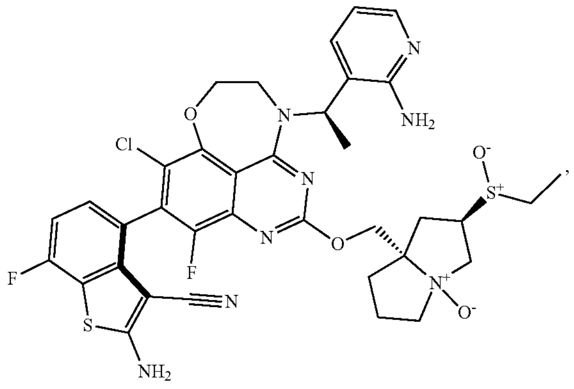
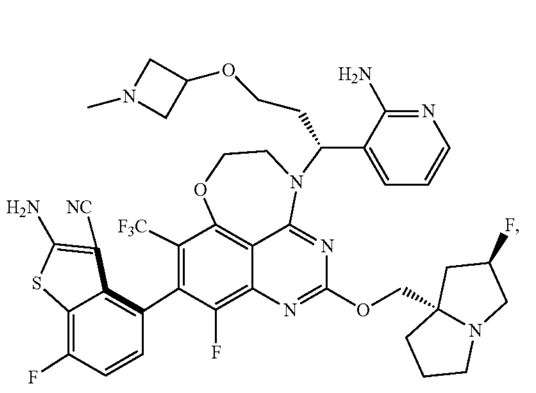
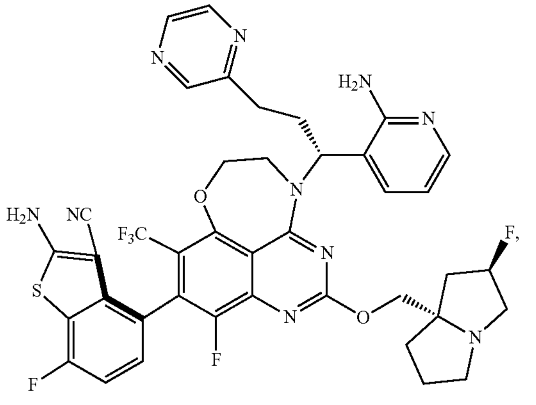
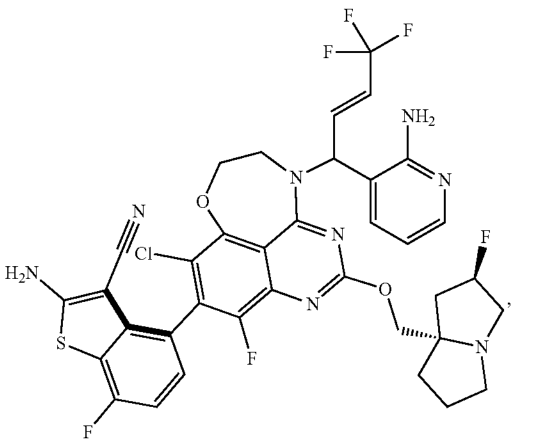
-continued
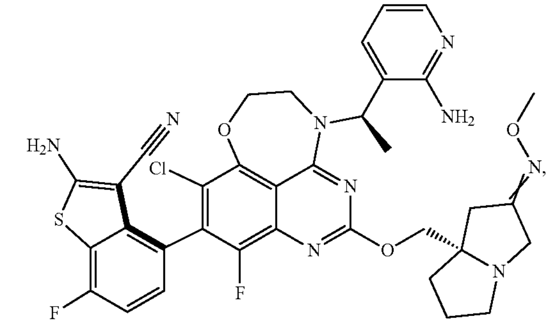
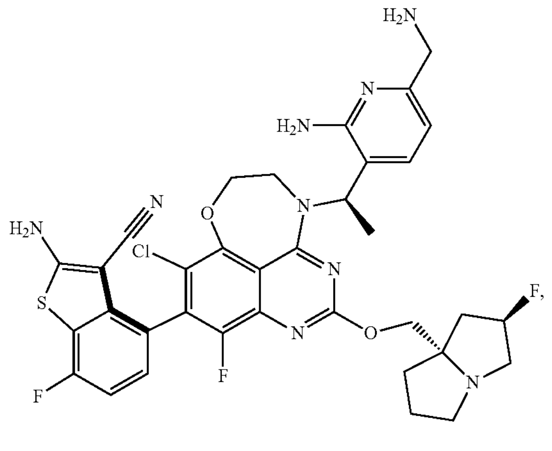
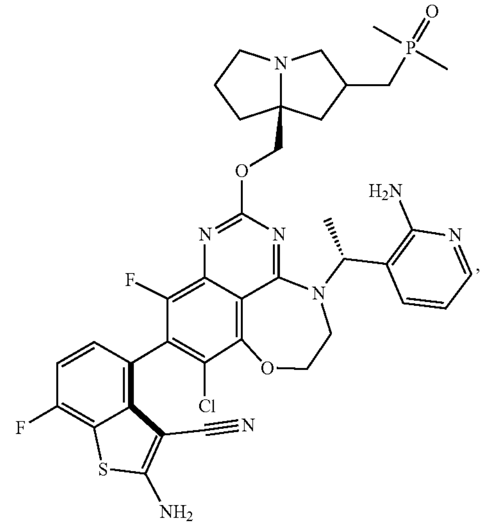
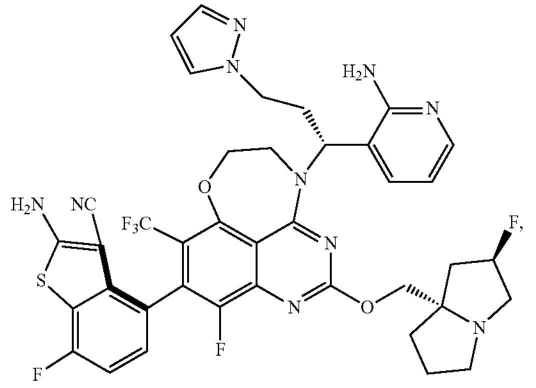

-continued
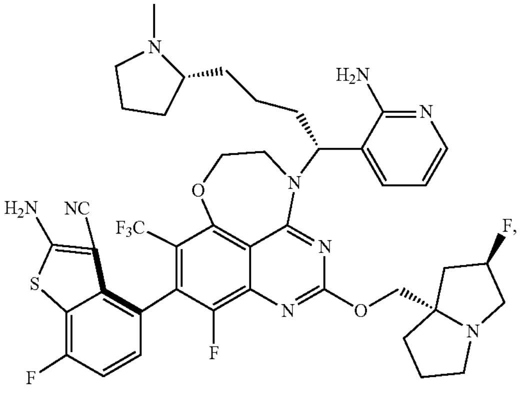
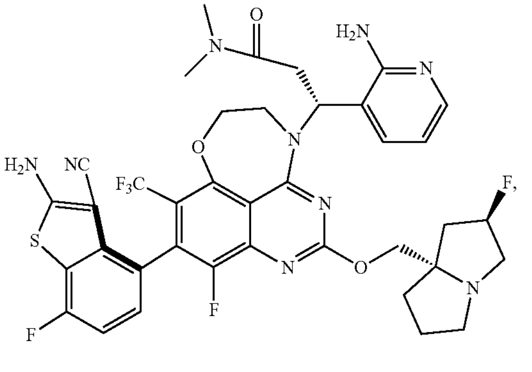
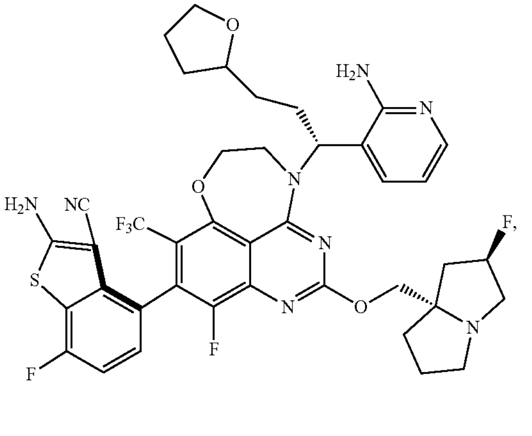
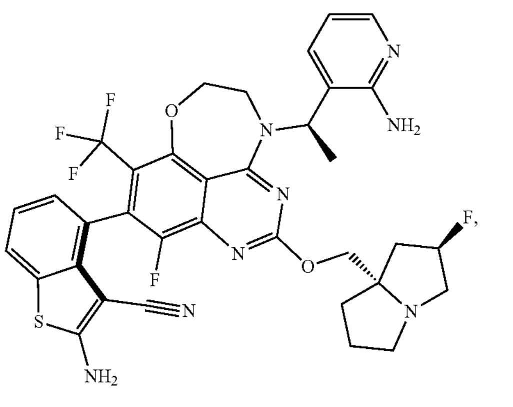
-continued
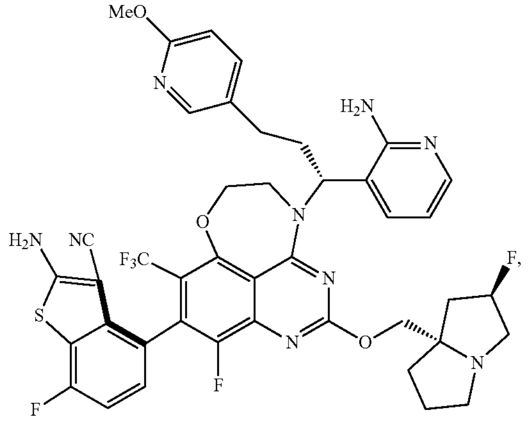
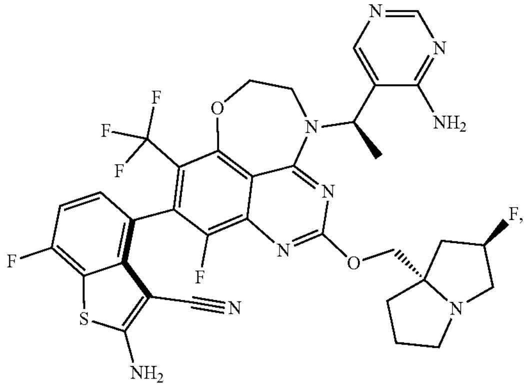
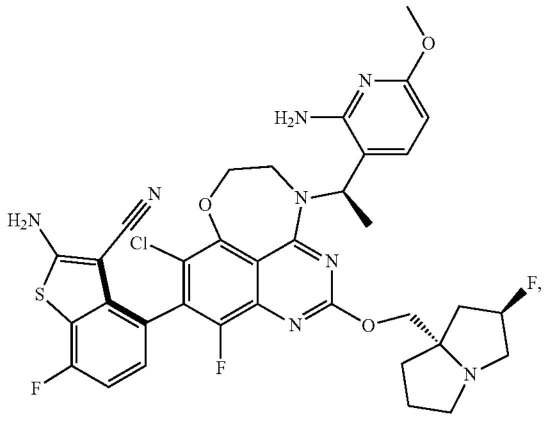
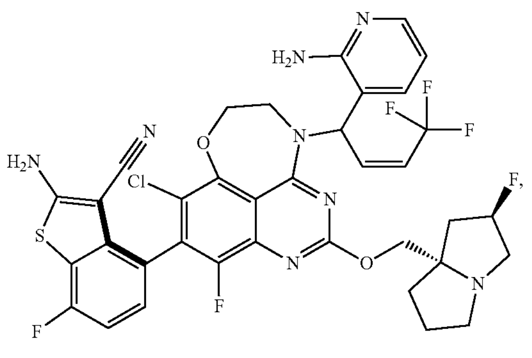

-continued
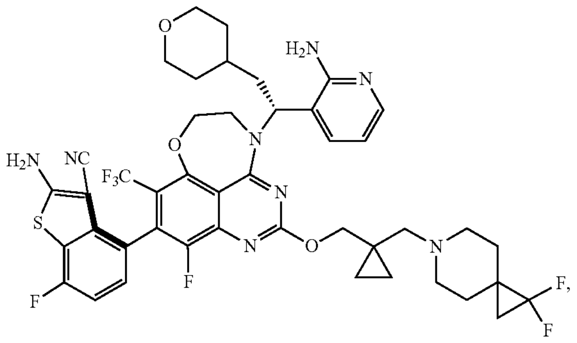
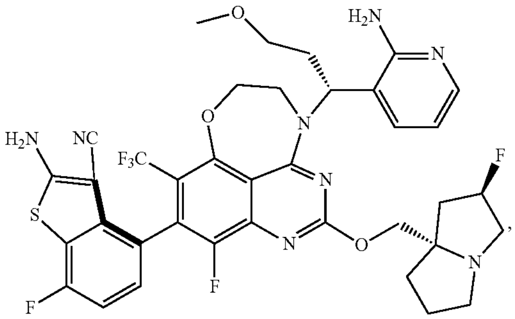
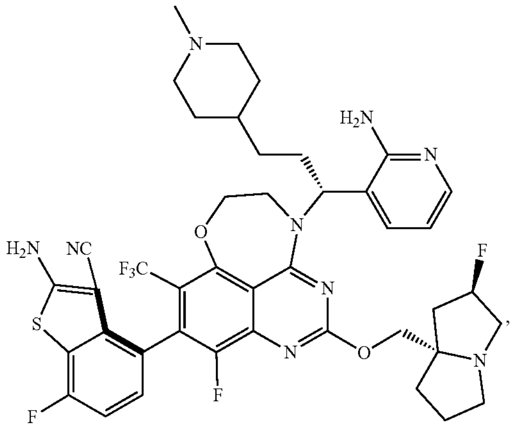
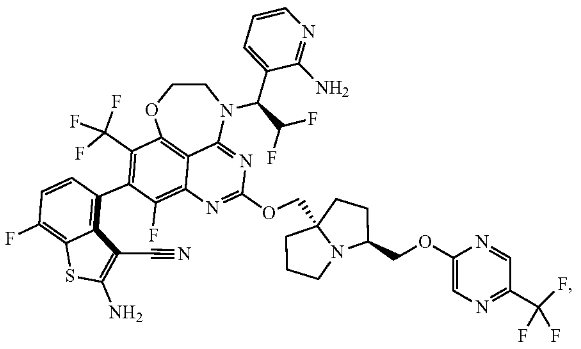
-continued
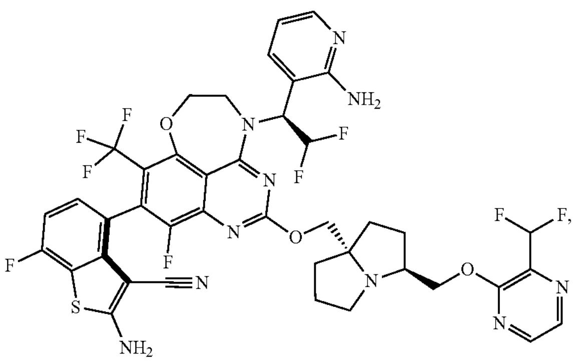
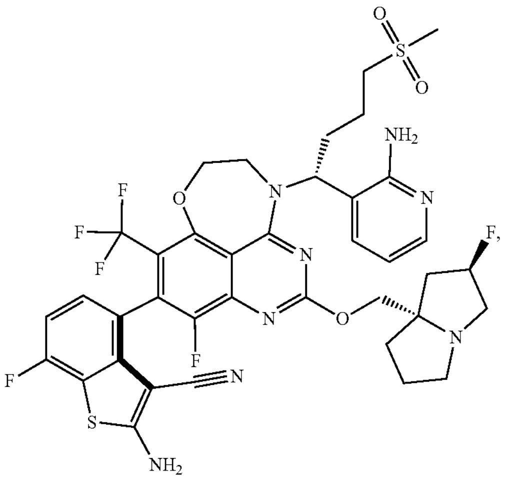
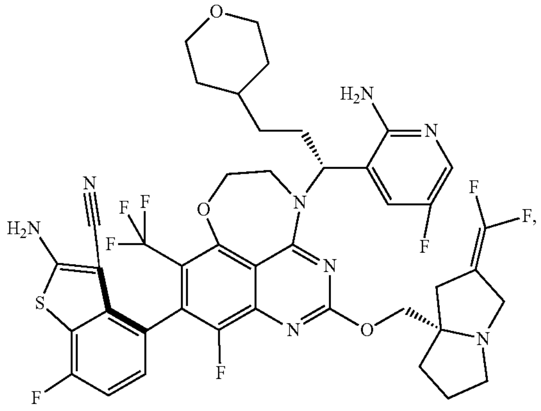
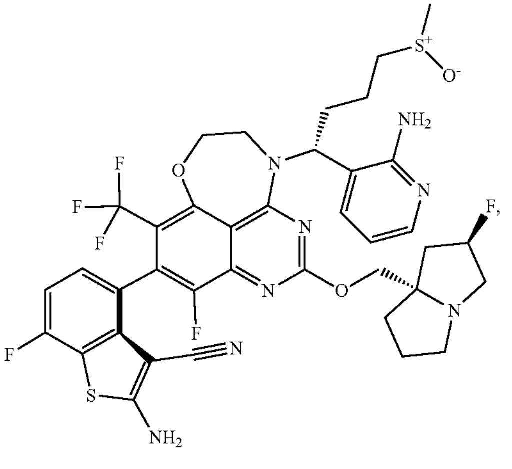

-continued
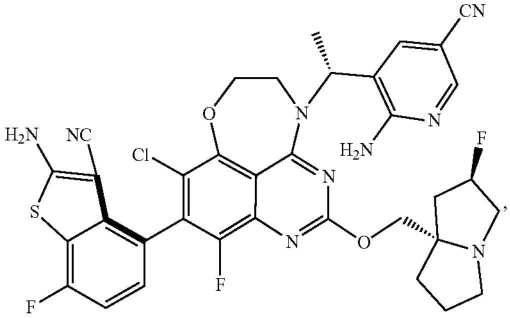
,
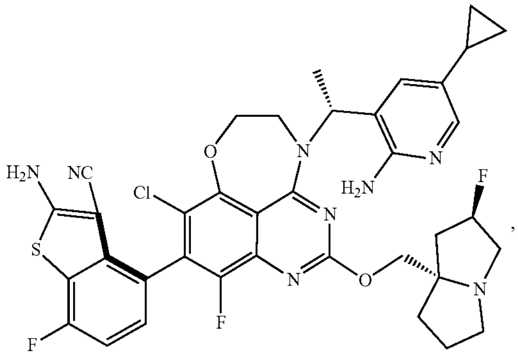
,
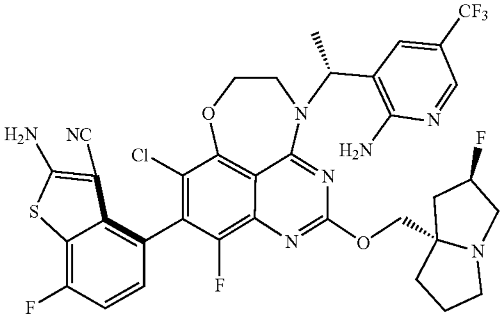
,
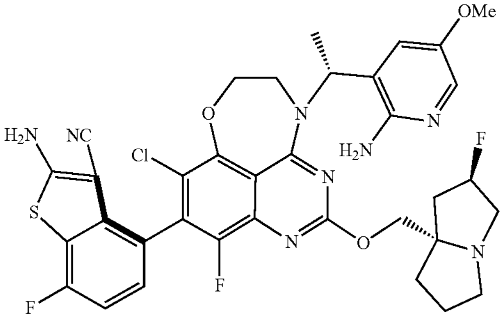
,
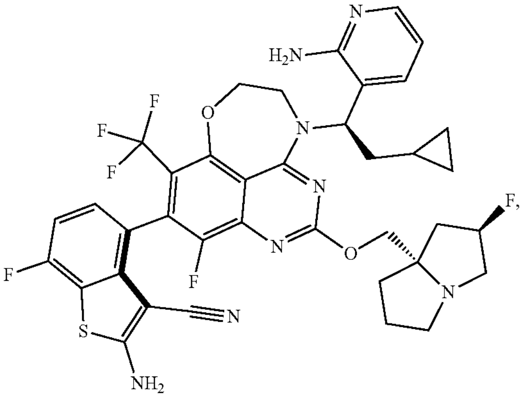
-continued
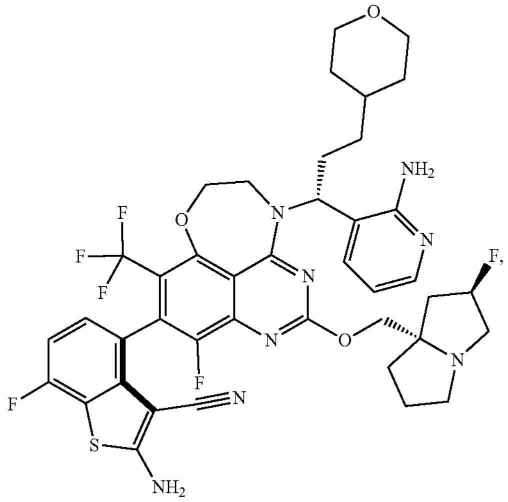
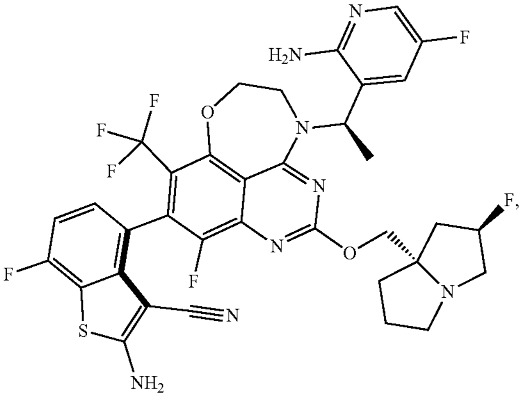
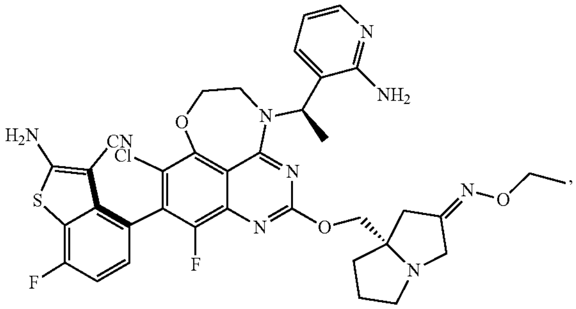
,
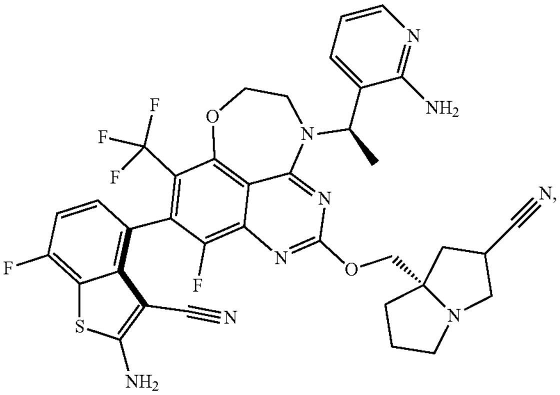

-continued
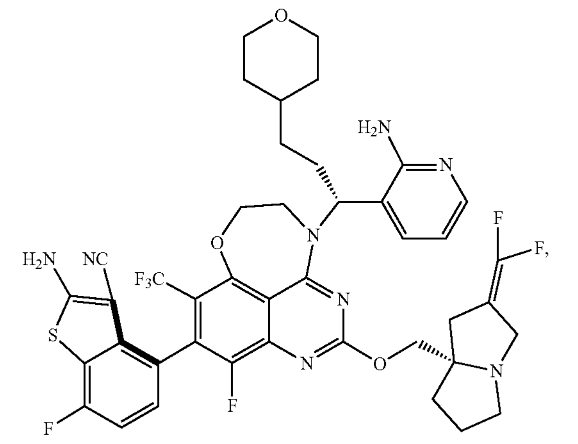
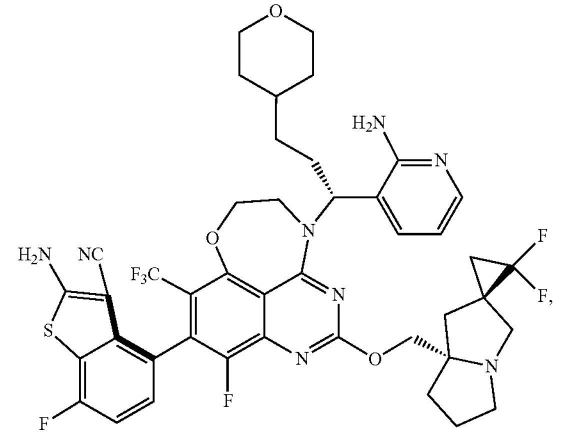
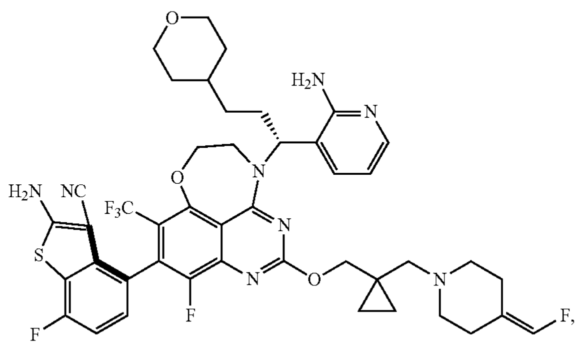
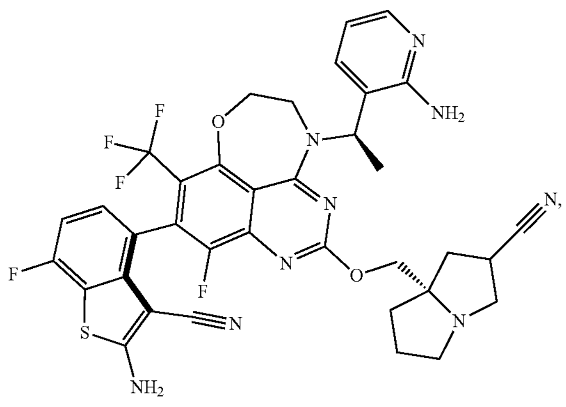
-continued
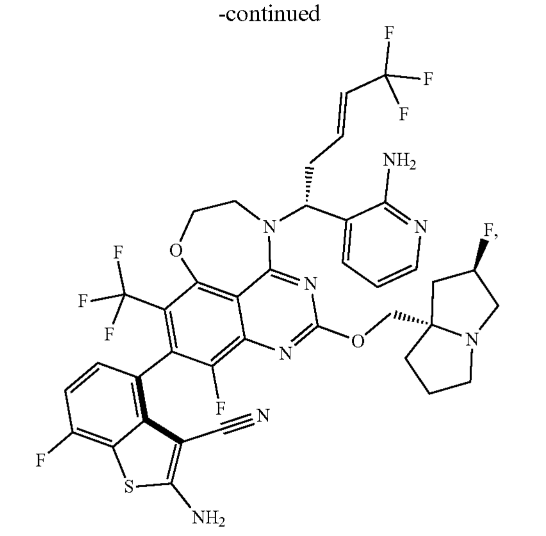
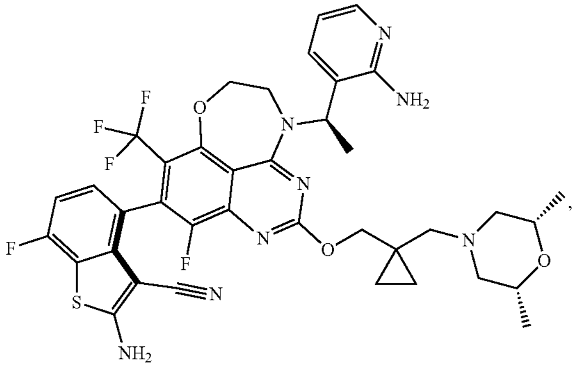
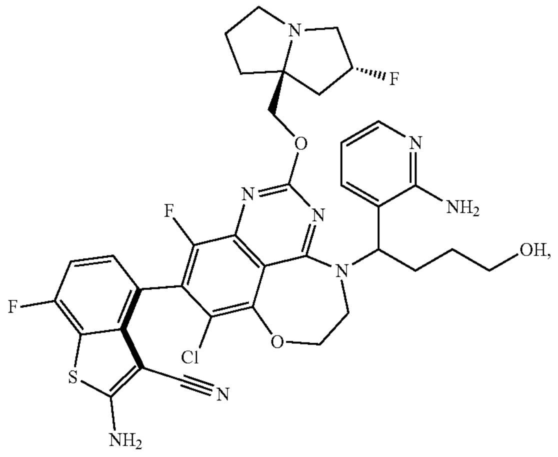
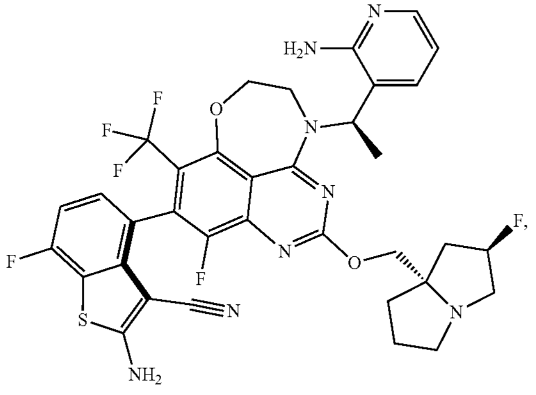

-continued
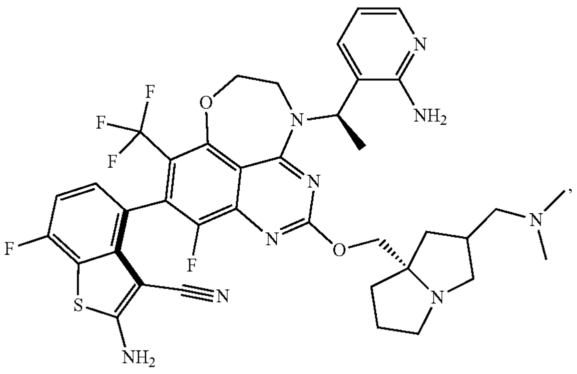
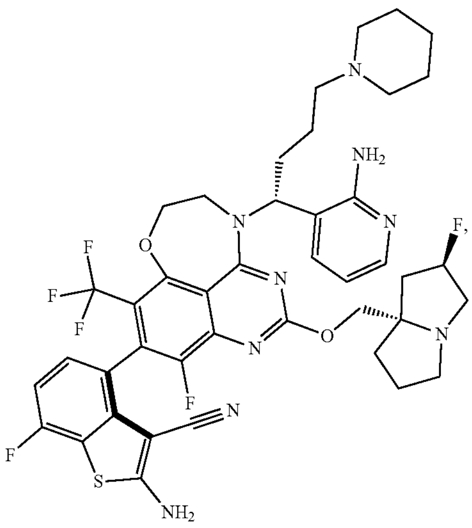
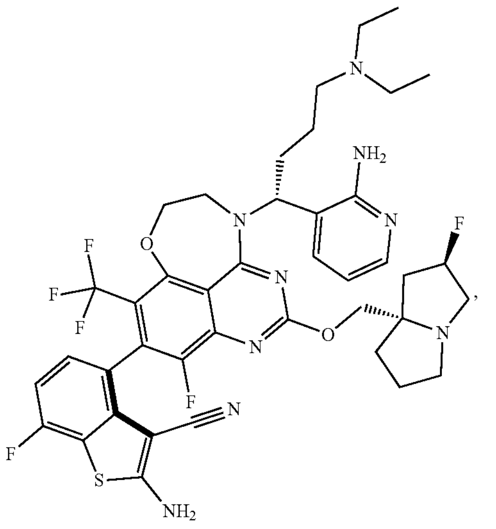
-continued
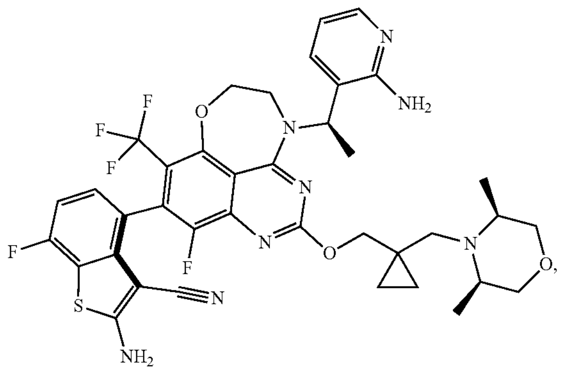
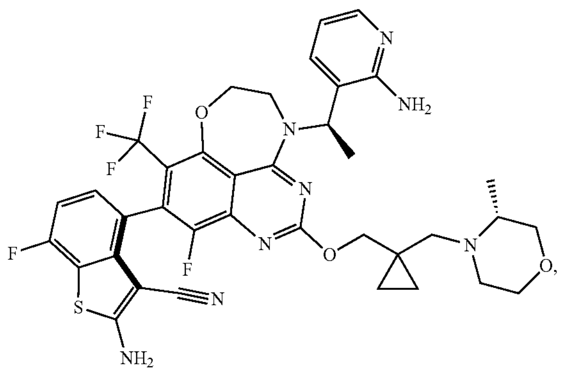
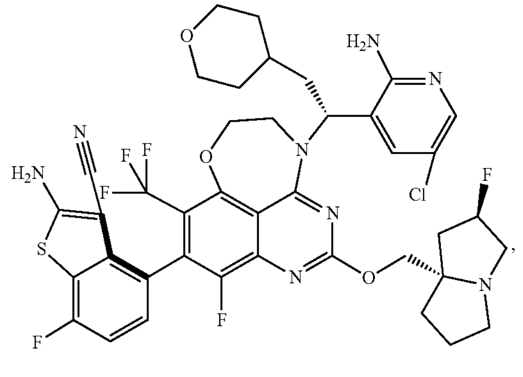
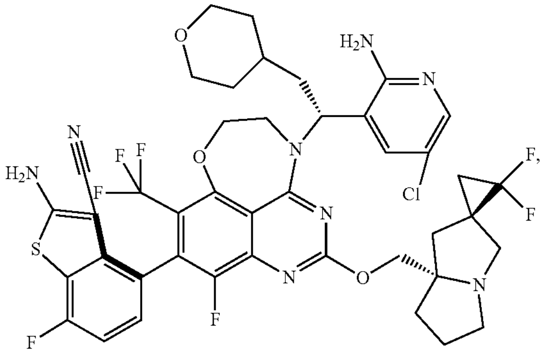

-continued
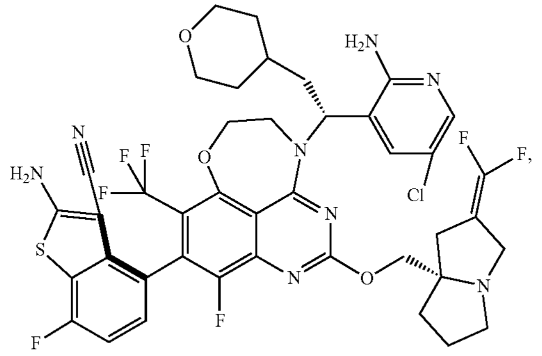
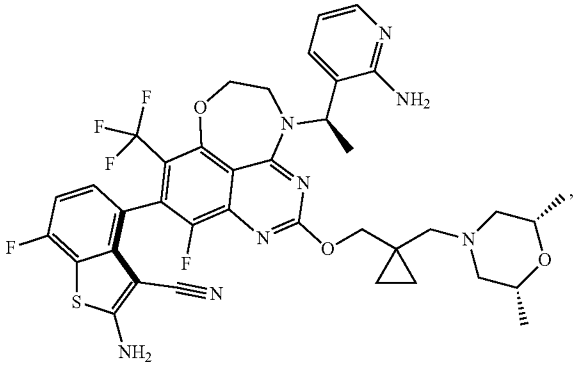
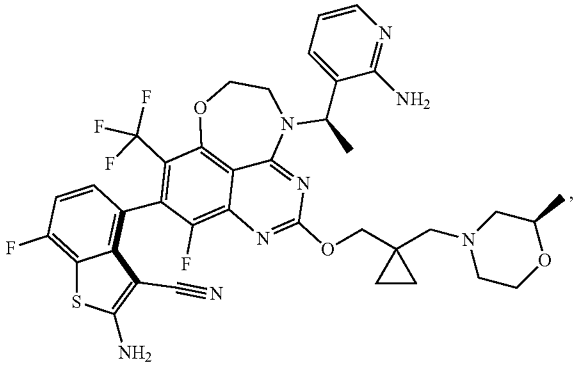
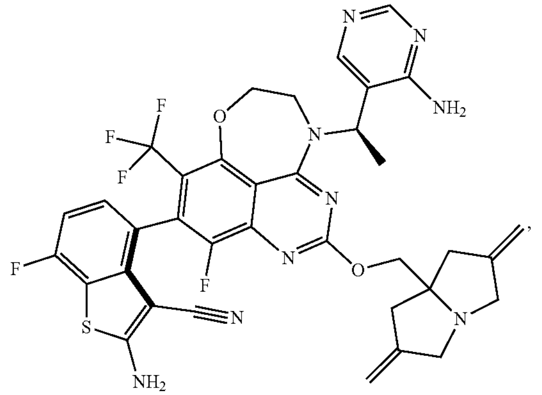
-continued
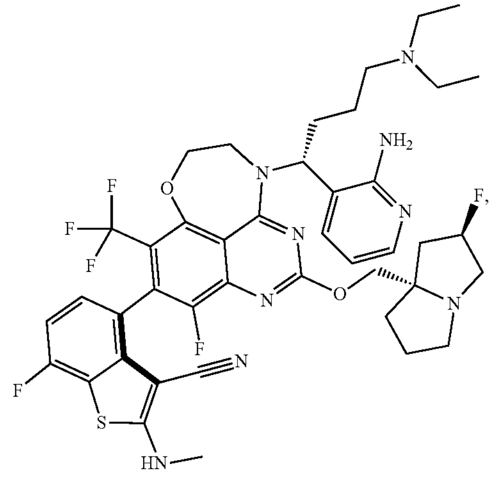
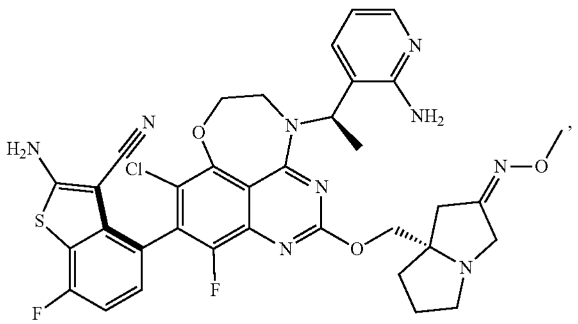
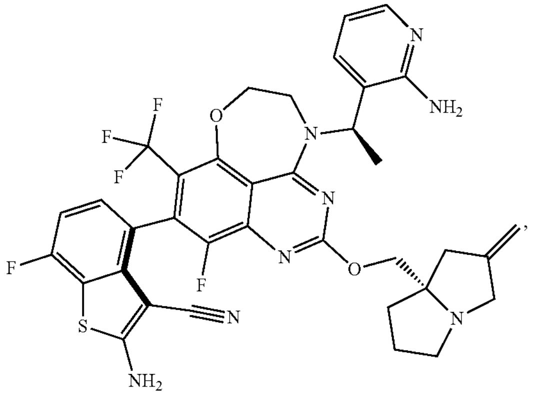
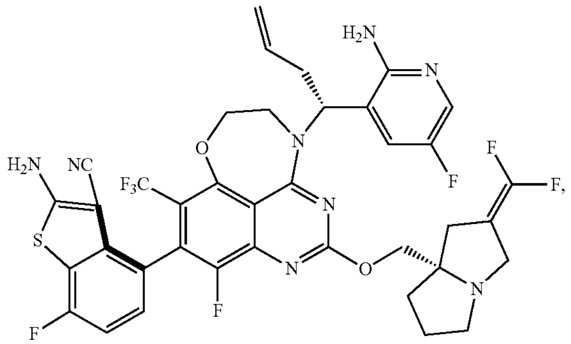

-continued
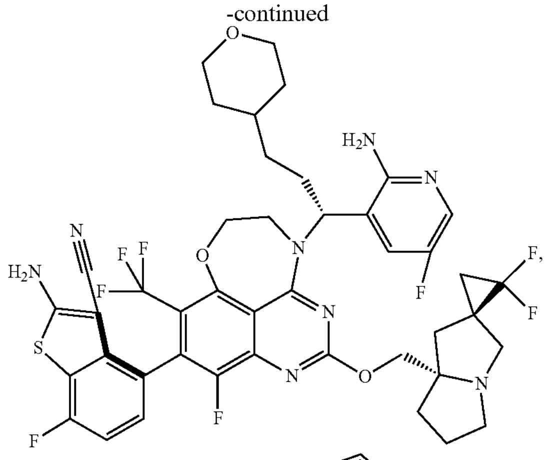
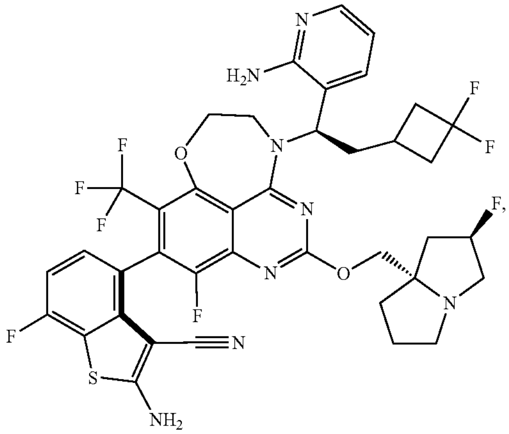
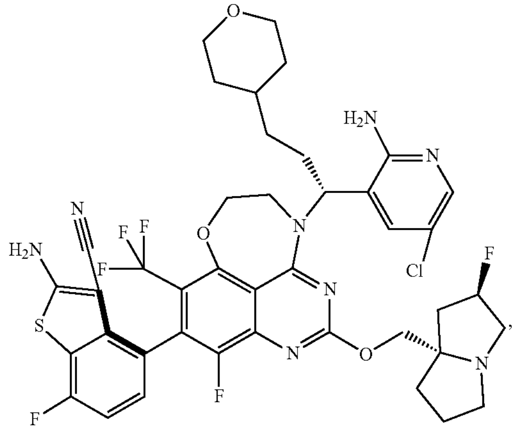
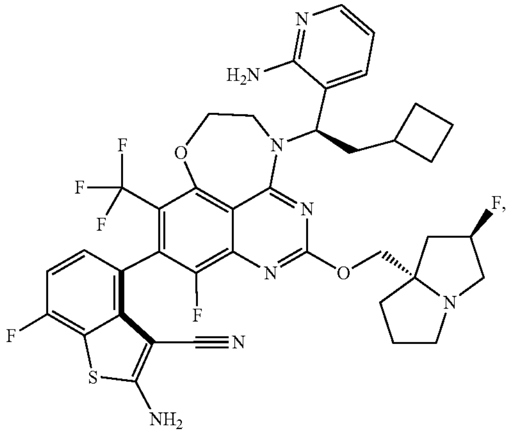
-continued
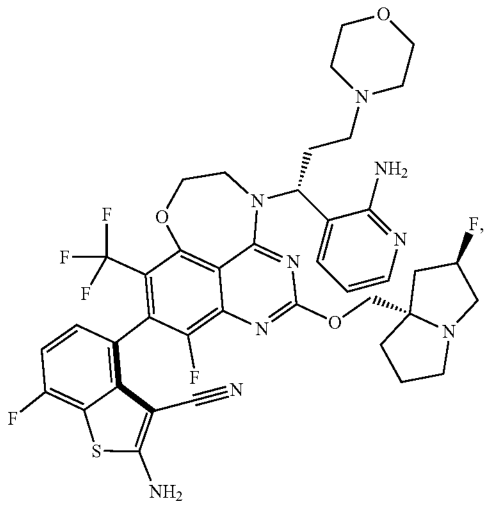
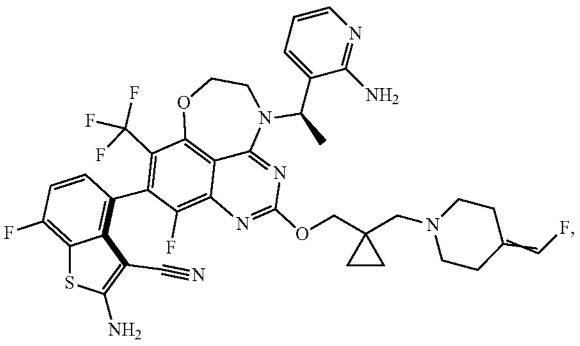
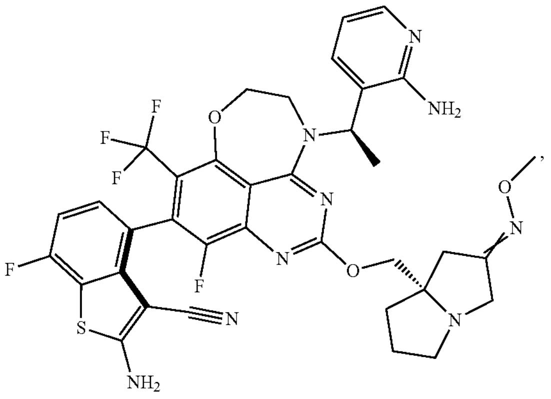
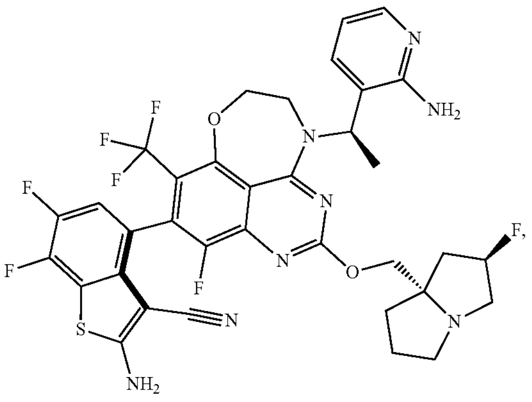

-continued
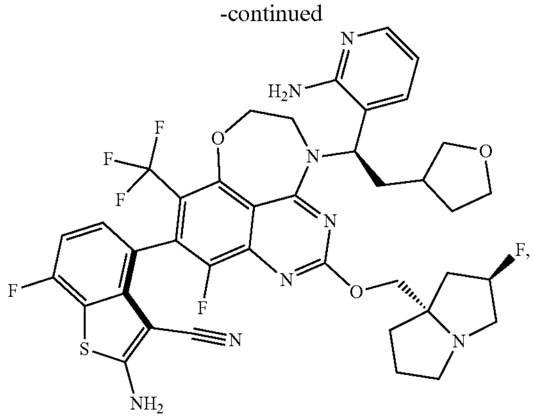
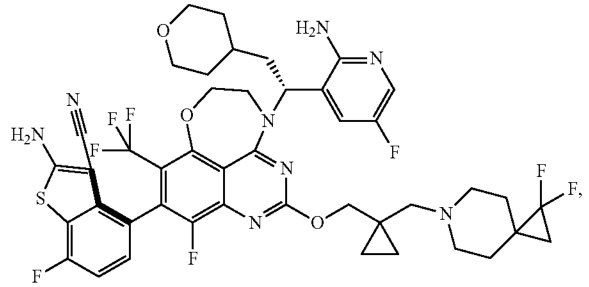
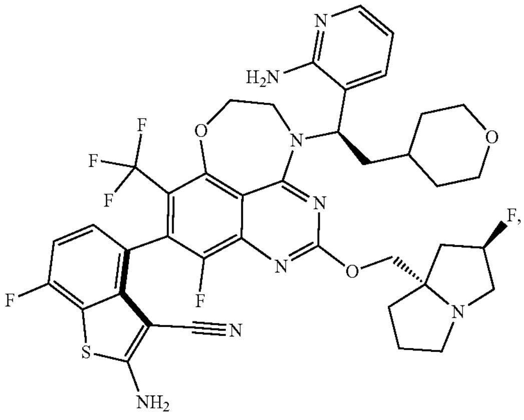
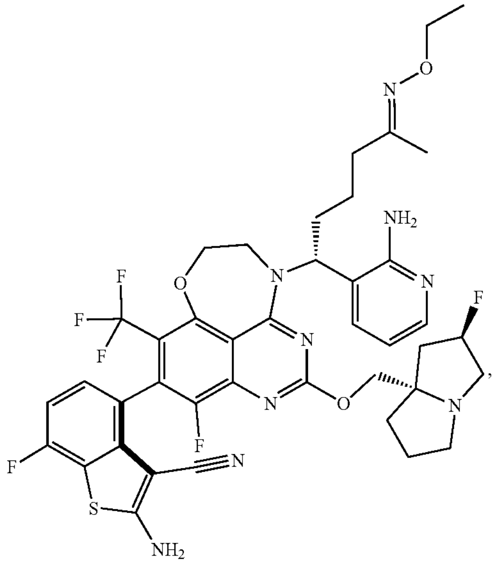
-continued
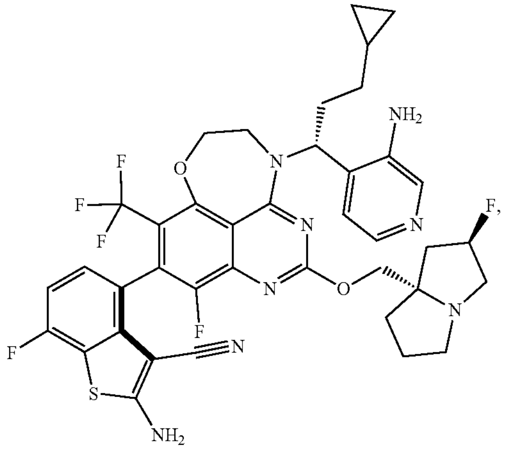
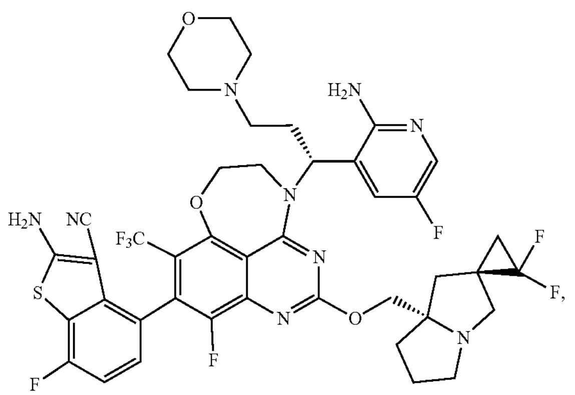
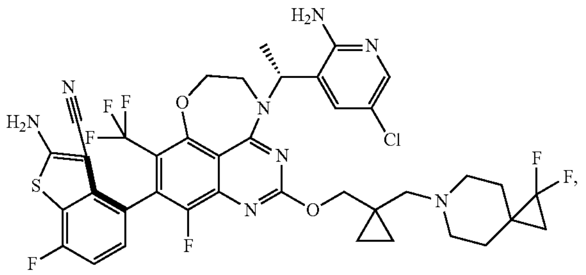
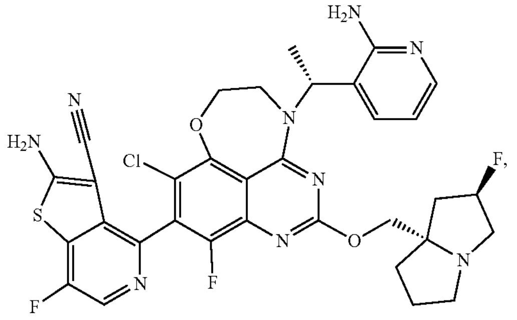

-continued
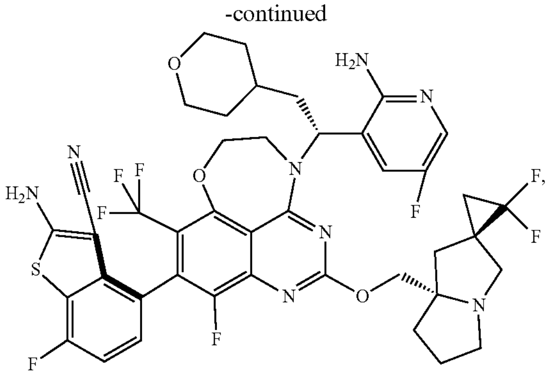
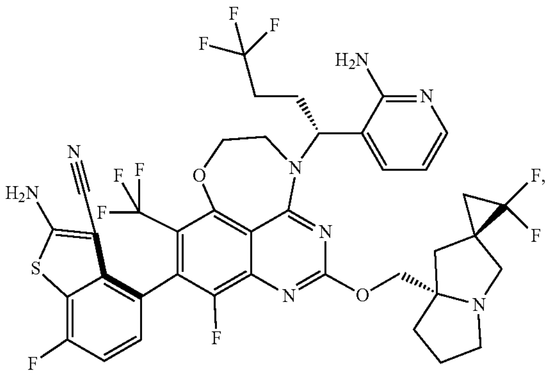
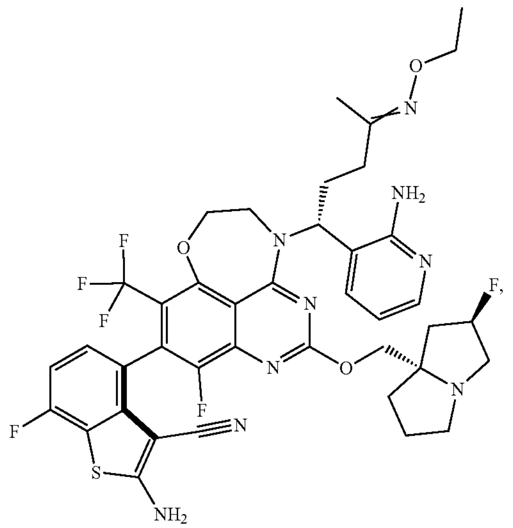
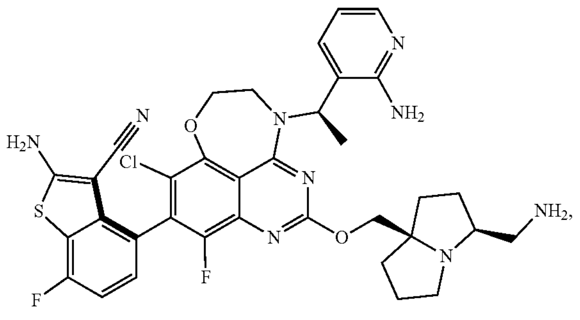
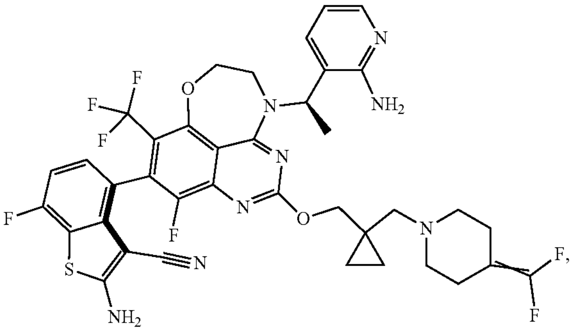
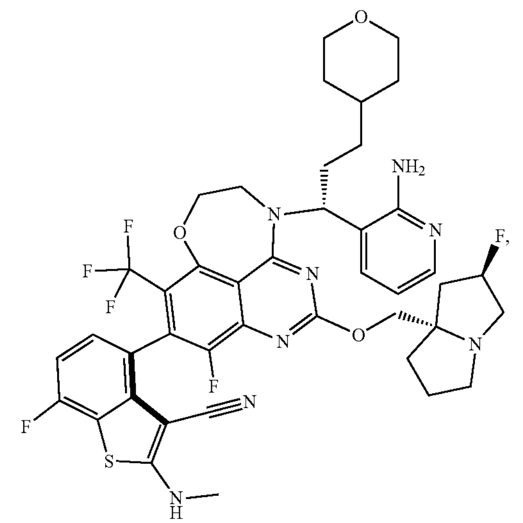
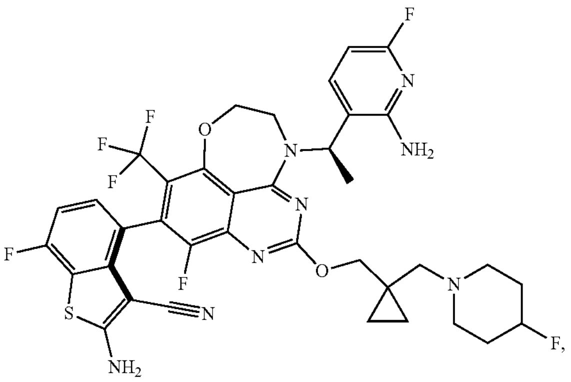
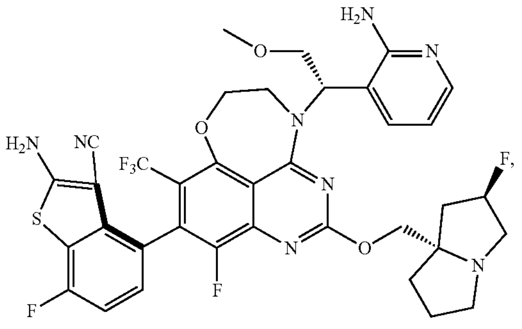

-continued
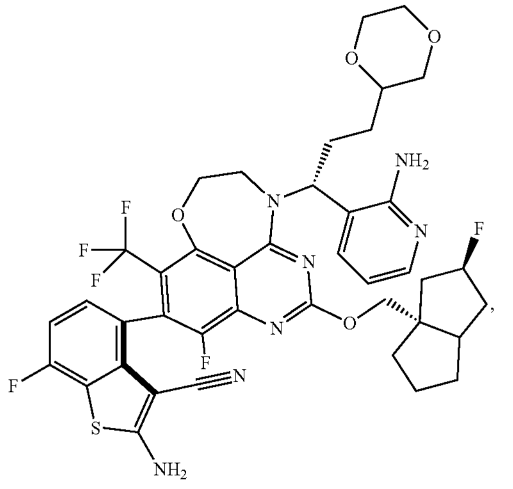
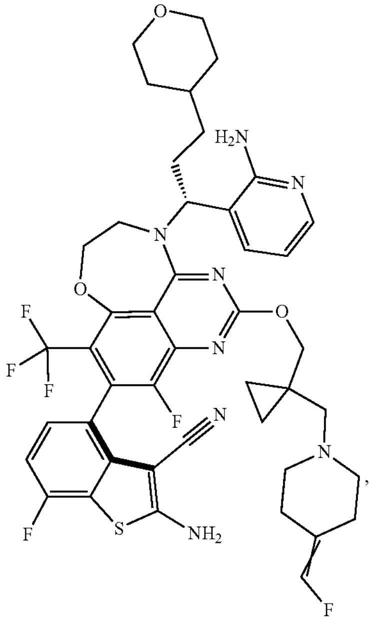
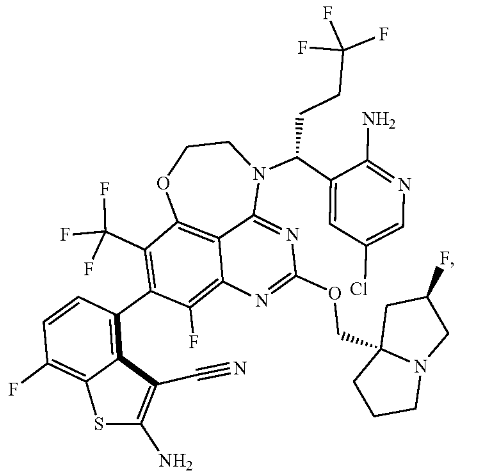
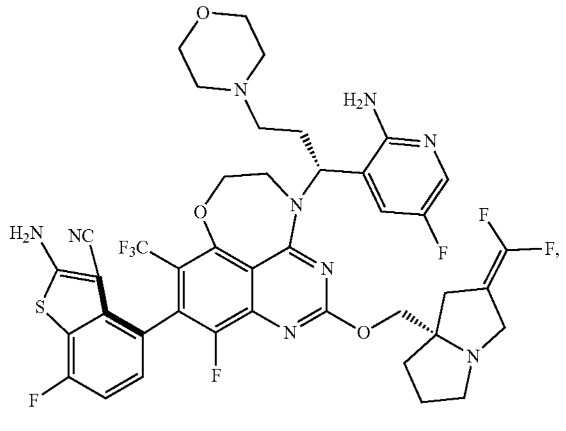
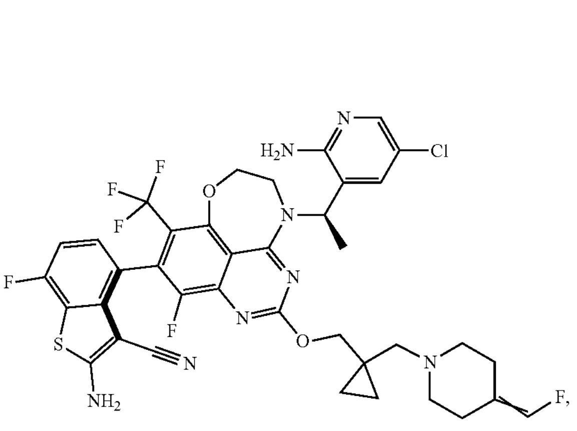
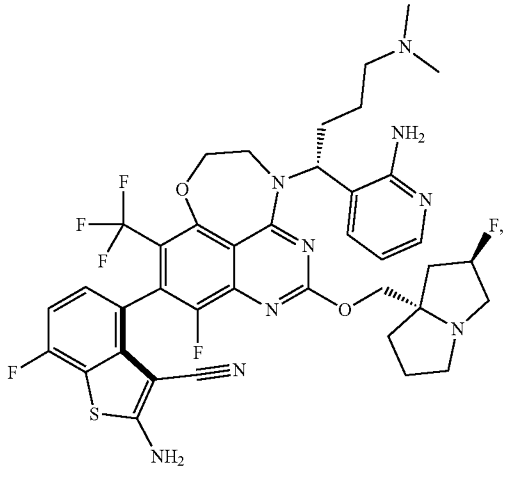

-continued
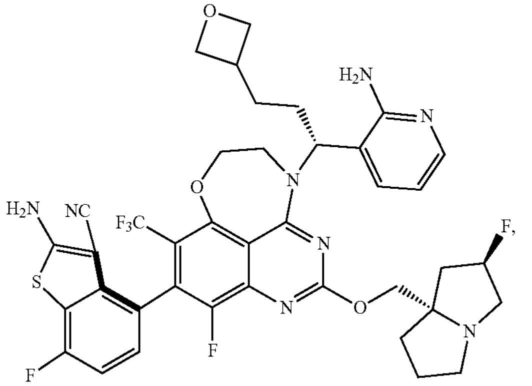
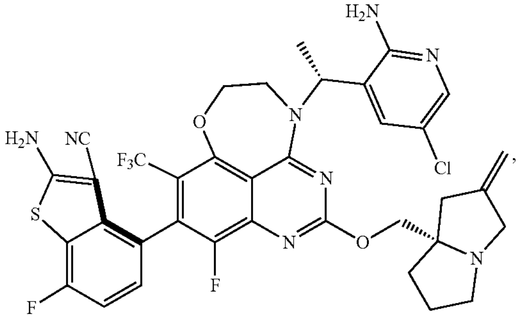
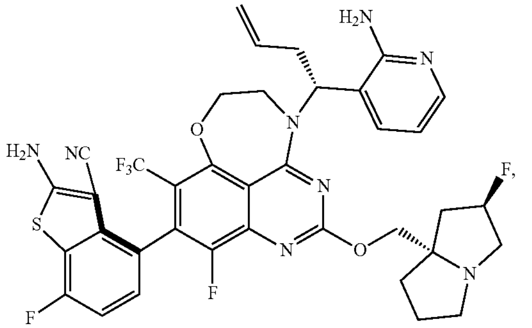
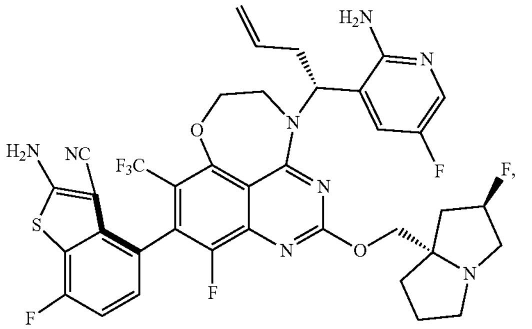
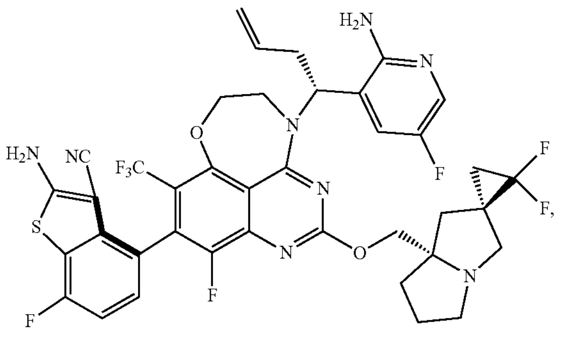
-continued
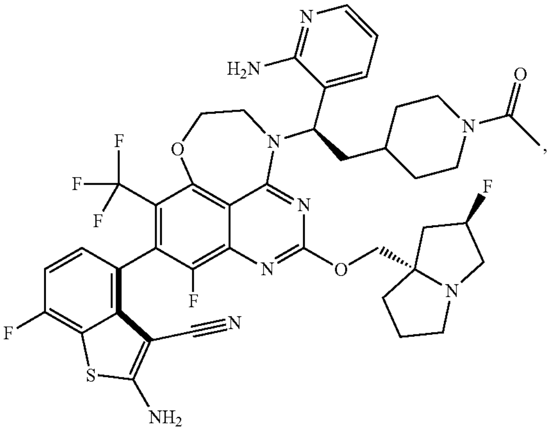
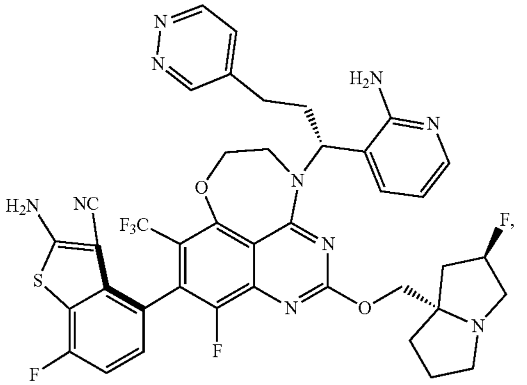
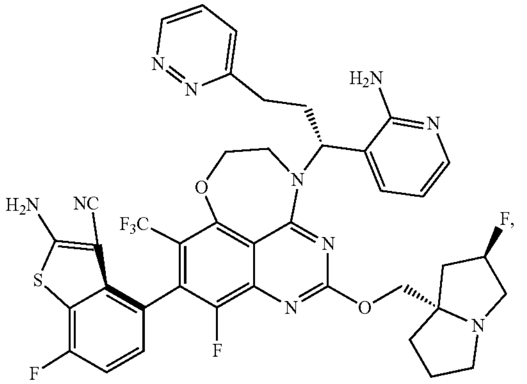
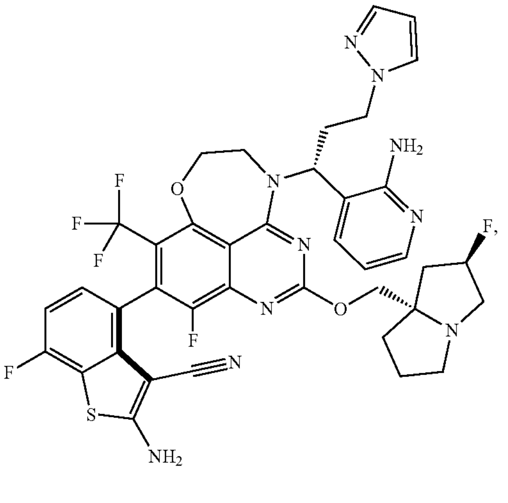

-continued
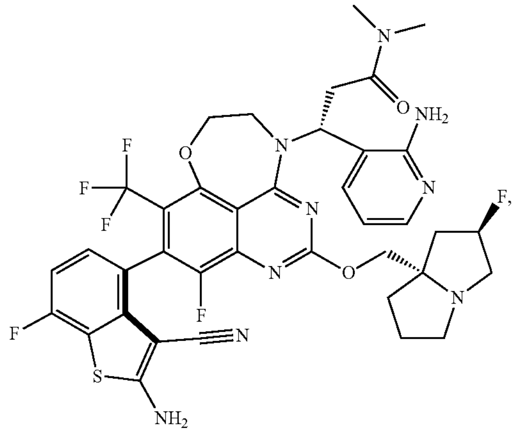
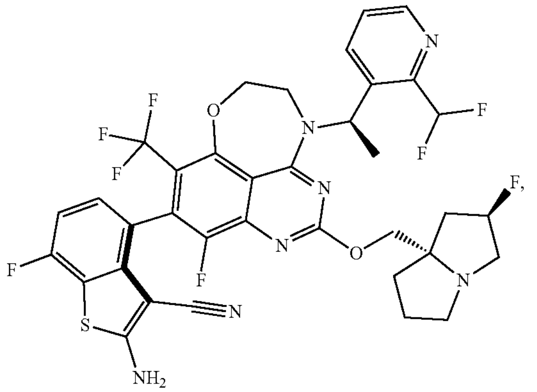
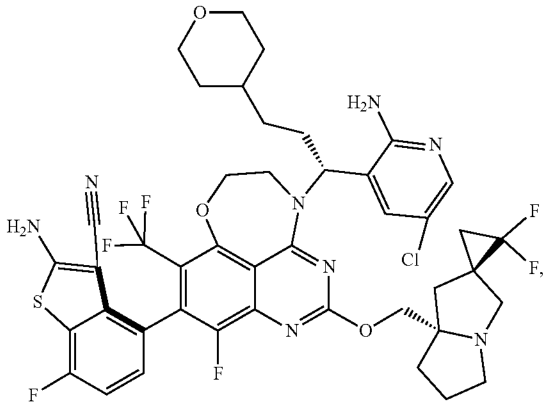
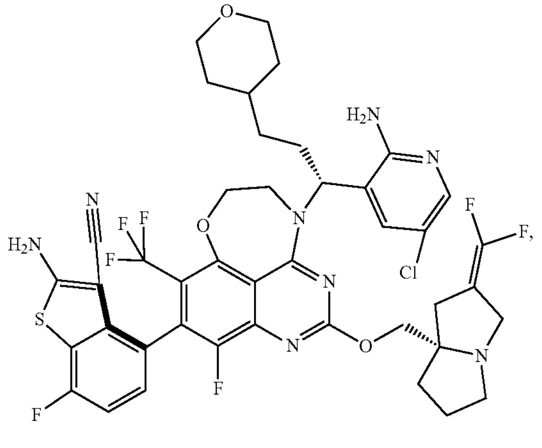
-continued
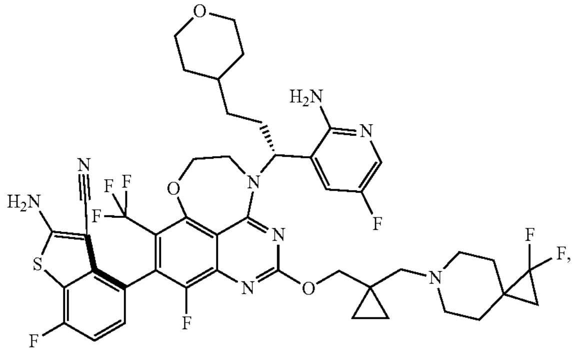
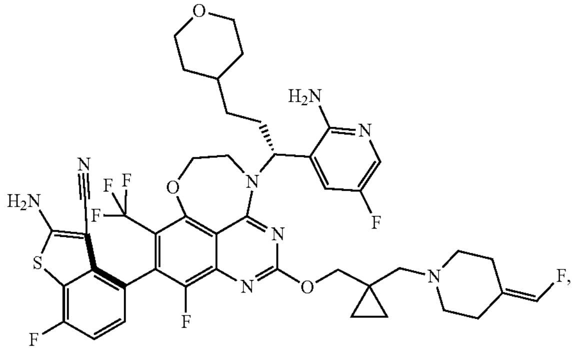
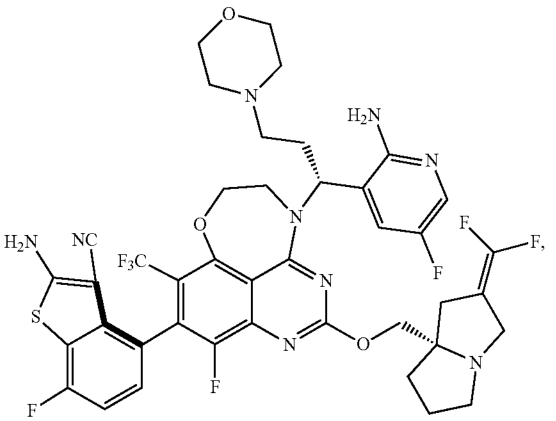
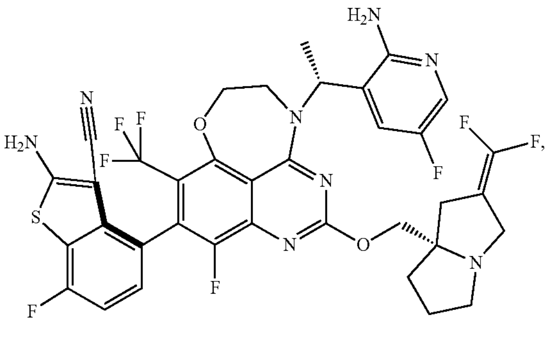

-continued
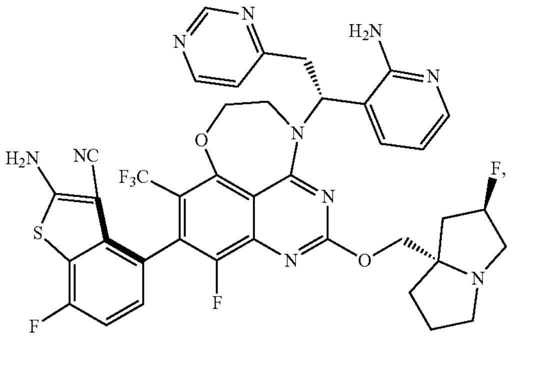
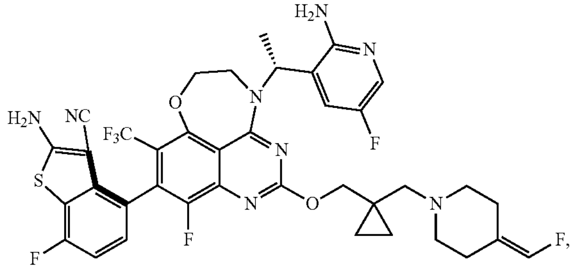
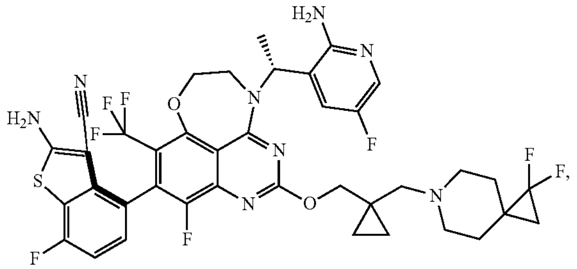
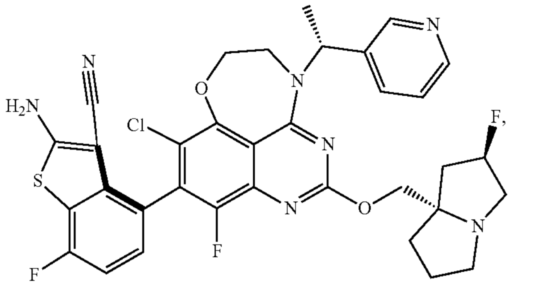
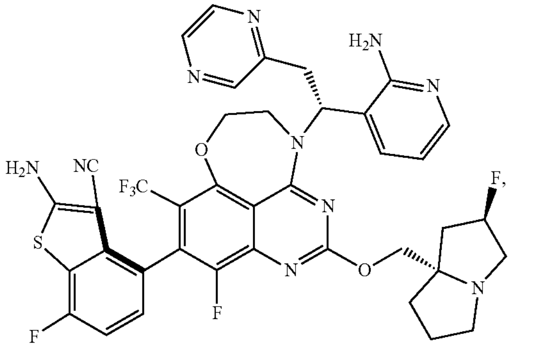
-continued
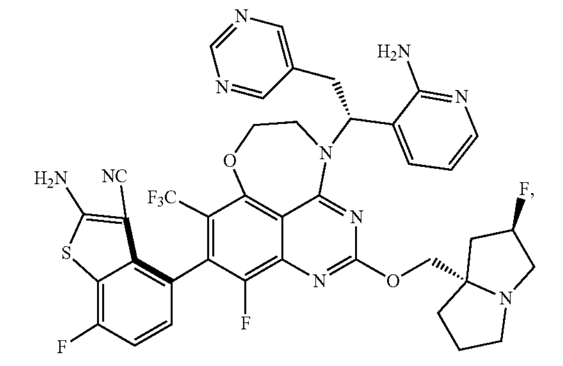
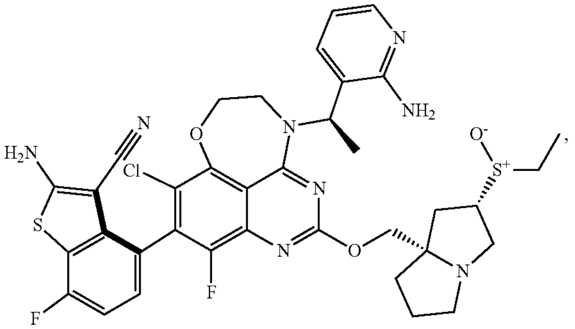
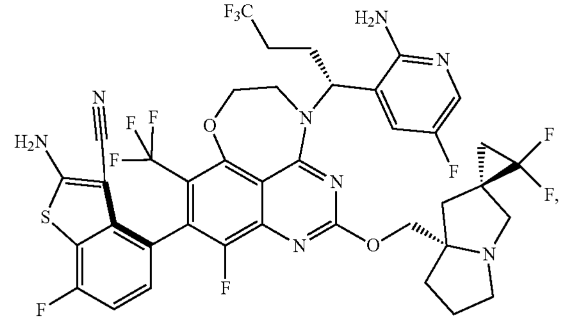
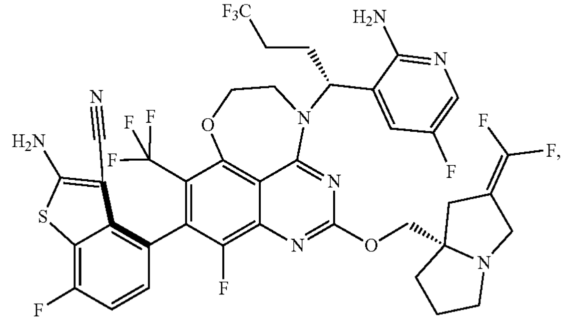
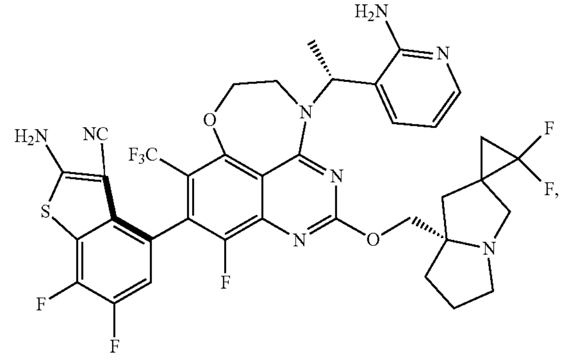

-continued
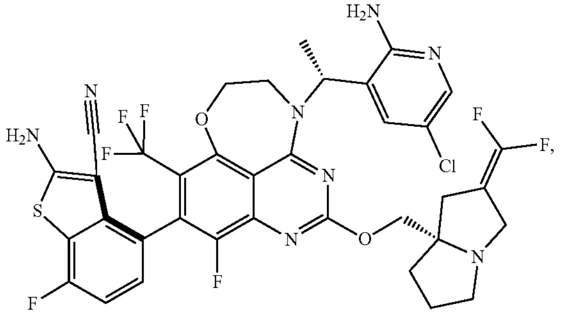
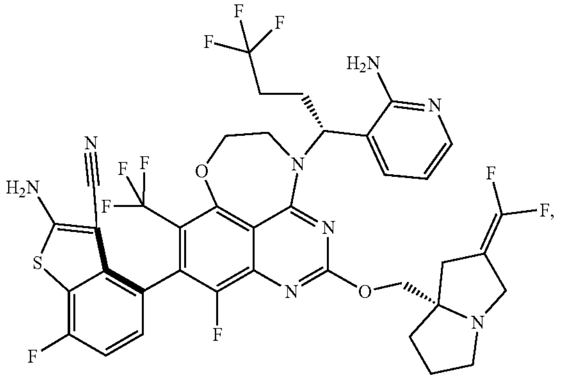
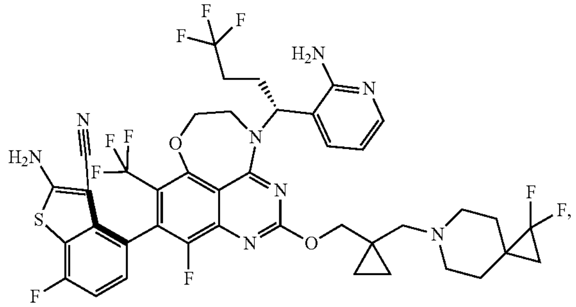
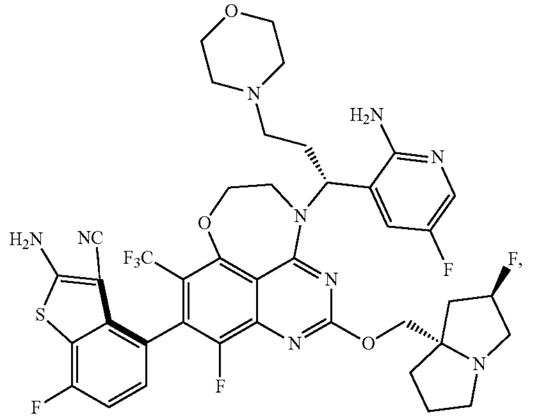
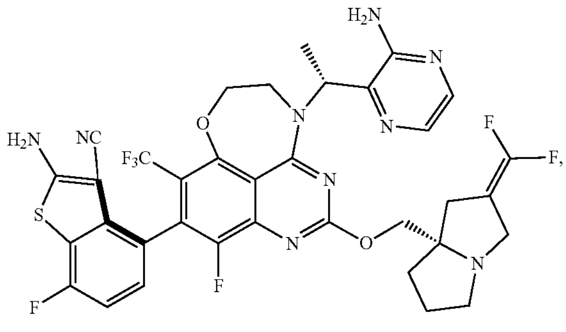
-continued
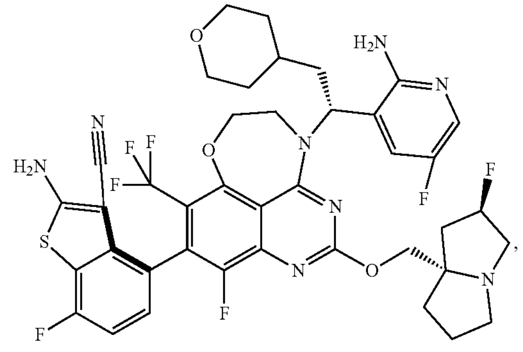
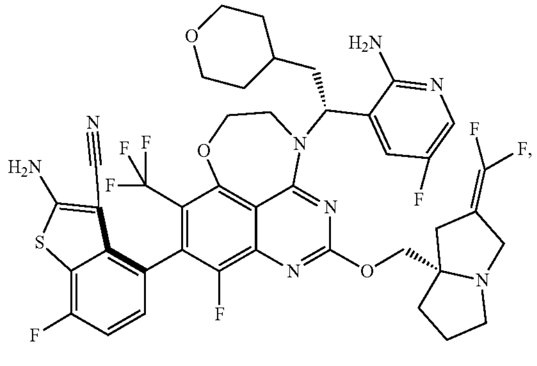
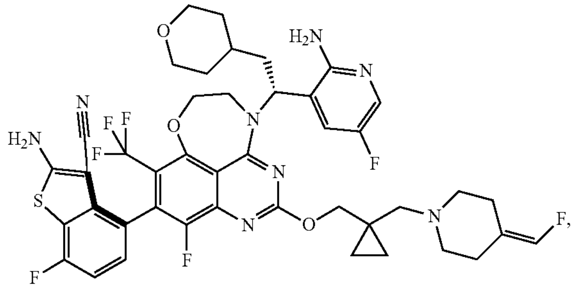
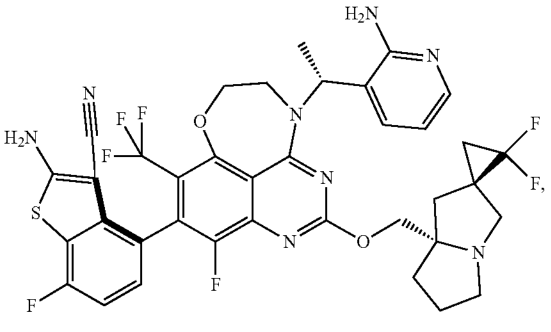

-continued
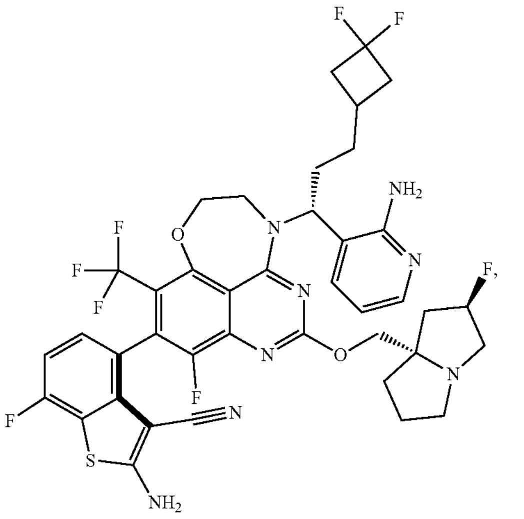
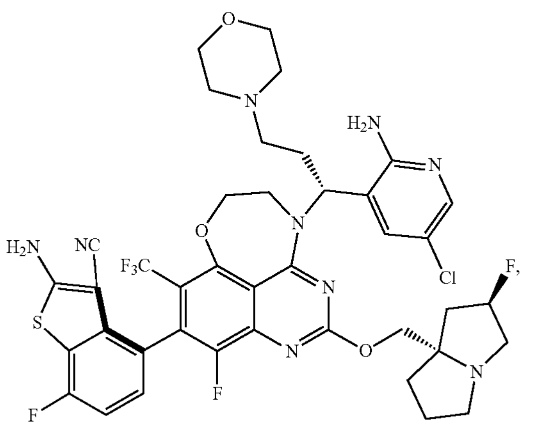
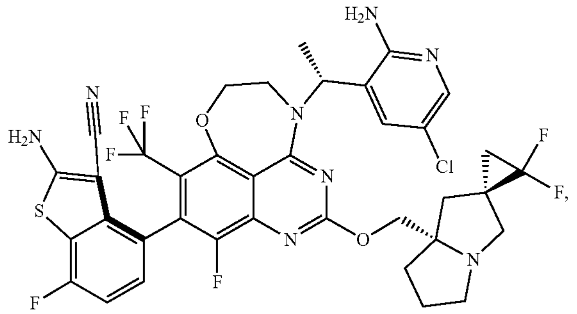
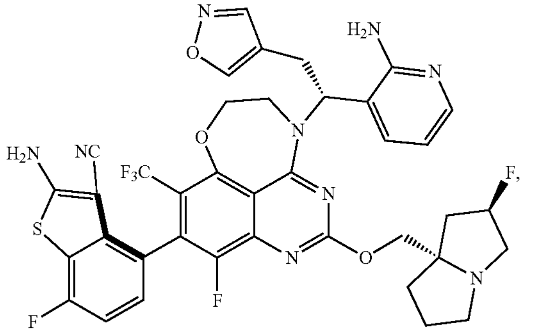
-continued
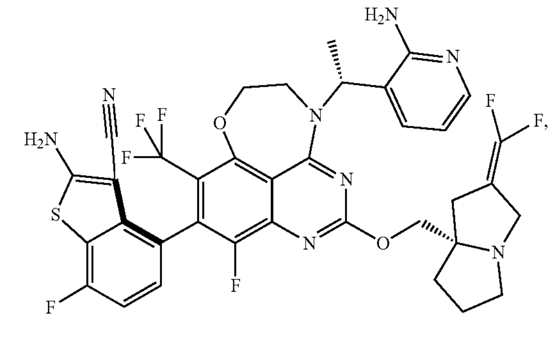
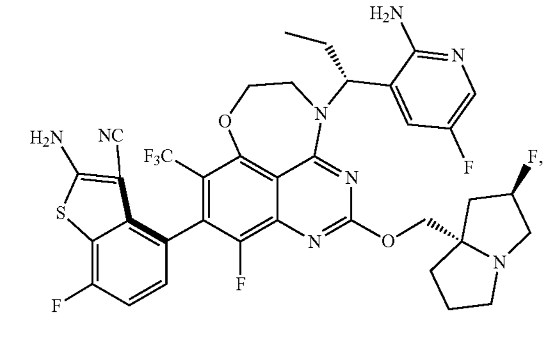
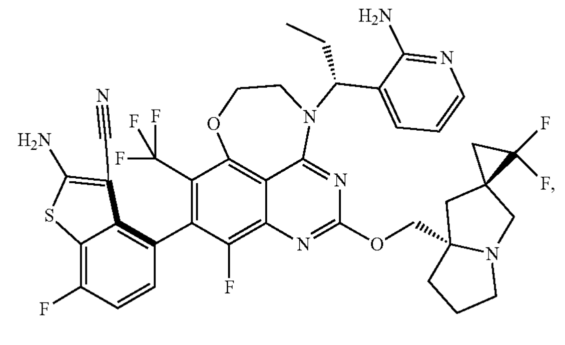
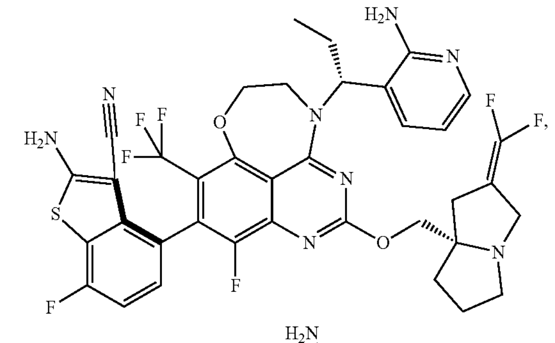
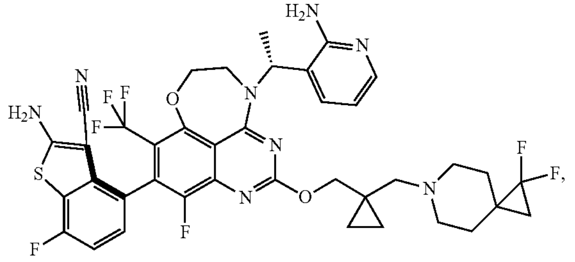

-continued
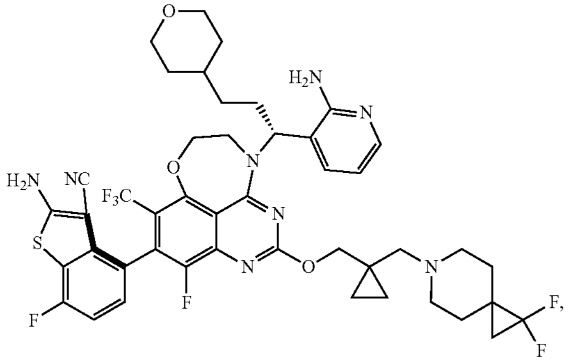
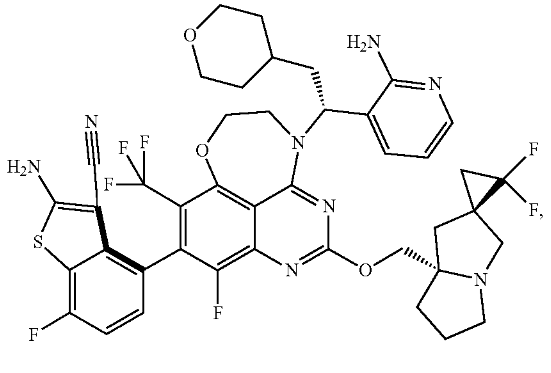
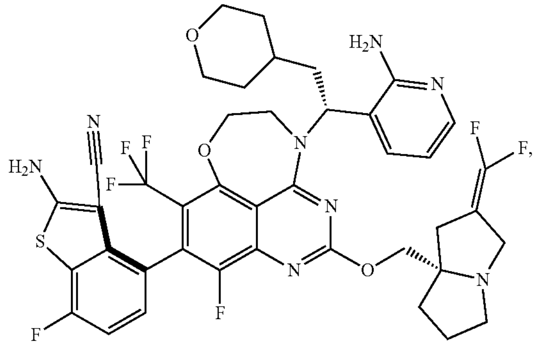
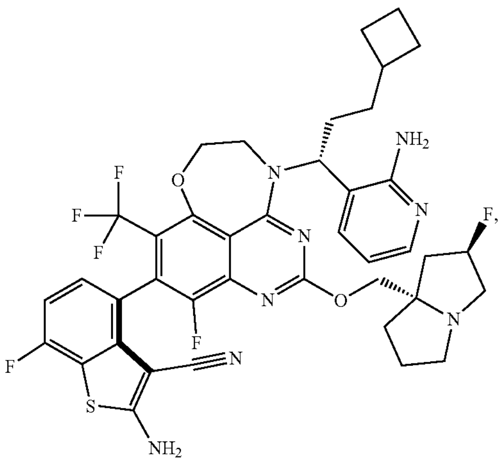
-continued
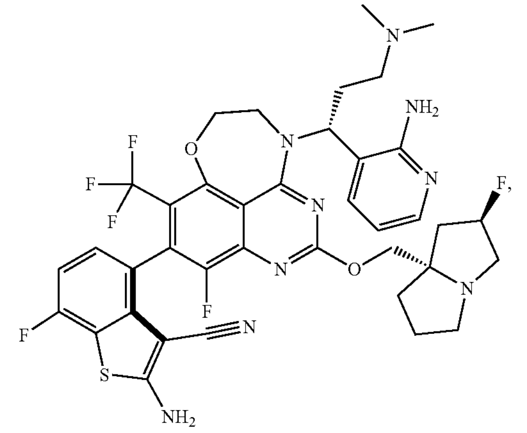
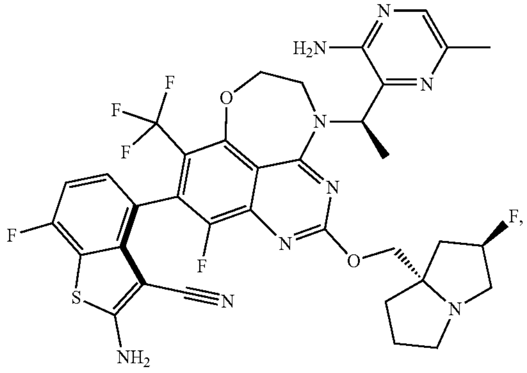
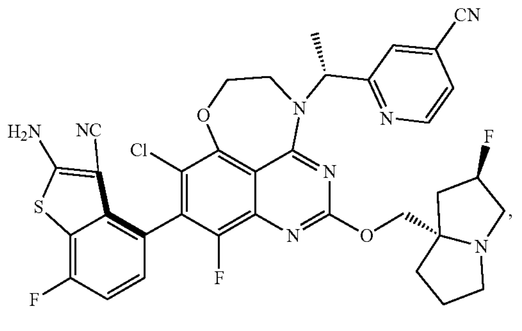
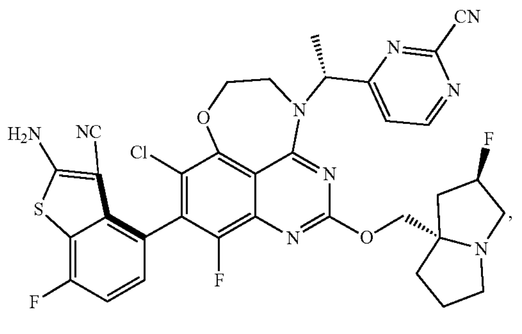

-continued
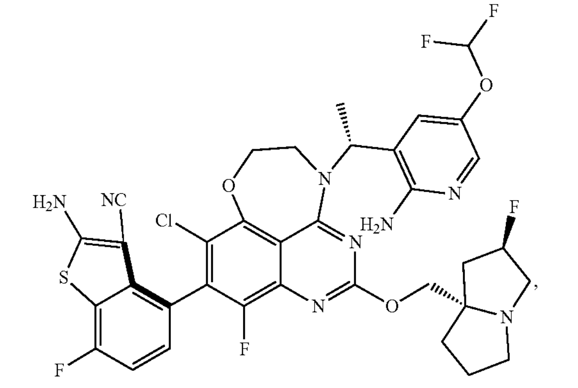
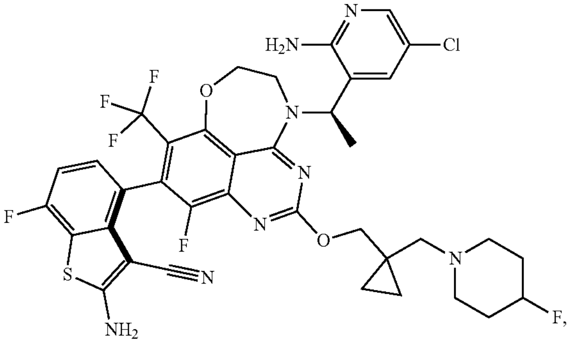
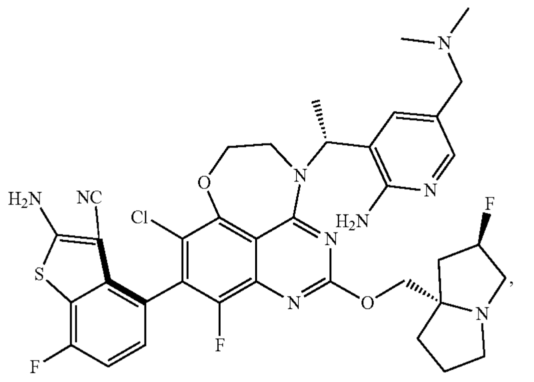
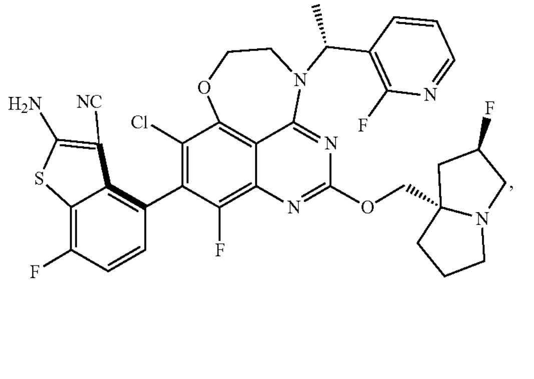
-continued
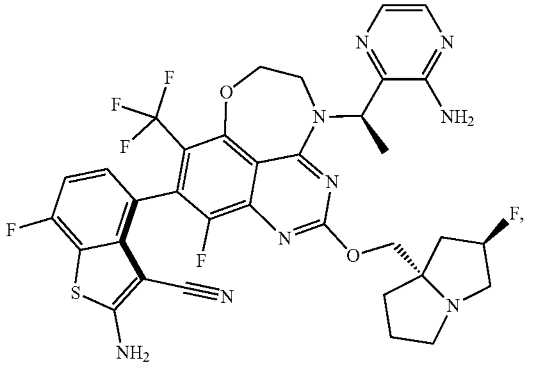
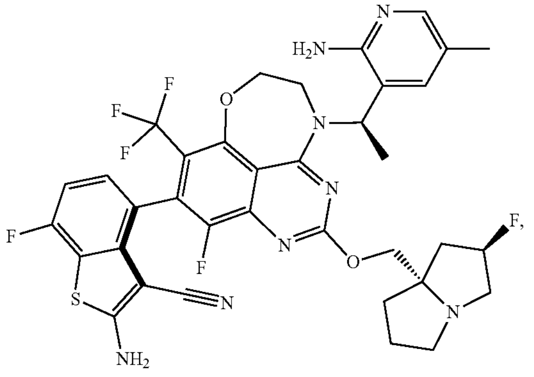
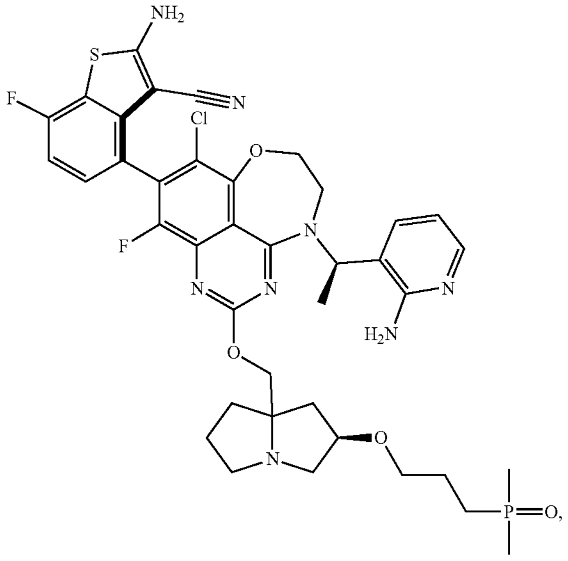
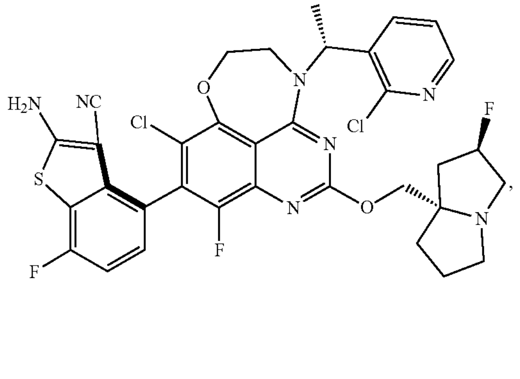

-continued
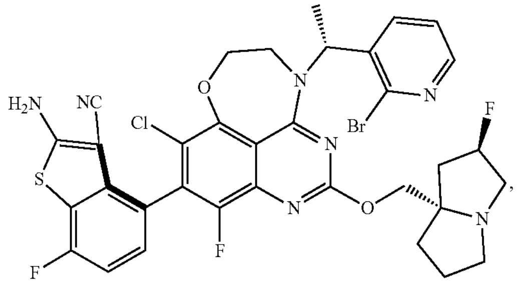
,
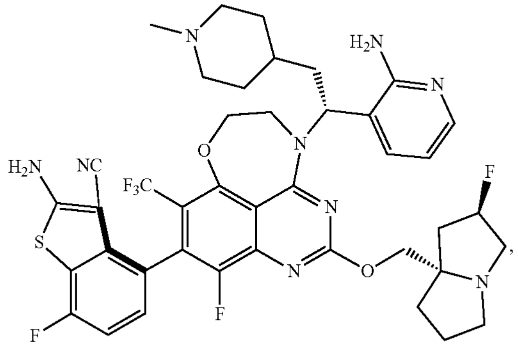
,
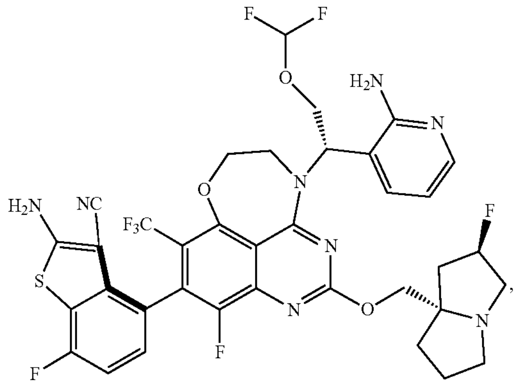
,
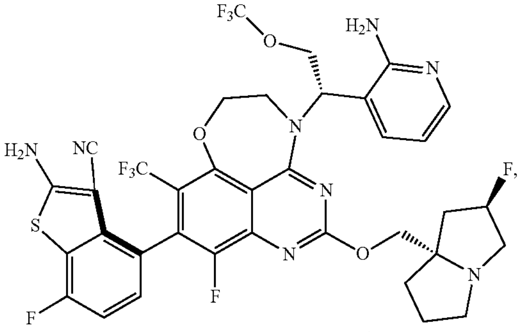
,
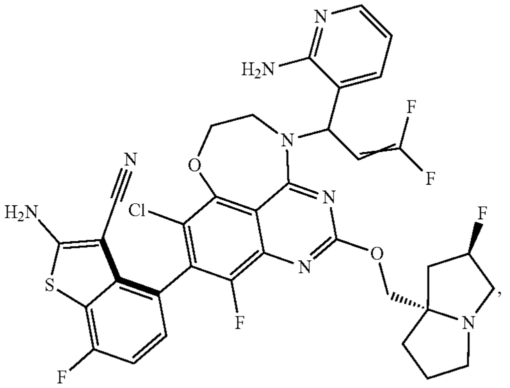
,
-continued
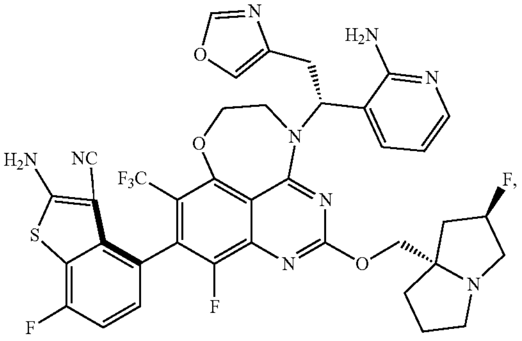
,
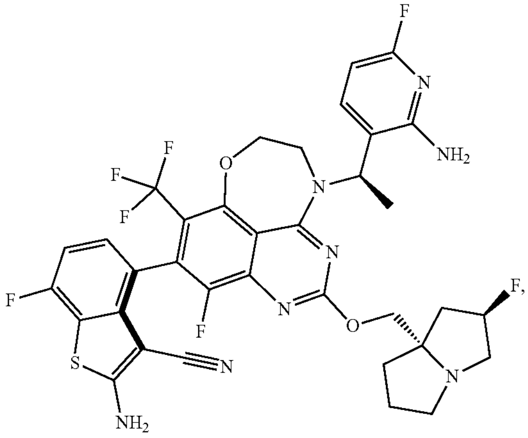
,
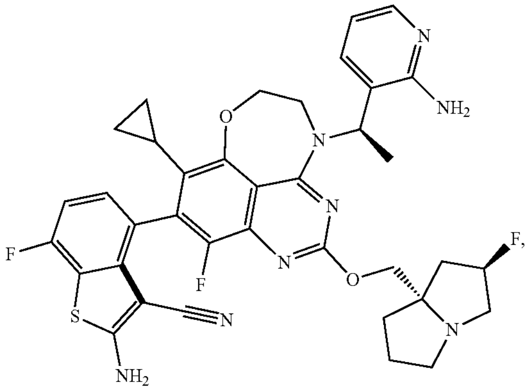
,
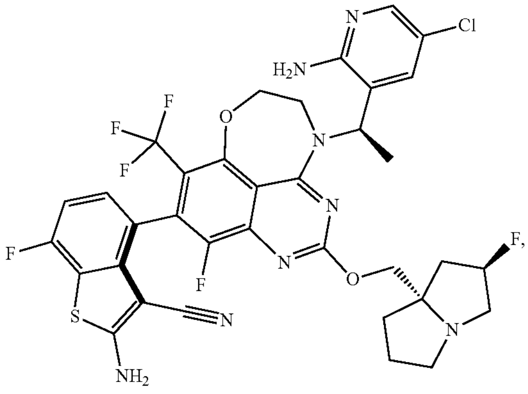
, -continued
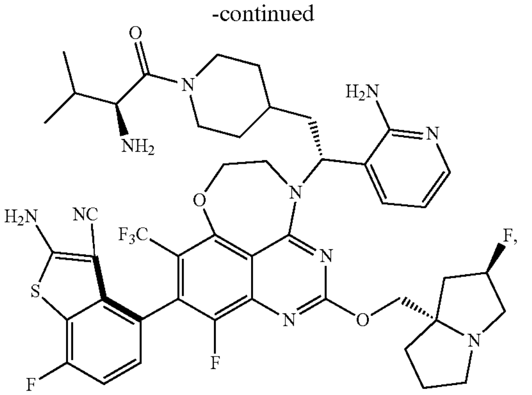
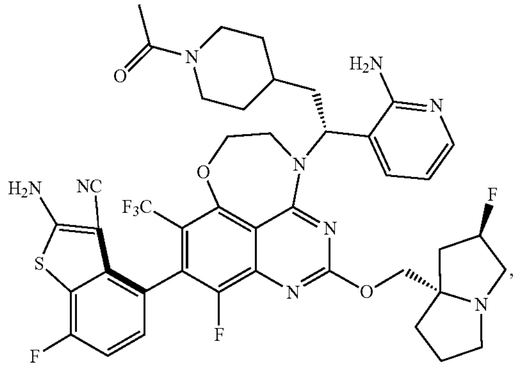
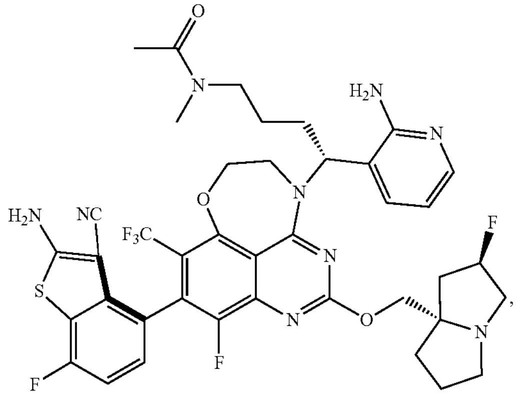
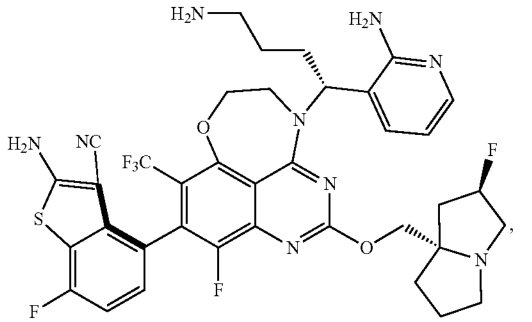
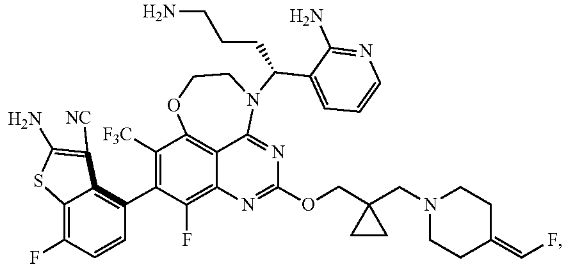
-continued
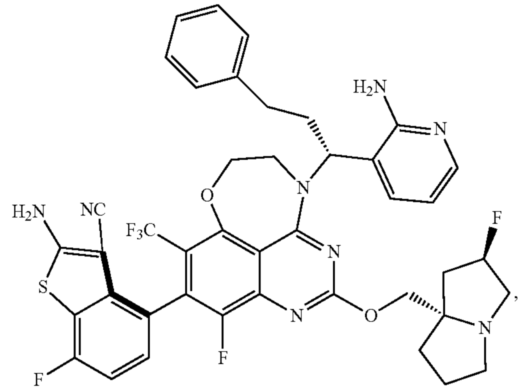
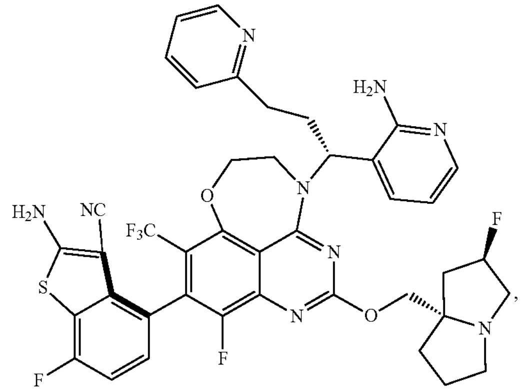
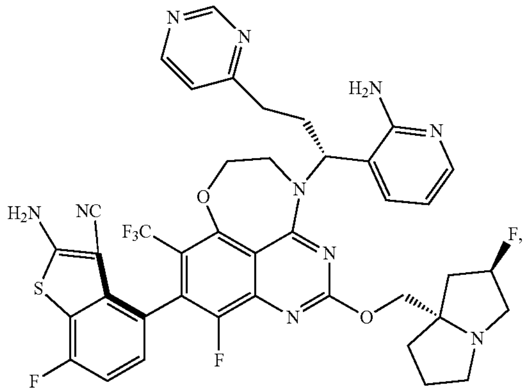
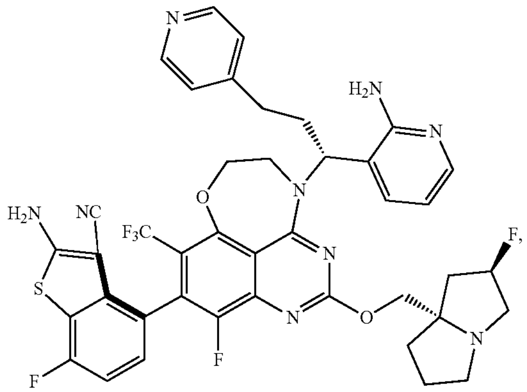

-continued
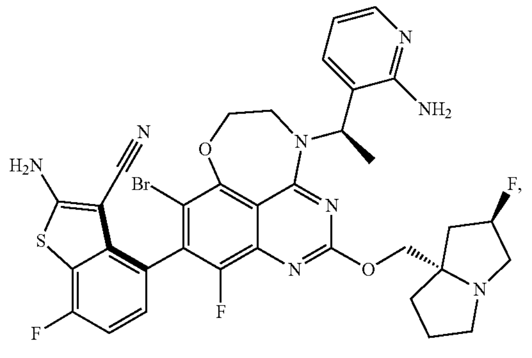
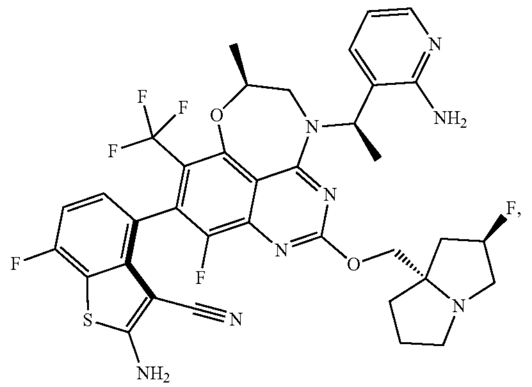
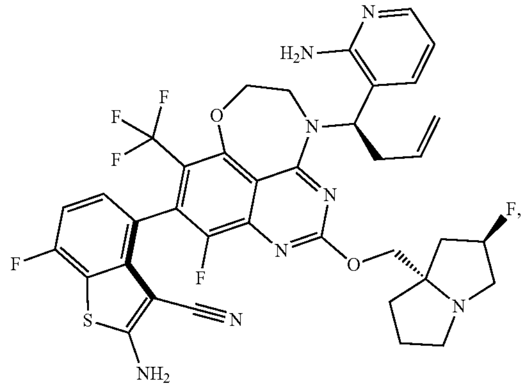
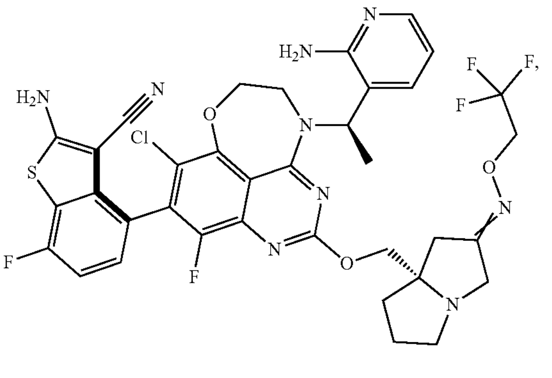
-continued
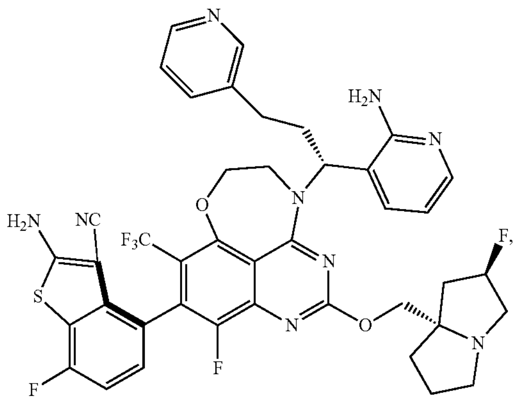
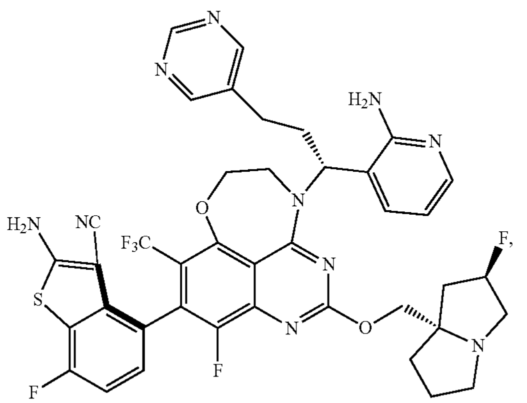
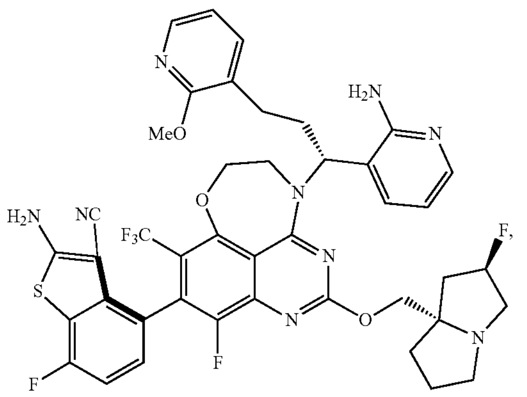
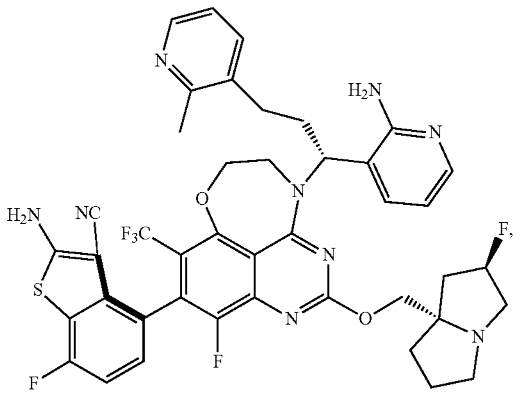

-continued
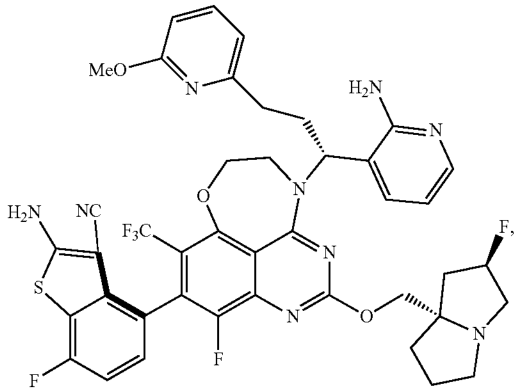
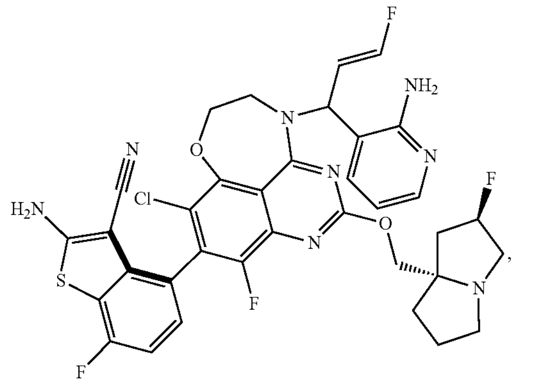
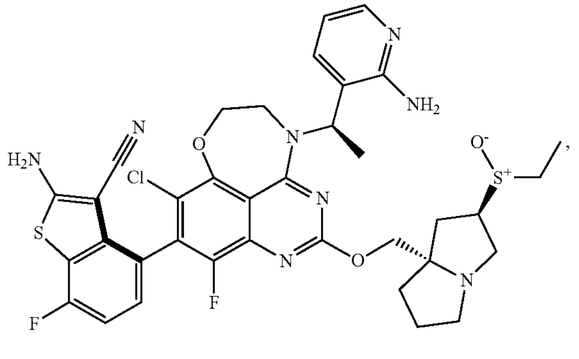
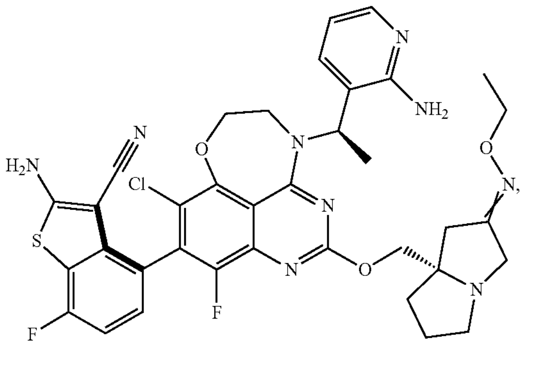
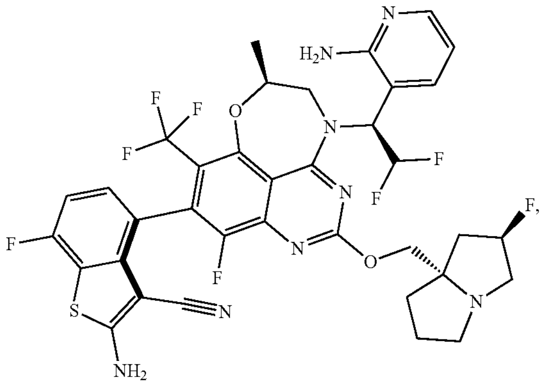
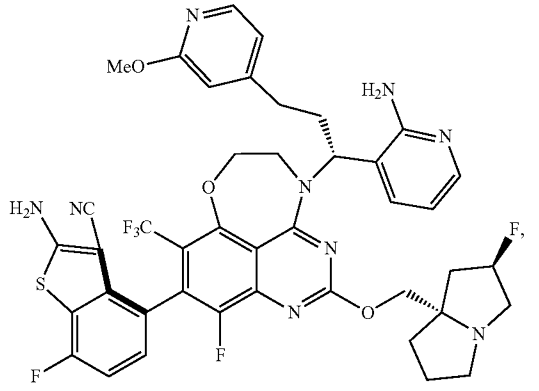
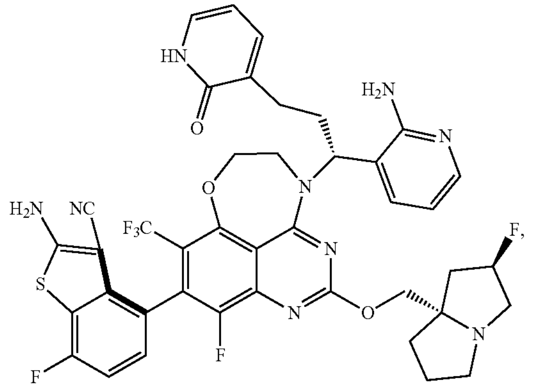
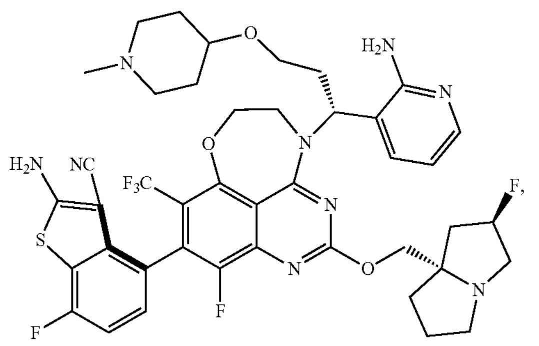

-continued
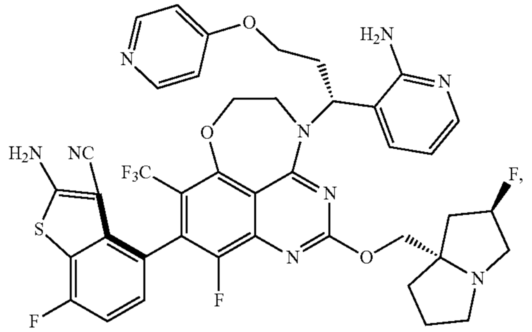
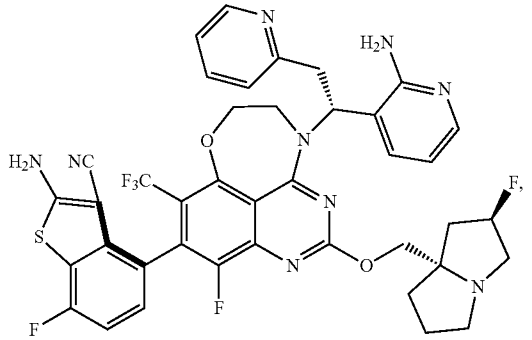
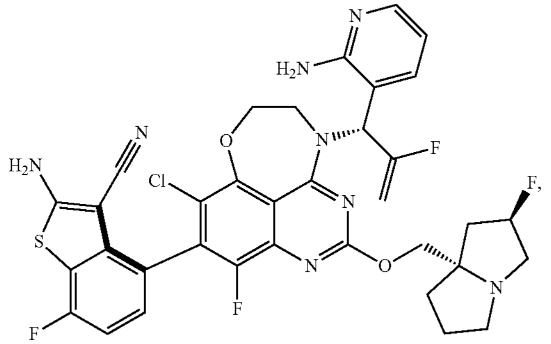
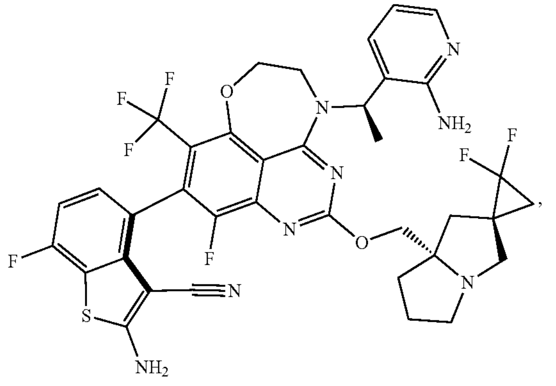
-continued
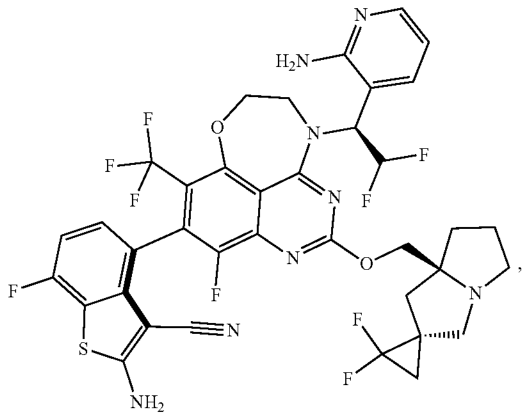
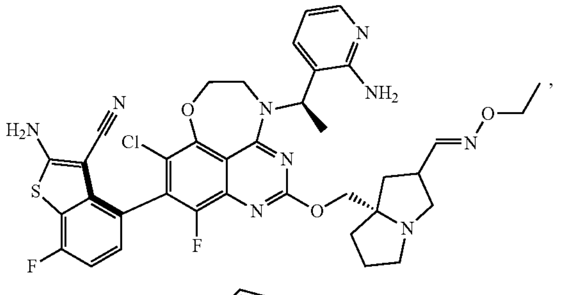
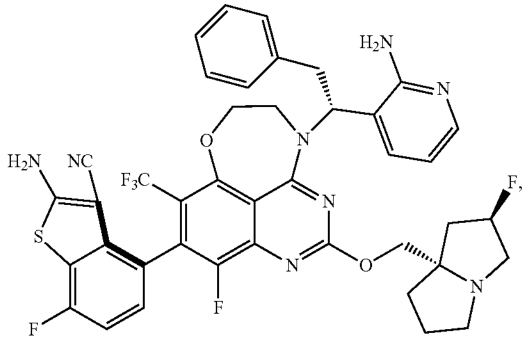
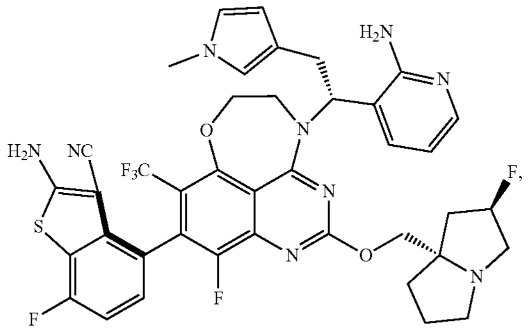
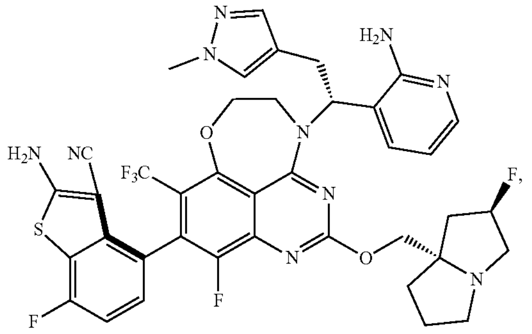

-continued
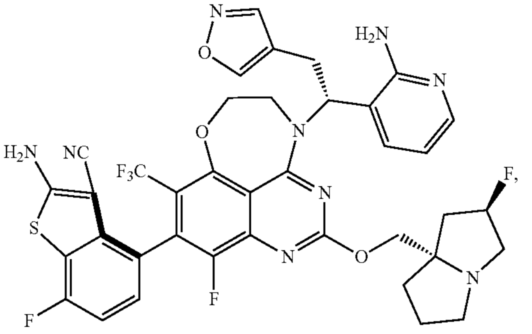
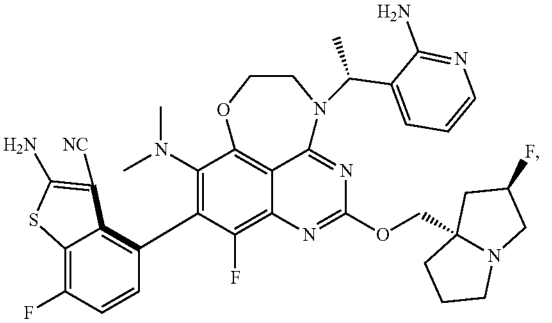
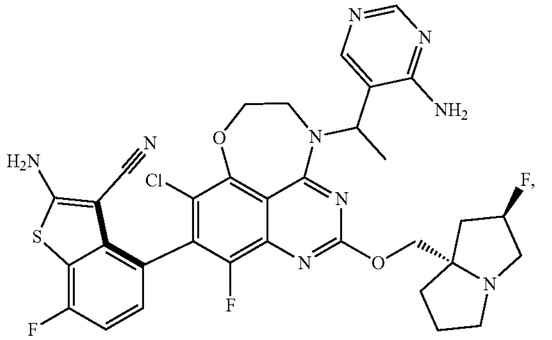
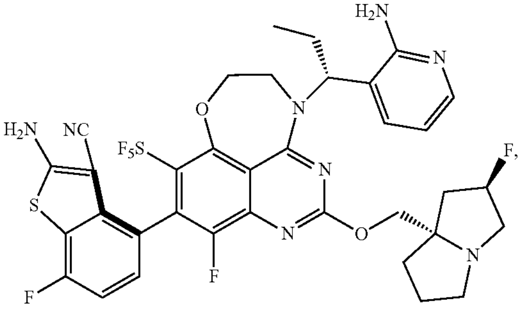
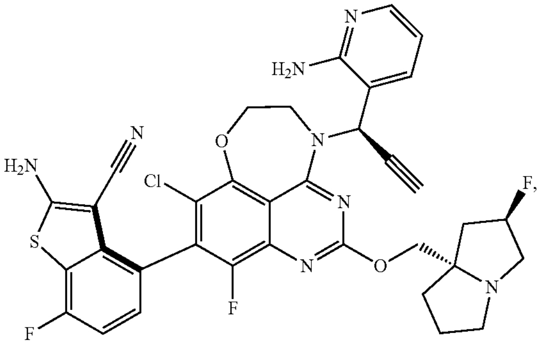
-continued
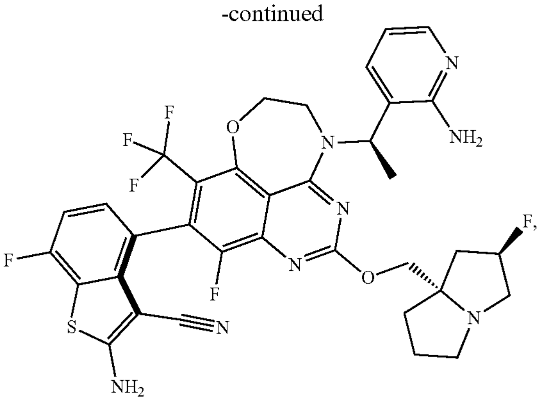
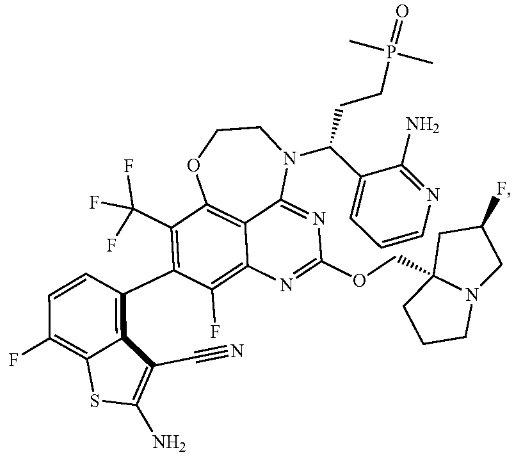
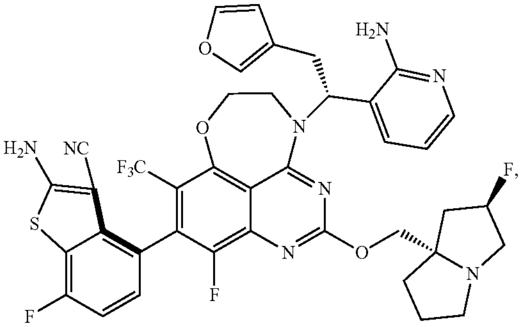
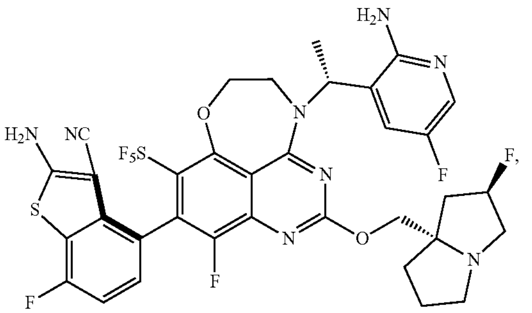
and -continued
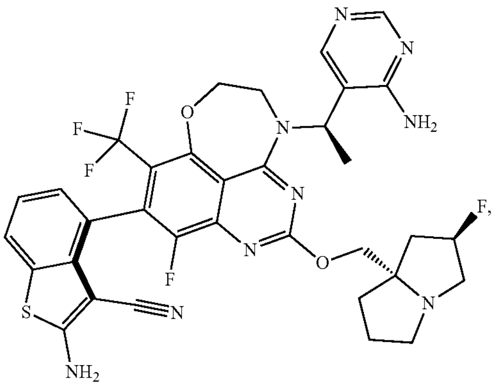
or a pharmaceutically acceptable salt or solvate thereof. In certain aspects, the present disclosure provides a compound selected from:
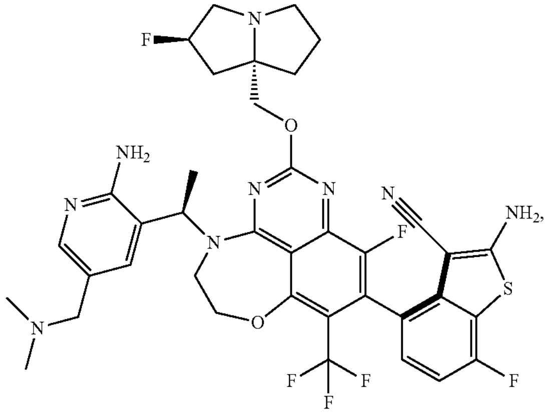
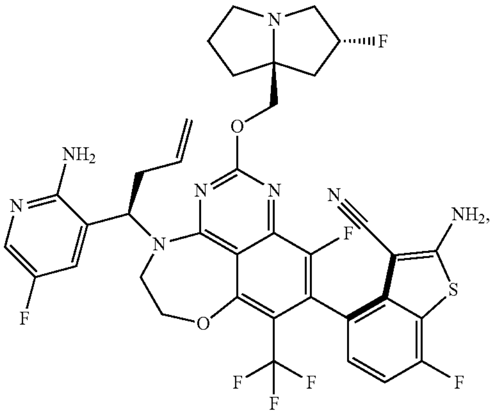
-continued
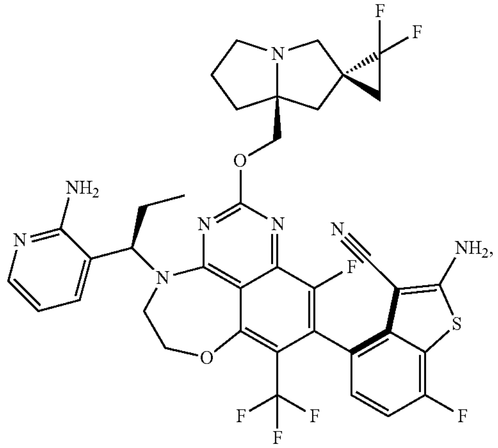
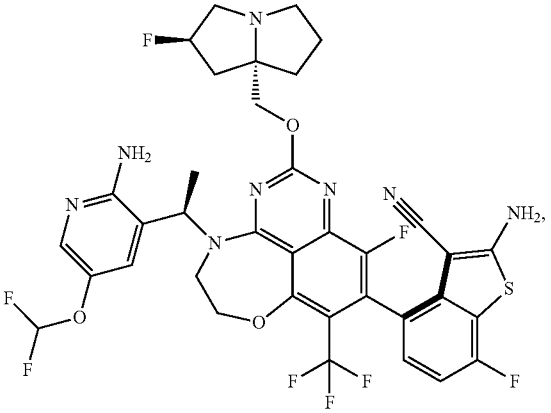
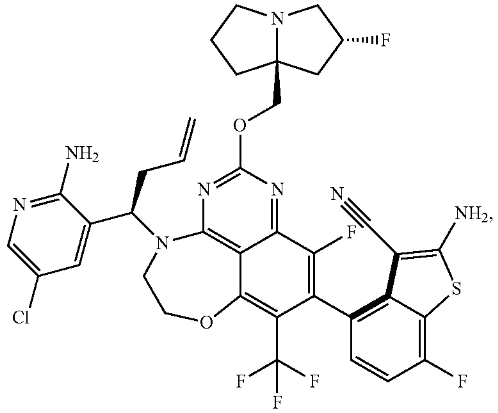
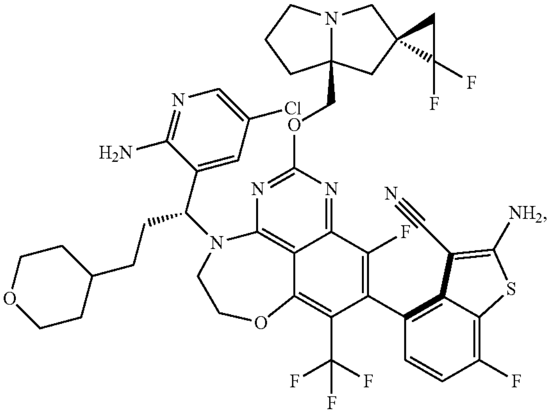

-continued
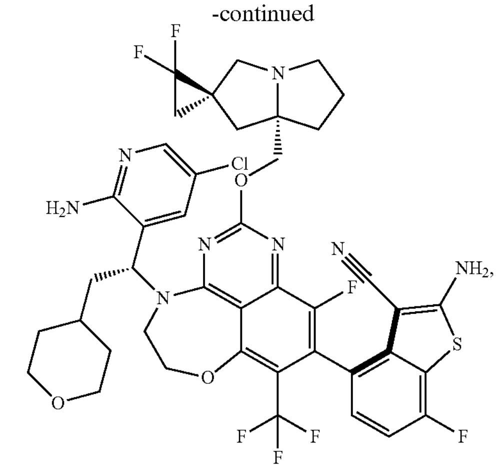
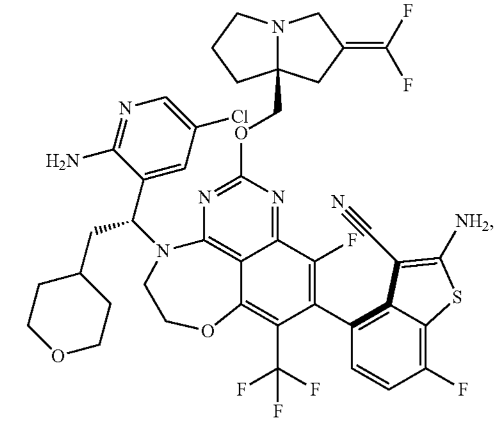
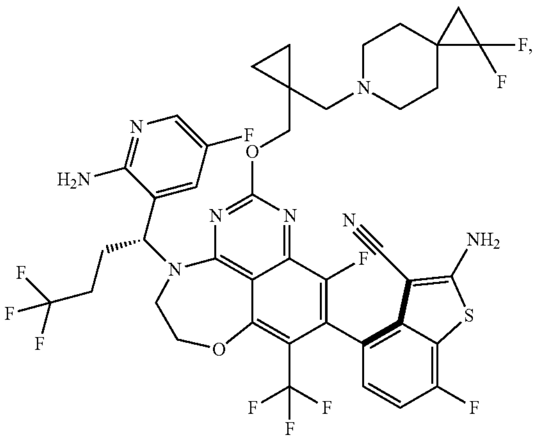
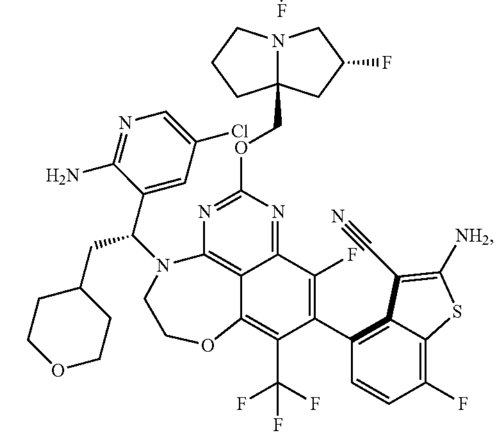
-continued
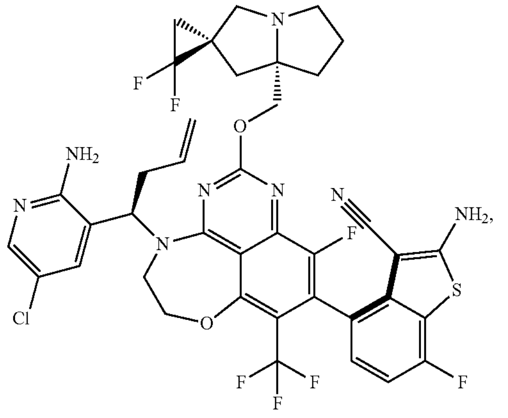
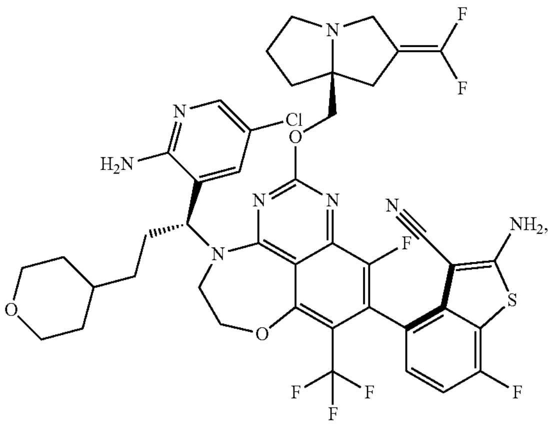
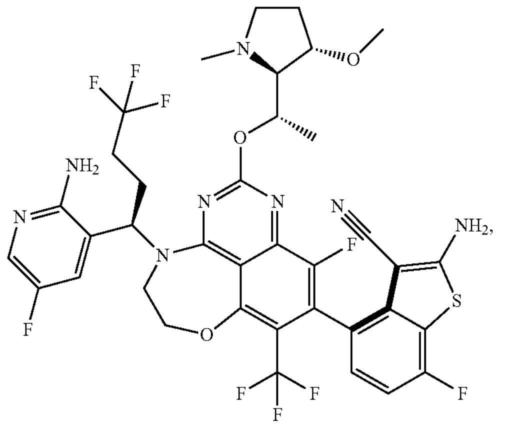
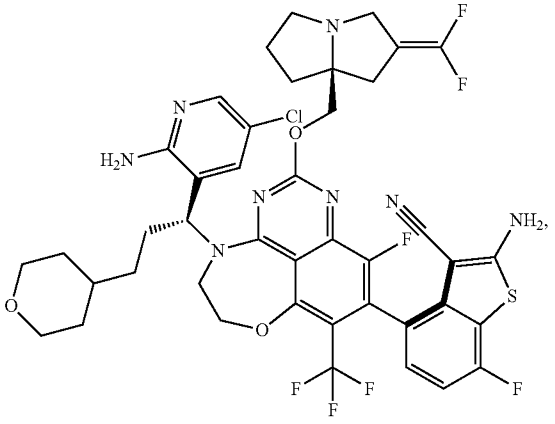

-continued
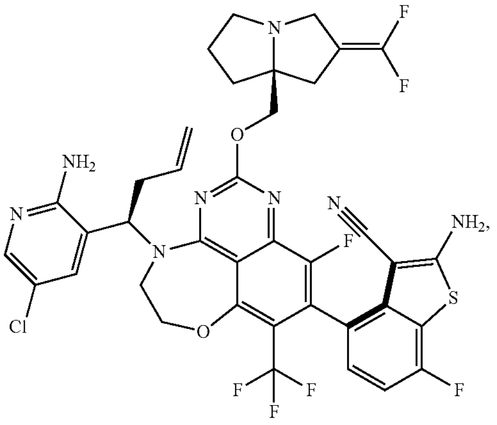
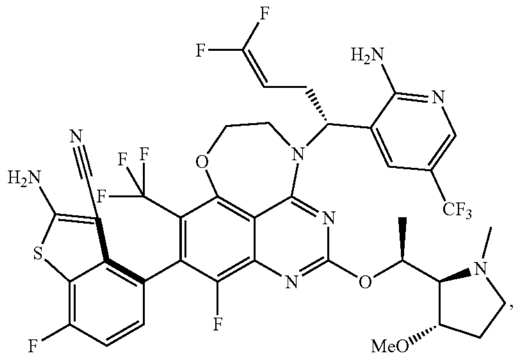
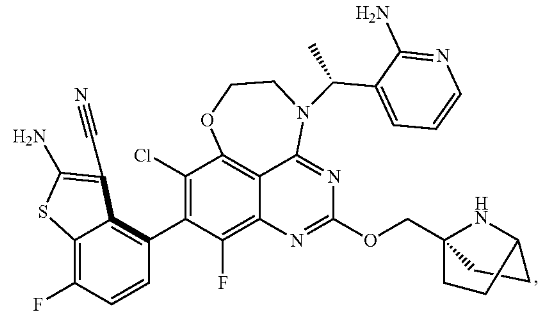
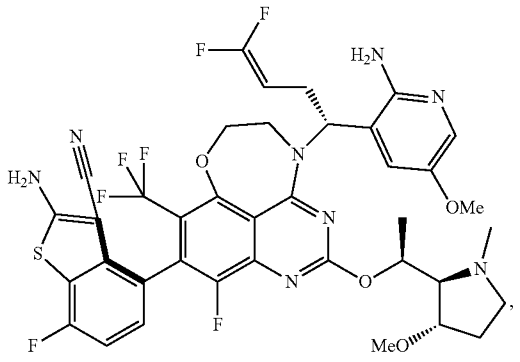
-continued
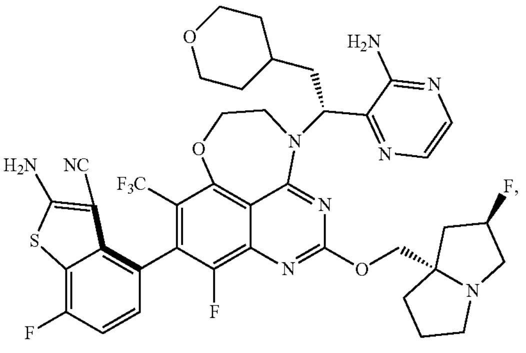
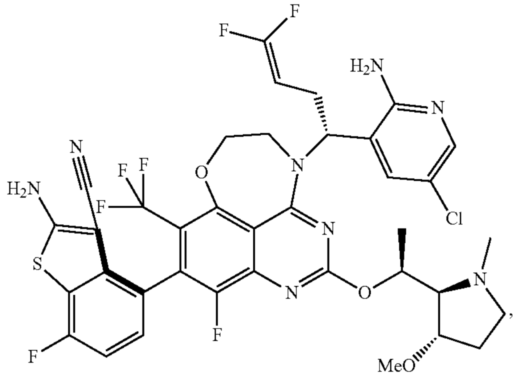
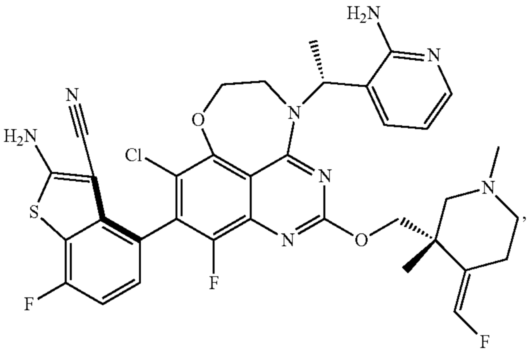
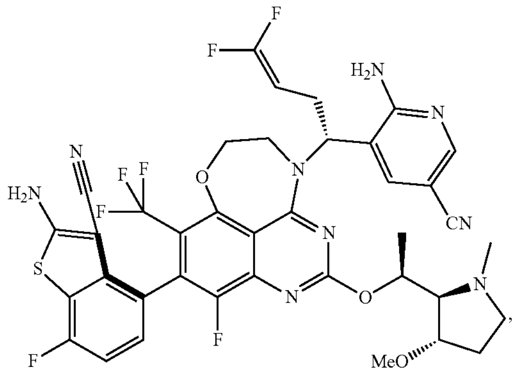

-continued
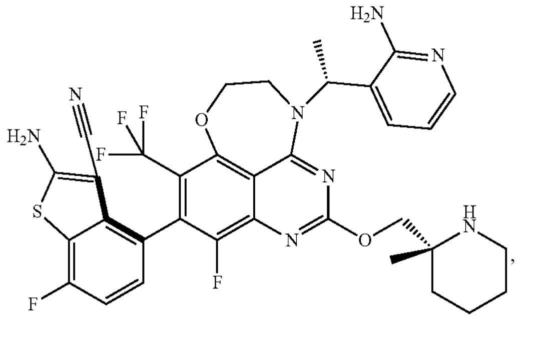
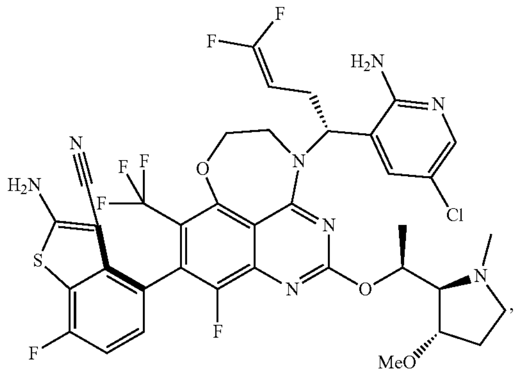
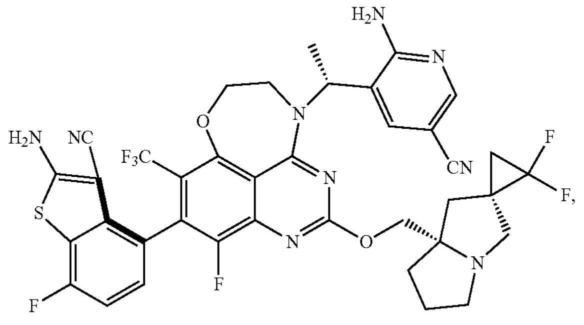
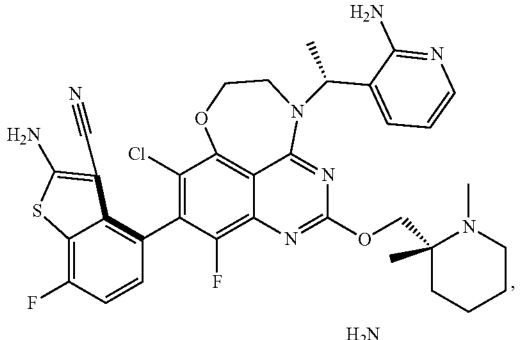
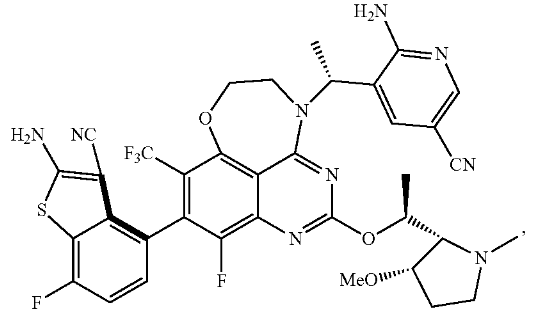
-continued
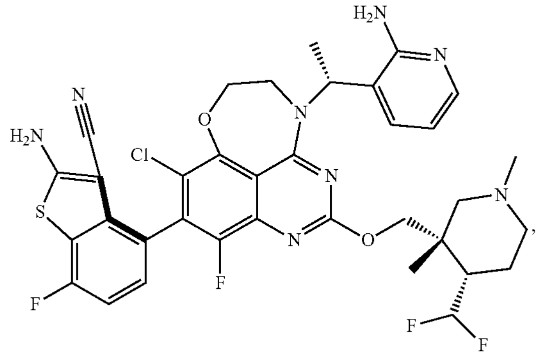
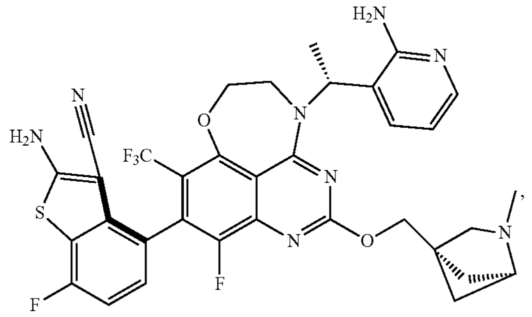
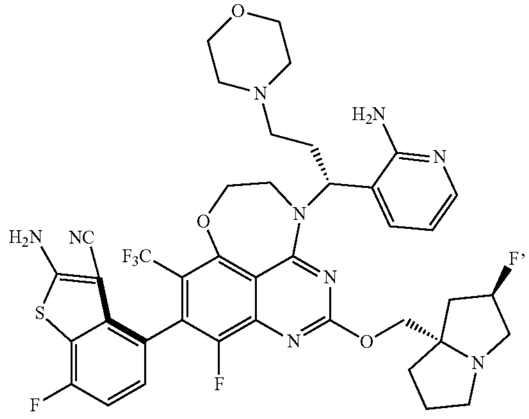
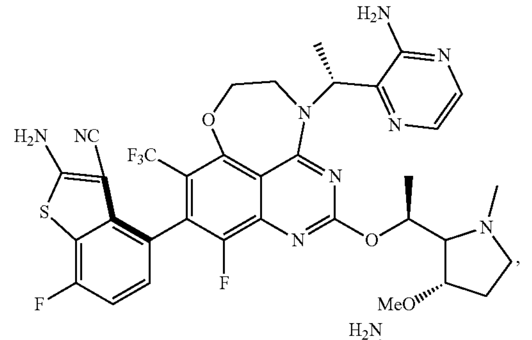
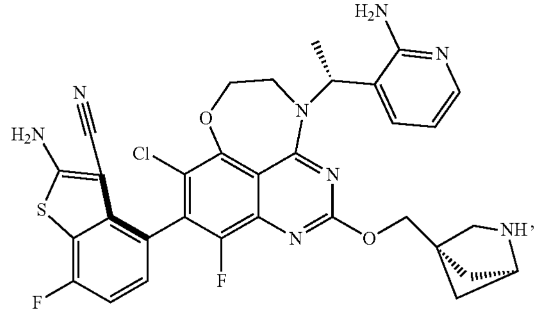

-continued
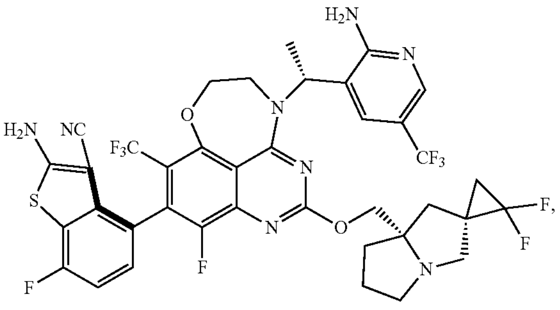
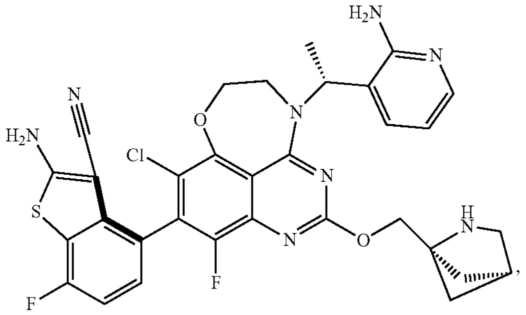
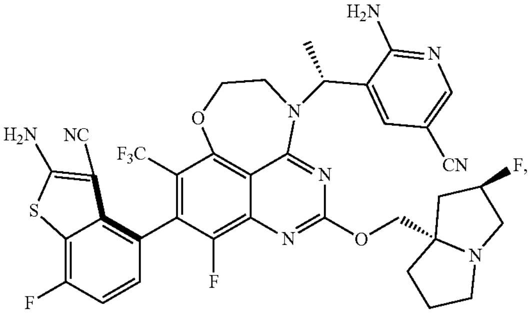
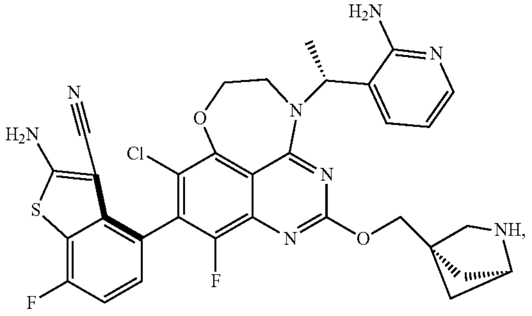
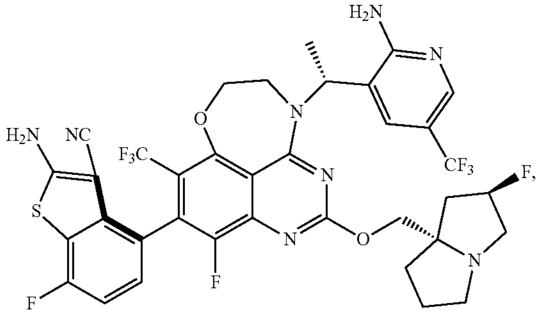
-continued
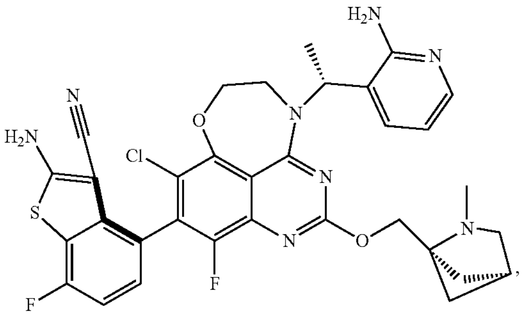
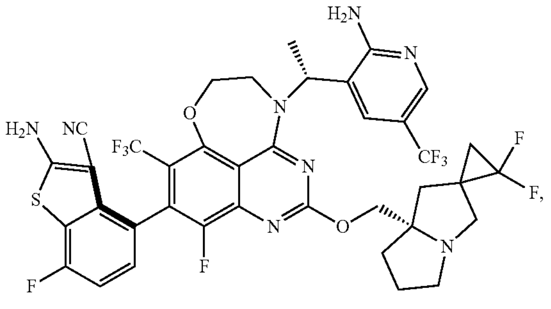
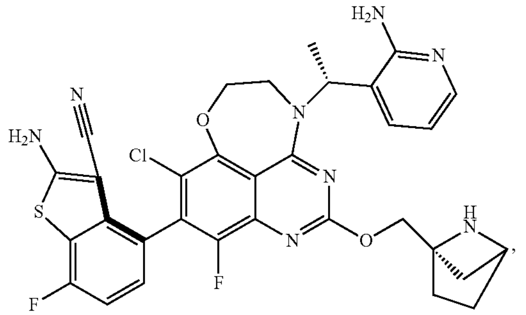
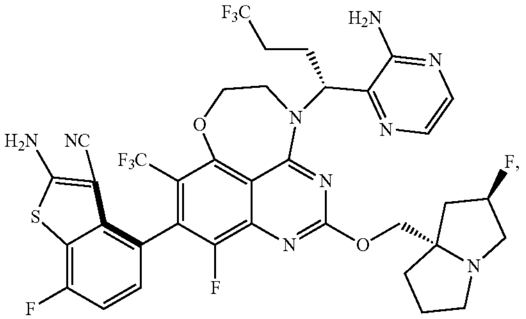
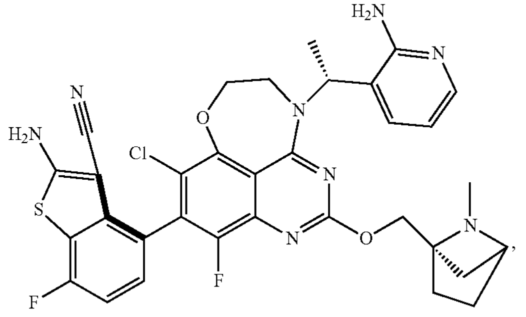

-continued
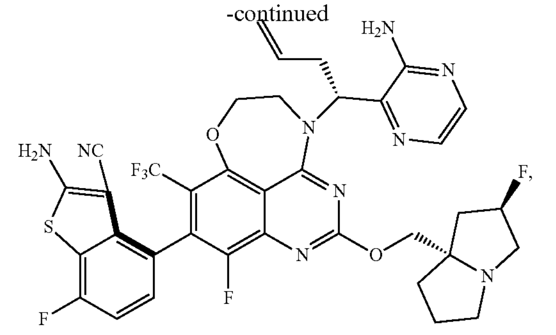
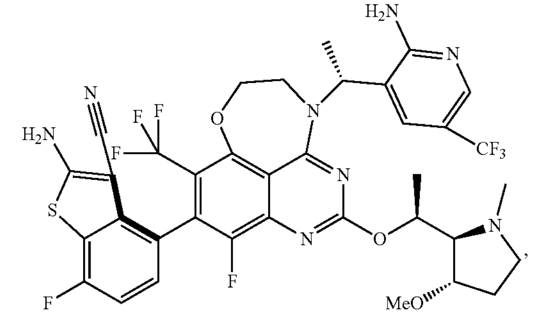
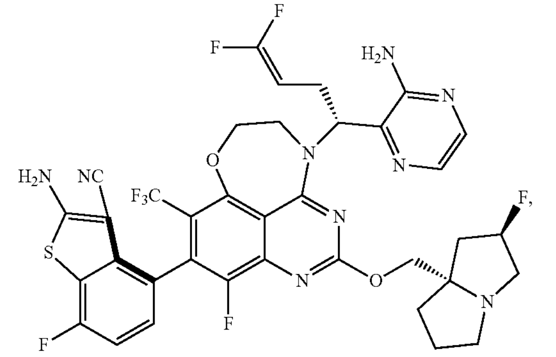
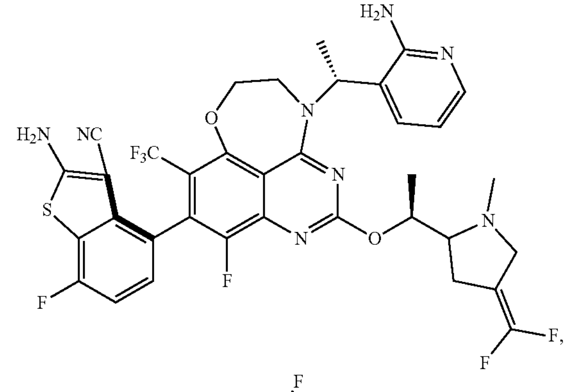
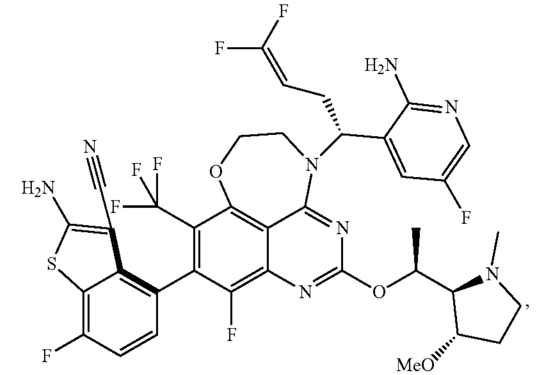
-continued
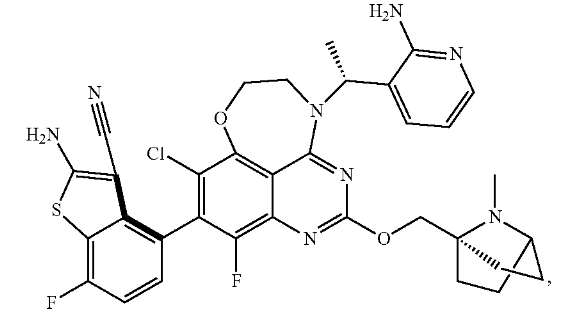
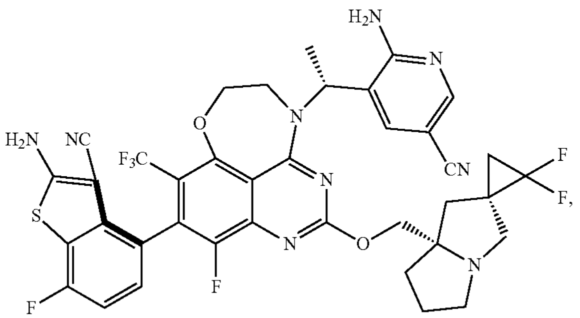
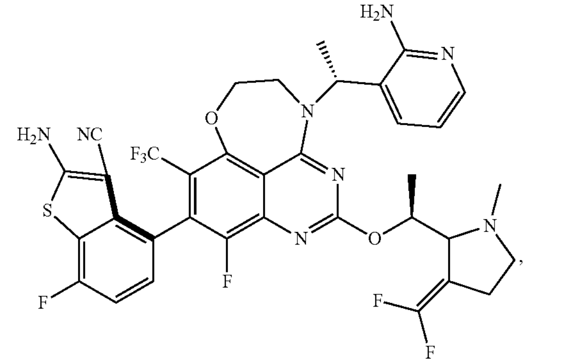
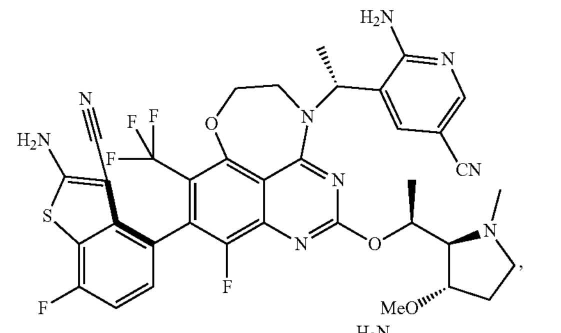
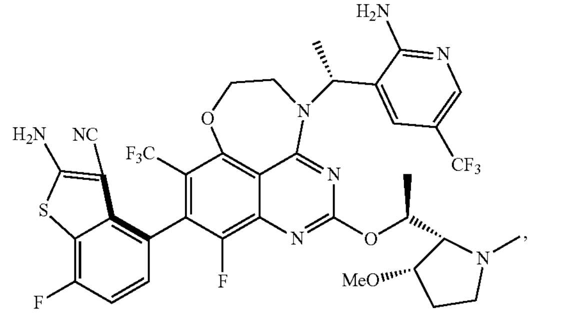

-continued
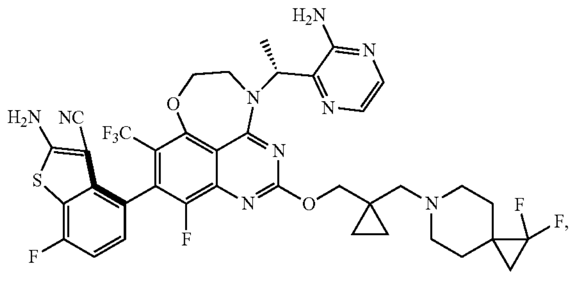
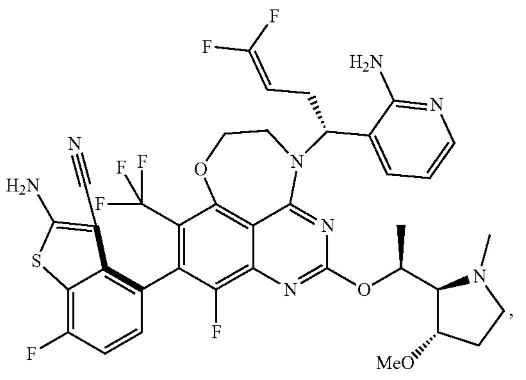
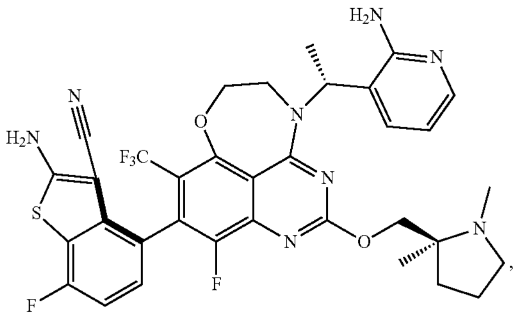
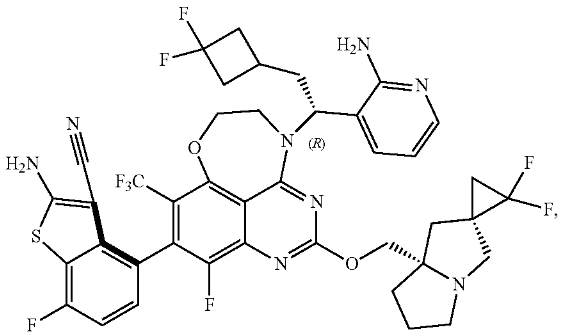
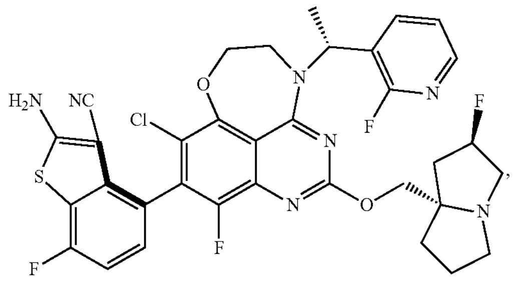
-continued
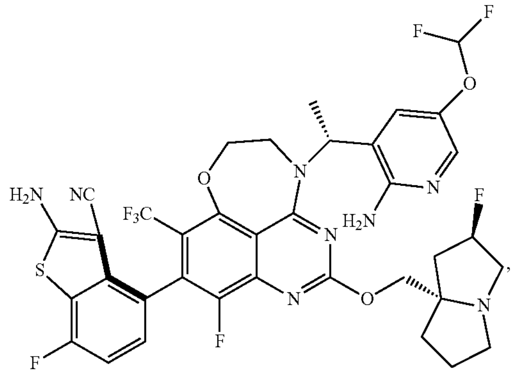
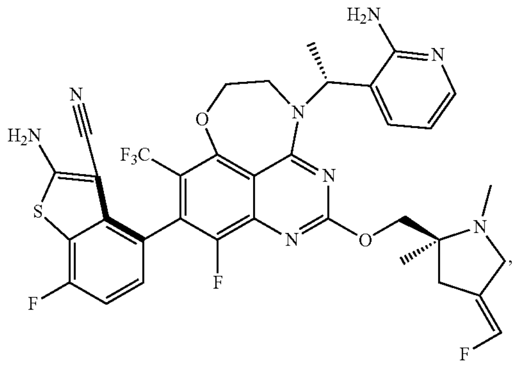
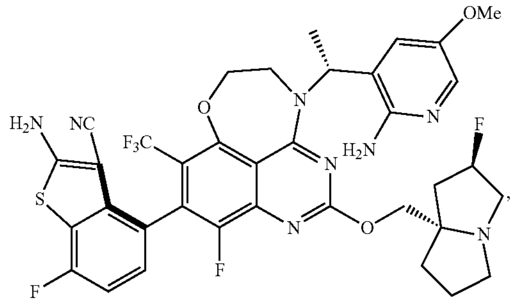
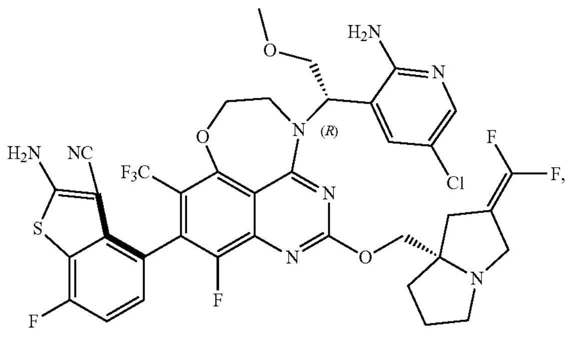

-continued
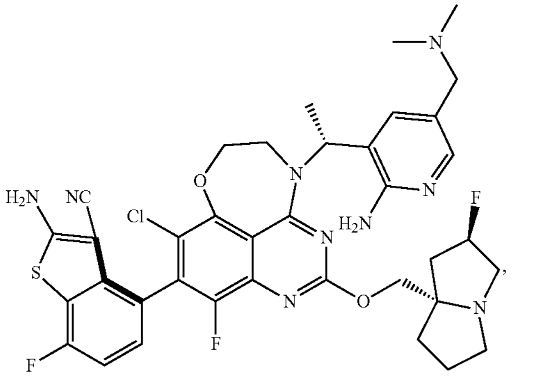
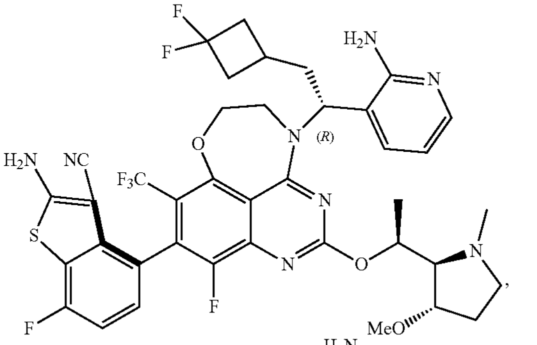
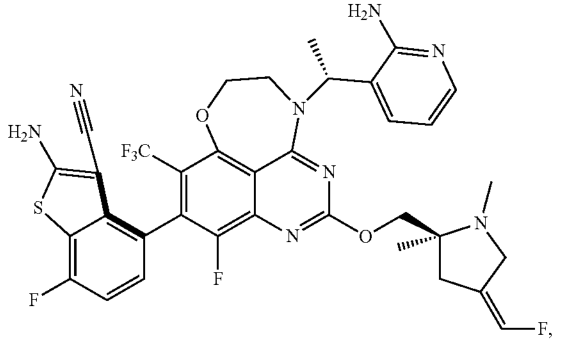
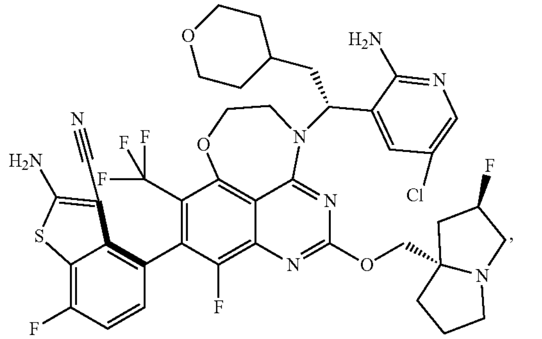
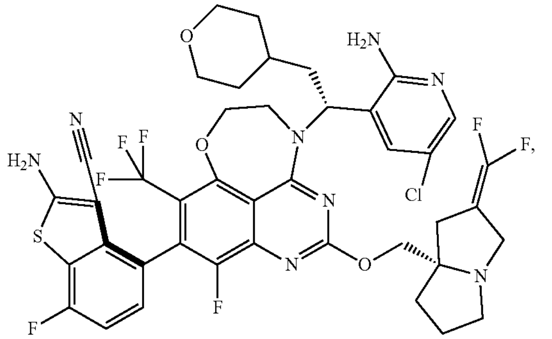
-continued
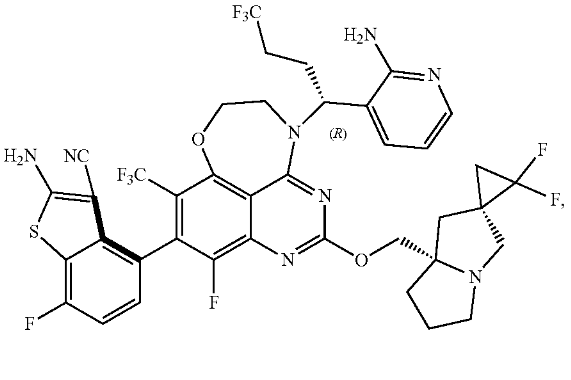
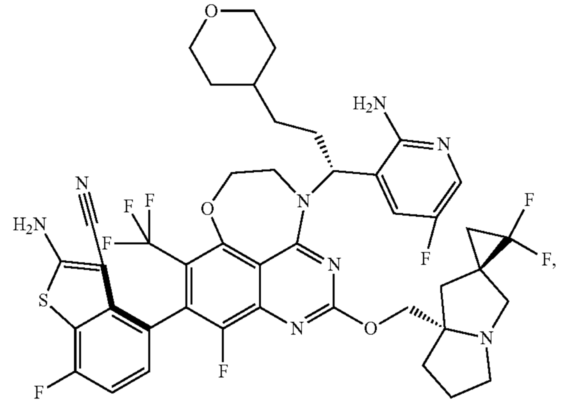
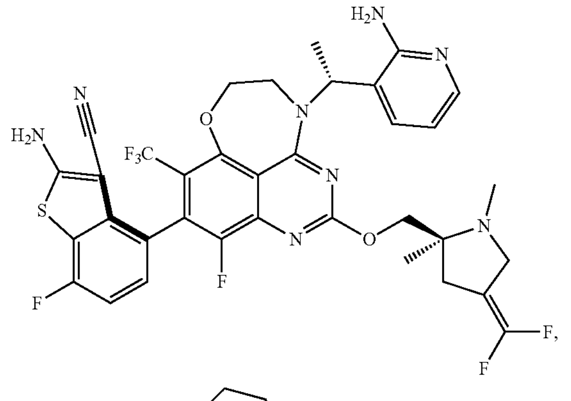
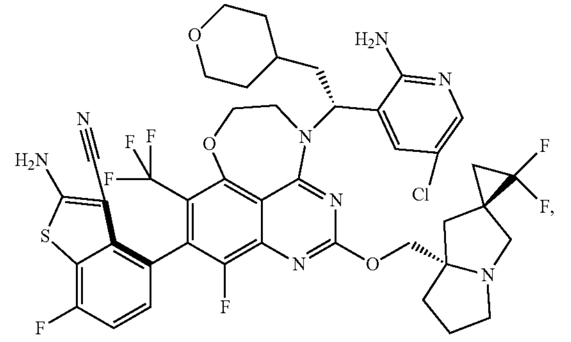

-continued
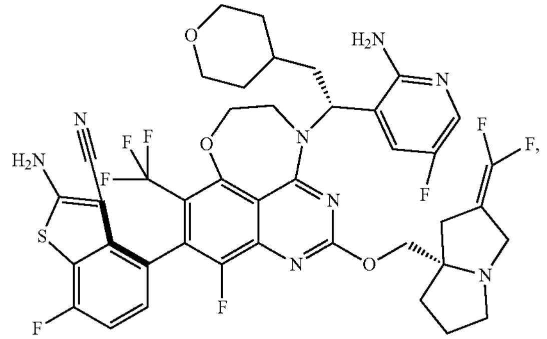
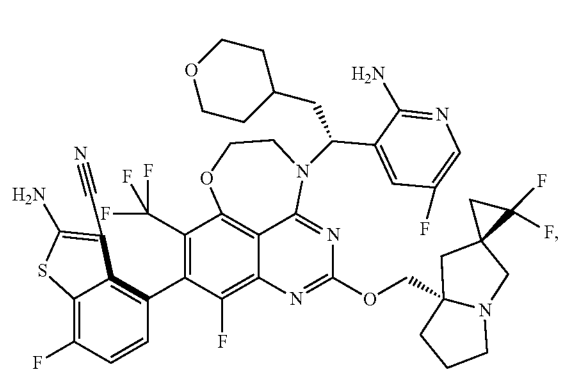
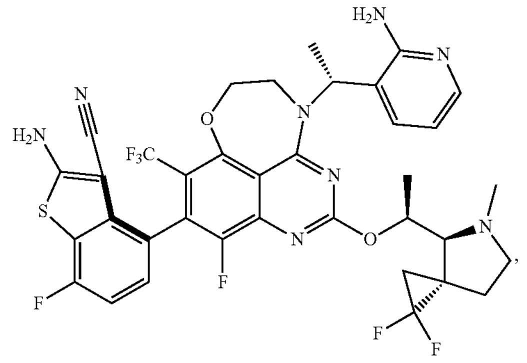
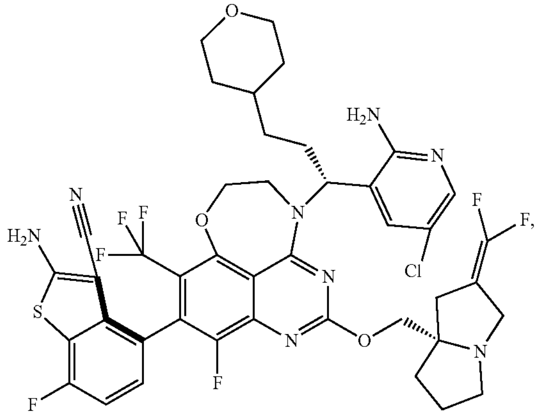
-continued
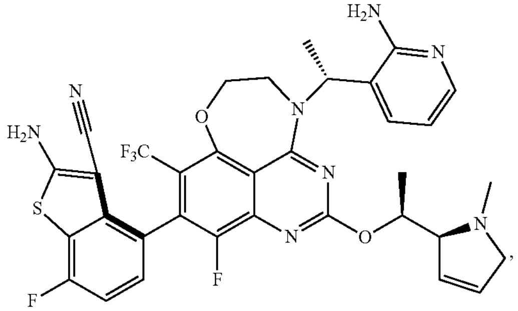
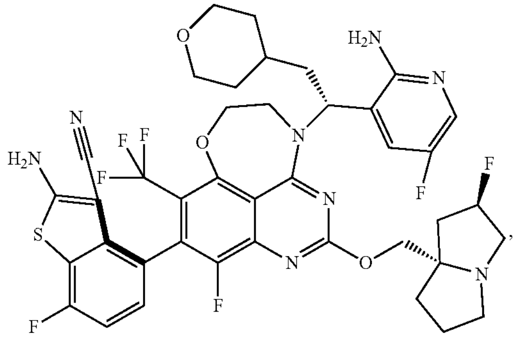
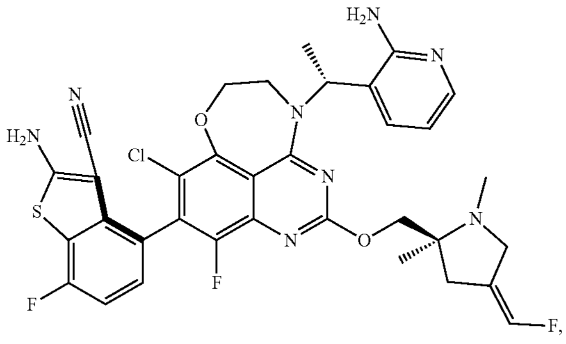
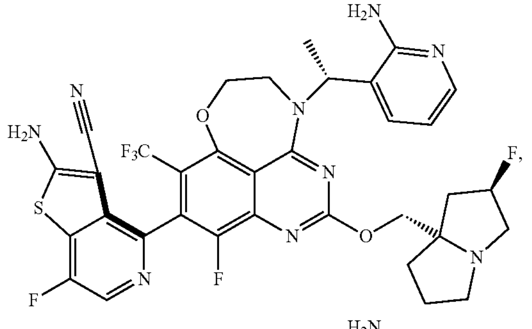
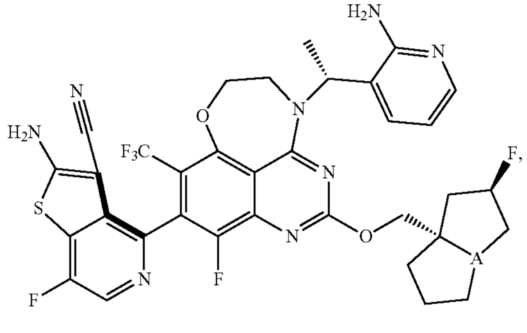

-continued
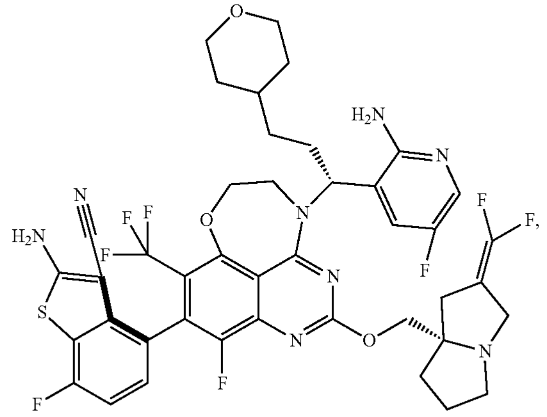
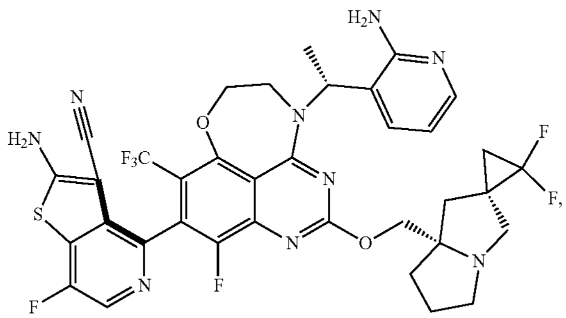
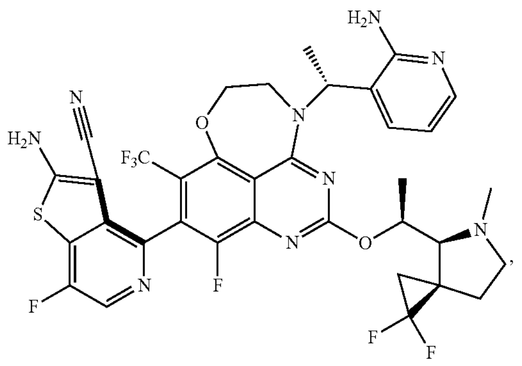
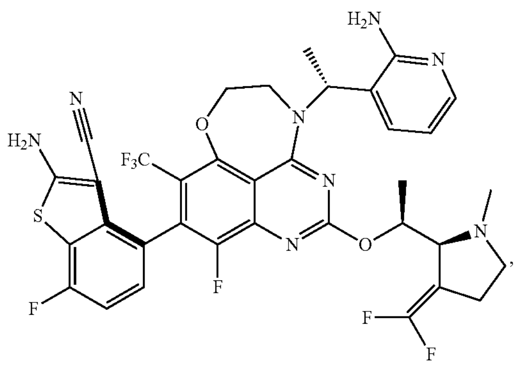
-continued
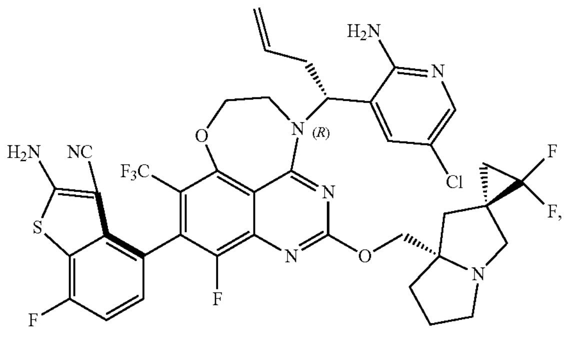
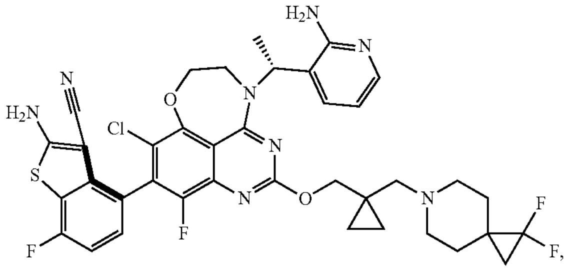
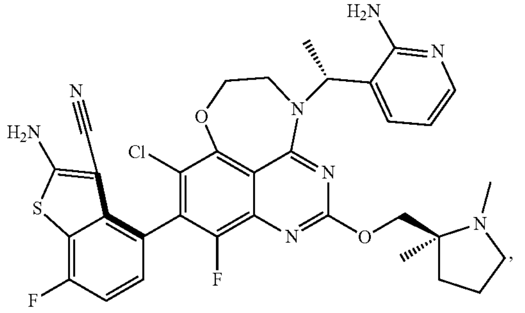
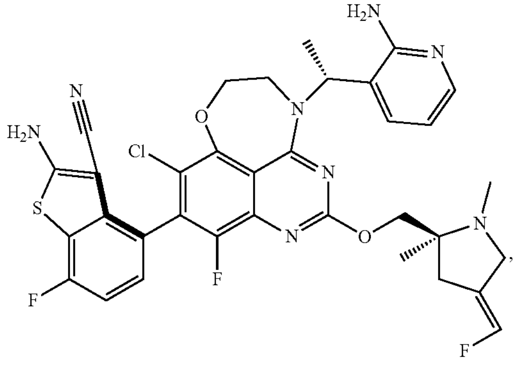
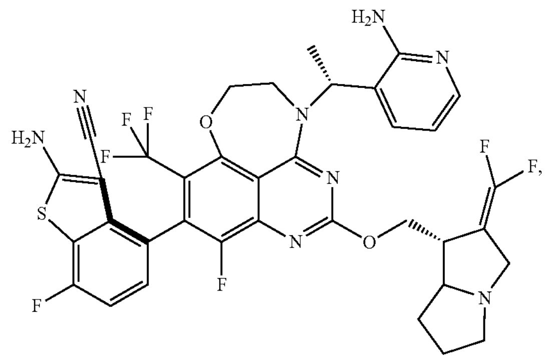

-continued
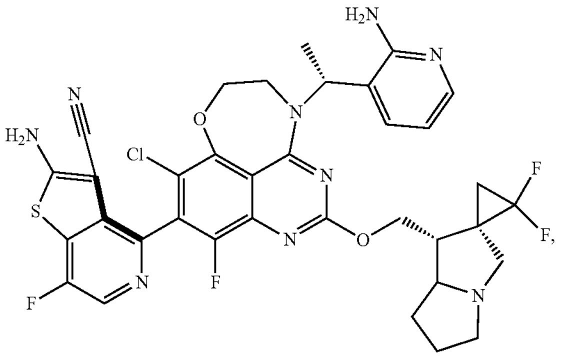
,
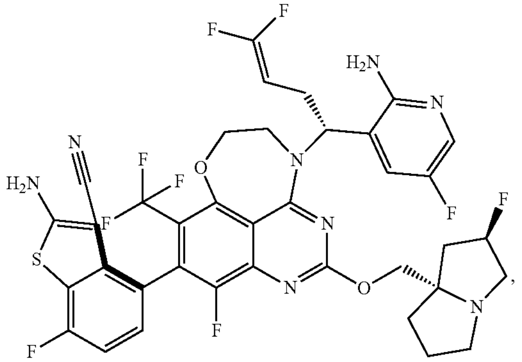
,
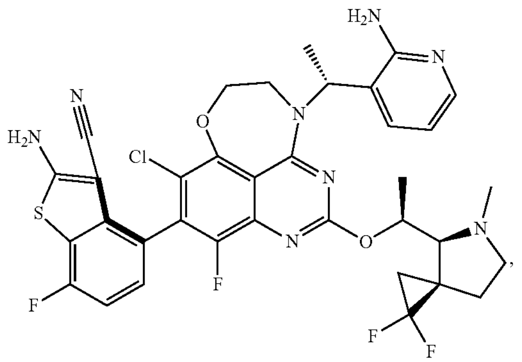
,
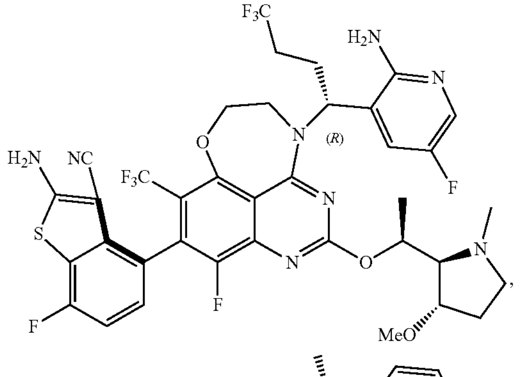
,
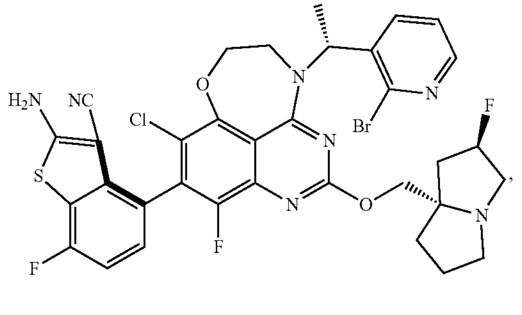
,
-continued
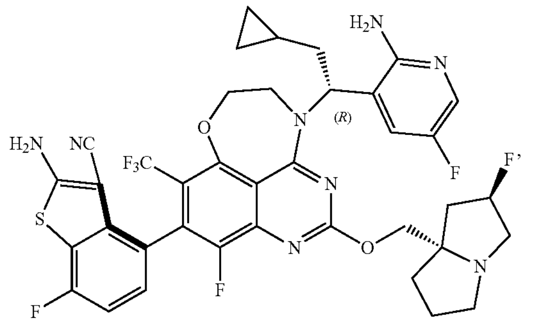
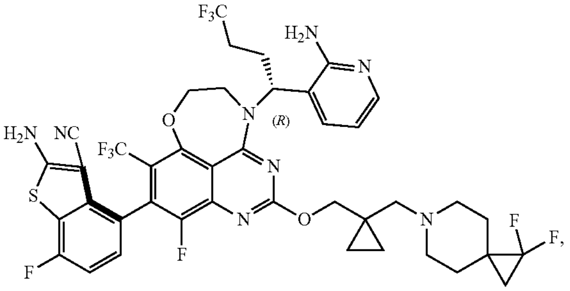
,
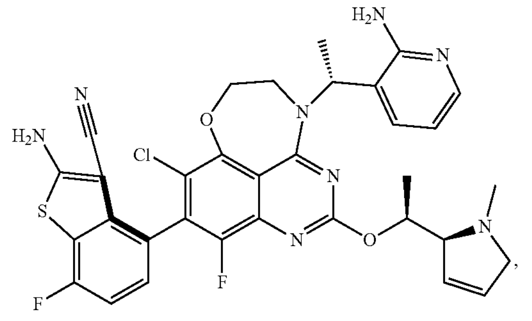
,
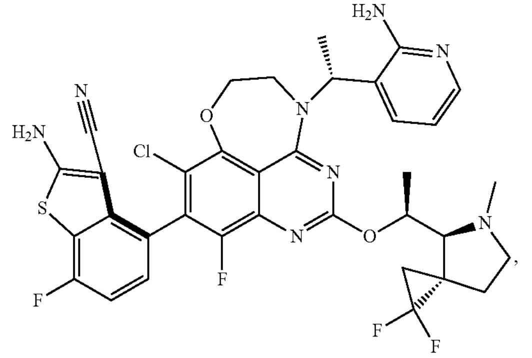
,
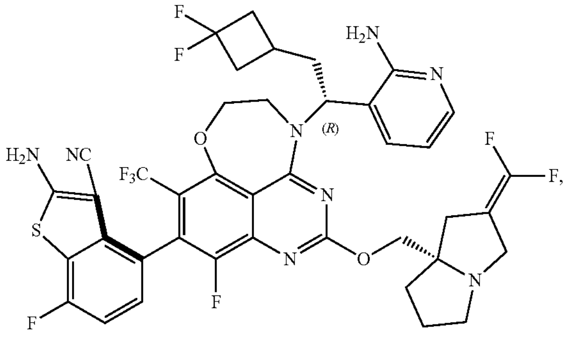
, -continued
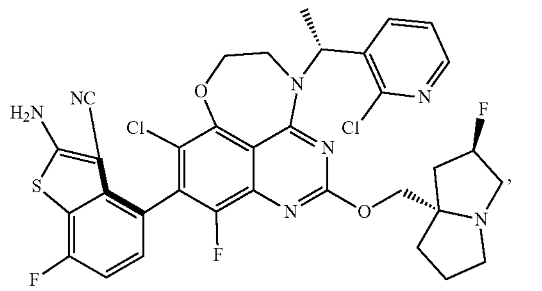
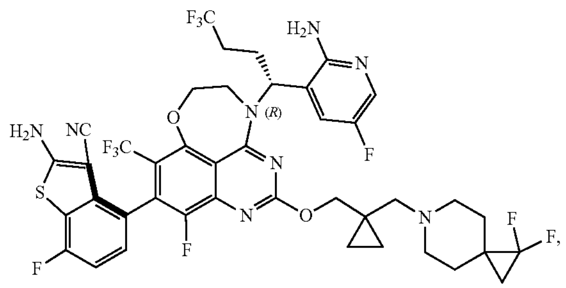
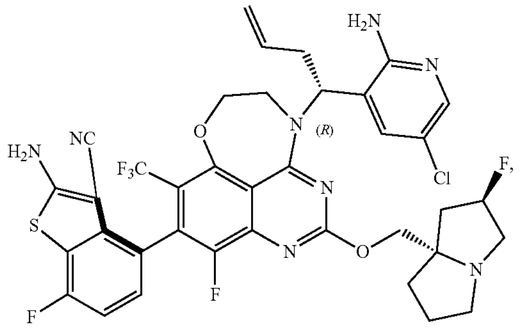
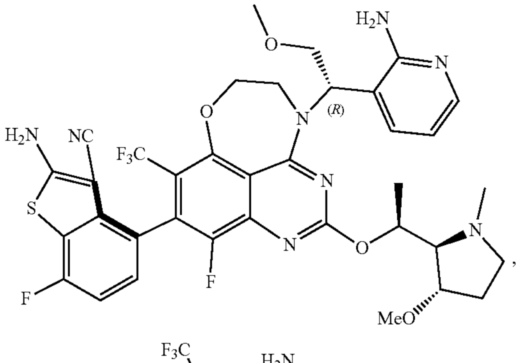
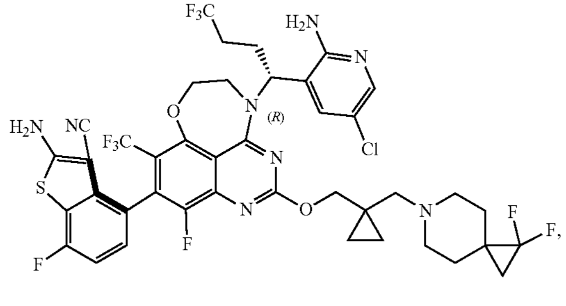
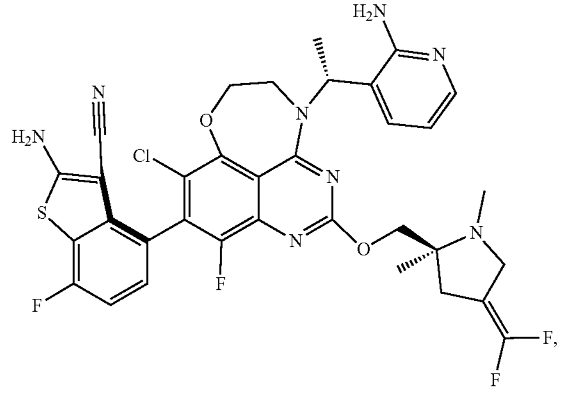
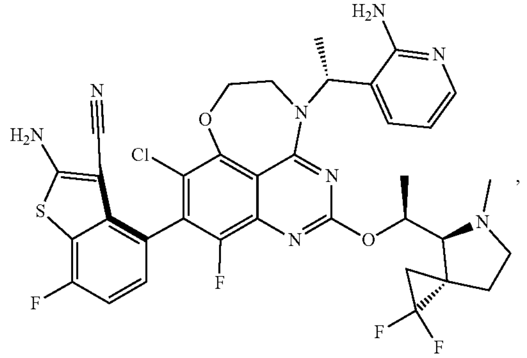
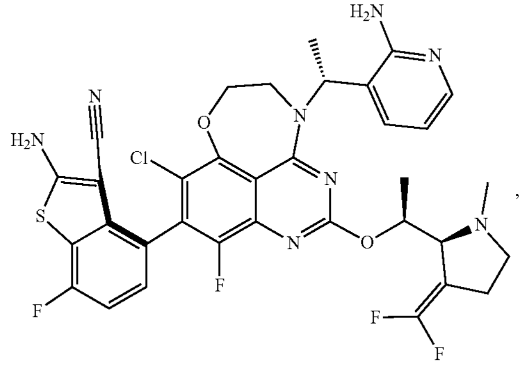
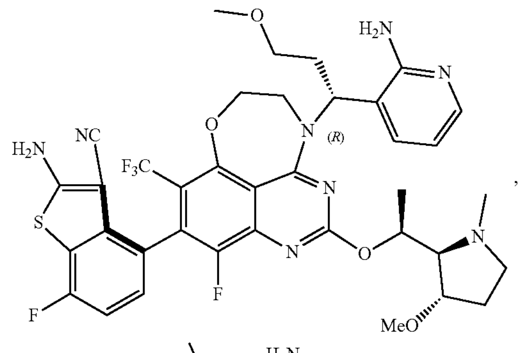
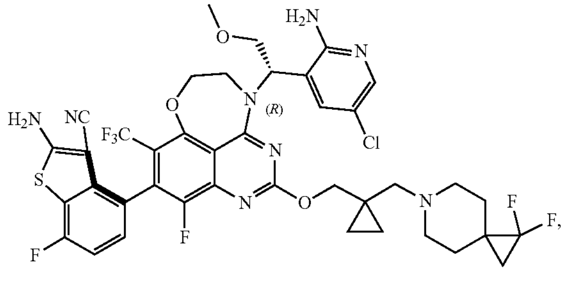

399
-continued
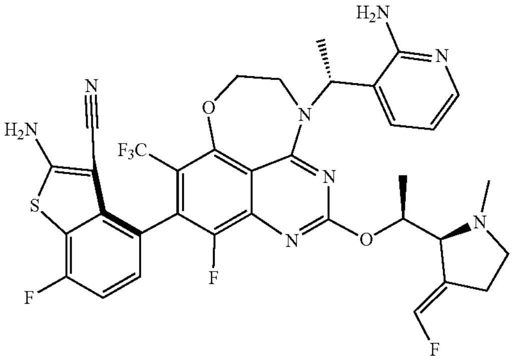
,
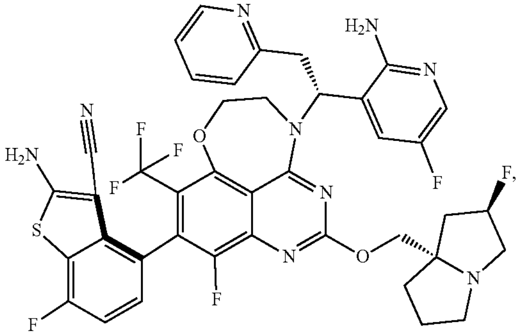
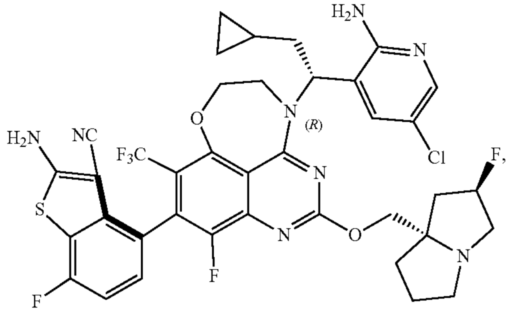
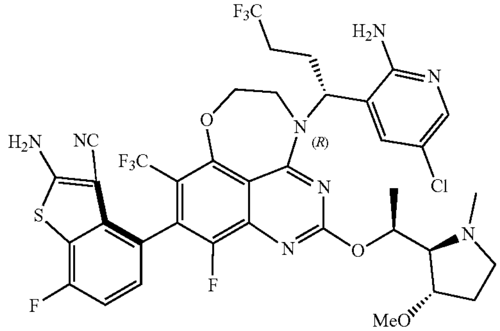
,
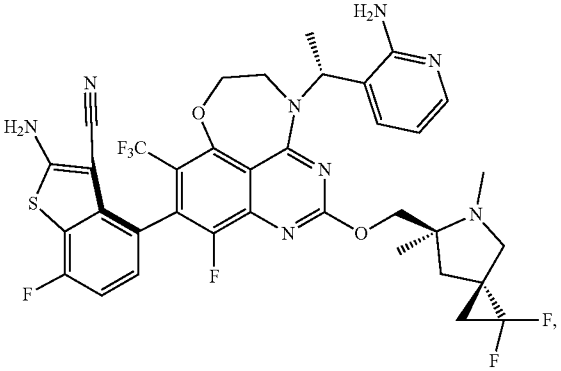
400
-continued
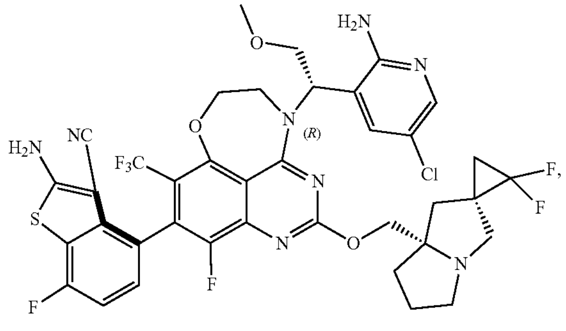
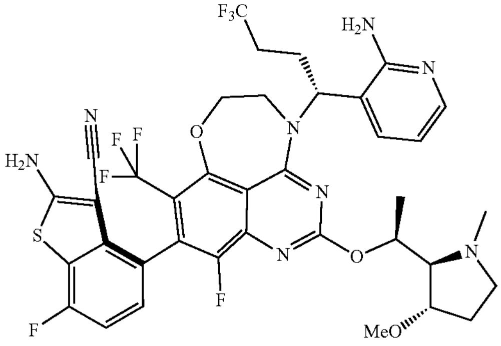
,
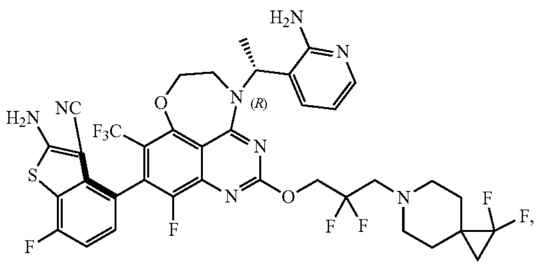
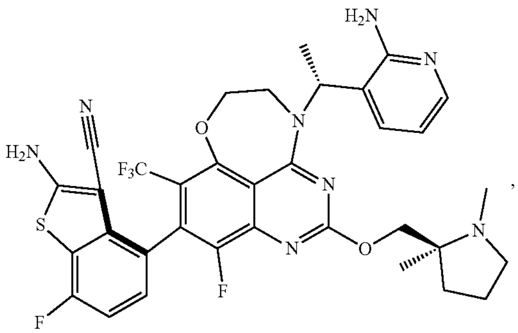
,
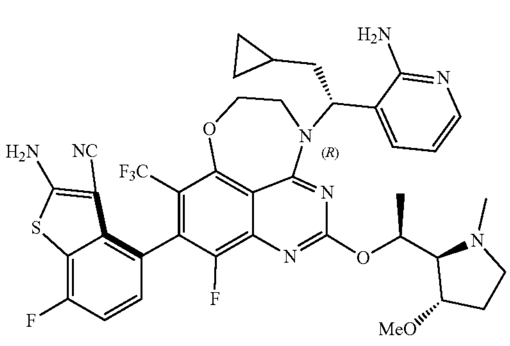
, -continued
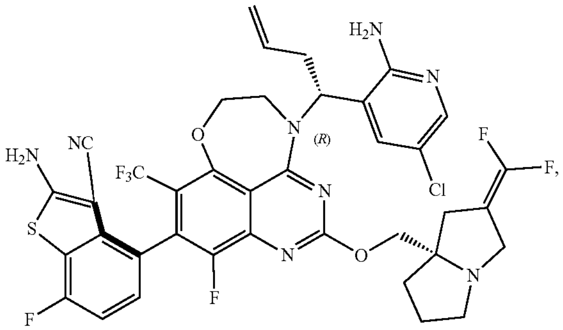
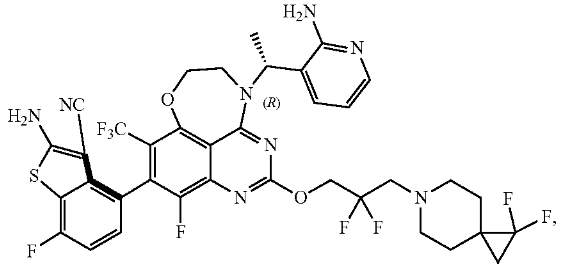
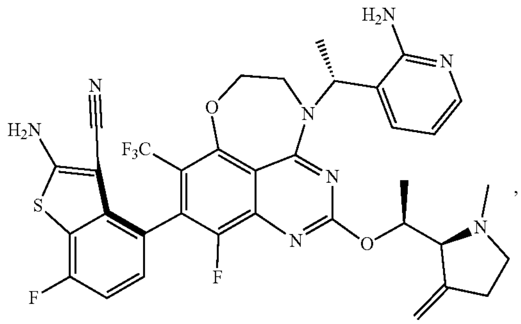
,
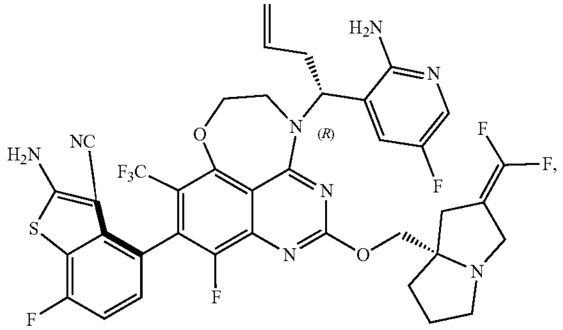
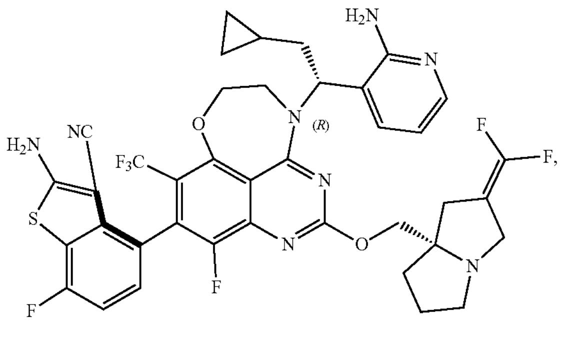
-continued
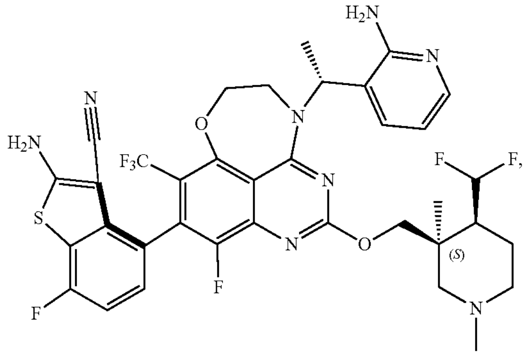
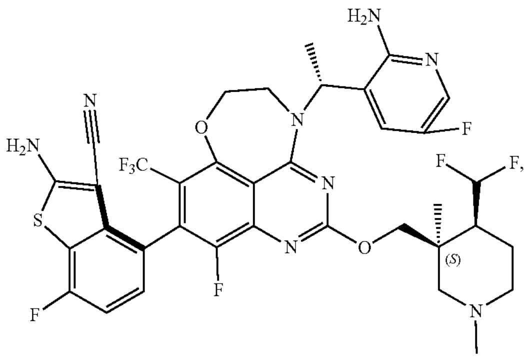
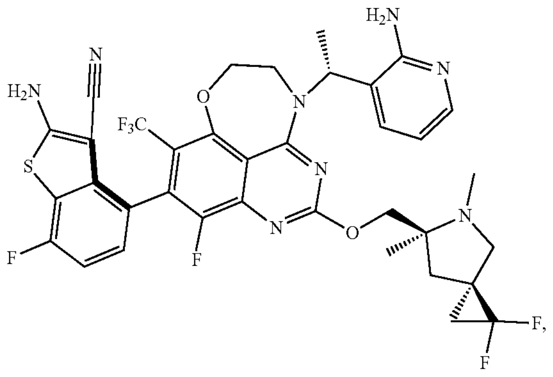
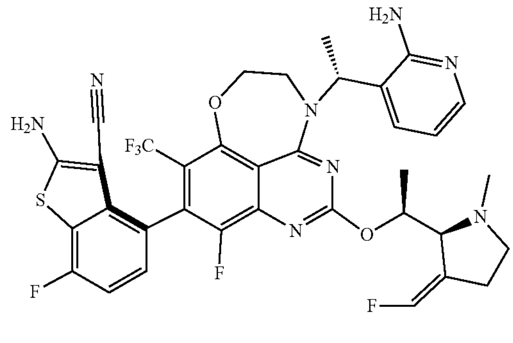
,

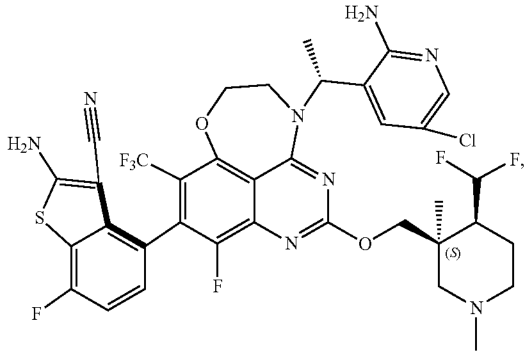
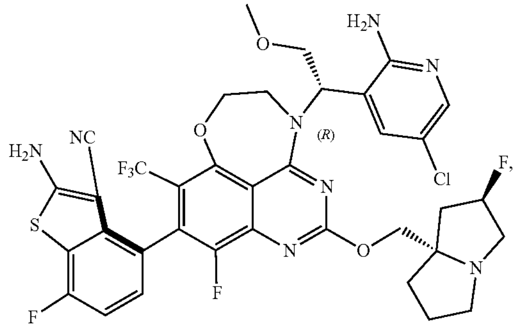
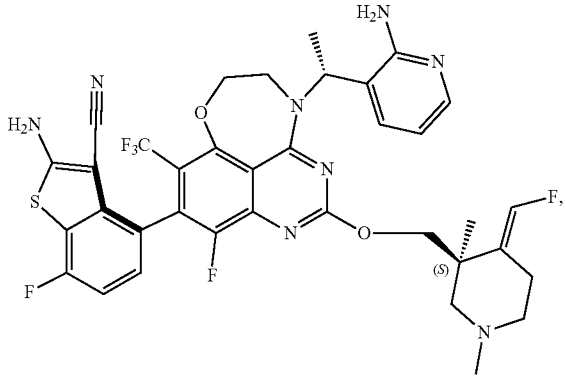
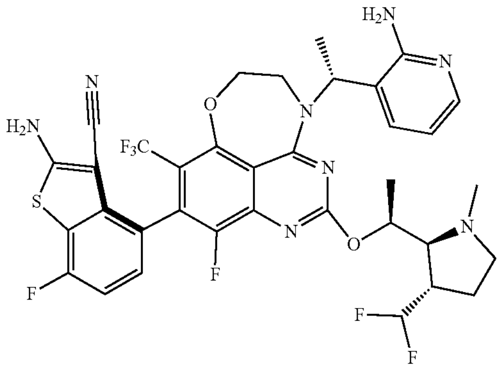
,
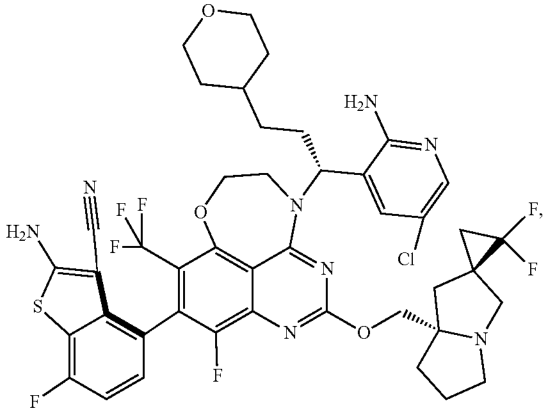
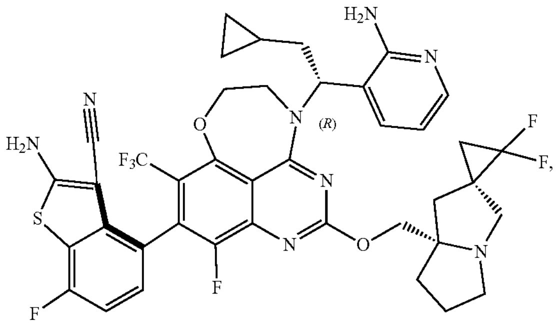
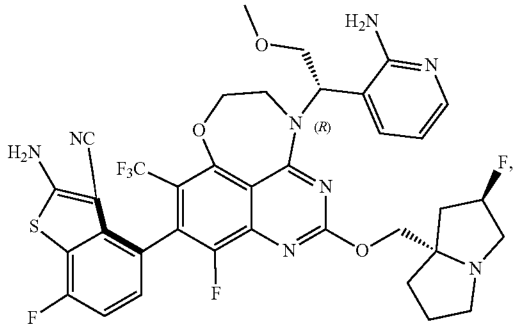
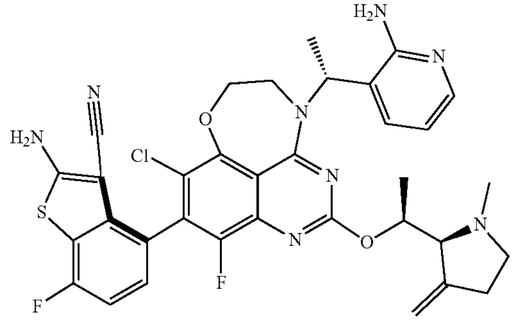
, -continued
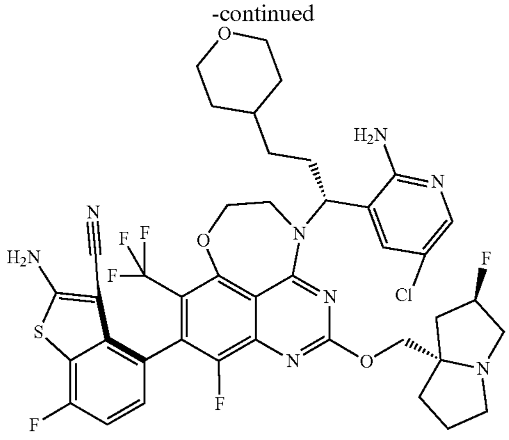
,
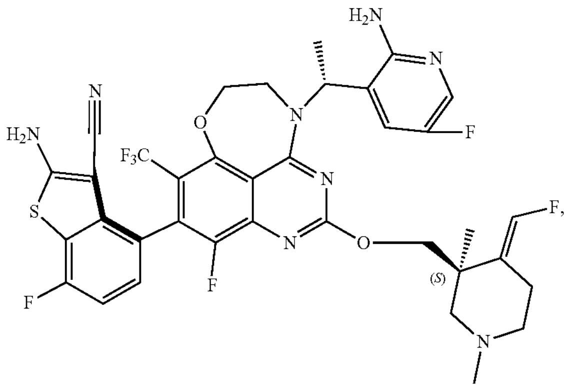
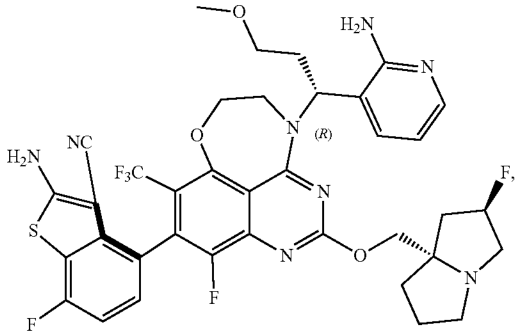
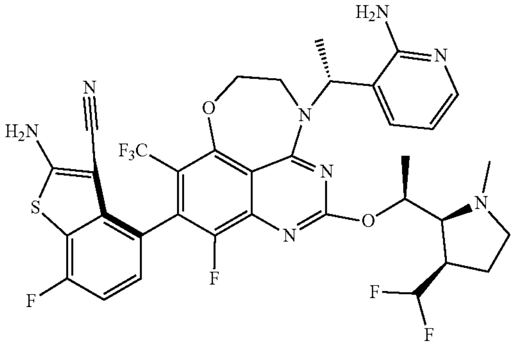
,
-continued
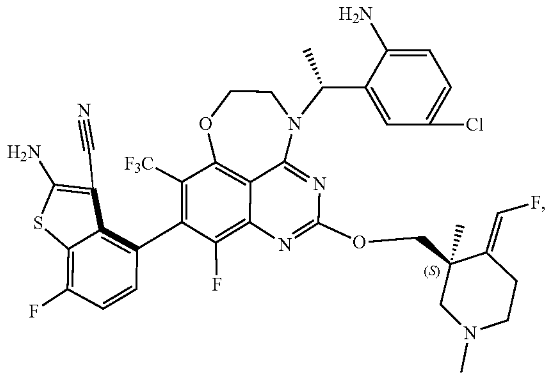
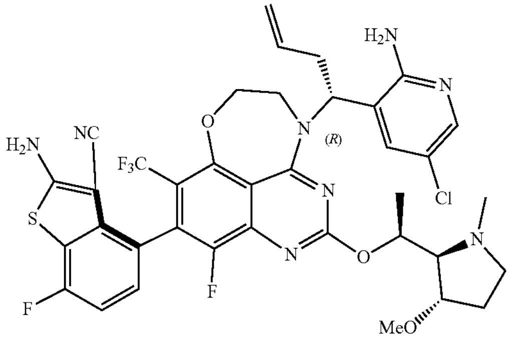
,
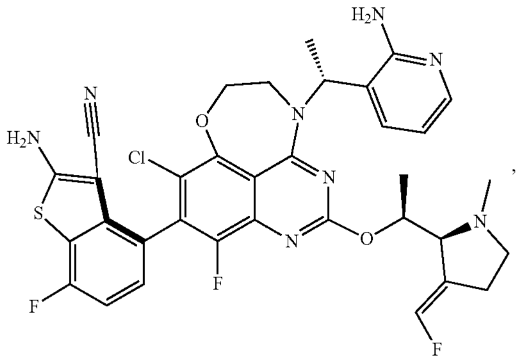
,
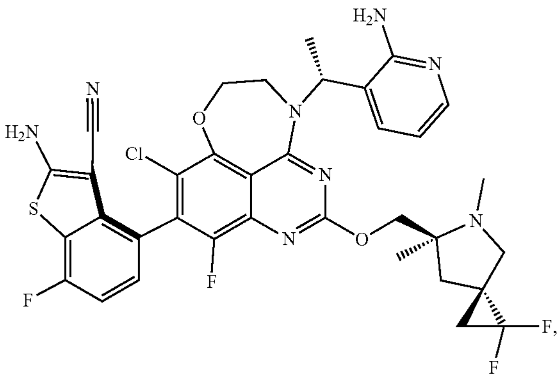

-continued
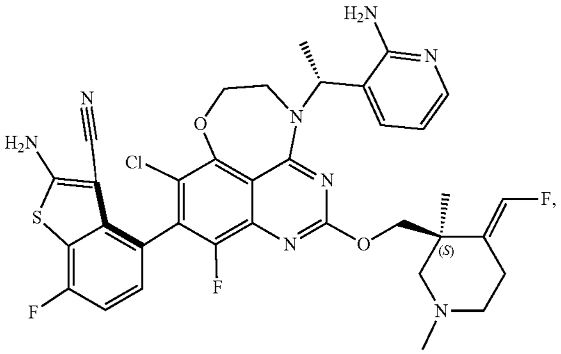
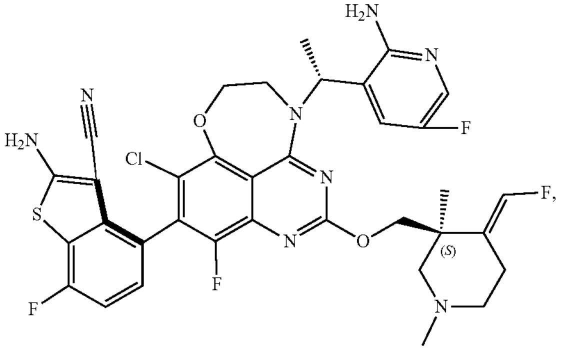
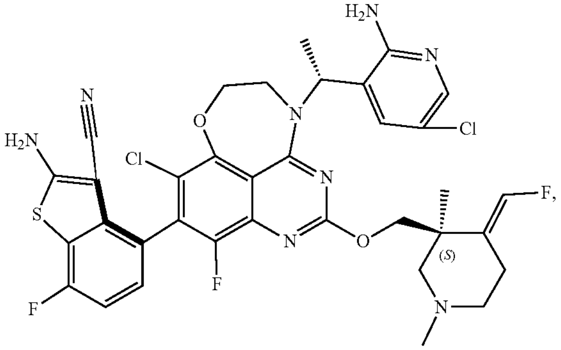
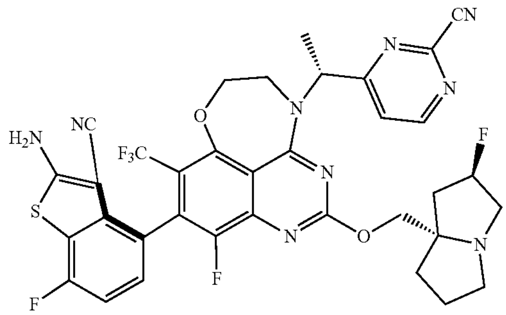
,
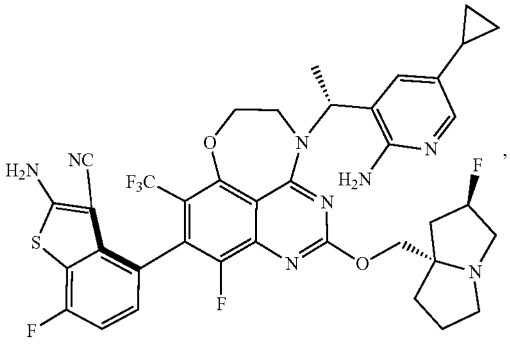
,
-continued
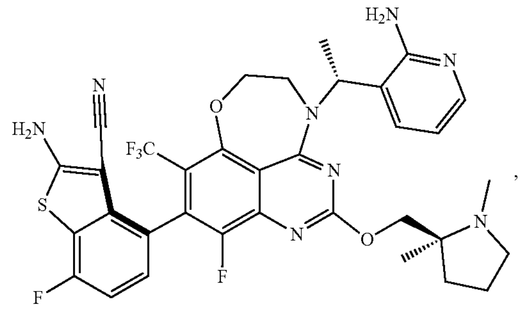
,
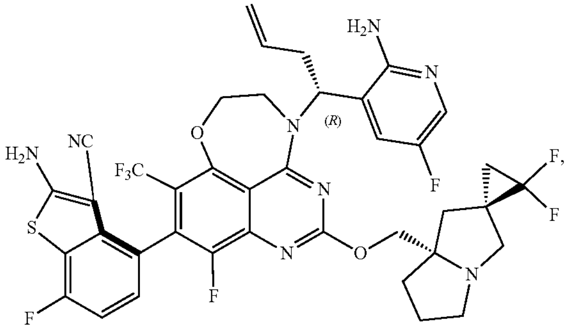
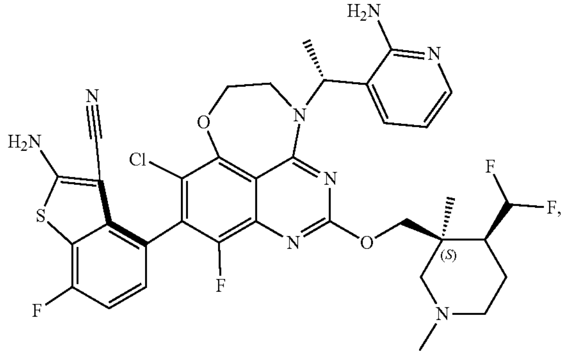
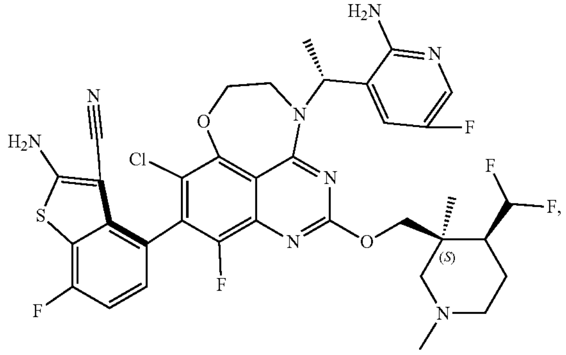
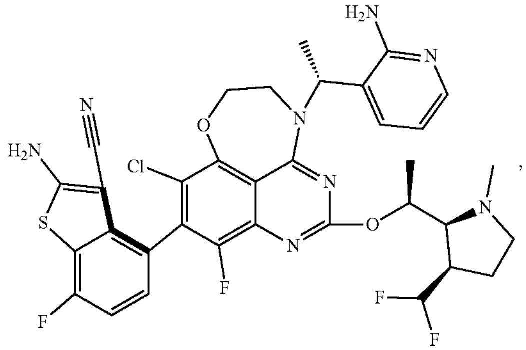
, -continued
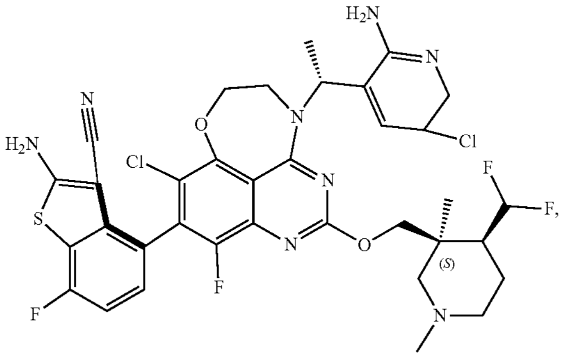
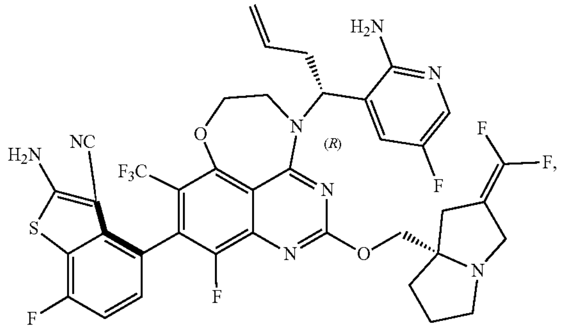
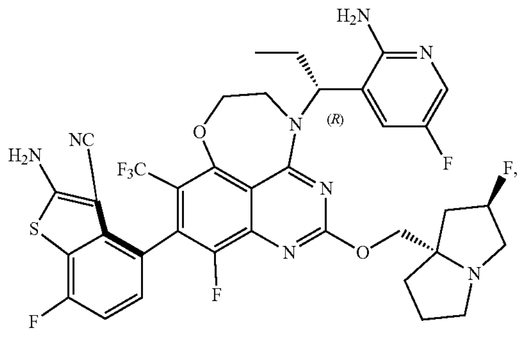
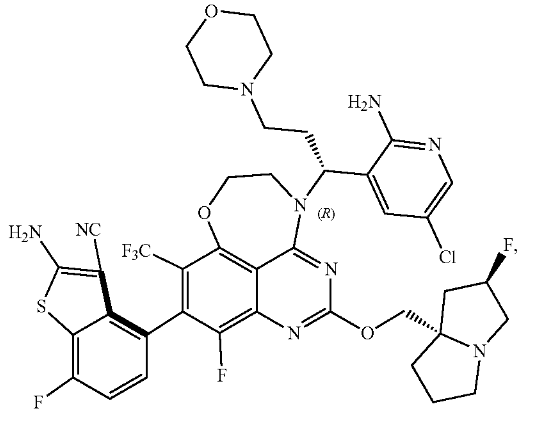
-continued
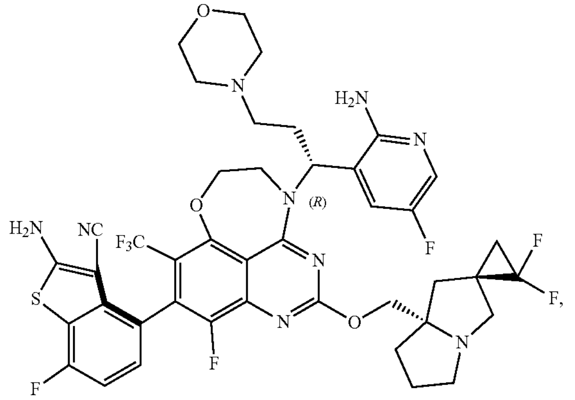
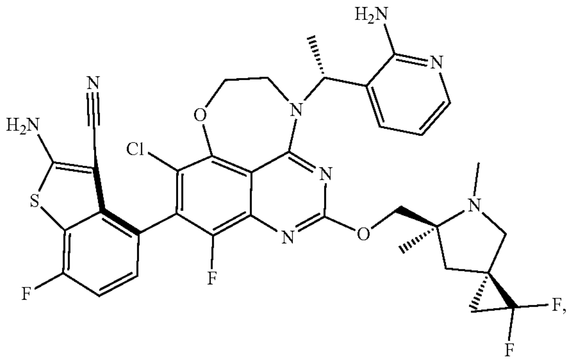
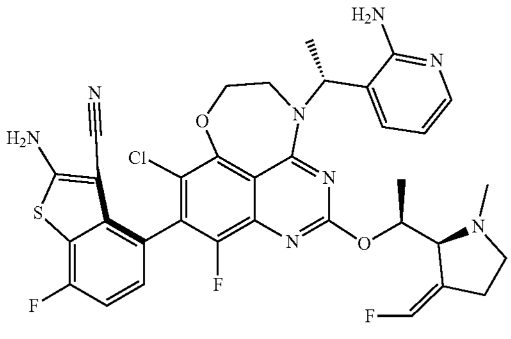
,
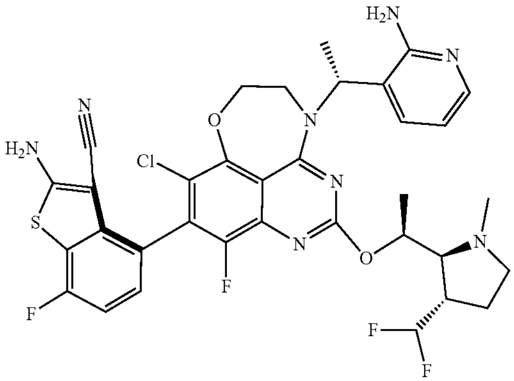
, -continued

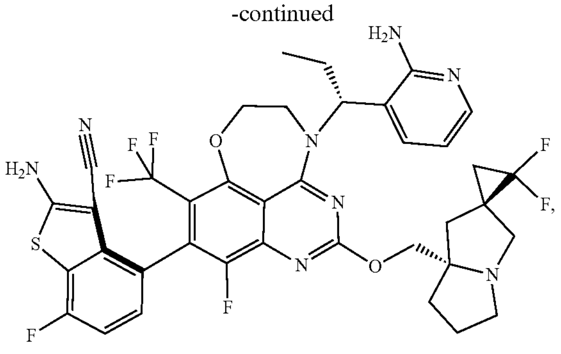

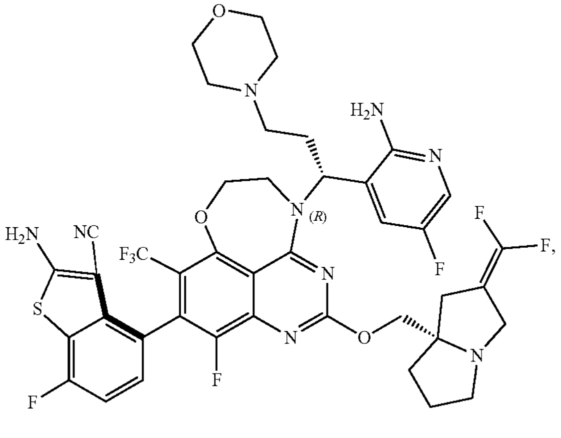

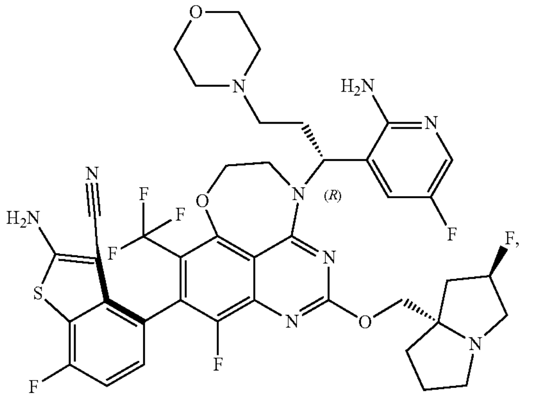

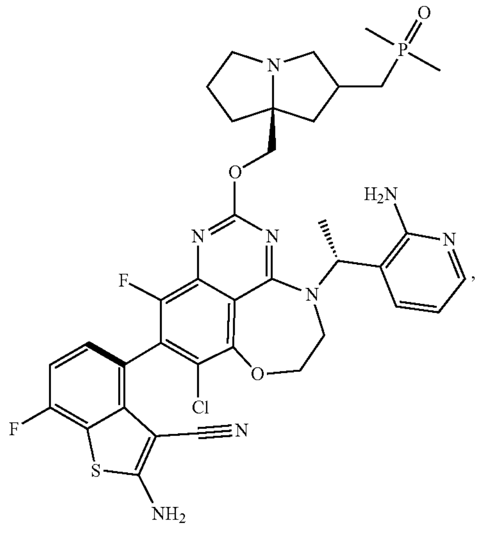

-continued

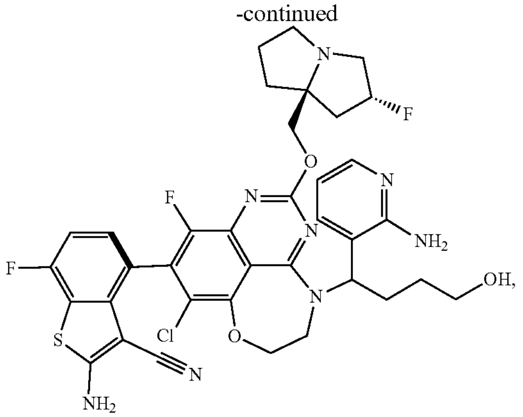

and

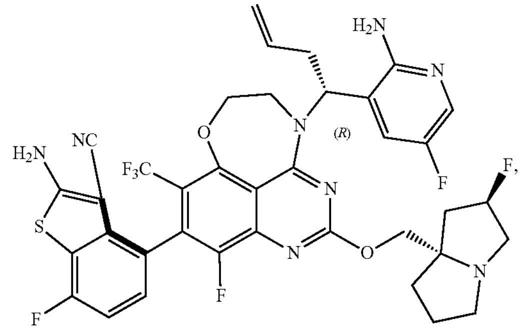

or a pharmaceutically acceptable salt or solvate thereof.

In some embodiments, a compound described herein, such as a compound of Formula (I), (II), (II-a), (III), or (IV), is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess.

In some embodiments, the present disclosure provides an atropisomer of a compound described herein, such as a compound of Formula (I), (II), (II-a), (III), or (IV). In some embodiments, the atropisomer is provided in enantiomeric excess. In some embodiments, the atropisomer is provided in at least 80% enantiomeric excess, such as at least 85%, at least 90%, at least 95%, at least 96%, at least 97%, at least 98%, at least 99%, or at least 99.9% enantiomeric excess. In some embodiments, the compound or modified protein of Formula (I), (II), (II-a), (III), or (IV) is preferably used as a non-racemic mixture, wherein one atropisomer is present in excess of its corresponding enantiomer or epimer. Typically, such mixture contains a mixture of the two isomers in a ratio of at least 9:1, preferably at least 19:1. In some embodiments, the atropisomer is provided in at least 96% enantiomeric excess, meaning the compound has less than 2% of the corresponding enantiomer. In some embodiments, the atropisomer is provided in at least 96% diastereomeric excess, meaning the compound has less than 2% of the corresponding diastereomer.

The term "atropisomers" refers to conformational stereoisomers which occur when rotation about a single bond in the molecule is prevented, restricted, or greatly slowed as a result of steric interactions with other parts of the molecule and wherein the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom. Atropisomers are typically considered stable if the barrier to interconversion is high enough to permit the atropisomers to undergo little or no interconversion at room temperature for a least a week, preferably at least a year. In some embodiments, an atropisomeric compound of the disclosure does not undergo more than about 5% interconversion to its opposite atropisomer at room temperature during one week when the atropisomeric compound is in substantially pure form, which is generally a solid state. In some embodiments, an atropisomeric compound of the disclosure does not undergo more than about 5% interconversion to its opposite atropisomer at room temperature (approximately 25° C.) during one year. The present chemical entities, pharmaceutical compositions, and methods are meant to include all such possible atropisomers, including racemic mixtures, diastereomeric mixtures, epimeric mixtures, optically pure forms of single atropisomers, and intermediate mixtures.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases or inorganic or organic acids to form a pharmaceutically acceptable salt. In some embodiments, such salts are prepared in situ during the final isolation and purification of the compounds described herein, or by separately reacting a purified compound in its free form with a suitable acid or base, and isolating the salt thus formed.

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

In certain aspects, the present disclosure provides a compound of the formula B-$L^{BE}$-E wherein:

B is a monovalent form of a compound described herein;

$L^{BE}$ is a covalent linker bonded to B and E; and

E is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In some embodiments, the degradation enhancer is capable of binding to an E3 ubiquitin ligase protein or a protein complex comprising an E3 ubiquitin ligase protein. In some embodiments, the degradation enhancer is capable of binding to an E2 ubiquitin-conjugating enzyme. In some embodiments, the degradation enhancer is capable of binding to a protein complex comprising an E2 ubiquitin-conjugating enzyme and an E3 ubiquitin ligase protein.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CULA-RBX1-DDB1-CRBN (CRLACRBN) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2W, UBE2Z, ATG3, BIRC6, and UFC1. In some embodiments, the degradation enhancer is a compound described in Ishida and Ciulli, SLAS Discovery 2021, Vol. 25 (4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In some embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Pat. Nos. 10,040,804, 9,938,302, 10,144,745, 10,145,848, 9,938,264, 9,632,089, 9,821,068, 9,758,522, 9,500,653, 9,765,019, 8,507,488, 8,299,057, US20180298027, US20180215731, US20170065719, US20170037004, US20160272639, US20150291562, or US20140356322, each of which is incorporated by reference in its entirety for any purpose.

In some embodiments, $L^{BE}$ is $-L^{BE1}-L^{BE2}-L^{BE3}-L^{BE4}-L^{BE5}-$;

$L^{BE1}$, $L^{BE2}$, $L^{BE3}$, $L^{BE4}$, and $L^{BE5}$ are independently a bond, —O—, —N($R^{12}$)—, —C(O)—, —N($R^{12}$)C(O)—, —C(O)N($R^{12}$)—, —S—, —S(O)$_2$—, —S(O)—, —S(O)$_2$N($R^{12}$)—, —S(O)N($R^{12}$)—, —N($R^{12}$) S(O)—, —N($R^{12}$)S(O)$_2$—, $C_{1-6}$ alkylene, (—O—$C_{1-6}$ alkyl)$_z$-, (—$C_{1-6}$ alkyl-O)$_z$—, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$; and wherein each $C_{1-6}$ alkyl of (—O—$C_{1-6}$ alkyl)$_z$- and (—$C_{1-6}$ alkyl-O)$_z$—is optionally substituted with one, two, or three $R^{20}$; and z is independently an integer from 0 to 10.

In some embodiments, $L^{BE}$ is —(O—$C_2$ alkyl), and z is an integer from 1 to 10. In some embodiments, $L^{BE}$ is —($C_2$ alkyl-O—)$_z$- and z is an integer from 1 to 10. In some embodiments, $L^{BE}$ is —$(CH_2)_{zz1}L^{BE2}(CH_2O)_{zz2}$—, wherein $L^{BE2}$ is a bond, a 5- or 6-membered heterocyclene, phenylene, —$C_{2-4}$ alkynylene, —$SO_2$—or —NH—; and zz1 and zz2 are independently an integer from 0 to 10. In some embodiments, $L^{BE}$ is —$(CH_2)_{zz1}(CH_2O)_{zz2}$—, wherein zz1 and zz2 are each independently an integer from 0 to 10. In some embodiments, $L^{BE}$ is a PEG linker (e.g., divalent linker of 1 to 10 ethylene glycol subunits). In some embodiments, E is a monovalent form of a compound selected from

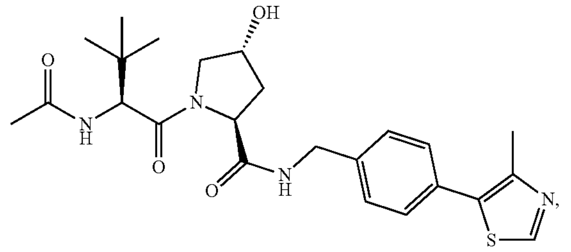

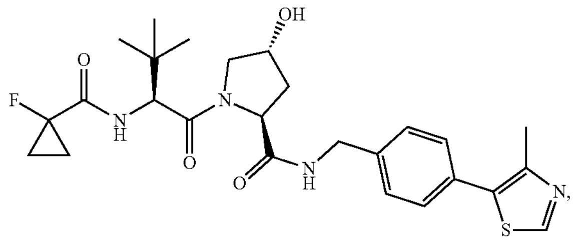

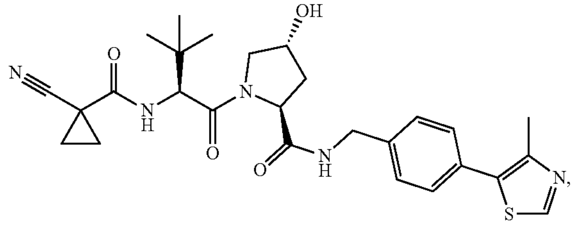

-continued

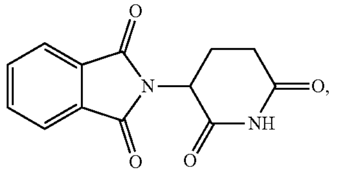

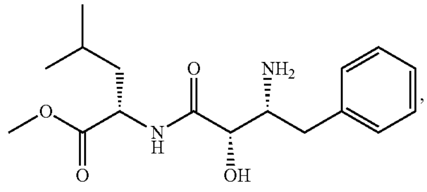

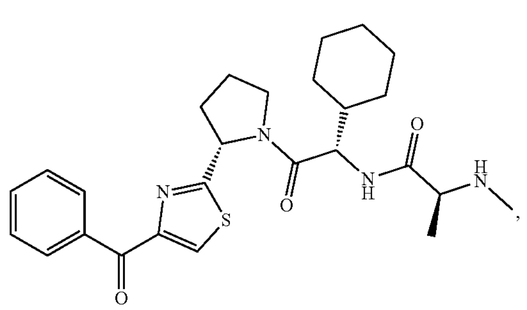

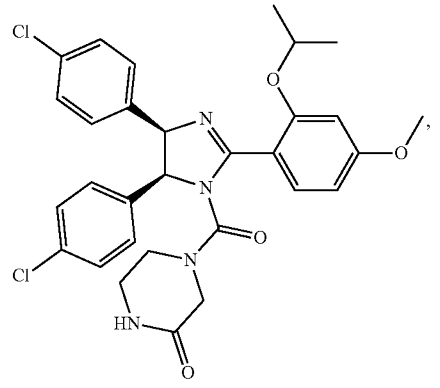

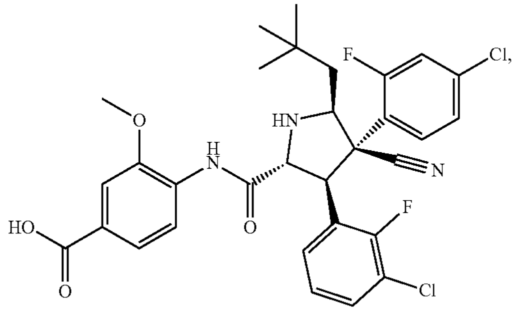

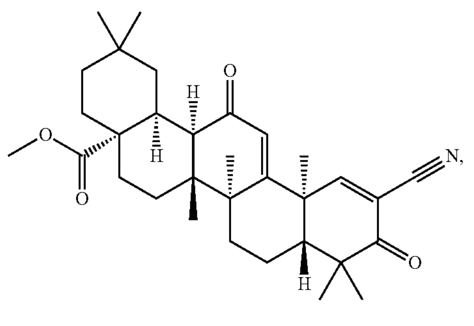

-continued
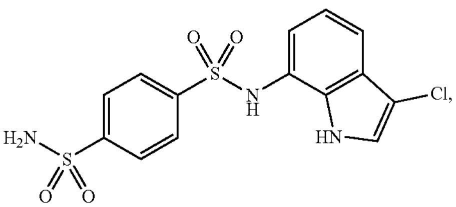
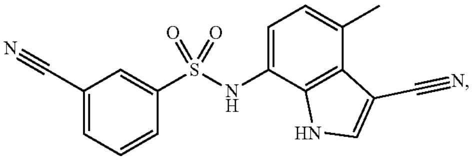
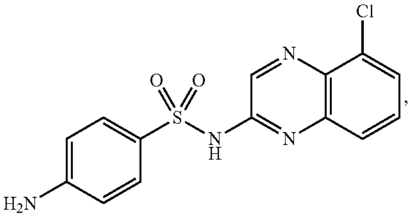
, and
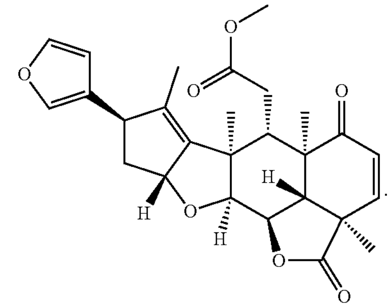
In some embodiments, E is a monovalent form of a compound selected from
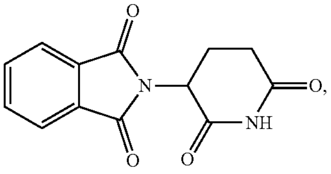
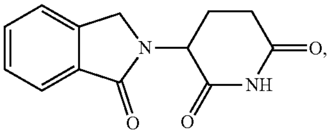
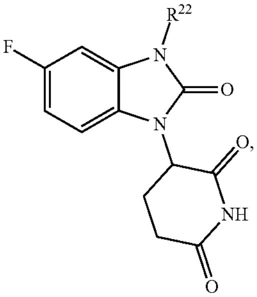
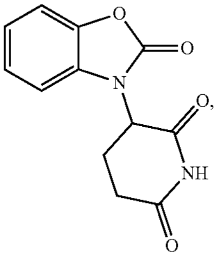
-continued
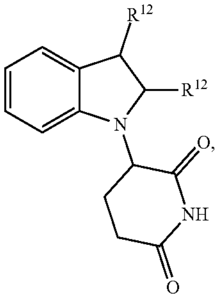
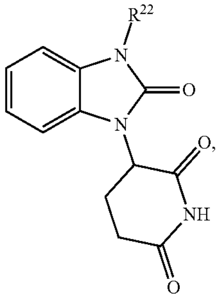
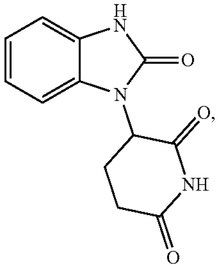
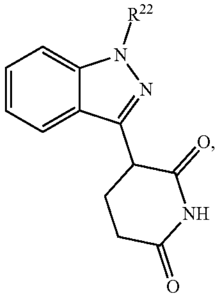
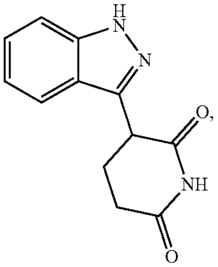
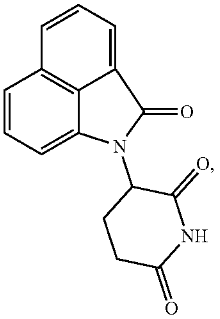
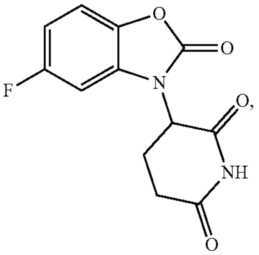
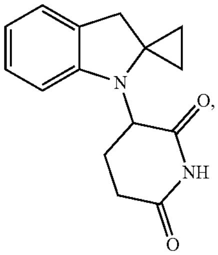
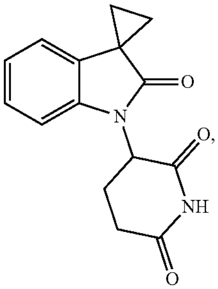
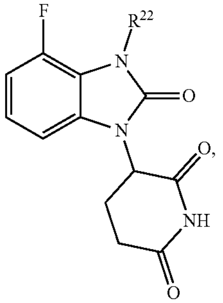

-continued
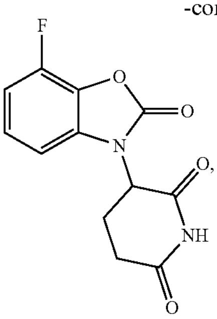
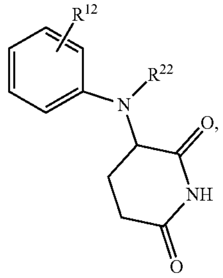
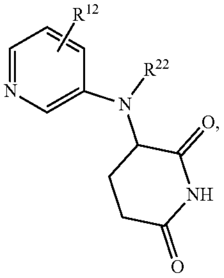
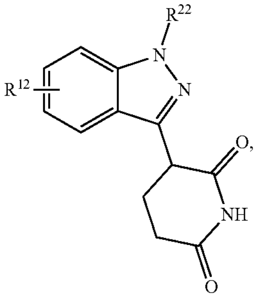
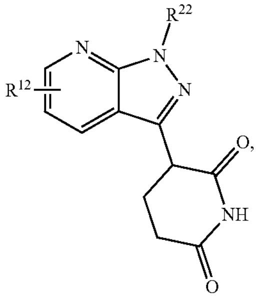
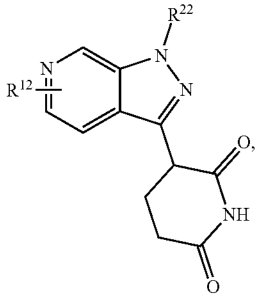
-continued
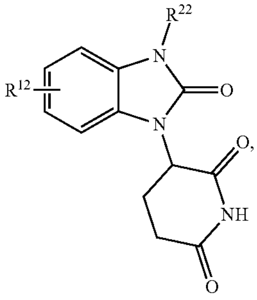
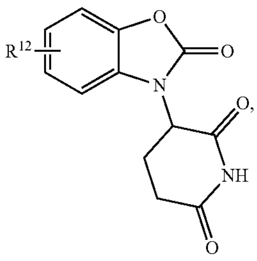
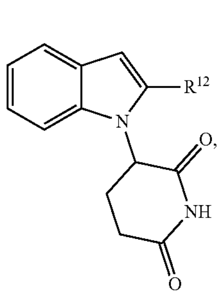
and
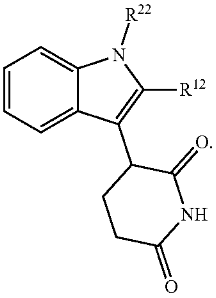
In some embodiments, the compound of formula B-$L^{BE}$-E is selected from:
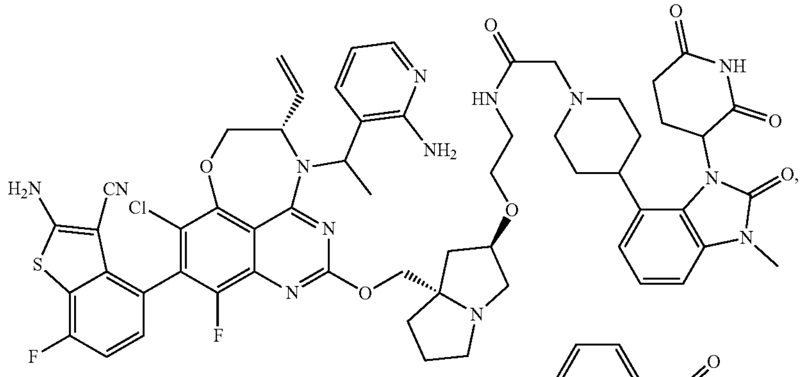
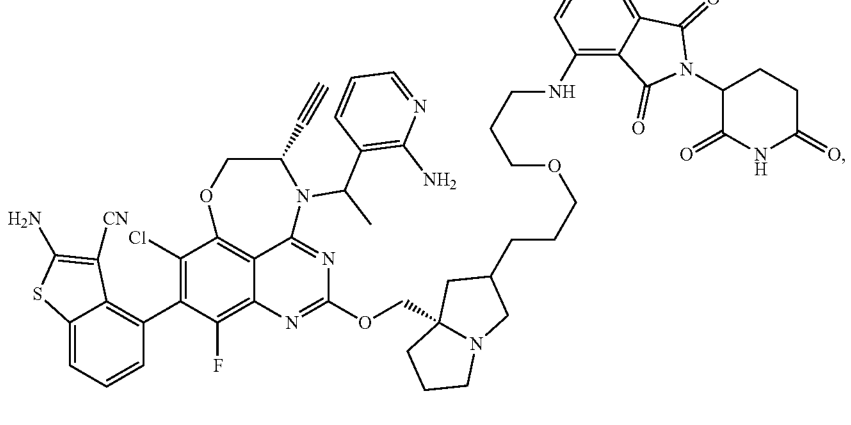

-continued
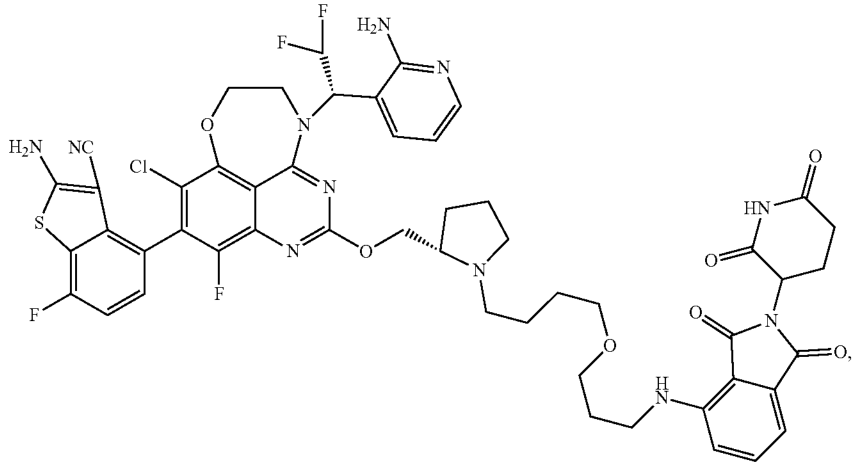
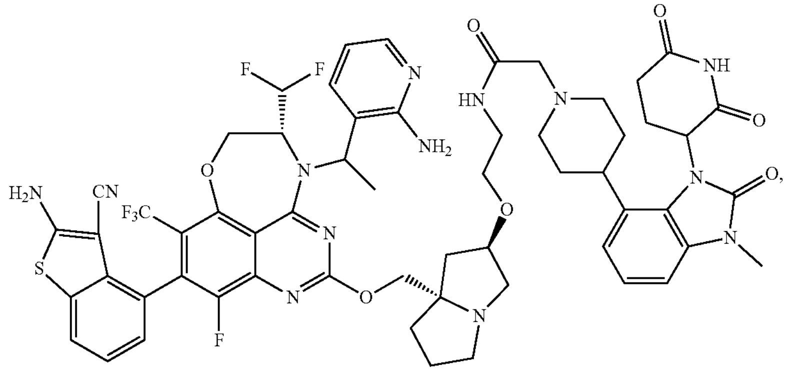
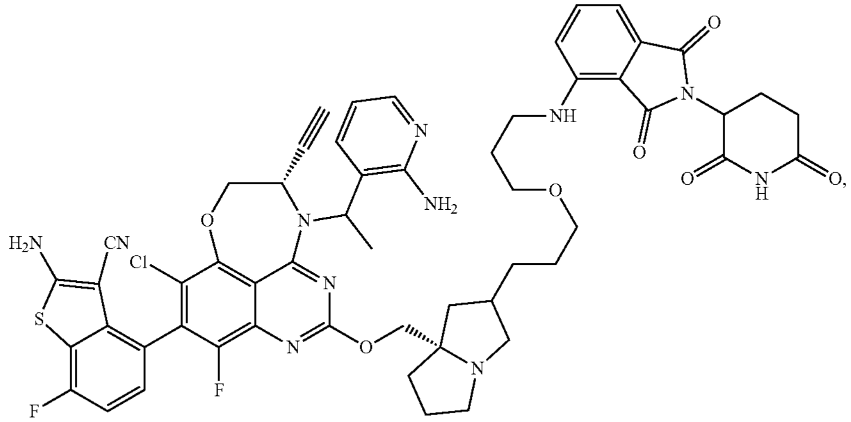
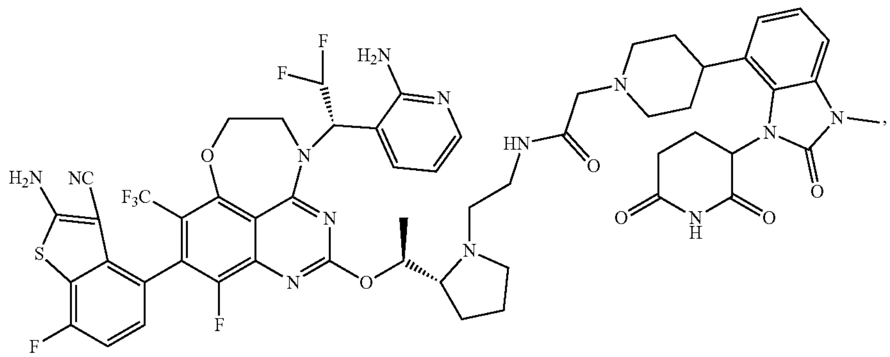

-continued
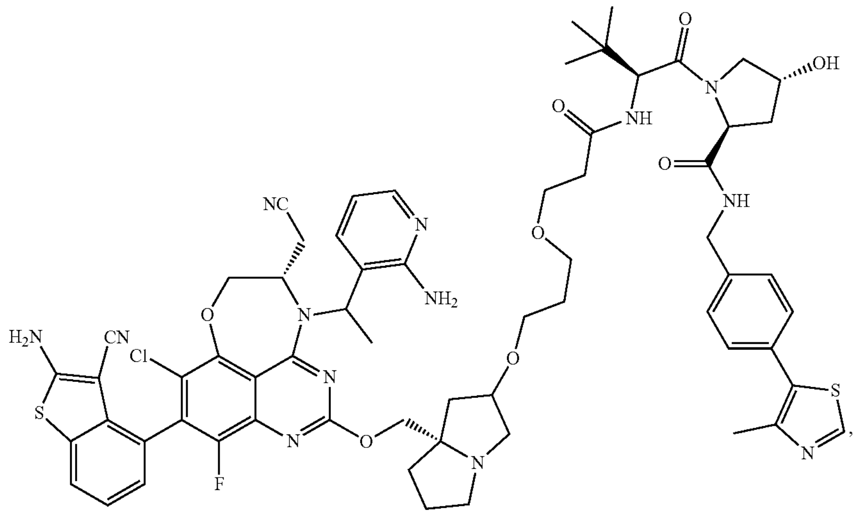
,
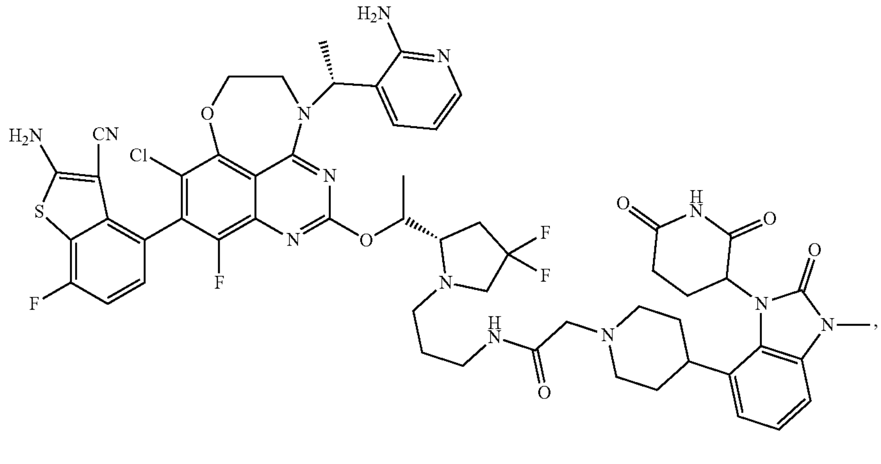
,
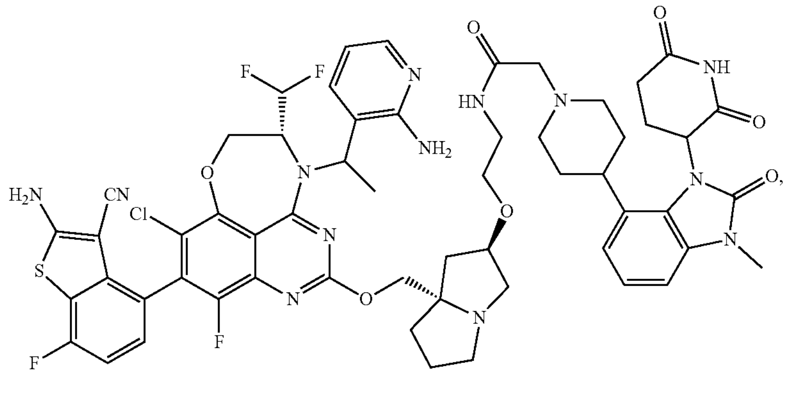
,

-continued
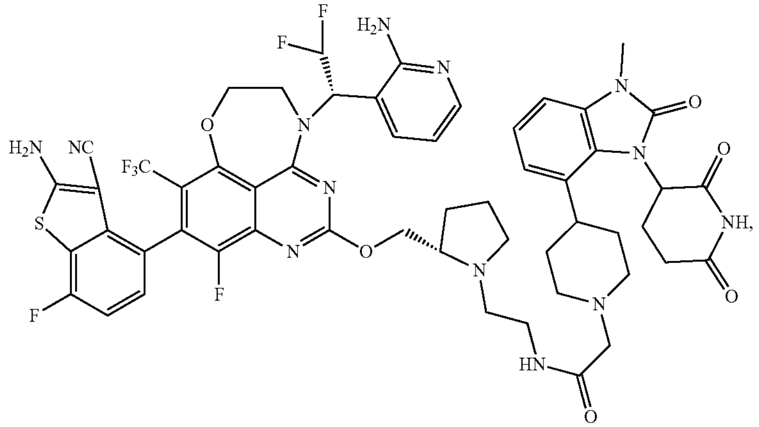
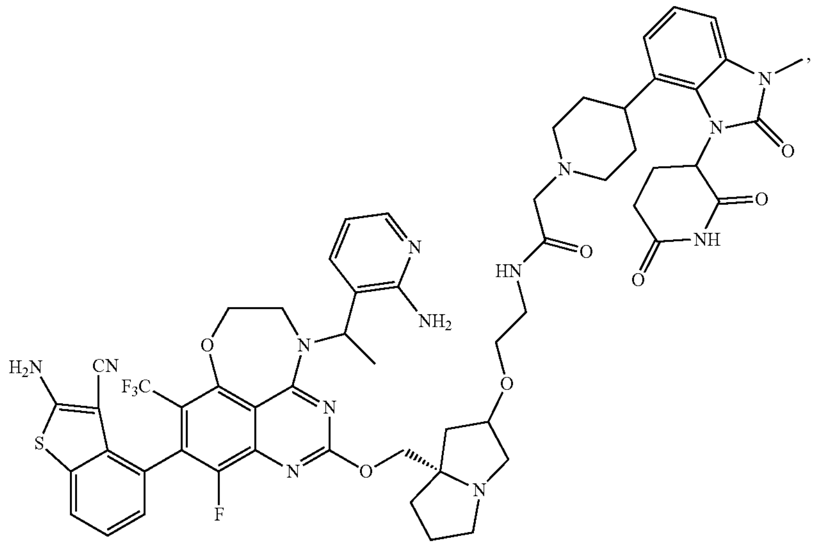 [SMILES: CC(c1cccnc1N)N1CCOc2c(Cl)c(-c3ccc(F)c4sc(N)c(C#N)c34)c(F)c3nc(OC[C@@]45CCCN4CC(OCCNC(=O)CN4CCC(c6cccc7c6n(C6CCC(=O)NC6=O)c(=O)n7C)CC4)C5)nc1c23]
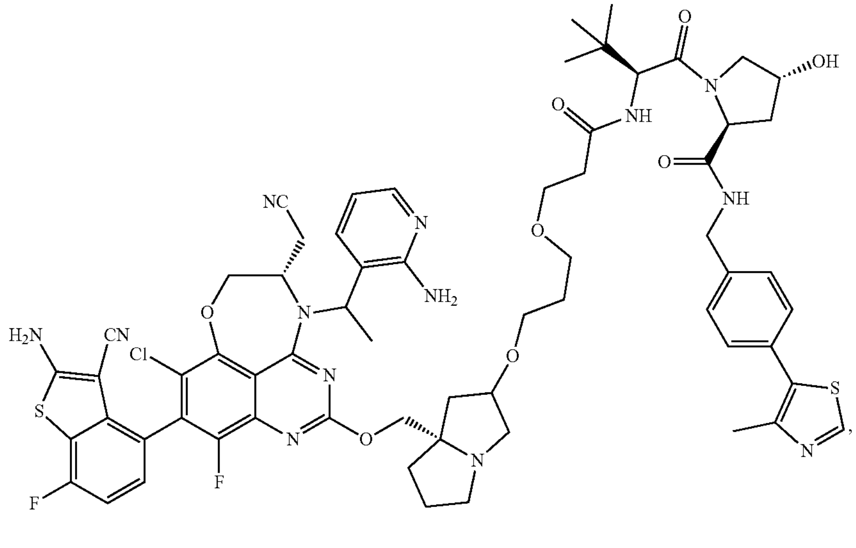

-continued

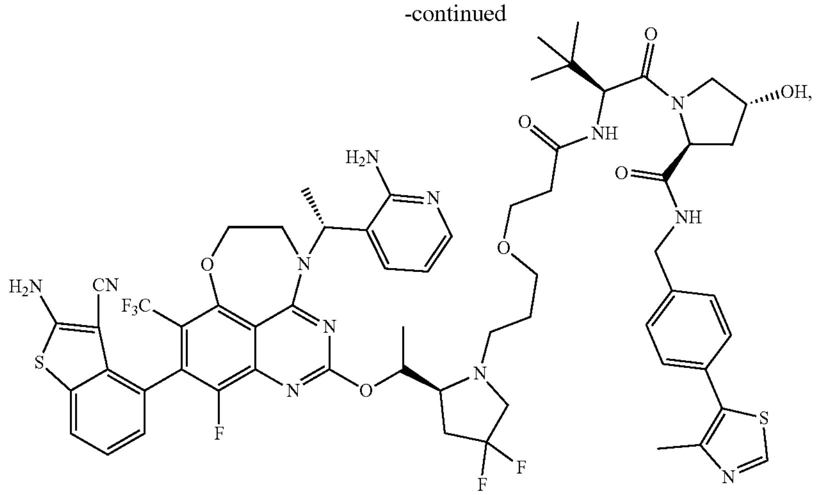

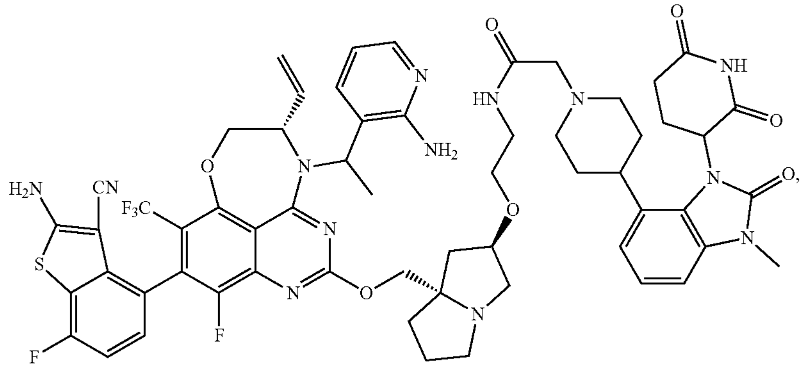

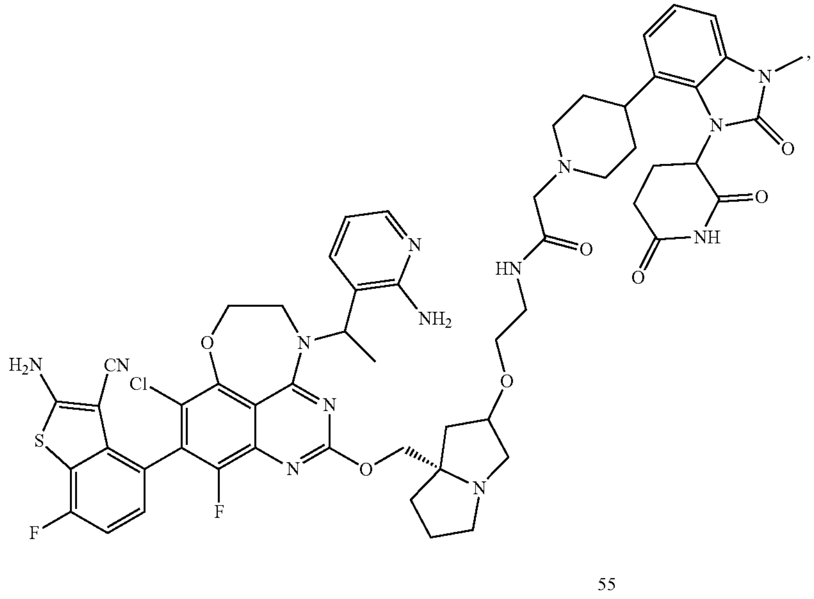

or a pharmaceutically acceptable salt or solvate thereof.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-7, the steps in some cases may be performed in a different order than the order shown in Schemes 1-7. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

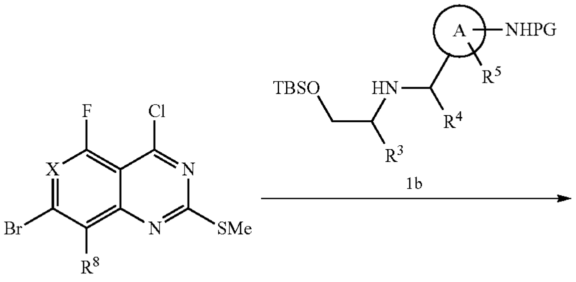

1a

1b

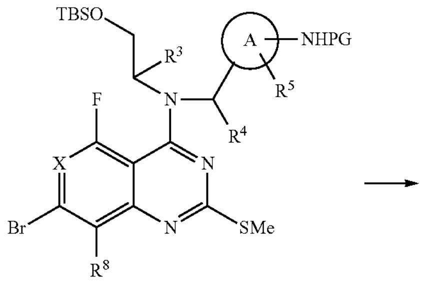

1c

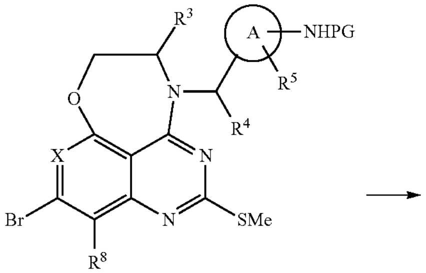

1d

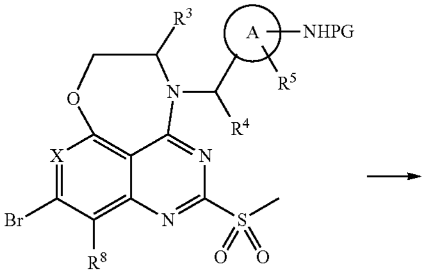

1e

-continued

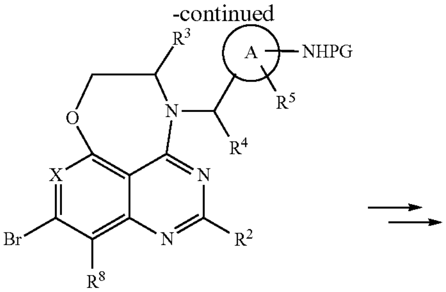

1f

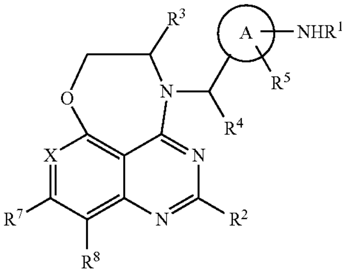

1g

In some embodiments, a compound of Formula 1 g may be prepared according to Scheme 1. For example, heteroaryl amine 1c can be formed from chloride 1a via a nucleophilic aromatic substitution reaction with amine 1b. Ring closure to 1d can be followed by an oxidation reaction to provide sulfone 1e, which can be substituted with $R^2$ upon addition of a suitable alcohol to afford 1f. Substitution of the aryl bromide with a suitable boronic ester can provide the corresponding $R^7$-substituted compound, which may optionally be subjected to one or more subsequent reactions, such as a deprotection, to provide a compound of Formula 1 g.

Scheme 2

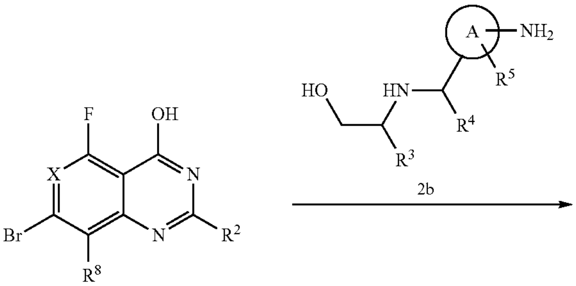

2a

2b

-continued

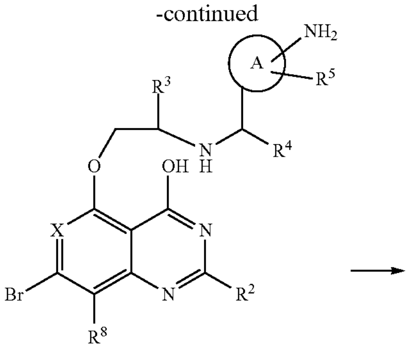

2c

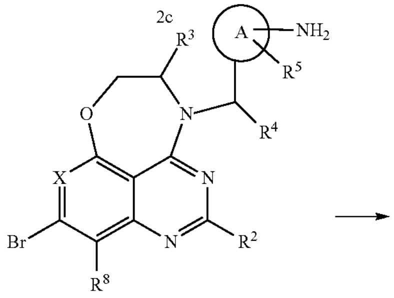

2d

-continued

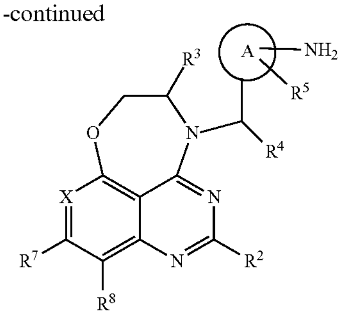

2e

In some embodiments, a compound of Formula 2e may be prepared according to Scheme 2. For example, heteroaryl ether 2c can be formed from fluoride 2a via a nucleophilic aromatic substitution reaction with alcohol 2b. Ring closure to 2d can be followed by substitution with a suitable boronic ester to provide the corresponding $R^7$-substituted compound, which may optionally be subjected to one or more protecting group manipulations to provide a compound of Formula 2e.

Scheme 3

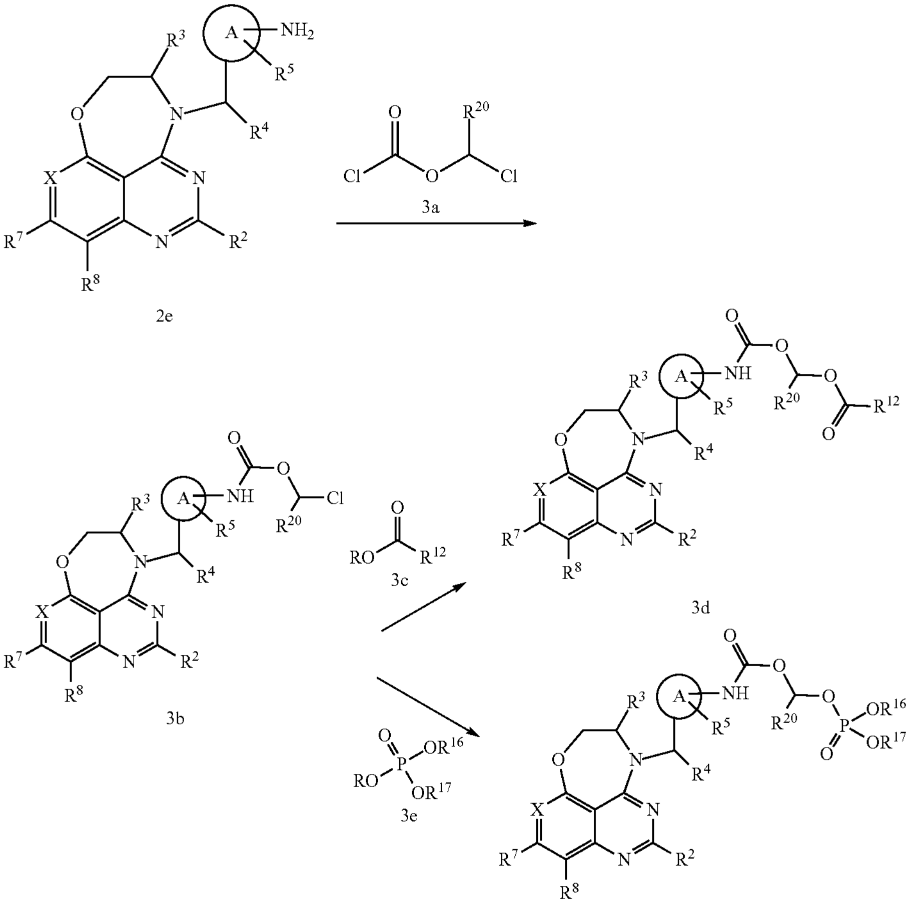

2e 3a 3b 3c 3d 3e 3f

In some embodiments, a compound of Formula 3d or 3f may be prepared according to Scheme 3. For example, 2e can be treated with chloroformate 3a to provide 3b. Substitution with 3c or 3e can provide a compound of Formula 3d or 3f, respectively.

Scheme 4

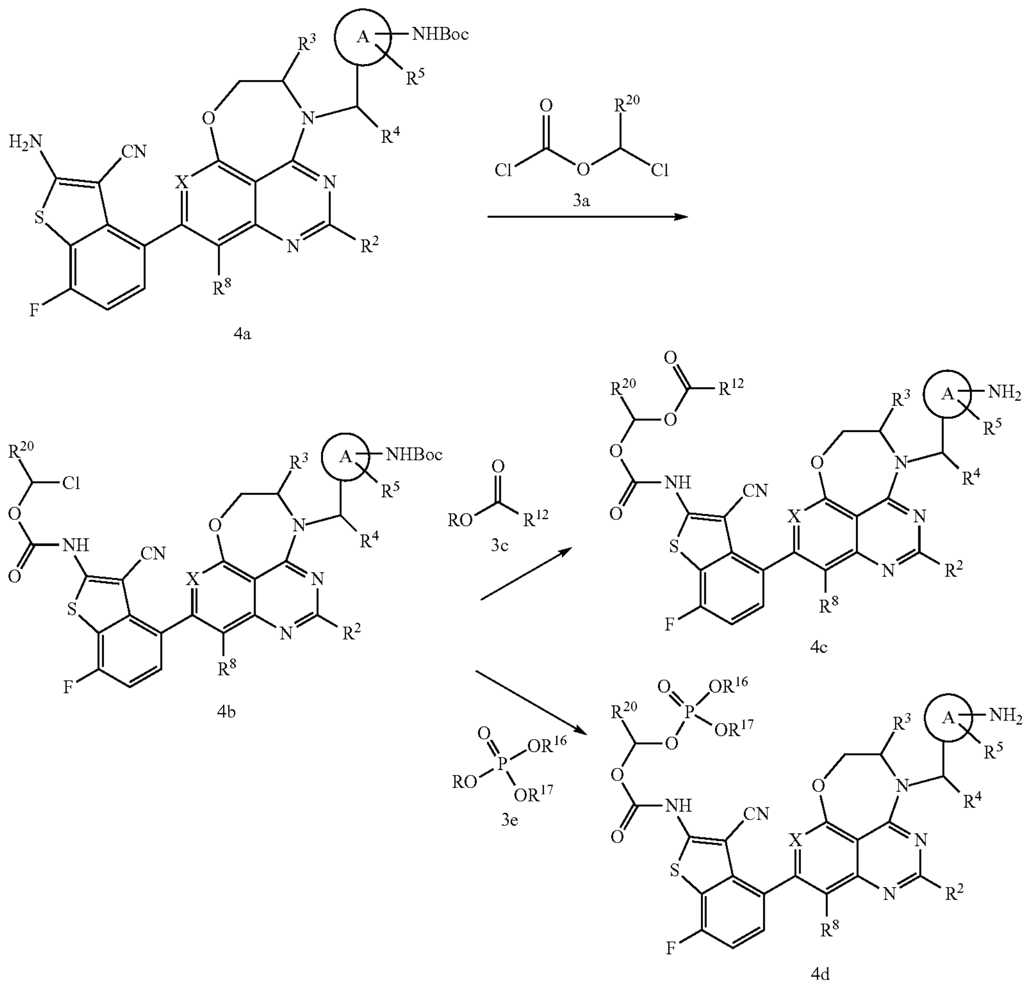

4a

4b

4c

4d

Similarly, in some embodiments, a compound of Formula 4c or 4d may be prepared according to Scheme 4. For example, 4a can be treated with chloroformate 3a to provide 4b. Substitution with 3c or 3e and subsequent Boc deprotection can provide a compound of Formula 4c or 4d, respectively.

Scheme 5

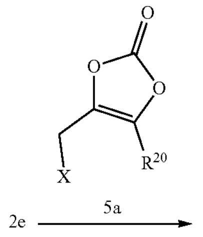

-continued

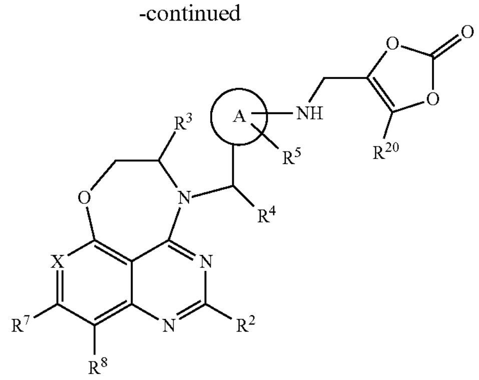

5b

In some embodiments, a compound of Formula 5b may be prepared according to Scheme 5. For example, 2e can be treated with base and a suitable alkyl halide, such as 5a, and optionally undergo one or more protecting group manipulations to provide a compound of Formula 5b.

Scheme 6

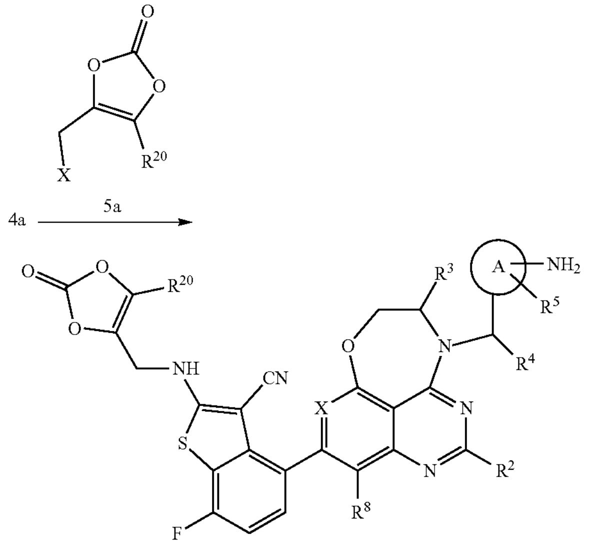

6a

Similarly, in some embodiments, a compound of Formula Ga may be prepared according to Scheme 6. For example, 4a can be treated with base and a suitable alkyl halide, such as 5a, and optionally undergo one or more protecting group manipulations to provide a compound of Formula 6a.

Scheme 7

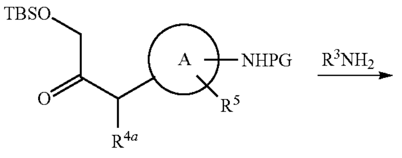

7a

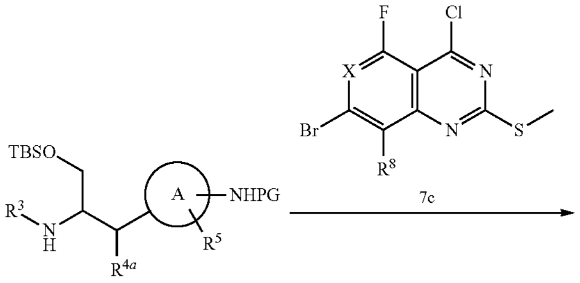

7b

-continued

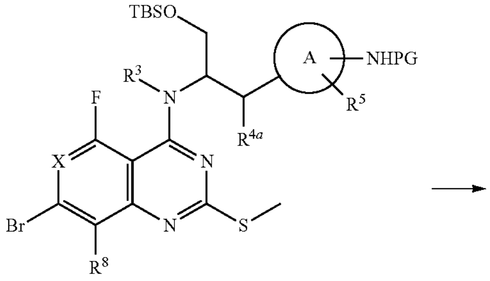

7d

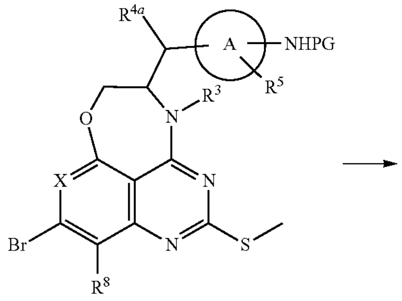

7e

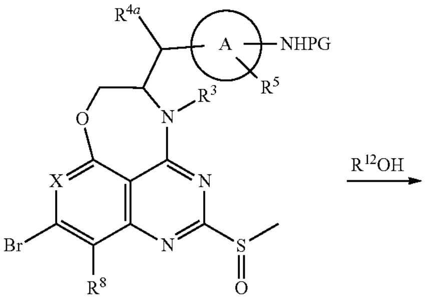

7f

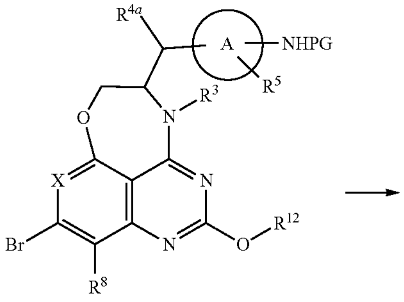

7g

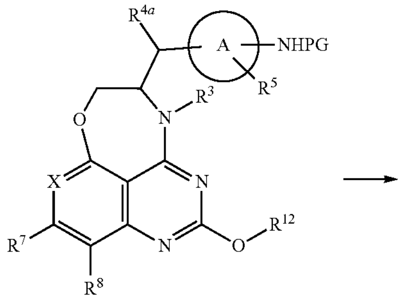

7h

-continued

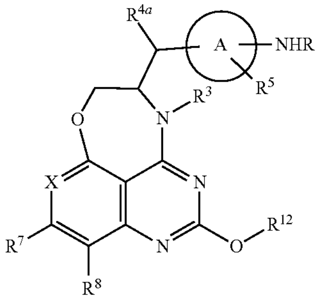

7i

In some embodiments, a compound of Formula 7i may be prepared according to Scheme 7. For example, 7a can undergo a reductive amination with a suitable $R^3$-substituted amine to provide 7b. Heteroaryl amine 7d can be formed from chloride 7c via a nucleophilic aromatic substitution reaction with amine 7b. Ring closure to 7e can be followed by an oxidation reaction to provide sulfoxide 7f, which can be substituted with —$OR^{12}$ upon addition of a suitable alcohol to afford 7 g. Substitution of the aryl bromide with a suitable boronic ester can provide the corresponding $R^7$-substituted compound, which may optionally be subjected to one or more subsequent reactions, such as a deprotection, to provide a compound of Formula 7i.

In some embodiments, a compound of the present disclosure, for example, a compound of a formula given in Table 1, was synthesized according to one of the general routes outlined in Schemes 1-7, Example 1, or by methods generally known in the art. In some embodiments, exemplary compounds may include, but are not limited to, a compound selected from Table 1, or a salt or solvate thereof.

TABLE 1

| No | Structure | Chemical Name | $[M + H]^+$ |
|---|---|---|---|
| 601 | 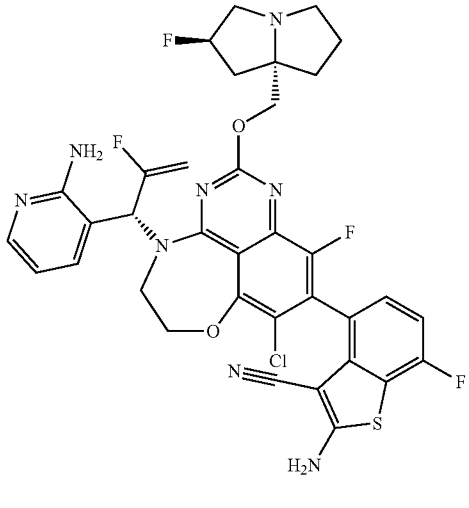 [SMILES: C=C(F)[C@@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-2-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 736.9 |
| 602 | 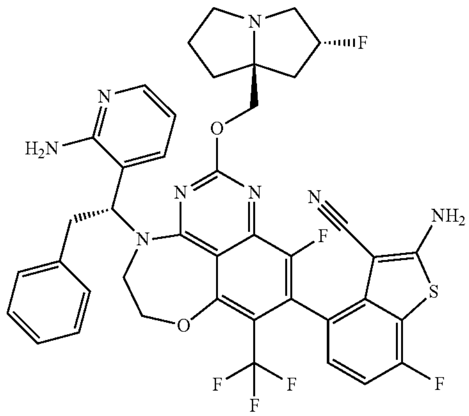 [SMILES: N#Cc1c(N)sc2c(F)ccc(-c3c(C(F)(F)F)c4c5c(nc(OC[C@@]67CCCN6C[C@H](F)C7)nc5c3F)N([C@H](Cc3ccccc3)c3cccnc3N)CCO4)c12] | 2-amino-4-(4-((R)-1-(2-aminopyridin-3-yl)-2-phenylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 817.3 |

TABLE 1-continued

| No | Structure | Chemical Name | [M + H]+ |
|---|---|---|---|
| 603 | 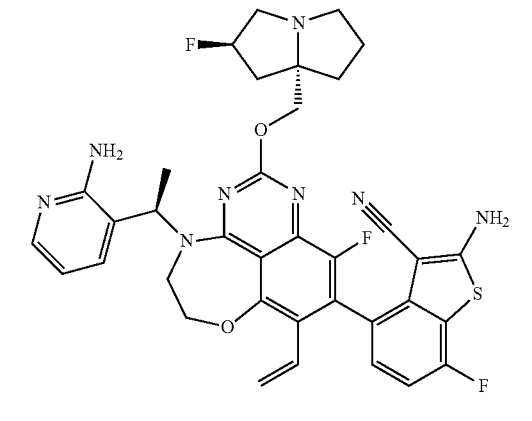 [SMILES: C=Cc1c(-c2ccc(F)c3sc(N)c(C#N)c23)c(F)c2nc(OC[C@@]34CCCN3C[C@H](F)C4)nc3c2c1OCCN3[C@H](C)c1cccnc1N] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-vinyl-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 699.0 |
| 604 | 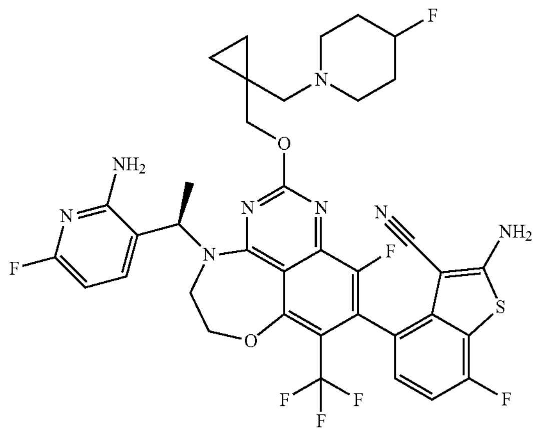 [SMILES: C[C@H](c1ccc(F)nc1N)N1CCOc2c(C(F)(F)F)c(-c3ccc(F)c4sc(N)c(C#N)c34)c(F)c3nc(OCC4(CN5CCC(F)CC5)CC4)nc1c23] | 2-amino-4-(4-((R)-1-(2-amino-6-fluoropyridin-3-yl)ethyl)-10-fluoro-2-((1-((4-fluoropiperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 787.3 |
| 605 | 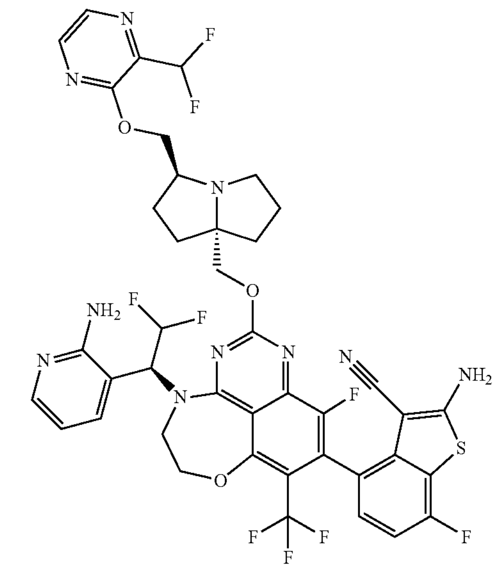 [SMILES: N#Cc1c(N)sc2c(F)ccc(-c3c(C(F)(F)F)c4c5c(nc(OC[C@@]67CCCN6[C@H](COc6nccnc6C(F)F)CC7)nc5c3F)N([C@@H](c3cccnc3N)C(F)F)CCO4)c12] | 2-amino-4-(4-((S)-1-(2-aminopyridin-3-yl)-2,2-difluoroethyl)-2-(((3S,7aS)-3-(((3-(difluoromethyl)pyrazin-2-yl)oxy)methyl)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 917.2 |

TABLE 1-continued

| No | Structure | Chemical Name | [M + H]+ |
|---|---|---|---|
| 606 | 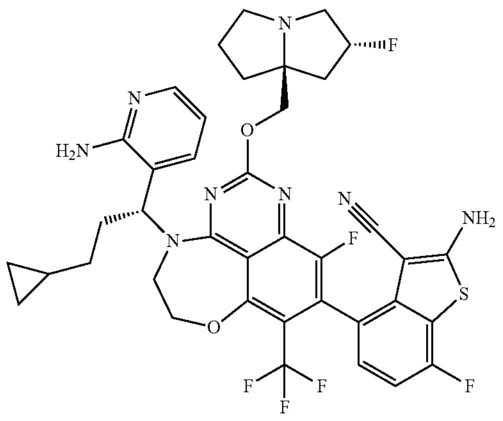 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CC3)c3cccnc3N)CCO4)c12] | 2-amino-4-(4-((R)-1-(2-aminopyridin-3-yl)-3-cyclopropylpropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 795.3 |
| 607 | 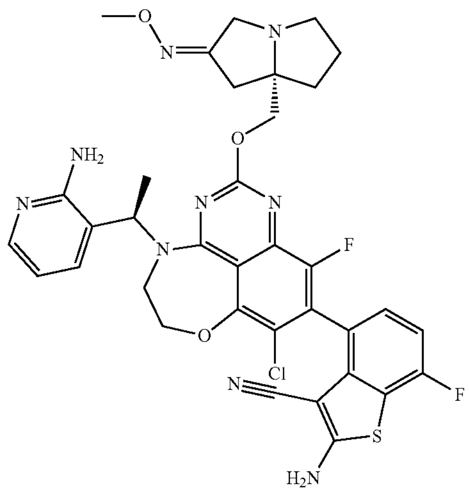 [SMILES: CO/N=C1\CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-10-fluoro-2-(((S,Z)-2-(methoxyimino)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 732.2 |
| 608 | 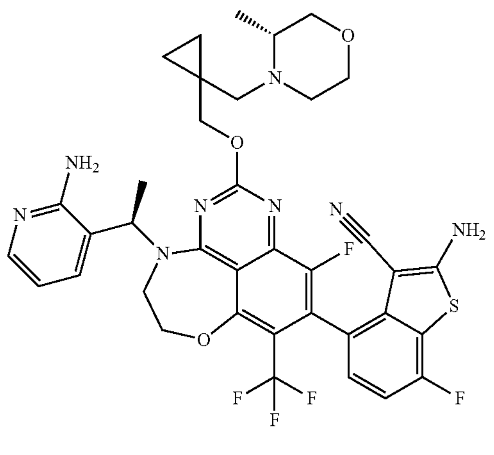 [SMILES: C[C@@H]1COCCN1CC1(COc2nc3c4c(c(C(F)(F)F)c(-c5ccc(F)c6sc(N)c(C#N)c56)c(F)c4n2)OCCN3[C@H](C)c2cccnc2N)CC1] | 2-amino-4-(4-((R)-1-(2-aminopyridin-3-yl)ethyl)-10-fluoro-2-((1-(((R)-3-methylmorpholino)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 767.2 |

TABLE 1-continued

| No | Structure | Chemical Name | [M + H]+ |
|---|---|---|---|
| 609 | 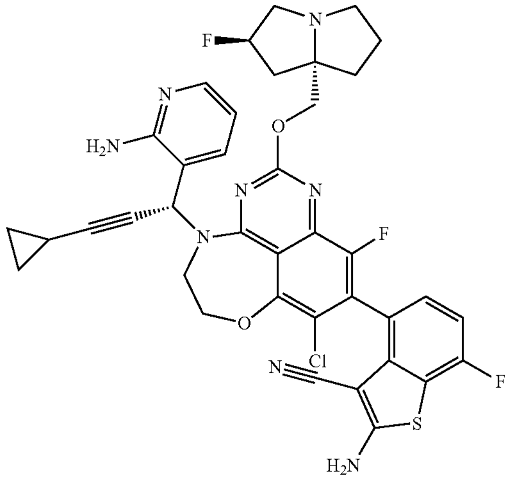 [SMILES: N#Cc1c(N)sc2c(F)ccc(-c3c(Cl)c4c5c(nc(OC[C@@]67CCCN6C[C@H](F)C7)nc5c3F)N([C@H](C#CC3CC3)c3cccnc3N)CCO4)c12] | 2-amino-4-(4-((R)-1-(2-aminopyridin-3-yl)-3-cyclopropylprop-2-yn-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 756.9 |
| 610 | 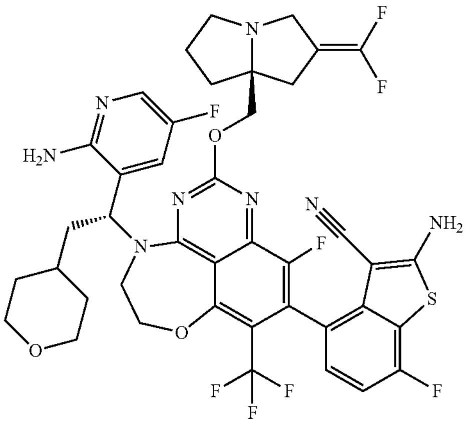 [SMILES: N#Cc1c(N)sc2c(F)ccc(-c3c(C(F)(F)F)c4c5c(nc(OC[C@@]67CCCN6CC(=C(F)F)C7)nc5c3F)N([C@H](CC3CCOCC3)c3cc(F)cnc3N)CCO4)c12] | 2-amino-4-(4-((R)-1-(2-amino-5-fluoropyridin-3-yl)-2-(tetrahydro-2H-pyran-4-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 873.4 |
| 611 | 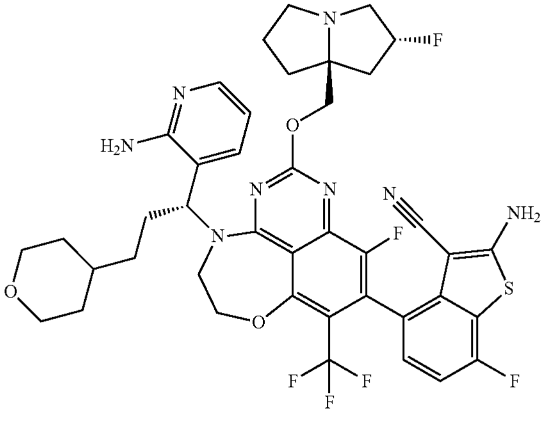 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 839.2 |

TABLE 1-continued

| No | Structure | Chemical Name | [M + H]+ |
|---|---|---|---|
| 612 | 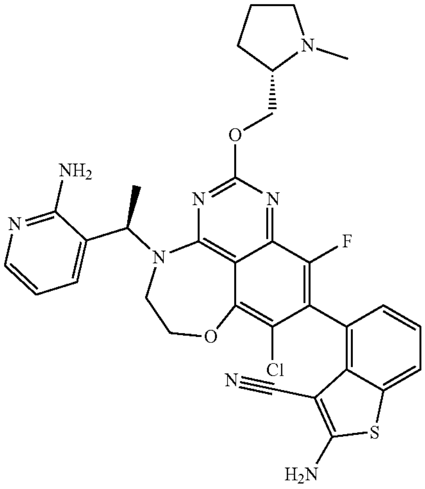 [SMILES: C[C@H](c1cccnc1N)N1CCOc2c(Cl)c(-c3cccc4sc(N)c(C#N)c34)c(F)c3nc(OC[C@@H]4CCCN4C)nc1c23] | 2-amino-4-(4-((R)-1-(2-aminopyridin-3-yl)ethyl)-8-chloro-10-fluoro-2-(((S)-1-methylpyrrolidin-2-yl)methoxy)-5,6-dihydro-4H-[1,4]oxazepino[5,6,7-de]quinazolin-9-yl)benzo[b]thiophene-3-carbonitrile (single diastereomer, R atropisomer at $R^7$ substituent) | 644.9 |
| 613 | 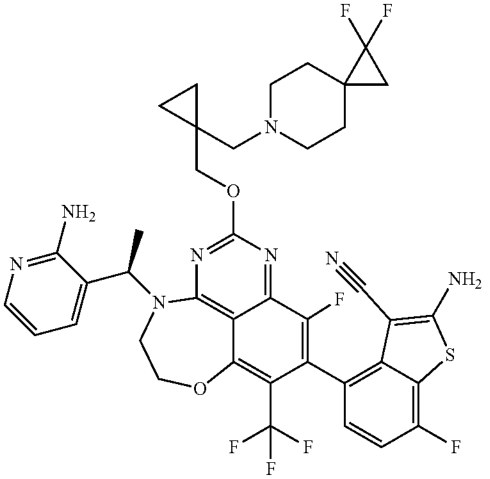 [SMILES: C[C@H](c1cccnc1N)N1CCOc2c(C(F)(F)F)c(-c3ccc(F)c4sc(N)c(C#N)c34)c(F)c3nc(OCC4(CN5CCC6(CC5)CC6(F)F)CC4)nc1c23] | 2-amino-4-(4-((R)-1-(2-aminopyridin-3-yl)ethyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 813.3 |
| 614 | 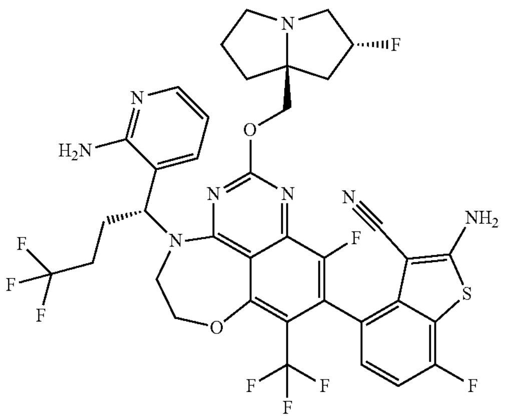 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC(F)(F)F)c3cccnc3N)CCO4)c12] | 2-amino-4-(4-((R)-1-(2-aminopyridin-3-yl)-4,4,4-trifluorobutyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 823.3 |

TABLE 1-continued

| No | Structure | Chemical Name | [M + H]+ |
|---|---|---|---|
| 615 | 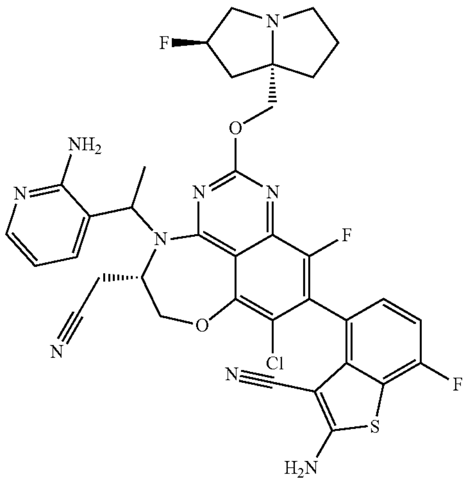 [SMILES: CC(c1cccnc1N)N1c2nc(OC[C@@]34CCCN3C[C@H](F)C4)nc3c(F)c(-c4ccc(F)c5sc(N)c(C#N)c45)c(Cl)c(c23)OC[C@@H]1CC#N] | 2-amino-4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 745.8 |
| 616 | 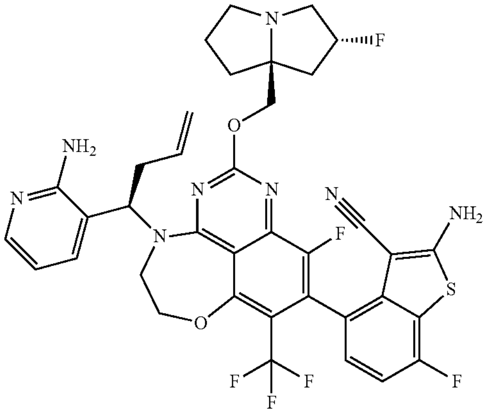 [SMILES: C=CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)but-3-en-1-yl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 766.9 |
| 617 | 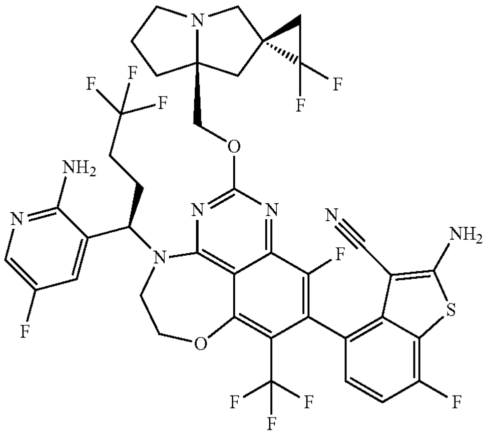 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CCC(F)(F)F)c3cc(F)cnc3N)CCO4)c12] | 2-amino-4-(4-((R)-1-(2-amino-5-fluoropyridin-3-yl)-4,4,4-trifluorobutyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 885.2 |

TABLE 1-continued

| No | Structure | Chemical Name | [M + H]+ |
|---|---|---|---|
| 618 | 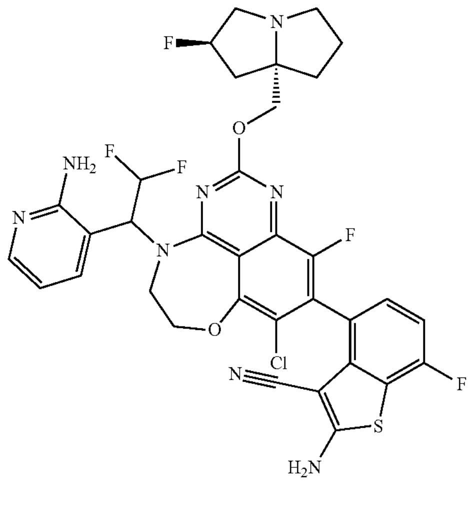 [SMILES: N#Cc1c(N)sc2c(F)ccc(-c3c(Cl)c4c5c(nc(OC[C@@]67CCCN6C[C@H](F)C7)nc5c3F)N(C(c3cccnc3N)C(F)F)CCO4)c12] | 2-amino-4-(4-(1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 742.7 |
| 619 | 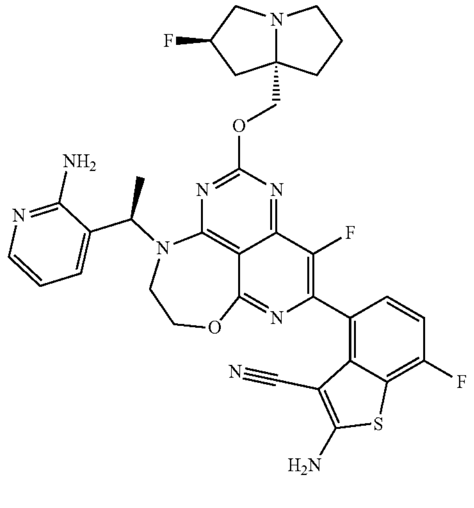 [SMILES: C[C@H](c1cccnc1N)N1CCOc2nc(-c3ccc(F)c4sc(N)c(C#N)c34)c(F)c3nc(OC[C@@]45CCCN4C[C@H](F)C5)nc1c23] | 2-amino-4-(10-((R)-1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-7-fluorobenzo[b]thiophene-3-carbonitrile (single diastereomer) | 674.3 |
| 620 | 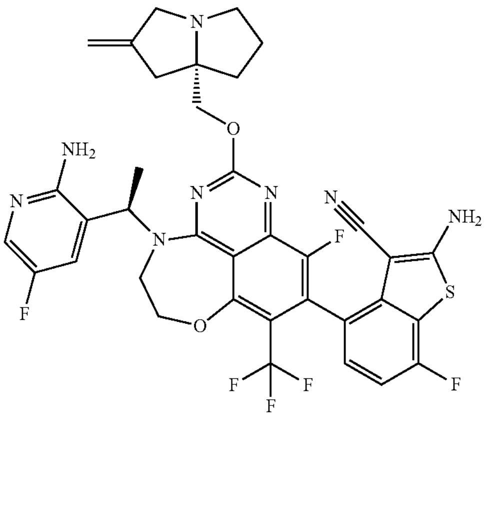 | 2-amino-4-(4-((R)-1-(2-amino-5-fluoropyridin-3-yl)ethyl)-10-fluoro-2-(((S)-2-methylenetetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 753.3 |

TABLE 1-continued

| No | Structure | Chemical Name | [M + H]+ |
| --- | --- | --- | --- |
| 621 | 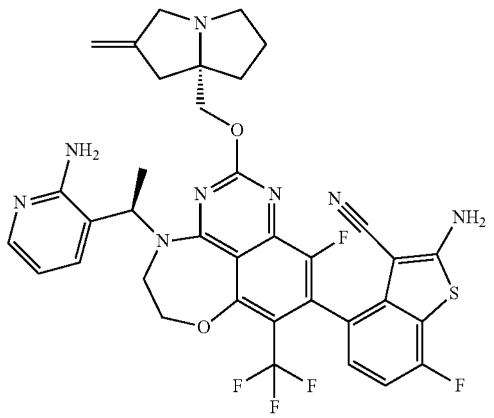 | 2-amino-4-(4-((R)-1-(2-aminopyridin-3-yl)ethyl)-10-fluoro-2-(((S)-2-methylenetetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 735.2 |
| 622 | 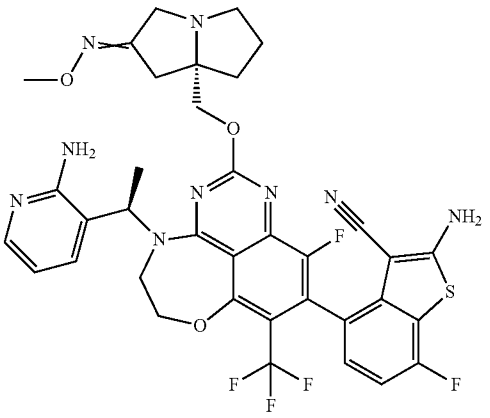 [SMILES: CON=C1CN2CCC[C@@]2(COc2nc3c4c(c(C(F)(F)F)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-10-fluoro-2-(((S)-2-(methoxyimino)tetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 766.3 |
| 623 | 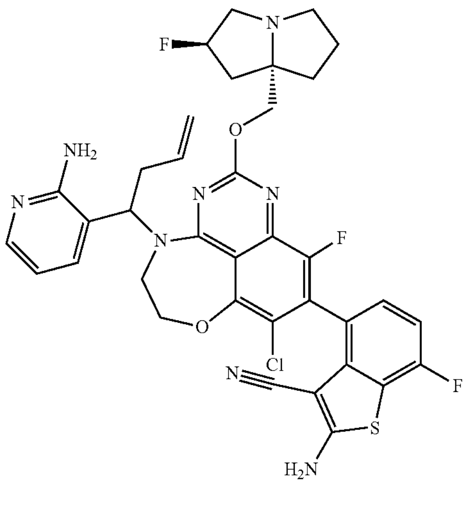 [SMILES: C=CCC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)but-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 733.2 |

TABLE 1-continued

| No | Structure | Chemical Name | [M + H]+ |
| --- | --- | --- | --- |
| 624 | 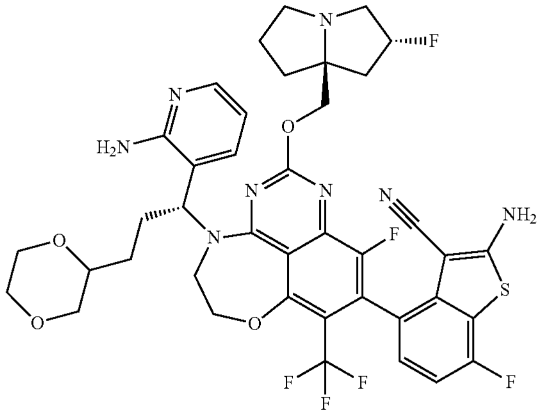 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3COCCO3)c3cccnc3N)CCO4)c12] | 2-amino-4-(4-((1R)-1-(2-aminopyridin-3-yl)-3-(1,4-dioxan-2-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 841.3 |
| 625 | 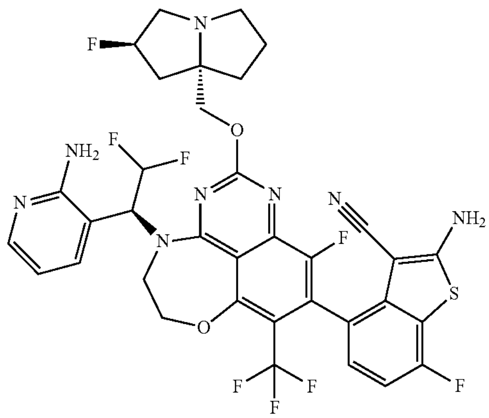 [SMILES: N#Cc1c(N)sc2c(F)ccc(-c3c(C(F)(F)F)c4c5c(nc(OC[C@@]67CCCN6C[C@H](F)C7)nc5c3F)N([C@@H](c3cccnc3N)C(F)F)CCO4)c12] | 2-amino-4-(4-((S)-1-(2-aminopyridin-3-yl)-2,2-difluoroethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 776.9 |
| 626 | 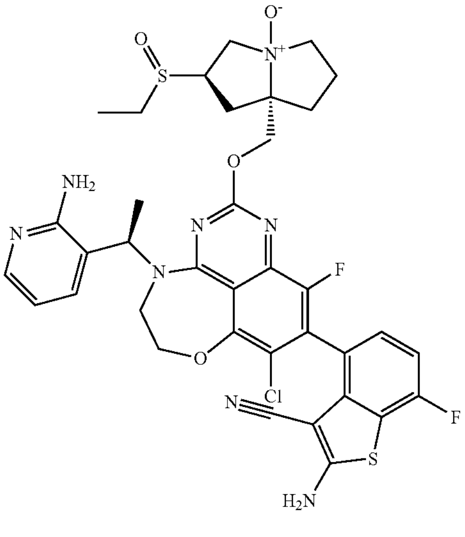 | (2R,7aS)-7a-(((9-(2-amino-3-cyano-7-fluorobenzo[b]thiophen-4-yl)-4-((R)-1-(2-aminopyridin-3-yl)ethyl)-8-chloro-10-fluoro-5,6-dihydro-4H-[1,4]oxazepino[5,6,7-de]quinazolin-2-yl)oxy)methyl)-2-(ethylsulfinyl)hexahydropyrrolizine 4(1H)-oxide (diastereomer mixture) | 781.0 |

TABLE 1-continued

| No | Structure | Chemical Name | [M + H]+ |
|---|---|---|---|
| 627 | 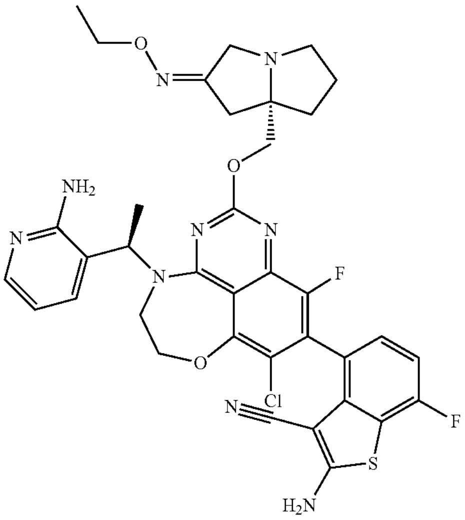 | 2-amino-4-(4-((R)-1-(2-aminopyridin-3-yl)ethyl)-8-chloro-2-(((S,Z)-2-(ethoxyimino)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 746.1 |
| 628 | 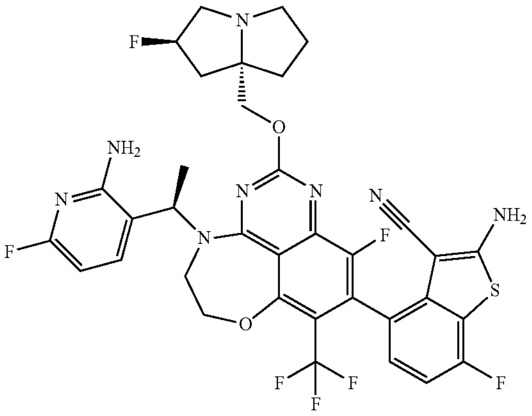 [SMILES: C[C@H](c1ccc(F)nc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-6-fluoropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 759.2 |
| 629 | 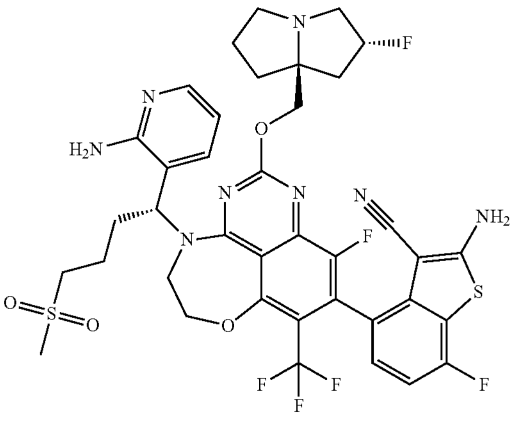 [SMILES: CS(=O)(=O)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-4-(methylsulfonyl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 847.1 |

TABLE 1-continued

| No | Structure | Chemical Name | [M + H]+ |
| --- | --- | --- | --- |
| 630 | 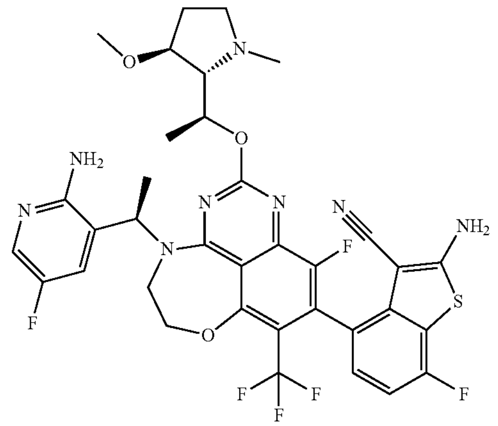 [SMILES: CO[C@H]1CCN(C)[C@@H]1[C@H](C)Oc1nc2c3c(c(C(F)(F)F)c(-c4ccc(F)c5sc(N)c(C#N)c45)c(F)c3n1)OCCN2[C@H](C)c1cc(F)cnc1N] | 2-amino-4-(4-((R)-1-(2-amino-5-fluoropyridin-3-yl)ethyl)-10-fluoro-2-((S)-1-((2R,3S)-3-methoxy-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 759.3 |
| 631 | 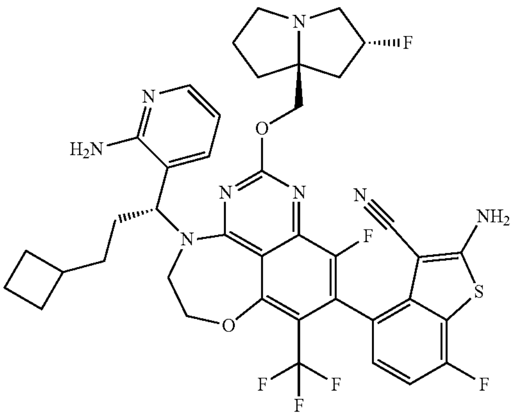 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CCC3)c3cccnc3N)CCO4)c12] | 2-amino-4-(4-((R)-1-(2-aminopyridin-3-yl)-3-cyclobutylpropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 809.3 |
| 632 | 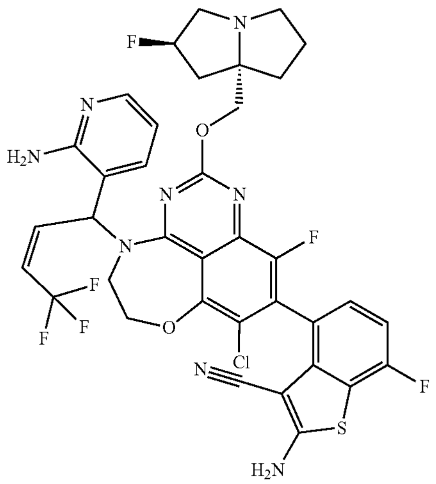 [SMILES: N#Cc1c(N)sc2c(F)ccc(-c3c(Cl)c4c5c(nc(OC[C@@]67CCCN6C[C@H](F)C7)nc5c3F)N(C(/C=C\C(F)(F)F)c3cccnc3N)CCO4)c12] | 2-amino-4-(4-((Z)-1-(2-aminopyridin-3-yl)-4,4,4-trifluorobut-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, absolute stereochemistry not determined) | 786.8 |

TABLE 1-continued

| No | Structure | Chemical Name | [M + H]+ |
|---|---|---|---|
| 633 | 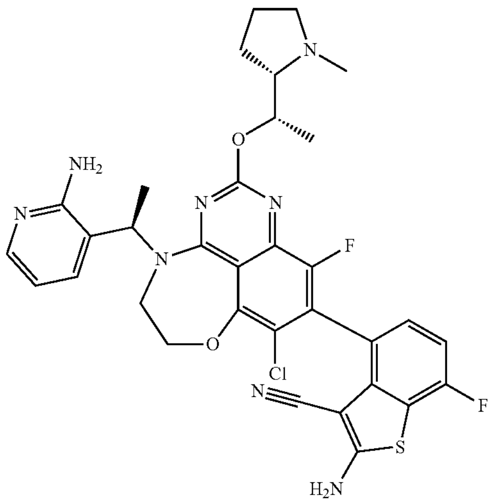 [SMILES: C[C@H](Oc1nc2c3c(c(Cl)c(-c4ccc(F)c5sc(N)c(C#N)c45)c(F)c3n1)OCCN2[C@H](C)c1cccnc1N)[C@@H]1CCCN1C] | 2-amino-4-(4-((R)-1-(2-aminopyridin-3-yl)ethyl)-8-chloro-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 677.1 |
| 634 | 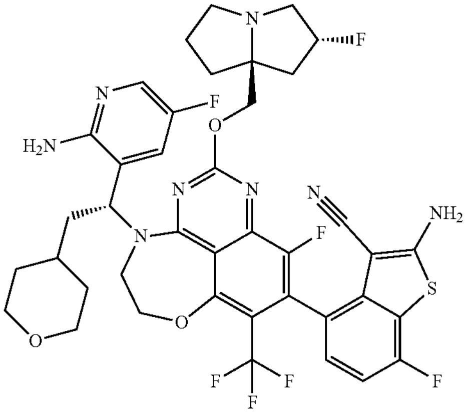 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOCC3)c3cc(F)cnc3N)CCO4)c12] | 2-amino-4-(4-((R)-1-(2-amino-5-fluoropyridin-3-yl)-2-(tetrahydro-2H-pyran-4-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 843.3 |
| 635 | 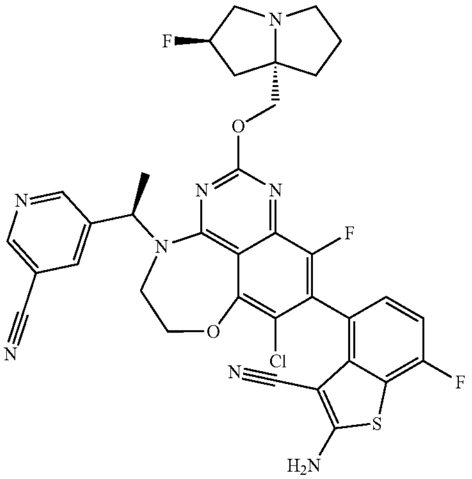 [SMILES: C[C@H](c1cncc(C#N)c1)N1CCOc2c(Cl)c(-c3ccc(F)c4sc(N)c(C#N)c34)c(F)c3nc(OC[C@@]45CCCN4C[C@H](F)C5)nc1c23] | 2-((1R)-1-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)isonicotinonitrile (single diastereomer, R atropisomer at $R^7$ substituent) | 717.3 |

TABLE 1-continued

| No | Structure | Chemical Name | [M + H]+ |
|---|---|---|---|
| 636 | 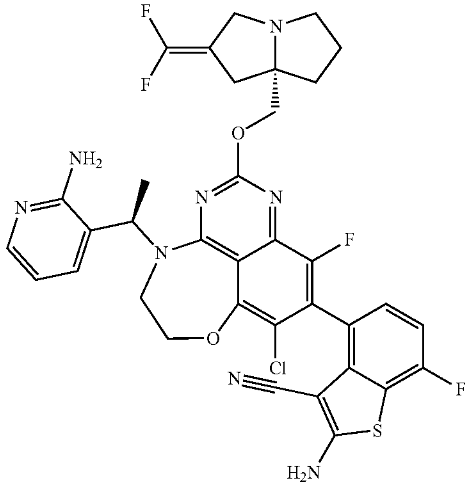 [SMILES: C[C@H](c1cccnc1N)N1CCOc2c(Cl)c(-c3ccc(F)c4sc(N)c(C#N)c34)c(F)c3nc(OC[C@@]45CCCN4CC(=C(F)F)C5)nc1c23] | 2-amino-4-(4-((R)-1-(2-aminopyridin-3-yl)ethyl)-8-chloro-2-(((S)-2-(difluoromethylene)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 736.8 |
| 637 | 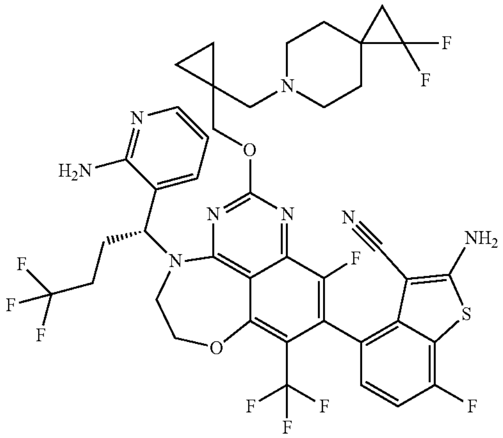 [SMILES: N#Cc1c(N)sc2c(F)ccc(-c3c(C(F)(F)F)c4c5c(nc(OCC6(CN7CCC8(CC7)CC8(F)F)CC6)nc5c3F)N([C@H](CCC(F)(F)F)c3cccnc3N)CCO4)c12] | 2-amino-4-(4-((R)-1-(2-aminopyridin-3-yl)-4,4,4-trifluorobutyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 895.4 |
| 638 | 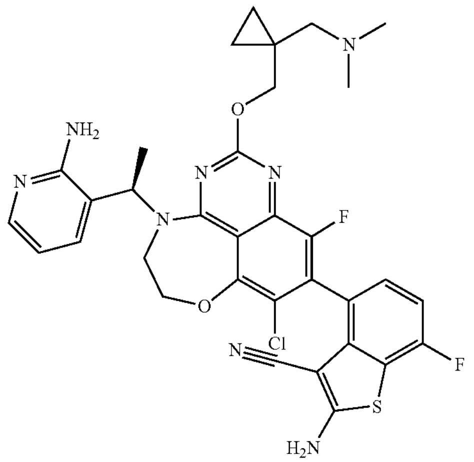 [SMILES: C[C@H](c1cccnc1N)N1CCOc2c(Cl)c(-c3ccc(F)c4sc(N)c(C#N)c34)c(F)c3nc(OCC4(CN(C)C)CC4)nc1c23] | 2-amino-4-(4-((R)-1-(2-aminopyridin-3-yl)ethyl)-8-chloro-2-((1-((dimethylamino)methyl)cyclopropyl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 676.8 |

TABLE 1-continued

| No | Structure | Chemical Name | [M + H]$^+$ |
|---|---|---|---|
| 639 | 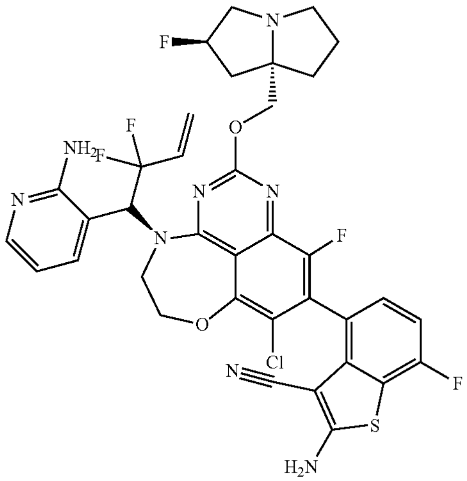 | 2-amino-4-(4-((S)-1-(2-aminopyridin-3-yl)-2,2-difluorobut-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 769.1 |
| 640 | 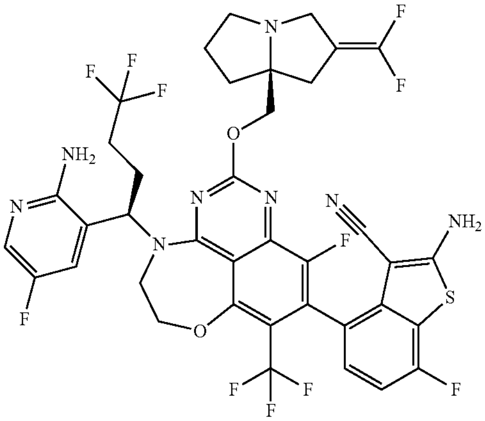 [SMILES: N#Cc1c(N)sc2c(F)ccc(-c3c(C(F)(F)F)c4c5c(nc(OC[C@@]67CCCN6CC(=C(F)F)C7)nc5c3F)N([C@H](CCC(F)(F)F)c3cc(F)cnc3N)CCO4)c12] | 2-amino-4-(4-((R)-1-(2-amino-5-fluoropyridin-3-yl)-4,4,4-trifluorobutyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 871.3 |
| 641 | 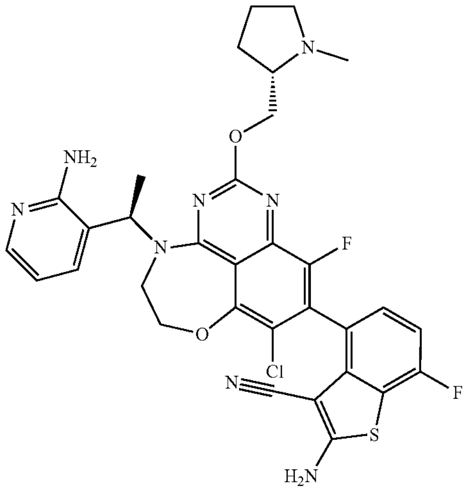 [SMILES: C[C@H](c1cccnc1N)N1CCOc2c(Cl)c(-c3ccc(F)c4sc(N)c(C#N)c34)c(F)c3nc(OC[C@@H]4CCCN4C)nc1c23] | 2-amino-4-(4-((R)-1-(2-aminopyridin-3-yl)ethyl)-8-chloro-10-fluoro-2-(((S)-1-methylpyrrolidin-2-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 663.0 |

TABLE 1-continued

| No | Structure | Chemical Name | [M + H]+ |
|---|---|---|---|
| 642 | 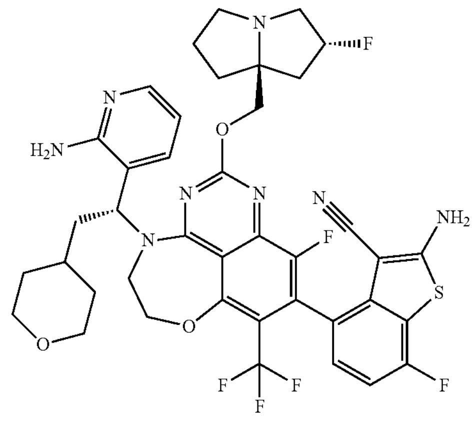 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOCC3)c3cccnc3N)CCO4)c12] | 2-amino-4-(4-((R)-1-(2-aminopyridin-3-yl)-2-(tetrahydro-2H-pyran-4-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 825.4 |
| 643 | 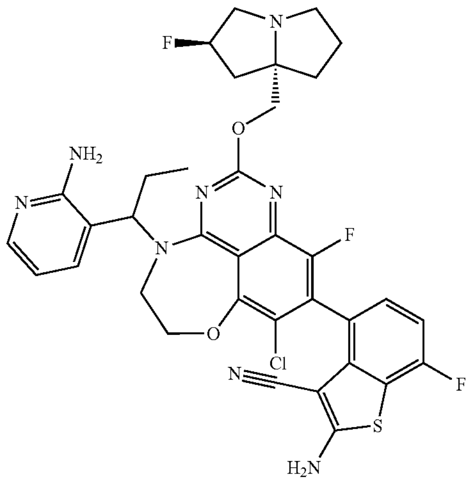 [SMILES: CCC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)propyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 721.2 |
| 644 | 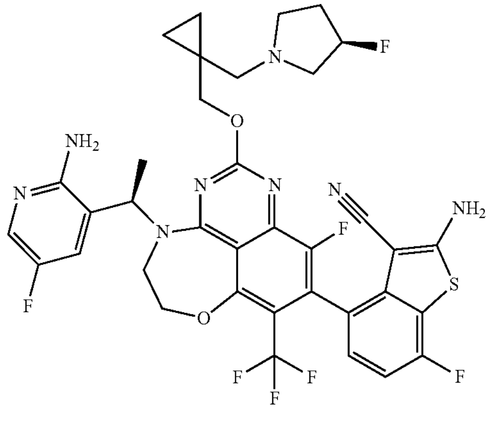 [SMILES: C[C@H](c1cc(F)cnc1N)N1CCOc2c(C(F)(F)F)c(-c3ccc(F)c4sc(N)c(C#N)c34)c(F)c3nc(OCC4(CN5CC[C@@H](F)C5)CC4)nc1c23] | 2-amino-4-(4-((R)-1-(2-amino-5-fluoropyridin-3-yl)ethyl)-10-fluoro-2-((1-(((R)-3-fluoropyrrolidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 773.3 |

TABLE 1-continued

| No | Structure | Chemical Name | [M + H]+ |
|---|---|---|---|
| 645 | 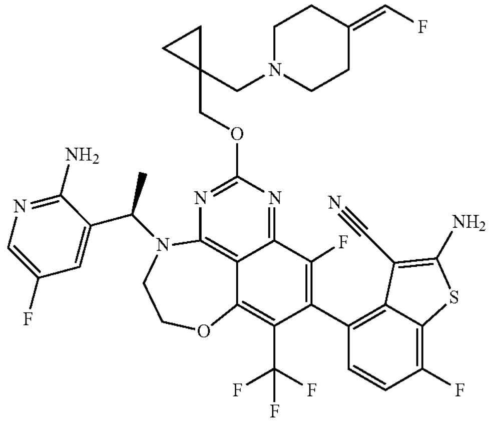 [SMILES: C[C@H](c1cc(F)cnc1N)N1CCOc2c(C(F)(F)F)c(-c3ccc(F)c4sc(N)c(C#N)c34)c(F)c3nc(OCC4(CN5CCC(=CF)CC5)CC4)nc1c23] | 2-amino-4-(4-((R)-1-(2-amino-5-fluoropyridin-3-yl)ethyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 799.3 |
| 646 | 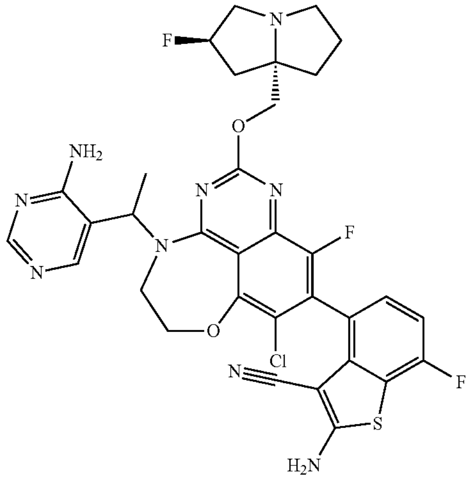 | 2-amino-4-(4-(1-(4-aminopyrimidin-5-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 707.9 |
| 647 | 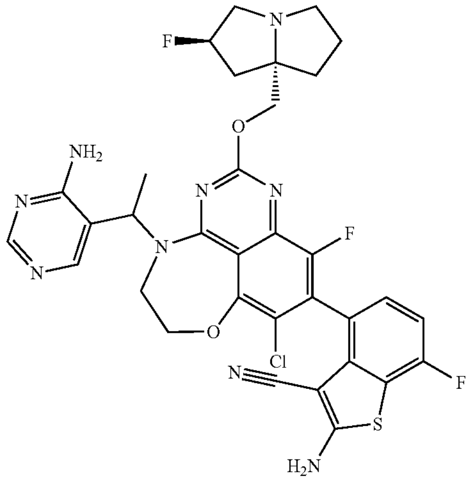 [SMILES: CC(c1cncnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(4-aminopyrimidin-5-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 708.1 |

TABLE 1-continued

| No | Structure | Chemical Name | [M + H]+ |
|---|---|---|---|
| 648 | 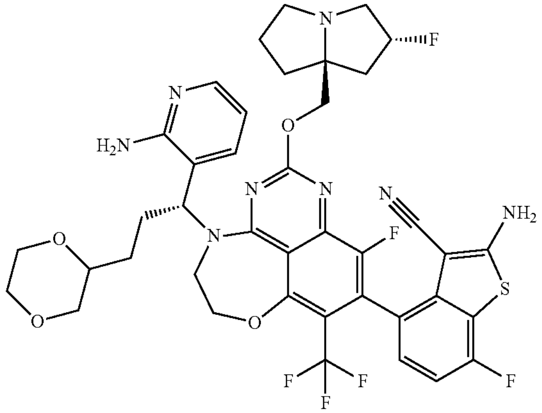 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3COCCO3)c3cccnc3N)CCO4)c12] | 2-amino-4-(4-((1R)-1-(2-aminopyridin-3-yl)-3-(1,4-dioxan-2-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (mixture of diastereomers) | 841.3 |
| 649 | 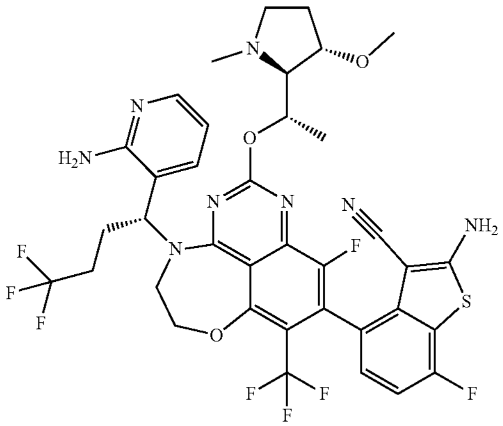 [SMILES: CO[C@H]1CCN(C)[C@@H]1[C@H](C)Oc1nc2c3c(c(C(F)(F)F)c(-c4ccc(F)c5sc(N)c(C#N)c45)c(F)c3n1)OCCN2[C@H](CCC(F)(F)F)c1cccnc1N] | 2-amino-4-(4-((R)-1-(2-aminopyridin-3-yl)-4,4,4-trifluorobutyl)-10-fluoro-2-((S)-1-((2R,3S)-3-methoxy-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 823.3 |
| 650 | 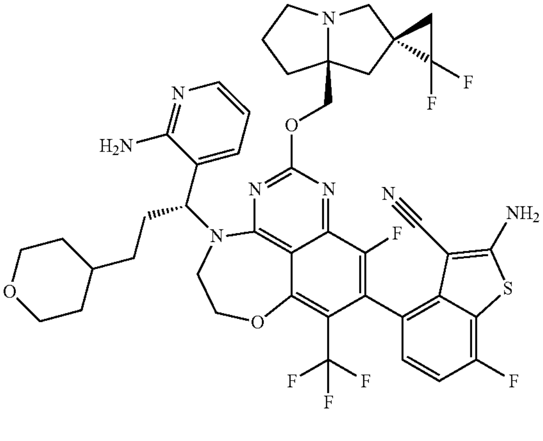 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 883.3 |

TABLE 1-continued

| No | Structure | Chemical Name | [M + H]$^+$ |
|---|---|---|---|
| 651 | 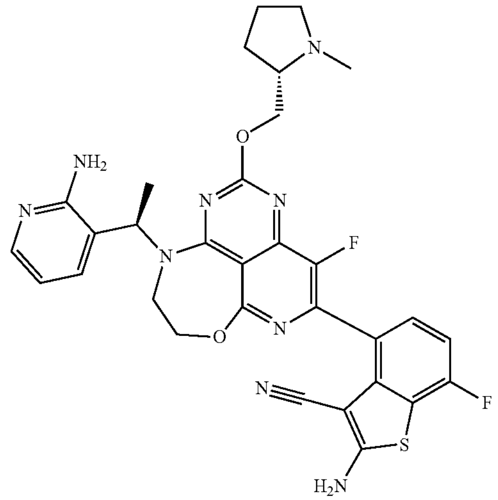 [SMILES: C[C@H](c1cccnc1N)N1CCOc2nc(-c3ccc(F)c4sc(N)c(C#N)c34)c(F)c3nc(OC[C@@H]4CCCN4C)nc1c23] | 2-amino-4-(10-((R)-1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-7-fluorobenzo[b]thiophene-3-carbonitrile (single diastereomer) | 630.3 |
| 652 | 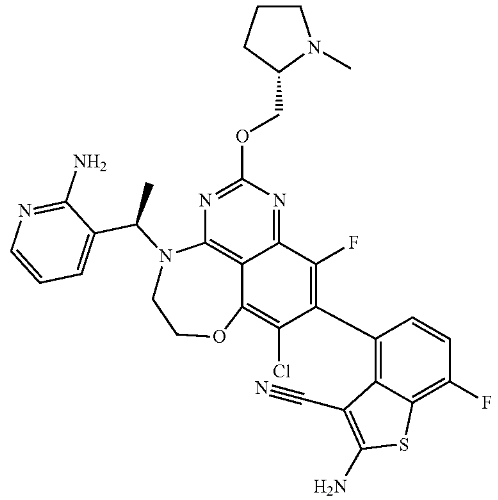 [SMILES: C[C@H](c1cccnc1N)N1CCOc2c(Cl)c(-c3ccc(F)c4sc(N)c(C#N)c34)c(F)c3nc(OC[C@@H]4CCCN4C)nc1c23] | 2-amino-4-(4-((R)-1-(2-aminopyridin-3-yl)ethyl)-8-chloro-10-fluoro-2-(((S)-1-methylpyrrolidin-2-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 663.0 |
| 653 | 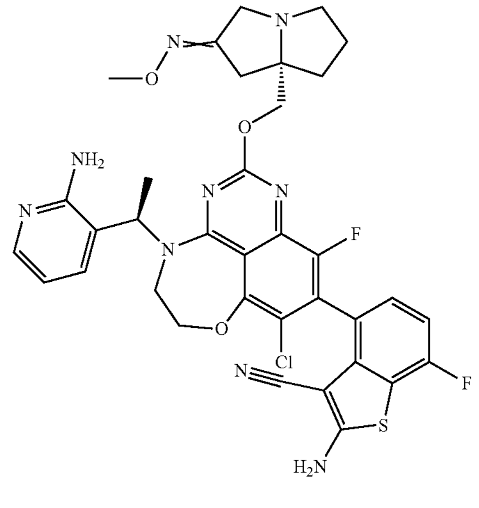 [SMILES: CON=C1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-10-fluoro-2-(((S)-2-(methoxyimino)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (diastereomer mixture) | 732.2 |

TABLE 1-continued

| No | Structure | Chemical Name | [M + H]+ |
| --- | --- | --- | --- |
| 654 | 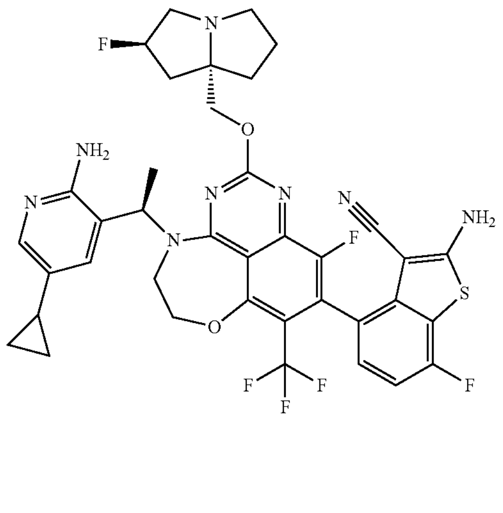 [SMILES: C[C@H](c1cc(C2CC2)cnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-cyclopropylpyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.3 |
| 655 | 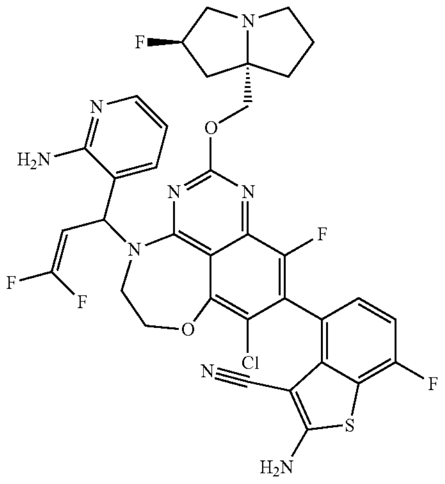 [SMILES: N#Cc1c(N)sc2c(F)ccc(-c3c(Cl)c4c5c(nc(OC[C@@]67CCCN6C[C@H](F)C7)nc5c3F)N(C(C=C(F)F)c3cccnc3N)CCO4)c12] | 2-amino-4-(4-(1-(2-aminopyridin-3-yl)-3,3-difluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 755.0 |
| 656 | 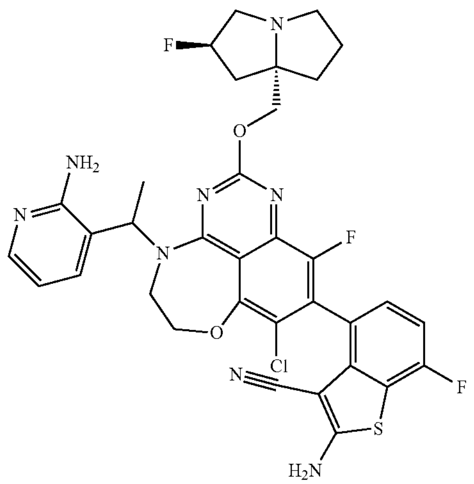 [SMILES: CC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 707.0 |

TABLE 1-continued

| No | Structure | Chemical Name | [M + H]+ |
| --- | --- | --- | --- |
| 657 | 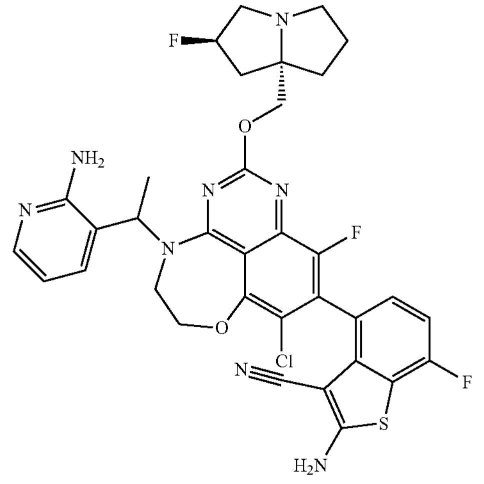 [SMILES: CC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 707.0 |
| 658 | 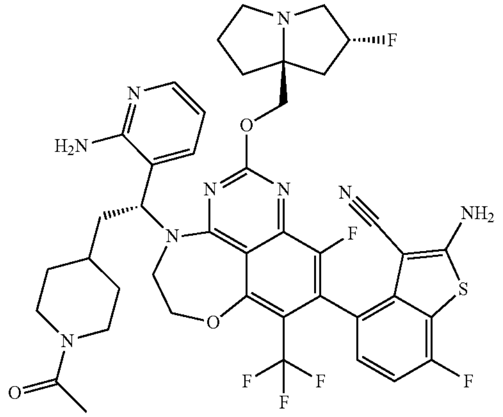 [SMILES: CC(=O)N1CCC(C[C@H](c2cccnc2N)N2CCOc3c(C(F)(F)F)c(-c4ccc(F)c5sc(N)c(C#N)c45)c(F)c4nc(OC[C@@]56CCCN5C[C@H](F)C6)nc2c34)CC1] | 4-(4-((R)-2-(1-acetylpiperidin-4-yl)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-2-amino-7-fluorobenzo[b]thiophene-3-carbonitrile (single diastereomer, S atropisomer at $R^7$ substituent) | 866.3 |
| 659 | 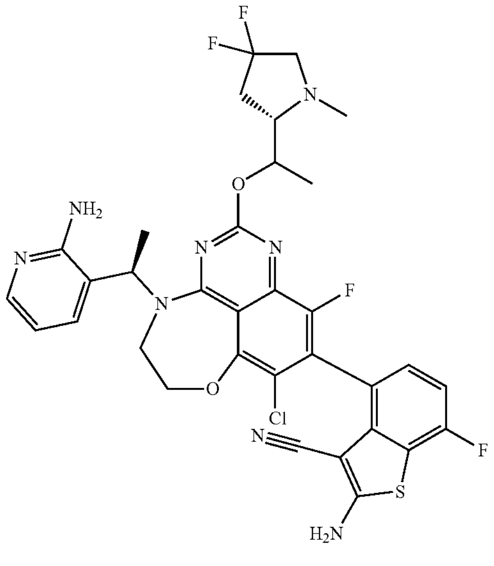 [SMILES: CC(Oc1nc2c3c(c(Cl)c(-c4ccc(F)c5sc(N)c(C#N)c45)c(F)c3n1)OCCN2[C@H](C)c1cccnc1N)[C@@H]1CC(F)(F)CN1C] | 2-amino-4-(4-((R)-1-(2-aminopyridin-3-yl)ethyl)-8-chloro-2-(1-((S)-4,4-difluoro-1-methylpyrrolidin-2-yl)ethoxy)-10-fluoro-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 712.8 |

TABLE 1-continued

| No | Structure | Chemical Name | [M + H]$^+$ |
|---|---|---|---|
| 660 | 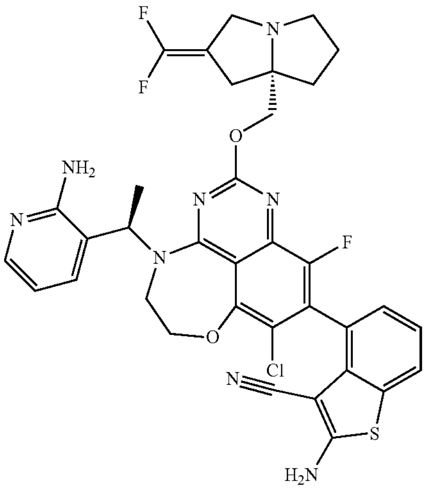 [SMILES: C[C@H](c1cccnc1N)N1CCOc2c(Cl)c(-c3cccc4sc(N)c(C#N)c34)c(F)c3nc(OC[C@@]45CCCN4CC(=C(F)F)C5)nc1c23] | 2-amino-4-(4-((R)-1-(2-aminopyridin-3-yl)ethyl)-8-chloro-2-(((S)-2-(difluoromethylene)tetrahydro-1H-pyrrolizin-7a(5H)-yl)methoxy)-10-fluoro-5,6-dihydro-4H-[1,4]oxazepino[5,6,7-de]quinazolin-9-yl)benzo[b]thiophene-3-carbonitrile (single diastereomer, R atropisomer at $R^7$ substituent) | 736.8 |
| 661 | 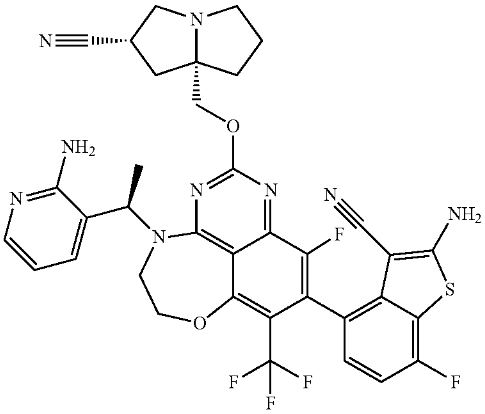 | (2S,7aS)-7a-(((9-(2-amino-3-cyano-7-fluorobenzo[b]thiophen-4-yl)-4-((R)-1-(2-aminopyridin-3-yl)ethyl)-10-fluoro-8-(trifluoromethyl)-5,6-dihydro-4H-[1,4]oxazepino[5,6,7-de]quinazolin-2-yl)oxy)methyl)hexahydro-1H-pyrrolizine-2-carbonitrile (single diastereomer, S atropisomer at $R^7$ substituent) | 748.3 |
| 662 | 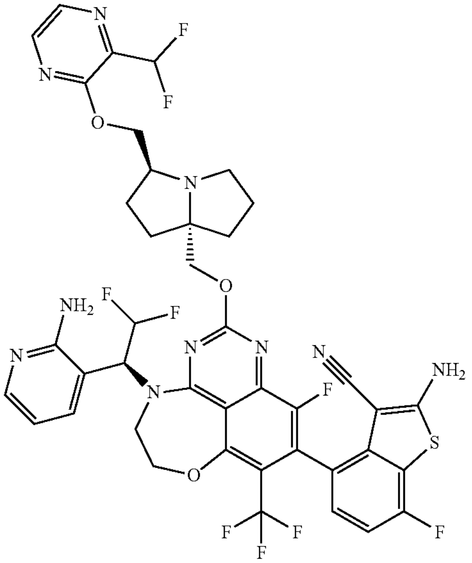 [SMILES: N#Cc1c(N)sc2c(F)ccc(-c3c(C(F)(F)F)c4c5c(nc(OC[C@@]67CCCN6[C@H](COc6nccnc6C(F)F)CC7)nc5c3F)N([C@@H](c3cccnc3N)C(F)F)CCO4)c12] | 2-amino-4-(4-((S)-1-(2-aminopyridin-3-yl)-2,2-difluoroethyl)-2-(((3S,7aS)-3-(((3-(difluoromethyl)pyrazin-2-yl)oxy)methyl)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 917.2 |

TABLE 1-continued

| No | Structure | Chemical Name | [M + H]+ |
|---|---|---|---|
| 663 | 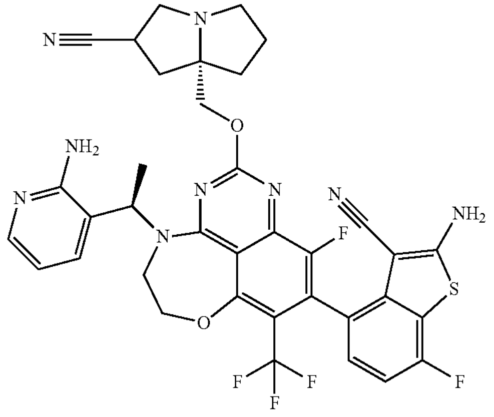 [SMILES: C[C@H](c1cccnc1N)N1CCOc2c(C(F)(F)F)c(-c3ccc(F)c4sc(N)c(C#N)c34)c(F)c3nc(OC[C@@]45CCCN4CC(C#N)C5)nc1c23] | (7aS)-7a-(((9-(2-amino-3-cyano-7-fluorobenzo[b]thiophen-4-yl)-4-((R)-1-(2-aminopyridin-3-yl)ethyl)-10-fluoro-8-(trifluoromethyl)-5,6-dihydro-4H-[1,4]oxazepino[5,6,7-de]quinazolin-2-yl)oxy)methyl)hexahydro-1H-pyrrolizine-2-carbonitrile (single diastereomer, absolute stereochemistry undetermined) | 748.3 |
| 664 | 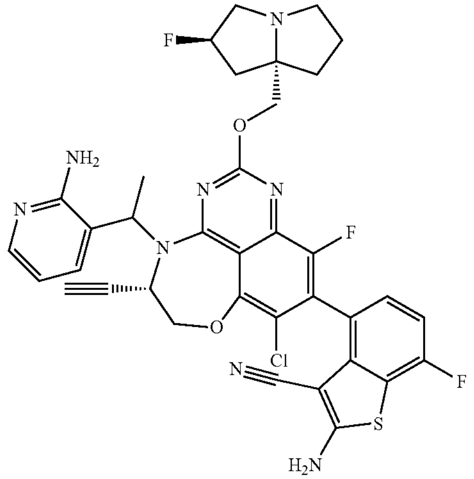 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 730.9 |
| 665 | 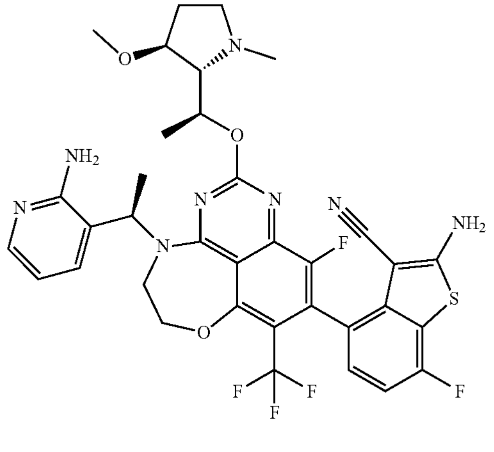 [SMILES: CO[C@H]1CCN(C)[C@@H]1[C@H](C)Oc1nc2c3c(c(C(F)(F)F)c(-c4ccc(F)c5sc(N)c(C#N)c45)c(F)c3n1)OCCN2[C@H](C)c1cccnc1N] | 2-amino-4-(4-((R)-1-(2-aminopyridin-3-yl)ethyl)-10-fluoro-2-((S)-1-((2R,3S)-3-methoxy-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 741.3 |

TABLE 1-continued

| No | Structure | Chemical Name | [M + H]+ |
|---|---|---|---|
| 666 | 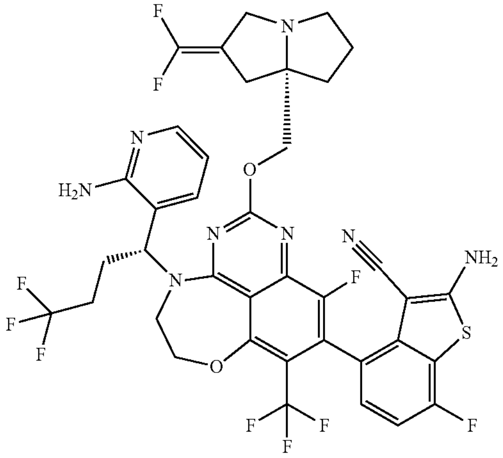 [SMILES: N#Cc1c(N)sc2c(F)ccc(-c3c(C(F)(F)F)c4c5c(nc(OC[C@@]67CCCN6CC(=C(F)F)C7)nc5c3F)N([C@H](CCC(F)(F)F)c3cccnc3N)CCO4)c12] | 2-amino-4-(4-((R)-1-(2-aminopyridin-3-yl)-4,4,4-trifluorobutyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 853.2 |
| 667 | 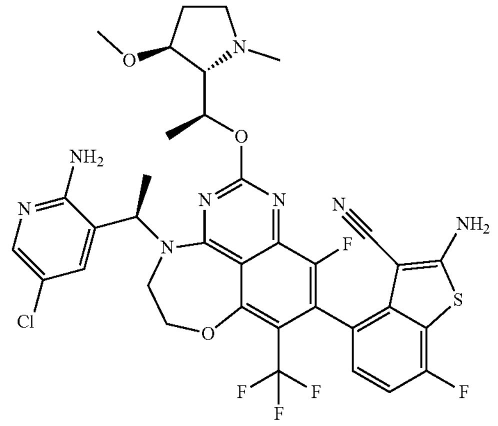 [SMILES: CO[C@H]1CCN(C)[C@@H]1[C@H](C)Oc1nc2c3c(c(C(F)(F)F)c(-c4ccc(F)c5sc(N)c(C#N)c45)c(F)c3n1)OCCN2[C@H](C)c1cc(Cl)cnc1N] | 2-amino-4-(4-((R)-1-(2-amino-5-chloropyridin-3-yl)ethyl)-10-fluoro-2-((S)-1-((2R,3S)-3-methoxy-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 775.2 |
| 668 | 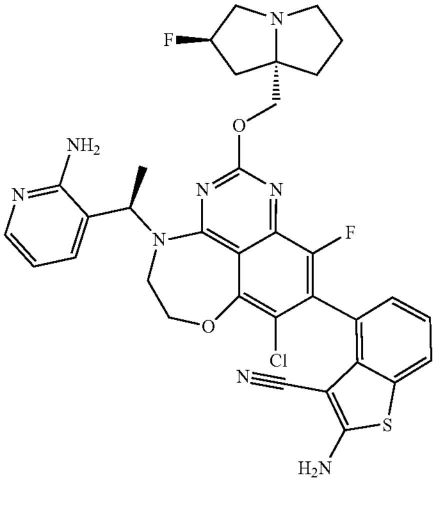 [SMILES: C[C@H](c1cccnc1N)N1CCOc2c(Cl)c(-c3cccc4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)benzo[b]thiophene-3-carbonitrile (single diastereomer, S atropisomer at $R^7$ substituent) | 689.1 |

TABLE 1-continued

| No | Structure | Chemical Name | [M + H]+ |
|---|---|---|---|
| 669 | 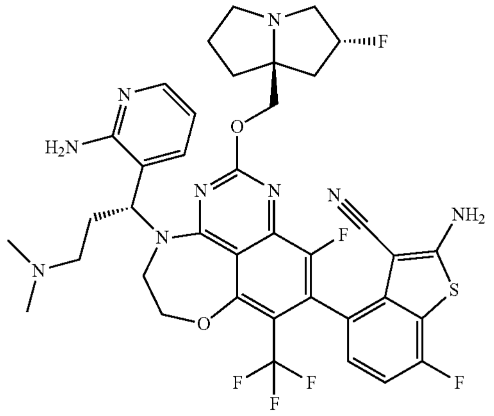 [SMILES: CN(C)CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-3-(dimethylamino)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 798.3 |
| 670 | 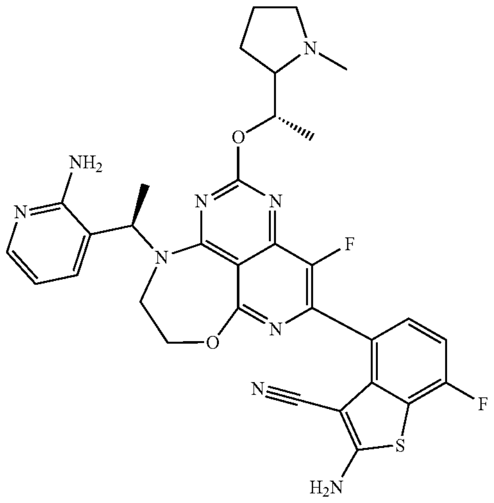 | 2-amino-4-(10-((R)-1-(2-aminopyridin-3-yl)ethyl)-4-fluoro-2-((1S)-1-(1-methylpyrrolidin-2-yl)ethoxy)-9,10-dihydro-8H-7-oxa-1,3,6,10-tetraazacyclohepta[de]naphthalen-5-yl)-7-fluorobenzo[b]thiophene-3-carbonitrile (single diastereomer) | 644.3 |
| 671 | 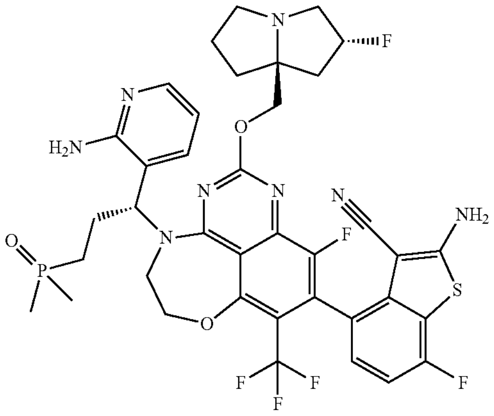 [SMILES: CP(C)(=O)CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-3-(dimethylphosphoryl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 831.1 |

TABLE 1-continued

| No | Structure | Chemical Name | [M + H]$^+$ |
|---|---|---|---|
| 672 | 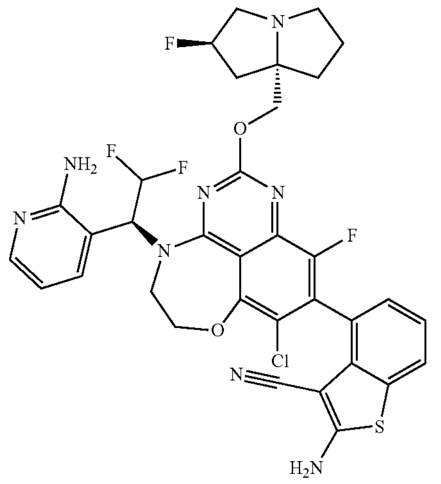 [SMILES: N#Cc1c(N)sc2cccc(-c3c(Cl)c4c5c(nc(OC[C@@]67CCCN6C[C@H](F)C7)nc5c3F)N([C@@H](c3cccnc3N)C(F)F)CCO4)c12] | 2-amino-4-(4-((S)-1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)benzo[b]thiophene-3-carbonitrile (single diastereomer, R atropisomer at $R^7$ substituent) | 724.9 |
| 673 | 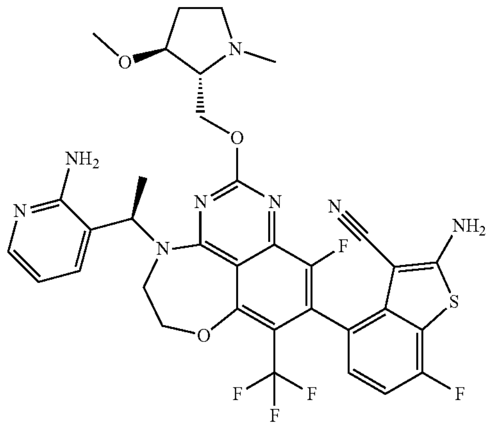 [SMILES: CO[C@H]1CCN(C)[C@@H]1COc1nc2c3c(c(C(F)(F)F)c(-c4ccc(F)c5sc(N)c(C#N)c45)c(F)c3n1)OCCN2[C@H](C)c1cccnc1N] | 2-amino-4-(4-((R)-1-(2-aminopyridin-3-yl)ethyl)-10-fluoro-2-(((2R,3S)-3-methoxy-1-methylpyrrolidin-2-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 727.2 |
| 674 | 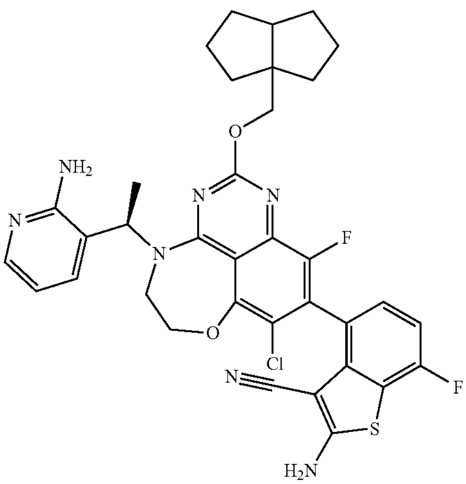 [SMILES: C[C@H](c1cccnc1N)N1CCOc2c(Cl)c(-c3ccc(F)c4sc(N)c(C#N)c34)c(F)c3nc(OCC45CCCC4CCC5)nc1c23] | 2-amino-4-(4-((R)-1-(2-aminopyridin-3-yl)ethyl)-8-chloro-10-fluoro-2-((hexahydropentalen-3a(1H)-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 688.1 |

TABLE 1-continued

| No | Structure | Chemical Name | [M + H]+ |
|---|---|---|---|
| 675 | 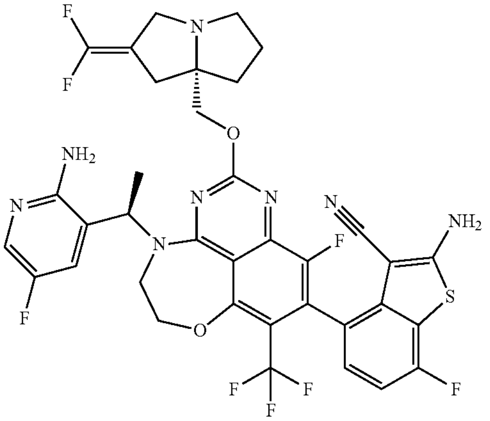 [SMILES: C[C@H](c1cc(F)cnc1N)N1CCOc2c(C(F)(F)F)c(-c3ccc(F)c4sc(N)c(C#N)c34)c(F)c3nc(OC[C@@]45CCCN4CC(=C(F)F)C5)nc1c23] | 2-amino-4-(4-((R)-1-(2-amino-5-fluoropyridin-3-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 789.3 |
| 676 | 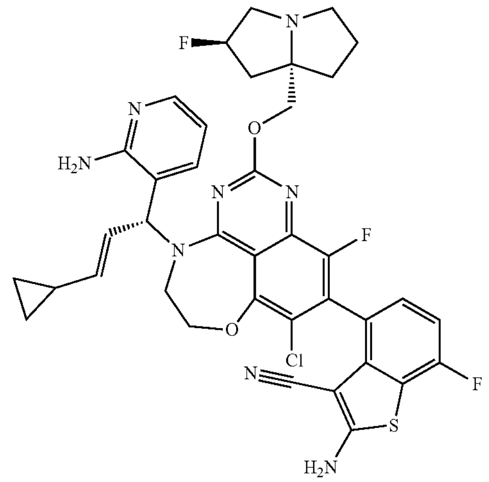 [SMILES: N#Cc1c(N)sc2c(F)ccc(-c3c(Cl)c4c5c(nc(OC[C@@]67CCCN6C[C@H](F)C7)nc5c3F)N([C@H](/C=C/C3CC3)c3cccnc3N)CCO4)c12] | 2-amino-4-(4-((R,E)-1-(2-aminopyridin-3-yl)-3-cyclopropylallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 759.0 |
| 677 | 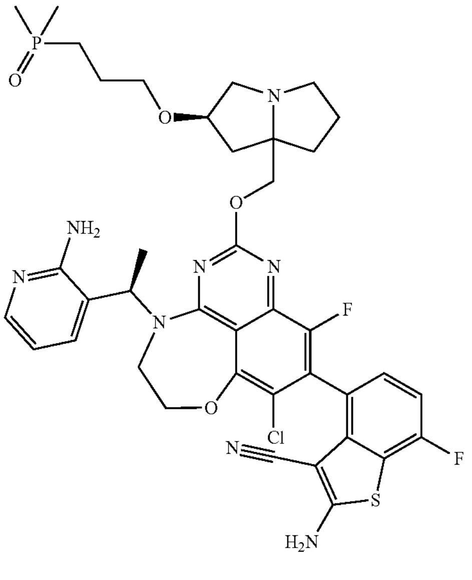 [SMILES: C[C@H](c1cccnc1N)N1CCOc2c(Cl)c(-c3ccc(F)c4sc(N)c(C#N)c34)c(F)c3nc(OCC45CCCN4C[C@H](OCCCP(C)(C)=O)C5)nc1c23] | 2-amino-4-(4-((R)-1-(2-aminopyridin-3-yl)ethyl)-8-chloro-2-(((2R)-2-(3-(dimethylphosphoryl)propoxy)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 824.2 |

TABLE 1-continued

| No | Structure | Chemical Name | [M + H]+ |
|---|---|---|---|
| 678 | 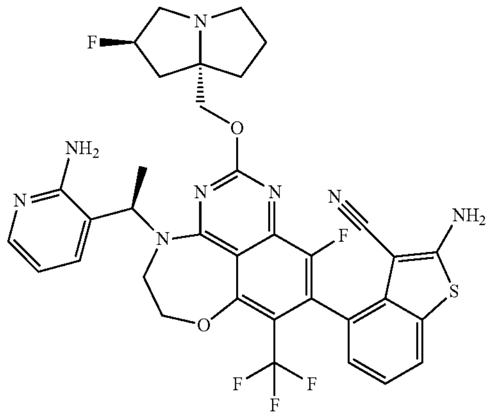 [SMILES: C[C@H](c1cccnc1N)N1CCOc2c(C(F)(F)F)c(-c3cccc4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)benzo[b]thiophene-3-carbonitrile (single diastereomer, R atropisomer at $R^7$ substituent) | 723.0 |
| 679 | 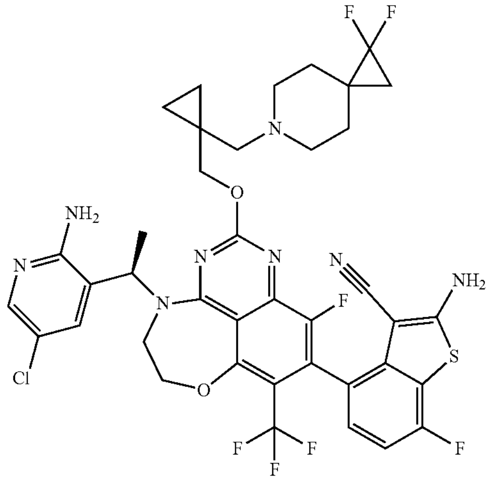 [SMILES: C[C@H](c1cc(Cl)cnc1N)N1CCOc2c(C(F)(F)F)c(-c3ccc(F)c4sc(N)c(C#N)c34)c(F)c3nc(OCC4(CN5CCC6(CC5)CC6(F)F)CC4)nc1c23] | 2-amino-4-(4-((R)-1-(2-amino-5-chloropyridin-3-yl)ethyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 847.1 |
| 680 | 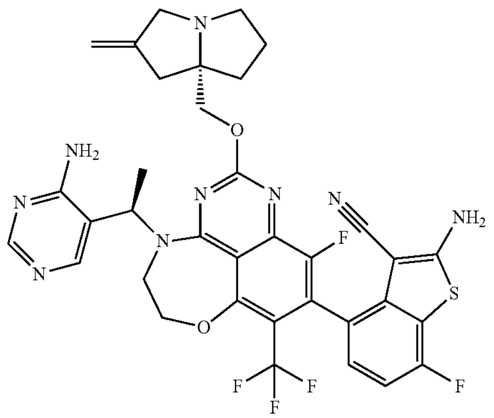 [SMILES: C=C1CN2CCC[C@@]2(COc2nc3c4c(c(C(F)(F)F)c(-c5ccc(F)c6sc(N)c(C#N)c56)c(F)c4n2)OCCN3[C@H](C)c2cncnc2N)C1] | 2-amino-4-(4-((R)-1-(4-aminopyrimidin-5-yl)ethyl)-10-fluoro-2-(((S)-2-methylenetetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 736.3 |

TABLE 1-continued

| No | Structure | Chemical Name | [M + H]+ |
|---|---|---|---|
| 681 | 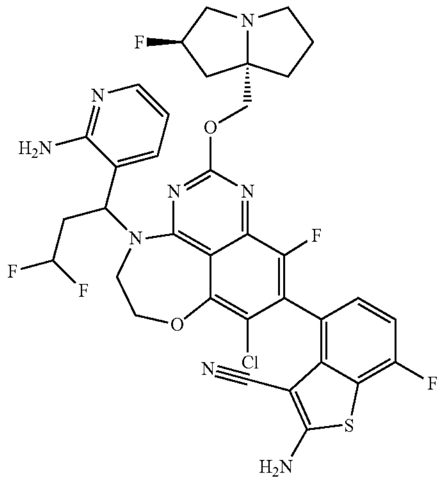 [SMILES: N#Cc1c(N)sc2c(F)ccc(-c3c(Cl)c4c5c(nc(OC[C@@]67CCCN6C[C@H](F)C7)nc5c3F)N(C(CC(F)F)c3cccnc3N)CCO4)c12] | 2-amino-4-(4-(1-(2-aminopyridin-3-yl)-3,3-difluoropropyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 756.9 |
| 682 | 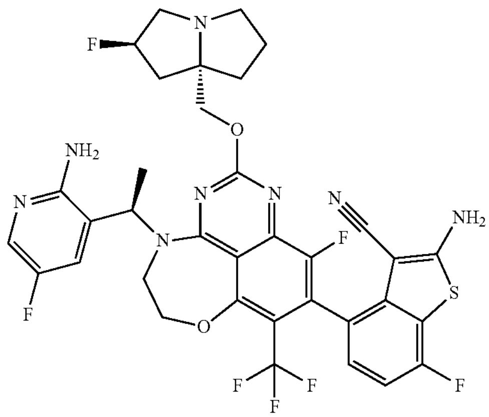 | 2-amino-4-(4-((R)-1-(2-amino-5-fluoropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 759.2 |
| 683 | 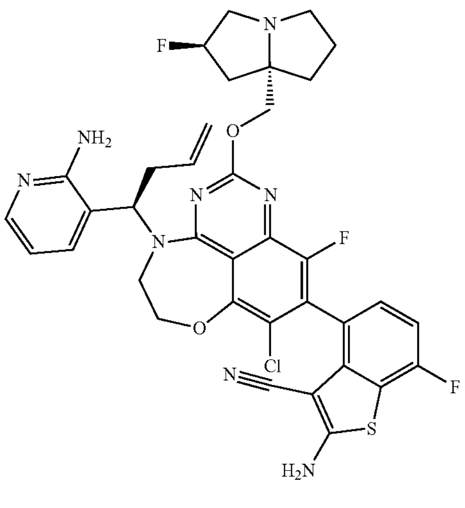 [SMILES: C=CC[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)but-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 732.9 |

TABLE 1-continued

| No | Structure | Chemical Name | [M + H]+ |
|---|---|---|---|
| 684 | 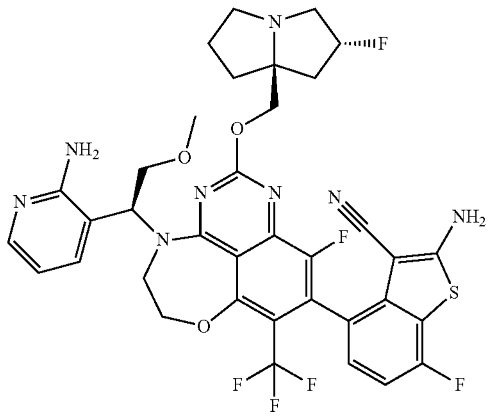 [SMILES: COC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((S)-1-(2-aminopyridin-3-yl)-2-methoxyethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 771.3 |
| 685 | 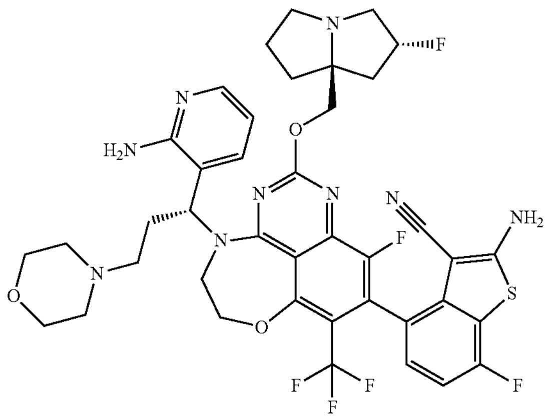 | 2-amino-4-(4-((R)-1-(2-aminopyridin-3-yl)-3-morpholinopropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 840.4 |
| 686 | 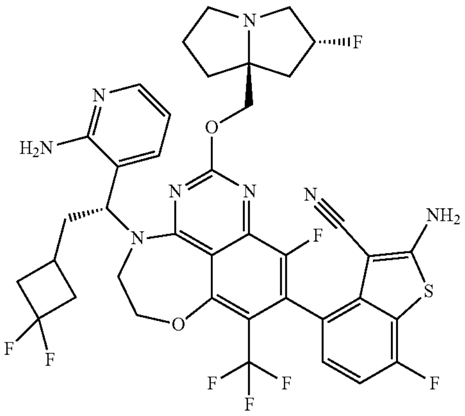 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CC(F)(F)C3)c3cccnc3N)CCO4)c12] | 2-amino-4-(4-((R)-1-(2-aminopyridin-3-yl)-2-(3,3-difluorocyclobutyl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 831.4 |

TABLE 1-continued

| No | Structure | Chemical Name | [M + H]+ |
|---|---|---|---|
| 687 | 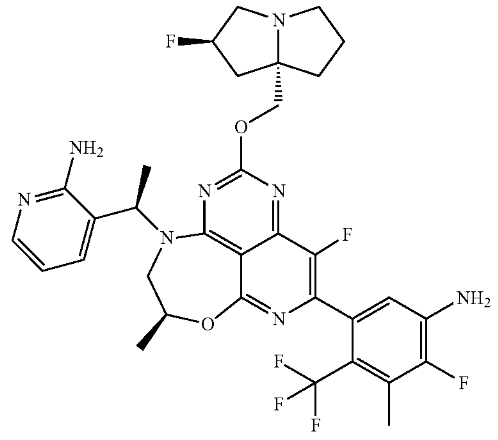 [SMILES: Cc1c(F)c(N)cc(-c2nc3c4c(nc(OC[C@@]56CCCN5C[C@H](F)C6)nc4c2F)N([C@H](C)c2cccnc2N)C[C@H](C)O3)c1C(F)(F)F] | 3-((R)-1-((S)-5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8-methyl-8,9-dihydro-10H-7-oxa-1,3,6,10-tetraazacyclohepta[de]naphthalen-10-yl)ethyl)pyridin-2-amine (single diastereomer) | 689.3 |
| 688 | 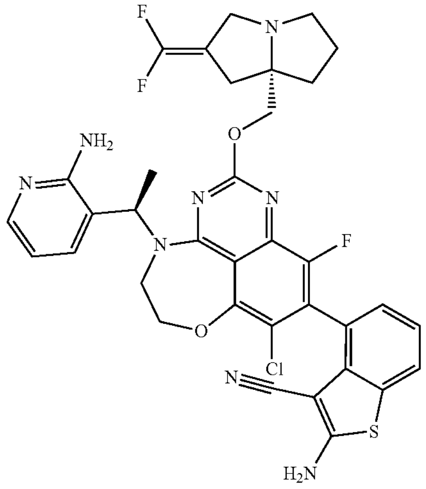 [SMILES: C[C@H](c1cccnc1N)N1CCOc2c(Cl)c(-c3cccc4sc(N)c(C#N)c34)c(F)c3nc(OC[C@@]45CCCN4CC(=C(F)F)C5)nc1c23] | 2-amino-4-(4-((R)-1-(2-aminopyridin-3-yl)ethyl)-8-chloro-2-(((S)-2-(difluoromethylene)tetrahydro-1H-pyrrolizin-7a(5H)-yl)methoxy)-10-fluoro-5,6-dihydro-4H-[1,4]oxazepino[5,6,7-de]quinazolin-9-yl)benzo[b]thiophene-3-carbonitrile (single diastereomer, S atropisomer at $R^7$ substituent) | 736.8 |
| 689 | 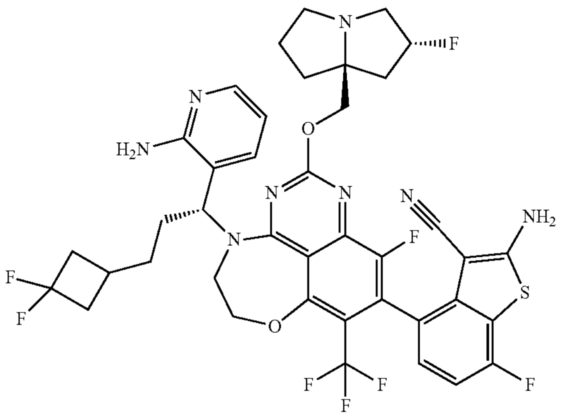 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CC(F)(F)C3)c3cccnc3N)CCO4)c12] | 2-amino-4-(4-((R)-1-(2-aminopyridin-3-yl)-3-(3,3-difluorocyclobutyl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 845.2 |

TABLE 1-continued

| No | Structure | Chemical Name | [M + H]+ |
|---|---|---|---|
| 690 | 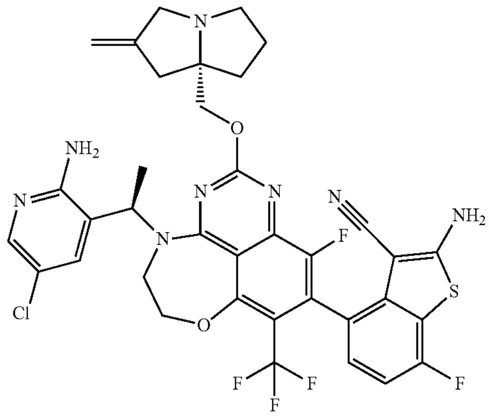 [SMILES: C=C1CN2CCC[C@@]2(COc2nc3c4c(c(C(F)(F)F)c(-c5ccc(F)c6sc(N)c(C#N)c56)c(F)c4n2)OCCN3[C@H](C)c2cc(Cl)cnc2N)C1] | 2-amino-4-(4-((R)-1-(2-amino-5-chloropyridin-3-yl)ethyl)-10-fluoro-2-(((S)-2-methylenetetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 769.3 |
| 691 | 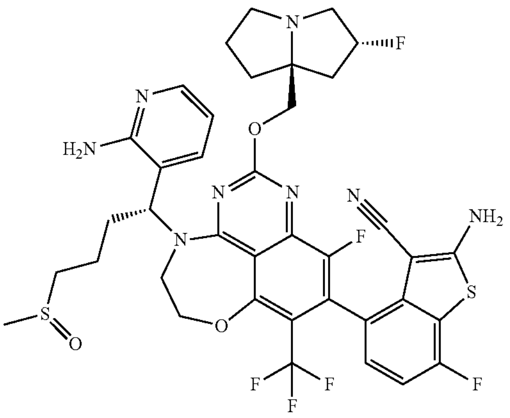 [SMILES: CS(=O)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((1R)-1-(2-aminopyridin-3-yl)-4-(methylsulfinyl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 831.1 |
| 692 | 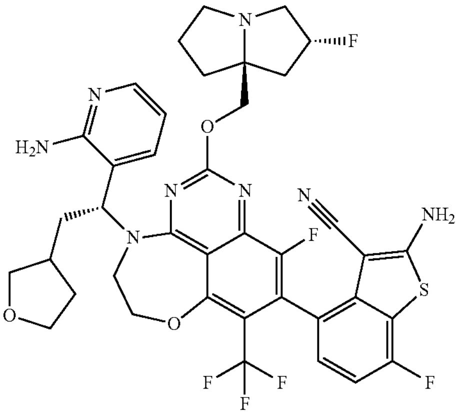 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOC3)c3cccnc3N)CCO4)c12] | 2-amino-4-(4-((1R)-1-(2-aminopyridin-3-yl)-2-(tetrahydrofuran-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 811.3 |

TABLE 1-continued

| No | Structure | Chemical Name | [M + H]$^+$ |
|---|---|---|---|
| 693 | 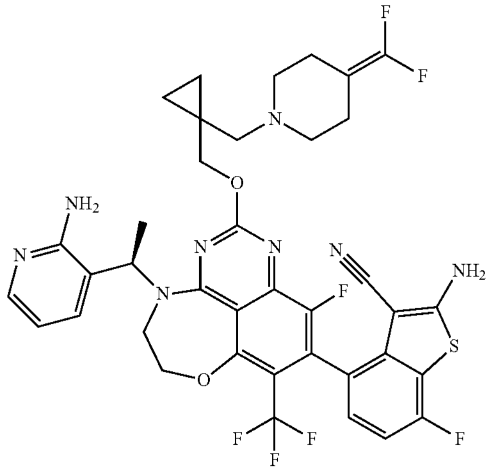 [SMILES: C[C@H](c1cccnc1N)N1CCOc2c(C(F)(F)F)c(-c3ccc(F)c4sc(N)c(C#N)c34)c(F)c3nc(OCC4(CN5CCC(=C(F)F)CC5)CC4)nc1c23] | 2-amino-4-(4-((R)-1-(2-aminopyridin-3-yl)ethyl)-2-((1-((4-(difluoromethylene)piperidin-1-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 799.2 |
| 694 | 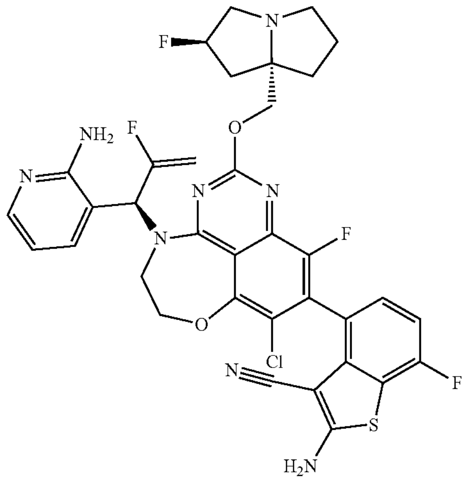 [SMILES: C=C(F)[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((S)-1-(2-aminopyridin-3-yl)-2-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 736.9 |
| 695 | 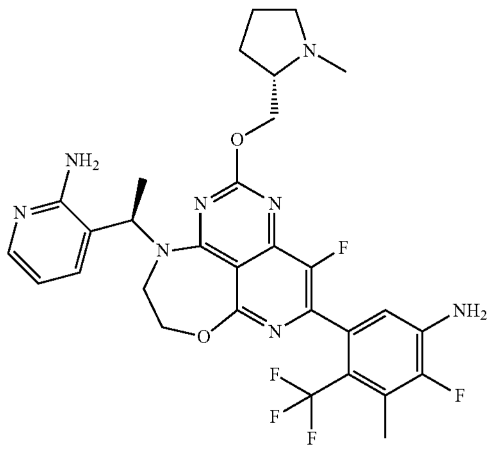 [SMILES: Cc1c(F)c(N)cc(-c2nc3c4c(nc(OC[C@@H]5CCCN5C)nc4c2F)N([C@H](C)c2cccnc2N)CCO3)c1C(F)(F)F] | 3-((R)-1-(5-(5-amino-4-fluoro-3-methyl-2-(trifluoromethyl)phenyl)-4-fluoro-2-(((S)-1-methylpyrrolidin-2-yl)methoxy)-8,9-dihydro-10H-7-oxa-1,3,6,10-tetraazacyclohepta[de]naphthalen-10-yl)ethyl)pyridin-2-amine (single diastereomer) | 631.3 |

TABLE 1-continued

| No | Structure | Chemical Name | [M + H]+ |
|---|---|---|---|
| 696 | 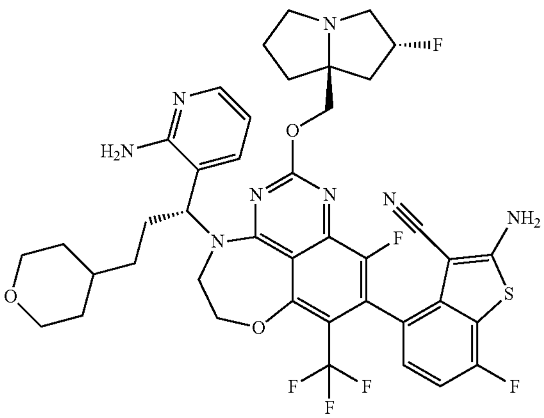 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 839.2 |
| 697 | 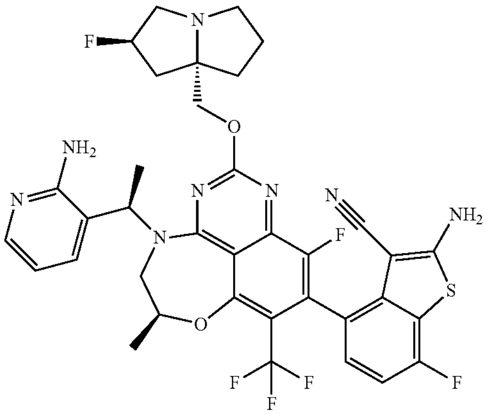 [SMILES: C[C@H](c1cccnc1N)N1C[C@H](C)Oc2c(C(F)(F)F)c(-c3ccc(F)c4sc(N)c(C#N)c34)c(F)c3nc(OC[C@@]45CCCN4C[C@H](F)C5)nc1c23] | 2-amino-4-((6S)-4-((R)-1-(2-aminopyridin-3-yl)ethyl)-10-fluoro-2-(((2R,7aS)-2-fluorotetrahydro-1H-pyrrolizin-7a(5H)-yl)methoxy)-6-methyl-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 755.0 |
| 698 | 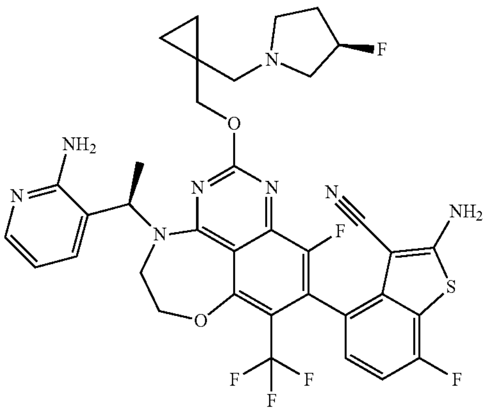 [SMILES: C[C@H](c1cccnc1N)N1CCOc2c(C(F)(F)F)c(-c3ccc(F)c4sc(N)c(C#N)c34)c(F)c3nc(OCC4(CN5CC[C@@H](F)C5)CC4)nc1c23] | 2-amino-4-(4-((R)-1-(2-aminopyridin-3-yl)ethyl)-10-fluoro-2-((1-(((R)-3-fluoropyrrolidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 755.3 |

TABLE 1-continued

| No | Structure | Chemical Name | [M + H]+ |
|---|---|---|---|
| 699 | 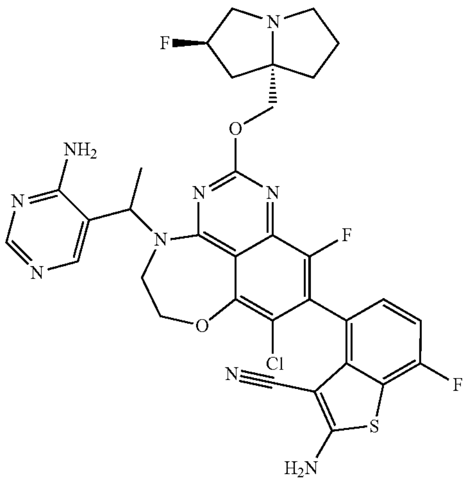 [SMILES: CC(c1cncnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(4-aminopyrimidin-5-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 707.9 |
| 700 | 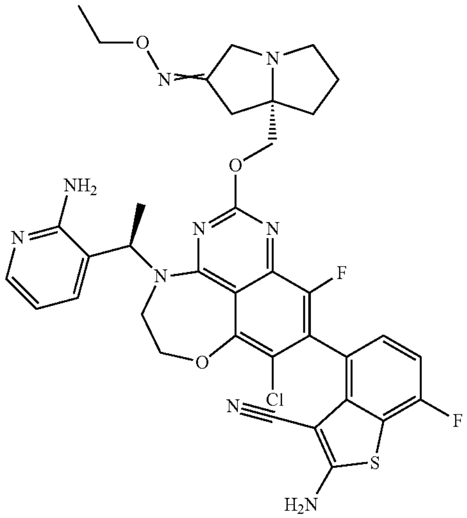 [SMILES: CCON=C1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-2-(((S)-2-(ethoxyimino)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 746.0 |
| 701 | 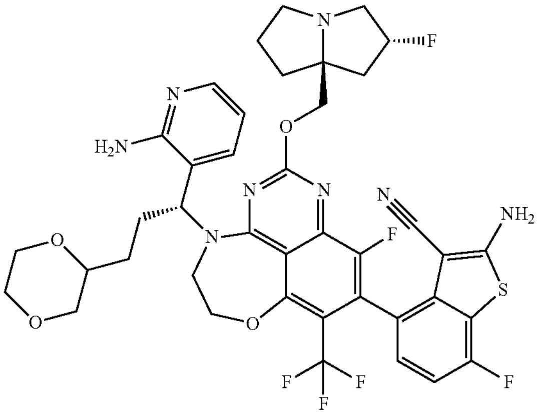 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3COCCO3)c3cccnc3N)CCO4)c12] | 2-amino-4-(4-((1R)-1-(2-aminopyridin-3-yl)-3-(1,4-dioxan-2-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 841.3 |

TABLE 1-continued

| No | Structure | Chemical Name | [M + H]+ |
|---|---|---|---|
| 702 | 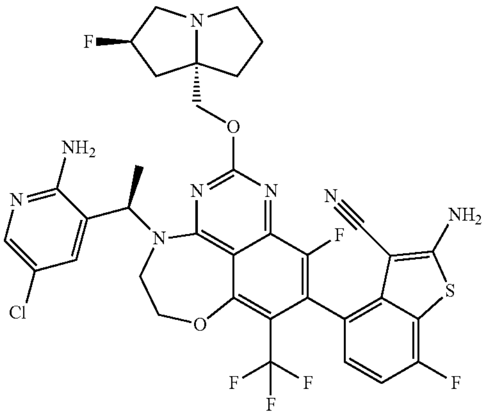 [SMILES: C[C@H](c1cc(Cl)cnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-chloropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 775.1 |
| 703 | 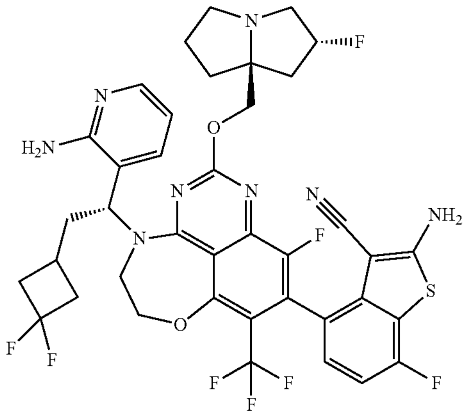 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CC(F)(F)C3)c3cccnc3N)CCO4)c12] | 2-amino-4-(4-((R)-1-(2-aminopyridin-3-yl)-2-(3,3-difluorocyclobutyl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 831.4 |
| 704 | 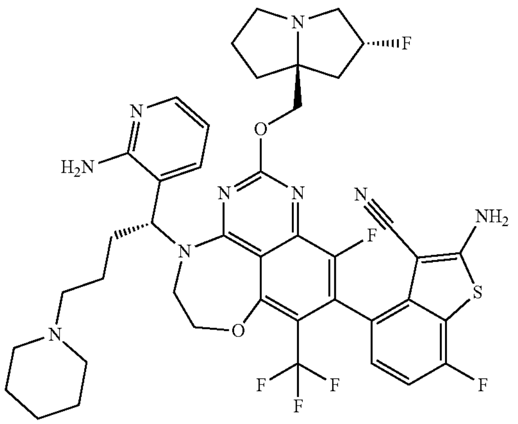 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCCN3CCCCC3)c3cccnc3N)CCO4)c12] | 2-amino-4-(4-((R)-1-(2-aminopyridin-3-yl)-4-(piperidin-1-yl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 852.3 |

TABLE 1-continued

| No | Structure | Chemical Name | [M + H]+ |
|---|---|---|---|
| 705 | 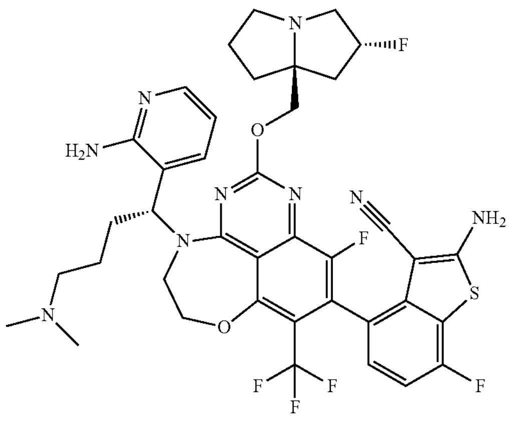 | 2-amino-4-(4-((R)-1-(2-aminopyridin-3-yl)-4-(dimethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 812.4 |
| 706 | 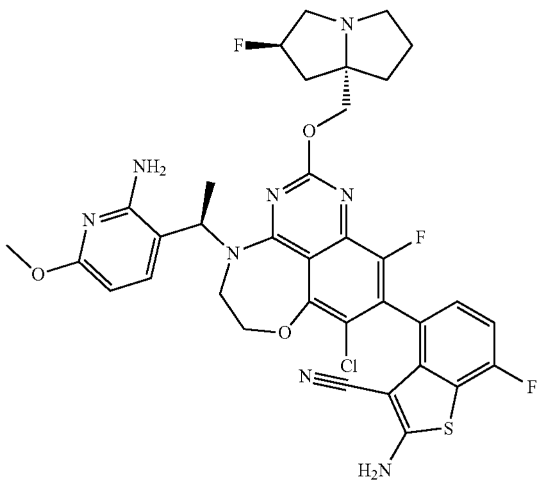 [SMILES: COc1ccc([C@@H](C)N2CCOc3c(Cl)c(-c4ccc(F)c5sc(N)c(C#N)c45)c(F)c4nc(OC[C@@]56CCCN5C[C@H](F)C6)nc2c34)c(N)n1] | 2-amino-4-(4-((R)-1-(2-amino-6-methoxypyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 736.9 |
| 707 | 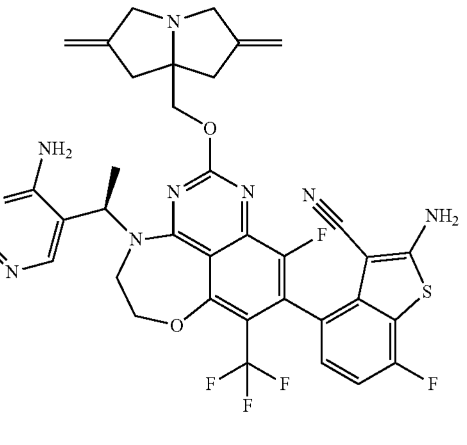 | 2-amino-4-(4-((R)-1-(4-aminopyrimidin-5-yl)ethyl)-2-((2,6-dimethylenetetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 748.3 |

TABLE 1-continued

| No | Structure | Chemical Name | [M + H]$^+$ |
|---|---|---|---|
| 708 | 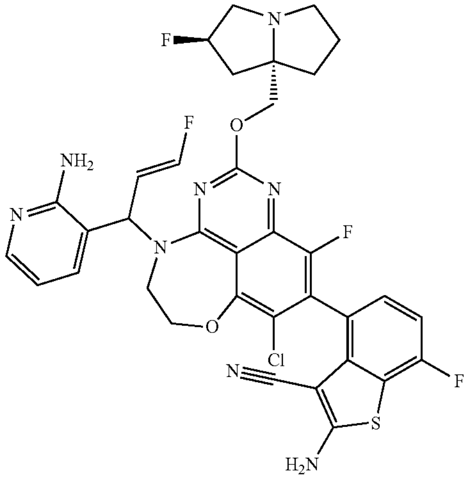 [SMILES: N#Cc1c(N)sc2c(F)ccc(-c3c(Cl)c4c5c(nc(OC[C@@]67CCCN6C[C@H](F)C7)nc5c3F)N(C(/C=C/F)c3cccnc3N)CCO4)c12] | 2-amino-4-(4-((E)-1-(2-aminopyridin-3-yl)-3-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 737.0 |
| 709 | 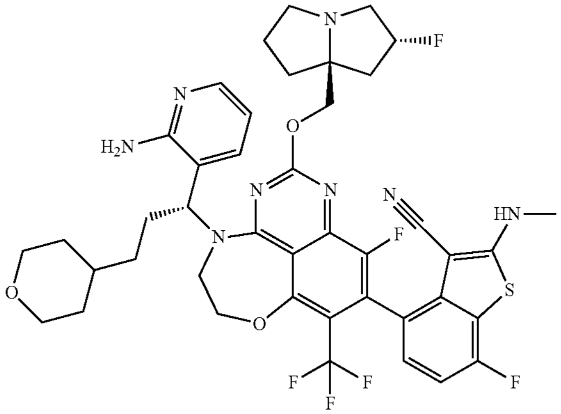 [SMILES: CNc1sc2c(F)ccc(-c3c(C(F)(F)F)c4c5c(nc(OC[C@@]67CCCN6C[C@H](F)C7)nc5c3F)N([C@H](CCC3CCOCC3)c3cccnc3N)CCO4)c2c1C#N] | 4-(4-((R)-1-(2-aminopyridin-3-yl)-3-(tetrahydro-2H-pyran-4-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluoro-2-(methylamino)benzo[b]thiophene-3-carbonitrile (single diastereomer, S atropisomer at $R^7$ substituent) | 853.3 |
| 710 | 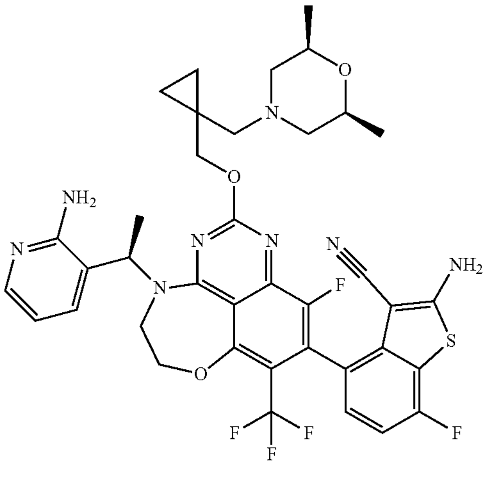 [SMILES: C[C@@H]1CN(CC2(COc3nc4c5c(c(C(F)(F)F)c(-c6ccc(F)c7sc(N)c(C#N)c67)c(F)c5n3)OCCN4[C@H](C)c3cccnc3N)CC2)C[C@H](C)O1] | 2-amino-4-(4-((R)-1-(2-aminopyridin-3-yl)ethyl)-2-((1-(((2S,6R)-2,6-dimethylmorpholino)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.2 |

TABLE 1-continued

| No | Structure | Chemical Name | [M + H]+ |
|---|---|---|---|
| 711 | 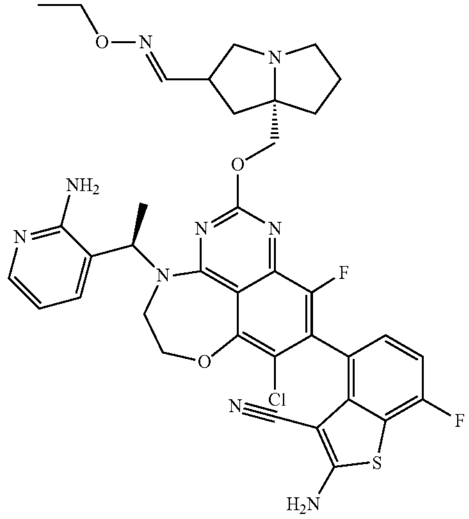 [SMILES: CCO/N=C/C1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-2-(((7aS)-2-((E)-(ethoxyimino)methyl)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (diastereomer mixture) | 760.0 |
| 712 | 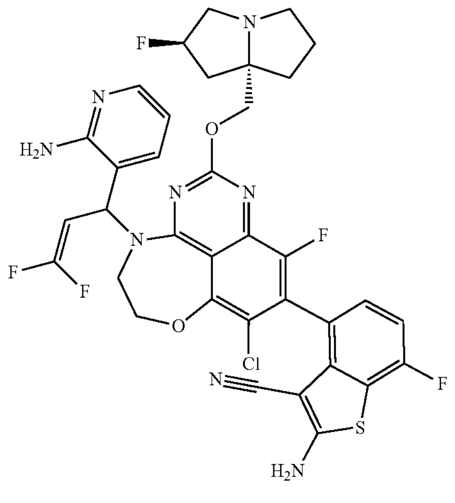 [SMILES: N#Cc1c(N)sc2c(F)ccc(-c3c(Cl)c4c5c(nc(OC[C@@]67CCCN6C[C@H](F)C7)nc5c3F)N(C(C=C(F)F)c3cccnc3N)CCO4)c12] | 2-amino-4-(4-(1-(2-aminopyridin-3-yl)-3,3-difluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 755.0 |
| 713 | 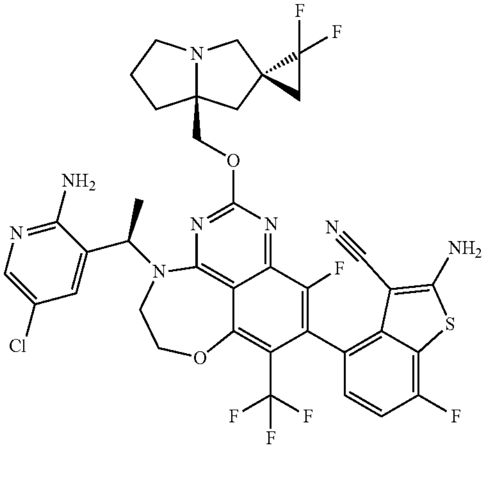 [SMILES: C[C@H](c1cc(Cl)cnc1N)N1CCOc2c(C(F)(F)F)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(2-amino-5-chloropyridin-3-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 819.2 |

TABLE 1-continued

| No | Structure | Chemical Name | $[M + H]^+$ |
|---|---|---|---|
| 714 | 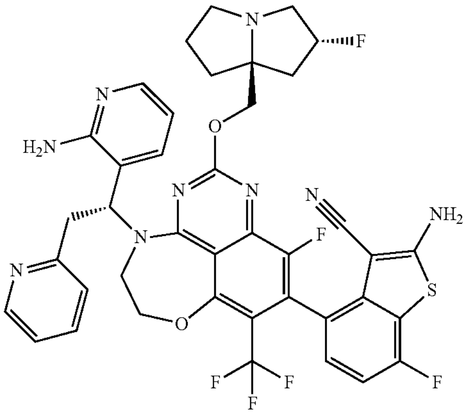 [SMILES: N#Cc1c(N)sc2c(F)ccc(-c3c(C(F)(F)F)c4c5c(nc(OC[C@@]67CCCN6C[C@H](F)C7)nc5c3F)N([C@H](Cc3ccccn3)c3cccnc3N)CCO4)c12] | 2-amino-4-(4-((R)-1-(2-aminopyridin-3-yl)-2-(pyridin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 818.3 |
| 715 | 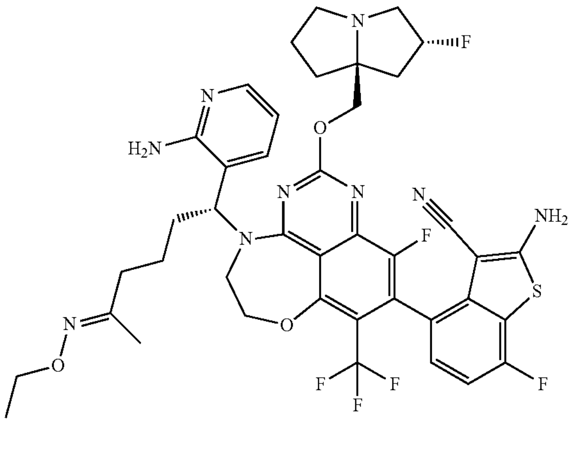 [SMILES: CCO/N=C(\C)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R,E)-1-(2-aminopyridin-3-yl)-5-(ethoxyimino)hexyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 854.3 |
| 716 | 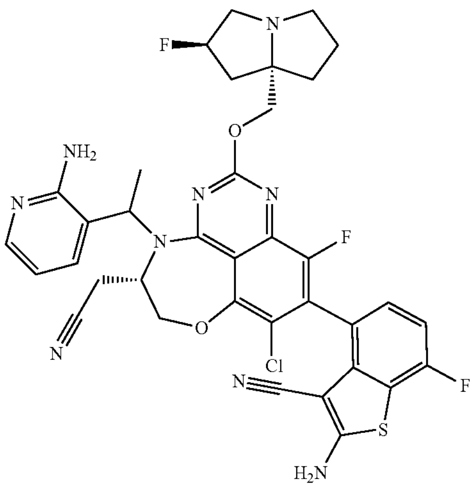 [SMILES: CC(c1cccnc1N)N1c2nc(OC[C@@]34CCCN3C[C@H](F)C4)nc3c(F)c(-c4ccc(F)c5sc(N)c(C#N)c45)c(Cl)c(c23)OC[C@@H]1CC#N] | 2-amino-4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 745.8 |

TABLE 1-continued

| No | Structure | Chemical Name | [M + H]+ |
|---|---|---|---|
| 717 | 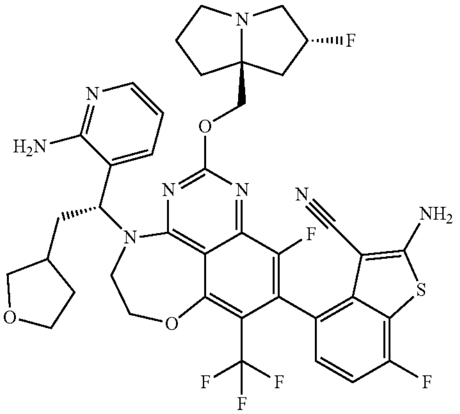 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOC3)c3cccnc3N)CCO4)c12] | 2-amino-4-(4-((1R)-1-(2-aminopyridin-3-yl)-2-(tetrahydrofuran-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 811.3 |
| 718 | 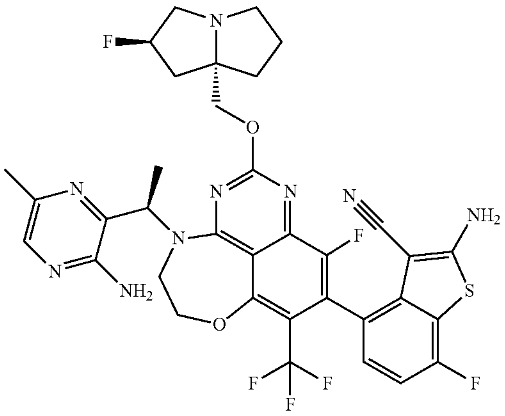 [SMILES: Cc1cnc(N)c([C@@H](C)N2CCOc3c(C(F)(F)F)c(-c4ccc(F)c5sc(N)c(C#N)c45)c(F)c4nc(OC[C@@]56CCCN5C[C@H](F)C6)nc2c34)n1] | 2-amino-4-(4-((R)-1-(3-amino-6-methylpyrazin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 756.3 |
| 719 | 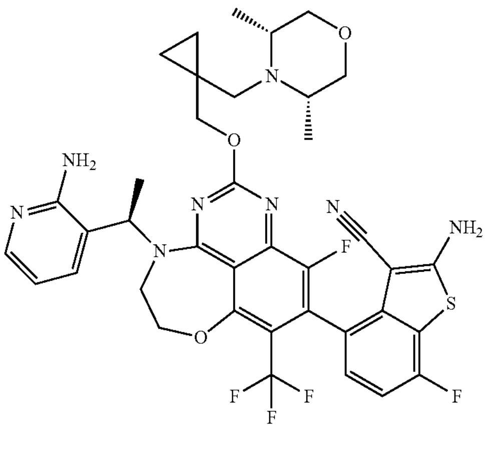 [SMILES: C[C@H](c1cccnc1N)N1CCOc2c(C(F)(F)F)c(-c3ccc(F)c4sc(N)c(C#N)c34)c(F)c3nc(OCC4(CN5[C@H](C)COC[C@@H]5C)CC4)nc1c23] | 2-amino-4-(4-((R)-1-(2-aminopyridin-3-yl)ethyl)-2-((1-(((3S,5R)-3,5-dimethylmorpholino)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 781.2 |

TABLE 1-continued

| No | Structure | Chemical Name | [M + H]+ |
|---|---|---|---|
| 720 | 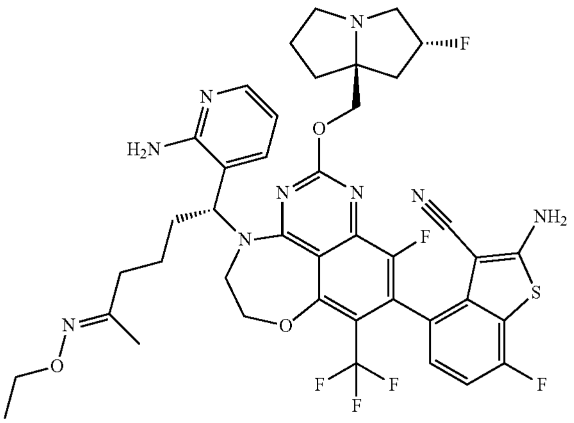 [SMILES: CCO/N=C(\C)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R,E)-1-(2-aminopyridin-3-yl)-5-(ethoxyimino)hexyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 854.3 |
| 721 | 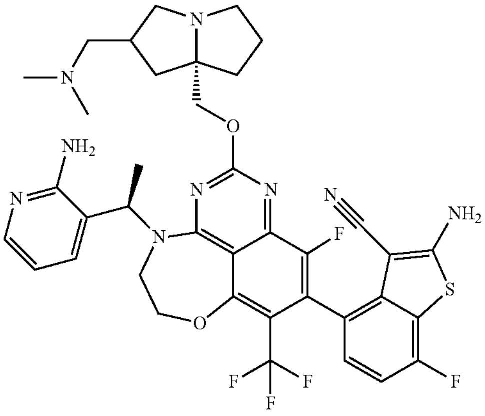 [SMILES: C[C@H](c1cccnc1N)N1CCOc2c(C(F)(F)F)c(-c3ccc(F)c4sc(N)c(C#N)c34)c(F)c3nc(OC[C@@]45CCCN4CC(CN(C)C)C5)nc1c23] | 2-amino-4-(4-((R)-1-(2-aminopyridin-3-yl)ethyl)-2-(((7aS)-2-((dimethylamino)methyl)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 780.2 |
| 722 | 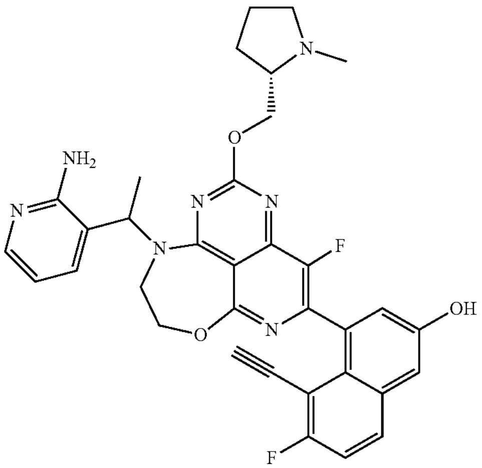 [SMILES: C#Cc1c(F)ccc2cc(O)cc(-c3nc4c5c(nc(OC[C@@H]6CCCN6C)nc5c3F)N(C(C)c3cccnc3N)CCO4)c12] | 4-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-5-ethynyl-6-fluoronaphthalen-2-ol (diastereomer mixture) | 623.9 |

TABLE 1-continued

| No | Structure | Chemical Name | [M + H]+ |
|---|---|---|---|
| 723 | 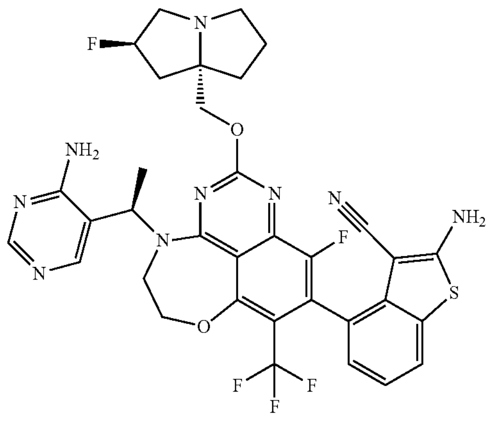 | 2-amino-4-(4-((R)-1-(4-aminopyrimidin-5-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)benzo[b]thiophene-3-carbonitrile (single diastereomer, S atropisomer at $R^7$ substituent) | 724.2 |
| 724 | 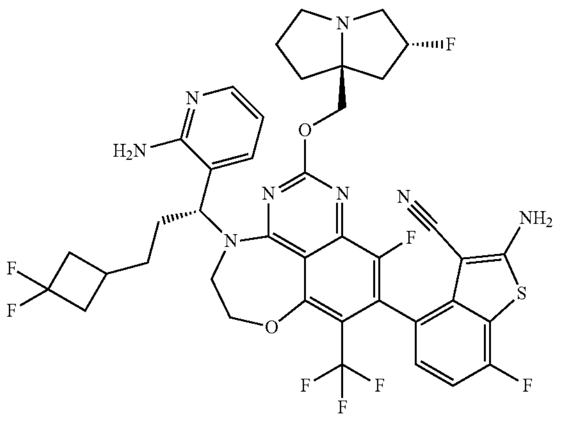 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CC(F)(F)C3)c3cccnc3N)CCO4)c12] | 2-amino-4-(4-((R)-1-(2-aminopyridin-3-yl)-3-(3,3-difluorocyclobutyl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 845.2 |
| 725 | 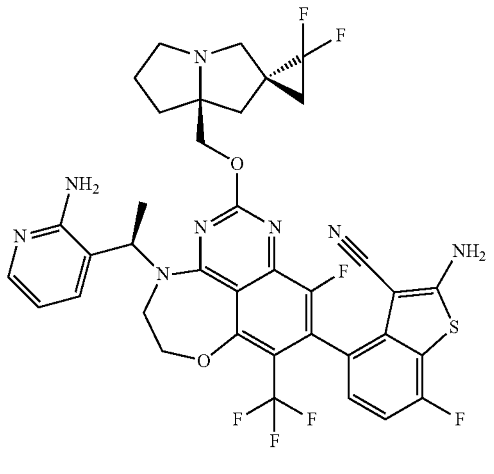 [SMILES: C[C@H](c1cccnc1N)N1CCOc2c(C(F)(F)F)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(2-aminopyridin-3-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 785.0 |

TABLE 1-continued

| No | Structure | Chemical Name | [M + H]+ |
|---|---|---|---|
| 726 | 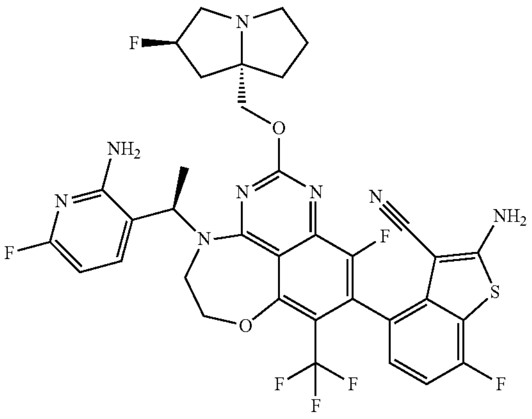 [SMILES: C[C@H](c1ccc(F)nc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-6-fluoropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 759.2 |
| 727 | 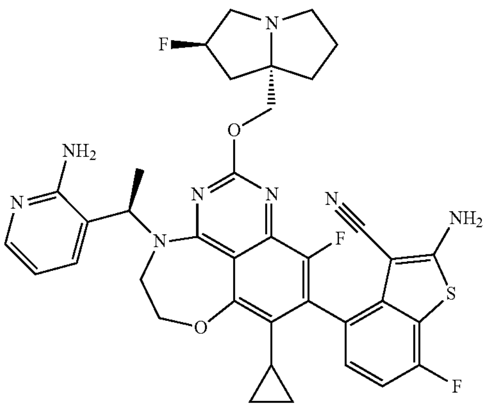 [SMILES: C[C@H](c1cccnc1N)N1CCOc2c(C3CC3)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-cyclopropyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 713.0 |
| 728 | 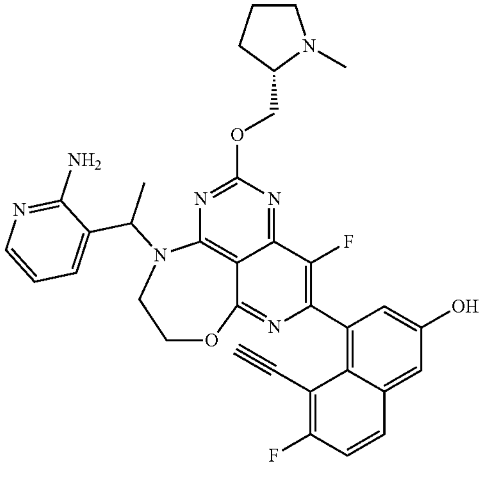 [SMILES: C#Cc1c(F)ccc2cc(O)cc(-c3nc4c5c(nc(OC[C@@H]6CCCN6C)nc5c3F)N(C(C)c3cccnc3N)CCO4)c12] | 4-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-5-ethynyl-6-fluoronaphthalen-2-ol (single diastereomer 1, absolute stereochemistry not determined) | 623.9 |

TABLE 1-continued

| No | Structure | Chemical Name | [M + H]+ |
|---|---|---|---|
| 729 | 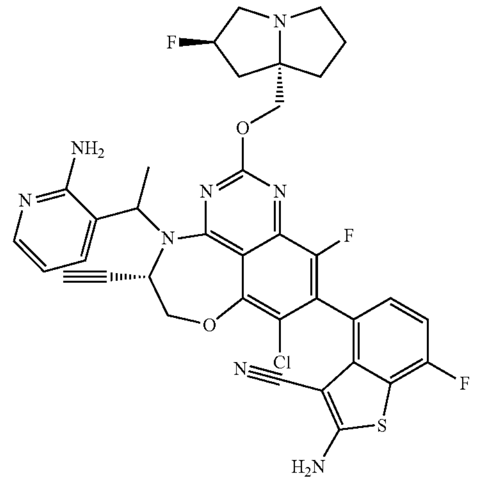 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-((R)-1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 730.9 |
| 730 | 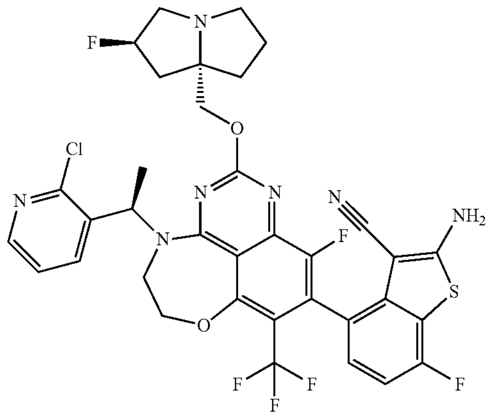 | 2-amino-4-(4-((R)-1-(2-chloropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 760.2 |
| 731 | 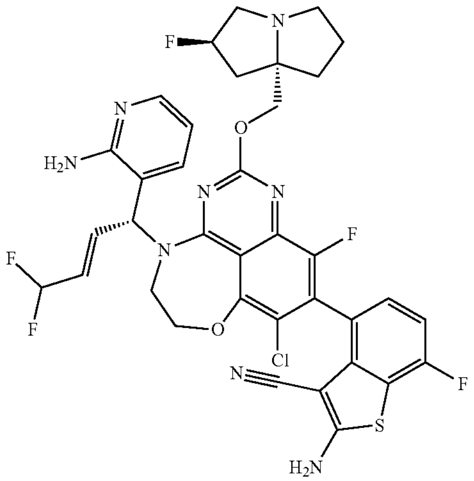 [SMILES: N#Cc1c(N)sc2c(F)ccc(-c3c(Cl)c4c5c(nc(OC[C@@]67CCCN6C[C@H](F)C7)nc5c3F)N([C@H](/C=C/C(F)F)c3cccnc3N)CCO4)c12] | 2-amino-4-(4-((R,E)-1-(2-aminopyridin-3-yl)-4,4-difluorobut-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 768.9 |

TABLE 1-continued

| No | Structure | Chemical Name | [M + H]+ |
|---|---|---|---|
| 732 | 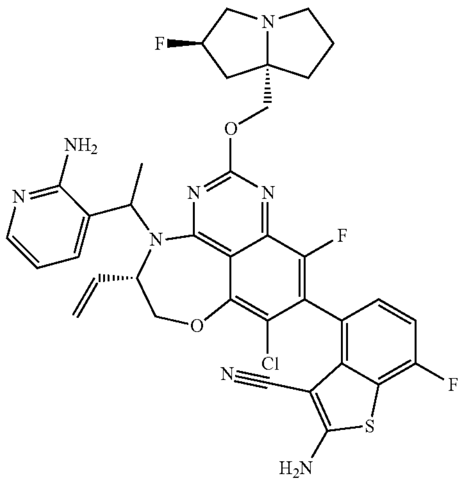 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (mixture of diastereomers) | 732.9 |
| 733 | 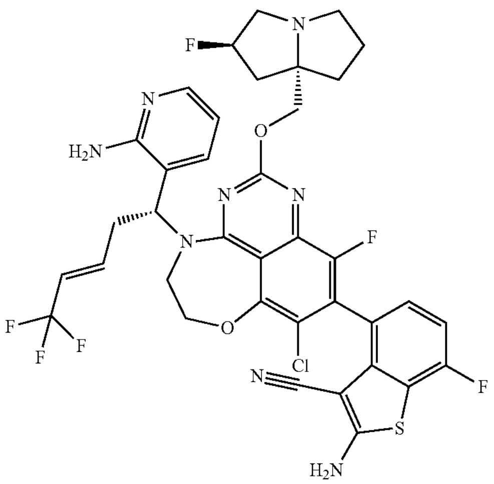 [SMILES: N#Cc1c(N)sc2c(F)ccc(-c3c(Cl)c4c5c(nc(OC[C@@]67CCCN6C[C@H](F)C7)nc5c3F)N([C@H](C/C=C/C(F)(F)F)c3cccnc3N)CCO4)c12] | 2-amino-4-(4-((R,E)-1-(2-aminopyridin-3-yl)-5,5,5-trifluoropent-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 800.9 |
| 734 | 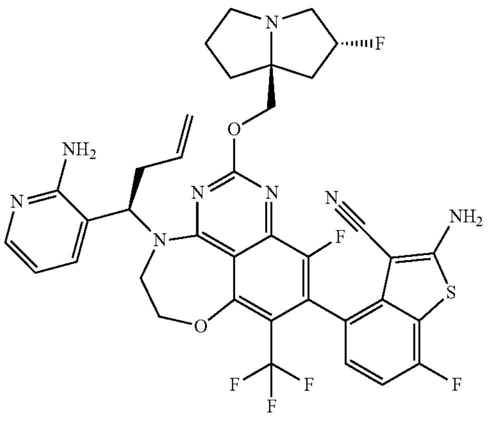 [SMILES: C=CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)but-3-en-1-yl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 766.9 |

TABLE 1-continued

| No | Structure | Chemical Name | [M + H]+ |
|---|---|---|---|
| 735 | 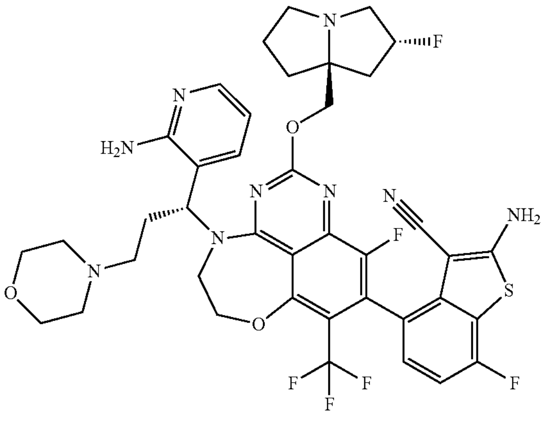 | 2-amino-4-(4-((R)-1-(2-aminopyridin-3-yl)-3-morpholinopropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 840.4 |
| 736 | 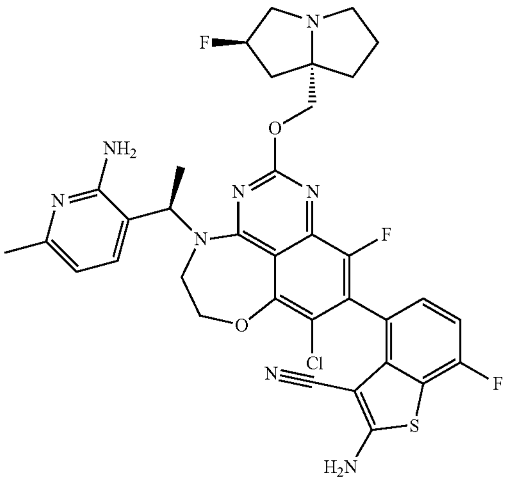 [SMILES: Cc1ccc([C@@H](C)N2CCOc3c(Cl)c(-c4ccc(F)c5sc(N)c(C#N)c45)c(F)c4nc(OC[C@@]56CCCN5C[C@H](F)C6)nc2c34)c(N)n1] | 2-amino-4-(4-((R)-1-(2-amino-6-methylpyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 721.0 |
| 737 | 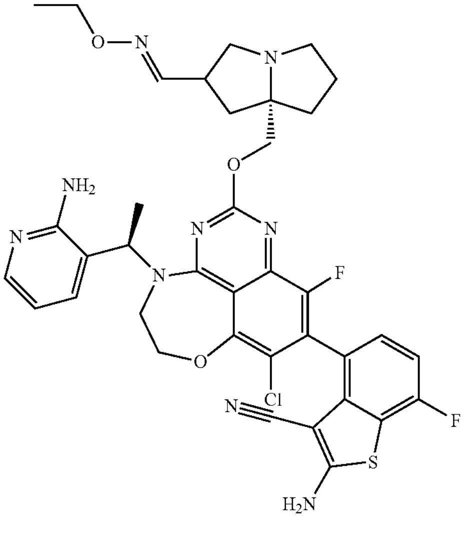 [SMILES: CCO/N=C/C1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-2-(((7aS)-2-((E)-(ethoxyimino)methyl)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (diastereomer mixture) | 760.0 |

TABLE 1-continued

| No | Structure | Chemical Name | [M + H]+ |
|---|---|---|---|
| 738 | 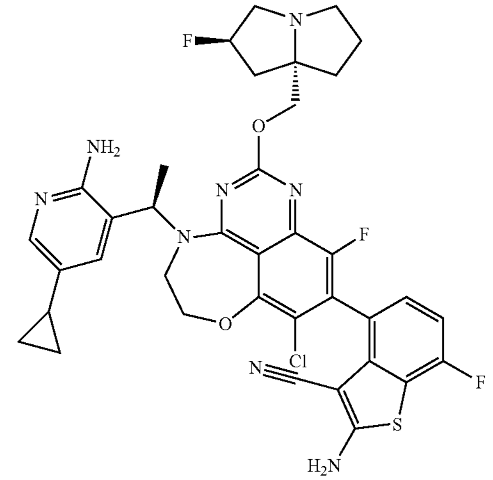 [SMILES: C[C@H](c1cc(C2CC2)cnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-cyclopropylpyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 747.3 |
| 739 | 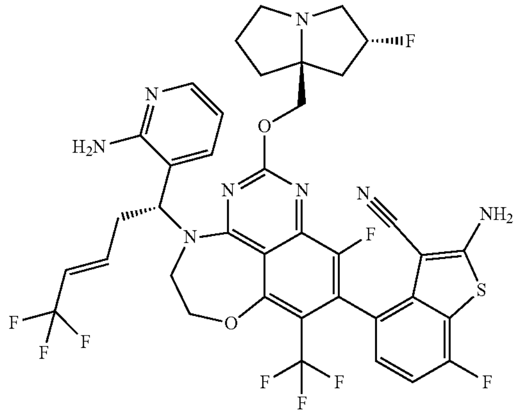 [SMILES: N#Cc1c(N)sc2c(F)ccc(-c3c(C(F)(F)F)c4c5c(nc(OC[C@@]67CCCN6C[C@H](F)C7)nc5c3F)N([C@H](C/C=C/C(F)(F)F)c3cccnc3N)CCO4)c12] | 2-amino-4-(4-((R,E)-1-(2-aminopyridin-3-yl)-5,5,5-trifluoropent-3-en-1-yl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 835.2 |
| 740 | 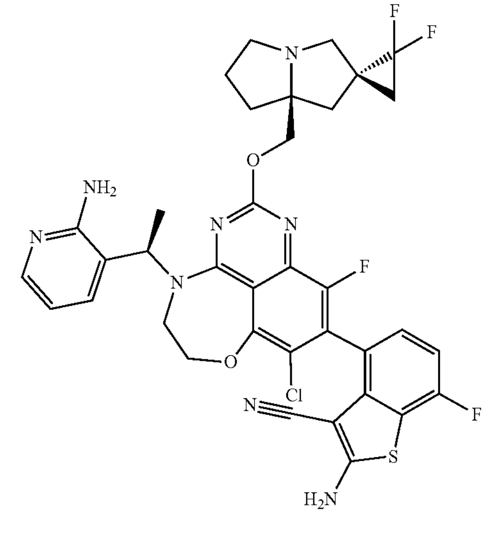 [SMILES: C[C@H](c1cccnc1N)N1CCOc2c(Cl)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(2-aminopyridin-3-yl)ethyl)-8-chloro-2-(((1S,7a'S)-2,2-difluorodihydro-1'H,3'H-spiro[cyclopropane-1,2'-pyrrolizin]-7a'(5'H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 750.9 |

TABLE 1-continued

| No | Structure | Chemical Name | [M + H]+ |
|---|---|---|---|
| 741 | 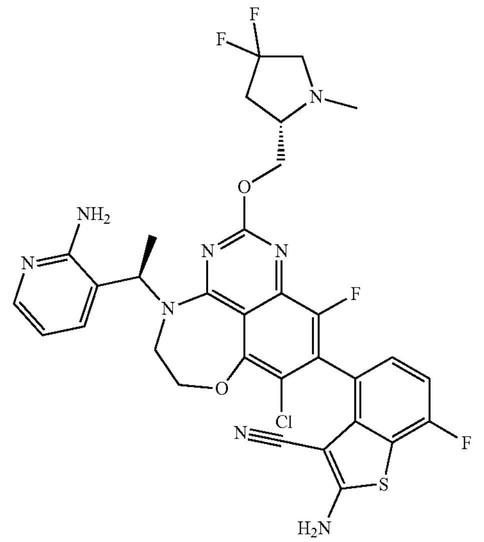 [SMILES: C[C@H](c1cccnc1N)N1CCOc2c(Cl)c(-c3ccc(F)c4sc(N)c(C#N)c34)c(F)c3nc(OC[C@@H]4CC(F)(F)CN4C)nc1c23] | 2-amino-4-(4-((R)-1-(2-aminopyridin-3-yl)ethyl)-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 712.8 |
| 742 | 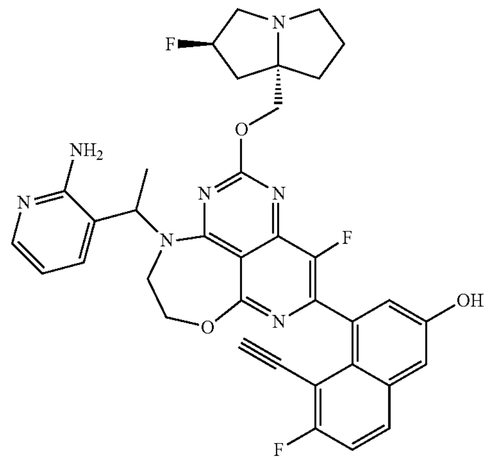 [SMILES: C#Cc1c(F)ccc2cc(O)cc(-c3nc4c5c(nc(OC[C@@]67CCCN6C[C@H](F)C7)nc5c3F)N(C(C)c3cccnc3N)CCO4)c12] | 4-(10-(1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-5-ethynyl-6-fluoronaphthalen-2-ol (mixture of diastereomers) | 667.8 |
| 743 | 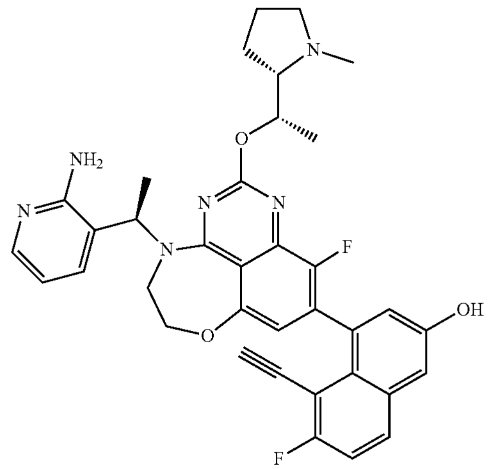 [SMILES: C#Cc1c(F)ccc2cc(O)cc(-c3cc4c5c(nc(O[C@@H](C)[C@@H]6CCCN6C)nc5c3F)N([C@H](C)c3cccnc3N)CCO4)c12] | 4-(10-((R)-1-(2-aminopyridin-3-yl)ethyl)-4-fluoro-2-((S)-1-((S)-1-methylpyrrolidin-2-yl)ethoxy)-9,10-dihydro-8H-7-oxa-1,3,6,10-tetraazacyclohepta[de]naphthalen-5-yl)-5-ethynyl-6-fluoronaphthalen-2-ol (single diastereomer) | 637.9 |

TABLE 1-continued

| No | Structure | Chemical Name | [M + H]+ |
|---|---|---|---|
| 744 | 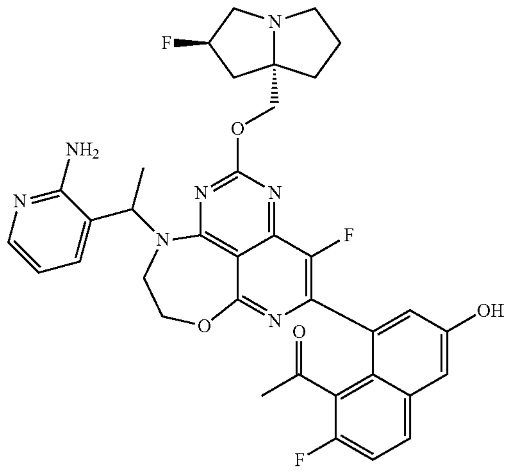 [SMILES: CC(=O)c1c(F)ccc2cc(O)cc(-c3nc4c5c(nc(OC[C@@]67CCCN6C[C@H](F)C7)nc5c3F)N(C(C)c3cccnc3N)CCO4)c12] | 1-(8-(10-(1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (mixture of diastereomers) | 685.8 |
| 745 | 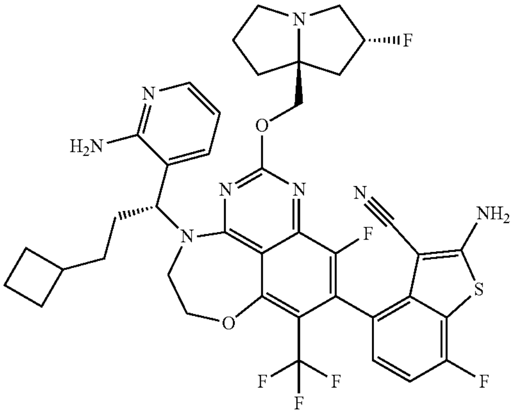 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CCC3)c3cccnc3N)CCO4)c12] | 2-amino-4-(4-((R)-1-(2-aminopyridin-3-yl)-3-cyclobutylpropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 809.3 |
| 746 | 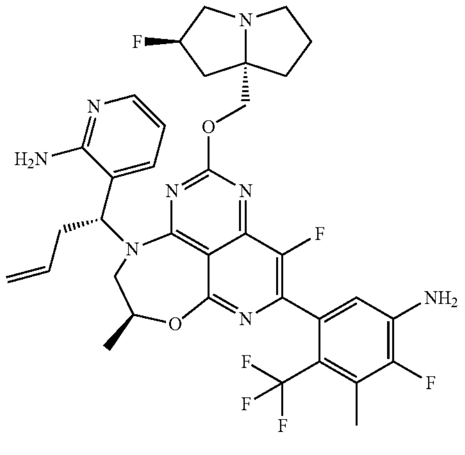 [SMILES: C=CC[C@H](c1cccnc1N)N1C[C@H](C)Oc2nc(-c3cc(N)c(F)c(C)c3C(F)(F)F)c(F)c3nc(OC[C@@]45CCCN4C[C@H](F)C5)nc1c23] | 3-((R)-1-((S)-5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8-methyl-8,9-dihydro-10H-7-oxa-1,3,6,10-tetraazacyclohepta[de]naphthalen-10-yl)but-3-en-1-yl)pyridin-2-amine (single diastereomer) | 715.0 |

TABLE 1-continued

| No | Structure | Chemical Name | [M + H]+ |
| --- | --- | --- | --- |
| 747 | 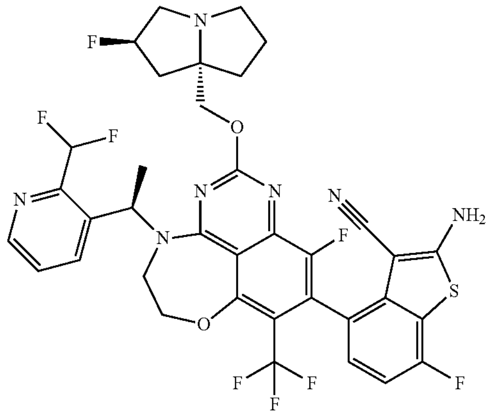 [SMILES: C[C@H](c1cccnc1C(F)F)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-(difluoromethyl)pyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 776.3 |
| 748 | 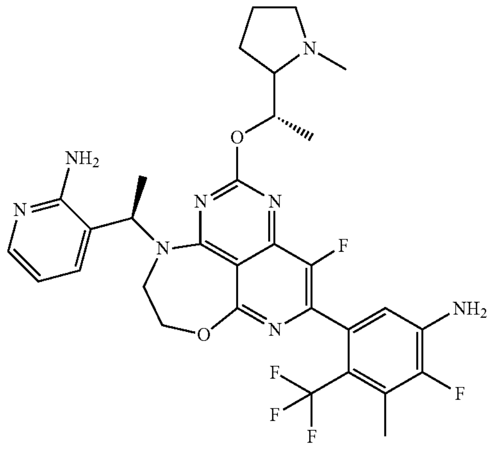 [SMILES: Cc1c(F)c(N)cc(-c2nc3c4c(nc(O[C@@H](C)C5CCCN5C)nc4c2F)N([C@H](C)c2cccnc2N)CCO3)c1C(F)(F)F] | 3-((1R)-1-(5-(5-amino-4-fluoro-3-methyl-2-(trifluoromethyl)phenyl)-4-fluoro-2-((1S)-1-(1-methylpyrrolidin-2-yl)ethoxy)-8,9-dihydro-10H-7-oxa-1,3,6,10-tetraazacyclohepta[de]naphthalen-10-yl)ethyl)pyridin-2-amine (single diastereomer) | 645.4 |
| 749 | 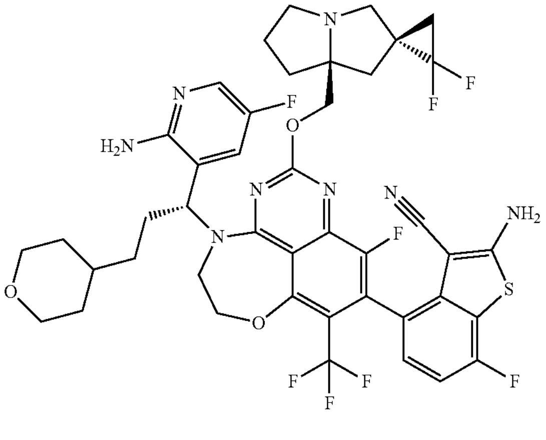 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CCC3CCOCC3)c3cc(F)cnc3N)CCO4)c12] | 2-amino-4-(4-((R)-1-(2-amino-5-fluoropyridin-3-yl)-3-(tetrahydro-2H-pyran-4-yl)propyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 901.2 |

TABLE 1-continued

| No | Structure | Chemical Name | [M + H]+ |
| --- | --- | --- | --- |
| 750 | 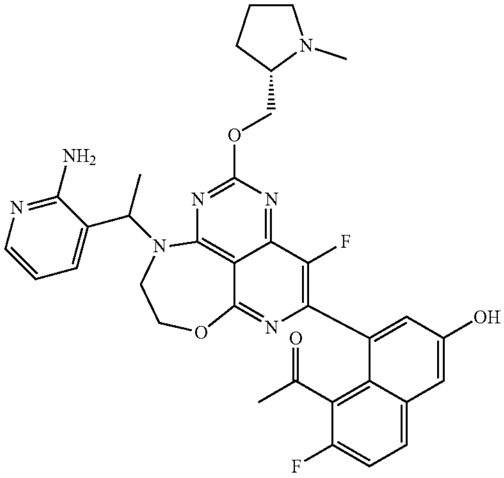 [SMILES: CC(=O)c1c(F)ccc2cc(O)cc(-c3nc4c5c(nc(OC[C@@H]6CCCN6C)nc5c3F)N(C(C)c3cccnc3N)CCO4)c12] | 1-(8-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (single diastereomer 1, absolute stereochemistry not determined) | 642.0 |
| 751 | 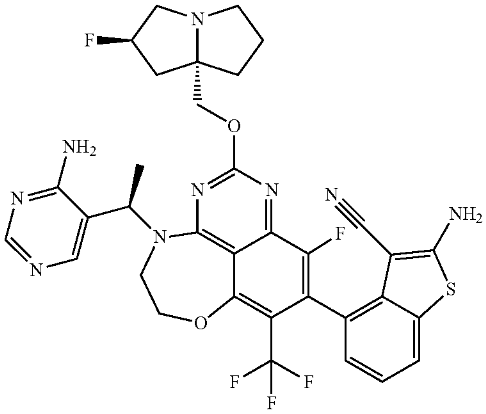 | 2-amino-4-(4-((R)-1-(4-aminopyrimidin-5-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)benzo[b]thiophene-3-carbonitrile (single diastereomer, R atropisomer at $R^7$ substituent) | 724.2 |
| 752 | 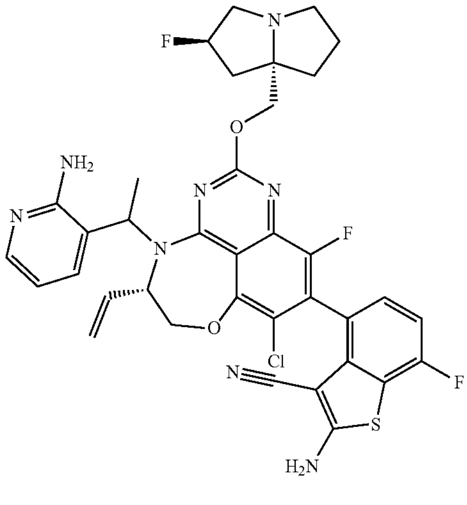 [SMILES: C=C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-10-fluoro-2-(((2R,7aS)-2-fluorotetrahydro-1H-pyrrolizin-7a(5H)-yl)methoxy)-5-vinyl-5,6-dihydro-4H-[1,4]oxazepino[5,6,7-de]quinazolin-9-yl)-7-fluorobenzo[b]thiophene-3-carbonitrile (mixture of diastereomers) | 732.9 |

TABLE 1-continued

| No | Structure | Chemical Name | [M + H]+ |
|---|---|---|---|
| 753 | 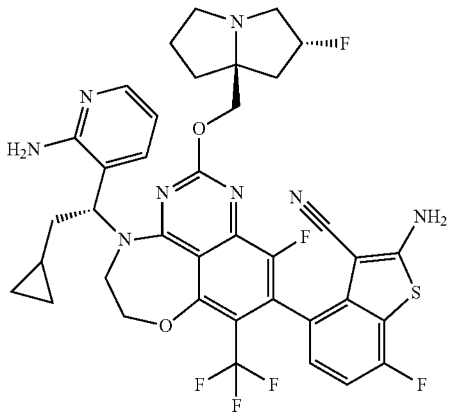 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CC3)c3cccnc3N)CCO4)c12] | 2-amino-4-(4-((R)-1-(2-aminopyridin-3-yl)-2-cyclopropylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.3 |
| 754 | 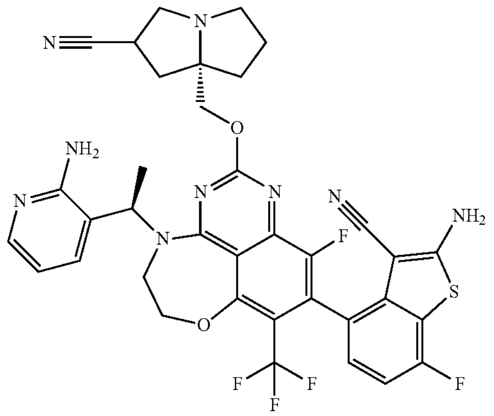 [SMILES: C[C@H](c1cccnc1N)N1CCOc2c(C(F)(F)F)c(-c3ccc(F)c4sc(N)c(C#N)c34)c(F)c3nc(OC[C@@]45CCCN4CC(C#N)C5)nc1c23] | (7aS)-7a-(((9-(2-amino-3-cyano-7-fluorobenzo[b]thiophen-4-yl)-4-((R)-1-(2-aminopyridin-3-yl)ethyl)-10-fluoro-8-(trifluoromethyl)-5,6-dihydro-4H-[1,4]oxazepino[5,6,7-de]quinazolin-2-yl)oxy)methyl)hexahydro-1H-pyrrolizine-2-carbonitrile (single diastereomer 1, absolute stereochemistry not determined) | 748.3 |
| 755 | 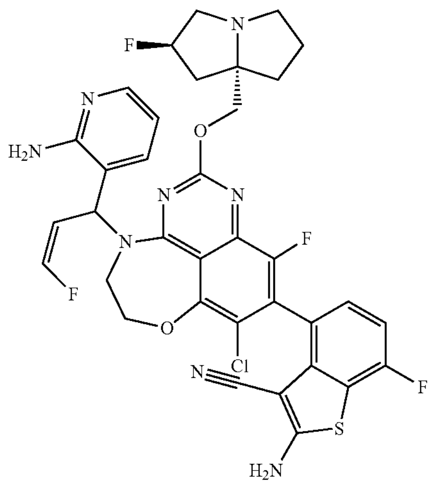 [SMILES: N#Cc1c(N)sc2c(F)ccc(-c3c(Cl)c4c5c(nc(OC[C@@]67CCCN6C[C@H](F)C7)nc5c3F)N(C(/C=C\F)c3cccnc3N)CCO4)c12] | 2-amino-4-(4-((Z)-1-(2-aminopyridin-3-yl)-3-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 737.0 |

TABLE 1-continued

| No | Structure | Chemical Name | [M + H]+ |
|---|---|---|---|
| 756 | 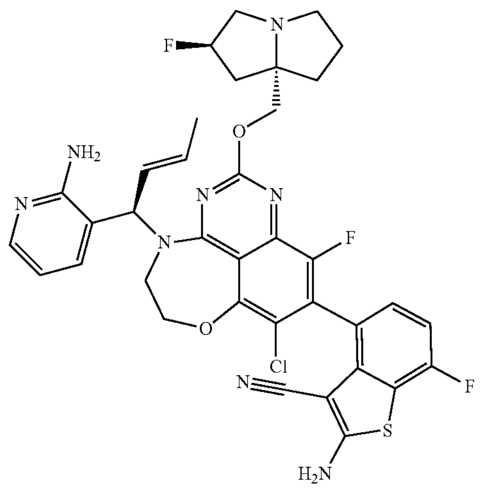 [SMILES: C/C=C/[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R,E)-1-(2-aminopyridin-3-yl)but-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 733.0 |
| 757 | 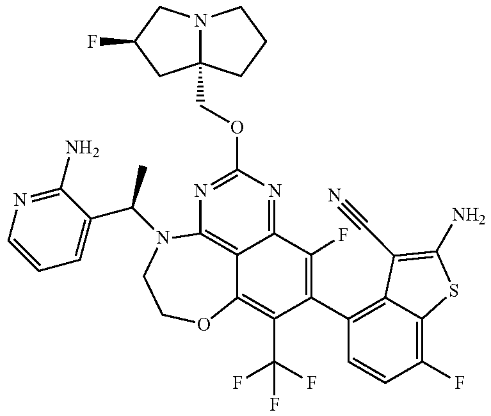 [SMILES: C[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 740.9 |
| 758 | 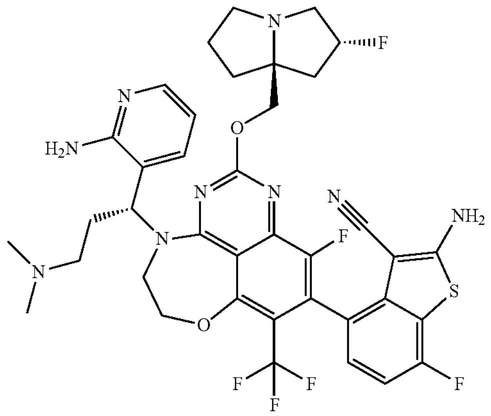 [SMILES: CN(C)CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-3-(dimethylamino)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 798.3 |

TABLE 1-continued

| No | Structure | Chemical Name | [M + H]+ |
|---|---|---|---|
| 759 | 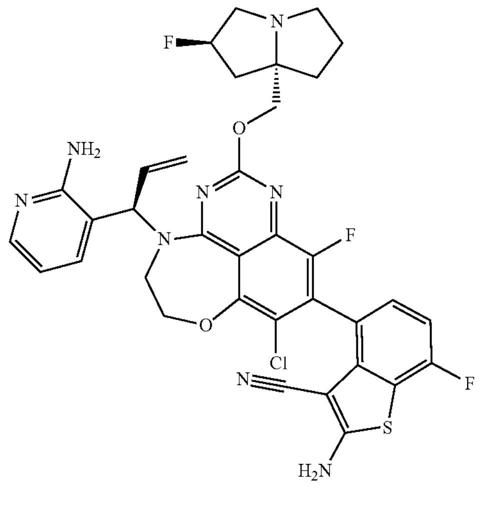 [SMILES: C=C[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)allyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 718.9 |
| 760 | 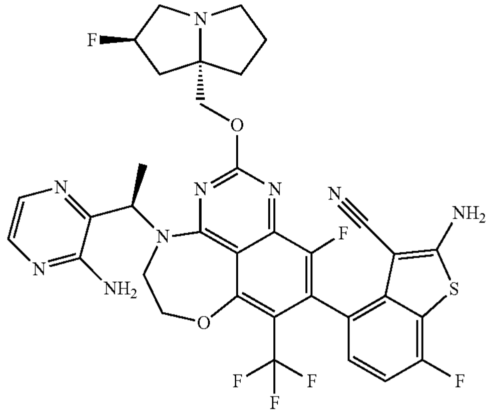 [SMILES: C[C@H](c1nccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(3-aminopyrazin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 742.2 |
| 761 | 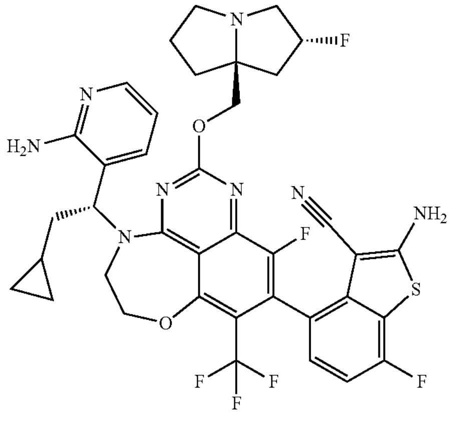 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CC3)c3cccnc3N)CCO4)c12] | 2-amino-4-(4-((R)-1-(2-aminopyridin-3-yl)-2-cyclopropylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 781.3 |

TABLE 1-continued

| No | Structure | Chemical Name | [M + H]+ |
|---|---|---|---|
| 762 | 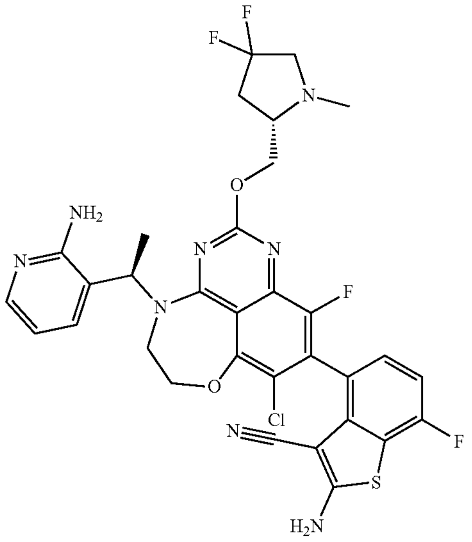 [SMILES: C[C@H](c1cccnc1N)N1CCOc2c(Cl)c(-c3ccc(F)c4sc(N)c(C#N)c34)c(F)c3nc(OC[C@@H]4CC(F)(F)CN4C)nc1c23] | 2-amino-4-(4-((R)-1-(2-aminopyridin-3-yl)ethyl)-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 2, absolute stereochemistry undetermined) | 712.8 |
| 763 | 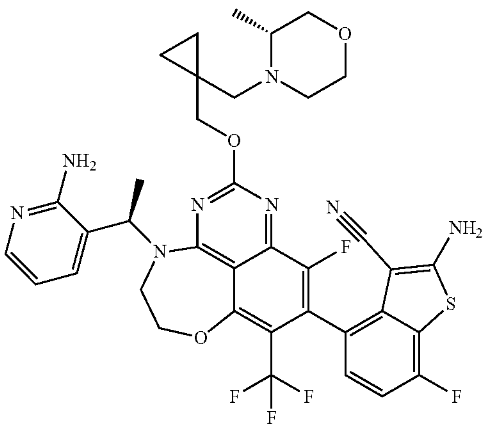 [SMILES: C[C@@H]1COCCN1CC1(COc2nc3c4c(c(C(F)(F)F)c(-c5ccc(F)c6sc(N)c(C#N)c56)c(F)c4n2)OCCN3[C@H](C)c2cccnc2N)CC1] | 2-amino-4-(4-((R)-1-(2-aminopyridin-3-yl)ethyl)-2-((1-(((3S,5R)-3,5-dimethylmorpholino)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.2 |
| 764 | 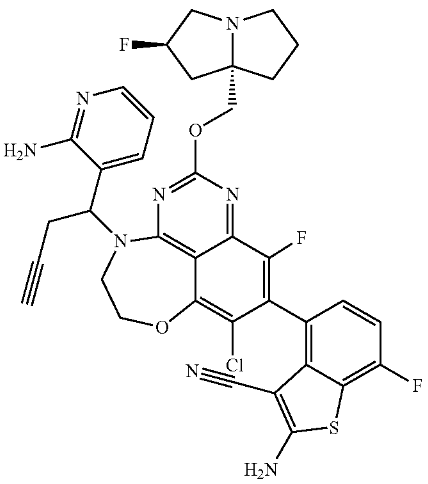 [SMILES: C#CCC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)but-3-yn-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 731.1 |

TABLE 1-continued

| No | Structure | Chemical Name | [M + H]+ |
|---|---|---|---|
| 765 | 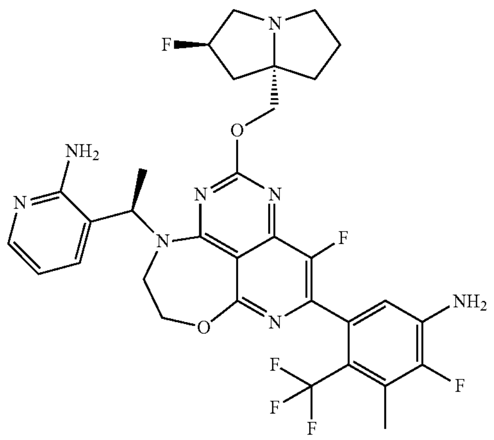 [SMILES: Cc1c(F)c(N)cc(-c2nc3c4c(nc(OC[C@@]56CCCN5C[C@H](F)C6)nc4c2F)N([C@H](C)c2cccnc2N)CCO3)c1C(F)(F)F] | 3-((R)-1-(5-(5-amino-4-fluoro-3-methyl-2-(trifluoromethyl)phenyl)-4-fluoro-2-(((2R,7aS)-2-fluorotetrahydro-1H-pyrrolizin-7a(5H)-yl)methoxy)-8,9-dihydro-10H-7-oxa-1,3,6,10-tetraazacyclohepta[de]naphthalen-10-yl)ethyl)pyridin-2-amine (single diastereomer) | 675.4 |
| 766 | 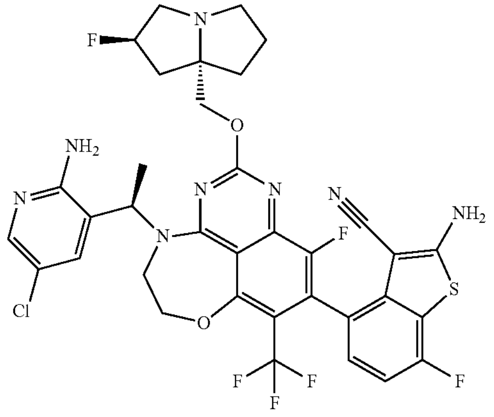 [SMILES: C[C@H](c1cc(Cl)cnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-chloropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 775.1 |
| 767 | 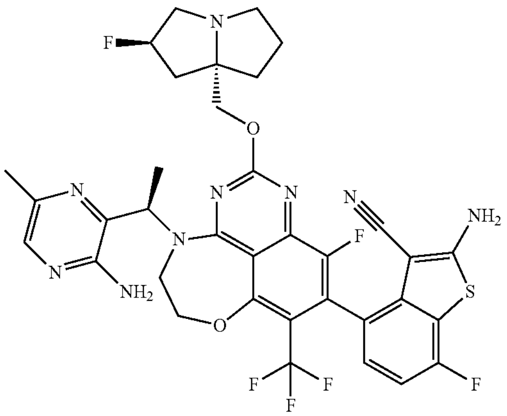 [SMILES: Cc1cnc(N)c([C@@H](C)N2CCOc3c(C(F)(F)F)c(-c4ccc(F)c5sc(N)c(C#N)c45)c(F)c4nc(OC[C@@]56CCCN5C[C@H](F)C6)nc2c34)n1] | 2-amino-4-(4-((R)-1-(3-amino-6-methylpyrazin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 756.3 |

TABLE 1-continued

| No | Structure | Chemical Name | [M + H]+ |
|---|---|---|---|
| 768 | 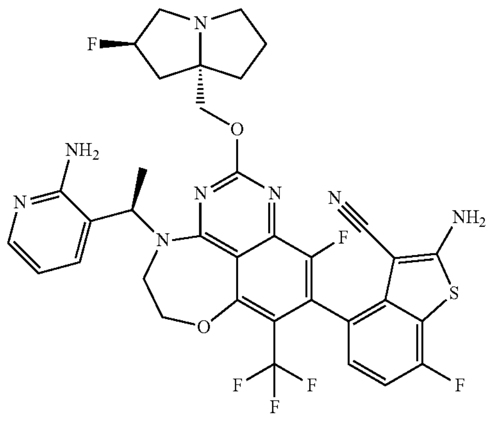 [SMILES: C[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 740.9 |
| 769 | 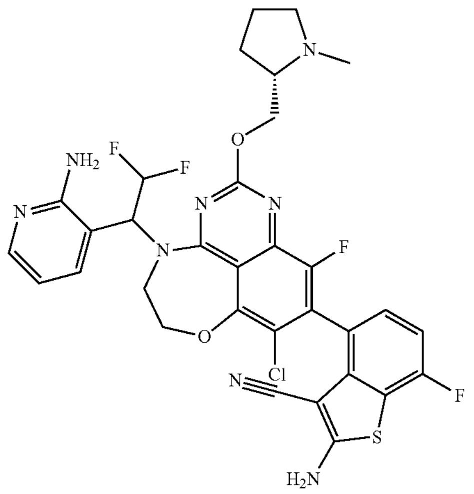 [SMILES: CN1CCC[C@H]1COc1nc2c3c(c(Cl)c(-c4ccc(F)c5sc(N)c(C#N)c45)c(F)c3n1)OCCN2C(c1cccnc1N)C(F)F] | 2-amino-4-(4-(1-(2-aminopyridin-3-yl)-2,2-difluoroethyl)-8-chloro-10-fluoro-2-(((S)-1-methylpyrrolidin-2-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 698.9 |
| 770 | 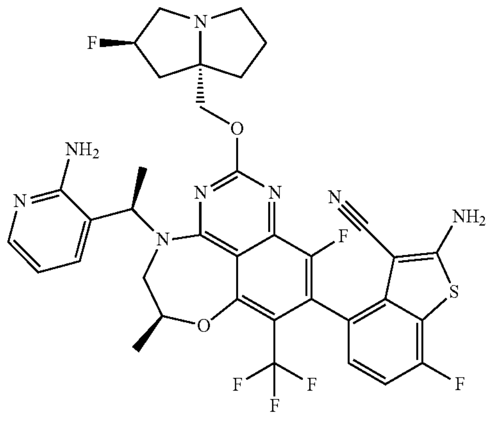 [SMILES: C[C@H](c1cccnc1N)N1C[C@H](C)Oc2c(C(F)(F)F)c(-c3ccc(F)c4sc(N)c(C#N)c34)c(F)c3nc(OC[C@@]45CCCN4C[C@H](F)C5)nc1c23] | 2-amino-4-((6S)-4-((R)-1-(2-aminopyridin-3-yl)ethyl)-10-fluoro-2-(((2R,7aS)-2-fluorotetrahydro-1H-pyrrolizin-7a(5H)-yl)methoxy)-6-methyl-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 755.0 |

TABLE 1-continued

| No | Structure | Chemical Name | [M + H]+ |
|---|---|---|---|
| 771 | 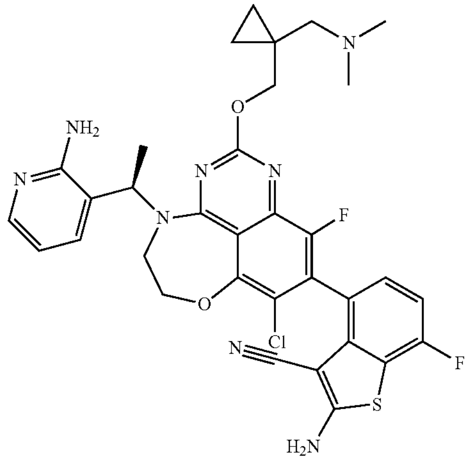 [SMILES: C[C@H](c1cccnc1N)N1CCOc2c(Cl)c(-c3ccc(F)c4sc(N)c(C#N)c34)c(F)c3nc(OCC4(CN(C)C)CC4)nc1c23] | 2-amino-4-(4-((R)-1-(2-aminopyridin-3-yl)ethyl)-8-chloro-2-((1-((dimethylamino)methyl)cyclopropyl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 676.8 |
| 772 | 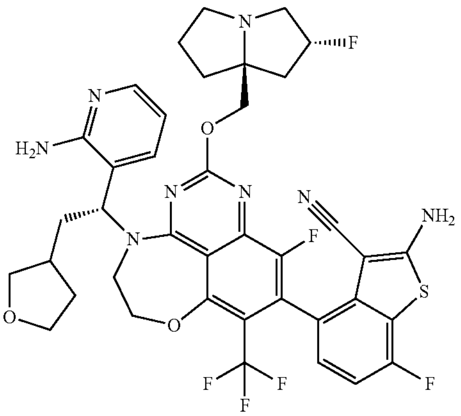 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOC3)c3cccnc3N)CCO4)c12] | 2-amino-4-(4-((1R)-1-(2-aminopyridin-3-yl)-2-(tetrahydrofuran-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 811.3 |
| 773 | 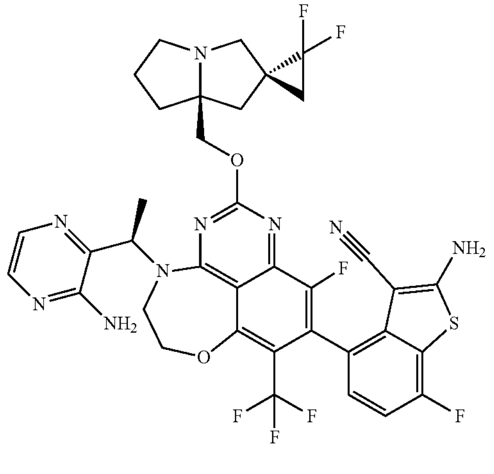 [SMILES: C[C@H](c1nccnc1N)N1CCOc2c(C(F)(F)F)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(3-aminopyrazin-2-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 786.2 |

TABLE 1-continued

| No | Structure | Chemical Name | [M + H]+ |
|---|---|---|---|
| 774 | 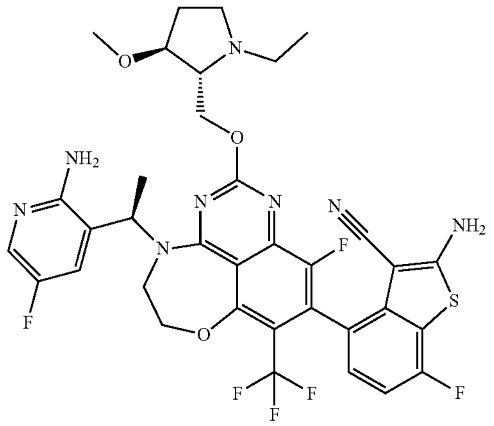 [SMILES: CCN1CC[C@H](OC)[C@H]1COc1nc2c3c(c(C(F)(F)F)c(-c4ccc(F)c5sc(N)c(C#N)c45)c(F)c3n1)OCCN2[C@H](C)c1cc(F)cnc1N] | 2-amino-4-(4-((R)-1-(2-amino-5-fluoropyridin-3-yl)ethyl)-10-fluoro-2-(((2R,3S)-3-methoxy-1-methylpyrrolidin-2-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 745.3 |
| 775 | 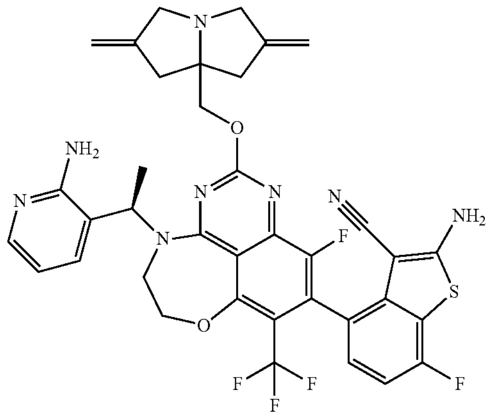 [SMILES: C=C1CN2CC(=C)CC2(COc2nc3c4c(c(C(F)(F)F)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-2-((2,6-dimethylenetetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 747.3 |
| 776 | 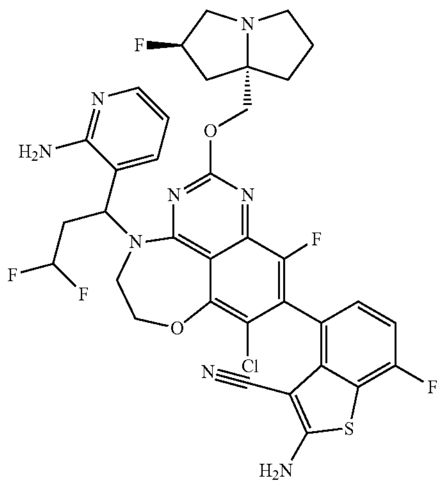 [SMILES: N#Cc1c(N)sc2c(F)ccc(-c3c(Cl)c4c5c(nc(OC[C@@]67CCCN6C[C@H](F)C7)nc5c3F)N(C(CC(F)F)c3cccnc3N)CCO4)c12] | 2-amino-4-(4-(1-(2-aminopyridin-3-yl)-3,3-difluoropropyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 756.9 |

TABLE 1-continued

| No | Structure | Chemical Name | [M + H]+ |
|---|---|---|---|
| 777 | 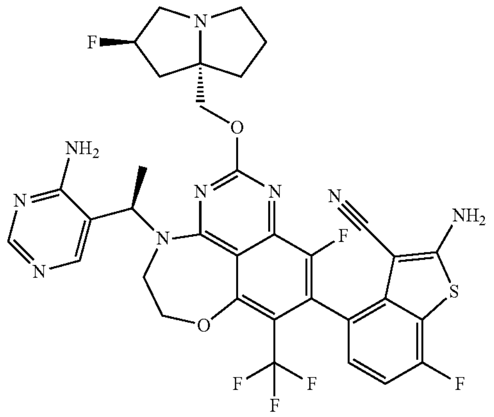 [SMILES: C[C@H](c1cncnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(4-aminopyrimidin-5-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 742.1 |
| 778 | 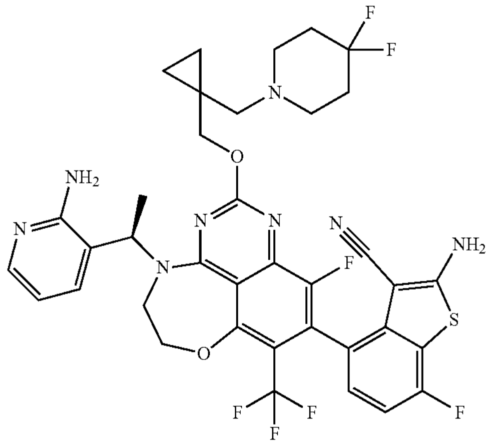 [SMILES: C[C@H](c1cccnc1N)N1CCOc2c(C(F)(F)F)c(-c3ccc(F)c4sc(N)c(C#N)c34)c(F)c3nc(OCC4(CN5CCC(F)(F)CC5)CC4)nc1c23] | 2-amino-4-(4-((R)-1-(2-aminopyridin-3-yl)ethyl)-2-((1-((4,4-difluoropiperidin-1-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 787.2 |
| 779 | 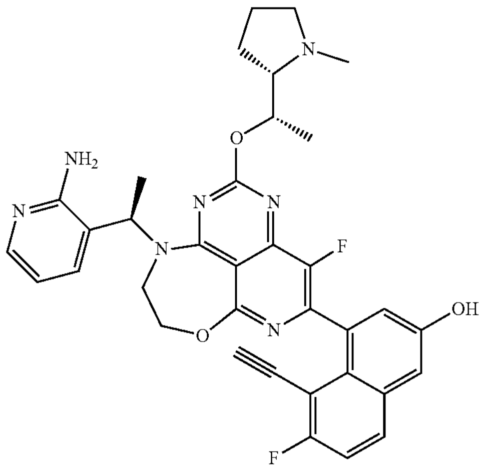 | 4-(10-((R)-1-(2-aminopyridin-3-yl)ethyl)-4-fluoro-2-((S)-1-((S)-1-methylpyrrolidin-2-yl)ethoxy)-9,10-dihydro-8H-7-oxa-1,3,6,10-tetraazacyclohepta[de]naphthalen-5-yl)-5-ethynyl-6-fluoronaphthalen-2-ol (single diastereomer 1, absolute stereochemistry not determined) | 637.9 |

TABLE 1-continued

| No | Structure | Chemical Name | [M + H]$^+$ |
|---|---|---|---|
| 780 | 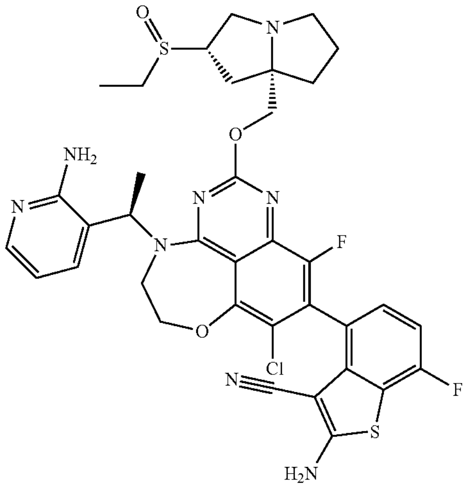 [SMILES: CCS(=O)[C@@H]1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-2-(((2S,7aS)-2-(ethylsulfinyl)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (diastereomer mixture) | 765.0 |
| 781 | 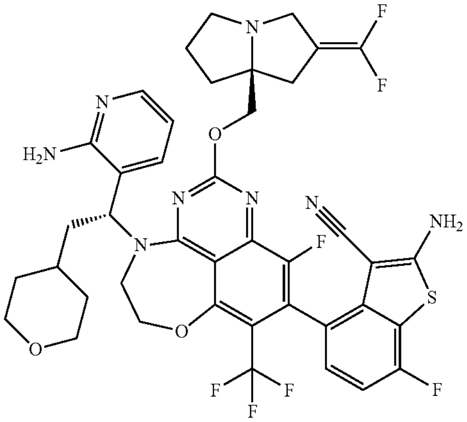 [SMILES: N#Cc1c(N)sc2c(F)ccc(-c3c(C(F)(F)F)c4c5c(nc(OC[C@@]67CCCN6CC(=C(F)F)C7)nc5c3F)N([C@H](CC3CCOCC3)c3cccnc3N)CCO4)c12] | 2-amino-4-(4-((R)-1-(2-aminopyridin-3-yl)-2-(tetrahydro-2H-pyran-4-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 855.3 |
| 782 | 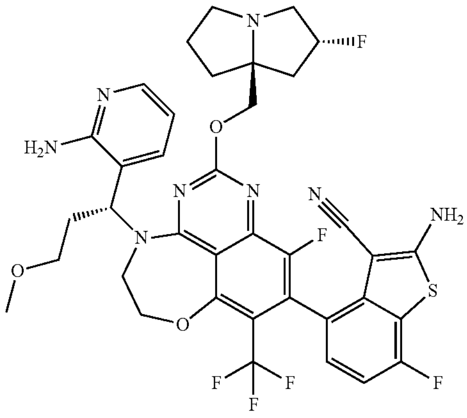 [SMILES: COCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-3-methoxypropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 785.4 |

TABLE 1-continued

| No | Structure | Chemical Name | [M + H]+ |
|---|---|---|---|
| 783 | 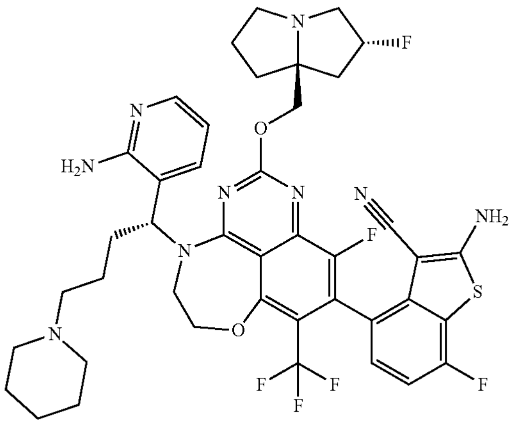 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCCN3CCCCC3)c3cccnc3N)CCO4)c12] | 2-amino-4-(4-((R)-1-(2-aminopyridin-3-yl)-4-(piperidin-1-yl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 852.3 |
| 784 | 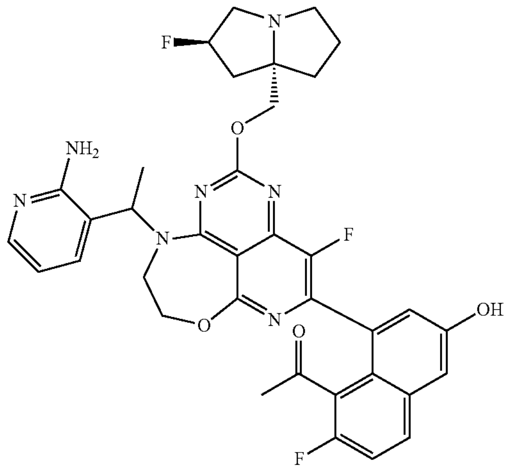 [SMILES: CC(=O)c1c(F)ccc2cc(O)cc(-c3nc4c5c(nc(OC[C@@]67CCCN6C[C@H](F)C7)nc5c3F)N(C(C)c3cccnc3N)CCO4)c12] | 1-(8-(10-(1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (diastereomer mixture) | 685.9 |
| 785 | 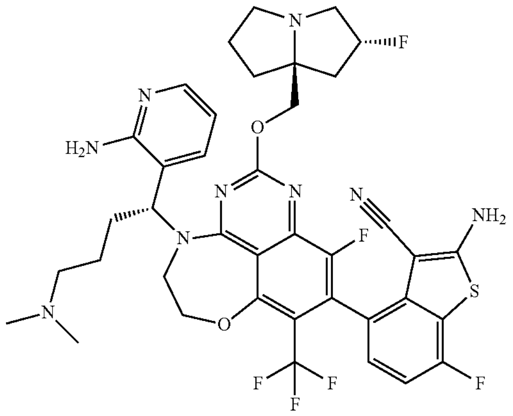 | 2-amino-4-(4-((R)-1-(2-aminopyridin-3-yl)-4-(dimethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 812.4 |

TABLE 1-continued

| No | Structure | Chemical Name | [M + H]+ |
|---|---|---|---|
| 786 | 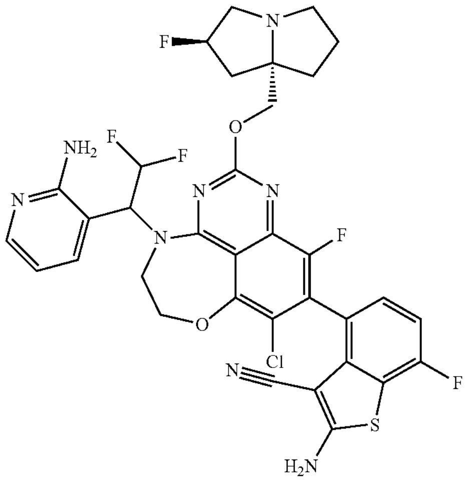 [SMILES: N#Cc1c(N)sc2c(F)ccc(-c3c(Cl)c4c5c(nc(OC[C@@]67CCCN6C[C@H](F)C7)nc5c3F)N(C(c3cccnc3N)C(F)F)CCO4)c12] | 2-amino-4-(4-(1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 4, absolute stereochemistry undetermined) | 742.7 |
| 787 | 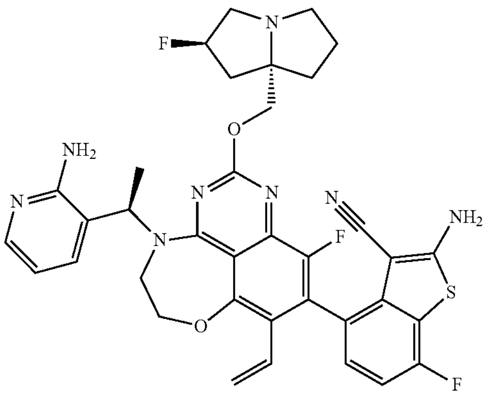 [SMILES: C=Cc1c(-c2ccc(F)c3sc(N)c(C#N)c23)c(F)c2nc(OC[C@@]34CCCN3C[C@H](F)C4)nc3c2c1OCCN3[C@H](C)c1cccnc1N] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-vinyl-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 699.0 |
| 788 | 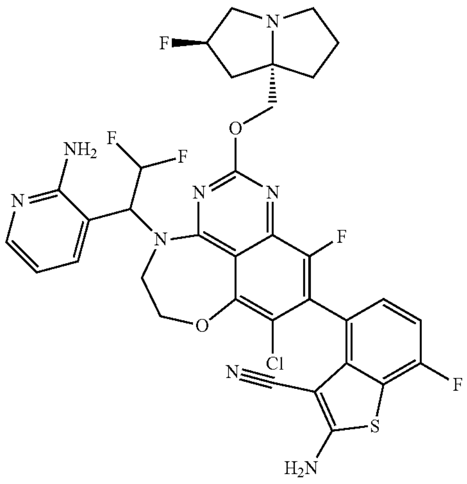 [SMILES: N#Cc1c(N)sc2c(F)ccc(-c3c(Cl)c4c5c(nc(OC[C@@]67CCCN6C[C@H](F)C7)nc5c3F)N(C(c3cccnc3N)C(F)F)CCO4)c12] | 2-amino-4-(4-(1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 742.7 |

TABLE 1-continued

| No | Structure | Chemical Name | $[M + H]^+$ |
|---|---|---|---|
| 789 | 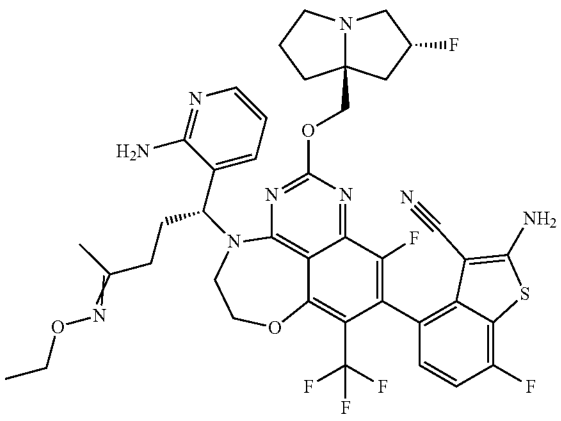 [SMILES: CCON=C(C)CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-4-(ethoxyimino)pentyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 840.4 |
| 790 | 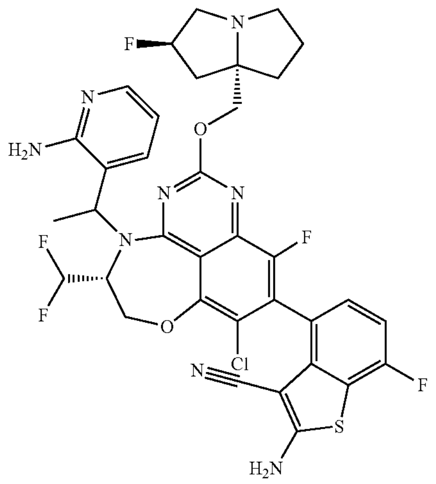 [SMILES: CC(c1cccnc1N)N1c2nc(OC[C@@]34CCCN3C[C@H](F)C4)nc3c(F)c(-c4ccc(F)c5sc(N)c(C#N)c45)c(Cl)c(c23)OC[C@@H]1C(F)F] | 2-amino-4-((5R)-4-(1-(2-aminopyridin-3-yl)ethyl)-8-chloro-5-(difluoromethyl)-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 756.8 |
| 791 | 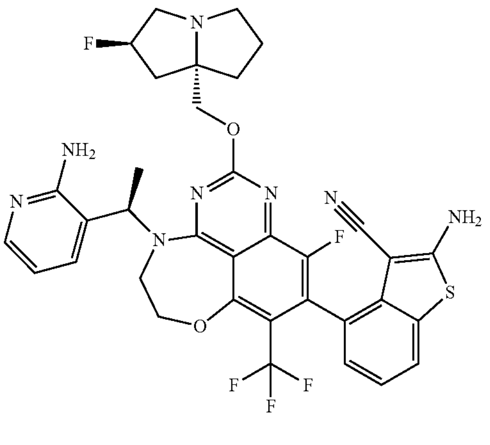 [SMILES: C[C@H](c1cccnc1N)N1CCOc2c(C(F)(F)F)c(-c3cccc4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)benzo[b]thiophene-3-carbonitrile (single diastereomer, S atropisomer at $R^7$ substituent) | 723.0 |

TABLE 1-continued

| No | Structure | Chemical Name | [M + H]+ |
|---|---|---|---|
| 792 | 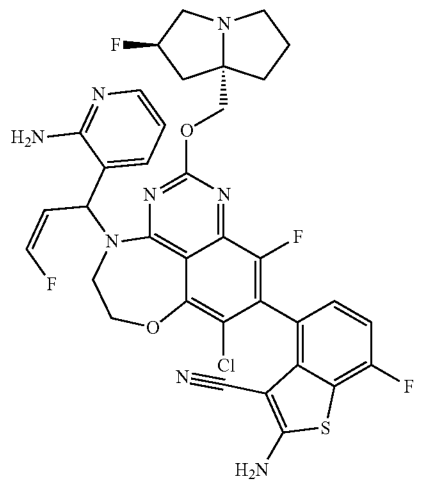 [SMILES: N#Cc1c(N)sc2c(F)ccc(-c3c(Cl)c4c5c(nc(OC[C@@]67CCCN6C[C@H](F)C7)nc5c3F)N(C(/C=C\F)c3cccnc3N)CCO4)c12] | 2-amino-4-(4-((Z)-1-(2-aminopyridin-3-yl)-3-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 737.0 |
| 793 | 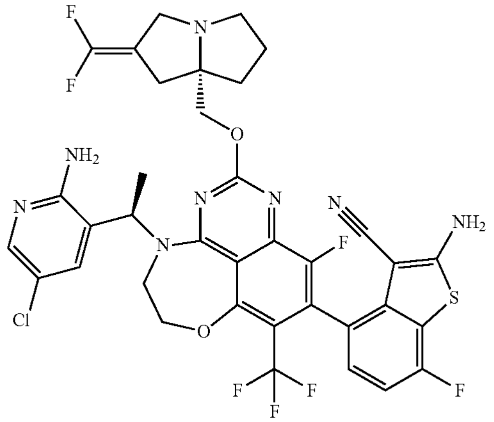 [SMILES: C[C@H](c1cc(Cl)cnc1N)N1CCOc2c(C(F)(F)F)c(-c3ccc(F)c4sc(N)c(C#N)c34)c(F)c3nc(OC[C@@]45CCCN4CC(=C(F)F)C5)nc1c23] | 2-amino-4-(4-((R)-1-(2-amino-5-chloropyridin-3-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 805.2 |
| 794 | 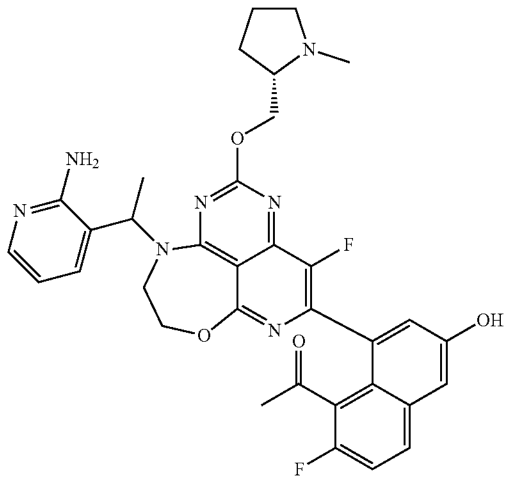 [SMILES: CC(=O)c1c(F)ccc2cc(O)cc(-c3nc4c5c(nc(OC[C@@H]6CCCN6C)nc5c3F)N(C(C)c3cccnc3N)CCO4)c12] | 1-(8-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (single diastereomer 2, absolute stereochemistry not determined) | 642.0 |

TABLE 1-continued

| No | Structure | Chemical Name | [M + H]+ |
|---|---|---|---|
| 795 | 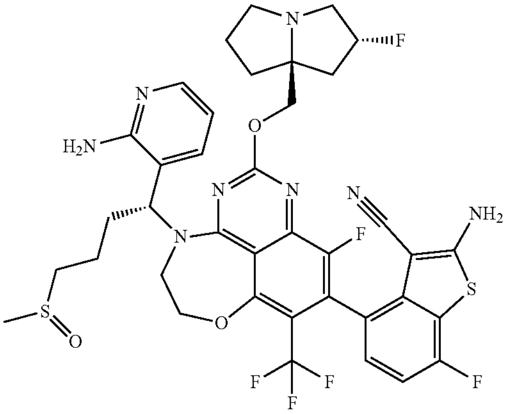 [SMILES: CS(=O)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((1R)-1-(2-aminopyridin-3-yl)-4-(methylsulfinyl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 831.1 |
| 796 | 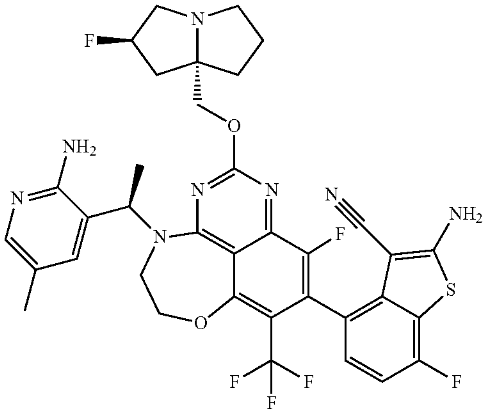 [SMILES: Cc1cnc(N)c([C@@H](C)N2CCOc3c(C(F)(F)F)c(-c4ccc(F)c5sc(N)c(C#N)c45)c(F)c4nc(OC[C@@]56CCCN5C[C@H](F)C6)nc2c34)c1] | 2-amino-4-(4-((R)-1-(2-amino-5-methylpyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 755.2 |
| 797 | 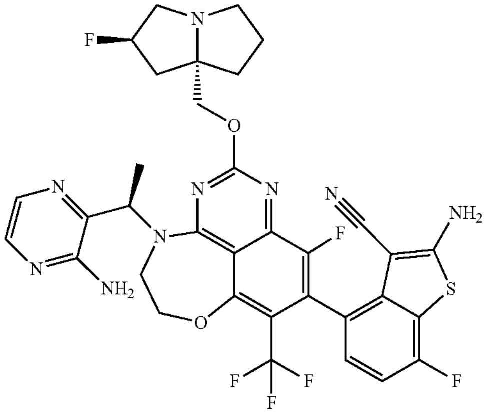 [SMILES: C[C@H](c1nccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(3-aminopyrazin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 742.2 |

TABLE 1-continued

| No | Structure | Chemical Name | [M + H]$^+$ |
|---|---|---|---|
| 798 | 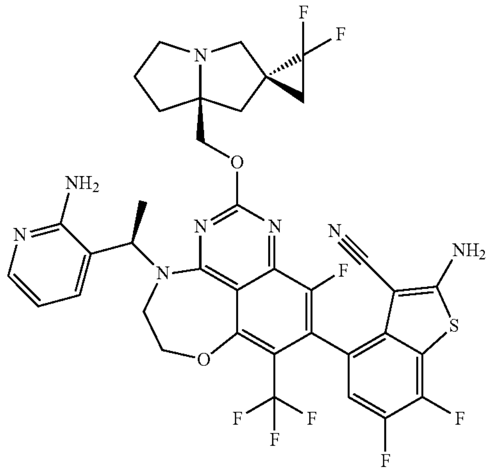 [SMILES: C[C@H](c1cccnc1N)N1CCOc2c(C(F)(F)F)c(-c3cc(F)c(F)c4sc(N)c(C#N)c34)c(F)c3nc(OC[C@@]45CCCN4C[C@@]4(CC4(F)F)C5)nc1c23] | 2-amino-4-(4-((R)-1-(2-aminopyridin-3-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-6,7-difluorobenzo[b]thiophene-3-carbonitrile (single diastereomer, S atropisomer at $R^7$ substituent) | 803.3 |
| 799 | 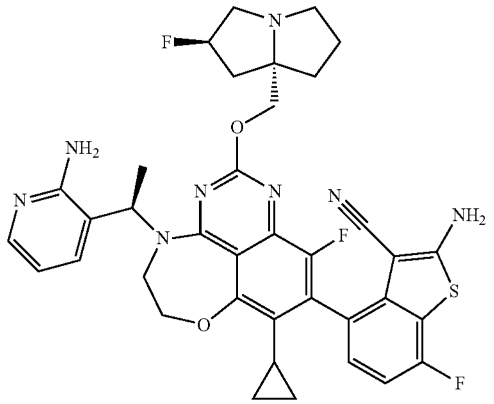 [SMILES: C[C@H](c1cccnc1N)N1CCOc2c(C3CC3)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-cyclopropyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 713.0 |
| 800 | 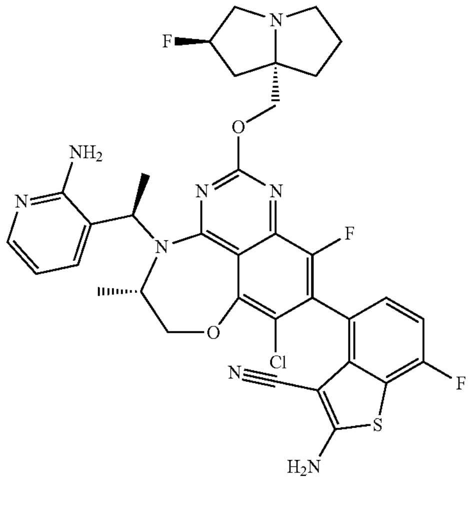 [SMILES: C[C@H](c1cccnc1N)N1c2nc(OC[C@@]34CCCN3C[C@H](F)C4)nc3c(F)c(-c4ccc(F)c5sc(N)c(C#N)c45)c(Cl)c(c23)OC[C@@H]1C] | 2-amino-4-((5S)-4-((R)-1-(2-aminopyridin-3-yl)ethyl)-8-chloro-10-fluoro-2-(((2R,7aS)-2-fluorotetrahydro-1H-pyrrolizin-7a(5H)-yl)methoxy)-5-methyl-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 721.1 |

TABLE 1-continued

| No | Structure | Chemical Name | [M + H]+ |
|---|---|---|---|
| 801 | 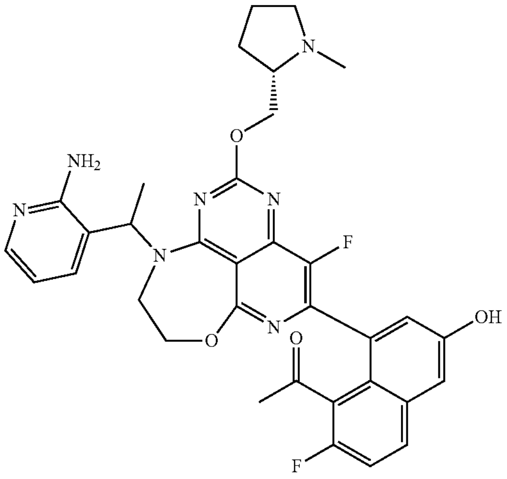 [SMILES: CC(=O)c1c(F)ccc2cc(O)cc(-c3nc4c5c(nc(OC[C@@H]6CCCN6C)nc5c3F)N(C(C)c3cccnc3N)CCO4)c12] | 1-(8-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (diastereomer mixture) | 641.9 |
| 802 | 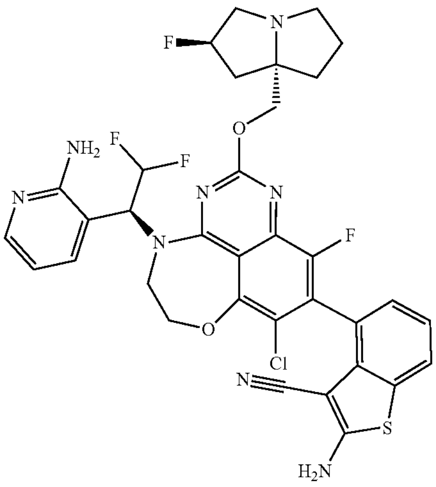 [SMILES: N#Cc1c(N)sc2cccc(-c3c(Cl)c4c5c(nc(OC[C@@]67CCCN6C[C@H](F)C7)nc5c3F)N([C@@H](c3cccnc3N)C(F)F)CCO4)c12] | 2-amino-4-(4-((S)-1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)benzo[b]thiophene-3-carbonitrile (single diastereomer, S atropisomer at $R^7$ substituent) | 724.9 |
| 803 | 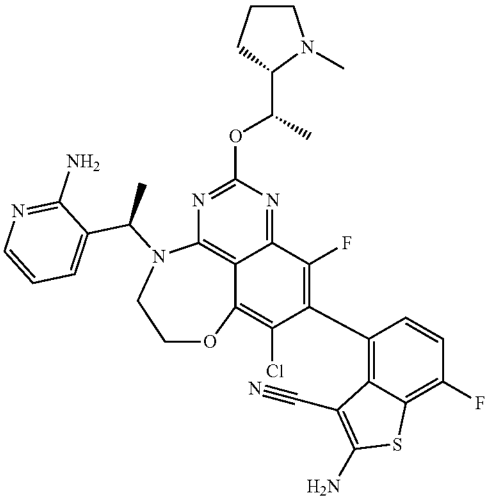 [SMILES: C[C@H](Oc1nc2c3c(c(Cl)c(-c4ccc(F)c5sc(N)c(C#N)c45)c(F)c3n1)OCCN2[C@H](C)c1cccnc1N)[C@@H]1CCCN1C] | 2-amino-4-(4-((R)-1-(2-aminopyridin-3-yl)ethyl)-8-chloro-10-fluoro-2-((S)-1-((S)-1-methylpyrrolidin-2-yl)ethoxy)-5,6-dihydro-4H-[1,4]oxazepino[5,6,7-de]quinazolin-9-yl)-7-fluorobenzo[b]thiophene-3-carbonitrile (mixture of diastereomers) | 677.0 |

TABLE 1-continued

| No | Structure | Chemical Name | [M + H]+ |
|---|---|---|---|
| 804 | 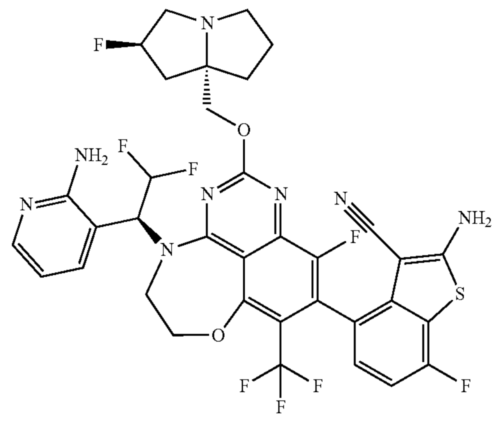 [SMILES: N#Cc1c(N)sc2c(F)ccc(-c3c(C(F)(F)F)c4c5c(nc(OC[C@@]67CCCN6C[C@H](F)C7)nc5c3F)N([C@@H](c3cccnc3N)C(F)F)CCO4)c12] | 2-amino-4-(4-((S)-1-(2-aminopyridin-3-yl)-2,2-difluoroethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 776.9 |
| 805 | 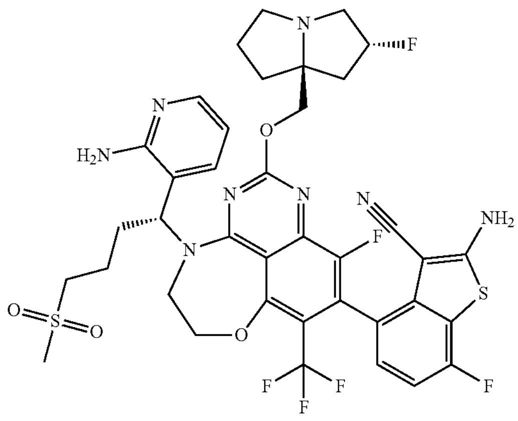 [SMILES: CS(=O)(=O)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-4-(methylsulfonyl)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 847.1 |
| 806 | 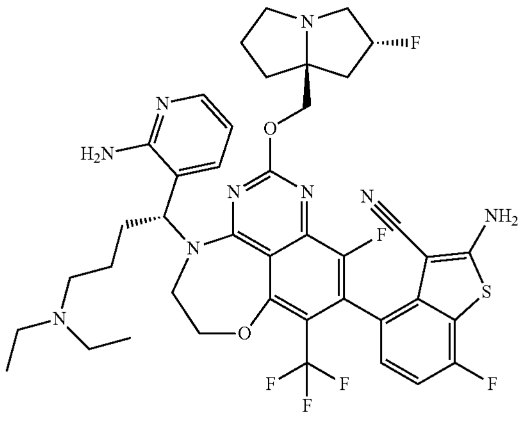 [SMILES: CCN(CC)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-4-(diethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 840.3 |

TABLE 1-continued

| No | Structure | Chemical Name | [M + H]+ |
|---|---|---|---|
| 807 | 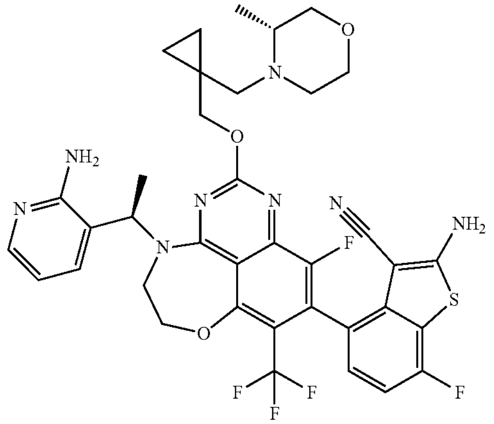 | 2-amino-4-(4-((R)-1-(2-aminopyridin-3-yl)ethyl)-10-fluoro-2-((1-(((R)-3-methylmorpholino)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 767.2 |
| 808 | 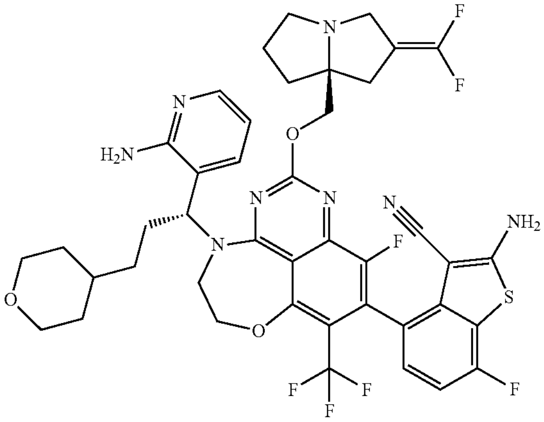 [SMILES: N#Cc1c(N)sc2c(F)ccc(-c3c(C(F)(F)F)c4c5c(nc(OC[C@@]67CCCN6CC(=C(F)F)C7)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 869.8 |
| 809 | 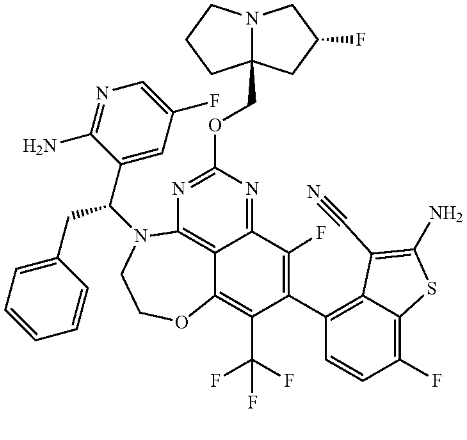 [SMILES: N#Cc1c(N)sc2c(F)ccc(-c3c(C(F)(F)F)c4c5c(nc(OC[C@@]67CCCN6C[C@H](F)C7)nc5c3F)N([C@H](Cc3ccccc3)c3cc(F)cnc3N)CCO4)c12] | 2-amino-4-(4-((R)-1-(2-amino-5-fluoropyridin-3-yl)-2-phenylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 835.2 |

TABLE 1-continued

| No | Structure | Chemical Name | [M + H]+ |
|---|---|---|---|
| 810 | 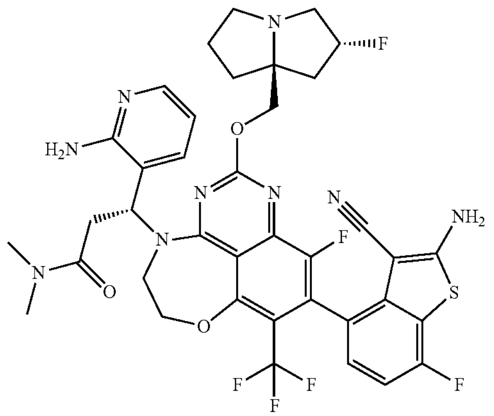 [SMILES: CN(C)C(=O)C[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | (3R)-3-(9-(2-amino-3-cyano-7-fluorobenzo[b]thiophen-4-yl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-4-yl)-3-(2-aminopyridin-3-yl)-N,N-dimethylpropanamide (single diastereomer, S atropisomer at $R^7$ substituent) | 812.3 |
| 811 | 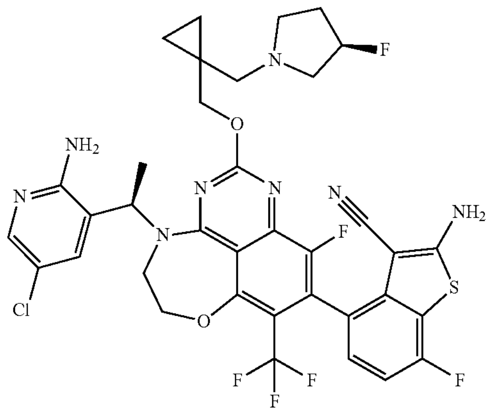 | 2-amino-4-(4-((R)-1-(2-amino-5-chloropyridin-3-yl)ethyl)-10-fluoro-2-((1-(((R)-3-fluoropyrrolidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 789.4 |
| 812 | 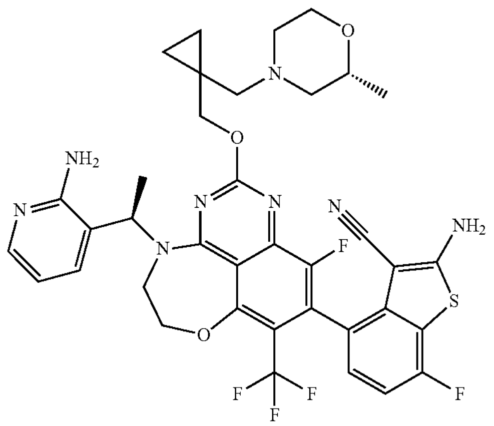 [SMILES: C[C@@H]1CN(CC2(COc3nc4c5c(c(C(F)(F)F)c(-c6ccc(F)c7sc(N)c(C#N)c67)c(F)c5n3)OCCN4[C@H](C)c3cccnc3N)CC2)CCO1] | 2-amino-4-(4-((R)-1-(2-aminopyridin-3-yl)ethyl)-10-fluoro-2-((1-(((R)-2-methylmorpholino)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 767.2 |

TABLE 1-continued

| No | Structure | Chemical Name | [M + H]+ |
|---|---|---|---|
| 813 | 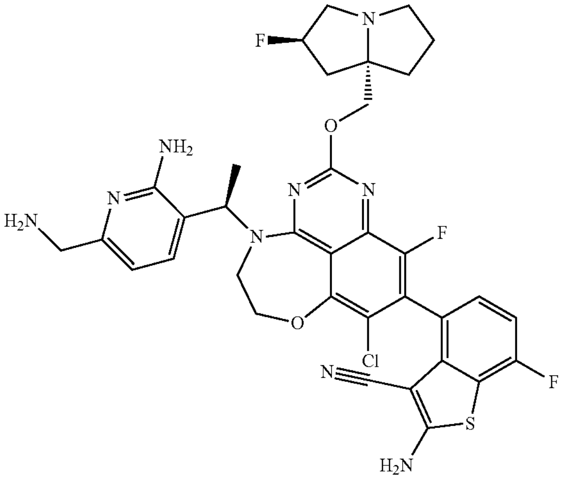 [SMILES: C[C@H](c1ccc(CN)nc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-6-(aminomethyl)pyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 736.0 |
| 814 | 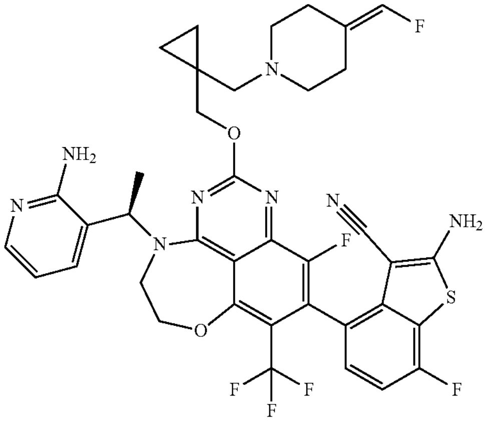 | 2-amino-4-(4-((R)-1-(2-aminopyridin-3-yl)ethyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.2 |
| 815 | 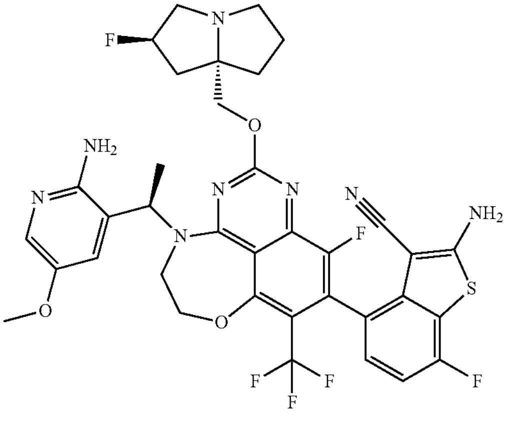 [SMILES: COc1cnc(N)c([C@@H](C)N2CCOc3c(C(F)(F)F)c(-c4ccc(F)c5sc(N)c(C#N)c45)c(F)c4nc(OC[C@@]56CCCN5C[C@H](F)C6)nc2c34)c1] | 2-amino-4-(4-((R)-1-(2-amino-5-methoxypyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 771.3 |

TABLE 1-continued

| No | Structure | Chemical Name | [M + H]+ |
|---|---|---|---|
| 816 | 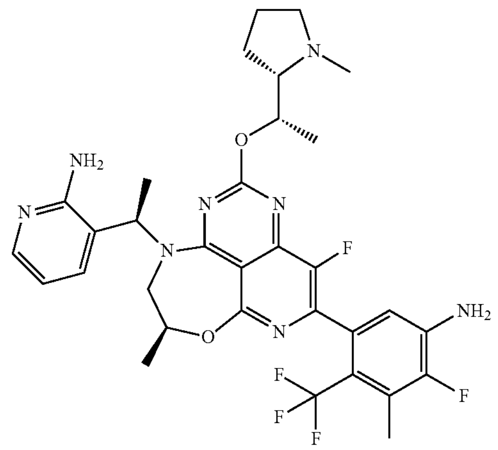 [SMILES: Cc1c(F)c(N)cc(-c2nc3c4c(nc(O[C@@H](C)[C@@H]5CCCN5C)nc4c2F)N([C@H](C)c2cccnc2N)C[C@H](C)O3)c1C(F)(F)F] | 3-((R)-1-((S)-5-(5-amino-4-fluoro-3-methyl-2-(trifluoromethyl)phenyl)-4-fluoro-8-methyl-2-((S)-1-((S)-1-methylpyrrolidin-2-yl)ethoxy)-8,9-dihydro-10H-7-oxa-1,3,6,10-tetraazacyclohepta[de]naphthalen-10-yl)ethyl)pyridin-2-amine (single diastereomer) | 658.7 |
| 817 | 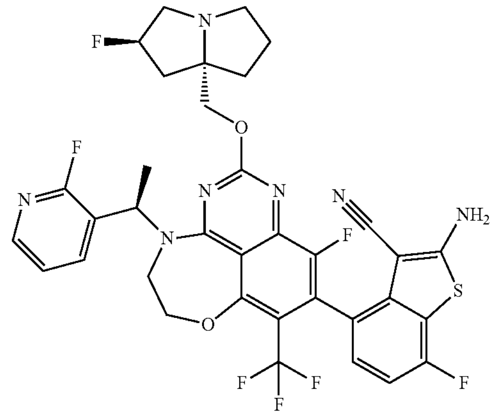 [SMILES: C[C@H](c1cccnc1F)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-7-fluoro-4-(10-fluoro-4-((R)-1-(2-fluoropyridin-3-yl)ethyl)-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)benzo[b]thiophene-3-carbonitrile (single diastereomer, S atropisomer at $R^7$ substituent) | 744.2 |
| 818 | 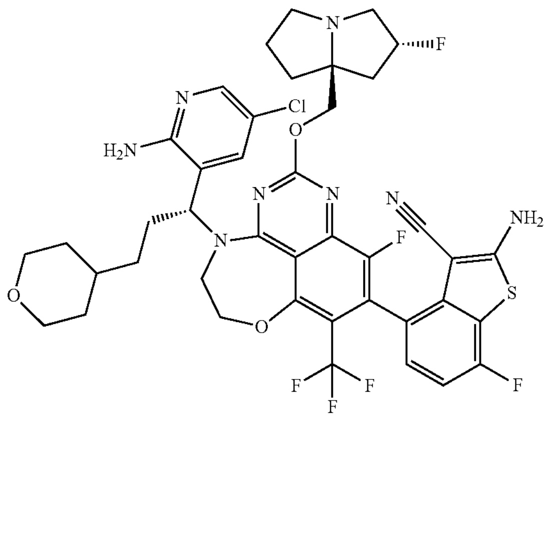 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CCOCC3)c3cc(Cl)cnc3N)CCO4)c12] | 2-amino-4-(4-((R)-1-(2-amino-5-chloropyridin-3-yl)-3-(tetrahydro-2H-pyran-4-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 873.3 |

TABLE 1-continued

| No | Structure | Chemical Name | [M + H]+ |
|---|---|---|---|
| 819 | 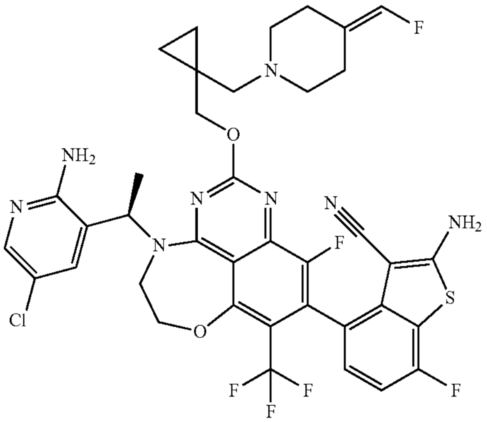 | 2-amino-4-(4-((R)-1-(2-amino-5-chloropyridin-3-yl)ethyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 815.3 |
| 820 | 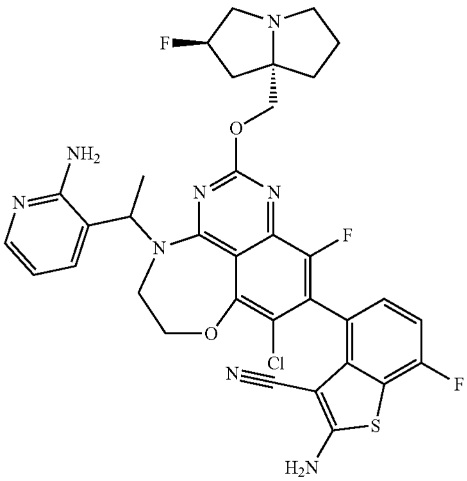 [SMILES: CC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 4, absolute stereochemistry not determined) | 707.0 |
| 821 | 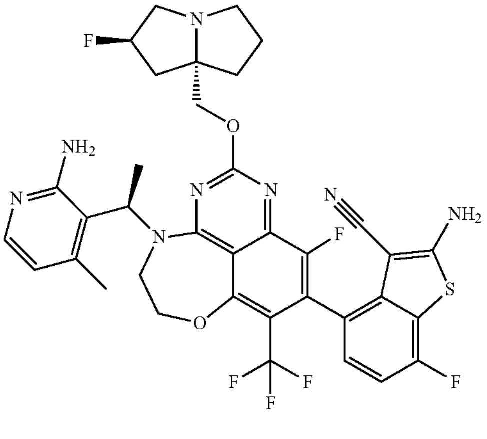 [SMILES: Cc1ccnc(N)c1[C@@H](C)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-4-methylpyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 755.3 |

TABLE 1-continued

| No | Structure | Chemical Name | [M + H]+ |
|---|---|---|---|
| 822 | 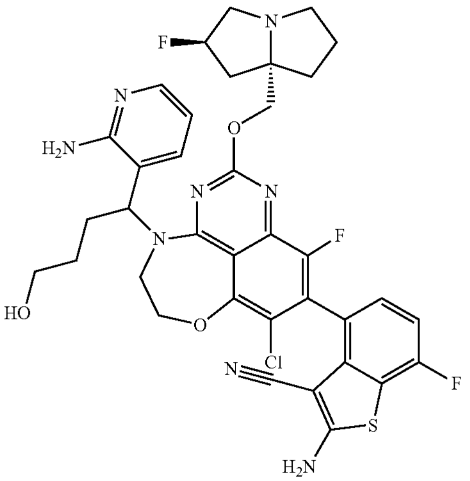 [SMILES: N#Cc1c(N)sc2c(F)ccc(-c3c(Cl)c4c5c(nc(OC[C@@]67CCCN6C[C@H](F)C7)nc5c3F)N(C(CCCO)c3cccnc3N)CCO4)c12] | 2-amino-4-(4-(1-(2-aminopyridin-3-yl)-4-hydroxybutyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (diastereomer mixture) | 751.2 |
| 823 | 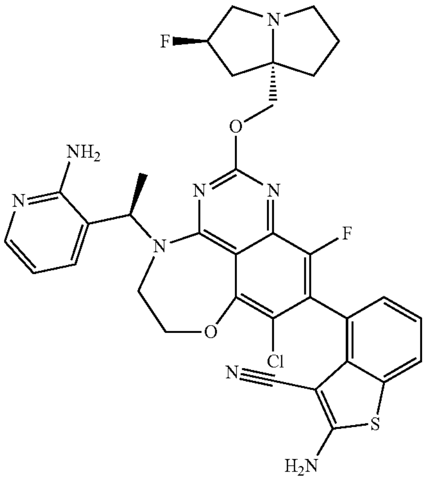 [SMILES: C[C@H](c1cccnc1N)N1CCOc2c(Cl)c(-c3cccc4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)benzo[b]thiophene-3-carbonitrile (single diastereomer, R atropisomer at $R^7$ substituent) | 689.1 |
| 824 | 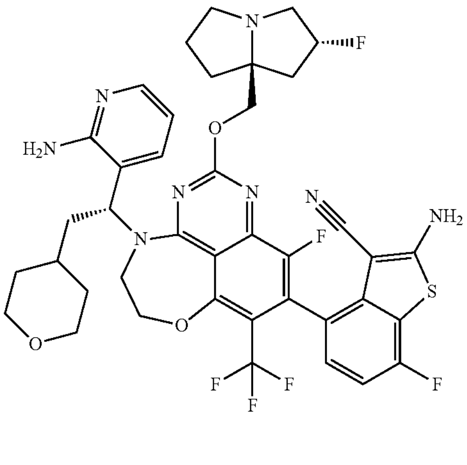 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOCC3)c3cccnc3N)CCO4)c12] | 2-amino-4-(4-((R)-1-(2-aminopyridin-3-yl)-2-(tetrahydro-2H-pyran-4-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 825.4 |

TABLE 1-continued

| No | Structure | Chemical Name | [M + H]+ |
|---|---|---|---|
| 825 | 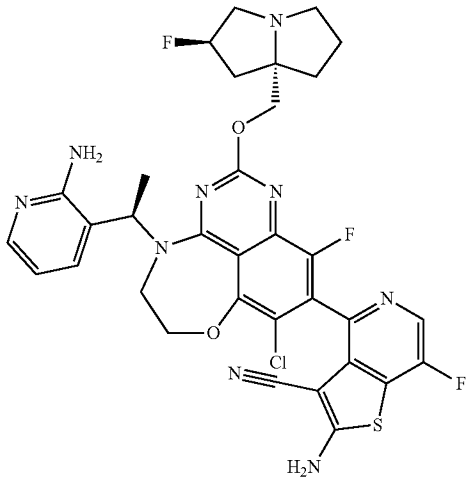 [SMILES: C[C@H](c1cccnc1N)N1CCOc2c(Cl)c(-c3ncc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorothieno[3,2-c]pyridine-3-carbonitrile (single diastereomer 1, R atropisomer at $R^7$ substituent) | 708.5 |
| 826 | 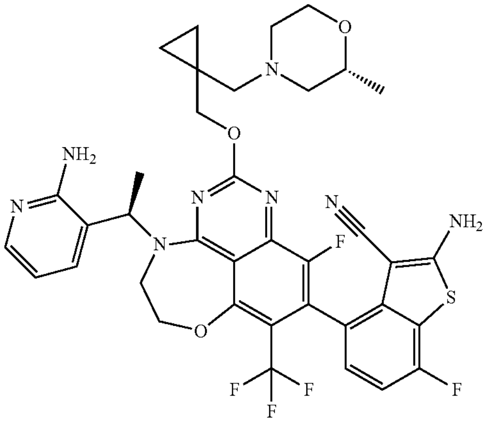 [SMILES: C[C@@H]1CN(CC2(COc3nc4c5c(c(C(F)(F)F)c(-c6ccc(F)c7sc(N)c(C#N)c67)c(F)c5n3)OCCN4[C@H](C)c3cccnc3N)CC2)CCO1] | 2-amino-4-(4-((R)-1-(2-aminopyridin-3-yl)ethyl)-10-fluoro-2-((1-(((R)-2-methylmorpholino)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 767.2 |
| 827 | 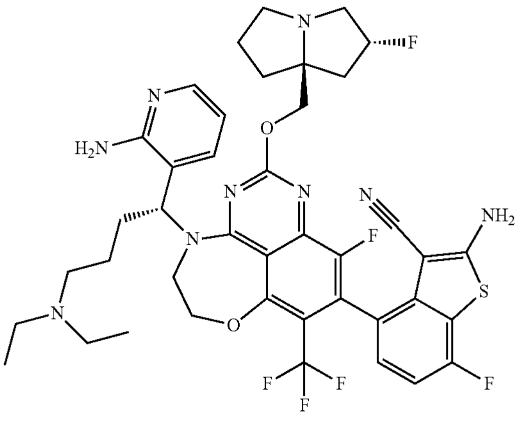 [SMILES: CCN(CC)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-4-(diethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 840.3 |

TABLE 1-continued

| No | Structure | Chemical Name | [M + H]+ |
|---|---|---|---|
| 828 | 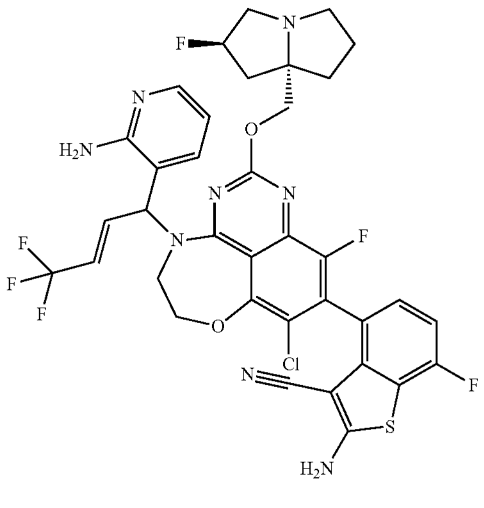 [SMILES: N#Cc1c(N)sc2c(F)ccc(-c3c(Cl)c4c5c(nc(OC[C@@]67CCCN6C[C@H](F)C7)nc5c3F)N(C(/C=C/C(F)(F)F)c3cccnc3N)CCO4)c12] | 2-amino-4-(4-((E)-1-(2-aminopyridin-3-yl)-4,4,4-trifluorobut-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 787.0 |
| 829 | 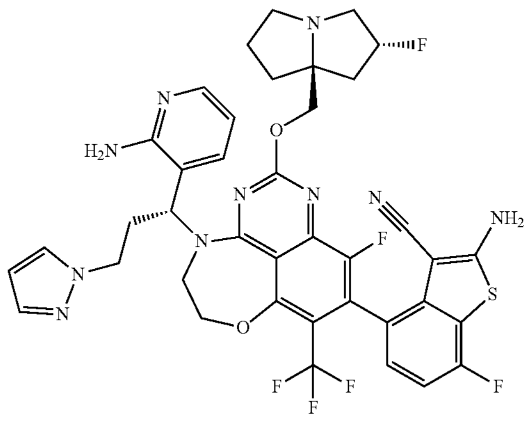 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCn3cccn3)c3cccnc3N)CCO4)c12] | 2-amino-4-(4-((R)-1-(2-aminopyridin-3-yl)-3-(1H-pyrazol-1-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 821.4 |
| 830 | 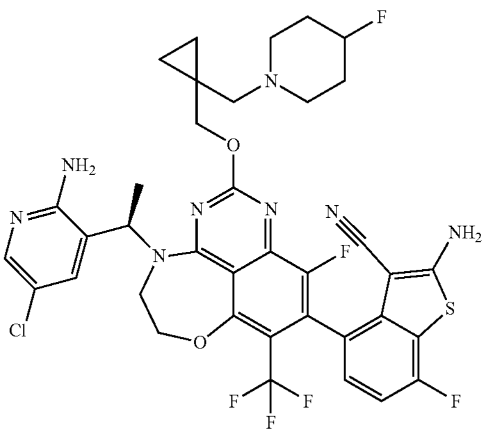 [SMILES: C[C@H](c1cc(Cl)cnc1N)N1CCOc2c(C(F)(F)F)c(-c3ccc(F)c4sc(N)c(C#N)c34)c(F)c3nc(OCC4(CN5CCC(F)CC5)CC4)nc1c23] | 2-amino-4-(4-((R)-1-(2-amino-5-chloropyridin-3-yl)ethyl)-10-fluoro-2-((1-((4-fluoropiperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 803.2 |

TABLE 1-continued

| No | Structure | Chemical Name | [M + H]+ |
|---|---|---|---|
| 831 | 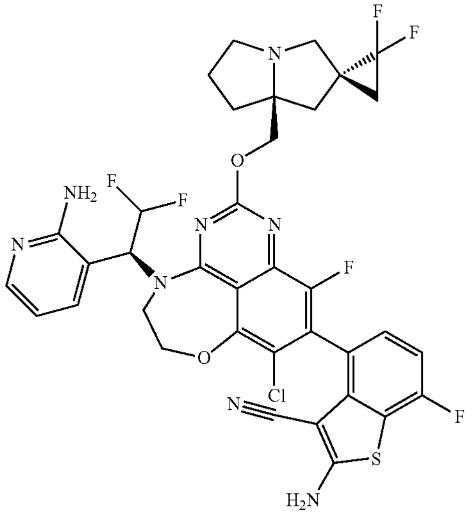 [SMILES: N#Cc1c(N)sc2c(F)ccc(-c3c(Cl)c4c5c(nc(OC[C@@]67CCCN6C[C@@]6(CC6(F)F)C7)nc5c3F)N([C@@H](c3cccnc3N)C(F)F)CCO4)c12] | 2-amino-4-(4-((S)-1-(2-aminopyridin-3-yl)-2,2-difluoroethyl)-8-chloro-2-(((1S,7a'S)-2,2-difluorodihydro-1'H,3'H-spiro[cyclopropane-1,2'-pyrrolizin]-7a'(5'H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 786.9 |
| 832 | 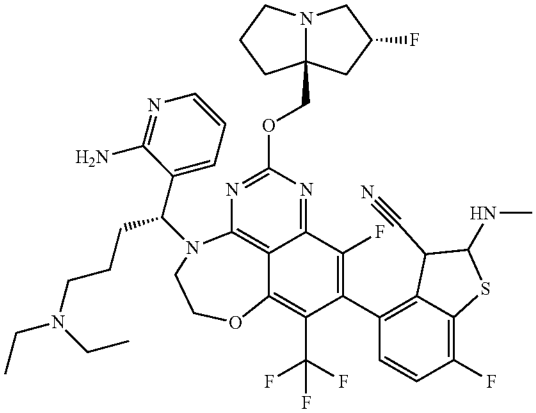 [SMILES: CCN(CC)CCC[C@H](c1cccnc1N)N1CCOc2c(C(F)(F)F)c(-c3ccc(F)c4c3C(C#N)C(NC)S4)c(F)c3nc(OC[C@@]45CCCN4C[C@H](F)C5)nc1c23] | 4-(4-((R)-1-(2-aminopyridin-3-yl)-4-(diethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluoro-2-(methylamino)benzo[b]thiophene-3-carbonitrile (single diastereomer, R atropisomer at $R^7$ substituent) | 854.3 |
| 833 | 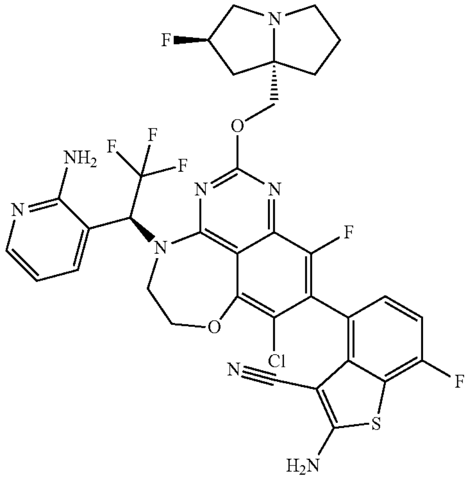 [SMILES: N#Cc1c(N)sc2c(F)ccc(-c3c(Cl)c4c5c(nc(OC[C@@]67CCCN6C[C@H](F)C7)nc5c3F)N([C@@H](c3cccnc3N)C(F)(F)F)CCO4)c12] | 2-amino-4-(4-((S)-1-(2-aminopyridin-3-yl)-2,2,2-trifluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 760.9 |

TABLE 1-continued

| No | Structure | Chemical Name | [M + H]+ |
|---|---|---|---|
| 834 | 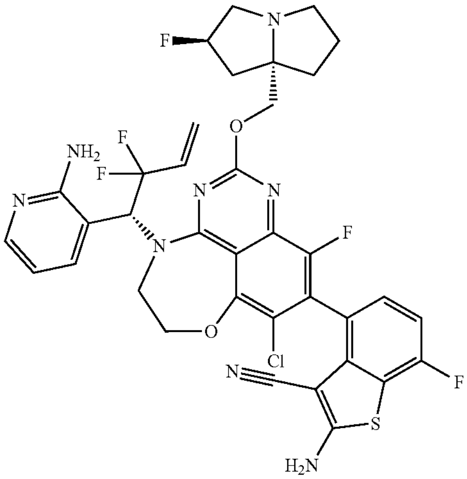 [SMILES: C=CC(F)(F)[C@@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-2,2-difluorobut-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at R7 substituent) | 769.2 |
| 835 | 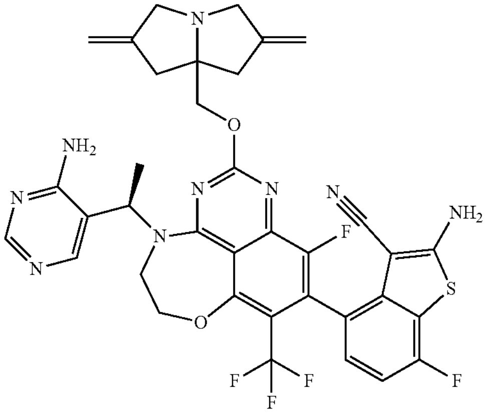 [SMILES: C=C1CN2CC(=C)CC2(COc2nc3c4c(c(C(F)(F)F)c(-c5ccc(F)c6sc(N)c(C#N)c56)c(F)c4n2)OCCN3[C@H](C)c2cncnc2N)C1] | 2-amino-4-(4-((R)-1-(4-aminopyrimidin-5-yl)ethyl)-2-((2,6-dimethylenetetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at R7 substituent) | 748.3 |
| 836 | 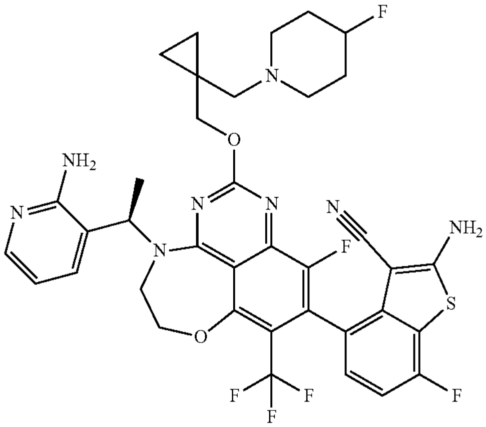 | 2-amino-4-(4-((R)-1-(2-aminopyridin-3-yl)ethyl)-10-fluoro-2-((1-((4-fluoropiperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at R7 substituent) | 796.4 |

TABLE 1-continued

| No | Structure | Chemical Name | [M + H]+ |
|---|---|---|---|
| 837 | 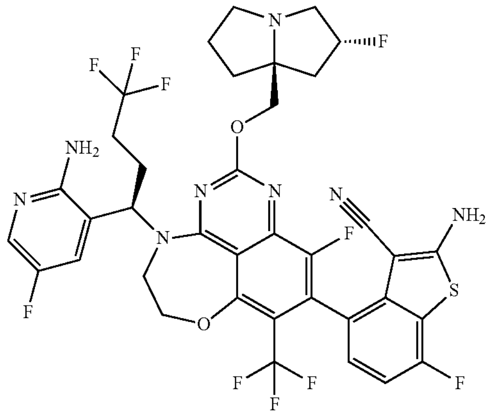 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC(F)(F)F)c3cc(F)cnc3N)CCO4)c12] | 2-amino-4-(4-((R)-1-(2-amino-5-fluoropyridin-3-yl)-4,4,4-trifluorobutyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 841.4 |
| 838 | 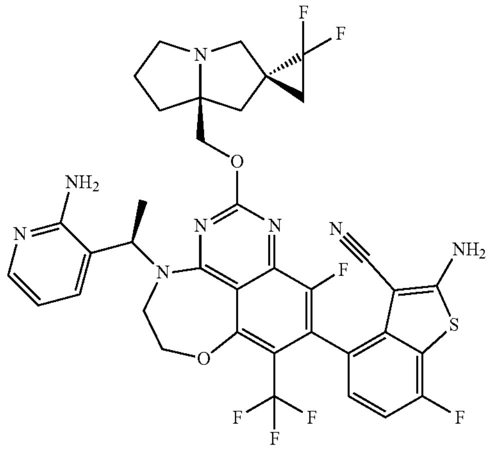 [SMILES: C[C@H](c1cccnc1N)N1CCOc2c(C(F)(F)F)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(2-aminopyridin-3-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 785.0 |
| 839 | 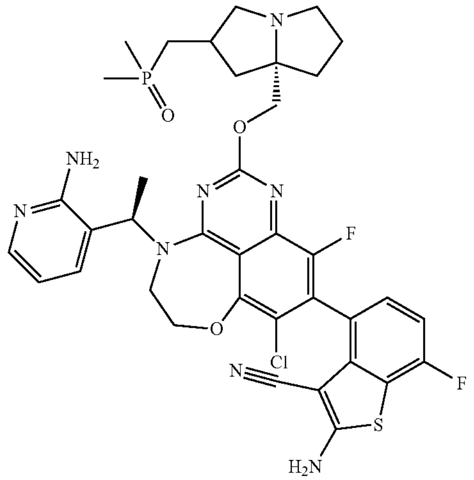 [SMILES: C[C@H](c1cccnc1N)N1CCOc2c(Cl)c(-c3ccc(F)c4sc(N)c(C#N)c34)c(F)c3nc(OC[C@@]45CCCN4CC(CP(C)(C)=O)C5)nc1c23] | 2-amino-4-(4-((R)-1-(2-aminopyridin-3-yl)ethyl)-8-chloro-2-(((7aS)-2-((dimethylphosphoryl)methyl)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (diastereomer mixture) | 780.5 |

TABLE 1-continued

| No | Structure | Chemical Name | [M + H]+ |
|---|---|---|---|
| 840 | 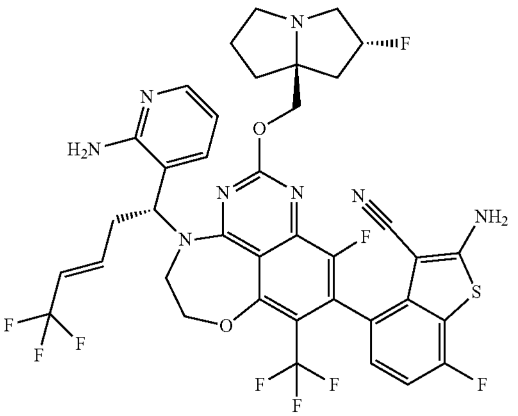 [SMILES: N#Cc1c(N)sc2c(F)ccc(-c3c(C(F)(F)F)c4c5c(nc(OC[C@@]67CCCN6C[C@H](F)C7)nc5c3F)N([C@H](C/C=C/C(F)(F)F)c3cccnc3N)CCO4)c12] | 2-amino-4-(4-((R,E)-1-(2-aminopyridin-3-yl)-5,5,5-trifluoropent-3-en-1-yl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 835.2 |
| 841 | 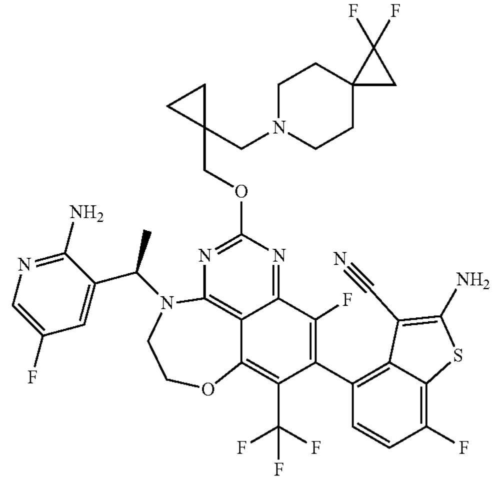 | 2-amino-4-(4-((R)-1-(2-amino-5-fluoropyridin-3-yl)ethyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 831.2 |
| 842 | 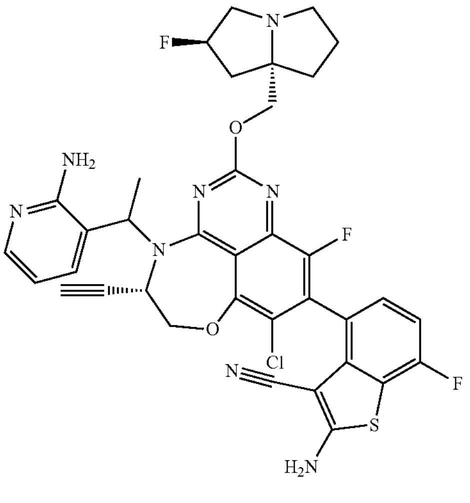 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 730.9 |

TABLE 1-continued

| No | Structure | Chemical Name | [M + H]+ |
|---|---|---|---|
| 843 | 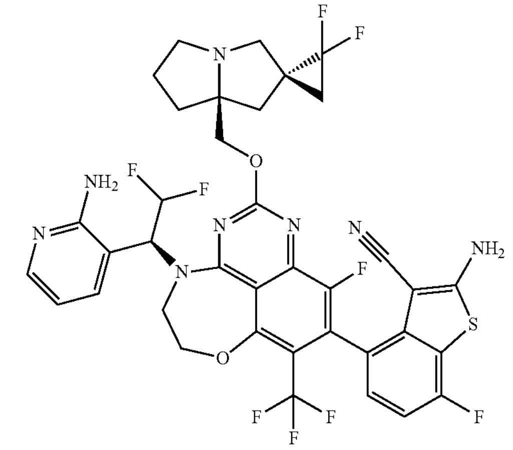 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@@H](c3cccnc3N)C(F)F)CCO4)c12] | 2-amino-4-(4-((S)-1-(2-aminopyridin-3-yl)-2,2-difluoroethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 821.1 |
| 844 | 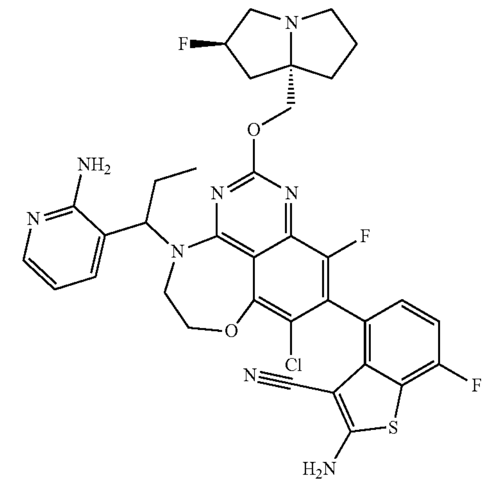 [SMILES: CCC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)propyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 721.2 |
| 845 | 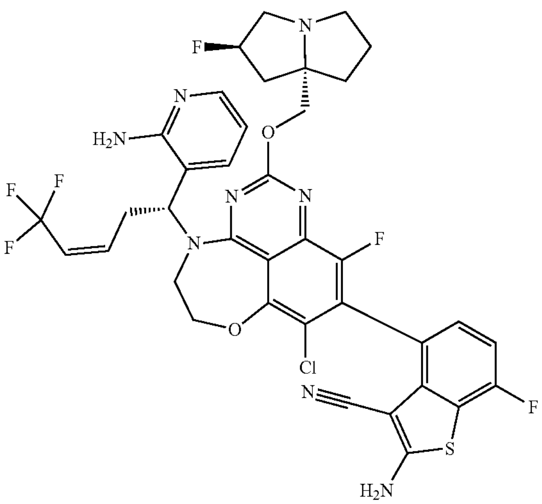 [SMILES: N#Cc1c(N)sc2c(F)ccc(-c3c(Cl)c4c5c(nc(OC[C@@]67CCCN6C[C@H](F)C7)nc5c3F)N([C@H](C/C=C\C(F)(F)F)c3cccnc3N)CCO4)c12] | 2-amino-4-(4-((R,Z)-1-(2-aminopyridin-3-yl)-5,5,5-trifluoropent-3-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 800.9 |

TABLE 1-continued

| No | Structure | Chemical Name | [M + H]+ |
| --- | --- | --- | --- |
| 846 | 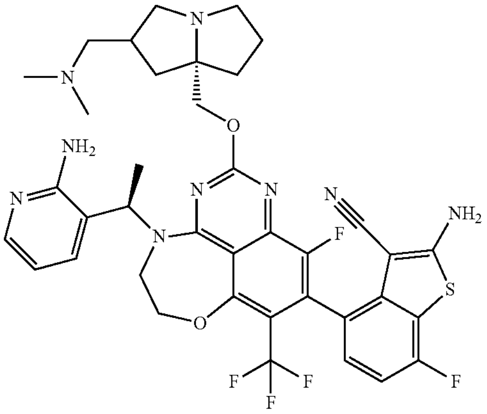 [SMILES: C[C@H](c1cccnc1N)N1CCOc2c(C(F)(F)F)c(-c3ccc(F)c4sc(N)c(C#N)c34)c(F)c3nc(OC[C@@]45CCCN4CC(CN(C)C)C5)nc1c23] | 2-amino-4-(4-((R)-1-(2-aminopyridin-3-yl)ethyl)-2-(((7aS)-2-((dimethylamino)methyl)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (diastereomer mixture) | 780.2 |
| 847 | 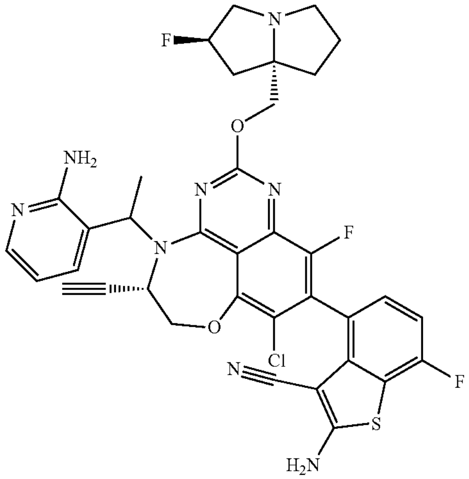 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 730.9 |
| 848 | 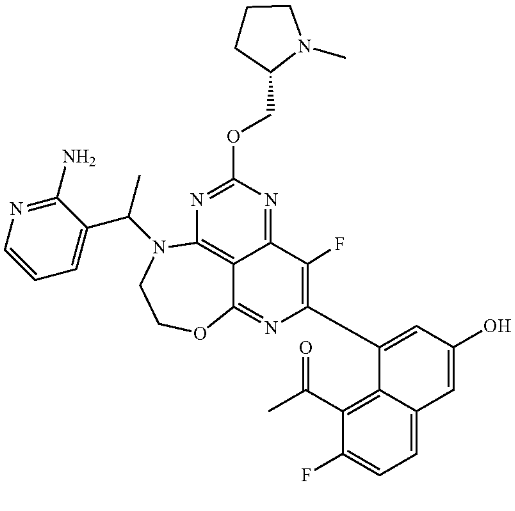 [SMILES: CC(=O)c1c(F)ccc2cc(O)cc(-c3nc4c5c(nc(OC[C@@H]6CCCN6C)nc5c3F)N(C(C)c3cccnc3N)CCO4)c12] | 1-(8-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-2-fluoro-6-hydroxynaphthalen-1-yl)ethan-1-one (diastereomer mixture) | 642.1 |

TABLE 1-continued

| No | Structure | Chemical Name | [M + H]+ |
|---|---|---|---|
| 849 | 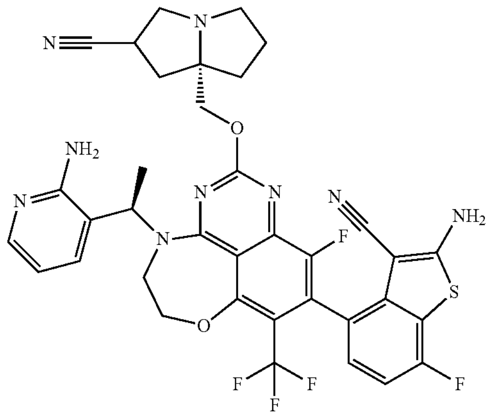 | (7aS)-7a-(((9-(2-amino-3-cyano-7-fluorobenzo[b]thiophen-4-yl)-4-((R)-1-(2-aminopyridin-3-yl)ethyl)-10-fluoro-8-(trifluoromethyl)-5,6-dihydro-4H-[1,4]oxazepino[5,6,7-de]quinazolin-2-yl)oxy)methyl)hexahydro-1H-pyrrolizine-2-carbonitrile (single diastereomer 2, absolute stereochemistry not determined) | 748.3 |
| 850 | 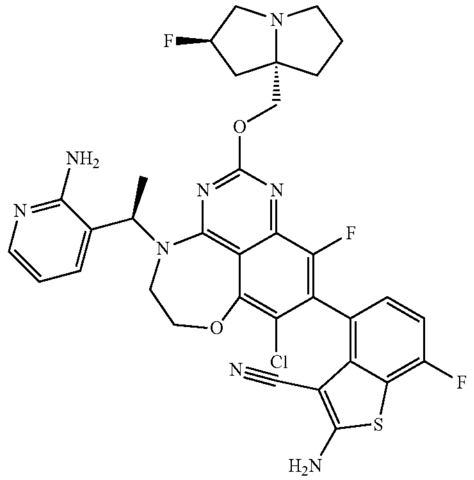 [SMILES: C[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 707.0 |
| 851 | 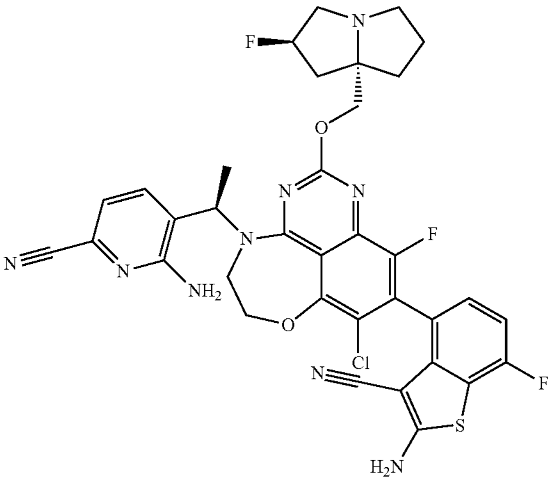 [SMILES: C[C@H](c1ccc(C#N)nc1N)N1CCOc2c(Cl)c(-c3ccc(F)c4sc(N)c(C#N)c34)c(F)c3nc(OC[C@@]45CCCN4C[C@H](F)C5)nc1c23] | 6-amino-5-((1R)-1-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)picolinonitrile (single diastereomer, R atropisomer at $R^7$ substituent) | 732.1 |

TABLE 1-continued

| No | Structure | Chemical Name | [M + H]+ |
|---|---|---|---|
| 852 | 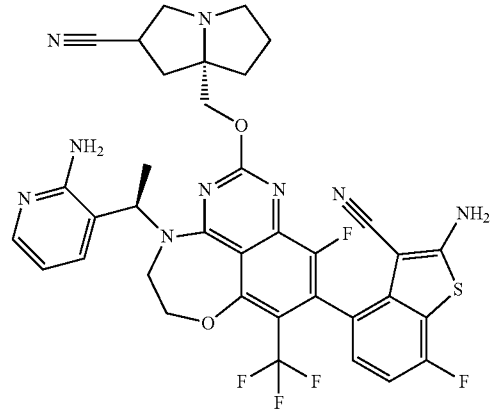 | (7aS)-7a-(((9-(2-amino-3-cyano-7-fluorobenzo[b]thiophen-4-yl)-4-((R)-1-(2-aminopyridin-3-yl)ethyl)-10-fluoro-8-(trifluoromethyl)-5,6-dihydro-4H-[1,4]oxazepino[5,6,7-de]quinazolin-2-yl)oxy)methyl)hexahydro-1H-pyrrolizine-2-carbonitrile | 748.3 |
| 853 | 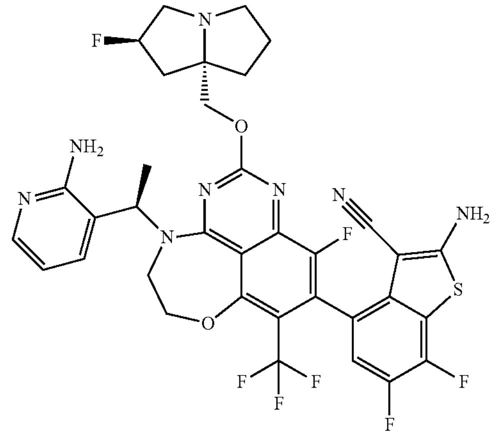 [SMILES: C[C@H](c1cccnc1N)N1CCOc2c(C(F)(F)F)c(-c3cc(F)c(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-6,7-difluorobenzo[b]thiophene-3-carbonitrile (single diastereomer, S atropisomer at $R^7$ substituent) | 759.3 |
| 854 | 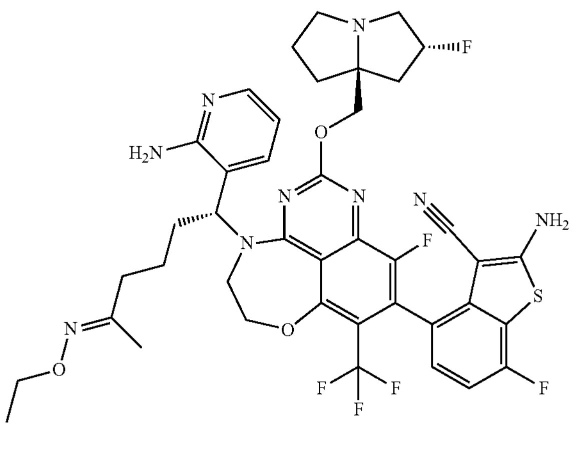 [SMILES: CCO/N=C(\C)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R,E)-1-(2-aminopyridin-3-yl)-5-(ethoxyimino)hexyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile | 854.3 |

TABLE 1-continued

| No | Structure | Chemical Name | [M + H]+ |
|---|---|---|---|
| 855 | 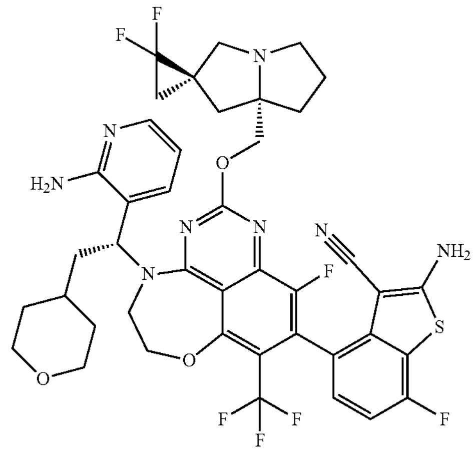 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CC3CCOCC3)c3cccnc3N)CCO4)c12] | 2-amino-4-(4-((R)-1-(2-aminopyridin-3-yl)-2-(tetrahydro-2H-pyran-4-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 869.3 |
| 856 | 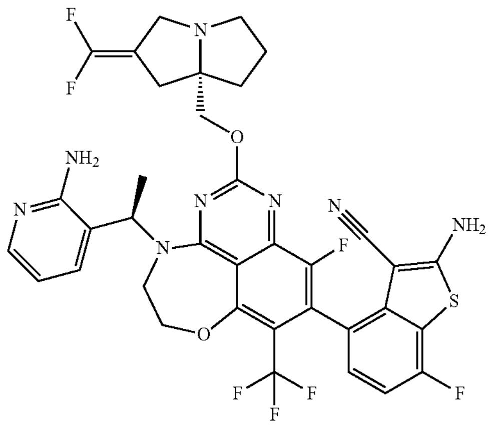 [SMILES: C[C@H](c1cccnc1N)N1CCOc2c(C(F)(F)F)c(-c3ccc(F)c4sc(N)c(C#N)c34)c(F)c3nc(OC[C@@]45CCCN4CC(=C(F)F)C5)nc1c23] | 2-amino-4-(4-((R)-1-(2-aminopyridin-3-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 771.3 |
| 857 | 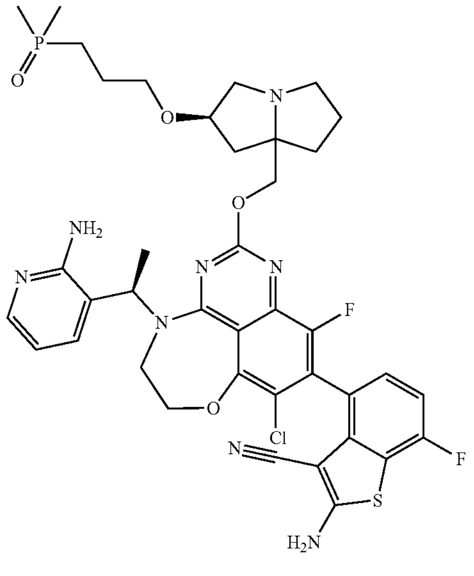 [SMILES: C[C@H](c1cccnc1N)N1CCOc2c(Cl)c(-c3ccc(F)c4sc(N)c(C#N)c34)c(F)c3nc(OCC45CCCN4C[C@H](OCCCP(C)(C)=O)C5)nc1c23] | 2-amino-4-(4-((R)-1-(2-aminopyridin-3-yl)ethyl)-8-chloro-2-(((2R)-2-(3-(dimethylphosphoryl)propoxy)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 824.2 |

TABLE 1-continued

| No | Structure | Chemical Name | [M + H]+ |
| --- | --- | --- | --- |
| 858 | 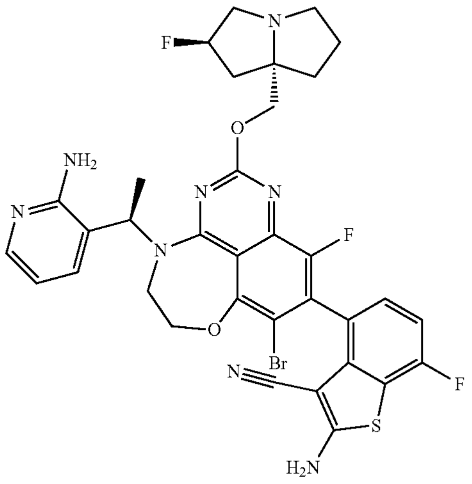 | 2-amino-4-(4-((R)-1-(2-aminopyridin-3-yl)ethyl)-8-bromo-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 752.8 |
| 859 | 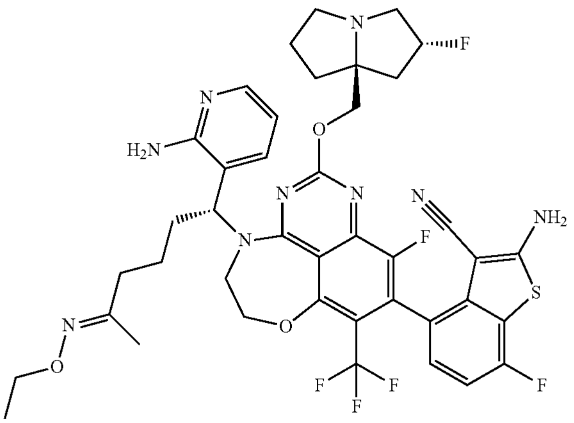 [SMILES: CCO/N=C(\C)CCC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R,E)-1-(2-aminopyridin-3-yl)-5-(ethoxyimino)hexyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 3, absolute stereochemistry not determined) | 854.3 |
| 860 | 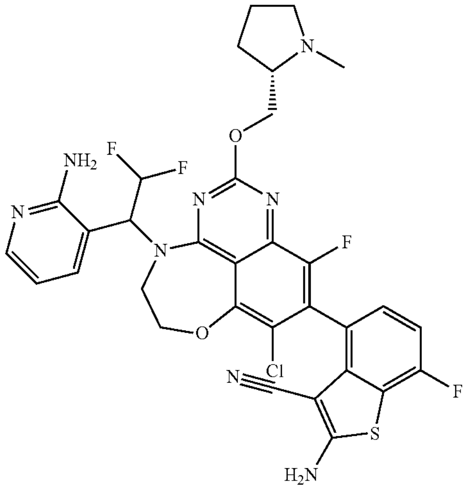 [SMILES: CN1CCC[C@H]1COc1nc2c3c(c(Cl)c(-c4ccc(F)c5sc(N)c(C#N)c45)c(F)c3n1)OCCN2C(c1cccnc1N)C(F)F] | 2-amino-4-(4-(1-(2-aminopyridin-3-yl)-2,2-difluoroethyl)-8-chloro-10-fluoro-2-(((S)-1-methylpyrrolidin-2-yl)methoxy)-5,6-dihydro-4H-[1,4]oxazepino[5,6,7-de]quinazolin-9-yl)-7-fluorobenzo[b]thiophene-3-carbonitrile (mixture of diastereomers) | 698.9 |

TABLE 1-continued

| No | Structure | Chemical Name | [M + H]+ |
|---|---|---|---|
| 861 | 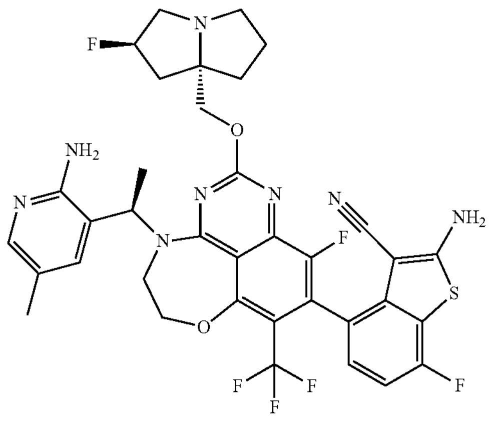 | 2-amino-4-(4-((R)-1-(2-amino-5-methylpyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 755.2 |
| 862 | 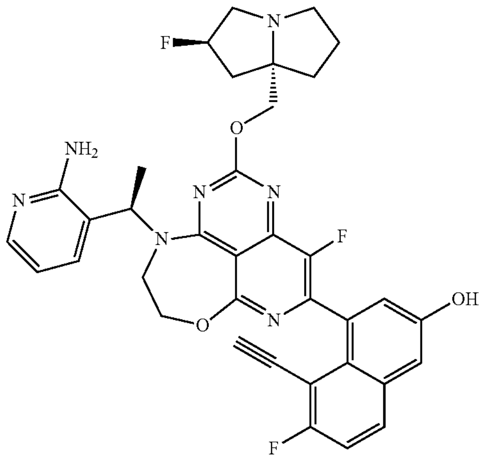 [SMILES: C#Cc1c(F)ccc2cc(O)cc(-c3nc4c5c(nc(OC[C@@]67CCCN6C[C@H](F)C7)nc5c3F)N([C@H](C)c3cccnc3N)CCO4)c12] | 4-(10-((R)-1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-5-ethynyl-6-fluoronaphthalen-2-ol (single diastereomer) | 668.2 |
| 863 | 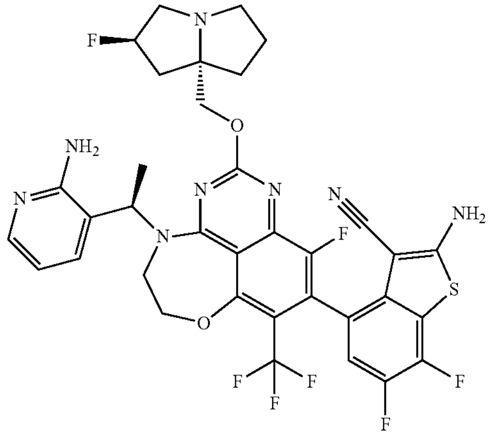 [SMILES: C[C@H](c1cccnc1N)N1CCOc2c(C(F)(F)F)c(-c3cc(F)c(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-6,7-difluorobenzo[b]thiophene-3-carbonitrile (single diastereomer, R atropisomer at $R^7$ substituent) | 759.3 |

TABLE 1-continued

| No | Structure | Chemical Name | [M + H]+ |
|---|---|---|---|
| 864 | 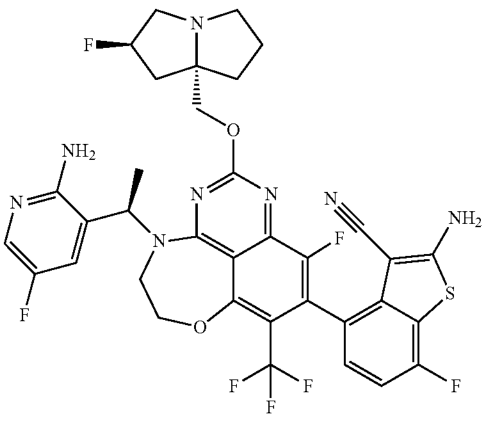 | 2-amino-4-(4-((R)-1-(2-amino-5-fluoropyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 759.2 |
| 865 | 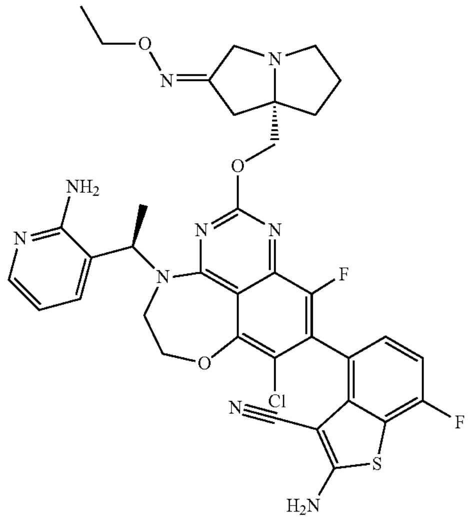 | 2-amino-4-(4-((R)-1-(2-aminopyridin-3-yl)ethyl)-8-chloro-2-(((S,Z)-2-(ethoxyimino)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 746.1 |
| 866 | 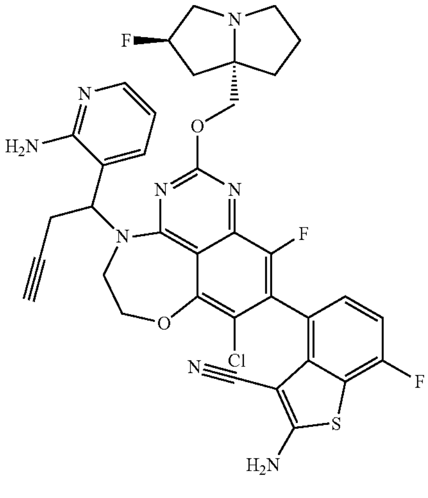 [SMILES: C#CCC(c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(2-aminopyridin-3-yl)but-3-yn-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 731.1 |

TABLE 1-continued

| No | Structure | Chemical Name | [M + H]$^+$ |
|---|---|---|---|
| 867 | 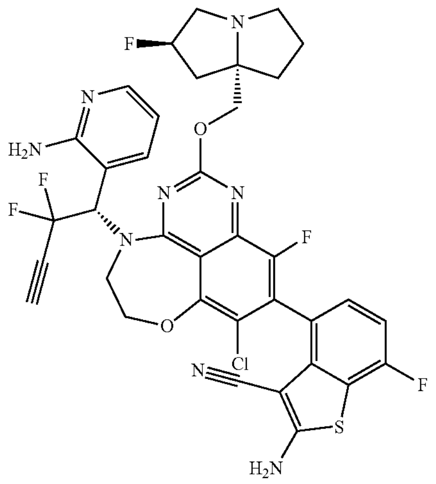 [SMILES: C#CC(F)(F)[C@H](c1cccnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((S)-1-(2-aminopyridin-3-yl)-2,2-difluorobut-3-yn-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 767.1 |
| 868 | 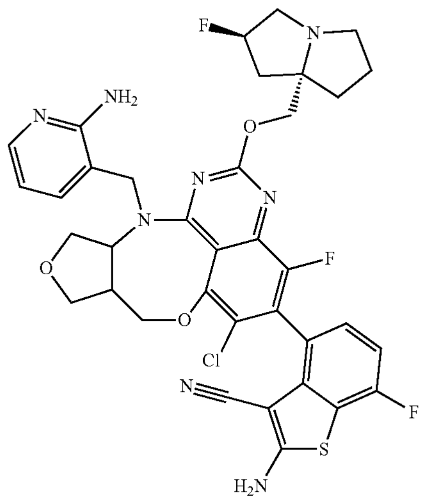 [SMILES: N#Cc1c(N)sc2c(F)ccc(-c3c(Cl)c4c5c(nc(OC[C@@]67CCCN6C[C@H](F)C7)nc5c3F)N(Cc3cccnc3N)C3COCC3CO4)c12] | 2-amino-4-(12-((2-aminopyridin-3-yl)methyl)-6-chloro-4-fluoro-2-(((2R,7aS)-2-fluorotetrahydro-1H-pyrrolizin-7a(5H)-yl)methoxy)-8a,9,11a,12-tetrahydro-8H,11H-furo[3',4':6,7][1,5]oxazocino[4,3,2-de]quinazolin-5-yl)-7-fluorobenzo[b]thiophene-3-carbonitrile (mixture of diastereomers) | 749.0 |
| 869 | 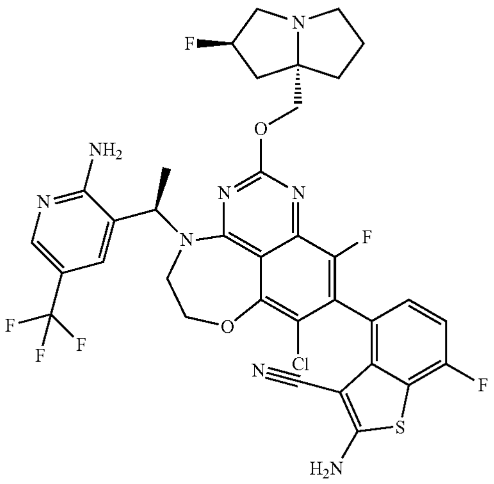 [SMILES: C[C@H](c1cc(C(F)(F)F)cnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-(trifluoromethyl)pyridin-3-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 775.2 |

TABLE 1-continued

| No | Structure | Chemical Name | [M + H]+ |
|---|---|---|---|
| 870 | 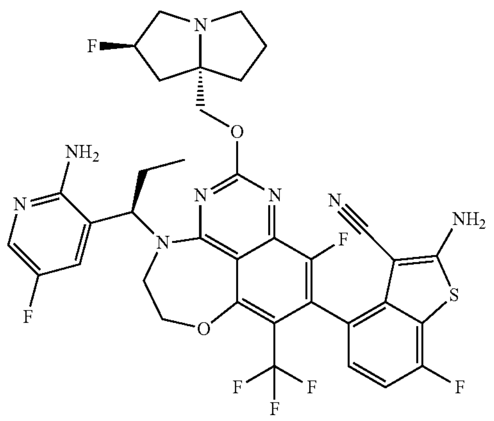 [SMILES: CC[C@H](c1cc(F)cnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-5-fluoropyridin-3-yl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at R7 substituent) | 773.3 |
| 871 | 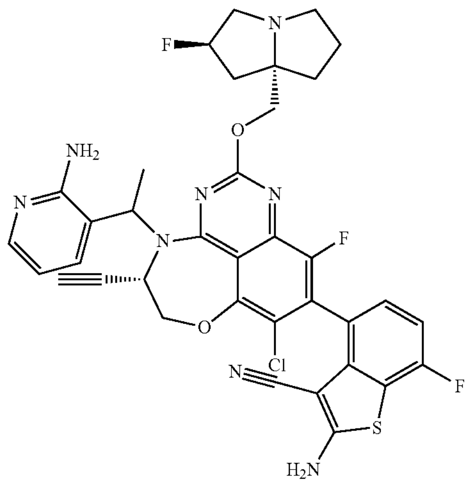 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 5, absolute stereochemistry not determined) | 730.9 |
| 872 | 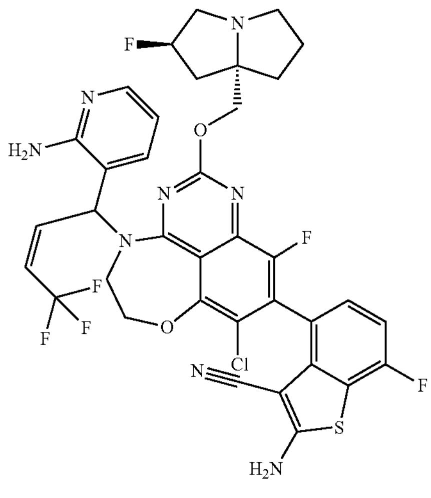 [SMILES: N#Cc1c(N)sc2c(F)ccc(-c3c(Cl)c4c5c(nc(OC[C@@]67CCCN6C[C@H](F)C7)nc5c3F)N(C(/C=C\C(F)(F)F)c3cccnc3N)CCO4)c12] | 2-amino-4-(4-((Z)-1-(2-aminopyridin-3-yl)-4,4,4-trifluorobut-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at R7 substituent) | 786.9 |

TABLE 1-continued

| No | Structure | Chemical Name | [M + H]+ |
|---|---|---|---|
| 873 | 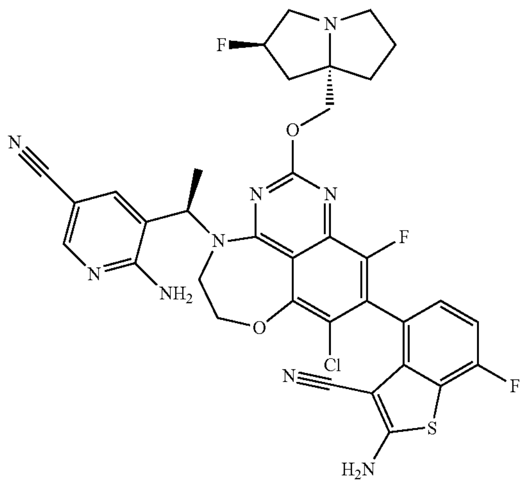 [SMILES: C[C@H](c1cc(C#N)cnc1N)N1CCOc2c(Cl)c(-c3ccc(F)c4sc(N)c(C#N)c34)c(F)c3nc(OC[C@@]45CCCN4C[C@H](F)C5)nc1c23] | 6-amino-5-((1R)-1-(9-(2-amino-3-cyano-7-fluorobenzo[b]thiophen-4-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-4-yl)ethyl)nicotinonitrile (single diastereomer, R atropisomer at $R^7$ substituent) | 732.1 |
| 874 | 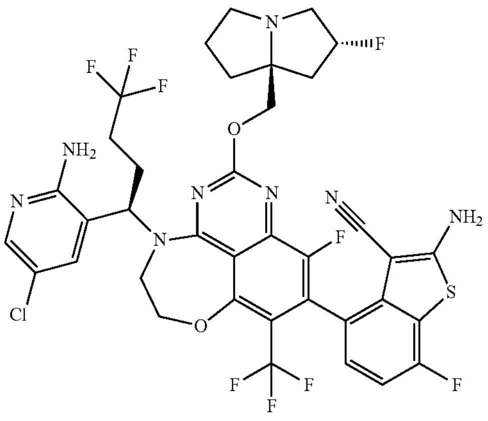 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC(F)(F)F)c3cc(Cl)cnc3N)CCO4)c12] | 2-amino-4-(4-((R)-1-(2-amino-5-chloropyridin-3-yl)-4,4,4-trifluorobutyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 857.1 |
| 875 | 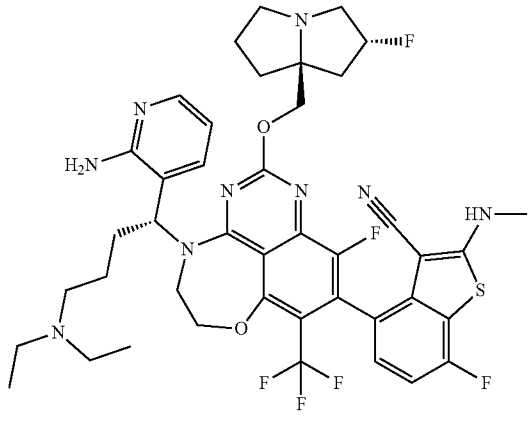 [SMILES: CCN(CC)CCC[C@H](c1cccnc1N)N1CCOc2c(C(F)(F)F)c(-c3ccc(F)c4sc(NC)c(C#N)c34)c(F)c3nc(OC[C@@]45CCCN4C[C@H](F)C5)nc1c23] | 4-(4-((R)-1-(2-aminopyridin-3-yl)-4-(diethylamino)butyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluoro-2-(methylamino)benzo[b]thiophene-3-carbonitrile (single diastereomer, S atropisomer at $R^7$ substituent) | 854.3 |

TABLE 1-continued

| No | Structure | Chemical Name | [M + H]+ |
|---|---|---|---|
| 876 | 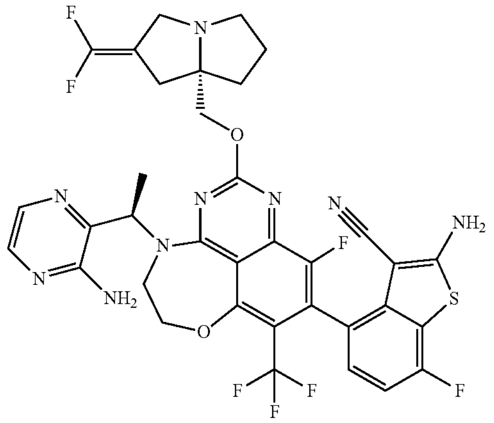 [SMILES: C[C@H](c1nccnc1N)N1CCOc2c(C(F)(F)F)c(-c3ccc(F)c4sc(N)c(C#N)c34)c(F)c3nc(OC[C@@]45CCCN4CC(=C(F)F)C5)nc1c23] | 2-amino-4-(4-((R)-1-(3-aminopyrazin-2-yl)ethyl)-2-(((S)-2-(difluoromethylene)tetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 772.3 |
| 877 | 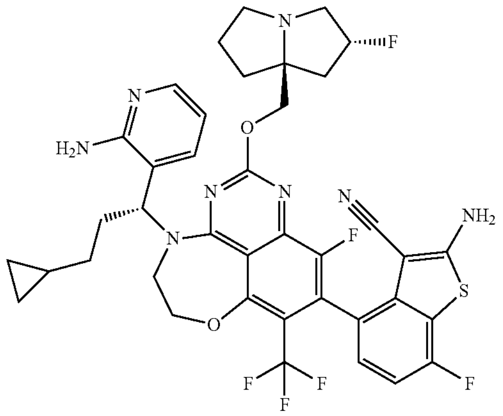 [SMILES: N#Cc1c(N)sc2c(F)ccc(-c3c(C(F)(F)F)c4c5c(nc(OC[C@@]67CCCN6C[C@H](F)C7)nc5c3F)N([C@H](CCC3CC3)c3cccnc3N)CCO4)c12] | 2-amino-4-(4-((R)-1-(2-aminopyridin-3-yl)-3-cyclopropylpropyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 795.3 |
| 878 | 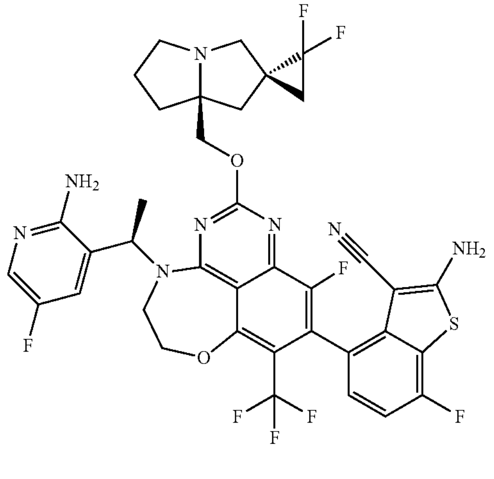 [SMILES: C[C@H](c1cc(F)cnc1N)N1CCOc2c(C(F)(F)F)c(-c3ccc(F)c4sc(N)c(C#N)c34)c(F)c3nc(OC[C@@]45CCCN4C[C@@]4(CC4(F)F)C5)nc1c23] | 2-amino-4-(4-((R)-1-(2-amino-5-fluoropyridin-3-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 803.3 |

TABLE 1-continued

| No | Structure | Chemical Name | [M + H]+ |
|---|---|---|---|
| 879 | 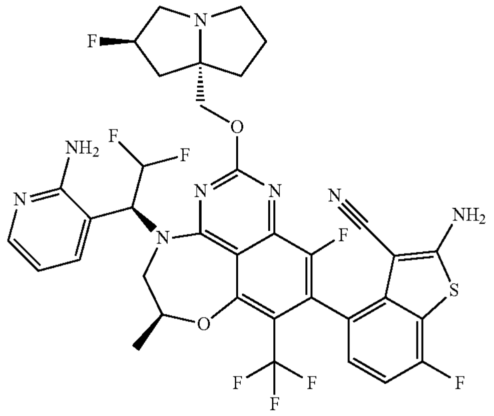 [SMILES: C[C@H]1CN([C@@H](c2cccnc2N)C(F)F)c2nc(OC[C@@]34CCCN3C[C@H](F)C4)nc3c(F)c(-c4ccc(F)c5sc(N)c(C#N)c45)c(C(F)(F)F)c(c23)O1] | 2-amino-4-((6S)-4-((S)-1-(2-aminopyridin-3-yl)-2,2-difluoroethyl)-10-fluoro-2-(((2R,7aS)-2-fluorotetrahydro-1H-pyrrolizin-7a(5H)-yl)methoxy)-6-methyl-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 790.9 |
| 880 | 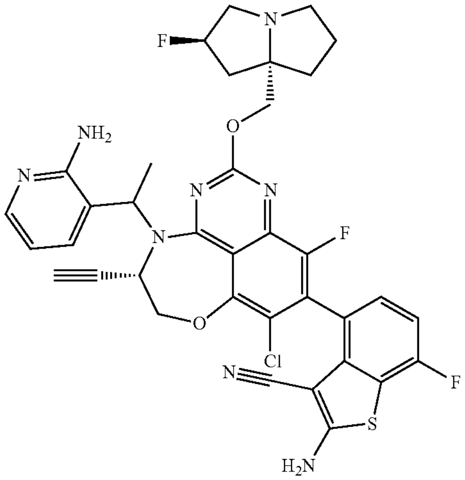 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 6, absolute stereochemistry not determined) | 730.8 |
| 881 | 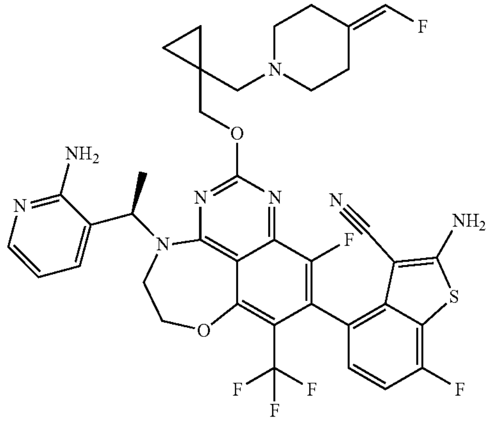 [SMILES: C[C@H](c1cccnc1N)N1CCOc2c(C(F)(F)F)c(-c3ccc(F)c4sc(N)c(C#N)c34)c(F)c3nc(OCC4(CN5CCC(=CF)CC5)CC4)nc1c23] | 2-amino-4-(4-((R)-1-(2-aminopyridin-3-yl)ethyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile | 781.2 |

TABLE 1-continued

| No | Structure | Chemical Name | [M + H]+ |
| --- | --- | --- | --- |
| 882 | 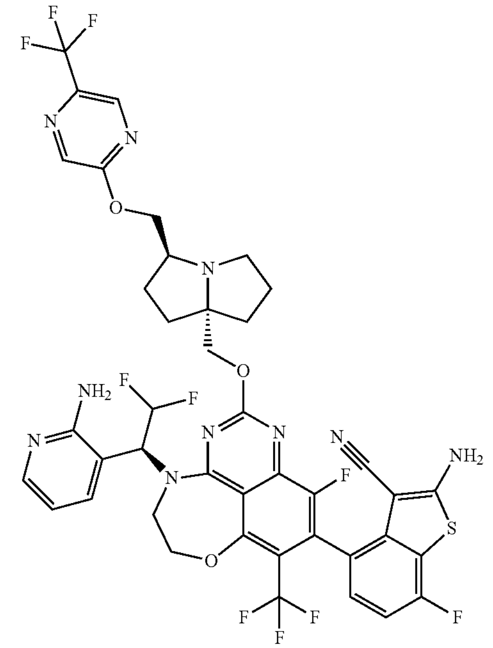 [SMILES: N#Cc1c(N)sc2c(F)ccc(-c3c(C(F)(F)F)c4c5c(nc(OC[C@@]67CCCN6[C@H](COc6cnc(C(F)(F)F)cn6)CC7)nc5c3F)N([C@@H](c3cccnc3N)C(F)F)CCO4)c12] | 2-amino-4-(4-((S)-1-(2-aminopyridin-3-yl)-2,2-difluoroethyl)-10-fluoro-8-(trifluoromethyl)-2-(((3S,7aS)-3-(((5-(trifluoromethyl)pyrazin-2-yl)oxy)methyl)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 935.2 |
| 883 | 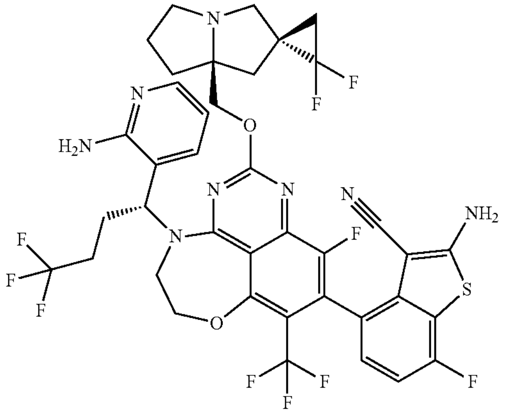 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CCC(F)(F)F)c3cccnc3N)CCO4)c12] | 2-amino-4-(4-((R)-1-(2-aminopyridin-3-yl)-4,4,4-trifluorobutyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 876.3 |
| 884 | 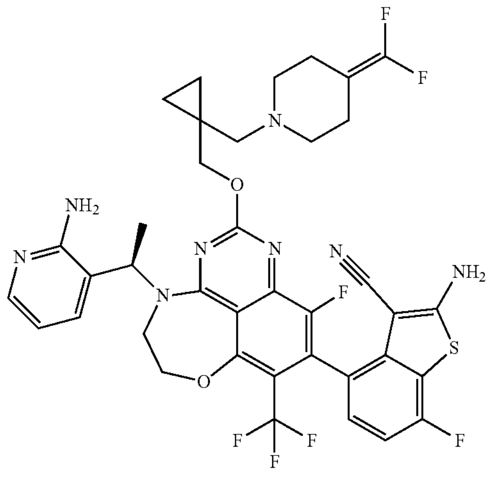 [SMILES: C[C@H](c1cccnc1N)N1CCOc2c(C(F)(F)F)c(-c3ccc(F)c4sc(N)c(C#N)c34)c(F)c3nc(OCC4(CN5CCC(=C(F)F)CC5)CC4)nc1c23] | 2-amino-4-(4-((R)-1-(2-aminopyridin-3-yl)ethyl)-2-((1-((4-(difluoromethylene)piperidin-1-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 799.2 |

TABLE 1-continued

| No | Structure | Chemical Name | [M + H]+ |
|---|---|---|---|
| 885 | 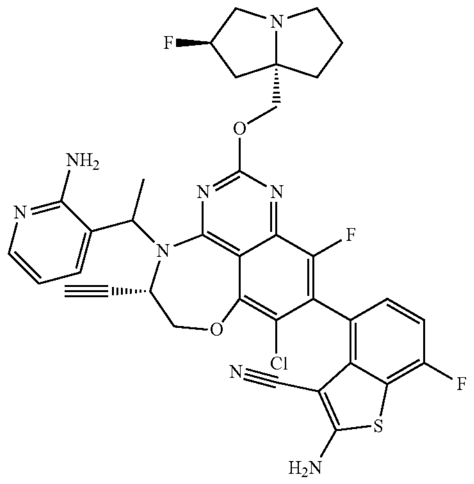 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 730.9 |
| 886 | 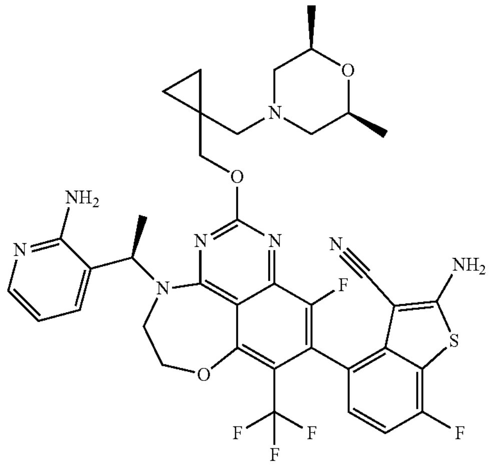 [SMILES: C[C@@H]1CN(CC2(COc3nc4c5c(c(C(F)(F)F)c(-c6ccc(F)c7sc(N)c(C#N)c67)c(F)c5n3)OCCN4[C@H](C)c3cccnc3N)CC2)C[C@H](C)O1] | 2-amino-4-(4-((R)-1-(2-aminopyridin-3-yl)ethyl)-2-((1-(((2S,6R)-2,6-dimethylmorpholino)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 781.2 |
| 887 | 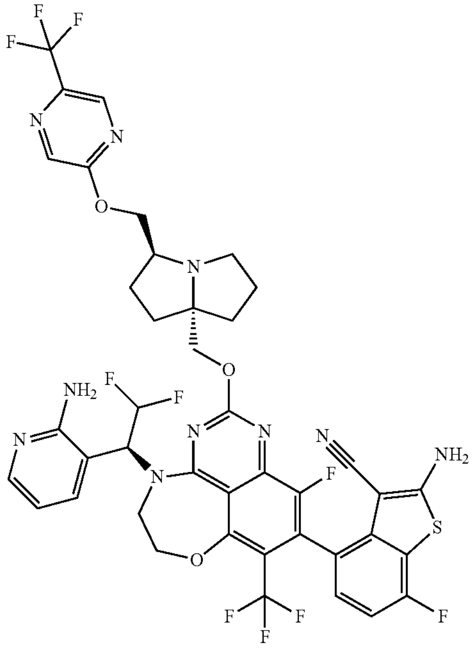 [SMILES: N#Cc1c(N)sc2c(F)ccc(-c3c(C(F)(F)F)c4c5c(nc(OC[C@@]67CCCN6[C@H](COc6cnc(C(F)(F)F)cn6)CC7)nc5c3F)N([C@@H](c3cccnc3N)C(F)F)CCO4)c12] | 2-amino-4-(4-((S)-1-(2-aminopyridin-3-yl)-2,2-difluoroethyl)-10-fluoro-8-(trifluoromethyl)-2-(((3S,7aS)-3-(((5-(trifluoromethyl)pyrazin-2-yl)oxy)methyl)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 935.2 |

TABLE 1-continued

| No | Structure | Chemical Name | [M + H]+ |
|---|---|---|---|
| 888 | 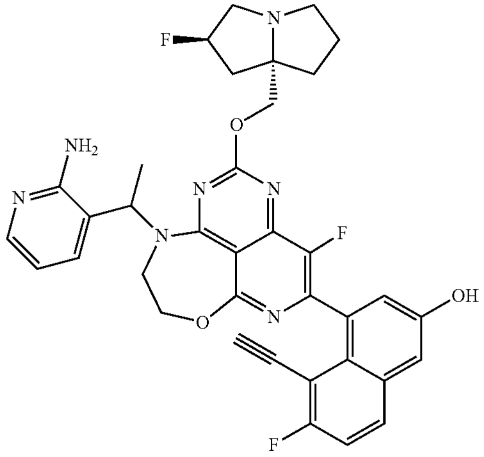 [SMILES: C#Cc1c(F)ccc2cc(O)cc(-c3nc4c5c(nc(OC[C@@]67CCCN6C[C@H](F)C7)nc5c3F)N(C(C)c3cccnc3N)CCO4)c12] | 4-(10-(1-(2-aminopyridin-3-yl)ethyl)-4-fluoro-2-(((2R,7aS)-2-fluorotetrahydro-1H-pyrrolizin-7a(5H)-yl)methoxy)-9,10-dihydro-8H-7-oxa-1,3,6,10-tetraazacyclohepta[de]naphthalen-5-yl)-5-ethynyl-6-fluoronaphthalen-2-ol (diastereomer mixture) | 667.9 |
| 889 | 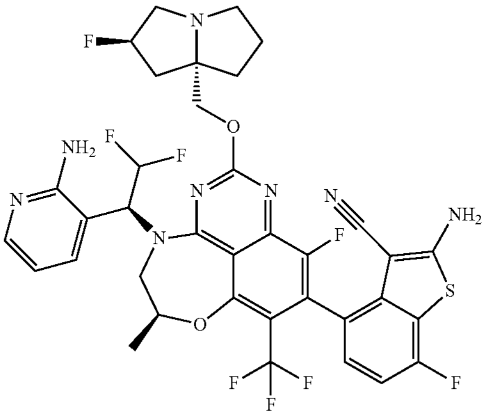 [SMILES: C[C@H]1CN([C@@H](c2cccnc2N)C(F)F)c2nc(OC[C@@]34CCCN3C[C@H](F)C4)nc3c(F)c(-c4ccc(F)c5sc(N)c(C#N)c45)c(C(F)(F)F)c(c23)O1] | 2-amino-4-((6S)-4-((S)-1-(2-aminopyridin-3-yl)-2,2-difluoroethyl)-10-fluoro-2-(((2R,7aS)-2-fluorotetrahydro-1H-pyrrolizin-7a(5H)-yl)methoxy)-6-methyl-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 790.9 |
| 890 | 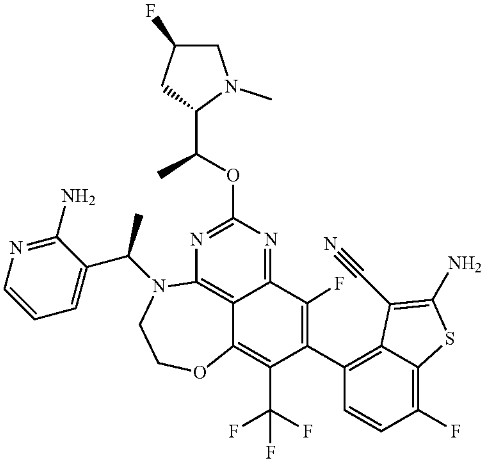 [SMILES: C[C@H](Oc1nc2c3c(c(C(F)(F)F)c(-c4ccc(F)c5sc(N)c(C#N)c45)c(F)c3n1)OCCN2[C@H](C)c1cccnc1N)[C@@H]1C[C@@H](F)CN1C] | 2-amino-4-(4-((R)-1-(2-aminopyridin-3-yl)ethyl)-10-fluoro-2-((S)-1-((2S,4R)-4-fluoro-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 729.2 |

TABLE 1-continued

| No | Structure | Chemical Name | [M + H]+ |
|---|---|---|---|
| 891 | 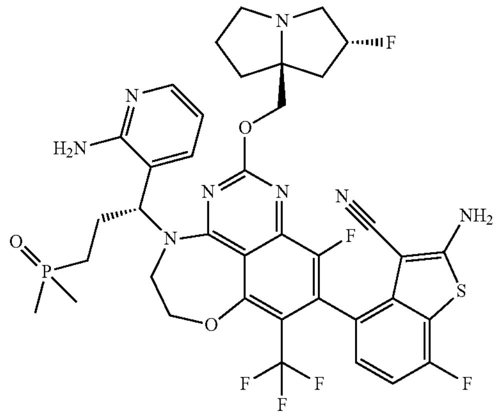 [SMILES: CP(C)(=O)CC[C@H](c1cccnc1N)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-aminopyridin-3-yl)-3-(dimethylphosphoryl)propyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 831.1 |
| 892 | 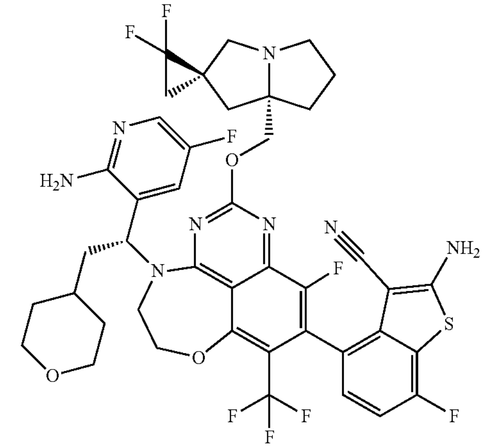 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@H](CC3CCOCC3)c3cc(F)cnc3N)CCO4)c12] | 2-amino-4-(4-((R)-1-(2-amino-5-fluoropyridin-3-yl)-2-(tetrahydro-2H-pyran-4-yl)ethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 887.3 |
| 893 | 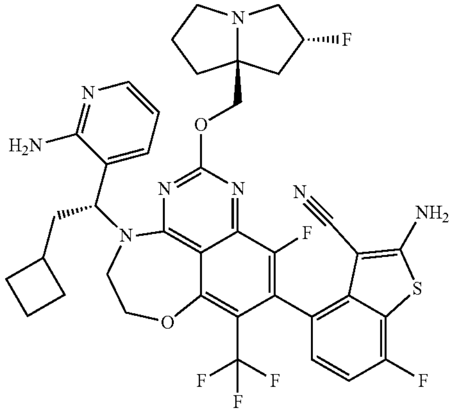 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCC3)c3cccnc3N)CCO4)c12] | 2-amino-4-(4-((R)-1-(2-aminopyridin-3-yl)-2-cyclobutylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 795.3 |

TABLE 1-continued

| No | Structure | Chemical Name | [M + H]+ |
|---|---|---|---|
| 894 | 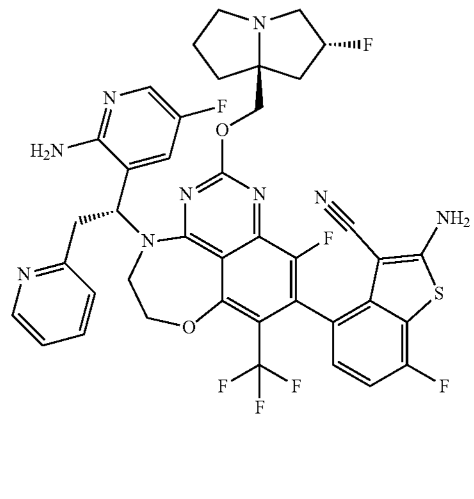 [SMILES: N#Cc1c(N)sc2c(F)ccc(-c3c(C(F)(F)F)c4c5c(nc(OC[C@@]67CCCN6C[C@H](F)C7)nc5c3F)N([C@H](Cc3ccccn3)c3cc(F)cnc3N)CCO4)c12] | 2-amino-4-(4-((R)-1-(2-amino-5-fluoropyridin-3-yl)-2-(pyridin-2-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 836.3 |
| 895 | 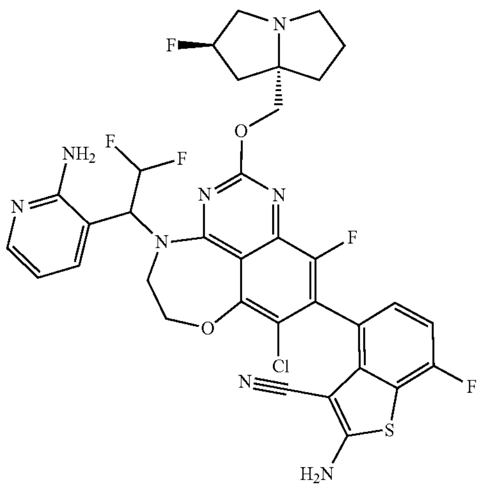 [SMILES: N#Cc1c(N)sc2c(F)ccc(-c3c(Cl)c4c5c(nc(OC[C@@]67CCCN6C[C@H](F)C7)nc5c3F)N(C(c3cccnc3N)C(F)F)CCO4)c12] | 2-amino-4-(4-(1-(2-aminopyridin-3-yl)-2,2-difluoroethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 2, absolute stereochemistry not determined) | 742.7 |
| 896 | 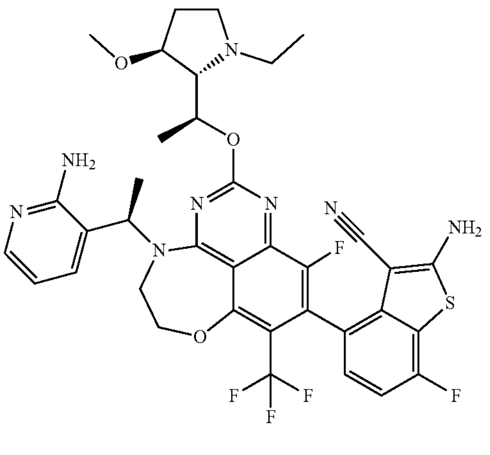 [SMILES: CCN1CC[C@H](OC)[C@H]1[C@H](C)Oc1nc2c3c(c(C(F)(F)F)c(-c4ccc(F)c5sc(N)c(C#N)c45)c(F)c3n1)OCCN2[C@H](C)c1cccnc1N] | 2-amino-4-(4-((R)-1-(2-aminopyridin-3-yl)ethyl)-2-((S)-1-((2R,3S)-1-ethyl-3-methoxypyrrolidin-2-yl)ethoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 755.3 |

TABLE 1-continued

| No | Structure | Chemical Name | [M + H]+ |
|---|---|---|---|
| 897 | 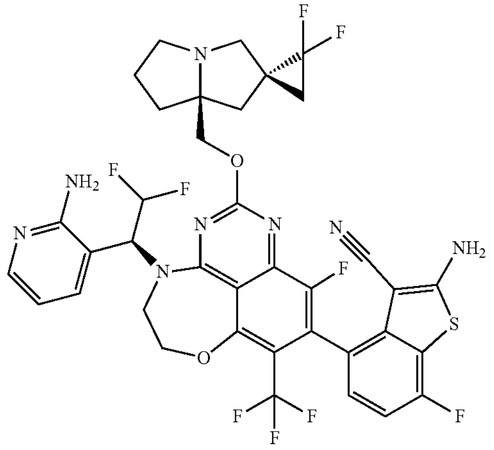 [SMILES: N#Cc1c(N)sc2c(F)ccc(-c3c(C(F)(F)F)c4c5c(nc(OC[C@@]67CCCN6C[C@@]6(CC6(F)F)C7)nc5c3F)N([C@@H](c3cccnc3N)C(F)F)CCO4)c12] | 2-amino-4-(4-((S)-1-(2-aminopyridin-3-yl)-2,2-difluoroethyl)-2-(((1S,7a'S)-2,2-difluorodihydro-1'H,3'H-spiro[cyclopropane-1,2'-pyrrolizin]-7a'(5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 821.1 |
| 898 | 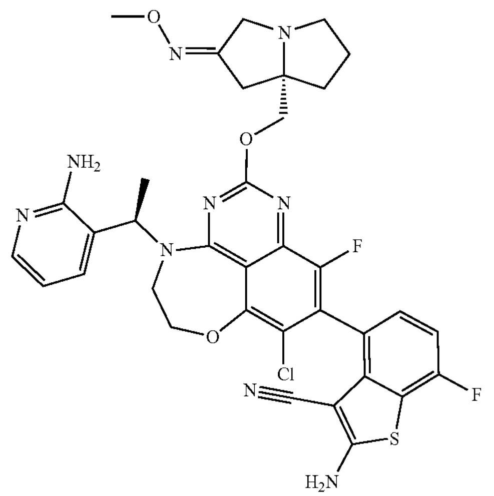 [SMILES: CO/N=C1\CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-10-fluoro-2-(((S,Z)-2-(methoxyimino)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 732.2 |
| 899 | 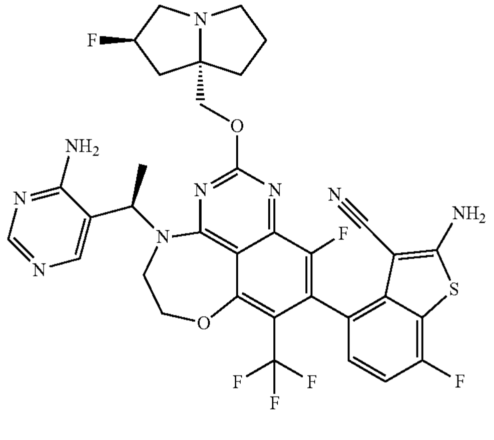 | 2-amino-4-(4-((R)-1-(4-aminopyrimidin-5-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 742.1 |

TABLE 1-continued

| No | Structure | Chemical Name | [M + H]+ |
|---|---|---|---|
| 900 | 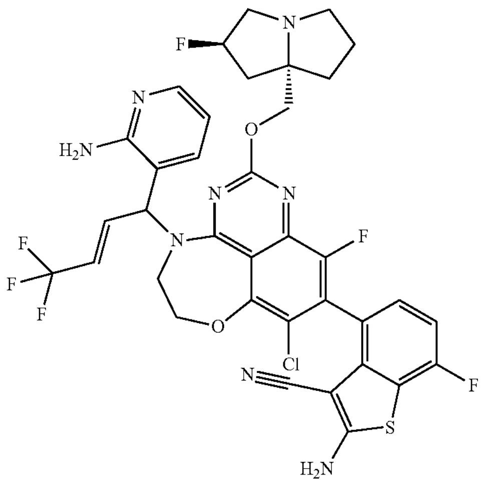 [SMILES: N#Cc1c(N)sc2c(F)ccc(-c3c(Cl)c4c5c(nc(OC[C@@]67CCCN6C[C@H](F)C7)nc5c3F)N(C(/C=C/C(F)(F)F)c3cccnc3N)CCO4)c12] | 2-amino-4-(4-((E)-1-(2-aminopyridin-3-yl)-4,4,4-trifluorobut-2-en-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (diastereomer mixture) | 787.0 |
| 901 | 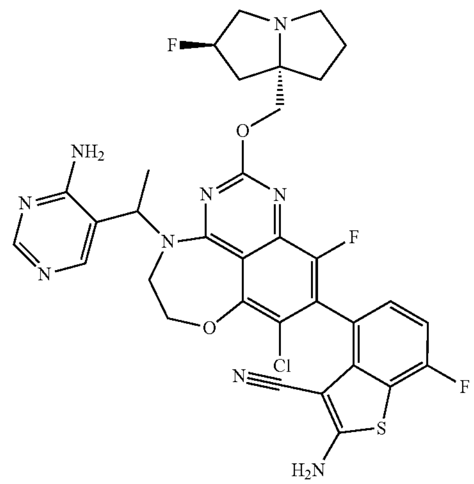 [SMILES: CC(c1cncnc1N)N1CCOc2c(Cl)c(-c3ccc(F)c4sc(N)c(C#N)c34)c(F)c3nc(OC[C@@]45CCCN4C[C@H](F)C5)nc1c23] | 2-amino-4-(4-(1-(4-aminopyrimidin-5-yl)ethyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 707.9 |
| 902 | 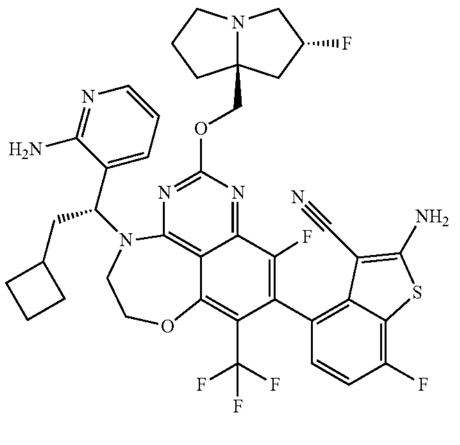 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCC3)c3cccnc3N)CCO4)c12] | 2-amino-4-(4-((R)-1-(2-aminopyridin-3-yl)-2-cyclobutylethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 795.3 |

TABLE 1-continued

| No | Structure | Chemical Name | [M + H]+ |
|---|---|---|---|
| 903 | 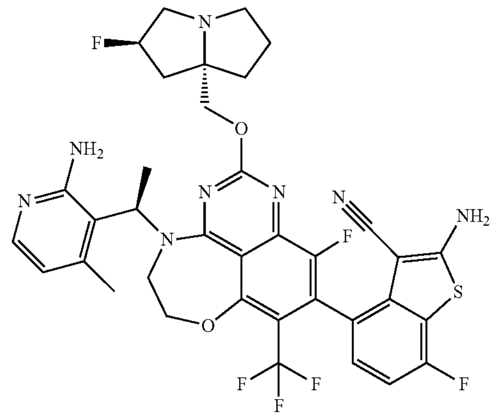 [SMILES: Cc1ccnc(N)c1[C@@H](C)N1CCOc2c(C(F)(F)F)c(-c3ccc(F)c4sc(N)c(C#N)c34)c(F)c3nc(OC[C@@]45CCCN4C[C@H](F)C5)nc1c23] | 2-amino-4-(4-((R)-1-(2-amino-4-methylpyridin-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 755.3 |
| 904 | 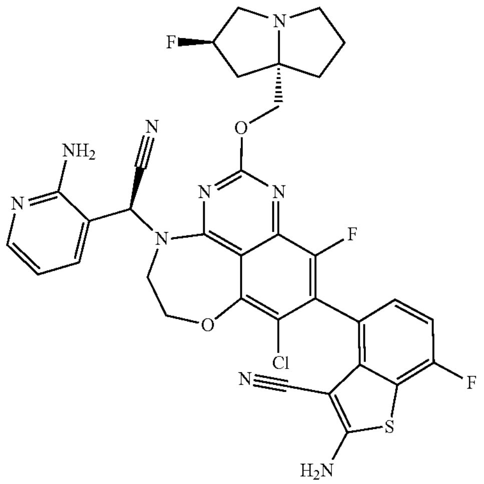 [SMILES: N#Cc1c(N)sc2c(F)ccc(-c3c(Cl)c4c5c(nc(OC[C@@]67CCCN6C[C@H](F)C7)nc5c3F)N([C@H](C#N)c3cccnc3N)CCO4)c12] | 2-amino-4-(4-((R)-1-(2-aminopyridin-3-yl)prop-2-yn-1-yl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 717.1 |
| 905 | 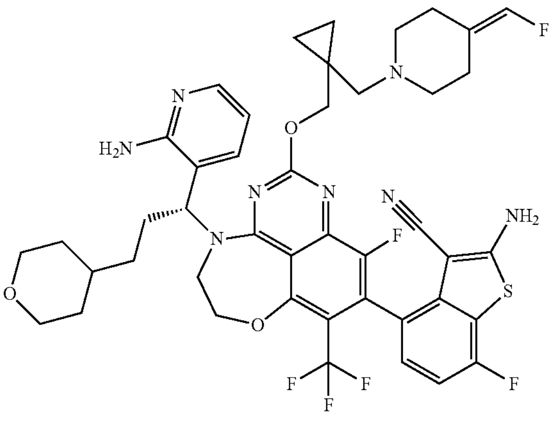 [SMILES: N#Cc1c(N)sc2c(F)ccc(-c3c(C(F)(F)F)c4c5c(nc(OCC6(CN7CCC(=CF)CC7)CC6)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 879.4 |

TABLE 1-continued

| No | Structure | Chemical Name | [M + H]+ |
|---|---|---|---|
| 906 | 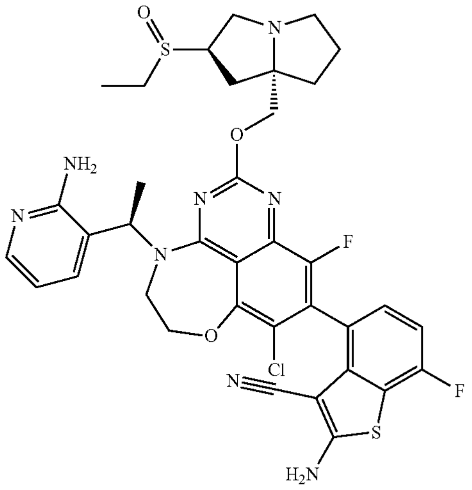 [SMILES: CCS(=O)[C@H]1CN2CCC[C@@]2(COc2nc3c4c(c(Cl)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-8-chloro-2-(((2R,7aS)-2-(ethylsulfinyl)tetrahydro-1H-pyrrolizin-7a(5H)-yl)methoxy)-10-fluoro-5,6-dihydro-4H-[1,4]oxazepino[5,6,7-de]quinazolin-9-yl)-7-fluorobenzo[b]thiophene-3-carbonitrile (diastereomer mixture) | 764.9 |
| 907 | 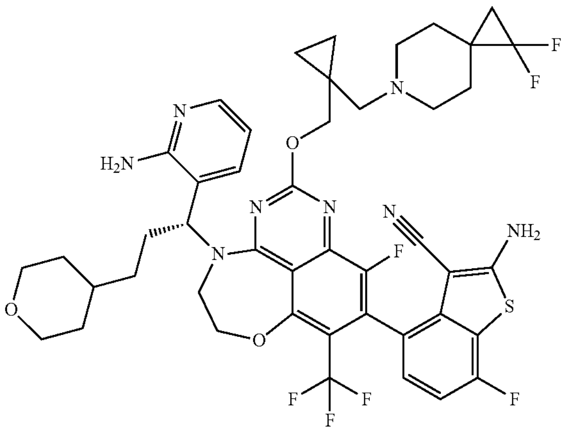 [SMILES: N#Cc1c(N)sc2c(F)ccc(-c3c(C(F)(F)F)c4c5c(nc(OCC6(CN7CCC8(CC7)CC8(F)F)CC6)nc5c3F)N([C@H](CCC3CCOCC3)c3cccnc3N)CCO4)c12] | 2-amino-4-(4-((R)-1-(2-aminopyridin-3-yl)-3-(tetrahydro-2H-pyran-4-yl)propyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 911.4 |
| 908 | 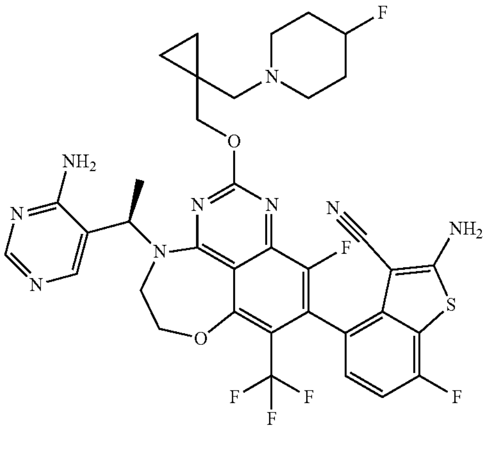 [SMILES: C[C@H](c1cncnc1N)N1CCOc2c(C(F)(F)F)c(-c3ccc(F)c4sc(N)c(C#N)c34)c(F)c3nc(OCC4(CN5CCC(F)CC5)CC4)nc1c23] | 2-amino-4-(4-((R)-1-(4-aminopyrimidin-5-yl)ethyl)-10-fluoro-2-((1-((4-fluoropiperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 770.3 |

TABLE 1-continued

| No | Structure | Chemical Name | [M + H]+ |
|---|---|---|---|
| 909 | 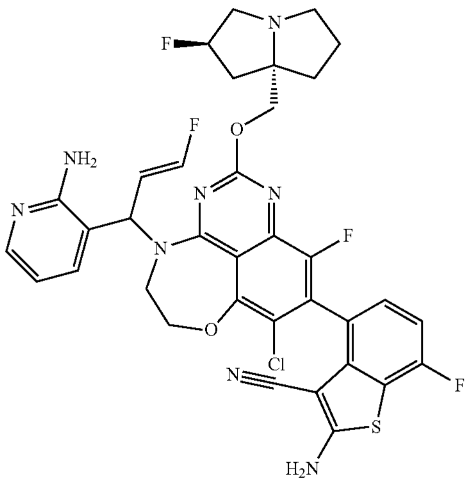 [SMILES: N#Cc1c(N)sc2c(F)ccc(-c3c(Cl)c4c5c(nc(OC[C@@]67CCCN6C[C@H](F)C7)nc5c3F)N(C(/C=C/F)c3cccnc3N)CCO4)c12] | 2-amino-4-(4-((E)-1-(2-aminopyridin-3-yl)-3-fluoroallyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 737.0 |
| 910 | 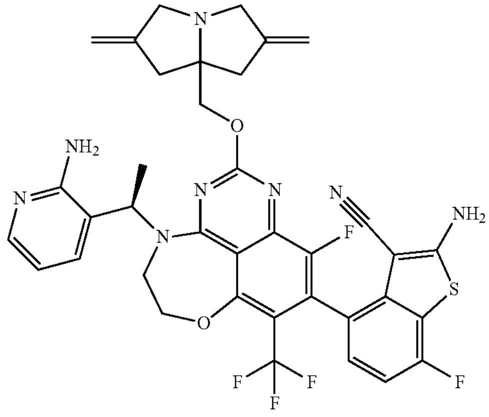 [SMILES: C=C1CN2CC(=C)CC2(COc2nc3c4c(c(C(F)(F)F)c(-c5ccc(F)c6sc(N)c(C#N)c56)c(F)c4n2)OCCN3[C@H](C)c2cccnc2N)C1] | 2-amino-4-(4-((R)-1-(2-aminopyridin-3-yl)ethyl)-2-((2,6-dimethylenetetrahydro-1H-pyrrolizin-7a(5H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 747.3 |
| 911 | 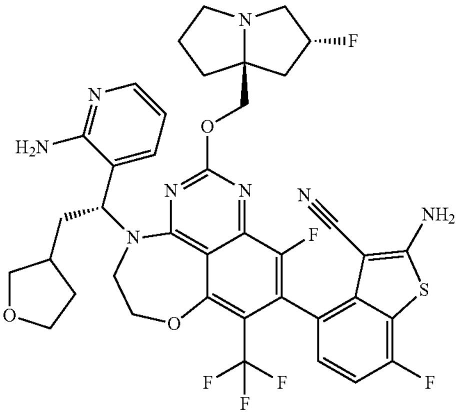 [SMILES: N#Cc1c(N)sc2c(F)ccc(-c3c(C(F)(F)F)c4c5c(nc(OC[C@@]67CCCN6C[C@H](F)C7)nc5c3F)N([C@H](CC3CCOC3)c3cccnc3N)CCO4)c12] | 2-amino-4-(4-((1R)-1-(2-aminopyridin-3-yl)-2-(tetrahydrofuran-3-yl)ethyl)-10-fluoro-2-(((2R,7aS)-2-fluorotetrahydro-1H-pyrrolizin-7a(5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 811.3 |

TABLE 1-continued

| No | Structure | Chemical Name | [M + H]+ |
|---|---|---|---|
| 912 | 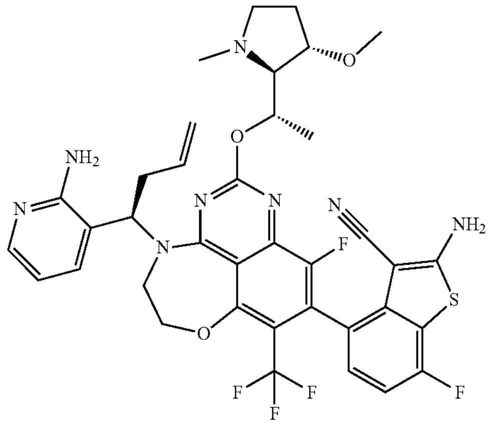 [SMILES: C=CC[C@H](c1cccnc1N)N1CCOc2c(C(F)(F)F)c(-c3ccc(F)c4sc(N)c(C#N)c34)c(F)c3nc(O[C@@H](C)[C@@H]4[C@@H](OC)CCN4C)nc1c23] | 2-amino-4-(4-((R)-1-(2-aminopyridin-3-yl)but-3-en-1-yl)-10-fluoro-2-((S)-1-((2R,3S)-3-methoxy-1-methylpyrrolidin-2-yl)ethoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 767.2 |
| 913 | 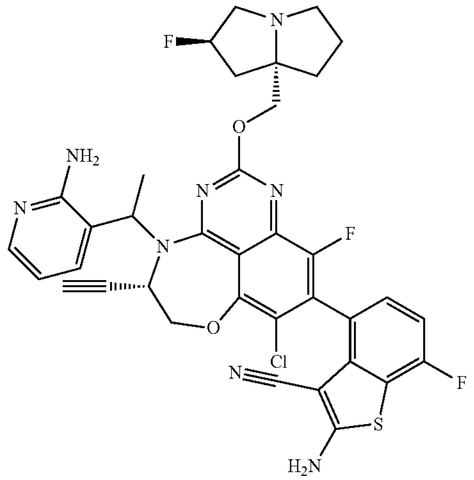 [SMILES: C#C[C@H]1COc2c(Cl)c(-c3ccc(F)c4sc(N)c(C#N)c34)c(F)c3nc(OC[C@@]45CCCN4C[C@H](F)C5)nc(c23)N1C(C)c1cccnc1N] | 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (single diastereomer 7, absolute stereochemistry not determined) | 730.9 |
| 914 | 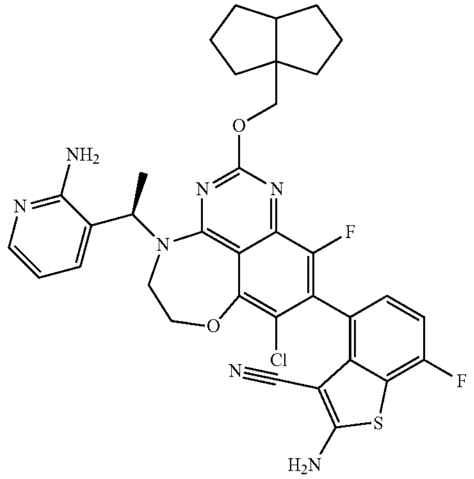 [SMILES: C[C@H](c1cccnc1N)N1CCOc2c(Cl)c(-c3ccc(F)c4sc(N)c(C#N)c34)c(F)c3nc(OCC45CCCC4CCC5)nc1c23] | 2-amino-4-(4-((R)-1-(2-aminopyridin-3-yl)ethyl)-8-chloro-10-fluoro-2-((hexahydropentalen-3a(1H)-yl)methoxy)-5,6-dihydro-4H-[1,4]oxazepino[5,6,7-de]quinazolin-9-yl)-7-fluorobenzo[b]thiophene-3-carbonitrile (single diastereomer 1, absolute stereochemistry not determined) | 688.1 |

TABLE 1-continued

| No | Structure | Chemical Name | [M + H]+ |
|---|---|---|---|
| 915 | 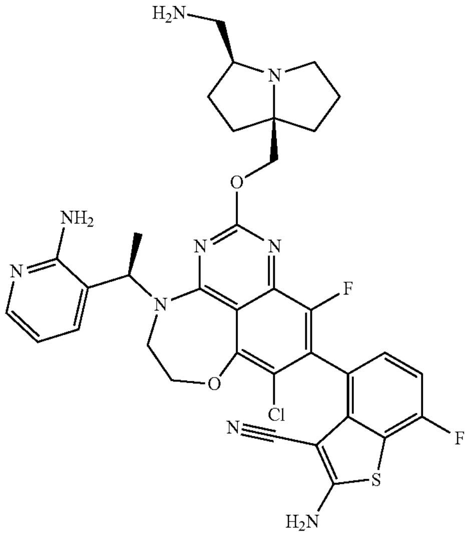 [SMILES: C[C@H](c1cccnc1N)N1CCOc2c(Cl)c(-c3ccc(F)c4sc(N)c(C#N)c34)c(F)c3nc(OC[C@]45CCCN4[C@H](CN)CC5)nc1c23] | 2-amino-4-(2-(((3S,7aR)-3-(aminomethyl)tetrahydro-1H-pyrrolizin-7a(5H)-yl)methoxy)-4-((R)-1-(2-aminopyridin-3-yl)ethyl)-8-chloro-10-fluoro-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 718.3 |
| 916 | 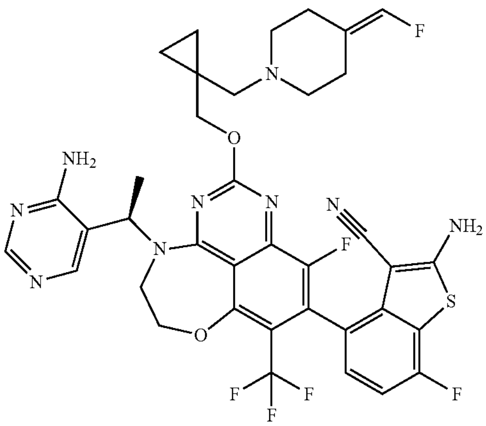 [SMILES: C[C@H](c1cncnc1N)N1CCOc2c(C(F)(F)F)c(-c3ccc(F)c4sc(N)c(C#N)c34)c(F)c3nc(OCC4(CN5CCC(=CF)CC5)CC4)nc1c23] | 2-amino-4-(4-((R)-1-(4-aminopyrimidin-5-yl)ethyl)-10-fluoro-2-((1-((4-(fluoromethylene)piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (single diastereomer, S atropisomer at $R^7$ substituent) | 782.3 |
| 917 | 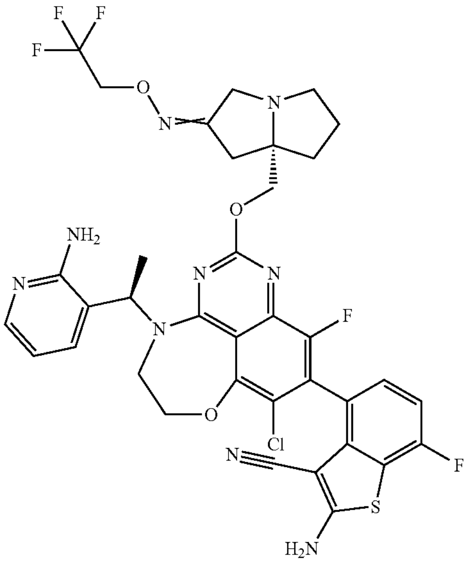 [SMILES: C[C@H](c1cccnc1N)N1CCOc2c(Cl)c(-c3ccc(F)c4sc(N)c(C#N)c34)c(F)c3nc(OC[C@@]45CCCN4CC(=NOCC(F)(F)F)C5)nc1c23] | 2-amino-4-(4-((R)-1-(2-aminopyridin-3-yl)ethyl)-8-chloro-10-fluoro-2-(((S)-2-((2,2,2-trifluoroethoxy)imino)tetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (diastereomer mixture) | 799.9 |

TABLE 1-continued

| No | Structure | Chemical Name | [M + H]+ |
|---|---|---|---|
| 918 | 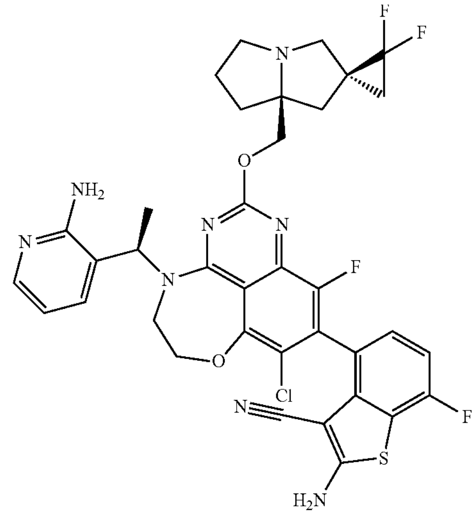 [SMILES: C[C@H](c1cccnc1N)N1CCOc2c(Cl)c(-c3ccc(F)c4sc(N)c(C#N)c34)c(F)c3nc(OC[C@@]45CCCN4C[C@]4(CC4(F)F)C5)nc1c23] | 2-amino-4-(4-((R)-1-(2-aminopyridin-3-yl)ethyl)-8-chloro-2-(((1R,7a'S)-2,2-difluorodihydro-1'H,3'H-spiro[cyclopropane-1,2'-pyrrolizin]-7a'(5'H)-yl)methoxy)-10-fluoro-5,6-dihydro-4H-[1,4]oxazepino[5,6,7-de]quinazolin-9-yl)-7-fluorobenzo[b]thiophene-3-carbonitrile (single diastereomer, R atropisomer at $R^7$ substituent) | 750.9 |
| 919 | 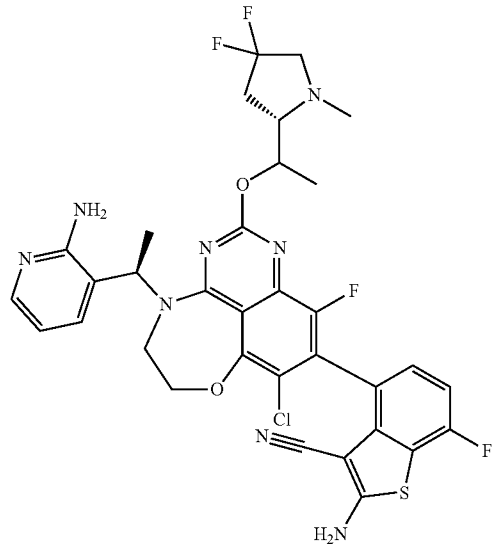 [SMILES: CC(Oc1nc2c3c(c(Cl)c(-c4ccc(F)c5sc(N)c(C#N)c45)c(F)c3n1)OCCN2[C@H](C)c1cccnc1N)[C@@H]1CC(F)(F)CN1C] | 2-amino-4-(4-((R)-1-(2-aminopyridin-3-yl)ethyl)-8-chloro-2-(1-((S)-4,4-difluoro-1-methylpyrrolidin-2-yl)ethoxy)-10-fluoro-5,6-dihydro-4H-[1,4]oxazepino[5,6,7-de]quinazolin-9-yl)-7-fluorobenzo[b]thiophene-3-carbonitrile (single diastereomer, absolute stereochemistry undetermined) | 712.8 |

Compounds of Table 1 are depicted with flat, wedged, and/or hashed wedged bonds. It is understood that compounds depicted in Table 1 encompass all possible stereoisomers, including atropisomers, of the compounds of Table 1. In some instances, the relative stereochemistry at one or more stereocenters of a compound has been determined; in some instances, the absolute stereochemistry has been determined. In some instances, a single compound number represents a mixture of stereoisomers, including atropisomers. In some instances, a single compound number represents a single stereoisomer, such as a single atropisomer. As such, it is understood that if two or more compound numbers in Table 1 are provided with the same depicted structure, then different stereoisomers or mixtures of stereoisomers of the depicted structure are represented by each compound number.

In some embodiments, the compounds of the present disclosure exhibit one or more functional characteristics disclosed herein. For example, a subject compound binds to a Ras protein, KRAS protein or a mutant form thereof. In some embodiments, a subject compound binds specifically and also inhibits a Ras protein, KRAS protein or a mutant form thereof. In some embodiments, a subject compound selectively inhibits a KRAS mutant relative to a wildtype KRAS. In some embodiments, the IC50 of a subject compound for a KRAS mutant (e.g., including G12C, G12S, G12D, G12V) is less than about 5 μM, less than about 1 μM, less than about 500 nM, less than 250 nM, less than 100 nM, less than 50 nM, or even less, as measured in an in vitro assay known in the art or exemplified herein.

In some embodiments, a compound of the present disclosure is capable of reducing Ras signaling output. Such reduction may be evidenced by one or more of the following: (i) an increase in steady state level of GDP-bound Ras protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, and (vi) reduction (e.g., inhibition) of cell growth of Ras-driven tumor cells (e.g., those derived from a tumor cell line disclosed herein). In some cases, the reduction in Ras signaling output can be evidenced by two, three, four, five, or all of (i)-(vi) above.

It shall be understood that different aspects of the disclosure can be appreciated individually, collectively, or in combination with each other. Various aspects described herein may be applied to any of the particular applications disclosed herein. The compositions of matter, including compounds of any formulae disclosed in the compound section, of the present disclosure may be utilized in the method section, including methods of use and production disclosed herein, or vice versa.

In embodiments a subject compound encompasses any compound disclosed herein, including a compound of Formula (I), (II), (III), (IV), (V), (VI), (VII), (VIII), (IX), (X), (XI), and (XII), and further including any compound disclosed in Table 1, an aspect, an embodiment, or any other compound disclosed herein.

Compounds disclosed herein exhibit desired properties, including, but not limited to, high potency in reducing Ras signaling output, advantageous solubility, and DMPK properties. Fine-tuned pharmacological properties embodied in the subject compounds are of great significance for improving efficacy and safety of Ras inhibitors for therapeutic clinical applications. In some embodiments, compounds of Formula (I), (II), (III), (IV), (V), (VI), (VII), (VIII), (IX), (X), (XI), (XII), or embodiments thereof, exhibit at least one, two, three or multiple salient superior pharmacological and/or safety properties as compared to compounds having the same core scaffold with a different substituent at the position corresponding to $R^4$, $R^5$, $R^6$, and/or $R^7$. Exemplary superior DMPK properties associated with the subject compounds include but are not limited to improved metabolic stability, increased bioavailability, decreased clearance, increased oral exposure, and decreased serum protein binding (hence increasing the free and available compounds circulating in a subject's blood upon administration of the compounds).

In some embodiments, compounds of Formula (I), (II), (III), (IV), (V), (VI), (VII), (VIII), (IX), (X), (XI), (XII), or embodiments thereof, exhibit at least one, two, three or multiple salient superior pharmacological and/or safety properties as compared to compounds having the same core scaffold with a different substituent at the position corresponding to $R^4$, $R^5$, $R^6$, and/or $R^7$, when measured in an animal model (e.g., a model selected from mouse, human, rat, dog, and monkey). In some embodiments, compounds of Formula (I), (II), (III), (IV), (V), (VI), (VII), (VIII), (IX), (X), (XI), (XII), or embodiments thereof, exhibit at least one, two, three or multiple salient superior pharmacological and/or safety properties as compared to compounds having the same core scaffold with a different substituent at the position corresponding to $R^4$, $R^5$, $R^6$, and/or $R^7$, when measured in two or more animal models (e.g., a model selected from mouse, human, rat, dog, and monkey). In embodiments, the animal model is mouse. In embodiments, the animal model is human. In embodiments, the animal model is rat. In embodiments, the animal model is dog. In embodiments, the animal model is monkey.

In some embodiments, superior DMPK properties are observed with compounds of Formula (I), (II), (III), (IV), (V), (VI), (VII), (VIII), (IX), (X), (XI), (XII), or embodiments thereof. Non-limiting examples of compounds exhibiting such superior DMPK properties include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, -$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

Such unexpected, superior structure and correlated functional attributes described in the three paragraphs immediately above are observed in a variety of compounds of Formula (I), (II), (III), (IV), (V), (VI), (VII), (VIII), (IX), (X), (XI), or (XII), or embodiments thereof, wherein (i) a substituent at $R^4$ is selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ is equal to halogen; and/or (iii) a substituent at $R^5$ is non-hydrogen; and/or (iv) a substituent at $R^6$ is equal to —$CF_3$; and/or (v) a substituent at $R^7$ is equal to benzothiophenyl optionally substituted with one or more substituents independently selected from —$NH_2$, —CN, and —F. In particular, such unexpected property is observed in compounds of Formula (I), (II), (III), (IV), (V), (VI), (VII), (VIII), (IX), (X), (XI), or (XII), or embodiments thereof, wherein a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I. In particular, such unexpected property is observed in compounds of Formula (I), (II), (III), (IV), (V), (VI), (VII), (VIII), (IX), (X), (XI), or (XII), or embodiments thereof, wherein a substituent at $R^5$ is equal to halogen. In particular, such unexpected property is observed in compounds of Formula (I), (II), (III), (IV), (V), (VI), (VII), (VIII), (IX), (X), (XI), (XII), or embodiments thereof, wherein a substituent at $R^5$ is non-hydrogen. In particular, such unexpected property is observed in compounds of Formula (I), (II), (III), (IV), (V), (VI), (VII), (VIII), (IX), (X), (XI), or (XII), or embodiments thereof, wherein a substituent at $R^6$ is equal to haloalkyl (e.g., —$CF_3$). In particular, such unexpected property is observed in compounds of Formula (I), (II), (III), (IV), (V), (VI), (VII), (VIII), (IX), (X), (XI), or (XII), or embodiments thereof, wherein a substituent at $R^7$ is equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits decreased serum protein binding as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals an increase in unbound/free compound present in plasma by at least, 1%, 5%, 10%, or even higher.

In some embodiments, an increase in unbound/free compound present in plasma is associated with compounds of Formula (I), (II), (III), (IV), (V), (VI), (VII), (VIII), (IX), (X), (XI), (XII), or embodiments thereof. Non-limiting examples of compounds exhibiting such an increase in unbound/free compound present in plasma include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits improvements in microsomal metabolic stability as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in microsomal metabolic stability by at least, 1%, 5%, 10%, or even higher.

In some embodiments, improvements in microsomal metabolic stability are associated with compounds of Formula (I), (II), (III), (IV), (V), (VI), (VII), (VIII), (IX), (X), (XI), (XII), or embodiments thereof. Non-limiting examples of compounds exhibiting such improvements in microsomal metabolic stability include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior oral bioavailability as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in oral bioavailability by at least, 1.1-fold, 1.2, 1.3, 1.4, 1.5, 1.6, 1.7, 1.8, 1.9, 2, 3, 4, 5, 6, 7, 8, 9, 10-fold, or even greater.

In some embodiments, superior oral bioavailability is associated with compounds of Formula (I), (II), (III), (IV), (V), (VI), (VII), (VIII), (IX), (X), (XI), (XII), or embodiments thereof. Non-limiting examples of compounds exhibiting such superior oral bioavailability include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, -$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior oral exposure (e.g., measured as AUC) as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in oral exposure (e.g., measured as AUC) by at least, 1.1-fold, 1.2, 1.3, 1.4, 1.5, 1.6, 1.7, 1.8, 1.9, 2, 3, 4, 5, 6, 7, 8-fold or even greater.

In some embodiments, superior oral exposure (e.g., measured as AUC) is associated with compounds of Formula (I), (II), (III), (IV), (V), (VI), (VII), (VIII), (IX), (X), (XI), (XII), or embodiments thereof. Non-limiting examples of compounds exhibiting such superior oral exposure (e.g., measured as AUC) include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior clearance as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in clearance by at least, 1.1-fold, 1.2, 1.3, 1.4, 1.5, 1.6, 1.7, 1.8, 1.9, 2, 3-fold or even greater reduction in clearance.

In some embodiments, superior clearance is associated with compounds of Formula (I), (II), (III), (IV), (V), (VI), (VII), (VIII), (IX), (X), (XI), (XII), or embodiments thereof. Non-limiting examples of compounds exhibiting such superior clearance include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior oral exposure (e.g., measured as Cmax) as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in oral exposure (e.g., measured as Cmax) by at least, 1.1-fold, 1.2, 1.3, 1.4, 1.5, 1.6, 1.7, 1.8, 1.9, 2, 3, 4, 5, 6, 7, 8, 9, 10-fold or even greater.

In some embodiments, superior oral exposure (e.g., measured as Cmax) is associated with compounds of Formula (I), (II), (III), (IV), (V), (VI), (VII), (VIII), (IX), (X), (XI), (XII), or embodiments thereof. Non-limiting examples of compounds exhibiting such superior oral exposure (e.g., measured as Cmax) include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior solubility as compared to a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals improvements in solubility by at least, 1%, 5%, 10%, or even higher.

In some embodiments, superior solubility is associated with compounds of Formula (I), (II), (III), (IV), (V), (VI), (VII), (VIII), (IX), (X), (XI), (XII), or embodiments thereof. Non-limiting examples of compounds exhibiting such superior solubility include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle), wherein $C_{1-3}$ alkyl, $C_{2-4}$ alkenyl, $C_{2-3}$ alkynyl, —$C_{1-2}$ alkyl-($C_{3-4}$ saturated carbocycle), and —$C_{1-2}$ alkyl-(5- to 6-membered saturated heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$; and/or (iv) a substituent at $R^7$ equal to benzothiophenyl optionally substituted with one or more substituents independently selected from —$NH_2$, —CN, and —F.

In some embodiments, a compound of Formula (I), (II), (III), (IV), (V), (VI), (VII), (VIII), (IX), (X), (XI), (XII), or embodiments thereof, exhibits superior compound exposure in a tumor compared to plasma in the same animal (e.g., ng/mL, mouse). In some embodiments, a compound of Formula (I), (II), (III), (IV), (V), (VI), (VII), (VIII), (IX), (X), (XI), (XII), or embodiments thereof, exhibits superior compound exposure in a tumor compared to plasma in the same animal (e.g., ng/mL, mouse) as compared to the relative tumor/plasma exposure of a compound having the same core scaffold with a different substituent at the position corresponding to $R^4$, $R^5$, $R^6$, and/or $R^7$. In embodiments, a comparison of such subject compound of Formula (I), (II), (III), (IV), (V), (VI), (VII), (VIII), (IX), (X), (XI), (XII), or embodiments thereof, to compounds of the same core where the compound has a different substituent at the position corresponding to $R^4$, $R^5$, $R^6$, and/or $R^7$ reveals increased tumor exposure compared to plasma exposure (e.g., ng/ml) by at least, 1.1-fold, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4, 5, 6, 7, 8, 9, or 10-fold, or even greater.

In some embodiments, superior tumor exposure compared to plasma exposure in the same animal (e.g., mouse) is associated with compounds of Formula (I), (II), (III), (IV), (V), (VI), (VII), (VIII), (IX), (X), (XI), (XII), or embodiments thereof. Non-limiting examples of compounds exhibiting such superior tumor exposure compared to plasma exposure in the same animal (e.g., mouse) include compounds having (i) a substituent at $R^4$ selected from $C_{1-3}$ alkyl, $C_{2-4}$ alkenyl, $C_{2-3}$ alkynyl, —$C_{1-2}$ alkyl-($C_{3-4}$ carbocycle), and —$C_{1-2}$ alkyl-(5- to 6-membered heterocycle), wherein $C_{1-3}$ alkyl, $C_{2-4}$ alkenyl, $C_{2-3}$ alkynyl, —$C_{1-2}$ alkyl-($C_{3-4}$ carbocycle), and —$C_{1-2}$ alkyl-(5- to 6-membered heterocycle) are each optionally substituted with one or more halogen selected from —F, —Cl, —Br, and I; and/or (ii) a substituent at $R^5$ equal to halogen; and/or (iii) a substituent at $R^6$ equal to —$CF_3$, a substituent at $R^6$ equal to —Cl, or a substituent at $R^6$ equal to halogen; and/or (iv) a substituent at $R^7$ equal to benzothiophenyl optionally substituted with one or more substituents independently selected from —$NH_2$, —CN, and —F.

Besides the inhibitory effect and high potency in reducing Kras signaling output, compounds disclosed herein exhibit advantageous solubility and DMPK properties. Fine-tuned pharmacological properties embodied in the subject compounds are of great significance for improving efficacy and safety of Kras inhibitors for therapeutic clinical applications. In some embodiments, compounds of Formula (I), (II), (II-a), (IV), (V), (Va), (Vb), (Vc), (VIII), (IX), (X), and/or (XI), exhibit at least one, two, three or multiple salient superior pharmacological and/or safety properties as compared to compounds having the same core scaffold with a different substituent at Ring A, $R^4$, $R^5$, $R^6$, and/or $R^7$. Exemplary superior DMPK properties associated with the subject compounds include but are not limited to improved metabolic stability, increased oral exposure (measured through multiple parameters such as AUC and bioavailability (% F)), and increased compound exposure in tumor relative to circulation.

In some embodiments, a compound of Formula (I), (II), (II-a), (IV), (V), (Va), (Vb), (Vc), (VIII), (IX), (X), and/or (XI) exhibits increased cellular growth inhibition of a Kras- or mutant Kras-mediated cell line as compared to a compound having the same core scaffold with $R^7$ being a substituent other than substituted benzothiophenyl. In an embodiment, such compound of Formula (I), (II), (II-a), (IV), (V), (Va), (Vb), (Vc), (VIII), (IX), (X), and/or (XI) exhibits increased cellular growth inhibition of a Kras- or mutant Kras-mediated cell line as compared to a compound having the same core scaffold wherein $R^7$ is replaced with a monocyclic aromatic ring optionally substituted with one or more $R^{20}$. In an embodiment, increased cellular growth inhibition of a Kras- or mutant Kras-mediated cell line is observed for a compound of Formula (I), (II), and/or (II-a) when compared to a compound having the same core scaffold wherein $R^7$ is replaced with substituted pyridyl. In embodiments, a comparison of such compound of Formula (I), (II), and/or (II-a) to a compound of the same core where $R^7$ is not benzothiophenyl reveals a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, 5, 6, 7, or 8-fold, or even greater for the compound wherein $R^7$ is benzothiophenyl. In embodiments, a comparison of such compound of Formula (I), (II), and/or (II-a) to a compound of the same core where $R^7$ is not a benzothiophenyl reveals a remarkable increase in cellular growth inhibition of a G12D mutant expressing cell line (e.g., SW1990), as evidenced by a reduction in IC50 of at least 1.1, 1.2, 1.3, 1.4, 1.5, 1.6, 1.7, 1.8, 1.9, 2, 3, 4, 5, 6, 7, or 8-fold, or even greater for the compound wherein $R^7$ is benzothiophenyl. In embodiments, a compound of Formula (I), (II), and/or (II-a) wherein $R^7$ is

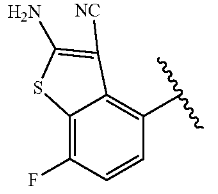 [SMILES: *c1ccc(F)c2sc(N)c(C#N)c12]

exhibits a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, 5, 6, 7, or 8-fold, or even greater, relative to an identical compound wherein $R^7$ is replaced with

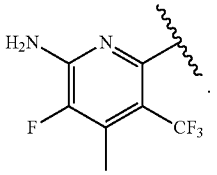

In embodiments, a compound of Formula (I), (II), and/or (II-a) wherein $R^7$ is

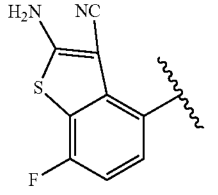 [SMILES: *c1ccc(F)c2sc(N)c(C#N)c12]

exhibits a remarkable increase in cellular growth inhibition of a G12D mutant expressing cell line (e.g., SW1990), as evidenced by a reduction in IC50 of at least 1.1, 1.2, 1.3, 1.4, 1.5, 1.6, 1.7, 1.8, 1.9, 2, 3, 4, 5, 6, 7, or 8-fold, or even greater, relative to an identical compound wherein $R^7$ is replaced with

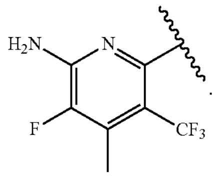

In some embodiments, a compound of Formula (I), (II), (II-a), (IV), (V), (Va), (Vb), (Vc), (VIII), (IX), (X), and/or (XI) wherein the X position of the tricyclic core is carbon exhibits increased cellular growth inhibition of a Kras- or mutant Kras-mediated cell line as compared to a compound having the same core scaffold wherein the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is substituted carbon exhibits increased cellular growth inhibition of a Kras- or mutant Kras-mediated cell line as compared to a compound having the same core scaffold wherein the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is C(Cl) exhibits increased cellular growth inhibition of a Kras- or mutant Kras-mediated cell line as compared to a compound having the same core scaffold wherein the X position of the tricyclic core is replaced with nitrogen. In embodiments, a comparison of a compound of Formula (I), (II), (II-a), (IV), (V), (Va), (Vb), (Vc), (VIII), (IX), (X), and/or (XI) wherein the X position of the tricyclic core is carbon against an identical compound wherein the X position of the tricyclic core is replaced with nitrogen reveals a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon. In embodiments, a comparison of a compound of Formula (I), (II), (II-a), (IV), (V), (Va), (Vb), (Vc), (VIII), (IX), (X), and/or (XI) wherein the X position of the tricyclic core is carbon against an identical compound wherein the X position of the tricyclic core is replaced with nitrogen reveals a remarkable increase in cellular growth inhibition of a G12D mutant expressing cell line (e.g., SW1990), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon.

In some embodiments, a compound of Formula (I), (II), (II-a), (IV), (V), (Va), (Vb), (Vc), (VIII), (IX), (X), and/or (XI) wherein the X position of the tricyclic core is carbon and $R^7$ is substituted benzothiophenyl exhibits increased cellular growth inhibition of a Kras- or mutant Kras-mediated cell line as compared to a compound having the same core scaffold wherein the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is substituted carbon and $R^7$ is substituted benzothiophenyl exhibits increased cellular growth inhibition of a Kras- or mutant Kras-mediated cell line as compared to a compound having the same core scaffold wherein the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is C(Cl) and $R^7$ is substituted benzothiophenyl exhibits increased cellular growth inhibition of a Kras- or mutant Kras-mediated cell line as compared to a compound having the same core scaffold wherein the X position of the tricyclic core is replaced with nitrogen. In embodiments, a comparison of a compound of Formula (I), (II), (II-a), (IV), (V), (Va), (Vb), (Vc), (VIII), (IX), (X), and/or (XI) wherein the X position of the tricyclic core is carbon and $R^7$ is a substituted benzothiophenyl against an identical compound wherein the X position of the tricyclic core is replaced with nitrogen reveals a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon. In embodiments, a comparison of a compound of Formula (I), (II), (II-a), (IV), (V), (Va), (Vb), (Vc), (VIII), (IX), (X), and/or (XI) wherein the X position of the tricyclic core is carbon and $R^7$ is substituted benzothiophenyl against an identical compound wherein the X position of the tricyclic core is replaced with nitrogen reveals a remarkable increase in cellular growth inhibition of a G12D mutant expressing cell line (e.g., SW1990), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon.

In some embodiments, a compound of Formula (I), (II), (II-a), (IV), (V), (Va), (Vb), (Vc), (VIII), (IX), (X), and/or (XI) wherein the X position of the tricyclic core is carbon and $R^7$ is

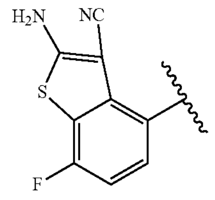 [SMILES: *c1ccc(F)c2sc(N)c(C#N)c12]

exhibits increased cellular growth inhibition of a Kras- or mutant Kras-mediated cell line as compared to a compound having the same overall compound structure except that the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is substituted carbon and $R^7$ is

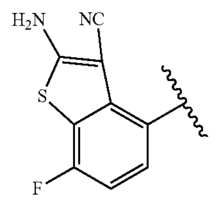 [SMILES: *c1ccc(F)c2sc(N)c(C#N)c12]

exhibits increased cellular growth inhibition of a Kras- or mutant Kras-mediated cell line as compared to a compound having the same core scaffold wherein the X position of the tricyclic core is replaced with nitrogen. In an embodiment, a compound of Formula (I), (II), (II-a), (IV), (V), (Va), (Vb), (Vc), (VIII), (IX), (X), and/or (XI) wherein the X position of the tricyclic core is C(Cl) and $R^7$ is

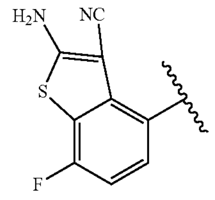 [SMILES: *c1ccc(F)c2sc(N)c(C#N)c12]

exhibits increased cellular growth inhibition of a Kras- or mutant Kras-mediated cell line as compared to a compound having the same core scaffold wherein the X position of the tricyclic core is replaced with nitrogen. In embodiments, a comparison of a compound of Formula (I), (II), (II-a), (IV), (V), (Va), (Vb), (Vc), (VIII), (IX), (X), and/or (XI) wherein the X position of the tricyclic core is a carbon and $R^7$ is

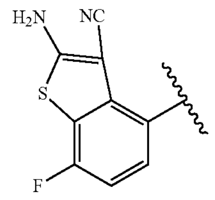 [SMILES: *c1ccc(F)c2sc(N)c(C#N)c12]

against an identical compound wherein the X position of the tricyclic core is replaced with nitrogen reveals a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon. In embodiments, a comparison of a compound of Formula (I), (II), (II-a), (IV), (V), (Va), (Vb), (Vc), (VIII), (IX), (X), and/or (XI) wherein the X position of the tricyclic core is carbon and $R^7$ is

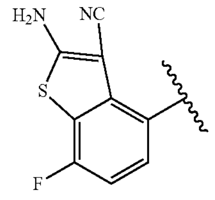 [SMILES: *c1ccc(F)c2sc(N)c(C#N)c12]

against an identical compound wherein the X position of the tricyclic core is replaced with nitrogen reveals a remarkable increase in cellular growth inhibition of a G12D mutant expressing cell line (e.g., SW1990), as evidenced by a reduction in IC50 of at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, or 45-fold, or even greater for the compound wherein the X position of the tricyclic core is carbon.

In some embodiments, a compound of Formula (I), (II), (II-a), (IV), (V), (Va), (Vb), (Vc), (VIII), (IX), (X), and/or (XI) wherein $R^6$ is haloalkyl exhibits increased metabolic stability as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl exhibits increased metabolic stability as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased metabolic stability as compared to a compound having the same core scaffold except that $R^6$ is replaced with halogen. In an embodiment, such subject compound of Formula (I), (II), (II-a), (IV), (V), (Va), (Vb), (Vc), (VIII), (IX), (X), and/or (XI) wherein $R^6$ is —$CF_3$ exhibits increased metabolic stability as compared to a compound having the same core scaffold except that $R^6$ is replaced with Cl. In embodiments, a comparison of a compound of Formula (I), (II), (II-a), (IV), (V), (Va), (Vb), (Vc), (VIII), (IX), (X), and/or (XI) wherein $R^6$ is haloalkyl against an identical compound wherein $R^6$ is replaced with halogen reveals remarkable increased metabolic stability, as evidenced by an increase in the percent of compound remaining (e.g., in mice) of at least 1.1, 1.2, 1.3, 1.4, 1.5, 1.6, 1.7, 1.8, or 1.9-fold, or even greater for the compound wherein $R^6$ is haloalkyl. In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl against an identical compound wherein $R^6$ is replaced with halogen reveals remarkable increased metabolic stability, as evidenced by an increase in the percent of compound remaining (e.g., in mice) of at least 1.1, 1.2, 1.3, 1.4, 1.5, 1.6, 1.7, 1.8, or 1.9-fold, or even greater for the compound wherein $R^6$ is $C_1$-$C_3$ haloalkyl. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with halogen reveals remarkable increased metabolic stability, as evidenced by an increase in the percent of compound remaining (e.g., in mice) of at least 1.1, 1.2, 1.3, 1.4, 1.5, 1.6, 1.7, 1.8, or 1.9-fold, or even greater for the compound wherein $R^6$ is —$CF_3$.

In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with —Cl reveals remarkable increased metabolic stability, as evidenced by an increase in the percent of compound remaining (e.g., in mice) of at least 1.1, 1.2, 1.3, 1.4, 1.5, 1.6, 1.7, 1.8, or 1.9-fold, or even greater for the compound wherein $R^6$ is —$CF_3$. In embodiments, a comparison of a compound of Formula (I), (II), (II-a), (IV), (V), (Va), (Vb), (Vc), (VIII), (IX), (X), and/or (XI) wherein $R^6$ is haloalkyl against an identical compound wherein $R^6$ is replaced with halogen reveals remarkable increased metabolic stability, as evidenced by an increase in the percent of compound remaining (e.g., in humans) of at least 1.1, 1.2, 1.3, 1.4, 1.5, 1.6, 1.7, 1.8, 1.9-fold, or even greater for the compound wherein $R^6$ is haloalkyl. In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl against an identical compound wherein $R^6$ is replaced with halogen reveals remarkable increased metabolic stability, as evidenced by an increase in the percent of compound remaining (e.g., in humans) of at least 1.1, 1.2, 1.3, 1.4, 1.5, 1.6, 1.7, 1.8, or 1.9-fold, or even greater for the compound wherein $R^6$ is $C_1$-$C_3$ haloalkyl. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is halogen reveals remarkable increased metabolic stability, as evidenced by an increase in the percent of compound remaining (e.g., in humans) of at least 1.1, 1.2, 1.3, 1.4, 1.5, 1.6, 1.7, 1.8, or 1.9-fold, or even greater for the compound wherein $R^6$ is —$CF_3$. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is —Cl reveals remarkable increased metabolic stability, as evidenced by an increase in the percent of compound remaining (e.g., in humans) of at least 1.1, 1.2, 1.3, 1.4, 1.5, 1.6, 1.7, 1.8, or 1.9-fold, or even greater for the compound wherein $R^6$ is —$CF_3$.

In some embodiments, a compound of Formula (I), (II), (II-a), (IV), (V), (Va), (Vb), (Vc), (VIII), (IX), (X), and/or (XI) wherein $R^6$ is haloalkyl exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased oral exposure (e.g., in dog) as compared to a compound having the same core scaffold except that $R^6$ is replaced with Cl. In embodiments, a comparison of a compound of Formula (I), (II), (II-a), (IV), (V), (Va), (Vb), (Vc), (VIII), (IX), (X), and/or (XI) wherein $R^6$ is haloalkyl against an identical compound wherein $R^6$ is replaced with halogen reveals a remarkable increase in oral exposure, as evidenced by an AUC (e.g., in dog) greater than 250 hr/ng/mL when $R^6$ is haloalkyl and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl against an identical compound wherein $R^6$ is replaced with halogen reveals a remarkable increase in oral exposure, as evidenced by an AUC (e.g., in dog) greater than 250 hr/ng/ml when $R^6$ is $C_1$-$C_3$ haloalkyl and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with halogen reveals a remarkable increase in oral exposure, as evidenced by an AUC (e.g., in dog) greater than 250 hr/ng/ml when $R^6$ is —$CF_3$ and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with —Cl reveals a remarkable increase in oral exposure, as evidenced by an AUC (e.g., in dog) greater than 250 hr/ng/ml when $R^6$ is —$CF_3$ and less than 50 hr/ng/ml when $R^6$ is —Cl.

In some embodiments, a compound of Formula (I), (II), (II-a), (IV), (V), (Va), (Vb), (Vc), (VIII), (IX), (X), and/or (XI) wherein $R^6$ is haloalkyl exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased oral bioavailability (e.g., in dog) as compared to a compound having the same core scaffold except that $R^6$ is replaced with Cl. In embodiments, a comparison of a compound of Formula (I), (II), (II-a), (IV), (V), (Va), (Vb), (Vc), (VIII), (IX), (X), and/or (XI) wherein $R^6$ is haloalkyl against an identical compound wherein $R^6$ is replaced with halogen reveals remarkable increased oral bioavailability (e.g., in dog) when $R^6$ is haloalkyl, as evidenced by an observed oral bioavailability in dogs of greater than 10% when $R^6$ is haloalkyl and less than 1% when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl against an identical compound wherein $R^6$ is replaced with halogen reveals remarkable increased oral bioavailability (e.g., in dog) when $R^6$ is $C_1$-$C_3$ haloalkyl, as evidenced by an observed oral bioavailability in dogs of greater than 10% when $R^6$ is $C_1$-$C_3$ haloalkyl and less than 1% when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with halogen reveals remarkable increased oral bioavailability (e.g., in dog) when $R^6$ is —$CF_3$, as evidenced by an observed oral bioavailability in dogs of greater than 10% when $R^6$ is —$CF_3$ and less than 1% when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ against an identical compound wherein $R^6$ is replaced with —Cl reveals remarkable increased oral bioavailability (e.g., in dog) when $R^6$ is —$CF_3$, as evidenced by an observed oral bioavailability in dogs of greater than 10% when $R^6$ is —$CF_3$ and less than 1% when $R^6$ is —Cl.

In some embodiments, a compound of Formula (I), (II), (II-a), (IV), (V), (Va), (Vb), (Vc), (VIII), (IX), (X), and/or (XI) wherein the $R^6$ is haloalkyl and $R^7$ is

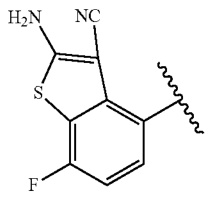 [SMILES: *c1ccc(F)c2sc(N)c(C#N)c12]

exhibits increased metabolic stability as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl and $R^7$ is

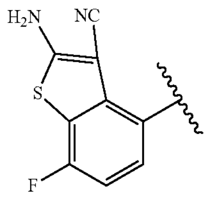

exhibits increased metabolic stability as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ and $R^7$ is

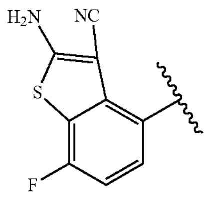 [SMILES: *c1ccc(F)c2sc(N)c(C#N)c12]

exhibits increased metabolic stability as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ and $R^7$ is

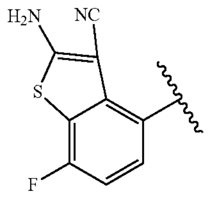 [SMILES: *c1ccc(F)c2sc(N)c(C#N)c12]

exhibits increased metabolic stability as compared to a compound having the same core scaffold except that $R^6$ is replaced with Cl. In embodiments, a compound of Formula (I), (II), (II-a), (IV), (V), (Va), (Vb), (Vc), (VIII), (IX), (X), and/or (XI) wherein $R^6$ is haloalkyl and $R^7$ is

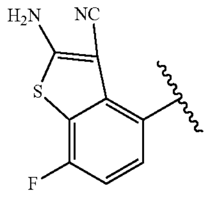 [SMILES: *c1ccc(F)c2sc(N)c(C#N)c12]

exhibits remarkable increased metabolic stability as evidenced by an increase in the percent of compound remaining (e.g., in mice) of at least 1.1, 1.2, 1.3, 1.4, 1.5, 1.6, 1.7, 1.8, or 1.9-fold, or even greater when compared to an identical compound wherein $R^6$ is replaced with halogen. In embodiments, a compound of Formula (I), (II), (II-a), (IV), (V), (Va), (Vb), (Vc), (VIII), (IX), (X), and/or (XI) wherein $R^6$ is $C_1$-$C_3$ haloalkyl and $R^7$ is

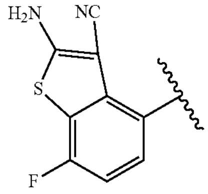 [SMILES: *c1ccc(F)c2sc(N)c(C#N)c12]

exhibits remarkable increased metabolic stability as evidenced by an increase in the percent of compound remaining (e.g., in mice) of at least 1.1, 1.2, 1.3, 1.4, 1.5, 1.6, 1.7, 1.8, or 1.9-fold, or even greater when compared to an identical compound wherein $R^6$ is replaced with halogen. In embodiments, a compound of Formula (I), (II), (II-a), (IV), (V), (Va), (Vb), (Vc), (VIII), (IX), (X), and/or (XI) wherein $R^6$ is —$CF_3$ and $R^7$ is

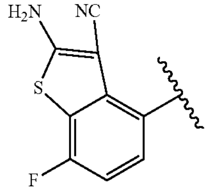 [SMILES: *c1ccc(F)c2sc(N)c(C#N)c12]

exhibits remarkable increased metabolic stability as evidenced by an increase in the percent of compound remaining (e.g., in mice) of at least 1.1, 1.2, 1.3, 1.4, 1.5, 1.6, 1.7, 1.8, or 1.9-fold, or even greater when compared to an identical compound wherein $R^6$ is replaced with halogen. In embodiments, a compound of Formula (I), (II), (II-a), (IV), (V), (Va), (Vb), (Vc), (VIII), (IX), (X), and/or (XI) wherein $R^6$ is —$CF_3$ and $R^7$ is

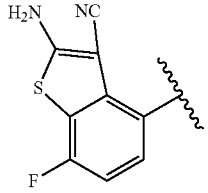 [SMILES: *c1ccc(F)c2sc(N)c(C#N)c12]

exhibits remarkable increased metabolic stability as evidenced by an increase in the percent of compound remaining (e.g., in mice) of at least 1.1, 1.2, 1.3, 1.4, 1.5, 1.6, 1.7, 1.8, or 1.9-fold, or even greater when compared to an identical compound wherein $R^6$ is replaced with —Cl.

In embodiments, a comparison of a compound of Formula (I), (II), (II-a), (IV), (V), (Va), (Vb), (Vc), (VIII), (IX), (X), and/or (XI) wherein $R^6$ is

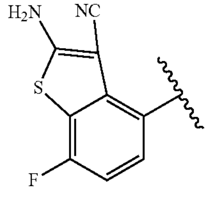 [SMILES: *c1ccc(F)c2sc(N)c(C#N)c12]

haloalkyl and $R^7$ is against an identical compound wherein $R^6$ is halogen reveals remarkable increased metabolic stability, as evidenced by an increase in the percent of compound remaining (e.g., in human) of at least 1.1, 1.2, 1.3, 1.4, 1.5, 1.6, 1.7, 1.8, or 1.9-fold, or even greater for the compound wherein $R^6$ is haloalkyl. In embodiments, a comparison of a compound of Formula (I), (II), (II-a), (IV), (V), (Va), (Vb), (Vc), (VIII), (IX), (X), and/or (XI) wherein the $R^6$ is $C_1$-$C_3$ haloalkyl and $R^7$ is

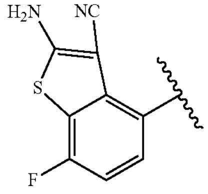 [SMILES: *c1ccc(F)c2sc(N)c(C#N)c12]

against an identical compound wherein $R^6$ is replaced with halogen reveals remarkable increased metabolic stability, as evidenced by an increase in the percent of compound remaining (e.g., in human) of at least 1.1, 1.2, 1.3, 1.4, 1.5, 1.6, 1.7, 1.8, or 1.9-fold, or even greater for the compound wherein $R^6$ is $C_1$-$C_3$ haloalkyl. In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$ is

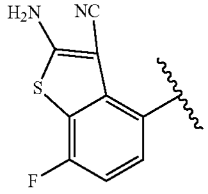 [SMILES: *c1ccc(F)c2sc(N)c(C#N)c12]

against an identical compound wherein $R^6$ is replaced with halogen reveals remarkable increased metabolic stability, as evidenced by an increase in the percent of compound remaining (e.g., in human) of at least 1.1, 1.2, 1.3, 1.4, 1.5, 1.6, 1.7, 1.8, or 1.9-fold, or even greater for the compound wherein $R^6$ is —$CF_3$. In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$ is

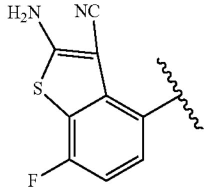 [SMILES: *c1ccc(F)c2sc(N)c(C#N)c12]

against an identical compound wherein $R^6$ is replaced with —Cl reveals remarkable increased metabolic stability, as evidenced by an increase in the percent of compound remaining (e.g., in human) of at least 1.1, 1.2, 1.3, 1.4, 1.5, 1.6, 1.7, 1.8, or 1.9-fold, or even greater for the compound wherein $R^6$ is —$CF_3$.

In some embodiments, a compound of Formula (I), (II), (II-a), (IV), (V), (Va), (Vb), (Vc), (VIII), (IX), (X), and/or (XI) wherein $R^6$ is haloalkyl and $R^7$ is

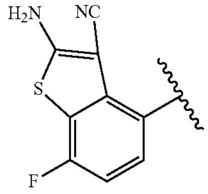 [SMILES: *c1ccc(F)c2sc(N)c(C#N)c12]

exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl and $R^7$ is

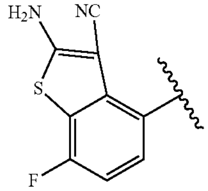 [SMILES: *c1ccc(F)c2sc(N)c(C#N)c12]

exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ exhibits increased oral exposure (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ and $R^7$

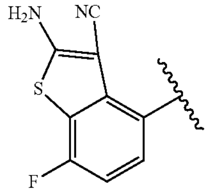 [SMILES: *c1ccc(F)c2sc(N)c(C#N)c12]

exhibits increased oral exposure (e.g., in dog) as compared to a compound having the same core scaffold except that $R^6$ is replaced with Cl. In embodiments, a comparison of a compound of Formula (I), (II), (II-a), (IV), (V), (Va), (Vb), (Vc), (VIII), (IX), (X), and/or (XI) wherein $R^6$ is haloalkyl and $R^7$ is

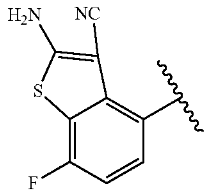 [SMILES: *c1ccc(F)c2sc(N)c(C#N)c12]

against an identical compound wherein $R^6$ is replaced with halogen reveals a remarkable increased oral exposure (e.g., in dog) when $R^6$ is haloalkyl, as evidenced by an AUC in dog of greater than 250 hr/ng/ml when $R^6$ is haloalkyl and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl and $R^7$ is

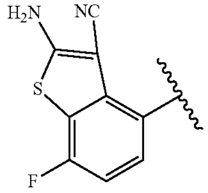 [SMILES: *c1ccc(F)c2sc(N)c(C#N)c12]

against an identical compound wherein $R^6$ is replaced with halogen reveals a remarkable increased oral exposure (e.g., in dog) when $R^6$ is $C_1$-$C_3$ haloalkyl, as evidenced by an AUC in dog of greater than 250 hr/ng/ml when $R^6$ is $C_1$-$C_3$ haloalkyl and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$ is

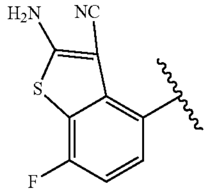 [SMILES: *c1ccc(F)c2sc(N)c(C#N)c12]

against an identical compound wherein $R^6$ is replaced with halogen reveals a remarkable increased oral exposure (e.g., in dog) when $R^6$ is —$CF_3$, as evidenced by an AUC in dog of greater than 250 hr/ng/ml when $R^6$ is —$CF_3$ and less than 50 hr/ng/ml when $R^6$ is halogen. In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$ is

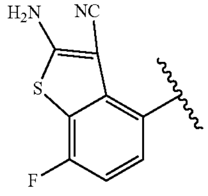 [SMILES: *c1ccc(F)c2sc(N)c(C#N)c12]

against an identical compound wherein $R^6$ is replaced with —Cl reveals a remarkable increased oral exposure (e.g., in dog) when $R^6$ is —$CF_3$, as evidenced by an AUC in dog of greater than 250 hr/ng/ml when $R^6$ is —$CF_3$ and less than 50 hr/ng/ml when $R^6$ is —Cl.

In some embodiments, a compound of Formula (I), (II), (II-a), (IV), (V), (Va), (Vb), (Vc), (VIII), (IX), (X), and/or (XI) wherein $R^6$ is haloalkyl and $R^7$ is

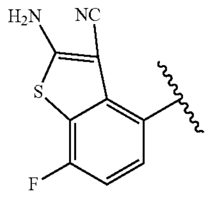 [SMILES: *c1ccc(F)c2sc(N)c(C#N)c12]

exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is $C_1$-$C_3$ haloalkyl exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ and $R^7$ is

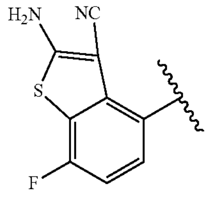 [SMILES: *c1ccc(F)c2sc(N)c(C#N)c12]

exhibits increased oral bioavailability (e.g., in dog) as compared to a compound having the same core scaffold except that $R^6$ is replaced with halogen. In an embodiment, a compound of Formula (I), (II), (II-a), (IV), (V), (Va), (Vb), (Vc), (VIII), (IX), (X), and/or (XI) wherein $R^6$ is —$CF_3$ and $R^7$ is

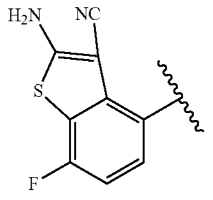 [SMILES: *c1ccc(F)c2sc(N)c(C#N)c12]

exhibits increased oral bioavailability (e.g., in dog) as compared to a compound having the same core scaffold except that $R^6$ is replaced with Cl. In embodiments, a comparison of a compound of Formula (I), (II), (II-a), (IV), (V), (Va), (Vb), (Vc), (VIII), (IX), (X), and/or (XI) wherein $R^6$ is haloalkyl and $R^7$ is

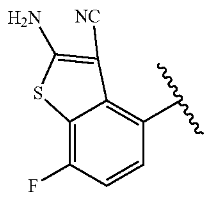 [SMILES: *c1ccc(F)c2sc(N)c(C#N)c12]

against an identical compound wherein $R^6$ is replaced with halogen reveals a remarkable increased oral bioavailability (e.g., in dog) when $R^6$ is haloalkyl. In embodiments, oral bioavailability in dogs is greater than 10% when $R^6$ is haloalkyl and $R^7$ is

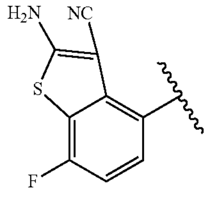 [SMILES: *c1ccc(F)c2sc(N)c(C#N)c12]

and less than 1% when $R^6$ is halogen and $R^7$ is

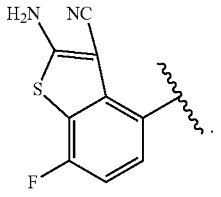 [SMILES: *c1ccc(F)c2sc(N)c(C#N)c12]

In embodiments, a comparison of a compound of Formula (I), (II), (II-a), (IV), (V), (Va), (Vb), (Vc), (VIII), (IX), (X), and/or (XI) wherein $R^6$ is $C_1$-$C_3$ haloalkyl and $R^7$ is

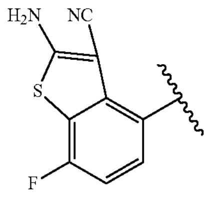 [SMILES: *c1ccc(F)c2sc(N)c(C#N)c12]

against an identical compound wherein $R^6$ is replaced with halogen reveals a remarkable increased oral bioavailability (e.g., in dog) when $R^6$ is $C_1$-$C_3$ haloalkyl. In embodiments, oral bioavailability in dogs is greater than 10% when $R^6$ is $C_1$-$C_3$ haloalkyl and $R^7$ is

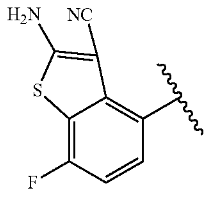 [SMILES: *c1ccc(F)c2sc(N)c(C#N)c12]

and less than 1% when $R^6$ is halogen and $R^7$ is

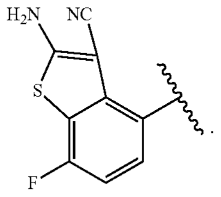 [SMILES: *c1ccc(F)c2sc(N)c(C#N)c12]

In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$ is

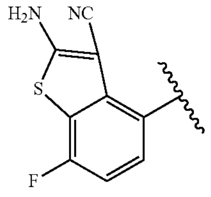

against an identical compound wherein $R^6$ is replaced with halogen reveals a remarkable increased oral bioavailability (e.g., in dog) when $R^6$ is —$CF_3$. In embodiments, oral bioavailability in dogs is greater than 10% when $R^6$ is —$CF_3$ and $R^7$ is

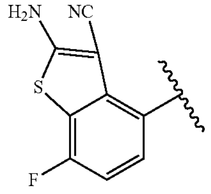 [SMILES: *c1ccc(F)c2sc(N)c(C#N)c12]

and less than 1% when $R^6$ is halogen and $R^7$ is

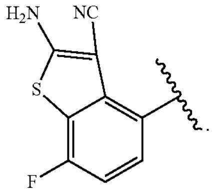 [SMILES: *c1ccc(F)c2sc(N)c(C#N)c12]

In embodiments, a comparison of a compound of Formula (I), (II), (II-a), (IV), (V), (Va), (Vb), (Vc), (VIII), (IX), (X), and/or (XI) wherein $R^6$ is —$CF_3$ and $R^7$

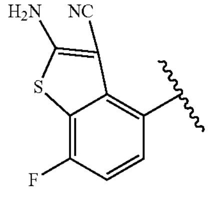 [SMILES: *c1ccc(F)c2sc(N)c(C#N)c12]

against an identical compound wherein $R^6$ is replaced with —Cl reveals a remarkable increased oral bioavailability (e.g., in dog) when $R^6$ is —$CF_3$. In embodiments, oral bioavailability in dogs is greater than 10% when $R^6$ is —$CF_3$ and $R^7$ is

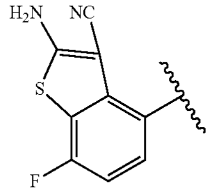 [SMILES: *c1ccc(F)c2sc(N)c(C#N)c12]

and less than 1% when $R^6$ is —Cl and $R^7$ is

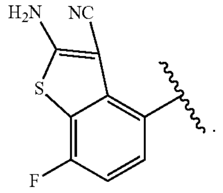 [SMILES: *c1ccc(F)c2sc(N)c(C#N)c12]

In some embodiments, a compound of Formula (I), (IV), (V), (Va), (Vb), (Vc), (VIII), (IX), (X), and/or (XI) wherein $R^5$ is halogen exhibits increased oral exposure (e.g., in mice) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —F exhibits increased oral exposure (e.g., in mice) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —Cl exhibits increased oral exposure (e.g., in mice) as compared to a compound having the same core scaffold except that $R^5$ is replaced with hydrogen.

In embodiments, a comparison of a compound of Formula (I), (IV), (V), (Va), (Vb), (Vc), (VIII), (IX), (X), and/or (XI) wherein $R^5$ is halogen against an identical compound wherein $R^5$ is replaced with hydrogen reveals a remarkable increased oral exposure (e.g., in mice) when $R^5$ is halogen, as evidenced by an observed AUC in mice of greater than 1000 hr/ng/ml when $R^5$ is halogen and less than 500 hr/ng/mL when $R^5$ is hydrogen. In embodiments, a comparison of a compound of Formula (I), (IV), (V), (Va), (Vb), (Vc), (VIII), (IX), (X), and/or (XI) wherein $R^5$ is —F against an identical compound wherein $R^5$ is replaced with hydrogen reveals a remarkable increased oral exposure (e.g., in mice) when $R^5$ is —F, as evidenced by an observed AUC in mice of greater than 1000 hr/ng/mL when $R^5$ is —F and less than 500 hr/ng/ml when $R^5$ is hydrogen. In embodiments, a comparison of a compound of Formula (I), (IV), (V), (Va), (Vb), (Vc), (VIII), (IX), (X), and/or (XI) wherein $R^5$ is —Cl against an identical compound wherein $R^5$ is replaced with hydrogen reveals a remarkable increased oral exposure (e.g., in mice) when $R^5$ is —Cl, as evidenced by an observed AUC in mice of greater than 1000 hr/ng/ml when $R^5$ is —Cl and less than 500 hr/ng/ml when $R^5$ is hydrogen.

In some embodiments, a compound of Formula (I), (IV), (V), (Va), (Vb), (Vc), (VIII), (IX), (X), and/or (XI) wherein $R^5$ is halogen exhibits increased oral bioavailability (e.g., in rat) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —Cl exhibits increased oral bioavailability (e.g., in rat) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —F exhibits increased oral bioavailability (e.g., in rat) as compared to a compound having the same core scaffold except that $R^5$ is replaced with hydrogen. In embodiments, a comparison of a compound of Formula (I), (IV), (V), (Va), (Vb), (Vc), (VIII), (IX), (X), and/or (XI) wherein $R^5$ is halogen against an identical compound wherein $R^5$ is replaced with hydrogen reveals remarkable increased oral bioavailability (e.g., in rat) when $R^5$ is halogen. In embodiments, bioavailability in rats is greater than 10% when $R^5$ is halogen and less than 5% when $R^5$ is hydrogen. In embodiments, a comparison of a compound of Formula (I), (IV), (V), (Va), (Vb), (Vc), (VIII), (IX), (X), and/or (XI) wherein $R^5$ is —Cl against an identical compound wherein $R^5$ is replaced with hydrogen reveals remarkable increased oral bioavailability (e.g., in rat) when $R^5$ is —Cl. In embodiments, oral bioavailability in rats is greater than 10% when $R^5$ is —Cl and less than 5% when $R^5$ is hydrogen. In embodiments, a comparison of a compound of Formula (I), (IV), (V), (Va), (Vb), (Vc), (VIII), (IX), (X), and/or (XI) wherein $R^5$ is —F against an identical compound wherein $R^5$ is replaced with hydrogen reveals remarkable increased oral bioavailability (e.g., in rat) when $R^5$ is —F. In embodiments, oral bioavailability in rats is greater than 10% when $R^5$ is —F and less than 5% when $R^5$ is hydrogen.

In some embodiments, a compound of Formula (I), (IV), (V), (Va), (Vb), (Vc), (VIII), (IX), (X), and/or (XI) wherein $R^5$ is halogen and $R^7$ is

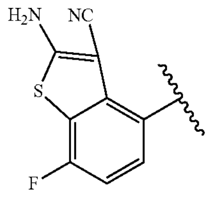

exhibits increased oral exposure (e.g., in mice) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —Cl and $R^7$ is

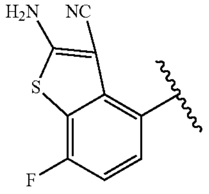
, exhibits increased oral exposure (e.g., in mice) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —F and $R^7$ is

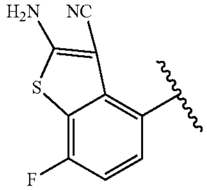 [SMILES: *c1ccc(F)c2sc(N)c(C#N)c12]

exhibits increased oral exposure (e.g., in mice) as compared to a compound having the same core scaffold except that $R^5$ is replaced with hydrogen. In embodiments, a comparison of a compound of Formula (I), (IV), (V), (Va), (Vb), (Vc), (VIII), (IX), (X), and/or (XI) wherein $R^5$ is halogen and $R^7$ is

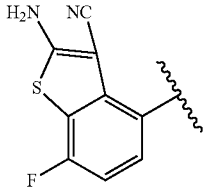 [SMILES: *c1ccc(F)c2sc(N)c(C#N)c12]

against an identical compound wherein $R^5$ is replaced with hydrogen reveals remarkable increased oral exposure (e.g., in mice) when $R^5$ is halogen, as evidenced by an observed AUC in mice greater than 1000 hr/ng/ml when $R^5$ is halogen and less than 500 hr/ng/ml when $R^5$ is hydrogen. In embodiments, a comparison of a compound of Formula (I), (IV), (V), (Va), (Vb), (Vc), (VIII), (IX), (X), and/or (XI) wherein $R^5$ is —Cl and $R^7$ is

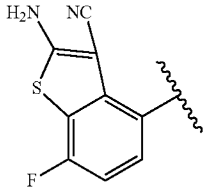 [SMILES: *c1ccc(F)c2sc(N)c(C#N)c12]

against an identical compound wherein $R^5$ is replaced with hydrogen reveals a remarkable increased oral exposure (e.g., in mice) when $R^5$ is —Cl, as evidenced by an observed AUC in mice greater than 1000 hr/ng/ml when $R^5$ is —Cl and less than 500 hr/ng/ml when $R^5$ is hydrogen. In embodiments, a comparison of a compound of Formula (I), (IV), (V), (Va), (Vb), (Vc), (VIII), (IX), (X), and/or (XI) wherein $R^5$ is —F and $R^7$ is

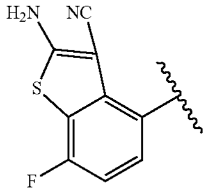 [SMILES: *c1ccc(F)c2sc(N)c(C#N)c12]

against an identical compound wherein $R^5$ is replaced with hydrogen reveals a remarkable increased oral exposure (e.g., in mice) when $R^5$ is —F, as evidenced by an observed AUC in mice greater than 1000 hr/ng/ml when $R^5$ is —F and less than 500 hr/ng/ml when $R^5$ is hydrogen.

In some embodiments, a compound of Formula (I), (IV), (V), (Va), (Vb), (Vc), (VIII), (IX), (X), and/or (XI) wherein $R^5$ is halogen and $R^7$ is

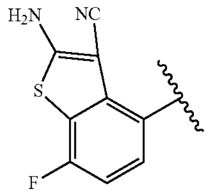 [SMILES: *c1ccc(F)c2sc(N)c(C#N)c12]

exhibits increased oral bioavailability (e.g., in rat) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —Cl and $R^7$ is

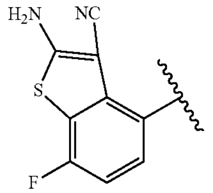 [SMILES: *c1ccc(F)c2sc(N)c(C#N)c12]

exhibits increased oral bioavailability (e.g., in rat) as compared to a compound having the same core scaffold except that $R^5$ is replaced with hydrogen. In an embodiment, a compound of Formula (I), (IV), (V), (Va), (Vb), (Vc), (VIII), (IX), (X), and/or (XI) wherein $R^5$ is —F and $R^7$ is

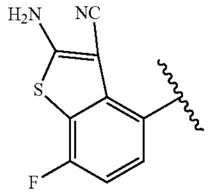 [SMILES: *c1ccc(F)c2sc(N)c(C#N)c12]

exhibits increased oral bioavailability (e.g., in rat) as compared to a compound having the same core scaffold except that $R^5$ is replaced with hydrogen. In embodiments, a comparison of a compound of Formula (I), (IV), (V), (Va), (Vb), (Vc), (VIII), (IX), (X), and/or (XI) wherein $R^5$ is halogen and $R^7$ is

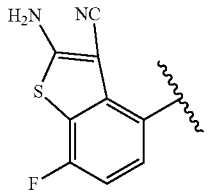 [SMILES: *c1ccc(F)c2sc(N)c(C#N)c12]

against an identical compound wherein $R^5$ is replaced with hydrogen reveals remarkable increased oral bioavailability (e.g., in rat) when $R^5$ is halogen. In embodiments, oral bioavailability in rats is greater than 10% when $R^5$ is halogen and $R^7$ is

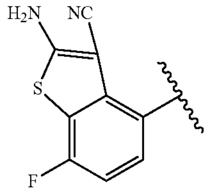 [SMILES: *c1ccc(F)c2sc(N)c(C#N)c12]

and less than 5% when $R^5$ is hydrogen and $R^7$ is

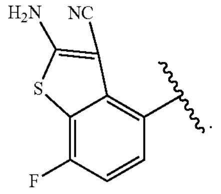 [SMILES: *c1ccc(F)c2sc(N)c(C#N)c12]

In embodiments, a comparison of a compound of Formula (I), (IV), (V), (Va), (Vb), (Vc), (VIII), (IX), (X), and/or (XI) wherein $R^5$ is —Cl and $R^7$ is

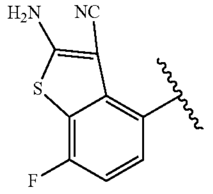 [SMILES: *c1ccc(F)c2sc(N)c(C#N)c12]

against an identical compound wherein $R^5$ is replaced with hydrogen reveals remarkable increased oral bioavailability (e.g., in rat) when $R^5$ is —Cl. In embodiments, oral bioavailability in rats is greater than 10% when $R^5$ is —Cl and $R^7$ is

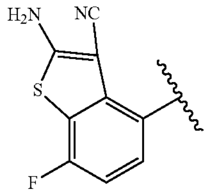 [SMILES: *c1ccc(F)c2sc(N)c(C#N)c12]

and less than 5% when $R^5$ is hydrogen and $R^7$ is

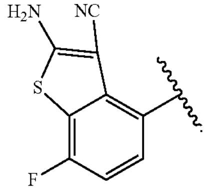 [SMILES: *c1ccc(F)c2sc(N)c(C#N)c12]

In embodiments, a comparison of a compound of Formula (I), (IV), (V), (Va), (Vb), (Vc), (VIII), (IX), (X), and/or (XI) wherein $R^5$ is —F and $R^7$ is

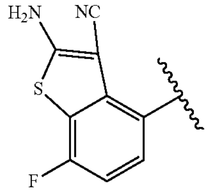 [SMILES: *c1ccc(F)c2sc(N)c(C#N)c12]

against an identical compound wherein $R^5$ is replaced with hydrogen reveals remarkable increased oral bioavailability (e.g., in rat) when $R^5$ is —F. In embodiments, bioavailability in rats is greater than 10% when $R^5$ is —F and $R^7$ is

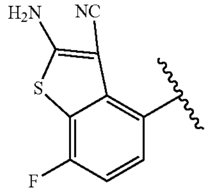

and less than 5% when $R^5$ is hydrogen and $R^7$ is

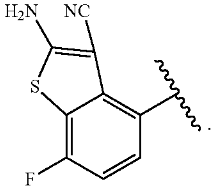 [SMILES: *c1ccc(F)c2sc(N)c(C#N)c12]

In some embodiments, a compound of Formula (I), (IV), (V), (Va), (Vb), (Vc), (X), and/or (XI) wherein $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$ exhibits increased oral exposure (e.g., in rat) as compared to a compound having the same core scaffold except that $R^4$ is replaced with —$CH_3$. In embodiments, a compound of Formula (I), (IV), (V), (Va), (Vb), (Vc), (X), and/or (XI) wherein $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$ exhibits remarkable increased oral exposure (e.g., in rat) compared to an identical compound wherein $R^4$ is replaced with —$CH_3$. In embodiments, the oral AUC in rats is greater than 3000 hr/ng/ml when $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$; and less than 500 hr/ng/ml when $R^4$ is —$CH_3$.

In some embodiments, a compound of Formula (I), (IV), (V), (Va), (Vb), (Vc), (X), and/or (XI) wherein the $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$ exhibits increased oral bioavailability (e.g., in rat) as compared to a compound having the same core scaffold except that $R^4$ is replaced with —$CH_3$. In embodiments, a compound of Formula (I), (IV), (V), (Va), (Vb), (Vc), (X), and/or (XI) wherein $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$ exhibits remarkable increased oral bioavailability (e.g., in rat) compared to an identical compound wherein $R^4$ is replaced with —$CH_3$. In embodiments, the oral bioavailability in rats is greater than 10% when $R^4$ is selected from $C_{1-3}$ alkyl substituted with one or more $R^{20}$, $C_{2-4}$ alkenyl, and $C_{2-3}$ alkynyl, wherein $C_{2-4}$ alkenyl and $C_{2-3}$ alkynyl are each optionally substituted with one or more $R^{20}$; and less than 5% when $R^4$ is —$CH_3$.

In some embodiments, a compound of Formula (I), (IV), (V), (Va), (Vb), (Vc), (X), and/or (XI) wherein $R^4$ is $C_{1-3}$ alkyl substituted with one or more $R^{20}$ exhibits increased oral exposure (e.g., in rat) as compared to a compound having the same core scaffold except that $R^4$ is replaced with —$CH_3$. In embodiments, a compound of Formula (I), (IV), (V), (Va), (Vb), (Vc), (X), and/or (XI) wherein $R^4$ is $C_{1-3}$ alkyl substituted with one or more $R^{20}$, such as compound 611, exhibits remarkable increased oral exposure (e.g., in rats) compared to a compound wherein $R^4$ is —$CH_3$, such as compound 850. In embodiments, and as shown in Table 2, oral AUC in rats is greater than 3000 hr/ng/ml when $R^4$ is $C_{1-3}$ alkyl substituted with one or more $R^{20}$ and less than 500 hr/ng/ml when $R^4$ is —$CH_3$.

In some embodiments, a compound of Formula (I), (IV), (V), (Va), (Vb), (Vc), (X), and/or (XI) wherein $R^4$ is $C_{1-3}$ alkyl substituted with one or more $R^{20}$ exhibits increased oral bioavailability (e.g., in rat) as compared to a compound wherein $R^4$ is —$CH_3$. In embodiments, a compound of Formula (I), (IV), (V), (Va), (Vb), (Vc), (X), and/or (XI) wherein $R^4$ is $C_{1-3}$ alkyl substituted with one or more $R^{20}$, such as compound 611, exhibits remarkable increased oral bioavailability (e.g., in rats) compared to a compound wherein $R^4$ is —$CH_3$, such as compound 850. In embodiments, and as shown in Table 2, oral bioavailability in rats is greater than 10% when $R^4$ is $C_{1-3}$ alkyl substituted with one or more $R^{20}$ and less than 5% when $R^4$ is —$CH_3$.

TABLE 2

| Compound | AUC (PO, hr/ng/mL) | Bioavailability (% F) |
|---|---|---|
| 850 | <500 | <5 |
| 611 | >3000 | >10 |

In embodiments, a comparison of a compound of Formula (I), (IV), (V), (Va), (Vb), (Vc), (X), and/or (XI) wherein $R^4$ is $C_1$-3 alkyl substituted with one or more $R^{20}$ against a compound wherein $R^4$ is replaced with —$CH_3$ reveals remarkable increased oral exposure (e.g., in rat) when $R^4$ is $C_{1-3}$ alkyl substituted with one or more $R^{20}$. In embodiments, oral AUC is greater than 3000 hr/ng/ml when $R^4$ is $C_{1-3}$ alkyl substituted with one or more $R^{20}$ and less than 500 hr/ng/ml when $R^4$ is —$CH_3$.

In some embodiments, a compound of Formula (I), (IV), (V), (Va), (Vb), (Vc), (X), and/or (XI) wherein $R^4$ is

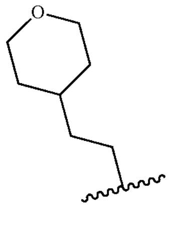 [SMILES: *CCC1CCOCC1]

exhibits increased oral bioavailability (e.g., in rat) as compared to a compound wherein $R^4$ is —$CH_3$. In embodiments, a comparison of a compound of Formula (I), (IV), (V), (Va), (Vb), (Vc), (X), and/or (XI) wherein $R^4$ is

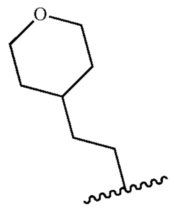 [SMILES: *CCC1CCOCC1]

against a compound wherein $R^4$ is —$CH_3$ reveals a remarkable increased oral bioavailability (e.g., in rat) when $R^4$ is

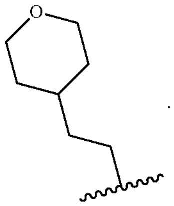 [SMILES: *CCC1CCOCC1]

In embodiments, oral bioavailability in rats is greater than 10% when $R^4$ is

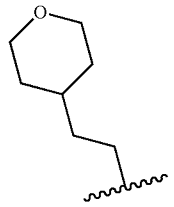 [SMILES: *CCC1CCOCC1]

and less than 5% when $R^4$ is —$CH_3$.

In some embodiments, a compound of Formula (I), (IV), (V), (Va), (Vb), (Vc), (VIII), (IX), (X), and/or (XI) wherein $R^4$ is a substituent other than unsubstituted methyl exhibits increased cellular growth inhibition of a Kras- or mutant Kras-mediated cell line as compared to a compound having the same core scaffold wherein $R^4$ is replaced with unsubstituted methyl. In some embodiments, a compound of Formula (I), (IV), (V), (Va), (Vb), (Vc), (VIII), (IX), (X), and/or (XI) wherein $R^4$ is a $C_{1-3}$ alkyl substituted with one, two, or three $R^{20}$ exhibits increased cellular growth inhibition of a Kras- or mutant Kras-mediated cell line as compared to a compound having the same core scaffold wherein $R^4$ is replaced with unsubstituted methyl. In some embodiments, a compound of Formula (I), (IV), (V), (Va), (Vb), (Vc), (VIII), (IX), (X), and/or (XI) wherein $R^4$ is a $C_{1-3}$ alkyl substituted with one, two, or three halogen exhibits increased cellular growth inhibition of a Kras- or mutant Kras-mediated cell line as compared to a compound having the same core scaffold wherein $R^4$ is replaced with unsubstituted methyl. In embodiments, a comparison of a compound of Formula (I), (IV), (V), (Va), (Vb), (Vc), (VIII), (IX), (X), and/or (XI) wherein $R^4$ is $C_{1-3}$ alkyl substituted with one, two, or three $R^{20}$ (e.g., halogen) to a compound of the same core where $R^4$ is replaced with unsubstituted methyl reveals a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, 4, or 5-fold, or even greater for the compound wherein $R^4$ is $C_{1-3}$ alkyl substituted with one, two, or three $R^{20}$ (e.g., halogen). In some embodiments, a compound of Formula (I), (IV), (V), (Va), (Vb), (Vc), (VIII), (IX), (X), and/or (XI) wherein $R^7$ is a substituent other than

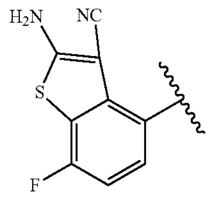 [SMILES: *c1ccc(F)c2sc(N)c(C#N)c12]

exhibits increased cellular growth inhibition of a Kras- or mutant Kras-mediated cell line as compared to a compound having the same core scaffold wherein $R^7$ is replaced with

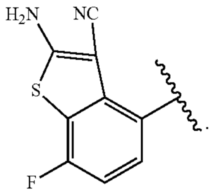 [SMILES: *c1ccc(F)c2sc(N)c(C#N)c12]

In some embodiments, a compound of Formula (I), (IV), (V), (Va), (Vb), (Vc), (VIII), (IX), (X), and/or (XI) wherein $R^7$ is benzothiophenyl optionally substituted with one or more substituents independently selected from —$NH_2$, —CN, and —F exhibits increased cellular growth inhibition of a Kras- or mutant Kras-mediated cell line as compared to a compound having the same core scaffold wherein $R^7$ is replaced with

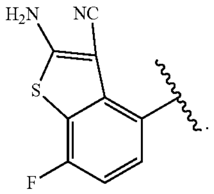 [SMILES: *c1ccc(F)c2sc(N)c(C#N)c12]

In some embodiments, a compound of Formula (I), (IV), (V), (Va), (Vb), (Vc), (VIII), (IX), (X), and/or (XI) wherein $R^7$ is benzothiophenyl optionally substituted with one or more $R^{20}$ exhibits increased cellular growth inhibition of a Kras- or mutant Kras-mediated cell line as compared to a compound having the same core scaffold wherein $R^7$ replaced with

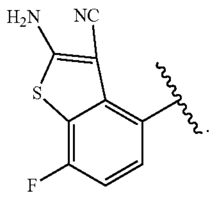

In embodiments, a compound of Formula (I), (IV), (V), (Va), (Vb), (Vc), (VIII), (IX), (X), and/or (XI) wherein $R^7$ is a benzothiophenyl optionally substituted with one or more $R^{20}$ (e.g., selected from —$NH_2$, —CN, and —F) exhibits a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, or 4-fold, or even greater compared to a compound of the same core where $R^7$ is replaced with

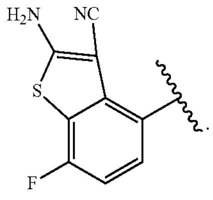 [SMILES: *c1ccc(F)c2sc(N)c(C#N)c12]

In some embodiments, a compound of Formula (I), (IV), (V), (Va), (Vb), (Vc), (VIII), (IX), (X), and/or (XI) wherein $R^2$ is a substituent other than

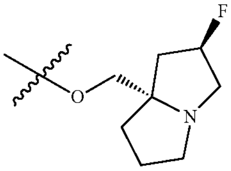 [SMILES: *OC[C@@]12CCCN1C[C@H](F)C2]

exhibits increased cellular growth inhibition of a Kras- or mutant Kras-mediated cell line as compared to a compound having the same core scaffold wherein $R^2$ is replaced with

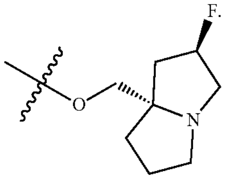 [SMILES: *OC[C@@]12CCCN1C[C@H](F)C2]

In some embodiments, a compound of Formula (I), (IV), (V), (Va), (Vb), (Vc), (VIII), (IX), (X), and/or (XI) wherein $R^2$ is —O—$CH_2$-(8- to 10-membered saturated heterocycle) optionally substituted with one or more substituents independently selected from —$CF_2$, —$CH_2$, and —CHF exhibits increased cellular growth inhibition of a Kras- or mutant Kras-mediated cell line as compared to a compound having the same core scaffold wherein $R^2$ is replaced with

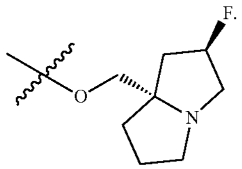 [SMILES: *OC[C@@]12CCCN1C[C@H](F)C2]

In some embodiments, a compound of Formula (I), (IV), (V), (Va), (Vb), (Vc), (VIII), (IX), (X), and/or (XI) wherein $R^2$ is —O—$CH_2$-(8- to 10-membered saturated heterocycle) optionally substituted with one or more substituents independently selected from $R^{20}$ exhibits increased cellular growth inhibition of a Kras- or mutant Kras-mediated cell line as compared to a compound having the same core scaffold wherein $R^2$ is replaced with

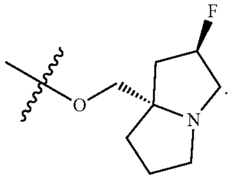 [SMILES: *OC[C@@]12CCCN1C[C@H](F)C2]

In embodiments, a compound of Formula (I), (IV), (V), (Va), (Vb), (Vc), (VIII), (IX), (X), and/or (XI) wherein $R^2$ is —O—$CH_2$-(8- to 10-membered saturated heterocycle) optionally substituted with one or more substituents independently selected from $R^{20}$ (e.g., selected from —$CF_2$, —$CH_2$, and =CHF) exhibits a remarkable increase in cellular growth inhibition of a G12D mutant expressing cell line (e.g., GP2d), as evidenced by a reduction in IC50 of at least 1.1, 1.2, 1.3, 1.4, 1.5, 1.6, 1.7, 1.8, 1.9, 2, 3, or 4-fold, or even greater compared to a compound of the same core where $R^2$ is replaced with

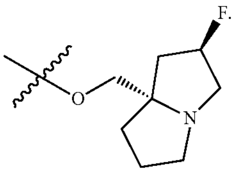 [SMILES: *OC[C@@]12CCCN1C[C@H](F)C2]

In some embodiments, a compound of Formula (I), (IV), (V), (Va), (Vb), (Vc), (VIII), (IX), (X), and/or (XI) wherein $R^4$ is

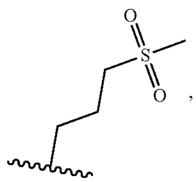 ,

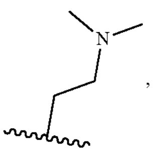 ,

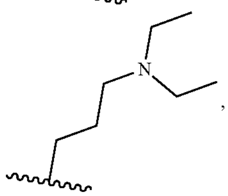 , or

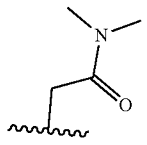

exhibits an IC50 of less than 5 nM against each of KRas G12D, wtKRas, and KRas G12V as assessed by an HTRF biochemical assay described herein. In some embodiments, a compound of Formula (I), (IV), (V), (Va), (Vb), (Vc), (VIII), (IX), (X), and/or (XI) wherein $R^5$ is $—CH_2NH_2$ exhibits an IC50 of less than 5 nM against each of KRas G12D, wtKRas, and KRas G12V as assessed by an HTRF biochemical assay described herein. In some embodiments, a compound of Formula (I), (IV), (V), (Va), (Vb), (Vc), (VIII), (IX), (X), and/or (XI) wherein $R^2$ is

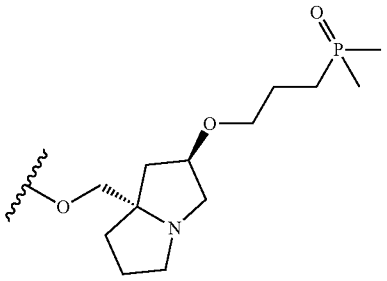

or

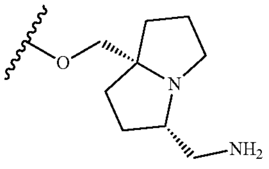

exhibits an IC50 of less than 5 nM against each of KRas G12D, wtKRas, and KRas G12V as assessed by an HTRF biochemical assay described herein. In some embodiments, a compound of Formula (I), (IV), (V), (Va), (Vb), (Vc), (VIII), (IX), (X), and/or (XI) wherein

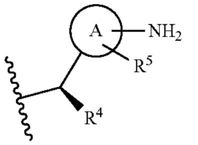

is

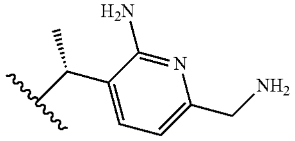

,

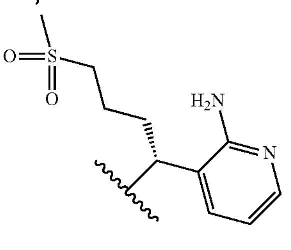

,

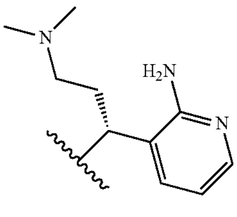

,

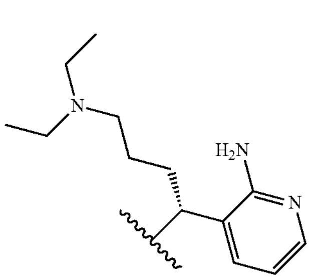

,

-continued

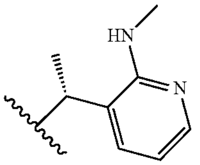

, or

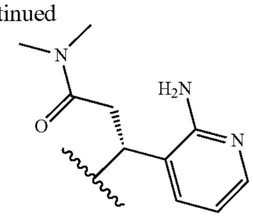

exhibits an IC50 of less than 5 nM against each of KRas G12D, wtKRas, and KRas G12V as assessed by an HTRF biochemical assay described herein.

In some embodiments is provided a compound of Formula (A), or a pharmaceutically acceptable salt or solvate thereof:

Formula (A)

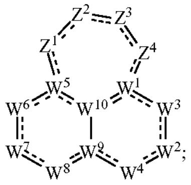

wherein:

$Z^1$, $Z^2$, and $Z^3$ are each independently selected from $N(R^{B4})$, $N(R^{11c})$, $N(R^{11d})$, N, $C(R^{B4})$, $C(R^{11c})$, $C(R^{11d})$, $C(R^{B4})(R^{11c})$, $C(R^{11c})(R^{11c})$, $C(R^{B4})(R^{B4})$, $C(R^{11c})(R^{11d})$, S, O, and C(O);

$Z^4$ is selected from $N(R^{B4})$, $N(R^{11c})$, $N(R^{11d})$, N, $C(R^{B4})$, $C(R^{11c})$, $C(R^{11d})$, $C(R^{B4})(R^{11c})$, $C(R^{11c})(R^{11c})$, $C(R^{B4})(R^{B4})$, $C(R^{11c})(R^{11d})$, S, and O;

wherein at least one of $Z^1$, $Z^2$, $Z^3$ and $Z^4$ is $N(R^{B4})$, $N(R^{11d})$, $C(R^{B4})$, $C(R^{11d})$, $C(R^{B4})(R^{11c})$, $C(R^{B4})(R^{B4})$, or $C(R^{11c})(R^{11d})$;

$W^1$ is $C(R^{B1})$, C, or N;

$W^2$ is $N(R^{2a})$, N, $C(R^2)$, $C(R^2)(R^{2a})$, C(O), $S(O)_2$, or S(O);

$R^{B1}$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—OR^{12}$, $—O—(C_{1-6}$ alkyl)-$OR^{15}$, $—SR^{12}$, $—N(R^{12})(R^{13})$, $—C(O)OR^{12}$, $—N—(R^{12})$, $—OC(O)N(R^{12})(R^{13})$, $—N(R^{12})C(O)N(R^{12})(R^{13})$, $—N(R^{12})C(O)OR^{12}$, $—N(R^{12})$ $S(O)_2R^{12}$, $—C(O)R^{12}$, $—S(O)R^{12}$, $—OC(O)R^{12}$, $—C(O)N(R^{12})(R^{13})$, $—C(O)C(O)N(R^{12})(R^{13})$, $—N(R^{12})C(O)R^{12}$, $—S(O)_2R^{12}$, $—S(O)(NR^{12})R^{12}$, $—S(O)_2N(R^{12})(R^{13})$, $—S(O)(NR^{12})N(R^{12})(R^{13})$, $—CH_2C(O)N(R^{12})(R^{13})$, $—CH_2N(R^{12})C(O)R^{12}$, $—CH_2S(O)_2R^{12}$, and $—OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl are optionally substituted with one, two, or three $R^{20}$;

$R^2$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, $—C_{0-6}$ alkyl-($C_{3-12}$ carbocycle), -(2- to 6-membered heteroalkyl)-($C_{3-12}$ carbocycle), $—C_{0-6}$ alkyl-(3- to 12-membered heterocycle), -(2- to 6-membered heteroalkyl)-(3- to 12-membered heterocycle), $—OR^{12}$, $—O—(C_1$-6 alkyl)-$OR^{15}$, $—SR^{12}$, $—N(R^{12})(R^{13})$, $—C(O)OR^{12}$, $—N{=}(R^{12})$, $—OC(O)N(R^{12})(R^{13})$, $—N(R^{12})C(O)N(R^{12})(R^{13})$, $—N(R^{12})C(O)$ $OR^{12}$, —N ($R^{12}$) $S(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2N(R^{12})(R^{13})$, —S(O)($NR^{12}$)N($R^{12}$)($R^{13}$), —$CH_2C(O)N(R^{12})(R^{13})$, —$CH_2N(R^{12})C(O)R^{12}$, —$CH_2S(O)_2R^{12}$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{2a}$, $R^{B3}$, $R^{3a}$, $R^{4c}$, $R^6$, $R^{6a}$, $R^{7a}$, $R^{7c}$, $R^8$, and $R^{8a}$ are independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —O—($C_{1-6}$ alkyl)-$OR^{15}$, —$SR^{12}$, —N($R^{12}$)($R^{13}$), —C(O)$OR^{12}$, —N═($R^{12}$), —OC(O)N($R^{12}$)($R^{13}$), —N($R^{12}$)C(O)N($R^{12}$)($R^{13}$), —N($R^{12}$)C(O)$OR^{12}$, —N($R^{12}$) $S(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2N(R^{12})(R^{13})$, —S(O)($NR^{12}$)N($R^{12}$)($R^{13}$), —$CH_2C(O)N(R^{12})(R^{13})$, —$CH_2N(R^{12})C(O)R^{12}$, —$CH_2S(O)_2R^{12}$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{3b}$, $R^{3c}$, $R^{4d}$, $R^{6b}$, $R^{7d}$, and $R^{8b}$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —O—($C_{1-6}$ alkyl)-$OR^{15}$, —$SR^{12}$, —N($R^{12}$)($R^{13}$), —C(O)$OR^{12}$, —N═($R^{12}$), —OC(O)N($R^{12}$)($R^{13}$), —C(O)$R^{12}$, —S(O)$R^{12}$, —OC(O)$R^{12}$, —C(O)N($R^{12}$)($R^{13}$), —C(O)C(O)N($R^{12}$)($R^{13}$), —$S(O)_2R^{12}$, —S(O)($NR^{12}$)$R^{12}$, —$S(O)_2N(R^{12})(R^{13})$, —S(O)($NR^{12}$)N($R^{12}$)($R^{13}$), —$CH_2C(O)N(R^{12})(R^{13})$, —$CH_2N(R^{12})C(O)R^{12}$, —$CH_2S(O)_2R^{12}$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$W^3$ is N($R^{3b}$), N, C($R^3$), C($R^{B3}$)($R^{3a}$), C(O), $S(O)_2$, or S(O);

$W^4$ is N or N($R^{3c}$);

$W^5$ is C($R^{B5}$), C, or N;

$R^{B5}$ is selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$OR^{12}$, —O—($C_{1-6}$ alkyl)-$OR^{15}$, —$SR^{12}$, —N($R^{12}$)($R^{13}$), —C(O)$OR^{12}$, —N═($R^{12}$), —OC(O)N($R^{12}$)($R^{13}$), —N($R^{12}$)C(O)N($R^{12}$)($R^{13}$), —N($R^{12}$)C(O)$OR^{12}$, —N($R^{12}$) $S(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2N(R^{12})(R^{13})$, —S(O)($NR^{12}$)N($R^{12}$)($R^{13}$), —$CH_2C(O)N(R^{12})(R^{13})$, —$CH_2N(R^{12})C(O)R^{12}$, —$CH_2S(O)_2R^{12}$, and —$OCH_2C(O)OR^{12}$, wherein $C_{1-6}$ alkyl, $C_{2-6}$ alkenyl, $C_{2-6}$ alkynyl, 2- to 6-membered heteroalkyl, 3- to 6-membered heteroalkenyl, and 3- to 6-membered heteroalkynyl, are optionally substituted with one, two, or three $R^{20}$ $W^6$ is N($R^6$%), N, C($R^6$), C($R^6$)($R^{6a}$), C(O), S(O), or $S(O)_2$;

$W^7$ is N($R^7$), C($R^7$), or C($R^7$)($R^{7a}$);

$R^7$ is -$L^7$-$R^{17}$;

$L^7$ is a bond, —O—, —N($R^{74}$)—, —C(O)—, —S—, —$S(O)_2$—, —S(O)—, —P(O)$R^{7d}$—, $CR^{7c}R^{7c}$, —$OCR^{7c}GR^{7c}$, —N($R^{7d}$)$CR^{7c}GR^{7c}$-, —C(O)$CR^{7c}CR^{7c}$—, —$SCR^{7c}CR^{7c}$—, —$S(O)_2CR^{7c}GR^{7c}$-, —S(O)$CR^{7c}CR^{7c}$—, —P(O)$R^{7d}CR^{7c}CR^{7c}$—, —$CR^{7c}CR^{7c}CR^{7c}CR^{7c}$, —$CR^{7c}CR^{7c}$CO—, —$CR^{7c}R^{7c}$N($R^{7d}$)—, —$CR^{7c}CR^{7c}$C, (O)—, —$CR^{7c}CR^{7c}$S—, —$CR^{7c}CR^{7c}S(O)_2$—, —$CR^{7c}CR^{7c}$S(O)—, —$CR^{7c}GR^{7c}$P(O)$R^{7d}$—, —N($R^{7d}$)C(O)—, —N($R^{7d}$) $S(O)_2$—, —N($R^{7d}$) S(O)—, —N($R^{7d}$) P(O)$R^{7d}$—, —C(O)N($R^{7d}$)—, —$S(O)_2$N($R^{7d}$)—, —S(O)N($R^{7d}$)—, —P(O)$R^{7c}$ON($R^{7d}$)—, —OC(O)—, —$OS(O)_2$—, —OS(O)—, —OP(O)$R^{7d}$—, —C(O)O—, —$S(O)_2$O—, —S(O)O—, or —P(O)$R^{7d}$O—;

$R^{17}$ is selected from $C_{3-12}$ carbocycle and 3- to 12-membered heterocycle, wherein $C_{3-12}$ carbocycle and 3- to 12-membered heterocycle are optionally substituted with one, two, or three $R^{20}$;

$W^8$ is C($R^8$), C($R^8$)($R^{8a}$), N, N($R^{8b}$), C(O), S(O), or $S(O)_2$;

$W^9$ is C($R^9$), C, or N;

$W^{10}$ is C($R^9$), C, or N;

each $R^9$ is independently selected from hydrogen, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{B4}$ is -$L^4$-$R^{4a}$;

$L^4$ is a bond, —O—, —N($R^{4d}$)—, —C(O)—, —S—, —$S(O)_2$—, —S(O)—, —P(O)$R^{4d}$—, $CR^{4c}R^{4c}$, —$OCR^{4c}R^{4c}$—, —N($R^{4d}$)$CR^{4c}R^{4c}$—, —C(O)$CR^{4c}R^{4c}$—, —$SCR^{4c}R^{4c}$—, —$S(O)_2CR^{4c}R^{4c}$—, —S(O)$CR^{4c}R^{4c}$—, —P(O)$R^{4d}CR^{4c}R^{4c}$—, —$CR^{4c}CR^{4c}CR^{4c}R^{4c}$, —$CR^{4c}R^{4c}$CO—, —$CR^{4c}R^{4c}$CN ($R^{4d}$)—, —$CR^{4c}R^{4c}$C(O)—, —$CR^{4c}R^{4c}$S—, —$CR^{4c}R^{4c}S(O)_2$—, —$CR^{4c}R^{4c}$S(O)—, —$CR^{4c}GR^{4c}$P(O)$R^{4d}$—, —N($R^{4d}$)C(O)—, —$N(R^{4d})$ $S(O)_2$—, —$N(R^{4d})$ $S(O)$—, —$N(R^{4d})$ $P(O)R^{4d}$—, —$C(O)N(R^{4d})$—, —$S(O)_2N(R^{4d})$—, —$S(O)N(R^{4d})$—, —$P(O)R^{4d}ON(R^{4d})$—, —$OC(O)$—, —$OS(O)_2$—, —$OS(O)$—, —$OP(O)R^{4d}$—, —$C(O)O$—, —$S(O)_2O$—, —$S(O)O$—, or —$P(O)R^{4d}O$—;

each $R^{4a}$ is independently selected from $C_{3-12}$ carbocycle and 3- to 12-membered heterocycle, wherein $C_{3-12}$ carbocycle and 3- to 12-membered heterocycle are optionally substituted with one, two, three, or four $R^{4b}$;

each $R^{4b}$ and $R^{11d}$ is independently selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, =$NR^{12}$, —$SF_5$, —N—$OR^{12}$, =N—$N(R^{12})(R^{13})$, —$P(O)(R^{12})(R^{13})$, —ON=$R^{12}$, =$C(R^{14})_2$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})$ $S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$OCH_2C(O)OR^{12}$, —($C_{1-6}$alkyl)-$C(O)N(R^{12})(R^{13})$, —($C_{1-6}$alkyl)-$OC(O)R^{12}$, —($C_{1-6}$alkyl)-$N(R^{12})C(O)R^{12}$, —($C_{1-6}$alkyl)-$N(R^{12})(R^{13})$, —($C_{1-6}$alkyl)-$S(O)_2R^{12}$, and —($C_{1-6}$alkyl)-$S(O)_2N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, three, four, or five $R^{20}$;

each $R^{11c}$ is independently selected from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$OR^{15}$, —O—($C_{1-6}$ alkyl)-$OR^{15}$, —$SR^{12}$, =$NR^{12}$, —$SF_5$, =N—$OR^{12}$, =N—$N(R^{12})(R^{13})$, —$P(O)(R^{12})(R^{13})$, —ON=$R^{12}$, =$C(R^{14})_2$, —N $(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})$ $S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$OCH_2C(O)OR^{12}$, —($C_{1-6}$alkyl)-$C(O)N(R^{12})(R^{13})$, —($C_{1-6}$alkyl)-$OC(O)R^{12}$, —($C_{1-6}$alkyl)-$N(R^{12})C(O)R^{12}$, —($C_{1-6}$ alkyl)-$N(R^{12})(R^{13})$, —($C_{1-6}$alkyl)-$S(O)_2R^{12}$, and —($C_{1-6}$alkyl)-$S(O)_2N(R^{12})(R^{13})$, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, three, four, or five $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)OR^{12}$, —$C(O)R^{12}$, —P(O)(Y—$R^{16}$)(Z—$R^{17}$), and —$CH_2P(O)$(Y—$R^{16}$)(Z—$R^{17}$);

Y and Z are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —N $(R^{12})C(O)OR^{12}$, —$N(R^{12})$ $S(O)_2R^{12}$, —$N(R^{12})$ $S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, —O, —S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$SF_5$, =N—$OR^{22}$, —N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})$ $S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$—, —$S(O)(NR^{22})N(R^{22})(R^{23})$, —$OCH_2C(O)OR^{22}$; —$OR^{25}$, —O—($C_{1-6}$ alkyl)-$OR^{25}$, —NH($C_{1-6}$ alkyl)-$OR^{25}$, —NHC(O)O—($C_{1-6}$ alkyl)-$OR^{25}$, (5-methyl-2-oxo-1,3-dioxol-4-yl)methyl-NH—, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$SF_5$, =N—$OR^{22}$, =N—$N(R^{22})(R^{23})$, —$P(O)(R^{22})(R^{23})$, —ON=$R^{22}$, —$C(O)OR^{22}$, —$OC(O)N(R^{22})(R^{23})$, —$N(R^{22})C(O)N(R^{22})(R^{23})$, —N $(R^{22})C(O)OR^{22}$, —$N(R^{22})$ $S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$OS(O)_2R^{22}$, —$S(O)_2R^{22}$, —$S(O)(NR^{22})R^{22}$, —$S(O)_2N(R^{22})(R^{23})$, and —$S(O)(NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle); and $R^{23}$ is independently selected at each occurrence from hydrogen and $C_{1-6}$ alkyl; or $R^{22}$ and $R^{23}$ attached to the same nitrogen atom form 3- to 10 membered heterocycle.

$R^{25}$ is independently selected at each occurrence from (5-methyl-2-oxo-1,3-dioxol-4-yl)methyl, —$C(O)OR^{12}$, —$C(O)R^{12}$, —$P(O)(Y—R^{16})(Z—R^{17})$, and —$CH_2P(O)(Y—R^{16})(Z—R^{17})$; ------ indicates a single or double bond such that all valences are satisfied.

Embodiments disclosed herein that refer to a compound of Formula (I), (II), (II-a), (III), (IV), (V), or (VI) are also intended to apply to a compound of Formula (A). If any provision of an embodiment that refers to a compound of Formula (I), (II), (II-a), (III), (IV), (V), or (VI) recites a substituent or variable not depicted in the compound of Formula (A), then the remainder of said embodiment shall be considered severable and not affected by the missing substituent or variable.

Methods

The compounds described herein, or a pharmaceutically acceptable salt or solvate thereof, are Ras inhibitors capable of inhibiting a Ras protein, such as wild-type Ras or a Ras mutant protein (e.g., G12S, G12C, G12D, G12V, G13C, and/or G13D) from K-Ras, H-Ras or N-Ras. Compounds, including pharmaceutically acceptable salts or solvates thereof, disclosed herein have a wide range of applications in therapeutics, diagnostics, and other biomedical research.

In certain aspects, the present disclosure provides a method of treating cancer in a subject in need thereof, comprising administering to the subject a therapeutically effective amount of a compound described herein, or a pharmaceutically acceptable salt or solvate thereof.

In certain aspects, the present disclosure provides a method of treating a cancer comprising amplified wildtype Ras or a Ras mutant (e.g., G12S, G12C, G12D, G12V, G13C, and/or G13D) protein in a subject, comprising inhibiting amplified wildtype Ras or the Ras mutant protein of said subject by administering to said subject a compound, wherein the compound is characterized in that upon contacting the Ras protein, the Ras protein activity or function is inhibited (e.g., partially inhibited or completely inhibited), such that said inhibited Ras protein exhibits reduced Ras signaling output (e.g., compared to a corresponding Ras protein not contacted by the compound).

In certain aspects, the present disclosure provides a method of modulating activity of a Ras protein (e.g., K-Ras, mutant K-Ras, K-Ras G12S, K-Ras G12C, K-Ras G12D, K-Ras G12V, K-Ras G13C, and/or K-Ras G13D), comprising contacting a Ras protein with an effective amount of a compound described herein, or a pharmaceutically acceptable salt or solvate thereof, thereby modulating the activity of the Ras protein.

In certain aspects, the present disclosure provides a method of inhibiting cell growth, comprising administering an effective amount of a compound described herein, or a pharmaceutically acceptable salt or solvate thereof, to a cell expressing a Ras (e.g., K-Ras) protein, thereby inhibiting growth of said cells. In some embodiments, the subject method comprises administering an additional agent to said cell.

In certain aspects, the present disclosure provides a method of treating a disease mediated at least in part by a Ras protein, such as K-Ras or a mutant thereof, in a subject in need thereof, comprising administering to the subject an effective amount of a compound disclosed herein, or a pharmaceutically acceptable salt or solvate thereof. In some embodiments, the disease is cancer, such as a solid tumor or a hematological cancer. In some embodiments, the method further comprises administering an additional agent to the subject, such as a SHP2 inhibitor, a SOS inhibitor, an EGFR inhibitor, a MEK inhibitor, an ERK inhibitor, a CDK4/6 inhibitor, a BRAF inhibitor, or a combination thereof.

In certain aspects, the present disclosure provides a method of inhibiting activity of a Ras protein, such as K-Ras or a mutant thereof, comprising contacting the Ras protein with a compound disclosed herein, or a pharmaceutically acceptable salt or solvate thereof. In some embodiments, the compound exhibits an IC50 against the Ras protein of less than 10 μM, such as less than 5 μM, 1 μM, 500 nM, 100 nM, 50 nM, 10 nM, 5 nM, 1 nM, 500 μM, 50 μM, 10 μM or less.

In certain aspects, the present disclosure provides a method of treating a Ras-mediated cancer in a subject in need thereof, comprising administering to the subject a SHP2 inhibitor, a SOS inhibitor, an EGFR inhibitor, a MEK inhibitor, an ERK inhibitor, a CDK4/6 inhibitor, or a BRAF inhibitor and an effective amount of a compound disclosed herein, such as a compound of Formula (I), (II), (II-a), (III), (IV), (V), (Va), (Vb), (Vc), (VI), (VII), (VIII), (IX), (X), (XI), or (XII), or embodiments thereof, or a pharmaceutically acceptable salt or solvate thereof. In some embodiments, the cancer is a solid tumor. In some embodiments, the cancer is a hematological cancer.

In practicing any of the methods disclosed herein, the Ras target to which a subject compound binds, either covalently or reversibly, can be a Ras mutant (e.g., G12S, G12C, G12D, G12V, G13C, and/or G13D), including a mutant of K-Ras, H-Ras, or N-Ras. In some embodiments, the methods of treating cancer can be applied to treat a solid tumor or a hematological cancer. In some embodiments, the cancer being treated can be, without limitation, prostate cancer, brain cancer, colon cancer, rectal cancer, renal-cell carcinoma, liver cancer, various lung cancers including non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer. In some embodiments is a method of treating cancer in a subject in need thereof, comprising administering to the subject a therapeutically effective amount of a compound described herein, or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound described herein, or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, or (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiments, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof. In one embodiment, a subject treatment method is combined with a chemotherapeutic agent.

Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present disclosure include: anthracyclines; alkylating agents; antimetabolites; drugs that inhibit either the calcium dependent phosphatase calcineurin or the p70S6 kinase FK506 or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors: methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes: uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In certain aspects, compositions provided herein can be administered in combination with radiotherapy, such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-$L^1$, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-$L^1$ antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab, cemiplimab), anti-LAG3 antibodies (e.g., C9B7W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-$L^1$ antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldesleukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, a compound described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, is administered in combination or in conjunction with one or more pharmacologically active agents selected from (1) an inhibitor of MEK (e.g., MEK1, MEK2) or of mutants thereof (e.g., trametinib, cobimetinib, binimetinib, selumetinib, refametinib, AZD6244); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or FGFR4 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120, sorafenib, vemurafenib, dabrafenib, encorafenib, regorafenib, GDC-879); (19) an inhibitor of ERK and/or of mutants thereof (e.g., ulixertinib, MK-8353, LTT462, AZD0364, SCH772984, BIX02189, LY3214996, ravoxertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor, as well as SHIP1 inhibitors; (27) an inhibitor of SRC (e.g., dasatinib); (28) an inhibitor of JAK (e.g. tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of Src, FLT3, HDAC, VEGFR, PDGFR, LCK, Bcr-Abl or AKT, (33) an inhibitor of KRAS G12C mutant (e.g., including but not limited to AMG510, MRTX849, and any covalent inhibitors binding to the cysteine residue 12 of KRAS, the structures of which are publicly known)(e.g., an inhibitor of Ras G12C as described in US20180334454, US20190144444, US20150239900, U.S. Pat. No. 10,246,424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety), (34) an SHC inhibitor (e.g., PP2, AID371185), (35) a GAB inhibitor (e.g., GAB-0001), (36) a GRB inhibitor, (37) a PI-3 kinase inhibitor (e.g., idelalisib, copanlisib, duvelisib, alpelisib, taselisib, perifosine, buparlisib, umbralisib, NVP-BEZ235-AN), (38) a MARPK inhibitor, (39) a CDK4/6 inhibitor (e.g., palbociclib, ribociclib, abemaciclib), (40) a MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (41) a SHP pathway inhibitor, such as a SHP2 inhibitor (e.g., RMC-4630, ERAS-601,

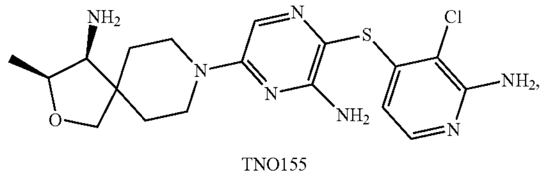

TNO155

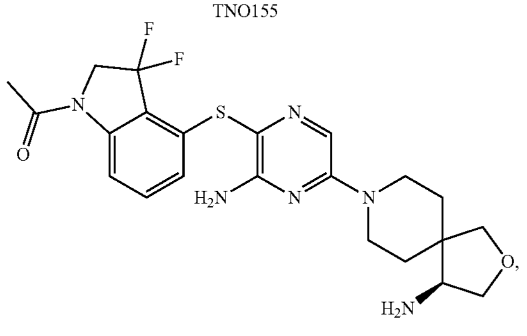

JAB-3068

-continued

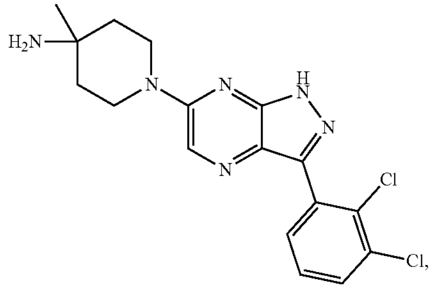

IACS-13909/BBP-398

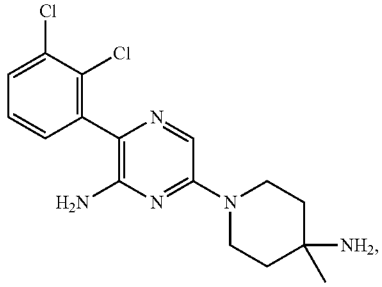

and

SHP099

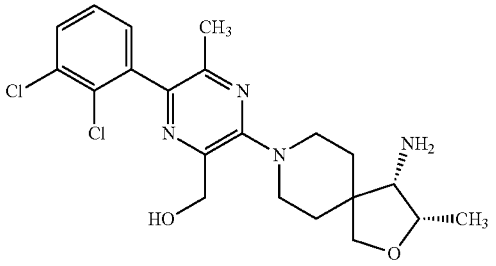

RMC-4550 )

or a SHP1 inhibitor. In some embodiments, a Ras inhibitor described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, is administered in combination or in conjunction with one or more checkpoint immune blockade agents (e.g., anti-PD-1 and/or anti-PD-L[1] antibody, anti-CLTA-4 antibody). In some embodiments, a Ras inhibitor described herein, such as a compound, salt, or solvate of Formula (I), (II), (II-a), (III), or (IV), is administered in combination or in conjunction with one or more pharmacologically active agents comprising an inhibitor against one or more targets selected from: MEK, epidermal growth factor receptor (EGFR), FGFR1, FGFR2, FGFR3, mitotic kinase, topoisomerase, ALK, ALK5, c-MET, ErbB2, AXL, NTRK1, RET, A-Raf, B-Raf, C-Raf, ERK, MDM2, mTOR, BET, IGF1/2, IGF1-R, CDK9, SHIP1, SHIP2, SHP2, SRC, JAK, PARP, BTK, FLT3, HDAC, VEGFR, PDGFR, LCK, Bcr-Abl, AKT, KRAS G12C mutant, and ROS1. In some embodiments, a Ras inhibitor described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, is administered in combination or in conjunction with one or more additional pharmacologically active agents comprising an inhibitor of SOS (e.g., SOS1, SOS2) or of mutants thereof, such as

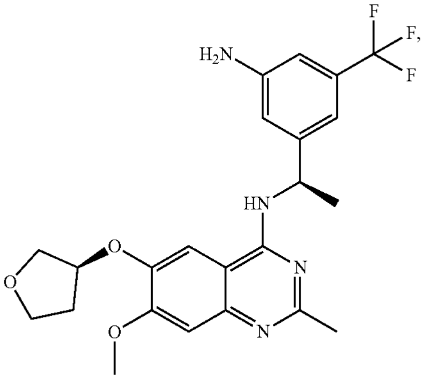

BI-3406

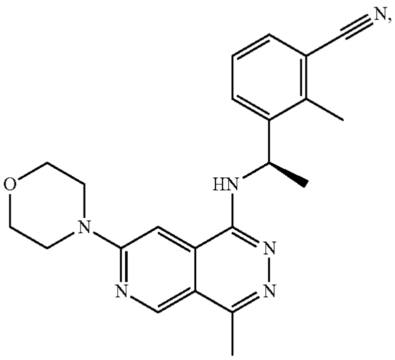

and

MRTX0902

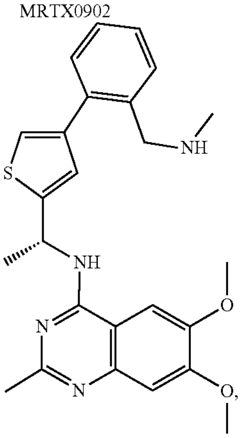

BAY 293

RMC-5845, or BI-1701963. In some embodiments, a Ras inhibitor described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, is administered in combination or in conjunction with an inhibitor of SOS described in WO2021092115, WO2018172250, WO2019201848, WO2019122129, WO2018115380, WO2021127429, WO2020180768, or WO2020180770, each of which is herein incorporated by reference in its entirety for all purposes.

In some embodiments, a Ras inhibitor described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, is administered in combination or in conjunction with one or more checkpoint immune blockade agents (e.g., anti-PD-1 and/or anti-PD-L1 antibody, anti-CLTA-4 antibody).

In some embodiments, a compound described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, and one or more pharmacologically active agents are administered either simultaneously, concurrently or sequentially with no specific time limits, wherein such administration provides therapeutically effective levels of the two or more compounds in the body of the patient.

In some embodiments, a compound described herein, such as a compound, salt, or solvate of Formula (I), (II), (II-a), (III), (IV), (V), (Va), (Vb), (Vc), (VI), (VII), (VIII), (IX), (X), (XI), or (XII), or embodiments thereof, and one or more pharmacologically active agents are administered sequentially in any order by a suitable route, such as infusion or orally. The dosing regimen may vary depending upon the stage of the disease, physical fitness of the patient, safety profiles of the individual drugs, and tolerance of the individual drugs, as well as other criteria known to the attending physician and medical practitioner(s) administering the combination. The compound of the present disclosure and other pharmacologically active agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In some cases, a treatment regime may be dosed according to a body weight of a subject. In subjects who are determined obese (BMI>35) a practical weight may need to be utilized. BMI is calculated by: BMI=weight (kg)/[height (m)]$^2$. Body weight may be calculated for men as 50 kg+2.3*(number of inches over 60 inches) or for women 45.5 kg+2.3*(number of inches over 60 inches). An adjusted body weight may be calculated for subjects who are more than 20% of their ideal body weight. An adjusted body weight may be the sum of an ideal body weight+(0.4*(Actual body weight-ideal body weight)). In some cases, a body surface area may be utilized to calculate a dosage. A body surface area (BSA) may be calculated by: BSA (m$^2$)=√Height (cm)*Weight (kg)/3600.

In certain aspects, the present disclosure provides a method of modulating activity of a Ras (e.g., K-Ras) protein, comprising contacting a Ras protein with an effective amount of a compound described herein, or a pharmaceutically acceptable salt or solvate thereof, thereby modulating the activity of the Ras (e.g., K-Ras) protein. In some embodiments, the subject method comprises administering an additional agent or therapy.

In certain aspects, the present disclosure provides a method of modulating activity of a Ras protein, comprising contacting a Ras protein with an effective amount of a compound described, or a pharmaceutically acceptable salt or solvate thereof, wherein said modulating comprises inhibiting the Ras (e.g., K-Ras) protein activity. In certain aspects, the present disclosure provides a method of modulating activity of a Ras protein, such as Ras mutant (e.g., G12S, G12C, G12D, G12V, G13C, and/or G13D) proteins of K-Ras, H-Ras, and N-Ras, comprising contacting the Ras protein with an effective amount of a compound described herein, or a pharmaceutically acceptable salt or solvate thereof.

In certain aspects, the present disclosure provides a method of reducing Ras signaling output in a cell by contacting the cell with a compound described herein. A reduction in Ras signaling can be evidenced by one or more of the following: (i) an increase in steady state level of GDP-bound modified protein; (ii) a reduction in steady state level of GTP-bound Ras protein; (iii) a reduction of phosphorylated AKTs473, (iv) a reduction of phosphorylated ERKT202/y204, (v) a reduction of phosphorylated S6S235/236, (vi) a reduction of cell growth of a tumor cell expressing a Ras mutant (e.g., G12S, G12C, G12D, G12V, G13C, and/or G13D) protein, and (vii) a reduction in Ras interaction with a Ras-pathway signaling protein. Non-limiting examples of Ras-pathway signaling proteins include SOS (including SOS1 and SOS2), RAF, SHC, SHP (including SHP1 and SHP2), MEK, MAPK, ERK, GRB, RASA1, and GNAQ. In some embodiments, the reduction in Ras signaling output can be evidenced by two, three, four, five, six, or all of (i)-(vii) above. In some embodiments, the reduction of any one or more of (i)-(vii) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to a control not treated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine, colon), endometrium, stomach, hematopoietic tissue (e.g., lymphoid tissue), etc. Examples of tumor cell lines comprising a K-Ras mutation include, but are not limited to, A549 (e.g., K-Ras G12S), AGS (e.g., K-Ras G12D), ASPC1 (e.g., K-Ras G12D), Calu-6 (e.g., K-Ras Q61K), CFPAC-1 (e.g., K-Ras G12V), CL40 (e.g., K-Ras G12D), COLO678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HECIA (e.g., K-Ras G12D), HEC1B (e.g., K-Ras G12F), HEC50B (e.g., K-Ras G12F), HEYA8 (e.g., K-Ras G12D or G13D), HPAC (e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS (e.g., K-Ras G12D), NB4 (e.g., K-Ras A$^{18}$D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK—CO-1 (e.g., K-Ras G12V), SKLU1 (e.g., K-Ras G12D), SKM-1 (e.g., K-Ras K117N), SNU1 (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-C2A (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras Q61L), T3M10 (e.g., K-Ras G12D), TCC-PAN2 (e.g., K-Ras G12R), TGBC11TKB (e.g., K-Ras G12D), and MIA Pa—Ca (e.g., MIA Pa—Ca 2 (e.g., K-Ras G12C)).

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

In some embodiments, a compound described herein, or a pharmaceutically acceptable salt or solvate thereof, is administered to a subject in a biologically compatible form suitable for administration to treat or prevent diseases, disorders, or conditions. Administration of a compound described herein can be in any pharmacological form including a therapeutically effective amount of a compound described herein, or a pharmaceutically acceptable salt or solvate thereof, alone or in combination with a pharmaceutically acceptable carrier.

In some embodiments, a compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s)(or carrier(s)) is acceptable or suitable if the excipient is compatible with the other ingredients of the composition and not deleterious to the recipient (i.e., the subject) of the composition.

In some embodiments of the methods described herein, a compound described herein is administered either alone or in combination with pharmaceutically acceptable carriers, excipients or diluents, in a pharmaceutical composition. Administration of a compound or composition described herein can be affected by any method that enables delivery of the compound to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, a compound described herein can be administered locally to the area in need of treatment, by, for example, local infusion during surgery, topical application such as creams or ointments, injection, catheter, or implant. The administration can also be by direct injection at the site of a diseased tissue or organ. In some embodiments, a compound described herein, or a pharmaceutically acceptable salt or solvate thereof, is administered orally.

In some embodiments of the methods described herein, a pharmaceutical composition suitable for oral administration is presented as a discrete unit such as a capsule, cachet or tablet, each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary, or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compound which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

EXAMPLES

The following examples are provided for illustrative purposes only and not to limit the scope of the claims provided herein. Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or 1H-NMR spectroscopy. For NMR measurement, samples were dissolved in deuterated solvent ($CD_3OD$, $CDCl_3$, or DMSO-$d_6$).

Example 1a: Synthesis of 2-amino-4-(4-(1-(2-aminopyridin-3-yl)-3,3-difluoropropyl)-8-chloro-10-fluoro-2-(((2R,7aS)-2-fluorotetrahydro-1H-pyrrolizin-7a(5H)-yl)methoxy)-5,6-dihydro-4H-[1,4]oxazepino[5,6,7-de]quinazolin-9-yl)-7-fluorobenzo[b]thiophene-3-carbonitrile (776).

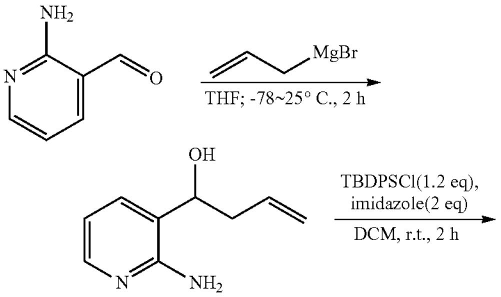

-continued

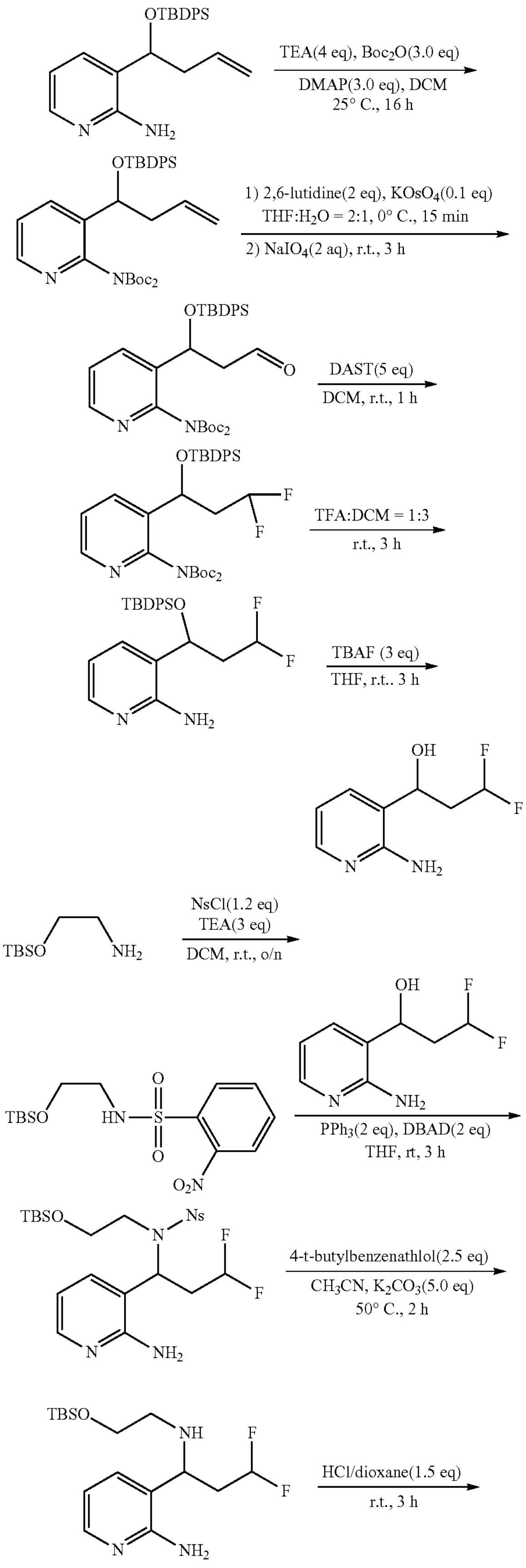

-continued

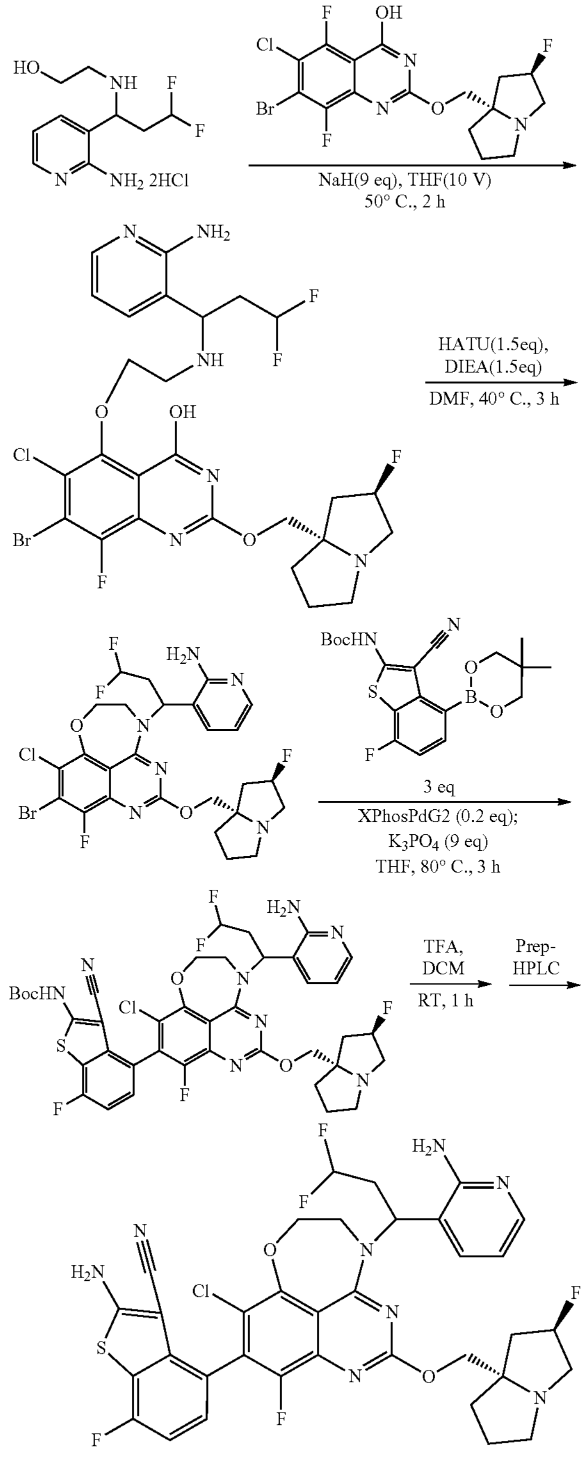

Step A: Synthesis of 1-(2-aminopyridin-3-yl) but-3-en-1-ol. To a solution of 2-aminopyridine-3-carbaldehyde (10 g, 81.882 mmol) in THF (100 mL) was added allylmagnesium bromide (35.69 g, 245.646 mmol) slowly at −78° C. The mixture was stirred at 25° C. for 2 hours, quenched with sat. $NH_4Cl$ (200 mL), and extracted with EtOAc (200 mL×2). The combined organic phase was washed with brine (200 mL) and dried over $Na_2SO_4$. The product was filtered and the filtrate was concentrated in vacuo. The resulting residue was purified by silica gel column chromatography (EA in PE from 0% to 100%) to give the desired product as a colorless oil. (ESI, m/z): 165 $[M+H]^+$.

Step B: Synthesis of 3-(1-((tert-butyldiphenylsilyl)oxy) but-3-en-1-yl) pyridin-2-amine. To a solution of 1-(2-aminopyridin-3-yl) but-3-en-1-ol (10.8 g, 65.770 mmol) in dichloromethane (200 mL) was added imidazole (8.96 g, 131.540 mmol) and TBDPSCl (21.69 g, 78.924 mmol). The mixture was stirred at 25° C. for 2 hours. Water (100 mL) was added slowly and the mixture was extracted with dichloromethane (200 mL×2). The combined organic phase was washed with brine (200 mL), dried with over $Na_2SO_4$, and concentrated in vacuo. The resulting residue was purified by silica gel column chromatography (ethyl acetate in petroleum ether from 0% to 50%) to give the desired product as a colorless oil. (ESI, m/z): 403 $[M+H]^+$.

Step C: Synthesis of di-tert-butyl (3-(1-((tert-butyldiphenylsilyl)oxy) but-3-en-1-yl) pyridin-2-yl)imidodicarbonate. To a solution of 3-[1-((2-[(tert-butyldimethylsilyl)oxy]ethylamino) but-3-en-1-yl]pyridin-2-amine (6 g, 18.660 mmol) in dichloromethane (60.0 mL) were added $Boc_2O$ (12.22 g, 55.980 mmol), TEA (7.55 g, 74.640 mmol) and DMAP (6.84 g, 55.980 mmol). The mixture was stirred at 25° C. for 16 hours, quenched with water (100 mL), and extracted with dichloromethane (100 mL×2). The combined organic phase was washed with brine (100 mL), dried with over $Na_2SO_4$, and concentrated in vacuo. The resulting residue was purified by silica gel column chromatography (ethyl acetate in petroleum ether from 0% to 20%) to give the desired product as a colorless oil. (ESI, m/z): 603 $[M+H]^+$.

Step D: Synthesis of di-tert-butyl (3-(1-((tert-butyldiphenylsilyl)oxy)-3-oxopropyl)pyridin-2-yl)iminodicarbonate. To a mixture of tert-butyl N-(tert-butoxycarbonyl)-N-(3-(1-[(tert-butyldiphenylsilyl)oxy]but-3-en-1-ylpyridin-2-yl)carbamate (12 g, 19.906 mmol) and 2,6-lutidine (4266.0 mg, 39.812 mmol) in dioxane (120.0 mL) and $H_2O$ (60.0 mL) at 0° C. was added $K_2OsO_4·2H_2O$ (733.42 mg, 1.991 mmol) in portions. The mixture was stirred for 15 minutes at 0° C. and $NaIO_4$ (8.52 g, 39.812 mmol) was added in portions. The reaction was stirred at room temperature for 3 hours, then cooled to 0° C. and treated with saturated aqueous $Na_2SO_3$ (50 mL). The mixture was extracted with EtOAc (3×100 mL). The combined organic layers were washed with 2M HCl, dried over anhydrous $Na_2SO_4$, and filtered. The filtrate was concentrated under reduced pressure to give the desired product as an oil. (ESI, m/z): 605 $[M+H]^+$.

Step E: Synthesis of di-tert-butyl (3-(1-((tert-butyldiphenylsilyl)oxy)-3,3-difluoropropyl)pyridin-2-yl)iminodicarbonate. To a solution of tert-butyl N-(tert-butoxycarbonyl)-N-(3-(1-[(tert-butyldiphenylsilyl)oxy]-3-oxopropylpyridin-2-yl)carbamate (10 g, 16.534 mmol) in dichloromethane (100.0 mL) was added DAST (13.33 g, 82.670 mmol) dropwise. The mixture was stirred at 25° C. for 1 hour, treated with water (200 mL), and extracted with dichloromethane (200 mL×2). The combined organic phase was washed with brine (200 mL), dried over $Na_2SO_4$, and concentrated in vacuo. The resulting residue was purified by silica gel column chromatography (ethyl acetate in petroleum ether from 0% to 20%) to give the desired product as a colorless oil. (ESI, m/z): 627 $[M+H]^+$.

Step F: Synthesis of 3-(1-((tert-butyldiphenylsilyl)oxy)-3,3-difluoropropyl)pyridin-2-amine. To a solution of tert-butyl N-(tert-butoxycarbonyl)-N-(3-(1-[(tert-butyldiphenylsilyl)oxy]-3,3-difluoropropylpyridin-2-yl)carbamate (10 g, 15.954 mmol) in dichloromethane (90 mL) was added TFA (30 mL). The mixture was stirred at 25° C. for 3 hours, then treated with sat $NaHCO_3$ to adjust the pH to 8~9. The mixture was extracted with dichloromethane, washed with brine, and dried over sodium sulfate. The product was then filtered and the filtrate was concentrated. The resulting residue was purified by silica gel column chromatography (ethyl acetate in petroleum ether from 0% to 100%) to give the desired product as a yellow oil. (ESI, m/z): 427 $[M+H]^+$.

Step G: Synthesis of 1-(2-aminopyridin-3-yl)-3,3-difluoropropan-1-ol. To a solution of 3-(1-[(tert-butyldiphenylsilyl)oxy]-3,3-difluoropropylpyridin-2-amine (6.4 g, 15.003 mmol) in THF (64.0 mL) was added TBAF (11.77 g, 45.009 mmol) and the mixture was stirred at 25° C. for 3 hours. The product was then concentrated to give a residue. The residue was purified by silica gel column chromatography (ethyl acetate in petroleum ether from 0% to 100%) to give the desired product as a light yellow solid. (ESI, m/z): 189 $[M+H]^+$.

Step H: Synthesis of N-(2-((tert-butyldimethylsilyl)oxy)ethyl)-2-nitrobenzenesulfonamide. A solution of (2-aminoethoxy)(tert-butyl)dimethylsilane (10 g, 57.030 mmol), 4-nitrobenzene-1-sulfonyl chloride (15.17 g, 68.436 mmol) and TEA (17.31 g, 171.090 mmol) in DCM (150 mL) was stirred overnight at room temperature under nitrogen atmosphere. The resulting mixture was extracted with EtOAc (3×200 mL). The combined organic layers were washed with brine (1×200 mL) and dried over anhydrous $Na_2SO_4$. After filtration, the filtrate was concentrated under reduced pressure. The resulting residue was purified by silica gel column chromatography and eluted with petroleum ether/ethyl acetate (3:1) to afford the desired product as a light solid. (ESI, m/z): 361 $[M+H]^+$.

Step I: Synthesis of N-(1-(2-aminopyridin-3-yl)-3,3-difluoropropyl)-N-(2-((tert-butyldimethylsilyl)oxy)ethyl)-4-nitrobenzenesulfonamide. To a solution of N-(2-[(tert-butyldimethylsilyl)oxy]ethyl-2-nitrobenzenesulfonamide (4.98 g, 13.816 mmol) in THF (52.0 mL) were added 1-(2-aminopyridin-3-yl)-3,3-difluoropropan-1-ol (1.3 g, 6.908 mmol) and $PPh_3$ (3.62 g, 13.816 mmol), followed by the addition of DBAD (3.18 g, 13.816 mmol). The mixture was stirred at 25° C. for 3 hours, slowly treated with water (100 mL), and extracted with dichloromethane (100 mL×2). The combined organic phase was washed with brine (100 mL), dried with over $Na_2SO_4$, and concentrated in vacuo. The resulting residue was purified by silica gel column chromatography (ethyl acetate in petroleum ether from 0% to 35%) to give the desired product as a colorless oil. (ESI, m/z): 531 $[M+H]^+$.

Step J: Synthesis of 3-(1-((2-((tert-butyldimethylsilyl)oxy)ethyl)amino)-3,3-difluoropropyl)pyridin-2-amine. To a solution of N-[1-(2-aminopyridin-3-yl)-3,3-difluoropropyl]-N-(2-[(tert-butyldimethylsilyl)oxy]ethyl-4-nitrobenzenesulfonamide (680 mg, 1.281 mmol) in $CH_3CN$ (13.6 mL) were added 4-tert-butylbenzene-1-thiol (0.53 g, 3.202 mmol) and $K_2CO_3$ (0.89 g, 6.405 mmol). The mixture was stirred at 50° C. for 2 hours and cooled to room temperature. The mixture was slowly treated with water (100 mL) and extracted with dichloromethane (100 mL×2). The combined organic phase was washed with brine (100 mL), dried with over $Na_2SO_4$, and concentrated in vacuo. The resulting residue was purified by silica gel column chromatography (ethyl acetate in petroleum ether from 0% to 100%) to give the desired product as a colorless oil. (ESI, m/z): 346 $[M+H]^+$.

Step K: To a mixture of 3-difluoropropyl]pyridin-2-amine (420 mg, 1.216 mmol) in dioxane (4.2 mL) was added HCl in 1,4-dioxane (4M, 4.2 mL). The mixture was stirred at 25° C. for 3 hours, then concentrated in vacuo to give the desired product as a white solid: (ESI, m/z): 232 $[M+H]^+$.

Step L: Synthesis of 5-(2-((1-(2-aminopyridin-3-yl)-3,3-difluoropropyl)amino) ethoxy)-7-bromo-6-chloro-8-fluoro-2-(((2R,7aS)-2-fluorotetrahydro-1H-pyrrolizin-7a (5H)-yl) methoxy) quinazolin-4-ol. To a solution of 2-([1-(2-aminopyridin-3-yl)-3,3-difluoropropyl]aminoethanol (0.35 g, 1.514 mmol) in THF (14.0 mL) were added 2-([(2R,7aS)-2-fluoro-hexahydropyrrolizin-7a-yl]methoxy-7-bromo-6-chloro-5,8-difluoroquinazolin-4-ol (0.69 g, 1.514 mmol) and NaH (0.54 g, 13.626 mmol, 60%). The mixture was stirred at 50° C. for 2 hours and cooled to room temperature. The product was treated with water (100 mL) slowly and extracted with dichloromethane (100 mL×2). The combined organic phase was washed with brine (100 mL) and dried with over $Na_2SO_4$. The product was filtered and the filtrate was concentrated in vacuo to give the desired product a brown oil. (ESI, m/z): 663 $[M+H]^+$.

Step M: Synthesis of 3-(1-(9-bromo-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de]quinazolin-4-yl)-3,3-difluoropropyl)pyridin-2-amine. To a solution of 2-([(2R,7aS)-2-fluoro-hexahydropyrrolizin-7a-yl]methoxy-5-(2-([1-(2-aminopyridin-3-yl)-3,3-difluoropropyl]aminoethoxy)-7-bromo-6-chloro-8-fluoroquinazolin-4-ol (0.8 g, 1.205 mmol) in DMF (18 mL) was added HATU (0.69 g, 1.808 mmol) and DIPEA (0.23 g, 1.808 mmol). The mixture was stirred at 40° C. for 3 hours and cooled to room temperature. The product was slowly treated with water (100 mL) and extracted with dichloromethane (100 mL×2). The combined organic phase was washed with brine (100 mL), dried with over $Na_2SO_4$, and concentrated in vacuo. The resulting residue was purified by silica gel column chromatography (MeOH in dichloromethane from 0% to 10%) to give the desired product as a yellow solid. (ESI, m/z): 645 $[M+H]^+$.

Step N: Synthesis of tert-butyl (4-(4-(1-(2-aminopyridin-3-yl)-3,3-difluoropropyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate. To a solution of 3-(1-(9-bromo-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl)-3,3-difluoropropyl)pyridin-2-amine (165 mg, 0.255 mmol) in THF (1 mL) were added tert-butyl N-[3-cyano-4-(5,5-dimethyl-1,3,2-dioxaborinan-2-yl)-7-fluoro-1-benzothiophen-2-yl]carbamate (309.82 mg, 0.765 mmol), $K_3PO_4$ (488.04 mg, 2.295 mmol), and 2nd Generation XPhos Precatalyst (40.2 mg, 0.051 mmol). The mixture was stirred at 80° C. for 3 hours and cooled to room temperature. The mixture was slowly treated with water (100 mL) and extracted with dichloromethane (100 mL×2). The combined organic phase was washed with brine (100 mL), dried over $Na_2SO_4$, and concentrated in vacuo. The resulting residue was purified by silica gel column chromatography (MeOH in dichloromethane from 0% to 12%) to give the desired product as a light brown solid. (ESI, m/z): 857 $[M+H]^+$.

Step O: Synthesis of 2-amino-4 (4-(1-(2-aminopyridin-3-yl)-3,3-difluoropropyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile. To a solution of tert-butyl (4-(4-(1-(2-aminopyridin-3-yl)-3,3-difluoropropyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate (0.1 g, 0.117 mmol) in dichloromethane (3 mL) was added TFA (1 mL). The mixture was stirred at 25° C. for 1 hour and concentrated. The resulting residue was purified by Prep-HPLC(Column: Sunfire C18 5 m, 30 mm*150 mm; Mobile Phase A: Water (0.1% FA), Mobile Phase B: MeOH; Flow rate: 60 mL/min; Gradient: 25% B to 45% B in 10 min; Wave Length: UV 254 nm/220 nm; RT1 (min): 7.17/9.35) to give the desired product as a light yellow solid: (ESI, m/z): 757 $[M+H]^+$. $^1H$ NMR: (400 MHZ, DMSO-d6, ppm): δ 8.08 (s, 2H), 8.00 (dd, J=4.9, 1.7 Hz, 1H), 7.72 (dd, J=7.6, 1.8 Hz, 1H), 7.20 (dd, J=8.4, 5.3 Hz, 1H), 7.13 (dd, J=9.4, 8.4 Hz, 1H), 6.69 (dd, J=7.6, 4.9 Hz, 1H), 6.52 (dd, J=9.5, 5.2 Hz, 1H), 6.28-6.00 (m, 1H), 5.84 (d, J=6.3 Hz, 2H), 5.41 (d, J=53.6 Hz, 1H), 4.55-4.44 (m, 1H), 4.42-4.14 (m, 3H), 3.75 (dd, J=15.5, 6.4 Hz, 1H), 2.32-2.11 (m, 2H), 1.93 (s, 3H).

Example 1b: Synthesis of 2-amino-4-(4-(1-(2-aminopyridin-3-yl)ethyl)-8-chloro-10-fluoro-2-(((2R,7aS)-2-fluoro-tetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (656 and 850).

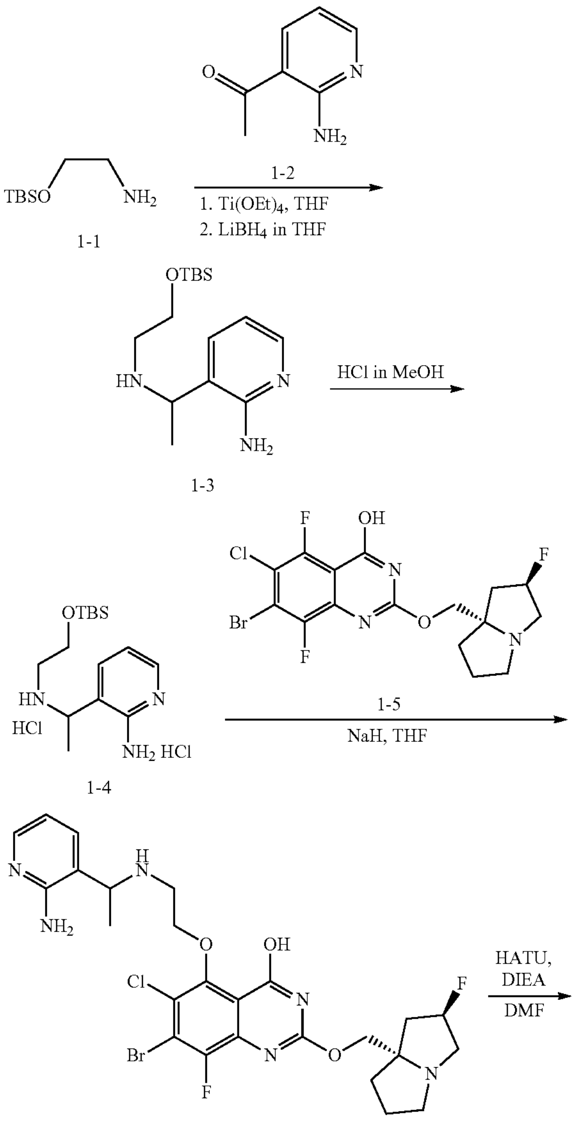

1-6

-continued

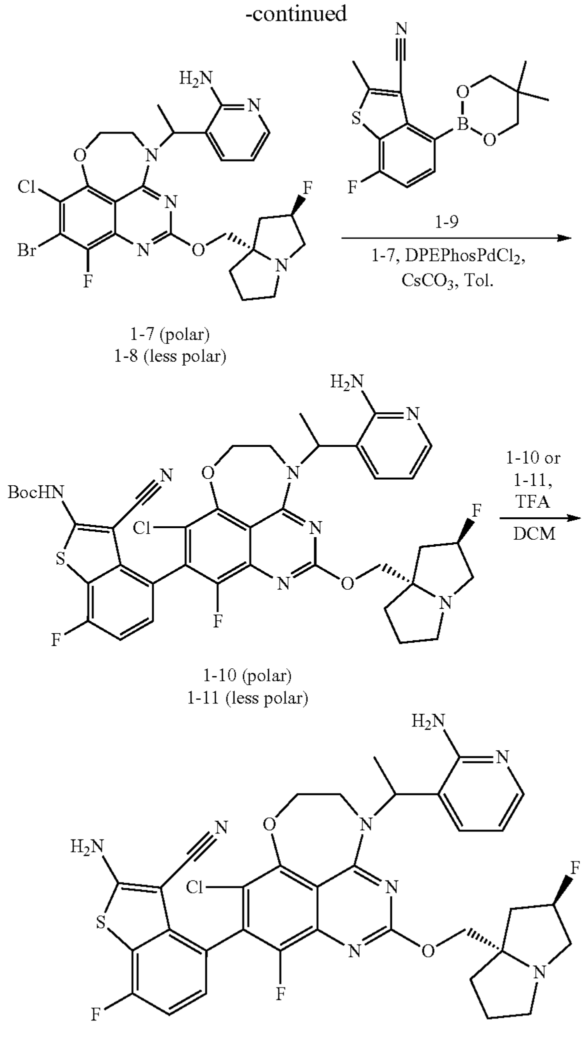

850 (polar)
656 (less polar)

Step A: Synthesis of 3-(1-((2-((tert-butyldimethylsilyl) oxy)ethyl)amino)ethyl) pyridin-2-amine (1-3). A solution of (2-aminoethoxy)(tert-butyl)dimethylsilane (1-1)(1.00 g, 5.7 mmol), 1-(2-aminopyridin-3-yl) ethanone (1-2)(0.85 g, 6.27 mmol) and $Ti(OEt)_4$ (10.41 g, 45.62 mmol) in THF (19 mL) was stirred overnight at 65° C. The reaction mixture was cooled to room temperature, then $LiBH_4$ in THF (5.69 mL, 11.38 mmol) was added and the resulting mixture stirred for 24 hours at 65° C. The reaction mixture was cooled to room temperature, quenched with water, filtered, and the filter cake was washed with ethyl acetate (3×10 mL). The filtrate was extracted with ethyl acetate (3×15 mL) and the combined organic layers were washed with brine (1×40 mL), dried over anhydrous $Na_2SO_4$, filtered, and concentrated under reduced pressure to give a residue. The residue was purified by silica gel column chromatography, eluting with petroleum ether/ethyl acetate (5:1) to afford the desired product as a yellow oil. (ESI, m/z): 296 $[M+H]^+$.

Step B: Synthesis of 2-((1-(2-aminopyridin-3-yl)ethyl) amino) ethan-1-ol dihydrochloride (1-4). A solution of 1-3 (578 mg, 1.95 mmol) and HCl in MeOH (5.8 mL) was stirred for 3 hours at room temperature. The resulting mixture was concentrated under reduced pressure to afford the desired product as an off-white solid. (ESI, m/z): 182 $[M+H]^+$.

Step C: Synthesis of 5-(2-((1-(2-aminopyridin-3-yl)ethyl) amino) ethoxy)-7-bromo-6-chloro-8-fluoro-2-(((2R,7aS)-2-fluorotetrahydro-1H-pyrrolizin-7a (5H)-yl)methoxy) quinazolin-4-ol (1-6). To a stirred solution of 1-4 (486 mg, 1.91 mmol) and 2-([(2R,7aS)-2-fluoro-hexahydropyrrolizin-7a-yl]methoxy)-7-bromo-6-chloro-5,8-difluoroquinazolin-4-ol (1-5)(606 mg, 1.33 mmol) in THF (10 mL) was added NaH (688 mg, 17.20 mmol, 60%) at 0° C. under nitrogen atmosphere. The resulting mixture was stirred for 2 hours at room temperature, then quenched with sat. $NH_4Cl$ (aq.) at 0° C. and extracted with ethyl acetate (3×20 mL). The combined organic layers were washed with brine (1×40 mL), dried over anhydrous $Na_2SO_4$, filtered, and concentrated under reduced pressure to give a residue. The residue was purified by reverse-phase flash chromatography (column, C18; mobile phase, MeCN in water (10 mmol/L $NH_4HCO_3$), 20% to 60% gradient in 20 min; detector, UV 254 nm) to give the desired product as a yellow solid. (ESI, m/z): 613 $[M+H]^+$.

Step D: Synthesis of 3-(1-(9-bromo-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de]quinazolin-4-yl)ethyl) pyridin-2-amine (1-7 and 1-8). A solution of 1-6 (250 mg, 0.4 mmol), HATU (464 mg, 1.22 mmol) and DIEA (78 mg, 0.61 mmol) in DMF (6 mL) was stirred for 2 hours at 40° C., then concentrated under reduced pressure to give a residue. The residue was purified by reverse-phase flash chromatography (column, C18; mobile phase, MeCN in water (10 mmol/L $NH_4HCO_3$), 30% to 90% gradient in 20 min). The product (235.0 mg) was purified by chiral prep-HPLC (Column: CHIRALPAK IA, 2*25 cm, 5 um; Mobile Phase A: Hex (0.1% FA), Mobile Phase B: EtOH: DCM=1:1; Flow rate: 20 mL/min; Gradient: isocratic 30; Wave Length: UV 254/220 nm; RT1 (min): 7.34; RT2 (min): 12.61; Number Of Runs: 4) to afford desired products as peak 1 (1-7) and peak 2 (1-8) as a yellow solids. 1-7: (ESI, m/z): 595 $[M+H]^+$; 1-8: (ESI, m/z): 595 $[M+H]^+$.

Step E: Synthesis of tert-butyl (4-(4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate (1-10 and 1-11). To a stirred solution of 1-7 (66 mg, 0.11 mmol) and tert-butyl N-[3-cyano-4-(5,5-dimethyl-1,3,2-dioxaborinan-2-yl)-7-fluoro-1-benzothiophen-2-yl]carbamate (1-9)(134 mg, 0.33 mmol) in toluene (6.6 mL) were added $Cs_2CO_3$ (108 mg, 0.33 mmol) and $DPEPhosPdCl_2$ (31 mg, 0.04 mmol) in portions. The resulting mixture was stirred 3 hours at 100° C., then cooled to room temperature and extracted with ethyl acetate (3×15 mL). The combined organic layers were washed with brine (1×50 mL), dried over anhydrous $Na_2SO_4$, filtered, and concentrated under reduced pressure to give a residue. The residue was purified by reverse-phase flash chromatography (column, C18; mobile phase, MeCN in water (10 mmol/L $NH_4HCO_3$), 30% to 95% gradient in 25 min; detector, UV 254 nm) to give desired products 1-10 (peak 1) and 1-11 (peak 2) as yellow solids. 1-10: (ESI, m/z): 807 $[M+H]^+$; 1-11: (ESI, m/z): 807 $[M+H]^+$.

Step F-1: Synthesis of 2-amino-4-(4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b] thiophene-3-carbonitrile (850). A solution of 1-10 (51 mg, 0.063 mmol) and TFA (1.5 mL) in DCM (4.5 mL) was stirred for 2 hours at room temperature, then concentrated under reduced pressure. The crude product (60.0 mg) was purified by Prep-HPLC(Column: XBridge BEH Shield RP18 5 m, 30 mm*150 mm; Mobile Phase A: water (10 mmol/L $NH_4HCO_3$), Mobile Phase B: ACN; Flow rate: 60 mL/min; Gradient: 40% B to 70% B in 8 min; Wave Length: UV 254 nm/220 nm; RT1 (min): 7.35) to afford the desired product as a white solid. (ESI, m/z): 707 $[M+H]^+$. $^1H$ NMR: (400 MHZ, DMSO-d6, ppm) δ 8.07 (s, 2H), 7.97 (dd, J=4.9, 1.8 Hz, 1H), 7.63 (dd, J=7.6, 1.7 Hz, 1H), 7.20 (dd, J=8.4, 5.3 Hz, 1H), 7.13 (dd, J=9.4, 8.4 Hz, 1H), 6.67 (dd, J=7.5, 4.9 Hz, 1H), 6.25 (q, J=6.8 Hz, 1H), 5.70 (s, 2H), 5.28 (d, J=54.4 Hz, 1H), 4.42 (dd, J=11.5, 6.3 Hz, 1H), 4.30 (dd, J=11.5, 6.7 Hz, 1H), 4.15-4.03 (m, 2H), 3.61 (dd, J=15.2, 6.6 Hz, 1H), 3.41 (d, J=5.6 Hz, 1H), 3.16-3.02 (m, 2H), 3.02-2.98 (m, 1H), 2.82 (d, J=6.5 Hz, 1H), 2.22-2.10 (m, 1H), 2.09-2.00 (m, 2H), 1.87-1.68 (m, 3H), 1.60 (d, J=6.8 Hz, 3H).

Step F-2: Synthesis of 2-amino-4-(4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b] thiophene-3-carbonitrile (656). The procedures provided in Step F-1 were repeated, replacing 1-10 with 1-11, to afford the desired product. (ESI, m/z): 707 $[M+H]^+$. $^1H$ NMR: (400 MHZ, DMSO-d6, ppm) δ 8.06 (s, 2H), 7.97 (dd, J=4.9, 1.7 Hz, 1H), 7.67-7.60 (m, 1H), 7.19 (dd, J=8.4, 5.3 Hz, 1H), 7.13 (t, J=8.9 Hz, 1H), 6.66 (dd, J=7.5, 4.9 Hz, 1H), 6.31 (m, 1H), 5.83 (s, 2H), 5.28 (d, J=54.3 Hz, 1H), 4.53 (dd, J=11.6, 6.6 Hz, 1H), 4.20 (dd, J=11.8, 6.7 Hz, 1H), 4.13-4.02 (m, 2H), 3.71 (dd, J=15.4, 6.8 Hz, 1H), 3.34-3.37 (m, 1H), 3.13-3.05 (m, 2H), 3.01 (s, 1H), 2.82 (d, J=6.8 Hz, 1H), 2.23-2.10.

Example 1c: Synthesis of 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (847, 871, and 729).

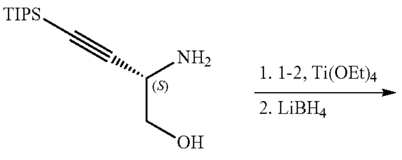

2-1

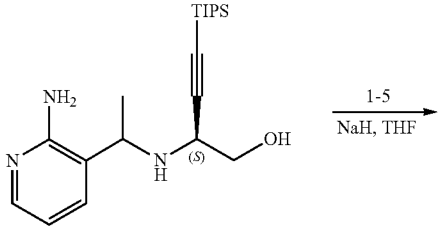

2-2

-continued

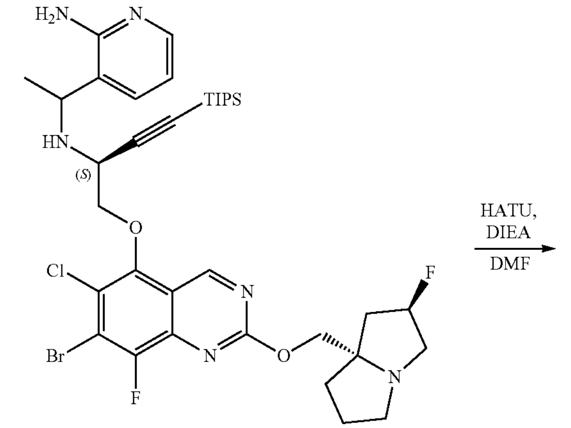

2-3

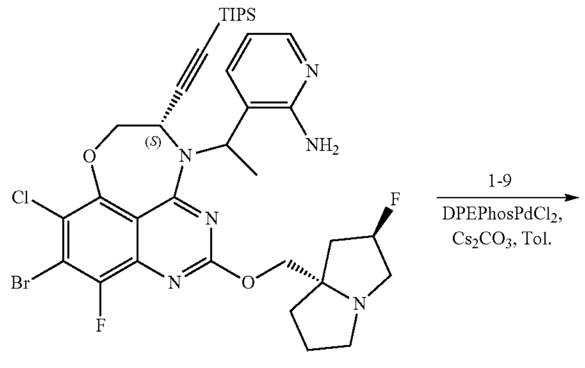

2-4

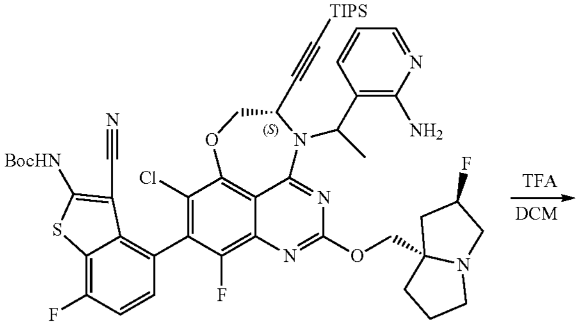

2-5

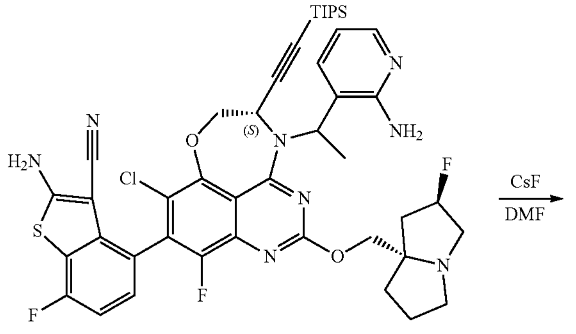

2-6

-continued

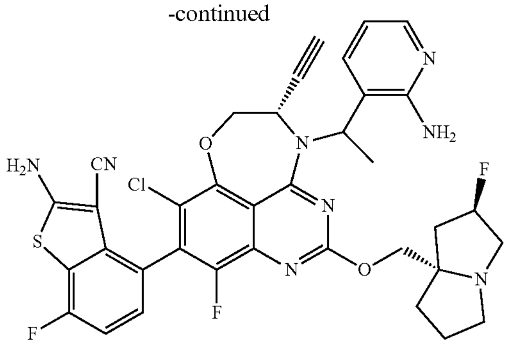

729(peak 1-first polar)
847(peak 2-second polar)
871(peak 3-third polar)

Step A: Synthesis of (2S)-2-((1-(2-aminopyridin-3-yl) ethyl)amino)-4-(triisopropylsilyl) but-3-yn-1-ol (2-2). A solution of (2S)-2-amino-4-(triisopropylsilyl) but-3-yn-1-ol (2-1)(1 g, 4.142 mmol) and 1-2 (0.85 g, 6.213 mmol) and Ti (OEt) 4 (7.56 g, 33.136 mmol) in THF (10 mL) was stirred for 20 hours at 70° C. To the resulting mixture was then added $LiBH_4$ (0.27 g, 12.42 mmol) dropwise over 2 minutes at room temperature. The resulting mixture was stirred for 2 hours, then quenched with water, filtered, and the filter cake washed with ethyl acetate (3×20 mL). The filtrate was extracted with ethyl acetate (3×50 mL) and the combined organic layers were washed with brine (1×150 mL), dried over anhydrous $Na_2SO_4$, filtered, and concentrated under reduced pressure. The resulting residue was purified by reverse-phase flash chromatography (column, C18; mobile phase, MeOH in water (0.1% TFA), 10% to 100% gradient in 20 min; detector, UV 254 nm) to afford the desired product as a yellow solid. (ESI, m/z): 362 $[M+H]^+$.

Step B: Synthesis of 5-(((2S)-2-((1-(2-aminopyridin-3-yl) ethyl)amino)-4-(triisopropylsilyl) but-3-yn-1-yl)oxy)-7-bromo-6-chloro-8-fluoro-2-(((2R,7aS)-2-fluorotetrahydro-1H-pyrrolizin-7a (5H)-yl)methoxy) quinazolin-4-ol (2-3). A solution of 2-2 (350 mg, 0.968 mmol) in THF (7.0 mL) was treated with 1-5 (350.5 mg, 0.774 mmol) for 30 minutes at 0° C., then NaH (209.0 mg, 8.712 mmol) was added in portions at 0° C. The resulting mixture was stirred overnight at 0° C. The crude product was used in the next step directly without further purification. (ESI, m/z): 794 $[M+H]^+$.

Step C: Synthesis of 3-(1-((S)-9-bromo-8-chloro-10-fluoro-2-(((2R,7aS)-2-fluorotetrahydro-1H-pyrrolizin-7a (5H)-yl)methoxy)-5-((triisopropylsilyl) ethynyl)-5,6-dihydro-4H-[1,4]oxazepino[5,6,7-de]quinazolin-4-yl)ethyl) pyridin-2-amine (2-4). A solution of 2-3 (500 mg, 0.630 mmol), HATU (359.05 mg, 0.945 mmol), and DIEA (244 mg, 1.890 mmol) in DMF (5 mL) was stirred for 1 hour at 40° C., then cooled and concentrated to give a residue. The residue was purified by reverse-phase flash chromatography (column, C18; mobile phase, MeCN in water (10 mmol/L $NH_4HCO_3$), 10% to 100% gradient in 30 min; detector, UV 254 nm) to afford the desired product as a yellow solid. (ESI, m/z): 776 $[M+H]^+$.

Step D: Synthesis of tert-butyl (4-((5S)-4-(1-(2-amino-pyridin-3-yl)ethyl)-8-chloro-10-fluoro-2-(((2R,7aS)-2-fluorotetrahydro-1H-pyrrolizin-7a (5H)-yl)methoxy)-5-((triisopropylsilyl) ethynyl)-5,6-dihydro-4H-[1,4]oxazepino[5,6,7-de]quinazolin-9-yl)-3-cyano-7-fluorobenzo[b]thiophen-2-yl)carbamate (2-5). A solution of 2-4 (150 mg, 0.193 mmol), 1-9 (156 mg, 0.386 mmol), DPEPhosPdCl$_2$ (55 mg, 0.077 mmol), and $Cs_2CO_3$ (189 mg, 0.579 mmol) in toluene (1.5 mL) was stirred for 1 hour at 100° C. The resulting mixture was cooled to room temperature and filtered. The filtrate was concentrated under reduced pressure to give a residue. The residue was purified by silica gel column chromatography, eluting with petroleum ether/ethyl acetate (5:1) to afford the desired product as a yellow solid. (ESI, m/z): 988 $[M+H]^+$.

Step E: Synthesis of 2-amino-4-((5S)-4-(1-(2-aminopyridin-3-yl)ethyl)-8-chloro-10-fluoro-2-(((2R,7aS)-2-fluoro-tetrahydro-1H-pyrrolizin-7a (5H)-yl)methoxy)-5-((triisopropylsilyl) ethynyl)-5,6-dihydro-4H-[1,4]oxazepino[5,6,7-de]quinazolin-9-yl)-7-fluorobenzo[b]thiophene-3-carbonitrile (2-6). A solution of 2-5 (75 mg, 0.076 mmol) and TFA (1 mL) in DCM (2 mL) was stirred for 2 hours at 0° C. The resulting mixture was diluted with DCM (3 mL), then concentrated under reduced pressure. The crude product was used in the next step directly without further purification. (ESI, m/z): 888 $[M+H]^+$.

Step F: Synthesis of 2-amino-4-((5S)-4-(1-(2-aminopyridin-3-yl)ethyl)-8-chloro-5-ethynyl-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (847, 871, and 729). A solution of 2-6 (75 mg, 0.085 mmol) and CsF (256 mg, 1.70 mmol) in DMF (1.09 mL) was stirred for 1 hour. The resulting mixture was purified by Prep-HPLC(Column: YMC Triart C18 ExRs 5 m, 30 mm×150 mm; Mobile Phase A: water (10 mmol/L $NH_4HCO_3$), Mobile Phase B: ACN; Flow rate: 60 mL/min; Gradient: 50% B to 70% B in 10 min; UV 254 nm/221 nm; RT1 (min): 5.13/7.45/9.28) to afford the first eluting (729-peak 1, first polar), second eluting (847-peak 2, second polar) and third eluting (871-peak 3, third polar) products as a white solids. 729: (ESI, m/z): 730.80 $[M+H]^+$. 1H NMR: (400 MHZ, DMSO-d6, ppm) δ 8.09 (s, 2H), 7.98-7.93 (m, 1H), 7.68 (d, J=7.6 Hz, 1H), 7.21 (dd, J=8.4, 5.3 Hz, 1H), 7.17-7.08 (m, 1H), 6.65 (dd, J=7.5, 4.9 Hz, 1H), 6.56-6.47 (m, 1H), 5.63 (s, 2H), 5.29 (d, J=53.6 Hz, 1H), 4.98 (s, 1H), 4.76 (dd, J=12.3, 5.1 Hz, 1H), 4.39 (d, J=12.4 Hz, 1H), 4.12 (s, 2H). 2.93 (d, J=2.4 Hz, 2H), 3.13 (s, 1H), 2.84 (s, 1H), 2.67 (d, J=1.9 Hz, 1H), 2.06 (d, J=19.8 Hz, 3H), 1.78 (d, J=17.9 Hz, 3H), 1.63 (d, J=6.9 Hz, 3H), 1.23 (s, 1H). 847: (ESI, m/z): 730.85 $[M+H]^+$. $^1H$ NMR: (400 MHZ, DMSO-d6, ppm) δ 8.07 (d, J=17.5 Hz, 2H), 7.96 (d, J=4.9 Hz, 1H), 7.78-7.65 (m, 1H), 7.22 (dd, J=8.4, 5.3 Hz, 1H), 7.19-7.08 (m, 1H), 6.64 (t, J=6.2 Hz, 1H), 6.59-6.06 (m, 1H), 5.95-5.07 (m, 4H), 4.86 (s, 1H), 4.49-3.85 (m, 3H), 3.70 (s, 1H), 2.85 (s, 2H), 2.67 (d, J=1.8 Hz, 1H), 2.51 (s, 1H), 2.21-1.94 (m, 3H), 1.89 (d, J=6.9 Hz, 3H), 1.83-1.65 (m, 3H), 1.24 (s, 1H). 871: (ESI, m/z): 730.85 $[M+H]^+$. $^1H$ NMR: (400 MHZ, DMSO-d6, ppm) δ 8.12 (s, 2H), 7.95 (d, J=4.9 Hz, 1H), 7.74 (d, J=7.5 Hz, 1H), 7.29 (dd, J=8.4, 5.2 Hz, 1H), 7.15 (t, J=8.9 Hz, 1H), 6.64 (d, J=8.1 Hz, 1H), 6.52 (s, 3H), 5.64 (s, 2H), 5.46-5.06 (m, 1H), 4.09 (d, J=5.3 Hz, 2H), 4.04 (s, 1H), 3.17 (s, 1H), 3.16 (s, 2H), 2.83 (s, 1H), 2.67 (s, 1H), 2.07 (s, 3H), 1.91 (d, J=6.8 Hz, 3H), 1.86-1.63 (m, 3H), 1.23 (s, 1H).

Example 1d: Synthesis of 4-(10-(1-(2-aminopyridin-3-yl) ethyl)-4-fluoro-2-(((2R,7aS)-2-fluorotetrahydro-1H-pyrrolizin-7a (5H)-yl)methoxy)-9,10-dihydro-8H-7-oxa-1,3,6,10-tetraazacyclohepta[de]naphthalen-5-yl)-5-ethynyl-6-fluoronaphthalen-2-ol (742 and 744).

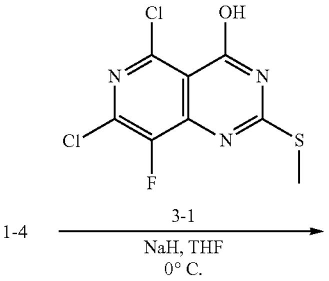

1-4
3-1

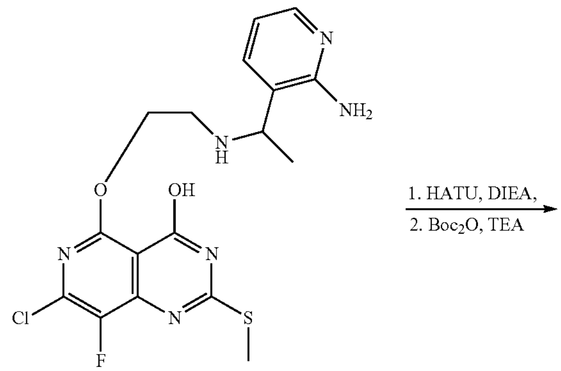

3-2

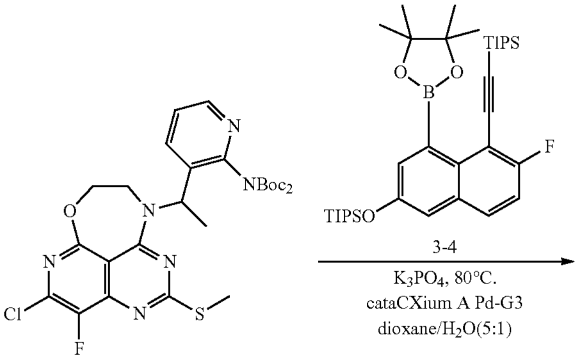

3-4
3-3

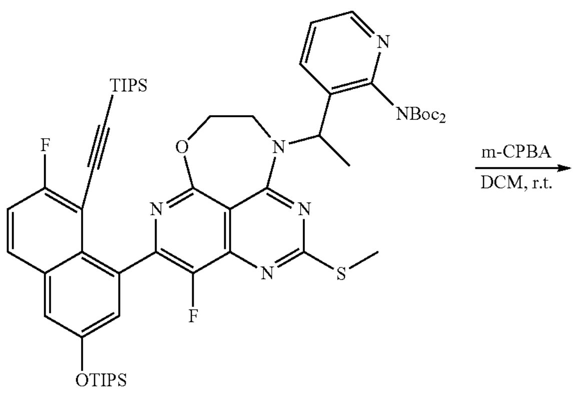

3-5

-continued

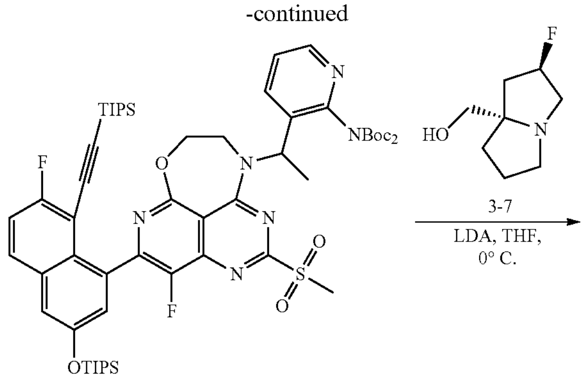

3-6

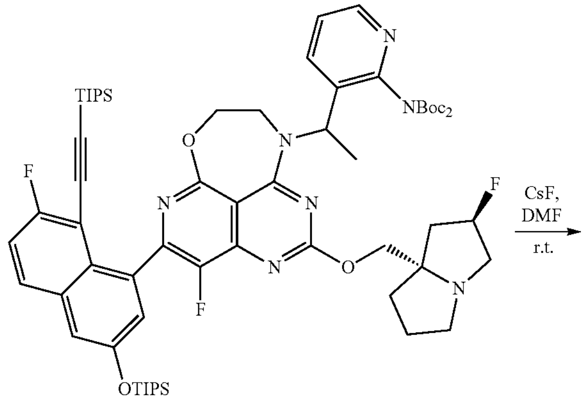

3-8

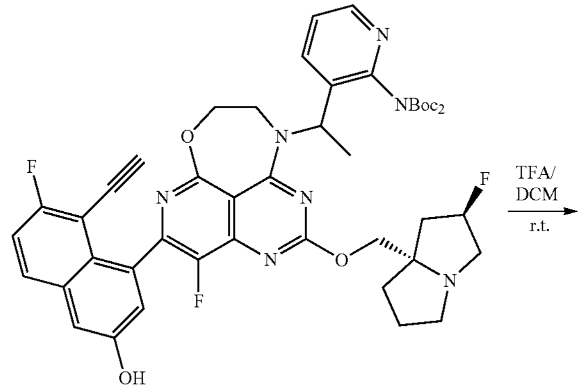

3-9

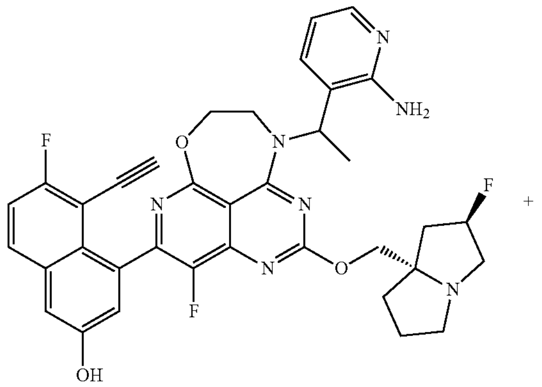

742

-continued

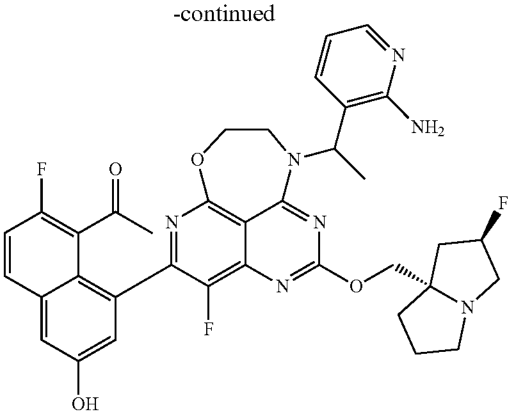

744

Step A: Synthesis of 5-(2-((1-(2-aminopyridin-3-yl)ethyl) amino) ethoxy)-7-chloro-8-fluoro-2-(methylthio)pyrido[4,3-d]pyrimidin-4-ol (3-2). To a solution of 1-4 (0.77 g, 4.24 mmol) and 5,7-dichloro-8-fluoro-2-(methylsulfanyl)pyrido [4,3-d]pyrimidin-4-ol (3-1)(1.07 g, 3.82 mmol) in THF (20.0 mL) was added NaH (1.53 g, 38.24 mmol, 60%) and the resulting solution was stirred for 2 hours at 0° C. The reaction was quenched with sat. $NH_4Cl$ (aq.) and the resulting mixture was extracted with ethyl acetate (3×15 mL). The combined organic layers were washed with brine (1×40 mL), dried over anhydrous $Na_2SO_4$, filtered, and concentrated under reduced pressure to give the desired product, which was used in the next step directly without further purification. (ESI, m/z): 425 $[M+H]^+$.

Step B-1: Synthesis of 3-(1-(5-chloro-4-fluoro-2-(methylthio)-8,9-dihydro-10H-7-oxa-1,3,6, 10-tetraazacyclohepta [de]naphthalen-10-yl)ethyl) pyridin-2-amine. To a solution of 3-2 (2.60 g, 6.12 mmol) and HATU (3.49 g, 9.18 mmol) in DMF (45.0 mL) was added DIEA (1.19 g, 9.18 mmol) and the mixture was stirred for 1 hour at 50° C. The reaction was then cooled to room temperature and diluted with water (135 mL). The precipitated solids were collected by filtration and washed with water (3×25 mL), followed by air drying to give the desired product as a yellow solid. (ESI, m/z): 407 $[M+H]^+$.

Step B-2: Synthesis of tert-butyl (tert-butoxycarbonyl)(3-(1-(5-chloro-4-fluoro-2-(methylthio)-8,9-dihydro-10H-7-oxa-1,3,6,10-tetraazacyclohepta[de]naphthalen-10-yl)ethyl) pyridin-2-yl)carbamate (3-3). A solution of 3-(1-(5-chloro-4-fluoro-2-(methylthio)-8,9-dihydro-10H-7-oxa-1,3,6,10-tetraazacyclohepta[de]naphthalen-10-yl)ethyl) pyridin-2-amine (1.51 g, 3.71 mmol), $Boc_2O$ (12.15 g, 55.66 mmol), triethylamine (3.76 g, 37.11 mmol) and DMAP (272.0 mg, 2.22 mmol) in dichloromethane (22.0 mL) was stirred for 2 hours at room temperature, then extracted with dichloromethane (3×15 mL). The combined organic layers were washed with brine (1×25 mL), dried over anhydrous $Na_2SO_4$, filtered, and concentrated under reduced pressure to give a residue, which was purified by silica gel column chromatography and eluted with $CH_2Cl_2$/ethyl acetate (4:1) to afford the desired product as a yellow solid. (ESI, m/z): 607 $[M+H]^+$.

Step C: Synthesis of tert-butyl (tert-butoxycarbonyl)(3-(1-(4-fluoro-5-(7-fluoro-8-((triisopropylsilyl) ethynyl)-3-((triisopropylsilyl)oxy) naphthalen-1-yl)-2-(methylthio)-8,9-dihydro-10H-7-oxa-1,3,6,10-tetraazacyclohepta[de] naphthalen-10-yl)ethyl) pyridin-2-yl)carbamate (3-5). A solution of 3-3 (460 mg, 0.75 mmol), (2-[2-fluoro-8-(4,4,5, 5-tetramethyl-1,3,2-dioxaborolan-2-yl)-6-[(triisopropylsilyl)oxy]naphthalen-1-yl]ethynyltriisopropylsilane (3-4)(710 mg, 1.13 mmol), $K_3PO_4$ (482 mg, 2.27 mmol) and cataCXium-A-Pd-G3 (55 mg, 0.07 mmol) in dioxane (8.0 mL) and water (1.6 mL) was stirred for 2 hours at 80° C., then cooled to room temperature and extracted with ethyl acetate (3×15 mL). The combined organic layers were washed with brine (1×20 mL), dried over anhydrous $Na_2SO_4$, filtered, and concentrated under reduced pressure to give a residue, which was purified by prep-TLC (petroleum ether/ethyl acetate 3:1) to afford the desired product as a yellow solid. (ESI, m/z): 1069.5 $[M+H]^+$.

Step D: Synthesis of tert-butyl (tert-butoxycarbonyl)(3-(1-(4-fluoro-5-(7-fluoro-8-((triisopropylsilyl) ethynyl)-3-((triisopropylsilyl)oxy) naphthalen-1-yl)-2-(methylsulfonyl)-8,9-dihydro-10H-7-oxa-1,3,6,10-tetraazacyclohepta [de]naphthalen-10-yl)ethyl) pyridin-2-yl)carbamate (3-6). A solution of 3-5 (790 mg, 0.73 mmol) and m-CPBA (359 mg, 1.77 mmol, 85%) in DCM (16 mL) was stirred for 2 hours at room temperature, then extracted with $CH_2Cl_2$ (3×30 mL). The combined organic layers were washed with sat. $NaHCO_3$ (1×60 mL) and dried over anhydrous $Na_2SO_4$. After filtration, the filtrate was concentrated under reduced pressure to give the desired product, which was used in the next step directly without further purification. (ESI, m/z): 1101.5 $[M+H]^+$.

Step E: Synthesis of tert-butyl (tert-butoxycarbonyl)(3-(1-(4-fluoro-5-(7-fluoro-8-((triisopropylsilyl) ethynyl)-3-((triisopropylsilyl)oxy) naphthalen-1-yl)-2-(((2R,7aS)-2-fluorotetrahydro-1H-pyrrolizin-7a (5H)-yl)methoxy)-8,9-dihydro-10H-7-oxa-1,3,6,10-tetraazacyclohepta[de] naphthalen-10-yl)ethyl) pyridin-2-yl)carbamate (3-8). To a stirred solution of 3-6 (300 mg, 0.27 mmol) and [(2R,7aS)-2-fluoro-hexahydropyrrolizin-7a-yl]methanol (3-7)(130 mg, 0.81 mmol) in THF (6 mL) was added LDA (544 µL, 1.08 mmol) dropwise at 0° C. The resulting mixture was stirred for an additional 2 hours at 0° C., then quenched with sat. $NH_4Cl$ (aq.) at room temperature. The resulting mixture was extracted with ethyl acetate (3×25 mL). The combined organic layers were washed with brine (1×50 mL) and dried over anhydrous $Na_2SO_4$. After filtration, the filtrate was concentrated under reduced pressure to give the desired product, which was used in the next step directly without further purification. (ESI, m/z): 1180.5 $[M+H]^+$.

Step F: Synthesis of tert-butyl (tert-butoxycarbonyl)(3-(1-(5-(8-ethynyl-7-fluoro-3-hydroxynaphthalen-1-yl)-4-fluoro-2-(((2R,7aS)-2-fluorotetrahydro-1H-pyrrolizin-7a (5H)-yl)methoxy)-8,9-dihydro-10H-7-oxa-1,3,6,10-tetraazacyclohepta[de]naphthalen-10-yl)ethyl) pyridin-2-yl) carbamate (3-9). A solution of 3-8 (435 mg, 0.36 mmol) and CsF (559 mg, 3.68 mmol) in DMF (9 mL) was stirred for 4 hours at room temperature, then extracted with ethyl acetate (3×20 mL). The combined organic layers were washed with brine (1×40 mL) and dried over anhydrous $Na_2SO_4$. After filtration, the filtrate was concentrated under reduced pressure to give the desired product, which was used in the next step directly without further purification. (ESI, m/z): 868.5 $[M+H]^+$.

Step G: Synthesis of 4-(10-(1-(2-aminopyridin-3-yl) ethyl)-4-fluoro-2-(((2R,7aS)-2-fluorotetrahydro-1H-pyrrolizin-7a (5H)-yl)methoxy)-9,10-dihydro-8H-7-oxa-1,3,6,10-tetraazacyclohepta[de]naphthalen-5-yl)-5-ethynyl-6-fluoronaphthalen-2-ol (742) and 1-(8-(10-(1-(2-aminopyridin-3-yl)ethyl)-4-fluoro-2-(((2R,7aS)-2-fluorotetrahydro-1H-pyrrolizin-7a (5H)-yl)methoxy)-9,10-dihydro-8H-7-oxa-1,3,6,10-tetraazacyclohepta[de] naphthalen-5-yl)-2-fluoro-6-hydroxynaphthalen-1-yl) ethan-1-one (744). A solution of 3-9 (349 mg, 0.4 mmol) and TFA (2.0 mL) in DCM (6.0 mL) was stirred for 2 hours at room temperature, then concentrated under reduced pressure to give the desired crude products. The crude products were purified by prep-HPLC with the following conditions (Column: Sunfire C18 5 m, 30 mm*150 mm; Mobile Phase A: water (0.1% FA), Mobile Phase B: ACN; Flow rate: 60 mL/min; Gradient: 7% B to 20% B in 10 min; Wave Length: UV 254 nm/220 nm; RT1 (min): 8.43) to afford 742 (formic acid) as an off-white solid and 744 as an off-white solid. 742: (ESI, m/z): 668 $[M+H]^+$. $^1$H NMR: (400 MHZ, DMSO-d6, ppm) § 12.73 (s, 1H), 10.82 (s, 1H), 10.15 (s, 1H), 8.02-7.92 (m, 2H), 7.66 (d, J=7.5 Hz, 1H), 7.50-7.41 (m, 1H), 7.40-7.35 (m, 1H), 7.14 (d, J=2.6 Hz, 1H), 6.69 (t, J=6.3 Hz, 1H), 6.33 (dd, J=14.5, 7.1 Hz, 1H), 5.86 (s, 1H), 5.76 (s, 1H), 5.48 (d, J=52.8 Hz, 1H), 4.44 (s, 3H), 4.26 (s, 1H), 4.09 (s, 1H), 3.96 (d, J=2.7 Hz, 1H), 3.76 (m, 2H), 3.52 (s, 1H), 2.07 (s, 6H), 1.61 (t, J=5.6 Hz, 3H). 744: (ESI, m/z): 686 $[M+H]^+$. $^1$H NMR: (400 MHz, DMSO-d6, ppm) § 10.20 (s, 1H), 8.18 (s, 1H), 8.04-7.94 (m, 2H), 7.62 (d, J=7.6 Hz, 1H), 7.44 (t, J=9.5 Hz, 1H), 7.38 (d, J=2.6 Hz, 1H), 7.23 (s, 1H), 6.67 (dd, J=7.5, 4.9 Hz, 1H), 6.36 (d, J=6.8 Hz, 1H), 5.71 (s, 2H), 5.31 (d, J=54.5 Hz, 1H), 4.44 (dd, J=12.5, 6.7 Hz, 1H), 4.31 (s, 1H), 4.27-4.03 (m, 2H), 3.69 (dd, J=16.1, 6.5 Hz, 1H), 3.12 (d, J=9.5 Hz, 2H), 3.03 (s, 1H), 2.84 (d, J=7.5 Hz, 1H), 2.34 (d, J=3.3 Hz, 3H), 2.17 (d, J=11.0 Hz, 1H), 2.07 (d, J=16.2 Hz, 2H), 1.84 (dd, J=19.5, 11.0 Hz, 3H), 1.57 (d, J=6.8 Hz, 3H).

Example 1e: Synthesis of 2-amino-4-((R)-4-((R)-1-(2-aminopyridin-3-yl)ethyl)-8-chloro-2-(((S)-2-(difluoromethylene)tetrahydro-1H-pyrrolizin-7a (5H)-yl)methoxy)-10-fluoro-5,6-dihydro-4H-[1,4]oxazepino[5,6,7-de]quinazolin-9-yl)-7-fluorobenzo[b]thiophene-3-carbonitrile (636).

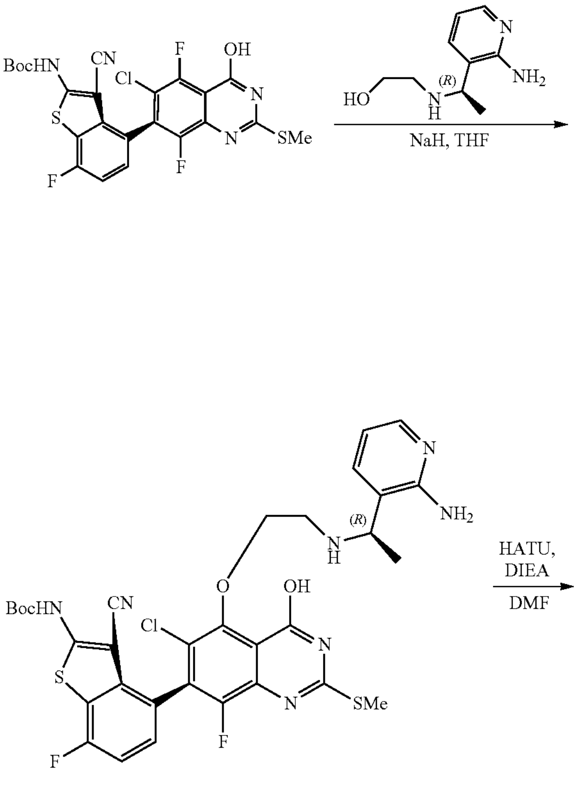

-continued

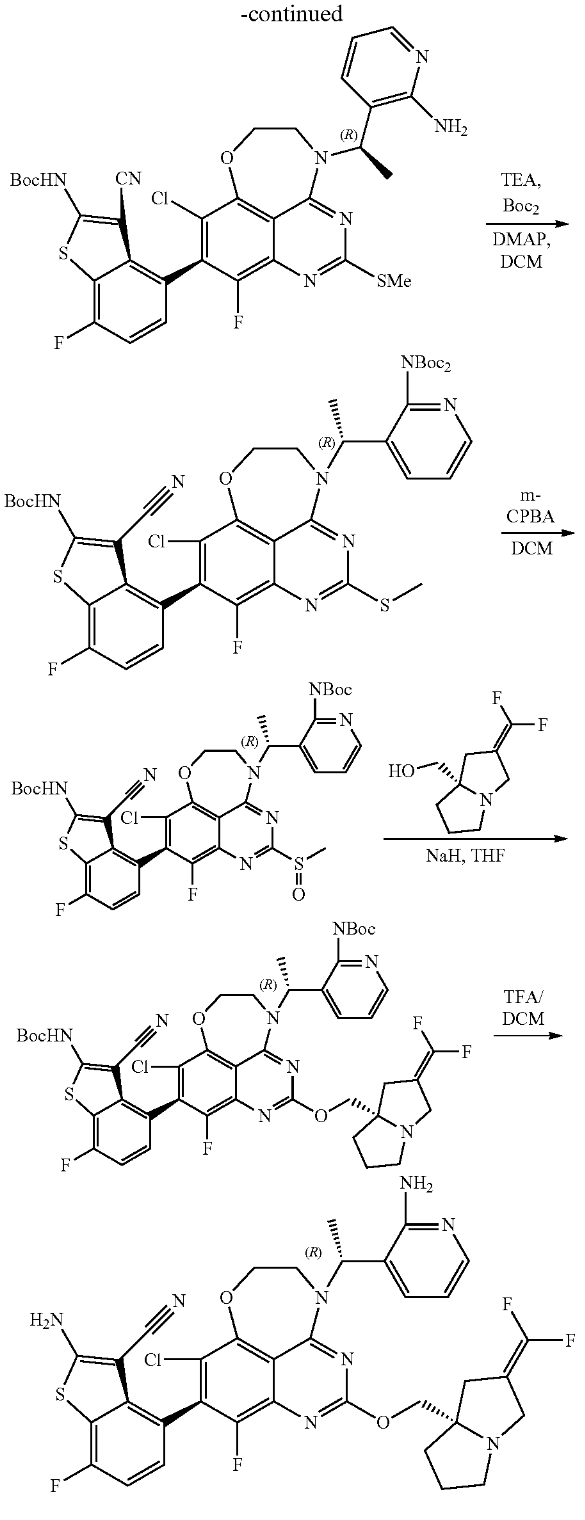

Step A: Synthesis of tert-butyl (4-((R)-5-(2-(((R)-1-(2-aminopyridin-3-yl)ethyl)amino) ethoxy)-6-chloro-8-fluoro-4-hydroxy-2-(methylthio) quinazolin-7-yl)-3-cyano-7-fluorobenzo[b]thiophen-2-yl)carbamate. A solution of tert-butyl N-{4-[6-chloro-5,8-difluoro-4-hydroxy-2-(methylsulfanyl) quinazolin-7-yl]-3-cyano-7-fluoro-1-benzothiophen-2-yl}carbamate (1.38 g, 2.49 mmol) in THF (28 mL) was treated with 2-{[(1R)-1-(2-aminopyridin-3-yl)ethyl] amino}ethanol (0.50 g, 2.75 mmol) at room temperature under argon atmosphere, followed by the addition of NaH (0.54 g, 22.46 mmol) at 0° C. The resulting mixture was stirred for an additional 3 hours at 50° C. The reaction was cooled to room temperature, quenched with sat. $NH_4Cl$ (aq.) at 0° C., and extracted with EtOAc (3×50 mL). The combined organic layers were washed with brine (50 mL) and dried over anhydrous $Na_2SO_4$. After filtration, the filtrate was concentrated under reduced pressure to give the crude product which was used in the next step directly without further purification: (ESI, m/z): 714 $[M+H]^+$.

Step B: Synthesis of tert-butyl (4-((R)-4-((R)-1-(2-aminopyridin-3-yl)ethyl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl)carbamate. A solution of tert-butyl (4-((R)-5-(2-(((R)-1-(2-aminopyridin-3-yl) ethyl)amino) ethoxy)-6-chloro-8-fluoro-4-hydroxy-2-(methylthio) quinazolin-7-yl)-3-cyano-7-fluorobenzo[b] thiophen-2-yl)carbamate (3.60 g, 5.04 mmol) in DMF (72 mL) was treated with HATU (2.87 g, 7.56 mmol) and DIEA (0.98 g, 7.56 mmol) at room temperature. The resulting mixture was stirred an additional 1 hour at 50° C. The mixture was allowed to cool to room temperature and diluted with ethyl acetate (150 mL). The organic layers were washed with brine (3×30 mL) and dried over anhydrous $Na_2SO_4$. After filtration, the filtrate was concentrated under reduced pressure to give the crude product (2.97 g) which was used in the next step directly without further purification. (ESI, m/z): 696 $[M+H]^+$.

Step C: Synthesis of tert-butyl (tert-butoxycarbonyl)(3-((R)-1-((R)-9-(2-((tert-butoxycarbonyl)amino)-3-cyano-7-fluorobenzo[b]thiophen-4-yl)-8-chloro-10-fluoro-2-(methylthio)-5,6-dihydro-4H-[1,4]oxazepino[5,6,7-de] quinazolin-4-yl)ethyl) pyridin-2-yl)carbamate. A solution of (4-((R)-4-((R)-1-(2-aminopyridin-3-yl)ethyl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl)carbamate (2.70 g, 3.88 mmol) and $Boc_2O$ (2.54 g, 11.63 mmol) in dichloromethane (54 mL) was treated with triethylamine (1.96 g, 19.39 mmol) at room temperature followed by the addition of DMAP (1.42 g, 11.63 mmol). The resulting mixture was stirred an additional 1 hour at room temperature and diluted with water (20 mL). The resulting mixture was extracted with dichloromethane (3×30 mL). The combined organic layers were washed with brine (30 mL) and dried over anhydrous $Na_2SO_4$. After filtration, the filtrate was concentrated under reduced pressure to give a residue. The residue was purified by silica gel column chromatography, eluted with petroleum ether/ethyl acetate (1:1) to afford the desired product as a yellow solid. (ESI, m/z): 896 $[M+H]^+$.

Step D: Synthesis of tert-butyl (tert-butoxycarbonyl)(3-((1R)-1-((9R)-9-(2-((tert-butoxycarbonyl)amino)-3-cyano-7-fluorobenzo[b]thiophen-4-yl)-8-chloro-10-fluoro-2-(methylsulfinyl)-5,6-dihydro-4H-[1,4]oxazepino[5,6,7-de] quinazolin-4-yl)ethyl) pyridin-2-yl)carbamate. A solution of tert-butyl (tert-butoxycarbonyl)(3-((R)-1-((R)-9-(2-((tert-butoxycarbonyl)amino)-3-cyano-7-fluorobenzo[b]thiophen-4-yl)-8-chloro-10-fluoro-2-(methylthio)-5,6-dihydro-4H-[1,4]oxazepino[5,6,7-de]quinazolin-4-yl)ethyl) pyridin-2-yl) carbamate (1.4 g, 2.00 mmol) in dichloromethane (14 mL) was treated with m-CPBA (0.27 g, 2.00 mmol) at 0° C. The resulting mixture was stirred for an additional 1 hour at 0° C. and quenched with $NaHSO_3$. The mixture was adjusted to pH 9 with saturated $NaHCO_3$(aq.) and extracted with dichloromethane (3×30 mL). The combined organic layers were washed with brine (30 mL) and dried over anhydrous $Na_2SO_4$. After filtration, the filtrate was concentrated under reduced pressure to give the desired product which was used in the next step directly without further purification. (ESI, m/z): 912 $[M+H]^+$.

Step E: Synthesis of Synthesis of tert-butyl (4-((R)-4-((R)-1-(2-((tert-butoxycarbonyl)amino)pyridin-3-yl)ethyl)-8-chloro-2-(((S)-2-(difluoromethylene)tetrahydro-1H-pyrrolizin-7a (5H)-yl)methoxy)-10-fluoro-5,6-dihydro-4H-[1,4]oxazepino[5,6,7-de]quinazolin-9-yl)-3-cyano-7-fluorobenzo[b]thiophen-2-yl)carbamate. A solution of tert-butyl (tert-butoxycarbonyl)(3-((1R)-1-((9R)-9-(2-((tert-butoxycarbonyl)amino)-3-cyano-7-fluorobenzo[b]thiophen-4-yl)-8-chloro-10-fluoro-2-(methylsulfinyl)-5,6-dihydro-4H-[1,4]oxazepino[5,6,7-de]quinazolin-4-yl)ethyl) pyridin-2-yl)carbamate (180.0 mg, 0.2 mmol) in THF (3.6 mL) was treated with [(7aS)-2-(difluoromethylidene)-tetrahydro-1H-pyrrolizin-7a-yl]methanol (74.65 mg, 0.394 mmol) and NaH (42.6 mg, 1.77 mmol) at 0° C. under nitrogen atmosphere. The resulting mixture was stirred for 1 hour at 0° C., quenched with sat. $NH_4Cl$ (aq.), and extracted with EtOAc (3x30 mL). The combined organic layers were washed with brine (30 mL) and dried over anhydrous $Na_2SO_4$. After filtration, the filtrate was concentrated under reduced pressure to give a residue. The residue was purified by reverse-phase flash chromatography (column, C18; mobile phase, MeCN in Water (10 mmol/L $NH_4HCO_3$), 50% to 90% gradient in 25 min; detector, UV 220 nm) to afford the desired product as a light yellow solid. (ESI, m/z): 937 $[M+H]^+$.

Step F: Synthesis of 2-amino-4-((R)-4-((R)-1-(2-aminopyridin-3-yl)ethyl)-8-chloro-2-(((S)-2-(difluoromethylene) tetrahydro-1H-pyrrolizin-7a (5H)-yl)methoxy)-10-fluoro-5,6-dihydro-4H-[1,4]oxazepino[5,6,7-de]quinazolin-9-yl)-7-fluorobenzo[b]thiophene-3-carbonitrile. A solution of tert-butyl (4-((R)-4-((R)-1-(2-((tert-butoxycarbonyl)amino) pyridin-3-yl)ethyl)-8-chloro-2-(((S)-2-(difluoromethylene) tetrahydro-1H-pyrrolizin-7a (5H)-yl)methoxy)-10-fluoro-5,6-dihydro-4H-[1,4]oxazepino[5,6,7-de]quinazolin-9-yl)-3-cyano-7-fluorobenzo[b]thiophen-2-yl)carbamate (77.0 mg, 0.07 mmol) in dichloromethane (2 mL) was treated with TFA (0.4 mL) at room temperature. The resulting mixture was stirred for 1 hour at room temperature and adjusted to pH 8 with saturated $NaHCO_3$ (aq.). The product was extracted with dichloromethane (3x15 mL). The combined organic layers were washed with brine (10 mL) and dried over anhydrous $Na_2SO_4$. After filtration, the filtrate was concentrated under reduced pressure. The crude product (85 mg) was purified by Prep-HPLC(Column: XBridge BEH Shield RP18 5 m, 30 mm*150 mm; Mobile Phase A: Water (10 mmol/L $NH_4HCO_3$), Mobile Phase B: ACN; Flow rate: 60 mL/min; Gradient: 40% B to 75% B in 7 min; Wave Length: UV 254 nm/220 nm; RT1 (min): 7.05) to afford the desired product as a white solid. (ESI, m/z): 737 $[M+H]^+$. $^1H$ NMR: (400 MHZ, DMSO-d6, ppm) δ 8.08 (s, 2H), 7.97 (dd, J=4.8, 1.7 Hz, 1H), 7.66-7.61 (m, 1H), 7.22-7.10 (m, 2H), 6.67 (dd, J=7.5, 4.9 Hz, 1H), 6.23 (d, J=6.8 Hz, 1H), 5.68 (s, 2H), 4.41 (dd, J=11.7, 6.4 Hz, 1H), 4.29 (dd, J=11.4, 6.6 Hz, 1H), 4.18-4.10 (m, 2H), 3.67-3.56 (m, 2H), 3.51-3.37 (m, 2H), 3.00 (q, J=5.4, 4.1 Hz, 1H), 2.65 (s, 1H), 2.43-2.39 (m, 2H), 2.03-1.97 (m, 1H), 1.89-1.73 (m, 3H), 1.60 (d, J=6.8 Hz, 3H).

Example 1f: Synthesis of 4-(10-(1-(2-aminopyridin-3-yl) ethyl)-4-fluoro-2-(((S)-1-methylpyrrolidin-2-yl)methoxy)-9,10-dihydro-8H-7-oxa-1,3,6,10-tetraazacyclohepta[de] naphthalen-5-yl)-5-ethynyl-6-fluoronaphthalen-2-ol (728).

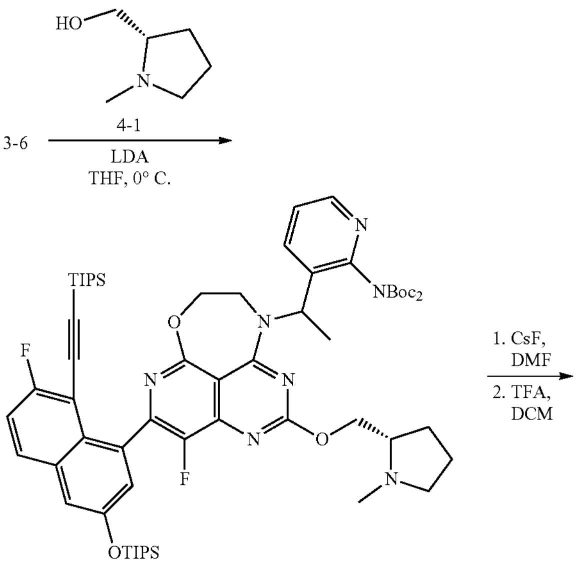

4-2

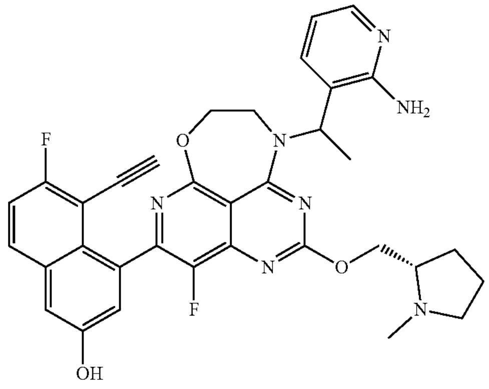

728

Step A: Synthesis of tert-butyl (tert-butoxycarbonyl)(3-(1-(4-fluoro-5-(7-fluoro-8-((triisopropylsilyl) ethynyl)-3-((triisopropylsilyl)oxy) naphthalen-1-yl)-2-(((S)-1-methylpyrrolidin-2-yl)methoxy)-8,9-dihydro-10H-7-oxa-1,3,6,10-tetraazacyclohepta[de]naphthalen-10-yl)ethyl) pyridin-2-yl)carbamate (4-2). To a stirred mixture of 3-6 (as shown in Example 1c; 290 mg, 0.26 mmol) and [(2S)-1-methylpyrrolidin-2-yl]methanol (4-1)(90 mg, 0.78 mmol) in THF (6 mL, 74.05 mmol) was added LDA (526 μL, 1.05 mmol) dropwise at 0° C. The resulting mixture was stirred an additional 2 hours at 0° C., then quenched with sat. $NH_4Cl$ (aq.) at room temperature. The resulting mixture was extracted with ethyl acetate (3x25 mL) and the combined organic layers were washed with brine (1x50 mL), dried over anhydrous $Na_2SO_4$, filtered, and concentrated under reduced pressure to give the desired product, which was used in the next step directly without further purification. (ESI, m/z): 1136.5 $[M+H]^+$.

Step B-1: Synthesis of tert-butyl (tert-butoxycarbonyl)(3-(1-(5-(8-ethynyl-7-fluoro-3-hydroxynaphthalen-1-yl)-4-fluoro-2-(((S)-1-methylpyrrolidin-2-yl)methoxy)-8,9-dihydro-10H-7-oxa-1,3,6,10-tetraazacyclohepta[de]naphthalen-10-yl)ethyl) pyridin-2-yl)carbamate. A solution of 4-2 (480 mg, 0.42 mmol) and CsF (641 mg, 4.22 mmol) in DMF (10.0 mL) was stirred for 4 hours. The resulting mixture was extracted with ethyl acetate (3×20 mL) and the combined organic layers were washed with brine (1×40 mL), dried over anhydrous $Na_2SO_4$, filtered, and concentrated under reduced pressure to give the desired product, which was used in the next step directly without further purification. (ESI, m/z): 824 $[M+H]^+$.

Step B-2: Synthesis of 4-(10-(1-(2-aminopyridin-3-yl)ethyl)-4-fluoro-2-(((S)-1-methylpyrrolidin-2-yl)methoxy)-9,10-dihydro-8H-7-oxa-1,3,6,10-tetraazacyclohepta[de]naphthalen-5-yl)-5-ethynyl-6-fluoronaphthalen-2-ol (728). A solution of tert-butyl (tert-butoxycarbonyl)(3-(1-(5-(8-ethynyl-7-fluoro-3-hydroxynaphthalen-1-yl)-4-fluoro-2-(((S)-1-methylpyrrolidin-2-yl)methoxy)-8,9-dihydro-10H-7-oxa-1,3,6,10-tetraazacyclohepta[de]naphthalen-10-yl)ethyl) pyridin-2-yl)carbamate (360 mg, 0.43 mmol) and TFA (2 mL) in DCM (6 mL) was stirred for 2 hours at room temperature. The resulting mixture was concentrated under reduced pressure to give a crude residue, which was purified by Prep-HPLC(Column: Xselect CSH™ Prep C18 5 μm 30*150 mm OBD; Mobile Phase A: Water (0.1% FA), Mobile Phase B: ACN; Flow rate: 60 mL/min; Gradient: 2% B to 20% B in 10 min; Wave Length: UV 254 nm/220 nm; RT1 (min): 8.42/9.17/10.6) to afford the desired product as a brown solid. (ESI, m/z): 624 $[M+H]^+$. $^1H$ NMR (400 MHz, DMSO-d6, ppm) δ 10.13 (s, 1H), 8.14 (s, 1H), 8.01-7.92 (m, 2H), 7.69-7.62 (m, 1H), 7.46 (t, J=9.0 Hz, 1H), 7.40-7.34 (m, 1H), 7.14 (t, J=3.1 Hz, 1H), 6.68 (dd, J=7.3, 5.1 Hz, 1H), 6.35 (m, 1H), 5.74 (d, J=11.9 Hz, 1H), 5.67 (d, J=7.4 Hz, 1H), 4.42 (q, J=10.8, 8.0 Hz, 2H), 4.31-4.18 (m, 2H), 4.14-3.91 (m, 1H), 3.81-3.61 (m, 1H), 3.46-3.40 (m, 1H), 3.00 (s, 1H), 2.70 (s, 1H), 2.41 (s, 3H), 2.26 (s, 1H), 1.99 (s, 1H), 1.73-1.66 (m, 3H), 1.60 (dd, J=6.9, 4.4 Hz, 3H).

Example 1g: Synthesis of 2-amino-4-(4-((R)-1-(2-aminopyridin-3-yl)ethyl)-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-9-yl)-7-fluorobenzo[b]thiophene-3-carbonitrile (741 and 762).

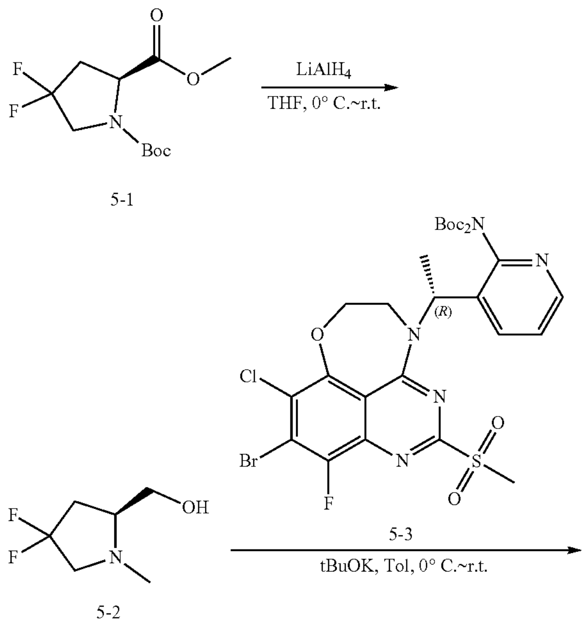

5-1
5-3
5-2

-continued

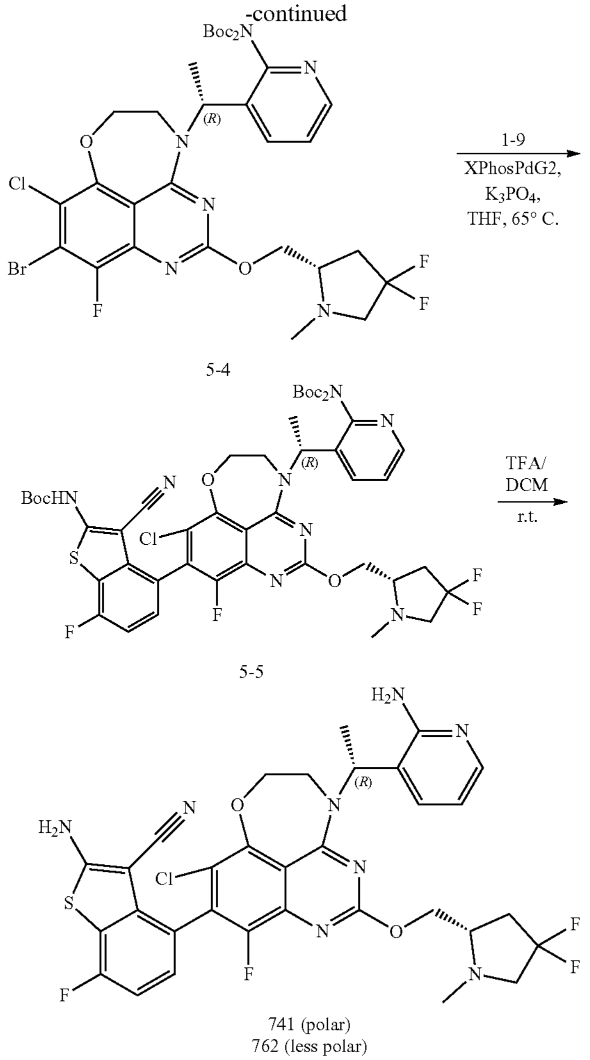

5-4
5-5
741 (polar)
762 (less polar)

Step A: Synthesis of(S)-(4,4-difluoro-1-methylpyrrolidin-2-yl) methanol (5-2). To a solution of 1-tert-butyl 2-methyl (2S)-4,4-difluoropyrrolidine-1,2-dicarboxylate (5-1)(1 g, 3.77 mmol) in THF (10 mL) was added $LiAlH_4$ (5.65 mL, 11.31 mmol) dropwise at 0° C. and the mixture was stirred for 3 hours at room temperature. The reaction was quenched with sodium sulfate decahydrate at 0° C. The precipitated solids were collected by filtration and washed with $CH_2Cl_2$ (3×10 mL). The resulting mixture was concentrated under vacuum to give the desired product as a colorless liquid. (ESI, m/z): 152 $[M+H]^+$.

Step B: Synthesis of tert-butyl (3-((R)-1-(9-bromo-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-4-yl)ethyl) pyridin-2-yl)(tert-butoxycarbonyl)carbamate (5-4). To a stirred solution of tert-butyl (R)-(3-(1-(9-bromo-8-chloro-10-fluoro-2-(methylsulfonyl)-5,6-dihydro-4H-[1,4]oxazepino[5,6,7-de]quinazolin-4-yl)ethyl) pyridin-2-yl)(tert-butoxycarbonyl)carbamate (5-3)(200 mg, 0.27 mmol) in toluene (4 mL, 37.59 mmol) was added t-BuOK (156 mg, 1.39 mmol) and(S)-(4,4-difluoro-1-methylpyrrolidin-2-yl) methanol (5-2) in portions at 0° C. The resulting mixture was stirred for an additional 2 hours at room temperature, then extracted with ethyl acetate (3×10 mL). The combined organic layers were washed with brine (3×10 mL), dried over anhydrous $Na_2SO_4$, filtered, and concentrated under reduced pressure to give a residue, which was purified by silica gel column chromatography, eluted with $CH_2Cl_2$/MeOH (12:1) to afford the desired product as a light-yellow solid. (ESI, m/z): 787/789 $[M+H]^+$.

Step C: Synthesis of tert-butyl (4-(4-((R)-1-(2-((tert-butoxycarbonyl)amino)pyridin-3-yl)ethyl)-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-9-yl)-3-cyano-7-fluorobenzo[b]thiophen-2-yl)carbamate (5-5). To a stirred solution of 5-4 (130 mg, 0.165 mmol) and 1-9 (200 mg, 0.49 mmol) in THF (3 mL) were added $K_3PO_4$ (315.14 mg, 1.485 mmol) and 2nd Generation XPhos Precatalyst/X-Phos aminobiph (51 mg, 0.065 mmol) in portions at room temperature. The resulting mixture was stirred for an additional 2 hours at 65° C., then cooled to room temperature and extracted with ethyl acetate (3×10 mL). The combined organic layers were washed with brine (3×10 mL), dried over anhydrous $Na_2SO_4$, filtered, and concentrated under reduced pressure to give a residue, which was purified by reverse-phase flash chromatography (column: C18 silica gel; mobile phase: MeCN in water (10 mmol/L $NH_4HCO_3$), 60% to 80% gradient in 10 min; detector: UV 254 nm) to give the desired product as a yellow solid. (ESI, m/z): 899/901 $[M+H]^+$.

Step D: Synthesis of 2-amino-4-(4-((R)-1-(2-aminopyridin-3-yl)ethyl)-8-chloro-2-(((S)-4,4-difluoro-1-methylpyrrolidin-2-yl)methoxy)-10-fluoro-5,6-dihydro-4H-[1,4]oxazepino[5,6,7-de]quinazolin-9-yl)-7-fluorobenzo[b]thiophene-3-carbonitrile (741 and 762). To a stirred solution of 5-5 (85 mg, 0.085 mmol) in DCM (0.9 mL, 14.158 mmol) was added TFA (0.3 mL, 4.03 mmol) dropwise. The resulting mixture was stirred an additional 1 hour at room temperature and basified to pH 8 with saturated $NaHCO_3$(aq.). The resulting mixture was extracted with $CH_2Cl_2$ (2×6 mL). The combined organic layers were washed with brine (2×6 mL) and dried over anhydrous $Na_2SO_4$. After filtration, the filtrate was concentrated under reduced pressure to give a crude residue, which was purified by prep-HPLC(Column: Kinetex 5 m EVO C18, 30 mm*150 mm; Mobile Phase A: water (10 mmol/L $NH_4HCO_3$), Mobile Phase B: ACN; Flow rate: 60 mL/min; Gradient: 40% B to 61% B in 10 min; Wave Length: 254 nm/220 nm; RT1 (min): 7.32/9.12) to afford 741 (polar) as an off-white solid and 762 (less polar) as an off-white solid. 741: (ESI, m/z): 699 $[M+H]^+$. $^1H$ NMR: (400 MHZ, DMSO-d6, ppm) δ 8.08 (s, 1H), 7.97 (d, J=4.9 Hz, 1H), 7.64 (d, J=7.5 Hz, 1H), 7.21 (dd, J=8.4, 5.3 Hz, 1H), 7.14 (t, J=8.9 Hz, 1H), 6.68 (dd, J=7.5, 4.9 Hz, 1H), 6.24 (q, J=6.9 Hz, 1H), 5.64 (s, 2H), 4.49-4.42 (m, 1H), 4.41-4.37 (m, 2H), 4.36-4.31 (m, 1H), 3.19-3.12 (m, 2H), 3.02-2.93 (m, 2H), 2.71 (d, J=4.5 Hz, 2H), 2.38 (s, 3H), 1.60 (d, J=6.8 Hz, 3H), 1.24 (s, 2H). 762: (ESI, m/z): 699 $[M+H]^+$. $^1H$ NMR: (400 MHZ, DMSO-d6, ppm) δ 8.08 (s, 1H), 7.97 (dd, J=4.9, 1.8 Hz, 1H), 7.64 (dd, J=7.6, 1.8 Hz, 1H), 7.20 (dd, J=8.4, 5.3 Hz, 1H), 7.14 (t, J=8.9 Hz, 1H), 6.67 (dd, J=7.5, 4.9 Hz, 1H), 6.30 (d, J=6.9 Hz, 1H), 5.76 (d, J=9.7 Hz, 2H), 4.57-4.48 (m, 1H), 4.47-4.35 (m, 2H), 4.22 (dd, J=11.9, 6.8 Hz, 1H), 4.03 (m, 1H), 3.17 (d, J=5.2 Hz, 2H), 2.98 (dt, J=12.8, 7.1 Hz, 2H), 2.74-2.56 (m, 3H), 2.38 (s, 3H), 1.57 (d, J=6.8 Hz, 2H), 1.23 (s, 1H).

Example 1h: Synthesis of 2-amino-4-((5S)-4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5-vinyl-5,6-dihydro-4H-[1,4]oxazepino[5,6,7-de]quinazolin-9-yl)-7-fluorobenzo[b]thiophene-3-carbonitrile (732 and 752).

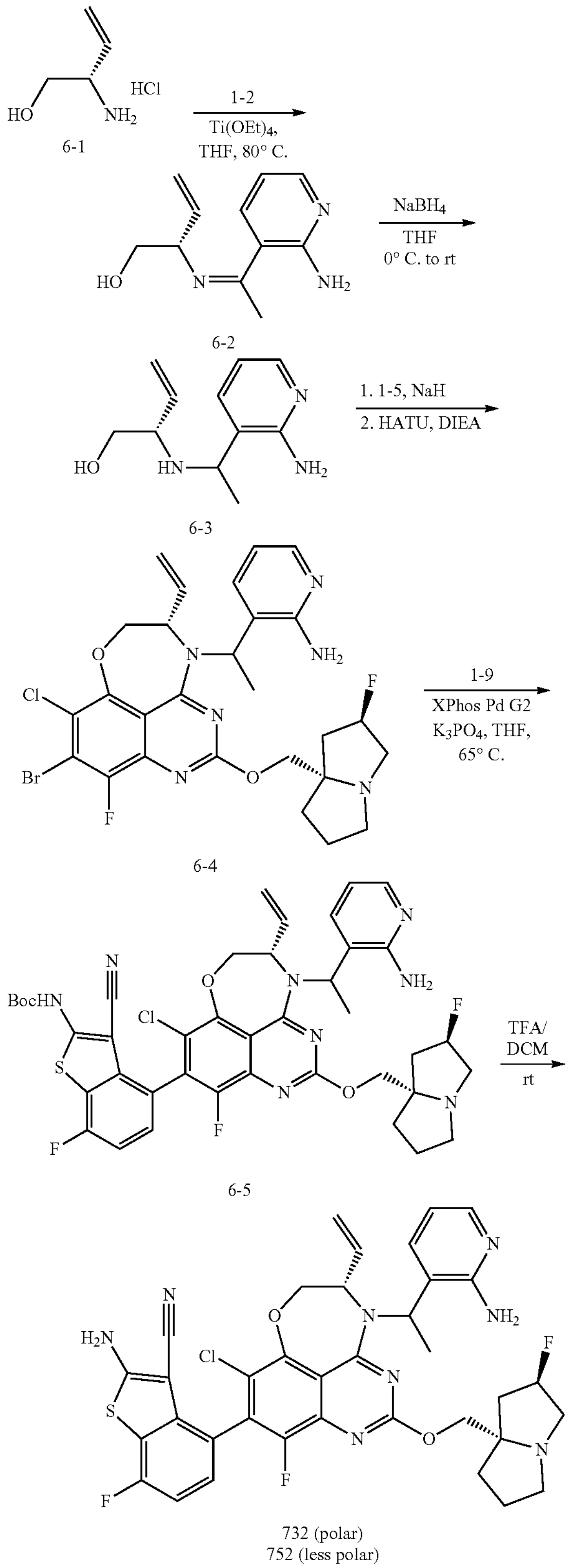

6-1
6-2
6-3
6-4
6-5
732 (polar)
752 (less polar)

Step A: Synthesis of (S,Z)-2-((1-(2-aminopyridin-3-yl)ethylidene)amino) but-3-en-1-ol (6-2). A solution of (2S)-2-aminobut-3-en-1-ol hydrochloride (6-1)(1 g, 8.09 mmol), 1-2 (1.65 g, 12.13 mmol) and Ti (OEt) 4 (9.2 g, 40.46 mmol)

in THF (30 mL) was stirred overnight at 80° C., then cooled to room temperature. The resulting mixture was used in the next step directly without further purification. (ESI, m/z): 206 [M+H]+.

Step B: Synthesis of (2S)-2-((1-(2-aminopyridin-3-yl) ethyl)amino) but-3-en-1-ol (6-3). A solution of 6-2 (1.3 g, 6.33 mmol) in THF (40 mL) was treated with $NaBH_4$ (718.78 mg, 18.99 mmol) for 10 minutes at 0° C. The resulting mixture was stirred for 3 hours at room temperature, then quenched with water at 0° C. and concentrated under vacuum to give a residue. The residue was purified by reverse-phase flash chromatography (column: C18; mobile phase: MeCN in water (10 mmol/L $NH_4HCO_3$), 10% to 40% gradient in 10 min; detector: UV 254 nm) to provided the desired product as a yellow oil. (ESI, m/z): 208 [M+H]+.

Step C-1: Synthesis of 5-(((2S)-2-((1-(2-aminopyridin-3-yl)ethyl)amino) but-3-en-1-yl)oxy)-7-bromo-6-chloro-8-fluoro-2-(((2R,7aS)-2-fluorotetrahydro-1H-pyrrolizin-7a (5H)-yl)methoxy) quinazolin-4-ol. A solution of 6-3 (250 mg, 1.20 mmol) and 1-5 (382 mg, 0.84 mmol) in THF (4 mL) was treated with NaH (434 mg, 10.85 mmol, 60%) for 20 minutes at 0° C. The resulting mixture was stirred for 3 hours at 50° C., then quenched with water at 0° C. and extracted with dichloromethane (3×10 mL). The combined organic layers were dried over anhydrous $Na_2SO_4$, filtered, and concentrated under reduced pressure to give the desired product, which was used in the next step directly without further purification. (ESI, m/z): 639 [M+H]+.

Step C-2: Synthesis of 3-(1-((S)-9-bromo-8-chloro-10-fluoro-2-(((2R,7aS)-2-fluorotetrahydro-1H-pyrrolizin-7a (5H)-yl)methoxy)-5-vinyl-5,6-dihydro-4H-[1,4]oxazepino [5,6,7-de]quinazolin-4-yl)ethyl) pyridin-2-amine (6-4). A solution of 5-(((2S)-2-((1-(2-aminopyridin-3-yl)ethyl) amino) but-3-en-1-yl)oxy)-7-bromo-6-chloro-8-fluoro-2-(((2R,7aS)-2-fluorotetrahydro-1H-pyrrolizin-7a (5H)-yl) methoxy) quinazolin-4-ol (660 mg, 0.31 mmol, 60%), HATU (176.47 mg, 0.46 mmol) and diisopropyl ethylamine (59.99 mg, 0.46 mmol) in DMF (10 mL) was stirred for 2 hours at 40° C. The resulting mixture was extracted with ethyl acetate (3×30 mL) and the combined organic layers were dried over anhydrous $Na_2SO_4$, filtered, and concentrated under reduced pressure to give a residue, which was purified by reverse-phase flash chromatography (column: C18; mobile phase: MeCN in water (10 mmol/L $NH_4HCO_3$), 80% to 100% gradient in 10 min; detector: UV 254 nm) to provide desired product as a brown solid. (ESI, m/z): 621 [M+H]+.

Step D: Synthesis of tert-butyl (4-((5S)-4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5-vinyl-5,6-dihydro-4H-[1,4]oxazepino[5,6,7-de]quinazolin-9-yl)-3-cyano-7-fluorobenzo[b]thiophen-2-yl)carbamate (6-5). A solution of 6-4 (160 mg, 0.25 mmol), 1-9 (312.01 mg, 0.771 mmol), $K_3PO_4$ (327.66 mg, 1.542 mmol) and Xphos Pd G2 (60.66 mg, 0.0771 mmol) in THF (16.0 mL) was stirred for 3 h at 65° C. The resulting mixture was extracted with ethyl acetate (3×30 mL). The combined organic layers were dried over anhydrous $Na_2SO_4$, filtered, and concentrated under reduced pressure to afford a residue, which was purified by reverse-phase flash chromatography (column: C18; mobile phase: MeCN in water (10 mmol/L $NH_4HCO_3$), 70% to 100% gradient in 10 min; detector: UV 254 nm) to give the desired product as a brown solid. (ESI, m/z): 833 [M+H]+.

Step E: Synthesis of 2-amino-4-((5S)-4-(1-(2-aminopyridin-3-yl)ethyl)-8-chloro-10-fluoro-2-(((2R,7aS)-2-fluorotetrahydro-1H-pyrrolizin-7a (5H)-yl)methoxy)-5-vinyl-5,6-dihydro-4H-[1,4]oxazepino[5,6,7-de]quinazolin-9-yl)-7-fluorobenzo[b]thiophene-3-carbonitrile (732 and 752). A solution of 6-5 (100 mg, 0.120 mmol) and TFA (1 mL) in DCM (3 mL) was stirred for 1 hour. The resulting mixture was concentrated under reduced pressure. The crude product (150 mg) was purified by prep-HPLC(Column: Kinetex 5 m EVO C18, 30 mm*150 mm; Mobile Phase A: water (10 mmol/L $NH_4HCO_3$), Mobile Phase B: ACN; Flow rate: 60 mL/min; Gradient: 40% B to 64% B in 10 min; Wave Length: UV 254 nm/222 nm; RT1 (min): 6.37/8.07) to afford 732 (peak 1; polar) and 752 (peak 2; less polar), each as a white solid. 732: (ESI, m/z): 733 [M+H]+. $^1$H NMR: (400 MHZ, DMSO-d6, ppm) δ 8.08 (d, J=9.8 Hz, 2H), 7.90 (dd, J=4.8, 1.6 Hz, 1H), 7.64 (d, J=7.4 Hz, 1H), 7.25-7.15 (m, 1H), 7.14-7.06 (m, 1H), 6.73-6.63 (m, 1H), 6.61-6.50 (m, 1H), 5.89-5.67 (m, 2H), 5.55-5.42 (m, 1H), 5.40-5.17 (m, 1H), 5.12-4.83 (m, 1H), 4.68-4.56 (m, 2H), 4.33 (d, J=12.4 Hz, 1H), 4.16-3.99 (m, 2H), 3.11 (s, 2H), 3.03 (s, 1H), 2.84 (s, 2H), 2.20-1.99 (m, 3H), 1.90-1.76 (m, 3H), 1.64 (d, J=6.8 Hz, 3H). 752: (ESI, m/z): 733 [M+H]+. $^1$H NMR: (400 MHZ, DMSO-d6, ppm) δ 8.06 (d, J=12.7 Hz, 2H), 8.01-7.85 (m, 1H), 7.68-7.60 (m, 1H), 7.25-7.17 (m, 1H), 7.16-7.06 (m, 1H), 6.71-6.62 (m, 1H), 6.61-6.47 (m, 1H), 6.01-5.42 (m, 3H), 5.41-5.20 (m, 1H), 5.19-4.94 (m, 1H), 4.87-4.69 (m, 1H), 4.56 (d, J=10.2 Hz, 1H), 4.48-4.38 (m, 1H), 4.10 (s, 1H), 3.98 (d, J=12.1 Hz, 1H), 3.10 (s, 2H), 3.03 (s, 1H), 2.84 (s, 1H), 2.18-2.00 (m, 3H), 1.87-1.75 (m, 3H), 1.64-1.50 (m, 3H), 1.23-1.22 (m, 1H).

Example 1i: Synthesis of 2-amino-4-((R)-4-((S)-1-(2-aminopyridin-3-yl)-2,2-difluoroethyl)-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (618).

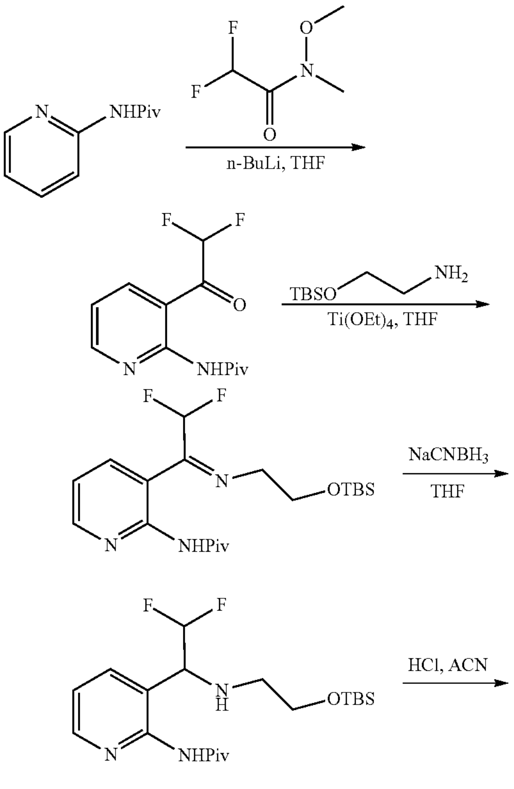

-continued

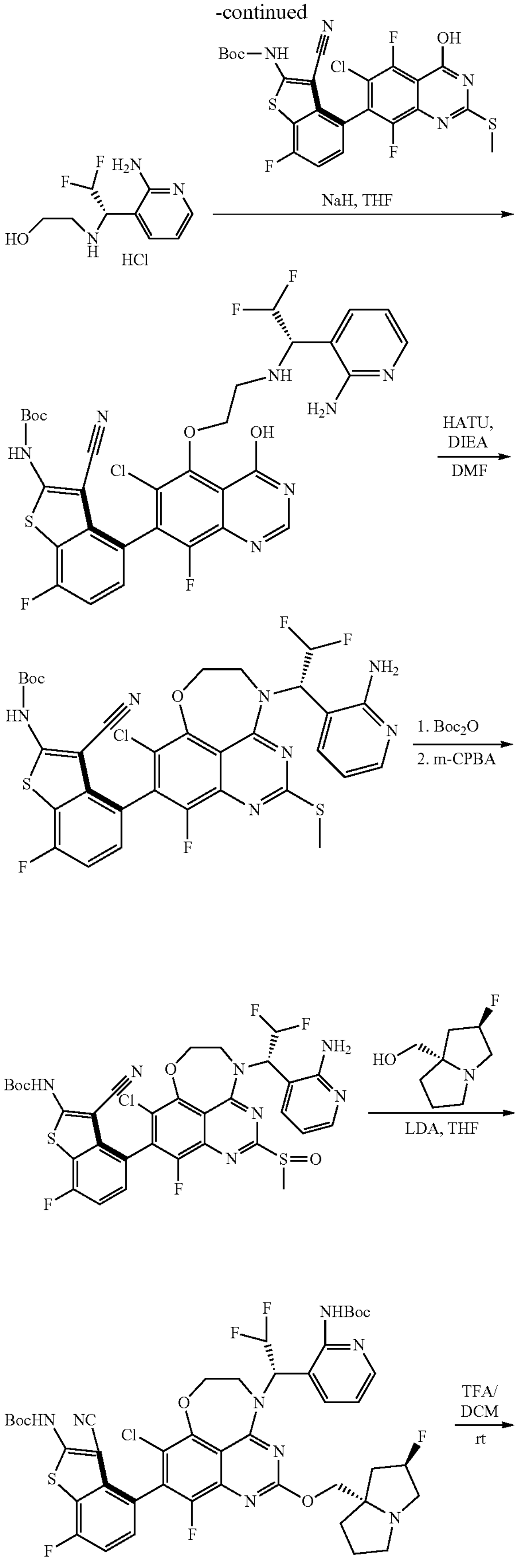

-continued

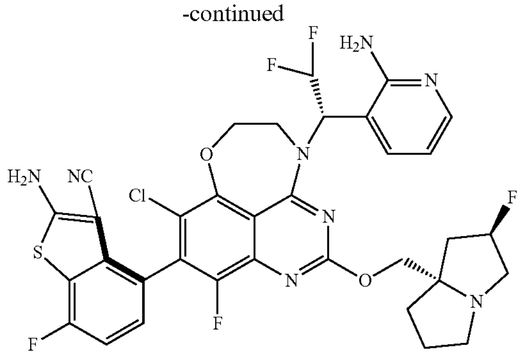

Step A: Synthesis of N-(3-(2,2-difluoroacetyl)pyridin-2-yl) pivalamide. To a solution of 2,2-dimethyl-N-(pyridin-2-yl) propanamide (10 g, 56.106 mmol) in THF (30 mL) was added n-BuLi (47.13 mL, 117.823 mmol) at −78° C. under nitrogen atmosphere and the reaction was stirred for 1 hour at 0° C. 2,2-difluoro-N-methoxy-N-methylacetamide (8.58 g, 61.717 mmol) was added to the solution at −78° C. and the reaction mixture was stirred overnight at room temperature. The reaction was quenched with MeOH (2 eq) at 0° C. and concentrated under vacuum to give a residue. The residue was purified by silica gel column chromatography, eluted with $CH_2Cl_2$/MeOH (10:1) to afford the desired product as a yellow oil. (ESI, m/z): 257.05 $[M+H]^+$.

Step B: Synthesis of (Z)—N-(3-(1-((2-((tert-butyldimethylsilyl)oxy)ethyl)imino)-2,2-difluoroethyl) pyridin-2-yl) pivalamide. A solution of N-(3-(2,2-difluoroacetyl)pyridin-2-yl) pivalamide (6 g, 23.414 mmol), Ti (OEt) 4 (32.05 g, 140.484 mmol) and (2-aminoethoxy)(tert-butyl)dimethylsilane (5.75 g, 32.780 mmol) in THF (40 mL) was stirred for 1 hour at 60° C. under nitrogen atmosphere. The reaction was then cooled to room temperature and quenched with water. The resulting mixture was filtered and the filter cake was washed with dichloromethane (3×10 mL). The filtrate was concentrated under reduced pressure to give the desired product which was used in the next step directly without further purification. (ESI, m/z): 414.10 $[M+H]^+$.

Step C: Synthesis of N-(3-(1-((2-((tert-butyldimethylsilyl)oxy)ethyl)amino)-2,2-difluoroethyl) pyridin-2-yl) pivalamide. A mixture of N-(3-[(1Z)-1-((2-[(tert-butyldimethylsilyl)oxy]ethylimino)-2,2-difluoroethyl]pyridin-2-yl-2,2-dimethylpropanamide (8 g, 19.343 mmol) and $NaBH_3CN$ (12.16 g, 193.430 mmol) in THF (80.0 mL) was stirred overnight at 60° C. under nitrogen atmosphere. The reaction was cooled to room temperature and quenched with water. The aqueous layer was extracted with dichloromethane (3×30 mL). The extracts were combined, washed with brine and dried over sodium sulfate. The product was filtered and the filtrate was concentrated under vacuum to give a residue. The residue was purified by silica gel column chromatography and eluted with petroleum ether/ethyl acetate (1:1) to afford the desired product as a yellow semi-solid. (ESI, m/z): 417.10 $[M+H]^+$.

Step D: Synthesis of(S)-2-((1-(2-aminopyridin-3-yl)-2,2-difluoroethyl)amino) ethan-1-ol. A solution of N-(3-(1-((2-((tert-butyldimethylsilyl)oxy)ethyl)amino)-2,2-difluoroethyl) pyridin-2-yl) pivalamide (3 g, 7.218 mmol) in hydrogen chloride (20 mL in dioxane, 40.000 mmol) and ACN (5 mL) was stirred overnight at 100° C. under nitrogen atmosphere. The reaction was cooled to room temperature, quenched with sat. $NaHCO_3$(aq.), and extracted with ethyl acetate (3×5 mL). The resulting mixture was concentrated under vacuum to give the crude product. The crude product (3 g) was purified by Prep-HPLC(Column: CHIRAL ART Cellulose-SB 3*25 cm, 5 m; Mobile Phase A: HEX (0.1% DEA), Mobile Phase B: EtOH; Flow rate: 20 mL/min; Gradient: isocratic 20; Wave Length: UV 254/220 nm; RT1 (min): 4.62; RT2 (min): 5.81; Sample Solvent: EtOH; Injection Volume: 0.6 mL; Number of Runs: 42) to afford the desired product as a yellow oil. (ESI, m/z): 218.00 $[M+H]^+$.

Step E: Synthesis of tert-butyl (4-((R)-5-(2-(((S)-1-(2-aminopyridin-3-yl)-2,2-difluoroethyl)amino)ethoxy)-6-chloro-8-fluoro-4-hydroxy-2-(methylthio) quinazolin-7-yl)-3-cyano-7-fluorobenzo[b]thiophen-2-yl)carbamate. A solution of(S)-2-((1-(2-aminopyridin-3-yl)-2,2-difluoroethyl)amino) ethan-1-ol (500 mg, 2.302 mmol) in THF (5 mL) was treated with NaH (497.15 mg, 20.718 mmol) for 30 minutes at 0° C. followed by the addition of tert-butyl N-(4-[6-chloro-5,8-difluoro-4-hydroxy-2-(methylsulfanyl) quinazolin-7-yl]-3-cyano-7-fluoro-1-benzothiophen-2-yl-carbamate (1018.27 mg, 1.842 mmol) in THF (1 mL). The resulting mixture was stirred for 2 hours at 50° C., cooled to room temperature, and quenched with sat. $NH_4Cl$ (aq.) at 0° C. The resulting mixture was extracted with EtOAc (3×30 mL). The combined organic layers were washed with brine (1×100 mL) and dried over anhydrous $Na_2SO_4$. After filtration, the filtrate was concentrated under reduced pressure to give the desired product which was used in the next step directly without further purification.

Step F: Synthesis of tert-butyl (4-((R)-4-((S)-1-(2-amino-pyridin-3-yl)-2,2-difluoroethyl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl) carbamate. A solution of tert-butyl (4-((R)-5-(2-(((S)-1-(2-aminopyridin-3-yl)-2,2-difluoroethyl)amino)ethoxy)-6-chloro-8-fluoro-4-hydroxy-2-(methylthio) quinazolin-7-yl)-3-cyano-7-fluorobenzo[b]thiophen-2-yl)carbamate (1.4 g, 1.866 mmol), HATU (1.42 g, 3.732 mmol) and DIEA (0.72 g, 5.598 mmol) in DMF (14.0 mL) was stirred for 1 hour at 50° C. under nitrogen atmosphere. The reaction was cooled to room temperature and quenched with water. The precipitated solids were collected by filtration and washed with water (3×10 mL). The resulting solid was dried under vacuum and purified by reverse-phase flash chromatography (column, C18; mobile phase, MeCN in Water (10 mmol/L $NH_4HCO_3$), 10% to 100% gradient in 15 minutes; detector, UV 254 nm) to afford the desired product as a brown solid. (ESI, m/z): 731.95 $[M+H]^+$.

Step G: Synthesis of di-tert-butyl (3-((S)-1-((R)-9-(2-((tert-butoxycarbonyl)amino)-3-cyano-7-fluorobenzo[b] thiophen-4-yl)-8-chloro-10-fluoro-2-(methylthio)-5,6-dihydro-4H-[1,4]oxazepino[5,6,7-de]quinazolin-4-yl)-2,2-difluoroethyl) pyridin-2-yl)iminodicarbonate. A solution of (4-((R)-4-((S)-1-(2-aminopyridin-3-yl)-2,2-difluoroethyl)-8-chloro-10-fluoro-2-(methylthio)-5,6 dihydro-4H-[1,4] oxazepino[5,6,7-de]quinazolin-9-yl)-3-cyano-7-fluorobenzo[b]thiophen-2-yl)carbamate (3.5 g, 4.780 mmol), $(Boc)_2O$ (10.43 g, 47.800 mmol), DMAP (0.58 g, 4.780 mmol) and DIEA (1.85 g, 14.340 mmol) in dichloromethane (35 mL) was stirred for 2 hour at 50° C. under nitrogen atmosphere. The reaction mixture was cooled to room temperature, quenched with water, and extracted with dichloromethane (3×20 mL). The combined organic layers were washed with brine (1×60 mL) and dried over anhydrous $Na_2SO_4$. After filtration, the filtrate was concentrated under reduced pressure. The resulting residue was purified by silica gel column chromatography and eluted with petroleum ether/ethyl acetate (1:1) to afford the desired product as a yellow solid. (ESI, m/z): 932.10 $[M+H]^+$.

Step H: Synthesis of di-tert-butyl (3-((1S)-1-((9R)-9-(2-((tert-butoxycarbonyl)amino)-3-cyano-7-fluorobenzo[b] thiophen-4-yl)-8-chloro-10-fluoro-2-(methylsulfinyl)-5,6-dihydro-4H-[1,4]oxazepino[5,6,7-de]quinazolin-4-yl)-2,2-difluoroethyl) pyridin-2-yl)iminodicarbonate. A solution of di-tert-butyl (3-((S)-1-((R)-9-(2-((tert-butoxycarbonyl) amino)-3-cyano-7-fluorobenzo[b]thiophen-4-yl)-8-chloro-10-fluoro-2-(methylthio)-5,6-dihydro-4H-[1,4]oxazepino[5,6,7-de]quinazolin-4-yl)-2,2-difluoroethyl) pyridin-2-yl) iminodicarbonate (740 mg, 0.717 mmol) and m-CPBA (111.31 mg, 0.645 mmol) in ethyl acetate (7.4 mL) was stirred for 1 hour at room temperature, quenched with saturated $NaHCO_3$(aq.), and extracted with EtOAc (3×50 mL). The combined organic layers were washed with brine (1×100 mL) and dried over anhydrous $Na_2SO_4$. After filtration, the filtrate was concentrated under reduced pressure to give the desired product which was used in the next step directly without further purification. (ESI, m/z): 948.10 $[M+H]^+$.

Step I: Synthesis of tert-butyl (4-((R)-4-((S)-1-(2-((tert-butoxycarbonyl)amino)pyridin-3-yl)-2,2-difluoroethyl)-8-chloro-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-9-yl)-3-cyano-7-fluorobenzo[b]thiophen-2-yl)carbamate. A solution of [(2R, 7aS)-2-fluoro-hexahydropyrrolizin-7a-yl]methanol (236.87 mg, 1.488 mmol) and LDA (239.08 mg, 2.232 mmol) in THF (7.8 mL) was stirred for 30 minutes at 0° C. under nitrogen atmosphere. To the above mixture was added di-tert-butyl (3-((1S)-1-((9R)-9-(2-((tert-butoxycarbonyl) amino)-3-cyano-7-fluorobenzo[b]thiophen-4-yl)-8-chloro-10-fluoro-2-(methylsulfinyl)-5,6-dihydro-4H-[1,4]oxazepino[5,6,7-de]quinazolin-4-yl)-2,2-difluoroethyl) pyridin-2-yl)iminodicarbonate (780 mg, 0.744 mmol) dropwise at 0° C. and the resulting mixture was stirred for an additional 1 hour at room temperature. The reaction was quenched with sat. $NH_4Cl$ (aq.) at room temperature and extracted with EtOAc (3×30 mL). The combined organic layers were washed with brine (1×100 mL) and dried over anhydrous $Na_2SO_4$. After filtration, the filtrate was concentrated under reduced pressure to give the desired product which was used in the next step directly without further purification. (ESI, m/z): 943.15 $[M+H]^+$.

Step J: Synthesis of 2-amino-4-((R)-4-((S)-1-(2-amino-pyridin-3-yl)-2,2-difluoroethyl)-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile. To a solution of tert-butyl (4-((R)-4-((S)-1-(2-((tert-butoxy-carbonyl)amino)pyridin-3-yl)-2,2-difluoroethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate (1.5 g, 1.779 mmol) in dichloromethane (10 mL) was added TFA (5 mL) and the mixture was stirred for 30 minutes at 0° C. under nitrogen atmosphere. The reaction was quenched with sat. $NaHCO_3$(aq.) at room temperature and extracted with EtOAc (3×10 mL). The combined extracts were washed with brine and dried over sodium sulfate. The product was filtered and the filtrate was concentrated under vacuum to give the crude product. The crude product was purified by Prep-HPLC(Column: Kinetex 5 m EVO C18, 30 mm*150 mm; Mobile Phase A: Water (10 mmol/L $NH_4HCO_3$), Mobile Phase B: ACN; Flow rate: 60 mL/min; Gradient: 42% B to 56% B in 10 min; Wave Length: UV 254 nm/220 nm; RT1 (min): 7.53/10.03) to afford the desired product as a white solid. (ESI, m/z):

742.80 [M+H]$^+$. $^1$H NMR: (400 MHZ, DMSO-d6, ppm) δ 8.26-7.95 (m, 3H), 7.75 (dd, J=7.4, 1.6 Hz, 1H), 7.36-6.84 (m, 3H), 6.70 (dd, J=7.6, 4.8 Hz, 1H), 6.58 (m, 1H), 6.03 (s, 2H), 5.38-5.14 (m, 1H), 4.57 (ddd, J=12.2, 7.6, 2.0 Hz, 1H), 4.40 (ddd, J=12.0, 5.8, 2.0 Hz, 1H), 4.11 (s, 2H), 3.79 (m, 1H), 3.57 (m, 1H), 3.17-2.95 (m, 3H), 2.82 (td, J=9.2, 8.6, 4.0 Hz, 1H), 2.23-2.13 (m, 1H), 2.07 (d, J=2.0 Hz, 1H), 2.04-1.97 (m, 1H), 1.89-1.72 (m, 3H).

Example 1j: Synthesis of 2-amino-4-((9R)-4-(1-(2-aminopyridin-3-yl) but-3-en-1-yl)-8-chloro-10-fluoro-2-(((2R, 7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (623).

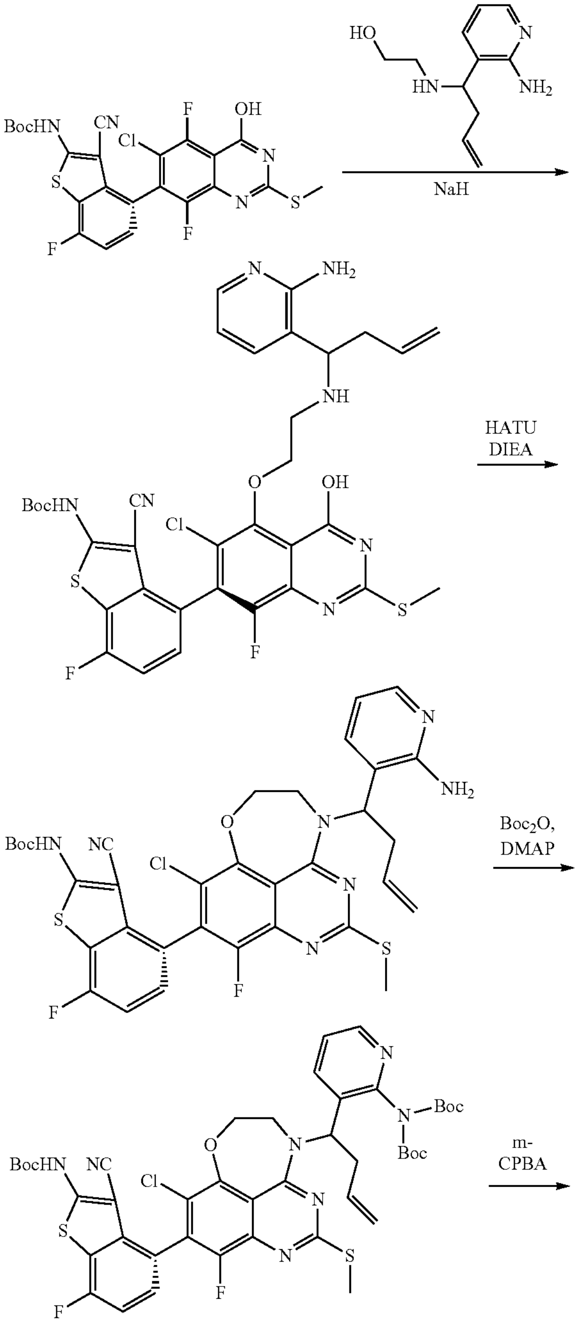

-continued

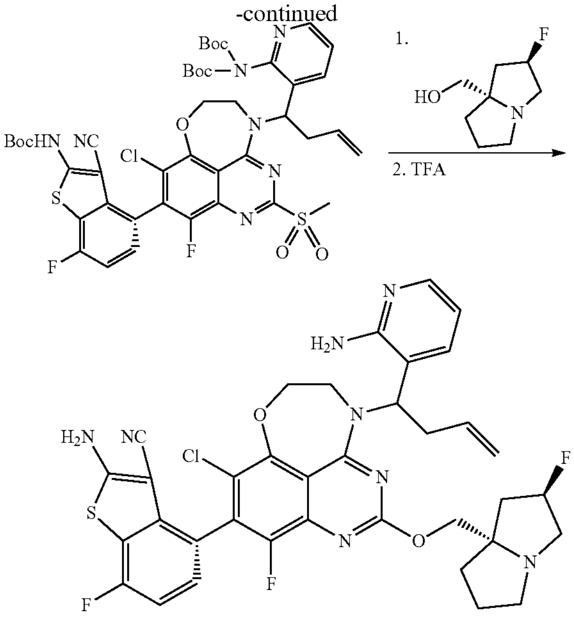

Step A: Synthesis of tert-butyl (4-((7R)-5-(2-((1-(2-aminopyridin-3-yl) but-3-en-1-yl)amino) ethoxy)-6-chloro-8-fluoro-4-hydroxy-2-(methylthio) quinazolin-7-yl)-3-cyano-7-fluorobenzo[b]thiophen-2-yl)carbamate. A mixture of tert-butyl (R)-(4-(6-chloro-5,8-difluoro-4-hydroxy-2-(methylthio) quinazolin-7-yl)-3-cyano-7-fluorobenzo[b] thiophen-2-yl)carbamate (150 mg, 0.27 mmol) and 2-((1-(2-aminopyridin-3-yl) but-3-en-1-yl)amino) ethan-1-ol (56 mg, 0.27 mmol) was stirred in dioxane (8 mL) at 0° C. NaH (97 mg, 2.43 mmol, 60% suspension in mineral oil) was added to the mixture in portions. Upon completing the addition, the mixture was heated to 80° C. for 2 hours. The reaction was cooled to room temperature and quenched with sat. $NH_4Cl$, which was followed by the addition of ethyl acetate. The organics were separated and dried over $Na_2SO_4$. The product was filtered and the filtrate was concentrated. The resulting residue was purified by silica gel chromatography eluting with 0-10% MeOH/DCM. The desired fractions were concentrated to yield the title compound as a white solid. ESI [M+H]$^+$: 739.1.

Step B: Synthesis of tert-butyl (4-((9R)-4-(1-(2-aminopyridin-3-yl) but-3-en-1-yl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl)carbamate. A mixture of tert-butyl (4-((7R)-5-(2-((1-(2-aminopyridin-3-yl) but-3-en-1-yl)amino) ethoxy)-6-chloro-8-fluoro-4-hydroxy-2-(methylthio) quinazolin-7-yl)-3-cyano-7-fluorobenzo[b]thiophen-2-yl)carbamate (95 mg, 0.128 mmol), (1-[Bis(dimethylamino)methylene]-1H-1,2,3-triazolo[4,5-b]pyridinium 3-oxid hexafluorophosphate)(HATU)(74 mg, 0.193 mmol), and N,N-Diisopropylethylamine (68 μL, 0.384 mmol) was stirred in dichloromethane (5 mL) for 2 hours. Water (5 mL) was added and the organics were separated. The aqueous layer was extracted with DCM (5 mL×2). The combined organics were dried over $Na_2SO_4$, filtered and concentrated. The residue was purified by silica gel chromatography eluting with 0-50% EtOAc/hexanes to afford the desired product as white solid. ESI [M+H]$^+$: m/z: 722.2.

Step C: Synthesis of tert-butyl (tert-butoxycarbonyl)(3-(1-((R)-9-(2-((tert-butoxycarbonyl)amino)-3-cyano-7-fluorobenzo[b]thiophen-4-yl)-8-chloro-10-fluoro-2-(methylthio)-5,6-dihydro-4H-[1,4]oxazepino[5,6,7-de]quinazolin- 4-yl) but-3-en-1-yl) pyridin-2-yl)carbamate. A mixture of tert-butyl (4-((9R)-4-(1-(2-aminopyridin-3-yl) but-3-en-1-yl)-8-chloro-10-fluoro-2-(methylthio)-5,6-dihydro-4H-[1,4] oxazepino[5,6,7-de]quinazolin-9-yl)-3-cyano-7-fluorobenzo[b]thiophen-2-yl)carbamate (34 mg, 0.047 mmol), di-tert-butyl decarbonate (51 mg, 0.235 mmol), and 4-dimethylaminopyridine (29 mg, 0.235 mmol) was stirred in DCM (3 mL) for 3 hours. Water (3 mL) was added and the organic layer was separated. The aqueous layer was extracted with dichloromethane (3 mL×2). The combined organics were dried over $Na_2SO_4$, filtered, and concentrated. The resulting residue was purified by silica gel chromatography eluting with 0-30% EtOAc/hexanes to afford the desired product as a white solid. ESI $[M+H]^+$: 922.2.

Step D: Synthesis of tert-butyl (tert-butoxycarbonyl)(3-(1-((R)-9-(2-((tert-butoxycarbonyl)amino)-3-cyano-7-fluorobenzo[b]thiophen-4-yl)-8-chloro-10-fluoro-2-(methylsulfonyl)-5,6-dihydro-4H-[1,4]oxazepino[5,6,7-de] quinazolin-4-yl) but-3-en-1-yl) pyridin-2-yl)carbamate. To a solution of tert-butyl (tert-butoxycarbonyl)(3-(1-((R)-9-(2-((tert-butoxycarbonyl)amino)-3-cyano-7-fluorobenzo[b] thiophen-4-yl)-8-chloro-10-fluoro-2-(methylthio)-5,6-dihydro-4H-[1,4]oxazepino[5,6,7-de]quinazolin-4-yl) but-3-en-1-yl) pyridin-2-yl)carbamate (22 mg, 0.024 mmol) in DCM (3 mL) at 0° C. was slowly added meta-chloroperoxybenzoic acid (13 mg, 0.05 mmol). The product was warmed to room temperature and stirred for 1 hour. Water (3 mL) was added and the organic layers were separated. The aqueous layer was extracted with DCM (3 mL×2). The combined organics were dried over $Na_2SO_4$, filtered and concentrated. The residue was purified by silica gel chromatography eluting with 0-100% EtOAc/hexanes to afford the desired compound as white solid. ESI $[M+H]^+$: m/z 954.2.

Step E: Synthesis of tert-butyl (tert-butoxycarbonyl)(3-(1-((R)-9-(2-((tert-butoxycarbonyl)amino)-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-4-yl) but-3-en-1-yl) pyridin-2-yl)carbamate. A mixture of tert-butyl (tert-butoxycarbonyl)(3-(1-((R)-9-(2-((tert-butoxycarbonyl) amino)-3-cyano-7-fluorobenzo[b]thiophen-4-yl)-8-chloro-10-fluoro-2-(methylsulfonyl)-5,6-dihydro-4H-[1,4]oxazepino[5,6,7-de]quinazolin-4-yl) but-3-en-1-yl) pyridin-2-yl) carbamate (16 mg, 0.017 mmol) and ((2R,7aS)-2-fluorotetrahydro-1H-pyrrolizin-7a (5H)-yl) methanol (6.7 mg, 0.051 mmol) with molecular sieves in toluene (3 mL) was stirred at 0° C. for 10 minutes. Sodium tert-butoxide (5.0 mg, 0.051 mmol) was added to the reaction, and the mixture was stirred for another hour at room temperature. The product was filtered, and the filtrate was dried on a rotatory evaporator. The residue was purified by silica gel chromatography eluting with 0-20% MeOH/DCM to afford the title compound. $[M+2H]^+$: m/z=517.2; Found: 517.0.

Step F: Synthesis of 2-amino-4-((9R)-4-(1-(2-aminopyridin-3-yl) but-3-en-1-yl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile. To a solution of tert-butyl (tert-butoxycarbonyl)(3-(1-((R)-9-(2-((tert-butoxycarbonyl)amino)-3-cyano-7-fluorobenzo[b]thiophen-4-yl)-8-chloro-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-4-yl) but-3-en-1-yl) pyridin-2-yl)carbamate (5 mg, 0.005 mmol) in DCM (2 mL) at 0° C. was slowly added trifluoroacetic acid (0.5 mL). The mixture was warmed to room temperature and stirred for an additional 30 minutes. Solvent was removed and the crude product was purified via prep-HPLC on a C18 column (0-60% $MeCN/H_2O$ containing 0.1% HCOOH) to afford the title compound. ESI $[M+H]^+$: m/z 732.2.

Example 1k: Synthesis of 2-amino-4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (615).

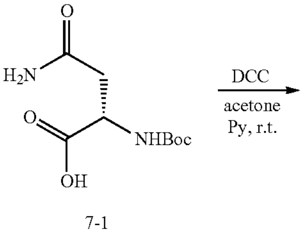

7-1

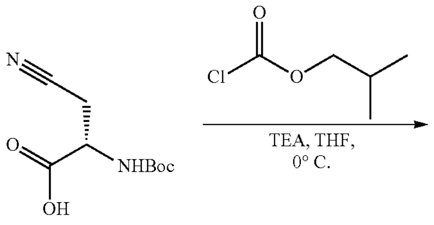

7-2

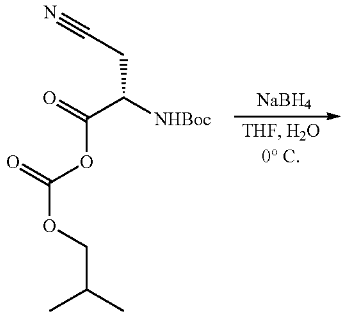

7-3

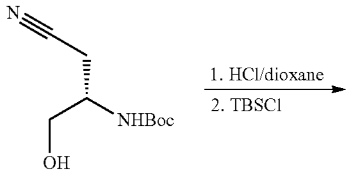

7-4

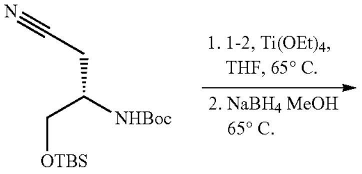

7-5

-continued

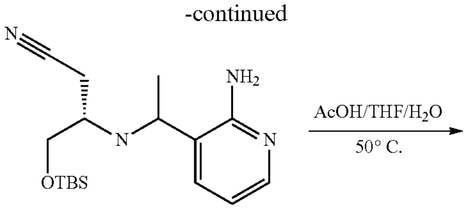

7-6

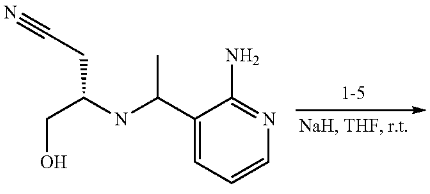

7-7

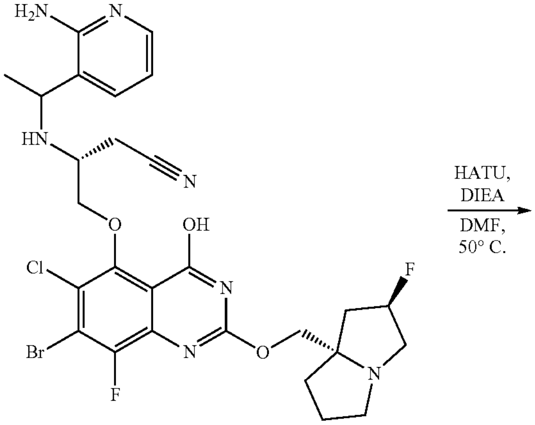

7-8

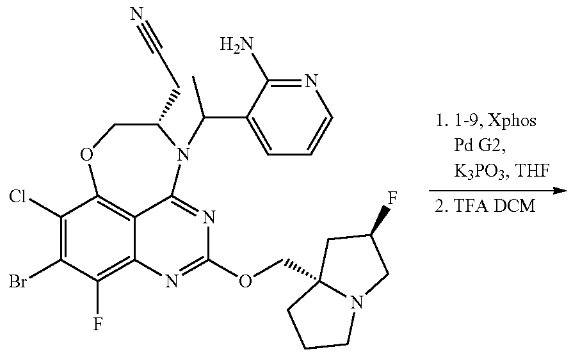

7-9

-continued

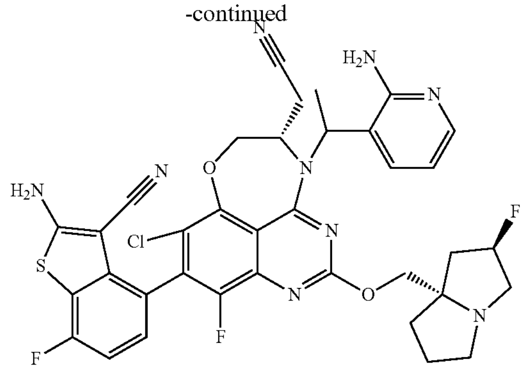

615

Step A: Synthesis of(S)-2-((tert-butoxycarbonyl)amino)-3-cyanopropanoic acid (7-2). To a stirred solution of Boc-Asn (7-1) (9 g, 38.75 mmol) in anhydrous pyridine (50 mL) was added a solution of DCC (8.80 g, 42.62 mmol) in acetone (90 mL) and the resulting mixture was stirred for 3 hours. The mixture was then filtered and most of the pyridine was removed under reduced pressure to give a residue. The residue was dissolved in dichloromethane, washed with 2N HCl and water, dried over magnesium sulfate, filtered, and concentrated under reduced pressure to provide the desired product as an oil, which was used in the next step without further purification. (ESI, m/z): 215 $[M+H]^+$.

Step B: Synthesis of(S)—(S)-2-((tert-butoxycarbonyl) amino)-3-cyanopropanoic (isobutyl carbonic) anhydride (7-3). A solution of 7-2 (4.4 g, 20.54 mmol) in THF (44 mL) was treated with TEA (2.08 g, 20.54 mmol) at 0° C., followed by addition of 2-methylpropyl carbonochloridate (3.09 g, 22.59 mmol) dropwise. The reaction mixture was stirred for 2 hours at 0° C., then filtered through a coarse scintered glass funnel to afford the desired product in THF (44 mL), which was used in the next step directly without further purification.

Step C: Synthesis of tert-butyl(S)-(1-cyano-3-hydroxy-propan-2-yl)carbamate (7-4). In a flask, a solution of $NaBH_4$ (1.54 g, 40.72 mmol) in water (18 mL) cooled in an ice water bath. The filtered solution of the mixed anhydride (7-3) from the previous step in THF (44 mL) was added dropwise to the cold sodium borohydride solution and the resulting mixture was stirred for 3 hour at 0° C. The reaction was quenched with water and the mixture was extracted with ethyl acetate. The extracts were combined, washed with brine, dried over sodium sulfate, filtered, and concentrated under reduced pressure to give a residue. The residue was purified by silica gel column chromatography, eluted with petroleum ether/ethyl acetate (3:1) to afford the desired product as a colorless oil. (ESI, m/z): 201 $[M+H]^+$.

Step D-1: Synthesis of(S)-3-amino-4-hydroxybutanenitrile. A solution of 7-4 (1.4 g, 6.99 mmol) in HCl in 1,4-dioxane (4 M, 15 mL) was stirred at room temperature for 4 hours. The reaction mixture was concentrated to give the desired product, which was used directly in the next step without purification. (ESI, m/z): 101 $[M+H]^+$.

Step D-2: Synthesis of(S)-3-amino-4-((tert-butyldimethylsilyl)oxy) butanenitrile (7-5). To a stirred solution of (3S)-3-amino-4-hydroxybutanenitrile (1.6 g, 15.98 mmol) in anhydrous DCM (16 mL) were added imidazole (4.35 g, 63.92 mmol) and TBSCl (4.82 g, 31.96 mmol) and the mixture was stirred for 2 hours. The resulting mixture was extracted with DCM (3×20 mL), dried over anhydrous $Na_2SO_4$, filtered, and concentrated under reduced pressure to give crude product, which was purified by silica gel column chromatography and eluted with petroleum ether/ethyl acetate (3:1 to 1:1) to afford the desired compound. (ESI, m/z): 215 $[M+H]^+$.

Step E: Synthesis of (3S)-3-((1-(2-aminopyridin-3-yl)ethyl)amino)-4-((tert-butyldimethylsilyl)oxy) butanenitrile (7-6). A solution of 7-5 (890 mg, 4.15 mmol), 1-2 (847 mg, 6.22 mmol), and Ti (OEt) 4 (7.58 g, 33.20 mmol) in THF (45 mL) was stirred overnight at 65° C. The reaction mixture was cooled to room temperature, quenched with water, extracted with DCM (3×20 mL), dried over anhydrous $Na_2SO_4$, filtered, and concentrated under reduced pressure to afford the intermediate imide. Then, to a stirred solution of this intermediate in anhydrous MeOH (20 mL) was added $NaBH_4$ (471.15 mg, 12.454 mmol) at 0° C. and the resulting mixture was stirred for 3 hours at 65° C. The reaction mixture was cooled with an ice-water bath and quenched with water at 0° C. The resulting mixture was extracted with DCM (3×20 mL), dried over anhydrous $Na_2SO_4$, filtered, and concentrated under reduced pressure to give crude product, which was purified by silica gel column chromatography and eluted with petroleum ether/ethyl acetate (10:1 to 1:1) to afford the desired product. (ESI, m/z): 335 $[M+H]^+$.

Step F: Synthesis of (3S)-3-((1-(2-aminopyridin-3-yl)ethyl)amino)-4-hydroxybutanenitrile (7-7). To a stirred solution of 7-6 (380 mg, 1.13 mmol) in anhydrous acetic acid (1.8 mL) were added THF (0.6 mL) and water (0.6 mL) at room temperature and the mixture was stirred overnight at 50° C. The reaction mixture was cooled to room temperature and concentrated under reduced pressure to give the desired product, which was used in the next step directly without further purification. (ESI, m/z): 221 $[M+H]^+$.

Step G: Synthesis of (3R)-3-((1-(2-aminopyridin-3-yl)ethyl)amino)-4-((7-bromo-6-chloro-8-fluoro-2-(((2R,7aS)-2-fluorotetrahydro-1H-pyrrolizin-7a (5H)-yl)methoxy)-4-hydroxyquinazolin-5-yl)oxy) butanenitrile (7-8). To a stirred solution of 7-7 (350 mg, 1.58 mmol) and 1-5 (575.39 mg, 1.27 mmol, 0.8 equiv) in anhydrous THF (3.5 mL) was added NaH (571 mg, 14.3 mmol, 60%) at 0° C. and the mixture was stirred for 3 hours. The reaction was then quenched with water (5 mL) at 0° C. and the aqueous layer was extracted with EtOAc (10 mL×3). The extracts were combined, washed with brine, dried over sodium sulfate, filtered, and concentrated under reduced pressure to give crude product, which was purified by column chromatography using 10 to 20% MeOH in DCM to afford the desired compound. (ESI, m/z): 652 $[M+H]^+$.

Step H: Synthesis of 2-((5S)-4-(1-(2-aminopyridin-3-yl)ethyl)-9-bromo-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-5-yl) acetonitrile (7-9). To a stirred solution of 7-8 (400 mg, 0.61 mmol) in anhydrous DMF was added HATU (349 mg, 0.91 mmol) and DIEA (118 mg, 0.91 mmol). The mixture was stirred for 2 hours at 50° C., then cooled to room temperature and quenched with water. The resulting mixture was extracted with ethyl acetate (3×10 mL), dried over anhydrous $Na_2SO_4$, filtered, and concentrated under reduced pressure to give crude product, which was purified by column chromatography using 10 to 20% MeOH in DCM to afford the desired product, which was further purified by prep-HPLC(Column: Kinetex 5 m EVO C18, 30 mm*150 mm; Mobile Phase A: water (10 mmol/L $NH_4HCO_3$), Mobile Phase B: ACN; Flow rate: 60 mL/min; Gradient: 45% B to 61% B in 10 min; Wave Length: UV 254 nm/220 nm; RT1 (min): 7.88) to afford the desired product as an off-white solid. (ESI, m/z): 634 $[M+H]^+$.

Step I-1: Synthesis of tert-butyl (4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate. To a stirred solution of 7-9 (37 mg, 0.058 mmol) in anhydrous THF (3.7 mL) were added 1-9 (70 mg, 0.174 mmol) and $K_3PO_4$ (37 mg, 0.17 mmol) followed by a catalytic amount of 2nd Generation XPhos precatalyst (13 mg, 0.017 mmol). The reaction mixture was stirred at 65° C. for 6 hours, then cooled to room temperature and quenched by the addition of water (8 mL) and extracted with ethyl acetate (3×15 mL). The combined organic phase was washed with brine (3×10 mL), dried over anhydrous sodium sulfate, filtered, and concentrated under reduced pressure to give crude product, which was further purified by reverse-phase flash chromatography (column: C18; mobile phase, MeCN in water (10 mmol/L $NH_4HCO_3$), 10% to 100% gradient in 20 min; detector: UV 254 nm) to afford the desired product as an off-white solid. (ESI, m/z): 846 $[M+H]^+$.

Step I-2: Synthesis of 2-amino-4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorobenzo[b]thiophene-3-carbonitrile (615). To a stirred solution of tert-butyl (4-((5S)-4-(1-(2-aminopyridin-3-yl)ethyl)-8-chloro-5-(cyanomethyl)-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-3-cyano-7-fluorobenzo[b]thiophen-2-yl)carbamate (20 mg, 0.014 mmol, 60%) in anhydrous DCM (2 mL) was added TFA (0.6 mL) at 0° C. The reaction mixture was stirred at room temperature for 1 hour. The resulting mixture was filtered and the filter cake was washed with DCM (5×8 mL). The filtrate was concentrated under reduced pressure to give a residue, which was purified by prep-HPLC(Column: XBridge BEH C18 OBD Prep Column 130, 5 m, 30 mm*150 mm; Mobile Phase A: water (10 mmol/L $NH_4HCO_3$), Mobile Phase B: ACN; Flow rate: 60 mL/min; Gradient: 33% B to 68% B in 10 min; Wave Length: UV 254 nm/220 nm; RT1 (min): 6.62/7.15/7.57/9.1) to afford desired product as an off-white solid. (ESI, m/z): 745.80 $[M+H]^+$. $^1H$ NMR: (400 MHZ, DMSO-d6, ppm) δ 7.97-7.94 (m, 1H), 7.86 (s, 2H), 7.71-7.69 (m, 1H), 7.11-7.02 (m, 2H), 6.67 (dd, J=7.5, 4.7 Hz, 1H), 6.55-6.54 (m, 1H), 5.56 (s, 2H), 5.28-5.14 (m, 1H), 4.82-4.78 (m, 1H), 4.30-4.24 (m, 2H), 4.17-3.99 (m, 2H), 2.98-2.91 (m, 4H), 2.79-2.76 (m, 1H), 2.61-2.59 (m, 1H), 2.33-1.96 (m, 3H), 1.81-1.69 (m, 3H), 1.56-1.48 (m, 3H).

Example 11: Synthesis of 2-amino-4-(12-((2-aminopyridin-3-yl)methyl)-6-chloro-4-fluoro-2-(((2R,7aS)-2-fluorotetrahydro-1H-pyrrolizin-7a (5H)-yl)methoxy)-8a,9,11a,12-tetrahydro-8H, 11H-furo[3',4': 6,7][1,5]oxazocino[4,3,2-de]quinazolin-5-yl)-7-fluorobenzo[b]thiophene-3-carbonitrile (868).

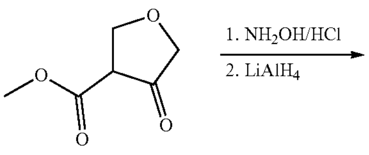

8-1

-continued

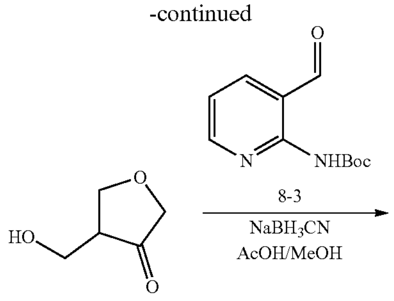

8-2

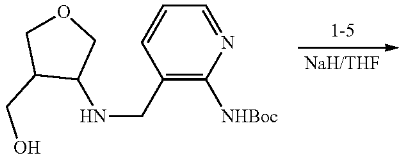

8-4

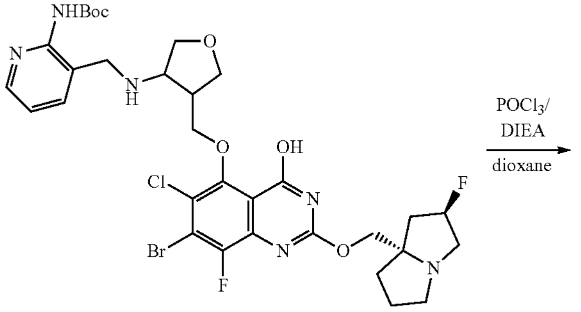

8-5

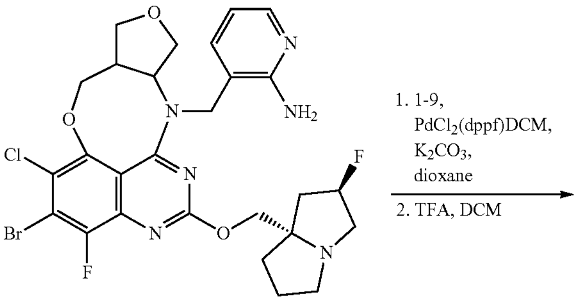

8-6

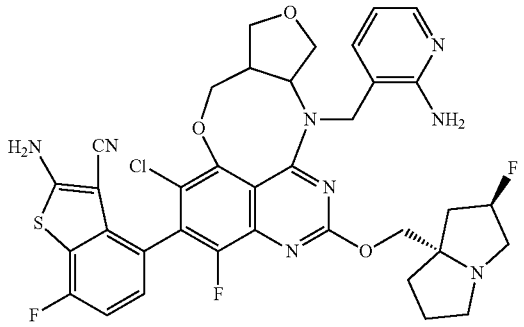

868

Step A-1: Synthesis of methyl-4-(hydroxyimino)tetrahydrofuran-3-carboxylate. To a stirred solution of methyl 4-oxotetrahydrofuran-3-carboxylate (8-1)(10 g, 69.4 mmol) in EtOH (20 mL) were added $NH_2OH/HCl$ (4.78 g, 69.4 mmol) and $Na_2CO_3$ (22 g, 208.2 mmol), and the resulting mixture was stirred at 85° C. for 12 hours. The mixture was cooled to room temperature and partitioned between water and ethyl acetate. The organic layer was washed with brine, dried over $Na_2SO_4$, and concentrated in vacuo. The residue was purified by flash column chromatography on silica gel to afford the desired product. ESI-MS m/z: 159.1 $[M+H]^+$.

Step A-2: Synthesis of (4-aminotetrahydrofuran-3-yl) methanol (8-2). To a stirred solution of methyl-4-(hydroxyimino)tetrahydrofuran-3-carboxylate (8 g, 50.3 mmol) in THF (200 mL) was added $LiAlH_4$ (3.8 g, 100.6 mmol), and the resulting mixture was stirred for 4 hours. The reaction was quenched with $H_2O$ and NaOH (15% solution). The organic layer was washed with brine, dried over $Na_2SO_4$, and concentrated in vacuo. The residue was purified by flash column chromatography on silica gel to afford the desired product. ESI-MS m/z: 117.1 $[M+H]^+$.

Step B: Synthesis of tert-butyl (3-(((4-(hydroxymethyl) tetrahydrofuran-3-yl)amino)methyl)pyridin-2-yl)carbamate (8-4). To a stirred solution of 8-2 (300 mg, 2.56 mmol) in EtOH (20 mL) were added tert-butyl (3-formylpyridin-2-yl) carbamate (8-3)(568 mg, 2.56 mmol) and $NaBH_3CN$ (238 g, 3.84 mmol) and the resulting mixture was stirred for 4 hours. The mixture was partitioned between water and ethyl acetate. The organic layer was washed with brine, dried over $Na_2SO_4$, and concentrated in vacuo. The residue was purified by flash column chromatography on silica gel to afford the desired product. ESI-MS m/z: 323.2 $[M+H]^+$.

Step C: Synthesis of tert-butyl (3-(((4-(((7-bromo-6-chloro-8-fluoro-2-(((2R,7aS)-2-fluorotetrahydro-1H-pyrrolizin-7a (5H)-yl)methoxy)-4-hydroxyquinazolin-5-yl) oxy)methyl)tetrahydrofuran-3-yl)amino)methyl)pyridin-2-yl)carbamate (8-5). To a solution of 8-4 (170 mg, 0.52 mmol) in THF (20 mL) was added NaH (100 mg, 2.5 mmol). The resulting solution was stirred for 30 minutes at 0° C. Compound 1-5 (400 mg, 1.17 mmol) was added and the resulting mixture was stirred at room temperature for 2 hours, then extracted with ethyl acetate. The combined organic layer was washed with water and concentrated in vacuo. The residue was purified by flash column chromatography on silica gel to afford the desired product. ESI-MS m/z: 754.2 $[M+H]^+$.

Step D: Synthesis of 3-((5-bromo-6-chloro-4-fluoro-2-(((2R,7aS)-2-fluorotetrahydro-1H-pyrrolizin-7a (5H)-yl) methoxy)-8a,9,11,11a-tetrahydro-8H, 12H-furo[3',4': 6,7][1, 5]oxazocino[4,3,2-de]quinazolin-12-yl)methyl) pyridin-2-amine (8-6). To a stirred solution of 8-5 (165 mg, 0.21 mmol) in dioxane (20 mL) were added $BOPCl_3$ (106 mg, 0.42 mmol) and DIEA (108 mg, 0.84 mmol), and the resulting mixture was stirred at 75° C. for 12 hours. The mixture was cooled to room temperature and partitioned between water and ethyl acetate. The organic layer was washed with brine, dried over $Na_2SO_4$, and concentrated in vacuo. The residue was purified by flash column chromatography on silica gel to afford the desired product. ESI-MS m/z: 636.1 $[M+H]^+$.

Step E-1: Synthesis of tert-butyl (4-(12-((2-((tert-butoxycarbonyl)amino)pyridin-3-yl)methyl)-6-chloro-4-fluoro-2-(((2R,7aS)-2-fluorotetrahydro-1H-pyrrolizin-7a (5H)-yl) methoxy)-8a,9,11a, 12-tetrahydro-8H,11H-furo[3',4': 6,7][1, 5]oxazocino[4,3,2-de]quinazolin-5-yl)-3-cyano-7-fluorobenzo[b]thiophen-2-yl)carbamate. A mixture of 8-6 (100 mg, 0.13 mmol), 1-9 (110 mg, 0.27 mmol), $K_2CO_3$ (110 mg, 0.84 mmol), and $PdCl_2$ (dtbpf)(22 mg, 0.027 mmol) in dioxane (10 mL) was stirred at 105° C. for 4 hours. The resulting mixture was cooled to room temperature, diluted with water (20 mL) and extracted with ethyl acetate (15 mL×2). The combined organic layer was washed with water and brine, dried over anhydrous $Na_2SO_4$, filtered, and concentrated in vacuo. The residue was purified by prep-TLC to afford the desired product. ESI-MS m/z: 948.30 $[M+H]^+$.

Step E-2: Synthesis of 2-amino-4-(12-((2-aminopyridin-3-yl)methyl)-6-chloro-4-fluoro-2-(((2R,7aS)-2-fluorotetrahydro-1H-pyrrolizin-7a (5H)-yl)methoxy)-8a,9,11a, 12-tetrahydro-8H, 11H-furo[3',4': 6,7][1,5]oxazocino[4,3,2-de]quinazolin-5-yl)-7-fluorobenzo[b]thiophene-3-carbonitrile (868). To a solution of tert-butyl (4-(12-((2-((tert-butoxycarbonyl)amino)pyridin-3-yl)methyl)-6-chloro-4-fluoro-2-(((2R,7aS)-2-fluorotetrahydro-1H-pyrrolizin-7a (5H)-yl)methoxy)-8a,9,11a,12-tetrahydro-8H,11H-furo[3',4': 6,7][1,5]oxazocino[4,3,2-de]quinazolin-5-yl)-3-cyano-7-fluorobenzo[b]thiophen-2-yl)carbamate (24 mg) in DCM (6 mL) was added TFA (2 mL), and the resulting mixture was stirred for 30 minutes. The mixture was concentrated in vacuo to remove the solvent. The residue was purified by flash column chromatography on silica gel to afford the desired product. ESI-MS m/z: 748.20 $[M+H]^+$.

Example 1m: Synthesis of 2-amino-4-(4-((R)-1-(2-aminopyridin-3-yl)ethyl)-8-chloro-10-fluoro-2-((hexahydropentalen-3a (1H)-yl)methoxy)-5,6-dihydro-4H-[1,4]oxazepino[5,6,7-de]quinazolin-9-yl)-7-fluorobenzo[b]thiophene-3-carbonitrile (914 and 674).

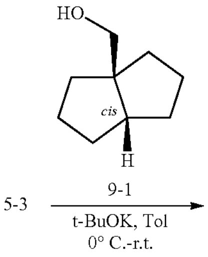

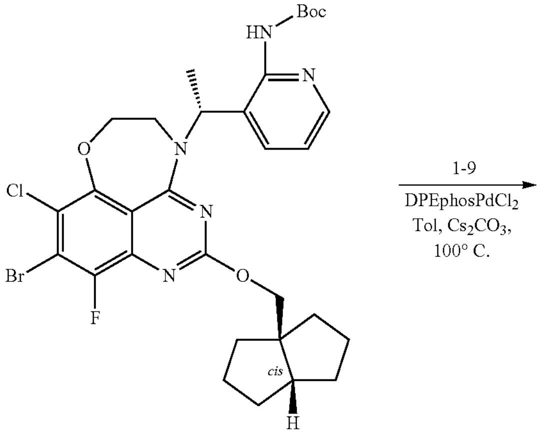

9-2

-continued

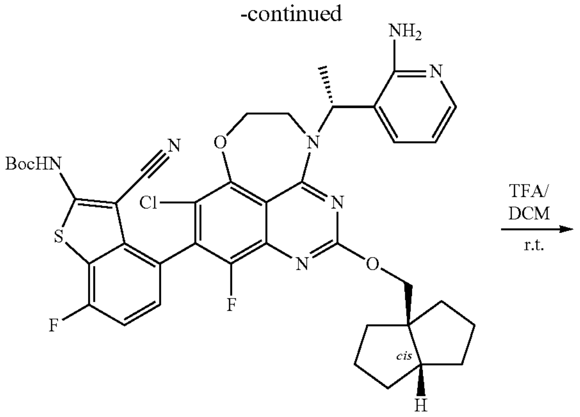

9-3

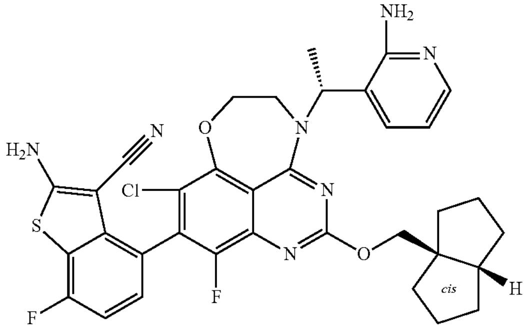

914 (polar)
674 (less polar)

Step A: Synthesis of tert-butyl (3-((R)-1-(9-bromo-8-chloro-10-fluoro-2-(((3ar,6aR)-hexahydropentalen-3a (1H)-yl)methoxy)-5,6-dihydro-4H-[1,4]oxazepino[5,6,7-de]quinazolin-4-yl)ethyl) pyridin-2-yl)carbamate. (9-2). To a stirred mixture of 5-3 (200 mg, 0.28 mmol) and (cis)-hexahydro-1H-pentalen-3a-ylmethanol (9-1)(120 mg, 0.85 mmol) in toluene (2 mL) was added t-BuOK (160 mg, 1.42 mmol) in portions at 0° C. The resulting mixture was stirred for 2 hours at room temperature, then diluted with $NH_4Cl$ (3 mL) and extracted with ethyl acetate (3x3 mL). The combined organic layers were washed with brine (3 mL), dried over anhydrous $Na_2SO_4$, filtered, and concentrated under reduced pressure to give a residue, which was purified by prep-TLC (petroleum ether/ethyl acetate 1:2) to afford the desired product as a white solid. (ESI-MS m/z): 676 $[M+H]^+$.

Step B: Synthesis of tert-butyl (4-(4-((R)-1-(2-aminopyridin-3-yl)ethyl)-8-chloro-10-fluoro-2-(((3ar,6aR)-hexahydropentalen-3a (1H)-yl)methoxy)-5,6-dihydro-4H-[1,4]oxazepino[5,6,7-de]quinazolin-9-yl)-3-cyano-7-fluorobenzo[b]thiophen-2-yl)carbamate (9-3). To a stirred mixture of 9-2 (80 mg, 0.11 mmol), 1-9 (143 mg, 0.35 mmol) and $Cs_2CO_3$ (115 mg, 0.35 mmol) in toluene (8.0 mL) was added dichloropalladium; (2-[2-(diphenylphosphanyl)phenoxy]phenyldiphenylphosphane (33 mg, 0.04 mmol) in portions. The resulting mixture was stirred for 2 hours at 100° C., then cooled to room temperature and diluted with water (5 mL). The resulting mixture was extracted with ethyl acetate (3x5 mL). The combined organic layers were washed with brine (5 mL), dried over anhydrous $Na_2SO_4$, filtered, and concentrated under reduced pressure to give a residue, which was purified by reverse-phase flash chromatography (column: C18; mobile phase: MeCN in water (10 mmol/L $NH_4HCO_3$), 50% to 100% gradient in 10 min; detector: UV 254 nm) to give the desired product as a yellow solid. (ESI, m/z): 788 $[M+H]^+$.

Step C: Synthesis of 2-amino-4-(4-((R)-1-(2-aminopyridin-3-yl)ethyl)-8-chloro-10-fluoro-2-((hexahydropentalen-3a (1H)-yl)methoxy)-5,6-dihydro-4H-[1,4]oxazepino[5,6,7-de]quinazolin-9-yl)-7-fluorobenzo[b]thiophene-3-carbonitrile (914 and 674). A solution of 9-3 (50 mg, 0.057 mmol) in DCM (2 mL) and TFA (0.5 mL) was stirred for 1 hour. The resulting mixture was concentrated under reduced pressure to give a residue, the pH of which was adjusted to pH 8 with $NH_3 \cdot H_2O$. The mixture was concentrated to give the crude product, which was purified by prep-HPLC(Column: YMC Triart C18 ExRs 5 m, 30 mm*150 mm; Mobile Phase A: water (10 mmol/L $NH_4HCO_3$), Mobile Phase B: ACN; Flow rate: 60 mL/min; Gradient: 70% B to 90% B in 10 min; Wave Length: UV 254 nm/220 nm; RT1 (min): 6.83/9.28) to afford 914 (polar) and 674 (less polar) as a white solid. 914: (ESI, m/z): 688 $[M+H]^+$; 1H NMR: (400 MHZ, DMSO-d6, ppm) δ 8.09 (s, 2H), 7.96 (dd, J=4.9, 1.7 Hz, 1H), 7.62 (d, J=7.6 Hz, 1H), 7.25-7.11 (m, 2H), 6.66 (dd, J=7.5, 4.9 Hz, 1H), 6.23 (d, J=6.7 Hz, 1H), 5.73 (s, 2H), 4.43 (dd, J=11.6, 6.1 Hz, 1H), 4.31 (d, J=11.2 Hz, 1H), 4.22 (d, J=10.4 Hz, 1H), 4.14 (d, J=10.4 Hz, 1H), 3.63 (dd, J=15.4, 6.7 Hz, 1H), 3.41 (dd, J=15.9, 6.1 Hz, 1H), 1.72 (ddt, J=24.2, 11.7, 6.2 Hz, 3H), 1.61 (q, J=6.0, 4.5 Hz, 5H), 1.54 (td, J=12.1, 11.3, 5.3 Hz, 2H), 1.44 (dd, J=12.0, 6.3 Hz, 2H), 1.31-1.22 (m, 4H). 674: (ESI, m/z): 688 $[M+H]^+$; 1H NMR: (400 MHz, DMSO-d6, ppm) δ 8.08 (s, 2H), 7.96 (dd, J=4.9, 1.7 Hz, 1H), 7.67-7.58 (m, 1H), 7.24-7.08 (m, 2H), 6.66 (dd, J=7.5, 4.9 Hz, 1H), 6.28 (d, J=6.9 Hz, 1H), 5.85 (s, 2H), 4.54 (dd, J=11.9, 6.4 Hz, 1H), 4.26-4.19 (m, 2H), 4.14 (d, J=10.3 Hz, 1H), 3.73 (dd, J=15.6, 6.7 Hz, 1H), 3.41-3.35 (m, 1H), 2.2-2.1 (m, 1H), 1.73 (ddq, J=24.3, 12.2, 6.5, 6.1 Hz, 4H), 1.57 (tt, J=12.3, 5.9 Hz, 7H), 1.43 (dt, J=12.2, 6.2 Hz, 2H), 1.35-1.21 (m, 2H).

Example 1n: Synthesis of 2-amino-4-((R)-4-((R)-1-(2-aminopyridin-3-yl)ethyl)-8-chloro-2-(((1S,7a'S)-2,2-difluorodihydro-1'H,3'H-spiro[cyclopropane-1,2'-pyrrolizin]-7a' (5'H)-yl)methoxy)-10-fluoro-5,6-dihydro-4H-[1,4]oxazepino[5,6,7-de]quinazolin-9-yl)-7-fluorobenzo[b]thiophene-3-carbonitrile (740).

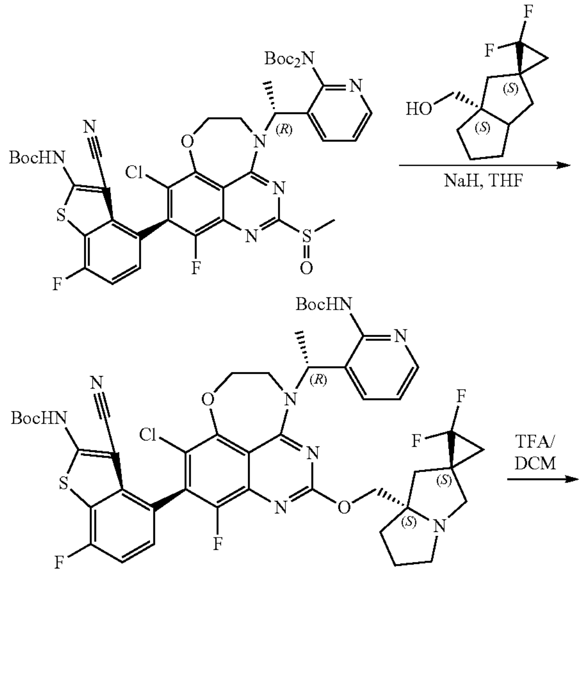

-continued

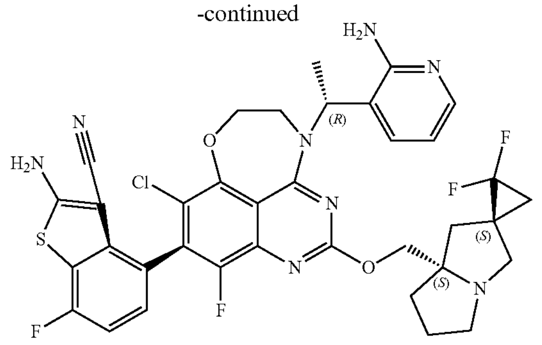

Step A: Synthesis of tert-butyl (4-((R)-4-((R)-1-(2-((tert-butoxycarbonyl)amino)pyridin-3-yl)ethyl)-8-chloro-2-(((1S,7a'S)-2,2-difluorodihydro-1'H,3'H-spiro[cyclopropane-1,2'-pyrrolizin]-7a' (5'H)-yl)methoxy)-10-fluoro-5,6-dihydro-4H-[1,4]oxazepino[5,6,7-de]quinazolin-9-yl)-3-cyano-7-fluorobenzo[b]thiophen-2-yl)carbamate. To a stirred solution of (1S,7'aS)-2,2-difluoro-tetrahydro-1'H-spiro[cyclopropane-1,2'-pyrrolizin]-7'a-ylmethanol (70.0 mg, 0.34 mmol) and tert-butyl (tert-butoxycarbonyl)(3-((1R)-1-((9R)-9-(2-((tert-butoxycarbonyl)amino)-3-cyano-7-fluorobenzo[b]thiophen-4-yl)-8-chloro-10-fluoro-2-(methylsulfinyl)-5,6-dihydro-4H-[1,4]oxazepino[5,6,7-de] quinazolin-4-yl)ethyl) pyridin-2-yl)carbamate (188.5 mg, 0.2 mmol) in THF (3.5 mL) was added NaH (123.9 mg, 3.09 mmol) at 0° C. The resulting mixture was stirred for 1 hour at room temperature, quenched by the addition of sat. $NH_4Cl$ (aq.)(50 mL) at 0° C., and extracted with EtOAc (3×50 mL). The combined organic layers were washed with brine (1×30 mL) and dried over anhydrous $Na_2SO_4$. After filtration, the filtrate was concentrated under reduced pressure to give the desired product as a yellow solid. (ESI, m/z): 951 $[M+H]^+$.

Step B: Synthesis of 2-amino-4-((R)-4-((R)-1-(2-aminopyridin-3-yl)ethyl)-8-chloro-2-(((1S,7a'S)-2,2-difluorodihydro-1'H,3'H-spiro[cyclopropane-1,2'-pyrrolizin]-7a' (5'H)-yl)methoxy)-10-fluoro-5,6-dihydro-4H-[1,4]oxazepino[5,6,7-de]quinazolin-9-yl)-7-fluorobenzo[b]thiophene-3-carbonitrile. To a 20 mL vial were added tert-butyl (4-((R)-4-((R)-1-(2-((tert-butoxycarbonyl)amino)pyridin-3-yl) ethyl)-8-chloro-2-(((1S,7a'S)-2,2-difluorodihydro-1'H,3'H-spiro[cyclopropane-1,2'-pyrrolizin]-7a' (5'H)-yl)methoxy)-10-fluoro-5,6-dihydro-4H-[1,4]oxazepino[5,6,7-de] quinazolin-9-yl)-3-cyano-7-fluorobenzo[b]thiophen-2-yl) carbamate (240.0 mg, 0.25 mmol), dichloromethane (5.0 mL), and TFA (1.0 mL) at room temperature. The resulting mixture was stirred for 1 hour at room temperature and quenched by sat. $NaHCO_3$(aq.)(50 mL) at 0° C. The resulting mixture was extracted with EtOAc (3×50 mL). The combined organic layers were washed with brine (1×30 mL) and dried over anhydrous $Na_2SO_4$. After filtration, the filtrate was concentrated under reduced pressure to give a crude. The crude product was purified by Prep-HPLC (Column: XBridge BEH C18 OBD Prep Column 130, 5 m, 30 mm*150 mm; Mobile Phase A: Water (17 mmol/L $NH_4HCO_3$), Mobile Phase B: ACN; Flow rate: 60 mL/min; Gradient: 44% B to 60% B in 10 min; Wave Length: UV 254 nm/220 nm; RT1 (min): 7.78) to afford the desired product as an off-white solid. (ESI, m/z): 751 $[M+H]^+$. $^1H$ NMR: (400 MHZ, DMSO-d6, ppm) δ 8.09 (s, 2H), 7.97 (dd, J=4.9, 1.7 Hz, 1H), 7.64 (dd, J=7.5, 1.8 Hz, 1H), 7.20 (dd, J=8.4, 5.3 Hz, 1H), 7.13 (dd, J=9.4, 8.4 Hz, 1H), 6.67 (dd, J=7.5, 4.9 Hz, 1H), 6.26 (q, J=6.8 Hz, 1H), 5.72 (s, 2H), 4.42 (dd, J=11.4, 6.4 Hz, 1H), 4.34-4.21 (m, 2H), 4.17 (d, J=10.4 Hz, 1H), 3.61 (dd, J=15.1, 6.6 Hz, 1H), 3.41 (d, J=6.7 Hz, 1H), 3.09 (dd, J=11.8, 6.8 Hz, 1H), 3.01 (ddd, J=9.6, 6.1, 3.6 Hz, 1H), 2.71 (d, J=11.9 Hz, 1H), 2.56 (s, 1H), 2.09 (dd, J=13.4, 5.7 Hz, 1H), 2.01 (ddd, J=11.7, 7.0, 3.9 Hz, 1H), 1.90 (d, J=13.3 Hz, 1H), 1.82-1.67 (m, 2H), 1.59 (t, J=9.7 Hz, 4H), 1.58-1.41 (m, 2H).

Example 10: Synthesis of 2-amino-4-((S)-4-((R)-1-(2-aminopyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile bis(2,2,2-trifluoroacetate)(768).

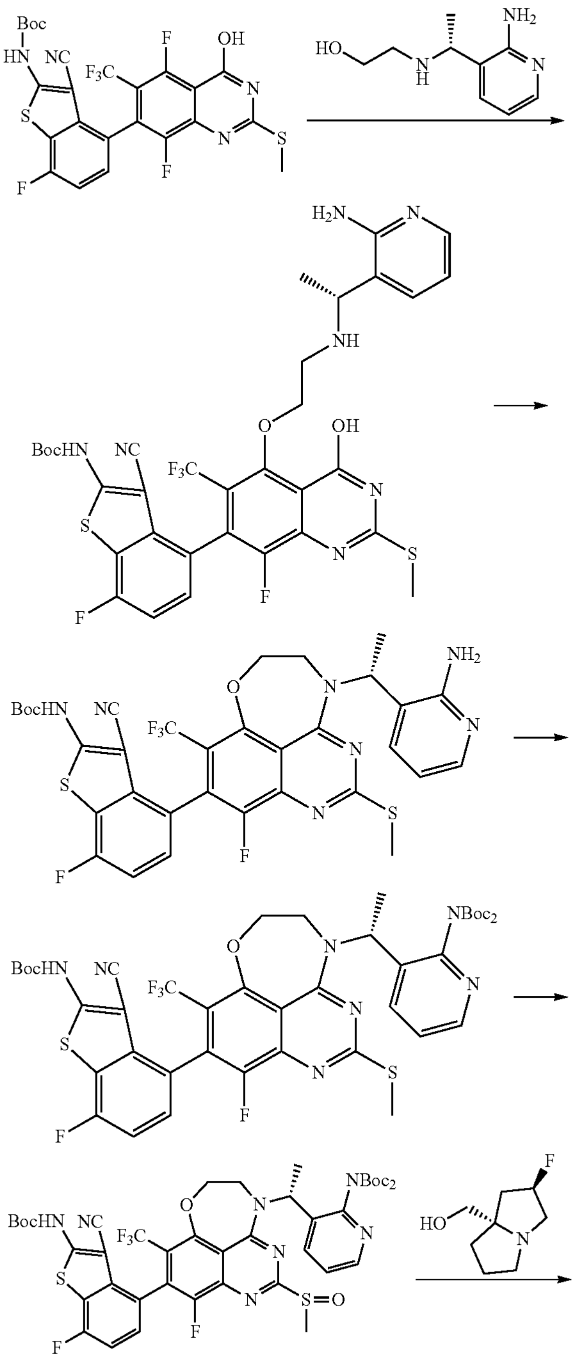

-continued

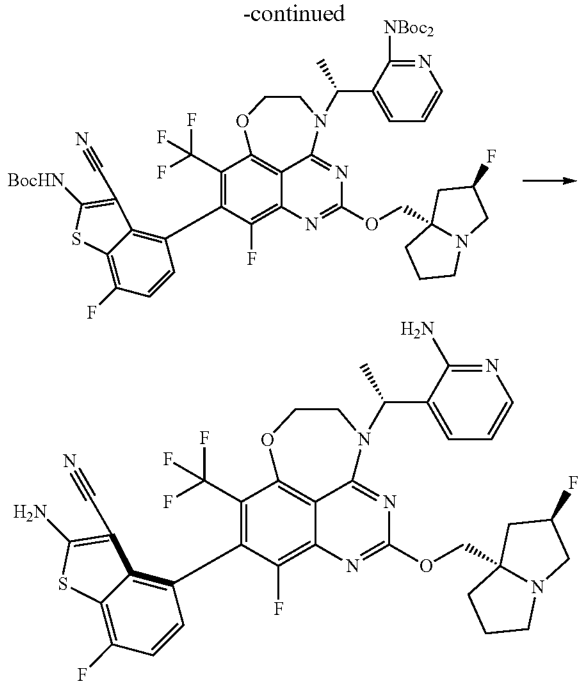

Step A: Synthesis of tert-butyl (4-(5-(2-(((R)-1-(2-aminopyridin-3-yl)ethyl)amino) ethoxy)-8-fluoro-4-hydroxy-2-(methylthio)-6-(trifluoromethyl) quinazolin-7-yl)-3-cyano-7-fluorobenzo[b]thiophen-2-yl)carbamate. To a stirred solution of tert-butyl (3-cyano-4-(5,8-difluoro-4-hydroxy-2-(methylthio)-6-(trifluoromethyl) quinazolin-7-yl)-7-fluorobenzo[b]thiophen-2-yl)carbamate (410 mg, 0.350 mmol) and 2-([(1R)-1-(2-aminopyridin-3-yl)ethyl]aminoethanol (79.18 mg, 0.438 mmol) in anhydrous THF (8 mL) was added NaH (94.36 mg, 3.937 mmol) in portions at 0° C. and the resulting mixture was stirred for 1 hour at room temperature. The reaction was quenched with water at 0° C. The product was extracted with EtOAc (3×50 mL) and the combined organic layers were dried over anhydrous $Na_2SO_4$. After filtration, the filtrate was concentrated under reduced pressure to give the desired product which was used in the next step directly without further purification. (ESI, m/z): 748 $[M+H]^+$.

Step B: Synthesis of tert-butyl (4-(4-((R)-1-(2-aminopyridin-3-yl)ethyl)-10-fluoro-2-(methylthio)-8-(trifluoromethyl)-5,6-dihydro-4H-[1,4]oxazepino[5,6,7-de]quinazolin-9-yl)-3-cyano-7-fluorobenzo[b]thiophen-2-yl)carbamate. A solution of tert-butyl (4-(5-(2-(((R)-1-(2-aminopyridin-3-yl) ethyl)amino) ethoxy)-8-fluoro-4-hydroxy-2-(methylthio)-6-(trifluoromethyl) quinazolin-7-yl)-3-cyano-7-fluorobenzo [b]thiophen-2-yl)carbamate (720 mg, 0.770 mmol, 80%), HATU (585.79 mg, 1.540 mmol) and DIEA (398.24 mg, 3.080 mmol) in DMF (10 mL) was stirred for 1 hour at room temperature and the resulting mixture was extracted with EtOAc (3×50 mL). The combined organic layers were washed with water (3×30 mL) and dried over anhydrous $Na_2SO_4$. After filtration, the filtrate was concentrated under reduced pressure. The resulting residue was purified by reverse-phase flash chromatography (column, C18; mobile phase, MeCN in Water (0.1% TFA), 50% to 60% gradient in 10 min; detector, UV 254 nm) to afford the desired product as a yellow solid. (ESI, m/z): 730 $[M+H]^+$.

Step C: Synthesis of tert-butyl (tert-butoxycarbonyl)(3-((1R)-1-(9-(2-((tert-butoxycarbonyl)amino)-3-cyano-7- fluorobenzo[b]thiophen-4-yl)-10-fluoro-2-(methylthio)-8-(trifluoromethyl)-5,6-dihydro-4H-[1,4]oxazepino[5,6,7-de] quinazolin-4-yl)ethyl) pyridin-2-yl)carbamate. To a stirred solution of tert-butyl (4-(4-((R)-1-(2-aminopyridin-3-yl) ethyl)-10-fluoro-2-(methylthio)-8-(trifluoromethyl)-5,6-dihydro-4H-[1,4]oxazepino[5,6,7-de]quinazolin-9-yl)-3-cyano-7-fluorobenzo[b]thiophen-2-yl)carbamate (170 mg, 0.233 mmol), DMAP (142.3 mg, 1.165 mmol) and TEA (235.74 mg, 2.330 mmol) in anhydrous DCM (5 mL) was added $Boc_2O$ (254.21 mg, 1.165 mmol) at room temperature and the reaction mixture was stirred for 2 hours. The resulting mixture was extracted with DCM (3×30 mL) and the combined organic layers were dried over anhydrous $Na_2SO_4$. After filtration, the filtrate was concentrated under reduced pressure to give a residue. The residue was purified by silica gel column chromatography, eluted with petroleum ether/ethyl acetate (10:1) to afford the desired product as a yellow solid. (ESI, m/z): 930 $[M+H]^+$.

Step D: Synthesis of tert-butyl (tert-butoxycarbonyl)(3-((1R)-1-(9-(2-((tert-butoxycarbonyl)amino)-3-cyano-7-fluorobenzo[b]thiophen-4-yl)-10-fluoro-2-(methylsulfinyl)-8-(trifluoromethyl)-5,6-dihydro-4H-[1,4]oxazepino[5,6,7-de]quinazolin-4-yl)ethyl) pyridin-2-yl)carbamate. A solution of tert-butyl (tert-butoxycarbonyl)(3-((1R)-1-(9-(2-((tert-butoxycarbonyl)amino)-3-cyano-7-fluorobenzo[b] thiophen-4-yl)-10-fluoro-2-(methylthio)-8-(trifluoromethyl)-5,6-dihydro-4H-[1,4]oxazepino[5,6,7-de]quinazolin-4-yl)ethyl) pyridin-2-yl)carbamate (260 mg, 0.280 mmol) and m-CPBA (48.24 mg, 0.280 mmol) in DCM (10 mL) was stirred for 1 hour at room temperature and the resulting mixture was extracted with DCM (3×20 mL). The combined organic layers were washed with brine and dried over anhydrous $Na_2SO_4$. After filtration, the filtrate was concentrated under reduced pressure to give the desired product which was used in the next step directly without further purification. (ESI, m/z): 946 $[M+H]^+$.

Step E: Synthesis of tert-butyl (tert-butoxycarbonyl)(3-((1R)-1-(9-(2-((tert-butoxycarbonyl)amino)-3-cyano-7-fluorobenzo[b]thiophen-4-yl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-4-yl)ethyl) pyridin-2-yl)carbamate. To a stirred solution of tert-butyl (tert-butoxycarbonyl)(3-((1R)-1-(9-(2-((tert-butoxycarbonyl)amino)-3-cyano-7-fluorobenzo[b] thiophen-4-yl)-10-fluoro-2-(methylsulfinyl)-8-(trifluoromethyl)-5,6-dihydro-4H-[1,4]oxazepino[5,6,7-de]quinazolin-4-yl)ethyl) pyridin-2-yl)carbamate (245 mg, 0.259 mmol) and [(2R,7aS)-2-fluoro-hexahydropyrrolizin-7a-yl]methanol (61.85 mg, 0.389 mmol) in anhydrous THF (10 mL) was added NaH (55.94 mg, 2.331 mmol) in portions at 0° C. and the mixture was stirred for 1 hour and quenched with water. The resulting mixture was extracted with EtOAc (3×20 mL). The combined organic layers were washed with brine and dried over anhydrous $Na_2SO_4$. After filtration, the filtrate was concentrated under reduced pressure to give the desired product which was used directly in the next step without further purification. (ESI, m/z): 941 $[M+H]^+$.

Step F: Synthesis of 2-amino-4-((S)-4-((R)-1-(2-aminopyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile. A solution of tert-butyl (tert-butoxycarbonyl)(3-((1R)-1-(9-(2-((tert-butoxycarbonyl)amino)-3-cyano-7-fluorobenzo[b]thiophen-4-yl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-4-yl)ethyl) pyridin-2-yl)carbamate (290 mg, 0.279 mmol) and TFA (3 mL) in DCM (9 mL) was stirred for 1 hour at room temperature. The resulting mixture was concentrated under reduced pressure. The crude product (260 mg) was purified by Prep-HPLC(Column: Xselect CSH™ Prep C18 5 μm 30*150 mm OBD; Mobile Phase A: Water (0.1% FA), Mobile Phase B: ACN; Flow rate: 60 mL/min; Gradient: 15% B to 27% B in 10 min; Wavelength: UV 254 nm/220 nm; RT1 (min): 6.7/8.62) to afford the first eluting as desired product as a yellow solid. (ESI, m/z): 741 $[M+H]^+$. $^1H$ NMR: (400 MHZ, DMSO-d6, ppm) δ 10.80 (s, 1H), 8.09 (s, 2H), 8.02 (dd, J=5.6, 1.6 Hz, 1H), 7.87 (s, 1H), 7.14-7.10 (m, 2H), 6.90-6.79 (m, 1H), 6.12-6.03 (m, 1H), 5.67-5.48 (m, 1H), 4.60 (d, J=12.0 Hz, 1H), 4.53 (d, J=11.6 Hz, 2H), 4.46-4.37 (m, 1H), 3.91-3.62 (m, 6H), 2.61-2.53 (m, 2H), 2.45-2.43 (m, 1H), 2.32-2.27 (m, 1H), 2.23-2.11 (m, 2H), 2.09-1.99 (m, 1H), 1.67 (d, J=6.8 Hz, 3H).

Example 1p: Synthesis of 2-amino-4-((R)-4-((R)-1-(2-aminopyridin-3-yl) but-3-en-1-yl)-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile (683).

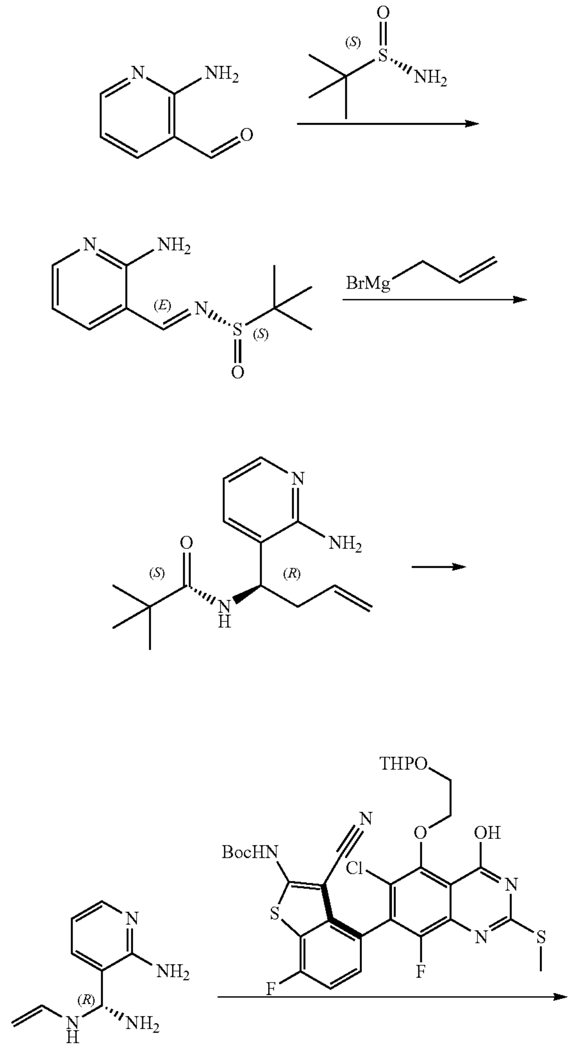

-continued

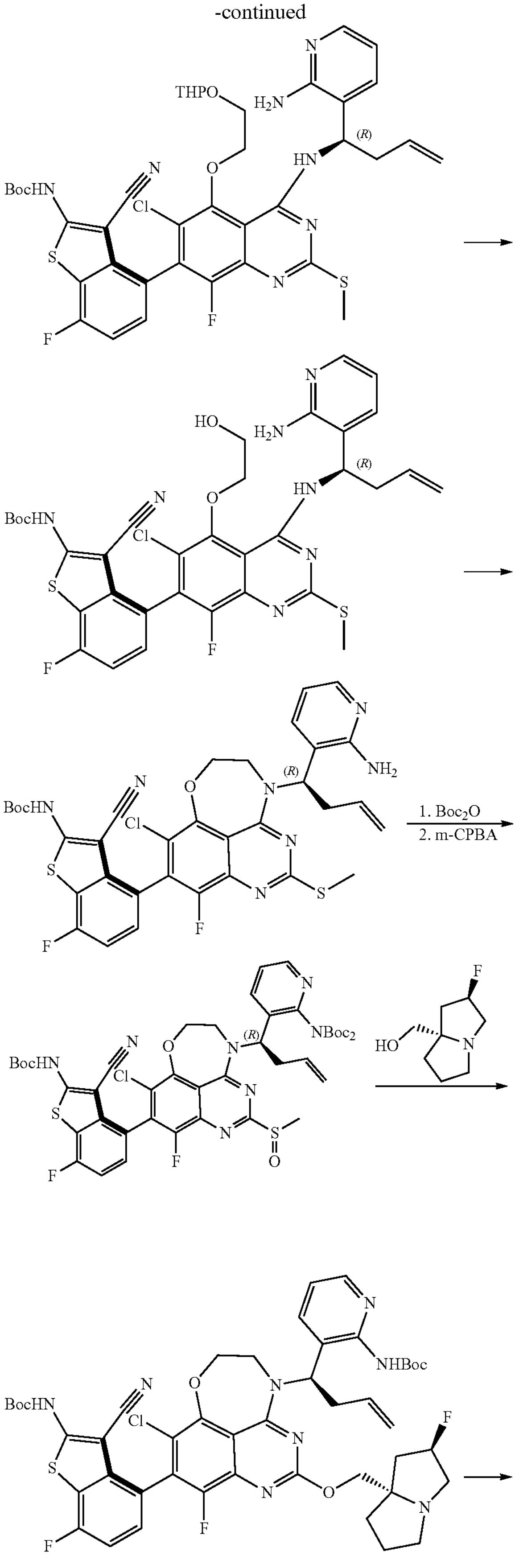

-continued

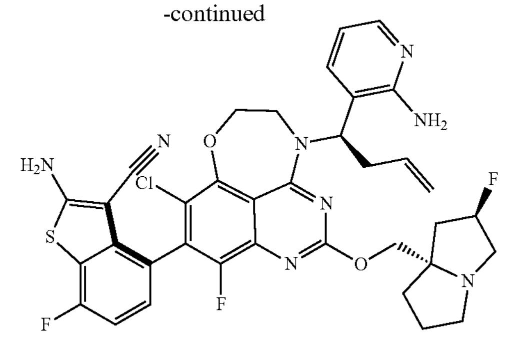

Step A: Synthesis of (S,E)-N-((2-aminopyridin-3-yl) methylene)-2-methylpropane-2-sulfinamide. To a solution of 2-aminopyridine-3-carbaldehyde (10 g, 81.882 mmol) and(S)-2-methylpropane-2-sulfinamide (13.89 g, 114.635 mmol) in THF (120 mL) was added Ti $(Oi\text{-}Pr)_4$ (93.09 g, 327.528 mmol) at 25° C. and the mixture was stirred for 12 hours at 66° C. The mixture was cooled to room temperature and water (30 mL) was added. The mixture was extracted with ethyl acetate (3×40 mL) and extracts were combined, washed with brine and dried over sodium sulfate. The product was filtered and the filtrates were concentrated to give a residue which was purified by flash chromatography to give the desired product as a yellow solid. (ESI, m/z): 226 $[M+H]^+$.

Step B: Synthesis of(S)—N—((R)-1-(2-aminopyridin-3-yl) but-3-en-1-yl)-2-methylpropane-2-sulfinamide. To a solution of(S)—N-[(2-aminopyridin-3-yl)methylidene]-2-methylpropane-2-sulfinamide (15.5 g, 68.794 mmol) in THF (155.00 mL) was added allylmagnesium bromide (343.97 mL, 343.970 mmol) at −78° C. and the mixture was stirred for 3 hours. The mixture was quenched with water and extracted with ethyl acetate (3×40 mL). The extracts were combined, washed with brine and dried over sodium sulfate. The product was filtered and the filtrates were concentrated to give a residue which was purified by flash chromatography to afford the desired product as a yellow solid. (ESI, m/z): 268 $[M+H]^+$.

Step C: Synthesis of (R)-3-(1-aminobut-3-en-1-yl) pyridin-2-amine hydrochloride. HCl in 1,4-dioxane (24 mL, 789.907 mmol) was added to(S)—N-[(1R)-1-(2-aminopyridin-3-yl) but-3-en-1-yl]-2-methylpropane-2-sulfinamide (6 g, 22.439 mmol) at 25° C. and the mixture was stirred for 1 hour followed by the addition of methanol (10 mL). The mixture was then concentrated to provide the desired product which was used directly in the next step without further purification. (ESI, m/z): 200 $[M+H]^+$.

Step D: Synthesis of tert-butyl (4-((7R)-4-(((R)-1-(2-aminopyridin-3-yl) but-3-en-1-yl)amino)-6-chloro-8-fluoro-2-(methylthio)-5-(2-((tetrahydro-2H-pyran-2-yl)oxy) ethoxy) quinazolin-7-yl)-3-cyano-7-fluorobenzo[b]thiophen-2-yl) carbamate. A solution of tert-butyl N-(4-[6-chloro-8-fluoro-4-hydroxy-2-(methylsulfanyl)-5-[2-(oxan-2-yloxy) ethoxy] quinazolin-7-yl]-3-cyano-7-fluoro-1-benzothiophen-2-ylcarbamate (952.33 mg, 1.402 mmol) in DMF (20 mL) was treated with HATU (1332.96 mg, 3.506 mmol) and DIEA (906.18 mg, 7.012 mmol) at room temperature under nitrogen atmosphere followed by the addition of 3-[(1R)-1-aminobut-3-en-1-yl]pyridin-2-amine hydrochloride (350 mg, 1.753 mmol) dropwise. The resulting mixture was stirred for 1 hour at room temperature and extracted with EtOAc (3×100 mL). The combined organic layers were washed with brine (3×50 mL) and dried over anhydrous $Na_2SO_4$. The product was filtered and the filtrates were concentrated to give a residue which was purified by silica gel column chromatography and eluted with petroleum ether/ethyl acetate (1:2) to give the desired product as a yellow solid. (ESI, m/z): 824 $[M+H]^+$.

Step E: Synthesis of tert-butyl (4-((R)-4-((R)-1-(2-aminopyridin-3-yl) but-3-en-1-yl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl) carbamate. A solution of tert-butyl (4-((7R)-4-(((R)-1-(2-aminopyridin-3-yl) but-3-en-1-yl)amino)-6-chloro-8-fluoro-2-(methylthio)-5-(2-((tetrahydro-2H-pyran-2-yl)oxy) ethoxy) quinazolin-7-yl)-3-cyano-7-fluorobenzo[b]thiophen-2-yl)carbamate (850 mg, 1.031 mmol) in MeOH (8.5 mL) was treated with HCl in MeOH (8.50 mL, 279.731 mmol) at room temperature under nitrogen atmosphere. The resulting mixture was stirred for 20 minutes. The pH was adjusted to 8 with saturated aq. $NaHCO_3$ and the mixture extracted with EtOAc (3×100 mL). The combined organic layers were washed with brine (3×50 mL) and dried over anhydrous $Na_2SO_4$. After filtration, the filtrate was concentrated under reduced pressure to give a residue. The residue was purified by silica gel column chromatography to give the desired product as a yellow solid. (ESI, m/z): 740 $[M+H]^+$.

Step F: Synthesis of tert-butyl (4-((R)-4-((R)-1-(2-aminopyridin-3-yl) but-3-en-1-yl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl)carbamate. A solution of $PPh_3$ (467.72 mg, 1.782 mmol) in THF (4.4 mL) was treated with DIAD (360.58 mg, 1.782 mmol) for 30 minutes at 0° C. under nitrogen atmosphere followed by the addition of tert-butyl (4-((R)-4-((R)-1-(2-aminopyridin-3-yl) but-3-en-1-yl)-8-chloro-10-fluoro-2-(methylthio)-5,6 dihydro-4H-[1,4]oxazepino[5,6,7-de]quinazolin-9-yl)-3-cyano-7-fluorobenzo[b]thiophen-2-yl)carbamate (440 mg, 0.594 mmol) dropwise at room temperature. The resulting mixture was stirred for 1 hour at room temperature under nitrogen atmosphere and extracted with EtOAc (3×100 mL). The combined organic layers were washed with brine (3×50 mL) and dried over anhydrous $Na_2SO_4$. After filtration, the filtrate was concentrated under reduced pressure to give a residue. The residue was purified by silica gel column chromatography to afford the desired product as a yellow solid. (ESI, m/z): 722 $[M+H]^+$.

Step G: Synthesis of tert-butyl (tert-butoxycarbonyl)(3-((R)-1-((R)-9-(2-((tert-butoxycarbonyl)amino)-3-cyano-7-fluorobenzo[b]thiophen-4-yl)-8-chloro-10-fluoro-2-(methylthio)-5,6-dihydro-4H-[1,4]oxazepino[5,6,7-de] quinazolin-4-yl) but-3-en-1-yl) pyridin-2-yl)carbamate. A solution of tert-butyl (4-((R)-4-((R)-1-(2-aminopyridin-3-yl) but-3-en-1-yl)-8-chloro-10-fluoro-2-(methylthio)-5,6-dihydro-4H-[1,4]oxazepino[5,6,7-de]quinazolin-9-yl)-3-cyano-7-fluorobenzo[b]thiophen-2-yl)carbamate (165 mg, 0.228 mmol) in DCM (3.3 mL, 51.911 mmol) was treated with $Boc_2O$ (747.91 mg, 3.420 mmol) at room temperature under nitrogen atmosphere followed by the addition of DMAP (16.75 mg, 0.137 mmol) and TEA (231.18 mg, 2.280 mmol). The resulting mixture was stirred overnight and extracted with $CH_2Cl_2$ (3×100 mL). The combined organic layers were washed with brine (3×50 mL) and dried over anhydrous $Na_2SO_4$. After filtration, the filtrate was concentrated under reduced pressure to give a residue. The residue was purified by silica gel column chromatography to provide the desired product as a yellow solid. (ESI, m/z): 922 $[M+H]^+$.

Step H: Synthesis of tert-butyl (tert-butoxycarbonyl)(3-((1R)-1-((9R)-9-(2-((tert-butoxycarbonyl)amino)-3-cyano-7-fluorobenzo[b]thiophen-4-yl)-8-chloro-10-fluoro-2-(methylsulfinyl)-5,6-dihydro-4H-[1,4]oxazepino[5,6,7-de] quinazolin-4-yl) but-3-en-1-yl) pyridin-2-yl)carbamate. A solution of tert-butyl (tert-butoxycarbonyl)(3-((R)-1-((R)-9-(2-((tert-butoxycarbonyl)amino)-3-cyano-7-fluorobenzo[b] thiophen-4-yl)-8-chloro-10-fluoro-2-(methylthio)-5,6-dihydro-4H-[1,4]oxazepino[5,6,7-de]quinazolin-4-yl) but-3-en-1-yl) pyridin-2-yl)carbamate (130 mg, 0.139 mmol) in DCM (2.60 mL, 41.040 mmol) was treated with m-CPBA (28.68 mg, 0.167 mmol) at 0° C. under nitrogen atmosphere. The mixture was stirred for 1 hour at 0° C. and quenched with $NaHSO_3$. The resulting mixture was extracted with EtOAc (3×50 mL). The combined organic layers were washed with brine (2×20 mL) and dried over anhydrous $Na_2SO_4$. After filtration, the filtrate was concentrated under reduced pressure to give desired product as a yellow solid which was used directly in the next step without further purification. (ESI m/z): 938 $[M+H]^+$.

Step I: Synthesis of tert-butyl (4-((R)-4-((R)-1-(2-((tert-butoxycarbonyl)amino)pyridin-3-yl) but-3-en-1-yl)-8-chloro-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-9-yl)-3-cyano-7-fluorobenzo[b]thiophen-2-yl)carbamate. A solution of tert-butyl (tert-butoxycarbonyl)(3-((1R)-1-((9R)-9-(2-((tert-butoxycarbonyl)amino)-3-cyano-7-fluorobenzo[b]thiophen-4-yl)-8-chloro-10-fluoro-2-(methylsulfinyl)-5,6-dihydro-4H-[1,4]oxazepino[5,6,7-de]quinazolin-4-yl) but-3-en-1-yl) pyridin-2-yl)carbamate (150 mg, 0.160 mmol) in THF (3.00 mL, 37.066 mmol) was treated with [(2R,7aS)-2-fluorohexahydropyrrolizin-7a-yl]methanol (76.34 mg, 0.480 mmol) for 5 minutes at 0° C. under nitrogen atmosphere followed by the addition of NaH (34.52 mg, 1.440 mmol) in portions at 0° C. The resulting mixture was stirred for 2 hours at 0° C. and quenched with sat. $NH_4Cl$. The resulting mixture was extracted with EtOAc (3×50 mL). The combined organic layers were washed with brine (2×20 mL) and dried over anhydrous $Na_2SO_4$. After filtration, the filtrate was concentrated under reduced pressure. The resulting residue was purified by reverse-phase flash chromatography (column, C18 silica gel; mobile phase, MeCN in Water (10 mmol/L $NH_4HCO_3$), 10% to 50% gradient in 10 min; detector, UV 254 nm) to afford the desired product as a yellow solid. (ESI, m/z): 933 $[M+H]^+$.

Step J: Synthesis of 2-amino-4-((R)-4-((R)-1-(2-aminopyridin-3-yl) but-3-en-1-yl)-8-chloro-10-fluoro-2-(((2R,7aS)-2-fluorotetrahydro-1H-pyrrolizin-7a (5H)-yl) methoxy)-5,6-dihydro-4H-[1,4]oxazepino[5,6,7-de] quinazolin-9-yl)-7-fluorobenzo[b]thiophene-3-carbonitrile. In a reaction vial were added tert-butyl (4-((R)-4-((R)-1-(2-((tert-butoxycarbonyl)amino)pyridin-3-yl) but-3-en-1-yl)-8-chloro-10-fluoro-2-(((2R,7aS)-2-fluorotetrahydro-1H-pyrrolizin-7a (5H)-yl)methoxy)-5,6-dihydro-4H-[1,4] oxazepino[5,6,7-de]quinazolin-9-yl)-3-cyano-7-fluorobenzo[b]thiophen-2-yl)carbamate (95 mg, 0.103 mmol), TFA (2 mL) and DCM (4 mL, 31.461 mmol) at room temperature. The resulting mixture was stirred for 1 hour at room temperature and concentrated under reduced pressure. The mixtures was diluted with acetonitrile (3 mL) and purified by Prep-HPLC (Column: XBridge BEH Shield RP18 5 m, 30 mm*150 mm; Mobile Phase A: Water (10 mmol/L $NH_4HCO_3$), Mobile Phase B: ACN; Flow rate: 60 ml/min mL/min; Gradient: 50% B to 65% B in 8 min; Wave Length: 254 nm/220 nm nm; RT1 (min): 6.28) to afford the desired product as a white solid. (ESI, m/z): 733 $[M+H]^+$. $^1H$ NMR (400 MHZ, DMSO-d6) δ 8.09 (s, 2H), 8.00-7.94 (m, 1H), 7.67 (d, J=7.5 Hz, 1H), 7.20 (dd, J=8.4, 5.3 Hz, 1H), 7.13 (t, J=8.9 Hz, 1H), 6.65 (dd, J=7.5, 4.8 Hz, 1H), 6.33 (dd, J=9.2, 6.1 Hz, 1H), 5.95 (s, 2H), 5.79-5.65 (m, 1H), 5.29 (d, J=54.4 Hz, 1H), 5.17 (d, J=17.0 Hz, 1H), 4.97 (d, J=10.2 Hz, 1H), 4.49 (dd, J=12.2, 6.6 Hz, 1H), 4.27 (dd, J=12.1, 6.7 Hz, 1H), 4.15-4.05 (m, 2H), 3.67 (dd, J=15.5, 6.7 Hz, 1H), 3.42 (dd, J=15.6, 6.6 Hz, 1H), 3.16-3.05 (m, 2H), 3.01 (s, 1H), 2.95 (q, J=8.7, 7.8 Hz, 1H), 2.80 (dt, J=13.5, 5.9 Hz, 2H), 2.22-2.09 (m, 1H), 2.09-1.99 (m, 2H), 1.89-1.76 (m, 3H).

Example 1q: Synthesis of 2-amino-4-((S)-4-((R)-1-(2-amino-5-fluoropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (864).

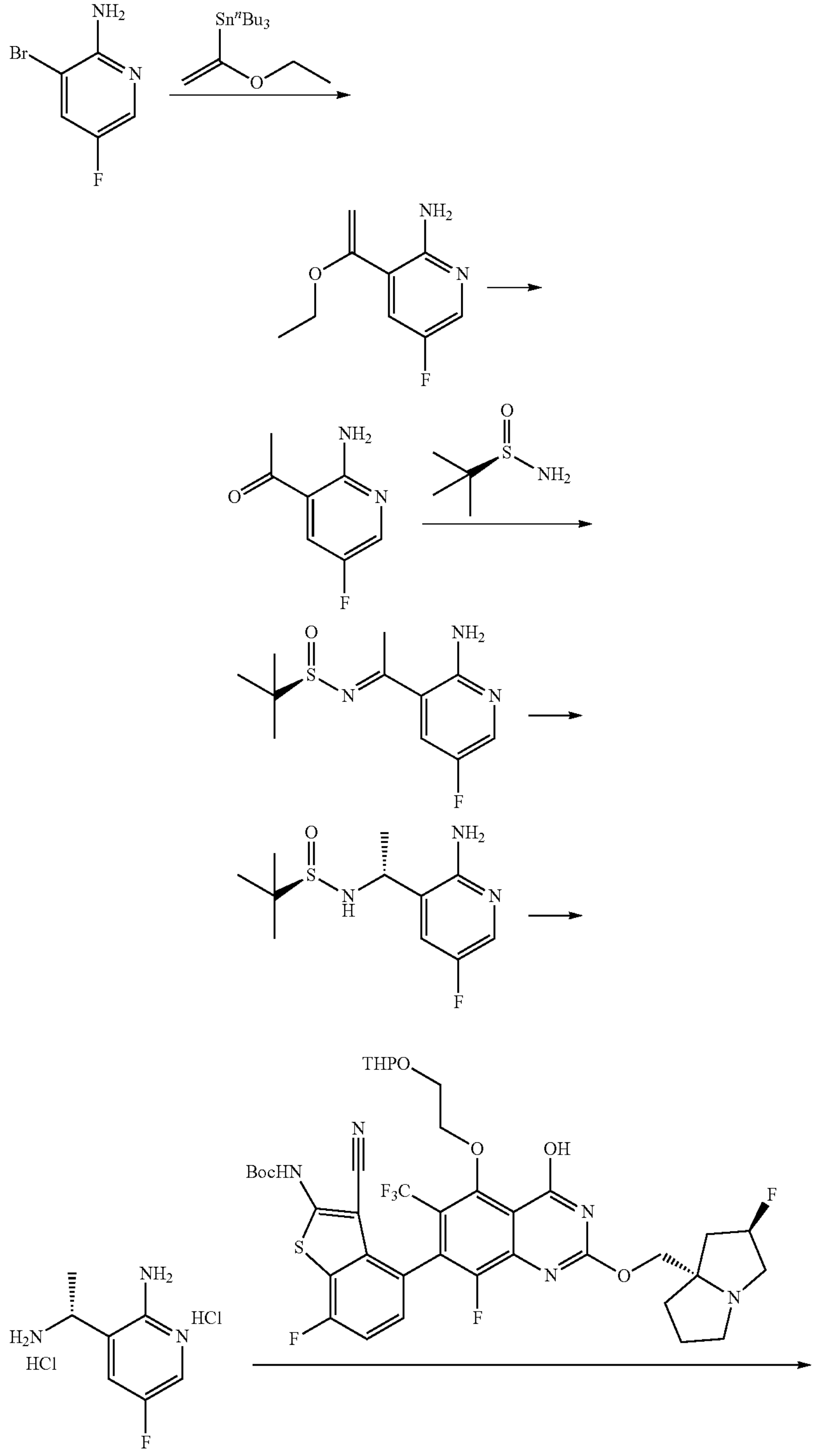

-continued

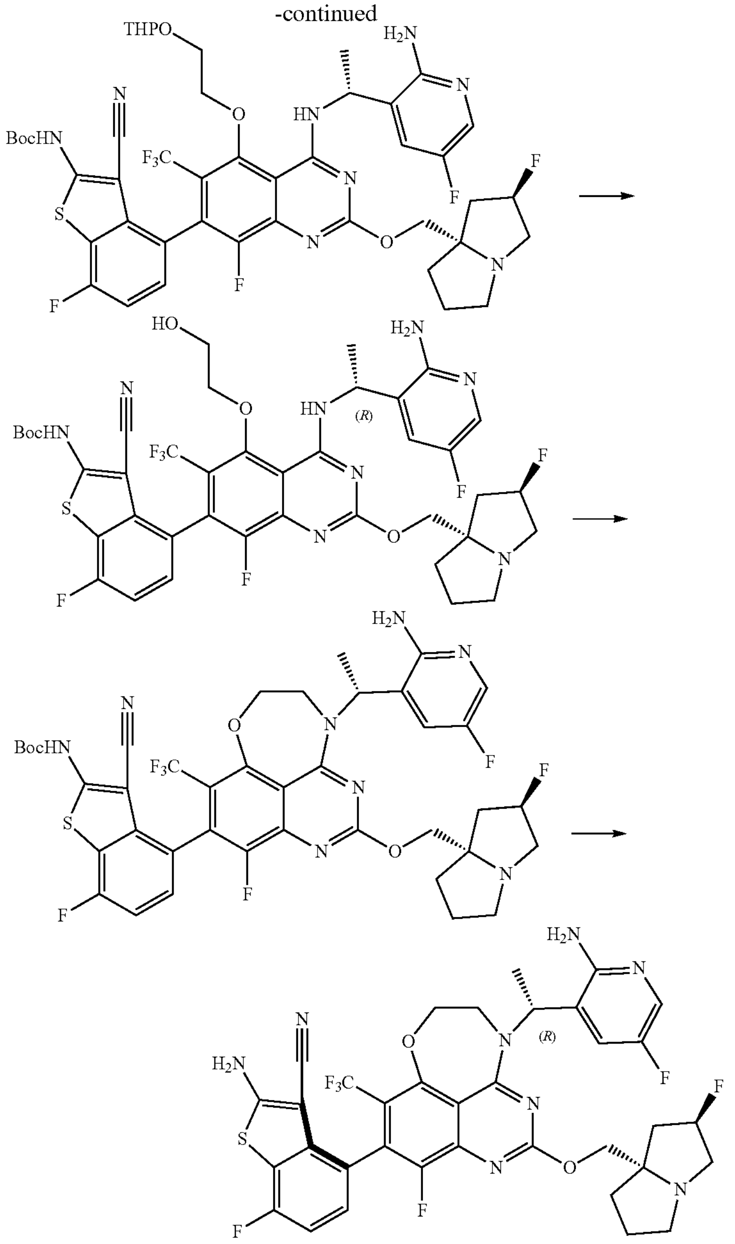

Step A: Synthesis of 3-(1-ethoxyvinyl)-5-fluoropyridin-2-amine. A solution of 3-bromo-5-fluoropyridin-2-amine (6 g, 31.413 mmol), tributyl(1-ethoxyethenyl) stannane (13.61 g, 37.696 mmol) and Pd $(PPh_3)_2Cl_2$ (4.41 g, 6.283 mmol) in toluene (60 mL) was stirred at 100° C. for 3 hours under nitrogen atmosphere. The mixture was allowed to cool to room temperature and extracted with EtOAc (3×300 mL). The combined organic layers were washed with water (3×100 mL) and dried over anhydrous $Na_2SO_4$. After filtration, the filtrate was concentrated under reduced pressure to give the desired product which was used in the next step directly without further purification. (ESI, m/z): 183 $[M+H]^+$.

Step B: Synthesis of 1-(2-amino-5-fluoropyridin-3-yl) ethan-1-one. To a stirred solution of 3-(1-ethoxyethenyl)-5-fluoropyridin-2-amine (9.8 g, 53.788 mmol) in THF (50 mL) was added 2M HCl (50 mL, 100.000 mmol) dropwise at room temperature. The resulting mixture was stirred at room temperature for 2 hours and extracted with EtOAc (3×200 mL). The combined organic layers were washed with water (3×100 mL) and dried over anhydrous $Na_2SO_4$. After filtration, the filtrate was concentrated under reduced pressure. The resulting residue was purified by silica gel column chromatography, eluted with petroleum ether/ethyl acetate (3:1) to give the desired product as a yellow solid. (ESI, m/z): 155 $[M+H]^+$.

Step C: Synthesis of (R,E)-N-(1-(2-amino-5-fluoropyridin-3-yl)ethylidene)-2-methylpropane-2-sulfinamide. A solution of 1-(2-amino-5-fluoropyridin-3-yl) ethanone (2.6 g, 16.867 mmol), (R)-2-methylpropane-2-sulfinamide (5.11 g, 42.168 mmol) and Ti (OEt) 4 (19.24 g, 84.335 mmol) in THF (26 mL) was stirred at 70° C. for 3 hours. The mixture was allowed to cool to room temperature and diluted with water (50 mL). The resulting mixture was filtered and the filter cake was washed with EtOAc (6×50 mL). The filtrate was concentrated under reduced pressure. The resulting residue was purified by silica gel column chromatography to afford the desired product as a yellow solid. (ESI, m/z): 258 [M+H]$^+$.

Step D: Synthesis of (R)—N—((R)-1-(2-amino-5-fluoropyridin-3-yl)ethyl)-2-methylpropane-2-sulfinamide. To a stirred solution of (R)—N-[(1E)-1-(2-amino-5-fluoropyridin-3-yl)ethylidene]-2-methylpropane-2-sulfinamide (3.7 g, 14.378 mmol) in THF (65 mL) was added 1M DIBAl-H in DCM (57.51 mL, 57.512 mmol) dropwise at −78° C. under nitrogen atmosphere and the mixture was stirred for 1 hour. The reaction was then quenched with water at −20° C. The resulting mixture was warmed to room temperature, filtered, and the filter cake was washed with EtOAc (3×80 mL). The filtrate was concentrated under reduced pressure. The resulting residue was purified by silica gel column chromatography, eluting with $CH_2Cl2$/MeOH (10:1) to afford the desired product as a yellow oil. (ESI, m/z): 260 [M+H]$^+$.

Step E: Synthesis of (R)-3-(1-aminoethyl)-5-fluoropyridin-2-amine. A solution of (R)—N-[(1R)-1-(2-amino-5-fluoropyridin-3-yl)ethyl]-2-methylpropane-2-sulfinamide (3.2 g, 12.339 mmol) and HCl in MeOH (2.70 g, 74.034 mmol) in ethyl acetate (32.00 mL) was stirred at room temperature for 1 hour. The resulting mixture was concentrated under vacuum to provide the desired product as a yellow solid. (ESI, m/z): 156 [M+H]$^+$.

Step F: Synthesis of tert-butyl (4-(4-(((R)-1-(2-amino-5-fluoropyridin-3-yl)ethyl)amino)-8-fluoro-2-(((2R,7aS)-2-fluorotetrahydro-1H-pyrrolizin-7a (5H)-yl)methoxy)-5-(2-((tetrahydro-2H-pyran-2-yl)oxy) ethoxy)-6-(trifluoromethyl) quinazolin-7-yl)-3-cyano-7-fluorobenzo[b]thiophen-2-yl)carbamate. A solution of tert-butyl (3-cyano-7-fluoro-4-(8-fluoro-2-(((2R,7aS)-2-fluorotetrahydro-1H-pyrrolizin-7a (5H)-yl)methoxy)-4-hydroxy-5-(2-((tetrahydro-2H-pyran-2-yl)oxy) ethoxy)-6-(trifluoromethyl) quinazolin-7-yl)benzo[b]thiophen-2-yl)carbamate (200 mg, 0.243 mmol), HATU (110.77 mg, 0.292 mmol), DIEA (62.76 mg, 0.486 mmol) in THF (10.00 mL), and DMA (2.00 mL) was stirred at room temperature for 3 hours. To the above mixture were added 3-[(1R)-1-aminoethyl]-5-fluoropyridin-2-amine dihydrochloride (166.12 mg, 0.729 mmol) and DIEA (62.76 mg, 0.486 mmol) at room temperature. The resulting mixture was stirred an additional 1 hour, then quenched with water at room temperature and extracted with EtOAc (3×20 mL). The combined organic layers were washed with brine (2×50 mL) and dried over anhydrous $Na_2SO_4$. After filtration, the filtrate was concentrated under reduced pressure. The resulting residue was purified by silica gel column chromatography, eluted with $CH_2Cl2$/MeOH (10:1) to afford the desired product as a yellow solid. (ESI, m/z): 961 [M+H]$^+$.

Step G: Synthesis of tert-butyl (4-(4-(((R)-1-(2-amino-5-fluoropyridin-3-yl)ethyl)amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo[b]thiophen-2-yl)carbamate. A solution of tert-butyl (4-(4-(((R)-1-(2-amino-5-fluoropyridin-3-yl) ethyl)amino)-8-fluoro-2-(((2R,7aS)-2-fluorotetrahydro-1H-pyrrolizin-7a (5H)-yl)methoxy)-5-(2-((tetrahydro-2H-pyran-2-yl)oxy) ethoxy)-6-(trifluoromethyl) quinazolin-7-yl)-3-cyano-7-fluorobenzo[b]thiophen-2-yl)carbamate (190 mg, 0.198 mmol) and HCl in MeOH (43.25 mg, 1.188 mmol) in ethyl acetate (2 mL) was stirred at room temperature for 1 hour. The pH of the mixture was adjusted to ~8 with saturated $NaHCO_3$(aq.) and extracted with EtOAc (3×30 mL). The combined organic layers were washed with brine (1×100 mL) and dried over anhydrous $Na_2SO_4$. After filtration, the filtrate was concentrated under reduced pressure to give the desired product which was used directly in the next step without further purification. (ESI, m/z): 877 [M+H]$^+$.

Step H: Synthesis of tert-butyl (4-(4-((R)-1-(2-amino-5-fluoropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate. A solution of tert-butyl (4-(4-(((R)-1-(2-amino-5-fluoropyridin-3-yl)ethyl)amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo[b]thiophen-2-yl)carbamate (100 mg, 0.114 mmol) and $PPh_3$ (89.74 mg, 0.342 mmol) in THF (1 mL) was stirred at 0° C. for 10 minutes under nitrogen atmosphere. To the above mixture was added DIAD (69.2 mg, 0.342 mmol) dropwise at 0° C. and the resulting mixture was stirred at room temperature for an additional 7 hours. The mixture was quenched with water and extracted with EtOAc (3×20 mL). The combined organic layers were washed with brine (1×60 mL) and dried over anhydrous $Na_2SO_4$. After filtration, the filtrate was concentrated under reduced pressure and the resulting residue was purified by silica gel column chromatography, eluting with $CH_2Cl2$/MeOH (10:1) to afford the desired product as a yellow solid. (ESI, m/z): 859 [M+H]$^+$.

Step I: Synthesis of 2-amino-4-((S)-4-((R)-1-(2-amino-5-fluoropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile. A solution of tert-butyl (4-(4-((R)-1-(2-amino-5-fluoropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-3-cyano-7-fluorobenzo[b]thiophen-2-yl)carbamate (35 mg, 0.041 mmol) and TFA (0.5 mL, 6.732 mmol) in DCM (1 mL) was stirred at room temperature for 1 hour. The pH of the mixture was adjusted to ~8 with saturated $NaHCO_3$(aq.) and extracted with $CH_2Cl_2$ (3×20 mL). The combined organic layers were washed with brine (1×60 mL) and dried over anhydrous $Na_2SO_4$. After filtration, the filtrate was concentrated under reduced pressure and the resulting residue was purified by Prep-HPLC (Column: YMC-Actus Triart C18 ExRS 30*150 mm, 5 m; Mobile Phase A: Water (10 mmol/L $NH_4HCO_3$), Mobile Phase B: ACN; Flow rate: 60 mL/min mL/min; Gradient: 47% B to 67% B in 8 min; Wave Length: 254 nm/220 nm nm; RT1 (min): 8.97/11.15) to afford the desired product as the first elute as a white solid. (ESI, m/z): 759 [M+H]$^+$. $^1$H NMR (400 MHZ, DMSO-d6) δ 8.08 (s, 2H), 7.98 (d, J=2.8 Hz, 1H), 7.60 (d, J=9.6 Hz, 1H), 7.20-7.04 (m, 2H), 6.08 (d, J=7.0 Hz, 1H), 5.69 (s, 2H), 5.27 (d, J=54.2 Hz, 1H), 4.42 (s, 1H), 4.25 (d, J=8.5 Hz, 1H), 4.14-4.04 (m, 2H), 3.70-3.51 (m, 2H), 3.07 (d, J=7.8 Hz, 2H), 2.99 (s, 1H), 2.81 (d, J=7.7 Hz, 1H), 2.16-1.98 (m, 3H), 1.88-1.74 (m, 3H), 1.62 (d, J=6.7 Hz, 3H).

Example 1r: Synthesis of 2-amino-4-((S)-4-((R)-1-(2-aminopyridin-3-yl)-3-(tetrahydro-2H-pyran-4-yl) propyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4] oxazepino[5,6,7-de]quinazolin-9-yl)-7-fluorobenzo[b]thiophene-3-carbonitrile (611).

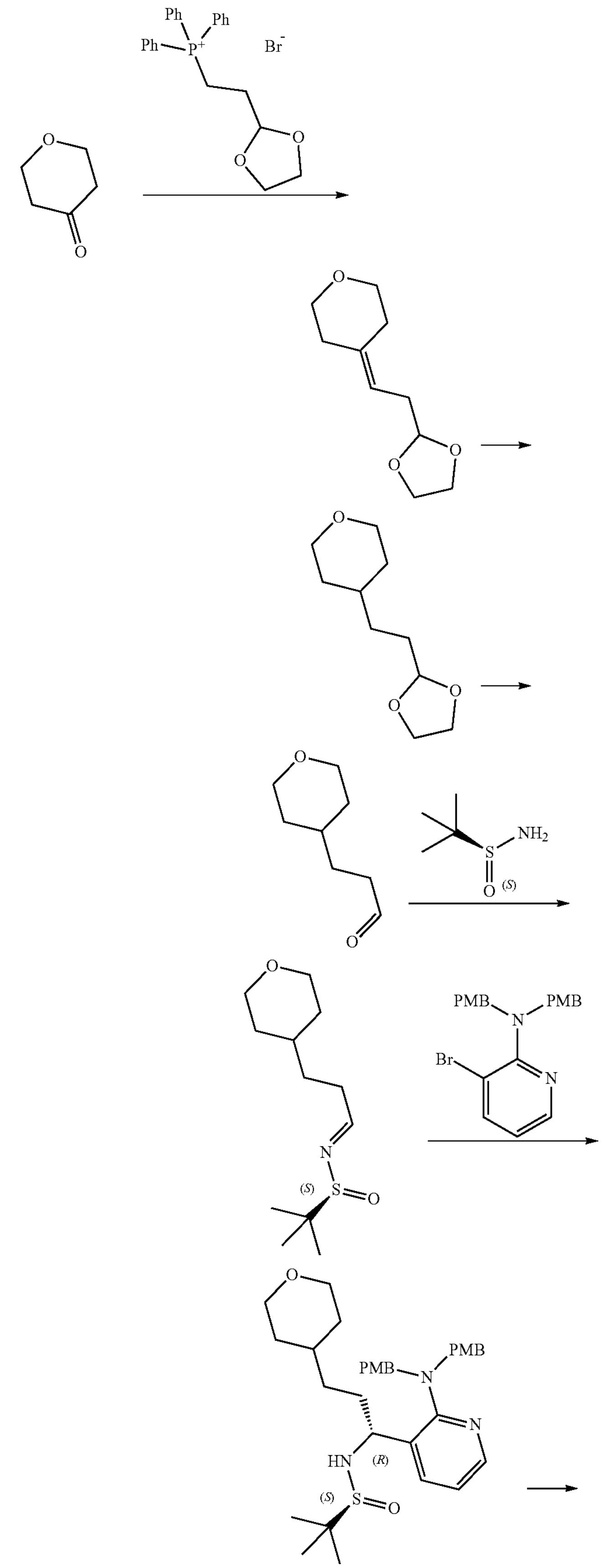

-continued
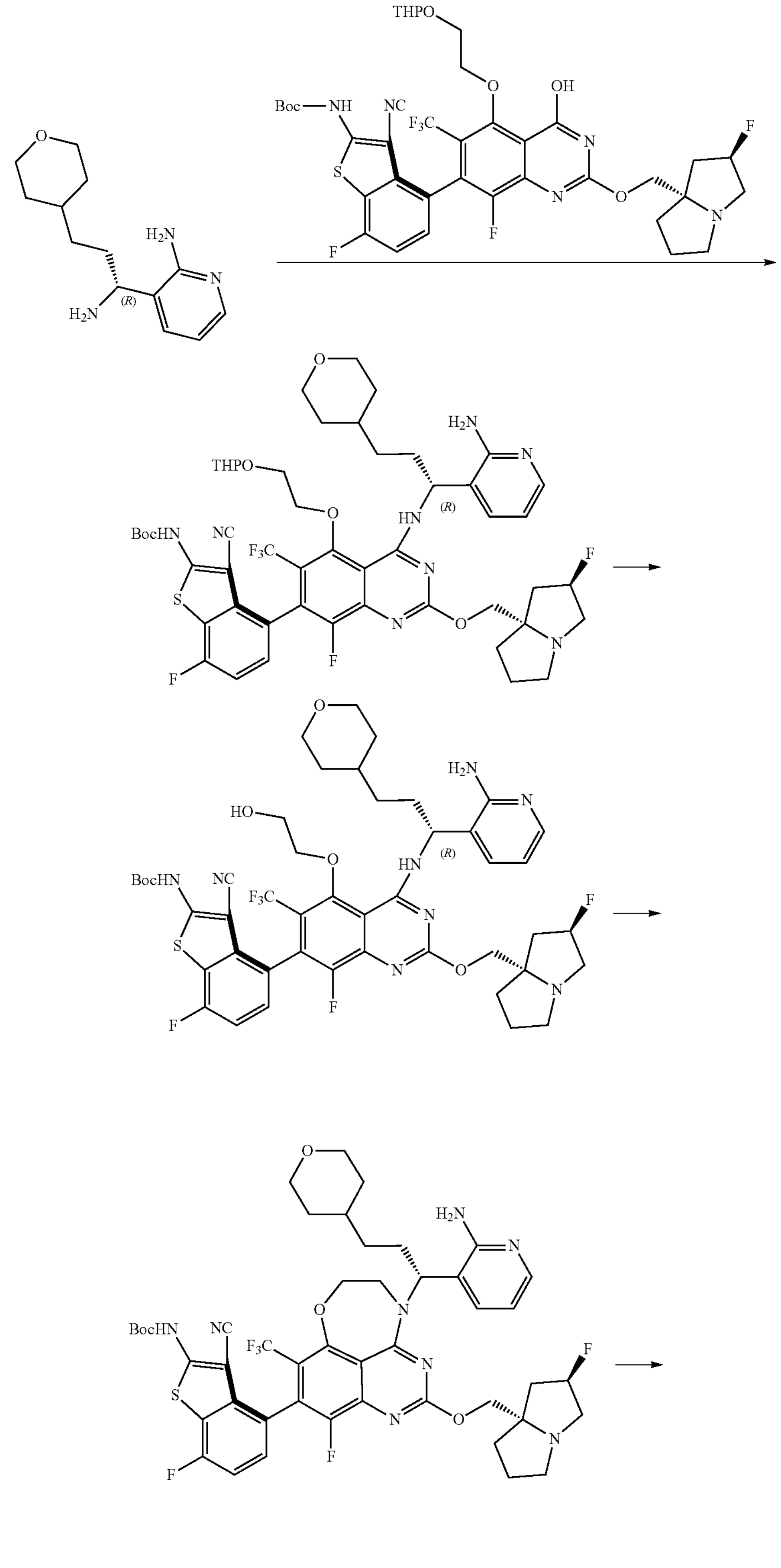

-continued

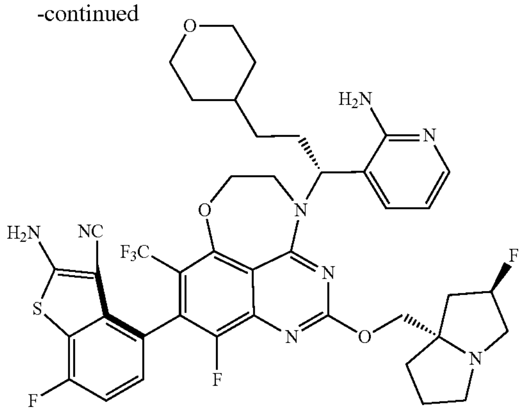

Step A: Synthesis of 4-(2-(1,3-dioxolan-2-yl)ethylidene) tetrahydro-2H-pyran. To a stirred solution of [2-(1,3-dioxolan-2-yl)ethyl]triphenylphosphanium bromide (26.6 g, 59.9 mmol) in THF (60 mL) was added sodium bis(trimethylsilyl) azanide (30 ml, 2 mol/L, 59.9 mmol) dropwise at 0° C. under nitrogen atmosphere. The resulting mixture was stirred at 0° C. for 1 hour. To the above mixture was added 4H-pyran-4-one, tetrahydro-(5.0 g, 49.9 mmol, dissolved in 10 mL THF) dropwise over 5 minutes at 0° C. The resulting mixture was stirred at room temperature for an additional 2 hours, then quenched by the addition of water (150 mL) at 0° C. and extracted with diethyl ether (3×150 mL). The combined organic layers were washed with brine (2×70 mL) and dried over anhydrous $Na_2SO_4$. After filtration, the filtrate was concentrated under reduced pressure to give a mixture. The mixture was purified by silica gel column chromatography to afford the desired product as a colorless liquid. 1H NMR (300 MHZ, Chloroform-d) δ 5.26 (tt, J=7.3, 1.3 Hz, 1H), 4.87 (t, J=4.8 Hz, 1H), 4.02-3.95 (m, 2H), 3.90-3.83 (m, 2H), 3.67 (q, J=5.4 Hz, 4H), 2.41 (dd, J=7.3, 4.8 Hz, 2H), 2.33-2.19 (m, 4H).

Step B: Synthesis of 4-(2-(1,3-dioxolan-2-yl)ethyl)tetrahydro-2H-pyran. A mixture of 4-[2-(1,3-dioxolan-2-yl)ethylidene]oxane (5.0 g, 27.1 mmol) and Pd/C (0.5 g, 4.6 mmol) in MeOH (50 mL) was stirred at 30° C. for 12 hours under hydrogen (1 atm) atmosphere. The resulting mixture was filtered and the filter cake was washed with MeOH (2×10 mL). The filtrate was concentrated under reduced pressure to afford the desired product as a colorless liquid which was used directly in the next step without further purification. 1H NMR (400 MHZ, Chloroform-d) δ 4.77 (t, J=4.8 Hz, 1H), 3.93-3.84 (m, 4H), 3.81-3.75 (m, 2H), 3.30 (td, J=11.8, 2.1 Hz, 2H), 1.65-1.49 (m, 4H), 1.48-1.37 (m, J=14.6, 10.6, 7.1, 3.4 Hz, 1H), 1.35-1.15 (m, 4H).

Step C: Synthesis of 3-(tetrahydro-2H-pyran-4-yl) propanal. A solution of 4-[2-(1,3-dioxolan-2-yl)ethyl]oxane (5.0 g, 26.8 mmol) and HCl (50 mL, 3 M in water) in THF (50 mL) was stirred at room temperature for 12 hours under air atmosphere. The mixture was extracted with diethyl ether (3×100 mL). The combined organic layers were washed with brine (2×50 mL) and dried over anhydrous $Na_2SO_4$. After filtration, the filtrate was concentrated under reduced pressure to afford the desired product as a colorless liquid which used directly in next step. 1H NMR (400 MHZ, Chloroform-d) δ 9.79 (t, J=1.7 Hz, 1H), 3.96 (dtd, J=11.5, 2.5, 1.1 Hz, 3H), 3.75 (ddt, J=7.0, 5.1, 1.9 Hz, 2H), 3.36 (tt, J=11.8, 2.5 Hz, 3H), 2.47 (td, J=7.5, 1.7 Hz, 2H), 1.88-1.83 (m, 2H), 1.53-1.46 (m, 1H).

Step D: Synthesis of (S,E)-2-methyl-N-(3-(tetrahydro-2H-pyran-4-yl) propylidene) propane-2-sulfinamide. To a solution of 3-(oxan-4-yl) propanal (3.2 g, 22.5 mmol) and (S)-2-methylpropane-2-sulfinamide (3.0 g, 24.8 mmol) in THF (60 mL) was added titanium (IV) ethoxide (7.7 g, 33.8 mmol) at room temperature. The resulting mixture was stirred for 2 hours at room temperature and quenched by the addition of water (30 mL) at 0° C. The resulting mixture was filtered, the filter cake was washed with EtOAc (3×100 mL), and the combined organic layers were washed with brine (2×100 mL) and dried over anhydrous $Na_2SO_4$. After filtration, the filtrate was concentrated under reduced pressure. The resulting residue was purified by normal-phase flash chromatography (column, silica gel; mobile phase, EtOAc in petroleum ether, 20% to 45% gradient in 15 min; detector, UV 254 nm) to afford the desired product as a colorless liquid. (ESI, m/z): $[M+H]^+$246.10. $^1H$ NMR (400 MHz, Chloroform-d) δ 8.08 (t, J=4.7 Hz, 1H), 3.96 (dd, J=11.6, 4.5 Hz, 2H), 3.79-3.71 (m, 2H), 3.36 (tt, J=11.7, 2.1 Hz, 2H), 2.55 (td, J=7.4, 4.7 Hz, 2H), 1.89-1.82 (m, 2H), 1.52 (dtd, J=10.6, 6.8, 3.3 Hz, 1H), 1.31 (qd, J=12.3, 4.4 Hz, 2H), 1.20 (s, 9H).

Step E: Synthesis of (R)-3-(1-amino-3-(tetrahydro-2H-pyran-4-yl) propyl)pyridin-2-amine. To a stirred solution of 3-bromo-N,N-bis[(4-methoxyphenyl)methyl]pyridin-2-amine (2.7 g, 6.5 mmol) in THF (80 mL) was added n-BuLi (4.24 mL, 10.6 mmol, 2.5 M in hexane) dropwise at −78° C. under nitrogen atmosphere. The resulting mixture was stirred at −78° C. for 30 minutes. To the above mixture was added(S)-2-methyl-N-[3-(oxan-4-yl) propylidene]propane-2-sulfinamide (2.0 g, 8.2 mmol) dropwise at −78° C. and the resulting mixture was stirred for an additional 1 hour. The reaction was quenched by the addition of sat. $NH_4Cl$ (aq. 30 mL) at 0° C. The resulting mixture was diluted with water (80 mL) and extracted with $CH_2Cl_2$ (3×90 mL). The combined organic layers were washed with brine (2×50 mL) and dried over anhydrous $Na_2SO_4$. After filtration, the filtrate was concentrated under reduced pressure. The resulting residue was purified by reverse-phase flash chromatography (column, C18; mobile phase, MeCN in Water (0.1% FA), 30% to 60% gradient in 30 min; detector, UV 254 nm) to afford the crude product. The crude product (2.5 g) was purified by Prep-HPLC(Column: XSelect CSH Prep C18 OBD Column, 30*150 mm, 5 m; Mobile Phase A: Water (0.1% FA), Mobile Phase B: ACN; Flow rate: 60 mL/min mL/min; Gradient: 40% B to 59% B in 9 min; Wave Length: 254 nm/220 nm nm; RT1 (min): 8.28) to afford the desired product as a white solid. (ESI, m/z): $[M+H]^+$580.25. $^1H$ NMR (400 MHZ, DMSO-d6) δ 8.18 (dd, J=4.7, 1.8 Hz, 1H), 7.81 (dd, J=7.6, 1.9 Hz, 1H), 7.18-7.13 (m, 4H), 7.08 (dd, J=7.6, 4.7 Hz, 1H), 6.87-6.79 (m, 4H), 5.42 (d, J=7.8 Hz, 1H), 4.77 (q, J=7.3 Hz, 1H), 4.16 (d, J=13.9 Hz, 2H), 4.00 (d, J=13.9 Hz, 2H), 3.80-3.73 (m, 2H), 3.70 (s, 6H), 3.17 (dtd, J=13.9, 11.6, 2.0 Hz, 2H), 1.83-1.70 (m, 1H), 1.50 (td, J=11.6, 10.9, 5.3 Hz, 1H), 1.46-1.37 (m, 2H), 1.36-1.22 (m, 2H), 1.03 (dt, J=12.2, 5.4 Hz, 2H), 0.96 (s, 9H), 0.93-0.86 (m, 1H).

Step F: Synthesis of (R)-3-(1-amino-3-(tetrahydro-2H-pyran-4-yl) propyl)pyridin-2-amine. A solution of(S)—N-[(1R)-1-(2-(bis[(4-methoxyphenyl)methyl]aminopyridin-3-yl)-3-(oxan-4-yl) propyl]-2-methylpropane-2-sulfinamide (500 mg, 0.9 mmol) and HCl (15 mL, 6M in $H_2O$) was stirred at 100° C. for 2 hours under air atmosphere. The resulting mixture was cooled to room temperature and diluted with water (50 mL). The resulting mixture was extracted with EtOAc (2×50 mL). The pH of the aqueous layer was adjusted to ~10 with $NH_3$. $H_2O$ and extracted with $CH_2Cl2$/MeOH (10/1)(3×100 mL). The combined organic layers were washed with brine (2×50 mL) and dried over anhydrous $Na_2SO_4$. After filtration, the filtrate was concentrated under reduced pressure to afford the desired product (230 mg, crude) as a yellow solid which was used in the next step directly without further purification. (ESI, m/z): $[M+H]^+$236.25. $^1$H NMR (400 MHZ, DMSO-d6) δ 7.84-7.71 (m, 1H), 7.28 (dd, J=7.3, 1.9 Hz, 1H), 6.48 (dd, J=7.2, 4.9 Hz, 1H), 6.03 (s, 2H), 3.85-3.73 (m, 3H), 3.22 (tt, J=11.6, 1.9 Hz, 2H), 1.92 (s, 2H), 1.67 (tdd, J=12.0, 7.0, 5.2 Hz, 1H), 1.60-1.44 (m, 3H), 1.44-1.32 (m, 1H), 1.22 (dddd, J=16.0, 11.8, 7.0, 5.0 Hz, 1H), 1.16-0.96 (m, 3H).

Step G: Synthesis of tert-butyl (4-((S)-4-(((R)-1-(2-aminopyridin-3-yl)-3-(tetrahydro-2H-pyran-4-yl) propyl) amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo [b]thiophen-2-yl)carbamate. A solution of tert-butyl (4-((7S)-4-(((R)-1-(2-aminopyridin-3-yl)-3-(tetrahydro-2H-pyran-4-yl) propyl)amino)-8-fluoro-2-(((2R,7aS)-2-fluorotetrahydro-1H-pyrrolizin-7a (5H)-yl)methoxy)-5-(2-((tetrahydro-2H-pyran-2-yl)oxy) ethoxy)-6-(trifluoromethyl) quinazolin-7-yl)-3-cyano-7-fluorobenzo [b]thiophen-2-yl)carbamate (900 mg, 1.1 mmol), $Et_3N$ (0.55 g, 5.4 mmol), 3-[(1R)-1-amino-3-(oxan-4-yl) propyl]pyridin-2-amine (514 mg, 2.2 mmol) and hexafluoro-l^[5]-phosphanuide tris(pyrrolidin-1-yl)phosphanium bromide (0.76 g, 1.627 mmol) in 1,4-dioxane (25 mL) was stirred at room temperature for 3 hours. The resulting mixture was diluted with water (150 mL) and extracted with $CH_2Cl_2$ (3×150 mL). The combined organic layers were washed with brine (2×50 mL) and dried over anhydrous $Na_2SO_4$. After filtration, the filtrate was concentrated under reduced pressure to give a residue. The residue was purified by reverse-phase flash chromatography (column, C18; mobile phase, MeOH in Water (10 mmol/L $NH_4HCO_3$), 70% to 90% gradient in 20 min; detector, UV 254 nm) to afford the desired product as a yellow solid. (ESI, m/z): $[M+H]^+$1041.4. $^1$H NMR (400 MHZ, DMSO-d6) δ 8.46 (t, J=9.3 Hz, 1H), 7.88 (dt, J=4.5, 2.1 Hz, 1H), 7.60 (ddd, J=21.0, 7.5, 1.8 Hz, 1H), 7.17 (d, J=22.1 Hz, 2H), 6.58 (ddd, J=7.3, 4.9, 2.3 Hz, 1H), 6.00 (d, J=7.3 Hz, 2H), 5.76 (s, 1H), 5.50-5.27 (m, 2H), 4.59 (dd, J=13.6, 4.5 Hz, 1H), 4.35-4.11 (m, 4H), 4.08-3.94 (m, 1H), 3.79 (ddd, J=22.1, 11.6, 5.6 Hz, 4H), 3.49-3.40 (m, 2H), 3.25 (dd, J=13.0, 10.7 Hz, 3H), 3.01 (dq, J=6.7, 3.9 Hz, 1H), 2.34-2.03 (m, 4H), 2.03-1.82 (m, 5H), 1.75-1.53 (m, 5H), 1.46 (s, 9H), 1.42 (s, 4H), 1.27 (d, J=25.6 Hz, 2H), 1.20-1.07 (m, 2H).

Step H: Synthesis of tert-butyl (4-((S)-4-(((R)-1-(2-aminopyridin-3-yl)-3-(tetrahydro-2H-pyran-4-yl) propyl) amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo [b]thiophen-2-yl)carbamate. To a stirred solution of tert-butyl (4-((S)-4-(((R)-1-(2-aminopyridin-3-yl)-3-(tetrahydro-2H-pyran-4-yl) propyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate (600 mg, 0.6 mmol) in $CH_2Cl2$ (20 mL) was added hydrogen chloride (4.0 M in methanol)(2 mL, 8.000 mmol) dropwise at 0° C. The resulting mixture was stirred at 0° C. for 1 hour and the pH was adjusted to ~10 with saturated $NaHCO_3$(aq.) at 0° C. The resulting mixture was extracted with $CH_2Cl_2$ (3×100 mL). The combined organic layers were washed with brine (2×50 mL) and dried over anhydrous $Na_2SO_4$. After filtration, the filtrate was concentrated under reduced pressure to afford the desired product as a yellow solid. (ESI, m/z): $[M+H]^+$957.35.

Step I: Synthesis of tert-butyl (4-((S)-4-((R)-1-(2-aminopyridin-3-yl)-3-(tetrahydro-2H-pyran-4-yl) propyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4] oxazepino[5,6,7-de]quinazolin-9-yl)-3-cyano-7-fluorobenzo[b]thiophen-2-yl)carbamate. To a stirred solution of $PPh_3$ (0.99 g, 3.8 mmol) in THF (22 mL) was added DIAD (0.63 g, 3.1 mmol, dissolved in 22 mL THF) dropwise at room temperature under nitrogen atmosphere. The resulting mixture was stirred for 40 minutes, then added to a solution of tert-butyl (4-((S)-4-(((R)-1-(2-aminopyridin-3-yl)-3-(tetrahydro-2H-pyran-4-yl) propyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate (600 mg, 0.627 mmol) in THF (6 mL) under nitrogen atmosphere and the resulting mixture was stirred at 40° C. for an additional 2 hours. The mixture was cooled to room temperature and the reaction was quenched with water, then extracted with $CH_2Cl_2$ (3×100 mL). The combined organic layers were washed with brine (2×50 mL) and dried over anhydrous $Na_2SO_4$. After filtration, the filtrate was concentrated under reduced pressure. The resulting residue was purified by silica gel column chromatography, eluted with $CH_2Cl2$/MeOH (13:1) to afford the desired product as a yellow solid. (ESI, m/z): $[M+H]^+$939.4. $^1$H NMR (400 MHZ, DMSO-d6) δ 7.99 (dd, J=4.9, 1.7 Hz, 1H), 7.70 (dd, J=7.5, 1.8 Hz, 1H), 7.20 (s, 2H), 6.68 (dd, J=7.5, 4.9 Hz, 1H), 6.06 (t, J=7.4 Hz, 1H), 5.91 (s, 2H), 5.76 (s, 1H), 5.38 (d, J=53.5 Hz, 1H), 4.49 (td, J=8.7, 8.1, 3.7 Hz, 1H), 4.40-4.09 (m, 3H), 3.87-3.74 (m, 2H), 3.69-3.45 (m, 2H), 3.26 (td, J=11.7, 2.0 Hz, 3H), 2.99 (s, 1H), 2.35-2.04 (m, 5H), 1.96 (d, J=25.2 Hz, 3H), 1.59 (d, J=33.0 Hz, 3H), 1.48 (s, 9H), 1.37-1.01 (m, 6H).

Step J: Synthesis of 2-amino-4-((S)-4-((R)-1-(2-aminopyridin-3-yl)-3-(tetrahydro-2H-pyran-4-yl) propyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4] oxazepino[5,6,7-de]quinazolin-9-yl)-7-fluorobenzo[b]thiophene-3-carbonitrile. To a stirred solution of tert-butyl (4-((S)-4-((R)-1-(2-aminopyridin-3-yl)-3-(tetrahydro-2H-pyran-4-yl) propyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate (450 mg, 0.5 mmol) in $CH_2Cl_2$ (15 mL) was added trifluoroacetic acid (3 mL) dropwise at 0° C. The resulting mixture was stirred at room temperature for 1 hour and diluted with $CH_2Cl_2$ (15 mL) and $NH_3 \cdot H_2O$ at 0° C. The resulting mixture was extracted with $CH_2Cl_2$ (3×100 mL). The combined organic layers were washed with brine (2×50 mL) and dried over anhydrous $Na_2SO_4$. After filtration, the filtrate was concentrated under reduced pressure. The resulting residue was purified by reverse-phase flash chromatography (column, C18; mobile phase, MeCN in Water (10 mmol/L $NH_4HCO_3$), 50% to 80% gradient in 20 min; detector, UV 254 nm) to afford the desired product as a white solid. (ESI, m/z): $[M+H]^+$839.20. $^1H$ NMR (400 MHZ, DMSO-d6) δ 8.06 (s, 2H), 7.98 (dd, J=4.9, 1.6 Hz, 1H), 7.69 (dd, J=7.6, 1.7 Hz, 1H), 7.18-7.05 (m, 2H), 6.67 (dd, J=7.5, 4.9 Hz, 1H), 6.06 (t, J=7.4 Hz, 1H), 5.88 (s, 2H), 5.28 (d, J=54.4 Hz, 1H), 4.52-4.42 (m, 1H), 4.21-4.12 (m, 2H), 4.07 (d, J=10.3 Hz, 1H), 3.86-3.75 (m, 2H), 3.64-3.43 (m, 2H), 3.25 (td, J=11.7, 2.0 Hz, 2H), 3.09 (d, J=9.2 Hz, 2H), 3.02 (s, 1H), 2.83 (q, J=7.9 Hz, 1H), 2.22-1.95 (m, 5H), 1.89-1.73 (m, 3H), 1.64-1.47 (m, J=26.0, 12.7 Hz, 3H), 1.30-1.09 (m, 4H).

Example 1s: Synthesis of 2-amino-4-((S)-4-((R)-1-(2-aminopyridin-3-yl)-2-cyclobutylethyl)-10-fluoro-2-(((2R, 7aS)-2-fluorotetrahydro-1H-pyrrolizin-7a (5H)-yl) methoxy)-8-(trifluoromethyl)-5,6-dihydro-4H-[1,4] oxazepino[5,6,7-de]quinazolin-9-yl)-7-fluorobenzo[b] thiophene-3-carbonitrile (893).

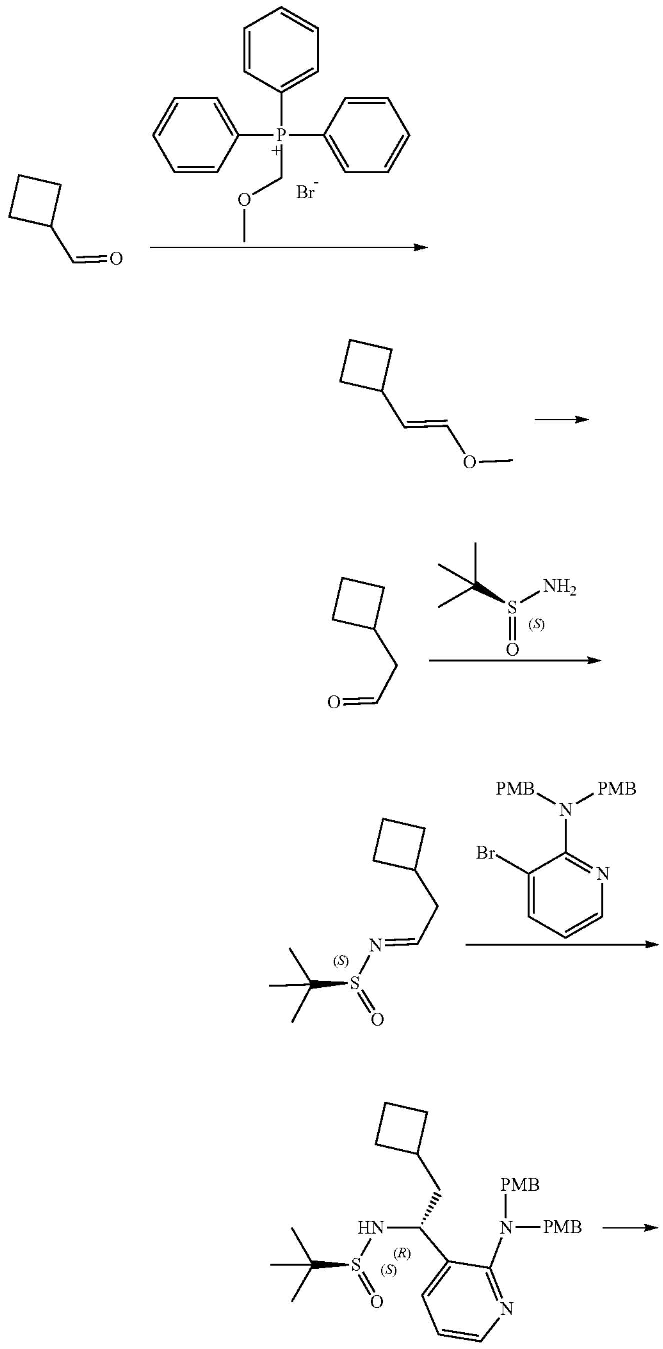

-continued

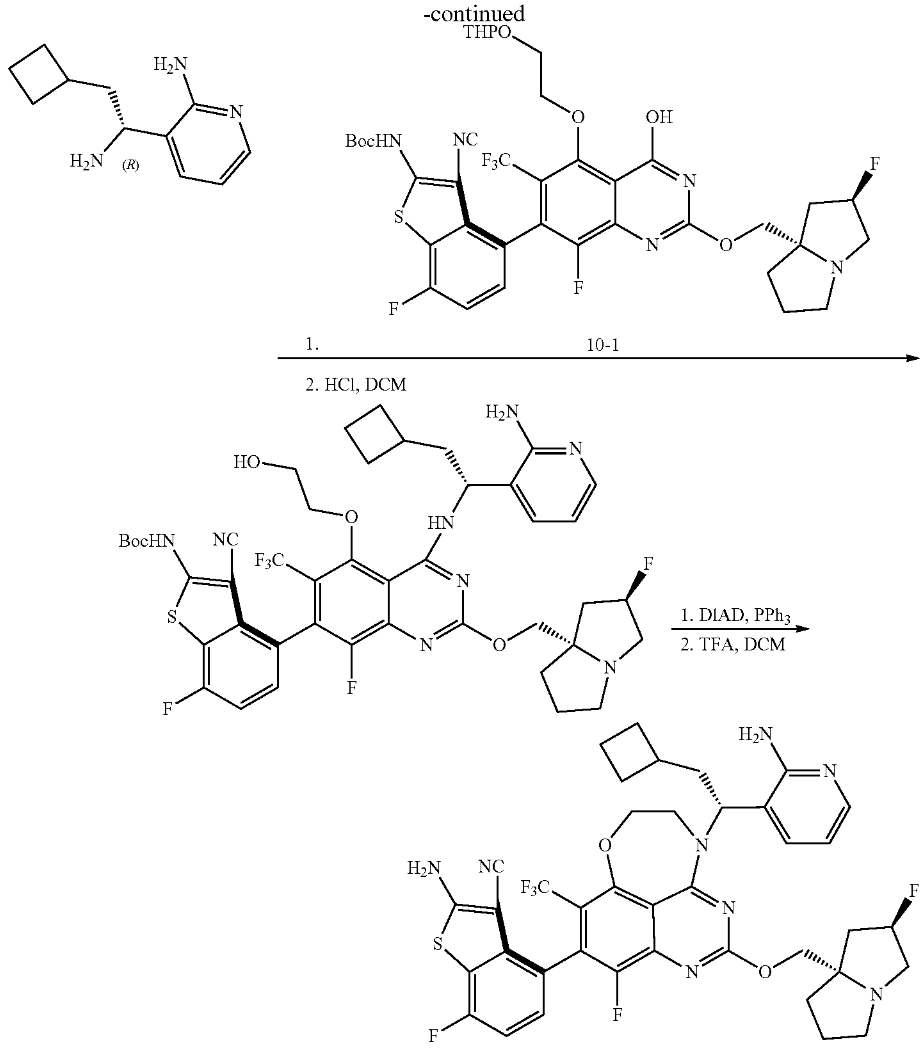

Step A: Synthesis of (E)-(2-methoxyvinyl)cyclobutene. To a stirred solution of (methoxymethyl)triphenylphosphanium bromide (55.2 g, 142.6 mmol) in THF (200 mL) was added NaHMDS (72 mL, 142.6 mmol, 1M in THF) dropwise at 0° C. under nitrogen atmosphere. The resulting mixture was stirred for 1 hour at 0° C. To the above mixture was added cyclobutyral (10.0 g, 118.8 mmol) dropwise and the resulting mixture was stirred for an additional 2 hours at room temperature. The reaction was quenched with sat. $NH_4Cl$ (aq.) at 0° C. and the resulting mixture was extracted with $Et_2O$ (3×200 mL). The combined organic layers were washed with brine (3×100 mL) and dried over anhydrous $Na_2SO_4$. After filtration, the filtrate was concentrated under reduced pressure to give the desired product which was used directly in the next step without further purification.

Step B: Synthesis of 2-cyclobutylacetaldehyde. To (E)-(2-methoxyvinyl)cyclobutene were added THF (50 mL) and HCl (3M)(50 mL) at room temperature. The resulting mixture was stirred overnight at room temperature under nitrogen atmosphere, then extracted with $Et_2O$ (3×200 mL). The combined organic layers were washed with brine (3×100 mL) and dried over anhydrous $Na_2SO_4$. After filtration, the filtrate was used in the next step directly without further purification.

Step C: Synthesis of (S,E)-N-(2-cyclobutylethylidene)-2-methylpropane-2-sulfinamide. To the above mixture in THF (150 mL) was added(S)-2-methylpropane-2-sulfinamide (18.5 g, 152.8 mmol), followed by the addition of tetrakis (propan-2-yloxy) titanium (43.4 g, 152.8 mmol) dropwise at 0° C. under nitrogen atmosphere. The resulting mixture was stirred overnight at room temperature and concentrated under reduced pressure to give a residue. The residue was purified by silica gel column chromatography, eluted with petroleum ether/ethyl acetate (0% to 20% gradient in 30 min) to afford the desired product as a yellow solid. (ES+H, m/z): $[M+H]^+$202.24.

Step D: Synthesis of(S)—N—((R)-1-(2-(bis(4-methoxybenzyl)amino)pyridin-3-yl)-2-cyclobutylethyl)-2-methylpropane-2-sulfinamide. To a stirred solution of 3-bromo-N,N-bis[(4-methoxyphenyl)methyl]pyridin-2-amine (2.4 g, 6.0 mmol) in THF (15 mL) was added n-BuLi (2.4 mL, 6.0 mmol) dropwise at −78° C. under nitrogen atmosphere. The resulting mixture was stirred for 1 h at −78° C., then(S)—N-(2-cyclobutylethylidene)-2-methylpropane-2-sulfinamide (1.0 g, 5.0 mmol) in THF (10 ml) was added dropwise at −78° C. and the resulting mixture was stirred an additional 1 hour. The reaction was quenched with sat. $NH_4Cl$ (aq.) at −78° C. and extracted with EtOAc (3×100 mL). The combined organic layers were washed with brine (3×50 mL) and dried over anhydrous $Na_2SO_4$. After filtration, the filtrate was concentrated under reduced pressure. The resulting residue was purified by silica gel column chromatography, eluted with petroleum ether/ethyl acetate (0% to 100% gradient in 30 min) to afford the desired product as a yellow oil. (ES+H, m/z): $[M+H]^+$536.34. $^1$H NMR (400 MHZ, DMSO-d6) δ 8.16 (dd, J=4.7, 1.9 Hz, 1H), 7.82 (dd, J=7.7, 1.9 Hz, 1H), 7.18-7.14 (m, 4H), 7.05 (dd, J=7.6, 4.7 Hz, 1H), 6.86-6.82 (m, 4H), 5.37 (d, J=7.7 Hz, 1H), 4.76-4.70 (m, 1H), 4.17 (d, J=13.9 Hz, 2H), 3.71 (s, 7H), 2.38-2.27 (m, 1H), 1.93 (ddd, J=13.8, 8.5, 5.9 Hz, 2H), 1.71-1.62 (m, 3H), 1.58-1.44 (m, 3H), 1.37 (p, J=6.9, 6.4 Hz, 1H), 0.96 (s, 9H).

Step E: Synthesis of (R)-3-(1-amino-2-cyclobutylethyl) pyridin-2-amine. Into a 20 mL vial was added(S)—N-[(1R)-1-(2-{bis[(4-methoxyphenyl)methyl]amino}pyridin-3-yl)-2-cyclobutylethyl]-2-methylpropane-2-sulfinamide (400 mg, 0.3 mmol) and HCl (6M)(4 mL) at room temperature. The resulting mixture was stirred at 100° C. for 2 hours under nitrogen atmosphere, then cooled to room temperature. The pH of the mixture was adjusted to ~10 with $NH_3{\cdot}H_2O$ and the mixture was extracted with $CH_2Cl2$/MeOH (10:1)(4×10 mL). The combined extracts were washed with brine and dried over sodium sulfate. The product was filtered and concentrated under reduced pressure to give the desired product which was used directly in the next step without further purification. (ES+H, m/z): $[M+H]^+$192.15. $^1$H NMR (400 MHZ, DMSO-d6) δ 7.78 (dd, J=5.0, 1.9 Hz, 1H), 7.21 (dd, J=7.3, 1.9 Hz, 1H), 6.47 (dd, J=7.3, 4.9 Hz, 1H), 6.06 (s, 2H), 3.75 (t, J=7.0 Hz, 1H), 2.15 (h, J=7.7 Hz, 2H), 1.98 (dtt, J=12.0, 7.8, 3.9 Hz, 2H), 1.82-1.76 (m, 2H), 1.75-1.68 (m, 2H), 1.67-1.59 (m, 2H), 1.48 (q, J=8.8 Hz, 1H).

Step F: Synthesis of tert-butyl (4-((7S)-4-(((R)-1-(2-aminopyridin-3-yl)-2-cyclobutylethyl)amino)-8-fluoro-2-(((2R,7aS)-2-fluorotetrahydro-1H-pyrrolizin-7a (5H)-yl) methoxy)-5-(2-((tetrahydro-2H-pyran-2-yl)oxy) ethoxy)-6-(trifluoromethyl) quinazolin-7-yl)-3-cyano-7-fluorobenzo[b]thiophen-2-yl)carbamate. Into an 8 mL vial were added tert-butyl (3-cyano-7-fluoro-4-((7S)-8-fluoro-2-(((2R,7aS)-2-fluorotetrahydro-1H-pyrrolizin-7a (5H)-yl)methoxy)-4-hydroxy-5-(2-((tetrahydro-2H-pyran-2-yl)oxy) ethoxy)-6-(trifluoromethyl) quinazolin-7-yl)benzo[b]thiophen-2-yl) carbamate (10-1)(200 mg, 0.121 mmol), HATU (138 mg, 0.1 mmol), DIEA (157 mg, 1.2 mmol), and N-methyl-2-pyrrolidone (0.5 mL, 12.7 mmol) at room temperature. The resulting mixture was stirred at room temperature for 30 minutes under nitrogen atmosphere. To the above mixture was added 3-[(1R)-1-amino-2-cyclobutylethyl]pyridin-2-amine (232 mg, 0.6 mmol) and DIEA (157 mg, 1.2 mmol) dropwise over 3 minutes, followed by stirring for an additional 3 hours. The resulting mixture was extracted with EtOAc (3×30 mL). The combined organic layers were washed with brine (1×50 mL) and dried over anhydrous $Na_2SO_4$. After filtration, the filtrate was concentrated under reduced pressure. The resulting residue was purified by reverse-phase flash chromatography (column, C18 silica gel; mobile phase, MeCN in Water (0.1% $NH_3{\cdot}H2O$), 40% to 80% gradient in 30 min; detector, UV 254 nm) to give the desired product as a light-yellow solid. (ES+H, m/z): $[M+H]^+$997.25.

Step G: Synthesis of tert-butyl (4-((S)-4-(((R)-1-(2-aminopyridin-3-yl)-2-cyclobutylethyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate. Into a 20 mL vial were added tert-butyl (4-((7S)-4-(((R)-1-(2-aminopyridin-3-yl)-2-cyclobutylethyl)amino)-8-fluoro-2-(((2R,7aS)-2-fluorotetrahydro-1H-pyrrolizin-7a (5H)-yl)methoxy)-5-(2-((tetrahydro-2H-pyran-2-yl)oxy) ethoxy)-6-(trifluoromethyl) quinazolin-7-yl)-3-cyano-7-fluorobenzo[b]thiophen-2-yl)carbamate (230 mg, 0.231 mmol), hydrogen chloride (4.0 M in methanol)(0.5 mL), and DCM (2 mL) at room temperature. The resulting mixture was stirred at room temperature for 1 hour under nitrogen atmosphere. The pH of the mixture was adjusted to ~9 with $NH_3{\cdot}H_2O$ and the mixture was extracted with $CH_2Cl_2$ (3×50 mL). The combined organic layers were washed with brine (1×50 mL) and dried over anhydrous $Na_2SO_4$. After filtration, the filtrate was concentrated under reduced pressure to give the desired product as a brown oil. (ES+H, m/z): $[M+H]^+$913.25.

Step H: Synthesis of tert-butyl (4-((S)-4-((R)-1-(2-aminopyridin-3-yl)-2-cyclobutylethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate. Into a 20 mL vial was added $PPh_3$ (205 mg, 0.5 mmol) and THF (5 mL) at room temperature. To the above mixture was added DIAD (133 mg, 0.4 mmol) dropwise over 1 minute at room temperature. The resulting mixture was stirred an additional 1 hour, then added to a solution of tert-butyl (4-((S)-4-(((R)-1-(2-aminopyridin-3-yl)-2-cyclobutylethyl)amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo[b]thiophen-2-yl)carbamate (120 mg, 0.1 mmol) in THF (3 mL) dropwise at room temperature. The resulting mixture was stirred at 40° C. for an additional 2 hours, then cooled to room temperature. The resulting mixture was extracted with EtOAc (3×20 mL). The combined organic layers were washed with brine (1×30 mL) and dried over anhydrous $Na_2SO_4$. After filtration, the filtrate was concentrated under reduced pressure. The resulting residue was purified by silica gel column chromatography, eluted with $CH_2Cl2$/MeOH (10:1) to afford the desired product as a brown oil. (ES+H, m/z): $[M+H]^+$895.40.

Step I: Synthesis of 2-amino-4-((S)-4-((R)-1-(2-aminopyridin-3-yl)-2-cyclobutylethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile. Into an 8 mL vial were added tert-butyl (4-((S)-4-((R)-1-(2-aminopyridin-3-yl)-2-cyclobutylethyl)-10-fluoro-2-(((2R,7aS)-2-fluorotetrahydro-1H-pyrrolizin-7a (5H)-yl) methoxy)-8-(trifluoromethyl)-5,6-dihydro-4H-[1,4] oxazepino[5,6,7-de]quinazolin-9-yl)-3-cyano-7-fluorobenzo[b]thiophen-2-yl)carbamate (130 mg, 0.145 mmol), trifluoroacetic acid (0.3 mL), and DCM (0.9 mL) at room temperature. The resulting mixture was stirred at room temperature for 1 hour under nitrogen atmosphere and concentrated under reduced pressure. The pH of the mixture was adjusted to ~8 with $NH_3{\cdot}H2O$. The resulting mixture was concentrated under reduced pressure to give a crude. The crude product (110 mg) was purified by Prep-HPLC (Column: XBridge Prep OBD C18 Column 30*150 mm, 5 m; Mobile Phase A: 10 mmol/L $NH_4HCO3$+0.05% $NH_3H_2O$), Mobile Phase B: ACN; Flow rate: 60 mL/min mL/min; Gradient: 5% B to 5% B in 1 min, 5% B to 50% B in 2 min, 50% to 65% B in 11 min; Wave Length: 254 nm/220 nm nm; RT1 (min): 9.28) to afford the desired product as a white solid. (ESI, m/z): $[M+H]^+$795.30. 1H NMR (400 MHZ, DMSO-d6) δ 8.06 (s, 2H), 7.99 (dd, J=5.0, 1.7 Hz, 1H), 7.65-7.64 (m, 1H), 7.17-7.07 (t, J=8.8 Hz, 2H), 6.69 (dd, J=7.5, 4.9 Hz, 1H), 6.10 (t, J=7.1 Hz, 1H), 5.83 (s, 2H), 5.34 (s, 1H), 5.20 (s, 1H), 4.45-4.42 (m, 1H), 4.18 (d, J=10.2 Hz, 1H), 4.08 (t, J=10.3 Hz, 1H), 3.59-3.48 (d, J=12.6 Hz, 2H), 3.13-3.01 (m, 3H), 2.83 (s, 1H), 2.21-2.11 (m, 3H), 2.06 (d, J=13.5 Hz, 4H), 1.78-1.70 (m, 8H).
Example 1t: Synthesis of 2-amino-4-((S)-4-((R)-1-(2-aminopyridin-3-yl)ethyl)-10-fluoro-2-((1-((4-(fluoromethylene) piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (881).
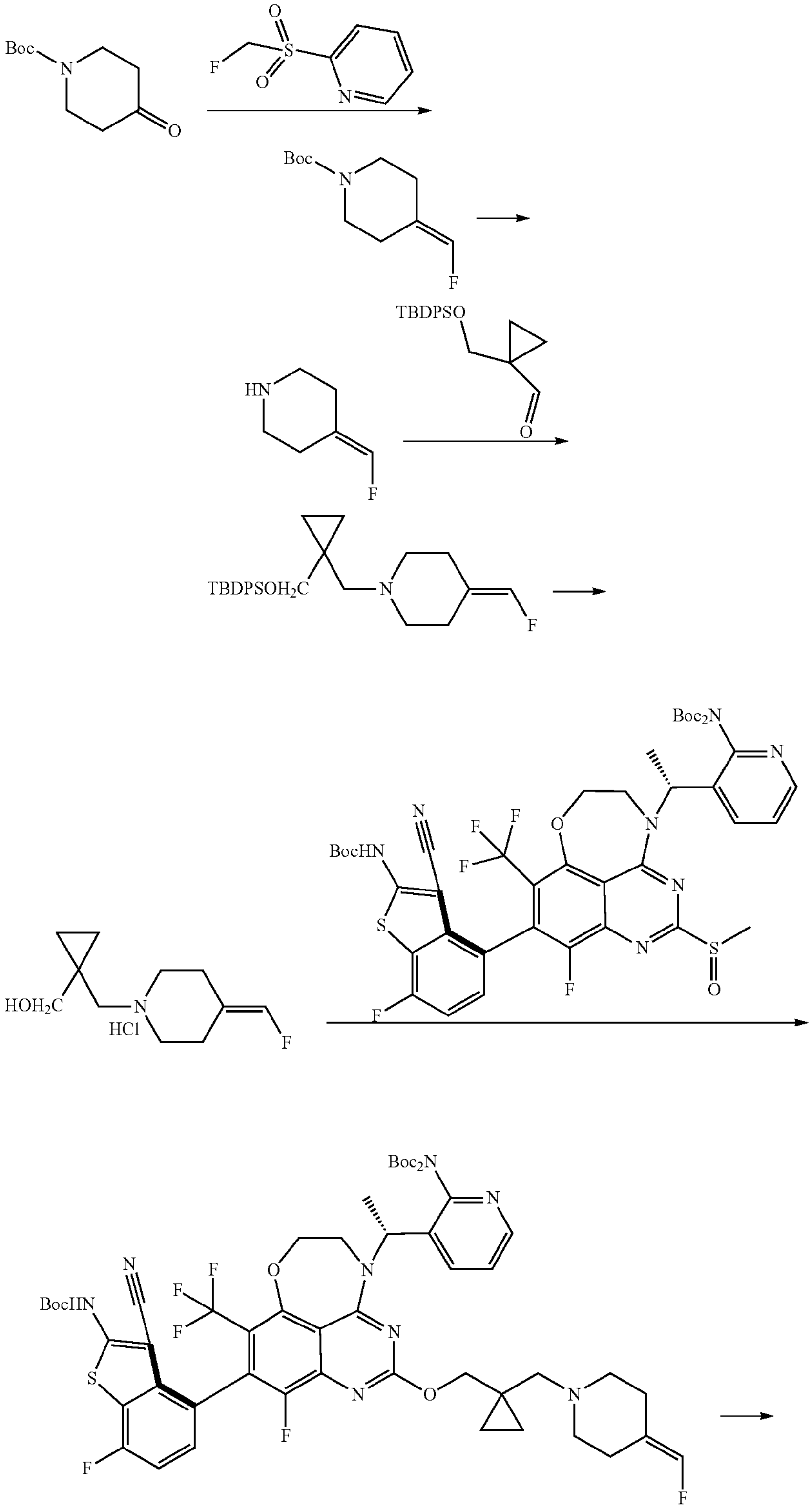

-continued

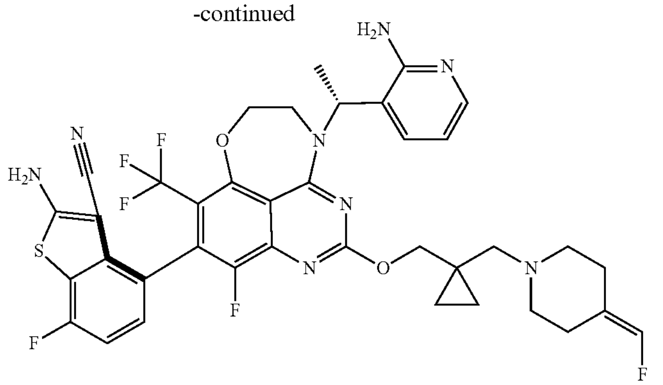

Step A: Synthesis of tert-butyl 4-(fluoromethylene) piperidine-1-carboxylate. To a stirred mixture of 2-fluoromethanesulfonylpyridine (3.87 g, 22.082 mmol) in THF (64.00 mL, 789.951 mmol) was added KHMDS (1M in THF)(24.09 mL, 24.090 mmol). The resulting mixture was stirred for 0.5 h at −78° C. followed by the addition of tert-butyl 4-oxopiperidine-1-carboxylate (4 g, 20.075 mmol). The resulting mixture was stirred for 1 hour at −78° C., treated with $NH_4Cl$ (20 mL) and extracted with ethyl acetate. The combined organic layers were washed with brine and dried over anhydrous $Na_2SO_4$. After filtration, the filtrate was concentrated under reduced pressure. The resulting residue was purified by silica gel column chromatography, eluted with petroleum ether and ethyl acetate (5:1) to afford the desired product as a white solid. (ESI, m/z): 201 $[M+H]^+$.

Step B: Synthesis of 4-(fluoromethylene) piperidine. To a stirred mixture of tert-butyl 4-(fluoromethylidene) piperidine-1-carboxylate (2.5 g, 11.613 mmol) in ACN (100 mL) was added hydrogen chloride (4.0 M in 1,4-dioxane)(20 mL) in portions at 0° C. The resulting mixture was stirred for 0.5 hours at 0° C. The mixture was concentrated to provide the desired product which was used in the next step directly without further purification. (ESI, m/z): 116 $[M+H]^+$.

Step C: Synthesis of 1-((1-(((tert-butyldiphenylsilyl)oxy) methyl)cyclopropyl)methyl)-4-(fluoromethylene) piperidine. To a stirred mixture of 4-(fluoromethylidene) piperidine (1.35 g, 11.698 mmol) and 1-{[(tert-butyldiphenylsilyl) oxy]methyl}cyclopropane-1-carbaldehyde (3.3 g, 9.748 mmol) in 1,2-dichloroethane (35 mL) was added AcOH (117.08 mg, 1.950 mmol). The resulting mixture was stirred for 20 minutes at 25° C., followed by the addition of sodium bis(acetyloxy) boranuidyl acetate (6.20 g, 29.244 mmol). The mixture was stirred for 1 hour, quenched by the addition of water (5 mL) and extracted with ethyl acetate. The combined organic layers were washed with brine and dried over anhydrous $Na_2SO_4$. After filtration, the filtrate was concentrated under reduced pressure. The resulting residue was purified by reverse-phase Combi-Flash chromatography, eluting with $CH_3CN$: $H_2O$ (0.5% $NH_4HCO_3$)=5%-60% to provide the desired product as a colorless oil. (ESI, m/z): 438 $[M+H]^+$.

Step D: Synthesis of tert-butyl (tert-butoxycarbonyl)(3-((1R)-1-((9S)-9-(2-((tert-butoxycarbonyl)amino)-3-cyano-7-fluorobenzo[b]thiophen-4-yl)-10-fluoro-2-(methylsulfinyl)-8-(trifluoromethyl)-5,6-dihydro-4H-[1,4]oxazepino[5,6,7-de]quinazolin-4-yl)ethyl) pyridin-2-yl)carbamate. (1-((4-(fluoromethylene) piperidin-1-yl)methyl)cyclopropyl) methanol 1-[(1-{[(tert-butyldiphenylsilyl)oxy]methyl} cyclopropyl)methyl]-4-(fluoromethylidene) piperidine (800 mg, 1.828 mmol) was added to hydrogen chloride (4.0 M in methanol)(8 mL). The mixture was stirred for 1 hour at 25° C., then quenched by the addition of water (15 mL). The resulting mixture was extracted with ethyl acetate. After filtration, the aqueous layer was concentrated under reduced pressure to afford the desired product as a colorless oil which was used directly in the next step without further purification. (ESI, m/z): 200 $[M+H]^+$.

Step E: Synthesis of tert-butyl (tert-butoxycarbonyl)(3-((R)-1-((S)-9-(2-((tert-butoxycarbonyl)amino)-3-cyano-7-fluorobenzo[b]thiophen-4-yl)-10-fluoro-2-((1-((4-(fluoromethylene) piperidin-1-yl)methyl)cyclopropyl)methoxy)-8-(trifluoromethyl)-5,6-dihydro-4H-[1,4]oxazepino[5,6,7-de] quinazolin-4-yl)ethyl) pyridin-2-yl)carbamate. To a stirred mixture of (1-{[4-(fluoromethylidene) piperidin-1-yl] methyl}cyclopropyl) methanol (46.34 mg, 0.232 mmol) in THF (2.5 mL) was added NaH (69.76 mg, 2.900 mmol). The resulting mixture was stirred for 20 minute at 0° C. followed by the addition of tert-butyl (tert-butoxycarbonyl)(3-((1R)-1-((9S)-9-(2-((tert-butoxycarbonyl)amino)-3-cyano-7-fluorobenzo[b]thiophen-4-yl)-10-fluoro-2-(methylsulfinyl)-8-(trifluoromethyl)-5,6-dihydro-4H-[1,4]oxazepino[5,6,7-de] quinazolin-4-yl)ethyl) pyridin-2-yl)carbamate (110 mg, 0.116 mmol). The mixture was stirred for 1 hour at 25° C., then quenched by the addition of $NH_4Cl$ (10 mL). The mixture was extracted with ethyl acetate and the combined organic layers were washed with brine and dried over anhydrous $Na_2SO_4$. After filtration, the filtrate was concentrated under reduced pressure. The resulting residue was purified by prep-TLC with DCM/MeOH (20:1) to afford the desired product as a yellow solid. (ESI, m/z): 1081 $[M+H]^+$.

Step F: Synthesis of 2-amino-4-((S)-4-((R)-1-(2-amino-pyridin-3-yl)ethyl)-10-fluoro-2-((1-((4-(fluoromethylene) piperidin-1-yl)methyl)cyclopropyl)methoxy)-8-(trifluoromethyl)-5,6-dihydro-4H-[1,4]oxazepino[5,6,7-de]quinazolin-9-yl)-7-fluorobenzo[b]thiophene-3-carbonitrile. To a stirred mixture of tert-butyl (tert-butoxycarbonyl)(3-((R)-1-((S)-9-(2-((tert-butoxycarbonyl)amino)-3-cyano-7-fluorobenzo[b] thiophen-4-yl)-10-fluoro-2-((1-((4-(fluoromethylene) piperidin-1-yl)methyl)cyclopropyl)methoxy)-8-(trifluoromethyl)-5,6-dihydro-4H-[1,4]oxazepino[5,6,7-de]quinazolin-4-yl)ethyl) pyridin-2-yl)carbamate (50 mg, 0.046 mmol) in DCM (2 mL) was added TFA (1 mL). The resulting mixture was stirred for 1 hour at 25° C., then quenched by the addition of sat. $NaHCO_3$ (10 mL). The mixture was extracted with dichloromethane. The combined organic layers were washed with brine and dried over anhydrous $Na_2SO_4$. After filtration, the filtrate was concentrated under reduced pressure. The resulting residue was purified by reverse-phase Combi-Flash chromatography, eluting with $CH_3CN$: $H_2O$ (0.5% $NH_4HCO_3$)=55%-70% to afford the desired product as a white solid. (ESI, m/z): 781 $[M+H]^+$. $^1H$ NMR (400 MHZ, DMSO-d6, ppm) δ 8.07 (s, 2H), 7.99 (d, J=4.9 Hz, 1H), 7.63 (d, J=7.5 Hz, 1H), 7.16-7.03 (m, 2H), 6.76-6.49 (m, 2H), 6.11 (q, J=6.9 Hz, 1H), 5.68 (s, 2H), 4.43-4.16 (m, 4H), 3.64-3.41 (m, 2H), 2.41 (q, J=6.6, 5.5 Hz, 4H), 2.37 (s, 1H), 2.27 (d, J=12.5 Hz, 1H), 2.21 (d, J=5.7 Hz, 2H), 2.00 (d, J=6.0 Hz, 2H), 1.61 (d, J=6.7 Hz, 3H), 0.65 (q, J=3.8 Hz, 2H), 0.40 (s, 2H).

Example 1u: Synthesis of 2-amino-4-(4-((R)-1-(2-aminopyridin-3-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorothieno[3,2-c]pyridine-3-carbonitrile (825).

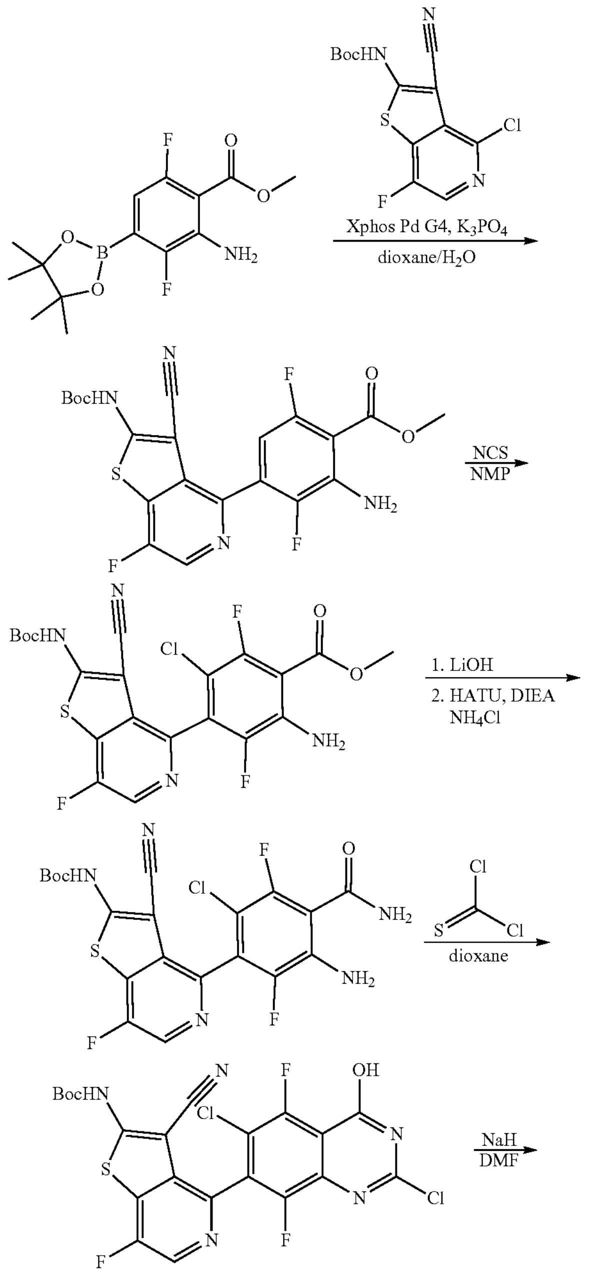

-continued

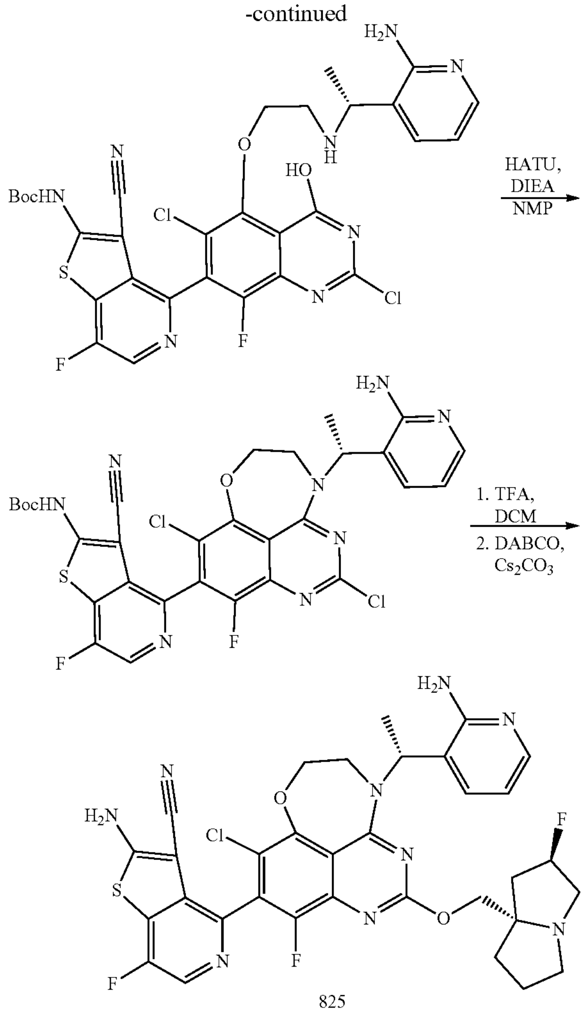

825

Step A: Synthesis of methyl 2-amino-4-(2-((tert-butoxycarbonyl)amino)-3-cyano-7-fluorothieno[3,2-c]pyridin-4-yl)-3,6-difluorobenzoate. To a solution of methyl 2-amino-3,6-difluoro-4-(4,4,5,5-tetramethyl-1,3,2-dioxaborolan-2-yl)benzoate (10 g, 31.949 mmol) in dioxane (80 mL) and water (8 mL) were added Xphos Pd G4 (5.49 g, 6.389 mmol), $K_3PO_4$ (20.3 g, 95.847 mmol) and tert-butyl (4-chloro-3-cyano-7-fluorothieno[3,2-c]pyridin-2-yl)carbamate (10.45 g, 31.949 mmol). The resulting mixture was stirred at 85° C. for 3 hours. The reaction was cooled to room temperature, quenched with water (200 mL), and extracted with ethyl acetate (80 mL×4). The combined organic layers were washed with brine (100 mL), dried over anhydrous sodium sulfate, filtered and the filtrate was concentrated to dryness under reduced pressure. The crude mixture was purified by flash chromatography to afford the desired product as a yellow solid. LCMS: (ESI, m/z): 479.3 $[M+H]^+$.

Step B: Synthesis of methyl 2-amino-4-(2-((tert-butoxycarbonyl)amino)-3-cyano-7-fluorothieno[3,2-c]pyridin-4-yl)-5-chloro-3,6-difluorobenzoate. To a solution of methyl 2-amino-4-(2-((tert-butoxycarbonyl)amino)-3-cyano-7-fluorothieno[3,2-c]pyridin-4-yl)-3,6-difluorobenzoate (1 g, 2.092 mmol) in NMP (10 mL) was added NCS (334 mg, 2.510 mmol). The resulting mixture was stirred for 16 hours, then quenched with water and extracted with ethyl acetate (30 mL×3). The combined organic layers were washed with brine (100 mL), dried over anhydrous sodium sulfate, filtered and the filtrate was concentrated to dryness under reduced pressure. The crude mixture was purified by flash chromatography to afford the deaired product as a yellow solid. MS m/z (ESI): 513.3 $[M+H]^+$.

Step C: Synthesis of 2-amino-4-(2-((tert-butoxycarbonyl) amino)-3-cyano-7-fluorothieno[3,2-c]pyridin-4-yl)-5-chloro-3,6-difluorobenzoic acid. To a solution of methyl 2-amino-4-(2-((tert-butoxycarbonyl)amino)-3-cyano-7-fluorothieno[3,2-c]pyridin-4-yl)-5-chloro-3,6-difluorobenzoate (200 mg, 0.391 mmol) in THF (5 mL) and $H_2O$ (0.5 mL) was added LiOH (47 mg, 1.955 mmol). The resulting mixture was stirred at 50° C. for 16 hours, then quenched with HCl (2 M) and extracted with ethyl acetate (20 mL×4). The combined organic layers were washed with brine (100 mL), dried over anhydrous sodium sulfate, filtered and the filtrate was concentrated to dryness under reduced pressure. The crude mixture was purified by flash chromatography to afford the desired product as a yellow solid. MS m/z (ESI): 443.0 [M-56+H]+.

Step D: Synthesis of tert-butyl (4-(3-amino-4-carbamoyl-6-chloro-2,5-difluorophenyl)-3-cyano-7-fluorothieno[3,2-c] pyridin-2-yl)carbamate. To a solution of 2-amino-4-(2-((tert-butoxycarbonyl)amino)-3-cyano-7-fluorothieno[3,2-c]pyridin-4-yl)-5-chloro-3,6-difluorobenzoic acid (150 mg, 0.301 mmol) in DMF (2 mL) were added HATU (171 mg, 0.452 mmol), $NH_4Cl$ (18 mg, 0.361 mmol) and DIEA (117 mg, 0.904 mmol). The resulting mixture was stirred for 2 hours. Upon completion, the reaction mixture was quenched with water and the aqueous phase was extracted with ethyl acetate. The combined organic layers were washed with brine, dried over $Na_2SO_4$, filtered and the filtrate was concentrated to dryness under reduced pressure. The crude mixture was purified by column chromatography to afford the desired product as yellow oil. MS m/z (ESI): 498.2 $[M+H]^+$.

Step E: Synthesis of tert-butyl (3-cyano-4-(2,6-dichloro-5,8-difluoro-4-hydroxyquinazolin-7-yl)-7-fluorothieno[3,2-c]pyridin-2-yl)carbamate. To a solution of tert-butyl (4-(3-amino-4-carbamoyl-6-chloro-2,5-difluorophenyl)-3-cyano-7-fluorothieno[3,2-c]pyridin-2-yl)carbamate (1.2 g, 2.414 mmol) in dioxane (30 mL) was added thiophosgene (1.666 g, 14.487 mmol). The resulting mixture was stirred at 85° C. for 2 h, then concentrated to dryness under reduced pressure. The crude mixture was purified by column chromatography to afford the desired product as yellow oil. MS m/z (ESI): 485.9 [M-56+H]+.

Step F: Synthesis of tert-butyl (4-(5-(2-(((R)-1-(2-amino-pyridin-3-yl)ethyl)amino) ethoxy)-2,6-dichloro-8-fluoro-4-hydroxyquinazolin-7-yl)-3-cyano-7-fluorothieno[3,2-c] pyridin-2-yl)carbamate. To a solution of (R)-2-((1-(2-aminopyridin-3-yl)ethyl)amino) ethan-1-ol (317 mg, 1.996 mmol) in DMF (15 mL) was added NaH (665 mg, 16.64 mmol). The reaction mixture was stirred for 10 min, then tert-butyl (3-cyano-4-(2,6-dichloro-5,8-difluoro-4-hydroxy-quinazolin-7-yl)-7-fluorothieno[3,2-c]pyridin-2-yl)carbamate (100 mg, 0.185 mmol) was added. The resulting mixture was stirred for 5 hours, then quenched with water (40 mL) and extracted with ethyl acetate (3×50 mL). The combined organic layers were washed with brine, dried over $Na_2SO_4$, filtered and the filtrate was concentrated to dryness under reduced pressure. The crude mixture was purified by flash chromatography to afford the desired product as yellow oil. MS m/z (ESI): 703.4 $[M+H]^+$.

Step G: Synthesis of tert-butyl (4-(4-((R)-1-(2-aminopyridin-3-yl)ethyl)-2,8-dichloro-10-fluoro-5,6-dihydro-4H-[1, 4]oxazepino[5,6,7-de]quinazolin-9-yl)-3-cyano-7-fluorothieno[3,2-c]pyridin-2-yl)carbamate. To a solution of tert-butyl (4-(5-(2-(((R)-1-(2-aminopyridin-3-yl)ethyl)amino) ethoxy)-2,6-dichloro-8-fluoro-4-hydroxyquinazolin-7-yl)-3-cyano-7-fluorothieno[3,2-c]pyridin-2-yl)carbamate (700 mg, 0.997 mmol) in DMF (20 mL) were added HATU (568 mg, 1.495 mmol) and DIEA (385 mg, 2.991 mmol). The resulting mixture was stirred for 2 hours, then quenched with water. The mixture was extracted with ethyl acetate (30 mL×3) and the combined organic layer was dried over anhydrous sodium sulfate, filtered and the filtrate was concentrated to dryness under reduced pressure. The crude mixture was purified by flash chromatography to afford the desired product as yellow oil. MS m/z (ESI): 685.4 $[M+H]^+$.

Step H: Synthesis of 2-amino-4-(4-((R)-1-(2-aminopyridin-3-yl)ethyl)-2,8-dichloro-10-fluoro-5,6-dihydro-4H-[1, 4]oxazepino[5,6,7-de]quinazolin-9-yl)-7-fluorothieno[3,2-c]pyridine-3-carbonitrile. To a solution of tert-butyl (4-(4-((R)-1-(2-aminopyridin-3-yl)ethyl)-2,8-dichloro-10-fluoro-5,6-dihydro-4H-[1,4]oxazepino[5,6,7-de]quinazolin-9-yl)-3-cyano-7-fluorothieno[3,2-c]pyridin-2-yl)carbamate (220 mg, 0.322 mmol) in DCM (1.5 mL) was added TFA (0.5 mL). The resulting mixture was stirred for 3 hours, then concentrated in vacuo. The crude mixture was purified by column chromatography to afford the desired product as yellow oil. MS m/z (ESI): 585.3 $[M+H]^+$.

Step I: Synthesis of 2-amino-4-((S)-4-((R)-1-(2-amino-pyridin-3-yl)ethyl)-8-chloro-10-fluoro-2-(((2R,7aS)-2-fluorotetrahydro-1H-pyrrolizin-7a (5H)-yl)methoxy)-5,6-dihydro-4H-[1,4]oxazepino[5,6,7-de]quinazolin-9-yl)-7-fluorothieno[3,2-c]pyridine-3-carbonitrile (825). To a solution of 2-amino-4-(4-((R)-1-(2-aminopyridin-3-yl) ethyl)-2,8-dichloro-10-fluoro-5,6-dihydro-4H-[1,4]oxazepino[5,6,7-de]quinazolin-9-yl)-7-fluorothieno[3,2-c]pyridine-3-carbonitrile (50 mg, 0.085 mmol) and ((2R,7aS)-2-fluorotetrahydro-1H-pyrrolizin-7a (5H)-yl) methanol (25 mg, 0.17 mmol) in DMF (1 mL) and THF (1 mL) were added DABCO (20 mg, 0.17 mmol) and $Cs_2CO_3$ (110 mg, 0.34 mmol). The resulting mixture was stirred for 2 hours, then quenched with water. The mixture was extracted with ethyl acetate (30 mL×3) and the combined organic layer was dried over anhydrous sodium sulfate, filtered and the filtrate was concentrated to dryness under reduced pressure. The crude mixture was purified by column chromatography to afford the desired product as a white solid. MS m/z (ESI): 708.5 $[M+H]^+$. $^1H$ NMR (400 MHZ, DMSO-d6) δ 8.43-8.42 (m, 3H), 7.97-7.96 (s, 1H), 7.63-7.62 (m, 1H), 6.67-6.65 (m, 1H), 6.24-6.22 (m, 1H), 5.74-5.72 (m, 2H), 5.28-5.26 (m, 1H), 4.39-4.37 (m, 2H), 4.08-4.06 (m, 2H), 3.63-3.62 (m, 1H), 3.43-3.42 (m, 1H), 3.11-2.99 (m, 3H), 2.87-2.76 (m, 1H), 2.23-1.95 (m, 4H), 1.79-1.75 (m, 3H), 1.61-1.59 (m, 3H).

Example 1v: Synthesis of 2-amino-4-((S)-4-((R)-1-(2-aminopyridin-3-yl)ethyl)-2-(((1S,7a'S)-2,2-difluorodihydro-1'H,3'H-spiro[cyclopropane-1,2'-pyrrolizin]-7a' (5'H)-yl)methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (725).

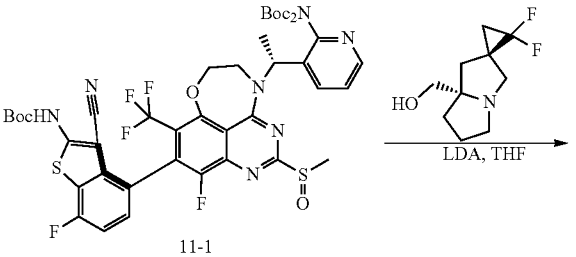

11-1

-continued

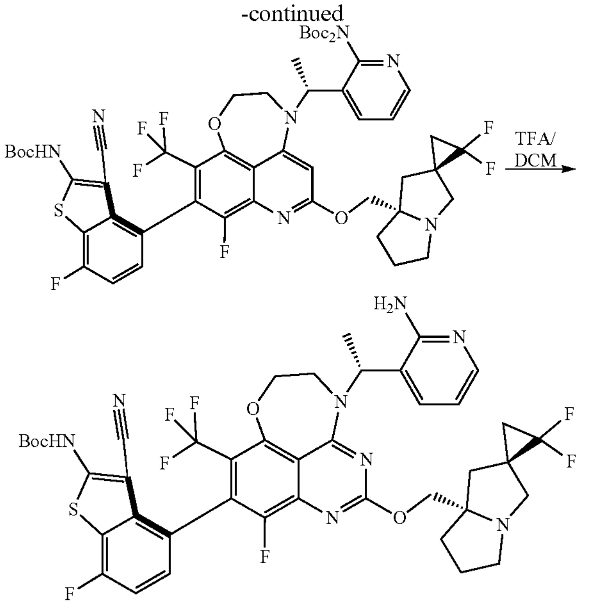

725

Step A: Synthesis of tert-butyl (tert-butoxycarbonyl)(3-((R)-1-((S)-9-(2-((tert-butoxycarbonyl)amino)-3-cyano-7-fluorobenzo[b]thiophen-4-yl)-2-(((1S,7a'S)-2,2-difluorodihydro-1'H,3'H-spiro[cyclopropane-1,2'-pyrrolizin]-7a' (5'H)-yl)methoxy)-10-fluoro-8-(trifluoromethyl)-5,6-dihydro-4H-[1,4]oxazepino[5,6,7-de]quinazolin-4-yl)ethyl) pyridin-2-yl)carbamate. A solution of ((1S,7a'S)-2,2-difluorodihydro-1'H,3'H-spiro[cyclopropane-1,2'-pyrrolizin]-7a' (5'H)-yl) methanol (161.13 mg, 0.794 mmol) in THF (5 mL) was treated with LDA (2.0M in THF/heptane)(0.66 mL, 1.323 mmol) at 0° C. followed by the addition of a solution of tert-butyl (tert-butoxycarbonyl)(3-((1R)-1-((9S)-9-(2-((tert-butoxycarbonyl)amino)-3-cyano-7-fluorobenzo[b]thiophen-4-yl)-10-fluoro-2-(methylsulfinyl)-8-(trifluoromethyl)-5,6-dihydro-4H-[1,4]oxazepino[5,6,7-de]quinazolin-4-yl)ethyl) pyridin-2-yl)carbamate (11-1) (500 mg, 0.529 mmol) in THF (1 mL) dropwise at 0° C. The resulting mixture was stirred at room temperature for 1 hour, then neutralized to pH 7 with saturated $NH_4Cl$ (aq.) and extracted with EtOAc (3×10 mL). The combined organic layers were washed with brine (2×10 mL), dried over anhydrous $Na_2SO_4$, filtered, and the filtrate concentrated under reduced pressure. The crude residue was purified by silica gel column chromatography, eluting with dichloromethane/ethyl acetate to afford the desired product as a light-yellow solid. (ESI, m/z): 1085 $[M+H]^+$.

Step B: Synthesis of 2-amino-4-((S)-4-((R)-1-(2-aminopyridin-3-yl)ethyl)-2-(((1S,7a'S)-2,2-difluorodihydro-1'H,3'H-spiro[cyclopropane-1,2'-pyrrolizin]-7a' (5'H)-yl) methoxy)-10-fluoro-8-(trifluoromethyl)-5,6-dihydro-4H-[1,4]oxazepino[5,6,7-de]quinazolin-9-yl)-7-fluorobenzo[b]thiophene-3-carbonitrile (725). A solution of tert-butyl (tert-butoxycarbonyl)(3-((R)-1-((S)-9-(2-((tert-butoxycarbonyl)amino)-3-cyano-7-fluorobenzo[b]thiophen-4-yl)-2-(((1S,7a'S)-2,2-difluorodihydro-1'H,3'H-spiro[cyclopropane-1,2'-pyrrolizin]-7a' (5'H)-yl)methoxy)-10-fluoro-8-(trifluoromethyl)-5,6-dihydro-4H-[1,4]oxazepino[5,6,7-de]quinazolin-4-yl)ethyl) pyridin-2-yl)carbamate (475 mg, 0.438 mmol) and trifluoroacetic acid (1 mL) in DCM (3 mL) was stirred for 1 hour under air atmosphere, then basified to pH~8 with saturated $NaHCO_3$ (aq.). The resulting mixture was extracted with EtOAc (3×10 mL). The combined organic layers were washed with brine (2×10 mL), dried over anhydrous $Na_2SO_4$, filtered, and the filtrate concentrated under reduced pressure. The crude residue was purified by reverse-phase flash chromatography (column, C18 silica gel; mobile phase, MeCN in water (10 mmol/L $NH_4HCO_3$), 10% to 50% gradient in 10 min; detector, UV 254 nm) to afford the desired product as a solid. (ESI, m/z): 785 $[M+H]^+$. $^1H$ NMR (400 MHZ, DMSO-d6) δ 8.06 (s, 2H), 7.99 (dd, J=4.9, 1.7 Hz, 1H), 7.64 (dd, J=7.4, 1.8 Hz, 1H), 7.18-7.05 (m, 2H), 6.68 (dd, J=7.5, 4.9 Hz, 1H), 6.13 (q, J=6.8 Hz, 1H), 5.69 (s, 2H), 4.44-4.36 (m, 1H), 4.32-4.15 (m, 3H), 3.58 (dd, J=13.8, 7.9 Hz, 1H), 3.52-3.42 (m, 1H), 3.08 (dd, J=11.9, 6.7 Hz, 1H), 3.00 (ddd, J=9.7, 6.2, 3.7 Hz, 1H), 2.71 (d, J=11.8 Hz, 1H), 2.55 (s, 1H), 2.11-2.04 (m, 1H), 2.00 (ddd, J=11.6, 6.9, 4.0 Hz, 1H), 1.90 (d, J=13.4 Hz, 1H), 1.85-1.70 (m, 2H), 1.62 (d, J=6.6 Hz, 3H), 1.60-1.52 (m, 2H), 1.46 (ddd, J=12.6, 8.1, 4.1 Hz, 1H).

Example 1w: Synthesis of 2-amino-4-((S)-4-((R)-1-(2-amino-5-chloropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (766).

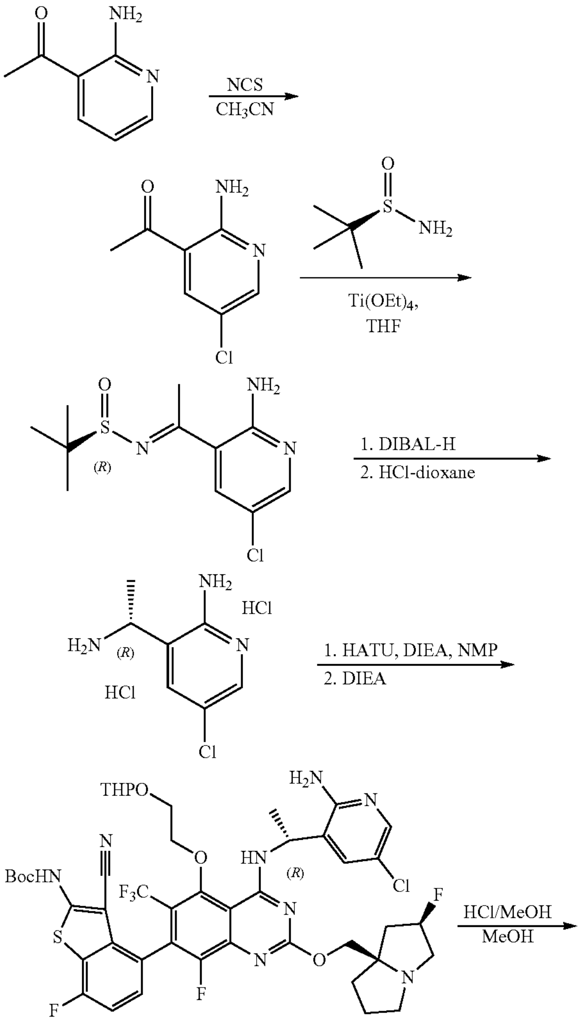

-continued

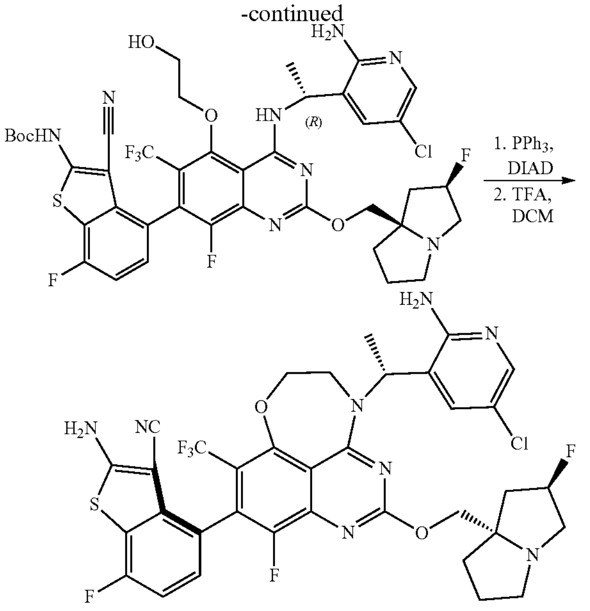

766

Step A: Synthesis of 1-(2-amino-5-chloropyridin-3-yl) ethan-1-one. A solution of 1-(2-aminopyridin-3-yl) ethanone (10 g, 73.446 mmol) and NCS (10.79 g, 80.791 mmol) in MeCN (100 mL) was stirred for 2 hours at 60° C. The reaction was quenched by the addition of $Na_2SO_3$ (100 mL) at room temperature, then extracted with $CH_2Cl_2$ (3×100 mL). The combined organic layers were washed with $NaHCO_3$(aq) and NaCl (aq), dried over anhydrous $Na_2SO_4$, filtered, and the filtrate concentrated under reduced pressure to give the desired product as a yellow solid: (ESI, m/z): 170.85 $[M+H]^+$.

Step B: Synthesis of (R)—N-(1-(2-amino-5-chloropyridin-3-yl)ethylidene)-2-methylpropane-2-sulfinamide. A solution of 1-(2-amino-5-chloropyridin-3-yl) ethanone (5 g, 29.308 mmol), (R)-2-methylpropane-2-sulfinamide (8.88 g, 73.270 mmol) and Ti (OEt) 4 (16.71 g, 73.270 mmol) in THF (50 mL) was stirred overnight at 65° C. The resulting mixture was cooled to room temperature and extracted with EtOAc (3×50 mL). The combined organic layers were washed with $H_2O$ (3×10 mL), dried over anhydrous $Na_2SO_4$, filtered, and the filtrate concentrated under reduced pressure to afford the desired product as a light-yellow solid which was used directly in the next step without further purification. (ESI, m/z): 273.90 $[M+H]^+$.

Step C: Synthesis of (R)—N—((R)-1-(2-amino-5-chloropyridin-3-yl)ethyl)-2-methylpropane-2-sulfinamide. To a stirred solution of (R)—N-[1-(2-amino-5-chloropyridin-3-yl)ethylidene]-2-methylpropane-2-sulfinamide (9 g, 32.873 mmol) in THF (90 mL) was added bis(2-methylpropyl) aluminum hydride (25% in toluene)(18.70 g, 131.492 mmol) dropwise at −78° C. The mixture was stirred at −78° C. for 1 hour, then quenched with sat. $NH_4Cl$ (aq.) at room temperature. The resulting mixture was filtered, the filter cake was washed with DCM (100 mL×3), and the filtrate was extracted with DCM (100 mL×3). The combined organic layers were washed with water (100 mL×3), dried over anhydrous $Na_2SO_4$, filtered, and the filtrate concentrated under reduced pressure. The crude residue was purified by silica gel column chromatography, eluting with petroleum ether/ethyl acetate (1:2) to afford the desired product as a yellow solid. (ESI, m/z): 275.90 $[M+H]^+$.

Step D: Synthesis of (R)-3-(1-aminoethyl)-5-chloropyridin-2-amine dihydrochloride. A solution of (R)—N—((R)-1-(2-amino-5-chloropyridin-3-yl)ethyl)-2-methylpropane-2-sulfinamide (8 g, 29.007 mmol) and hydrochloric titrant (29.01 mL, 116.028 mmol) in ethyl acetate (80 mL) was stirred for 2 hours, then concentrated under reduced pressure. The resulting residue was dissolved in petroleum ether (80 mL). The precipitated solids were collected by filtration and washed with petroleum ether (3×80 mL) to afford the desired product as a yellow solid. (ESI, m/z): 172.00 $[M+H]^+$.

Step E: Synthesis of tert-butyl (4-((7S)-4-(((R)-1-(2-amino-5-chloropyridin-3-yl)ethyl)amino)-8-fluoro-2-(((2R,7aS)-2-fluorotetrahydro-1H-pyrrolizin-7a (5H)-yl) methoxy)-5-(2-((tetrahydro-2H-pyran-2-yl)oxy) ethoxy)-6-(trifluoromethyl) quinazolin-7-yl)-3-cyano-7-fluorobenzo [b]thiophen-2-yl)carbamate. A solution tert-butyl (3-cyano-7-fluoro-4-((7S)-8-fluoro-2-(((2R,7aS)-2-fluorotetrahydro-1H-pyrrolizin-7a (5H)-yl)methoxy)-4-hydroxy-5-(2-((tetrahydro-2H-pyran-2-yl)oxy) ethoxy)-6-(trifluoromethyl) quinazolin-7-yl)benzo[b]thiophen-2-yl)carbamate (260 mg, 0.316 mmol) in NMP (2 mL) was treated with HATU (144.01 mg, 0.379 mmol) and DIEA (203.96 mg, 1.580 mmol) for 30 minutes, then (R)-3-(1-aminoethyl)-5-chloropyridin-2-amine dihydrochloride (270.84 mg, 1.580 mmol) and DIEA (203.96 mg, 1.580 mmol) in N-methyl-2-pyrrolidone (3 mL) were added dropwise. The reaction mixture was stirred for 1 hour, then quenched by addition of water (5 mL). The aqueous layer was extracted with ethyl acetate (3×5 mL). The combined organic phase was washed with brine (10 mL), dried over anhydrous sodium sulfate and concentrated under reduced pressure to give a crude product which was further purified by column chromatography using a 0% to 10% MeOH in DCM gradient to afford the desired product as a yellow solid. (ESI, m/z): 977.35 $[M+H]^+$.

Step F: Synthesis of tert-butyl (4-((S)-4-(((R)-1-(2-amino-5-chloropyridin-3-yl)ethyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate. A solution of tert-butyl (4-((7S)-4-(((R)-1-(2-amino-5-chloropyridin-3-yl)ethyl)amino)-8-fluoro-2-(((2R,7aS)-2-fluorotetrahydro-1H-pyrrolizin-7a (5H)-yl) methoxy)-5-(2-((tetrahydro-2H-pyran-2-yl)oxy) ethoxy)-6-(trifluoromethyl) quinazolin-7-yl)-3-cyano-7-fluorobenzo [b]thiophen-2-yl)carbamate (230 mg, 0.235 mmol) in MeOH (2.30 mL) was treated with HCl (g) in MeOH (0.29 mL, 1.175 mmol) for 1 hour. The reaction was quenched with $NaHCO_3$(aq), then extracted with DCM (3×5 mL), dried over anhydrous $Na_2SO_4$, filtered, and concentrated under reduced pressure to afford the desired product as a yellow solid which was used directly in the next step without further purification. (ESI, m/z): 893.30 $[M+H]^+$.

Step G: Synthesis of tert-butyl (4-((S)-4-((R)-1-(2-amino-5-chloropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate. To a stirred solution of $PPh_3$ (334.73 mg, 1.278 mmol) in THF (2 mL) was added DIAD (215.04 mg, 1.065 mmol) dropwise. The reaction mixture was stirred for 1 hour, then tert-butyl (4-((S)-4-(((R)-1-(2-amino-5-chloropyridin-3-yl)ethyl)amino)-8-fluoro-2-(((2R,7aS)-2-fluorotetrahydro-1H-pyrrolizin-7a (5H)-yl)methoxy)-5-(2-hydroxyethoxy)-6-(trifluoromethyl) quinazolin-7-yl)-3-cyano-7-fluorobenzo[b]thiophen-2-yl)carbamate (190 mg, 0.213 mmol) in THF (2 mL) was added. The reaction mixture was stirred at 40° C. for 2 hours, then cooled to room temperature, filtered, and the filter cake washed with DCM (3×10 mL). The filtrate was concentrated under reduced pressure and the resulting residue was purified by silica gel column chromatography, eluting with DCM/MeOH (10:1) to afford the desired product as a yellow solid. (ESI, m/z): 875.25 $[M+H]^+$.

Step H: Synthesis of 2-amino-4-((S)-4-((R)-1-(2-amino-5-chloropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile (766). A solution of tert-butyl (4-((S)-4-((R)-1-(2-amino-5-chloropyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate (150 mg, 0.175 mmol) in trifluoroacetic acid (1 mL) and DCM (3 mL) was stirred for 1 hour, then basified to pH ~8 with $NaHCO_3$(aq) and extracted with ethyl acetate (5 mL×3). The combined organic layers were washed with water (10 mL×3), dried over anhydrous $Na_2SO_4$, filtered, and the filtrate concentrated under reduced pressure. The resulting residue was purified by reverse-phase flash chromatography (column, C18 silica gel; mobile phase, water (0.1% $NH_4HCO_3$) in ACN, 30% to 50% gradient in 15 min; detector, UV 254 nm) to afford the desired product as a white solid. (ESI, m/z): 775.25 $[M+H]^+$. $^1$HNMR (400 MHZ, DMSO-d6): δ 8.08 (s, 2H), 7.99 (d, J=2.4 Hz, 1H), 7.65 (d, J=2.5 Hz, 1H), 7.17-7.05 (m, 2H), 6.07 (q, J=6.8 Hz, 1H), 5.99 (s, 2H), 5.38-5.18 (m, 1H), 4.45 (ddd, J=11.7, 6.3, 2.8 Hz, 1H), 4.28 (dq, J=10.0, 3.5, 3.0 Hz, 1H), 4.15-4.05 (m, 2H), 3.70-3.49 (m, 2H), 3.14-2.98 (m, 3H), 2.86-2.76 (m, 1H), 2.17-1.96 (m, 3H), 1.86-1.72 (m, 3H), 1.63 (d, J=6.8 Hz, 3H).

Example 1x: Synthesis of 2-amino-4-((S)-4-((R)-1-(2-aminopyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-6,7-difluorobenzo[b]thiophene-3-carbonitrile (853).

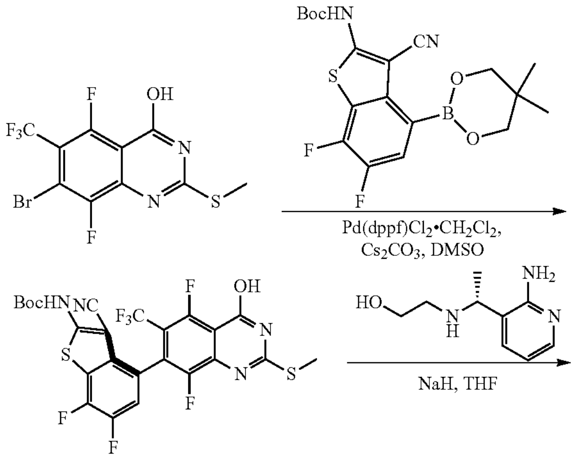

-continued

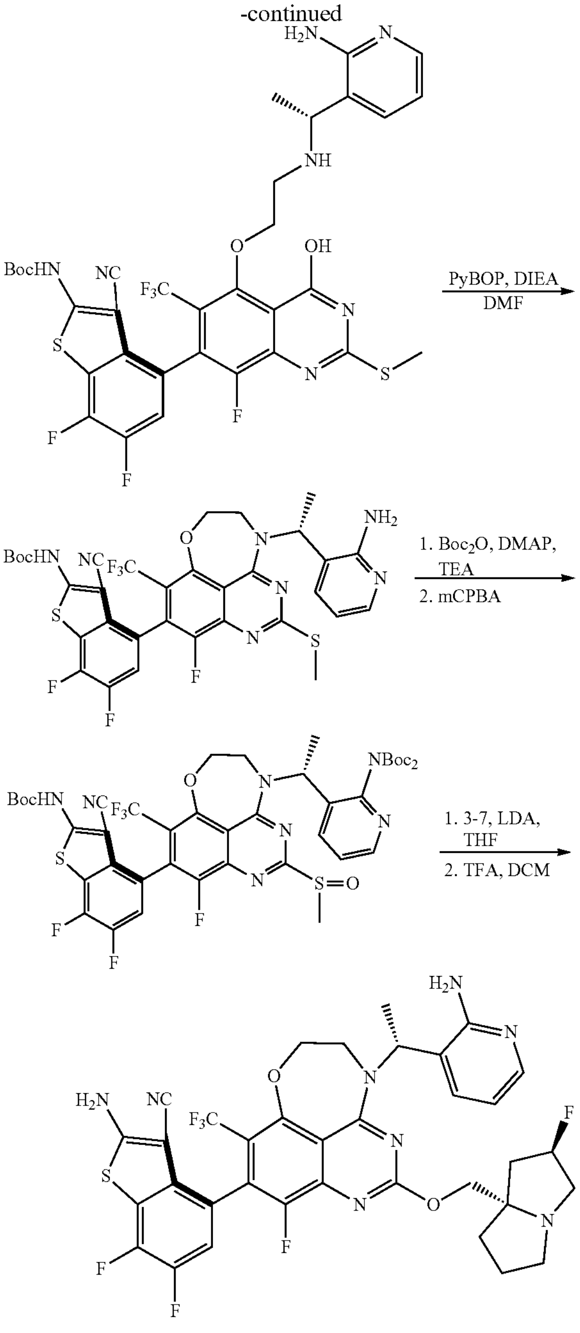

853

Step A: Synthesis of tert-butyl(S)-(3-cyano-4-(5,8-difluoro-4-hydroxy-2-(methylthio)-6-(trifluoromethyl) quinazolin-7-yl)-6,7-difluorobenzo[b]thiophen-2-yl)carbamate. A mixture of 7-bromo-5,8-difluoro-2-(methylsulfanyl)-6-(trifluoromethyl) quinazolin-4-ol (1.8 g, 4.799 mmol), tert-butyl N-[3-cyano-4-(5,5-dimethyl-1,3,2-dioxaborinan-2-yl)-6,7-difluoro-1-benzothiophen-2-yl]carbamate (6.08 g, 14.397 mmol), Pd (dppf) $Cl2CH_2Cl_2$ (1.18 g, 1.440 mmol) and $Cs_2CO_3$ (4.69 g, 14.397 mmol) in DMSO (45 mL) was stirred at 80° C. for 12 hour, then cooled to room temperature, filtered and basified to pH=5 with HCl (6M). The filter cake was washed with ethyl acetate (3×100 mL), then extracted with EtOAc (3×100 mL). The combined organic layers were washed with brine (2×100 mL), dried over anhydrous $Na_2SO_4$, filtered, and the filtrate concentrated under reduced pressure. The resulting residue was purified by silica gel column chromatography, eluting with DCM/EA/MeOH=10/1/1 to afford a crude product as a yellow solid. The product was further separated by SFC with the following conditions (Column: (S, S)-Whelk-01, 4.6*50 mm, 3 um; Mobile Phase B: MeOH (0.1% DEA); Gradient: isocratic % B) to afford the desired product. (ESI, m/z): 605.15 $[M+H]^+$.

Step B: Synthesis of tert-butyl (4-((S)-5-(2-(((R)-1-(2-aminopyridin-3-yl)ethyl)amino) ethoxy)-8-fluoro-4-hydroxy-2-(methylthio)-6-(trifluoromethyl) quinazolin-7-yl)-3-cyano-6,7-difluorobenzo[b]thiophen-2-yl)carbamate. To a solution of 2-([(1R)-1-(2-aminopyridin-3-yl)ethyl]amino-ethanol (554.64 mg, 3.060 mmol) in THF (14.8 mL) was added sodium hydride (264.39 mg, 11.016 mmol)(60% in oil, 440 mg) at 0° C. The mixture was stirred for 30 min, then tert-butyl(S)-(3-cyano-4-(5,8-difluoro-4-hydroxy-2-(methylthio)-6-(trifluoromethyl) quinazolin-7-yl)-6,7-difluorobenzo[b]thiophen-2-yl)carbamate (740 mg, 1.224 mmol) was added and the mixture was allowed to warm to room temperature and stirred for 2 hours. The reaction mixture was quenched by $NH_4Cl$ (aq) and extracted with ethyl acetate (3×20 mL). The combined organic layers were washed with brine (2×20 mL), dried over anhydrous $Na_2SO_4$, filtered, and the filtrate concentrated under reduced pressure to afford the desired product as a yellow solid which was used in the next step directly without further purification. (ESI, m/z): 766.25 $[M+H]^+$.

Step C: Synthesis of tert-butyl (4-((S)-4-((R)-1-(2-aminopyridin-3-yl)ethyl)-10-fluoro-2-(methylthio)-8-(trifluoromethyl)-5,6-dihydro-4H-[1,4]oxazepino[5,6,7-de]quinazolin-9-yl)-3-cyano-6,7-difluorobenzo[b]thiophen-2-yl) carbamate. A mixture of tert-butyl (4-((S)-5-(2-(((R)-1-(2-aminopyridin-3-yl)ethyl)amino) ethoxy)-8-fluoro-4-hydroxy-2-(methylthio)-6-(trifluoromethyl) quinazolin-7-yl)-3-cyano-6,7-difluorobenzo[b]thiophen-2-yl)carbamate (600 mg, 0.784 mmol), benzotriazole-1-yl-oxytripyrrolidinophosphonium hexafluorophosphate (611.64 mg, 1.176 mmol) and DIEA (506.35 mg, 3.920 mmol) in DMF (12 mL) was stirred at 50° C. for 1 hour. The resulting mixture was cooled to room temperature and extracted with ethyl acetate (3×20 mL). The combined organic layers were washed with brine (2×20 mL), dried over anhydrous $Na_2SO_4$, filtered, and the filtrate concentrated under reduced pressure to afford the desired product as a yellow solid which was used directly in the next step without further purification. (ESI, m/z): 748.25 $[M+H]^+$.

Step D: Synthesis of tert-butyl (tert-butoxycarbonyl)(3-((R)-1-((S)-9-(2-((tert-butoxycarbonyl)amino)-3-cyano-6,7-difluorobenzo[b]thiophen-4-yl)-10-fluoro-2-(methylthio)-8-(trifluoromethyl)-5,6-dihydro-4H-[1,4]oxazepino[5,6,7-de] quinazolin-4-yl)ethyl) pyridin-2-yl)carbamate. A mixture of tert-butyl (4-((S)-4-((R)-1-(2-aminopyridin-3-yl)ethyl)-10-fluoro-2-(methylthio)-8-(trifluoromethyl)-5,6-dihydro-4H-[1,4]oxazepino[5,6,7-de]quinazolin-9-yl)-3-cyano-6,7-difluorobenzo[b]thiophen-2-yl)carbamate (1.2 g, 1.605 mmol), di-tert-butyl dicarbonate (2.80 g, 12.840 mmol), DMAP (0.59 g, 4.815 mmol), and $Et_3N$ (0.81 g, 8.025 mmol) in DCM (14 mL) was stirred for 3 hours, then extracted with DCM (3×20 mL). The combined organic layers were washed with brine (2×20 mL), dried over anhydrous $Na_2SO_4$, filtered, and the filtrate concentrated under reduced pressure. The resulting residue was purified by silica gel column chromatography, eluting with DCM/ethyl acetate (10:1) to afford the desired product as a yellow solid. (ESI, m/z): 748.35 $[M+H]^+$.

Step E: Synthesis of tert-butyl (tert-butoxycarbonyl)(3-((1R)-1-((9S)-9-(2-((tert-butoxycarbonyl)amino)-3-cyano-6,7-difluorobenzo[b]thiophen-4-yl)-10-fluoro-2-(methylsulfinyl)-8-(trifluoromethyl)-5,6-dihydro-4H-[1,4] oxazepino[5,6,7-de]quinazolin-4-yl)ethyl) pyridin-2-yl) carbamate. To a stirred solution of tert-butyl (tert-butoxycarbonyl)(3-((R)-1-((S)-9-(2-((tert-butoxycarbonyl) amino)-3-cyano-6,7-difluorobenzo[b]thiophen-4-yl)-10-fluoro-2-(methylthio)-8-(trifluoromethyl)-5,6-dihydro-4H-[1,4]oxazepino[5,6,7-de]quinazolin-4-yl)ethyl) pyridin-2-yl)carbamate (359 mg, 0.379 mmol) in DCM (4 mL) was added 3-chlorobenzene-1-carboperoxoic acid (78.42 mg, 0.455 mmol) in portions at 0° C. The resulting mixture was stirred for 1 hour, then quenched by the addition of sat. $NaHCO_3$(aq.)(5 mL) at 0° C. The aqueous layer was extracted with $CH_2Cl_2$ (3×5 mL) and the combined organic layers were concentrated under reduced pressure to give the desired product as a yellow solid which was used directly in the next step without further purification. (ESI, m/z): 964.25 $[M+H]^+$.

Step F: Synthesis of tert-butyl (tert-butoxycarbonyl)(3-((R)-1-((S)-9-(2-((tert-butoxycarbonyl)amino)-3-cyano-6,7-difluorobenzo[b]thiophen-4-yl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-4-yl)ethyl) pyridin-2-yl)carbamate. To a stirred solution of tert-butyl (tert-butoxycarbonyl)(3-((1R)-1-((9S)-9-(2-((tert-butoxycarbonyl)amino)-3-cyano-6,7-difluorobenzo[b]thiophen-4-yl)-10-fluoro-2-(methylsulfinyl)-8-(trifluoromethyl)-5,6-dihydro-4H-[1,4]oxazepino[5,6,7-de] quinazolin-4-yl)ethyl) pyridin-2-yl)carbamate (200 mg, 0.207 mmol) and 3-7 (49.55 mg, 0.310 mmol) in THF (0.4 mL) was added LDA (2.0M in THF/heptane)(0.23 mL, 0.455 mmol) dropwise at 0° C. The resulting mixture was stirred at room temperature for 1 hour, then quenched with $NH_4Cl$ (aq), extracted with $CH_2Cl_2$ (3×10 mL), dried over anhydrous $Na_2SO_4$, filtered, and the filtrate concentrated under reduced pressure. The resulting residue was purified by silica gel column chromatography, eluting with DCM/MeOH (20/1) to afford the desired product as a yellow solid. (ESI, m/z): 959.30 $[M+H]^+$.

Step G: Synthesis of 2-amino-4-((S)-4-((R)-1-(2-aminopyridin-3-yl)ethyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-6,7-difluorobenzo[b]thiophene-3-carbonitrile (853). A solution of tert-butyl (tert-butoxycarbonyl)(3-((R)-1-((S)-9-(2-((tert-butoxycarbonyl)amino)-3-cyano-6,7-difluorobenzo[b]thiophen-4-yl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-4-yl)ethyl) pyridin-2-yl)carbamate (130 mg, 0.123 mmol) in trifluoroacetic acid (1 mL) and DCM (3 mL) was stirred for 1 hour, then basified to pH=8 with $NaHCO_3$ (aq). The resulting mixture was extracted with ethyl acetate (5 mL×3) and the combined organic layers were washed with water (10 mL×3), dried over anhydrous $Na_2SO_4$, filtered, and the filtrate concentrated under reduced pressure. The resulting crude residue was purified by prep-HPLC (Column: HPH Column 21.2*150 mm, 4 m; Mobile Phase A: Water (10 mmol/L $NH_4HCO_3$), Mobile Phase B: ACN; Flow rate: 25 mL/min; Gradient: 5% B to 5% B in 1 min, 5% B to 50% B in 2 min, 45% to 60% B in 20 min; Wave Length: 254 nm/220 nm) to afford the desired product as a white solid. (ESI, m/z): 959.30 $[M+H]^+$. $^1$H-NMR (400 MHZ, DMSO-d6): δ 8.09 (s, 2H), 7.99 (dd, J=4.9, 1.8 Hz, 1H), 7.64 (dd, J=7.6, 1.8 Hz, 1H), 7.37 (dd, J=11.1, 7.4 Hz, 1H), 6.68 (dd, J=7.5, 4.9 Hz, 1H), 6.13 (q, J=6.8 Hz, 1H), 5.67 (s, 2H), 5.36-5.19 (m, 1H), 4.41 (ddd, J=11.6, 6.0, 2.5 Hz, 1H), 4.22 (dt, J=6.8, 3.2 Hz, 1H), 4.19-4.06 (m, 2H), 3.63-3.53 (m, 1H), 3.48 (s, 1H), 3.16-3.04 (m, 2H), 3.00 (s, 1H), 2.87-2.79 (m, 1H), 2.15 (dd, J=13.8, 9.5 Hz, 1H), 2.11-1.97 (m, 2H), 1.89-1.72 (m, 3H), 1.62 (d, J=6.8 Hz, 3H).

Example 1y: Synthesis of 2-amino-4 ((S)-4-((R)-1-(2-aminopyridin-3-yl)ethyl)-10-fluoro-2-(((S)-2-(methoxyimino)tetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile (622).

11-1

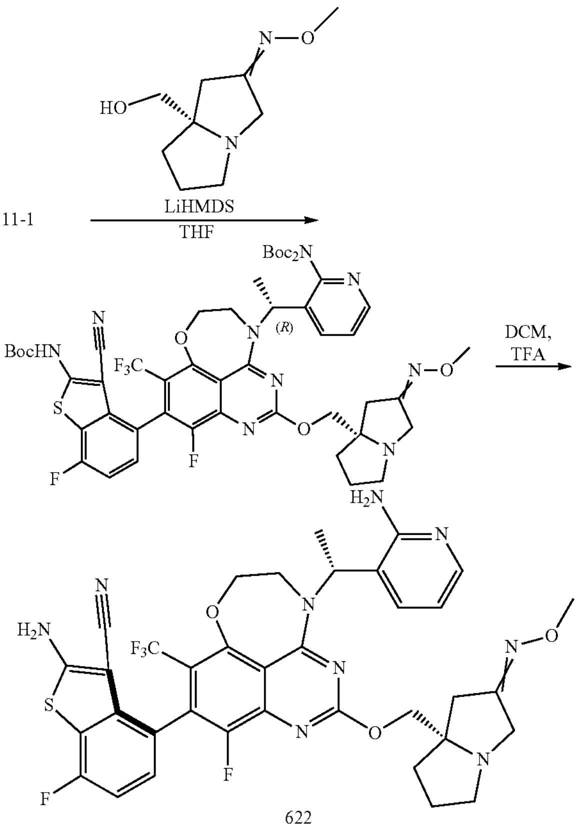

622

Step A: Synthesis of tert-butyl (tert-butoxycarbonyl)(3-((1R)-1-(9-(2-((tert-butoxycarbonyl)amino)-3-cyano-7-fluorobenzo[b]thiophen-4-yl)-10-fluoro-2-(((S)-2-(methoxyimino)tetrahydro-1H-pyrrolizin-7a (5H)-yl) methoxy)-8-(trifluoromethyl)-5,6-dihydro-4H-[1,4] oxazepino[5,6,7-de]quinazolin-4-yl)ethyl) pyridin-2-yl) carbamate. A solution of 11-1 (100 mg, 0.106 mmol) in THF (2 mL) was treated with [(7aS)-2-(methoxyimino)-tetrahydro-1H-pyrrolizin-7a-yl]methanol (38.95 mg, 0.212 mmol) and 4A MS at 0° C. for 5 minutes, then LiHMDS (1.0 M in THF)(0.21 mL, 0.212 mmol) was added dropwise at 0° C. The resulting mixture was stirred at 0° C. for 2 hours, then quenched by the addition of sat. $NH_4Cl$ (aq.)(2 mL) at room temperature. The resulting mixture was extracted with EtOAc (3×10 mL). The combined organic layers were washed with brine (3×10 mL), dried over anhydrous $Na_2SO_4$, filtered, and the filtrate concentrated under reduced pressure. The resulting residue was purified by prep-TLC ($CH_2Cl2$/MeOH 16:1) to afford the desired product as a yellow solid. (ESI, m/z): 1066.4 $[M+H]^+$.

Step B: Synthesis of 2-amino-4-((S)-4-((R)-1-(2-amino-pyridin-3-yl)ethyl)-10-fluoro-2-(((S)-2-(methoxyimino)tetrahydro-1H-pyrrolizin-7a (5H)-yl)methoxy)-8-(trifluoromethyl)-5,6-dihydro-4H-[1,4]oxazepino[5,6,7-de]quinazolin-9-yl)-7-fluorobenzo[b]thiophene-3-carbonitrile (622). To a stirred solution of tert-butyl (tert-butoxycarbonyl)(3-((1R)-1-(9-(2-((tert-butoxycarbonyl)amino)-3-cyano-7-fluorobenzo[b]thiophen-4-yl)-10-fluoro-2-(((S)-2-(methoxyimino)tetrahydro-1H-pyrrolizin-7a (5H)-yl)methoxy)-8-(trifluoromethyl)-5,6-dihydro-4H-[1,4]oxazepino[5,6,7-de] quinazolin-4-yl)ethyl) pyridin-2-yl)carbamate (50 mg, 0.052 mmol) in DCM (2 mL) was added trifluoroacetic acid (0.5 mL) dropwise at 0° C. The resulting mixture was stirred at room temperature for 1.5 hours, then basified to pH~8 with saturated $NaHCO_3$(aq.) and extracted with $CH_2Cl_2$ (3×10 mL). The combined organic layers were washed with brine (3×10 mL), dried over anhydrous $Na_2SO_4$, filtered, and the filtrate concentrated under reduced pressure. The resulting crude residue was purified by prep-HPLC(Column: XBridge Prep Phenyl OBD Column 19*250 mm, 5 m; Mobile Phase A: water (10 mmol/L $NH_4HCO_3$), Mobile Phase B: ACN; Gradient: 5% B to 5% B in 1 min, 5% B to 40% B in 2 min, 40% to 58% B in 11 min; Wavelength: 254 nm/220 nm nm) to afford the desired product as a white solid. (ESI, m/z): 766.2 $[M+H]^+$. $^1H$ NMR (400 MHZ, DMSO-d6) δ 8.01 (s, 2H), 7.92 (d, J=4.8 Hz, 1H), 7.58 (d, J=7.2 Hz, 1H), 7.13-6.97 (m, 2H), 6.62 (dd, J=7.5, 4.8 Hz, 1H), 6.04 (d, J=7.2 Hz, 1H), 5.63 (s, 2H), 4.33 (s, 1H), 4.16 (q, J=10.4, 9.6 Hz, 3H), 3.67 (d, J=8.8 Hz, 4H), 3.35 (m, 3H), 3.05 (s, 1H) 2.69 (d, J=28.6 Hz, 3H), 1.94 (d, J=7.5 Hz, 1H), 1.79 (d, J=19.3 Hz, 3H), 1.55 (d, J=6.8 Hz, 3H).

Example 1z: Synthesis of 2-amino-4-((S)-4-((R)-1-(2-aminopyridin-3-yl)-4,4,4-trifluorobutyl)-10-fluoro-2-(((2R, 7aS)-2-fluorotetrahydro-1H-pyrrolizin-7a (5H)-yl) methoxy)-8-(trifluoromethyl)-5,6-dihydro-4H-[1,4] oxazepino[5,6,7-de]quinazolin-9-yl)-7-fluorobenzo[b] thiophene-3-carbonitrile (614).

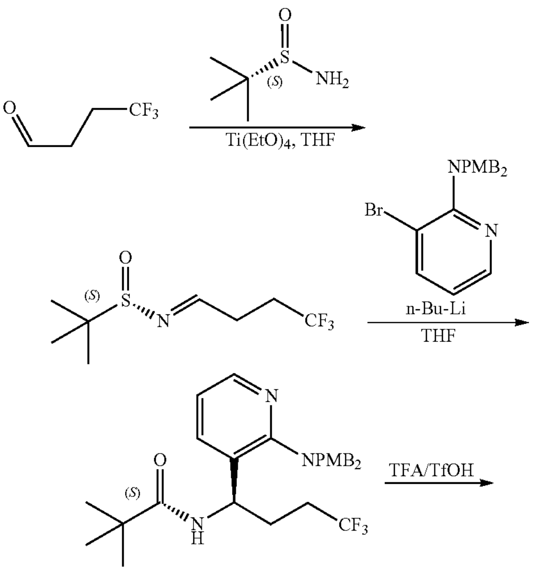

-continued

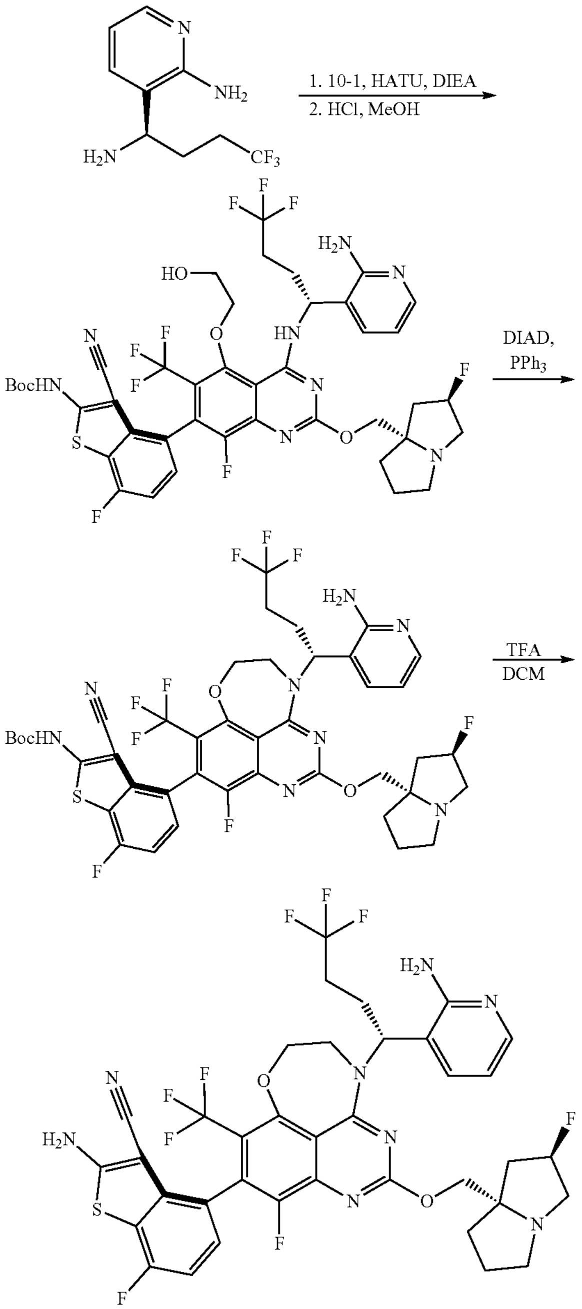

614

Step A: Synthesis of(S)-2-methyl-N-(4,4,4-trifluorobutylidene) propane-2-sulfinamide. To a stirred solution of(S)-2-methyl-N-(4,4,4-trifluorobutylidene) propane-2-sulfinamide (45.46 g, 198.290 mmol) in 1,4-dioxane (150 mL) were added titanium (4+) ion tetrakis(ethanolate)(72.37 g, 317.264 mmol) and 4,4,4-trifluorobutanal (10 g, 79.316 mmol). The resulting mixture was stirred for 2 hours at 70° C., then cooled to room temperature and quenched with water/ice. The precipitates were collected by filtration and washed with $CH_2Cl_2$ (3×50 mL). The resulting mixture was extracted with $CH_2Cl_2$ (3×50 mL), dried over anhydrous $Na_2SO_4$, filtered, and the filtrate concentrated under reduced pressure. The resulting residue was purified by silica gel column chromatography, eluting with $CH_2Cl2$/MeOH (10:1) to afford the desired product as a yellow solid. (ESI, m/z): 230 $[M+H]^+$.

Step B: Synthesis of(S)—N—((R)-1-(2-(bis(4-methoxybenzyl)amino)pyridin-3-yl)-4,4,4-trifluorobutyl)-2-methylpropane-2-sulfinamide. A solution of 3-bromo-N,N-bis[(4-methoxyphenyl)methyl]pyridin-2-amine (3 g, 7.258 mmol) in THF (75 mL) was treated with butyllithium (1.6M in n-hexane)(0.24 mL, 9.435 mmol) for 30 minutes at −78° C. followed by the addition of(S)-2-methyl-N-(4,4,4-trifluorobutylidene) propane-2-sulfinamide (0.83 g, 3.629 mmol) in portions. The resulting mixture was stirred for 2 hours at 25° C., then diluted with saturated aqueous $NH_4Cl$ and extracted with EtOAc. The combined organic layers were washed with brine, dried over anhydrous sodium sulfate, filtered, and the filtrate concentrated under reduced pressure. The resulting residue was purified by silica gel column chromatography, eluting with 0% to 60% EtOAc in PE to afford the desired product as a yellow solid. (ESI, m/z): 564 $[M+H]^+$.

Step C: Synthesis of (R)-3-(1-amino-4,4,4-trifluorobutyl) pyridin-2-amine. To a stirred solution of(S)—N-[1-(2-(bis [(4-methoxyphenyl)methyl]aminopyridin-3-yl)-4,4,4-trifluorobutyl]-2-methylpropane-2-sulfinamide (1 g, 1.774 mmol) in trifluoroacetic acid (10 mL) was added trifluoromethanesulfonic acid (5 mL). The resulting mixture was stirred for 5 hours at 40° C., then cooled to room temperature and concentrated under reduced pressure to give a crude product which was purified by C18 column, eluting with $CH_3CN$: $H_2O$ (0.1% $NH_4HCO_3$)=5-55% to afford the desired product as a yellow solid. (ESI, m/z): 220 $[M+H]^+$.

Step D: Synthesis of tert-butyl (4-((7S)-4-(((R)-1-(2-aminopyridin-3-yl)-4,4,4-trifluorobutyl)amino)-8-fluoro-2-(((2R,7aS)-2-fluorotetrahydro-1H-pyrrolizin-7a (5H)-yl) methoxy)-5-(2-((tetrahydro-2H-pyran-2-yl)oxy) ethoxy)-6-(trifluoromethyl) quinazolin-7-yl)-3-cyano-7-fluorobenzo [b]thiophen-2-yl)carbamate. To a stirred solution of 3-[(1R)-1-amino-4,4,4-trifluorobutyl]pyridin-2-amine (39.91 mg, 0.181 mmol) in DMA (4 mL) were added 10-1 (100 mg, 0.121 mmol), HATU (92.31 mg, 0.242 mmol) and DIEA (94.13 mg, 0.726 mmol) in portions. The resulting mixture was stirred for 2 hours at 40° C., then cooled to room temperature, diluted with saturated aqueous $NH_4Cl$, and extracted with EtOAc. The combined organic layers were washed with brine, dried over anhydrous sodium sulfate, filtered, and the filtrate concentrated under reduced pressure. The resulting residue was purified by reverse flash chromatography (column, C18 silica gel; mobile phase, MeCN in water, 5% to 50% gradient in 30 min; detector, UV 254 nm) to give the desired product as a white solid. (ESI, m/z): 1025 $[M+H]^+$.

Step E: Synthesis of tert-butyl (4-((S)-4-(((R)-1-(2-aminopyridin-3-yl)-4,4,4-trifluorobutyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate. To a stirred solution of tert-butyl N-[4-(2-{[(2R, 7aS)-2-fluoro-hexahydropyrrolizin-7a-yl]methoxy}-4-{[(1R)-1-(2-aminopyridin-3-yl)-4,4,4-trifluorobutyl] amino}-8-fluoro-5-[2-(oxan-2-yloxy) ethoxy]-6-(trifluoromethyl) quinazolin-7-yl)-3-cyano-7-fluoro-1-benzothiophen-2-yl]carbamate (150 mg, 0.146 mmol) in DCM (2 mL) was added 4M HCl in 1,4-dioxane (0.18 mL, 0.730 mmol). The resulting mixture was stirred for 1 hour, then diluted with saturated aqueous $NaHCO_3$ (20 mL) and extracted with EtOAc. The combined organic layers were washed with brine, dried over anhydrous sodium sulfate, filtered, and the filtrate concentrated under reduced pressure. The resulting residue was purified by reverse flash chromatography (column, C18 silica gel; mobile phase, MeCN in water, 5% to 50% gradient in 30 min; detector, UV 254 nm) to afford the desired product as a yellow solid. (ESI, m/z): 941 $[M+H]^+$.

Step F: Synthesis of tert-butyl (4-((S)-4-((R)-1-(2-aminopyridin-3-yl)-4,4,4-trifluorobutyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-3-cyano-7-fluorobenzo[b]thiophen-2-yl) carbamate. A solution of $PPh_3$ (66.90 mg, 0.258 mmol) in THF (1 mL) was treated with DIAD (42.98 mg, 0.215 mmol) for 1 hour at 0° C., then tert-butyl N-[4-(2-([(2R, 7aS)-2-fluoro-hexahydropyrrolizin-7a-yl]methoxy-4-([(1R)-1-(2-aminopyridin-3-yl)-4,4,4-trifluorobutyl]amino-8-fluoro-5-(2-hydroxyethoxy)-6-(trifluoromethyl) quinazolin-7-yl)-3-cyano-7-fluoro-1-benzothiophen-2-yl] carbamate (40 mg, 0.043 mmol) was added. The resulting mixture was stirred for 1 hour at 25° C., then concentrated and the residue purified by silica gel column chromatography, eluting with 0% to 10% MeOH in petroleum ether to afford the desired product as a yellow solid. (ESI, m/z): 923 $[M+H]^+$.

Step G: Synthesis of 2-amino-4-((S)-4-((R)-1-(2-aminopyridin-3-yl)-4,4,4-trifluorobutyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de] quinazolin-9-yl)-7-fluorobenzo[b]thiophene-3-carbonitrile (614). To a stirred solution of tert-butyl (4-((S)-4-((R)-1-(2-aminopyridin-3-yl)-4,4,4-trifluorobutyl)-10-fluoro-2-(((2R, 7aS)-2-fluorotetrahydro-1H-pyrrolizin-7a (5H)-yl) methoxy)-8-(trifluoromethyl)-5,6-dihydro-4H-[1,4] oxazepino[5,6,7-de]quinazolin-9-yl)-3-cyano-7-fluorobenzo[b]thiophen-2-yl)carbamate (20 mg, 0.022 mmol) in DCM (1 mL) was added trifluoroacetic acid (0.3 mL). The resulting mixture was stirred for 1 hour, then diluted with saturated aqueous $NaHCO_3$ (20 mL) and extracted with DCM (2x15 mL). The combined organic layers were washed with brine (2x15 mL), dried over anhydrous sodium sulfate, filtered, and the filtrate concentrated under reduced pressure. The resulting residue was purified by reverse flash chromatography (column, C18 silica gel; mobile phase, MeCN in water ($NH_4HCO_3$), 5% to 70% gradient in 30 min; detector, UV 254 nm) to afford the desired product as a white solid. (ESI, m/z): 823.2 $[M+H]^+$. $^1H$ NMR (400 MHZ, DMSO-d6) δ 8.08 (s, 2H), 8.01 (d, J=4.8 Hz, 1H), 7.71 (d, J=7.6 Hz, 1H), 7.27-7.03 (m, 2H), 6.69 (dd, J=7.6, 4.8 Hz, 1H), 6.15 (t, J=6.4 Hz, 1H), 5.86 (s, 2H), 5.28 (d, J=54.4 Hz, 1H), 4.49 (t, J=9.2 Hz, 1H), 4.28-4.04 (m, 3H), 3.74-3.62 (m, 1H), 3.59-3.43 (m, 1H), 3.21-2.97 (m, 3H), 2.83 (q, J=9.2, 8.0 Hz, 1H), 2.49-1.95 (m, 7H), 1.95-1.72 (m, 3H).

Example 1aa: Synthesis of 2-amino-4-((S)-4-((R)-1-(2-aminopyridin-3-yl)ethyl)-2-((1-((1,1-difluoro-6-azaspiro [2.5]octan-6-yl)methyl)cyclopropyl)methoxy)-10-fluoro-8-(trifluoromethyl)-5,6-dihydro-4H-[1,4]oxazepino[5,6,7-de] quinazolin-9-yl)-7-fluorobenzo[b]thiophene-3-carbonitrile (613).

11-1

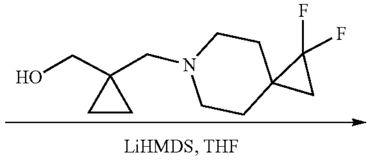

-continued

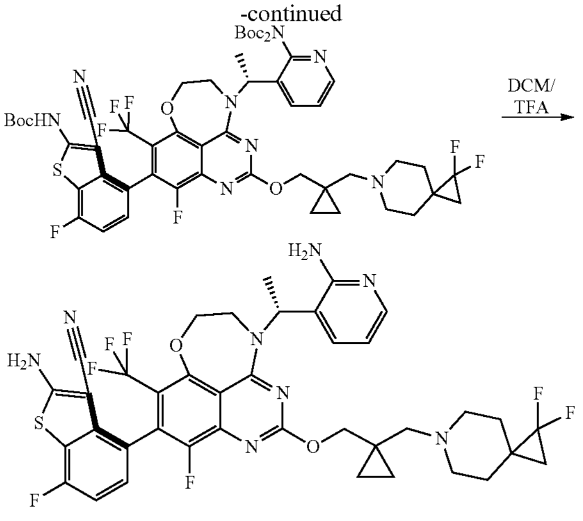

613

Step A: Synthesis of tert-butyl (tert-butoxycarbonyl)(3-((R)-1-((S)-9-(2-((tert-butoxycarbonyl)amino)-3-cyano-7-fluorobenzo[b]thiophen-4-yl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino [5,6,7-de]quinazolin-4-yl)ethyl) pyridin-2-yl)carbamate. To a stirred solution of 11-1 (400 mg, 0.423 mmol) and [1-((1, 1-difluoro-6-azaspiro[2.5]octan-6-ylmethyl)cyclopropyl] methanol (195.60 mg, 0.846 mmol) in THF (8 mL, 246.947 mmol) was added LiHMDS (1.0 M in THF)(141.51 mg, 0.846 mmol) at 0° C. The resulting mixture was stirred for 1 hour, then quenched with $H_2O$ at 0° C. and extracted with EtOAc (3x10 mL). The combined organic layers were washed with brine (2x10 mL), dried over anhydrous $Na_2SO_4$, filtered, and the filtrate concentrated under reduced pressure. The resulting residue was purified by silica gel column chromatography, eluting with petroleum ether/ethyl acetate (1:1) to afford the desired product as a yellow solid. (ESI, m/z): 1113.50 $[M+H]^+$.

Step B: Synthesis of 2-amino-4-((S)-4-((R)-1-(2-aminopyridin-3-yl)ethyl)-2-((1-((1,1-difluoro-6-azaspiro[2.5]octan-6-yl)methyl)cyclopropyl)methoxy)-10-fluoro-8-(trifluoromethyl)-5,6-dihydro-4H-[1,4]oxazepino[5,6,7-de] quinazolin-9-yl)-7-fluorobenzo[b]thiophene-3-carbonitrile (613). A solution tert-butyl (tert-butoxycarbonyl)(3-((R)-1-((S)-9-(2-((tert-butoxycarbonyl)amino)-3-cyano-7-fluorobenzo[b]thiophen-4-yl)-2-((1-((1,1-difluoro-6-azaspiro [2.5]octan-6-yl)methyl)cyclopropyl)methoxy)-10-fluoro-8-(trifluoromethyl)-5,6-dihydro-4H-[1,4]oxazepino[5,6,7-de] quinazolin-4-yl)ethyl) pyridin-2-yl)carbamate (350 mg, 0.314 mmol) in DCM (15 mL) and trifluoroacetic acid (5 mL) was stirred for 1 hour, then basified to pH~8 with saturated $NaHCO_3$(aq.) and extracted with EtOAc (3x10 mL). The combined organic layers were washed with NaCl (aq.)(2x10 mL), dried over anhydrous $Na_2SO_4$, filtered, and the filtrate concentrated under reduced pressure. The resulting residue was purified by reverse-phase flash chromatography (column, C18 silica gel; mobile phase, 0.001% $NH_4HCO3$ in ACN, 10% to 100% gradient in 30 min; detector, UV 254 nm) to afford the desired product as a white solid. (ESI, m/z): 813.30 $[M+H]^+$. $^1H$ NMR (400 MHZ, DMSO-d6) δ 8.07 (s, 2H), 7.99 (m, J=4.9, 1.7 Hz, 1H), 7.63 (m, J=7.6, 1.8 Hz, 1H), 7.17-7.02 (m, 2H), 6.67 (m, J=7.5, 4.9 Hz, 1H), 6.11 (q, J=6.8 Hz, 1H), 5.68 (s, 2H), 4.43-4.16

(m, 4H), 3.66-3.43 (m, 2H), 2.34 (m, J=55.0, 12.6 Hz, 6H), 1.62 (d, J=6.8 Hz, 3H), 1.60-1.40 (m, 4H), 1.17 (t, J=8.5 Hz, 2H), 0.75-0.59 (m, 2H), 0.41 (s, 2H).

Example 1bb: Synthesis of 2-amino-4-((S)-4-((R)-1-(2-aminopyridin-3-yl)-4-(piperidin-1-yl)butyl)-10-fluoro-2-(((2R,7aS)-2-fluorotetrahydro-1H-pyrrolizin-7a (5H)-yl) methoxy)-8-(trifluoromethyl)-5,6-dihydro-4H-[1,4] oxazepino[5,6,7-de]quinazolin-9-yl)-7-fluorobenzo[b] thiophene-3-carbonitrile (704).

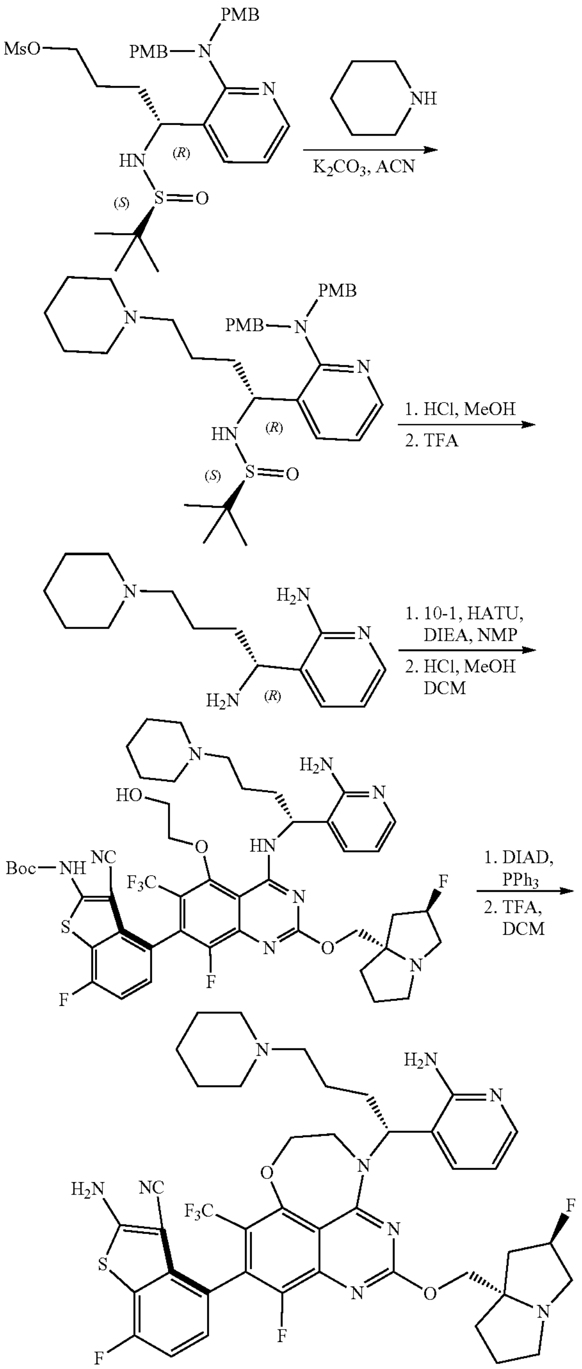

704

Step A: Synthesis of(S)—N—((R)-1-(2-(bis(4-methoxybenzyl)amino)pyridin-3-yl)-4-(piperidin-1-yl)butyl)-2-methylpropane-2-sulfinamide. To a stirred solution of (4R)-4-(2-{bis[(4-methoxyphenyl)methyl]amino}pyridin-3-yl)-4-{[(S)-2-methylpropane-2-sulfinyl]amino}butyl methanesulfonate (5.0 g, 8.1 mmol) and piperidine (1.4 g, 16.56 mmol) in ACN (100 mL) was added $K_2CO_3$ (3.45 g, 25.2 mmol). The resulting mixture was stirred at 80° C. for 1 hour, then cooled to room temperature and concentrated under reduced pressure. The resulting residue was purified by silica gel column chromatography, eluting with $CH_2Cl2$/MeOH (5:1) to afford the desired product as a colorless oil (ESI, m/z): $[M+H]^+$=593.30.

Step B: Synthesis of (R)-3-(1-amino-4-(piperidin-1-yl) butyl)pyridin-2-amine. To a stirred solution of(S)—N-[(1R)-1-(2-{bis[(4-methoxyphenyl)methyl]amino}pyridin-3-yl)-4-(piperidin-1-yl)butyl]-2-methylpropane-2-sulfinamide (2.0 g, 3.3 mmol) was added 4M HCl (g) in MeOH (10 mL, 4M). The resulting mixture was stirred for 20 minutes, then concentrated under reduced pressure. TFA (10 mL) was added and the resulting mixture was stirred an additional 3 hours, then concentrated under reduced pressure. The resulting residue was dissolved in DCM (100 mL) and washed with of $H_2O$ (2×100 mL). The aqueous layer was basified to pH 9 with saturated $NaHCO_3$(aq.) and extracted with DCM (100 mL). The combined organic layers were dried over sodium sulfate and filtered, then the filter cake was washed with DCM (2×50 mL) and the filtrate concentrated under reduced pressure to give the desired product as a yellow oil. (ESI, m/z): $[M+H]^+$=249.10.

Step C: Synthesis of tert-butyl (4-(4-(((R)-1-(2-amino-pyridin-3-yl)-4-(piperidin-1-yl)butyl)amino)-8-fluoro-2-(((2R,7aS)-2-fluorotetrahydro-1H-pyrrolizin-7a (5H)-yl) methoxy)-5-(2-((tetrahydro-2H-pyran-2-yl)oxy) ethoxy)-6-(trifluoromethyl) quinazolin-7-yl)-3-cyano-7-fluorobenzo [b]thiophen-2-yl)carbamate. To a stirred solution of 10-1 (200 mg, 0.25 mmol) in NMP (15 mL) were added HATU (140 mg, 0.36 mmol) and DIEA (157 mg, 1.22 mmol) in portions. The resulting mixture was stirred at 40° C. for 40 minutes, then 3-[(1R)-1-amino-4-(piperidin-1-yl)butyl]pyridin-2-amine (120 mg, 0.48 mmol) was added and the resulting mixture stirred at 40° C. for 1 hour. The reaction mixture was cooled to room temperature, then diluted with water (50 mL) and extracted with $CH_2Cl_2$ (2×50 mL). The combined organic layers were washed with brine (40 mL), dried over anhydrous $Na_2SO_4$, filtered, and the filtrate concentrated under reduced pressure. The resulting residue was purified by silica gel column chromatography, eluting with $CH_2Cl2$/MeOH (3:1) to afford the desired product as a yellow solid. (ESI, m/z): $[M+H]^+$=1054.25.

Step D: Synthesis of tert-butyl (4-(4-(((R)-1-(2-amino-pyridin-3-yl)-4-(piperidin-1-yl)butyl)amino)-8-fluoro-2-(((2R,7aS)-2-fluorotetrahydro-1H-pyrrolizin-7a (5H)-yl) methoxy)-5-(2-hydroxyethoxy)-6-(trifluoromethyl) quinazolin-7-yl)-3-cyano-7-fluorobenzo[b]thiophen-2-yl) carbamate. To a stirred solution of tert-butyl N-[4-(2-{[(2R, 7aS)-2-fluoro-hexahydropyrrolizin-7a-yl]methoxy}-4-{[(1R)-1-(2-aminopyridin-3-yl)-4-(piperidin-1-yl)butyl] amino}-8-fluoro-5-[2-(oxan-2-yloxy) ethoxy]-6-(trifluoromethyl) quinazolin-7-yl)-3-cyano-7-fluoro-1-benzothiophen-2-yl]carbamate (200 mg, 0.19 mmol) in DCM (8 mL) was added 4M HCl (g) in MeOH (0.8 mL, 3.20 mmol). The resulting mixture was stirred for 20 minutes, then treated with saturated $NaHCO_3$(aq.)(50 mL) and extracted with DCM (2×40 mL). The combined organic layers were washed with brine (2×20 mL), dried over anhydrous $Na_2SO_4$, filtered, and the filtrate concentrated under reduced pressure to give the desired product as a yellow solid which was used directly in the next step without further purification. (ESI, m/z): $[M+H]^{+}$=970.20.

Step E: Synthesis of tert-butyl (4-(4-((R)-1-(2-aminopyridin-3-yl)-4-(piperidin-1-yl)butyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4]oxazepino[5,6,7-de]quinazolin-9-yl)-3-cyano-7-fluorobenzo[b]thiophen-2-yl) carbamate. To a stirred solution of $PPh_3$ (540.7 mg, 2.060 mmol) in THF (20.00 mL) was added DIAD (416.9 mg, 2.06 mmol) dropwise. The resulting mixture was stirred for 0.5 hours, then tert-butyl N-[4-(2-{[(2R,7aS)-2-fluoro-hexahydropyrrolizin-7a-yl]methoxy}-4-{[(1R)-1-(2-aminopyridin-3-yl)-4-(piperidin-1-yl)butyl]amino}-8-fluoro-5-(2-hydroxyethoxy)-6-(trifluoromethyl) quinazolin-7-yl)-3-cyano-7-fluoro-1-benzothiophen-2-yl]carbamate (200 mg, 0.21 mmol) was added. The resulting mixture was stirred for 1 hour, then diluted with water (50 mL) and extracted with $CH_2Cl_2$ (2×40 mL). The combined organic layers were washed with brine (50 mL), dried over anhydrous $Na_2SO_4$, filtered, and the filtrate concentrated under reduced pressure. The resulting residue was purified by silica gel column chromatography, eluting with $CH_2Cl2$/MeOH (2:1) to afford the desired product as a yellow solid. (ESI, m/z): [M–H]— =950.30.

Step F: Synthesis of 2-amino-4-((S)-4-((R)-1-(2-aminopyridin-3-yl)-4-(piperidin-1-yl)butyl)-10-fluoro-2-(((2R, 7aS)-2-fluorotetrahydro-1H-pyrrolizin-7a (5H)-yl)

methoxy)-8-(trifluoromethyl)-5,6-dihydro-4H-[1,4] oxazepino[5,6,7-de]quinazolin-9-yl)-7-fluorobenzo[b] thiophene-3-carbonitrile. To a stirred solution tert-butyl (4-(4-((R)-1-(2-aminopyridin-3-yl)-4-(piperidin-1-yl)butyl)-10-fluoro-2-(((2R,7aS)-2-fluorotetrahydro-1H-pyrrolizin-7a (5H)-yl)methoxy)-8-(trifluoromethyl)-5,6-dihydro-4H-[1,4] oxazepino[5,6,7-de]quinazolin-9-yl)-3-cyano-7-fluorobenzo[b]thiophen-2-yl)carbamate (150 mg, 0.158 mmol) in DCM (5 mL) was added TFA (1 mL). The resulting mixture was stirred for 1 hour, then concentrated under reduced pressure. The resulting residue (120 mg) was purified by prep-HPLC(Column: XBridge Shield RP18 OBD Column 19*250 mm, 10 um; Mobile Phase A: 10 mmol/L $NH_4HCO_3$+0.05% $NH_3$: $H_2O$, Mobile Phase B: ACN; Flow rate: 60 mL/min; Gradient: 5% B to 5% B in 1 min, 5% B to 45% B in 2 min, 45% to 66% B in 11 min; Wave Length: 254 nm/220 nm; RT1 (min): 7.87) to afford the desired product as a white solid. (ESI, m/z): $[M+H]^{+}$=852.30. $^1$H NMR: (400 MHZ, DMSO-d6, ppm) δ 8.04 (s, 2H), 7.97 (dd, J=4.9, 1.7 Hz, 1H), 7.62 (dd, J=7.7, 1.8 Hz, 1H), 7.18-7.05 (m, 2H), 6.65 (dd, J=7.5, 4.9 Hz, 1H), 6.12 (t, J=7.3 Hz, 1H), 5.94 (s, 2H), 5.36-5.19 (m, 1H), 4.51 (dd, J=11.6, 6.3 Hz, 1H), 4.23-4.12 (m, 2H), 4.05 (d, J=10.4 Hz, 1H), 3.66-3.54 (m, 2H), 3.13-2.97 (m, 3H), 2.82 (d, J=6.6 Hz, 1H), 2.34-2.11 (m, 8H), 2.04 (ddd, J=15.1, 9.8, 5.6 Hz, 3H), 1.89-1.71 (m, 3H), 1.47 (t, J=6.3 Hz, 6H), 1.35 (s, 2H).

Example 2: Ras Sequences

```
Human K-Ras Wildtype sequence (SEQ ID NO. 1)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12D (SEQ ID NO. 2)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12V (SEQ ID NO. 3)
  1 MTEYKLVVVG AVGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human K-Ras G12S (SEQ ID NO. 4):
  1 MTEYKLVVVG ASGVGKSALT IQLIQNHFVD EYDPTIEDSY RKQVVIDGET

 51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM

Human N-Ras wildtype (SEQ ID NO. 5)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM
```

-continued

```
H-Ras G12D (SEQ ID NO. 6)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

H-Ras wildtype (SEQ ID NO. 7)
  1 MTEYKLVVVG AGGVGKSALT IQLIQNHFVD EYDPTIEDSY RKQVVIDGET

 51 CLLDILDTAG QEEYSAMRDQ YMRTGEGFLC VFAINNTKSF EDIHQYREQI

101 KRVKDSDDVP MVLVGNKCDL AARTVESRQA QDLARSYGIP YIETSAKTRQ

151 GVEDAFYTLV REIRQHKLRK LNPPDESGPG CMSCKCVLS

Human N-Ras G12D (SEQ ID NO. 8)
  1 MTEYKLVVVG ADGVGKSALT IQLIQNHFVD EYDPTIEDSY RKQVVIDGET

 51 CLLDILDTAG QEEYSAMRDQ YMRTGEGFLC VFAINNSKSF ADINLYREQI

101 KRVKDSDDVP MVLVGNKCDL PTRTVDTKQA HELAKSYGIP FIETSAKTRQ

151 GVEDAFYTLV REIRQYRMKK LNSSDDGTQG CMGLPCVVM
```

Example 3: Protein Expression

DNA expression constructs encoding one or more protein sequences of interest (e.g., KRAS fragments thereof, mutant variants thereof, etc.) and its corresponding DNA sequences are optimized for expression in *E. coli* and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides an N-terminal fusion of a HIS-tag to the integrated gene. To generate the final expression vectors, the expression construct of the protein of interest is cloned into any of the applied destination vectors. The expression vectors are transformed into an *E. coli* strain, e.g., BL21 (DE3). Cultivation of the transformed strains for expression is performed in a 10 L or 1 L fermenter. The cultures are grown, for example, in Terrific Broth media (MP Biomedicals, Kat. #1 13045032) with 200 μg/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed *E. coli* cells are harvested by centrifugation and the resulting pellet is suspended in a lysis buffer, as provided below, and lysed by passing three-times through a high-pressure device. The lysate is centrifuged (49000 g, 45 min, 4° C.) and the supernatant is used for further purification.

Example 4: Ras Protein Purification

A Ras (e.g., K-Ras wildtype or a mutant such as K-Ras G12S, K-Ras G12D, K-Ras G12V or K-Ras G12C) construct or a variant thereof is tagged with GST. *E. coli* culture from a 10L fermenter is lysed in lysis buffer (50 mM Tris HCl 7.5, 500 mM NaCl, 1 mM DTT, 0.5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 10° C.). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM glutathione). The main fractions of the elution peak (monitored by OD280) are pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

Example 5: HTRF (Homogenous Time-Resolved Fluorescence) Resonance Energy Transfer Assay The ability of a compound of the present disclosure to reduce Ras signaling output can be demonstrated by an HTRF assay. This assay can be also used to assess a selective inhibition or reduction of signaling output of a mutant Ras protein relative to a wildtype, or relative to a different mutant Ras protein. For example, the equilibrium interaction of wildtype KRAS or K-Ras mutant (e.g., wildtype or a mutant thereof) with SOS1 (e.g., hSOS1) can be assessed as a proxy or an indication for the ability of a subject compound to bind and inhibit Ras protein. The HTRF assay detects from (i) a fluorescence resonance energy transfer (FRET) donor (e.g., antiGST-Europium) that is bound to GST-tagged K-Ras mutant to (ii) a FRET acceptor (e.g., anti-6His-XL665) bound to a His-tagged hSOS1.

The assay buffer can contain ~5 mM HEPES pH 7.4, ~150 mM NaCl, ~1 mM DTT, 0.05% BSA and 0.0025% (v/v) Igepal. A Ras working solution is prepared in an assay buffer containing typically a suitable amount of the protein construct (e.g., GST-tagged K-Ras mutant) and the FRET donor (e.g., antiGST-Eu (K) from Cisbio, France). A SOS1 working solution is prepared in an assay buffer containing suitable amount of the protein construct (e.g., His-hSOS1) and the FRET acceptor (e.g., anti-6His-XL665 from Cisbio, France). A suitable amount of the protein construct will depend on the range of activity or range of IC50 values being detected or under investigation. For detecting an IC50 within a range of 500 nM, the protein constructs of the same range of molarity can be utilized. An inhibitor control solution is prepared in an assay buffer containing a comparable amount of the FRET acceptor without the SOS1 protein.

A fixed volume of DMSO with or without test compound is transferred into a 384-well plate. Ras working solution is added to all wells of the test plate. SOS1 working solution is added to all wells except for those that are subsequently filled with inhibitor control solution. Upon incubation for about 10 minutes or longer, the fluorescence is measured with a M1000Pro plate reader (Tecan) using HTRF detection (excitation 337 nm, emission 1:620 nm, emission 2:665 nm). Compounds are tested in duplicate at different concentrations (for example, 10 μM, 2.5 μM, 0.63 μM, 0.16 μM, 0.04 μM, 0.01 μM test compound). The ratiometric data (i.e., emission 2 divided by emission 1) is used to calculate IC50 values against Ras using GraphPad Prism (GraphPad software). Signaling output measured in terms of IC50 values can be obtained and a ratio of IC50 against one mutant relative to another mutant can be calculated. In some embodiments, one or more subject compounds disclosed herein exhibits an IC50 against one or more KRas mutants (e.g., G12C, G12D, G12V, or G12S) less than 500 nM, such as less than 100 nM, 50 nM, 10 nM, 1 nM, or even less.

The ability of one or more compounds exemplified in Table 1 to inhibit wildtype KRAS or a KRAS mutant is demonstrated utilizing the procedures described above. Table 3 shows the resulting IC50 values of exemplary compounds against KRAS G12D, KRAS G12V, KRAS G12S, and wildtype KRAS using the HTRF assay described herein. Compound numbers correspond to the numbers and structures provided in Table 1 and Example 1.

TABLE 3

| | ≤2 μM | >2 μM |
|---|---|---|
| Inhibition of KRAS G12D ($IC_{50}$) | 601, 603, 604, 605, 607, 608, 609, 611, 612, 613, 614, 615, 616, 617, 618, 619, 620, 621, 622, 623, 624, 625, 626, 627, 628, 629, 630, 632, 633, 634, 635, 636, 637, 638, 639, 640, 641, 642, 643, 644, 646, 647, 648, 649, 650, 651, 652, 653, 654, 655, 656, 657, 658, 660, 662, 663, 664, 665, 666, 667, 668, 669, 670, 671, 672, 673, 675, 676, 677, 678, 679, 680, 681, 683, 684, 685, 686, 687, 688, 690, 691, 692, 693, 694, 695, 696, 697, 698, 699, 700, 701, 703, 704, 705, 706, 707, 708, 709, 711, 712, 713, 715, 716, 720, 721, 722, 723, 724, 725, 726, 727, 728, 729, 730, 731, 732, 733, 734, 735, 736, 737, 738, 739, 740, 741, 742, 743, 744, 745, 746, 747, 748, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 799, 800, 801, 803, 804, 805, 806, 808, 810, 811, 812, 813, 814, 815, 816, 817, 819, 820, 821, 822, 823, 824, 825, 827, 828, 829, 830, 831, 832, 833, 835, 836, 838, 839, 840, 841, 842, 843, 844, 845, 846, 847, 848, 849, 850, 851, 853, 854, 855, 856, 857, 858, 860, 862, 864, 865, 866, 867, 868, 869, 870, 871, 872, 873, 874, 875, 876, 877, 878, 879, 880, 881, 882, 883, 885, 886, 887, 888, 889, 890, 891, 893, 895, 896, 898, 899, 900, 901, 903, 904, 905, 906, 907, 908, 909, 910, 911, 913, 914, 915, 916, 917, 918, 919 | 606, 631, 659, 674, 682, 689, 702, 710, 717, 718, 719, 797, 802, 807, 826, 834, 852, 859, 861, 863, 884, 897, 902 |
| Inhibition of KRAS WT ($IC_{50}$) | 601, 603, 604, 605, 607, 608, 609, 611, 612, 613, 614, 615, 616, 617, 618, 619, 620, 621, 622, 623, 624, 625, 626, 627, 628, 629, 630, 632, 633, 634, 635, 636, 637, 638, 639, 640, 641, 642, 643, 644, 646, 647, 648, 649, 650, 651, 652, 653, 654, 655, 656, 657, 658, 660, 662, 663, 664, 665, 666, 667, 668, 669, 670, 671, 672, 673, 675, 676, 677, 678, 679, 680, 681, 683, 684, 685, 686, 687, 688, 689, 690, 691, 692, 693, 694, 695, 696, 697, 698, 699, 700, 701, 703, 704, 705, 706, 707, 708, 709, 710, 711, 712, 713, 715, 716, 718, 720, 721, 722, 723, 724, 725, 726, 727, 728, 729, 730, 731, 732, 733, 735, 736, 737, 738, 739, 740, 741, 742, 743, 744, 745, 746, 747, 748, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 799, 800, 801, 803, 804, 805, 806, 808, 810, 811, 812, 813, 814, 815, 816, 817, 819, 820, 821, 822, 823, 824, 825, 827, 828, 829, 830, 831, 832, 833, 834, 835, 836, 838, 839, 840, 841, 842, 843, 844, 845, 846, 847, 848, 849, 850, 851, 852, 853, 854, 855, 856, 857, 858, 860, 862, 864, 865, 866, 867, 868, 869, 870, 871, 872, 873, 874, 875, 876, 877, 878, 879, 880, 881, 882, 883, 885, 886, 887, 888, 889, 890, 891, 893, 895, 896, 898, 899, 900, 901, 903, 904, 905, 906, 907, 908, 909, 910, 911, 913, 914, 915, 916, 917, 918, 919 | 606, 631, 659, 674, 682, 702, 717, 719, 734, 797, 802, 807, 826, 859, 861, 863, 884, 897, 902 |

TABLE 3-continued

| | ≤2 μM | >2 μM |
|---|---|---|
| Inhibition of KRAS G12V ($IC_{50}$) | 601, 603, 604, 605, 607, 608, 609, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 646, 647, 648, 649, 650, 651, 652, 653, 654, 655, 656, 657, 658, 660, 662, 663, 664, 665, 666, 667, 668, 669, 670, 671, 672, 673, 675, 676, 677, 678, 679, 680, 681, 683, 684, 685, 686, 687, 688, 689, 690, 691, 692, 693, 694, 695, 696, 697, 698, 699, 700, 701, 703, 704, 705, 706, 707, 708, 709, 710, 711, 712, 713, 715, 716, 718, 720, 721, 722, 723, 724, 725, 726, 727, 728, 729, 730, 731, 732, 733, 735, 736, 737, 738, 739, 740, 741, 742, 743, 744, 745, 746, 747, 748, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 799, 800, 801, 803, 804, 805, 806, 808, 810, 811, 812, 813, 814, 815, 816, 817, 819, 820, 821, 822, 823, 824, 825, 827, 828, 829, 830, 831, 832, 833, 834, 835, 836, 838, 839, 840, 841, 842, 843, 844, 845, 846, 847, 848, 849, 850, 851, 853, 854, 855, 856, 857, 858, 860, 861, 862, 863, 864, 865, 866, 867, 868, 869, 870, 871, 872, 873, 874, 875, 876, 877, 878, 879, 880, 881, 882, 883, 885, 886, 887, 888, 889, 890, 891, 893, 895, 896, 898, 899, 900, 901, 903, 904, 905, 906, 907, 908, 909, 910, 911, 913, 914, 915, 916, 917, 918, 919 | 606, 659, 674, 682, 702, 717, 719, 734, 797, 802, 807, 826, 852, 859, 884, 897, 902 |
| Inhibition of KRAS G12S ($IC_{50}$) | 601, 603, 604, 605, 607, 608, 609, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 646, 647, 648, 649, 650, 651, 652, 653, 654, 655, 656, 657, 658, 660, 662, 663, 664, 665, 666, 667, 668, 669, 670, 671, 672, 673, 675, 676, 677, 678, 679, 680, 681, 683, 684, 685, 686, 687, 688, 689, 690, 691, 692, 693, 694, 695, 696, 697, 698, 699, 700, 701, 703, 704, 705, 706, 707, 708, 709, 710, 711, 712, 713, 715, 716, 717, 718, 720, 721, 722, 723, 724, 725, 726, 727, 728, 729, 730, 731, 732, 733, 734, 735, 736, 737, 738, 739, 740, 741, 742, 743, 744, 745, 746, 747, 748, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 799, 800, 801, 803, 804, 805, 806, 808, 810, 811, 812, 813, 814, 815, 816, 817, 819, 820, 821, 822, 823, 824, 825, 827, 828, 829, 830, 831, 832, 833, 834, 835, 836, 838, 839, 840, 841, 842, 843, 844, 845, 846, 847, 848, 849, 850, 851, 853, 854, 855, 856, 857, 858, 859, 860, 862, 864, 865, 866, 867, 868, 869, 870, 871, 872, 873, 874, 875, 876, 877, 878, 879, 880, 881, 882, 883, 885, 886, 887, 888, 889, 890, 891, 893, 895, 896, 898, 899, 900, 901, 903, 904, 905, 906, 907, 908, 909, 910, 911, 913, 914, 915, 916, 917, 918, 919 | 606, 659, 674, 682, 702, 719, 797, 802, 807, 826, 852, 861, 863, 884, 897, 902 |

Example 6: GTPase Activity Assay

The ability of a compound of the present disclosure to inhibit Ras protein signaling can be demonstrated by a reduced GTPase activity. This assay can also be used to assess selective inhibition of a mutant Ras protein relative to a wildtype or different mutant Ras protein. In particular, intrinsic and GTPase-activating protein (GAP)-stimulated GTPase activity for a K-Ras construct or a mutant thereof can be measured using EnzCheck phosphate assay system (Life Technologies). For example, K-Ras WT, K-Ras D154Q mutant, K-Ras G12D mutant, K-Ras G12S mutant, and K-Ras G12D/D154Q mutant proteins (2.5 mg/mL) in buffer (20 mmol/L Tris, pH 8.0, 50 mM NaCl) are loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/mL. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methyl-purine ribonucleoside (MESG)(200 mM final), and purine nucleotide phosphorylase (5 U/mL final). GTP hydrolysis is initiated by the addition of MgCl2 at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein to assess the ability of each compound to inhibit signaling of a given Ras protein (e.g., a given mutant KRAS) of interest.

Example 7: Nucleotide Exchange Assay

The ability of a compound of the present disclosure to inhibit Ras protein signaling can be demonstrated by reduced nucleotide exchange activity. This assay can be also used to assess selective inhibition of a mutant Ras protein relative to a wildtype or different mutant Ras protein. For example, 250 nM or 500 nM GDP-loaded K-Ras protein (e.g., wildtype or a mutant thereof, including those mentioned in Example 4) is incubated with different concentrations of compounds (for example ~60 μM, ~20 μM, ~6.7 UM, ~2.2 μM, ~0.7 μM, or ~0.2 μM subject compound). A control reaction without subject compound is also included. SOS1 (catalytic domain) protein is added to the K-Ras protein solution. The nucleotide exchange reaction is initiated by adding fluorescent labelled GDP (guanosine 5'-diphosphate, BODIPY™ FL 2'-(or-3')—O—(N-(2-aminoethyl) urethane) to a final concentration of 0.36 μM. Fluorescence is measured every 30 s for 70 minutes at 490 nm/515 nm (excitation/emission) in a M1000Pro plate reader (Tecan). Data is exported and analyzed to calculate an IC50 using GraphPad Prism (GraphPad Software). Sample(s) can be tested with or without a subject compound disclosed herein to assess the ability of the compound to inhibit K-Ras signaling or its IC50 against a given Ras protein (e.g., a given mutant K-Ras) of interest.

Example 8: Testing for Modification of Ras Protein Via Covalent Binding

Test compounds are prepared as 10 mM stock solutions in DMSO (Fisher cat #BP231-100). KRAS protein (His-tagged GDP-loaded wildtype 1-169, His-tagged GDP-loaded G12S 1-169 or His-tagged GDP-loaded G12D 1-169) is diluted to ~2 μM in appropriate buffer (e.g., a Hepes buffer at physiological conditions). For testing KRAS modification, compounds are diluted to 50× final test concentration in DMSO in 96-well storage plates. 2 μL of the diluted 50× compounds are added to appropriate wells in the PCR plate (Fisher cat #AB-0800). ~49 μL of the stock protein solution is added to each well of the 96-well PCR plate. Reactions are mixed carefully. The plate is sealed well with aluminum plate seal and stored in a drawer at room temperature for 24 hrs. 5 μL of 2% formic acid (Fisher cat #A117-50) in MilliQ $H_2O$ is then added to each well followed by mixing with a pipette. The plate is then resealed with aluminum seal and stored until mass spectrometry analysis.

The extent of covalent modification of KRAS proteins can be determined by liquid chromatography electrospray mass spectrometry analysis of the intact proteins on a Thermo Q-Exactive Plus mass spectrometer. 20 μL of sample is injected onto a bioZen 3.6 μm Intact C4 column (Phenomenex cat #00B-4767-AN) placed in a column oven set to 40° C. and separated using a suitable LC gradient from ~20% to ~60% solvent B. Solvent A is 0.1% formic acid and solvent B is 0.1% formic acid in acetonitrile. HESI source settings are set to 40, 5 and 1 for the sheath, auxiliary and sweep gas flow, respectively. The spray voltage is 4 kV, and the capillary temperature is 320° C. S-lens RF level is 50 and auxiliary gas heater temperature is set to 200° C. The mass spectrometry is acquired using a scan range from 650 to 1750 m/z using positive polarity at a mass resolution of 70,000, AGC target of 1e6 ions and maximum injection time of 250 ms. The recorded protein mass spectrum is deconvoluted from the raw data file using Protein Deconvolution v4.0 (Thermo). The protein mass and adduct masses are exported with their peak intensities. The peak intensities for the unmodified and modified protein are used to calculate the percent covalent modification of the KRAS protein based on the following equation: % KRAS protein modification=((KRAS-compound)/(KRAS)+ (KRAS-Compound))*100.

Example 9: Ras Cellular Assay

The ability of a compound of the present disclosure to inhibit Ras protein signaling can be demonstrated by inhibiting growth of a given KRAS mutant cell line. For example, this assay can be also used to assess selective growth inhibition of a mutant Ras protein relative to a wildtype or different mutant Ras protein.

a. Growth of Cells with K-Ras G12C Mutation

MIA PaCa-2 (ATCC CRL-1420) and NCI-H1792 (ATCC CRL-5895) cell lines comprise a G12C mutation and can be used to assess Ras cellular signaling in vitro, e.g., in response to an inhibitor compound of the present disclosure. This cellular assay can also be used to discern selective inhibition of a subject compound against certain types of KRAS mutants, e.g., more potent inhibition against KRAS G12C relative to KRAS G12D mutant, by comparing inhibition of MIA PaCa-2 (G12C driven tumor cell line) to inhibition of GP2d (G12D driven tumor cell line). MIA PaCa-2 culture medium is prepared with DMEM/Ham's F12 (e.g., with stable glutamine, 10% FCS, and 2.5% horse serum. NCI-H1792 culture medium is prepared with RPMI 1640 (e.g., with stable glutamine) and 10% FCS.

On a first day (e.g., Day 1), Softagar (Select Agar, Invitrogen, 3% in $ddH_2O$ autoclaved) is boiled and tempered at 48° C. Appropriate culture medium (i.e., medium) is tempered to 37° C. Agar (3%) is diluted 1:5 in medium (–0.6%) and plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-H1792 at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a tenth day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the test compound to reduce cell growth of Ras-driven cells (e.g., tumor cell lines) in vitro and/or in vivo. In some embodiments, one or more compounds disclosed herein exhibits an IC50 value less than 1 μM, 100 nM, 10 nM, 1 nM, or even less, against one or more KRAS G12C cell line (such as MIA PaCa-2 or NCI-H1792).

b. Growth of Cells with K-Ras G12D Mutation

ASPC-1 (ATCC CRL-1682), Panc-10.05 (ATCC CRL-2547), A427, and GP2d cell lines, or any other cell lines comprising a G12D mutation, can be used to assess Ras cellular signaling in vitro, e.g., in response to a compound described herein. For example, ASPC-1 culture medium is prepared with RPMI-1640 and 10% heat-inactivated FBS. Panc-10.05 culture medium is prepared with RPMI-1640, 10 units/mL human recombinant insulin, and 10% FBS. A427 cell culture is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384UZ). The day after plating, cells are treated with a dilution series (e.g., a 9 point, 3-fold dilution series) of the compounds herein (e.g., approximately 40 μL final volume per well). Cell viability can be monitored (e.g., approximately 5 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four-parameter fit. The resulting IC50 value is a measurement of the ability of the test compound to reduce cell growth of Ras-driven cells (e.g., tumor cell lines) in vitro and/or in vivo. In some embodiments, one or more compounds disclosed herein exhibits an IC50 value less than 1 μM, 100 nM, 10 nM, 1 nM, or even less, against one or more KRAS G12D cell line (such as AsPC-1, Panc-10.05, 1427, or GP2d).

c. Growth of Cells with K-Ras G12S Mutation

A549 (ATCC CRL-185) and LS123 (ATCC CRL-255) cell lines comprise a G12S mutation and can be used to assess Ras cellular signaling in vitro, e.g., in response to treatment with a compound described herein. A549 culture medium is prepared with RPMI-1640 and 10% heat-inactivated FBS. LS123 culture medium is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800 per well) are seeded in their respective culture medium in standard tissue culture-treated 384-well format plates (Falcon #08-772-116) or ultra-low attachment surface 384-well format plates (S-Bio #MS-9384WZ). The day after plating, cells are treated with a dilution series (e.g., a 10 point, 3-fold dilution series) of the compounds herein (e.g., approximately 40 μL final volume per well). Cell viability can be monitored (e.g., approximately 6 days later) according to the manufacturer's recommended instructions, where CellTiter-Glo reagent is added (e.g., approximately 10 μL), vigorously mixed, covered, and placed on a plate shaker (e.g., approximately for 20 min) to ensure sufficient cell lysis prior to assessment of luminescent signal. The IC50 values are determined using the four parameter fit. The resulting IC50 value is a measurement of the ability of the test compound to reduce cell growth of Ras-driven cells (e.g., tumor cell lines) in vitro and/or in vivo. In some embodiments, one or more compounds disclosed herein exhibits an IC50 value less than 1 μM, 100 nM, 10 nM, 1 nM, or even less, against one or more KRAS G12S cell line (such as A549 or LS123).

Example 10: In Vivo Ras Inhibition

The in vivo reduction in Ras signaling output by a compound of the present disclosure is determined in a mouse tumor xenograft model, particularly by using a mutant K-Ras model including without limitation a K-Ras G12S model, a K-Ras G12C model, a K-Ras G12D model, a K-Ras G13D model, and a K-Ras G13C model. These models can be generated by the methods and procedures described below. In particular, the methods disclosed below involving the use of a K-Ras G12S mutant cell line for generating a K-Ras G12S xenograft model can be applied to other K-Ras mutant animal models using the respective K-Ras mutant cell lines described above.

Xenograft with K-Ras G12D, G12C, or G12S Mutation

Tumor xenografts are established by administration of tumor cells with a K-Ras G12D mutation (e.g., ASPC-1 cells), a K-Ras G12C mutation (e.g., MIA PaCa-2 cells), or a K-Ras G12S mutation (e.g., A549 or LS123 cells) into mice. Female 6- to 8-week-old athymic BALB/c nude (NCr) nu/nu mice are used for xenografts. The tumor cells (e.g., approximately $5\times10^6$) are harvested on the day of use and injected in growth-factor-reduced Matrigel/PBS (e.g., 50% final concentration in 100 μL). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: $(L\times w^2)/2$, in which L and w refer to the length and width of the tumor, respectively. Percent tumor volume change can be calculated using the following formula: $(V_{final}-V_{initial})/V_{initial}\times100$. Percent of tumor growth inhibition (% TGI) can be calculated using the following formula: % TGI=100×(1−(average $V_{final}-V_{initial}$ of treatment group)/(average $V_{final}-V_{initial}$ of control group). When tumors reach a threshold average size (e.g., approximately 200-400 $mm^3$), mice are randomized into 3-10 mice per group and are treated with vehicle (e.g., 100% Labrasol®) or a compound disclosed herein, using, for example, a daily schedule by oral gavage. Results can be expressed as mean and standard deviation of the mean.

Example 11: Metabolic (Microsomal) Stability Assay

The metabolic stability of a test compound is assayed at 37° C. using pooled liver microsomes (mouse or human liver microsomes). An aliquot of 10 μL of 50 μM test compound is mixed with 490 μL of 0.611 mg/mL liver microsomes, then 50 μL of the mixtures are dispensed to the 96 well tubes and warmed at 37° C. for 10 minutes. The reactions are initiated by adding 50 μL of the pre-warmed NADPH regeneration system solution (add 1.2 μL solution, 240 μL solution B, mix with 10.56 mL KPBS) and then incubated at 37° C. The final incubation solution contains 100 mM potassium phosphate (pH 7.4), 1.3 mM NADP+, 3.3 mM glucose 6-phosphate, 0.4 unit/mL of glucose 6-phosphate dehydrogenase, 3.3 mM magnesium chloride, 0.3 mg/mL liver microsomes and 0.5 μM test article. After 0, 15, 30 and 60 minutes in a shaking incubator, the reactions are terminated by adding 100 μL of acetonitrile containing 200 nM buspirone as an internal standard. All incubations are conducted in duplicate. Plates are vortexed vigorously by using Fisher Scientific microplate vortex mixer (Henry Troemner, US). Samples are then centrifuged at 3500 rpm for 10 minutes (4° C.) using Sorvall Legend XRT Centrifuge (Thermo Scientific, GE). Supernatants (40 μL) are transferred into clean 96-deep well plates. To each well is added with 160 μL of ultrapure water (Milli-Q, Millipore Corporation) with 0.1% (v/v) formic acid (Fisher Chemical) and the resulting solutions mixed thoroughly and subjected to LC/MS/MS analysis in MRM positive ionization mode.

All samples are measured using a mass spectrometer (QTrap 5500 quadrupole/ion trap) coupled with a Shimadzu HPLC system. The HPLC system consists of a Shimadzu series degasser, binary quaternary gradient pumps, column heater coupled to an autosampler, and a Phenomenex Gemini-NX, C18, 3.0 μm or Phenomenex Lunar, C8, 5.0 μM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+).

The half-life for the metabolic degradation of the test compound is calculated by plotting the time-course disappearance of the test compound during the incubation with liver microsomes. Each plot is fitted to a first-order equation for the elimination of the test compound (% remaining compound) versus time using non-linear regression (Equation 1).

$$\frac{C_t}{C_0} = e^{-kt} \quad \text{Equation 1}$$

where $C_t$ is the mean relative substrate concentration at time t and $C_0$ is the initial concentration (0.5 μM) at time 0. Note that the area ratio of the substrate peak to an internal standard peak is proportional to the analyte concentration and is used for regression analysis to derive a value of k.

The half-life $t_{1/2}$ for metabolic (microsome) stability is derived from the test compound elimination constant k using Equation 2 below.

$$t_{1/2} = \frac{0.693}{k} \quad \text{Equation 2}$$

Example 12: CYP2C19 Inhibition Assay

Some xenobiotics can inhibit cytochrome P450 (CYP) enzyme function, which alters their ability to metabolize drugs. Administration of a CYP inhibitor with a drug whose clearance is dependent on CYP metabolism can result in increased plasma concentrations of this concomitant drug, leading to potential toxicity. The inhibition of CYP2C19 by a test compound is assayed in human liver microsomes using S-mephenytoin as a CYP2C19 substrate. The stock solution of the test compound or known CYP2C19 inhibitor as a positive control (10 mM) is diluted with KPBS to 40 μM. In a similar way, the stock solutions of the human liver microsomes and S-mephenytoin are diluted with KPBS buffer. The pre-incubations are started by incubating a plate containing 25 μL human liver microsomes (final concentration of 0.2 mg/mL), 25 μL NADPH-generating system, and a 25 μL test compound (final concentration 10 μM) or the positive control for 30 min at 37±1° C. After the pre-incubation, 25 μL S-mephenytoin (final concentration 200 μM) is added and incubated another 12 minutes at 37±1° C. for substrate metabolism. The reactions are terminated by addition of 100 μL of ice-cold acetonitrile containing an internal standard (buspirone). Precipitated proteins are removed by centrifugation at 3500 rpm for 10 minutes at 4° C. (Allegra 25R, Beckman Co. Fullerton, CA), then an aliquot of the supernatant is transferred to an assay plate.

All the samples are assessed using a mass spectrometer (QTrap 5500 quadrupole/ion trap) coupled with a Shimadzu HPLC system following the manufacturer's instructions. The metabolism of S-mephenytoin in human liver microsomes is monitored by LC/MS/MS as representative of CYP2C19 inhibitory activity. The amount of metabolite formed is assessed by the peak area ratio (metabolite/IS) and % inhibition at 10 μM is expressed as a percentage of the metabolite signal reduced compared to the control (i.e. an incubation that contained no inhibitor and represented 100% enzyme activity): % inhibition=(1-A/B)×100%, where A is the metabolite peak area ratio formed in the presence of test compound or inhibitor at 10 UM and B is the metabolite peak area ratio formed without test compound or inhibitor in the incubation.

Example 13: Mouse and Human Protein Binding Assay to Assess Free Drug Concentration This assay can be used to determine the plasma protein binding of the test compound in the plasma of human and animal species using a Rapid Equilibrium Dialysis (RED) device for equilibrium dialysis and LC-MS/MS for sample analysis. Test compound is spiked in. The stock solution of the test compound is prepared at 5 mM concentration. One μL of 5 mM working solution is added into 1000 μL plasma to achieve a final concentration of 5 μM. The spiked plasma is placed on a rocker and gently agitated for approximately 20 minutes. A volume of 300 μL of the plasma sample containing 5 μM test compound from each species is added to designated RED device donor chambers followed by addition of 500 μL of potassium phosphate buffer to the corresponding receiver chambers in duplicate. The RED device is then sealed with sealing tape and shaken at 150 RPM for 4 hours at 37° C. Post-dialysis donor and receiver compartment samples are prepared for LC-MS/MS analysis, including spiking samples with an internal standard for the bioanalytical analysis. Warfarin and propranolol are purchased from Sigma-Aldrich (St. Louis, MO), and used as positive controls for low and high plasma protein binding, respectively.

All the samples are analyzed using an Agilent Technologies 6430 Triple Quad LC/MS system. The HPLC system consists of an Agilent 1290 Infinity Liquid Chromatograph coupled to an autosampler (Agilent 1290 Infinity LC Injector HTC), and a Phenomenex Gemini-NX, C18, 3.0 μm or Phenomenex Lunar, C8, 5.0 μM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All the analytes are detected with positive-mode electrospray ionization (ES+). The percentage of the test compound bound to plasma is calculated following Equations 3 and 4.

Equation 3

$$\%\text{ Free test compound} = \frac{\text{Peak ratio}\left(\frac{\text{test compound}}{\text{Internal standard}}\right)\text{, receiver compartment}}{\text{Peak ratio}\left(\frac{\text{test compound}}{\text{Internal standard}}\right)\text{, donor compartment}} * 100$$

Equation 4

$$\%\text{ Plasma protein bound test compound} = 100 - \%\text{ Free test compound}$$

Example 14: HERG (Automated Patch-Clamp) Assay

The human ether-a-go-go related gene (hERG) encodes the voltage gated potassium channel in the heart (IKr) which is involved in cardiac repolarization. Inhibition of the hERG causes QT interval prolongation and can lead to potential fatal events in humans. It is thus important to assess hERG inhibition early in drug discovery. A hERG automated patch-clamp assay is done using a hERG CHO-K1 cell line using an incubation time of 5 min. The degree of hERG inhibition (%) is obtained by measuring the tail current amplitude, which is induced by a one second test pulse to −40 mV after a two second pulse to +20 mV, before and after drug incubation (the current difference is normalized to control and multiplied by 100 to obtain the percent of inhibition). The percent hERG inhibition is measured in the presence of 10 μM test compound.

Example 15: Rat Oral Exposure (% F)

A pharmacokinetic profile for a test compound is measured by single dosing in jugular vein cannulated male Sprague-Dawley rats. Animal weights are typically over 200 grams, and animals are allowed to acclimate to their new environment for at least 3 days prior to the initiation of any studies. One set of animals is dosed intravenously (IV) with test compound (2 mg/kg in 20% HP-beta-CD or 20% Captisol, pH adjusted to ~4 by citric acid). The IV dosing solution concentration is 0.4 mg/mL test compound. Blood is sampled at 5 minutes, 15 minutes, 30 minutes, 90 minutes, 360 minutes, and 24 hours following IV dosing. Another set of animals is dosed oral (po) with test compound (10 mg/kg in 20% HP-beta-CD or 20% Captisol, pH adjusted to ~4 by citric acid). The oral dosing solution concentration is 1 mg/mL test compound. Blood is sampled at 15 minutes, 30 minutes, 90 minutes, 180 minutes, 360 minutes and 24 hours following oral (po) dosing. Blood samples (~0.2 mL/sample) is collected via the jugular vein, placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

The plasma samples are analyzed using an Agilent Technologies 6430 Triple Quad LC/MS system, following the manufacturer's instructions. The analytes are detected with positive-mode electrospray ionization (ES+). A standard curve for each test compound is generated and used to measure test compound concentrations in the rat plasma samples. Based on the time course sampling, an area under the curve is calculated for the oral dose group and the intravenous dose group. Percentage rat bioavailability is calculated based on equation 5.

$$\%\ F\ (\text{rat}) = 100 \times \frac{AUC_{po} * \text{Dose}_{IV}}{AUC_{IV} * \text{Dose}_{po}}, \qquad \text{Equation 5}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

Example 16: Mouse Oral Exposure (% F)

A pharmacokinetic profile for a test compound is assessed by single dosing in female CD-1 mice. Animal weights are typically between 20-50 grams, and animals are allowed to acclimate to their new environment for at least 3 days prior to the initiation of any studies. One set of animals is dosed intravenous (IV) with test compound, 2 mg/kg in 20% HP-beta-CD or 20% Captisol, pH adjusted to above 4 by citric acid at 10 mL/kg. Blood is sampled at 5 minutes, 15 minutes, 30 minutes, 90 minutes, 360 minutes, and 24 hours following IV dosing. Another set of animals is dosed oral (PO) with test compound, 10 mg/kg in 20% HP-beta-CD or 20% Captisol, pH adjusted to ~3-4 by citric acid at 10 mg/mL. The oral dosing solution concentration is 1 mg/mL test compound and 10 mL/kg. Blood is sampled at 15 minutes, 30 minutes, 90 minutes, 180 minutes, 360 minutes and 24 hours following PO dosing. Blood samples (~0.1 mL/sample) are collected via submandibular facial vein and placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

Plasma samples are analyzed using an Agilent Technologies 6430 Triple Quad LC/MS system, following the manufacturer instructions. All the analytes are detected with positive-mode electrospray ionization (ESI). A standard curve for each test compound is generated and used to measure test compound concentrations in the mouse plasma samples. Based on the time course sampling, an area under the curve is calculated for the oral dose group and the intravenous dose group. Percentage mouse bioavailability is calculated based on equation 6.

$$\%\ F\ (\text{mouse}) = 100 \times \frac{AUC_{po} * \text{Dose}_{IV}}{AUC_{IV} * \text{Dose}_{po}}, \qquad \text{Equation 6}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

Example 17: Dog Oral Exposure (% F)

A pharmacokinetic profile for a test compound is measured by single dosing in male Beagle dogs. Animal weights are typically between 8-12 kilograms, and animals are allowed to acclimate to their new environment for at least 3 days prior to the initiation of any studies. One set of animals is dosed intravenously (IV) with test compound (1 mg/kg in 20% HP-beta-CD or 20% Captisol, pH adjusted to above 4 by citric acid). The IV dosing solution concentration is 0.5 mg/mL test compound. Blood is sampled at 5 minutes, 15 minutes, 30 minutes, 1 hour, 2 hours, 4 hours, 8 hours, and 24 hours following IV dosing. Another set of animals is dosed oral (PO) with test compound (5 mg/kg in 20% HP-beta-CD or 20% Captisol, pH adjusted to ~4 by citric acid). The oral dosing solution concentration is 1 mg/mL test compound. Blood is sampled at 15 minutes, 30 minutes, 1 hour, 2 hours, 4 hours, 6 hours, 8 hours and 24 hours following PO dosing. Blood samples (~1 mL/sample) are collected via the jugular vein or other suitable vein, placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

The plasma samples are analyzed using an Agilent Technologies 6430 Triple Quad LC/MS system, following the manufacturer's instructions. The analytes are detected with positive-mode electrospray ionization (ESI). A standard curve for each test compound is generated and used to measure test compound concentrations in the dog plasma samples. Based on the time course sampling, an area under the curve is calculated for the oral dose group and the intravenous dose group. Percentage dog bioavailability is calculated based on equation 7.

$$\% \ F\,(\text{dog}) = 100 \times \frac{AUC_{po} * \text{Dose}_{IV}}{AUC_{IV} * \text{Dose}_{po}}, \qquad \text{Equation 7}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

Example 18: Monkey Oral Exposure (% F)

A pharmacokinetic profile for a test compound is assessed by single dosing in male Cynomolgus monkeys. Animal weights are typically between 2-5 kilograms, and animals are allowed to acclimate to their new environment for at least 3 days prior to the initiation of any studies. One set of animals is dosed intravenously (IV) with test compound (1 mg/kg in 20% HP-beta-CD or 20% Captisol, pH adjusted to above 4 by citric acid). The IV dosing solution concentration is 0.5 mg/mL test compound. Blood is sampled at 5 minutes, 15 minutes, 30 minutes, 1 hour, 2 hours, 4 hours, 8 hours, and 24 hours following IV dosing. Another set of animals is dosed oral (PO) with test compound (5 mg/kg in 20% HP-beta-CD or 20% Captisol, pH adjusted to ~4 by citric acid). The oral dosing solution concentration is 1 mg/mL test compound. Blood is sampled at 15 minutes, 30 minutes, 1 hour, 2 hours, 4 hours, 6 hours, 8 hours and 24 hours following PO dosing. Blood samples (~1 mL/sample) are collected via femoral vein or other suitable vein and placed in tubes containing EDTA-K2 and stored on ice until centrifuged. The blood samples are centrifuged at approximately 6800 g for 6 minutes at 2-8° C. and the resulting plasma is separated and stored frozen at approximately −80° C.

Plasma samples are analyzed using an Agilent Technologies 6430 Triple Quad LC/MS system, following the manufacturer instructions. The analytes are detected with positive-mode electrospray ionization (ESI). A standard curve for each test compound is generated and used to measure test compound concentrations in the monkey plasma samples. Based on the time course sampling, an area under the curve is calculated for the oral dose group and the intravenous dose group. Percentage monkey bioavailability is calculated based on equation 8.

$$\% \ F\,(\text{monkey}) = 100 \times \frac{AUC_{po} * \text{Dose}_{IV}}{AUC_{IV} * \text{Dose}_{po}}, \qquad \text{Equation 8}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

Example 19: Compound Tumor Exposure

This assay can be used to determine the exposure of a test compound in a tumor of an animal species. For a test compound tumor exposure study, the test compound is administered to tumor-bearing mice for a certain period. The tumor is harvested at the end of the in-vivo study (e.g., 1 hour to multiple weeks depending on the study) and subjected to bioanalysis to quantify the amount of test compound in the tumor. To quantify the amount of test compound distributed into the tumor, a certain amount of tumor is weighed and combined with 5-fold of deionized water (weight by weight) and homogenized into tissue homogenate by a Bead Mill Homogenizer (Omni International) into tissue suspension in de-ionized water. An aliquot of 40 μL from each individual homogenized tissue sample is combined with 10 μL blank DMSO and 20 μL of internal standard solution (e.g., verapamil 150 nM in water acidified by 0.1% formic acid) and crushed with 200 μL acetonitrile containing 0.1% formic acid, followed by vortex-mixing for 1 minute. Calibration standard and QC samples are made by adding 10 μL stock solution of different amounts of test compound in DMSO into 40 μL blank tumor homogenate solution suspension to make calibration standard samples at a series of nominal concentrations of test compound in blank tumor homogenate. Similarly, 20 μL of internal standard solution (e.g., verapamil 150 nM in water acidified by 0.1% formic acid) and 200 μL acetonitrile containing 0.1% formic acid are added to each of the calibration standard and QC samples, followed by vortex-mixing for 1 minute. The mixed samples are centrifuged at 4000 rpm for 6 min to obtain supernatant. A volume of 10 μL supernatant from each sample is combined with 190 μL of dilution solution (20% acetonitrile in water containing 0.1% formic acid) and transferred into a well in a 96-well analytical plate prior to a 2-5 μL injection into LC-MS/MS instrument system composed of Sciex Qtrap 6500+ and Shimadzu HPLC for analysis. The concentration of test compound in tumor homogenate determined is corrected by a dilution factor of 6 to obtain the test compound concentration in tumor is expressed in ng/mg of tumor.

What is claimed is:

1. A compound of Formula:

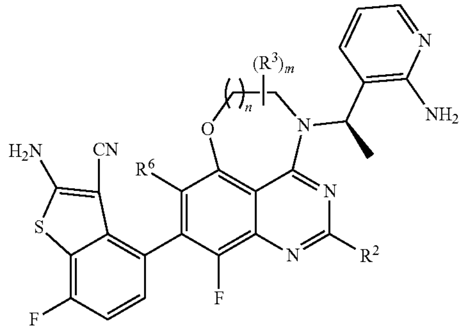

or a pharmaceutically acceptable salt or solvate thereof, wherein:

$R^2$ is selected from

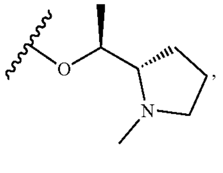

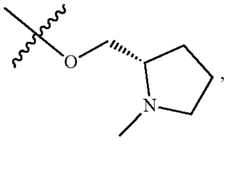

-continued

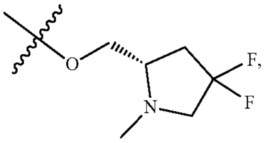

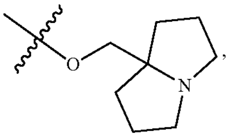

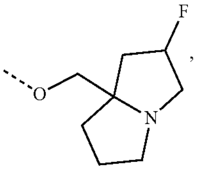

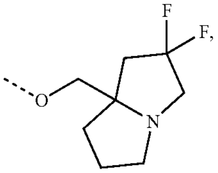

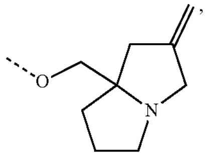

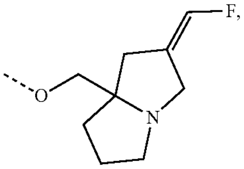

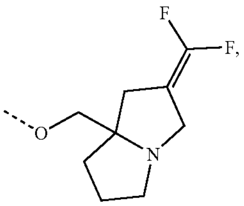

-continued

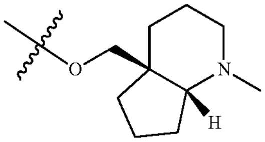

, and

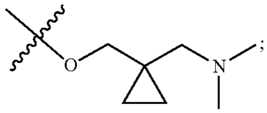

$R^3$ is independently selected at each occurrence from $C_{1-6}$ alkyl, $C_{2-6}$ alkenyl, and $C_{2-6}$ alkynyl, each of which is optionally substituted with one, two, or three substituents independently selected from halogen and —CN;

$R^6$ is selected from hydrogen, halogen, and $C_{1-3}$ haloalkyl;

m is 0, 1, 2, or 3; and n is 1 or 2.

2. The compound, salt, or solvate of claim 1, wherein $R^2$ is selected from

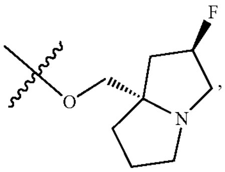

,

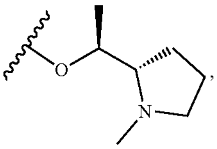

,

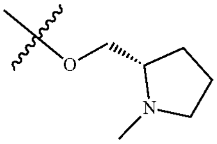

,

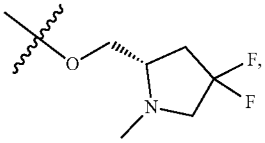

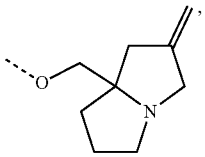

,

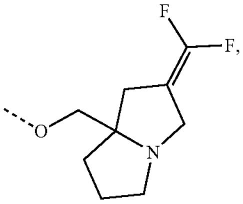

and

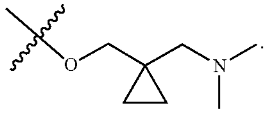

3. The compound, salt, or solvate of claim 1, wherein m is 0 or 1.

4. The compound, salt, or solvate of claim 1, wherein $R^6$ is chlorine.

5. The compound, salt, or solvate of claim 1, wherein n is 1.

6. The compound of claim 1 having the formula

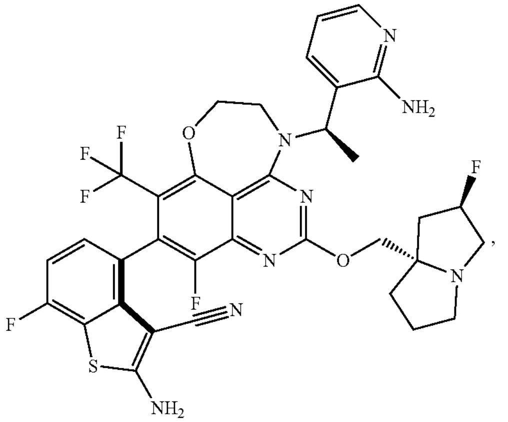

or a salt or solvate thereof.

7. The compound of claim 1, wherein the compound is selected from

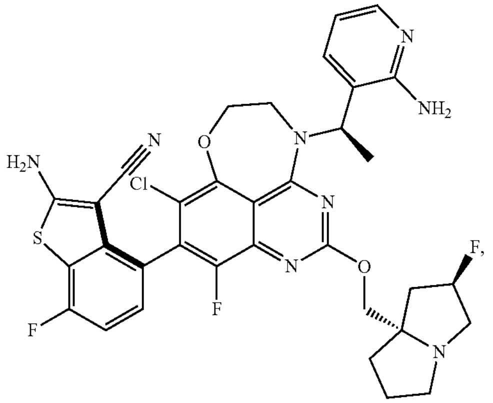

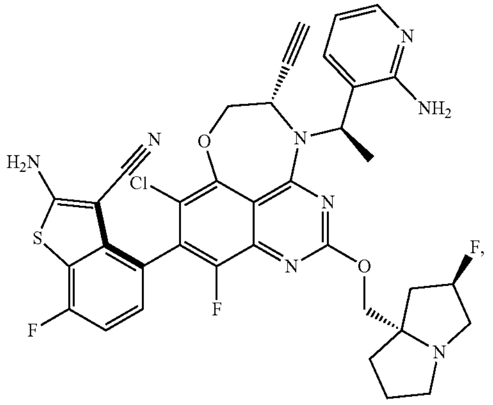

-continued
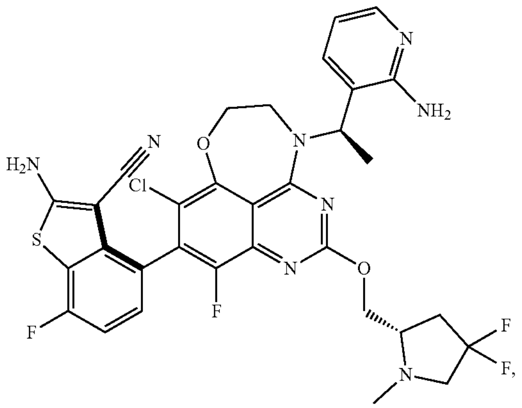
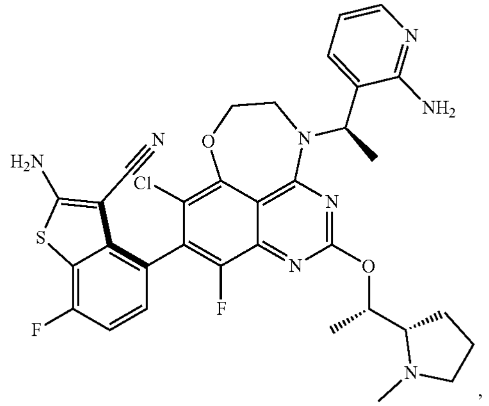
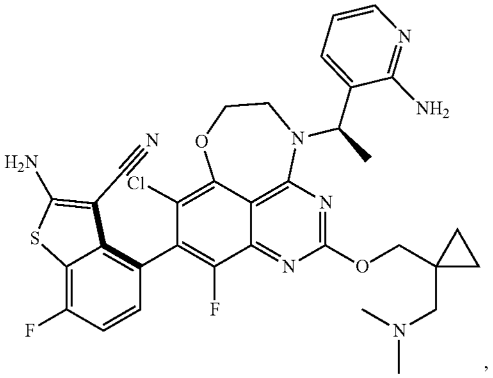
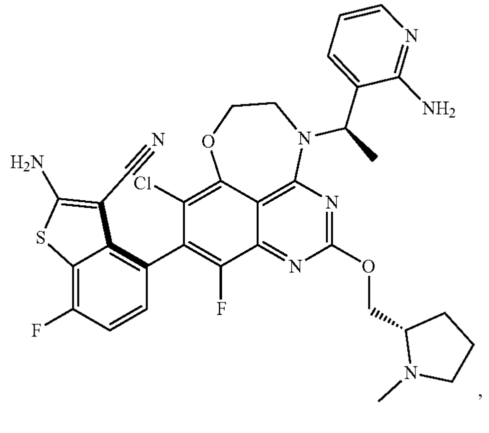
-continued
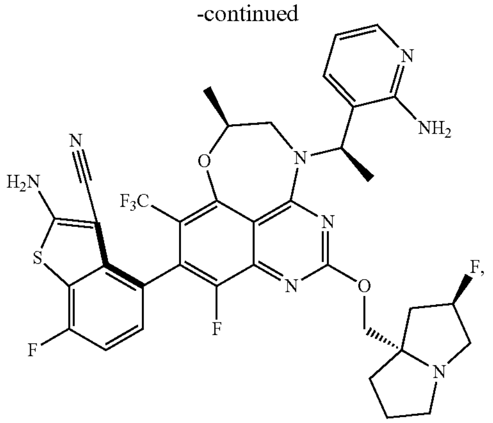
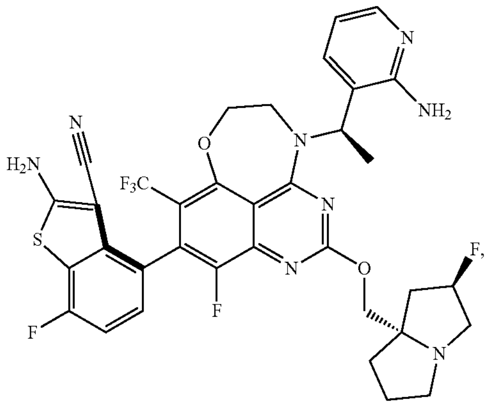
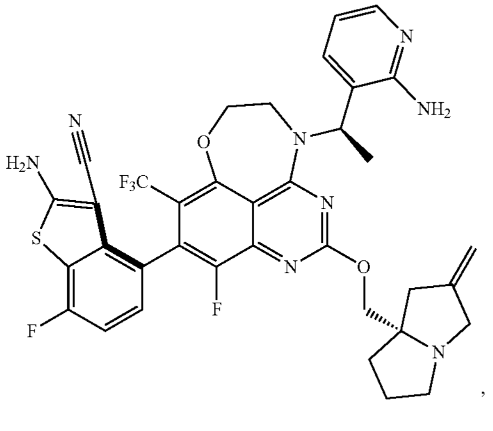

-continued
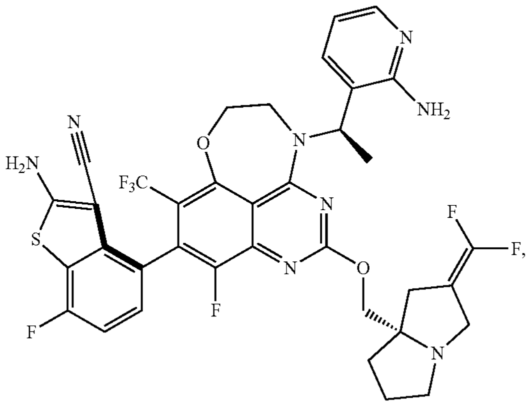
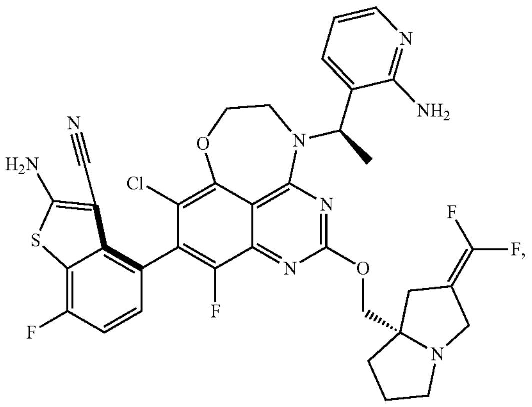
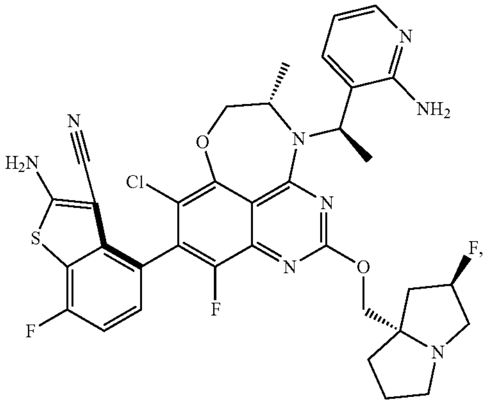
or a salt or solvate thereof.
8. A compound having the formula
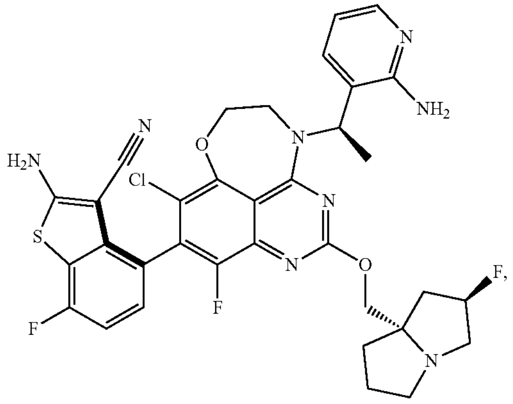
or a salt or solvate thereof.
9. A compound having the formula
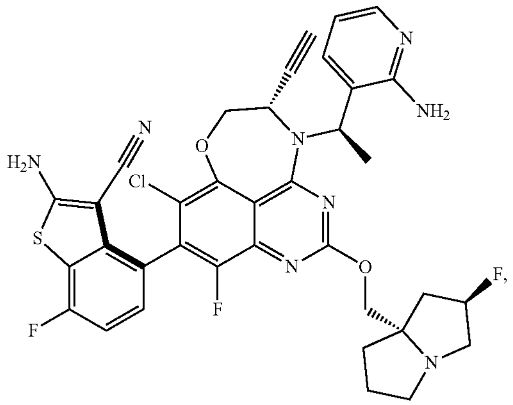
or a salt or solvate thereof.
10. The compound of claim 7 having the formula
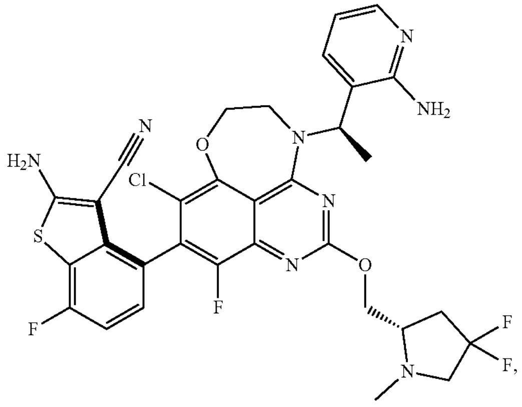
or a salt or solvate thereof.

11. The compound of claim 7 having the formula

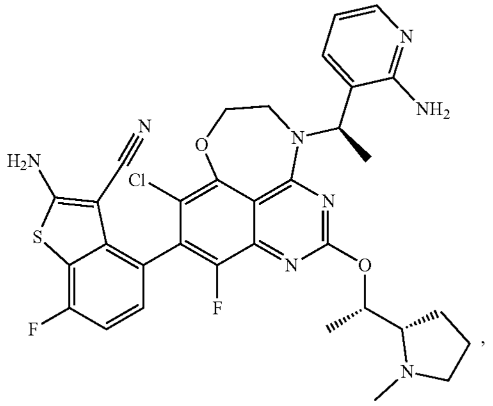 [SMILES: C[C@H](Oc1nc2c3c(c(Cl)c(-c4ccc(F)c5sc(N)c(C#N)c45)c(F)c3n1)OCCN2[C@H](C)c1cccnc1N)[C@@H]1CCCN1C]

or a salt or solvate thereof.

12. The compound of claim 7 having the formula

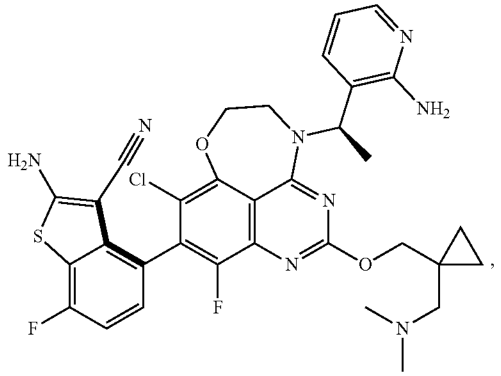

or a salt or solvate thereof.

13. The compound of claim 7 having the formula

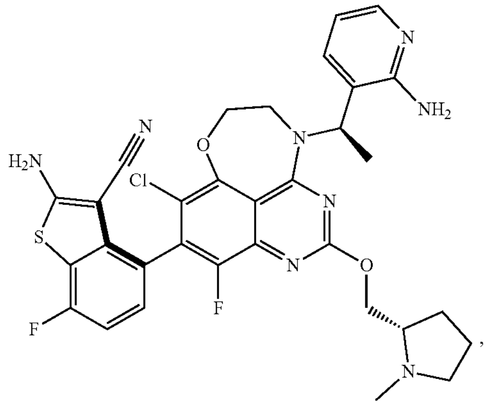

or a salt or solvate thereof.

14. A pharmaceutical composition comprising a compound of claim 1, or a pharmaceutically acceptable salt or solvate thereof, and a pharmaceutically acceptable excipient.

15. A pharmaceutical composition comprising a compound of claim 7, or a pharmaceutically acceptable salt or solvate thereof, and a pharmaceutically acceptable excipient.

16. A method of treating cancer having amplified wildtype Ras or a Ras mutant protein in a subject, the method comprising: inhibiting amplified wildtype Ras or the Ras mutant protein by administering to said subject an effective amount of a compound of claim 1, or a pharmaceutically acceptable salt or solvate thereof.

* * * * *